(12) United States Patent
Bradner et al.

(10) Patent No.: US 11,311,609 B2
(45) Date of Patent: Apr. 26, 2022

(54) REGULATING CHIMERIC ANTIGEN RECEPTORS

(71) Applicant: DANA-FARBER CANCER INSTITUTE, INC., Boston, MA (US)

(72) Inventors: James Bradner, Weston, MA (US); Justin Roberts, Cambridge, MA (US); Behnam Nabet, Boston, MA (US); Georg Winter, Vienna (AT); Andrew J. Phillips, Cambridge, MA (US); Timothy P. Heffernan, Cambridge, MA (US); Dennis Buckley, Jamaica Plain, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/483,204

(22) PCT Filed: Feb. 8, 2018

(86) PCT No.: PCT/US2018/017464
§ 371 (c)(1),
(2) Date: Aug. 2, 2019

(87) PCT Pub. No.: WO2018/148440
PCT Pub. Date: Aug. 16, 2018

(65) Prior Publication Data
US 2019/0365875 A1 Dec. 5, 2019

Related U.S. Application Data

(60) Provisional application No. 62/456,649, filed on Feb. 8, 2017, provisional application No. 62/457,124, filed on Feb. 9, 2017.

(51) Int. Cl.
| | | |
|---|---|---|
| *A61K 38/52* | (2006.01) | |
| *A61P 37/06* | (2006.01) | |
| *A61K 35/17* | (2015.01) | |
| *C07D 401/04* | (2006.01) | |
| *C07D 401/14* | (2006.01) | |
| *C07D 495/04* | (2006.01) | |
| *C07D 495/14* | (2006.01) | |
| *C07J 43/00* | (2006.01) | |
| *C07K 14/535* | (2006.01) | |
| *C07K 14/725* | (2006.01) | |

(Continued)

(52) U.S. Cl.
CPC .............. *A61K 38/52* (2013.01); *A61K 35/17* (2013.01); *A61P 37/06* (2018.01); *C07D 401/04* (2013.01); *C07D 401/14* (2013.01); *C07D 495/04* (2013.01); *C07D 495/14* (2013.01); *C07J 43/003* (2013.01); *C07K 14/535* (2013.01); *C07K 14/7051* (2013.01); *C07K 14/70517* (2013.01); *C07K 14/70521* (2013.01); *C07K 14/70578* (2013.01); *C07K 16/2803* (2013.01); *C07K 16/2878* (2013.01); *C07K 16/2896* (2013.01); *C07K 16/32* (2013.01); *C12N 5/0636* (2013.01); *C12N 5/0638* (2013.01); *C12N 9/90* (2013.01); *C12Y 502/01008* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
CPC .............. A61K 38/52; A61K 35/17; A61K 39/001112; A61K 45/06; A61K 2039/5156; A61K 39/0011; A61P 37/06; A61P 35/02; C07D 401/04; C07D 401/14; C07D 495/04; C07D 495/14; C07D 487/04; C07J 43/003; C07K 14/535; C07K 14/7051; C07K 14/70517; C07K 14/70521; C07K 14/70578; C07K 16/2803; C07K 16/2878; C07K 16/2896; C07K 16/32; C07K 2317/622; C07K 2317/76; C07K 2319/02; C07K 2319/03; C07K 2319/30; C07K 2319/33; C07K 2317/73; C07K 2319/70; C07K 2319/95; C07K 2319/20; C12N 5/0636; C12N 5/0638; C12N 9/90; C12N 9/104; C12Y 502/01008
See application file for complete search history.

(56) References Cited

U.S. PATENT DOCUMENTS

| | | |
|---|---|---|
| 5,763,590 A | 6/1998 | Peattie |
| 7,371,539 B2 | 5/2008 | Church |

(Continued)

FOREIGN PATENT DOCUMENTS

| | | |
|---|---|---|
| WO | 1995/026200 A1 | 10/1995 |
| WO | 1996/010038 A1 | 4/1996 |

(Continued)

OTHER PUBLICATIONS

Lloyd et al., Protein Engineering, Design & Selection 22:159-168 (Year: 2009).*

(Continued)

*Primary Examiner* — Phuong Huynh
(74) *Attorney, Agent, or Firm* — Burns & Levinson, LLP; Daniel W. Clarke; Shawn P. Foley

(57) ABSTRACT

This invention is in the area of compositions and methods for regulating chimeric antigen receptor immune effector cell, for example T-cell (CAR-T), therapy to modulate associated adverse inflammatory responses, for example, cytokine release syndrome and tumor lysis syndrome, using targeted protein degradation.

29 Claims, 164 Drawing Sheets

Specification includes a Sequence Listing.

(51) Int. Cl.
*C07K 14/705* (2006.01)
*C07K 16/28* (2006.01)
*C12N 5/0783* (2010.01)
*C12N 9/90* (2006.01)
*C07K 16/32* (2006.01)

(56) References Cited

U.S. PATENT DOCUMENTS

| | | | |
|---|---|---|---|
| 8,697,359 | B1 | 4/2014 | Zhang |
| 8,771,945 | B1 | 7/2014 | Zhang |
| 9,023,649 | B2 | 5/2015 | Mail |
| 9,228,208 | B2 | 1/2016 | Frendewey et al. |
| 9,260,752 | B1 | 2/2016 | May et al. |
| 9,694,084 | B2 | 7/2017 | Bradner et al. |
| 9,809,603 | B1 | 11/2017 | Jacques |
| 10,189,858 | B2 | 1/2019 | Jacques |
| 2003/0235889 | A1 | 12/2003 | Rivera et al. |
| 2004/0072319 | A1 | 4/2004 | Nash et al. |
| 2013/0280285 | A1 | 10/2013 | Schonfeld et al. |
| 2014/0068797 | A1 | 3/2014 | Doudna et al. |
| 2014/0273226 | A1 | 9/2014 | Wu |
| 2014/0273230 | A1 | 9/2014 | Chen et al. |
| 2014/0273235 | A1 | 9/2014 | Voytas et al. |
| 2014/0302523 | A1 | 10/2014 | Crews et al. |
| 2016/0045607 | A1 | 2/2016 | Crew et al. |
| 2016/0053272 | A1 | 2/2016 | Wurtzel et al. |
| 2016/0058872 | A1 | 3/2016 | Crew et al. |
| 2016/0176916 | A1 | 6/2016 | Bradner et al. |
| 2016/0199412 | A1 | 7/2016 | Tareen |
| 2016/0214972 | A1 | 7/2016 | Jin et al. |
| 2016/0235730 | A1 | 8/2016 | Bradner et al. |
| 2016/0272639 | A1 | 9/2016 | Crew et al. |
| 2016/0362472 | A1 | 12/2016 | Bitter et al. |
| 2017/0008904 | A1 | 1/2017 | Crew et al. |
| 2018/0085465 | A1 | 3/2018 | Bradner et al. |
| 2018/0134684 | A1 | 5/2018 | Bradner et al. |
| 2018/0169109 | A1 | 6/2018 | Bradner et al. |
| 2018/0179522 | A1 | 6/2018 | Buckley et al. |
| 2018/0327419 | A1 | 11/2018 | Bradner et al. |

FOREIGN PATENT DOCUMENTS

| | | | | |
|---|---|---|---|---|
| WO | 1997/018185 | A1 | 5/1997 | |
| WO | 1997/025329 | A1 | 7/1997 | |
| WO | 1997/030170 | A1 | 8/1997 | |
| WO | 1997/031934 | A1 | 9/1997 | |
| WO | 2000/001836 | A1 | 1/2000 | |
| WO | 2000/047220 | | 8/2000 | |
| WO | 2005002526 | A2 | 1/2005 | |
| WO | 2012078559 | A2 | 6/2012 | |
| WO | 2013/090921 | A1 | 6/2013 | |
| WO | 2013106643 | A2 | 7/2013 | |
| WO | 2013/170147 | A1 | 11/2013 | |
| WO | 2014015175 | A1 | 1/2014 | |
| WO | 2014/099744 | A1 | 6/2014 | |
| WO | 2014127261 | A1 | 8/2014 | |
| WO | 2014/191726 | A1 | 12/2014 | |
| WO | 2014/203129 | A1 | 12/2014 | |
| WO | 2014/203132 | A1 | 12/2014 | |
| WO | 2014/204729 | A1 | 12/2014 | |
| WO | 2014/205136 | A1 | 12/2014 | |
| WO | 2014/205138 | A1 | 12/2014 | |
| WO | 2015/071474 | A2 | 5/2015 | |
| WO | 2015/090229 | A1 | 6/2015 | |
| WO | 2015/095895 | A1 | 6/2015 | |
| WO | 2015/160845 | A2 | 10/2015 | |
| WO | WO-2015160845 | A2 * | 10/2015 | .............. A61P 37/02 |
| WO | 2016/011070 | A2 | 1/2016 | |
| WO | 2016/100236 | A2 | 6/2016 | |
| WO | 2016/105518 | A1 | 6/2016 | |
| WO | 2016/115177 | A1 | 7/2016 | |
| WO | 2016149254 | A1 | 9/2016 | |
| WO | 2017024318 | A1 | 2/2017 | |

OTHER PUBLICATIONS

Edwards et al., J Mol Biol. 334(1): 103-118 (Year: 2003).*
Rudikoff et al., Proc Natl Acad Sci USA 79: 1979-1983 (Year: 1982).*
Winter et al., Science 348: 1376-1381 (Year: 2015).*
Yu et al., Investigative Ophthalmology & Visual Science 49(2): 522-527 (Year: 2008).*
Dotti et al., Immunol Rev 257(1): 1-35 (Year: 2014).*
Sadelain et al., Current Opinion in Immunology 21: 215-223 (Year: 2009).*
Abate-Daga, Daniel, et al., "CAR Models: Net-Generation CAR Modifications for Enhanced T-Cell Function", Mol. Ther. Oncolytics, 2016, vol. 3, No. 16014.
Berge, I.J.M. Ten, et al., "Selective Expansion of a Peripheral Bood CD8+ Memory T Cell Subset Expressing Both Granzyme B and L-Selectin During Primary Viral Infection in Renal Allograft Recipients", Transplant Proc., 1998, vol. 30, pp. 3975-3977.
Bird, Robert E., et al., "Single-Chain Antigen-Binding Proteins", Science, 1988, vol. 242, No. 4877, pp. 423-426.
Bondeson, Daniel P., et al., "Catalytic in vivo Protein Knockdown by Small-Molecule PROTACs", Nat. Chem. Biol., 2015, vol. 11, No. 8, pp. 611-617.
Brentjens, Renier, et al., "Treatment of Chronic Lymphocytic Leukemia with Genetically Targeted Autologous T Cells: Case Report of an Unforseen Adverse Event in a Phase 1 Clinical Trial", Mol. Ther., 2010, vol. 18, No. 4, pp. 666-668.
Buckley, Dennis L., et al., "Use of Small Molecule PROTACs to Induce Degradation of HaloTag Fusion Proteins", ACS Chem. Biol., 2015, vol. 10, pp. 1831-1837.
Buckley, Dennis L., et al., "Small-Molecule Control of Intracellular Protein Levels through Modulation of the Ubiquitin Proteasome System", Angew. Chem. Int. Ed. Engl., 2014, vol. 53, No. 9, pp. 2312-2330.
Cabantous, Stephanie, et al., "A New Protein-Protein Interaction Sensor Based on Tripartite Split-GFP Association", Scientific Reports, 2013, vol. 3, No. 2854.
Chang, Xiu-bao, et al., "What is the Functional Role of the Thalidomide Binding Protein Cereblon?", Int. J. Biochem. Mol. Biol, 2011, vol. 2, No. 3, pp. 287-294.
Cho, Seung Woo, et al., "Analysis of Off-Target Effects of CRISPS/Cas-Derived RNA-Guided Endonucleases and Nickases", Genome Research, 2014, vol. 24, pp. 132-141.
Clackson, Tim, et al., "Redesigning an FKBP-Ligand Interface to Generate Chemical Dimerizers with Novel Specificity", Proc. Natl. Acad. Sci. USA, 1998, vol. 95, pp. 10437-10442.
Corson, Timothy W., et al., "Design and Applications of Bifunctional Small Molecules: Why Two Heads are Better Than One", ACS Chem. Biol., 2008, vol. 3, No. 11, pp. 677-692.
Crews, Craig M., "Targeting the Undruggable Proteome: The Small Molecule of My Dreams", Chem. Biol., 2010, vol. 17, No. 6, pp. 551-555.
Daniels, Danette L., et al., "Discovering Protein Interactions and Characterizing Protein Function Using HaloTag Technology", Journal of Visualized Experiments, 2014, vol. 89, pp. 1-9.
Danos, Olivier, et al., "Safe and Efficient Generation of recombinant Retroviruses with Amphotropic and Ecotropic Host Ranges", Proc. Natl. Acad. Sci., USA, 1988, vol. 85, pp. 6460-6464.
Doessegger, Lucette, et al., "Clinical Development Methodology for Infusion-Related Reactions with Monoclonal Antibodies", Clin. Transl. Immunology, 2015, vol. 4, No. 7, pp. e39.
England, Christopher G., et al., "HaloTag Technology: A Versatile Platform for Biomedical Applications", Bioconjugate Chem., 2015, vol. 26, No. 6, pp. 975-986.
Garland, R.J., et al., "The Use of Teflon Cell Culture Bags to Expand Functionally Active CD8+ Cytotoxic T Lymphocytes", Elsevier, J. Immunol. Methods, 1999, vol. 227, pp. 53-63.
Grupp, Stephan A., et al. "Chimeric Antigen Receptor-Modified T Cells for Acute Lymphoid Leukemia", N. Engl. J. Med., 2013, vol. 368, pp. 1509-1518.
Gustafson, Jeffrey L., et al. "Small-Molecule-Mediated Degradation of the Androgen Receptor Through Hydrophobic Tagging", Angew. Chem. Int. Ed., 2015, vol. 54, pp. 9659-9662.

(56) References Cited

OTHER PUBLICATIONS

Haanen, John B.A.G., et al., "Selective Expansion of Cross-Reactive CD8+ Memory T Cells by Viral Variants", J. Exp. Med., 1999, vol. 190, No. 9, pp. 1319-1328.

Huston, James S., et al., "Protein Engineering of Antibody Binding Sites: Recovery of Specific Activity in an Anti-Digoxin Single-Chain Fv Analogue Produced in *Escherichia coli*", Proc. Natl. Acad. Sci. USA, 1988, vol. 85, pp. 5879-5883.

Itoh, Yukihiro, et al., "Protein Knockdown Using Methyl Bestatin-Ligand Hybrid Molecules: Design and Synthesis of Inducers of Ubiquitination-Mediated Degradation of Cellular Retinoic Acid-Binding Proteins", J. Am. Chem. Soc., 2010, vol. 132, pp. 5820-5826.

Kamiyama, Daichi, et al., "Versatile Protein Tagging in Cells with Split Fluorescent Protein", Nat. Commun., 2015, vol. 7:, No. 11046.

Koles, Kate, et al., "Tissue-Specific Tagging of Endogenous Loci in *Drosophila melanogaster*", Biol. Open, 2015, vol. 5, No. 1, pp. 83-89.

Lackner, Daniel H., et al., "A Generic Strategy for CRISPR-Cas9-Mediated Gene Tagging", Nat. Commun., 2015, vol. 6, No. 10237.

Lai, Ashton C., et al., "Modular PROTAC Design for the Degradation of Oncogenic BCR-ABL", Angew. Chem. Int. Ed., 2016, vol. 55, pp. 807-810.

Li, Hao, et al., "TGF-B Induces Degradation of PTHrP Through Ubiquitin-Proteasome System in Hepatocellular Carcinoma", Journal of Cancer, 2015, vol. 6, pp. 511-518.

Lo, Te-Wen, et al., "Precise and Heritable Genome Editing in Evolutionarily Diverse Nematodes Using TALENs and CRISPR/Cas9 to Engineer Insertions and Deletions", Genetics, Oct. 2013, vol. 195, pp. 331-348.

Los, Georgyi V., et al., "HaloTag: A Novel Protein Labeling Technology for Cell Imaging and Protein Analysis", ACS Chem. Biol., 2008, vol. 3, No. 6, pp. 373-382.

Louis, Chrystal U., et al., "Antitumor Activity and Long-Term Fate of Chimeric Antigen Receptor-Positive T Cells in Patients with Neuroblastoma", Blood, 2011, vol. 118, No. 23, p. 6050.

Minagawa, Kentaro, et al., "Seatbelts in CAR Therapy: How Safe are CARS?", Pharmaceuticals (Basel), 2015, vol. 8, No. 2, pp. 230-249.

Mirzaei, Hamid Reza, et al., "Prospects for Chimeric Antigen Receptor (CAR) Y δ T Cells: A Potential Game Changer for Adoptive T Cell Cancer Immunotherapy", Cancer Lett., 2016, vol. 380, pp. 413-423.

Morgan, Richard A., et al., "Case Report of a Serious Adverse Event Following the Administration of T Cells Transduced with a Chimeric Antigen Receptor Recognizing ERBB2", Mol. Thera., 2010, vol. 18, No. 4, pp. 843-851.

Natsume, Toyoaki, et al., "Rapid Protein Depletion in Human Cells by Auxin-Inducible Degron Tagging with Short Homology Donors", Cell Reports, 2016, vol. 15, pp. 210-218.

Paix, Alexandre, et al., "Scalable and Versatile Genome Editing Using Linear DNAs with Microhomology to Cas9 Sites in Caenorhabditis Elegans", Genetics, 2014, vol. 198, pp. 1347-1356.

Park, Arnold, et al., "CRISPR/Cas9 Allows Efficient and Complete Knock-In of a Destabilization Domain-Tagged Essential Protein in a Human Cell Line, Allowing Rapid Knockdown of Protein Function", PLOS One, 2014, vol. 9, No. 4.

Porter, David L., et al., "Chimeric Antigen Receptor-Modified T Cells in Chronic Lymphoid Leukemia", N. Engl. J. Med., 2011, vol. 365, pp. 725-733.

Rakhit, Rishi, et al., "Chemical Biology Strategies for Post-translational Control of Protein Function", Chem. Biol., 2014, vol. 21, No. 9, pp. 1238-1252.

Robers, Matt, et al., "Fluorescent Labeling of Proteins in Living Cells Using the FKBP12(F36V) Tag", Cytometry Part A, 2009, vol. 75A, pp. 207-224.

Rodriguez-Gonzalez, A, et al., "Targeting Steroid Hormone Receptors for Ubiquitination and Degradation in Breast and Prostate Cancer", Oncogene, 2008, vol. 27, No. 57, pp. 7201-7211.

Sakamoto, Kathleen M., et al., "Chimeric Molecules that Target Proteins to the Skp1-Cullin-F Box Complex for Ubiquitination and Degradation", PNAS, 2001, vol. 98, No. 15, pp. 8554-8559.

Sakamoto, Kathleen M., et al., "Development of Protacs to Target Cancer-Promoting Proteins for Ubiquitination and Degradation", Mol. Cell Proteomics, 2003, vol. 2, No. 12, pp. 1350-1358.

Schneekloth, John S., et al., "Chemical Approaches to Controlling Intracellular Protein Degradation", ChemBioChem, 2005, vol. 6, pp. 40-46.

Schwartz, Matthew L., et al., "SapTrap, a Toolkit for High-Throughput CRISPR/Cas9 Gene Modification in Caenorhabditis Elegans", Genetics, 2016, vol. 202, pp. 1277-1288.

Sheridan, Ryan M., et al., "Selectable One-Step PCR-Mediated Integration of a Degron for Rapid Depletion of Endogenous Human Proteins", BioTechniques, 2016, vol. 60, pp. 69-74.

Skerra, Arne, et al., "Assembly of a Functional Immunoglobulin Fv Fragment in *Escherichia Coli*", Science, 1988, vol. 240, No. 4855, pp. 1038-1041.

Till, Brian G., et al., "CD20-Specific adoptive Immunotherapy for Lymphoma Using a Chimeric Antigen Receptor with Both CD28 and 4-1BB Domains: Pilot Clinical Trial Results", Blood, 2012, vol. 119, No. 17, pp. 3940-3950.

Toure, Momar, et al., "Small-Molecule PROTACS: New Approaches to Protein Degradation", Angew. Chem. Int. Ed. 2016, vol. 55, pp. 1966-1973.

Ui-Tei, Kumiko, et al., Sensitive Assay of RNA Interference in *Drosophila* and Chinese Hamster Cultured Cells Using Firefly Luciferase Gene as Target, FEBS Letters, 2000, vol. 4799, pp. 79-82.

Agaugue, Sophie, et al, "Development of an Inducible CAR-T Cell Platform Using Lentiviral Vector Background", Jan. 1, 2015, retrieved from the Internet: URL:http://www.theravectys.com/wp-constent/uploads/Publications/150506_CARs_ASGCT_72dpi.pdf.

Ang, Sonny O., et al., "Conditional Activation of T Cells to Specifically Target c-Met Under Hypoxia", Molecular Therapy, Cell Press, US, May 1, 2009, vol. 17, No. Suppl. 1, pp. S25-S26.

Garnier, Jean-Marc, et al., "BET Bromodomain Inhibitors: A Patent Review", Expert Opinion on Therapeutic Patents, Feb. 1, 2014, vol. 24, No. 2, pp. 185-199.

Wu, Chia-Yung, et al., "Remote Control of Therapeutic T Cells Through a Small Molecule-Gated Chimeric Receptor", SCIENCE, Sep. 24, 2015, vol. 350, No. 6258, p. aab4077.

Rivera et al., "A Humanized System for Pharmacologic Control of Gene Expression", Nature Medicine, Sep. 1, 1996, vol. 2, pp. 1028-1032.

Standaert et al. "Molecular Cloning and Overexpression of the Human FK506-Binding Protein FKBP", Nature, Aug. 16, 1990, vol. 346, pp. 671-674.

Hruscha, A., et al., "Efficient CRISPR/Cas9 Genome Editing with Low Off-Target Effects in Zebrafish", DEVELOPMENT, vol. 140, No. 24, Nov. 20, 2013, pp. 4982-4987.

Edwards, B., et al. "The Remarkable Flexibility of the Human Antibody Repertoire; Isolation of Over One Thousand Different Antibodies to a Single Protein, BLyS", J. Mol. Biol., 2003, vol. 334, No. 1, pp. 103-118.

Lloyd, C., et al., "Modelling the Human Immune Response: Performance of a 10" Human Antibody Repertoire Against a Broad Panel of Therapeutically Relevant Antigens", Protein Eng. Des. Sel., 2009, vol. 22, No. 3, pp. 159-168.

Lu, J., et al., "Hijacking the E3 Ubiquitin Ligase Cereblon to Efficiently Target BRD4", Chem. Biol., 2015, vol. 22, No. 6, pp. 755-763.

Rudikoff, S., et al., "Single Amino Acid Substitution Altering Antigen-Binding Specificity", Proc. Natl. Acad. Sci. USA, 1982, vol. 79, No. 6, pp. 1979-1983.

Schneekloth, J., et al., "Chemical Genetic Control of Protein Levels: Selective in Vivo Targeted Degradation", J. Am. Chem. Soc., 2004, vol. 126, No. 12, pp. 3748-3754.

Winter, G., et al., "Phthalimide Conjugation as a Strategy for in Vivo Target Protein Degradation", Research, 2015, vol. 348, No. 6241, pp. 1376-1381.

(56) References Cited

OTHER PUBLICATIONS

Janse, Daniel M., et al., "Localization to the Proteasome is Sufficient for Degradation", The Journal of Biological Chemistry, 2004, vol. 279, No. 20, pp. 21415-21420.

Xie, Youming, et al., "Physical Association of Ubiquitin Ligases and the 26S Proteasome", PNAS, 2000, vol. 97, No. 6, pp. 2497-2502.

Jensen, M.C., et al., "Design and Implementation of Adoptive Therapy with Chimeric Antigen Receptor-Modified T Cells", Immunological Review, Jan. 2014, vol. 257, pp. 127-144.

Wang, Xiao, et al., "CRISPR-Cas9 Targeting of PCSK9 in Human Hepatocytes In Vivo—Brief Report", Arterioscler Thromb. Vasc. Biol., 2016, vol. 36, No. 5, pp. 783-786.

Ward, Sally E., "Binding Activities of a Repertoire of Single Immunoglobulin Variable Domains Secreted from *Escherichia coli*", Nature, 1989, vol. 341, No. 6242, pp. 544-546.

Xu, Xiao-Jun, et al., "Efficacy and Safety of Adoptive Immunotherapy Using Anti-CD19 Chimeric Antigen Receptor Transduced T-Cells: A Systematic Review of Phase 1 Clinical Trials", Leuk. Lymphoma, 2013, vol. 54, No. 2, pp. 255-260.

Yu, Zhongshene, et al., "Various Applications of TALEN- and CRSPR/Cas9-Mediated Homologous Recombination to Modify the *Drosophila* Genome", Biol. Open, 2014, vol. 3, No. 4, pp. 271-280.

Zhang, Liangyu, et al., "The Auxin-Inducible Degradation (AID) System Enables Versatile Conditional Protein Depletion in C. Elegans", Development, 2015, vol. 142, No. 24, pp. 4374-4384.

Zhou, Qianhe, et al., "A Chemical Genetics Approach for the Functional Assessment of Novel Cancer Genes", Cancer Res., 2015, vol. 75, No. 10, pp. 1949-1958.

Bondeson, et al., "Lessons in PROTAC Design from Selective Degradation with a Promiscuous Warhead," Cell Chem Biol., Jan. 18, 2015, 25(1): 78-87.

Huang, et al., "A Chemoproteomic Approach to Query the Degradable Kinome Using A Multi-Kinase Degrader," Cell Chem. Biol., Jan. 18, 2018, vol. 25, No. 1, pp. 88-89.

Nowak, et al., "Plasticity in Binding Confers Selectivity in Ligand Induced Protein Degradation," Nat. Chem. Biol., Jul. 2018, vol. 14, No. 7 pp. 706-714.

Pettersson, et al., "PROteolysis Tageting Chimeras (PROTACs)—Past, Present and Future," Elsevier Ltd., Drug Discovery Today: Technologies, 2019, vol. 31, pp. 15-27.

Sakamoto, et al., "Protacs: Chimeric Molecules that Target Proteins to the SKP1-Cullin-F Box Complex for Ubiquitination and Degradation," PNAS, Jul. 17, 2001, vol. 98, No. 15, 8554-8559.

Smith, et al., "Targeted Intracellular Protein Degradation Induced by a Small Molecule: En Route to Chemical Proteomics,"Bioorganic & Medicinal Chemistry Letters 18 (2008)) 5904-5908.

* cited by examiner

| | |
|---|---|
|  | dBET15 |
|  | dBET16 |
|  | dBET17 |
|  | dBET18 |
|  | dGR1 |
|  | dGR2 |

| Cmpd. No. | Structure |
|---|---|
| dBET19 | 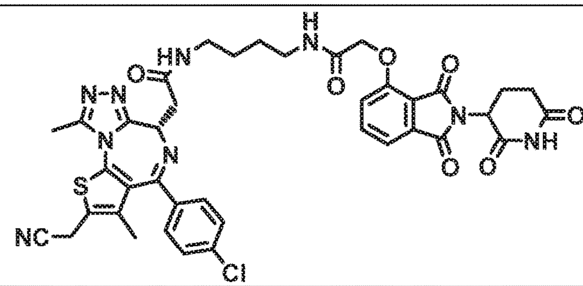 |
| dBET20 | 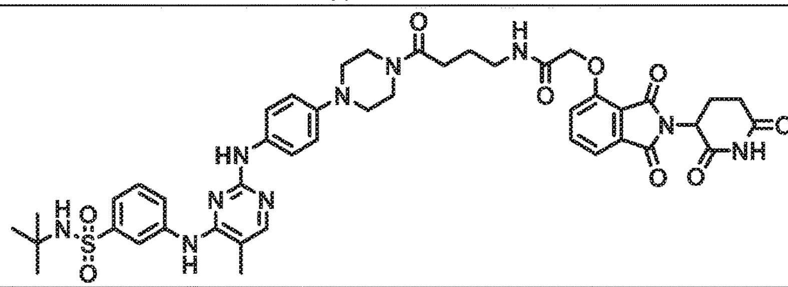 |
| dBET21 | 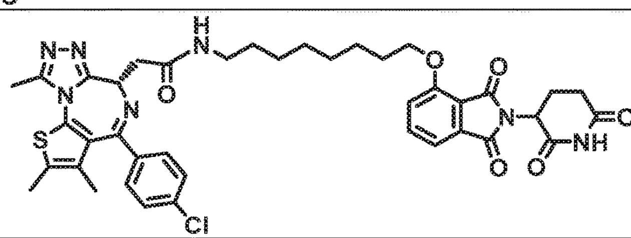 |
| dBET22 | 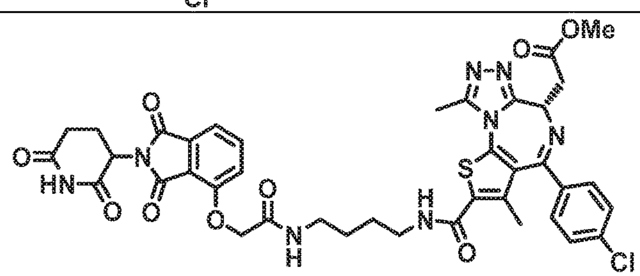 |
| dBET23 | 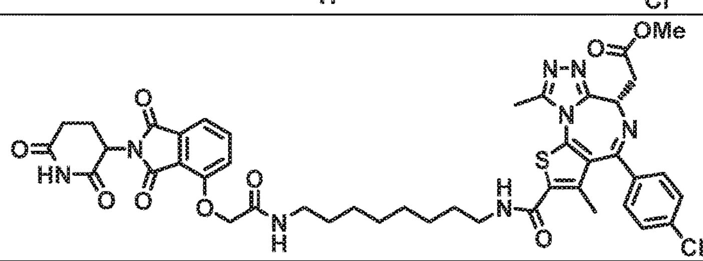 |

| | |
|---|---|
| dBET24 | |
| dBET25 | |
| dBET26 | |
| dBET27 | |
| dBET28 | |

FIG. 51B

| | |
|---|---|
| dBET29 |  |
| dBET30 |  |
| dBET31 |  |
| dBET32 |  |
| dBET33 |  |

| | |
|---|---|
| dBET34 |  |
| dBET35 |  |
| dBET36 |  |
| dBET37 |  |
| dBET38 |  |
| dBET39 |  |

| | |
|---|---|
| dBET40 |  |
| dBET41 |  |
| dBET42 |  |
| dBET43 |  |
| dBET44 |  |

FIG. 51F

| dBET100 |  |
| --- | --- |
| dBET101 |  |
| dBET102 |  |
| dBET103 |  |
| dBET104 |  |

| | |
|---|---|
| dFKBP-18 |  |
| dFKBP-19 |  |
| dFKBP-20 |  |

| | |
|---|---|
| dFKBP-27 |  |
| dFKBP-28 |  |
| dFKBP-29 |  |
| dFKBP-30 |  |
| dFKBP-31 |  |

| | |
|---|---|
| dFKBP-32 |  |
| dFKBP-33 |  |
| dFKBP-34 |  |
| dKFBP-35 |  |

| dFKBP-36 | |
| --- | --- |
| dFKBP-37 | |
| dFKBP-38 | |
| dFKBP100 | |

FIG. 51P

| Cmpd. No. | Structure |
|---|---|
| dBET200 | 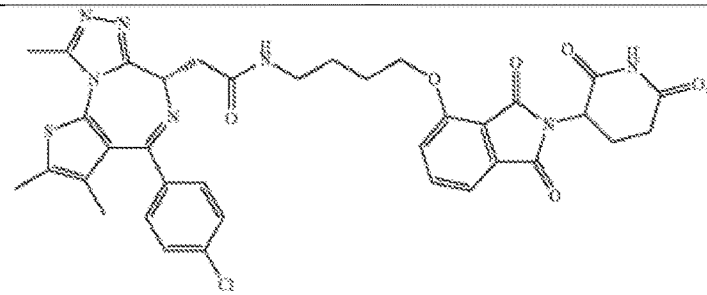 |
| dBET201 | 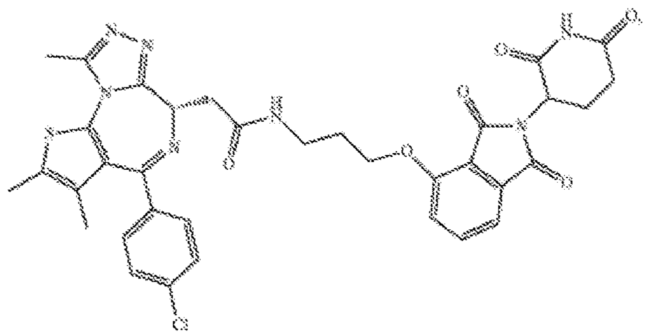 |
| dBET202 | 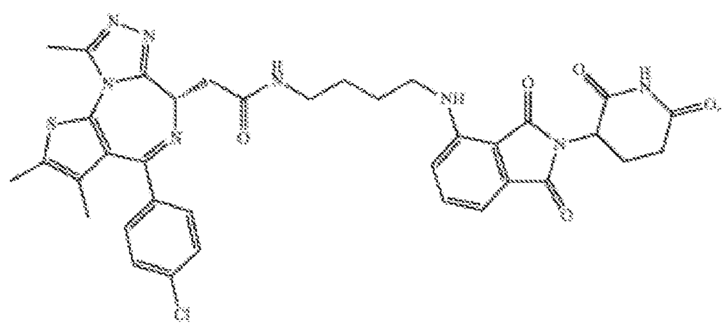 |
| dBET203 | 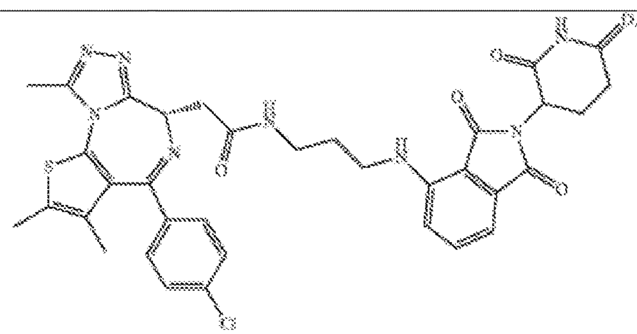 |

| dBET223 |  |
| dBET224 |  |
| dBET225 |  |
| dBET226 |  |

FIG. 53A

| | | |
|---|---|---|
| dFKBP-3-I-o |  |  |
| dFKBP-3-I-o" |  |  |
| dFKBP-3-I-p |  |  |
| dFKBP-3-I-p" |  |  |
| dFKBP-4-I-m |  |  |
| dFKBP-4-I-m" |  |  |
| dFKBP-4-I-o |  |  |

| | | |
|---|---|---|
| dFKBP-4-I-o" |  |  |
| dFKBP-4-I-p |  |  |
| dFKBP-4-I-p" |  |  |
| dFKBP-5-I-m |  |  |
| dFKBP-5-I-m" |  |  |
| dFKBP-5-I-o |  |  |
| dFKBP-5-I-o" |  |  |

| | | |
|---|---|---|
| dFKBP-17-I-o |  |  |
| dFKBP-17-I-o″ |  |  |
| dFKBP-17-I-p |  |  |
| dFKBP-17-I-p″ |  |  |
| dFKBP-26-I-m |  |  |
| dFKBP-26-I-m″ |  |  |
| dFKBP-26-I-o |  |  |

| | | |
|---|---|---|
| dFKBP-26-I-o″ |  |  |
| dFKBP-26-I-p |  |  |
| dFKBP-26-I-p″ |  |  |
| dFKBP-24-I-m |  |  |
| dFKBP-24-I-m″ |  |  |
| dFKBP-24-I-o |  |  |
| dFKBP-24-I-o″ |  |  |

| | | |
|---|---|---|
| dFKBP-16-I-m |  |  |
| dFKBP-16-I-m" |  |  |
| dFKBP-16-I-o |  |  |
| dFKBP-16-I-o" |  |  |
| dFKBP-16-I-p |  |  |

| | | |
|---|---|---|
| dFKBP-16-I-p" |  |  |
| dFKBP-20-I-m |  |  |
| dFKBP-20-I-m" |  |  |
| dFKBP-20-I-o |  |  |
| dFKBP-20-I-o" |  |  |
| dFKBP-20-I-p |  |  |
| dFKBP-20-I-p" |  |  |

| | | |
|---|---|---|
| dFKBP-18-I-m |  |  |
| dFKBP-18-I-m″ |  |  |
| dFKBP-18-I-o |  |  |
| dFKBP-18-I-o″ |  |  |
| dFKBP-18-I-p |  |  |
| dFKBP-18-I-p″ |  |  |

| | | |
|---|---|---|
| dFKBP-A-o |  |  |
| dFKBP-A-o" |  |  |
| dFKBP-A-p |  |  |
| dFKBP-A-p" |  |  |
| dFKBP-34-I-m |  |  |
| dFKBP-34-I-m" |  |  |
| dFKBP-34-I-o |  |  |

| | | |
|---|---|---|
| dFKBP-34-I-o″ |  |  |
| dFKBP-34-I-p |  |  |
| dFKBP-34-I-p″ |  |  |
| dFKBP-36-I-m |  |  |
| dFKBP-36-I-m″ |  |  |
| dFKBP-36-I-o |  |  |
| dFKBP-36-I-o″ |  |  |

FIG. 53Y

| | | |
|---|---|---|
| dFKBP-35-I-p″ |  |  |
| dFKBP-37-I-m |  |  |
| dFKBP-37-I-m″ |  |  |
| dFKBP-37-I-o |  |  |
| dFKBP-37-I-o″ |  |  |
| dFKBP-37-I-p |  |  |
| dFKBP-37-I-p″ |  |  |

| | | |
|---|---|---|
| dFKBP-30-I-m |  |  |
| dFKBP-30-I-m" |  |  |
| dFKBP-30-I-o |  |  |
| dFKBP-30-I-o" |  |  |
| dFKBP-30-I-p |  |  |
| dFKBP-30-I-p" |  |  |

| | | |
|---|---|---|
| dFKBP-32-I-m |  |  |
| dFKBP-32-I-m" |  |  |
| dFKBP-32-I-o |  |  |
| dFKBP-32-I-o" |  |  |
| dFKBP-32-I-p |  |  |
| dFKBP-32-I-p" |  |  |

| | | |
|---|---|---|
| dFKBP-33-I-m |  |  |
| dFKBP-33-I-m″ |  |  |
| dFKBP-33-I-o |  |  |
| dFKBP-33-I-o″ |  |  |
| dFKBP-33-I-p |  |  |
| dFKBP-33-I-p″ |  |  |
| dFKBP-38-I-m |  |  |

FIG. 53EE dFKBP-1-o dFKBP-1-p dFKBP-2-o dFKBP-2-*p* dFKBP*6-*o* dFKBP*6-*p* dFKBP*7-*o* dFKBP*7-p dFKBP*8-o dFKBP*9-o dFKBP*9-p

X2-o

X2-p dFKBP13-o dFKBP13-p dFKBP14-o dFKBP14-p dFKBP15-o dFKBP15-p dFKBP16-o dFKBP16-p dFKBP17-o dFKBP17-p dFKBP18-o dFKBP18-p dFKBP25-p dFKBP26-o dFKBP26-p dFKBP27-o dFKBP27-p dFKBP28-o dFKBP30-o dFKBP30-p dFKBP31-o dFKBP33-o dFKBP33-p dFKBP34-o dFKBP34-p dFKBP38-p dFKBP38-o dFKBP49-p dFKBP49-m dFKBP49-o

SEQUENCE LISTING

```
<160> NUMBER OF SEQ ID NOS: 115

<210> SEQ ID NO 1
<211> LENGTH: 107
<212> TYPE: PRT
<213> ORGANISM: Homo sapiens

<400> SEQUENCE: 1

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 2
<211> LENGTH: 107
<212> TYPE: PRT
<213> ORGANISM: Artificial Sequence
<220> FEATURE:
<223> OTHER INFORMATION: FKBP12 derived amino acid sequence with a
      mutation of phenylalanine (F) at amino acid position 36 to valine
      (V)

<400> SEQUENCE: 2
```

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
            85                  90                  95

Leu Val Phe Asp Val Glu Leu Leu Lys Leu Glu
            100                 105

<210> SEQ ID NO 3
<211> LENGTH: 1362
<212> TYPE: PRT
<213> ORGANISM: Homo sapiens

<400> SEQUENCE: 3

Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
            20                  25                  30

Ala Gln Pro Gln Pro Ala Asn Ala Ala Ser Thr Asn Pro Pro Pro Pro
            35                  40                  45

Glu Thr Ser Asn Pro Asn Lys Pro Lys Arg Gln Thr Asn Gln Leu Gln
50                  55                  60

Tyr Leu Leu Arg Val Val Leu Lys Thr Leu Trp Lys His Gln Phe Ala
65                  70                  75                  80

Trp Pro Phe Gln Gln Pro Val Asp Ala Val Lys Leu Asn Leu Pro Asp
            85                  90                  95

Tyr Tyr Lys Ile Ile Lys Thr Pro Met Asp Met Gly Thr Ile Lys Lys
            100                 105                 110

Arg Leu Glu Asn Asn Tyr Tyr Trp Asn Ala Gln Glu Cys Ile Gln Asp
            115                 120                 125

Phe Asn Thr Met Phe Thr Asn Cys Tyr Ile Tyr Asn Lys Pro Gly Asp
            130                 135                 140

Asp Ile Val Leu Met Ala Glu Ala Leu Glu Lys Leu Phe Leu Gln Lys
145                 150                 155                 160

Ile Asn Glu Leu Pro Thr Glu Glu Thr Glu Ile Met Ile Val Gln Ala
            165                 170                 175

Lys Gly Arg Gly Arg Gly Arg Lys Glu Thr Gly Thr Ala Lys Pro Gly
            180                 185                 190

Val Ser Thr Val Pro Asn Thr Thr Gln Ala Ser Thr Pro Pro Gln Thr
            195                 200                 205

Gln Thr Pro Gln Pro Asn Pro Pro Val Gln Ala Thr His Pro
            210                 215                 220

Phe Pro Ala Val Thr Pro Asp Leu Ile Val Gln Thr Pro Val Met Thr
225                 230                 235                 240

Val Val Pro Pro Gln Pro Leu Gln Thr Pro Pro Val Pro Pro Gln
            245                 250                 255

Pro Gln Pro Pro Pro Ala Pro Ala Pro Gln Pro Val Gln Ser His Pro
            260                 265                 270
```

```
Pro Ile Ile Ala Ala Thr Pro Gln Pro Val Lys Thr Lys Lys Gly Val
        275                 280                 285

Lys Arg Lys Ala Asp Thr Thr Thr Pro Thr Thr Ile Asp Pro Ile His
    290                 295                 300

Glu Pro Pro Ser Leu Pro Pro Glu Pro Lys Thr Thr Lys Leu Gly Gln
305                 310                 315                 320

Arg Arg Glu Ser Ser Arg Pro Val Lys Pro Pro Lys Lys Asp Val Pro
                325                 330                 335

Asp Ser Gln Gln His Pro Ala Pro Glu Lys Ser Ser Lys Val Ser Glu
                340                 345                 350

Gln Leu Lys Cys Cys Ser Gly Ile Leu Lys Glu Met Phe Ala Lys Lys
                355                 360                 365

His Ala Ala Tyr Ala Trp Pro Phe Tyr Lys Pro Val Asp Val Glu Ala
                370                 375                 380

Leu Gly Leu His Asp Tyr Cys Asp Ile Ile Lys His Pro Met Asp Met
385                 390                 395                 400

Ser Thr Ile Lys Ser Lys Leu Glu Ala Arg Glu Tyr Arg Asp Ala Gln
                405                 410                 415

Glu Phe Gly Ala Asp Val Arg Leu Met Phe Ser Asn Cys Tyr Lys Tyr
                420                 425                 430

Asn Pro Pro Asp His Glu Val Val Ala Met Ala Arg Lys Leu Gln Asp
                435                 440                 445

Val Phe Glu Met Arg Phe Ala Lys Met Pro Asp Glu Pro Glu Glu Pro
450                 455                 460

Val Val Ala Val Ser Ser Pro Ala Val Pro Pro Thr Lys Val Val
465                 470                 475                 480

Ala Pro Pro Ser Ser Ser Asp Ser Ser Ser Asp Ser Ser Ser Asp Ser
                485                 490                 495

Asp Ser Ser Thr Asp Asp Ser Glu Glu Glu Arg Ala Gln Arg Leu Ala
                500                 505                 510

Glu Leu Gln Glu Gln Leu Lys Ala Val His Glu Gln Leu Ala Ala Leu
    515                 520                 525

Ser Gln Pro Gln Gln Asn Lys Pro Lys Lys Glu Lys Asp Lys Lys
    530                 535                 540

Glu Lys Lys Lys Glu Lys His Lys Arg Lys Glu Glu Val Glu Glu Asn
545                 550                 555                 560

Lys Lys Ser Lys Ala Lys Glu Pro Pro Lys Lys Thr Lys Lys Asn
                565                 570                 575

Asn Ser Ser Asn Ser Asn Val Ser Lys Lys Glu Pro Ala Pro Met Lys
                580                 585                 590

Ser Lys Pro Pro Pro Thr Tyr Glu Ser Glu Glu Glu Asp Lys Cys Lys
    595                 600                 605

Pro Met Ser Tyr Glu Glu Lys Arg Gln Leu Ser Leu Asp Ile Asn Lys
610                 615                 620

Leu Pro Gly Glu Lys Leu Gly Arg Val Val His Ile Ile Gln Ser Arg
625                 630                 635                 640

Glu Pro Ser Leu Lys Asn Ser Asn Pro Asp Glu Ile Glu Ile Asp Phe
                645                 650                 655

Glu Thr Leu Lys Pro Ser Thr Leu Arg Glu Leu Glu Arg Tyr Val Thr
                660                 665                 670

Ser Cys Leu Arg Lys Lys Arg Lys Pro Gln Ala Glu Lys Val Asp Val
675                 680                 685
```

```
Ile Ala Gly Ser Ser Lys Met Lys Gly Phe Ser Ser Glu Ser Glu
    690             695             700
Ser Ser Ser Glu Ser Ser Ser Asp Ser Glu Asp Ser Glu Thr Glu
705             710             715             720
Met Ala Pro Lys Ser Lys Lys Lys Gly His Pro Gly Arg Glu Gln Lys
            725             730             735
Lys His His His His His Gln Gln Met Gln Gln Ala Pro Ala Pro
        740             745             750
Val Pro Gln Gln Pro Pro Pro Pro Gln Gln Pro Pro Pro Pro
        755             760             765
Pro Pro Gln Gln Gln Gln Gln Pro Pro Pro Pro Pro Pro Pro Ser
770             775             780
Met Pro Gln Gln Ala Ala Pro Ala Met Lys Ser Ser Pro Pro Phe
785             790             795             800
Ile Ala Thr Gln Val Pro Val Leu Glu Pro Gln Leu Pro Gly Ser Val
            805             810             815
Phe Asp Pro Ile Gly His Phe Thr Gln Pro Ile Leu His Leu Pro Gln
            820             825             830
Pro Glu Leu Pro Pro His Leu Pro Gln Pro Glu His Ser Thr Pro
        835             840             845
Pro His Leu Asn Gln His Ala Val Val Ser Pro Ala Leu His Asn
850             855             860
Ala Leu Pro Gln Gln Pro Ser Arg Pro Ser Asn Arg Ala Ala Ala Leu
865             870             875             880
Pro Pro Lys Pro Ala Arg Pro Pro Ala Val Ser Pro Ala Leu Thr Gln
            885             890             895
Thr Pro Leu Leu Pro Gln Pro Pro Met Ala Gln Pro Pro Gln Val Leu
            900             905             910
Leu Glu Asp Glu Glu Pro Pro Ala Pro Pro Leu Thr Ser Met Gln Met
        915             920             925
Gln Leu Tyr Leu Gln Gln Leu Gln Lys Val Gln Pro Pro Thr Pro Leu
        930             935             940
Leu Pro Ser Val Lys Val Gln Ser Gln Pro Pro Pro Leu Pro Pro
945             950             955             960
Pro Pro His Pro Ser Val Gln Gln Leu Gln Gln Gln Pro Pro Pro
        965             970             975
Pro Pro Pro Pro Gln Pro Gln Pro Pro Gln Gln Gln His Gln Pro
        980             985             990
Pro Pro Arg Pro Val His Leu Gln Pro Met Gln Phe Ser Thr His Ile
        995             1000            1005
Gln Gln Pro Pro Pro Pro Gln Gly Gln Gln Pro Pro His Pro Pro
    1010             1015             1020
Pro Gly Gln Gln Pro Pro Pro Gln Pro Ala Lys Pro Gln Gln
    1025             1030             1035
Val Ile Gln His His His Ser Pro Arg His His Lys Ser Asp Pro
    1040             1045             1050
Tyr Ser Thr Gly His Leu Arg Glu Ala Pro Ser Pro Leu Met Ile
    1055             1060             1065
His Ser Pro Gln Met Ser Gln Phe Gln Ser Leu Thr His Gln Ser
    1070             1075             1080
Pro Pro Gln Gln Asn Val Gln Pro Lys Lys Gln Glu Leu Arg Ala
    1085             1090             1095
Ala Ser Val Val Gln Pro Gln Pro Leu Val Val Val Lys Glu Glu
```

-continued

| | 1100 | | | 1105 | | | 1110 | | | |
|---|---|---|---|---|---|---|---|---|---|---|
| Lys | Ile | His | Ser | Pro | Ile | Ile | Arg | Ser | Glu | Pro | Phe | Ser | Pro | Ser |
| | 1115 | | | | 1120 | | | | 1125 | |

Leu Arg Pro Glu Pro Pro Lys His Pro Glu Ser Ile Lys Ala Pro
    1130                1135                1140

Val His Leu Pro Gln Arg Pro Glu Met Lys Pro Val Asp Val Gly
    1145                1150                1155

Arg Pro Val Ile Arg Pro Pro Glu Gln Asn Ala Pro Pro Pro Gly
    1160                1165                1170

Ala Pro Asp Lys Asp Lys Gln Lys Gln Glu Pro Lys Thr Pro Val
    1175                1180                1185

Ala Pro Lys Lys Asp Leu Lys Ile Lys Asn Met Gly Ser Trp Ala
    1190                1195                1200

Ser Leu Val Gln Lys His Pro Thr Thr Pro Ser Ser Thr Ala Lys
    1205                1210                1215

Ser Ser Ser Asp Ser Phe Glu Gln Phe Arg Arg Ala Ala Arg Glu
    1220                1225                1230

Lys Glu Glu Arg Glu Lys Ala Leu Lys Ala Gln Ala Glu His Ala
    1235                1240                1245

Glu Lys Glu Lys Glu Arg Leu Arg Gln Glu Arg Met Arg Ser Arg
    1250                1255                1260

Glu Asp Glu Asp Ala Leu Glu Gln Ala Arg Arg Ala His Glu Glu
    1265                1270                1275

Ala Arg Arg Arg Gln Glu Gln Gln Gln Gln Arg Gln Glu Gln
    1280                1285                1290

Gln Gln Gln Gln Gln Gln Ala Ala Val Ala Ala Ala Ala
    1295                1300                1305

Thr Pro Gln Ala Gln Ser Ser Gln Pro Gln Ser Met Leu Asp Gln
    1310                1315                1320

Gln Arg Glu Leu Ala Arg Lys Arg Glu Gln Glu Arg Arg Arg Arg
    1325                1330                1335

Glu Ala Met Ala Ala Thr Ile Asp Met Asn Phe Gln Ser Asp Leu
    1340                1345                1350

Leu Ser Ile Phe Glu Glu Asn Leu Phe
    1355                1360

<210> SEQ ID NO 4
<211> LENGTH: 595
<212> TYPE: PRT
<213> ORGANISM: Homo sapiens

<400> SEQUENCE: 4

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

-continued

```
Phe Pro Pro Leu Asn Ser Val Ser Pro Ser Pro Leu Met Leu Leu His
            100                 105                 110
Pro Pro Pro Gln Leu Ser Pro Phe Leu Gln Pro His Gly Gln Gln Val
        115                 120                 125
Pro Tyr Tyr Leu Glu Asn Glu Pro Ser Gly Tyr Thr Val Arg Glu Ala
    130                 135                 140
Gly Pro Pro Ala Phe Tyr Arg Pro Asn Ser Asp Asn Arg Arg Gln Gly
145                 150                 155                 160
Gly Arg Glu Arg Leu Ala Ser Thr Asn Asp Lys Gly Ser Met Ala Met
                165                 170                 175
Glu Ser Ala Lys Glu Thr Arg Tyr Cys Ala Val Cys Asn Asp Tyr Ala
            180                 185                 190
Ser Gly Tyr His Tyr Gly Val Trp Ser Cys Glu Gly Cys Lys Ala Phe
        195                 200                 205
Phe Lys Arg Ser Ile Gln Gly His Asn Asp Tyr Met Cys Pro Ala Thr
    210                 215                 220
Asn Gln Cys Thr Ile Asp Lys Asn Arg Arg Lys Ser Cys Gln Ala Cys
225                 230                 235                 240
Arg Leu Arg Lys Cys Tyr Glu Val Gly Met Met Lys Gly Gly Ile Arg
                245                 250                 255
Lys Asp Arg Arg Gly Gly Arg Met Leu Lys His Lys Arg Gln Arg Asp
            260                 265                 270
Asp Gly Glu Gly Arg Gly Val Gly Ser Ala Gly Asp Met Arg Ala
        275                 280                 285
Ala Asn Leu Trp Pro Ser Pro Leu Met Ile Lys Arg Ser Lys Lys Asn
    290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
        355                 360                 365
Asp Leu Thr Leu His Asp Gln Val His Leu Leu Glu Cys Ala Trp Leu
    370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
```

```
                515                 520                 525
Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Gly Phe Pro
                580                 585                 590

Ala Thr Val
        595

<210> SEQ ID NO 5
<211> LENGTH: 245
<212> TYPE: PRT
<213> ORGANISM: Artificial Sequence
<220> FEATURE:
<223> OTHER INFORMATION: estrogen receptor ligand-binding domain

<400> SEQUENCE: 5

Ser Leu Ala Leu Ser Leu Thr Ala Asp Gln Met Val Ser Ala Leu Leu
1               5                   10                  15

Asp Ala Glu Pro Pro Ile Leu Tyr Ser Glu Tyr Asp Pro Thr Arg Pro
                20                  25                  30

Phe Ser Glu Ala Ser Met Met Gly Leu Leu Thr Asn Leu Ala Asp Arg
            35                  40                  45

Glu Leu Val His Met Ile Asn Trp Ala Lys Arg Val Pro Gly Phe Val
    50                  55                  60

Asp Leu Thr Leu His Asp Gln Val His Leu Leu Glu Cys Ala Trp Leu
65                  70                  75                  80

Glu Ile Leu Met Ile Gly Leu Val Trp Arg Ser Met Glu His Pro Gly
                85                  90                  95

Lys Leu Leu Phe Ala Pro Asn Leu Leu Leu Asp Arg Asn Gln Gly Lys
            100                 105                 110

Cys Val Glu Gly Met Val Glu Ile Phe Asp Met Leu Leu Ala Thr Ser
        115                 120                 125

Ser Arg Phe Arg Met Met Asn Leu Gln Gly Glu Glu Phe Val Cys Leu
    130                 135                 140

Lys Ser Ile Ile Leu Leu Asn Ser Gly Val Tyr Thr Phe Leu Ser Ser
145                 150                 155                 160

Thr Leu Lys Ser Leu Glu Glu Lys Asp His Ile His Arg Val Leu Asp
                165                 170                 175

Lys Ile Thr Asp Thr Leu Ile His Leu Met Ala Lys Ala Gly Leu Thr
            180                 185                 190

Leu Gln Gln Gln His Gln Arg Leu Ala Gln Leu Leu Leu Ile Leu Ser
        195                 200                 205

His Ile Arg His Met Ser Asn Lys Gly Met Glu His Leu Tyr Ser Met
    210                 215                 220

Lys Cys Lys Asn Val Val Pro Leu Tyr Asp Leu Leu Leu Glu Met Leu
225                 230                 235                 240

Asp Ala His Arg Leu
                245

<210> SEQ ID NO 6
<211> LENGTH: 920
<212> TYPE: PRT
```

-continued

<213> ORGANISM: Homo sapiens

<400> SEQUENCE: 6

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Tyr Asn Phe Pro
        355                 360                 365

Leu Ala Leu Ala Gly Pro Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400
```

```
Ala Ala Ala Ala Gln Cys Arg Tyr Gly Asp Leu Ala Ser Leu His Gly
                405                 410                 415
Ala Gly Ala Ala Gly Pro Gly Ser Gly Ser Pro Ser Ala Ala Ala Ser
            420                 425                 430
Ser Ser Trp His Thr Leu Phe Thr Ala Glu Glu Gly Gln Leu Tyr Gly
        435                 440                 445
Pro Cys Gly Gly Gly Gly Gly Gly Gly Gly Gly Gly Gly Gly Gly Gly
    450                 455                 460
Gly Gly Gly Gly Gly Gly Gly Glu Ala Gly Ala Val Ala Pro
465                 470                 475                 480
Tyr Gly Tyr Thr Arg Pro Pro Gln Gly Leu Ala Gly Gln Glu Ser Asp
                485                 490                 495
Phe Thr Ala Pro Asp Val Trp Tyr Pro Gly Gly Met Val Ser Arg Val
            500                 505                 510
Pro Tyr Pro Ser Pro Thr Cys Val Lys Ser Glu Met Gly Pro Trp Met
        515                 520                 525
Asp Ser Tyr Ser Gly Pro Tyr Gly Asp Met Arg Leu Glu Thr Ala Arg
    530                 535                 540
Asp His Val Leu Pro Ile Asp Tyr Tyr Phe Pro Pro Gln Lys Thr Cys
545                 550                 555                 560
Leu Ile Cys Gly Asp Glu Ala Ser Gly Cys His Tyr Gly Ala Leu Thr
                565                 570                 575
Cys Gly Ser Cys Lys Val Phe Phe Lys Arg Ala Ala Glu Gly Lys Gln
            580                 585                 590
Lys Tyr Leu Cys Ala Ser Arg Asn Asp Cys Thr Ile Asp Lys Phe Arg
        595                 600                 605
Arg Lys Asn Cys Pro Ser Cys Arg Leu Arg Lys Cys Tyr Glu Ala Gly
    610                 615                 620
Met Thr Leu Gly Ala Arg Lys Leu Lys Lys Leu Gly Asn Leu Lys Leu
625                 630                 635                 640
Gln Glu Glu Gly Glu Ala Ser Ser Thr Thr Ser Pro Thr Glu Glu Thr
                645                 650                 655
Thr Gln Lys Leu Thr Val Ser His Ile Glu Gly Tyr Glu Cys Gln Pro
            660                 665                 670
Ile Phe Leu Asn Val Leu Glu Ala Ile Glu Pro Gly Val Val Cys Ala
        675                 680                 685
Gly His Asp Asn Asn Gln Pro Asp Ser Phe Ala Ala Leu Leu Ser Ser
    690                 695                 700
Leu Asn Glu Leu Gly Glu Arg Gln Leu Val His Val Val Lys Trp Ala
705                 710                 715                 720
Lys Ala Leu Pro Gly Phe Arg Asn Leu His Val Asp Asp Gln Met Ala
                725                 730                 735
Val Ile Gln Tyr Ser Trp Met Gly Leu Met Val Phe Ala Met Gly Trp
            740                 745                 750
Arg Ser Phe Thr Asn Val Asn Ser Arg Met Leu Tyr Phe Ala Pro Asp
        755                 760                 765
Leu Val Phe Asn Glu Tyr Arg Met His Lys Ser Arg Met Tyr Ser Gln
    770                 775                 780
Cys Val Arg Met Arg His Leu Ser Gln Glu Phe Gly Trp Leu Gln Ile
785                 790                 795                 800
Thr Pro Gln Glu Phe Leu Cys Met Lys Ala Leu Leu Leu Phe Ser Ile
                805                 810                 815
Ile Pro Val Asp Gly Leu Lys Asn Gln Lys Phe Phe Asp Glu Leu Arg
```

```
                820                 825                 830
Met Asn Tyr Ile Lys Glu Leu Asp Arg Ile Ile Ala Cys Lys Arg Lys
            835                 840                 845

Asn Pro Thr Ser Cys Ser Arg Arg Phe Tyr Gln Leu Thr Lys Leu Leu
    850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
            915                 920

<210> SEQ ID NO 7
<211> LENGTH: 462
<212> TYPE: PRT
<213> ORGANISM: Homo sapiens

<400> SEQUENCE: 7

Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
        35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Ser Glu Asp Ile Lys Pro Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
        195                 200                 205

Arg Gln Arg Gly Lys Asp Arg Asn Glu Asn Glu Val Glu Ser Thr Ser
    210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270
```

```
Asp Lys Gln Leu Phe Thr Leu Val Glu Trp Ala Lys Arg Ile Pro His
        275                 280                 285

Phe Ser Glu Leu Pro Leu Asp Asp Gln Val Ile Leu Leu Arg Ala Gly
    290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
                340                 345                 350

Leu Val Ser Lys Met Arg Asp Met Gln Met Asp Lys Thr Glu Leu Gly
            355                 360                 365

Cys Leu Arg Ala Ile Val Leu Phe Asn Pro Asp Ser Lys Gly Leu Ser
    370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
                420                 425                 430

Leu Glu His Leu Phe Phe Phe Lys Leu Ile Gly Asp Thr Pro Ile Asp
            435                 440                 445

Thr Phe Leu Met Glu Met Leu Glu Ala Pro His Gln Met Thr
        450                 455                 460
```

<210> SEQ ID NO 8
<211> LENGTH: 165
<212> TYPE: PRT
<213> ORGANISM: Escherichia coli

<400> SEQUENCE: 8

```
Met Asn Ser Glu Ser Val Arg Ile Tyr Leu Val Ala Ala Met Gly Ala
1               5                   10                  15

Asn Arg Val Ile Gly Asn Gly Pro Asn Ile Pro Trp Lys Ile Pro Gly
                20                  25                  30

Glu Gln Lys Ile Phe Arg Arg Leu Thr Glu Gly Lys Val Val Val Met
            35                  40                  45

Gly Arg Lys Thr Phe Glu Ser Ile Gly Lys Pro Leu Pro Asn Arg His
        50                  55                  60

Thr Leu Val Ile Ser Arg Gln Ala Asn Tyr Arg Ala Thr Gly Cys Val
65                  70                  75                  80

Val Val Ser Thr Leu Ser His Ala Ile Ala Leu Ala Ser Glu Leu Gly
                85                  90                  95

Asn Glu Leu Tyr Val Ala Gly Gly Ala Glu Ile Tyr Thr Leu Ala Leu
                100                 105                 110

Pro His Ala His Gly Val Phe Leu Ser Glu Val His Gln Thr Phe Glu
            115                 120                 125

Gly Asp Ala Phe Phe Pro Met Leu Asn Glu Thr Glu Phe Glu Leu Val
        130                 135                 140

Ser Thr Glu Thr Ile Gln Ala Val Ile Pro Tyr Thr His Ser Val Tyr
145                 150                 155                 160

Ala Arg Arg Asn Gly
                165
```

<210> SEQ ID NO 9

```
<211> LENGTH: 297
<212> TYPE: PRT
<213> ORGANISM: Artificial Sequence
<220> FEATURE:
<223> OTHER INFORMATION: amino acid sequence deried from a bacterial
      dehalogenase

<400> SEQUENCE: 9
```

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
290                 295

```
<210> SEQ ID NO 10
<211> LENGTH: 267
<212> TYPE: PRT
<213> ORGANISM: Artificial Sequence
<220> FEATURE:
<223> OTHER INFORMATION: CD19 scFv

<400> SEQUENCE: 10
```

Met Leu Leu Leu Val Thr Ser Leu Leu Leu Cys Glu Leu Pro His Pro
1               5                   10                  15

```
Ala Phe Leu Leu Ile Pro Asp Ile Gln Met Thr Gln Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser
            260                 265

<210> SEQ ID NO 11
<211> LENGTH: 22
<212> TYPE: PRT
<213> ORGANISM: Artificial Sequence
<220> FEATURE:
<223> OTHER INFORMATION: GMCSF signal peptide

<400> SEQUENCE: 11

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 12
<211> LENGTH: 107
<212> TYPE: PRT
<213> ORGANISM: Artificial Sequence
<220> FEATURE:
<223> OTHER INFORMATION: scFv to CD19 variable light chain (VL)

<400> SEQUENCE: 12

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30
```

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
                100                 105

<210> SEQ ID NO 13
<211> LENGTH: 18
<212> TYPE: PRT
<213> ORGANISM: Artificial Sequence
<220> FEATURE:
<223> OTHER INFORMATION: Whitlow linker

<400> SEQUENCE: 13

Gly Ser Thr Ser Gly Ser Gly Lys Pro Gly Ser Gly Glu Gly Ser Thr
1               5                   10                  15

Lys Gly

<210> SEQ ID NO 14
<211> LENGTH: 120
<212> TYPE: PRT
<213> ORGANISM: Artificial Sequence
<220> FEATURE:
<223> OTHER INFORMATION: scFv to CD19 variable heavy chain (VH)

<400> SEQUENCE: 14

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser
            115                 120

<210> SEQ ID NO 15
<211> LENGTH: 61
<212> TYPE: PRT
<213> ORGANISM: Artificial Sequence
<220> FEATURE:
<223> OTHER INFORMATION: modified CD8 alpha chain hinge region

<400> SEQUENCE: 15

Ala Leu Ser Asn Ser Ile Tyr Phe Ser His Phe Val Pro Val Phe Leu
1               5                   10                  15

Pro Ala Lys Pro Thr Thr Thr Pro Ala Pro Arg Pro Pro Thr Pro Ala

```
                    20                  25                  30

Pro Thr Ile Ala Ser Gln Pro Leu Ser Leu Arg Pro Glu Ala Cys Arg
            35                  40                  45

Pro Ala Ala Gly Gly Ala Val His Thr Arg Gly Leu Asp
        50                  55                  60

<210> SEQ ID NO 16
<211> LENGTH: 69
<212> TYPE: PRT
<213> ORGANISM: Artificial Sequence
<220> FEATURE:
<223> OTHER INFORMATION: fragment of the co-stimulatory CD28 protein

<400> SEQUENCE: 16

Lys Pro Phe Trp Val Leu Val Trp Gly Gly Val Leu Ala Cys Tyr Ser
1               5                  10                  15

Leu Leu Val Thr Val Ala Phe Ile Ile Phe Trp Val Arg Ser Lys Arg
            20                  25                  30

Ser Arg Leu Leu His Ser Asp Tyr Met Asn Met Thr Pro Arg Arg Pro
        35                  40                  45

Gly Pro Thr Arg Lys His Tyr Gln Pro Tyr Ala Pro Pro Arg Asp Phe
    50                  55                  60

Ala Ala Tyr Arg Ser
65

<210> SEQ ID NO 17
<211> LENGTH: 112
<212> TYPE: PRT
<213> ORGANISM: Artificial Sequence
<220> FEATURE:
<223> OTHER INFORMATION: CD3-zeta domain

<400> SEQUENCE: 17

Arg Val Lys Phe Ser Arg Ser Ala Asp Ala Pro Ala Tyr Gln Gln Gly
1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 18
<211> LENGTH: 107
<212> TYPE: PRT
<213> ORGANISM: Artificial Sequence
<220> FEATURE:
<223> OTHER INFORMATION: dTAG derivative of FKBP12 with F36V mutation

<400> SEQUENCE: 18

Gly Val Gln Val Glu Thr Ile Ser Pro Gly Asp Gly Arg Thr Phe Pro
1               5                  10                  15

Lys Arg Gly Gln Thr Cys Val Val His Tyr Thr Gly Met Leu Glu Asp
            20                  25                  30
```

```
Gly Lys Lys Val Asp Ser Ser Arg Asp Arg Asn Lys Pro Phe Lys Phe
            35                  40                  45
Val Leu Gly Lys Gln Glu Val Ile Arg Gly Trp Glu Gly Val Ala
 50                  55                  60
Gln Met Ser Val Gly Gln Arg Ala Lys Leu Thr Ile Ser Pro Asp Tyr
 65                  70                  75                  80
Ala Tyr Gly Ala Thr Gly His Pro Gly Ile Ile Pro Pro Asn Ala Thr
                85                  90                  95
Leu Ile Phe Asp Val Glu Leu Leu Lys Leu Glu
            100                 105
```

<210> SEQ ID NO 19
<211> LENGTH: 619
<212> TYPE: PRT
<213> ORGANISM: Artificial Sequence
<220> FEATURE:
<223> OTHER INFORMATION: CD19-CAR-dTAG

<400> SEQUENCE: 19

```
Met Leu Leu Leu Val Thr Ser Leu Leu Leu Cys Glu Leu Pro His Pro
 1               5                  10                  15
Ala Phe Leu Leu Ile Pro Asp Ile Gln Met Thr Gln Thr Thr Ser Ser
                20                  25                  30
Leu Ser Ala Ser Leu Gly Asp Arg Val Thr Ile Ser Cys Arg Ala Ser
            35                  40                  45
Gln Asp Ile Ser Lys Tyr Leu Asn Trp Tyr Gln Gln Lys Pro Asp Gly
 50                  55                  60
Thr Val Lys Leu Leu Ile Tyr His Thr Ser Arg Leu His Ser Gly Val
 65                  70                  75                  80
Pro Ser Arg Phe Ser Gly Ser Gly Ser Gly Thr Asp Tyr Ser Leu Thr
                85                  90                  95
Ile Ser Asn Leu Glu Gln Glu Asp Ile Ala Thr Tyr Phe Cys Gln Gln
            100                 105                 110
Gly Asn Thr Leu Pro Tyr Thr Phe Gly Gly Gly Thr Lys Leu Glu Ile
            115                 120                 125
Thr Gly Ser Thr Ser Gly Ser Gly Lys Pro Gly Ser Gly Glu Gly Ser
130                 135                 140
Thr Lys Gly Glu Val Lys Leu Gln Glu Ser Gly Pro Gly Leu Val Ala
145                 150                 155                 160
Pro Ser Gln Ser Leu Ser Val Thr Cys Thr Val Ser Gly Val Ser Leu
                165                 170                 175
Pro Asp Tyr Gly Val Ser Trp Ile Arg Gln Pro Pro Arg Lys Gly Leu
            180                 185                 190
Glu Trp Leu Gly Val Ile Trp Gly Ser Glu Thr Thr Tyr Tyr Asn Ser
            195                 200                 205
Ala Leu Lys Ser Arg Leu Thr Ile Ile Lys Asp Asn Ser Lys Ser Gln
            210                 215                 220
Val Phe Leu Lys Met Asn Ser Leu Gln Thr Asp Asp Thr Ala Ile Tyr
225                 230                 235                 240
Tyr Cys Ala Lys His Tyr Tyr Tyr Gly Gly Ser Tyr Ala Met Asp Tyr
                245                 250                 255
Trp Gly Gln Gly Thr Ser Val Thr Val Ser Ser Ala Leu Ser Asn Ser
            260                 265                 270
Ile Tyr Phe Ser His Phe Val Pro Val Phe Leu Pro Ala Lys Pro Thr
            275                 280                 285
```

```
Thr Thr Pro Ala Pro Arg Pro Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Lys Pro Phe Trp Val Leu Val Trp
                325                 330                 335

Gly Gly Val Leu Ala Cys Tyr Ser Leu Leu Val Thr Val Ala Phe Ile
                340                 345                 350

Ile Phe Trp Val Arg Ser Lys Arg Ser Arg Leu Leu His Ser Asp Tyr
                355                 360                 365

Met Asn Met Thr Pro Arg Arg Pro Gly Pro Thr Arg Lys His Tyr Gln
    370                 375                 380

Pro Tyr Ala Pro Pro Arg Asp Phe Ala Ala Tyr Arg Ser Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
                420                 425                 430

Asp Lys Arg Arg Gly Arg Asp Pro Glu Met Gly Gly Lys Pro Arg Arg
            435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg Gly Gly Gly
                500                 505                 510

Gly Val Gln Val Glu Thr Ile Ser Pro Gly Asp Gly Arg Thr Phe Pro
            515                 520                 525

Lys Arg Gly Gln Thr Cys Val Val His Tyr Thr Gly Met Leu Glu Asp
    530                 535                 540

Gly Lys Lys Val Asp Ser Ser Arg Asp Arg Asn Lys Pro Phe Lys Phe
545                 550                 555                 560

Val Leu Gly Lys Gln Glu Val Ile Arg Gly Trp Glu Glu Gly Val Ala
                565                 570                 575

Gln Met Ser Val Gly Gln Arg Ala Lys Leu Thr Ile Ser Pro Asp Tyr
            580                 585                 590

Ala Tyr Gly Ala Thr Gly His Pro Gly Ile Ile Pro Pro Asn Ala Thr
                595                 600                 605

Leu Ile Phe Asp Val Glu Leu Leu Lys Leu Glu
    610                 615

<210> SEQ ID NO 20
<211> LENGTH: 213
<212> TYPE: PRT
<213> ORGANISM: Artificial Sequence
<220> FEATURE:
<223> OTHER INFORMATION: ERB2 scFv variable light chain (VL)

<400> SEQUENCE: 20

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30
```

```
Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
             100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
         130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
        210

<210> SEQ ID NO 21
<211> LENGTH: 107
<212> TYPE: PRT
<213> ORGANISM: Artificial Sequence
<220> FEATURE:
<223> OTHER INFORMATION: scFv to ERB2 variable heavy chain (VH)

<400> SEQUENCE: 21

Asp Ile Gln Met Thr Gln Thr Thr Ser Ser Leu Ser Ala Ser Leu Gly
1               5                  10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr
            100                 105

<210> SEQ ID NO 22
<211> LENGTH: 221
<212> TYPE: PRT
<213> ORGANISM: Artificial Sequence
<220> FEATURE:
<223> OTHER INFORMATION: scFv to Erb-B2 variable heavy chain (VH)

<400> SEQUENCE: 22

Gln Val Gln Leu Lys Gln Ser Gly Pro Gly Leu Val Gln Pro Ser Gln
```

-continued

```
 1               5                   10                  15
Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
                35                  40                  45

Gly Val Ile Trp Ser Gly Gly Asn Thr Asp Tyr Asn Thr Pro Phe Thr
                50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser
210                 215                 220

<210> SEQ ID NO 23
<211> LENGTH: 690
<212> TYPE: PRT
<213> ORGANISM: Artificial Sequence
<220> FEATURE:
<223> OTHER INFORMATION: ERB2-CAR-dTAG

<400> SEQUENCE: 23

Asp Ile Leu Leu Thr Gln Ser Pro Val Ile Leu Ser Val Ser Pro Gly
 1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
                35                  40                  45

Lys Tyr Ala Ser Glu Ser Ile Ser Gly Ile Pro Ser Arg Phe Ser Gly
                50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
```

```
            145                 150                 155                 160
Glu Ser Val Thr Glu Gln Asp Ser Lys Asp Ser Thr Tyr Ser Leu Ser
                    165                 170                 175
Ser Thr Leu Thr Leu Ser Lys Ala Asp Tyr Glu Lys His Lys Val Tyr
                    180                 185                 190
Ala Cys Glu Val Thr His Gln Gly Leu Ser Ser Pro Val Thr Lys Ser
                    195                 200                 205
Phe Asn Arg Gly Glu Gly Ser Thr Ser Gly Ser Gly Lys Pro Gly Ser
210                 215                 220
Gly Glu Gly Ser Thr Lys Gly Asp Ile Gln Met Thr Gln Thr Thr Ser
225                 230                 235                 240
Ser Leu Ser Ala Ser Leu Gly Asp Arg Val Thr Ile Ser Cys Arg Ala
                    245                 250                 255
Ser Gln Asp Ile Ser Lys Tyr Leu Asn Trp Tyr Gln Gln Lys Pro Asp
                    260                 265                 270
Gly Thr Val Lys Leu Leu Ile Tyr His Thr Ser Arg Leu His Ser Gly
                    275                 280                 285
Val Pro Ser Arg Phe Ser Gly Ser Gly Ser Gly Thr Asp Tyr Ser Leu
                    290                 295                 300
Thr Ile Ser Asn Leu Glu Gln Glu Asp Ile Ala Thr Tyr Phe Cys Gln
305                 310                 315                 320
Gln Gly Asn Thr Leu Pro Tyr Thr Phe Gly Gly Gly Thr Lys Leu Glu
                    325                 330                 335
Ile Thr Ala Leu Ser Asn Ser Ile Tyr Phe Ser His Phe Val Pro Val
                    340                 345                 350
Phe Leu Pro Ala Lys Pro Thr Thr Thr Pro Ala Pro Arg Pro Pro Thr
                    355                 360                 365
Pro Ala Pro Thr Ile Ala Ser Gln Pro Leu Ser Leu Arg Pro Glu Ala
                    370                 375                 380
Cys Arg Pro Ala Ala Gly Gly Ala Val His Thr Arg Gly Leu Asp Lys
385                 390                 395                 400
Pro Phe Trp Val Leu Val Trp Gly Gly Val Leu Ala Cys Tyr Ser Leu
                    405                 410                 415
Leu Val Thr Val Ala Phe Ile Ile Phe Trp Val Arg Ser Lys Arg Ser
                    420                 425                 430
Arg Leu Leu His Ser Asp Tyr Met Asn Met Thr Pro Arg Arg Pro Gly
                    435                 440                 445
Pro Thr Arg Lys His Tyr Gln Pro Tyr Ala Pro Pro Arg Asp Phe Ala
                    450                 455                 460
Ala Tyr Arg Ser Arg Val Lys Phe Ser Arg Ser Ala Asp Ala Pro Ala
465                 470                 475                 480
Tyr Gln Gln Gly Gln Asn Gln Leu Tyr Asn Glu Leu Asn Leu Gly Arg
                    485                 490                 495
Arg Glu Glu Tyr Asp Val Leu Asp Lys Arg Arg Gly Arg Asp Pro Glu
                    500                 505                 510
Met Gly Gly Lys Pro Arg Arg Lys Asn Pro Gln Glu Gly Leu Tyr Asn
                    515                 520                 525
Glu Leu Gln Lys Asp Lys Met Ala Glu Ala Tyr Ser Glu Ile Gly Met
                    530                 535                 540
Lys Gly Glu Arg Arg Arg Gly Lys Gly His Asp Gly Leu Tyr Gln Gly
545                 550                 555                 560
Leu Ser Thr Ala Thr Lys Asp Thr Tyr Asp Ala Leu His Met Gln Ala
                    565                 570                 575
```

```
Leu Pro Pro Arg Gly Gly Gly Val Gln Val Glu Thr Ile Ser Pro
            580                 585                 590
Gly Asp Gly Arg Thr Phe Pro Lys Arg Gly Gln Thr Cys Val Val His
            595                 600                 605
Tyr Thr Gly Met Leu Glu Asp Gly Lys Val Asp Ser Ser Arg Asp
            610                 615                 620
Arg Asn Lys Pro Phe Lys Phe Val Leu Gly Lys Gln Glu Val Ile Arg
625                 630                 635                 640
Gly Trp Glu Glu Gly Val Ala Gln Met Ser Val Gly Gln Arg Ala Lys
                    645                 650                 655
Leu Thr Ile Ser Pro Asp Tyr Ala Tyr Gly Ala Thr Gly His Pro Gly
                660                 665                 670
Ile Ile Pro Pro Asn Ala Thr Leu Ile Phe Asp Val Glu Leu Leu Lys
                675                 680                 685
Leu Glu
    690

<210> SEQ ID NO 24
<211> LENGTH: 229
<212> TYPE: PRT
<213> ORGANISM: Artificial Sequence
<220> FEATURE:
<223> OTHER INFORMATION: androgen receptor ligand-binding domain

<400> SEQUENCE: 24

Asp Asn Asn Gln Pro Asp Ser Phe Ala Ala Leu Leu Ser Ser Leu Asn
1               5                   10                  15
Glu Leu Gly Glu Arg Gln Leu Val His Val Val Lys Trp Ala Lys Ala
                20                  25                  30
Leu Pro Gly Phe Arg Asn Leu His Val Asp Asp Gln Met Ala Val Ile
            35                  40                  45
Gln Tyr Ser Trp Met Gly Leu Met Val Phe Ala Met Gly Trp Arg Ser
    50                  55                  60
Phe Thr Asn Val Asn Ser Arg Met Leu Tyr Phe Ala Pro Asp Leu Val
65                  70                  75                  80
Phe Asn Glu Tyr Arg Met His Lys Ser Arg Met Tyr Ser Gln Cys Val
                85                  90                  95
Arg Met Arg His Leu Ser Gln Glu Phe Gly Trp Leu Gln Ile Thr Pro
            100                 105                 110
Gln Glu Phe Leu Cys Met Lys Ala Leu Leu Leu Phe Ser Ile Ile Pro
        115                 120                 125
Val Asp Gly Leu Lys Asn Gln Lys Phe Phe Asp Glu Leu Arg Met Asn
130                 135                 140
Tyr Ile Lys Glu Leu Asp Arg Ile Ile Ala Cys Lys Arg Lys Asn Pro
145                 150                 155                 160
Thr Ser Cys Ser Arg Arg Phe Tyr Gln Leu Thr Lys Leu Leu Asp Ser
                165                 170                 175
Val Gln Pro Ile Ala Arg Glu Leu His Gln Phe Thr Phe Asp Leu Leu
            180                 185                 190
Ile Lys Ser His Met Val Ser Val Asp Phe Pro Glu Met Met Ala Glu
        195                 200                 205
Ile Ile Ser Val Gln Val Pro Lys Ile Leu Ser Gly Lys Val Lys Pro
    210                 215                 220
Ile Tyr Phe His Thr
225
```

```
<210> SEQ ID NO 25
<211> LENGTH: 238
<212> TYPE: PRT
<213> ORGANISM: Artificial Sequence
<220> FEATURE:
<223> OTHER INFORMATION: Retinoic Receptor ligand-binding domain

<400> SEQUENCE: 25

Ser Ala Asn Glu Asp Met Pro Val Glu Arg Ile Leu Glu Ala Glu Leu
1               5                   10                  15

Ala Val Glu Pro Lys Thr Glu Thr Tyr Val Glu Ala Asn Met Gly Leu
            20                  25                  30

Asn Pro Ser Ser Pro Asn Asp Pro Val Thr Asn Ile Cys Gln Ala Ala
        35                  40                  45

Asp Lys Gln Leu Phe Thr Leu Val Glu Trp Ala Lys Arg Ile Pro His
    50                  55                  60

Phe Ser Glu Leu Pro Leu Asp Asp Gln Val Ile Leu Leu Arg Ala Gly
65                  70                  75                  80

Trp Asn Glu Leu Leu Ile Ala Ser Phe Ser His Arg Ser Ile Ala Val
                85                  90                  95

Lys Asp Gly Ile Leu Leu Ala Thr Gly Leu His Val His Arg Asn Ser
            100                 105                 110

Ala His Ser Ala Gly Val Gly Ala Ile Phe Asp Arg Val Leu Thr Glu
        115                 120                 125

Leu Val Ser Lys Met Arg Asp Met Gln Met Asp Lys Thr Glu Leu Gly
    130                 135                 140

Cys Leu Arg Ala Ile Val Leu Phe Asn Pro Asp Ser Lys Gly Leu Ser
145                 150                 155                 160

Asn Pro Ala Glu Val Glu Ala Leu Arg Glu Lys Val Tyr Ala Ser Leu
                165                 170                 175

Glu Ala Tyr Cys Lys His Lys Tyr Pro Glu Gln Pro Gly Arg Phe Ala
            180                 185                 190

Lys Leu Leu Leu Arg Leu Pro Ala Leu Arg Ser Ile Gly Leu Lys Cys
        195                 200                 205

Leu Glu His Leu Phe Phe Phe Lys Leu Ile Gly Asp Thr Pro Ile Asp
    210                 215                 220

Thr Phe Leu Met Glu Met Leu Glu Ala Pro His Gln Met Thr
225                 230                 235

<210> SEQ ID NO 26
<211> LENGTH: 110
<212> TYPE: PRT
<213> ORGANISM: Artificial Sequence
<220> FEATURE:
<223> OTHER INFORMATION: N-terminus of MDM2

<400> SEQUENCE: 26

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
```

```
              65                  70                  75                  80
Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val
               100                 105                 110

<210> SEQ ID NO 27
<211> LENGTH: 801
<212> TYPE: PRT
<213> ORGANISM: Homo sapiens

<400> SEQUENCE: 27

Met Leu Gln Asn Val Thr Pro His Asn Lys Leu Pro Gly Glu Gly Asn
 1               5                  10                  15

Ala Gly Leu Leu Gly Leu Gly Pro Glu Ala Ala Pro Gly Lys Arg
                20                  25                  30

Ile Arg Lys Pro Ser Leu Leu Tyr Glu Gly Phe Glu Ser Pro Thr Met
                35                  40                  45

Ala Ser Val Pro Ala Leu Gln Leu Thr Pro Ala Asn Pro Pro Pro
     50                  55                  60

Glu Val Ser Asn Pro Lys Lys Pro Gly Arg Val Thr Asn Gln Leu Gln
65                  70                  75                  80

Tyr Leu His Lys Val Val Met Lys Ala Leu Trp Lys His Gln Phe Ala
                85                  90                  95

Trp Pro Phe Arg Gln Pro Val Asp Ala Val Lys Leu Gly Leu Pro Asp
               100                 105                 110

Tyr His Lys Ile Ile Lys Gln Pro Met Asp Met Gly Thr Ile Lys Arg
               115                 120                 125

Arg Leu Glu Asn Asn Tyr Tyr Trp Ala Ala Ser Glu Cys Met Gln Asp
   130                 135                 140

Phe Asn Thr Met Phe Thr Asn Cys Tyr Ile Tyr Asn Lys Pro Thr Asp
145                 150                 155                 160

Asp Ile Val Leu Met Ala Gln Thr Leu Glu Lys Ile Phe Leu Gln Lys
                165                 170                 175

Val Ala Ser Met Pro Gln Glu Glu Gln Glu Leu Val Val Thr Ile Pro
                180                 185                 190

Lys Asn Ser His Lys Lys Gly Ala Lys Leu Ala Ala Leu Gln Gly Ser
                195                 200                 205

Val Thr Ser Ala His Gln Val Pro Ala Val Ser Ser Val Ser His Thr
    210                 215                 220

Ala Leu Tyr Thr Pro Pro Pro Glu Ile Pro Thr Thr Val Leu Asn Ile
225                 230                 235                 240

Pro His Pro Ser Val Ile Ser Ser Pro Leu Leu Lys Ser Leu His Ser
                245                 250                 255

Ala Gly Pro Pro Leu Leu Ala Val Thr Ala Ala Pro Ala Gln Pro
                260                 265                 270

Leu Ala Lys Lys Lys Gly Val Lys Arg Lys Ala Asp Thr Thr Thr Pro
                275                 280                 285

Thr Pro Thr Ala Ile Leu Ala Pro Gly Ser Pro Ala Ser Pro Pro Gly
    290                 295                 300

Ser Leu Glu Pro Lys Ala Ala Arg Leu Pro Pro Met Arg Arg Glu Ser
305                 310                 315                 320

Gly Arg Pro Ile Lys Pro Pro Arg Lys Asp Leu Pro Asp Ser Gln Gln
                325                 330                 335
```

```
Gln His Gln Ser Ser Lys Lys Gly Lys Leu Ser Glu Gln Leu Lys His
                340                 345                 350

Cys Asn Gly Ile Leu Lys Glu Leu Leu Ser Lys His Ala Ala Tyr
            355                 360                 365

Ala Trp Pro Phe Tyr Lys Pro Val Asp Ala Ser Ala Leu Gly Leu His
        370                 375                 380

Asp Tyr His Asp Ile Ile Lys His Pro Met Asp Leu Ser Thr Val Lys
385                 390                 395                 400

Arg Lys Met Glu Asn Arg Asp Tyr Arg Asp Ala Gln Glu Phe Ala Ala
                405                 410                 415

Asp Val Arg Leu Met Phe Ser Asn Cys Tyr Lys Tyr Asn Pro Pro Asp
            420                 425                 430

His Asp Val Val Ala Met Ala Arg Lys Leu Gln Asp Val Phe Glu Phe
        435                 440                 445

Arg Tyr Ala Lys Met Pro Asp Glu Pro Leu Glu Pro Gly Pro Leu Pro
    450                 455                 460

Val Ser Thr Ala Met Pro Pro Gly Leu Ala Lys Ser Ser Glu Ser
465                 470                 475                 480

Ser Ser Glu Glu Ser Ser Ser Glu Ser Ser Glu Glu Glu Glu
                485                 490                 495

Glu Asp Glu Glu Asp Glu Glu Glu Glu Ser Glu Ser Ser Asp Ser
            500                 505                 510

Glu Glu Glu Arg Ala His Arg Leu Ala Glu Leu Gln Glu Gln Leu Arg
        515                 520                 525

Ala Val His Glu Gln Leu Ala Ala Leu Ser Gln Gly Pro Ile Ser Lys
    530                 535                 540

Pro Lys Arg Lys Arg Glu Lys Lys Glu Lys Lys Lys Arg Lys Ala
545                 550                 555                 560

Glu Lys His Arg Gly Arg Ala Gly Ala Asp Glu Asp Lys Gly Pro
                565                 570                 575

Arg Ala Pro Arg Pro Pro Gln Pro Lys Lys Ser Lys Lys Ala Ser Gly
            580                 585                 590

Ser Gly Gly Gly Ser Ala Ala Leu Gly Pro Ser Gly Phe Gly Pro Ser
        595                 600                 605

Gly Gly Ser Gly Thr Lys Leu Pro Lys Lys Ala Thr Lys Thr Ala Pro
    610                 615                 620

Pro Ala Leu Pro Thr Gly Tyr Asp Ser Glu Glu Glu Glu Glu Ser Arg
625                 630                 635                 640

Pro Met Ser Tyr Asp Glu Lys Arg Gln Leu Ser Leu Asp Ile Asn Lys
                645                 650                 655

Leu Pro Gly Glu Lys Leu Gly Arg Val Val His Ile Ile Gln Ala Arg
            660                 665                 670

Glu Pro Ser Leu Arg Asp Ser Asn Pro Glu Glu Ile Glu Ile Asp Phe
        675                 680                 685

Glu Thr Leu Lys Pro Ser Thr Leu Arg Glu Leu Glu Arg Tyr Val Leu
    690                 695                 700

Ser Cys Leu Arg Lys Lys Pro Arg Lys Pro Tyr Thr Ile Lys Lys Pro
705                 710                 715                 720

Val Gly Lys Thr Lys Glu Glu Leu Ala Leu Glu Lys Lys Arg Glu Leu
                725                 730                 735

Glu Lys Arg Leu Gln Asp Val Ser Gly Gln Leu Asn Ser Thr Lys Lys
            740                 745                 750

Pro Pro Lys Lys Ala Asn Glu Lys Thr Glu Ser Ser Ser Ala Gln Gln
```

```
               755                 760                 765
Val Ala Val Ser Arg Leu Ser Ala Ser Ser Ser Ser Asp Ser Ser
        770                 775                 780

Ser Ser Ser Ser Ser Ser Ser Ser Asp Thr Ser Asp Ser Asp Ser
785                 790                 795                 800

Gly

<210> SEQ ID NO 28
<211> LENGTH: 726
<212> TYPE: PRT
<213> ORGANISM: Homo sapiens

<400> SEQUENCE: 28

Met Ser Thr Ala Thr Val Ala Pro Ala Gly Ile Pro Ala Thr Pro
1               5                  10                  15

Gly Pro Val Asn Pro Pro Pro Glu Val Ser Asn Pro Ser Lys Pro
            20                  25                  30

Gly Arg Lys Thr Asn Gln Leu Gln Tyr Met Gln Asn Val Val Lys
        35                  40                  45

Thr Leu Trp Lys His Gln Phe Ala Trp Pro Phe Tyr Gln Pro Val Asp
50                  55                  60

Ala Ile Lys Leu Asn Leu Pro Asp Tyr His Lys Ile Ile Lys Asn Pro
65                  70                  75                  80

Met Asp Met Gly Thr Ile Lys Lys Arg Leu Glu Asn Asn Tyr Tyr Trp
                85                  90                  95

Ser Ala Ser Glu Cys Met Gln Asp Phe Asn Thr Met Phe Thr Asn Cys
            100                 105                 110

Tyr Ile Tyr Asn Lys Pro Thr Asp Asp Ile Val Leu Met Ala Gln Ala
        115                 120                 125

Leu Glu Lys Ile Phe Leu Gln Lys Val Ala Gln Met Pro Gln Glu Glu
    130                 135                 140

Val Glu Leu Leu Pro Pro Ala Pro Lys Gly Lys Gly Arg Lys Pro Ala
145                 150                 155                 160

Ala Gly Ala Gln Ser Ala Gly Thr Gln Gln Val Ala Ala Val Ser Ser
                165                 170                 175

Val Ser Pro Ala Thr Pro Phe Gln Ser Val Pro Pro Thr Val Ser Gln
            180                 185                 190

Thr Pro Val Ile Ala Ala Thr Pro Val Pro Thr Ile Thr Ala Asn Val
        195                 200                 205

Thr Ser Val Pro Val Pro Pro Ala Ala Ala Pro Pro Pro Ala Thr
    210                 215                 220

Pro Ile Val Pro Val Val Pro Thr Pro Val Val Lys Lys
225                 230                 235                 240

Gly Val Lys Arg Lys Ala Asp Thr Thr Thr Pro Thr Thr Ser Ala Ile
                245                 250                 255

Thr Ala Ser Arg Ser Glu Ser Pro Pro Pro Leu Ser Asp Pro Lys Gln
            260                 265                 270

Ala Lys Val Val Ala Arg Arg Glu Ser Gly Gly Arg Pro Ile Lys Pro
        275                 280                 285

Pro Lys Lys Asp Leu Glu Asp Gly Glu Val Pro Gln His Ala Gly Lys
    290                 295                 300

Lys Gly Lys Leu Ser Glu His Leu Arg Tyr Cys Asp Ser Ile Leu Arg
305                 310                 315                 320

Glu Met Leu Ser Lys Lys His Ala Ala Tyr Ala Trp Pro Phe Tyr Lys
```

```
                    325                 330                 335
Pro Val Asp Ala Glu Ala Leu Glu Leu His Asp Tyr His Asp Ile Ile
            340                 345                 350
Lys His Pro Met Asp Leu Ser Thr Val Lys Arg Lys Met Asp Gly Arg
            355                 360                 365
Glu Tyr Pro Asp Ala Gln Gly Phe Ala Ala Asp Val Arg Leu Met Phe
            370                 375                 380
Ser Asn Cys Tyr Lys Tyr Asn Pro Pro Asp His Glu Val Val Ala Met
385                 390                 395                 400
Ala Arg Lys Leu Gln Asp Val Phe Glu Met Arg Phe Ala Lys Met Pro
            405                 410                 415
Asp Glu Pro Val Glu Ala Pro Ala Leu Pro Ala Pro Ala Ala Pro Met
            420                 425                 430
Val Ser Lys Gly Ala Glu Ser Ser Arg Ser Ser Glu Glu Ser Ser Ser
            435                 440                 445
Asp Ser Gly Ser Ser Asp Ser Glu Gly Glu Arg Ala Thr Arg Leu Ala
            450                 455                 460
Glu Leu Gln Glu Gln Leu Lys Ala Val His Glu Gln Leu Ala Ala Leu
465                 470                 475                 480
Ser Gln Ala Pro Val Asn Lys Pro Lys Lys Lys Glu Lys Glu
            485                 490                 495
Lys Glu Lys Lys Lys Lys Asp Lys Glu Lys Lys Lys Lys His Lys
            500                 505                 510
Val Lys Ala Glu Glu Lys Lys Ala Lys Val Ala Pro Pro Ala Lys
            515                 520                 525
Gln Ala Gln Gln Lys Lys Ala Pro Ala Lys Lys Ala Asn Ser Thr Thr
            530                 535                 540
Thr Ala Gly Arg Gln Leu Lys Lys Gly Gly Lys Gln Ala Ser Ala Ser
545                 550                 555                 560
Tyr Asp Ser Glu Glu Glu Glu Gly Leu Pro Met Ser Tyr Asp Glu
            565                 570                 575
Lys Arg Gln Leu Ser Leu Asp Ile Asn Arg Leu Pro Gly Glu Lys Leu
            580                 585                 590
Gly Arg Val Val His Ile Ile Gln Ser Arg Glu Pro Ser Leu Arg Asp
            595                 600                 605
Ser Asn Pro Asp Glu Ile Glu Ile Asp Phe Glu Thr Leu Lys Pro Thr
            610                 615                 620
Thr Leu Arg Glu Leu Glu Arg Tyr Val Lys Ser Cys Leu Gln Lys Lys
625                 630                 635                 640
Gln Arg Lys Pro Phe Ser Ala Ser Gly Lys Lys Gln Ala Ala Lys Ser
            645                 650                 655
Lys Glu Glu Leu Ala Gln Glu Lys Lys Glu Leu Glu Lys Arg Leu
            660                 665                 670
Gln Asp Val Ser Gly Gln Leu Ser Ser Lys Lys Pro Ala Arg Lys
            675                 680                 685
Glu Lys Pro Gly Ser Ala Pro Ser Gly Gly Pro Ser Arg Leu Ser Ser
            690                 695                 700
Ser Ser Ser Ser Glu Ser Gly Ser Ser Ser Ser Gly Ser Ser Ser
705                 710                 715                 720
Asp Ser Ser Asp Ser Glu
            725

<210> SEQ ID NO 29
```

```
<211> LENGTH: 947
<212> TYPE: PRT
<213> ORGANISM: Homo sapiens

<400> SEQUENCE: 29

Met Ser Leu Pro Ser Arg Gln Thr Ala Ile Ile Val Asn Pro Pro
1               5                   10                  15

Pro Glu Tyr Ile Asn Thr Lys Lys Asn Gly Arg Leu Thr Asn Gln Leu
            20                  25                  30

Gln Tyr Leu Gln Lys Val Val Leu Lys Asp Leu Trp Lys His Ser Phe
        35                  40                  45

Ser Trp Pro Phe Gln Arg Pro Val Asp Ala Val Lys Leu Gln Leu Pro
50                  55                  60

Asp Tyr Tyr Thr Ile Ile Lys Asn Pro Met Asp Leu Asn Thr Ile Lys
65                  70                  75                  80

Lys Arg Leu Glu Asn Lys Tyr Ala Lys Ala Ser Glu Cys Ile Glu
                85                  90                  95

Asp Phe Asn Thr Met Phe Ser Asn Cys Tyr Leu Tyr Asn Lys Pro Gly
            100                 105                 110

Asp Asp Ile Val Leu Met Ala Gln Ala Leu Glu Lys Leu Phe Met Gln
        115                 120                 125

Lys Leu Ser Gln Met Pro Gln Glu Glu Gln Val Val Gly Val Lys Glu
130                 135                 140

Arg Ile Lys Lys Gly Thr Gln Gln Asn Ile Ala Val Ser Ser Ala Lys
145                 150                 155                 160

Glu Lys Ser Ser Pro Ser Ala Thr Glu Lys Val Phe Lys Gln Gln Glu
                165                 170                 175

Ile Pro Ser Val Phe Pro Lys Thr Ser Ile Ser Pro Leu Asn Val Val
            180                 185                 190

Gln Gly Ala Ser Val Asn Ser Ser Ser Gln Thr Ala Ala Gln Val Thr
        195                 200                 205

Lys Gly Val Lys Arg Lys Ala Asp Thr Thr Thr Pro Ala Thr Ser Ala
210                 215                 220

Val Lys Ala Ser Ser Glu Phe Ser Pro Thr Phe Thr Glu Lys Ser Val
225                 230                 235                 240

Ala Leu Pro Pro Ile Lys Glu Asn Met Pro Lys Asn Val Leu Pro Asp
                245                 250                 255

Ser Gln Gln Gln Tyr Asn Val Val Lys Thr Val Lys Val Thr Glu Gln
            260                 265                 270

Leu Arg His Cys Ser Glu Ile Leu Lys Glu Met Leu Ala Lys Lys His
        275                 280                 285

Phe Ser Tyr Ala Trp Pro Phe Tyr Asn Pro Val Asp Val Asn Ala Leu
290                 295                 300

Gly Leu His Asn Tyr Tyr Asp Val Val Lys Asn Pro Met Asp Leu Gly
305                 310                 315                 320

Thr Ile Lys Glu Lys Met Asp Asn Gln Glu Tyr Lys Asp Ala Tyr Lys
                325                 330                 335

Phe Ala Ala Asp Val Arg Leu Met Phe Met Asn Cys Tyr Lys Tyr Asn
            340                 345                 350

Pro Pro Asp His Glu Val Val Thr Met Ala Arg Met Leu Gln Asp Val
        355                 360                 365

Phe Glu Thr His Phe Ser Lys Ile Pro Ile Glu Pro Val Glu Ser Met
370                 375                 380

Pro Leu Cys Tyr Ile Lys Thr Asp Ile Thr Glu Thr Thr Gly Arg Glu
```

```
            385                 390                 395                 400
Asn Thr Asn Glu Ala Ser Ser Glu Gly Asn Ser Ser Asp Asp Ser Glu
                405                 410                 415
Asp Glu Arg Val Lys Arg Leu Ala Lys Leu Gln Glu Gln Leu Lys Ala
                420                 425                 430
Val His Gln Gln Leu Gln Val Leu Ser Gln Val Pro Phe Arg Lys Leu
                435                 440                 445
Asn Lys Lys Lys Glu Lys Ser Lys Lys Glu Lys Lys Lys Glu Lys Val
                450                 455                 460
Asn Asn Ser Asn Glu Asn Pro Arg Lys Met Cys Glu Gln Met Arg Leu
465                 470                 475                 480
Lys Glu Lys Ser Lys Arg Asn Gln Pro Lys Arg Lys Gln Gln Phe
                485                 490                 495
Ile Gly Leu Lys Ser Glu Asp Glu Asp Asn Ala Lys Pro Met Asn Tyr
                500                 505                 510
Asp Glu Lys Arg Gln Leu Ser Leu Asn Ile Asn Lys Leu Pro Gly Asp
                515                 520                 525
Lys Leu Gly Arg Val Val His Ile Ile Gln Ser Arg Glu Pro Ser Leu
                530                 535                 540
Ser Asn Ser Asn Pro Asp Glu Ile Glu Ile Asp Phe Glu Thr Leu Lys
545                 550                 555                 560
Ala Ser Thr Leu Arg Glu Leu Glu Lys Tyr Val Ser Ala Cys Leu Arg
                565                 570                 575
Lys Arg Pro Leu Lys Pro Ala Lys Lys Ile Met Met Ser Lys Glu
                580                 585                 590
Glu Leu His Ser Gln Lys Lys Gln Glu Leu Glu Lys Arg Leu Leu Asp
                595                 600                 605
Val Asn Asn Gln Leu Asn Ser Arg Lys Arg Gln Thr Lys Ser Asp Lys
                610                 615                 620
Thr Gln Pro Ser Lys Ala Val Glu Asn Val Ser Arg Leu Ser Glu Ser
625                 630                 635                 640
Ser Ser Ser Ser Ser Ser Ser Glu Ser Glu Ser Ser Ser Asp
                645                 650                 655
Leu Ser Ser Ser Asp Ser Ser Asp Ser Glu Ser Glu Met Phe Pro Lys
                660                 665                 670
Phe Thr Glu Val Lys Pro Asn Asp Ser Pro Ser Lys Glu Asn Val Lys
                675                 680                 685
Lys Met Lys Asn Glu Cys Ile Pro Pro Glu Gly Arg Thr Gly Val Thr
                690                 695                 700
Gln Ile Gly Tyr Cys Val Gln Asp Thr Thr Ser Ala Asn Thr Thr Leu
705                 710                 715                 720
Val His Gln Thr Thr Pro Ser His Val Met Pro Pro Asn His His Gln
                725                 730                 735
Leu Ala Phe Asn Tyr Gln Glu Leu Glu His Leu Gln Thr Val Lys Asn
                740                 745                 750
Ile Ser Pro Leu Gln Ile Leu Pro Pro Ser Gly Asp Ser Glu Gln Leu
                755                 760                 765
Ser Asn Gly Ile Thr Val Met His Pro Ser Gly Asp Ser Asp Thr Thr
                770                 775                 780
Met Leu Glu Ser Glu Cys Gln Ala Pro Val Gln Lys Asp Ile Lys Ile
785                 790                 795                 800
Lys Asn Ala Asp Ser Trp Lys Ser Leu Gly Lys Pro Val Lys Pro Ser
                805                 810                 815
```

```
Gly Val Met Lys Ser Ser Asp Glu Leu Phe Asn Gln Phe Arg Lys Ala
            820                 825                 830

Ala Ile Glu Lys Glu Val Lys Ala Arg Thr Gln Glu Leu Ile Arg Lys
            835                 840                 845

His Leu Glu Gln Asn Thr Lys Glu Leu Lys Ala Ser Gln Glu Asn Gln
        850                 855                 860

Arg Asp Leu Gly Asn Gly Leu Thr Val Glu Ser Phe Ser Asn Lys Ile
865                 870                 875                 880

Gln Asn Lys Cys Ser Gly Glu Gln Lys Glu His Gln Gln Ser Ser
                885                 890                 895

Glu Ala Gln Asp Lys Ser Lys Leu Trp Leu Leu Lys Asp Arg Asp Leu
            900                 905                 910

Ala Arg Gln Lys Glu Gln Glu Arg Arg Arg Glu Ala Met Val Gly
            915                 920                 925

Thr Ile Asp Met Thr Leu Gln Ser Asp Ile Met Thr Met Phe Glu Asn
930                 935                 940

Asn Phe Asp
945

<210> SEQ ID NO 30
<211> LENGTH: 233
<212> TYPE: PRT
<213> ORGANISM: Homo sapiens

<400> SEQUENCE: 30

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
```

<210> SEQ ID NO 31
<211> LENGTH: 404
<212> TYPE: PRT
<213> ORGANISM: Homo sapiens

<400> SEQUENCE: 31

Met Ser Asp Ser Lys Glu Pro Arg Leu Gln Gln Leu Gly Leu Leu Glu
1               5                   10                  15

Glu Glu Gln Leu Arg Gly Leu Gly Phe Arg Gln Thr Arg Gly Tyr Lys
                20                  25                  30

Ser Leu Ala Gly Cys Leu Gly His Gly Pro Leu Val Leu Gln Leu Leu
            35                  40                  45

Ser Phe Thr Leu Leu Ala Gly Leu Leu Val Gln Val Ser Lys Val Pro
    50                  55                  60

Ser Ser Ile Ser Gln Glu Gln Ser Arg Gln Asp Ala Ile Tyr Gln Asn
65                  70                  75                  80

Leu Thr Gln Leu Lys Ala Ala Val Gly Glu Leu Ser Glu Lys Ser Lys
                85                  90                  95

Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
        115                 120                 125

Arg Leu Lys Ala Ala Val Gly Glu Leu Pro Glu Lys Ser Lys Leu Gln
130                 135                 140

Glu Ile Tyr Gln Glu Leu Thr Trp Leu Lys Ala Ala Val Gly Glu Leu
145                 150                 155                 160

Pro Glu Lys Ser Lys Met Gln Glu Ile Tyr Gln Glu Leu Thr Arg Leu
                165                 170                 175

Lys Ala Ala Val Gly Glu Leu Pro Glu Lys Ser Lys Gln Gln Glu Ile
            180                 185                 190

Tyr Gln Glu Leu Thr Arg Leu Lys Ala Ala Val Gly Glu Leu Pro Glu
        195                 200                 205

Lys Ser Lys Gln Gln Glu Ile Tyr Gln Glu Leu Thr Arg Leu Lys Ala
210                 215                 220

Ala Val Gly Glu Leu Pro Glu Lys Ser Lys Gln Gln Glu Ile Tyr Gln
225                 230                 235                 240

Glu Leu Thr Gln Leu Lys Ala Ala Val Glu Arg Leu Cys His Pro Cys
                245                 250                 255

Pro Trp Glu Trp Thr Phe Phe Gln Gly Asn Cys Tyr Phe Met Ser Asn
            260                 265                 270

Ser Gln Arg Asn Trp His Asp Ser Ile Thr Ala Cys Lys Glu Val Gly
        275                 280                 285

Ala Gln Leu Val Val Ile Lys Ser Ala Glu Glu Gln Asn Phe Leu Gln
290                 295                 300

Leu Gln Ser Ser Arg Ser Asn Arg Phe Thr Trp Met Gly Leu Ser Asp
305                 310                 315                 320

Leu Asn Gln Glu Gly Thr Trp Gln Trp Val Asp Gly Ser Pro Leu Leu
                325                 330                 335

Pro Ser Phe Lys Gln Tyr Trp Asn Arg Gly Glu Pro Asn Asn Val Gly
            340                 345                 350

Glu Glu Asp Cys Ala Glu Phe Ser Gly Asn Gly Trp Asn Asp Asp Lys
        355                 360                 365

```
Cys Asn Leu Ala Lys Phe Trp Ile Cys Lys Lys Ser Ala Ala Ser Cys
        370                 375                 380

Ser Arg Asp Glu Glu Gln Phe Leu Ser Pro Ala Pro Thr Pro Asn
385                 390                 395                 400

Pro Pro Pro Ala

<210> SEQ ID NO 32
<211> LENGTH: 497
<212> TYPE: PRT
<213> ORGANISM: Homo sapiens

<400> SEQUENCE: 32

Met Thr Phe Asn Ser Phe Glu Gly Ser Lys Thr Cys Val Pro Ala Asp
1               5                   10                  15

Ile Asn Lys Glu Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
                35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Cys Gly Gly Lys Leu Lys
        195                 200                 205

Asn Trp Glu Pro Cys Asp Arg Ala Trp Ser Glu His Arg Arg His Phe
210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
    290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335
```

```
Glu Tyr Ile Asn Asn Ile His Leu Thr His Ser Leu Glu Glu Cys Leu
                340                 345                 350
Val Arg Thr Thr Glu Lys Thr Pro Ser Leu Thr Arg Arg Ile Asp Asp
            355                 360                 365
Thr Ile Phe Gln Asn Pro Met Val Gln Glu Ala Ile Arg Met Gly Phe
        370                 375                 380
Ser Phe Lys Asp Ile Lys Lys Ile Met Glu Glu Lys Ile Gln Ile Ser
385                 390                 395                 400
Gly Ser Asn Tyr Lys Ser Leu Glu Val Leu Val Ala Asp Leu Val Asn
                405                 410                 415
Ala Gln Lys Asp Ser Met Gln Asp Glu Ser Ser Gln Thr Ser Leu Gln
            420                 425                 430
Lys Glu Ile Ser Thr Glu Gln Leu Arg Arg Leu Gln Glu Glu Lys
        435                 440                 445
Leu Cys Lys Ile Cys Met Asp Arg Asn Ile Ala Ile Val Phe Val Pro
    450                 455                 460
Cys Gly His Leu Val Thr Cys Lys Gln Cys Ala Glu Ala Val Asp Lys
465                 470                 475                 480
Cys Pro Met Cys Tyr Thr Val Ile Thr Phe Lys Gln Lys Ile Phe Met
                485                 490                 495
Ser

<210> SEQ ID NO 33
<211> LENGTH: 618
<212> TYPE: PRT
<213> ORGANISM: Homo sapiens

<400> SEQUENCE: 33

Met His Lys Thr Ala Ser Gln Arg Leu Phe Pro Gly Pro Ser Tyr Gln
1               5                   10                  15
Asn Ile Lys Ser Ile Met Glu Asp Ser Thr Ile Leu Ser Asp Trp Thr
                20                  25                  30
Asn Ser Asn Lys Gln Lys Met Lys Tyr Asp Phe Ser Cys Glu Leu Tyr
            35                  40                  45
Arg Met Ser Thr Tyr Ser Thr Phe Pro Ala Gly Val Pro Val Ser Glu
        50                  55                  60
Arg Ser Leu Ala Arg Ala Gly Phe Tyr Tyr Thr Gly Val Asn Asp Lys
65                  70                  75                  80
Val Lys Cys Phe Cys Cys Gly Leu Met Leu Asp Asn Trp Lys Leu Gly
                85                  90                  95
Asp Ser Pro Ile Gln Lys His Lys Gln Leu Tyr Pro Ser Cys Ser Phe
            100                 105                 110
Ile Gln Asn Leu Val Ser Ala Ser Leu Gly Ser Thr Ser Lys Asn Thr
        115                 120                 125
Ser Pro Met Arg Asn Ser Phe Ala His Ser Leu Ser Pro Thr Leu Glu
    130                 135                 140
His Ser Ser Leu Phe Ser Gly Ser Tyr Ser Ser Leu Ser Pro Asn Pro
145                 150                 155                 160
Leu Asn Ser Arg Ala Val Glu Asp Ile Ser Ser Ser Arg Thr Asn Pro
                165                 170                 175
Tyr Ser Tyr Ala Met Ser Thr Glu Glu Ala Arg Phe Leu Thr Tyr His
            180                 185                 190
Met Trp Pro Leu Thr Phe Leu Ser Pro Ser Glu Leu Ala Arg Ala Gly
        195                 200                 205
```

```
Phe Tyr Tyr Ile Gly Pro Gly Asp Arg Val Ala Cys Phe Ala Cys Gly
    210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
                260                 265                 270

Met Arg Thr Phe Met Tyr Trp Pro Ser Ser Val Pro Val Gln Pro Glu
            275                 280                 285

Gln Leu Ala Ser Ala Gly Phe Tyr Tyr Val Gly Arg Asn Asp Asp Val
    290                 295                 300

Lys Cys Phe Cys Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
                340                 345                 350

Pro His Leu Leu Glu Gln Leu Leu Ser Thr Ser Asp Thr Thr Gly Glu
            355                 360                 365

Glu Asn Ala Asp Pro Ile Ile His Phe Gly Pro Gly Glu Ser Ser
    370                 375                 380

Ser Glu Asp Ala Val Met Met Asn Thr Pro Val Val Lys Ser Ala Leu
385                 390                 395                 400

Glu Met Gly Phe Asn Arg Asp Leu Val Lys Gln Thr Val Gln Ser Lys
                405                 410                 415

Ile Leu Thr Thr Gly Glu Asn Tyr Lys Thr Val Asn Asp Ile Val Ser
                420                 425                 430

Ala Leu Leu Asn Ala Glu Asp Glu Lys Arg Glu Glu Glu Lys Glu Lys
            435                 440                 445

Gln Ala Glu Glu Met Ala Ser Asp Asp Leu Ser Leu Ile Arg Lys Asn
    450                 455                 460

Arg Met Ala Leu Phe Gln Gln Leu Thr Cys Val Leu Pro Ile Leu Asp
465                 470                 475                 480

Asn Leu Leu Lys Ala Asn Val Ile Asn Lys Gln Glu His Asp Ile Ile
                485                 490                 495

Lys Gln Lys Thr Gln Ile Pro Leu Gln Ala Arg Glu Leu Ile Asp Thr
                500                 505                 510

Ile Leu Val Lys Gly Asn Ala Ala Ala Asn Ile Phe Lys Asn Cys Leu
            515                 520                 525

Lys Glu Ile Asp Ser Thr Leu Tyr Lys Asn Leu Phe Val Asp Lys Asn
    530                 535                 540

Met Lys Tyr Ile Pro Thr Glu Asp Val Ser Gly Leu Ser Leu Glu Glu
545                 550                 555                 560

Gln Leu Arg Arg Leu Gln Glu Glu Arg Thr Cys Lys Val Cys Met Asp
                565                 570                 575

Lys Glu Val Ser Val Val Phe Ile Pro Cys Gly His Leu Val Val Cys
                580                 585                 590

Gln Glu Cys Ala Pro Ser Leu Arg Lys Cys Pro Ile Cys Arg Gly Ile
            595                 600                 605

Ile Lys Gly Thr Val Arg Thr Phe Leu Ser
    610                 615
```

```
<210> SEQ ID NO 34
<211> LENGTH: 199
<212> TYPE: PRT
<213> ORGANISM: Homo sapiens

<400> SEQUENCE: 34

Met Pro Asn Tyr Lys Leu Thr Tyr Phe Asn Met Arg Gly Arg Ala Glu
1               5                   10                  15

Ile Ile Arg Tyr Ile Phe Ala Tyr Leu Asp Ile Gln Tyr Glu Asp His
                20                  25                  30

Arg Ile Glu Gln Ala Asp Trp Pro Glu Ile Lys Ser Thr Leu Pro Phe
            35                  40                  45

Gly Lys Ile Pro Ile Leu Glu Val Asp Gly Leu Thr Leu His Gln Ser
50                  55                  60

Leu Ala Ile Ala Arg Tyr Leu Thr Lys Asn Thr Asp Leu Ala Gly Asn
65                  70                  75                  80

Thr Glu Met Glu Gln Cys His Val Asp Ala Ile Val Asp Thr Leu Asp
                85                  90                  95

Asp Phe Met Ser Cys Phe Pro Trp Ala Glu Lys Lys Gln Asp Val Lys
            100                 105                 110

Glu Gln Met Phe Asn Glu Leu Leu Thr Tyr Asn Ala Pro His Leu Met
        115                 120                 125

Gln Asp Leu Asp Thr Tyr Leu Gly Gly Arg Glu Trp Leu Ile Gly Asn
130                 135                 140

Ser Val Thr Trp Ala Asp Phe Tyr Trp Glu Ile Cys Ser Thr Thr Leu
145                 150                 155                 160

Leu Val Phe Lys Pro Asp Leu Leu Asp Asn His Pro Arg Leu Val Thr
                165                 170                 175

Leu Arg Lys Lys Val Gln Ala Ile Pro Ala Val Ala Asn Trp Ile Lys
            180                 185                 190

Arg Arg Pro Gln Thr Lys Leu
        195

<210> SEQ ID NO 35
<211> LENGTH: 189
<212> TYPE: PRT
<213> ORGANISM: Homo sapiens

<400> SEQUENCE: 35

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
```

-continued

```
                130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 36
<211> LENGTH: 678
<212> TYPE: PRT
<213> ORGANISM: Homo sapiens

<400> SEQUENCE: 36

Met Ala Ala Pro Gly Pro Leu Pro Ala Ala Leu Ser Pro Gly Ala
1               5                   10                  15

Pro Thr Pro Arg Glu Leu Met His Gly Val Ala Gly Val Thr Ser Arg
                20                  25                  30

Ala Gly Arg Asp Arg Glu Ala Gly Ser Val Leu Pro Ala Gly Asn Arg
            35                  40                  45

Gly Ala Arg Lys Ala Ser Arg Ser Ser Ser Arg Ser Met Ser Arg
50                  55                  60

Asp Asn Lys Phe Ser Lys Lys Asp Cys Leu Ser Ile Arg Asn Val Val
65                  70                  75                  80

Ala Ser Ile Gln Thr Lys Glu Gly Leu Asn Leu Lys Leu Ile Ser Gly
                85                  90                  95

Asp Val Leu Tyr Ile Trp Ala Asp Val Ile Val Asn Ser Val Pro Met
            100                 105                 110

Asn Leu Gln Leu Gly Gly Gly Pro Leu Ser Arg Ala Phe Leu Gln Lys
        115                 120                 125

Ala Gly Pro Met Leu Gln Lys Glu Leu Asp Asp Arg Arg Arg Glu Thr
    130                 135                 140

Glu Glu Lys Val Gly Asn Ile Phe Met Thr Ser Gly Cys Asn Leu Asp
145                 150                 155                 160

Cys Lys Ala Val Leu His Ala Val Ala Pro Tyr Trp Asn Asn Gly Ala
                165                 170                 175

Glu Thr Ser Trp Gln Ile Met Ala Asn Ile Ile Lys Lys Cys Leu Thr
            180                 185                 190

Thr Val Glu Val Leu Ser Phe Ser Ile Thr Phe Pro Met Ile Gly
        195                 200                 205

Thr Gly Ser Leu Gln Phe Pro Lys Ala Val Phe Ala Lys Leu Ile Leu
    210                 215                 220

Ser Glu Val Phe Glu Tyr Ser Ser Ser Thr Arg Pro Ile Thr Ser Pro
225                 230                 235                 240

Leu Gln Glu Val His Phe Leu Val Tyr Thr Asn Asp Asp Glu Gly Cys
                245                 250                 255

Gln Ala Phe Leu Asp Glu Phe Thr Asn Trp Ser Arg Ile Asn Pro Asn
            260                 265                 270

Lys Ala Arg Ile Pro Met Ala Gly Asp Thr Gln Gly Val Val Gly Thr
        275                 280                 285

Val Ser Lys Pro Cys Phe Thr Ala Tyr Glu Met Lys Ile Gly Ala Ile
    290                 295                 300

Thr Phe Gln Val Ala Thr Gly Asp Ile Ala Thr Glu Gln Val Asp Val
305                 310                 315                 320
```

```
Ile Val Asn Ser Thr Ala Arg Thr Phe Asn Arg Lys Ser Gly Val Ser
            325                 330                 335

Arg Ala Ile Leu Glu Gly Ala Gly Gln Ala Val Glu Ser Glu Cys Ala
        340                 345                 350

Val Leu Ala Ala Gln Pro His Arg Asp Phe Ile Ile Thr Pro Gly Gly
    355                 360                 365

Cys Leu Lys Cys Lys Ile Ile Ile His Val Pro Gly Gly Lys Asp Val
370                 375                 380

Arg Lys Thr Val Thr Ser Val Leu Glu Glu Cys Glu Gln Arg Lys Tyr
385                 390                 395                 400

Thr Ser Val Ser Leu Pro Ala Ile Gly Thr Gly Asn Ala Gly Lys Asn
                405                 410                 415

Pro Ile Thr Val Ala Asp Asn Ile Ile Asp Ala Ile Val Asp Phe Ser
            420                 425                 430

Ser Gln His Ser Thr Pro Ser Leu Lys Thr Lys Val Val Ile Phe
        435                 440                 445

Gln Pro Glu Leu Leu Asn Ile Phe Tyr Asp Ser Met Lys Lys Arg Asp
    450                 455                 460

Leu Ser Ala Ser Leu Asn Phe Gln Ser Thr Phe Ser Met Thr Thr Cys
465                 470                 475                 480

Asn Leu Pro Glu His Trp Thr Asp Met Asn His Gln Leu Phe Cys Met
                485                 490                 495

Val Gln Leu Glu Pro Gly Gln Ser Glu Tyr Asn Thr Ile Lys Asp Lys
            500                 505                 510

Phe Thr Arg Thr Cys Ser Ser Tyr Ala Ile Glu Lys Ile Glu Arg Ile
        515                 520                 525

Gln Asn Ala Phe Leu Trp Gln Ser Tyr Gln Val Lys Lys Arg Gln Met
    530                 535                 540

Asp Ile Lys Asn Asp His Lys Asn Asn Glu Arg Leu Leu Phe His Gly
545                 550                 555                 560

Thr Asp Ala Asp Ser Val Pro Tyr Val Asn Gln His Gly Phe Asn Arg
                565                 570                 575

Ser Cys Ala Gly Lys Asn Ala Val Ser Tyr Gly Lys Gly Thr Tyr Phe
            580                 585                 590

Ala Val Asp Ala Ser Tyr Ser Ala Lys Asp Thr Tyr Ser Lys Pro Asp
        595                 600                 605

Ser Asn Gly Arg Lys His Met Tyr Val Val Arg Val Leu Thr Gly Val
    610                 615                 620

Phe Thr Lys Gly Arg Ala Gly Leu Val Thr Pro Pro Lys Asn Pro
625                 630                 635                 640

His Asn Pro Thr Asp Leu Phe Asp Ser Val Thr Asn Asn Thr Arg Ser
                645                 650                 655

Pro Lys Leu Phe Val Val Phe Asp Asn Gln Ala Tyr Pro Glu Tyr
            660                 665                 670

Leu Ile Thr Phe Thr Ala
        675

<210> SEQ ID NO 37
<211> LENGTH: 1801
<212> TYPE: PRT
<213> ORGANISM: Homo sapiens

<400> SEQUENCE: 37

Met Ala Val Pro Gly Ser Phe Pro Leu Leu Val Glu Gly Ser Trp Gly
1               5                   10                  15
```

```
Pro Asp Pro Lys Asn Leu Asn Thr Lys Leu Gln Met Tyr Phe Gln
         20                  25                  30

Ser Pro Lys Arg Ser Gly Gly Glu Cys Glu Val Arg Gln Asp Pro
         35                  40                  45

Arg Ser Pro Ser Arg Phe Leu Val Phe Tyr Pro Glu Asp Val Arg
 50                  55                  60

Gln Lys Val Leu Glu Arg Lys Asn His Glu Leu Val Trp Gln Gly Lys
 65                  70                  75                  80

Gly Thr Phe Lys Leu Thr Val Gln Leu Pro Ala Thr Pro Asp Glu Ile
                 85                  90                  95

Asp His Val Phe Glu Glu Leu Leu Thr Lys Glu Ser Lys Thr Lys
             100                 105                 110

Glu Asp Val Lys Glu Pro Asp Val Ser Glu Glu Leu Asp Thr Lys Leu
             115                 120                 125

Pro Leu Asp Gly Gly Leu Asp Lys Met Glu Asp Ile Pro Glu Glu Cys
130                 135                 140

Glu Asn Ile Ser Ser Leu Val Ala Phe Glu Asn Leu Lys Ala Asn Val
145                 150                 155                 160

Thr Asp Ile Met Leu Ile Leu Leu Val Glu Asn Ile Ser Gly Leu Ser
                 165                 170                 175

Asn Asp Asp Phe Gln Val Glu Ile Ile Arg Asp Phe Asp Val Ala Val
                 180                 185                 190

Val Thr Phe Gln Lys His Ile Asp Thr Ile Arg Phe Val Asp Asp Cys
             195                 200                 205

Thr Lys His His Ser Ile Lys Gln Leu Gln Leu Ser Pro Arg Leu Leu
210                 215                 220

Glu Val Thr Asn Thr Ile Arg Val Glu Asn Leu Pro Pro Gly Ala Asp
225                 230                 235                 240

Asp Tyr Ser Leu Lys Leu Phe Phe Glu Asn Pro Tyr Asn Gly Gly Gly
                 245                 250                 255

Arg Val Ala Asn Val Glu Tyr Phe Pro Glu Glu Ser Ser Ala Leu Ile
                 260                 265                 270

Glu Phe Phe Asp Arg Lys Val Leu Asp Thr Ile Met Ala Thr Lys Leu
             275                 280                 285

Asp Phe Asn Lys Met Pro Leu Ser Val Phe Pro Tyr Tyr Ala Ser Leu
290                 295                 300

Gly Thr Ala Leu Tyr Gly Lys Glu Lys Pro Leu Ile Lys Leu Pro Ala
305                 310                 315                 320

Pro Phe Glu Glu Ser Leu Asp Leu Pro Leu Trp Lys Phe Leu Gln Lys
                 325                 330                 335

Lys Asn His Leu Ile Glu Glu Ile Asn Asp Glu Met Arg Arg Cys His
             340                 345                 350

Cys Glu Leu Thr Trp Ser Gln Leu Ser Gly Lys Val Thr Ile Arg Pro
             355                 360                 365

Ala Ala Thr Leu Val Asn Glu Gly Arg Pro Arg Ile Lys Thr Trp Gln
             370                 375                 380

Ala Asp Thr Ser Thr Thr Leu Ser Ser Ile Arg Ser Lys Tyr Lys Val
385                 390                 395                 400

Asn Pro Ile Lys Val Asp Pro Thr Met Trp Asp Thr Ile Lys Asn Asp
                 405                 410                 415

Val Lys Asp Asp Arg Ile Leu Ile Glu Phe Asp Thr Leu Lys Glu Met
                 420                 425                 430
```

-continued

```
Val Ile Leu Ala Gly Lys Ser Glu Asp Val Gln Ser Ile Glu Val Gln
            435                 440                 445

Val Arg Glu Leu Ile Glu Ser Thr Thr Gln Lys Ile Lys Arg Glu Glu
450                 455                 460

Gln Ser Leu Lys Glu Lys Met Ile Ile Ser Pro Gly Arg Tyr Phe Leu
465                 470                 475                 480

Leu Cys His Ser Ser Leu Leu Asp His Leu Thr Glu Cys Pro Glu
                485                 490                 495

Ile Glu Ile Cys Tyr Asp Arg Val Thr Gln His Leu Cys Leu Lys Gly
                500                 505                 510

Pro Ser Ala Asp Val Tyr Lys Ala Lys Cys Glu Ile Gln Glu Lys Val
                515                 520                 525

Tyr Thr Met Ala Gln Lys Asn Ile Gln Val Ser Pro Glu Ile Phe Gln
                530                 535                 540

Phe Leu Gln Gln Val Asn Trp Lys Glu Phe Ser Lys Cys Leu Phe Ile
545                 550                 555                 560

Ala Gln Lys Ile Leu Ala Leu Tyr Glu Leu Glu Gly Thr Thr Val Leu
                565                 570                 575

Leu Thr Ser Cys Ser Ser Glu Ala Leu Leu Glu Ala Glu Lys Gln Met
                580                 585                 590

Leu Ser Ala Leu Asn Tyr Lys Arg Ile Glu Val Glu Asn Lys Glu Val
                595                 600                 605

Leu His Gly Lys Lys Trp Lys Gly Leu Thr His Asn Leu Leu Lys Lys
                610                 615                 620

Gln Asn Ser Ser Pro Asn Thr Val Ile Ile Asn Glu Leu Thr Ser Glu
625                 630                 635                 640

Thr Thr Ala Glu Val Ile Ile Thr Gly Cys Val Lys Glu Val Asn Glu
                645                 650                 655

Thr Tyr Lys Leu Leu Phe Asn Phe Val Glu Gln Asn Met Lys Ile Glu
                660                 665                 670

Arg Leu Val Glu Val Lys Pro Ser Leu Val Ile Asp Tyr Leu Lys Thr
                675                 680                 685

Glu Lys Lys Leu Phe Trp Pro Lys Ile Lys Lys Val Asn Val Gln Val
                690                 695                 700

Ser Phe Asn Pro Glu Asn Lys Gln Lys Gly Ile Leu Leu Thr Gly Ser
705                 710                 715                 720

Lys Thr Glu Val Leu Lys Ala Val Asp Ile Val Lys Gln Val Trp Asp
                725                 730                 735

Ser Val Cys Val Lys Ser Val His Thr Asp Lys Pro Gly Ala Lys Gln
                740                 745                 750

Phe Phe Gln Asp Lys Ala Arg Phe Tyr Gln Ser Glu Ile Lys Arg Leu
                755                 760                 765

Phe Gly Cys Tyr Ile Glu Leu Gln Glu Asn Glu Val Met Lys Glu Gly
                770                 775                 780

Gly Ser Pro Ala Gly Gln Lys Cys Phe Ser Arg Thr Val Leu Ala Pro
785                 790                 795                 800

Gly Val Val Leu Ile Val Gln Gln Gly Asp Leu Ala Arg Leu Pro Val
                805                 810                 815

Asp Val Val Asn Ala Ser Asn Glu Asp Leu Lys His Tyr Gly Gly
                820                 825                 830

Leu Ala Ala Ala Leu Ser Lys Ala Ala Gly Pro Glu Leu Gln Ala Asp
                835                 840                 845

Cys Asp Gln Ile Val Lys Arg Glu Gly Arg Leu Leu Pro Gly Asn Ala
```

```
                850              855              860
Thr Ile Ser Lys Ala Gly Lys Leu Pro Tyr His His Val Ile His Ala
865              870              875              880

Val Gly Pro Arg Trp Ser Gly Tyr Glu Ala Pro Arg Cys Val Tyr Leu
                885              890              895

Leu Arg Arg Ala Val Gln Leu Ser Leu Cys Leu Ala Glu Lys Tyr Lys
                900              905              910

Tyr Arg Ser Ile Ala Ile Pro Ala Ile Ser Ser Gly Val Phe Gly Phe
            915              920              925

Pro Leu Gly Arg Cys Val Glu Thr Ile Val Ser Ala Ile Lys Glu Asn
        930              935              940

Phe Gln Phe Lys Lys Asp Gly His Cys Leu Lys Glu Ile Tyr Leu Val
945              950              955              960

Asp Val Ser Glu Lys Thr Val Glu Ala Phe Ala Glu Ala Val Lys Thr
                965              970              975

Val Phe Lys Ala Thr Leu Pro Asp Thr Ala Ala Pro Pro Gly Leu Pro
                980              985              990

Pro Ala Ala Ala Gly Pro Gly Lys  Thr Ser Trp Glu Lys  Gly Ser Leu
            995              1000              1005

Val Ser  Pro Gly Gly Leu Gln  Met Leu Leu Val Lys  Glu Gly Val
    1010              1015              1020

Gln Asn  Ala Lys Thr Asp Val  Val Val Asn Ser Val  Pro Leu Asp
    1025              1030              1035

Leu Val  Leu Ser Arg Gly Pro  Leu Ser Lys Ser Leu  Leu Glu Lys
    1040              1045              1050

Ala Gly  Pro Glu Leu Gln Glu  Glu Leu Asp Thr Val  Gly Gln Gly
    1055              1060              1065

Val Ala  Val Ser Met Gly Thr  Val Leu Lys Thr Ser  Ser Trp Asn
    1070              1075              1080

Leu Asp  Cys Arg Tyr Val Leu  His Val Val Ala Pro  Glu Trp Arg
    1085              1090              1095

Asn Gly  Ser Thr Ser Ser Leu  Lys Ile Met Glu Asp  Ile Ile Arg
    1100              1105              1110

Glu Cys  Met Glu Ile Thr Glu  Ser Leu Ser Leu Lys  Ser Ile Ala
    1115              1120              1125

Phe Pro  Ala Ile Gly Thr Gly  Asn Leu Gly Phe Pro  Lys Asn Ile
    1130              1135              1140

Phe Ala  Glu Leu Ile Ile Ser  Glu Val Phe Lys Phe  Ser Ser Lys
    1145              1150              1155

Asn Gln  Leu Lys Thr Leu Gln  Glu Val His Phe Leu  Leu His Pro
    1160              1165              1170

Ser Asp  His Glu Asn Ile Gln  Ala Phe Ser Asp Glu  Phe Ala Arg
    1175              1180              1185

Arg Ala  Asn Gly Asn Leu Val  Ser Asp Lys Ile Pro  Lys Ala Lys
    1190              1195              1200

Asp Thr  Gln Gly Phe Tyr Gly  Thr Val Ser Ser Pro  Asp Ser Gly
    1205              1210              1215

Val Tyr  Glu Met Lys Ile Gly  Ser Ile Ile Phe Gln  Val Ala Ser
    1220              1225              1230

Gly Asp  Ile Thr Lys Glu Glu  Ala Asp Val Ile Val  Asn Ser Thr
    1235              1240              1245

Ser Asn  Ser Phe Asn Leu Lys  Ala Gly Val Ser Lys  Ala Ile Leu
    1250              1255              1260
```

-continued

```
Glu Cys Ala Gly Gln Asn Val Glu Arg Glu Cys Ser Gln Gln Ala
    1265             1270             1275

Gln Gln Arg Lys Asn Asp Tyr Ile Ile Thr Gly Gly Gly Phe Leu
    1280             1285             1290

Arg Cys Lys Asn Ile Ile His Val Ile Gly Gly Asn Asp Val Lys
    1295             1300             1305

Ser Ser Val Ser Ser Val Leu Gln Glu Cys Glu Lys Lys Asn Tyr
    1310             1315             1320

Ser Ser Ile Cys Leu Pro Ala Ile Gly Thr Gly Asn Ala Lys Gln
    1325             1330             1335

His Pro Asp Lys Val Ala Glu Ala Ile Ile Asp Ala Ile Glu Asp
    1340             1345             1350

Phe Val Gln Lys Gly Ser Ala Gln Ser Val Lys Lys Val Lys Val
    1355             1360             1365

Val Ile Phe Leu Pro Gln Val Leu Asp Val Phe Tyr Ala Asn Met
    1370             1375             1380

Lys Lys Arg Glu Gly Thr Gln Leu Ser Ser Gln Gln Ser Val Met
    1385             1390             1395

Ser Lys Leu Ala Ser Phe Leu Gly Phe Ser Lys Gln Ser Pro Gln
    1400             1405             1410

Lys Lys Asn His Leu Val Leu Glu Lys Lys Thr Glu Ser Ala Thr
    1415             1420             1425

Phe Arg Val Cys Gly Glu Asn Val Thr Cys Val Glu Tyr Ala Ile
    1430             1435             1440

Ser Trp Leu Gln Asp Leu Ile Glu Lys Glu Gln Cys Pro Tyr Thr
    1445             1450             1455

Ser Glu Asp Glu Cys Ile Lys Asp Phe Asp Glu Lys Glu Tyr Gln
    1460             1465             1470

Glu Leu Asn Glu Leu Gln Lys Lys Leu Asn Ile Asn Ile Ser Leu
    1475             1480             1485

Asp His Lys Arg Pro Leu Ile Lys Val Leu Gly Ile Ser Arg Asp
    1490             1495             1500

Val Met Gln Ala Arg Asp Glu Ile Glu Ala Met Ile Lys Arg Val
    1505             1510             1515

Arg Leu Ala Lys Glu Gln Glu Ser Arg Ala Asp Cys Ile Ser Glu
    1520             1525             1530

Phe Ile Glu Trp Gln Tyr Asn Asp Asn Asn Thr Ser His Cys Phe
    1535             1540             1545

Asn Lys Met Thr Asn Leu Lys Leu Glu Asp Ala Arg Arg Glu Lys
    1550             1555             1560

Lys Lys Thr Val Asp Val Lys Ile Asn His Arg His Tyr Thr Val
    1565             1570             1575

Asn Leu Asn Thr Tyr Thr Ala Thr Asp Thr Lys Gly His Ser Leu
    1580             1585             1590

Ser Val Gln Arg Leu Thr Lys Ser Lys Val Asp Ile Pro Ala His
    1595             1600             1605

Trp Ser Asp Met Lys Gln Gln Asn Phe Cys Val Val Glu Leu Leu
    1610             1615             1620

Pro Ser Asp Pro Glu Tyr Asn Thr Val Ala Ser Lys Phe Asn Gln
    1625             1630             1635

Thr Cys Ser His Phe Arg Ile Glu Lys Ile Glu Arg Ile Gln Asn
    1640             1645             1650
```

```
Pro Asp Leu Trp Asn Ser Tyr Gln Ala Lys Lys Thr Met Asp
    1655                1660                1665

Ala Lys Asn Gly Gln Thr Met Asn Glu Lys Gln Leu Phe His Gly
    1670                1675                1680

Thr Asp Ala Gly Ser Val Pro His Val Asn Arg Asn Gly Phe Asn
    1685                1690                1695

Arg Ser Tyr Ala Gly Lys Asn Ala Val Ala Tyr Gly Lys Gly Thr
    1700                1705                1710

Tyr Phe Ala Val Asn Ala Asn Tyr Ser Ala Asn Asp Thr Tyr Ser
    1715                1720                1725

Arg Pro Asp Ala Asn Gly Arg Lys His Val Tyr Tyr Val Arg Val
    1730                1735                1740

Leu Thr Gly Ile Tyr Thr His Gly Asn His Ser Leu Ile Val Pro
    1745                1750                1755

Pro Ser Lys Asn Pro Gln Asn Pro Thr Asp Leu Tyr Asp Thr Val
    1760                1765                1770

Thr Asp Asn Val His His Pro Ser Leu Phe Val Ala Phe Tyr Asp
    1775                1780                1785

Tyr Gln Ala Tyr Pro Glu Tyr Leu Ile Thr Phe Arg Lys
    1790                1795                1800

<210> SEQ ID NO 38
<211> LENGTH: 154
<212> TYPE: PRT
<213> ORGANISM: Homo sapiens

<400> SEQUENCE: 38

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
        50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
                100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
        130                 135                 140

Leu Ala Cys Gly Val Ile Gly Ile Ala Gln
145                 150

<210> SEQ ID NO 39
<211> LENGTH: 150
<212> TYPE: PRT
<213> ORGANISM: Homo sapiens

<400> SEQUENCE: 39

Met Ser Ala Lys Asp Glu Arg Ala Arg Glu Ile Leu Arg Gly Phe Lys
1               5                   10                  15
```

```
Leu Asn Trp Met Asn Leu Arg Asp Ala Glu Thr Gly Lys Ile Leu Trp
            20                  25                  30

Gln Gly Thr Glu Asp Leu Ser Val Pro Gly Val Glu His Glu Ala Arg
        35                  40                  45

Val Pro Lys Lys Ile Leu Lys Cys Lys Ala Val Ser Arg Glu Leu Asn
 50                  55                  60

Phe Ser Ser Thr Glu Gln Met Glu Lys Phe Arg Leu Glu Gln Lys Val
 65                  70                  75                  80

Tyr Phe Lys Gly Gln Cys Leu Glu Glu Trp Phe Phe Glu Phe Gly Phe
                 85                  90                  95

Val Ile Pro Asn Ser Thr Asn Thr Trp Gln Ser Leu Ile Glu Ala Ala
                100                 105                 110

Pro Glu Ser Gln Met Met Pro Ala Ser Val Leu Thr Gly Asn Val Ile
            115                 120                 125

Ile Glu Thr Lys Phe Phe Asp Asp Leu Leu Val Ser Thr Ser Arg
130                 135                 140

Val Arg Leu Phe Tyr Val
145                 150

<210> SEQ ID NO 40
<211> LENGTH: 350
<212> TYPE: PRT
<213> ORGANISM: Homo sapiens

<400> SEQUENCE: 40

Met Phe Gly Leu Lys Arg Asn Ala Val Ile Gly Leu Asn Leu Tyr Cys
 1               5                  10                  15

Gly Gly Ala Gly Leu Gly Ala Gly Ser Gly Gly Ala Thr Arg Pro Gly
                 20                  25                  30

Gly Arg Leu Leu Ala Thr Glu Lys Glu Ala Ser Ala Arg Arg Glu Ile
            35                  40                  45

Gly Gly Gly Glu Ala Gly Ala Val Ile Gly Ser Ala Gly Ala Ser
 50                  55                  60

Pro Pro Ser Thr Leu Thr Pro Asp Ser Arg Arg Val Ala Arg Pro Pro
 65                  70                  75                  80

Pro Ile Gly Ala Glu Val Pro Asp Val Thr Ala Thr Pro Ala Arg Leu
                 85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
            115                 120                 125

Tyr Glu Pro Glu Pro Leu Gly Lys Arg Pro Ala Val Leu Pro Leu Leu
130                 135                 140

Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
            195                 200                 205

Ala Leu Glu Thr Leu Arg Arg Val Gly Asp Gly Val Gln Arg Asn His
210                 215                 220

Glu Thr Ala Phe Gln Gly Met Leu Arg Lys Leu Asp Ile Lys Asn Glu
225                 230                 235                 240
```

```
Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
                260                 265                 270

Phe Val Ala Lys His Leu Lys Thr Ile Asn Gln Glu Ser Cys Ile Glu
                275                 280                 285

Pro Leu Ala Glu Ser Ile Thr Asp Val Leu Val Arg Thr Lys Arg Asp
                290                 295                 300

Trp Leu Val Lys Gln Arg Gly Trp Asp Gly Phe Val Glu Phe Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
                340                 345                 350

<210> SEQ ID NO 41
<211> LENGTH: 239
<212> TYPE: PRT
<213> ORGANISM: Homo sapiens

<400> SEQUENCE: 41

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
                35                  40                  45

Phe Ser Ser Gln Pro Gly His Thr Pro His Pro Ala Ala Ser Arg Asp
            50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
                100                 105                 110

Ala Glu Met Ser Ser Gln Leu His Leu Thr Pro Phe Thr Ala Arg Gly
                115                 120                 125

Arg Phe Ala Thr Val Val Glu Glu Leu Phe Arg Asp Gly Val Asn Trp
            130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
                180                 185                 190

Gly Gly Trp Asp Ala Phe Val Glu Leu Tyr Gly Pro Ser Met Arg Pro
            195                 200                 205

Leu Phe Asp Phe Ser Trp Leu Ser Leu Lys Thr Leu Leu Ser Leu Ala
210                 215                 220

Leu Val Gly Ala Cys Ile Thr Leu Gly Ala Tyr Leu Gly His Lys
225                 230                 235

<210> SEQ ID NO 42
<211> LENGTH: 163
<212> TYPE: PRT
```

<213> ORGANISM: Homo sapiens

<400> SEQUENCE: 42

Met Ala Asp Glu Glu Lys Leu Pro Pro Gly Trp Glu Lys Arg Met Ser
1               5                   10                  15

Arg Ser Ser Gly Arg Val Tyr Tyr Phe Asn His Ile Thr Asn Ala Ser
            20                  25                  30

Gln Trp Glu Arg Pro Ser Gly Asn Ser Ser Gly Gly Lys Asn Gly
        35                  40                  45

Gln Gly Glu Pro Ala Arg Val Arg Cys Ser His Leu Leu Val Lys His
    50                  55                  60

Ser Gln Ser Arg Arg Pro Ser Ser Trp Arg Gln Glu Lys Ile Thr Arg
65                  70                  75                  80

Thr Lys Glu Glu Ala Leu Glu Leu Ile Asn Gly Tyr Ile Gln Lys Ile
                85                  90                  95

Lys Ser Gly Glu Glu Asp Phe Glu Ser Leu Ala Ser Gln Phe Ser Asp
            100                 105                 110

Cys Ser Ser Ala Lys Ala Arg Gly Asp Leu Gly Ala Phe Ser Arg Gly
        115                 120                 125

Gln Met Gln Lys Pro Phe Glu Asp Ala Ser Phe Ala Leu Arg Thr Gly
    130                 135                 140

Glu Met Ser Gly Pro Val Phe Thr Asp Ser Gly Ile His Ile Ile Leu
145                 150                 155                 160

Arg Thr Glu

<210> SEQ ID NO 43
<211> LENGTH: 1327
<212> TYPE: PRT
<213> ORGANISM: Homo sapiens

<400> SEQUENCE: 43

Met Ala Ala Ser Arg Arg Ser Gln His His His His Gln Gln
1               5                   10                  15

Gln Leu Gln Pro Ala Pro Gly Ala Ser Ala Pro Pro Pro Pro Pro
            20                  25                  30

Pro Pro Leu Ser Pro Gly Leu Ala Pro Gly Thr Thr Pro Ala Ser Pro
        35                  40                  45

Thr Ala Ser Gly Leu Ala Pro Phe Ala Ser Pro Arg His Gly Leu Ala
    50                  55                  60

Leu Pro Glu Gly Asp Gly Ser Arg Asp Pro Pro Asp Arg Pro Arg Ser
65                  70                  75                  80

Pro Asp Pro Val Asp Gly Thr Ser Cys Cys Ser Thr Thr Ser Thr Ile
                85                  90                  95

Cys Thr Val Ala Ala Ala Pro Val Val Pro Ala Val Ser Thr Ser Ser
            100                 105                 110

Ala Ala Gly Val Ala Pro Asn Pro Ala Gly Ser Gly Ser Asn Asn Ser
        115                 120                 125

Pro Ser Ser Ser Ser Pro Thr Ser Ser Ser Ser Ser Pro Ser
    130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175

Pro Ala Val Ser Gly Ala Leu Arg Glu Leu Leu Glu Ala Cys Arg Asn
            180                 185                 190

```
Gly Asp Val Ser Arg Val Lys Arg Leu Val Asp Ala Ala Asn Val Asn
        195                 200                 205

Ala Lys Asp Met Ala Gly Arg Lys Ser Ser Pro Leu His Phe Ala Ala
    210                 215                 220

Gly Phe Gly Arg Lys Asp Val Val Glu His Leu Leu Gln Met Gly Ala
225                 230                 235                 240

Asn Val His Ala Arg Asp Gly Gly Leu Ile Pro Leu His Asn Ala
                245                 250                 255

Cys Ser Phe Gly His Ala Glu Val Val Ser Leu Leu Cys Gln Gly
                260                 265                 270

Ala Asp Pro Asn Ala Arg Asp Asn Trp Asn Tyr Thr Pro Leu His Glu
    275                 280                 285

Ala Ala Ile Lys Gly Lys Ile Asp Val Cys Ile Val Leu Leu Gln His
    290                 295                 300

Gly Ala Asp Pro Asn Ile Arg Asn Thr Asp Gly Lys Ser Ala Leu Asp
305                 310                 315                 320

Leu Ala Asp Pro Ser Ala Lys Ala Val Leu Thr Gly Glu Tyr Lys Lys
                325                 330                 335

Asp Glu Leu Leu Glu Ala Ala Arg Ser Gly Asn Glu Glu Lys Leu Met
                340                 345                 350

Ala Leu Leu Thr Pro Leu Asn Val Asn Cys His Ala Ser Asp Gly Arg
        355                 360                 365

Lys Ser Thr Pro Leu His Leu Ala Ala Gly Tyr Asn Arg Val Arg Ile
    370                 375                 380

Val Gln Leu Leu Leu Gln His Gly Ala Asp Val His Ala Lys Asp Lys
385                 390                 395                 400

Gly Gly Leu Val Pro Leu His Asn Ala Cys Ser Tyr Gly His Tyr Glu
                405                 410                 415

Val Thr Glu Leu Leu Lys His Gly Ala Cys Val Asn Ala Met Asp
                420                 425                 430

Leu Trp Gln Phe Thr Pro Leu His Glu Ala Ala Ser Lys Asn Arg Val
    435                 440                 445

Glu Val Cys Ser Leu Leu Leu Ser His Gly Ala Asp Pro Thr Leu Val
    450                 455                 460

Asn Cys His Gly Lys Ser Ala Val Asp Met Ala Pro Thr Pro Glu Leu
465                 470                 475                 480

Arg Glu Arg Leu Thr Tyr Glu Phe Lys Gly His Ser Leu Leu Gln Ala
                485                 490                 495

Ala Arg Glu Ala Asp Leu Ala Lys Val Lys Lys Thr Leu Ala Leu Glu
            500                 505                 510

Ile Ile Asn Phe Lys Gln Pro Gln Ser His Glu Thr Ala Leu His Cys
        515                 520                 525

Ala Val Ala Ser Leu His Pro Lys Arg Lys Gln Val Thr Glu Leu Leu
    530                 535                 540

Leu Arg Lys Gly Ala Asn Val Asn Glu Lys Asn Lys Asp Phe Met Thr
545                 550                 555                 560

Pro Leu His Val Ala Ala Glu Arg Ala His Asn Asp Val Met Glu Val
                565                 570                 575

Leu His Lys His Gly Ala Lys Met Asn Ala Leu Asp Thr Leu Gly Gln
                580                 585                 590

Thr Ala Leu His Arg Ala Ala Leu Ala Gly His Leu Gln Thr Cys Arg
        595                 600                 605
```

```
Leu Leu Leu Ser Tyr Gly Ser Asp Pro Ser Ile Ile Ser Leu Gln Gly
610                 615                 620

Phe Thr Ala Ala Gln Met Gly Asn Glu Ala Val Gln Gln Ile Leu Ser
625                 630                 635                 640

Glu Ser Thr Pro Ile Arg Thr Ser Asp Val Asp Tyr Arg Leu Leu Glu
                645                 650                 655

Ala Ser Lys Ala Gly Asp Leu Glu Thr Val Lys Gln Leu Cys Ser Ser
                660                 665                 670

Gln Asn Val Asn Cys Arg Asp Leu Glu Gly Arg His Ser Thr Pro Leu
                675                 680                 685

His Phe Ala Ala Gly Tyr Asn Arg Val Ser Val Glu Tyr Leu Leu
690                 695                 700

His His Gly Ala Asp Val His Ala Lys Asp Lys Gly Leu Val Pro
705                 710                 715                 720

Leu His Asn Ala Cys Ser Tyr Gly His Tyr Glu Val Ala Glu Leu Leu
                725                 730                 735

Val Arg His Gly Ala Ser Val Asn Val Ala Asp Leu Trp Lys Phe Thr
                740                 745                 750

Pro Leu His Glu Ala Ala Ala Lys Gly Lys Tyr Glu Ile Cys Lys Leu
                755                 760                 765

Leu Leu Lys His Gly Ala Asp Pro Thr Lys Lys Asn Arg Asp Gly Asn
770                 775                 780

Thr Pro Leu Asp Leu Val Lys Glu Gly Asp Thr Asp Ile Gln Asp Leu
785                 790                 795                 800

Leu Arg Gly Asp Ala Ala Leu Leu Asp Ala Ala Lys Lys Gly Cys Leu
                805                 810                 815

Ala Arg Val Gln Lys Leu Cys Thr Pro Glu Asn Ile Asn Cys Arg Asp
                820                 825                 830

Thr Gln Gly Arg Asn Ser Thr Pro Leu His Leu Ala Ala Gly Tyr Asn
                835                 840                 845

Asn Leu Glu Val Ala Glu Tyr Leu Leu Glu His Gly Ala Asp Val Asn
                850                 855                 860

Ala Gln Asp Lys Gly Gly Leu Ile Pro Leu His Asn Ala Ala Ser Tyr
865                 870                 875                 880

Gly His Val Asp Ile Ala Ala Leu Leu Ile Lys Tyr Asn Thr Cys Val
                885                 890                 895

Asn Ala Thr Asp Lys Trp Ala Phe Thr Pro Leu His Glu Ala Ala Gln
                900                 905                 910

Lys Gly Arg Thr Gln Leu Cys Ala Leu Leu Leu Ala His Gly Ala Asp
                915                 920                 925

Pro Thr Met Lys Asn Gln Glu Gly Gln Thr Pro Leu Asp Leu Ala Thr
930                 935                 940

Ala Asp Asp Ile Arg Ala Leu Leu Ile Asp Ala Met Pro Pro Glu Ala
945                 950                 955                 960

Leu Pro Thr Cys Phe Lys Pro Gln Ala Thr Val Val Ser Ala Ser Leu
                965                 970                 975

Ile Ser Pro Ala Ser Thr Pro Ser Cys Leu Ser Ala Ala Ser Ser Ile
                980                 985                 990

Asp Asn Leu Thr Gly Pro Leu Ala Glu Leu Ala Val Gly Gly Ala Ser
                995                 1000                1005

Asn Ala Gly Asp Gly Ala Ala Gly Thr Glu Arg Lys Glu Gly Glu
                1010                1015                1020

Val Ala Gly Leu Asp Met Asn Ile Ser Gln Phe Leu Lys Ser Leu
```

-continued

```
                1025                1030                1035

Gly Leu Glu His Leu Arg Asp Ile Phe Glu Thr Glu Gln Ile Thr
    1040                1045                1050

Leu Asp Val Leu Ala Asp Met Gly His Glu Glu Leu Lys Glu Ile
    1055                1060                1065

Gly Ile Asn Ala Tyr Gly His Arg His Lys Leu Ile Lys Gly Val
    1070                1075                1080

Glu Arg Leu Leu Gly Gly Gln Gln Gly Thr Asn Pro Tyr Leu Thr
    1085                1090                1095

Phe His Cys Val Asn Gln Gly Thr Ile Leu Leu Asp Leu Ala Pro
    1100                1105                1110

Glu Asp Lys Glu Tyr Gln Ser Val Glu Glu Met Gln Ser Thr
    1115                1120                1125

Ile Arg Glu His Arg Asp Gly Gly Asn Ala Gly Gly Ile Phe Asn
    1130                1135                1140

Arg Tyr Asn Val Ile Arg Ile Gln Lys Val Val Asn Lys Lys Leu
    1145                1150                1155

Arg Glu Arg Phe Cys His Arg Gln Lys Glu Val Ser Glu Glu Asn
    1160                1165                1170

His Asn His His Asn Glu Arg Met Leu Phe His Gly Ser Pro Phe
    1175                1180                1185

Ile Asn Ala Ile Ile His Lys Gly Phe Asp Glu Arg His Ala Tyr
    1190                1195                1200

Ile Gly Gly Met Phe Gly Ala Gly Ile Tyr Phe Ala Glu Asn Ser
    1205                1210                1215

Ser Lys Ser Asn Gln Tyr Val Tyr Gly Ile Gly Gly Gly Thr Gly
    1220                1225                1230

Cys Pro Thr His Lys Asp Arg Ser Cys Tyr Ile Cys His Arg Gln
    1235                1240                1245

Met Leu Phe Cys Arg Val Thr Leu Gly Lys Ser Phe Leu Gln Phe
    1250                1255                1260

Ser Thr Met Lys Met Ala His Ala Pro Pro Gly His His Ser Val
    1265                1270                1275

Ile Gly Arg Pro Ser Val Asn Gly Leu Ala Tyr Ala Glu Tyr Val
    1280                1285                1290

Ile Tyr Arg Gly Glu Gln Ala Tyr Pro Glu Tyr Leu Ile Thr Tyr
    1295                1300                1305

Gln Ile Met Lys Pro Glu Ala Pro Ser Gln Thr Ala Thr Ala Ala
    1310                1315                1320

Glu Gln Lys Thr
    1325

<210> SEQ ID NO 44
<211> LENGTH: 1166
<212> TYPE: PRT
<213> ORGANISM: Homo sapiens

<400> SEQUENCE: 44

Met Ser Gly Arg Arg Cys Ala Gly Gly Ala Ala Cys Ala Ser Ala
1               5                   10                  15

Ala Ala Glu Ala Val Glu Pro Ala Ala Arg Glu Leu Phe Glu Ala Cys
                20                  25                  30

Arg Asn Gly Asp Val Glu Arg Val Lys Arg Leu Val Thr Pro Glu Lys
            35                  40                  45
```

-continued

Val Asn Ser Arg Asp Thr Ala Gly Arg Lys Ser Thr Pro Leu His Phe
 50                  55                  60

Ala Ala Gly Phe Gly Arg Lys Asp Val Val Glu Tyr Leu Leu Gln Asn
 65                  70                  75                  80

Gly Ala Asn Val Gln Ala Arg Asp Gly Gly Leu Ile Pro Leu His
                 85                  90                  95

Asn Ala Cys Ser Phe Gly His Ala Glu Val Val Asn Leu Leu Leu Arg
                100                 105                 110

His Gly Ala Asp Pro Asn Ala Arg Asp Asn Trp Asn Tyr Thr Pro Leu
                115                 120                 125

His Glu Ala Ala Ile Lys Gly Lys Ile Asp Val Cys Ile Val Leu Leu
                130                 135                 140

Gln His Gly Ala Glu Pro Thr Ile Arg Asn Thr Asp Gly Arg Thr Ala
145                 150                 155                 160

Leu Asp Leu Ala Asp Pro Ser Ala Lys Ala Val Leu Thr Gly Glu Tyr
                165                 170                 175

Lys Lys Asp Glu Leu Leu Glu Ser Ala Arg Ser Gly Asn Glu Glu Lys
                180                 185                 190

Met Met Ala Leu Leu Thr Pro Leu Asn Val Asn Cys His Ala Ser Asp
                195                 200                 205

Gly Arg Lys Ser Thr Pro Leu His Leu Ala Ala Gly Tyr Asn Arg Val
                210                 215                 220

Lys Ile Val Gln Leu Leu Leu Gln His Gly Ala Asp Val His Ala Lys
225                 230                 235                 240

Asp Lys Gly Asp Leu Val Pro Leu His Asn Ala Cys Ser Tyr Gly His
                245                 250                 255

Tyr Glu Val Thr Glu Leu Leu Val Lys His Gly Ala Cys Val Asn Ala
                260                 265                 270

Met Asp Leu Trp Gln Phe Thr Pro Leu His Glu Ala Ala Ser Lys Asn
                275                 280                 285

Arg Val Glu Val Cys Ser Leu Leu Leu Ser Tyr Gly Ala Asp Pro Thr
                290                 295                 300

Leu Leu Asn Cys His Asn Lys Ser Ala Ile Asp Leu Ala Pro Thr Pro
305                 310                 315                 320

Gln Leu Lys Glu Arg Leu Ala Tyr Glu Phe Lys Gly His Ser Leu Leu
                325                 330                 335

Gln Ala Ala Arg Glu Ala Asp Val Thr Arg Ile Lys Lys His Leu Ser
                340                 345                 350

Leu Glu Met Val Asn Phe Lys His Pro Gln Thr His Glu Thr Ala Leu
                355                 360                 365

His Cys Ala Ala Ala Ser Pro Tyr Pro Lys Arg Lys Gln Ile Cys Glu
                370                 375                 380

Leu Leu Leu Arg Lys Gly Ala Asn Ile Asn Glu Lys Thr Lys Glu Phe
385                 390                 395                 400

Leu Thr Pro Leu His Val Ala Ser Glu Lys Ala His Asn Asp Val Val
                405                 410                 415

Glu Val Val Lys His Glu Ala Lys Val Asn Ala Leu Asp Asn Leu
                420                 425                 430

Gly Gln Thr Ser Leu His Arg Ala Ala Tyr Cys Gly His Leu Gln Thr
                435                 440                 445

Cys Arg Leu Leu Leu Ser Tyr Gly Cys Asp Pro Asn Ile Ile Ser Leu
450                 455                 460

Gln Gly Phe Thr Ala Leu Gln Met Gly Asn Glu Asn Val Gln Gln Leu

-continued

```
             465                 470                 475                 480
Leu Gln Glu Gly Ile Ser Leu Gly Asn Ser Glu Ala Asp Arg Gln Leu
                485                 490                 495

Leu Glu Ala Ala Lys Ala Gly Asp Val Glu Thr Val Lys Lys Leu Cys
                500                 505                 510

Thr Val Gln Ser Val Asn Cys Arg Asp Ile Glu Gly Arg Gln Ser Thr
                515                 520                 525

Pro Leu His Phe Ala Ala Gly Tyr Asn Arg Val Ser Val Val Glu Tyr
                530                 535                 540

Leu Leu Gln His Gly Ala Asp Val His Ala Lys Asp Lys Gly Gly Leu
545                 550                 555                 560

Val Pro Leu His Asn Ala Cys Ser Tyr Gly His Tyr Glu Val Ala Glu
                565                 570                 575

Leu Leu Val Lys His Gly Ala Val Val Asn Val Ala Asp Leu Trp Lys
                580                 585                 590

Phe Thr Pro Leu His Glu Ala Ala Lys Gly Lys Tyr Glu Ile Cys
                595                 600                 605

Lys Leu Leu Leu Gln His Gly Ala Asp Pro Thr Lys Lys Asn Arg Asp
                610                 615                 620

Gly Asn Thr Pro Leu Asp Leu Val Lys Asp Gly Asp Thr Asp Ile Gln
625                 630                 635                 640

Asp Leu Leu Arg Gly Asp Ala Ala Leu Leu Asp Ala Ala Lys Lys Gly
                645                 650                 655

Cys Leu Ala Arg Val Lys Lys Leu Ser Ser Pro Asp Asn Val Asn Cys
                660                 665                 670

Arg Asp Thr Gln Gly Arg His Ser Thr Pro Leu His Leu Ala Ala Gly
                675                 680                 685

Tyr Asn Asn Leu Glu Val Ala Glu Tyr Leu Leu Gln His Gly Ala Asp
                690                 695                 700

Val Asn Ala Gln Asp Lys Gly Gly Leu Ile Pro Leu His Asn Ala Ala
705                 710                 715                 720

Ser Tyr Gly His Val Asp Val Ala Ala Leu Leu Ile Lys Tyr Asn Ala
                725                 730                 735

Cys Val Asn Ala Thr Asp Lys Trp Ala Phe Thr Pro Leu His Glu Ala
                740                 745                 750

Ala Gln Lys Gly Arg Thr Gln Leu Cys Ala Leu Leu Leu Ala His Gly
                755                 760                 765

Ala Asp Pro Thr Leu Lys Asn Gln Glu Gly Gln Thr Pro Leu Asp Leu
                770                 775                 780

Val Ser Ala Asp Asp Val Ser Ala Leu Leu Thr Ala Ala Met Pro Pro
785                 790                 795                 800

Ser Ala Leu Pro Ser Cys Tyr Lys Pro Gln Val Leu Asn Gly Val Arg
                805                 810                 815

Ser Pro Gly Ala Thr Ala Asp Ala Leu Ser Ser Gly Pro Ser Ser Pro
                820                 825                 830

Ser Ser Leu Ser Ala Ala Ser Ser Leu Asp Asn Leu Ser Gly Ser Phe
                835                 840                 845

Ser Glu Leu Ser Ser Val Val Ser Ser Ser Gly Thr Glu Gly Ala Ser
                850                 855                 860

Ser Leu Glu Lys Lys Glu Val Pro Gly Val Asp Phe Ser Ile Thr Gln
865                 870                 875                 880

Phe Val Arg Asn Leu Gly Leu Glu His Leu Met Asp Ile Phe Glu Arg
                885                 890                 895
```

Glu Gln Ile Thr Leu Asp Val Leu Val Glu Met Gly His Lys Glu Leu
            900                 905                 910

Lys Glu Ile Gly Ile Asn Ala Tyr Gly His Arg His Lys Leu Ile Lys
            915                 920                 925

Gly Val Glu Arg Leu Ile Ser Gly Gln Gln Gly Leu Asn Pro Tyr Leu
            930                 935                 940

Thr Leu Asn Thr Ser Gly Ser Gly Thr Ile Leu Ile Asp Leu Ser Pro
945                 950                 955                 960

Asp Asp Lys Glu Phe Gln Ser Val Glu Glu Met Gln Ser Thr Val
            965                 970                 975

Arg Glu His Arg Asp Gly Gly His Ala Gly Gly Ile Phe Asn Arg Tyr
            980                 985                 990

Asn Ile Leu Lys Ile Gln Lys Val Cys Asn Lys Lys Leu Trp Glu Arg
            995                 1000                1005

Tyr Thr His Arg Arg Lys Glu Val Ser Glu Glu Asn His Asn His
        1010                1015                1020

Ala Asn Glu Arg Met Leu Phe His Gly Ser Pro Phe Val Asn Ala
        1025                1030                1035

Ile Ile His Lys Gly Phe Asp Glu Arg His Ala Tyr Ile Gly Gly
        1040                1045                1050

Met Phe Gly Ala Gly Ile Tyr Phe Ala Glu Asn Ser Ser Lys Ser
        1055                1060                1065

Asn Gln Tyr Val Tyr Gly Ile Gly Gly Gly Thr Gly Cys Pro Val
        1070                1075                1080

His Lys Asp Arg Ser Cys Tyr Ile Cys His Arg Gln Leu Leu Phe
        1085                1090                1095

Cys Arg Val Thr Leu Gly Lys Ser Phe Leu Gln Phe Ser Ala Met
        1100                1105                1110

Lys Met Ala His Ser Pro Pro Gly His His Ser Val Thr Gly Arg
        1115                1120                1125

Pro Ser Val Asn Gly Leu Ala Leu Ala Glu Tyr Val Ile Tyr Arg
        1130                1135                1140

Gly Glu Gln Ala Tyr Pro Glu Tyr Leu Ile Thr Tyr Gln Ile Met
        1145                1150                1155

Arg Pro Glu Gly Met Val Asp Gly
        1160                1165

<210> SEQ ID NO 45
<211> LENGTH: 197
<212> TYPE: PRT
<213> ORGANISM: Homo sapiens

<400> SEQUENCE: 45

Met Tyr Trp Ser Asn Gln Ile Thr Arg Arg Leu Gly Glu Arg Val Gln
1               5                   10                  15

Gly Phe Met Ser Gly Ile Ser Pro Gln Gln Met Gly Glu Pro Glu Gly
            20                  25                  30

Ser Trp Ser Gly Lys Asn Pro Gly Thr Met Gly Ala Ser Arg Leu Tyr
        35                  40                  45

Thr Leu Val Leu Val Leu Gln Pro Gln Arg Val Leu Leu Gly Met Lys
    50                  55                  60

Lys Arg Gly Phe Gly Ala Gly Arg Trp Asn Gly Phe Gly Gly Lys Val
65                  70                  75                  80

Gln Glu Gly Glu Thr Ile Glu Asp Gly Ala Arg Arg Glu Leu Gln Glu

```
                    85                  90                  95
Glu Ser Gly Leu Thr Val Asp Ala Leu His Lys Val Gly Gln Ile Val
                100                 105                 110
Phe Glu Phe Val Gly Glu Pro Glu Leu Met Asp Val His Val Phe Cys
                115                 120                 125
Thr Asp Ser Ile Gln Gly Thr Pro Val Glu Ser Asp Glu Met Arg Pro
                130                 135                 140
Cys Trp Phe Gln Leu Asp Gln Ile Pro Phe Lys Asp Met Trp Pro Asp
145                 150                 155                 160
Asp Ser Tyr Trp Phe Pro Leu Leu Gln Lys Lys Phe His Gly
                    165                 170                 175
Tyr Phe Lys Phe Gln Gly Gln Asp Thr Ile Leu Asp Tyr Thr Leu Arg
                180                 185                 190
Glu Val Asp Thr Val
                195

<210> SEQ ID NO 46
<211> LENGTH: 536
<212> TYPE: PRT
<213> ORGANISM: Homo sapiens

<400> SEQUENCE: 46

Met Gly Ser Asn Lys Ser Lys Pro Lys Asp Ala Ser Gln Arg Arg Arg
1               5                   10                  15
Ser Leu Glu Pro Ala Glu Asn Val His Gly Ala Gly Gly Gly Ala Phe
                20                  25                  30
Pro Ala Ser Gln Thr Pro Ser Lys Pro Ala Ser Ala Asp Gly His Arg
                35                  40                  45
Gly Pro Ser Ala Ala Phe Ala Pro Ala Ala Ala Glu Pro Lys Leu Phe
                50                  55                  60
Gly Gly Phe Asn Ser Ser Asp Thr Val Thr Ser Pro Gln Arg Ala Gly
65                  70                  75                  80
Pro Leu Ala Gly Gly Val Thr Thr Phe Val Ala Leu Tyr Asp Tyr Glu
                85                  90                  95
Ser Arg Thr Glu Thr Asp Leu Ser Phe Lys Lys Gly Glu Arg Leu Gln
                100                 105                 110
Ile Val Asn Asn Thr Glu Gly Asp Trp Trp Leu Ala His Ser Leu Ser
                115                 120                 125
Thr Gly Gln Thr Gly Tyr Ile Pro Ser Asn Tyr Val Ala Pro Ser Asp
                130                 135                 140
Ser Ile Gln Ala Glu Glu Trp Tyr Phe Gly Lys Ile Thr Arg Arg Glu
145                 150                 155                 160
Ser Glu Arg Leu Leu Leu Asn Ala Glu Asn Pro Arg Gly Thr Phe Leu
                165                 170                 175
Val Arg Glu Ser Glu Thr Thr Lys Gly Ala Tyr Cys Leu Ser Val Ser
                180                 185                 190
Asp Phe Asp Asn Ala Lys Gly Leu Asn Val Lys His Tyr Lys Ile Arg
                195                 200                 205
Lys Leu Asp Ser Gly Gly Phe Tyr Ile Thr Ser Arg Thr Gln Phe Asn
                210                 215                 220
Ser Leu Gln Gln Leu Val Ala Tyr Tyr Ser Lys His Ala Asp Gly Leu
225                 230                 235                 240
Cys His Arg Leu Thr Thr Val Cys Pro Thr Ser Lys Pro Gln Thr Gln
                245                 250                 255
```

```
Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
        275                 280                 285

Trp Asn Gly Thr Thr Arg Val Ala Ile Lys Thr Leu Lys Pro Gly Thr
    290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
        355                 360                 365

Met Ala Ala Gln Ile Ala Ser Gly Met Ala Tyr Val Glu Arg Met Asn
    370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
        435                 440                 445

Trp Ser Phe Gly Ile Leu Leu Thr Glu Leu Thr Thr Lys Gly Arg Val
    450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
        515                 520                 525

Gln Tyr Gln Pro Gly Glu Asn Leu
    530                 535

<210> SEQ ID NO 47
<211> LENGTH: 152
<212> TYPE: PRT
<213> ORGANISM: Homo sapiens

<400> SEQUENCE: 47

Met Pro Ala His Ser Leu Val Met Ser Ser Pro Ala Leu Pro Ala Phe
1               5                   10                  15

Leu Leu Cys Ser Thr Leu Leu Val Ile Lys Met Tyr Val Val Ala Ile
            20                  25                  30

Ile Thr Gly Gln Val Arg Leu Arg Lys Lys Ala Phe Ala Asn Pro Glu
        35                  40                  45

Asp Ala Leu Arg His Gly Gly Pro Gln Tyr Cys Arg Ser Asp Pro Asp
    50                  55                  60

Val Glu Arg Cys Leu Arg Ala His Arg Asn Asp Met Glu Thr Ile Tyr
65                  70                  75                  80

Pro Phe Leu Phe Leu Gly Phe Val Tyr Ser Phe Leu Gly Pro Asn Pro
                85                  90                  95
```

```
Phe Val Ala Trp Met His Phe Leu Val Phe Leu Val Gly Arg Val Ala
                100                 105                 110

His Thr Val Ala Tyr Leu Gly Lys Leu Arg Ala Pro Ile Arg Ser Val
            115                 120                 125

Thr Tyr Thr Leu Ala Gln Leu Pro Cys Ala Ser Met Ala Leu Gln Ile
130                 135                 140

Leu Trp Glu Ala Ala Arg His Leu
145                 150

<210> SEQ ID NO 48
<211> LENGTH: 161
<212> TYPE: PRT
<213> ORGANISM: Homo sapiens

<400> SEQUENCE: 48

Met Asp Gln Glu Thr Val Gly Asn Val Val Leu Leu Ala Ile Val Thr
1               5                   10                  15

Leu Ile Ser Val Val Gln Asn Gly Phe Phe Ala His Lys Val Glu His
                20                  25                  30

Glu Ser Arg Thr Gln Asn Gly Arg Ser Phe Gln Arg Thr Gly Thr Leu
            35                  40                  45

Ala Phe Glu Arg Val Tyr Thr Ala Asn Gln Asn Cys Val Asp Ala Tyr
        50                  55                  60

Pro Thr Phe Leu Ala Val Leu Trp Ser Ala Gly Leu Leu Cys Ser Gln
65                  70                  75                  80

Val Pro Ala Ala Phe Ala Gly Leu Met Tyr Leu Phe Val Arg Gln Lys
                85                  90                  95

Tyr Phe Val Gly Tyr Leu Gly Glu Arg Thr Gln Ser Thr Pro Gly Tyr
                100                 105                 110

Ile Phe Gly Lys Arg Ile Ile Leu Phe Leu Phe Leu Met Ser Val Ala
            115                 120                 125

Gly Ile Phe Asn Tyr Tyr Leu Ile Phe Phe Gly Ser Asp Phe Glu
        130                 135                 140

Asn Tyr Ile Lys Thr Ile Ser Thr Thr Ile Ser Pro Leu Leu Leu Ile
145                 150                 155                 160

Pro

<210> SEQ ID NO 49
<211> LENGTH: 132
<212> TYPE: PRT
<213> ORGANISM: Homo sapiens

<400> SEQUENCE: 49

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
                20                  25                  30

Val Ala Gly Met Ala Lys Pro Asn Met Ile Ile Ser Val Asn Gly Asp
            35                  40                  45

Val Ile Thr Ile Lys Ser Glu Ser Thr Phe Lys Asn Thr Glu Ile Ser
        50                  55                  60

Phe Ile Leu Gly Gln Glu Phe Asp Glu Val Thr Ala Asp Asp Arg Lys
65                  70                  75                  80

Val Lys Ser Thr Ile Thr Leu Asp Gly Gly Val Leu Val His Val Gln
                85                  90                  95
```

```
Lys Trp Asp Gly Lys Ser Thr Thr Ile Lys Arg Lys Arg Glu Asp Asp
            100                 105                 110

Lys Leu Val Val Glu Cys Val Met Lys Gly Val Thr Ser Thr Arg Val
            115                 120                 125

Tyr Glu Arg Ala
            130

<210> SEQ ID NO 50
<211> LENGTH: 1821
<212> TYPE: PRT
<213> ORGANISM: Homo sapiens

<400> SEQUENCE: 50

Met Ser Cys Glu Arg Lys Gly Leu Ser Glu Leu Arg Ser Glu Leu Tyr
1               5                   10                  15

Phe Leu Ile Ala Arg Phe Leu Glu Asp Gly Pro Cys Gln Gln Ala Ala
            20                  25                  30

Gln Val Leu Ile Arg Glu Val Ala Glu Lys Glu Leu Leu Pro Arg Arg
            35                  40                  45

Thr Asp Trp Thr Gly Lys Glu His Pro Arg Thr Tyr Gln Asn Leu Val
        50                  55                  60

Lys Tyr Tyr Arg His Leu Ala Pro Asp His Leu Gln Ile Cys His
65                  70                  75                  80

Arg Leu Gly Pro Leu Leu Glu Gln Glu Ile Pro Gln Ser Val Pro Gly
                85                  90                  95

Val Gln Thr Leu Leu Gly Ala Gly Arg Gln Ser Leu Leu Arg Thr Asn
            100                 105                 110

Lys Ser Cys Lys His Val Val Trp Lys Gly Ser Ala Leu Ala Ala Leu
            115                 120                 125

His Cys Gly Arg Pro Pro Glu Ser Pro Val Asn Tyr Gly Ser Pro Pro
        130                 135                 140

Ser Ile Ala Asp Thr Leu Phe Ser Arg Lys Leu Asn Gly Lys Tyr Arg
145                 150                 155                 160

Leu Glu Arg Leu Val Pro Thr Ala Val Tyr Gln His Met Lys Met His
                165                 170                 175

Lys Arg Ile Leu Gly His Leu Ser Ser Val Tyr Cys Val Thr Phe Asp
            180                 185                 190

Arg Thr Gly Arg Arg Ile Phe Thr Gly Ser Asp Asp Cys Leu Val Lys
            195                 200                 205

Ile Trp Ala Thr Asp Asp Gly Arg Leu Leu Ala Thr Leu Arg Gly His
        210                 215                 220

Ala Ala Glu Ile Ser Asp Met Ala Val Asn Tyr Glu Asn Thr Met Ile
225                 230                 235                 240

Ala Ala Gly Ser Cys Asp Lys Met Ile Arg Val Trp Cys Leu Arg Thr
                245                 250                 255

Cys Ala Pro Leu Ala Val Leu Gln Gly His Ser Ala Ser Ile Thr Ser
            260                 265                 270

Leu Gln Phe Ser Pro Leu Cys Ser Gly Ser Lys Arg Tyr Leu Ser Ser
            275                 280                 285

Thr Gly Ala Asp Gly Thr Ile Cys Phe Trp Leu Trp Asp Ala Gly Thr
        290                 295                 300

Leu Lys Ile Asn Pro Arg Pro Ala Lys Phe Thr Glu Arg Pro Arg Pro
305                 310                 315                 320

Gly Val Gln Met Ile Cys Ser Ser Phe Ser Ala Gly Gly Met Phe Leu
                325                 330                 335
```

```
Ala Thr Gly Ser Thr Asp His Ile Ile Arg Val Tyr Phe Phe Gly Ser
            340                 345                 350

Gly Gln Pro Glu Lys Ile Ser Glu Leu Glu Phe His Thr Asp Lys Val
        355                 360                 365

Asp Ser Ile Gln Phe Ser Asn Thr Ser Asn Arg Phe Val Ser Gly Ser
    370                 375                 380

Arg Asp Gly Thr Ala Arg Ile Trp Gln Phe Lys Arg Arg Glu Trp Lys
385                 390                 395                 400

Ser Ile Leu Leu Asp Met Ala Thr Arg Pro Ala Gly Gln Asn Leu Gln
                405                 410                 415

Gly Ile Glu Asp Lys Ile Thr Lys Met Lys Val Thr Met Val Ala Trp
            420                 425                 430

Asp Arg His Asp Asn Thr Val Ile Thr Ala Val Asn Asn Met Thr Leu
        435                 440                 445

Lys Val Trp Asn Ser Tyr Thr Gly Gln Leu Ile His Val Leu Met Gly
    450                 455                 460

His Glu Asp Glu Val Phe Val Leu Glu Pro His Pro Phe Asp Pro Arg
465                 470                 475                 480

Val Leu Phe Ser Ala Gly His Asp Gly Asn Val Ile Val Trp Asp Leu
                485                 490                 495

Ala Arg Gly Val Lys Ile Arg Ser Tyr Phe Asn Met Ile Glu Gly Gln
            500                 505                 510

Gly His Gly Ala Val Phe Asp Cys Lys Cys Ser Pro Asp Gly Gln His
        515                 520                 525

Phe Ala Cys Thr Asp Ser His Gly His Leu Leu Ile Phe Gly Phe Gly
    530                 535                 540

Ser Ser Ser Lys Tyr Asp Lys Ile Ala Asp Gln Met Phe Phe His Ser
545                 550                 555                 560

Asp Tyr Arg Pro Leu Ile Arg Asp Ala Asn Asn Phe Val Leu Asp Glu
                565                 570                 575

Gln Thr Gln Gln Ala Pro His Leu Met Pro Pro Phe Leu Val Asp
            580                 585                 590

Val Asp Gly Asn Pro His Pro Ser Arg Tyr Gln Arg Leu Val Pro Gly
        595                 600                 605

Arg Glu Asn Cys Arg Glu Glu Gln Leu Ile Pro Gln Met Gly Val Thr
    610                 615                 620

Ser Ser Gly Leu Asn Gln Val Leu Ser Gln Gln Ala Asn Gln Glu Ile
625                 630                 635                 640

Ser Pro Leu Asp Ser Met Ile Gln Arg Leu Gln Gln Glu Gln Asp Leu
                645                 650                 655

Arg Arg Ser Gly Glu Ala Val Ile Ser Asn Thr Ser Arg Leu Ser Arg
            660                 665                 670

Gly Ser Ile Ser Ser Thr Ser Glu Val His Ser Pro Asn Val Gly
        675                 680                 685

Leu Arg Arg Ser Gly Gln Ile Glu Gly Val Arg Gln Met His Ser Asn
    690                 695                 700

Ala Pro Arg Ser Glu Ile Ala Thr Glu Arg Asp Leu Val Ala Trp Ser
705                 710                 715                 720

Arg Arg Val Val Val Pro Glu Leu Ser Ala Gly Val Ala Ser Arg Gln
                725                 730                 735

Glu Glu Trp Arg Thr Ala Lys Gly Glu Glu Glu Ile Lys Thr Tyr Arg
            740                 745                 750
```

-continued

Ser Glu Glu Lys Arg Lys His Leu Thr Val Pro Lys Glu Asn Lys Ile
            755                 760                 765

Pro Thr Val Ser Lys Asn His Ala His Glu His Phe Leu Asp Leu Gly
770                 775                 780

Glu Ser Lys Lys Gln Gln Thr Asn Gln His Asn Tyr Arg Thr Arg Ser
785                 790                 795                 800

Ala Leu Glu Glu Thr Pro Arg Pro Ser Glu Ile Glu Asn Gly Ser
                805                 810                 815

Ser Ser Ser Asp Glu Gly Glu Val Ala Val Ser Gly Gly Thr Ser
            820                 825                 830

Glu Glu Glu Arg Ala Trp His Ser Asp Gly Ser Ser Ser Asp Tyr
            835                 840                 845

Ser Ser Asp Tyr Ser Asp Trp Thr Ala Asp Ala Gly Ile Asn Leu Gln
850                 855                 860

Pro Pro Lys Lys Val Pro Lys Asn Lys Thr Lys Lys Ala Glu Ser Ser
865                 870                 875                 880

Ser Asp Glu Glu Glu Ser Glu Lys Gln Lys Gln Lys Gln Ile Lys
            885                 890                 895

Lys Glu Lys Lys Lys Val Asn Glu Glu Lys Asp Gly Pro Ile Ser Pro
            900                 905                 910

Lys Lys Lys Lys Pro Lys Glu Arg Lys Gln Lys Arg Leu Ala Val Gly
            915                 920                 925

Glu Leu Thr Glu Asn Gly Leu Thr Leu Glu Glu Trp Leu Pro Ser Thr
            930                 935                 940

Trp Ile Thr Asp Thr Ile Pro Arg Arg Cys Pro Phe Val Pro Gln Met
945                 950                 955                 960

Gly Asp Glu Val Tyr Tyr Phe Arg Gln Gly His Glu Ala Tyr Val Glu
                965                 970                 975

Met Ala Arg Lys Asn Lys Ile Tyr Ser Ile Asn Pro Lys Lys Gln Pro
            980                 985                 990

Trp His Lys Met Glu Leu Arg Glu Gln Glu Leu Met Lys Ile Val Gly
            995                 1000                1005

Ile Lys Tyr Glu Val Gly Leu Pro Thr Leu Cys Cys Leu Lys Leu
    1010                1015                1020

Ala Phe Leu Asp Pro Asp Thr Gly Lys Leu Thr Gly Gly Ser Phe
    1025                1030                1035

Thr Met Lys Tyr His Asp Met Pro Asp Val Ile Asp Phe Leu Val
    1040                1045                1050

Leu Arg Gln Gln Phe Asp Asp Ala Lys Tyr Arg Arg Trp Asn Ile
    1055                1060                1065

Gly Asp Arg Phe Arg Ser Val Ile Asp Asp Ala Trp Trp Phe Gly
    1070                1075                1080

Thr Ile Glu Ser Gln Glu Pro Leu Gln Leu Glu Tyr Pro Asp Ser
    1085                1090                1095

Leu Phe Gln Cys Tyr Asn Val Cys Trp Asp Asn Gly Asp Thr Glu
    1100                1105                1110

Lys Met Ser Pro Trp Asp Met Glu Leu Ile Pro Asn Asn Ala Val
    1115                1120                1125

Phe Pro Glu Glu Leu Gly Thr Ser Val Pro Leu Thr Asp Gly Glu
    1130                1135                1140

Cys Arg Ser Leu Ile Tyr Lys Pro Leu Asp Gly Glu Trp Gly Thr
    1145                1150                1155

Asn Pro Arg Asp Glu Glu Cys Glu Arg Ile Val Ala Gly Ile Asn

```
            1160                1165               1170

Gln Leu Met Thr Leu Asp Ile Ala Ser Ala Phe Val Ala Pro Val
    1175                1180                1185

Asp Leu Gln Ala Tyr Pro Met Tyr Cys Thr Val Val Ala Tyr Pro
    1190                1195                1200

Thr Asp Leu Ser Thr Ile Lys Gln Arg Leu Glu Asn Arg Phe Tyr
    1205                1210                1215

Arg Arg Val Ser Ser Leu Met Trp Glu Val Arg Tyr Ile Glu His
    1220                1225                1230

Asn Thr Arg Thr Phe Asn Glu Pro Gly Ser Pro Ile Val Lys Ser
    1235                1240                1245

Ala Lys Phe Val Thr Asp Leu Leu Leu His Phe Ile Lys Asp Gln
    1250                1255                1260

Thr Cys Tyr Asn Ile Ile Pro Leu Tyr Asn Ser Met Lys Lys Lys
    1265                1270                1275

Val Leu Ser Asp Ser Glu Asp Glu Lys Asp Ala Asp Val Pro
    1280                1285                1290

Gly Thr Ser Thr Arg Lys Arg Lys Asp His Gln Pro Arg Arg Arg
    1295                1300                1305

Leu Arg Asn Arg Ala Gln Ser Tyr Asp Ile Gln Ala Trp Lys Lys
    1310                1315                1320

Gln Cys Glu Glu Leu Leu Asn Leu Ile Phe Gln Cys Glu Asp Ser
    1325                1330                1335

Glu Pro Phe Arg Gln Pro Val Asp Leu Leu Glu Tyr Pro Asp Tyr
    1340                1345                1350

Arg Asp Ile Ile Asp Thr Pro Met Asp Phe Ala Thr Val Arg Glu
    1355                1360                1365

Thr Leu Glu Ala Gly Asn Tyr Glu Ser Pro Met Glu Leu Cys Lys
    1370                1375                1380

Asp Val Arg Leu Ile Phe Ser Asn Ser Lys Ala Tyr Thr Pro Ser
    1385                1390                1395

Lys Arg Ser Arg Ile Tyr Ser Met Ser Leu Arg Leu Ser Ala Phe
    1400                1405                1410

Phe Glu Glu His Ile Ser Ser Val Leu Ser Asp Tyr Lys Ser Ala
    1415                1420                1425

Leu Arg Phe His Lys Arg Asn Thr Ile Thr Lys Arg Arg Lys Lys
    1430                1435                1440

Arg Asn Arg Ser Ser Ser Val Ser Ser Ser Ala Ala Ser Ser Pro
    1445                1450                1455

Glu Arg Lys Lys Arg Ile Leu Lys Pro Gln Leu Lys Ser Glu Ser
    1460                1465                1470

Ser Thr Ser Ala Phe Ser Thr Pro Thr Arg Ser Ile Pro Pro Arg
    1475                1480                1485

His Asn Ala Ala Gln Ile Asn Gly Lys Thr Glu Ser Ser Ser Val
    1490                1495                1500

Val Arg Thr Arg Ser Asn Arg Val Val Asp Pro Val Val Thr
    1505                1510                1515

Glu Gln Pro Ser Thr Ser Ser Ala Ala Lys Thr Phe Ile Thr Lys
    1520                1525                1530

Ala Asn Ala Ser Ala Ile Pro Gly Lys Thr Ile Leu Glu Asn Ser
    1535                1540                1545

Val Lys His Ser Lys Ala Leu Asn Thr Leu Ser Ser Pro Gly Gln
    1550                1555                1560
```

```
Ser Ser Phe Ser His Gly Thr Arg Asn Asn Ser Ala Lys Glu Asn
    1565                1570                1575

Met Glu Lys Glu Lys Pro Val Lys Arg Lys Met Lys Ser Ser Val
    1580                1585                1590

Leu Pro Lys Ala Ser Thr Leu Ser Lys Ser Ser Ala Val Ile Glu
    1595                1600                1605

Gln Gly Asp Cys Lys Asn Asn Ala Leu Val Pro Gly Thr Ile Gln
    1610                1615                1620

Val Asn Gly His Gly Gly Gln Pro Ser Lys Leu Val Lys Arg Gly
    1625                1630                1635

Pro Gly Arg Lys Pro Lys Val Glu Val Asn Thr Asn Ser Gly Glu
    1640                1645                1650

Ile Ile His Lys Lys Arg Gly Arg Lys Pro Lys Lys Leu Gln Tyr
    1655                1660                1665

Ala Lys Pro Glu Asp Leu Glu Gln Asn Asn Val His Pro Ile Arg
    1670                1675                1680

Asp Glu Val Leu Pro Ser Ser Thr Cys Asn Phe Leu Ser Glu Thr
    1685                1690                1695

Asn Asn Val Lys Glu Asp Leu Leu Gln Lys Lys Asn Arg Gly Gly
    1700                1705                1710

Arg Lys Pro Lys Arg Lys Met Lys Thr Gln Lys Leu Asp Ala Asp
    1715                1720                1725

Leu Leu Val Pro Ala Ser Val Lys Val Leu Arg Arg Ser Asn Arg
    1730                1735                1740

Lys Lys Ile Asp Asp Pro Ile Asp Glu Glu Glu Glu Phe Glu Glu
    1745                1750                1755

Leu Lys Gly Ser Glu Pro His Met Arg Thr Arg Asn Gln Gly Arg
    1760                1765                1770

Arg Thr Ala Phe Tyr Asn Glu Asp Asp Ser Glu Glu Glu Gln Arg
    1775                1780                1785

Gln Leu Leu Phe Glu Asp Thr Ser Leu Thr Phe Gly Thr Ser Ser
    1790                1795                1800

Arg Gly Arg Val Arg Lys Leu Thr Glu Lys Ala Lys Ala Asn Leu
    1805                1810                1815

Ile Gly Trp
    1820

<210> SEQ ID NO 51
<211> LENGTH: 158
<212> TYPE: PRT
<213> ORGANISM: Homo sapiens

<400> SEQUENCE: 51

Met Ser Gly Ile Ala Leu Ser Arg Leu Ala Gln Glu Arg Lys Ala Trp
1               5                   10                  15

Arg Lys Asp His Pro Phe Gly Phe Val Ala Val Pro Thr Lys Asn Pro
                20                  25                  30

Asp Gly Thr Met Asn Leu Met Asn Trp Glu Cys Ala Ile Pro Gly Lys
            35                  40                  45

Lys Gly Thr Pro Trp Glu Gly Gly Leu Phe Lys Leu Arg Met Leu Phe
        50                  55                  60

Lys Asp Asp Tyr Pro Ser Ser Pro Pro Lys Cys Lys Phe Glu Pro Pro
65                  70                  75                  80

Leu Phe His Pro Asn Val Tyr Pro Ser Gly Thr Val Cys Leu Ser Ile
```

```
            85                 90                  95
Leu Glu Glu Asp Lys Asp Trp Arg Pro Ala Ile Thr Ile Lys Gln Ile
            100                105                 110

Leu Leu Gly Ile Gln Glu Leu Leu Asn Glu Pro Asn Ile Gln Asp Pro
        115                120                 125

Ala Gln Ala Glu Ala Tyr Thr Ile Tyr Cys Gln Asn Arg Val Glu Tyr
    130                 135                 140

Glu Lys Arg Val Arg Ala Gln Ala Lys Lys Phe Ala Pro Ser
145                 150                 155

<210> SEQ ID NO 52
<211> LENGTH: 101
<212> TYPE: PRT
<213> ORGANISM: Homo sapiens

<400> SEQUENCE: 52

Met Ser Asn Thr Gln Ala Glu Arg Ser Ile Ile Gly Met Ile Asp Met
1               5                   10                  15

Phe His Lys Tyr Thr Arg Arg Asp Asp Lys Ile Glu Lys Pro Ser Leu
            20                  25                  30

Leu Thr Met Met Lys Glu Asn Phe Pro Asn Phe Leu Ser Ala Cys Asp
        35                  40                  45

Lys Lys Gly Thr Asn Tyr Leu Ala Asp Val Phe Glu Lys Lys Asp Lys
    50                  55                  60

Asn Glu Asp Lys Lys Ile Asp Phe Ser Glu Phe Leu Ser Leu Leu Gly
65                  70                  75                  80

Asp Ile Ala Thr Asp Tyr His Lys Gln Ser His Gly Ala Ala Pro Cys
                85                  90                  95

Ser Gly Gly Ser Gln
            100

<210> SEQ ID NO 53
<211> LENGTH: 144
<212> TYPE: PRT
<213> ORGANISM: Homo sapiens

<400> SEQUENCE: 53

Met Lys Thr Leu Leu Leu Ala Val Ile Met Ile Phe Gly Leu Leu
1               5                   10                  15

Gln Ala His Gly Asn Leu Val Asn Phe His Arg Met Ile Lys Leu Thr
            20                  25                  30

Thr Gly Lys Glu Ala Ala Leu Ser Tyr Gly Phe Tyr Gly Cys His Cys
        35                  40                  45

Gly Val Gly Gly Arg Gly Ser Pro Lys Asp Ala Thr Asp Arg Cys Cys
    50                  55                  60

Val Thr His Asp Cys Cys Tyr Lys Arg Leu Glu Lys Arg Gly Cys Gly
65                  70                  75                  80

Thr Lys Phe Leu Ser Tyr Lys Phe Ser Asn Ser Gly Ser Arg Ile Thr
                85                  90                  95

Cys Ala Lys Gln Asp Ser Cys Arg Ser Gln Leu Cys Glu Cys Asp Lys
            100                 105                 110

Ala Ala Ala Thr Cys Phe Ala Arg Asn Lys Thr Thr Tyr Asn Lys Lys
            115                 120                 125

Tyr Gln Tyr Tyr Ser Asn Lys His Cys Arg Gly Ser Thr Pro Arg Cys
            130                 135                 140
```

-continued

```
<210> SEQ ID NO 54
<211> LENGTH: 1215
<212> TYPE: PRT
<213> ORGANISM: Homo sapiens

<400> SEQUENCE: 54

Met Thr Ser Thr Gly Gln Asp Ser Thr Thr Arg Gln Arg Arg Ser
1               5                   10                  15

Arg Gln Asn Pro Gln Ser Pro Pro Gln Asp Ser Ser Val Thr Ser Lys
                20                  25                  30

Arg Asn Ile Lys Lys Gly Ala Val Pro Arg Ser Ile Pro Asn Leu Ala
            35                  40                  45

Glu Val Lys Lys Lys Gly Lys Met Lys Lys Leu Gly Gln Ala Met Glu
    50                  55                  60

Glu Asp Leu Ile Val Gly Leu Gln Gly Met Asp Leu Asn Leu Glu Ala
65                  70                  75                  80

Glu Ala Leu Ala Gly Thr Gly Leu Val Leu Asp Glu Gln Leu Asn Glu
                85                  90                  95

Phe His Cys Leu Trp Asp Asp Ser Phe Pro Glu Gly Pro Glu Arg Leu
            100                 105                 110

His Ala Ile Lys Glu Gln Leu Ile Gln Glu Gly Leu Leu Asp Arg Cys
        115                 120                 125

Val Ser Phe Gln Ala Arg Phe Ala Glu Lys Glu Glu Leu Met Leu Val
130                 135                 140

His Ser Leu Glu Tyr Ile Asp Leu Met Glu Thr Thr Gln Tyr Met Asn
145                 150                 155                 160

Glu Gly Glu Leu Arg Val Leu Ala Asp Thr Tyr Asp Ser Val Tyr Leu
                165                 170                 175

His Pro Asn Ser Tyr Ser Cys Ala Cys Leu Ala Ser Gly Ser Val Leu
            180                 185                 190

Arg Leu Val Asp Ala Val Leu Gly Ala Glu Ile Arg Asn Gly Met Ala
        195                 200                 205

Ile Ile Arg Pro Pro Gly His His Ala Gln His Ser Leu Met Asp Gly
    210                 215                 220

Tyr Cys Met Phe Asn His Val Ala Val Ala Ala Arg Tyr Ala Gln Gln
225                 230                 235                 240

Lys His Arg Ile Arg Arg Val Leu Ile Val Asp Trp Asp Val His His
                245                 250                 255

Gly Gln Gly Thr Gln Phe Thr Phe Asp Gln Asp Pro Ser Val Leu Tyr
            260                 265                 270

Phe Ser Ile His Arg Tyr Glu Gln Gly Arg Phe Trp Pro His Leu Lys
        275                 280                 285

Ala Ser Asn Trp Ser Thr Thr Gly Phe Gly Gln Gly Gln Gly Tyr Thr
    290                 295                 300

Ile Asn Val Pro Trp Asn Gln Val Gly Met Arg Asp Ala Asp Tyr Ile
305                 310                 315                 320

Ala Ala Phe Leu His Val Leu Leu Pro Val Ala Leu Glu Phe Gln Pro
                325                 330                 335

Gln Leu Val Leu Val Ala Ala Gly Phe Asp Ala Leu Gln Gly Asp Pro
            340                 345                 350

Lys Gly Glu Met Ala Ala Thr Pro Ala Gly Phe Ala Gln Leu Thr His
        355                 360                 365

Leu Leu Met Gly Leu Ala Gly Gly Lys Leu Ile Leu Ser Leu Glu Gly
    370                 375                 380
```

```
Gly Tyr Asn Leu Arg Ala Leu Ala Glu Gly Val Ser Ala Ser Leu His
385                 390                 395                 400

Thr Leu Leu Gly Asp Pro Cys Pro Met Leu Glu Ser Pro Gly Ala Pro
            405                 410                 415

Cys Arg Ser Ala Gln Ala Ser Val Ser Cys Ala Leu Glu Ala Leu Glu
            420                 425                 430

Pro Phe Trp Glu Val Leu Val Arg Ser Thr Glu Thr Val Glu Arg Asp
            435                 440                 445

Asn Met Glu Glu Asp Asn Val Glu Glu Ser Glu Glu Glu Gly Pro Trp
450                 455                 460

Glu Pro Pro Val Leu Pro Ile Leu Thr Trp Pro Val Leu Gln Ser Arg
465                 470                 475                 480

Thr Gly Leu Val Tyr Asp Gln Asn Met Met Asn His Cys Asn Leu Trp
            485                 490                 495

Asp Ser His His Pro Glu Val Pro Gln Arg Ile Leu Arg Ile Met Cys
            500                 505                 510

Arg Leu Glu Glu Leu Gly Leu Ala Gly Arg Cys Leu Thr Leu Thr Pro
            515                 520                 525

Arg Pro Ala Thr Glu Ala Glu Leu Leu Thr Cys His Ser Ala Glu Tyr
            530                 535                 540

Val Gly His Leu Arg Ala Thr Glu Lys Met Lys Thr Arg Glu Leu His
545                 550                 555                 560

Arg Glu Ser Ser Asn Phe Asp Ser Ile Tyr Ile Cys Pro Ser Thr Phe
                565                 570                 575

Ala Cys Ala Gln Leu Ala Thr Gly Ala Ala Cys Arg Leu Val Glu Ala
            580                 585                 590

Val Leu Ser Gly Glu Val Leu Asn Gly Ala Ala Val Val Arg Pro Pro
            595                 600                 605

Gly His His Ala Glu Gln Asp Ala Ala Cys Gly Phe Cys Phe Phe Asn
            610                 615                 620

Ser Val Ala Val Ala Ala Arg His Ala Gln Thr Ile Ser Gly His Ala
625                 630                 635                 640

Leu Arg Ile Leu Ile Val Asp Trp Asp Val His His Gly Asn Gly Thr
                645                 650                 655

Gln His Met Phe Glu Asp Asp Pro Ser Val Leu Tyr Val Ser Leu His
            660                 665                 670

Arg Tyr Asp His Gly Thr Phe Phe Pro Met Gly Asp Glu Gly Ala Ser
            675                 680                 685

Ser Gln Ile Gly Arg Ala Ala Gly Thr Gly Phe Thr Val Asn Val Ala
            690                 695                 700

Trp Asn Gly Pro Arg Met Gly Asp Ala Asp Tyr Leu Ala Ala Trp His
705                 710                 715                 720

Arg Leu Val Leu Pro Ile Ala Tyr Glu Phe Asn Pro Glu Leu Val Leu
            725                 730                 735

Val Ser Ala Gly Phe Asp Ala Ala Arg Gly Asp Pro Leu Gly Gly Cys
            740                 745                 750

Gln Val Ser Pro Glu Gly Tyr Ala His Leu Thr His Leu Leu Met Gly
            755                 760                 765

Leu Ala Ser Gly Arg Ile Ile Leu Ile Leu Glu Gly Gly Tyr Asn Leu
            770                 775                 780

Thr Ser Ile Ser Glu Ser Met Ala Ala Cys Thr Arg Ser Leu Leu Gly
785                 790                 795                 800

Asp Pro Pro Pro Leu Leu Thr Leu Pro Arg Pro Pro Leu Ser Gly Ala
```

```
                    805                 810                 815
Leu Ala Ser Ile Thr Glu Thr Ile Gln Val His Arg Arg Tyr Trp Arg
                820                 825                 830
Ser Leu Arg Val Met Lys Val Glu Asp Arg Glu Gly Pro Ser Ser Ser
                835                 840                 845
Lys Leu Val Thr Lys Lys Ala Pro Gln Pro Ala Lys Pro Arg Leu Ala
                850                 855                 860
Glu Arg Met Thr Thr Arg Glu Lys Lys Val Leu Glu Ala Gly Met Gly
865                 870                 875                 880
Lys Val Thr Ser Ala Ser Phe Gly Glu Ser Thr Pro Gly Gln Thr
                    885                 890                 895
Asn Ser Glu Thr Ala Val Val Ala Leu Thr Gln Asp Gln Pro Ser Glu
                900                 905                 910
Ala Ala Thr Gly Gly Ala Thr Leu Ala Gln Thr Ile Ser Glu Ala Ala
                    915                 920                 925
Ile Gly Gly Ala Met Leu Gly Gln Thr Thr Ser Glu Glu Ala Val Gly
                930                 935                 940
Gly Ala Thr Pro Asp Gln Thr Thr Ser Glu Glu Thr Val Gly Gly Ala
945                 950                 955                 960
Ile Leu Asp Gln Thr Thr Ser Glu Asp Ala Val Gly Gly Ala Thr Leu
                    965                 970                 975
Gly Gln Thr Thr Ser Glu Glu Ala Val Gly Gly Ala Thr Leu Ala Gln
                980                 985                 990
Thr Thr Ser Glu Ala Ala Met Glu  Gly Ala Thr Leu Asp  Gln Thr Thr
                    995                  1000                1005
Ser Glu  Glu Ala Pro Gly Gly  Thr Glu Leu Ile Gln  Thr Pro Leu
    1010                1015                1020
Ala Ser  Ser Thr Asp His Gln  Thr Pro Pro Thr Ser  Pro Val Gln
    1025                1030                1035
Gly Thr  Thr Pro Gln Ile Ser  Pro Ser Thr Leu Ile  Gly Ser Leu
    1040                1045                1050
Arg Thr  Leu Glu Leu Gly Ser  Glu Ser Gln Gly Ala  Ser Glu Ser
    1055                1060                1065
Gln Ala  Pro Gly Glu Glu Asn  Leu Leu Gly Glu Ala  Ala Gly Gly
    1070                1075                1080
Gln Asp  Met Ala Asp Ser Met  Leu Met Gln Gly Ser  Arg Gly Leu
    1085                1090                1095
Thr Asp  Gln Ala Ile Phe Tyr  Ala Val Thr Pro Leu  Pro Trp Cys
    1100                1105                1110
Pro His  Leu Val Ala Val Cys  Pro Ile Pro Ala Ala  Gly Leu Asp
    1115                1120                1125
Val Thr  Gln Pro Cys Gly Asp  Cys Gly Thr Ile Gln  Glu Asn Trp
    1130                1135                1140
Val Cys  Leu Ser Cys Tyr Gln  Val Tyr Cys Gly Arg  Tyr Ile Asn
    1145                1150                1155
Gly His  Met Leu Gln His His  Gly Asn Ser Gly His  Pro Leu Val
    1160                1165                1170
Leu Ser  Tyr Ile Asp Leu Ser  Ala Trp Cys Tyr Tyr  Cys Gln Ala
    1175                1180                1185
Tyr Val  His His Gln Ala Leu  Leu Asp Val Lys Asn  Ile Ala His
    1190                1195                1200
Gln Asn  Lys Phe Gly Glu Asp  Met Pro His Pro His
    1205                1210                1215
```

<210> SEQ ID NO 55
<211> LENGTH: 524
<212> TYPE: PRT
<213> ORGANISM: Homo sapiens

<400> SEQUENCE: 55

```
Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
```

```
                    370                 375                 380
Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
                420                 425                 430

Leu Ala Ala Leu Glu Lys Gly Cys Ser Phe Leu Pro Asp Pro Tyr Gln
                435                 440                 445

Lys Gln Cys Asp Gln Phe Val Ala Glu Tyr Glu Pro Val Leu Ile Glu
                450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
                500                 505                 510

Asn Ala Val Glu His Cys Lys Arg His Val Trp Asn
                515                 520

<210> SEQ ID NO 56
<211> LENGTH: 4548
<212> TYPE: PRT
<213> ORGANISM: Homo sapiens

<400> SEQUENCE: 56

Met Glu His Lys Glu Val Val Leu Leu Leu Leu Phe Leu Lys Ser
1               5                   10                  15

Ala Ala Pro Glu Gln Ser His Val Val Gln Asp Cys Tyr His Gly Asp
                20                  25                  30

Gly Gln Ser Tyr Arg Gly Thr Tyr Ser Thr Val Thr Gly Arg Thr
                35                  40                  45

Cys Gln Ala Trp Ser Ser Met Thr Pro His Gln His Asn Arg Thr Thr
    50                  55                  60

Glu Asn Tyr Pro Asn Ala Gly Leu Ile Met Asn Tyr Cys Arg Asn Pro
65                  70                  75                  80

Asp Ala Val Ala Ala Pro Tyr Cys Tyr Thr Arg Asp Pro Gly Val Arg
                85                  90                  95

Trp Glu Tyr Cys Asn Leu Thr Gln Cys Ser Asp Ala Glu Gly Thr Ala
                100                 105                 110

Val Ala Pro Pro Thr Val Thr Pro Val Pro Ser Leu Glu Ala Pro Ser
                115                 120                 125

Glu Gln Ala Pro Thr Glu Gln Arg Pro Gly Val Gln Glu Cys Tyr His
                130                 135                 140

Gly Asn Gly Gln Ser Tyr Arg Gly Thr Tyr Ser Thr Thr Val Thr Gly
145                 150                 155                 160

Arg Thr Cys Gln Ala Trp Ser Ser Met Thr Pro His Ser His Ser Arg
                165                 170                 175

Thr Pro Glu Tyr Tyr Pro Asn Ala Gly Leu Ile Met Asn Tyr Cys Arg
                180                 185                 190

Asn Pro Asp Ala Val Ala Ala Pro Tyr Cys Tyr Thr Arg Asp Pro Gly
                195                 200                 205

Val Arg Trp Glu Tyr Cys Asn Leu Thr Gln Cys Ser Asp Ala Glu Gly
    210                 215                 220
```

```
Thr Ala Val Ala Pro Pro Thr Val Thr Pro Val Pro Ser Leu Glu Ala
225                 230                 235                 240

Pro Ser Glu Gln Ala Pro Thr Glu Gln Arg Pro Gly Val Gln Glu Cys
            245                 250                 255

Tyr His Gly Asn Gly Gln Ser Tyr Arg Gly Thr Tyr Ser Thr Thr Val
        260                 265                 270

Thr Gly Arg Thr Cys Gln Ala Trp Ser Ser Met Thr Pro His Ser His
    275                 280                 285

Ser Arg Thr Pro Glu Tyr Tyr Pro Asn Ala Gly Leu Ile Met Asn Tyr
290                 295                 300

Cys Arg Asn Pro Asp Ala Val Ala Ala Pro Tyr Cys Tyr Thr Arg Asp
305                 310                 315                 320

Pro Gly Val Arg Trp Glu Tyr Cys Asn Leu Thr Gln Cys Ser Asp Ala
                325                 330                 335

Glu Gly Thr Ala Val Ala Pro Pro Thr Val Thr Pro Val Pro Ser Leu
            340                 345                 350

Glu Ala Pro Ser Glu Gln Ala Pro Thr Glu Gln Arg Pro Gly Val Gln
        355                 360                 365

Glu Cys Tyr His Gly Asn Gly Gln Ser Tyr Arg Gly Thr Tyr Ser Thr
370                 375                 380

Thr Val Thr Gly Arg Thr Cys Gln Ala Trp Ser Ser Met Thr Pro His
385                 390                 395                 400

Ser His Ser Arg Thr Pro Glu Tyr Tyr Pro Asn Ala Gly Leu Ile Met
                405                 410                 415

Asn Tyr Cys Arg Asn Pro Asp Ala Val Ala Ala Pro Tyr Cys Tyr Thr
            420                 425                 430

Arg Asp Pro Gly Val Arg Trp Glu Tyr Cys Asn Leu Thr Gln Cys Ser
        435                 440                 445

Asp Ala Glu Gly Thr Ala Val Ala Pro Pro Thr Val Thr Pro Val Pro
450                 455                 460

Ser Leu Glu Ala Pro Ser Glu Gln Ala Pro Thr Glu Gln Arg Pro Gly
465                 470                 475                 480

Val Gln Glu Cys Tyr His Gly Asn Gly Gln Ser Tyr Arg Gly Thr Tyr
                485                 490                 495

Ser Thr Thr Val Thr Gly Arg Thr Cys Gln Ala Trp Ser Ser Met Thr
            500                 505                 510

Pro His Ser His Ser Arg Thr Pro Glu Tyr Tyr Pro Asn Ala Gly Leu
        515                 520                 525

Ile Met Asn Tyr Cys Arg Asn Pro Asp Ala Val Ala Ala Pro Tyr Cys
530                 535                 540

Tyr Thr Arg Asp Pro Gly Val Arg Trp Glu Tyr Cys Asn Leu Thr Gln
545                 550                 555                 560

Cys Ser Asp Ala Glu Gly Thr Ala Val Ala Pro Pro Thr Val Thr Pro
                565                 570                 575

Val Pro Ser Leu Glu Ala Pro Ser Glu Gln Ala Pro Thr Glu Gln Arg
            580                 585                 590

Pro Gly Val Gln Glu Cys Tyr His Gly Asn Gly Gln Ser Tyr Arg Gly
        595                 600                 605

Thr Tyr Ser Thr Thr Val Thr Gly Arg Thr Cys Gln Ala Trp Ser Ser
            610                 615                 620

Met Thr Pro His Ser His Ser Arg Thr Pro Glu Tyr Tyr Pro Asn Ala
625                 630                 635                 640

Gly Leu Ile Met Asn Tyr Cys Arg Asn Pro Asp Ala Val Ala Ala Pro
```

```
                645                 650                 655
Tyr Cys Tyr Thr Arg Asp Pro Gly Val Arg Trp Glu Tyr Cys Asn Leu
            660                 665                 670

Thr Gln Cys Ser Asp Ala Glu Gly Thr Ala Val Ala Pro Pro Thr Val
            675                 680                 685

Thr Pro Val Pro Ser Leu Glu Ala Pro Ser Glu Gln Ala Pro Thr Glu
690                 695                 700

Gln Arg Pro Gly Val Gln Glu Cys Tyr His Gly Asn Gly Gln Ser Tyr
705                 710                 715                 720

Arg Gly Thr Tyr Ser Thr Thr Val Thr Gly Arg Thr Cys Gln Ala Trp
                725                 730                 735

Ser Ser Met Thr Pro His Ser His Ser Arg Thr Pro Glu Tyr Tyr Pro
            740                 745                 750

Asn Ala Gly Leu Ile Met Asn Tyr Cys Arg Asn Pro Asp Ala Val Ala
            755                 760                 765

Ala Pro Tyr Cys Tyr Thr Arg Asp Pro Gly Val Arg Trp Glu Tyr Cys
            770                 775                 780

Asn Leu Thr Gln Cys Ser Asp Ala Glu Gly Thr Ala Val Ala Pro Pro
785                 790                 795                 800

Thr Val Thr Pro Val Pro Ser Leu Glu Ala Pro Ser Glu Gln Ala Pro
                805                 810                 815

Thr Glu Gln Arg Pro Gly Val Gln Glu Cys Tyr His Gly Asn Gly Gln
            820                 825                 830

Ser Tyr Arg Gly Thr Tyr Ser Thr Thr Val Thr Gly Arg Thr Cys Gln
            835                 840                 845

Ala Trp Ser Ser Met Thr Pro His Ser His Ser Arg Thr Pro Glu Tyr
            850                 855                 860

Tyr Pro Asn Ala Gly Leu Ile Met Asn Tyr Cys Arg Asn Pro Asp Ala
865                 870                 875                 880

Val Ala Ala Pro Tyr Cys Tyr Thr Arg Asp Pro Gly Val Arg Trp Glu
                885                 890                 895

Tyr Cys Asn Leu Thr Gln Cys Ser Asp Ala Glu Gly Thr Ala Val Ala
            900                 905                 910

Pro Pro Thr Val Thr Pro Val Pro Ser Leu Glu Ala Pro Ser Glu Gln
            915                 920                 925

Ala Pro Thr Glu Gln Arg Pro Gly Val Gln Glu Cys Tyr His Gly Asn
            930                 935                 940

Gly Gln Ser Tyr Arg Gly Thr Tyr Ser Thr Thr Val Thr Gly Arg Thr
945                 950                 955                 960

Cys Gln Ala Trp Ser Ser Met Thr Pro His Ser His Ser Arg Thr Pro
                965                 970                 975

Glu Tyr Tyr Pro Asn Ala Gly Leu Ile Met Asn Tyr Cys Arg Asn Pro
            980                 985                 990

Asp Ala Val Ala Ala Pro Tyr Cys Tyr Thr Arg Asp Pro Gly Val Arg
            995                 1000                1005

Trp Glu Tyr Cys Asn Leu Thr Gln Cys Ser Asp Ala Glu Gly Thr
        1010                1015                1020

Ala Val Ala Pro Pro Thr Val Thr Pro Val Pro Ser Leu Glu Ala
        1025                1030                1035

Pro Ser Glu Gln Ala Pro Thr Glu Gln Arg Pro Gly Val Gln Glu
        1040                1045                1050

Cys Tyr His Gly Asn Gly Gln Ser Tyr Arg Gly Thr Tyr Ser Thr
        1055                1060                1065
```

-continued

```
Thr Val Thr Gly Arg Thr Cys Gln Ala Trp Ser Ser Met Thr Pro
    1070            1075                1080

His Ser His Ser Arg Thr Pro Glu Tyr Tyr Pro Asn Ala Gly Leu
    1085            1090                1095

Ile Met Asn Tyr Cys Arg Asn Pro Asp Ala Val Ala Ala Pro Tyr
    1100            1105                1110

Cys Tyr Thr Arg Asp Pro Gly Val Arg Trp Glu Tyr Cys Asn Leu
    1115            1120                1125

Thr Gln Cys Ser Asp Ala Glu Gly Thr Ala Val Ala Pro Pro Thr
    1130            1135                1140

Val Thr Pro Val Pro Ser Leu Glu Ala Pro Ser Glu Gln Ala Pro
    1145            1150                1155

Thr Glu Gln Arg Pro Gly Val Gln Glu Cys Tyr His Gly Asn Gly
    1160            1165                1170

Gln Ser Tyr Arg Gly Thr Tyr Ser Thr Thr Val Thr Gly Arg Thr
    1175            1180                1185

Cys Gln Ala Trp Ser Ser Met Thr Pro His Ser His Ser Arg Thr
    1190            1195                1200

Pro Glu Tyr Tyr Pro Asn Ala Gly Leu Ile Met Asn Tyr Cys Arg
    1205            1210                1215

Asn Pro Asp Ala Val Ala Ala Pro Tyr Cys Tyr Thr Arg Asp Pro
    1220            1225                1230

Gly Val Arg Trp Glu Tyr Cys Asn Leu Thr Gln Cys Ser Asp Ala
    1235            1240                1245

Glu Gly Thr Ala Val Ala Pro Pro Thr Val Thr Pro Val Pro Ser
    1250            1255                1260

Leu Glu Ala Pro Ser Glu Gln Ala Pro Thr Glu Gln Arg Pro Gly
    1265            1270                1275

Val Gln Glu Cys Tyr His Gly Asn Gly Gln Ser Tyr Arg Gly Thr
    1280            1285                1290

Tyr Ser Thr Thr Val Thr Gly Arg Thr Cys Gln Ala Trp Ser Ser
    1295            1300                1305

Met Thr Pro His Ser His Ser Arg Thr Pro Glu Tyr Tyr Pro Asn
    1310            1315                1320

Ala Gly Leu Ile Met Asn Tyr Cys Arg Asn Pro Asp Ala Val Ala
    1325            1330                1335

Ala Pro Tyr Cys Tyr Thr Arg Asp Pro Gly Val Arg Trp Glu Tyr
    1340            1345                1350

Cys Asn Leu Thr Gln Cys Ser Asp Ala Glu Gly Thr Ala Val Ala
    1355            1360                1365

Pro Pro Thr Val Thr Pro Val Pro Ser Leu Glu Ala Pro Ser Glu
    1370            1375                1380

Gln Ala Pro Thr Glu Gln Arg Pro Gly Val Gln Glu Cys Tyr His
    1385            1390                1395

Gly Asn Gly Gln Ser Tyr Arg Gly Thr Tyr Ser Thr Thr Val Thr
    1400            1405                1410

Gly Arg Thr Cys Gln Ala Trp Ser Ser Met Thr Pro His Ser His
    1415            1420                1425

Ser Arg Thr Pro Glu Tyr Tyr Pro Asn Ala Gly Leu Ile Met Asn
    1430            1435                1440

Tyr Cys Arg Asn Pro Asp Ala Val Ala Ala Pro Tyr Cys Tyr Thr
    1445            1450                1455
```

-continued

```
Arg Asp Pro Gly Val Arg Trp Glu Tyr Cys Asn Leu Thr Gln Cys
    1460                1465                1470

Ser Asp Ala Glu Gly Thr Ala Val Ala Pro Pro Thr Val Thr Pro
    1475                1480                1485

Val Pro Ser Leu Glu Ala Pro Ser Glu Gln Ala Pro Thr Glu Gln
    1490                1495                1500

Arg Pro Gly Val Gln Glu Cys Tyr His Gly Asn Gly Gln Ser Tyr
    1505                1510                1515

Arg Gly Thr Tyr Ser Thr Thr Val Thr Gly Arg Thr Cys Gln Ala
    1520                1525                1530

Trp Ser Ser Met Thr Pro His Ser His Ser Arg Thr Pro Glu Tyr
    1535                1540                1545

Tyr Pro Asn Ala Gly Leu Ile Met Asn Tyr Cys Arg Asn Pro Asp
    1550                1555                1560

Ala Val Ala Ala Pro Tyr Cys Tyr Thr Arg Asp Pro Gly Val Arg
    1565                1570                1575

Trp Glu Tyr Cys Asn Leu Thr Gln Cys Ser Asp Ala Glu Gly Thr
    1580                1585                1590

Ala Val Ala Pro Pro Thr Val Thr Pro Val Pro Ser Leu Glu Ala
    1595                1600                1605

Pro Ser Glu Gln Ala Pro Thr Glu Gln Arg Pro Gly Val Gln Glu
    1610                1615                1620

Cys Tyr His Gly Asn Gly Gln Ser Tyr Arg Gly Thr Tyr Ser Thr
    1625                1630                1635

Thr Val Thr Gly Arg Thr Cys Gln Ala Trp Ser Ser Met Thr Pro
    1640                1645                1650

His Ser His Ser Arg Thr Pro Glu Tyr Tyr Pro Asn Ala Gly Leu
    1655                1660                1665

Ile Met Asn Tyr Cys Arg Asn Pro Asp Ala Val Ala Ala Pro Tyr
    1670                1675                1680

Cys Tyr Thr Arg Asp Pro Gly Val Arg Trp Glu Tyr Cys Asn Leu
    1685                1690                1695

Thr Gln Cys Ser Asp Ala Glu Gly Thr Ala Val Ala Pro Pro Thr
    1700                1705                1710

Val Thr Pro Val Pro Ser Leu Glu Ala Pro Ser Glu Gln Ala Pro
    1715                1720                1725

Thr Glu Gln Arg Pro Gly Val Gln Glu Cys Tyr His Gly Asn Gly
    1730                1735                1740

Gln Ser Tyr Arg Gly Thr Tyr Ser Thr Thr Val Thr Gly Arg Thr
    1745                1750                1755

Cys Gln Ala Trp Ser Ser Met Thr Pro His Ser His Ser Arg Thr
    1760                1765                1770

Pro Glu Tyr Tyr Pro Asn Ala Gly Leu Ile Met Asn Tyr Cys Arg
    1775                1780                1785

Asn Pro Asp Ala Val Ala Ala Pro Tyr Cys Tyr Thr Arg Asp Pro
    1790                1795                1800

Gly Val Arg Trp Glu Tyr Cys Asn Leu Thr Gln Cys Ser Asp Ala
    1805                1810                1815

Glu Gly Thr Ala Val Ala Pro Pro Thr Val Thr Pro Val Pro Ser
    1820                1825                1830

Leu Glu Ala Pro Ser Glu Gln Ala Pro Thr Glu Gln Arg Pro Gly
    1835                1840                1845

Val Gln Glu Cys Tyr His Gly Asn Gly Gln Ser Tyr Arg Gly Thr
```

-continued

```
            1850                1855                1860

Tyr Ser Thr Thr Val Thr Gly Arg Thr Cys Gln Ala Trp Ser Ser
        1865                1870                1875

Met Thr Pro His Ser His Ser Arg Thr Pro Glu Tyr Tyr Pro Asn
        1880                1885                1890

Ala Gly Leu Ile Met Asn Tyr Cys Arg Asn Pro Asp Ala Val Ala
        1895                1900                1905

Ala Pro Tyr Cys Tyr Thr Arg Asp Pro Gly Val Arg Trp Glu Tyr
        1910                1915                1920

Cys Asn Leu Thr Gln Cys Ser Asp Ala Glu Gly Thr Ala Val Ala
        1925                1930                1935

Pro Pro Thr Val Thr Pro Val Pro Ser Leu Glu Ala Pro Ser Glu
        1940                1945                1950

Gln Ala Pro Thr Glu Gln Arg Pro Gly Val Gln Glu Cys Tyr His
        1955                1960                1965

Gly Asn Gly Gln Ser Tyr Arg Gly Thr Tyr Ser Thr Thr Val Thr
        1970                1975                1980

Gly Arg Thr Cys Gln Ala Trp Ser Ser Met Thr Pro His Ser His
        1985                1990                1995

Ser Arg Thr Pro Glu Tyr Tyr Pro Asn Ala Gly Leu Ile Met Asn
        2000                2005                2010

Tyr Cys Arg Asn Pro Asp Ala Val Ala Ala Pro Tyr Cys Tyr Thr
        2015                2020                2025

Arg Asp Pro Gly Val Arg Trp Glu Tyr Cys Asn Leu Thr Gln Cys
        2030                2035                2040

Ser Asp Ala Glu Gly Thr Ala Val Ala Pro Pro Thr Val Thr Pro
        2045                2050                2055

Val Pro Ser Leu Glu Ala Pro Ser Glu Gln Ala Pro Thr Glu Gln
        2060                2065                2070

Arg Pro Gly Val Gln Glu Cys Tyr His Gly Asn Gly Gln Ser Tyr
        2075                2080                2085

Arg Gly Thr Tyr Ser Thr Thr Val Thr Gly Arg Thr Cys Gln Ala
        2090                2095                2100

Trp Ser Ser Met Thr Pro His Ser His Ser Arg Thr Pro Glu Tyr
        2105                2110                2115

Tyr Pro Asn Ala Gly Leu Ile Met Asn Tyr Cys Arg Asn Pro Asp
        2120                2125                2130

Ala Val Ala Ala Pro Tyr Cys Tyr Thr Arg Asp Pro Gly Val Arg
        2135                2140                2145

Trp Glu Tyr Cys Asn Leu Thr Gln Cys Ser Asp Ala Glu Gly Thr
        2150                2155                2160

Ala Val Ala Pro Pro Thr Val Thr Pro Val Pro Ser Leu Glu Ala
        2165                2170                2175

Pro Ser Glu Gln Ala Pro Thr Glu Gln Arg Pro Gly Val Gln Glu
        2180                2185                2190

Cys Tyr His Gly Asn Gly Gln Ser Tyr Arg Gly Thr Tyr Ser Thr
        2195                2200                2205

Thr Val Thr Gly Arg Thr Cys Gln Ala Trp Ser Ser Met Thr Pro
        2210                2215                2220

His Ser His Ser Arg Thr Pro Glu Tyr Tyr Pro Asn Ala Gly Leu
        2225                2230                2235

Ile Met Asn Tyr Cys Arg Asn Pro Asp Ala Val Ala Ala Pro Tyr
        2240                2245                2250
```

```
Cys Tyr Thr Arg Asp Pro Gly Val Arg Trp Glu Tyr Cys Asn Leu
        2255                2260                2265

Thr Gln Cys Ser Asp Ala Glu Gly Thr Ala Val Ala Pro Pro Thr
    2270                2275                2280

Val Thr Pro Val Pro Ser Leu Glu Ala Pro Ser Glu Gln Ala Pro
    2285                2290                2295

Thr Glu Gln Arg Pro Gly Val Gln Glu Cys Tyr His Gly Asn Gly
    2300                2305                2310

Gln Ser Tyr Arg Gly Thr Tyr Ser Thr Val Thr Gly Arg Thr
    2315                2320                2325

Cys Gln Ala Trp Ser Ser Met Thr Pro His Ser His Ser Arg Thr
    2330                2335                2340

Pro Glu Tyr Tyr Pro Asn Ala Gly Leu Ile Met Asn Tyr Cys Arg
    2345                2350                2355

Asn Pro Asp Ala Val Ala Ala Pro Tyr Cys Tyr Thr Arg Asp Pro
    2360                2365                2370

Gly Val Arg Trp Glu Tyr Cys Asn Leu Thr Gln Cys Ser Asp Ala
    2375                2380                2385

Glu Gly Thr Ala Val Ala Pro Pro Thr Val Thr Pro Val Pro Ser
    2390                2395                2400

Leu Glu Ala Pro Ser Glu Gln Ala Pro Thr Glu Gln Arg Pro Gly
    2405                2410                2415

Val Gln Glu Cys Tyr His Gly Asn Gly Gln Ser Tyr Arg Gly Thr
    2420                2425                2430

Tyr Ser Thr Thr Val Thr Gly Arg Thr Cys Gln Ala Trp Ser Ser
    2435                2440                2445

Met Thr Pro His Ser His Ser Arg Thr Pro Glu Tyr Tyr Pro Asn
    2450                2455                2460

Ala Gly Leu Ile Met Asn Tyr Cys Arg Asn Pro Asp Ala Val Ala
    2465                2470                2475

Ala Pro Tyr Cys Tyr Thr Arg Asp Pro Gly Val Arg Trp Glu Tyr
    2480                2485                2490

Cys Asn Leu Thr Gln Cys Ser Asp Ala Glu Gly Thr Ala Val Ala
    2495                2500                2505

Pro Pro Thr Val Thr Pro Val Pro Ser Leu Glu Ala Pro Ser Glu
    2510                2515                2520

Gln Ala Pro Thr Glu Gln Arg Pro Gly Val Gln Glu Cys Tyr His
    2525                2530                2535

Gly Asn Gly Gln Ser Tyr Arg Gly Thr Tyr Ser Thr Thr Val Thr
    2540                2545                2550

Gly Arg Thr Cys Gln Ala Trp Ser Ser Met Thr Pro His Ser His
    2555                2560                2565

Ser Arg Thr Pro Glu Tyr Tyr Pro Asn Ala Gly Leu Ile Met Asn
    2570                2575                2580

Tyr Cys Arg Asn Pro Asp Ala Val Ala Ala Pro Tyr Cys Tyr Thr
    2585                2590                2595

Arg Asp Pro Gly Val Arg Trp Glu Tyr Cys Asn Leu Thr Gln Cys
    2600                2605                2610

Ser Asp Ala Glu Gly Thr Ala Val Ala Pro Pro Thr Val Thr Pro
    2615                2620                2625

Val Pro Ser Leu Glu Ala Pro Ser Glu Gln Ala Pro Thr Glu Gln
    2630                2635                2640
```

-continued

```
Arg Pro Gly Val Gln Glu Cys Tyr His Gly Asn Gly Gln Ser Tyr
    2645                2650                2655

Arg Gly Thr Tyr Ser Thr Thr Val Thr Gly Arg Thr Cys Gln Ala
    2660                2665                2670

Trp Ser Ser Met Thr Pro His Ser His Ser Arg Thr Pro Glu Tyr
    2675                2680                2685

Tyr Pro Asn Ala Gly Leu Ile Met Asn Tyr Cys Arg Asn Pro Asp
    2690                2695                2700

Ala Val Ala Ala Pro Tyr Cys Tyr Thr Arg Asp Pro Gly Val Arg
    2705                2710                2715

Trp Glu Tyr Cys Asn Leu Thr Gln Cys Ser Asp Ala Glu Gly Thr
    2720                2725                2730

Ala Val Ala Pro Pro Thr Val Thr Pro Val Pro Ser Leu Glu Ala
    2735                2740                2745

Pro Ser Glu Gln Ala Pro Thr Glu Gln Arg Pro Gly Val Gln Glu
    2750                2755                2760

Cys Tyr His Gly Asn Gly Gln Ser Tyr Arg Gly Thr Tyr Ser Thr
    2765                2770                2775

Thr Val Thr Gly Arg Thr Cys Gln Ala Trp Ser Ser Met Thr Pro
    2780                2785                2790

His Ser His Ser Arg Thr Pro Glu Tyr Tyr Pro Asn Ala Gly Leu
    2795                2800                2805

Ile Met Asn Tyr Cys Arg Asn Pro Asp Ala Val Ala Ala Pro Tyr
    2810                2815                2820

Cys Tyr Thr Arg Asp Pro Gly Val Arg Trp Glu Tyr Cys Asn Leu
    2825                2830                2835

Thr Gln Cys Ser Asp Ala Glu Gly Thr Ala Val Ala Pro Pro Thr
    2840                2845                2850

Val Thr Pro Val Pro Ser Leu Glu Ala Pro Ser Glu Gln Ala Pro
    2855                2860                2865

Thr Glu Gln Arg Pro Gly Val Gln Glu Cys Tyr His Gly Asn Gly
    2870                2875                2880

Gln Ser Tyr Arg Gly Thr Tyr Ser Thr Thr Val Thr Gly Arg Thr
    2885                2890                2895

Cys Gln Ala Trp Ser Ser Met Thr Pro His Ser His Ser Arg Thr
    2900                2905                2910

Pro Glu Tyr Tyr Pro Asn Ala Gly Leu Ile Met Asn Tyr Cys Arg
    2915                2920                2925

Asn Pro Asp Ala Val Ala Ala Pro Tyr Cys Tyr Thr Arg Asp Pro
    2930                2935                2940

Gly Val Arg Trp Glu Tyr Cys Asn Leu Thr Gln Cys Ser Asp Ala
    2945                2950                2955

Glu Gly Thr Ala Val Ala Pro Pro Thr Val Thr Pro Val Pro Ser
    2960                2965                2970

Leu Glu Ala Pro Ser Glu Gln Ala Pro Thr Glu Gln Arg Pro Gly
    2975                2980                2985

Val Gln Glu Cys Tyr His Gly Asn Gly Gln Ser Tyr Arg Gly Thr
    2990                2995                3000

Tyr Ser Thr Thr Val Thr Gly Arg Thr Cys Gln Ala Trp Ser Ser
    3005                3010                3015

Met Thr Pro His Ser His Ser Arg Thr Pro Glu Tyr Tyr Pro Asn
    3020                3025                3030

Ala Gly Leu Ile Met Asn Tyr Cys Arg Asn Pro Asp Ala Val Ala
```

```
                  3035              3040              3045
Ala Pro Tyr Cys Tyr Thr Arg Asp Pro Gly Val Arg Trp Glu Tyr
    3050              3055              3060
Cys Asn Leu Thr Gln Cys Ser Asp Ala Glu Gly Thr Ala Val Ala
    3065              3070              3075
Pro Pro Thr Val Thr Pro Val Pro Ser Leu Glu Ala Pro Ser Glu
    3080              3085              3090
Gln Ala Pro Thr Glu Gln Arg Pro Gly Val Gln Glu Cys Tyr His
    3095              3100              3105
Gly Asn Gly Gln Ser Tyr Arg Gly Thr Tyr Ser Thr Thr Val Thr
    3110              3115              3120
Gly Arg Thr Cys Gln Ala Trp Ser Ser Met Thr Pro His Ser His
    3125              3130              3135
Ser Arg Thr Pro Glu Tyr Tyr Pro Asn Ala Gly Leu Ile Met Asn
    3140              3145              3150
Tyr Cys Arg Asn Pro Asp Ala Val Ala Ala Pro Tyr Cys Tyr Thr
    3155              3160              3165
Arg Asp Pro Gly Val Arg Trp Glu Tyr Cys Asn Leu Thr Gln Cys
    3170              3175              3180
Ser Asp Ala Glu Gly Thr Ala Val Ala Pro Pro Thr Val Thr Pro
    3185              3190              3195
Val Pro Ser Leu Glu Ala Pro Ser Glu Gln Ala Pro Thr Glu Gln
    3200              3205              3210
Arg Pro Gly Val Gln Glu Cys Tyr His Gly Asn Gly Gln Ser Tyr
    3215              3220              3225
Arg Gly Thr Tyr Ser Thr Thr Val Thr Gly Arg Thr Cys Gln Ala
    3230              3235              3240
Trp Ser Ser Met Thr Pro His Ser His Ser Arg Thr Pro Glu Tyr
    3245              3250              3255
Tyr Pro Asn Ala Gly Leu Ile Met Asn Tyr Cys Arg Asn Pro Asp
    3260              3265              3270
Ala Val Ala Ala Pro Tyr Cys Tyr Thr Arg Asp Pro Gly Val Arg
    3275              3280              3285
Trp Glu Tyr Cys Asn Leu Thr Gln Cys Ser Asp Ala Glu Gly Thr
    3290              3295              3300
Ala Val Ala Pro Pro Thr Val Thr Pro Val Pro Ser Leu Glu Ala
    3305              3310              3315
Pro Ser Glu Gln Ala Pro Thr Glu Gln Arg Pro Gly Val Gln Glu
    3320              3325              3330
Cys Tyr His Gly Asn Gly Gln Ser Tyr Arg Gly Thr Tyr Ser Thr
    3335              3340              3345
Thr Val Thr Gly Arg Thr Cys Gln Ala Trp Ser Ser Met Thr Pro
    3350              3355              3360
His Ser His Ser Arg Thr Pro Glu Tyr Tyr Pro Asn Ala Gly Leu
    3365              3370              3375
Ile Met Asn Tyr Cys Arg Asn Pro Asp Pro Val Ala Ala Pro Tyr
    3380              3385              3390
Cys Tyr Thr Arg Asp Pro Ser Val Arg Trp Glu Tyr Cys Asn Leu
    3395              3400              3405
Thr Gln Cys Ser Asp Ala Glu Gly Thr Ala Val Ala Pro Pro Thr
    3410              3415              3420
Ile Thr Pro Ile Pro Ser Leu Glu Ala Pro Ser Glu Gln Ala Pro
    3425              3430              3435
```

-continued

```
Thr Glu Gln Arg Pro Gly Val Gln Glu Cys Tyr His Gly Asn Gly
    3440                3445                3450

Gln Ser Tyr Gln Gly Thr Tyr Phe Ile Thr Val Thr Gly Arg Thr
    3455                3460                3465

Cys Gln Ala Trp Ser Ser Met Thr Pro His Ser His Ser Arg Thr
    3470                3475                3480

Pro Ala Tyr Tyr Pro Asn Ala Gly Leu Ile Lys Asn Tyr Cys Arg
    3485                3490                3495

Asn Pro Asp Pro Val Ala Ala Pro Trp Cys Tyr Thr Thr Asp Pro
    3500                3505                3510

Ser Val Arg Trp Glu Tyr Cys Asn Leu Thr Arg Cys Ser Asp Ala
    3515                3520                3525

Glu Trp Thr Ala Phe Val Pro Pro Asn Val Ile Leu Ala Pro Ser
    3530                3535                3540

Leu Glu Ala Phe Phe Glu Gln Ala Leu Thr Glu Glu Thr Pro Gly
    3545                3550                3555

Val Gln Asp Cys Tyr Tyr His Tyr Gly Gln Ser Tyr Arg Gly Thr
    3560                3565                3570

Tyr Ser Thr Thr Val Thr Gly Arg Thr Cys Gln Ala Trp Ser Ser
    3575                3580                3585

Met Thr Pro His Gln His Ser Arg Thr Pro Glu Asn Tyr Pro Asn
    3590                3595                3600

Ala Gly Leu Thr Arg Asn Tyr Cys Arg Asn Pro Asp Ala Glu Ile
    3605                3610                3615

Arg Pro Trp Cys Tyr Thr Met Asp Pro Ser Val Arg Trp Glu Tyr
    3620                3625                3630

Cys Asn Leu Thr Gln Cys Leu Val Thr Glu Ser Ser Val Leu Ala
    3635                3640                3645

Thr Leu Thr Val Val Pro Asp Pro Ser Thr Glu Ala Ser Ser Glu
    3650                3655                3660

Glu Ala Pro Thr Glu Gln Ser Pro Gly Val Gln Asp Cys Tyr His
    3665                3670                3675

Gly Asp Gly Gln Ser Tyr Arg Gly Ser Phe Ser Thr Thr Val Thr
    3680                3685                3690

Gly Arg Thr Cys Gln Ser Trp Ser Ser Met Thr Pro His Trp His
    3695                3700                3705

Gln Arg Thr Thr Glu Tyr Tyr Pro Asn Gly Gly Leu Thr Arg Asn
    3710                3715                3720

Tyr Cys Arg Asn Pro Asp Ala Glu Ile Ser Pro Trp Cys Tyr Thr
    3725                3730                3735

Met Asp Pro Asn Val Arg Trp Glu Tyr Cys Asn Leu Thr Gln Cys
    3740                3745                3750

Pro Val Thr Glu Ser Ser Val Leu Ala Thr Ser Thr Ala Val Ser
    3755                3760                3765

Glu Gln Ala Pro Thr Glu Gln Ser Pro Thr Val Gln Asp Cys Tyr
    3770                3775                3780

His Gly Asp Gly Gln Ser Tyr Arg Gly Ser Phe Ser Thr Thr Val
    3785                3790                3795

Thr Gly Arg Thr Cys Gln Ser Trp Ser Ser Met Thr Pro His Trp
    3800                3805                3810

His Gln Arg Thr Thr Glu Tyr Tyr Pro Asn Gly Gly Leu Thr Arg
    3815                3820                3825
```

-continued

| | | | | | | | | | | | |
|---|---|---|---|---|---|---|---|---|---|---|---|
|Asn|Tyr|Cys|Arg|Asn|Pro|Asp|Ala|Glu|Ile|Arg|Pro|Trp|Cys|Tyr|
| 3830 | | | | 3835 | | | | 3840 | | | |

Asn Tyr Cys Arg Asn Pro Asp Ala Glu Ile Arg Pro Trp Cys Tyr
3830           3835           3840

Thr Met Asp Pro Ser Val Arg Trp Glu Tyr Cys Asn Leu Thr Gln
3845           3850           3855

Cys Pro Val Met Glu Ser Thr Leu Leu Thr Thr Pro Thr Val Val
3860           3865           3870

Pro Val Pro Ser Thr Glu Leu Pro Ser Glu Glu Ala Pro Thr Glu
3875           3880           3885

Asn Ser Thr Gly Val Gln Asp Cys Tyr Arg Gly Asp Gly Gln Ser
3890           3895           3900

Tyr Arg Gly Thr Leu Ser Thr Thr Ile Thr Gly Arg Thr Cys Gln
3905           3910           3915

Ser Trp Ser Ser Met Thr Pro His Trp His Arg Arg Ile Pro Leu
3920           3925           3930

Tyr Tyr Pro Asn Ala Gly Leu Thr Arg Asn Tyr Cys Arg Asn Pro
3935           3940           3945

Asp Ala Glu Ile Arg Pro Trp Cys Tyr Thr Met Asp Pro Ser Val
3950           3955           3960

Arg Trp Glu Tyr Cys Asn Leu Thr Arg Cys Pro Val Thr Glu Ser
3965           3970           3975

Ser Val Leu Thr Thr Pro Thr Val Ala Pro Val Pro Ser Thr Glu
3980           3985           3990

Ala Pro Ser Glu Gln Ala Pro Pro Glu Lys Ser Pro Val Val Gln
3995           4000           4005

Asp Cys Tyr His Gly Asp Gly Arg Ser Tyr Arg Gly Ile Ser Ser
4010           4015           4020

Thr Thr Val Thr Gly Arg Thr Cys Gln Ser Trp Ser Ser Met Ile
4025           4030           4035

Pro His Trp His Gln Arg Thr Pro Glu Asn Tyr Pro Asn Ala Gly
4040           4045           4050

Leu Thr Glu Asn Tyr Cys Arg Asn Pro Asp Ser Gly Lys Gln Pro
4055           4060           4065

Trp Cys Tyr Thr Thr Asp Pro Cys Val Arg Trp Glu Tyr Cys Asn
4070           4075           4080

Leu Thr Gln Cys Ser Glu Thr Glu Ser Gly Val Leu Glu Thr Pro
4085           4090           4095

Thr Val Val Pro Val Pro Ser Met Glu Ala His Ser Glu Ala Ala
4100           4105           4110

Pro Thr Glu Gln Thr Pro Val Val Arg Gln Cys Tyr His Gly Asn
4115           4120           4125

Gly Gln Ser Tyr Arg Gly Thr Phe Ser Thr Thr Val Thr Gly Arg
4130           4135           4140

Thr Cys Gln Ser Trp Ser Ser Met Thr Pro His Arg His Gln Arg
4145           4150           4155

Thr Pro Glu Asn Tyr Pro Asn Asp Gly Leu Thr Met Asn Tyr Cys
4160           4165           4170

Arg Asn Pro Asp Ala Asp Thr Gly Pro Trp Cys Phe Thr Met Asp
4175           4180           4185

Pro Ser Ile Arg Trp Glu Tyr Cys Asn Leu Thr Arg Cys Ser Asp
4190           4195           4200

Thr Glu Gly Thr Val Val Ala Pro Pro Thr Val Ile Gln Val Pro
4205           4210           4215

Ser Leu Gly Pro Pro Ser Glu Gln Asp Cys Met Phe Gly Asn Gly

```
            4220                4225                4230

Lys Gly Tyr Arg Gly Lys Lys Ala Thr Thr Val Thr Gly Thr Pro
            4235                4240                4245

Cys Gln Glu Trp Ala Ala Gln Glu Pro His Arg His Ser Thr Phe
            4250                4255                4260

Ile Pro Gly Thr Asn Lys Trp Ala Gly Leu Glu Lys Asn Tyr Cys
            4265                4270                4275

Arg Asn Pro Asp Gly Asp Ile Asn Gly Pro Trp Cys Tyr Thr Met
            4280                4285                4290

Asn Pro Arg Lys Leu Phe Asp Tyr Cys Asp Ile Pro Leu Cys Ala
            4295                4300                4305

Ser Ser Ser Phe Asp Cys Gly Lys Pro Gln Val Glu Pro Lys Lys
            4310                4315                4320

Cys Pro Gly Ser Ile Val Gly Gly Cys Val Ala His Pro His Ser
            4325                4330                4335

Trp Pro Trp Gln Val Ser Leu Arg Thr Arg Phe Gly Lys His Phe
            4340                4345                4350

Cys Gly Gly Thr Leu Ile Ser Pro Glu Trp Val Leu Thr Ala Ala
            4355                4360                4365

His Cys Leu Lys Lys Ser Ser Arg Pro Ser Ser Tyr Lys Val Ile
            4370                4375                4380

Leu Gly Ala His Gln Glu Val Asn Leu Glu Ser His Val Gln Glu
            4385                4390                4395

Ile Glu Val Ser Arg Leu Phe Leu Glu Pro Thr Gln Ala Asp Ile
            4400                4405                4410

Ala Leu Leu Lys Leu Ser Arg Pro Ala Val Ile Thr Asp Lys Val
            4415                4420                4425

Met Pro Ala Cys Leu Pro Ser Pro Asp Tyr Met Val Thr Ala Arg
            4430                4435                4440

Thr Glu Cys Tyr Ile Thr Gly Trp Gly Glu Thr Gln Gly Thr Phe
            4445                4450                4455

Gly Thr Gly Leu Leu Lys Glu Ala Gln Leu Leu Val Ile Glu Asn
            4460                4465                4470

Glu Val Cys Asn His Tyr Lys Tyr Ile Cys Ala Glu His Leu Ala
            4475                4480                4485

Arg Gly Thr Asp Ser Cys Gln Gly Asp Ser Gly Gly Pro Leu Val
            4490                4495                4500

Cys Phe Glu Lys Asp Lys Tyr Ile Leu Gln Gly Val Thr Ser Trp
            4505                4510                4515

Gly Leu Gly Cys Ala Arg Pro Asn Lys Pro Gly Val Tyr Ala Arg
            4520                4525                4530

Val Ser Arg Phe Val Thr Trp Ile Glu Gly Met Met Arg Asn Asn
            4535                4540                4545

<210> SEQ ID NO 57
<211> LENGTH: 184
<212> TYPE: PRT
<213> ORGANISM: Homo sapiens

<400> SEQUENCE: 57

Met Ala Glu Pro Gln Pro Pro Ser Gly Gly Leu Thr Asp Glu Ala Ala
1               5                   10                  15

Leu Ser Cys Cys Ser Asp Ala Asp Pro Ser Thr Lys Asp Phe Leu Leu
                20                  25                  30
```

```
Gln Gln Thr Met Leu Arg Val Lys Asp Pro Lys Lys Ser Leu Asp Phe
            35                  40                  45

Tyr Thr Arg Val Leu Gly Met Thr Leu Ile Gln Lys Cys Asp Phe Pro
 50                  55                  60

Ile Met Lys Phe Ser Leu Tyr Phe Leu Ala Tyr Glu Asp Lys Asn Asp
 65                  70                  75                  80

Ile Pro Lys Glu Lys Asp Glu Lys Ile Ala Trp Ala Leu Ser Arg Lys
                85                  90                  95

Ala Thr Leu Glu Leu Thr His Asn Trp Gly Thr Glu Asp Glu Thr
            100                 105                 110

Gln Ser Tyr His Asn Gly Asn Ser Asp Pro Arg Gly Phe Gly His Ile
            115                 120                 125

Gly Ile Ala Val Pro Asp Val Tyr Ser Ala Cys Lys Arg Phe Glu Glu
            130                 135                 140

Leu Gly Val Lys Phe Val Lys Lys Pro Asp Asp Gly Lys Met Lys Gly
145                 150                 155                 160

Leu Ala Phe Ile Gln Asp Pro Asp Gly Tyr Trp Ile Glu Ile Leu Asn
                165                 170                 175

Pro Asn Lys Met Ala Thr Leu Met
            180

<210> SEQ ID NO 58
<211> LENGTH: 1824
<212> TYPE: PRT
<213> ORGANISM: Homo sapiens

<400> SEQUENCE: 58

Met Ser Ala Gly Gly Arg Asp Glu Arg Arg Lys Leu Ala Asp Ile
1               5                   10                  15

Ile His His Trp Asn Ala Asn Arg Leu Asp Leu Phe Glu Ile Ser Gln
            20                  25                  30

Pro Thr Glu Asp Leu Glu Phe His Gly Val Met Arg Phe Tyr Phe Gln
            35                  40                  45

Asp Lys Ala Ala Gly Asn Phe Ala Thr Lys Cys Ile Arg Val Ser Ser
 50                  55                  60

Thr Ala Thr Thr Gln Asp Val Ile Glu Thr Leu Ala Glu Lys Phe Arg
 65                  70                  75                  80

Pro Asp Met Arg Met Leu Ser Ser Pro Lys Tyr Ser Leu Tyr Glu Val
                85                  90                  95

His Val Ser Gly Glu Arg Arg Leu Asp Ile Asp Glu Lys Pro Leu Val
            100                 105                 110

Val Gln Leu Asn Trp Asn Lys Asp Asp Arg Glu Gly Arg Phe Val Leu
            115                 120                 125

Lys Asn Glu Asn Asp Ala Ile Pro Pro Lys Lys Ala Gln Ser Asn Gly
            130                 135                 140

Pro Glu Lys Gln Glu Lys Glu Gly Val Ile Gln Asn Phe Lys Arg Thr
145                 150                 155                 160

Leu Ser Lys Lys Glu Lys Lys Glu Lys Lys Arg Glu Lys Glu Ala
                165                 170                 175

Leu Arg Gln Ala Ser Asp Lys Asp Arg Pro Phe Gln Gly Glu Asp
            180                 185                 190

Val Glu Asn Ser Arg Leu Ala Ala Glu Val Tyr Lys Asp Met Pro Glu
            195                 200                 205

Thr Ser Phe Thr Arg Thr Ile Ser Asn Pro Glu Val Val Met Lys Arg
            210                 215                 220
```

```
Arg Arg Gln Gln Lys Leu Glu Lys Arg Met Gln Glu Phe Arg Ser Ser
225                 230                 235                 240

Asp Gly Arg Pro Asp Ser Gly Gly Thr Leu Arg Ile Tyr Ala Asp Ser
            245                 250                 255

Leu Lys Pro Asn Ile Pro Tyr Lys Thr Ile Leu Leu Ser Thr Thr Asp
            260                 265                 270

Pro Ala Asp Phe Ala Val Ala Glu Ala Leu Glu Lys Tyr Gly Leu Glu
            275                 280                 285

Lys Glu Asn Pro Lys Asp Tyr Cys Ile Ala Arg Val Met Leu Pro Pro
            290                 295                 300

Gly Ala Gln His Ser Asp Glu Lys Gly Ala Lys Glu Ile Ile Leu Asp
305                 310                 315                 320

Asp Asp Glu Cys Pro Leu Gln Ile Phe Arg Glu Trp Pro Ser Asp Lys
                325                 330                 335

Gly Ile Leu Val Phe Gln Leu Lys Arg Arg Pro Asp His Ile Pro
                340                 345                 350

Lys Lys Thr Lys Lys His Leu Glu Gly Lys Thr Pro Lys Gly Lys Glu
            355                 360                 365

Arg Ala Asp Gly Ser Gly Tyr Gly Ser Thr Leu Pro Pro Glu Lys Leu
370                 375                 380

Pro Tyr Leu Val Glu Leu Ser Pro Gly Arg Arg Asn His Phe Ala Tyr
385                 390                 395                 400

Tyr Asn Tyr His Thr Tyr Glu Asp Gly Ser Asp Ser Arg Asp Lys Pro
                405                 410                 415

Lys Leu Tyr Arg Leu Gln Leu Ser Val Thr Glu Val Gly Thr Glu Lys
                420                 425                 430

Leu Asp Asp Asn Ser Ile Gln Leu Phe Gly Pro Gly Ile Gln Pro His
            435                 440                 445

His Cys Asp Leu Thr Asn Met Asp Gly Val Val Thr Val Thr Pro Arg
450                 455                 460

Ser Met Asp Ala Glu Thr Tyr Val Glu Gly Gln Arg Ile Ser Glu Thr
465                 470                 475                 480

Thr Met Leu Gln Ser Gly Met Lys Val Gln Phe Gly Ala Ser His Val
                485                 490                 495

Phe Lys Phe Val Asp Pro Ser Gln Asp His Ala Leu Ala Lys Arg Ser
            500                 505                 510

Val Asp Gly Gly Leu Met Val Lys Gly Pro Arg His Lys Pro Gly Ile
            515                 520                 525

Val Gln Glu Thr Thr Phe Asp Leu Gly Gly Asp Ile His Ser Gly Thr
            530                 535                 540

Ala Leu Pro Thr Ser Lys Ser Thr Thr Arg Leu Asp Ser Asp Arg Val
545                 550                 555                 560

Ser Ser Ala Ser Ser Thr Ala Glu Arg Gly Met Val Lys Pro Met Ile
                565                 570                 575

Arg Val Glu Gln Gln Pro Asp Tyr Arg Arg Gln Glu Ser Arg Thr Gln
                580                 585                 590

Asp Ala Ser Gly Pro Glu Leu Ile Leu Pro Ala Ser Ile Glu Phe Arg
            595                 600                 605

Glu Ser Ser Glu Asp Ser Phe Leu Ser Ala Ile Ile Asn Tyr Thr Asn
            610                 615                 620

Ser Ser Thr Val His Phe Lys Leu Ser Pro Thr Tyr Val Leu Tyr Met
625                 630                 635                 640
```

```
Ala Cys Arg Tyr Val Leu Ser Asn Gln Tyr Arg Pro Asp Ile Ser Pro
                645                 650                 655

Thr Glu Arg Thr His Lys Val Ile Ala Val Val Asn Lys Met Val Ser
        660                 665                 670

Met Met Glu Gly Val Ile Gln Lys Gln Lys Asn Ile Ala Gly Ala Leu
        675                 680                 685

Ala Phe Trp Met Ala Asn Ala Ser Glu Leu Leu Asn Phe Ile Lys Gln
        690                 695                 700

Asp Arg Asp Leu Ser Arg Ile Thr Leu Asp Ala Gln Asp Val Leu Ala
705                 710                 715                 720

His Leu Val Gln Met Ala Phe Lys Tyr Leu Val His Cys Leu Gln Ser
                725                 730                 735

Glu Leu Asn Asn Tyr Met Pro Ala Phe Leu Asp Asp Pro Glu Glu Asn
                740                 745                 750

Ser Leu Gln Arg Pro Lys Ile Asp Asp Val Leu His Thr Leu Thr Gly
                755                 760                 765

Ala Met Ser Leu Leu Arg Arg Cys Arg Val Asn Ala Ala Leu Thr Ile
        770                 775                 780

Gln Leu Phe Ser Gln Leu Phe His Phe Ile Asn Met Trp Leu Phe Asn
785                 790                 795                 800

Arg Leu Val Thr Asp Pro Asp Ser Gly Leu Cys Ser His Tyr Trp Gly
                805                 810                 815

Ala Ile Ile Arg Gln Gln Leu Gly His Ile Glu Ala Trp Ala Glu Lys
                820                 825                 830

Gln Gly Leu Glu Leu Ala Ala Asp Cys His Leu Ser Arg Ile Val Gln
        835                 840                 845

Ala Thr Thr Leu Leu Thr Met Asp Lys Tyr Ala Pro Asp Asp Ile Pro
850                 855                 860

Asn Ile Asn Ser Thr Cys Phe Lys Leu Asn Ser Leu Gln Leu Gln Ala
865                 870                 875                 880

Leu Leu Gln Asn Tyr His Cys Ala Pro Asp Glu Pro Phe Ile Pro Thr
                885                 890                 895

Asp Leu Ile Glu Asn Val Val Thr Val Ala Glu Asn Thr Ala Asp Glu
                900                 905                 910

Leu Ala Arg Ser Asp Gly Arg Glu Val Gln Leu Glu Glu Asp Pro Asp
        915                 920                 925

Leu Gln Leu Pro Phe Leu Leu Pro Glu Asp Gly Tyr Ser Cys Asp Val
        930                 935                 940

Val Arg Asn Ile Pro Asn Gly Leu Gln Glu Phe Leu Asp Pro Leu Cys
945                 950                 955                 960

Gln Arg Gly Phe Cys Arg Leu Ile Pro His Thr Arg Ser Pro Gly Thr
                965                 970                 975

Trp Thr Ile Tyr Phe Glu Gly Ala Asp Tyr Glu Ser His Leu Leu Arg
                980                 985                 990

Glu Asn Thr Glu Leu Ala Gln Pro Leu Arg Lys Glu Pro Glu Ile Ile
            995                1000                1005

Thr Val Thr Leu Lys Lys Gln Asn Gly Met Gly Leu Ser Ile Val
        1010                1015                1020

Ala Ala Lys Gly Ala Gly Gln Asp Lys Leu Gly Ile Tyr Val Lys
        1025                1030                1035

Ser Val Val Lys Gly Gly Ala Ala Asp Val Asp Gly Arg Leu Ala
        1040                1045                1050

Ala Gly Asp Gln Leu Leu Ser Val Asp Gly Arg Ser Leu Val Gly
```

-continued

```
            1055                1060                1065
Leu Ser Gln Glu Arg Ala Ala Glu Leu Met Thr Arg Thr Ser Ser
        1070                1075                1080
Val Val Thr Leu Glu Val Ala Lys Gln Gly Ala Ile Tyr His Gly
        1085                1090                1095
Leu Ala Thr Leu Leu Asn Gln Pro Ser Pro Met Met Gln Arg Ile
        1100                1105                1110
Ser Asp Arg Arg Gly Ser Gly Lys Pro Arg Pro Lys Ser Glu Gly
        1115                1120                1125
Phe Glu Leu Tyr Asn Asn Ser Thr Gln Asn Gly Ser Pro Glu Ser
        1130                1135                1140
Pro Gln Leu Pro Trp Ala Glu Tyr Ser Glu Pro Lys Lys Leu Pro
        1145                1150                1155
Gly Asp Asp Arg Leu Met Lys Asn Arg Ala Asp His Arg Ser Ser
        1160                1165                1170
Pro Asn Val Ala Asn Gln Pro Pro Ser Pro Gly Gly Lys Ser Ala
        1175                1180                1185
Tyr Ala Ser Gly Thr Thr Ala Lys Ile Thr Ser Val Ser Thr Gly
        1190                1195                1200
Asn Leu Cys Thr Glu Glu Gln Thr Pro Pro Arg Pro Glu Ala
        1205                1210                1215
Tyr Pro Ile Pro Thr Gln Thr Tyr Thr Arg Glu Tyr Phe Thr Phe
        1220                1225                1230
Pro Ala Ser Lys Ser Gln Asp Arg Met Ala Pro Pro Gln Asn Gln
        1235                1240                1245
Trp Pro Asn Tyr Glu Glu Lys Pro His Met His Thr Asp Ser Asn
        1250                1255                1260
His Ser Ser Ile Ala Ile Gln Arg Val Thr Arg Ser Gln Glu Glu
        1265                1270                1275
Leu Arg Glu Asp Lys Ala Tyr Gln Leu Glu Arg His Arg Ile Glu
        1280                1285                1290
Ala Ala Met Asp Arg Lys Ser Asp Ser Asp Met Trp Ile Asn Gln
        1295                1300                1305
Ser Ser Ser Leu Asp Ser Ser Thr Ser Ser Gln Glu His Leu Asn
        1310                1315                1320
His Ser Ser Lys Ser Val Thr Pro Ala Ser Thr Leu Thr Lys Ser
        1325                1330                1335
Gly Pro Gly Arg Trp Lys Thr Pro Ala Ala Ile Pro Ala Thr Pro
        1340                1345                1350
Val Ala Val Ser Gln Pro Ile Arg Thr Asp Leu Pro Pro Pro Pro
        1355                1360                1365
Pro Pro Pro Pro Val His Tyr Ala Gly Asp Phe Asp Gly Met Ser
        1370                1375                1380
Met Asp Leu Pro Leu Pro Pro Pro Ser Ala Asn Gln Ile Gly
        1385                1390                1395
Leu Pro Ser Ala Gln Val Ala Ala Ala Glu Arg Arg Lys Arg Glu
        1400                1405                1410
Glu His Gln Arg Trp Tyr Glu Lys Glu Lys Ala Arg Leu Glu Glu
        1415                1420                1425
Glu Arg Glu Arg Lys Arg Arg Glu Gln Glu Arg Lys Leu Gly Gln
        1430                1435                1440
Met Arg Thr Gln Ser Leu Asn Pro Ala Pro Phe Ser Pro Leu Thr
        1445                1450                1455
```

```
Ala Gln Gln Met Lys Pro Glu Lys Pro Ser Thr Leu Gln Arg Pro
    1460            1465            1470

Gln Glu Thr Val Ile Arg Glu Leu Gln Pro Gln Gln Gln Pro Arg
    1475            1480            1485

Thr Ile Glu Arg Arg Asp Leu Gln Tyr Ile Thr Val Ser Lys Glu
    1490            1495            1500

Glu Leu Ser Ser Gly Asp Ser Leu Ser Pro Asp Pro Trp Lys Arg
    1505            1510            1515

Asp Ala Lys Glu Lys Leu Glu Lys Gln Gln Met His Ile Val
    1520            1525            1530

Asp Met Leu Ser Lys Glu Ile Gln Glu Leu Gln Ser Lys Pro Asp
    1535            1540            1545

Arg Ser Ala Glu Glu Ser Asp Arg Leu Arg Lys Leu Met Leu Glu
    1550            1555            1560

Trp Gln Phe Gln Lys Arg Leu Gln Glu Ser Lys Gln Lys Asp Glu
    1565            1570            1575

Asp Asp Glu Glu Glu Glu Asp Asp Val Asp Thr Met Leu Ile
    1580            1585            1590

Met Gln Arg Leu Glu Ala Glu Arg Arg Ala Arg Leu Gln Asp Glu
    1595            1600            1605

Glu Arg Arg Arg Gln Gln Gln Leu Glu Glu Met Arg Lys Arg Glu
    1610            1615            1620

Ala Glu Asp Arg Ala Arg Gln Glu Glu Arg Arg Arg Gln Glu
    1625            1630            1635

Glu Glu Arg Thr Lys Arg Asp Ala Glu Lys Arg Arg Gln Glu
    1640            1645            1650

Glu Gly Tyr Tyr Ser Arg Leu Glu Ala Glu Arg Arg Gln His
    1655            1660            1665

Asp Glu Ala Ala Arg Arg Leu Leu Glu Pro Glu Ala Pro Gly Leu
    1670            1675            1680

Cys Arg Pro Pro Leu Pro Arg Asp Tyr Glu Pro Pro Ser Pro Ser
    1685            1690            1695

Pro Ala Pro Gly Ala Pro Pro Pro Pro Gln Arg Asn Ala Ser
    1700            1705            1710

Tyr Leu Lys Thr Gln Val Leu Ser Pro Asp Ser Leu Phe Thr Ala
    1715            1720            1725

Lys Phe Val Ala Tyr Asn Glu Glu Glu Glu Glu Asp Cys Ser
    1730            1735            1740

Leu Ala Gly Pro Asn Ser Tyr Pro Gly Ser Thr Gly Ala Ala Val
    1745            1750            1755

Gly Ala His Asp Ala Cys Arg Asp Ala Lys Glu Lys Arg Ser Lys
    1760            1765            1770

Ser Gln Asp Ala Asp Ser Pro Gly Ser Ser Gly Ala Pro Glu Asn
    1775            1780            1785

Leu Thr Phe Lys Glu Arg Gln Arg Leu Phe Ser Gln Gly Gln Asp
    1790            1795            1800

Val Ser Asn Lys Val Lys Ala Ser Arg Lys Leu Thr Glu Leu Glu
    1805            1810            1815

Asn Glu Leu Asn Thr Lys
    1820

<210> SEQ ID NO 59
<211> LENGTH: 327
```

<212> TYPE: PRT
<213> ORGANISM: Homo sapiens

<400> SEQUENCE: 59

```
Gly Glu Ala Pro Asn Gln Ala Leu Leu Arg Ile Leu Lys Glu Thr Glu
1               5                   10                  15

Phe Lys Lys Ile Lys Val Leu Gly Ser Gly Ala Phe Gly Thr Val Tyr
            20                  25                  30

Lys Gly Leu Trp Ile Pro Glu Gly Glu Lys Val Lys Ile Pro Val Ala
        35                  40                  45

Ile Lys Glu Leu Arg Glu Ala Thr Ser Pro Lys Ala Asn Lys Glu Ile
    50                  55                  60

Leu Asp Glu Ala Tyr Val Met Ala Ser Val Asp Asn Pro His Val Cys
65                  70                  75                  80

Arg Leu Leu Gly Ile Cys Leu Thr Ser Thr Val Gln Leu Ile Thr Gln
                85                  90                  95

Leu Met Pro Phe Gly Cys Leu Leu Asp Tyr Val Arg Glu His Lys Asp
            100                 105                 110

Asn Ile Gly Ser Gln Tyr Leu Leu Asn Trp Cys Val Gln Ile Ala Lys
        115                 120                 125

Gly Met Asn Tyr Leu Glu Asp Arg Arg Leu Val His Arg Asp Leu Ala
    130                 135                 140

Ala Arg Asn Val Leu Val Lys Thr Pro Gln His Val Lys Ile Thr Asp
145                 150                 155                 160

Phe Gly Arg Ala Lys Leu Leu Gly Ala Glu Glu Lys Glu Tyr His Ala
                165                 170                 175

Glu Gly Gly Lys Val Pro Ile Lys Trp Met Ala Leu Glu Ser Ile Leu
            180                 185                 190

His Arg Ile Tyr Thr His Gln Ser Asp Val Trp Ser Tyr Gly Val Thr
        195                 200                 205

Val Trp Glu Leu Met Thr Phe Gly Ser Lys Pro Tyr Asp Gly Ile Pro
    210                 215                 220

Ala Ser Glu Ile Ser Ser Ile Leu Glu Lys Gly Glu Arg Leu Pro Gln
225                 230                 235                 240

Pro Pro Ile Cys Thr Ile Asp Val Tyr Met Ile Met Val Lys Cys Trp
                245                 250                 255

Met Ile Asp Ala Asp Ser Arg Pro Lys Phe Arg Glu Leu Ile Ile Glu
            260                 265                 270

Phe Ser Lys Met Ala Arg Asp Pro Gln Arg Tyr Leu Val Ile Gln Gly
        275                 280                 285

Asp Glu Arg Met His Leu Pro Ser Pro Thr Asp Ser Asn Phe Tyr Arg
    290                 295                 300

Ala Leu Met Asp Glu Glu Asp Met Asp Asp Val Val Asp Ala Asp Glu
305                 310                 315                 320

Tyr Leu Ile Pro Gln Gln Gly
                325
```

<210> SEQ ID NO 60
<211> LENGTH: 327
<212> TYPE: PRT
<213> ORGANISM: Artificial Sequence
<220> FEATURE:
<223> OTHER INFORMATION: dTAG

<400> SEQUENCE: 60

Gly Glu Ala Pro Asn Gln Ala Leu Leu Arg Ile Leu Lys Glu Thr Glu

```
              1               5                  10                 15
            Phe Lys Lys Ile Lys Val Leu Gly Ser Gly Ala Phe Gly Thr Val Tyr
                        20                  25                 30
            Lys Gly Leu Trp Ile Pro Glu Gly Glu Lys Val Lys Ile Pro Val Ala
                        35                  40                 45
            Ile Lys Glu Leu Arg Glu Ala Thr Ser Pro Lys Ala Asn Lys Glu Ile
            50                      55                  60
            Leu Asp Glu Ala Tyr Val Met Ala Ser Val Asp Asn Pro His Val Cys
            65                      70                  75                 80
            Arg Leu Leu Gly Ile Cys Leu Thr Ser Thr Val Gln Leu Ile Met Gln
                        85                  90                  95
            Leu Met Pro Phe Gly Cys Leu Leu Asp Tyr Val Arg Glu His Lys Asp
                        100                 105                110
            Asn Ile Gly Ser Gln Tyr Leu Leu Asn Trp Cys Val Gln Ile Ala Lys
                        115                 120                125
            Gly Met Asn Tyr Leu Glu Asp Arg Arg Leu Val His Arg Asp Leu Ala
            130                     135                 140
            Ala Arg Asn Val Leu Val Lys Thr Pro Gln His Val Lys Ile Thr Asp
            145                     150                 155                160
            Phe Gly Arg Ala Lys Leu Leu Gly Ala Glu Glu Lys Glu Tyr His Ala
                        165                 170                175
            Glu Gly Gly Lys Val Pro Ile Lys Trp Met Ala Leu Glu Ser Ile Leu
                        180                 185                190
            His Arg Ile Tyr Thr His Gln Ser Asp Val Trp Ser Tyr Gly Val Thr
                        195                 200                205
            Val Trp Glu Leu Met Thr Phe Gly Ser Lys Pro Tyr Asp Gly Ile Pro
            210                     215                 220
            Ala Ser Glu Ile Ser Ser Ile Leu Glu Lys Gly Glu Arg Leu Pro Gln
            225                     230                 235                240
            Pro Pro Ile Cys Thr Ile Asp Val Tyr Met Ile Met Val Lys Cys Trp
                        245                 250                255
            Met Ile Asp Ala Asp Ser Arg Pro Lys Phe Arg Glu Leu Ile Ile Glu
                        260                 265                270
            Phe Ser Lys Met Ala Arg Asp Pro Gln Arg Tyr Leu Val Ile Gln Gly
                        275                 280                285
            Asp Glu Arg Met His Leu Pro Ser Pro Thr Asp Ser Asn Phe Tyr Arg
            290                     295                 300
            Ala Leu Met Asp Glu Glu Asp Met Asp Asp Val Val Asp Ala Asp Glu
            305                     310                 315                320
            Tyr Leu Ile Pro Gln Gln Gly
                        325

<210> SEQ ID NO 61
<211> LENGTH: 327
<212> TYPE: PRT
<213> ORGANISM: Artificial Sequence
<220> FEATURE:
<223> OTHER INFORMATION: dTAG

<400> SEQUENCE: 61

Gly Glu Ala Pro Asn Gln Ala Leu Leu Arg Ile Leu Lys Glu Thr Glu
            1               5                   10                 15

Phe Lys Lys Ile Lys Val Leu Gly Ser Gly Ala Phe Gly Thr Val Tyr
                        20                  25                 30

Lys Gly Leu Trp Ile Pro Glu Gly Glu Lys Val Lys Ile Pro Val Ala
```

-continued

```
                35                  40                  45
Ile Lys Glu Leu Arg Glu Ala Thr Ser Pro Lys Ala Asn Lys Glu Ile
 50                  55                  60

Leu Asp Glu Ala Tyr Val Met Ala Ser Val Asp Asn Pro His Val Cys
 65                  70                  75                  80

Arg Leu Leu Gly Ile Cys Leu Thr Ser Thr Val Gln Leu Ile Met Gln
                 85                  90                  95

Leu Met Pro Phe Gly Ser Leu Leu Asp Tyr Val Arg Glu His Lys Asp
                100                 105                 110

Asn Ile Gly Ser Gln Tyr Leu Leu Asn Trp Cys Val Gln Ile Ala Lys
            115                 120                 125

Gly Met Asn Tyr Leu Glu Asp Arg Arg Leu Val His Arg Asp Leu Ala
130                 135                 140

Ala Arg Asn Val Leu Val Lys Thr Pro Gln His Val Lys Ile Thr Asp
145                 150                 155                 160

Phe Gly Arg Ala Lys Leu Leu Gly Ala Glu Glu Lys Glu Tyr His Ala
                165                 170                 175

Glu Gly Gly Lys Val Pro Ile Lys Trp Met Ala Leu Glu Ser Ile Leu
            180                 185                 190

His Arg Ile Tyr Thr His Gln Ser Asp Val Trp Ser Tyr Gly Val Thr
        195                 200                 205

Val Trp Glu Leu Met Thr Phe Gly Ser Lys Pro Tyr Asp Gly Ile Pro
210                 215                 220

Ala Ser Glu Ile Ser Ser Ile Leu Glu Lys Gly Glu Arg Leu Pro Gln
225                 230                 235                 240

Pro Pro Ile Cys Thr Ile Asp Val Tyr Met Ile Met Val Lys Cys Trp
                245                 250                 255

Met Ile Asp Ala Asp Ser Arg Pro Lys Phe Arg Glu Leu Ile Ile Glu
            260                 265                 270

Phe Ser Lys Met Ala Arg Asp Pro Gln Arg Tyr Leu Val Ile Gln Gly
        275                 280                 285

Asp Glu Arg Met His Leu Pro Ser Pro Thr Asp Ser Asn Phe Tyr Arg
290                 295                 300

Ala Leu Met Asp Glu Glu Asp Met Asp Asp Val Val Asp Ala Asp Glu
305                 310                 315                 320

Tyr Leu Ile Pro Gln Gln Gly
                325

<210> SEQ ID NO 62
<211> LENGTH: 327
<212> TYPE: PRT
<213> ORGANISM: Artificial Sequence
<220> FEATURE:
<223> OTHER INFORMATION: dTAG

<400> SEQUENCE: 62

Gly Glu Ala Pro Asn Gln Ala Leu Leu Arg Ile Leu Lys Glu Thr Glu
1               5                   10                  15

Phe Lys Lys Ile Lys Val Leu Gly Ser Gly Ala Phe Gly Thr Val Tyr
            20                  25                  30

Lys Gly Leu Trp Ile Pro Glu Gly Glu Lys Val Lys Ile Pro Val Ala
        35                  40                  45

Ile Lys Glu Leu Arg Glu Ala Thr Ser Pro Lys Ala Asn Lys Glu Ile
 50                  55                  60

Leu Asp Glu Ala Tyr Val Met Ala Ser Val Asp Asn Pro His Val Cys
```

```
                65                  70                  75                  80
Arg Leu Leu Gly Ile Cys Leu Thr Ser Thr Val Gln Leu Ile Met Gln
                        85                  90                  95

Leu Met Pro Phe Gly Cys Gly Leu Asp Tyr Val Arg Glu His Lys Asp
                    100                 105                 110

Asn Ile Gly Ser Gln Tyr Leu Leu Asn Trp Cys Val Gln Ile Ala Lys
                115                 120                 125

Gly Met Asn Tyr Leu Glu Asp Arg Arg Leu Val His Arg Asp Leu Ala
            130                 135                 140

Ala Arg Asn Val Leu Val Lys Thr Pro Gln His Val Lys Ile Thr Asp
145                 150                 155                 160

Phe Gly Arg Ala Lys Leu Leu Gly Ala Glu Lys Glu Tyr His Ala
                    165                 170                 175

Glu Gly Gly Lys Val Pro Ile Lys Trp Met Ala Leu Glu Ser Ile Leu
                180                 185                 190

His Arg Ile Tyr Thr His Gln Ser Asp Val Trp Ser Tyr Gly Val Thr
            195                 200                 205

Val Trp Glu Leu Met Thr Phe Gly Ser Lys Pro Tyr Asp Gly Ile Pro
210                 215                 220

Ala Ser Glu Ile Ser Ser Ile Leu Glu Lys Gly Glu Arg Leu Pro Gln
225                 230                 235                 240

Pro Pro Ile Cys Thr Ile Asp Val Tyr Met Ile Met Val Lys Cys Trp
                245                 250                 255

Met Ile Asp Ala Asp Ser Arg Pro Lys Phe Arg Glu Leu Ile Ile Glu
            260                 265                 270

Phe Ser Lys Met Ala Arg Asp Pro Gln Arg Tyr Leu Val Ile Gln Gly
            275                 280                 285

Asp Glu Arg Met His Leu Pro Ser Pro Thr Asp Ser Asn Phe Tyr Arg
        290                 295                 300

Ala Leu Met Asp Glu Glu Asp Met Asp Asp Val Val Asp Ala Asp Glu
305                 310                 315                 320

Tyr Leu Ile Pro Gln Gln Gly
                325

<210> SEQ ID NO 63
<211> LENGTH: 272
<212> TYPE: PRT
<213> ORGANISM: Artificial Sequence
<220> FEATURE:
<223> OTHER INFORMATION: epidermal growth factor receptor (BCR-ABL)

<400> SEQUENCE: 63

Ser Pro Asn Tyr Asp Lys Trp Glu Met Glu Arg Thr Asp Ile Thr Met
1               5                   10                  15

Lys His Lys Leu Gly Gly Gly Gln Tyr Gly Glu Val Tyr Glu Gly Val
            20                  25                  30

Trp Lys Lys Tyr Ser Leu Thr Val Ala Val Lys Thr Leu Lys Glu Asp
        35                  40                  45

Thr Met Glu Val Glu Glu Phe Leu Lys Glu Ala Ala Val Met Lys Glu
    50                  55                  60

Ile Lys His Pro Asn Leu Val Gln Leu Leu Gly Val Cys Thr Arg Glu
65                  70                  75                  80

Pro Pro Phe Tyr Ile Ile Ile Glu Phe Met Thr Tyr Gly Asn Leu Leu
                85                  90                  95

Asp Tyr Leu Arg Glu Cys Asn Arg Gln Glu Val Asn Ala Val Val Leu
```

```
            100                 105                 110
Leu Tyr Met Ala Thr Gln Ile Ser Ser Ala Met Glu Tyr Leu Glu Lys
            115                 120                 125
Lys Asn Phe Ile His Arg Asp Leu Ala Ala Arg Asn Cys Leu Val Gly
            130                 135                 140
Glu Asn His Leu Val Lys Val Ala Asp Phe Gly Leu Ser Arg Leu Met
145                 150                 155                 160
Thr Gly Asp Thr Tyr Thr Ala His Ala Gly Ala Lys Phe Pro Ile Lys
                165                 170                 175
Trp Thr Ala Pro Glu Ser Leu Ala Tyr Asn Lys Phe Ser Ile Lys Ser
                180                 185                 190
Asp Val Trp Ala Phe Gly Val Leu Leu Trp Glu Ile Ala Thr Tyr Gly
            195                 200                 205
Met Ser Pro Tyr Pro Gly Ile Asp Leu Ser Gln Val Tyr Glu Leu Leu
            210                 215                 220
Glu Lys Asp Tyr Arg Met Glu Arg Pro Glu Gly Cys Pro Glu Lys Val
225                 230                 235                 240
Tyr Glu Leu Met Arg Ala Cys Trp Gln Trp Asn Pro Ser Asp Arg Pro
                245                 250                 255
Ser Phe Ala Glu Ile His Gln Ala Phe Glu Thr Met Phe Gln Glu Ser
            260                 265                 270

<210> SEQ ID NO 64
<211> LENGTH: 271
<212> TYPE: PRT
<213> ORGANISM: Artificial Sequence
<220> FEATURE:
<223> OTHER INFORMATION: BCR-ABL

<400> SEQUENCE: 64

Pro Asn Tyr Asp Lys Trp Glu Met Glu Arg Thr Asp Ile Thr Met Lys
1               5                   10                  15
His Lys Leu Gly Gly Gly Gln Tyr Gly Glu Val Tyr Glu Gly Val Trp
            20                  25                  30
Lys Lys Tyr Ser Leu Thr Val Ala Val Lys Thr Leu Lys Glu Asp Thr
            35                  40                  45
Met Glu Val Glu Glu Phe Leu Lys Glu Ala Ala Val Met Lys Glu Ile
        50                  55                  60
Lys His Pro Asn Leu Val Gln Leu Leu Gly Val Cys Thr Arg Glu Pro
65                  70                  75                  80
Pro Phe Tyr Ile Ile Thr Glu Phe Met Thr Tyr Gly Asn Leu Leu Asp
                85                  90                  95
Tyr Leu Arg Glu Cys Asn Arg Gln Glu Val Asn Ala Val Val Leu Leu
            100                 105                 110
Tyr Met Ala Thr Gln Ile Ser Ser Ala Met Glu Tyr Leu Glu Lys Lys
            115                 120                 125
Asn Phe Ile His Arg Asp Leu Ala Ala Arg Asn Cys Leu Val Gly Glu
        130                 135                 140
Asn His Leu Val Lys Val Ala Asp Phe Gly Leu Ser Arg Leu Met Thr
145                 150                 155                 160
Gly Asp Thr Tyr Thr Ala His Ala Gly Ala Lys Phe Pro Ile Lys Trp
                165                 170                 175
Thr Ala Pro Glu Ser Leu Ala Tyr Asn Lys Phe Ser Ile Lys Ser Asp
            180                 185                 190
Val Trp Ala Phe Gly Val Leu Leu Trp Glu Ile Ala Thr Tyr Gly Met
```

```
                195                 200                 205
Ser Pro Tyr Pro Gly Ile Asp Leu Ser Gln Val Tyr Glu Leu Leu Glu
210                 215                 220

Lys Asp Tyr Arg Met Glu Arg Pro Glu Gly Cys Pro Glu Lys Val Tyr
225                 230                 235                 240

Glu Leu Met Arg Ala Cys Trp Gln Trp Asn Pro Ser Asp Arg Pro Ser
                245                 250                 255

Phe Ala Glu Ile His Gln Ala Phe Glu Thr Met Phe Gln Glu Ser
            260                 265                 270

<210> SEQ ID NO 65
<211> LENGTH: 339
<212> TYPE: PRT
<213> ORGANISM: Homo sapiens

<400> SEQUENCE: 65

Glu Leu Gln Ser Pro Glu Tyr Lys Leu Ser Lys Leu Arg Thr Ser Thr
1               5                   10                  15

Ile Met Thr Asp Tyr Asn Pro Asn Tyr Cys Phe Ala Gly Lys Thr Ser
                20                  25                  30

Ser Ile Ser Asp Leu Lys Glu Val Pro Arg Lys Asn Ile Thr Leu Ile
            35                  40                  45

Arg Gly Leu Gly His Gly Ala Phe Gly Glu Val Tyr Glu Gly Gln Val
        50                  55                  60

Ser Gly Met Pro Asn Asp Pro Ser Pro Leu Gln Val Ala Val Lys Thr
65                  70                  75                  80

Leu Pro Glu Val Cys Ser Glu Gln Asp Glu Leu Asp Phe Leu Met Glu
                85                  90                  95

Ala Leu Ile Ile Ser Lys Phe Asn His Gln Asn Ile Val Arg Cys Ile
                100                 105                 110

Gly Val Ser Leu Gln Ser Leu Pro Arg Phe Ile Met Leu Glu Leu Met
            115                 120                 125

Ala Gly Gly Asp Leu Lys Ser Phe Leu Arg Glu Thr Arg Pro Arg Pro
        130                 135                 140

Ser Gln Pro Ser Ser Leu Ala Met Leu Asp Leu Leu His Val Ala Arg
145                 150                 155                 160

Asp Ile Ala Cys Gly Cys Gln Tyr Leu Glu Glu Asn His Phe Ile His
                165                 170                 175

Arg Asp Ile Ala Ala Arg Asn Cys Leu Leu Thr Cys Pro Gly Pro Gly
                180                 185                 190

Arg Val Ala Lys Ile Gly Asp Phe Gly Met Ala Arg Asp Ile Tyr Arg
            195                 200                 205

Ala Gly Tyr Tyr Arg Lys Gly Gly Cys Ala Met Leu Pro Val Lys Trp
210                 215                 220

Met Pro Pro Glu Ala Phe Met Glu Gly Ile Phe Thr Ser Lys Thr Asp
225                 230                 235                 240

Thr Trp Ser Phe Gly Val Leu Leu Trp Glu Ile Phe Ser Leu Gly Tyr
                245                 250                 255

Met Pro Tyr Pro Ser Lys Ser Asn Gln Glu Val Leu Glu Phe Val Thr
                260                 265                 270

Ser Gly Gly Arg Met Asp Pro Pro Lys Asn Cys Pro Gly Pro Val Tyr
            275                 280                 285

Arg Ile Met Thr Gln Cys Trp Gln His Gln Pro Glu Asp Arg Pro Asn
        290                 295                 300
```

```
Phe Ala Ile Ile Leu Glu Arg Ile Glu Tyr Cys Thr Gln Asp Pro Asp
305                 310                 315                 320

Val Ile Asn Thr Ala Leu Pro Ile Glu Tyr Gly Pro Leu Val Glu Glu
            325                 330                 335

Glu Glu Lys
```

<210> SEQ ID NO 66
<211> LENGTH: 277
<212> TYPE: PRT
<213> ORGANISM: Homo sapiens

<400> SEQUENCE: 66

```
Val Phe His Lys Ile Arg Asn Glu Asp Leu Ile Phe Asn Glu Ser Leu
1               5                   10                  15

Gly Gln Gly Thr Phe Thr Lys Ile Phe Lys Gly Val Arg Arg Glu Val
            20                  25                  30

Gly Asp Tyr Gly Gln Leu His Glu Thr Glu Val Leu Leu Lys Val Leu
        35                  40                  45

Asp Lys Ala His Arg Asn Tyr Ser Glu Ser Phe Phe Glu Ala Ala Ser
    50                  55                  60

Met Met Ser Lys Leu Ser His Lys His Leu Val Leu Asn Tyr Gly Val
65                  70                  75                  80

Cys Phe Cys Gly Asp Glu Asn Ile Leu Val Gln Glu Phe Val Lys Phe
                85                  90                  95

Gly Ser Leu Asp Thr Tyr Leu Lys Lys Asn Lys Asn Cys Ile Asn Ile
            100                 105                 110

Leu Trp Lys Leu Glu Val Ala Lys Gln Leu Ala Trp Ala Met His Phe
        115                 120                 125

Leu Glu Glu Asn Thr Leu Ile His Gly Asn Val Cys Ala Lys Asn Ile
130                 135                 140

Leu Leu Ile Arg Glu Glu Asp Arg Lys Thr Gly Asn Pro Pro Phe Ile
145                 150                 155                 160

Lys Leu Ser Asp Pro Gly Ile Ser Ile Thr Val Leu Pro Lys Asp Ile
                165                 170                 175

Leu Gln Glu Arg Ile Pro Trp Val Pro Pro Glu Cys Ile Glu Asn Pro
            180                 185                 190

Lys Asn Leu Asn Leu Ala Thr Asp Lys Trp Ser Phe Gly Thr Thr Leu
        195                 200                 205

Trp Glu Ile Cys Ser Gly Gly Asp Lys Pro Leu Ser Ala Leu Asp Ser
210                 215                 220

Gln Arg Lys Leu Gln Phe Tyr Glu Asp Arg His Gln Leu Pro Ala Pro
225                 230                 235                 240

Lys Ala Ala Glu Leu Ala Asn Leu Ile Asn Asn Cys Met Asp Tyr Glu
                245                 250                 255

Pro Asp His Arg Pro Ser Phe Arg Ala Ile Ile Arg Asp Leu Asn Ser
            260                 265                 270

Leu Phe Thr Pro Asp
        275
```

<210> SEQ ID NO 67
<211> LENGTH: 272
<212> TYPE: PRT
<213> ORGANISM: Homo sapiens

<400> SEQUENCE: 67

```
Asp Trp Glu Ile Pro Asp Gly Gln Ile Thr Val Gly Gln Arg Ile Gly
```

```
  1               5                  10                 15
Ser Gly Ser Phe Gly Thr Val Tyr Lys Gly Lys Trp His Gly Asp Val
             20                 25                 30

Ala Val Lys Met Leu Asn Val Thr Ala Pro Thr Pro Gln Gln Leu Gln
             35                 40                 45

Ala Phe Lys Asn Glu Val Gly Val Leu Arg Lys Thr Arg His Val Asn
             50                 55                 60

Ile Leu Leu Phe Met Gly Tyr Ser Thr Ala Pro Gln Leu Ala Ile Val
 65                 70                 75                 80

Thr Gln Trp Cys Glu Gly Ser Ser Leu Tyr His His Leu His Ala Ser
                 85                 90                 95

Glu Thr Lys Phe Glu Met Lys Lys Leu Ile Asp Ile Ala Arg Gln Thr
            100                105                110

Ala Arg Gly Met Asp Tyr Leu His Ala Lys Ser Ile Ile His Arg Asp
            115                120                125

Leu Lys Ser Asn Asn Ile Phe Leu His Glu Asp Asn Thr Val Lys Ile
        130                135                140

Gly Asp Phe Gly Leu Ala Thr Glu Lys Ser Arg Trp Ser Gly Ser His
145                150                155                160

Gln Phe Glu Gln Leu Ser Gly Ser Ile Leu Trp Met Ala Pro Glu Val
            165                170                175

Ile Arg Met Gln Asp Ser Asn Pro Tyr Ser Phe Gln Ser Asp Val Tyr
            180                185                190

Ala Phe Gly Ile Val Leu Tyr Glu Leu Met Thr Gly Gln Leu Pro Tyr
            195                200                205

Ser Asn Ile Asn Asn Arg Asp Gln Ile Ile Glu Met Val Gly Arg Gly
        210                215                220

Ser Leu Ser Pro Asp Leu Ser Lys Val Arg Ser Asn Cys Pro Lys Arg
225                230                235                240

Met Lys Arg Leu Met Ala Glu Cys Leu Lys Lys Lys Arg Asp Glu Arg
            245                250                255

Pro Ser Phe Pro Arg Ile Leu Ala Glu Ile Glu Glu Leu Ala Arg Glu
            260                265                270

<210> SEQ ID NO 68
<211> LENGTH: 111
<212> TYPE: PRT
<213> ORGANISM: Artificial Sequence
<220> FEATURE:
<223> OTHER INFORMATION: BCMA scFv variable light chain (VL)

<400> SEQUENCE: 68

Asp Ile Val Leu Thr Gln Ser Pro Pro Ser Leu Ala Met Ser Leu Gly
 1               5                  10                 15

Lys Arg Ala Thr Ile Ser Cys Arg Ala Ser Glu Ser Val Thr Ile Leu
             20                 25                 30

Gly Ser His Leu Ile Tyr Trp Tyr Gln Gln Lys Pro Gly Gln Pro Pro
             35                 40                 45

Thr Leu Leu Ile Gln Leu Ala Ser Asn Val Gln Thr Gly Val Pro Ala
             50                 55                 60

Arg Phe Ser Gly Ser Gly Ser Arg Thr Asp Phe Thr Leu Thr Ile Asp
 65                 70                 75                 80

Pro Val Glu Glu Asp Asp Val Ala Val Tyr Tyr Cys Leu Gln Ser Arg
                 85                 90                 95

Thr Ile Pro Arg Thr Phe Gly Gly Gly Thr Lys Leu Glu Ile Lys
```

<210> SEQ ID NO 69
<211> LENGTH: 22
<212> TYPE: PRT
<213> ORGANISM: Artificial Sequence
<220> FEATURE:
<223> OTHER INFORMATION: CD8a signal peptide

<400> SEQUENCE: 69

Met Ala Leu Pro Val Thr Ala Leu Leu Leu Pro Leu Ala Leu Leu Leu
1               5                   10                  15

His Ala Ala Arg Pro Asp
            20

<210> SEQ ID NO 70
<211> LENGTH: 117
<212> TYPE: PRT
<213> ORGANISM: Artificial Sequence
<220> FEATURE:
<223> OTHER INFORMATION: scFV to BCMA variable heavy chain (VH)

<400> SEQUENCE: 70

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg His Tyr
                20                  25                  30

Ser Met Asn Trp Val Lys Gln Ala Pro Gly Lys Gly Leu Lys Trp Met
            35                  40                  45

Gly Arg Ile Asn Thr Glu Ser Gly Val Pro Ile Tyr Ala Asp Asp Phe
        50                  55                  60

Lys Gly Arg Phe Ala Phe Ser Val Glu Thr Ser Ala Ser Thr Ala Tyr
65                  70                  75                  80

Leu Val Ile Asn Asn Leu Lys Asp Glu Asp Thr Ala Ser Tyr Phe Cys
                85                  90                  95

Ser Asn Asp Tyr Leu Tyr Ser Leu Asp Phe Trp Gly Gln Gly Thr Ala
            100                 105                 110

Leu Thr Val Ser Ser
        115

<210> SEQ ID NO 71
<211> LENGTH: 15
<212> TYPE: PRT
<213> ORGANISM: Artificial Sequence
<220> FEATURE:
<223> OTHER INFORMATION: Whitlow linker

<400> SEQUENCE: 71

Gly Gly Gly Gly Ser Gly Gly Gly Gly Ser Gly Gly Gly Gly Ser
1               5                   10                  15

<210> SEQ ID NO 72
<211> LENGTH: 69
<212> TYPE: PRT
<213> ORGANISM: Artificial Sequence
<220> FEATURE:
<223> OTHER INFORMATION: modified CD8 alpha chain hinge region

<400> SEQUENCE: 72

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly

```
                            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 73
<211> LENGTH: 42
<212> TYPE: PRT
<213> ORGANISM: Artificial Sequence
<220> FEATURE:
<223> OTHER INFORMATION: fragment of co-stimulatory 4-1BB protein

<400> SEQUENCE: 73

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 74
<211> LENGTH: 112
<212> TYPE: PRT
<213> ORGANISM: Artificial Sequence
<220> FEATURE:
<223> OTHER INFORMATION: CD-zeta domain

<400> SEQUENCE: 74

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 75
<211> LENGTH: 107
<212> TYPE: PRT
<213> ORGANISM: Artificial Sequence
<220> FEATURE:
<223> OTHER INFORMATION: dTAG derivative of FKBP12 with F36V mutation

<400> SEQUENCE: 75

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45
```

```
Met Leu Gly Lys Gln Glu Val Ile Arg Gly Trp Glu Glu Gly Val Ala
            50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                    85                  90                  95

Leu Val Phe Asp Val Glu Leu Leu Lys Leu Glu
                100                 105
```

<210> SEQ ID NO 76
<211> LENGTH: 9
<212> TYPE: PRT
<213> ORGANISM: Artificial Sequence
<220> FEATURE:
<223> OTHER INFORMATION: HA tag

<400> SEQUENCE: 76

```
Tyr Pro Tyr Asp Val Pro Asp Tyr Ala
 1               5
```

<210> SEQ ID NO 77
<211> LENGTH: 609
<212> TYPE: PRT
<213> ORGANISM: Artificial Sequence
<220> FEATURE:
<223> OTHER INFORMATION: BCMA-CAR-dTAG

<400> SEQUENCE: 77

```
Met Ala Leu Pro Val Thr Ala Leu Leu Leu Pro Leu Ala Leu Leu Leu
 1               5                  10                  15

His Ala Ala Arg Pro Asp Asp Ile Val Leu Thr Gln Ser Pro Pro Ser
                20                  25                  30

Leu Ala Met Ser Leu Gly Lys Arg Ala Thr Ile Ser Cys Arg Ala Ser
            35                  40                  45

Glu Ser Val Thr Ile Leu Gly Ser His Leu Ile Tyr Trp Tyr Gln Gln
 50                  55                  60

Lys Pro Gly Gln Pro Pro Thr Leu Leu Ile Gln Leu Ala Ser Asn Val
 65                  70                  75                  80

Gln Thr Gly Val Pro Ala Arg Phe Ser Gly Ser Gly Ser Arg Thr Asp
                    85                  90                  95

Phe Thr Leu Thr Ile Asp Pro Val Glu Glu Asp Asp Val Ala Val Tyr
                100                 105                 110

Tyr Cys Leu Gln Ser Arg Thr Ile Pro Arg Thr Phe Gly Gly Gly Thr
            115                 120                 125

Lys Leu Glu Ile Lys Gly Gly Gly Ser Gly Gly Gly Gly Ser Gly
 130                 135                 140

Gly Gly Gly Ser Gln Ile Gln Leu Val Gln Ser Gly Pro Glu Leu Lys
145                 150                 155                 160

Lys Pro Gly Glu Thr Val Lys Ile Ser Cys Lys Ala Ser Gly Tyr Thr
                165                 170                 175

Phe Arg His Tyr Ser Met Asn Trp Val Lys Gln Ala Pro Gly Lys Gly
            180                 185                 190

Leu Lys Trp Met Gly Arg Ile Asn Thr Glu Ser Gly Val Pro Ile Tyr
            195                 200                 205

Ala Asp Asp Phe Lys Gly Arg Phe Ala Phe Ser Val Glu Thr Ser Ala
        210                 215                 220

Ser Thr Ala Tyr Leu Val Ile Asn Asn Leu Lys Asp Glu Asp Thr Ala
```

```
             225                 230                 235                 240
     Ser Tyr Phe Cys Ser Asn Asp Tyr Leu Tyr Ser Leu Asp Phe Trp Gly
                     245                 250                 255

Gln Gly Thr Ala Leu Thr Val Ser Ser Thr Thr Pro Ala Pro Arg
                 260                 265                 270

Pro Pro Thr Pro Ala Pro Thr Ile Ala Ser Gln Pro Leu Ser Leu Arg
                 275                 280                 285

Pro Glu Ala Cys Arg Pro Ala Ala Gly Gly Ala Val His Thr Arg Gly
         290                 295                 300

Leu Asp Phe Ala Cys Asp Ile Tyr Ile Trp Ala Pro Leu Ala Gly Thr
     305                 310                 315                 320

Cys Gly Val Leu Leu Leu Ser Leu Val Ile Thr Leu Tyr Cys Lys Arg
                     325                 330                 335

Gly Arg Lys Lys Leu Leu Tyr Ile Phe Lys Gln Pro Phe Met Arg Pro
                 340                 345                 350

Val Gln Thr Thr Gln Glu Glu Asp Gly Cys Ser Cys Arg Phe Pro Glu
                 355                 360                 365

Glu Glu Glu Gly Gly Cys Glu Leu Arg Val Lys Phe Ser Arg Ser Ala
         370                 375                 380

Asp Ala Pro Ala Tyr Lys Gln Gly Gln Asn Gln Leu Tyr Asn Glu Leu
     385                 390                 395                 400

Asn Leu Gly Arg Arg Glu Glu Tyr Asp Val Leu Asp Lys Arg Arg Gly
                     405                 410                 415

Arg Asp Pro Glu Met Gly Gly Lys Pro Arg Arg Lys Asn Pro Gln Glu
                 420                 425                 430

Gly Leu Tyr Asn Glu Leu Gln Lys Asp Lys Met Ala Glu Ala Tyr Ser
                 435                 440                 445

Glu Ile Gly Met Lys Gly Glu Arg Arg Arg Gly Lys Gly His Asp Gly
         450                 455                 460

Leu Tyr Gln Gly Leu Ser Thr Ala Thr Lys Asp Thr Tyr Asp Ala Leu
     465                 470                 475                 480

His Met Gln Ala Leu Pro Pro Arg Gly Gly Gly Val Gln Val Glu
                     485                 490                 495

Thr Ile Ser Pro Gly Asp Gly Arg Thr Phe Pro Lys Arg Gly Gln Thr
                 500                 505                 510

Cys Val Val His Tyr Thr Gly Met Leu Glu Asp Gly Lys Lys Val Asp
                 515                 520                 525

Ser Ser Arg Asp Arg Asn Lys Pro Phe Lys Phe Met Leu Gly Lys Gln
         530                 535                 540

Glu Val Ile Arg Gly Trp Glu Glu Gly Val Ala Gln Met Ser Val Gly
     545                 550                 555                 560

Gln Arg Ala Lys Leu Thr Ile Ser Pro Asp Tyr Ala Tyr Gly Ala Thr
                     565                 570                 575

Gly His Pro Gly Ile Ile Pro Pro His Ala Thr Leu Val Phe Asp Val
                 580                 585                 590

Glu Leu Leu Lys Leu Glu Gly Gly Tyr Pro Tyr Asp Val Pro Asp Tyr
                 595                 600                 605

Ala

<210> SEQ ID NO 78
<211> LENGTH: 218
<212> TYPE: PRT
<213> ORGANISM: Artificial Sequence
<220> FEATURE:
```

<223> OTHER INFORMATION: BCMA scFv variable light chain (VL)

<400> SEQUENCE: 78

```
Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 79
<211> LENGTH: 446
<212> TYPE: PRT
<213> ORGANISM: Artificial Sequence
<220> FEATURE:
<223> OTHER INFORMATION: scFv to BCMA variable heavy chain (VH)

<400> SEQUENCE: 79

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg His Tyr
            20                  25                  30

Ser Met Asn Trp Val Lys Gln Ala Pro Gly Lys Gly Leu Lys Trp Met
        35                  40                  45

Gly Arg Ile Asn Thr Glu Ser Gly Val Pro Ile Tyr Ala Asp Asp Phe
    50                  55                  60

Lys Gly Arg Phe Ala Phe Ser Val Glu Thr Ser Ala Ser Thr Ala Tyr
65                  70                  75                  80

Leu Val Ile Asn Asn Leu Lys Asp Glu Asp Thr Ala Ser Tyr Phe Cys
                85                  90                  95

Ser Asn Asp Tyr Leu Tyr Ser Leu Asp Phe Trp Gly Gln Gly Thr Thr
            100                 105                 110

Leu Thr Val Ser Ser Ala Ser Thr Lys Gly Pro Ser Val Phe Pro Leu
        115                 120                 125
```

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 80
<211> LENGTH: 1045
<212> TYPE: PRT
<213> ORGANISM: Artificial Sequence
<220> FEATURE:
<223> OTHER INFORMATION: DCMA-CAR-dTAG

<400> SEQUENCE: 80

Met Ala Leu Pro Val Thr Ala Leu Leu Leu Pro Leu Ala Leu Leu Leu
1               5                   10                  15

His Ala Ala Arg Pro Asp Asp Ile Val Leu Thr Gln Ser Pro Pro Ser
            20                  25                  30

Leu Ala Met Ser Leu Gly Lys Arg Ala Thr Ile Ser Cys Arg Ala Ser
        35                  40                  45

```
Glu Ser Val Thr Ile Leu Gly Ser His Leu Ile Tyr Trp Tyr Gln Gln
 50                  55                  60
Lys Pro Gly Gln Pro Pro Thr Leu Leu Ile Gln Leu Ala Ser Asn Val
 65                  70                  75                  80
Gln Thr Gly Val Pro Ala Arg Phe Ser Gly Ser Gly Ser Arg Thr Asp
                 85                  90                  95
Phe Thr Leu Thr Ile Asp Pro Val Glu Glu Asp Asp Val Ala Val Tyr
            100                 105                 110
Tyr Cys Leu Gln Ser Arg Thr Ile Pro Arg Thr Phe Gly Gly Gly Thr
            115                 120                 125
Lys Leu Glu Ile Lys Arg Thr Val Ala Ala Pro Ser Val Phe Ile Phe
    130                 135                 140
Pro Pro Ser Asp Glu Gln Leu Lys Ser Gly Thr Ala Ser Val Val Cys
145                 150                 155                 160
Leu Leu Asn Asn Phe Tyr Pro Arg Glu Ala Lys Val Gln Trp Lys Val
                165                 170                 175
Asp Asn Ala Leu Gln Ser Gly Asn Ser Gln Glu Ser Val Thr Glu Gln
            180                 185                 190
Asp Ser Lys Asp Ser Thr Tyr Ser Leu Ser Ser Thr Leu Thr Leu Ser
            195                 200                 205
Lys Ala Asp Tyr Glu Lys His Lys Val Tyr Ala Cys Glu Val Thr His
    210                 215                 220
Gln Gly Leu Ser Ser Pro Val Thr Lys Ser Phe Asn Arg Gly Glu Cys
225                 230                 235                 240
Gly Gly Gly Gly Ser Gly Gly Gly Ser Gly Gly Gly Gly Ser Gln
                245                 250                 255
Ile Gln Leu Val Gln Ser Gly Pro Glu Leu Lys Lys Pro Gly Glu Thr
            260                 265                 270
Val Lys Ile Ser Cys Lys Ala Ser Gly Tyr Thr Phe Arg His Tyr Ser
            275                 280                 285
Met Asn Trp Val Lys Gln Ala Pro Gly Lys Gly Leu Lys Trp Met Gly
    290                 295                 300
Arg Ile Asn Thr Glu Ser Gly Val Pro Ile Tyr Ala Asp Asp Phe Lys
305                 310                 315                 320
Gly Arg Phe Ala Phe Ser Val Glu Thr Ser Ala Ser Thr Ala Tyr Leu
                325                 330                 335
Val Ile Asn Asn Leu Lys Asp Glu Asp Thr Ala Ser Tyr Phe Cys Ser
            340                 345                 350
Asn Asp Tyr Leu Tyr Ser Leu Asp Phe Trp Gly Gln Gly Thr Thr Leu
            355                 360                 365
Thr Val Ser Ser Ala Ser Thr Lys Gly Pro Ser Val Phe Pro Leu Ala
    370                 375                 380
Pro Ser Ser Lys Ser Thr Ser Gly Gly Thr Ala Ala Leu Gly Cys Leu
385                 390                 395                 400
Val Lys Asp Tyr Phe Pro Glu Pro Val Thr Val Ser Trp Asn Ser Gly
                405                 410                 415
Ala Leu Thr Ser Gly Val His Thr Phe Pro Ala Val Leu Gln Ser Ser
            420                 425                 430
Gly Leu Tyr Ser Leu Ser Ser Val Val Thr Val Pro Ser Ser Ser Leu
            435                 440                 445
Gly Thr Gln Thr Tyr Ile Cys Asn Val Asn His Lys Pro Ser Asn Thr
    450                 455                 460
```

```
Lys Val Asp Lys Lys Val Glu Pro Lys Ser Cys Asp Lys Thr His Thr
465                 470                 475                 480

Cys Pro Pro Cys Pro Ala Pro Glu Leu Leu Gly Gly Pro Ser Val Phe
            485                 490                 495

Leu Phe Pro Pro Lys Pro Lys Asp Thr Leu Met Ile Ser Arg Thr Pro
        500                 505                 510

Glu Val Thr Cys Val Val Val Asp Val Ser His Glu Asp Pro Glu Val
    515                 520                 525

Lys Phe Asn Trp Tyr Val Asp Gly Val Glu Val His Asn Ala Lys Thr
530                 535                 540

Lys Pro Arg Glu Glu Gln Tyr Asn Ser Thr Tyr Arg Val Val Ser Val
545                 550                 555                 560

Leu Thr Val Leu His Gln Asp Trp Leu Asn Gly Lys Glu Tyr Lys Cys
                565                 570                 575

Lys Val Ser Asn Lys Ala Leu Pro Ala Pro Ile Glu Lys Thr Ile Ser
                580                 585                 590

Lys Ala Lys Gly Gln Pro Arg Glu Pro Gln Val Tyr Thr Leu Pro Pro
            595                 600                 605

Ser Arg Asp Glu Leu Thr Lys Asn Gln Val Ser Leu Thr Cys Leu Val
610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Tyr Ser Lys Leu Thr Val Asp Lys Ser Arg Trp
            660                 665                 670

Gln Gln Gly Asn Val Phe Ser Cys Ser Val Met His Glu Ala Leu His
            675                 680                 685

Asn His Tyr Thr Gln Lys Ser Leu Ser Leu Ser Pro Gly Thr Thr Thr
            690                 695                 700

Pro Ala Pro Arg Pro Pro Thr Pro Ala Pro Thr Ile Ala Ser Gln Pro
705                 710                 715                 720

Leu Ser Leu Arg Pro Glu Ala Cys Arg Pro Ala Ala Gly Gly Ala Val
                725                 730                 735

His Thr Arg Gly Leu Asp Phe Ala Cys Asp Ile Tyr Ile Trp Ala Pro
            740                 745                 750

Leu Ala Gly Thr Cys Gly Val Leu Leu Leu Ser Leu Val Ile Thr Leu
            755                 760                 765

Tyr Cys Lys Arg Gly Arg Lys Lys Leu Leu Tyr Ile Phe Lys Gln Pro
770                 775                 780

Phe Met Arg Pro Val Gln Thr Thr Gln Glu Glu Asp Gly Cys Ser Cys
785                 790                 795                 800

Arg Phe Pro Glu Glu Glu Glu Gly Gly Cys Glu Leu Arg Val Lys Phe
            805                 810                 815

Ser Arg Ser Ala Asp Ala Pro Ala Tyr Lys Gln Gly Gln Asn Gln Leu
            820                 825                 830

Tyr Asn Glu Leu Asn Leu Gly Arg Arg Glu Glu Tyr Asp Val Leu Asp
835                 840                 845

Lys Arg Arg Gly Arg Asp Pro Glu Met Gly Gly Lys Pro Arg Arg Lys
            850                 855                 860

Asn Pro Gln Glu Gly Leu Tyr Asn Glu Leu Gln Lys Asp Lys Met Ala
865                 870                 875                 880

Glu Ala Tyr Ser Glu Ile Gly Met Lys Gly Glu Arg Arg Arg Gly Lys
```

```
                    885                 890                 895

Gly His Asp Gly Leu Tyr Gln Gly Leu Ser Thr Ala Thr Lys Asp Thr
            900                 905                 910

Tyr Asp Ala Leu His Met Gln Ala Leu Pro Pro Arg Gly Gly Gly Gly
        915                 920                 925

Val Gln Val Glu Thr Ile Ser Pro Gly Asp Gly Arg Thr Phe Pro Lys
    930                 935                 940

Arg Gly Gln Thr Cys Val Val His Tyr Thr Gly Met Leu Glu Asp Gly
945                 950                 955                 960

Lys Lys Val Asp Ser Ser Arg Asp Arg Asn Lys Pro Phe Lys Phe Met
                965                 970                 975

Leu Gly Lys Gln Glu Val Ile Arg Gly Trp Glu Gly Val Ala Gln
            980                 985                 990

Met Ser Val Gly Gln Arg Ala Lys  Leu Thr Ile Ser Pro  Asp Tyr Ala
        995                 1000                 1005

Tyr Gly  Ala Thr Gly His Pro  Gly Ile Ile Pro Pro  His Ala Thr
    1010                 1015                 1020

Leu Val  Phe Asp Val Glu Leu  Leu Lys Leu Glu Gly  Gly Tyr Pro
    1025                 1030                 1035

Tyr Asp  Val Pro Asp Tyr Ala
    1040                 1045

<210> SEQ ID NO 81
<211> LENGTH: 107
<212> TYPE: PRT
<213> ORGANISM: Artificial Sequence
<220> FEATURE:
<223> OTHER INFORMATION: CD38 scFV variable light chain (VL)

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 82
<211> LENGTH: 121
<212> TYPE: PRT
<213> ORGANISM: Artificial Sequence
<220> FEATURE:
<223> OTHER INFORMATION: scFv to CD38 variable heavy chain (VH)

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Ser Ser Tyr
            20                  25                  30
```

Ala Ile Ser Trp Val Arg Gln Ala Pro Gly Gln Gly Leu Glu Trp Met
         35                  40                  45

Gly Arg Ile Ile Arg Phe Leu Gly Ile Ala Asn Tyr Ala Gln Lys Phe
 50                  55                  60

Gln Gly Arg Val Thr Leu Ile Ala Asp Lys Ser Thr Asn Thr Ala Tyr
 65                  70                  75                  80

Met Glu Leu Ser Ser Leu Arg Ser Glu Asp Thr Ala Val Tyr Tyr Cys
             85                  90                  95

Ala Gly Glu Pro Gly Glu Arg Asp Pro Asp Ala Val Asp Ile Trp Gly
            100                 105                 110

Gln Gly Thr Met Val Thr Val Ser Ser
        115                 120

<210> SEQ ID NO 83
<211> LENGTH: 609
<212> TYPE: PRT
<213> ORGANISM: Artificial Sequence
<220> FEATURE:
<223> OTHER INFORMATION: CD38-CAR-dTAG

<400> SEQUENCE: 83

Met Ala Leu Pro Val Thr Ala Leu Leu Leu Pro Leu Ala Leu Leu Leu
 1               5                  10                  15

His Ala Ala Arg Pro Asp Asp Ile Gln Met Thr Gln Ser Pro Ser Ser
            20                  25                  30

Leu Ser Ala Ser Val Gly Asp Arg Val Thr Ile Thr Cys Arg Ala Ser
         35                  40                  45

Gln Gly Ile Arg Ser Trp Leu Ala Trp Tyr Gln Gln Lys Pro Glu Lys
 50                  55                  60

Ala Pro Lys Ser Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
             85                  90                  95

Ile Ser Ser Leu Gln Pro Glu Asp Phe Ala Thr Tyr Tyr Cys Gln Gln
            100                 105                 110

Tyr Asn Ser Tyr Pro Leu Thr Phe Gly Gly Gly Thr Lys Val Glu Ile
            115                 120                 125

Lys Gly Gly Gly Gly Ser Gly Gly Gly Gly Ser Gly Gly Gly Gly Ser
130                 135                 140

Gln Val Gln Leu Val Gln Ser Gly Ala Glu Val Lys Lys Pro Gly Ser
145                 150                 155                 160

Ser Val Lys Val Ser Cys Lys Ala Phe Gly Thr Phe Ser Ser Tyr
                165                 170                 175

Ala Ile Ser Trp Val Arg Gln Ala Pro Gly Gln Gly Leu Glu Trp Met
            180                 185                 190

Gly Arg Ile Ile Arg Phe Leu Gly Ile Ala Asn Tyr Ala Gln Lys Phe
        195                 200                 205

Gln Gly Arg Val Thr Leu Ile Ala Asp Lys Ser Thr Asn Thr Ala Tyr
    210                 215                 220

Met Glu Leu Ser Ser Leu Arg Ser Glu Asp Thr Ala Val Tyr Tyr Cys
225                 230                 235                 240

Ala Gly Glu Pro Gly Glu Arg Asp Pro Asp Ala Val Asp Ile Trp Gly
                245                 250                 255

Gln Gly Thr Met Val Thr Val Ser Ser Thr Thr Thr Pro Ala Pro Arg
            260                 265                 270

```
Pro Pro Thr Pro Ala Pro Thr Ile Ala Ser Gln Pro Ser Leu Arg
            275                 280                 285

Pro Glu Ala Cys Arg Pro Ala Ala Gly Gly Ala Val His Thr Arg Gly
290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Gly Gly Val Gln Val Glu
                485                 490                 495

Thr Ile Ser Pro Gly Asp Gly Arg Thr Phe Pro Lys Arg Gly Gln Thr
                500                 505                 510

Cys Val Val His Tyr Thr Gly Met Leu Glu Asp Gly Lys Lys Val Asp
                515                 520                 525

Ser Ser Arg Asp Arg Asn Lys Pro Phe Lys Phe Met Leu Gly Lys Gln
530                 535                 540

Glu Val Ile Arg Gly Trp Glu Glu Gly Val Ala Gln Met Ser Val Gly
545                 550                 555                 560

Gln Arg Ala Lys Leu Thr Ile Ser Pro Asp Tyr Ala Tyr Gly Ala Thr
                565                 570                 575

Gly His Pro Gly Ile Ile Pro Pro His Ala Thr Leu Val Phe Asp Val
                580                 585                 590

Glu Leu Leu Lys Leu Glu Gly Gly Tyr Pro Tyr Asp Val Pro Asp Tyr
                595                 600                 605

Ala

<210> SEQ ID NO 84
<211> LENGTH: 121
<212> TYPE: PRT
<213> ORGANISM: Artificial Sequence
<220> FEATURE:
<223> OTHER INFORMATION: scFv to CD38 variable heavy chain (VH)

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Ser Ser Tyr
```

```
            20                  25                  30
Ala Ile Ser Trp Val Arg Gln Ala Pro Gly Gln Gly Leu Glu Trp Met
        35                  40                  45

Gly Arg Ile Ile Arg Phe Leu Gly Lys Thr Asn His Ala Gln Lys Phe
    50                  55                  60

Gln Gly Arg Val Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Pro Gly Asp Arg Asp Pro Asp Ala Val Asp Ile Trp Gly
            100                 105                 110

Gln Gly Thr Met Val Thr Val Ser Ser
            115                 120

<210> SEQ ID NO 85
<211> LENGTH: 609
<212> TYPE: PRT
<213> ORGANISM: Artificial Sequence
<220> FEATURE:
<223> OTHER INFORMATION: CD38-CAR-dTAG

<400> SEQUENCE: 85

Met Ala Leu Pro Val Thr Ala Leu Leu Leu Pro Leu Ala Leu Leu Leu
1               5                   10                  15

His Ala Ala Arg Pro Asp Asp Ile Gln Met Thr Gln Ser Pro Ser Ser
                20                  25                  30

Leu Ser Ala Ser Val Gly Asp Arg Val Thr Ile Thr Cys Arg Ala Ser
        35                  40                  45

Gln Gly Ile Arg Ser Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Leu Thr Phe Gly Gly Gly Thr Lys Val Glu Ile
            115                 120                 125

Lys Gly Gly Gly Gly Ser Gly Gly Gly Gly Ser Gly Gly Gly Gly Ser
        130                 135                 140

Gln Val Gln Leu Val Gln Ser Gly Ala Glu Val Lys Lys Pro Gly Ser
145                 150                 155                 160

Ser Val Lys Val Ser Cys Lys Ala Phe Gly Gly Thr Phe Ser Ser Tyr
                165                 170                 175

Ala Ile Ser Trp Val Arg Gln Ala Pro Gly Gln Gly Leu Glu Trp Met
            180                 185                 190

Gly Arg Ile Ile Arg Phe Leu Gly Lys Thr Asn His Ala Gln Lys Phe
        195                 200                 205

Gln Gly Arg Val Thr Leu Thr Ala Asp Lys Ser Thr Asn Thr Ala Tyr
    210                 215                 220

Met Glu Leu Ser Ser Leu Arg Ser Glu Asp Thr Ala Val Tyr Tyr Cys
225                 230                 235                 240

Ala Gly Glu Pro Gly Asp Arg Asp Pro Asp Ala Val Asp Ile Trp Gly
                245                 250                 255

Gln Gly Thr Met Val Thr Val Ser Ser Thr Thr Thr Pro Ala Pro Arg
```

```
                260                 265                 270
Pro Pro Thr Pro Ala Pro Thr Ile Ala Ser Gln Pro Leu Ser Leu Arg
            275                 280                 285
Pro Glu Ala Cys Arg Pro Ala Ala Gly Gly Ala Val His Thr Arg Gly
            290                 295                 300
Leu Asp Phe Ala Cys Asp Ile Tyr Ile Trp Ala Pro Leu Ala Gly Thr
305                 310                 315                 320
Cys Gly Val Leu Leu Leu Ser Leu Val Ile Thr Leu Tyr Cys Lys Arg
                325                 330                 335
Gly Arg Lys Lys Leu Leu Tyr Ile Phe Lys Gln Pro Phe Met Arg Pro
                340                 345                 350
Val Gln Thr Thr Gln Glu Glu Asp Gly Cys Ser Cys Arg Phe Pro Glu
                355                 360                 365
Glu Glu Glu Gly Gly Cys Glu Leu Arg Val Lys Phe Ser Arg Ser Ala
            370                 375                 380
Asp Ala Pro Ala Tyr Lys Gln Gly Gln Asn Gln Leu Tyr Asn Glu Leu
385                 390                 395                 400
Asn Leu Gly Arg Arg Glu Glu Tyr Asp Val Leu Asp Lys Arg Arg Gly
                405                 410                 415
Arg Asp Pro Glu Met Gly Gly Lys Pro Arg Arg Lys Asn Pro Gln Glu
                420                 425                 430
Gly Leu Tyr Asn Glu Leu Gln Lys Asp Lys Met Ala Glu Ala Tyr Ser
                435                 440                 445
Glu Ile Gly Met Lys Gly Glu Arg Arg Arg Gly Lys Gly His Asp Gly
            450                 455                 460
Leu Tyr Gln Gly Leu Ser Thr Ala Thr Lys Asp Thr Tyr Asp Ala Leu
465                 470                 475                 480
His Met Gln Ala Leu Pro Pro Arg Gly Gly Gly Val Gln Val Glu
                485                 490                 495
Thr Ile Ser Pro Gly Asp Gly Arg Thr Phe Pro Lys Arg Gly Gln Thr
                500                 505                 510
Cys Val Val His Tyr Thr Gly Met Leu Glu Asp Gly Lys Lys Val Asp
                515                 520                 525
Ser Ser Arg Asp Arg Asn Lys Pro Phe Lys Phe Met Leu Gly Lys Gln
            530                 535                 540
Glu Val Ile Arg Gly Trp Glu Glu Gly Val Ala Gln Met Ser Val Gly
545                 550                 555                 560
Gln Arg Ala Lys Leu Thr Ile Ser Pro Asp Tyr Ala Tyr Gly Ala Thr
                565                 570                 575
Gly His Pro Gly Ile Ile Pro Pro His Ala Thr Leu Val Phe Asp Val
            580                 585                 590
Glu Leu Leu Lys Leu Glu Gly Gly Tyr Pro Tyr Asp Val Pro Asp Tyr
                595                 600                 605
Ala

<210> SEQ ID NO 86
<211> LENGTH: 107
<212> TYPE: PRT
<213> ORGANISM: Artificial Sequence
<220> FEATURE:
<223> OTHER INFORMATION: CD38 scFv variable light chain (VL)

<400> SEQUENCE: 86

Asp Ile Gln Met Thr Gln Ser Pro Ser Ser Leu Ser Ala Ser Val Gly
1               5                   10                  15
```

-continued

Asp Arg Val Thr Ile Thr Cys Arg Ala Ser Gln Gly Ile Arg Ser Trp
                20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Leu
                 85                  90                  95

Thr Phe Gly Gly Gly Thr Lys Val Glu Ile Lys
            100                 105

<210> SEQ ID NO 87
<211> LENGTH: 121
<212> TYPE: PRT
<213> ORGANISM: Artificial Sequence
<220> FEATURE:
<223> OTHER INFORMATION: scFv to CD38 variable heavy chain (VH)

<400> SEQUENCE: 87

Gln Val Gln Leu Val Gln Ser Gly Ala Glu Val Lys Lys Pro Gly Ser
1               5                  10                  15

Ser Val Lys Val Ser Cys Lys Pro Ser Gly Thr Phe Arg Ser Tyr
                20                  25                  30

Ala Ile Ser Trp Val Arg Gln Ala Pro Gly Gln Gly Leu Glu Trp Met
             35                  40                  45

Gly Arg Ile Ile Val Phe Leu Gly Lys Val Asn Tyr Ala Gln Arg Phe
 50                  55                  60

Gln Gly Arg Val Thr Leu Thr Ala Asp Lys Ser Thr Thr Thr Ala Tyr
65                  70                  75                  80

Met Glu Leu Ser Ser Leu Arg Ser Glu Asp Thr Ala Val Tyr Tyr Cys
                 85                  90                  95

Thr Gly Glu Pro Gly Ala Arg Asp Pro Asp Ala Phe Asp Ile Trp Gly
            100                 105                 110

Gln Gly Thr Met Val Thr Val Ser Ser
        115                 120

<210> SEQ ID NO 88
<211> LENGTH: 609
<212> TYPE: PRT
<213> ORGANISM: Artificial Sequence
<220> FEATURE:
<223> OTHER INFORMATION: CD38-CAR-dTAG

<400> SEQUENCE: 88

Met Ala Leu Pro Val Thr Ala Leu Leu Leu Pro Leu Ala Leu Leu Leu
1               5                  10                  15

His Ala Ala Arg Pro Asp Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Arg Ser Trp Leu Ala Trp Tyr Gln Gln Lys Pro Glu Lys
         50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr

```
                    85                  90                  95

Ile Ser Ser Leu Gln Pro Glu Asp Phe Ala Thr Tyr Tyr Cys Gln Gln
                100                 105                 110

Tyr Asn Asn Tyr Pro Leu Thr Phe Gly Gly Gly Thr Lys Val Glu Ile
                115                 120                 125

Lys Gly Gly Gly Gly Ser Gly Gly Gly Gly Ser Gly Gly Gly Gly Ser
130                 135                 140

Gln Val Gln Leu Val Gln Ser Gly Ala Glu Val Lys Lys Pro Gly Ser
145                 150                 155                 160

Ser Val Lys Val Ser Cys Lys Pro Ser Gly Gly Thr Phe Arg Ser Tyr
                165                 170                 175

Ala Ile Ser Trp Val Arg Gln Ala Pro Gly Gln Gly Leu Glu Trp Met
                180                 185                 190

Gly Arg Ile Ile Val Phe Leu Gly Lys Val Asn Tyr Ala Gln Arg Phe
                195                 200                 205

Gln Gly Arg Val Thr Leu Thr Ala Asp Lys Ser Thr Thr Thr Ala Tyr
                210                 215                 220

Met Glu Leu Ser Ser Leu Arg Ser Glu Asp Thr Ala Val Tyr Tyr Cys
225                 230                 235                 240

Thr Gly Glu Pro Gly Ala Arg Asp Pro Asp Ala Phe Asp Ile Trp Gly
                245                 250                 255

Gln Gly Thr Met Val Thr Val Ser Ser Thr Thr Thr Pro Ala Pro Arg
                260                 265                 270

Pro Pro Thr Pro Ala Pro Thr Ile Ala Ser Gln Pro Leu Ser Leu Arg
                275                 280                 285

Pro Glu Ala Cys Arg Pro Ala Ala Gly Gly Ala Val His Thr Arg Gly
                290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
                355                 360                 365

Glu Glu Glu Gly Gly Cys Glu Leu Arg Val Lys Phe Ser Arg Ser Ala
                370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
                450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Gly Gly Val Gln Val Glu
                485                 490                 495

Thr Ile Ser Pro Gly Asp Gly Arg Thr Phe Pro Lys Arg Gly Gln Thr
                500                 505                 510
```

```
Cys Val Val His Tyr Thr Gly Met Leu Glu Asp Gly Lys Lys Val Asp
            515                 520                 525

Ser Ser Arg Asp Arg Asn Lys Pro Phe Lys Phe Met Leu Gly Lys Gln
        530                 535                 540

Glu Val Ile Arg Gly Trp Glu Glu Gly Val Ala Gln Met Ser Val Gly
545                 550                 555                 560

Gln Arg Ala Lys Leu Thr Ile Ser Pro Asp Tyr Ala Tyr Gly Ala Thr
                565                 570                 575

Gly His Pro Gly Ile Ile Pro Pro His Ala Thr Leu Val Phe Asp Val
            580                 585                 590

Glu Leu Leu Lys Leu Glu Gly Gly Tyr Pro Tyr Asp Val Pro Asp Tyr
            595                 600                 605

Ala

<210> SEQ ID NO 89
<211> LENGTH: 106
<212> TYPE: PRT
<213> ORGANISM: Artificial Sequence
<220> FEATURE:
<223> OTHER INFORMATION: CD19 scFv variable light chain (VL)

<400> SEQUENCE: 89

Ile Gln Met Thr Gln Thr Thr Ser Ser Leu Ser Ala Ser Leu Gly Asp
1               5                   10                  15

Arg Val Thr Ile Ser Cys Arg Ala Ser Gln Asp Ile Ser Lys Tyr Leu
            20                  25                  30

Asn Trp Tyr Gln Gln Lys Pro Asp Gly Thr Val Lys Leu Leu Ile Tyr
        35                  40                  45

His Thr Ser Arg Leu His Ser Gly Val Pro Ser Arg Phe Ser Gly Ser
    50                  55                  60

Gly Ser Gly Thr Asp Tyr Ser Leu Thr Ile Ser Asn Leu Glu Gln Glu
65                  70                  75                  80

Asp Ile Ala Thr Tyr Phe Cys Gln Gln Gly Asn Thr Leu Pro Tyr Thr
                85                  90                  95

Phe Gly Gly Gly Thr Lys Leu Glu Ile Thr
            100                 105

<210> SEQ ID NO 90
<211> LENGTH: 120
<212> TYPE: PRT
<213> ORGANISM: Artificial Sequence
<220> FEATURE:
<223> OTHER INFORMATION: scFV to CD19 variable heavy chain (VH)

<400> SEQUENCE: 90

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95
```

-continued

Lys His Tyr Tyr Tyr Gly Gly Ser Tyr Ala Met Asp Tyr Trp Gly Gln
                100                 105                 110

Gly Thr Ser Val Thr Val Ser Ser
        115                 120

<210> SEQ ID NO 91
<211> LENGTH: 125
<212> TYPE: PRT
<213> ORGANISM: Artificial Sequence
<220> FEATURE:
<223> OTHER INFORMATION: dTAG derivative of BD1

<400> SEQUENCE: 91

Asn Pro Pro Pro Glu Thr Ser Asn Pro Asn Lys Pro Lys Arg Gln
1               5                   10                  15

Thr Asn Gln Leu Gln Tyr Leu Leu Arg Val Val Leu Lys Thr Leu Trp
        20                  25                  30

Lys His Gln Phe Ala Trp Pro Phe Gln Gln Pro Val Asp Ala Val Lys
    35                  40                  45

Leu Asn Leu Pro Asp Tyr Tyr Lys Ile Ile Lys Thr Pro Met Asp Met
50                  55                  60

Gly Thr Ile Lys Lys Arg Leu Glu Asn Asn Tyr Tyr Trp Asn Ala Gln
65                  70                  75                  80

Glu Cys Ile Gln Asp Phe Asn Thr Met Phe Thr Asn Cys Tyr Ile Tyr
                85                  90                  95

Asn Lys Pro Gly Asp Asp Ile Val Leu Met Ala Glu Ala Leu Glu Lys
            100                 105                 110

Leu Phe Leu Gln Lys Ile Asn Glu Leu Pro Thr Glu Glu
        115                 120                 125

<210> SEQ ID NO 92
<211> LENGTH: 625
<212> TYPE: PRT
<213> ORGANISM: Artificial Sequence
<220> FEATURE:
<223> OTHER INFORMATION: CD19-CAR-dTAG

<400> SEQUENCE: 92

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser

-continued

```
            145                 150                 155                 160
Leu Ser Val Thr Cys Thr Val Ser Gly Val Ser Leu Pro Asp Tyr Gly
                    165                 170                 175
Val Ser Trp Ile Arg Gln Pro Pro Arg Lys Gly Leu Glu Trp Leu Gly
                    180                 185                 190
Val Ile Trp Gly Ser Glu Thr Thr Tyr Tyr Asn Ser Ala Leu Lys Ser
                    195                 200                 205
Arg Leu Thr Ile Ile Lys Asp Asn Ser Lys Ser Gln Val Phe Leu Lys
                    210                 215                 220
Met Asn Ser Leu Gln Thr Asp Asp Thr Ala Ile Tyr Tyr Cys Ala Lys
225                 230                 235                 240
His Tyr Tyr Tyr Gly Gly Ser Tyr Ala Met Asp Tyr Trp Gly Gln Gly
                    245                 250                 255
Thr Ser Val Thr Val Ser Ser Thr Thr Pro Ala Pro Arg Pro Pro
                    260                 265                 270
Thr Pro Ala Pro Thr Ile Ala Ser Gln Pro Leu Ser Leu Arg Pro Glu
                    275                 280                 285
Ala Cys Arg Pro Ala Ala Gly Gly Ala Val His Thr Arg Gly Leu Asp
                    290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys Arg Gly Arg
                    325                 330                 335
Lys Lys Leu Leu Tyr Ile Phe Lys Gln Pro Phe Met Arg Pro Val Gln
                    340                 345                 350
Thr Thr Gln Glu Glu Asp Gly Cys Ser Cys Arg Phe Pro Glu Glu Glu
                    355                 360                 365
Glu Gly Gly Cys Glu Leu Arg Val Lys Phe Ser Arg Ser Ala Asp Ala
                    370                 375                 380
Pro Ala Tyr Lys Gln Gly Gln Asn Gln Leu Tyr Asn Glu Leu Asn Leu
385                 390                 395                 400
Gly Arg Arg Glu Glu Tyr Asp Val Leu Asp Lys Arg Arg Gly Arg Asp
                    405                 410                 415
Pro Glu Met Gly Gly Lys Pro Arg Arg Lys Asn Pro Gln Glu Gly Leu
                    420                 425                 430
Tyr Asn Glu Leu Gln Lys Asp Lys Met Ala Glu Ala Tyr Ser Glu Ile
                    435                 440                 445
Gly Met Lys Gly Glu Arg Arg Arg Gly Lys Gly His Asp Gly Leu Tyr
                    450                 455                 460
Gln Gly Leu Ser Thr Ala Thr Lys Asp Thr Tyr Asp Ala Leu His Met
465                 470                 475                 480
Gln Ala Leu Pro Pro Arg Gly Gly Asn Pro Pro Pro Glu Thr
                    485                 490                 495
Ser Asn Pro Asn Lys Pro Lys Arg Gln Thr Asn Gln Leu Gln Tyr Leu
                    500                 505                 510
Leu Arg Val Val Leu Lys Thr Leu Trp Lys His Gln Phe Ala Trp Pro
                    515                 520                 525
Phe Gln Gln Pro Val Asp Ala Val Lys Leu Asn Leu Pro Asp Tyr Tyr
                    530                 535                 540
Lys Ile Ile Lys Thr Pro Met Asp Met Gly Thr Ile Lys Lys Arg Leu
545                 550                 555                 560
Glu Asn Asn Tyr Tyr Trp Asn Ala Gln Glu Cys Ile Gln Asp Phe Asn
                    565                 570                 575
```

```
Thr Met Phe Thr Asn Cys Tyr Ile Tyr Asn Lys Pro Gly Asp Asp Ile
            580                 585                 590

Val Leu Met Ala Glu Ala Leu Glu Lys Leu Phe Leu Gln Lys Ile Asn
        595                 600                 605

Glu Leu Pro Thr Glu Gly Gly Tyr Pro Tyr Asp Val Pro Asp Tyr
    610                 615                 620

Ala
625

<210> SEQ ID NO 93
<211> LENGTH: 154
<212> TYPE: PRT
<213> ORGANISM: Artificial Sequence
<220> FEATURE:
<223> OTHER INFORMATION: dTAG derivative of MTH1

<400> SEQUENCE: 93

Gly Ala Ser Arg Leu Tyr Thr Leu Val Leu Val Leu Gln Pro Gln Arg
1               5                   10                  15

Val Leu Leu Gly Met Lys Lys Arg Gly Phe Gly Ala Gly Arg Trp Asn
            20                  25                  30

Gly Phe Gly Gly Lys Val Gln Glu Gly Glu Thr Ile Glu Asp Gly Ala
        35                  40                  45

Arg Arg Glu Leu Gln Glu Glu Ser Gly Leu Thr Val Asp Ala Leu His
    50                  55                  60

Lys Val Gly Gln Ile Val Phe Glu Phe Val Gly Glu Pro Glu Leu Met
65                  70                  75                  80

Asp Val His Val Phe Cys Thr Asp Ser Ile Gln Gly Thr Pro Val Glu
                85                  90                  95

Ser Asp Glu Met Arg Pro Cys Trp Phe Gln Leu Asp Gln Ile Pro Phe
            100                 105                 110

Lys Asp Met Trp Pro Asp Asp Ser Tyr Trp Phe Pro Leu Leu Leu Gln
        115                 120                 125

Lys Lys Lys Phe His Gly Tyr Phe Lys Phe Gln Gly Gln Asp Thr Ile
    130                 135                 140

Leu Asp Tyr Thr Leu Arg Glu Val Asp Thr
145                 150

<210> SEQ ID NO 94
<211> LENGTH: 655
<212> TYPE: PRT
<213> ORGANISM: Artificial Sequence
<220> FEATURE:
<223> OTHER INFORMATION: CD19-CAR-dTAG

<400> SEQUENCE: 94

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
```

-continued

```
                85                  90                  95
Ser Asn Leu Glu Gln Glu Asp Ile Ala Thr Tyr Phe Cys Gln Gln Gly
            100                 105                 110
Asn Thr Leu Pro Tyr Thr Phe Gly Gly Gly Thr Lys Leu Glu Ile Thr
            115                 120                 125
Gly Gly Gly Gly Ser Gly Gly Gly Ser Gly Gly Gly Gly Ser Glu
            130                 135                 140
Val Lys Leu Gln Glu Ser Gly Pro Gly Leu Val Ala Pro Ser Gln Ser
145                 150                 155                 160
Leu Ser Val Thr Cys Thr Val Ser Gly Val Ser Leu Pro Asp Tyr Gly
                165                 170                 175
Val Ser Trp Ile Arg Gln Pro Pro Arg Lys Gly Leu Glu Trp Leu Gly
                180                 185                 190
Val Ile Trp Gly Ser Glu Thr Thr Tyr Tyr Asn Ser Ala Leu Lys Ser
                195                 200                 205
Arg Leu Thr Ile Ile Lys Asp Asn Ser Lys Ser Gln Val Phe Leu Lys
            210                 215                 220
Met Asn Ser Leu Gln Thr Asp Asp Thr Ala Ile Tyr Tyr Cys Ala Lys
225                 230                 235                 240
His Tyr Tyr Tyr Gly Gly Ser Tyr Ala Met Asp Tyr Trp Gly Gln Gly
                245                 250                 255
Thr Ser Val Thr Val Ser Ser Thr Thr Thr Pro Ala Pro Arg Pro Pro
            260                 265                 270
Thr Pro Ala Pro Thr Ile Ala Ser Gln Pro Leu Ser Leu Arg Pro Glu
            275                 280                 285
Ala Cys Arg Pro Ala Ala Gly Gly Ala Val His Thr Arg Gly Leu Asp
            290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys Arg Gly Arg
                325                 330                 335
Lys Lys Leu Leu Tyr Ile Phe Lys Gln Pro Phe Met Arg Pro Val Gln
            340                 345                 350
Thr Thr Gln Glu Glu Asp Gly Cys Ser Cys Arg Phe Pro Glu Glu Glu
            355                 360                 365
Glu Gly Gly Cys Glu Leu Arg Val Lys Phe Ser Arg Ser Ala Asp Ala
            370                 375                 380
Pro Ala Tyr Lys Gln Gly Gln Asn Gln Leu Tyr Asn Glu Leu Asn Leu
385                 390                 395                 400
Gly Arg Arg Glu Glu Tyr Asp Val Leu Asp Lys Arg Arg Gly Arg Asp
                405                 410                 415
Pro Glu Met Gly Gly Lys Pro Arg Arg Lys Asn Pro Gln Glu Gly Leu
                420                 425                 430
Tyr Asn Glu Leu Gln Lys Asp Lys Met Ala Glu Ala Tyr Ser Glu Ile
            435                 440                 445
Gly Met Lys Gly Glu Arg Arg Arg Gly Lys Gly His Asp Gly Leu Tyr
            450                 455                 460
Gln Gly Leu Ser Thr Ala Thr Lys Asp Thr Tyr Asp Ala Leu His Met
465                 470                 475                 480
Gln Ala Leu Pro Pro Arg Gly Gly Gly Ala Ser Arg Leu Tyr Thr
                485                 490                 495
Leu Val Leu Val Leu Gln Pro Gln Arg Val Leu Leu Gly Met Lys Lys
            500                 505                 510
```

```
Arg Gly Phe Gly Ala Gly Arg Trp Asn Gly Phe Gly Lys Val Gln
        515                 520                 525

Glu Gly Glu Thr Ile Glu Asp Gly Ala Arg Arg Glu Leu Gln Glu Glu
530                 535                 540

Ser Gly Leu Thr Val Asp Ala Leu His Lys Val Gly Gln Ile Val Phe
545                 550                 555                 560

Glu Phe Val Gly Glu Pro Glu Leu Met Asp Val His Val Phe Cys Thr
                565                 570                 575

Asp Ser Ile Gln Gly Thr Pro Val Glu Ser Asp Glu Met Arg Pro Cys
            580                 585                 590

Trp Phe Gln Leu Asp Gln Ile Pro Phe Lys Asp Met Trp Pro Asp Asp
        595                 600                 605

Ser Tyr Trp Phe Pro Leu Leu Leu Gln Lys Lys Lys Phe His Gly Tyr
    610                 615                 620

Phe Lys Phe Gln Gly Gln Asp Thr Ile Leu Asp Tyr Thr Leu Arg Glu
625                 630                 635                 640

Val Asp Thr Val Gly Gly Tyr Pro Tyr Asp Val Pro Asp Tyr Ala
                645                 650                 655

<210> SEQ ID NO 95
<211> LENGTH: 125
<212> TYPE: PRT
<213> ORGANISM: Artificial Sequence
<220> FEATURE:
<223> OTHER INFORMATION: dTAG derived from BRD4

<400> SEQUENCE: 95

Asn Pro Pro Pro Glu Thr Ser Asn Pro Asn Lys Pro Lys Arg Gln
1               5                   10                  15

Thr Asn Gln Leu Gln Tyr Leu Leu Arg Val Val Leu Lys Thr Leu Trp
            20                  25                  30

Lys His Gln Phe Ala Trp Pro Phe Gln Gln Pro Val Asp Ala Val Lys
        35                  40                  45

Leu Asn Leu Pro Asp Tyr Tyr Lys Ile Ile Lys Thr Pro Met Asp Met
50                  55                  60

Gly Thr Ile Lys Lys Arg Leu Glu Asn Asn Tyr Tyr Trp Asn Ala Gln
65                  70                  75                  80

Glu Cys Ile Gln Asp Phe Asn Thr Met Phe Thr Asn Cys Tyr Ile Tyr
                85                  90                  95

Asn Lys Pro Gly Asp Asp Ile Val Leu Met Ala Glu Ala Leu Glu Lys
            100                 105                 110

Leu Phe Leu Gln Lys Ile Asn Glu Leu Pro Thr Glu Glu
        115                 120                 125

<210> SEQ ID NO 96
<211> LENGTH: 71
<212> TYPE: PRT
<213> ORGANISM: Homo sapiens

<400> SEQUENCE: 96

Ser Arg Gln Ala Leu Ala Ala Pro Leu Leu Asn Leu Pro Pro Lys Lys
1               5                   10                  15

Lys Asn Ala Asp Tyr Tyr Glu Lys Ile Ser Asp Pro Leu Asp Leu Ile
            20                  25                  30

Thr Ile Glu Lys Gln Ile Leu Thr Gly Tyr Tyr Lys Thr Val Glu Ala
        35                  40                  45
```

```
Phe Asp Ala Asp Met Leu Lys Val Phe Arg Asn Ala Glu Lys Tyr Tyr
            50                  55                  60

Gly Arg Lys Ser Pro Val Gly
65                  70

<210> SEQ ID NO 97
<211> LENGTH: 70
<212> TYPE: PRT
<213> ORGANISM: Homo sapiens

<400> SEQUENCE: 97

Ala Ile Asp Lys Arg Phe Arg Val Phe Thr Lys Pro Val Asp Pro Asp
1               5                   10                  15

Glu Val Pro Asp Tyr Val Thr Val Ile Lys Gln Pro Met Asp Leu Ser
                20                  25                  30

Ser Val Ile Ser Lys Ile Asp Leu His Lys Tyr Leu Thr Val Lys Asp
            35                  40                  45

Tyr Leu Arg Asp Ile Asp Leu Ile Cys Ser Asn Ala Leu Glu Tyr Asn
        50                  55                  60

Pro Asp Arg Asp Pro Gly
65                  70

<210> SEQ ID NO 98
<211> LENGTH: 71
<212> TYPE: PRT
<213> ORGANISM: Homo sapiens

<400> SEQUENCE: 98

Val Arg His Asp Asp Ser Trp Pro Phe Leu Lys Leu Val Ser Lys Ile
1               5                   10                  15

Gln Val Pro Asp Tyr Tyr Asp Ile Ile Lys Lys Pro Ile Ala Leu Asn
                20                  25                  30

Ile Ile Arg Glu Lys Val Asn Lys Cys Glu Tyr Lys Leu Ala Ser Glu
            35                  40                  45

Phe Ile Asp Asp Ile Glu Leu Met Phe Ser Asn Cys Phe Glu Tyr Asn
        50                  55                  60

Pro Arg Asn Thr Ser Glu Ala
65                  70

<210> SEQ ID NO 99
<211> LENGTH: 71
<212> TYPE: PRT
<213> ORGANISM: Homo sapiens

<400> SEQUENCE: 99

Val Lys Tyr Arg Phe Ser Trp Pro Phe Arg Glu Pro Val Thr Arg Asp
1               5                   10                  15

Glu Ala Glu Asp Tyr Tyr Asp Val Ile Thr His Pro Met Asp Phe Gln
                20                  25                  30

Thr Val Gln Asn Lys Cys Ser Cys Gly Ser Tyr Arg Ser Val Gln Glu
            35                  40                  45

Phe Leu Thr Asp Met Lys Gln Val Phe Thr Asn Ala Glu Val Tyr Asn
        50                  55                  60

Cys Arg Gly Ser His Val Leu
65                  70

<210> SEQ ID NO 100
<211> LENGTH: 71
<212> TYPE: PRT
```

-continued

<213> ORGANISM: Homo sapiens

<400> SEQUENCE: 100

Glu Ser His Asp Ala Ala Trp Pro Phe Leu Glu Pro Val Asn Pro Arg
1               5                   10                  15

Leu Val Ser Gly Tyr Arg Arg Ile Ile Lys Asn Pro Met Asp Phe Ser
            20                  25                  30

Thr Met Arg Glu Arg Leu Leu Arg Gly Gly Tyr Thr Ser Ser Glu Glu
        35                  40                  45

Phe Ala Ala Asp Ala Leu Leu Val Phe Asp Asn Cys Gln Thr Phe Asn
    50                  55                  60

Glu Asp Asp Ser Glu Val Gly
65                  70

<210> SEQ ID NO 101
<211> LENGTH: 71
<212> TYPE: PRT
<213> ORGANISM: Homo sapiens

<400> SEQUENCE: 101

Glu Thr His Glu Asp Ala Trp Pro Phe Leu Leu Pro Val Asn Leu Lys
1               5                   10                  15

Leu Val Pro Gly Tyr Lys Lys Val Ile Lys Lys Pro Met Asp Phe Ser
            20                  25                  30

Thr Ile Arg Glu Lys Leu Ser Ser Gly Gln Tyr Pro Asn Leu Glu Thr
        35                  40                  45

Phe Ala Leu Asp Val Arg Leu Val Phe Asp Asn Cys Glu Thr Phe Asn
    50                  55                  60

Glu Asp Asp Ser Asp Ile Gly
65                  70

<210> SEQ ID NO 102
<211> LENGTH: 71
<212> TYPE: PRT
<213> ORGANISM: Homo sapiens

<400> SEQUENCE: 102

Gln Asp Lys Asp Pro Ala Arg Ile Phe Ala Gln Pro Val Ser Leu Lys
1               5                   10                  15

Glu Val Pro Asp Tyr Leu Asp His Ile Lys His Pro Met Asp Phe Ala
            20                  25                  30

Thr Met Arg Lys Arg Leu Glu Ala Gln Gly Tyr Lys Asn Leu His Glu
        35                  40                  45

Phe Glu Glu Asp Phe Asp Leu Ile Ile Asp Asn Cys Met Lys Tyr Asn
    50                  55                  60

Ala Arg Asp Thr Val Phe Tyr
65                  70

<210> SEQ ID NO 103
<211> LENGTH: 71
<212> TYPE: PRT
<213> ORGANISM: Homo sapiens

<400> SEQUENCE: 103

Gln Arg Lys Asp Pro Ser Ala Phe Phe Ser Phe Pro Val Thr Asp Phe
1               5                   10                  15

Ile Ala Pro Gly Tyr Ser Met Ile Ile Lys His Pro Met Asp Phe Ser
            20                  25                  30

```
Thr Met Lys Glu Lys Ile Lys Asn Asn Asp Tyr Gln Ser Ile Glu Glu
            35                  40                  45

Leu Lys Asp Asn Phe Lys Leu Met Cys Thr Asn Ala Met Ile Tyr Asn
 50                      55                  60

Lys Pro Glu Thr Ile Tyr Tyr
 65                  70

<210> SEQ ID NO 104
<211> LENGTH: 71
<212> TYPE: PRT
<213> ORGANISM: Homo sapiens

<400> SEQUENCE: 104

Ala Asn His Arg Tyr Ala Asn Val Phe Leu Gln Pro Val Thr Asp Asp
 1               5                  10                  15

Ile Ala Pro Gly Tyr His Ser Ile Val Gln Arg Pro Met Asp Leu Ser
            20                  25                  30

Thr Ile Lys Lys Asn Ile Glu Asn Gly Leu Ile Arg Ser Thr Ala Glu
            35                  40                  45

Phe Gln Arg Asp Ile Met Leu Met Phe Gln Asn Ala Val Met Tyr Asn
 50                      55                  60

Ser Ser Asp His Asp Val Tyr
 65                  70

<210> SEQ ID NO 105
<211> LENGTH: 71
<212> TYPE: PRT
<213> ORGANISM: Homo sapiens

<400> SEQUENCE: 105

Ala Ser His Arg Phe Ser Ser Pro Phe Leu Lys Pro Val Ser Glu Arg
 1               5                  10                  15

Gln Ala Pro Gly Tyr Lys Asp Val Val Lys Arg Pro Met Asp Leu Thr
            20                  25                  30

Ser Leu Lys Arg Asn Leu Ser Lys Gly Arg Ile Arg Thr Met Ala Gln
            35                  40                  45

Phe Leu Arg Asp Leu Met Leu Met Phe Gln Asn Ala Val Met Tyr Asn
 50                      55                  60

Asp Ser Asp His His Val Tyr
 65                  70

<210> SEQ ID NO 106
<211> LENGTH: 71
<212> TYPE: PRT
<213> ORGANISM: Homo sapiens

<400> SEQUENCE: 106

Gln Arg Lys Asp Pro His Gly Phe Phe Ala Phe Pro Val Thr Asp Ala
 1               5                  10                  15

Ile Ala Pro Gly Tyr Ser Met Ile Ile Lys His Pro Met Asp Phe Gly
            20                  25                  30

Thr Met Lys Asp Lys Ile Val Ala Asn Glu Tyr Lys Ser Val Thr Glu
            35                  40                  45

Phe Lys Ala Asp Phe Lys Leu Met Cys Asp Asn Ala Met Thr Tyr Asn
 50                      55                  60

Arg Pro Asp Thr Val Tyr Tyr
 65                  70
```

```
<210> SEQ ID NO 107
<211> LENGTH: 73
<212> TYPE: PRT
<213> ORGANISM: Homo sapiens

<400> SEQUENCE: 107

Trp Lys His Ser Phe Ser Trp Pro Phe Gln Arg Pro Val Asp Ala Val
1               5                   10                  15

Lys Leu Gln Leu Pro Asp Tyr Tyr Thr Ile Ile Lys Asn Pro Met Asp
            20                  25                  30

Leu Asn Thr Ile Lys Lys Arg Leu Glu Asn Lys Tyr Tyr Ala Lys Ala
        35                  40                  45

Ser Glu Cys Ile Glu Asp Phe Asn Thr Met Phe Ser Asn Cys Tyr Leu
    50                  55                  60

Tyr Asn Lys Pro Gly Asp Asp Ile Val
65                  70

<210> SEQ ID NO 108
<211> LENGTH: 72
<212> TYPE: PRT
<213> ORGANISM: Homo sapiens

<400> SEQUENCE: 108

Lys His Phe Ser Tyr Ala Trp Pro Phe Tyr Asn Pro Val Asp Val Asn
1               5                   10                  15

Ala Leu Gly Leu His Asn Tyr Tyr Asp Val Val Lys Asn Pro Met Asp
            20                  25                  30

Leu Gly Thr Ile Lys Glu Lys Met Asp Asn Gln Glu Tyr Lys Asp Ala
        35                  40                  45

Tyr Lys Phe Ala Ala Asp Val Arg Leu Met Phe Met Asn Cys Tyr Lys
    50                  55                  60

Tyr Asn Pro Pro Asp His Glu Val
65                  70

<210> SEQ ID NO 109
<211> LENGTH: 71
<212> TYPE: PRT
<213> ORGANISM: Homo sapiens

<400> SEQUENCE: 109

Gln Glu Lys Asp Thr Gly Asn Ile Phe Ser Glu Pro Val Pro Leu Ser
1               5                   10                  15

Glu Val Pro Asp Tyr Leu Asp His Ile Lys Lys Pro Met Asp Phe Phe
            20                  25                  30

Thr Met Lys Gln Asn Leu Glu Ala Tyr Arg Tyr Leu Asn Phe Asp Asp
        35                  40                  45

Phe Glu Glu Asp Phe Asn Leu Ile Val Ser Asn Cys Leu Lys Tyr Asn
    50                  55                  60

Ala Lys Asp Thr Ile Phe Tyr
65                  70

<210> SEQ ID NO 110
<211> LENGTH: 71
<212> TYPE: PRT
<213> ORGANISM: Homo sapiens

<400> SEQUENCE: 110

Gln Glu Lys Asp Pro Ala His Ile Phe Ala Glu Pro Val Asn Leu Ser
1               5                   10                  15
```

Glu Val Pro Asp Tyr Leu Glu Phe Ile Ser Lys Pro Met Asp Phe Ser
                20                  25                  30

Thr Met Arg Arg Lys Leu Glu Ser His Leu Tyr Arg Thr Leu Glu Glu
            35                  40                  45

Phe Glu Glu Asp Phe Asn Leu Ile Val Thr Asn Cys Met Lys Tyr Asn
        50                  55                  60

Ala Lys Asp Thr Ile Phe His
65                  70

<210> SEQ ID NO 111
<211> LENGTH: 71
<212> TYPE: PRT
<213> ORGANISM: Homo sapiens

<400> SEQUENCE: 111

Leu Ser Leu Asp Phe Ala Ser Pro Phe Ala Val Pro Val Asp Leu Ser
1               5                   10                  15

Ala Tyr Pro Leu Tyr Cys Thr Val Val Ala Tyr Pro Thr Asp Leu Asn
                20                  25                  30

Thr Ile Arg Arg Arg Leu Glu Asn Arg Phe Tyr Arg Arg Ile Ser Ala
            35                  40                  45

Leu Met Trp Glu Val Arg Tyr Ile Glu His Asn Ala Arg Thr Phe Asn
        50                  55                  60

Glu Pro Asp Ser Pro Ile Val
65                  70

<210> SEQ ID NO 112
<211> LENGTH: 96
<212> TYPE: PRT
<213> ORGANISM: Homo sapiens

<400> SEQUENCE: 112

Tyr Glu Arg Glu Asp Ser Glu Pro Phe Arg Gln Pro Ala Asp Leu Leu
1               5                   10                  15

Ser Tyr Pro Gly His Gln Glu Gln Glu Gly Glu Ser Ser Glu Ser Val
                20                  25                  30

Val Pro Glu Arg Gln Gln Asp Ser Ser Leu Ser Glu Asp Tyr Gln Asp
            35                  40                  45

Val Ile Asp Thr Pro Val Asp Phe Ser Thr Val Lys Glu Thr Leu Glu
        50                  55                  60

Ala Gly Asn Tyr Gly Ser Pro Leu Glu Phe Tyr Lys Asp Val Arg Gln
65                  70                  75                  80

Ile Phe Asn Asn Ser Lys Ala Tyr Thr Ser Asn Lys Lys Ser Arg Ile
                85                  90                  95

<210> SEQ ID NO 113
<211> LENGTH: 71
<212> TYPE: PRT
<213> ORGANISM: Homo sapiens

<400> SEQUENCE: 113

Lys Ala His Lys Asp Ser Trp Pro Phe Leu Glu Pro Val Asp Glu Ser
1               5                   10                  15

Tyr Ala Pro Asn Tyr Tyr Gln Ile Ile Lys Ala Pro Met Asp Ile Ser
                20                  25                  30

Ser Met Glu Lys Lys Leu Asn Gly Gly Leu Tyr Cys Thr Lys Glu Glu
            35                  40                  45

Phe Val Asn Asp Met Lys Thr Met Phe Arg Asn Cys Arg Lys Tyr Asn

```
                  50                  55                  60

Gly Glu Ser Ser Glu Tyr Thr
 65                  70

<210> SEQ ID NO 114
<211> LENGTH: 254
<212> TYPE: PRT
<213> ORGANISM: Artificial Sequence
<220> FEATURE:
<223> OTHER INFORMATION: dTAG

<400> SEQUENCE: 114

Leu Arg Leu Glu Val Lys Leu Gly Gln Gly Cys Phe Gly Glu Val Trp
 1               5                  10                  15

Met Gly Thr Trp Asn Gly Thr Thr Arg Val Ala Ile Lys Thr Leu Lys
             20                  25                  30

Pro Gly Thr Met Ser Pro Glu Ala Phe Leu Gln Glu Ala Gln Val Met
         35                  40                  45

Lys Lys Leu Arg His Glu Lys Leu Val Gln Leu Tyr Ala Val Val Ser
     50                  55                  60

Glu Glu Pro Ile Tyr Ile Val Thr Glu Tyr Gly Ser Lys Gly Ser Leu
 65                  70                  75                  80

Leu Asp Phe Leu Lys Gly Glu Thr Gly Lys Tyr Leu Arg Leu Pro Gln
                 85                  90                  95

Leu Val Asp Met Ala Ala Gln Ile Ala Ser Gly Met Ala Tyr Val Glu
            100                 105                 110

Arg Met Asn Tyr Val His Arg Asp Leu Arg Ala Ala Asn Ile Leu Val
        115                 120                 125

Gly Glu Asn Leu Val Cys Lys Val Ala Asp Phe Gly Leu Ala Arg Leu
    130                 135                 140

Ile Glu Asp Asn Glu Tyr Thr Ala Arg Gln Gly Ala Lys Phe Pro Ile
145                 150                 155                 160

Lys Trp Thr Ala Pro Glu Ala Ala Leu Tyr Gly Arg Phe Thr Ile Lys
                165                 170                 175

Ser Asp Val Trp Ser Phe Gly Ile Leu Leu Thr Glu Leu Thr Thr Lys
            180                 185                 190

Gly Arg Val Pro Tyr Pro Gly Met Val Asn Arg Glu Val Leu Asp Gln
        195                 200                 205

Val Glu Arg Gly Tyr Arg Met Pro Cys Pro Pro Glu Cys Pro Glu Ser
    210                 215                 220

Leu His Asp Leu Met Cys Gln Cys Trp Arg Lys Glu Pro Glu Glu Arg
225                 230                 235                 240

Pro Thr Phe Glu Tyr Leu Gln Ala Phe Leu Glu Asp Tyr Phe
                245                 250

<210> SEQ ID NO 115
<211> LENGTH: 254
<212> TYPE: PRT
<213> ORGANISM: Artificial Sequence
<220> FEATURE:
<223> OTHER INFORMATION: dTAG

<400> SEQUENCE: 115

Leu Arg Leu Glu Val Lys Leu Gly Gln Gly Cys Phe Gly Glu Val Trp
 1               5                  10                  15

Met Gly Thr Trp Asn Gly Thr Thr Arg Val Ala Ile Lys Thr Leu Lys
             20                  25                  30
```

-continued

```
Pro Gly Thr Met Ser Pro Glu Ala Phe Leu Gln Glu Ala Gln Val Met
         35              40              45
Lys Lys Leu Arg His Glu Lys Leu Val Gln Leu Tyr Ala Val Val Ser
 50              55              60
Glu Glu Pro Ile Tyr Ile Val Thr Glu Tyr Ala Ser Lys Gly Ser Leu
 65              70              75              80
Leu Asp Phe Leu Lys Gly Glu Thr Gly Lys Tyr Leu Arg Leu Pro Gln
             85              90              95
Leu Val Asp Met Ala Ala Gln Ile Ala Ser Gly Met Ala Tyr Val Glu
            100             105             110
Arg Met Asn Tyr Val His Arg Asp Leu Arg Ala Ala Asn Ile Leu Val
            115             120             125
Gly Glu Asn Leu Val Cys Lys Val Ala Asp Phe Gly Leu Ala Arg Leu
    130             135             140
Ile Glu Asp Asn Glu Tyr Thr Ala Arg Gln Gly Ala Lys Phe Pro Ile
145             150             155             160
Lys Trp Thr Ala Pro Glu Ala Ala Leu Tyr Gly Arg Phe Thr Ile Lys
                165             170             175
Ser Asp Val Trp Ser Phe Gly Ile Leu Leu Thr Glu Leu Thr Thr Lys
            180             185             190
Gly Arg Val Pro Tyr Pro Gly Met Val Asn Arg Glu Val Leu Asp Gln
        195             200             205
Val Glu Arg Gly Tyr Arg Met Pro Cys Pro Pro Glu Cys Pro Glu Ser
    210             215             220
Leu His Asp Leu Met Cys Gln Cys Trp Arg Lys Glu Pro Glu Glu Arg
225             230             235             240
Pro Thr Phe Glu Tyr Leu Gln Ala Phe Leu Glu Asp Tyr Phe
                245             250
```

REGULATING CHIMERIC ANTIGEN RECEPTORS

RELATED APPLICATIONS

This application is a national stage application, filed under 35 U.S.C. § 371, of International Application No. PCT/US2018/017464, filed Feb. 8, 2018, which claims the benefit of provisional U.S. Application No. 62/456,649, filed Feb. 8, 2017, and provisional U.S. application No. 62/457,124, filed Feb. 9, 2017. The entirety of these applications are hereby incorporated by reference for all purposes.

GOVERNMENT LICENSE RIGHTS

This invention was made with government support under grant numbers R01 CA176745 and P01 CA066996 awarded by the National Institutes of Health. The government has certain rights in the invention.

INCORPORATION BY REFERENCE OF SEQUENCE LISTING

The contents of the text file named "52095_625N01US_SequenceListing_ST25.txt," which was created on Jun. 2, 2021, and is 361 KB in size, are hereby incorporated by reference in their entirety.

FIELD OF THE INVENTION

This invention is in the area of improving the safety profile of engineered immune effector cells, for example chimeric antigen receptor T-cells (CAR-T), by including regulatable and targeted protein degradation elements when a chimeric antigen receptor (CAR) or engineered T-cell receptor (TCR) that allow for the modulation of CAR or TCR expression, and thus CAR-T-cell or TCR-T-cell activation, in response to associated adverse effects, for example, off-target effects and inflammatory responses such as cytokine release syndrome and tumor lysis syndrome.

BACKGROUND

The adoptive transfer of genetically engineered immune effector cells aims to rapidly establish T-cell mediated tumor immunity. In this approach, the patient's own T-cells, or other immune effector cells, are targeted to bind to tumor cells through transgene-encoded chimeric antigen receptors (CARs) or engineered T-cell receptors (TCRs). When expressed in T-cells, CARs efficiently redirect T-cell specificity and cytotoxicity to tumor cells in a mechanism that is independent of antigen processing. Through this approach, CAR T-cells overcome issues with immune tolerance and the requirement of major histocompatibility complex (MEW) presentation of antigens. CARs are synthetic, engineered receptors that contain sequences that encode antibody-based recognition domains linked to intracellular T-cell signaling sequences. First generation CARs include an extracellular single chain variable fragment (scFv) derived from an antibody and directed against a tumor target antigen, linked to an intracellular CD3ζ signaling module. Second and third generation CARs have evolved to now include multiple co-stimulatory domains including, but not limited, to 4-1BB and CD28.

Results from early clinical trials have established the therapeutic efficacy of CAR-T therapy in a number of cancers, including lymphoma (Till et al., "CD20-specific adoptive immunotherapy for lymphoma using a chimeric antigen receptor with both CD28 and 4-1 BB domains: pilot clinical trial results." *Blood* 119 (2012): 3940-3950), chronic lymphocytic leukemia (CLL) (Porter et al., "Chimeric antigen receptor modified T-cells in chronic lymphoid leukemia." *NEJM* 365 (2011):725-733), acute lymphoblastic leukemia (ALL) (Grupp et al., "Chimeric antigen receptor modified T-cells for acute lymphoid leukemia." *NEJM* 368 (2013):1509-1518), and neuroblastoma (Louis et al., "Antitumor activity and long-term date of chimeric antigen receptor-positive T-cells in patients with neuroblastoma." *Blood* 118 (2011):6050-6056), among others.

In November 2014, the FDA granted orphan status to Juno Therapeutic, Inc.'s JCAR015. Kite Pharma, Inc.'s KTE-C19 for refractory aggressive non-Hodgkin's lymphoma also recently received the designation from both the FDA and the European Medicines Agency. The University of Pennsylvania/Novartis's CTL019 for ALL also received breakthrough status.

Recently, CAR-T cells containing γδ receptors targeting solid tumors such as melanoma and gastrointestinal tumors have been proposed. Mirzaei et al., "Prospects for chimeric antigen receptor (CAR) γδ T cells: A potential game changer for adoptive T cell cancer immunotherapy," Cancer Letters 380 (2016):413-423.

CAR T-cell therapy is not, however, without significant side effects. Although most adverse events with CAR-T are tolerable and acceptable, the administration of CAR T-cells has, in a number of cases, resulted in severe systemic inflammatory reactions, including cytokine release syndrome and tumor lysis syndrome (Xu et al., "Efficacy and safety of adoptive immunotherapy using anti-CD19 chimeric antigen receptor transduced T-cells: a systemic review of phase I clinical trials." *Leukemia Lymphoma* 54 (2013):255-260; Minagawa et al., "Seatbelts in CAR therapy: how safe are CARS?" *Pharmaceuticals* 8 (2015):230-249). For example, in 2010, two deaths were attributed to the development of cytokine release syndrome following administration of CAR T-cells in the clinical setting (Brentjens et al., "Treatment of chronic lymphocytic leukemia with genetically targeted autologous T-cells: case report of an unforeseen adverse event in a phase I clinical trial." *Mol. Ther.* 18 (2010):666-668; Morgan et al., "Case report of a serious adverse event following the administration of T-cells transduced with a chimeric antigen receptor recognizing ERBB2." *Mol. Ther.* 18 (2010):843-851).

Cytokine release syndrome (CRS) is an inflammatory response clinically manifesting with fever, nausea, headache, tachycardia, hypotension, hypoxia, as well as cardiac and/or neurologic manifestations. Severe cytokine release syndrome is described as a cytokine storm, and can be fatal. CRS is believed to be a result of the sustained activation of a variety of cell types such as monocytes and macrophages, T-cells and B cells, and is generally characterized by an increase in levels of TNFα and IFNγ within 1 to 2 hours of stimulus exposure, followed by increases in interleukin (IL)-6 and IL-10 and, in some cases, IL-2 and IL-8 (Doessegger et al., "Clinical development methodology for infusion-related reactions with monoclonal antibodies." *Nat. Clin. Transl. Immuno.* 4 (2015):e39).

Tumor lysis syndrome (TLS) is a metabolic syndrome that is caused by the sudden killing of tumor cells with chemotherapy, and subsequent release of cellular contents with the release of large amounts of potassium, phosphate, and nucleic acids into the systemic circulation. Catabolism of the nucleic acids to uric acid leads to hyperuricemia; the marked increase in uric acid excretion can result in the precipitation of uric acid in the renal tubules and renal vasoconstriction, impaired autoregulation, decreased renal flow, oxidation, and inflammation, resulting in acute kidney injury. Hyperphosphatemia with calcium phosphate deposition in the renal tubules can also cause acute kidney injury. High concentrations of both uric acid and phosphate potentiate the risk of acute kidney injury because uric acid precipitates more readily in the presence of calcium phosphate and vice versa that results in hyperkalemia, hyperphosphotemia, hypocalcemia, remia, and acute renal failure. It usually occurs in patients with bulky, rapidly proliferating, treatment-responsive tumors (Wintrobe M M, et al., "Complications of hematopoietic neoplasms." *Wintrobe's Clinical Hematology*, 11th ed. Philadelphia, Pa.: Lippincott Williams & Wilkins; Vol II (2003):1919-1944).

The dramatic clinical activity of CAR T-cell therapy necessitates the need to implement additional "safety" strategies to rapidly reverse or abort the T-cell responses in patients that are undergoing CRS or associated adverse events. Metabolic approaches including co-expression of Herpes simplex virus-thymidine kinase (HSV-TK) induce apoptosis of CAR T-cells upon treatment with ganciclovir. This approach is limited by the delayed kinetics of response and the potential for immunogenic reaction to HSV. Apoptosis promoting strategies have been developed in which a drug binding domain is expressed in frame with components of the apoptotic machinery, including Caspase 9 and FAS. This system allows for conditional activation of apoptosis upon administration of a small molecule inducer of dimerization. The effect is rapid, non-immunogenic, and reduces payload of transduced cells by 90%. Both approaches are currently being evaluated in clinical trials. While expression of "suicide" genes provides a mechanism to reverse the unwanted toxicities, both approaches are considered irreversible, effectively limiting any further therapeutic benefit to the patient.

Other strategies for controlling CAR T-cell activation include separating dual costimulatory domains from the antigen-recognition domain, wherein stimulation of the CAR T-cell is controlled by a small-molecule drug—rimiducid. These T-cells, known as GoCAR-Ts, can only be fully activated when they are exposed to both cancer cells and the drug. In addition, strategies incorporating bispecific CARs which includes a second binding domain on the CAR T-cell that can lead to either an inhibitory or amplifying signal, allows for decreased off-target effects, wherein the presence of one target protein leads to activation of the CAR T-cell while the presence of a second protein leads to inhibition.

WO2016/115177 to Juno Therapeutics, Inc. titled "Modified Hepatitis Post-Transcriptional Regulatory Elements" describes the inclusion of post-transcriptional regulatory elements (PREs) in administered proteins to hasten degradation by encouraging natural ubiquination of the protein and shorten half-life, including for example chimeric antigen receptors. The employed strategy, however, is not regulatable.

Jensen and Riddell, Design and implementation of adoptive therapy with chimeric antigen receptor-modified T cells, Immunol. Rev. 2014; 257(1):127-144 and WO2016/149254 to Chimera Bioengineering, Inc. titled "SMART CAR Devices, DE CAR Polypeptides, SIDE CARS and Uses Thereof describes the use of ligand-dependent destabilization domains (DD) and the Shield1 ligand to reversibly stabilize and destabilize a DD-tagged CAR. Jensen and Riddell, however, note that the use of such an approach is challenging due to the uncertainty of activation of the CAR in the presence of the small molecule and potential toxicity issues associated with such as strategy.

WO2016/200822 to Axiomx, Inc. titled "Methods and Compositions for Producing a Chimeric Polypeptide" describes the use of a mitotag and a small molecule, for example rapamycin or a rapamycin analogue, to sequester a chimeric antigen receptor to an intracellular region, for example mitochondrian, and thereby inactive the CAR. The use of rapamycin, however, It is an object of the present invention to provide effective, non-toxic reversible treatments which can modulate the activity of CAR T-cells and reduce adverse inflammatory responses.

SUMMARY OF THE INVENTION

Compositions, engineered cells, such as immune or immunostimulatory cells, and methods for mediating CAR immune effector cell stimulation, for example T-cell stimulation, through the incorporation of a heterobifunctional compound targeted protein, protein domain, or polypeptide sequence (the "heterobifunctional compound targeting domain" or "dTAG") within a synthetic chimeric antigen receptor (CAR) construct are provided that allow for reversible targeted protein degradation using a heterobifunctional compound (i.e., a heterobifunctional compound that binds to a ubiquitin ligase through its ubiquitin ligase binding moiety and also binds to the CAR that contains the dTAG through a dTAG Targeting Ligand in vivo, as defined in more detail below). Compared to modalities that incorporate suicide gene strategies that are used to rapidly induce cell death of, for example, CAR T-cells, the use of a heterobifunctional compound to target CAR ubiquitination and degradation within the immune effector cell allows for reversible control of the CAR expression and in turn the immune effector cell response while sparing the immune effector cell itself. The dTAG can be used as a rheostat of CAR expression and, thus, immune effector cell stimulation, affording the ability to regulate the expression of the CAR and degree of immune effector cell responses by administration of the heterobifunctional compound, and regeneration of the CAR upon clearance of the heterobifunctional compound. Furthermore, by incorporating a heterobifunctional compound targeted protein within, for example the CAR construct, adverse side effects associated with current CAR T-cell therapies such as inflammatory responses, including CRS, and metabolic responses, such as TIL, may be controlled through the administration of a heterobifunctional compound that controls CAR expression, all while allowing the CAR T-cell to retain its ability to reactivate upon re-expression of the CAR and clearance of the heterobifunctional compound.

The use of a dTAG and heterobifunctional compound to modulate CAR T-cell activation can be adapted for use with any clinical CAR T-cell strategy to provide additional safety mechanisms. For example, the dTAG can be incorporated into a CAR or within a CAR complex, for example a split or dual CAR construct, to modulate the activation of a CAR T-cell. By including a dTAG in a CAR, a further safety switch is available to ensure a controllable CAR T-cell response.

Therefore, in one embodiment, a method is provided that includes the steps of:
  (i) administering to a patient a transformed immune effector cell comprising a chimeric antigen receptor (CAR) having at least a sequence targeting a diseased cell surface antigen and an amino acid sequence that can be recognized by and bound to a dTAG Targeting Ligand of a heterobifunctional compound, wherein the patient has a disorder of diseased cells that can be treated by increasing the ability of an immune effector cell to recognize and bind to the diseased cells, and, (ii) administering to the patient, as needed, a heterobifunctional compound which binds to a) the dTAG and b) a ubiquitin ligase; in a manner that brings the dTAG (and thus the CAR) into proximity of the ubiquitin ligase, such that the CAR, or a portion thereof, is ubiquitinated, and then degraded by the proteasome.

By degrading at least a portion of the cytoplasmic signaling domain of the CAR, the ability of the CAR to activate the immune effector cell, for example a CAR T-cell, is diminished. As contemplated herein, sufficient degradation of the CAR occurs wherein the CAR's signaling functionality is disrupted.

In one aspect as contemplated herein, the synthetic CARs of the present invention, which can be expressed by engineered cells for use in adoptive cell therapies, include an extracellular ligand binding domain, a transmembrane domain, and a cytoplasmic domain having at least one intracellular signaling domain and a dTAG capable of being targeted and bound by a dTAG Targeting Ligand of a heterobifunctional compound, wherein the binding of the heterobifunctional compound to the dTAG leads to the degradation of the CAR through ubiquitination and ubiquitin-mediated degradation. In some embodiments, the intracellular signaling domain or domains include the cytoplasmic sequences of the T-cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability. In the context of a natural TCR, full activation generally requires not only signaling through the TCR, but also a costimulatory signal. Thus, in some embodiments, to promote full activation, a component for generating secondary or co-stimulatory signal is also included in the CAR. Generalized examples of CARs having a dTAG capable of being bound by a heterobifunctional compound resulting in degradation of at least a portion of the CAR in combination with one or more signaling domains are illustrated in FIG. 1. As shown in the figure, a dTAG can be incorporated to a CAR having a variety of conformations, for example, but not limited to, a single immunoreceptor activation domain (for example an ITAM), an activation domain and a costimulatory domain, or an activation domain and one or more costimulatory domains, wherein the CAR is degraded upon the administration of a heterobifunctional domain.

Alternatively, in one embodiment, the CAR does not include a component for generating a signal sufficient to activate the cell. In such multi-polypeptide CAR designs, a cytoplasmic costimulatory polypeptide comprising one or more signaling domains acts in concert with a CAR comprising, for example, an extracellular binding domain, a transmembrane domain, and a cytoplasmic domain having at least one intracellular signaling domain, to activate the cell. In one embodiment, the cytoplasmic costimulatory polypeptide and the CAR comprise a heterodimerization domain that dimerizes in the presence of a small molecule. (See for example, FIG. 3B, described in more detail below). Such a strategy provides for the activation of the cell only in the presence of the small molecule. In one embodiment, the CAR design includes multiple chains, wherein the CAR is activated by binding to the tumor target an additional inducer, such as an endogenous or exogenous small molecule. As contemplated herein, the dTAG can be incorporated into the cytoplasmic costimulatory polypeptide, the CAR, any of the multi-chains that comprise the CAR design, or all of them, allowing for an additional modulatory mechanism upon the administration of the heterobifunctional compound.

In other embodiments, the CAR does not include a component for generating a costimulatory signal. In some aspects, an additional CAR is expressed in the same cell and provides the component for generating the secondary or costimulatory signal. In some aspects, the cell comprises a first CAR which contains signaling domains to induce the primary signal and a second CAR which binds to a second antigen and contains the component for generating a costimulatory signal. For example, a first CAR can be an activating CAR and the second CAR can be a costimulatory CAR. In some aspects, both CARs must be ligated in order to induce a particular effector function in the cell, which can provide specificity and selectivity for the cell type being targeted. Accordingly, the dTAG can be incorporated into the first CAR or the second CAR, or both, and upon administration of the heterobifunctional compound, the activation of the cell is modulated by the degradation of one or both CARs.

In one embodiment, the cell comprises a first CAR which contains signaling domains to induce the primary signal and a costimulatory ligand polypeptide to stimulate other immune cells. See, e.g., Abate Daga et al., "CAR models: next generation CAR modifications for enhanced T-cell function," Molecular Therapy-Oncolytics (2016)3:1-7, incorporated herein by reference. Accordingly, the dTAG can be incorporated into the first CAR or the costimulatory ligand polypeptide, or both, and upon administration of a heterobifunctional compound, the CAR and/or the costimulatory ligand polypeptide is degraded and the activation of the cell modulated. An exemplary schematic of such a strategy is illustrated in FIG. 3A, wherein the dTAG is incorporated into the CAR.

Alternatively, a dTAG is incorporated into a CAR construct designed as a universal or switchable CAR. Universal CARs have an extracellular ligand binding domain targeting a label or a tag, wherein the label or tag is bound to, for example, an antibody capable of binding a target ligand such as a tumor antigen. Rather than engineering the CAR to have an extracellular ligand binding domain that recognizes specific tumor antigens one at a time and requiring a different CAR for every antigen, this technique engineers a T-cell receptor that can bind one invariant end of a bifunctional molecule. The molecule is constructed such that the other end can bind to whatever tumor cell surface marker is of interest. In this way, the CAR T cells can be constructed once and be directed to various tumor markers. See Kudo et al., "T Lymphocytes Expressing a CD16 Signaling Receptor Exert Antibody-Dependent Cancer Cell Killing," Cancer Res; 74(1) Jan. 1, 2014, incorporated herein by reference; Ma et al., "Versatile strategy for controlling the specificity and activity of engineered T cell," PNAS 2016 Jan. 26; 113(4):E450-8, incorporated herein by reference. One example of a universal CAR is illustrated in FIG. 2, wherein the CAR includes a costimulatory and activating domain, as well as a dTAG. As contemplated herein, the universal CAR may contain additional costimulatory domains or be adopted with any other aspect or strategy described herein.

In another alternative, the dTAG is incorporated into a CAR construct designed as a conditional or "split" CAR. See Wu et al., "Remote control of therapeutic T cells through a small molecule-gated chimeric receptor," Science. 2015

Oct. 16; 350(6258), incorporated herein by reference. A cell comprising a conditional or "split" CAR is by default unresponsive, or switched off, until the addition of a small molecule. The conditional or split CAR is generally a split receptor, wherein antigen binding and intracellular signaling components only assemble in the presence of a heterodimerizing small molecule. The split receptor comprises 1) a CAR having an extracellular antigen binding domain, e.g., a scFv, and one or more costimulatory domains incapable on its own to activate the cell, and 2) a cytoplasmic polypeptide comprising key downstream signaling elements, e.g., an ITAM. The two parts of the split receptor contain heterodimerization domains that conditionally interact upon binding of a heterodimerizing small molecule. Accordingly, the dTAG can be incorporated into the CAR or the cytoplasmic polypeptide, or both to effectuate modulation upon administration of the heterobifunctional compound. An illustration of a generalized split CAR is provided in FIG. 3B, wherein the CAR contains the dTAG. Common dimerization domains include the FK 506 Binding Protein (FKBP) domain and the T2089L mutant of FKBP-rapamycin binding (FRB) domains, which are incorporated into either the CAR or cytoplasmic polypeptide, respectively, and capable of dimerization with a rapalog such as rapamycin analog AP21967. Alternative dimerization domains include gibberelic acid based dimerization systems using GID1 and GAI which dimerizes in the presence of gibberellin. In an alternative embodiment, the dTAG is the heterodimerization domain itself, for example FKBP. Accordingly, a heterobifunctional compound capable of binding one of the heterodimerization domains allows for the degradation of one or both of the polypeptides, resulting in modulation of the cell activation activity. An illustration of an exemplary embodiment of such a strategy is provide in FIGS. 3C and 3D.

In a related aspect, the CAR does not contain a costimulation domain, but uses a CAR and activation domain, for example a ITAM such as a ON domain, together with a ligand-dependent costimulatory switch comprising inducible MyD88/CD40 (iMC). These so called "GoCARts" utilize tandem Rim-binding domains (FKBP12v36) in-frame with MyD88 and CD40 cytoplasmic signaling molecules, which are inducible with rimiducid (Rim). CAR antigen recognition and Rim-dependent iMC costimulation are required for cell activation. See Narayanan et al., "A Composite MyD88/CD40 switch synergistically activates mouse and human dendritic cells for enhanced antitumor efficacy," JCI 2011; 121(4):1524-1534, incorporated herein by reference; Foster et al., "Inducible MyD88/CD40 Allows AP1903-Dependent Costimulation to Control Proliferation and Survival of Chimeric Antigen Receptor-Modified T Cells," Blood 2014 124:1121, incorporated herein by reference; Foster et al., "Efficacy and safety of Her2-targeted chimeric antigen receptor (CAR) T cells using MyD88/CD40 costimulation and iCaspase-9 suicide switch", J Clin Oncol 34, 2016 (suppl; abstr 3050), incorporated herein by reference. Accordingly, the dTAG can be incorporated into either the CAR, the iMC costimulatory polypeptide, or both to further effectuate modulation when a heterobifunctional compound is administered.

In another alternative, the dTAG is incorporated into a CAR construct designed for use in a T cell that co-expresses an antitumor cytokine (T-cells directed for universal cytokine killing (TRUCKs)). Cytokine expression may be constitutive or induced by T call activation, e.g., IL-12. Localized production of pro-inflammatory cytokines recruits endogenous immune cells to tumor sites and potentiates an antitumor response. See Chmielewski et al., "TRUCKs: the fourth generation of CARs," Expert Opinion on Biological Therapy Vol. 15, Iss. 8, 2015, incorporated herein by reference. An illustration of an exemplary embodiment of such a strategy is provide in FIG. 3E, wherein the cell expresses both a CAR incorporating a dTAG and a anti-tumor cytokine.

In another alternative, the dTAG is incorporated into a CAR construct designed for use in a T cell that co-expresses a chemokine receptor (Self-driving CAR), for example a C—C motif chemokine receptor 2 (CCR2)-CC motif chemokine ligand 2 (CCL2), thereby increasing tumor homing. See Hong et al., "Chemotherapy induces intratumoral expression of chemokines in cutaneous melanoma favoring T-cell infiltration and tumor control," Cancer Res. 71, 6997-7009; 2011, incorporated by reference herein. FIG. 3F is a schematic of a self-driving CAR as contemplated herein which co-expresses a CAR incorporating a dTAG and a chemokine receptor which binds to a tumor ligand.

In another alternative, the dTAG is incorporated into a CAR construct designed for use in a cell engineered to be resistant to immunosuppression. These so-called Armored CARS are genetically modified to no longer express various immune checkpoint molecules, e.g., cytotoxic T lymphocyte-associated antigen 4 (CTLA4) or programmed cell death protein 1 (PD1), or be engineered with an immune checkpoint switch receptor, for example a dominant-negative transforming growth factor-β (TGF-β) receptor type II conferring T cell resistance to this suppressive cytokine (See Foster et al., "Antitumor activity of EBV-specific T lymphocytes transduced with a dominant negative TGF-β receptor," J. Immunother. 31, 500-505 (2008), incorporated herein by reference). In an alternative embodiment, a receptor comprising an IL-4 exodomain and an IL-7 alpha-receptor endodomain is co-expressed with the CAR. Tumor generated IL-4, a suppressive cytokine, produces an activating signal in these T cells through the stimulation of the IL-7alpha receptor endodomain (See Leen et al., "Reversal of tumor immune inhibition using a chimeric cytokine receptor," Mol. Ther. 22, 1211-1220 (2014), incorporated herein by reference). An illustration of an exemplary Armored CAR as contemplated herein is provided in FIG. 3G, wherein the dTAG is incorporated into the CAR. Alternatively, the dTAG can be incorporated into the IL-4αR/IL-7αR polypeptide.

In another alternative, the dTAG is incorporated into a CAR construct designed for use in a T cell that expresses a molecular switch which induces apoptosis, for example HSK-TK, which, when exposed to ganciclovir, induces the cell into apoptosis (see Jensen et al., "Antitransgene rejection responses contribute to attenuated persistence of adoptively transferred CD20/CD19-specific chimeric antigen receptor redirected T cells in humans," Biol. Blood Marrow Transp. 1, 1245-1256 (2010), incorporated herein by reference). An alternative suicide gene system is CaspaCIDe®, which consists of an inducible caspase 9 (iCasp9) gene together with the small-molecule, bio-inert, chemical induction of dimerization (CID) drug, AP1903. The iCasp9 gene contains the intracellular portion of the human caspase 9 protein, a pro-apoptotic molecule, fused to a drug-binding domain derived from human FK506-binding protein. Intravenous administration of AP1903 produces cross-linking of the drug-binding domains of this chimeric protein, which in turn dimerizes caspase9 and activates the downstream executioner caspase 3 molecule resulting in cellular apoptosis (see Gargett et al., "The inducible caspase-9 suicide gene system as a "safety switch" to limit on-target, off-tumor toxicities of chimeric antigen receptor T-cells," Front. Pharacol. 5, 235 (2014), incorporated herein by reference). An illustration of an exemplary CAR-T incorporating a suicide gene strategy as contemplated herein is provided in FIG. 3H, wherein the dTAG is incorporated into the CAR.

In an alternative strategy, the dTAG is incorporated into a CAR for use in a T-Cell also expressing a ligand capable of binding to a monoclonal antibody, for example a fusion of CD34 and CD20 epitopes (RQR8) which binds to rituximab (monoclonal CD20 antibody) (see Philip et al., "A highly compact epitope-based marker/suicide gene for easier and safer T-cell therapy," Blood 124, 1277-1287 (2014), incorporated herein by reference) or a truncated form of EGFR which binds to cetuximab (monoclonal EGFR antibody) (see Wang et al., "A transgene-encoded cell surface polypeptide for selection, in vivo tracking, and ablation of engineered cells," Blood 118, 1255-1263 (2011), incorporated herein by reference). An illustration of an exemplary CAR-T incorporating a monoclonal antibody binding motif as contemplated herein is provided in FIG. 3I.

In another alternative, the dTAG is incorporated into a CAR construct having two binding domains (a Tandem CAR), wherein the CAR T-Cell is only activated when target cells co-express both targets, for example CD19 and IL13Rα2 (see Grada et al., "TanCAR: a novel bispecific chimeric antigen receptor for cancer immunotherapy," Mol. Ther. Nucleic Acids 2, e105 (2013), incorporated herein by reference). An illustration of an exemplary TanCAR as contemplated herein is provided in FIG. 3J, wherein the dTAG is incorporated into the TanCAR.

In another alternative, the dTAG is incorporated into one or more CAR constructs expressed in a T Cell, for example, in a dual target strategy wherein the cell expresses two separate CARs with different ligand binding targets; one CAR includes only the co-stimulatory domain while the other CAR includes only an ITAM. Dual CAR cell activation requires expression of both targets on the tumor cell. See Lantis et al., "Chimeric antigen receptor T cells with dissociated signaling domains exhibit focused antitumor activity with reduced potential for toxicity in vivo," Cancer Immunol Res 1, 43-53 (2013), incorporated herein by reference. In such a strategy, the dTAG can be incorporated on either one of the CARs, or both CARs. An illustration of an exemplary Dual CAR as contemplated herein is provided in FIG. 3K.

In another alternative, the dTAG is incorporated into one or more CAR constructs expressed in a T Cell, for example, wherein one CAR comprises an inhibitory domain that is activated upon binding a ligand, for example on a normal cell, and a second CAR directed to a tumor target. This type of strategy provides for activation only when encountering a target cell that possess the tumor target but not the normal cell target. See Federov et al., "PD-1 and CTL-4 based inhibitory chimeric antigen receptors (iCARs) divert off-target immunotherapy responses," Sci Transl Med 5, 215ra172 (2013), incorporated herein by reference. An illustration of an exemplary inhibitory CAR as contemplated by this strategy is provided in FIG. 3L, which provides for the dTAG incorporated into the CAR. Alternatively, the dTAG can be incorporated into the CTLA4-inhibitory domain.

In another alternative, the dTAG is incorporated into a multi chain CAR (mcCAR), which comprises a spatio-temporal controlled CARs comprising multiple chains capable of responding to multiple inputs, for example enxogenous small molecules, monoclonal antibodies, or endogenous stimuli to regulate the CAR activation. These strategies may incorporate domains, for example FRB-protein, the FKBP12, or a fusion of FRB and FKBP12, inserted between the hinge and the scFv to create a "transient CAR-T cell" or incorporate a inducible signal domains capable of being induced in response to an endogenous stimuli, for example a hypoxia-inducible factor 1-alpha (HIF1α) modulated by variations in the oxygen level. See for example Juillerat et al., "An oxygen sensitive self-decision making engineered CAR T-cell," Scientific Reports 7:39833 (2017), doi: 10.1038/srep39833, incorporated herein by reference. The mcCAR may also include additional costimulatory polypeptides. The addition or presence of a small molecule induces a conformational change whereby the small molecule causes the protein to move from an "off-state," or inactive state, to an "on-state." This system allows for the preservation of the mcCAR during an inactivate state and allows for temporal control of the system. A transient CAR-T could simply be reactivated with the administration of a small molecule. See Juillerat et al. "Design of chimeric antigen receptors with integrated controllable transient functions," Scientific Reports, Vol. 6, 18950. In certain embodiments, the dTAG can be incorporated into any of the different chains, or all of the chains. An illustration of an exemplary embodiment of an mcCAR strategy is provided in FIG. 3M, wherein the dTAG is incorporated into the β-chain, but can be incorporated into any of the other polypeptides that comprise the CAR system.

Accordingly, the incorporation of a dTAG into the design of any of the known strategies of CAR design are contemplated herein. Exemplary CAR designs known in the art which the current dTAG strategy can be employed, in addition to the ones described herein, include but are not limited to those described, for example, in: Brentjens, R. J. et al., "CD19-targeted T cells rapidly induce molecular remissions in adults with chemotherapy-refractory acute lymphoblastic leukemia," Sci Transl Med 5, 177ra138 (2013); Grupp, S. A. et al., "Chimeric antigen receptor-modified T cells for acute lymphoid leukemia," N Engl J Med 368, 1509-1518 (2013); Kalos, M. et al., "T cells with chimeric antigen receptors have potent antitumor effects and can establish memory in patients with advanced leukemia," Sci Transl Med 3, 95ra73 (2011); Morgan, R. A. et al., "Case report of a serious adverse event following the administration of T cells transduced with a chimeric antigen receptor recognizing ERBB2," Mol Ther 18, 843-851 (2010); Chakravarti, D. & Wong, W. W., "Synthetic biology in cell-based cancer immunotherapy," Trends Biotechnol 33, 449-461 (2015); Juillerat, A. et al., "Design of chimeric antigen receptors with integrated controllable transient functions," Sci Rep 6, 18950 (2016); Wu, C. Y., Roybal, K. T., Puchner, E. M., Onuffer, J. & Lim, W. A., "Remote control of therapeutic T cells through a small molecule-gated chimeric receptor," Science 350, aab4077 (2015); Ma, J. S. et al., "Versatile strategy for controlling the specificity and activity of engineered T cells," Proc Natl Acad Sci USA 113, E450-458 (2016); Rodgers, D. T. et al. "Switch-mediated activation and retargeting of CAR-T cells for B-cell malignancies," Proc Natl Acad Sci USA 113, E459-468 (2016); Tamada, K. et al., "Redirecting gene-modified T cells toward various cancer types using tagged antibodies," Clin Cancer Res 18, 6436-6445 (2012); Urbanska, K. et al., "A universal strategy for adoptive immunotherapy of cancer through use of a novel T-cell antigen receptor," Cancer Res 72, 1844-1852 (2012); Marin, V. et al., "Comparison of different suicide-gene strategies for the safety improvement of genetically manipulated T cells," Hum Gene Ther Methods 23, 376-386 (2012); Poirot, L. et al., "Multiplex Genome-Edited T-cell Manufacturing Platform for "Off-the-Shelf" Adoptive T-cell Immunotherapies," Cancer Res 75, 3853-3864

(2015); Straathof, K. C. et al., "An inducible caspase 9 safety switch for T-cell therapy," Blood 105, 4247-4254 (2005); Duong, C. P., Westwood, J. A., Berry, L. J., Darcy, P. K. & Kershaw, M. H., "Enhancing the specificity of T-cell cultures for adoptive immunotherapy of cancer," Immunotherapy 3, 33-48 (2011); Wilkie, S. et al., "Dual targeting of ErbB2 and MUC1 in breast cancer using chimeric antigen receptors engineered to provide complementary signaling," J Clin Immunol 32, 1059-1070 (2012); Krause, A. et al., "Antigen-dependent CD28 signaling selectively enhances survival and proliferation in genetically modified activated human primary T lymphocytes," J Exp Med 188, 619-626 (1998); Fedorov, V. D., Themeli, M. & Sadelain, M., "PD-1- and CTLA-4-based inhibitory chimeric antigen receptors (iCARs) divert off-target immunotherapy responses," Sci Transl Med 5, 215ra172 (2013); Grada, Z. et al., "TanCAR: A Novel Bispecific Chimeric Antigen Receptor for Cancer Immunotherapy," Mol Ther Nucleic Acids 2, e105 (2013); Morsut, L. et al. "Engineering Customized Cell Sensing and Response Behaviors Using Synthetic Notch Receptors," Cell 164, 780-791 (2016), each of which is incorporated herein by reference.

The dTAG of the CAR is any amino acid sequence to which a heterobifunctional compound can be bound through its dTAG Targeting Ligand, which leads to ubiquitination and then proteasomal degradation of the CAR. Preferably, the dTAG should not interfere with the function of the CAR. In one embodiment, the dTAG is a non-endogenous peptide, leading to heterobifunctional compound selectivity and allowing for the avoidance of off target effects upon administration of the heterobifunctional compound. In one embodiment, the dTAG is an amino acid sequence derived from an endogenous protein which has been modified so that the heterobifunctional compound binds only to the modified amino acid sequence and not the endogenously expressed protein.

In particular embodiments, the dTAGs for use in the present invention include, but are not limited to, amino acid sequences derived from endogenously expressed proteins such as FK506 binding protein-12 (FKBP12), bromodomain-containing protein 4 (BRD4), CREB binding protein (CREBBP), or transcriptional activator BRG1 (SMARCA4). In other embodiments, dTAGs for use in the present invention may include, for example, a hormone receptor e.g. estrogen-receptor protein, androgen receptor protein, retinoid x receptor (RXR) protein, or dihydrofolate reductase (DHFR), including bacterial DHFR. In other embodiments, the dTAG may include, for example, an amino acid sequence derived from a bacterial dehalogenase. In other embodiments, the dTAG, may include, amino acid sequences derived from 7,8-dihydro-8-oxoguanin triphosphatase, AFAD, Arachidonate 5-lipoxygenase activating protein, apolipoprotein, ASH1L, ATAD2, baculoviral IAP repeat-containing protein 2, BAZ1A, BAZ1B, BAZ2A, BAZ2B, Bcl-2, Bcl-xL, BRD1, BRD2, BRD3, BRD4, BRD5, BRD6, BRD7, BRD8, BRD9, BRD10, BRDT, BRPF1, BRPF3, BRWD3, CD209, CECR2, CREBBP, E3 ligase XIAP, EP300, FALZ, fatty acid binding protein from adipocytes 4 (FABP4), GCN5L2, GTPase k-RAS, HDAC6, hematopoietic prostaglandin D synthase, KIAA1240, lactoglutathione lyase, LOC93349, Mcl-1, MLL, PA2GA, PB1, PCAF, peptidyl-prolyl cis-trans isomerase NIMA-interacting 1, PHIP, poly-ADP-ribose polymerase 14, poly-ADP-ribose polymerase 15, PRKCBP1, prosaposin, prostaglandin E synthase, retinal rod rhodopsin-sensitive cGMP 3',5- cyclic phosphodiesterase subunit delta, S100-A7, SMARCA2, SMARCA4, SP100, SP110, SP140, Src, Sumo- conjugating enzyme UBC9, superoxide dismutase, TAF1, TAF1L, tankyrase 1, tankyrase 2, TIF1a, TRIM28, TRIM33, TRIM66, WDR9, ZMYND11, or MLL4. In yet further embodiments, the dTAG may include, for example, an amino acid sequence derived from MDM2.

In a particular embodiment, the dTAGs for use in the present invention include an amino acid sequence derived from an endogenous protein kinase. In one embodiment, the endogenous protein kinase amino acid sequence includes a mutation rendering the kinase inactive. In one embodiment, the mutation in the protein kinase occurs within a conserved kinase catalytic triad amino acid sequence. In one embodiment, the conserved kinase catalytic triad amino acid sequence is TVS. In one embodiment, the conserved kinase catalytic triad amino acid sequence is HRD. In one embodiment, the conserved kinase catalytic triad amino acid sequence is DFG. In one embodiment, the conserved kinase catalytic triad amino acid sequence is TRD. See Kornev et al., "Surface comparison of active and inactive protein kinases identifies a conserved activation mechanism," PNAS 2006; 103(47):17783-17788, incorporated herein by reference. In one embodiment, at least one of the catalytic triad amino acids is substituted for an alanine. In one embodiment, at least one of the catalytic triad amino acids is substituted for a glycine. In one embodiment, the heterobifunctional compound contains an allelic-specific ligand capable of selectively binding the mutant protein kinase sequence. In one embodiment, the mutant kinase is as described in Roskoski et al., "Classification of small molecule protein kinase inhibitors based upon the structures of their drug-enzyme complexes," Pharmacological Research http://dx.doi.org/10.1016/j.phrs.2015.10.021, incorporated herein by reference and/or Roskoski et al., "A historical overview of protein kinases and their targeted small molecule inhibitors," Pharmaceutical Research (2015), http://dx.doi.org/10.1016/j.phrs.2015.07.10, incorporated herein by reference. In one embodiment, the dTAG is derived from a kinase that is an analog-sensitive kinase. In one embodiment, the mutant kinase is as described in Zhang et al., "Structure-guided inhibitor design expands the scope of analog-sensitive kinase technology," ACS Chem Biol. 2013: 8(9); 1931-1938, incorporated herein by reference.

In alternative embodiments, the dTAGs for use in the present invention include, but are not limited to, amino acid sequences derived from proteins selected from EGFR, BCR-ABL, ALK, JAK2, BRAF, LRRK2, PDGFRα, and RET. In one embodiment, the proteins contain one or more mutations. In one embodiment, the one or more mutations render the protein inactive.

In alternative embodiments, the dTAGs for use in the present invention include, but are not limited to, amino acid sequences derived from proteins selected from Src, Src, Pkd1, Kit, Jak2, Abl, Mek1, HIV integrase, and HIV reverse transcriptase.

In a particular embodiment, the dTAG is derived from BRD2, BRD3, BRD4, or BRDT. In certain embodiments, the dTAG is a modified or mutant BRD2, BRD3, BRD4, or BRDT protein. In certain embodiments, the one or more mutations of BRD2 include a mutation of the Tryptophan (W) at amino acid position 97, a mutation of the Valine (V) at amino acid position 103, a mutation of the Leucine (L) at amino acid position 110, a mutation of the W at amino acid position 370, a mutation of the V at amino acid position 376, or a mutation of the L at amino acid position 381.

In certain embodiments, the one or more mutations of BRD3 include a mutation of the W at amino acid position 57, a mutation of the V at amino acid position 63, a mutation of the L at amino acid position 70, a mutation of the W at amino acid position 332, a mutation of the V at amino acid position 338, or a mutation of the L at amino acid position 345. In certain embodiments, the one or more mutations of BRD4 include a mutation of the W at amino acid position 81, a mutation of the V at amino acid position 87, a mutation of the L at amino acid position 94, a mutation of the W at amino acid position 374, a mutation of the V at amino acid position 380, or a mutation of the L at amino acid position 387. In certain embodiments, the one or more mutations of BRDT include a mutation of the W at amino acid position 50, a mutation of the V at amino acid position 56, a mutation of the L at amino acid position 63, a mutation of the W at amino acid position 293, a mutation of the V at amino acid position 299, or a mutation of the L at amino acid position 306.

In a particular embodiment, the dTAG is derived from cytosolic signaling protein FKBP12. In certain embodiments, the dTAG is a modified or mutant cytosolic signaling protein FKBP12. In certain embodiments, the modified or mutant cytosolic signaling protein FKBP12 contains one or more mutations that create an enlarged binding pocket for FKBP12 ligands. In certain embodiments, the one or more mutations include a mutation of the phenylalanine (F) at amino acid position 36 to valine (V) (F36V) (referred to interchangeably herein as FKBP12* or FKBP*).

In one embodiment, the dTAG is derived from an amino acid sequence, or fragment thereof from any of SEQ. ID. NOs.: 1-9 or 24-58, or 59-67, or 95-113. In a particular embodiment, the dTAG is derived from an amino acid sequence, or fragment thereof of SEQ. ID. NO.: 1. In a particular embodiment, the dTAG is derived from an amino acid sequence, or fragment thereof of SEQ. ID. NO.: 2. In a particular embodiment, the dTAG is derived from an amino acid sequence, or fragment thereof of SEQ. ID. NO.: 3. In a particular embodiment, the dTAG is derived from an amino acid sequence, or fragment thereof of SEQ. ID. NO.: 4. In a particular embodiment, the dTAG is derived from an amino acid sequence, or fragment thereof of SEQ. ID. NO.: 5. In a particular embodiment, the dTAG is derived from an amino acid sequence, or fragment thereof of SEQ. ID. NO.: 6. In a particular embodiment, the dTAG is derived from an amino acid sequence, or fragment thereof of SEQ. ID. NO.: 7. In a particular embodiment, the dTAG is derived from an amino acid sequence, or fragment thereof of SEQ. ID. NO.: 8. In a particular embodiment, the dTAG is derived from an amino acid sequence, or fragment thereof of SEQ. ID. NO.: 9. In a particular embodiment, the dTAG is derived from an amino acid sequence, or fragment thereof of SEQ. ID. NO.: 24. In a particular embodiment, the dTAG is derived from an amino acid sequence, or fragment thereof of SEQ. ID. NO.: 25. In a particular embodiment, the dTAG is derived from an amino acid sequence, or fragment thereof of SEQ. ID. NO.: 26. In a particular embodiment, the dTAG is derived from an amino acid sequence, or fragment thereof of SEQ. ID. NO.: 27. In a particular embodiment, the dTAG is derived from an amino acid sequence, or fragment thereof of SEQ. ID. NO.: 28. In a particular embodiment, the dTAG is derived from an amino acid sequence, or fragment thereof of SEQ. ID. NO.: 29. In a particular embodiment, the dTAG is derived from an amino acid sequence, or fragment thereof of SEQ. ID. NO.: 30. In a particular embodiment, the dTAG is derived from an amino acid sequence, or fragment thereof of SEQ. ID. NO.: 31. In a particular embodiment, the dTAG is derived from an amino acid sequence, or fragment thereof of SEQ. ID. NO.: 32. In a particular embodiment, the dTAG is derived from an amino acid sequence, or fragment thereof of SEQ. ID. NO.: 33. In a particular embodiment, the dTAG is derived from an amino acid sequence, or fragment thereof of SEQ. ID. NO.: 34. In a particular embodiment, the dTAG is derived from an amino acid sequence, or fragment thereof of SEQ. ID. NO.: 35. In a particular embodiment, the dTAG is derived from an amino acid sequence, or fragment thereof of SEQ. ID. NO.: 36. In a particular embodiment, the dTAG is derived from an amino acid sequence, or fragment thereof of SEQ. ID. NO.: 37. In a particular embodiment, the dTAG is derived from an amino acid sequence, or fragment thereof of SEQ. ID. NO.: 38. In a particular embodiment, the dTAG is derived from an amino acid sequence, or fragment thereof of SEQ. ID. NO.: 39. In a particular embodiment, the dTAG is derived from an amino acid sequence, or fragment thereof of SEQ. ID. NO.: 40. In a particular embodiment, the dTAG is derived from an amino acid sequence, or fragment thereof of SEQ. ID. NO.: 41. In a particular embodiment, the dTAG is derived from an amino acid sequence, or fragment thereof of SEQ. ID. NO.: 42. In a particular embodiment, the dTAG is derived from an amino acid sequence, or fragment thereof of SEQ. ID. NO.: 43. In a particular embodiment, the dTAG is derived from an amino acid sequence, or fragment thereof of SEQ. ID. NO.: 44. In a particular embodiment, the dTAG is derived from an amino acid sequence, or fragment thereof of SEQ. ID. NO.: 45. In a particular embodiment, the dTAG is derived from an amino acid sequence, or fragment thereof of SEQ. ID. NO.: 46. In a particular embodiment, the dTAG is derived from an amino acid sequence, or fragment thereof of SEQ. ID. NO.: 47. In a particular embodiment, the dTAG is derived from an amino acid sequence, or fragment thereof of SEQ. ID. NO.: 48. In a particular embodiment, the dTAG is derived from an amino acid sequence, or fragment thereof of SEQ. ID. NO.: 49. In a particular embodiment, the dTAG is derived from an amino acid sequence, or fragment thereof of SEQ. ID. NO.: 50. In a particular embodiment, the dTAG is derived from an amino acid sequence, or fragment thereof of SEQ. ID. NO.: 51. In a particular embodiment, the dTAG is derived from an amino acid sequence, or fragment thereof of SEQ. ID. NO.: 52. In a particular embodiment, the dTAG is derived from an amino acid sequence, or fragment thereof of SEQ. ID. NO.: 53. In a particular embodiment, the dTAG is derived from an amino acid sequence, or fragment thereof of SEQ. ID. NO.: 54. In a particular embodiment, the dTAG is derived from an amino acid sequence, or fragment thereof of SEQ. ID. NO.: 55. In a particular embodiment, the dTAG is derived from an amino acid sequence, or fragment thereof of SEQ. ID. NO.: 56. In a particular embodiment, the dTAG is derived from an amino acid sequence, or fragment thereof of SEQ. ID. NO.: 57. In a particular embodiment, the dTAG is derived from an amino acid sequence, or fragment thereof of SEQ. ID. NO.: 58. In a particular embodiment, the dTAG is derived from an amino acid sequence, or fragment thereof of SEQ. ID. NO.: 59. In a particular embodiment, the dTAG is derived from an amino acid sequence, or fragment thereof of SEQ. ID. NO.: 60. In a particular embodiment, the dTAG is derived from an amino acid sequence, or fragment thereof of SEQ. ID. NO.: 61. In a particular embodiment, the dTAG is derived from an amino acid sequence, or fragment thereof of SEQ. ID. NO.: 62. In a particular embodiment, the dTAG is derived from an amino acid sequence, or fragment thereof of SEQ. ID. NO.: 63. In a particular embodiment, the dTAG is derived from an amino acid sequence, or fragment thereof of SEQ. ID. NO.: 64. In a particular embodiment, the dTAG is derived from an amino acid sequence, or fragment thereof of SEQ. ID. NO.: 65. In a particular embodiment, the dTAG is derived from an amino acid sequence, or fragment thereof of SEQ. ID. NO.: 66. In a particular embodiment, the dTAG is derived from an amino acid sequence, or fragment thereof of SEQ. ID. NO.: 67. In a particular embodiment, the dTAG is derived from an amino acid sequence, or fragment thereof of SEQ. ID. NO.: 95. In a particular embodiment, the dTAG is derived from an amino acid sequence, or fragment thereof of SEQ. ID. NO.: 96. In a particular embodiment, the dTAG is derived from an amino acid sequence, or fragment thereof of SEQ. ID. NO.: 97. In a particular embodiment, the dTAG is derived from an amino acid sequence, or fragment thereof of SEQ. ID. NO.: 98. In a particular embodiment, the dTAG is derived from an amino acid sequence, or fragment thereof of SEQ. ID. NO.: 99. In a particular embodiment, the dTAG is derived from an amino acid sequence, or fragment thereof of SEQ. ID. NO.: 100. In a particular embodiment, the dTAG is derived from an amino acid sequence, or fragment thereof of SEQ. ID. NO.: 101. In a particular embodiment, the dTAG is derived from an amino acid sequence, or fragment thereof of SEQ. ID. NO.: 102. In a particular embodiment, the dTAG is derived from an amino acid sequence, or fragment thereof of SEQ. ID. NO.: 103. In a particular embodiment, the dTAG is derived from an amino acid sequence, or fragment thereof of SEQ. ID. NO.: 104. In a particular embodiment, the dTAG is derived from an amino acid sequence, or fragment thereof of SEQ. ID. NO.: 105. In a particular embodiment, the dTAG is derived from an amino acid sequence, or fragment thereof of SEQ. ID. NO.: 106. In a particular embodiment, the dTAG is derived from an amino acid sequence, or fragment thereof of SEQ. ID. NO.: 107. In a particular embodiment, the dTAG is derived from an amino acid sequence, or fragment thereof of SEQ. ID. NO.: 108. In a particular embodiment, the dTAG is derived from an amino acid sequence, or fragment thereof of SEQ. ID. NO.: 109. In a particular embodiment, the dTAG is derived from an amino acid sequence, or fragment thereof of SEQ. ID. NO.: 110. In a particular embodiment, the dTAG is derived from an amino acid sequence, or fragment thereof of SEQ. ID. NO.: 111. In a particular embodiment, the dTAG is derived from an amino acid sequence, or fragment thereof of SEQ. ID. NO.: 112. In a particular embodiment, the dTAG is derived from an amino acid sequence, or fragment thereof of SEQ. ID. NO.: 113. In a particular embodiment, the dTAG is derived from an amino acid sequence, or fragment thereof of SEQ. ID. NO.: 114. In a particular embodiment, the dTAG is derived from an amino acid sequence, or fragment thereof of SEQ. ID. NO.: 115. In a particular embodiment, the fragment thereof refers to the minimum amino acid sequence needed to be bound by the heterobifunctional compound.

In a particular embodiment, the fragment thereof refers to a sequence comprising about 20, 25, 30, 35, 40, 45, 50, 55, 60, 65, 70, 75, 80, 85, 90, 95, 100, 120, 150, or 180 amino acids.

In an alternative embodiment, the dTAG for use in the present invention is an amino acid sequence derived from EGFR. In certain embodiments, the dTAG is a modified or mutant EGFR protein or fragment thereof. In certain embodiments, the one or more mutations of EGFR include a substitution of Leucine (L) with Arginine (R) at amino acid position 858, a deletion of the amino acid sequence LREA in exon 19, an insertion of amino acids VAIKEL in exon 19, a substitution of Glycine (G) with Alanine (A), Cysteine (C), or Serine (S) at amino acid position 719, a substitution of Leucine (L) with Alanine (A), Cysteine (C), or Serine (S) at amino acid position 861, a substitution of Valine (V) with Alanine (A) at amino acid position 765, a substitution of Threonine (T) with Alanine (A) at amino acid position 783, a substitution of Serine (S) with Proline (P) at amino acid position 784, a substitution of Threonine (T) with Methionine (M) at amino acid position 790 M, a substitution of Threonine (T) with Alanine (A) at amino acid position 854, a substitution of Aspartic Acid (D) with Tyrosine (Y) at amino acid 761, a substitution of Leucine (L) with Serine (S) at amino acid position 747, a substitution of Cysteine (C) with Serine (S) or Glycine (G) at amino acid position 797. In one embodiment, the dTAG is an amino acid sequence derived from, or a fragment thereof, of SEQ. ID. NO.: 59. In one embodiment, the dTAG is an amino acid sequence derived from, or a fragment thereof, of SEQ. ID. NO.: 60. In one embodiment, SEQ. ID. NO.: 60 has a Leucine at position 163. In one embodiment, the dTAG is an amino acid sequence derived from, or a fragment thereof, of SEQ. ID. NO.: 61. In one embodiment, SEQ. ID. NO.: 61 has a Leucine at position 163. In one embodiment, SEQ. ID. No.: 61 has a Threonine at position 95. In one embodiment, SEQ. ID. NO.: 61 has a Leucine at position 163 and a Threonine at position 95. In one embodiment, the dTAG is an amino acid sequence derived from, or a fragment thereof, of SEQ. ID. NO.: 62. In one embodiment, SEQ. ID. NO.: 62 has a Leucine at position 163. In one embodiment, SEQ. ID. NO.: 62 has a Threonine at position 95. In one embodiment, SEQ. ID. NO.: 62 has a Leucine at position 163 and a Threonine at position 95.

In an alternative embodiment, the dTAG for use in the present invention is an amino acid sequence derived from BCR-ABL. In certain embodiments, the dTAG is a modified or mutant BCR-ABL protein or fragment thereof. In certain embodiments, the one or more mutations of BCR-ABL include a substitution of Tyrosine (T) with Isoleucine (I) at amino acid position 315. In one embodiment, the dTAG is an amino acid sequence derived from, or a fragment thereof, of SEQ. ID. NO.: 63. In one embodiment, the dTAG is an amino acid sequence derived from, or a fragment thereof, of SEQ. ID. NO.: 64.

In an alternative embodiment, the dTAGs for use in the present invention is an amino acid sequence derived from ALK. In certain embodiments, the dTAG is a modified or mutant ALK protein or fragment thereof. In certain embodiments, the one or more mutations of ALK include a substitution of Leucine (L) with Methionine at amino acid position 1196. In one embodiment, the dTAG is an amino acid sequence derived from, or a fragment thereof, of SEQ. ID. NO.: 65.

In an alternative embodiment, the dTAGs for use in the present invention is an amino acid sequence derived from JAK2. In certain embodiments, the dTAG is a modified or mutant JAK2 protein or fragment thereof. In certain embodiments, the one or more mutations of JAK2 include a substitution of Valine (V) with Phenylalanine (F) at amino acid position 617. In one embodiment, the dTAG is an amino acid sequence derived from, or a fragment thereof, of SEQ. ID. NO.: 66.

In an alternative embodiment, the dTAGs for use in the present invention is an amino acid sequence derived from BRAF. In certain embodiments, the dTAG is a modified or mutant BRAF protein or fragment thereof. In certain embodiments, the one or more mutations of BRAF include a substitution of Valine (V) with Glutamic Acid (E) at amino acid position 600. In one embodiment, the dTAG is an amino acid sequence derived from, or a fragment thereof, of SEQ. ID. NO.: 67.

In an alternative embodiment, the dTAG for use in the present invention is an amino acid sequence derived from Src. In certain embodiments, the dTAG is a modified or mutant Src protein or fragment thereof. In certain embodiments, the one or more mutations or modifications of Src include a substitution of Threonine (T) with Glycine (G) or Alanine (A) at amino acid position 341. In one embodiment, the dTAG is an amino acid sequence derived from, or a fragment thereof, of SEQ. ID. NO.: 114. In one embodiment, the dTAG is an amino acid sequence derived from, or a fragment thereof, of SEQ. ID. NO.: 115.

In an alternative embodiment, the dTAG for use in the present invention is an amino acid sequence derived from LKKR2. In certain embodiments, the dTAG is a modified or mutant LKKR2 protein or fragment thereof. In certain embodiments, the one or more mutations of LKKR2 include a substitution of Arginine (R) with Cysteine (C) at amino acid 1441, a substitution of Glycine (G) with Serine (S) at amino acid 2019, a substitution of Isoleucine (I) with Threonine (T) at amino acid 2020.

In an alternative embodiment, the dTAG for use in the present invention is an amino acid sequence derived from PDGFRα. In certain embodiments, the dTAG is a modified or mutant PDGFRα protein or fragment thereof. In certain embodiments, the one or more mutations of PDGFRα include a substitution of Threonine (T) with Isoleucine (I) at amino acid 674.

In an alternative embodiment, the dTAG for use in the present invention is an amino acid sequence derived from RET. In certain embodiments, the dTAG is a modified or mutant RET protein or fragment thereof. In certain embodiments, the one or more mutations of RET include a substitution of Glycine (G) with Serine (S) at amino acid 691. In certain embodiments, the one or more mutations of RET include a substitution of Arginine (R) with Threonine (T) at amino acid 749. In certain embodiments, the one or more mutations of RET include a substitution of Glutamic acid (E) with Glutamine (Q) at amino acid 762. In certain embodiments, the one or more mutations of RET include a substitution of Tyrosine (Y) with Phenylalanine (F) at amino acid 791. In certain embodiments, the one or more mutations of RET include a substitution of Valine (V) with Methionine (M) at amino acid 804. In certain embodiments, the one or more mutations of RET include a substitution of Methionine (M) with Threonine (T) at amino acid 918.

In alternative embodiments, the dTAGs for use in the present invention include, but are not limited to, amino acid sequences derived from proteins selected from Kit, Jak3, Abl, Mek1, HIV reverse transcriptase, and HIV integrase.

In one embodiment, the dTAG is derived from any amino acid sequence described herein, or a fragment thereof, and the dTAG is capable of being bound by a corresponding heterobifunctional compound comprising a dTAG Targeting Ligand capable of binding the dTAG described herein. In one embodiment, the dTAG is an amino acid sequence capable of being bound by a heterobifunctional compound described in FIG. 50, FIG. 51, FIG. 52, FIG. 53, or FIG. 54, or any other heterobifunctional compound described herein. In one embodiment, the dTAG is an amino acid sequence capable of being bound by a heterobifunctional compound comprising a dTAG Targeting Ligand described in Table T. In a particular embodiment, the dTAG is derived from an amino acid sequence or fragment thereof of SEQ. ID. NO.: 1 and the dTAG is capable of being bound by a heterobifunctional compound selected from any of dFKBP-1-dFKBP-5. In a particular embodiment, the dTAG is derived from an amino acid sequence or fragment thereof of SEQ. ID. NO.: 2 and the dTAG is capable of being bound by a heterobifunctional compound selected from any of dFKBP-6-dFKBP-13. In a particular embodiment, the dTAG is derived from an amino acid sequence or fragment thereof of SEQ. ID. NO.: 3 and the dTAG is capable of being bound by a heterobifunctional compound selected from any of dBET1-dBET18. In a particular embodiment, the dTAG is derived from an amino acid sequence or fragment thereof of SEQ. ID. NO.: 3 and the dTAG is capable of being bound by a heterobifunctional compound selected from any of dBromo1-dBromo34. In a particular embodiment, the dTAG is derived from an amino acid sequence or fragment thereof of SEQ. ID. NO.: 9 and the dTAG is capable of being bound by a heterobifunctional compound selected from any of dHalo1-dHalo2. In a particular embodiment, the dTAG is derived from CREBBP and the heterobifunctional compound contains a CREBBP dTAG Targeting Ligand selected from Table T. In a particular embodiment, the dTAG is derived from SMARCA4, PB1, or SMARCA2 and the heterobifunctional compound contains a SMARCA4/PB1/SMARCA2 dTAG Targeting Ligand selected from Table T. In a particular embodiment, the dTAG is derived from TRIM24 or BRPF1 and the heterobifunctional compound contains a TRIM24/BRPF1 dTAG Targeting Ligand selected from Table T. In a particular embodiment, the dTAG is derived from a glucocorticoid receptor and the heterobifunctional compound contains a glucocorticoid dTAG Targeting Ligand selected from Table T. In a particular embodiment, the dTAG is derived from an estrogen or androgen receptor and the heterobifunctional compound contains an estrogen/androgen receptor dTAG Targeting Ligand selected from Table T. In a particular embodiment, the dTAG is derived from DOT1L and the heterobifunctional compound contains a DOT1L dTAG Targeting Ligand selected from Table T. In a particular embodiment, the dTAG is derived from Ras and the heterobifunctional compound contains a Ras dTAG Targeting Ligand selected from Table T. In a particular embodiment, the dTAG is derived from RasG12C and the heterobifunctional compound contains a RasG12C dTAG Targeting Ligand selected from Table T. In a particular embodiment, the dTAG is derived from HER3 and the heterobifunctional compound contains a HER3 dTAG Targeting Ligand selected from Table T. In a particular embodiment, the dTAG is derived from Bcl-2 or Bcl-XL and the heterobifunctional compound contains a Bcl-2/Bcl-XL dTAG Targeting Ligand selected from Table T. In a particular embodiment, the dTAG is derived from HDAC and the heterobifunctional compound contains a HDAC dTAG Targeting Ligand selected from Table T. In a particular embodiment, the dTAG is derived from PPAR and the heterobifunctional compound contains a PPAR dTAG Targeting Ligand selected from Table T. In a particular embodiment, the dTAG is derived from DHFR and the heterobifunctional compound contains a DHFR dTAG Targeting Ligand selected from Table T. In a particular embodiment, the dTAG is derived from an amino acid sequence or fragment thereof of SEQ. ID. NO.: 59 and the dTAG is capable of being bound by a heterobifunctional compound that contains an EGFR dTAG Targeting Ligand selected from Table T-P1. In a particular embodiment, the dTAG is derived from an amino acid sequence or fragment thereof of SEQ. ID. NO.: 60 and the dTAG is capable of being bound by a heterobifunctional compound that contains an EGFR dTAG Targeting Ligand selected from Table T-P2. In a particular embodiment, the dTAG is derived from an amino acid sequence or fragment thereof of SEQ. ID. NO.: 61 and the dTAG is capable of being bound by a heterobifunctional compound that contains an EGFR dTAG Targeting Ligand selected from Table T-P3. In a particular embodiment, the dTAG is derived from an amino acid sequence or fragment thereof of SEQ. ID. NO.: 62 and the dTAG is capable of being bound by a heterobifunctional compound that contains an EGFR dTAG Targeting Ligand selected from Table T-P3. In a particular embodiment, the dTAG is derived from an amino acid sequence or fragment thereof of SEQ. ID. NO.: 63 and the dTAG is capable of being bound by a heterobifunctional compound that contains a BCR-ABL dTAG Targeting Ligand selected from Table T-Q1. In a particular embodiment, the dTAG is derived from an amino acid sequence or fragment thereof of SEQ. ID. NO.: 64 and the dTAG is capable of being bound by a heterobifunctional compound that contains a BCR-ABL dTAG Targeting Ligand selected from Table T-Q1. In a particular embodiment, the dTAG is derived from an amino acid sequence or fragment thereof of SEQ. ID. NO.: 65 and the dTAG is capable of being bound by a heterobifunctional compound that contains a ALK dTAG Targeting Ligand selected from Table T-R1. In a particular embodiment, the dTAG is derived from an amino acid sequence or fragment thereof of SEQ. ID. NO.: 66 and the dTAG is capable of being bound by a heterobifunctional compound that contains a JAK2 dTAG Targeting Ligand selected from Table T-S1. In a particular embodiment, the dTAG is derived from an amino acid sequence or fragment thereof of SEQ. ID. NO.: 67 and the dTAG is capable of being bound by a heterobifunctional compound that contains a BRAF dTAG Targeting Ligand selected from Table T-T1. In a particular embodiment, the dTAG is derived from an amino acid sequence or fragment thereof of SEQ. ID. NO.: 114 and the dTAG is capable of being bound by a heterobifunctional compound that contains a Src dTAG Targeting Ligand selected from Table T-III2 In a particular embodiment, the dTAG is derived from an amino acid sequence or fragment thereof of SEQ. ID. NO.: 115 and the dTAG is capable of being bound by a heterobifunctional compound that contains a Src dTAG Targeting Ligand selected from Table T-III3. In one embodiment, the dTAG is derived from LRRK2 amino acid 1328 to 1511 (UnitPro-Q5 S007) and the dTAG Targeting Ligand in the heterobifunctional compound is selected from a ligand in Table T-U1. In one embodiment, the dTAG is derived from LRKK2 amino acid 1328 to 1511 (UniProt-Q5S007), wherein amino acid 1441 is Cysteine and the dTAG Targeting Ligand in the heterobifunctional compound is selected from a ligand in Table T-U1. In one embodiment, the dTAG is derived from LRRK2 amino acid 1879 to 2138 (UniProt-Q5S007). In one embodiment, the dTAG is derived from LRRK2 amino acid 1879 to 2138 (UniProt-Q5S007), wherein amino acid 2019 is Serine. In on embodiment, the dTAG is derived from amino acid 1879 to 2138 (UniProt-Q5S007), wherein amino acid 2020 is Threonine. In one embodiment, the dTAG is derived from LRRK2 amino acid 1879 to 2138 (UniProt-Q5S007) and the dTAG Targeting Ligand in the heterobifunctional compound is selected from a ligand in Table T-U2 or U3. In one embodiment, the dTAG is derived from LRRK2 amino acid 1879 to 2138 (UniProt-Q5S007), wherein amino acid 2019 is Serine and the dTAG Targeting Ligand in the heterobifunctional compound is selected from a ligand in Table T-U2. In one embodiment, the dTAG is derived from LRRK2 amino acid 1879 to 2138 (UniProt-Q5S007), wherein amino acid 2020 is Threonine and the dTAG Targeting Ligand in the heterobifunctional compound is selected from a ligand in Table T-U3. In one embodiment, the dTAG is derived from PDGFR amino acid 600 to 692 (UniProt-P09619) and the dTAG Targeting Ligand in the heterobifunctional compound is selected from a ligand in Table T-V1. In one embodiment, the dTAG is derived from PDGFR amino acid 600 to 692 (UniProt-P09619), wherein amino acid 674 is Isoleucine and the dTAG Targeting Ligand in the heterobifunctional compound is selected from a ligand in Table T-V1. In one embodiment, the dTAG is derived from RET amino acid 724 to 1016 (UniProtKB—P07949), and the dTAG Targeting Ligand in the heterobifunctional compound is selected from a ligand in Table T-W1-W6. In one embodiment, the dTAG is derived from RET amino acid 724 to 1016 (UniProtKB—P07949), wherein amino acid 691 is Serine and the dTAG Targeting Ligand in the heterobifunctional compound is selected from a ligand in Table T-W1. In one embodiment, the dTAG is derived from RET amino acid 724 to 1016 (UniProtKB—P07949), wherein amino acid 749 is Threonine and the dTAG Targeting Ligand in the heterobifunctional compound is selected from a ligand in Table T-W2. In one embodiment, the dTAG is derived from RET amino acid 724 to 1016 (UniProtKB—P07949), wherein amino acid 762 is Glutamine and the dTAG Targeting Ligand in the heterobifunctional compound is selected from a ligand in Table T-W3. In one embodiment, the dTAG is derived from RET amino acid 724 to 1016 (UniProtKB—P07949), wherein amino acid 791 is Phenylalanine and the dTAG Targeting Ligand in the heterobifunctional compound is selected from a ligand in Table T-W4. In one embodiment, the dTAG is derived from RET amino acid 724 to 1016 (UniProtKB—P07949), wherein amino acid 804 is Methionine and the dTAG Targeting Ligand in the heterobifunctional compound is selected from a ligand in Table T-W5. In one embodiment, the dTAG is derived from RET amino acid 724 to 1016 (UniProtKB—P07949), wherein amino acid 918 is Threonine and the dTAG Targeting Ligand in the heterobifunctional compound is selected from a ligand in Table T-W6. In one embodiment, the dTAG is derived from an JAK2, and the dTAG Targeting Ligand in the heterobifunctional compound is selected from a ligand in Table T-JJJ1. In one embodiment, the dTAG is derived from an Abl, and the dTAG Targeting Ligand in the heterobifunctional compound is selected from a ligand in Table T-KKK1. In one embodiment, the dTAG is derived from an MEK1, and the dTAG Targeting Ligand in the heterobifunctional compound is selected from a ligand in Table T-LLL1. In one embodiment, the dTAG is derived from an KIT, and the dTAG Targeting Ligand in the heterobifunctional compound is selected from a ligand in Table T-MMM1. In one embodiment, the dTAG is derived from an HIV reverse transcriptase, and the dTAG Targeting Ligand in the heterobifunctional compound is selected from a ligand in Table T-NNN1. In one embodiment, the dTAG is derived from an HIV integrase, and the dTAG Targeting Ligand in the heterobifunctional compound is selected from a ligand in Table T-OOO1.

In a particular embodiment, the dTAG is derived from a protein selected from EGFR, ErbB2, ErbB4, VEGFR1, VEGFR2, VEGFR3, Kit, BCR-Abl, Src, Lyn, Hck, RET, c-Met, TrkB, Flt3, Axl, Tie2, ALK, IGF-1R, InsR, ROS1, MST1R, B-Raf, Lck, Yes, Fyn, HER2-breast cancer, PNET, RCC, RAML, SEGA, BTK, FGFR1/2/3/4, DDR1, PDGFRα, PDGFRβ, CDK4, CDK6, Fms, Itk, T315I, Eph2A, JAK1, JAK2, JAK3 CDK8, CSF-1R, FKBP12/mTOR, MEK1, MEK2, Brk, EphR, A-Raf, B-Raf, C-Raf and the heterobifunctional compound contains a dTAG Targeting Ligand selected from Table Z.

As contemplated herein, the CARs of the present invention, in addition to a dTAG, include an extracellular ligand binding domain capable of binding a targeted protein, typically an antigen, for example a tumor antigen. In one embodiment, the extracellular ligand binding domain is an antigen binding domain, for example, an antibody or an antigen binding fragment thereof. In particular embodiments, the antigen-binding fragment is a Fab or scFv. In one embodiment, the extracellular ligand binding domain is a ligand for a tumor marker, for example, a ligand that binds a marker expressed on the cell surface of a tumor, for example IL13 which binds to the IL13 receptor (IL13R) on glioma cells or heregulin which binds to erb B2, B3, and B4 on breast cancer cells. In one embodiment, the extracellular ligand binding domain targets a labeled or tagged protein or molecule, for example biotin or fluorescein isothiocyanate, which is bound to an antibody targeting a tumor expressed protein. For example, the extracellular ligand binding domain can target a label on a tumor-specific antibody, for example biotin, so that when the antibody-label binds to the tumor cell, the extracellular binding ligand of the CAR T-cell binds the label, activating the T-cell, and killing the tumor cell. In this regard, a "universal CAR" can be generated capable of binding any tagged or labeled antibody. See, e.g., Abate Daga et al., "CAR models: next generation CAR modifications for enhanced T-cell function," Molecular Therapy-Oncolytics (2016)3:1-7. An exemplary illustration of such a strategy is depicted in FIG. 2

In one embodiment, the antigen binding domain in the CAR binds to a tumor antigen, for example, a tumor antigen associated with a hematological malignancy or a solid tumor. Tumor antigens capable of being targeted by CAR T-cells are known, and include, for example, but are not limited to, CD19, CD20, CD22, CD30, CD40, CD70, CD123, ErbB2 (HER2/neu), epithelial cell adhesion molecule (EpCAM), Epidermal growth factor receptor (EGFR), epidermal growth factor receptor variant III (EGFRvIII). Disialoganglioside GD2, disialoganglioside GD3, mesothelian, ROR1, mesothelin, CD33/IL3Ra, C-Met, PSMA, Glycolipid, F77, GD-2, NY-ESO-1 TCR, melanoma-associated antigen (MAGE) A3 TCR, melanoma-associated antigen (MAGE) A1 TCR, alphafetapotein (AFP), carcinoembryonic antigen (CEA), CA-125, MUC-1, epithelial tumor antigen (ETA), tyrosinase, CA15-3, CA27-29, CA19-9, calcitonin, calretinin CD34, CD99MIC2, CD7, chromogranin, cytokeratin, desmin, CD31 FL1, glial fibrillary acidic protein, gross cystic disease fluid protein, HMB-45, human chorionic gonadotropin inhibin, MART-1, Myo D1, neuron-specific enolast, placental alkaline phosphatase, prostate specific antigens, PSCA. PTPRC, S100 protein, synaptophysin, thyroglobulin, thyroid transcription factor 1, tumor M2-PK, vimentin, human telomerase reverse transcriptase (hTERT), surviving, mouse double minute 2 homolog (MDM2), kappa-light chain, LeY, L1 cell adhesion molecule, oncofetal antigen (h5T4), TAG-72, VEGF-R2, and combinations thereof, as well as others described herein. Other antigens to which the antigen binding domain of the CAR can be directed include, but are not limited to, tissue or cell lineage specific antigens including, but not limited to, CD3, CD4, CD8, CD24, CD25, CD33, CD34, CD133, CD138, or a combination thereof. Additional antigens to which the antigen binding domain of the CAR can be directed include, but are not limited to, CD174 (Lewis$^y$), NKG2D-L, BCMA, Igx, FR-α, L1-CAM (CD171), FAP (cell surface serine protease), CD38, CS1, CD44v6 (alternatively spliced variant of the hyaluronate receptor CD44), CD44v7/8 (alternatively spliced variant 7/8 of the hyaluronate receptor CD44), MUC1, IL-11Rα (the alpha subunit of the IL-11 receptor), EphA2, and CSPG4 (cell surface proteoglycan 4).

In one embodiment, the CARs, in addition to a dTAG, include a transmembrane domain spanning the extracellular ligand binding domain and the at least one intracellular signaling domain, such as a costimulatory motif and/or immunoreceptor tyrosine-based activation motif (ITAM). Transmembrane domains useful in the construction of CARs are known in the art, and can be derived from natural or synthetic sources. For example, transmembrane regions contemplated herein include, but are not limited to, those derived from (i.e. comprise at least the transmembrane region(s) of) the alpha, beta or zeta chain of the T-cell receptor, CD28, CD3 epsilon, CD8, CD45, CD4, CD5, CD5, CD9, CD 16, CD22, CD33, CD37, CD64, CD80, CD86, CD 134, CD137, CD 154, or KIR2DS2. Alternatively, the transmembrane domain in some embodiments is synthetic, for example, comprising predominantly hydrophobic residues such as leucine and valine. In some aspects, a triplet of phenylalanine, tryptophan and valine will be found at each end of a synthetic transmembrane domain.

In further embodiments, the CARs, in addition to a dTAG, include at least one intracellular (or cytoplasmic) signaling domain. The intracellular signaling domain of the CAR activates at least one of the normal effector functions or responses of the immune cell. For example, upon binding of the extracellular ligand domain to a target antigen, the signaling domain may act to activate the CAR T-cell, for example, by inducing a function of a T-cell such as cytolytic activity or T-helper activity, including the secretion of cytokines or other factors. In some embodiments, the CAR includes an intracellular component of the TCR complex, such as a TCR CD3+ chain that mediates T-cell activation and cytotoxicity, e.g., the immunoreceptor tyrosine-based activation motif (ITAM) domain CD3 zeta chain (CD3). Thus, in some aspects as contemplated herein, the antigen binding molecule is linked to one or more cell signaling domains. In some embodiments, cell signaling domains include CD3 transmembrane domain, CD3 intracellular signaling domains, and/or other CD transmembrane domains. In some embodiments, the CAR further includes a portion of one or more additional molecules such as Fc receptor γ, for example FcεRIγ, CD8, CD4, CD25, or CD16. For example, in some aspects, the CAR includes a chimeric molecule between CD3-zeta (CD3-ζ) or Fc receptor γ and CD8, CD4, CD25 or CD16. In one embodiment, the intracellular signaling domain is a Dap-12 derived signaling domain.

In some embodiments, the CAR, in addition to a dTAG, includes a signaling domain and/or transmembrane portion of a costimulatory receptor, such as CD28, 4-1BB, OX40, DAP10, and ICOS. In some aspects, the same CAR includes both the activating and costimulatory components; in other aspects, the activating domain is provided by one CAR whereas the costimulatory component is provided by another CAR or ligand recognizing another antigen.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD 137 (4-1BB, TNFRSF9) co-stimulatory domain, linked to a CD3 zeta intracellular domain. In some embodiments, the intracellular signaling domain comprises a chimeric CD28 or CD 137 (4-1BB, TNFRSF9) co-stimulatory domain. In some embodiments, the intracellular signaling domain comprises a chimeric CD28 and OX40 co-stimulatory domain. In some embodiments, the intracellular signaling domain comprises a chimeric CD27 co-stimulatory domain. In some embodiments, the intracellular signaling domain comprises a chimeric CD27 and DAP10 co-stimulatory domain.

In some embodiments, the CAR, in addition to a dTAG, encompasses two or more costimulatory domains combined with an activation domain, e.g., primary activation domain, in the cytoplasmic portion. One example is a receptor including intracellular components of CD3-zeta, CD28, and 4-1BB. Other examples include a receptor including intracellular components of CD3-zeta, CD28, and OX40. Other intracellular components contemplated herein include CD30, DR3, GITR, and HVEM, CD226, CD2, and combinations thereof. See Chen et al., "Molecular mechanisms of T cell co-stimulation and co-inhibition," Nat Rev. Immunol. 2013; 13(4):227-242.

As contemplated herein, the CARs of the present invention are expressed by an immune effector cell, for example a T-cell, and administered to a subject in order to treat a disease or disorder, for example, a cancer. Among the cell types that may be used to express the CARs of the present invention include, but are not limited to, T-cells, NK cells, CD4+ T-cells, CD8+ cells, and stem cells, such as an induced pluripotent stem cell (iPS cell). In one embodiment, the cell is an autologous T-cell. In one embodiment, the cell shows anti-tumor activity when cross-reacted with a tumor cell containing an antigen capable of being bound by the extracellular ligand binding domain. In another alternative, the dTAG can be incorporated into a CAR construct designed for use in a T cell that co-expresses a chemokine receptor, which binds to a tumor ligand, e.g., C—C motif chemokine receptor 3 (CCR2)-C—C motif chemokine ligand 2 (CCL2).

In one embodiment, the cell is an allogeneic cell derived from a healthy donor that has been genetically modified. In one embodiment, the cells are CD52 knock-out cells. In one embodiment, the cells are dCK knock-out cells. In one embodiment, the cells are PD-1 knock-out cells. In one embodiment, the cells are TCR knock-out cells. In one embodiment, the cells are double TCR knock-out and CD52-knockout cells. In one embodiment, the cells are double TCR knock-out and dCK-knockout cells. In one embodiment, the CAR-T cell is an allogeneic CAR-T cell derived from healthy donors that has been genetically modified. In one embodiment, the CAR-T cells are CD52 knock-out CAR-T cells. In one embodiment, the CAR-T cells are dCK knock-out CAR-T cells. In one embodiment, the CAR-T cells are PD-1 knock-out CAR-T cells. In one embodiment, the CAR-T cells are TCR knock-out CAR-T cells. In one embodiment, the CAR-T cells are double TCR knock-out and CD52-knockout CAR-T cells. In one embodiment, the CAR-T cells are double TCR knock-out and dCK-knockout CAR-T cells.

Further contemplated herein is the use of heterobifunctional compound molecules capable of binding to the dTAG of the CARs of the present invention and inducing degradation through ubiquitination. By administering to a subject a heterobifunctional compound directed to a dTAG, the immune effector cell response can be modulated in a subject who has previously received an immune effector cell expressing the CARs of the present invention. The heterobifunctional compounds for use in the present invention are small molecule antagonists capable of disabling the biological function of the CAR through degradation. In certain embodiments, the heterobifunctional compounds for use in the present invention provide prompt ligand-dependent target protein degradation via chemical conjugation with derivatized phthalimides that hijack the function of the Cereblon E3 ubiquitin ligase complex. Using this approach, the CARs of the present invention can be degraded rapidly with a high specificity and efficiency.

The heterobifunctional compounds that can be used in the present invention include those that include a small molecule E3 ligase ligand which is covalently linked to a dTAG Targeting Ligand through a Linker of varying length and/or functionality as described in more detail below. The heterobifunctional compound is able to bind to the dTAG and recruit an E3 ligase, for example, via binding to a Cereblon (CRBN) containing ligase or Von Hippel-Lindau tumor suppressor (VHL) to the CAR for ubiquitination and subsequent proteasomal degradation.

Moreover, by combining the chemical strategy of protein degradation via the bifunctional molecules of the present application with the effectiveness of CAR T-cell therapy, the activity of the CAR T-cell, and thus the side effects, can be regulated in a precise, temporal manner by rapidly turning on and off ubiquitination, and proteasomal degradation of the CAR.

Examples of heterobifunctional compounds useful in the present invention are exemplified in detail below.

In one aspect, a nucleic acid is provided that encodes a CAR having an extracellular ligand binding domain, a transmembrane domain, and a cytoplasmic domain having at least one intracellular signaling domain and a dTAG capable of being bound by a heterobifunctional compound. In one aspect, a nucleic acid is provided that encodes a costimulatory polypeptide having a cytoplasmic domain having at least one intracellular signaling domain and a dTAG capable of being bound by a heterobifunctional compound.

In a particular embodiment, a nucleic acid encoding a CAR is provided that has an extracellular ligand binding domain, a transmembrane domain, and a cytoplasmic domain having at least one intracellular signaling domain and a dTAG, wherein the dTAG is derived from an amino acid sequence or fragment thereof of SEQ. ID. NO.: 1 and the dTAG is capable of being bound by a heterobifunctional compound selected from any of dFKBP-1-dFKBP-5. In a particular embodiment, a nucleic acid encoding a CAR is provided that has an extracellular ligand binding domain, a transmembrane domain, and a cytoplasmic domain having at least one intracellular signaling domain and a dTAG, wherein the dTAG is derived from an amino acid sequence or fragment thereof of SEQ. ID. NO.: 2 and the dTAG is capable of being bound by a heterobifunctional compound selected from any of dFKBP-6-dFKBP-13. In a particular embodiment, a nucleic acid encoding a CAR is provided that has an extracellular ligand binding domain, a transmembrane domain, and a cytoplasmic domain having at least one intracellular signaling domain and a dTAG, wherein the dTAG is derived from an amino acid sequence or fragment thereof of SEQ. ID. NO.: 3 and the dTAG is capable of being bound by a heterobifunctional compound selected from any of dBET1-dBET18. In a particular embodiment, a nucleic acid encoding a CAR is provided that has an extracellular ligand binding domain, a transmembrane domain, and a cytoplasmic domain having at least one intracellular signaling domain and a dTAG, wherein the dTAG is derived from an amino acid sequence or fragment thereof of SEQ. ID. NO.: 3 and the dTAG is capable of being bound by a heterobifunctional compound selected from any of dBromo1-dBromo34. In a particular embodiment, a nucleic acid encoding a CAR is provided that has an extracellular ligand binding domain, a transmembrane domain, and a cytoplasmic domain having at least one intracellular signaling domain and a dTAG, wherein the dTAG is derived from an amino acid sequence or fragment thereof of SEQ. ID. NO.: 9 and the dTAG is capable of being bound by a heterobifunctional compound selected from any of dHalo1-dHalo2.

In a particular embodiment, a nucleic acid encoding a costimulatory polypeptide is provided that has a cytoplasmic domain having at least one intracellular signaling domain and a dTAG, wherein the dTAG is derived from an amino acid sequence or fragment thereof of SEQ. ID. NO.: 1 and the dTAG is capable of being bound by a heterobifunctional compound selected from any of dFKBP-1-dFKBP-5. In a particular embodiment, a nucleic acid encoding a costimulatory polypeptide is provided that has a cytoplasmic domain having at least one intracellular signaling domain and a dTAG, wherein the dTAG is derived from an amino acid sequence or fragment thereof of SEQ. ID. NO.: 2 and the dTAG is capable of being bound by a heterobifunctional compound selected from any of dFKBP-6-dFKBP-13. In a particular embodiment, a nucleic acid a nucleic acid encoding a costimulatory polypeptide is provided that has a cytoplasmic domain having at least one intracellular signaling domain and a dTAG, wherein the dTAG is derived from an amino acid sequence or fragment thereof of SEQ. ID. NO.: 3 and the dTAG is capable of being bound by a heterobifunctional compound selected from any of dBET1-dBET18. In a particular embodiment, a nucleic acid a nucleic acid encoding a costimulatory polypeptide is provided that has a cytoplasmic domain having at least one intracellular signaling domain and a dTAG, wherein the dTAG is derived from an amino acid sequence or fragment thereof of SEQ. ID. NO.: 3 and the dTAG is capable of being bound by a heterobifunctional compound selected from any of dBromo1-dBromo34. In a particular embodiment, a nucleic acid a nucleic acid encoding a costimulatory polypeptide is provided that has a cytoplasmic domain having at least one intracellular signaling domain and a dTAG, wherein the dTAG is derived from an amino acid sequence or fragment thereof of SEQ. ID. NO.: 9 and the dTAG is capable of being bound by a heterobifunctional compound selected from any of dHalo1-dHalo2.

In one aspect, an amino acid is provided that encodes a CAR having an extracellular ligand binding domain, a transmembrane domain, and a cytoplasmic domain having at least one intracellular signaling domain and a dTAG capable of being bound by a heterobifunctional compound.

In one aspect, an amino acid is provided that encodes a costimulatory polypeptide having a cytoplasmic domain having at least one intracellular signaling domain and a dTAG capable of being bound by a heterobifunctional compound.

In one aspect, a CAR expressing cell is provided, for example a natural killer (NK) cell or T lymphocyte, wherein the CAR has an extracellular ligand binding domain, a transmembrane domain, and a cytoplasmic domain having at least one intracellular signaling domain and a dTAG capable of being bound by a heterobifunctional compound.

In one aspect, a CAR expressing cell is provided, for example a natural killer (NK) cell or T lymphocyte, further expresses a costimulatory polypeptide having at least one intracellular signaling domain and a dTAG capable of being bound by a heterobifunctional compound.

In one aspect, a CAR expressing cell is provided, for example a natural killer (NK) cell or T lymphocyte, wherein the CAR has a first polypeptide comprising an extracellular ligand binding domain, a transmembrane domain, and a cytoplasmic domain having at least one intracellular signaling domain and a second costimulatory polypeptide having a cytoplasmic domain having at least one intracellular signaling domain and a dTAG capable of being bound by a heterobifunctional compound.

In one aspect, a CAR expressing cell is provided, for example a natural killer (NK) cell or T lymphocyte, wherein the cell has a first CAR comprising an extracellular ligand binding domain, a transmembrane domain, and a cytoplasmic domain having at least one intracellular signaling domain and a second CAR comprising an extracellular ligand binding domain, a transmembrane domain, and a cytoplasmic domain having at least one intracellular signaling domain wherein either the first CAR, the second CAR, or both CARs have a dTAG capable of being bound by a heterobifunctional compound.

In a particular aspect, a method of modulating the activity of a cell expressing the CARs of the present invention is provided that includes administering to a subject administered the CAR expressing cell a heterobifunctional compound.

Other aspects of the invention include polynucleotide sequences, plasmids, and vectors encoding the CARs of the present invention, and immune effector cells, for example T-cells or NK cells, expressing the CARs of the present invention. Other aspects include a system for modulating the activity of a cell expressing a CAR or CAR complex as described herein, wherein the CAR or CAR complex includes a dTAG and a heterobifunctional compound capable of degrading the dTAG and or second polypeptide to inhibit cellular activation or signaling.

Additional aspects include methods of modulating T lymphocyte or natural killer (NK) cell activity in a patient and treating the patient suffering from cancer by introducing into the individual a T lymphocyte or NK cell that includes a CAR of the present invention, and subsequently administering to the subject a heterobifunctional compound that is capable of degrading the CAR. These aspects particularly include the treatment of renal cell carcinoma, cervical carcinoma, osteosarcoma, glioblastoma, lung cancer, melanoma, breast cancer, prostate cancer, bladder cancer, salivary gland cancer, endometrial cancer, colon cancer, renal cell carcinoma, ovarian cancer, neuroblastoma, rhabdomyosarcoma, leukemia, and lymphoma. Examples of cancer targets for use with the present invention are cancers of B cell origin, particularly including acute lymphoblastic leukemia, B-cell chronic lymphocytic leukemia and B-cell non-Hodgkin's lymphoma.

Although many of the embodiments are described with respect to CARs, as contemplated herein, the modulation strategies utilizing a dTAG and a heterobifunctional compound described herein are applicable for modulating immune effector cells that express engineered T-cell receptors (TCRs) as well. Furthermore, as contemplated herein, the expression of a CAR or TCR is not limited to a T-cell, but includes any immune effector cell capable of targeting tumor cells while expressing a CAR or TCR.

BRIEF DESCRIPTION OF THE FIGURES

FIG. 17A illustrates the experimental design to measure the ability to control the expression CD19-CAR-dTAG in T-cells upon addition and removal of dFKBP7. Jurkat cells expressing CD19-CAR-dTAG were treated with 250 nM of dFKBP7 at the indicated time points (0 and 8 hours). At 4 and 12 hours, the dFKBP7 was washed out of the Jurkat cells. At each indicated timepoint, Jurkat cells were harvest to monitor CD19-CAR-dTAG expression levels via immunoblot analysis. FIG. 17B is the resulting immunoblot from the experimental design in FIG. 17A. The heterobifunctional compounds dFKBP7 molecule allows for exquisite chemical control of CD19-CAR-dTAG protein levels allowing for modulation within hours. These data, further described in Example 14, support the rheostat mechanism described in the current invention.

Figure 51B:
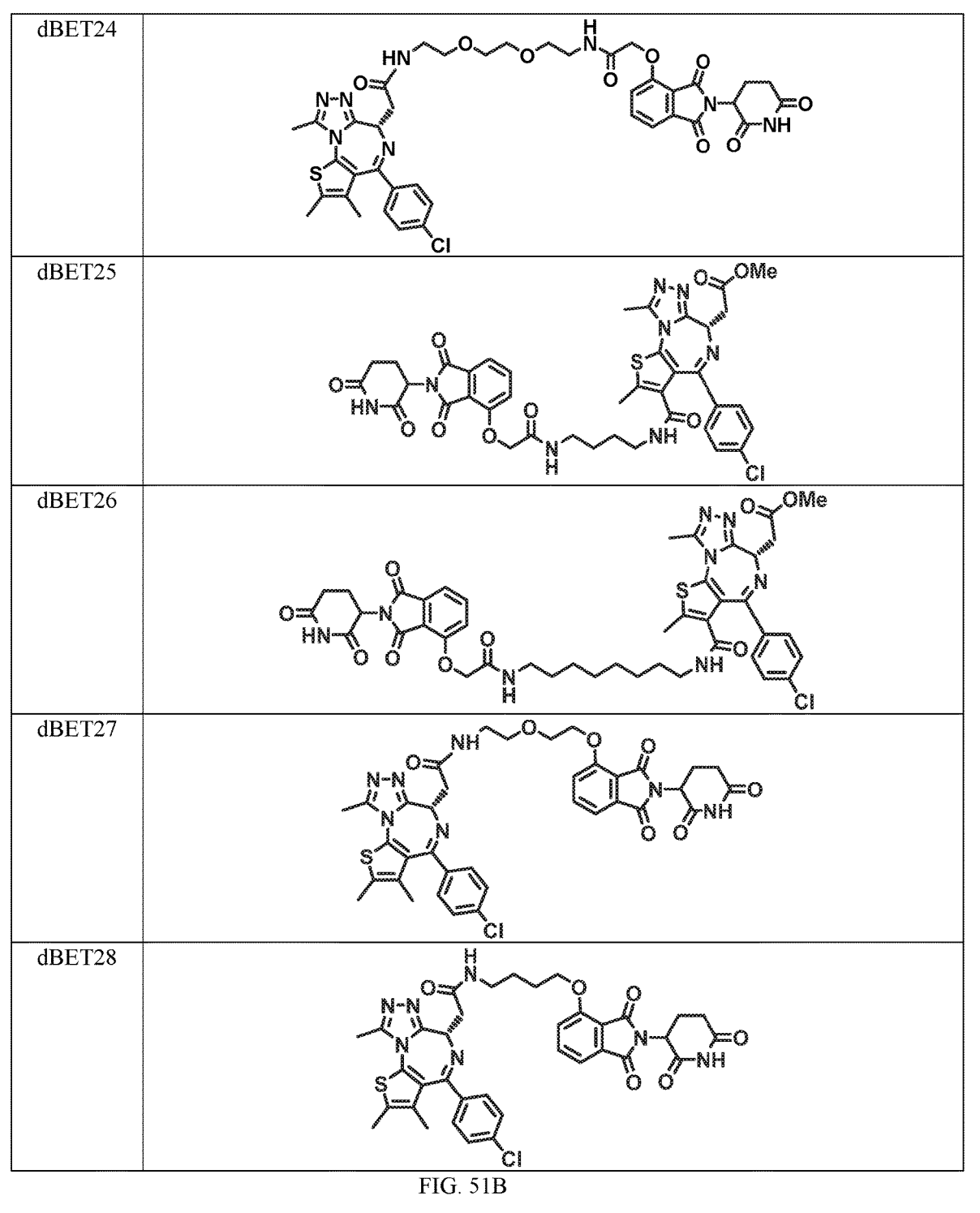
Figure 51F:
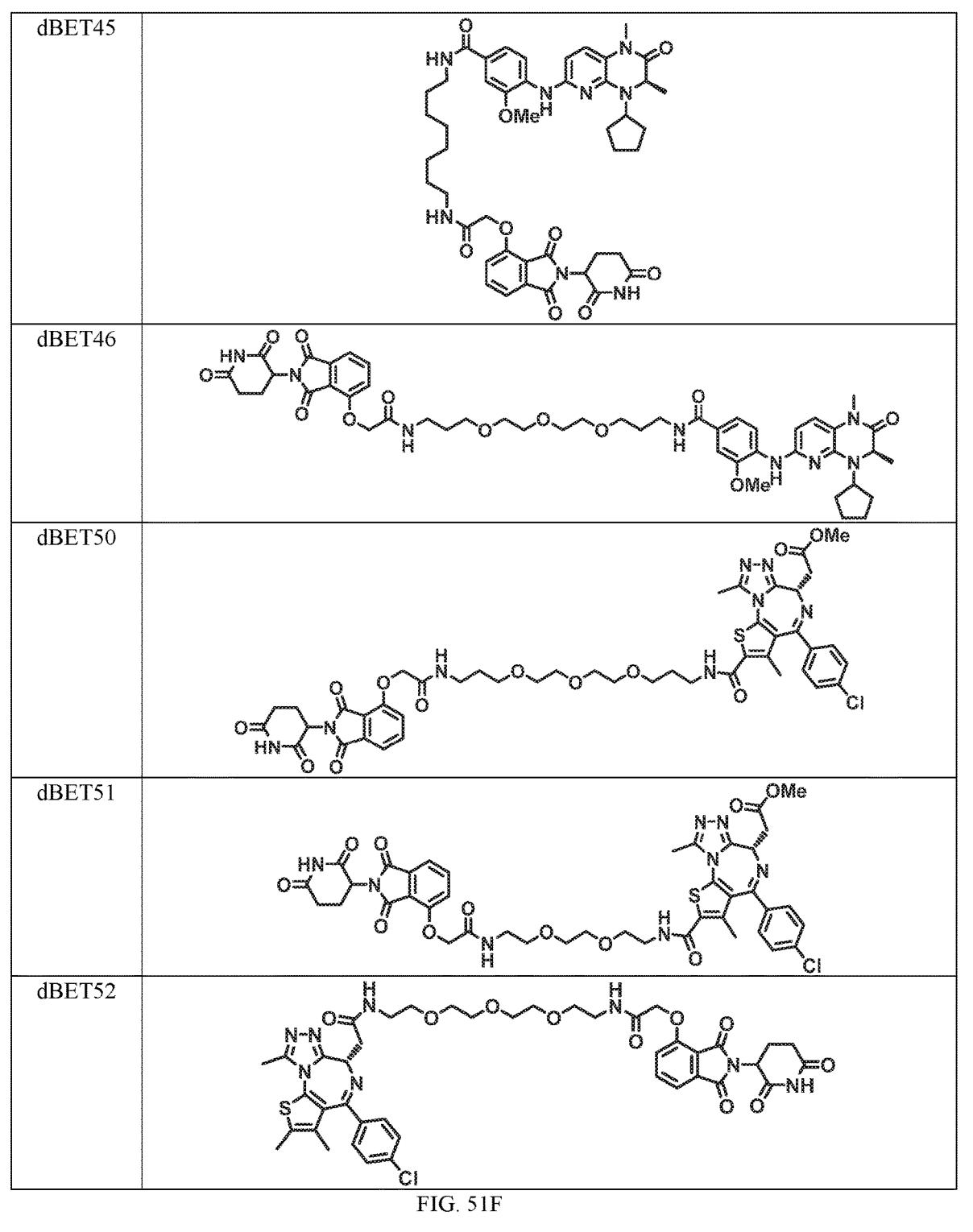
Figure 51P:
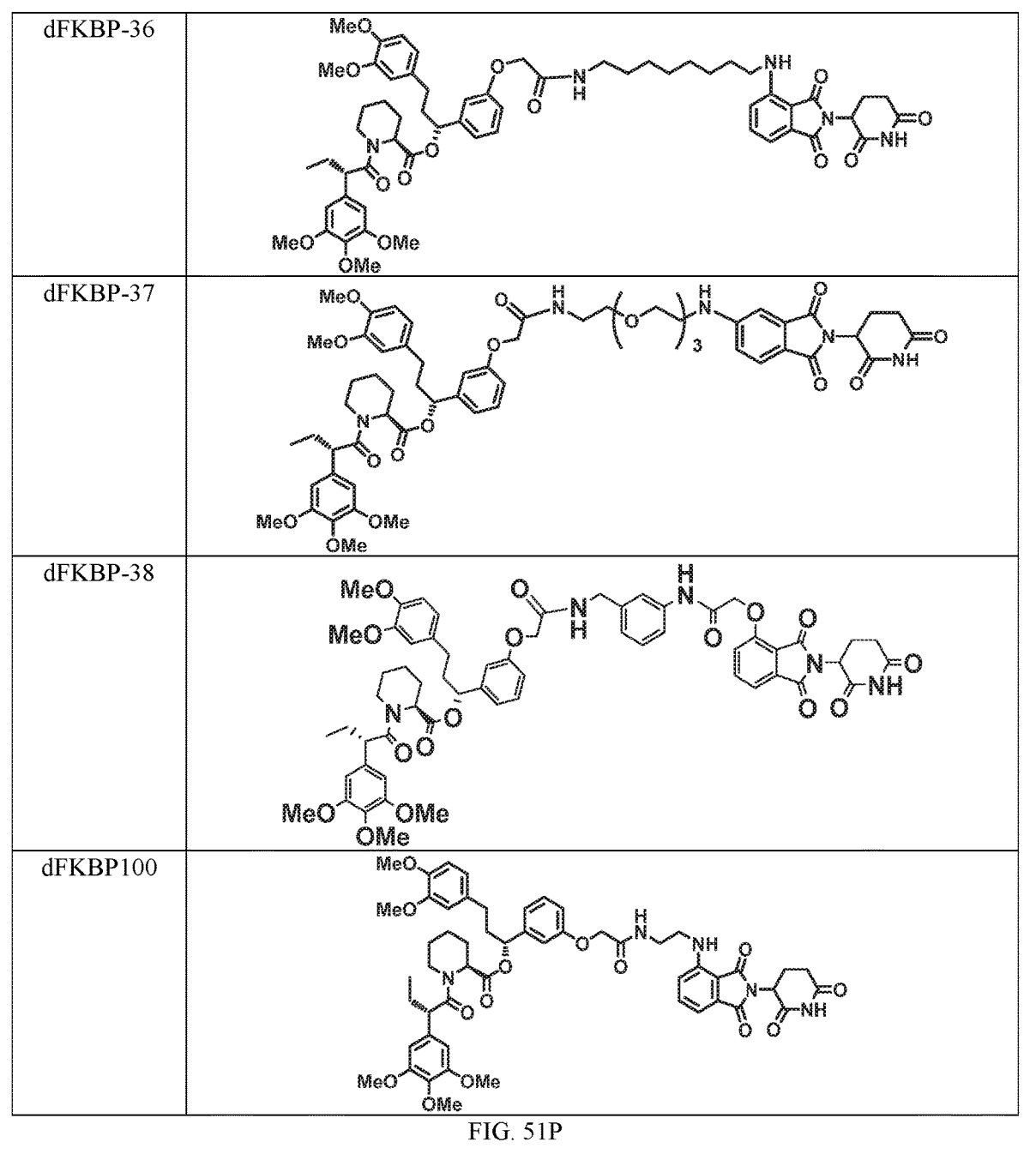

FIG. 51A, FIG. 51B, FIG. 51C, FIG. 51D, FIG. 51E, FIG. 51F, FIG. 51G, FIG. 51H, FIG. 51I, FIG. 51J, FIG. 51K, FIG. 51L, FIG. 51M, FIG. 51N, FIG. 51O, and FIG. 51P provide specific heterobifunctional compounds for use in the present invention, wherein X in the above structures is a halogen chosen from F, Cl, Br, and I.

Figure 53E:
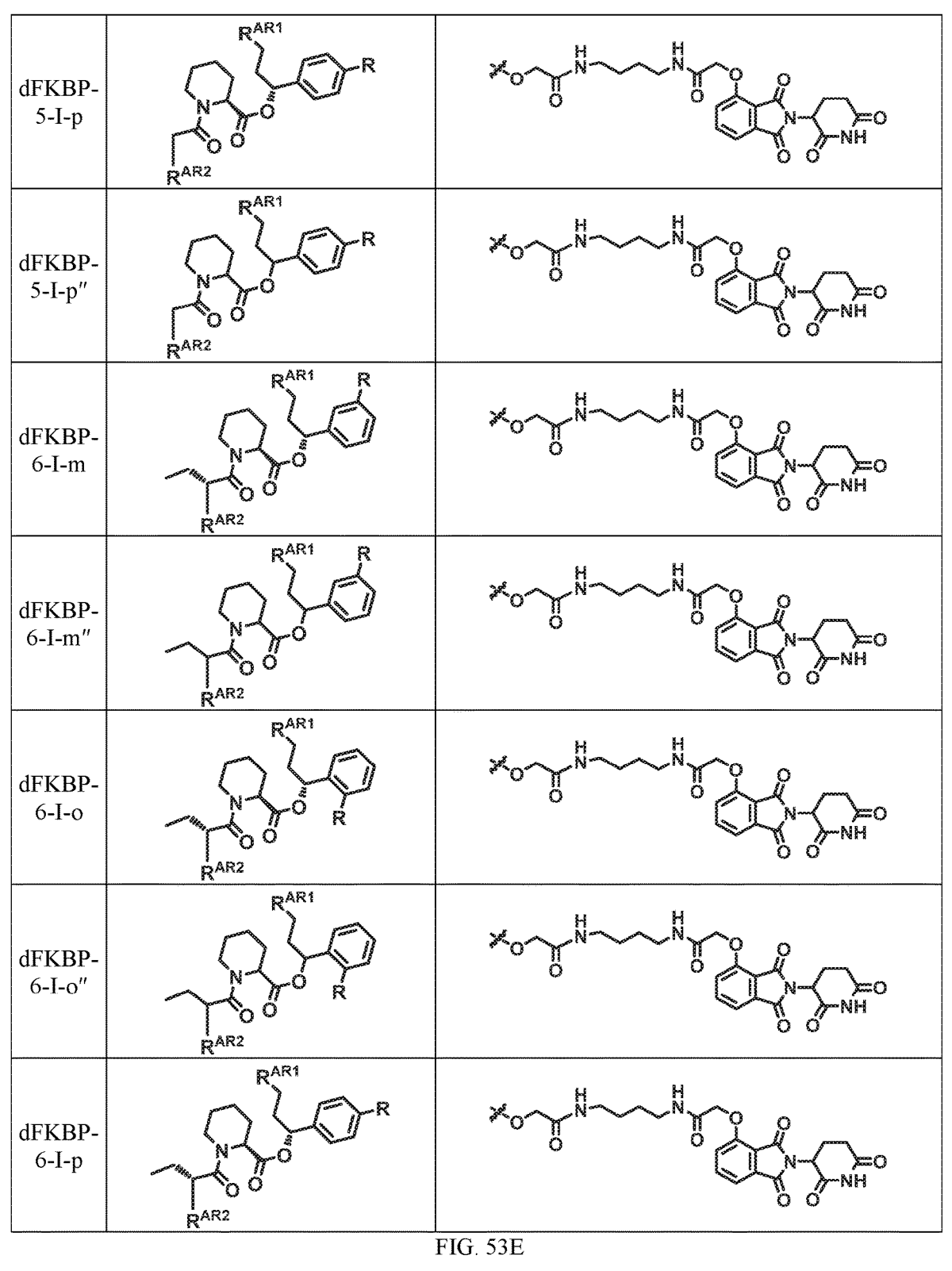
Figure 53F:
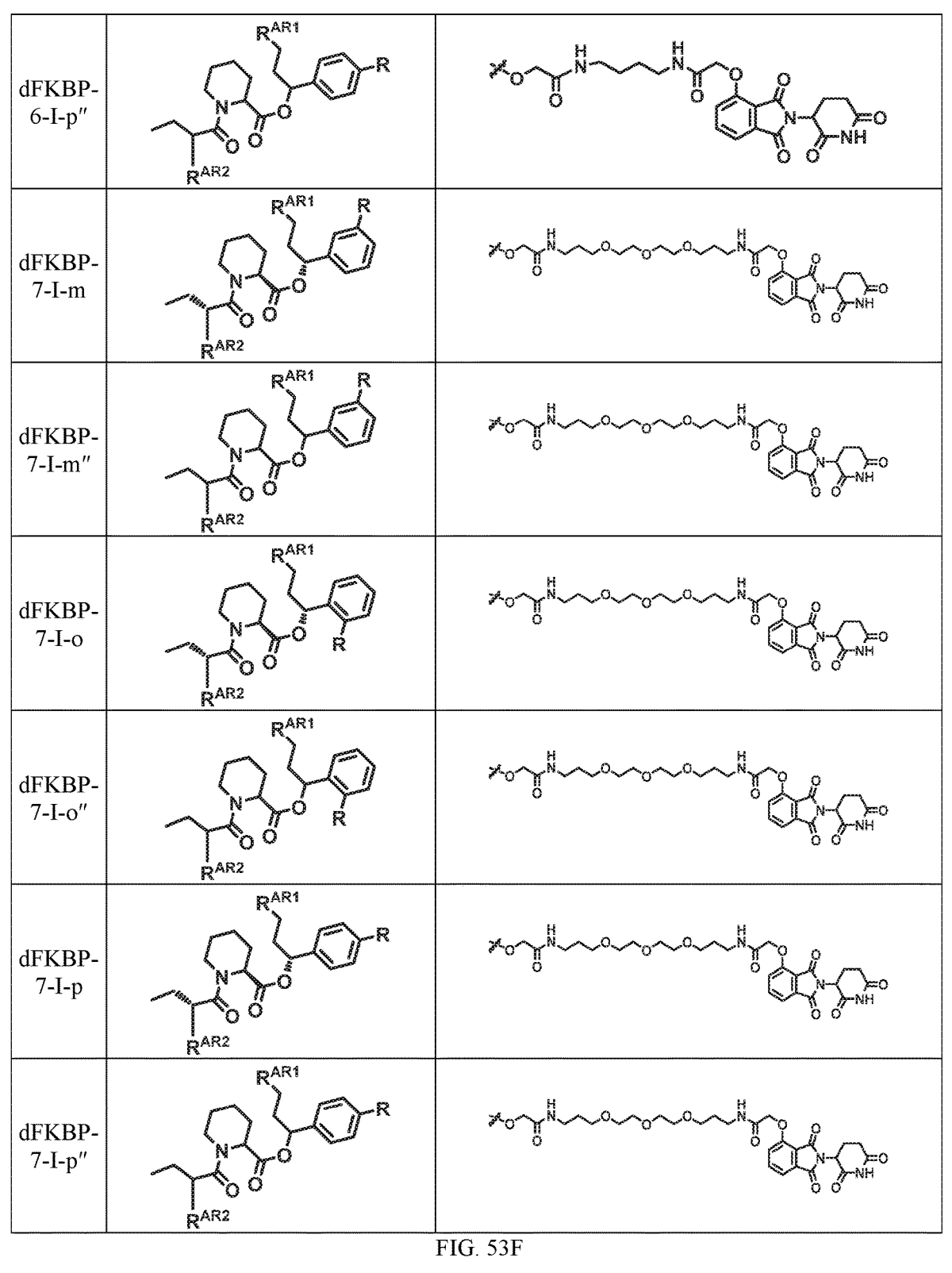
Figure 53G:
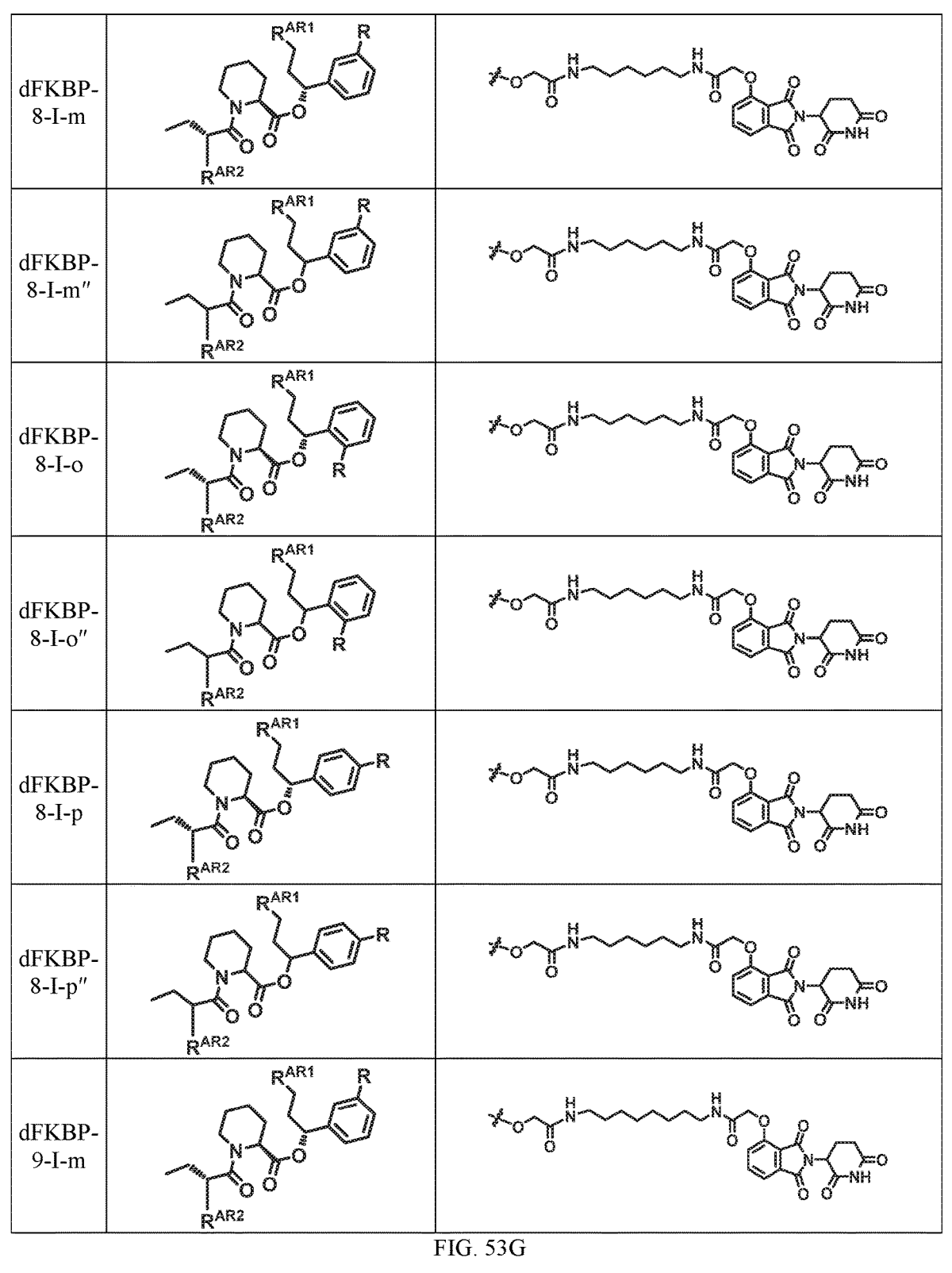
Figure 53S:
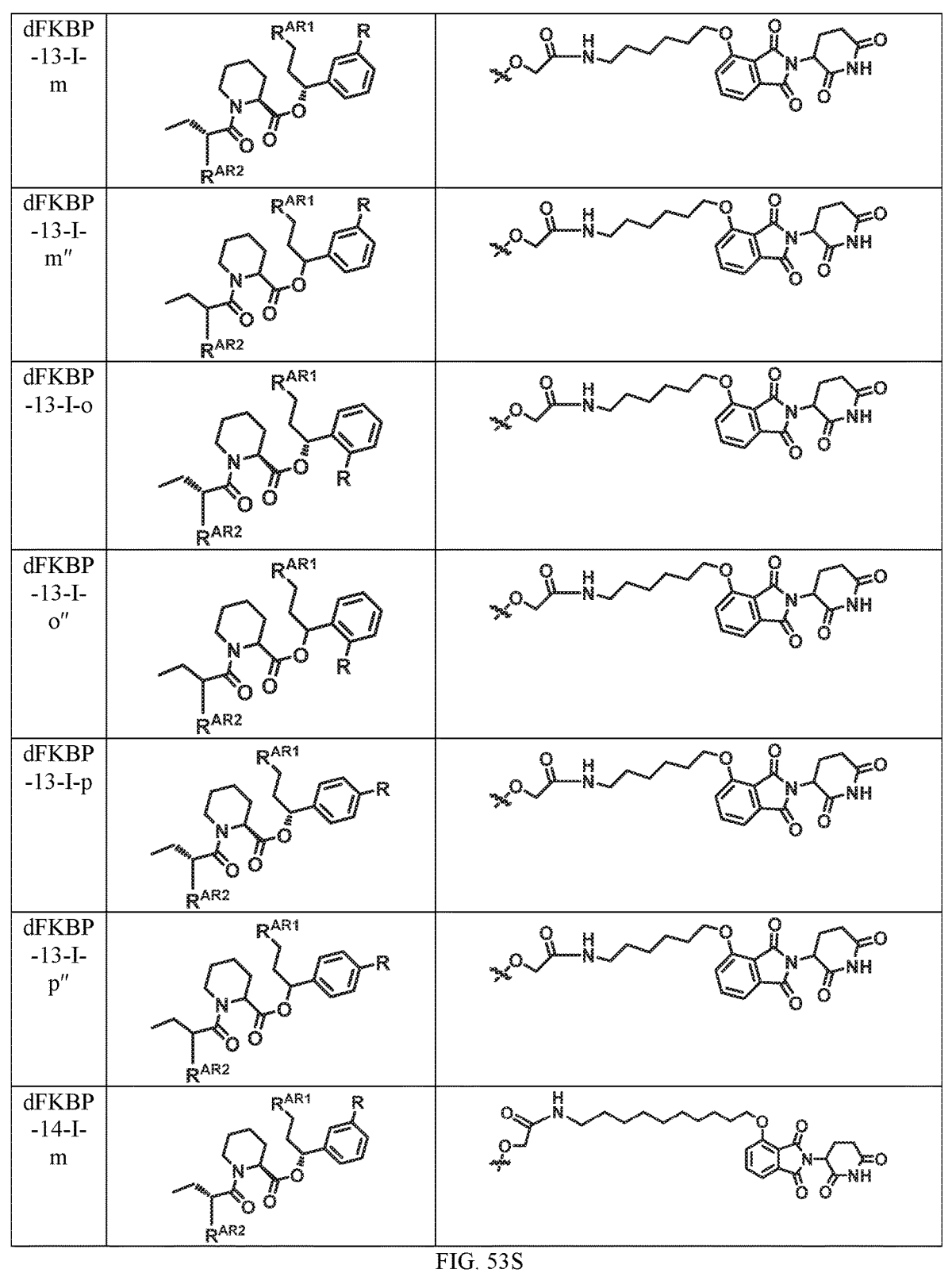
Figure 53V:
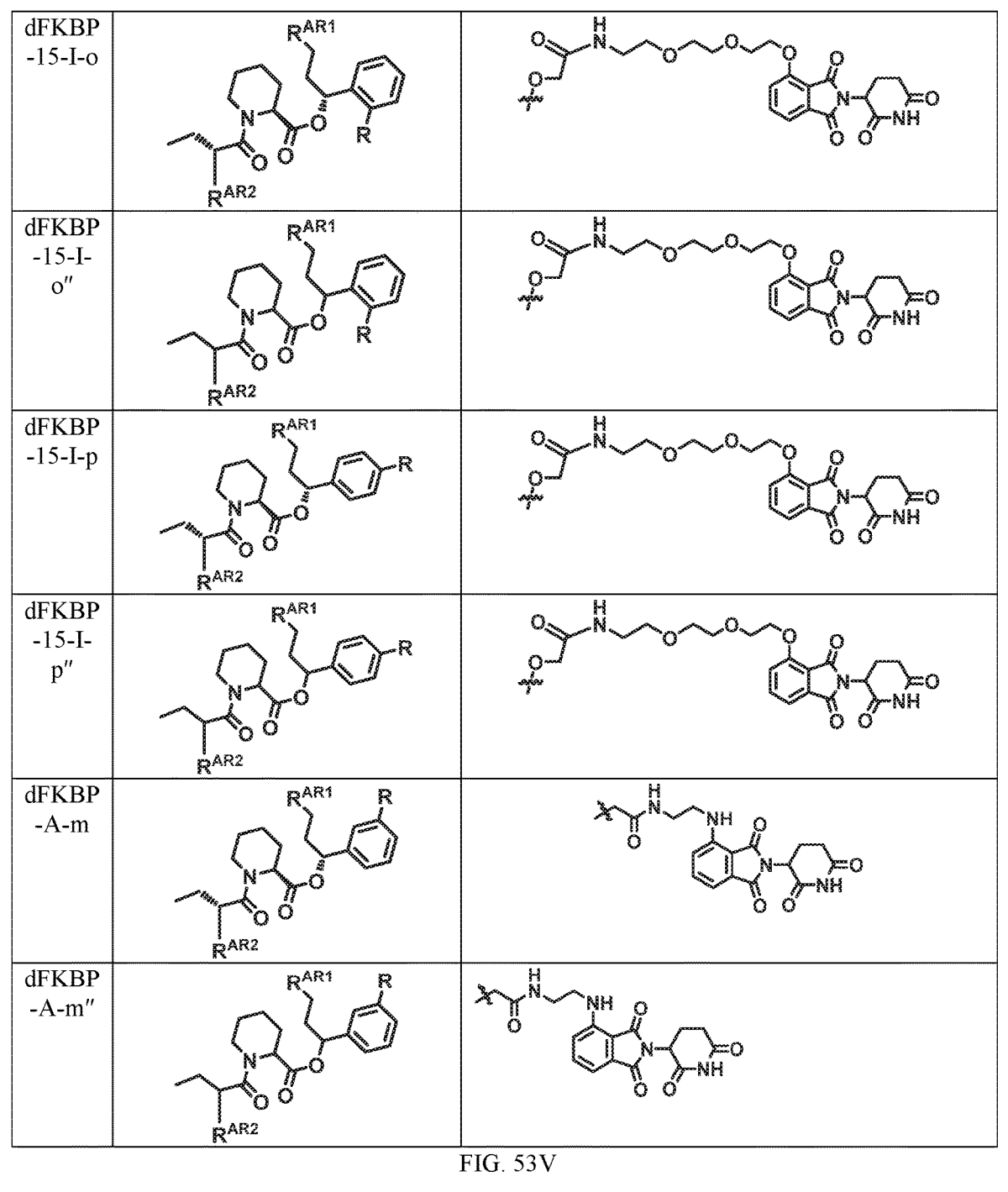
Figure 53Y:
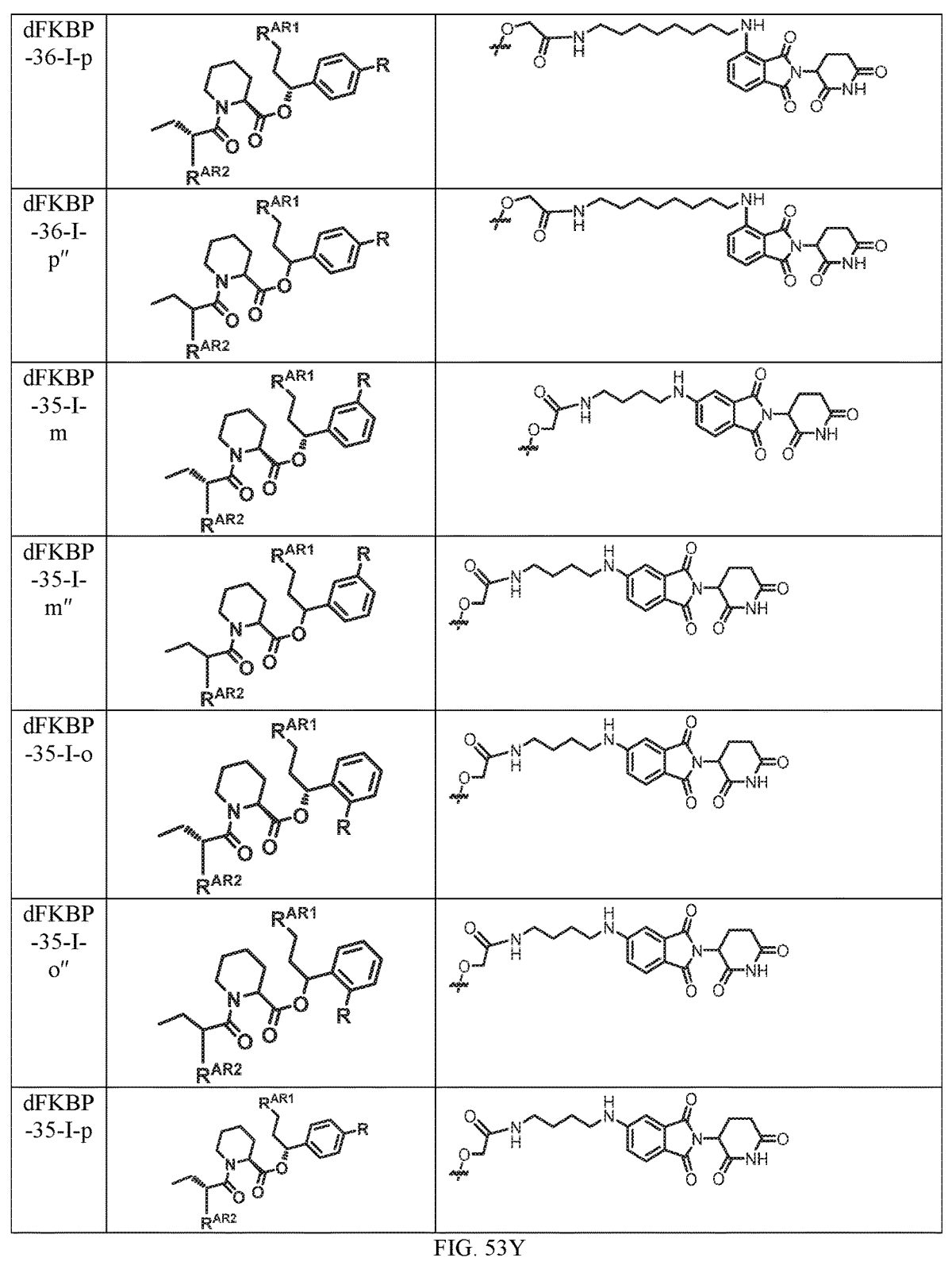

FIG. 53A, FIG. 53B, FIG. 53C, FIG. 53D, FIG. 53E, FIG. 53F, FIG. 53G, FIG. 53H, FIG. 53I, FIG. 53J, FIG. 53K, FIG. 53L, FIG. 53M, FIG. 53N, FIG. 53O, FIG. 53P, FIG. 53Q, FIG. 53R, FIG. 53S, FIG. 53T, FIG. 53U, FIG. 53V, FIG. 53W, FIG. 53X, FIG. 53Y, FIG. 53Z, FIG. 53AA, FIG. 53BB, FIG. 53CC, FIG. 53DD, and FIG. 53EE provide specific heterobifunctional compounds for use in the present invention, wherein $R^{AR1}$ and $R^{AR2}$ are described herein.

DETAILED DESCRIPTION OF THE INVENTION

Figure 1:
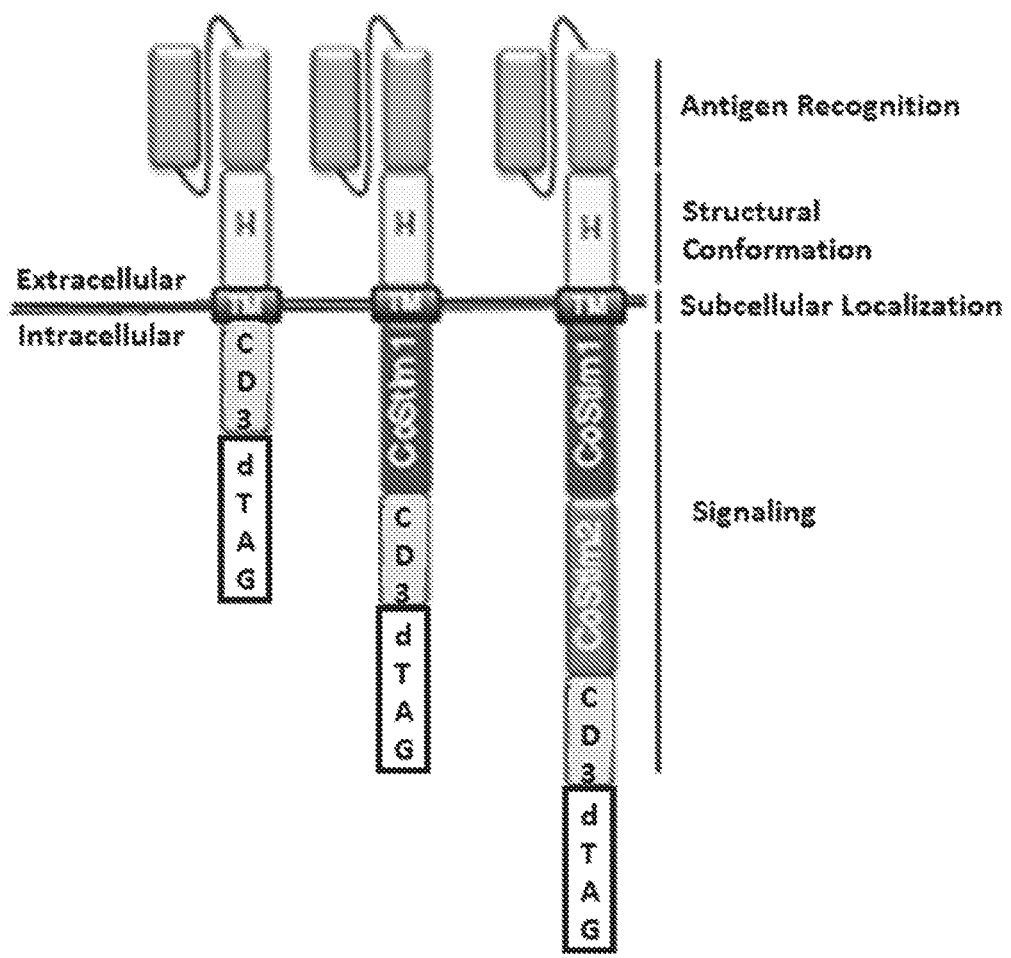
FIG. 1 is a schematic of generalized exemplary chimeric antigen receptors (CARs) of the invention which include a single chain antibody, hinge domain (H), transmembrane domain (TM), signaling domains responsible for T-cell activation, and a dTAG capable of being bound by a heterobifunctional compound resulting in degradation of at least a portion of the CAR. From left to right, the illustrative CARs include a CD3-derived signaling domain, a costimulatory domain and CD3-derived domain, and two costimulatory domains and a CD3-derived domain all with a 3' fused dTAG.
Figure 2:
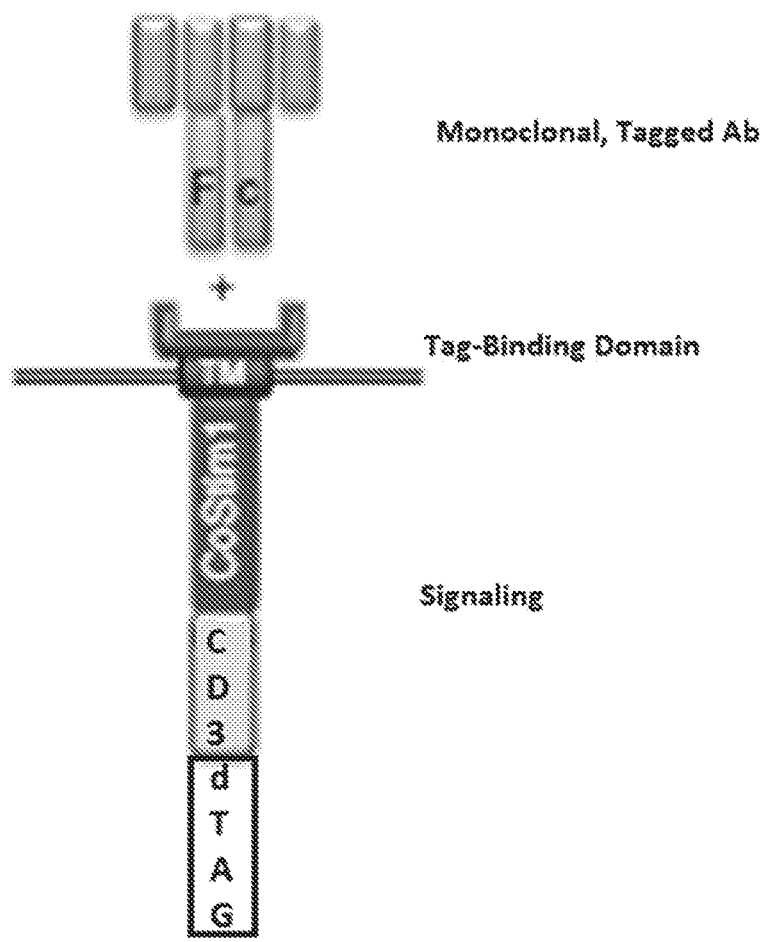
FIG. 2 is a schematic of a generalized example of a universal CAR having a dTAG capable of being bound by a heterobifunctional compound resulting in degradation of at least a portion of the CAR, wherein the extracellular ligand binding domain targets a label or a tag, wherein the label or tag is bound to, for example, and antibody capable of binding a target ligand such as a tumor antigen.
Figure 3A:
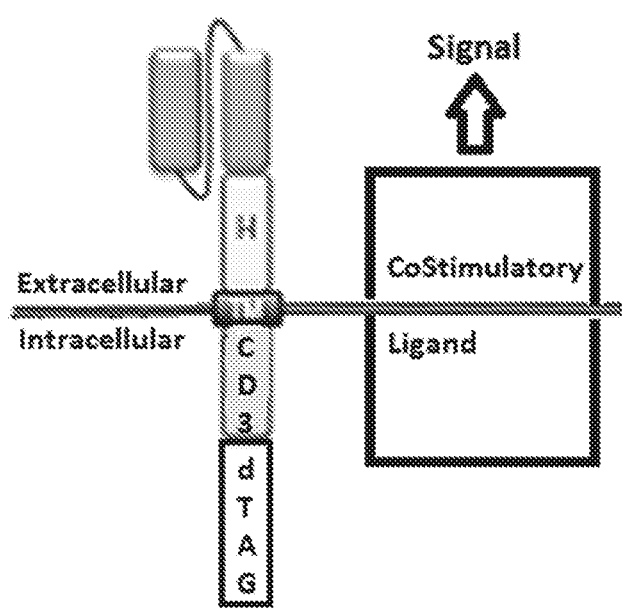
FIG. 3A is a schematic of a generalized example of a CAR having a dTAG capable of being bound by a heterobifunctional compound resulting in degradation of at least a portion of the CAR in a trans signaling combination with a costimulatory ligand including a costimulatory ligand capable of stimulating other immune effector cells.
Figure 3B:
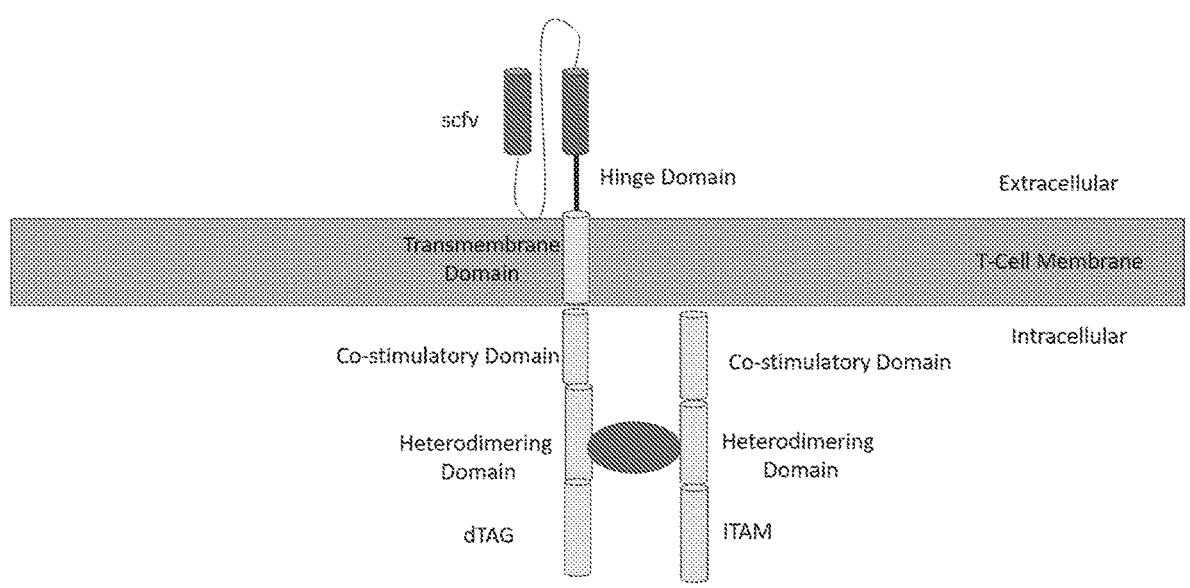
FIG. 3B is a schematic of a generalized example of a conditional or split CAR incorporating a dTAG. The dTAG can be on either part of the split CAR. The conditional or split CAR is generally a split receptor, wherein antigen binding and intracellular signaling components only assemble in the presence of a heterodimerizing small molecule
Figure 3C:
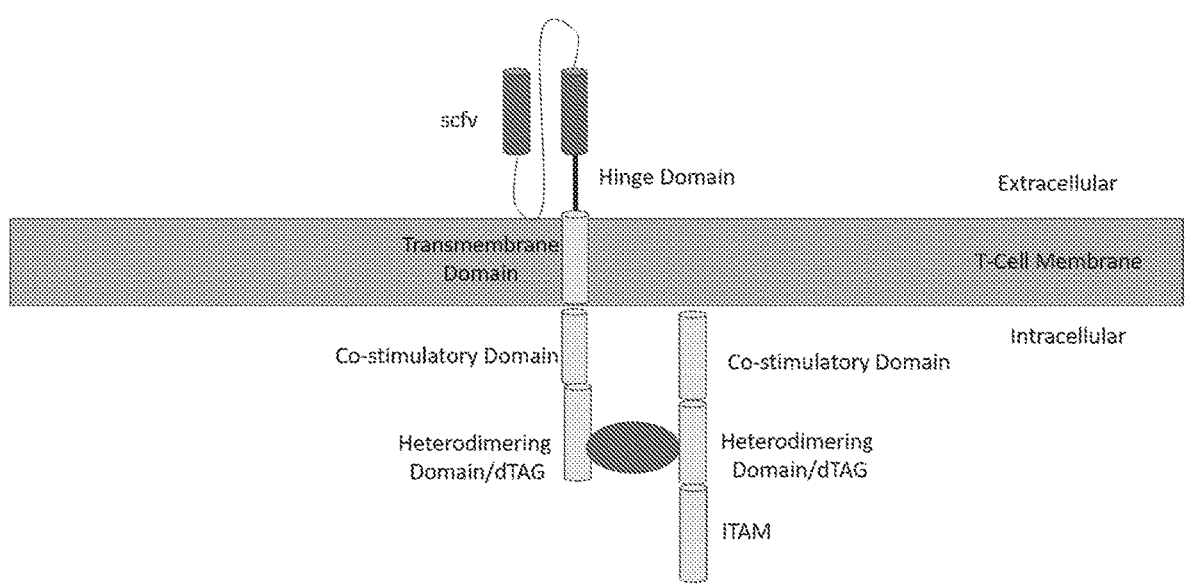
FIG. 3C is a schematic of a generalized conditional or split CAR wherein incorporating a dTAG.
Figure 3D:
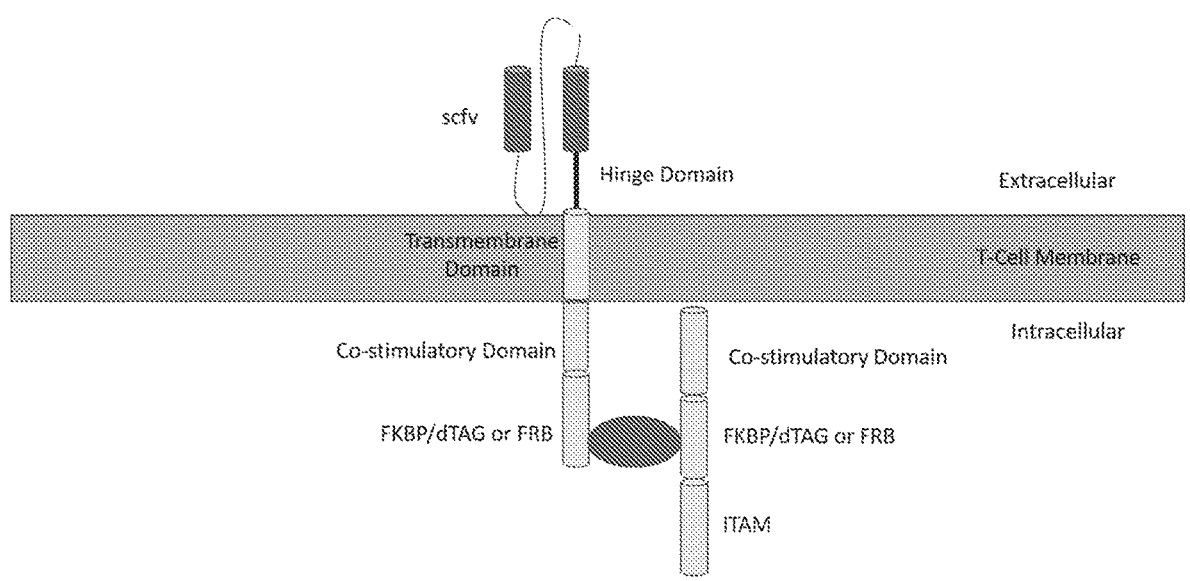
FIG. 3D is a schematic of a conditional or split CAR wherein the common dimerization domains include the FK 506 Binding Protein (FKBP) domain and the T2089L mutant of FKBP-rapamycin binding (FRB) domains, which are included on separate parts and capable of dimerization with a rapalog such as rapamycin analog AP21967, wherein the dTAG can be the heterodimerization domain itself, for example FKBP.
Figure 3E:
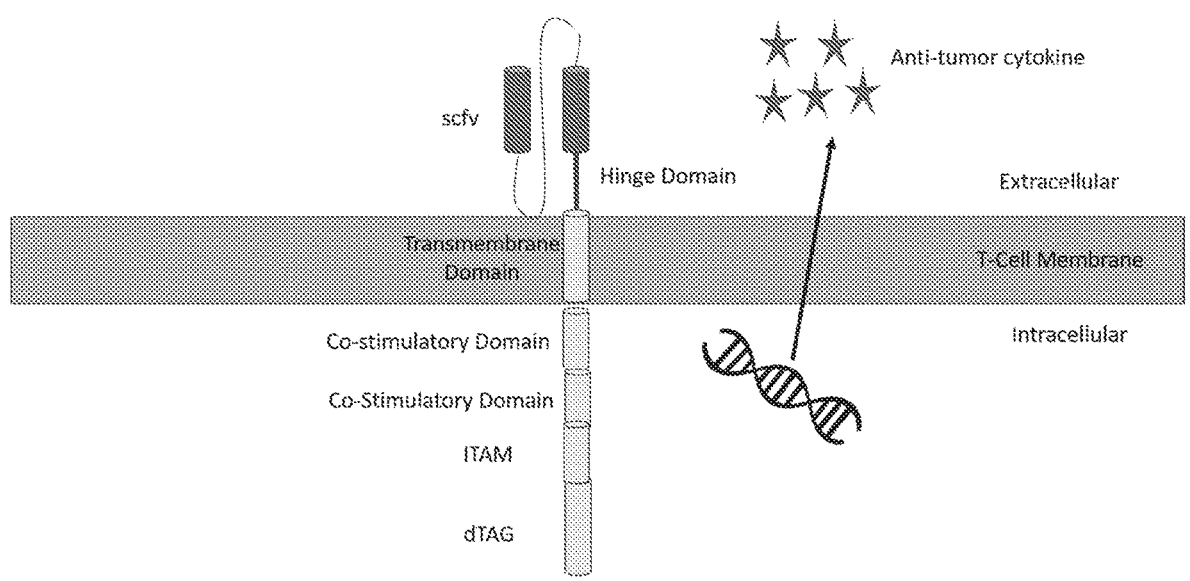
FIG. 3E is a schematic of a TRUCK strategy incorporating a dTAG. The TRUCK T-Cell co-expresses a CAR incorporating a dTAG and an anti-tumor cytokine, for example IL-12, which induces innate antitumor responses and alleviates immunosuppression in the tumor microenvironment. By modifying the tumor stroma, TRUCKs have the ability to enhance tumor infiltration by endogenous immune cells.
Figure 3F:
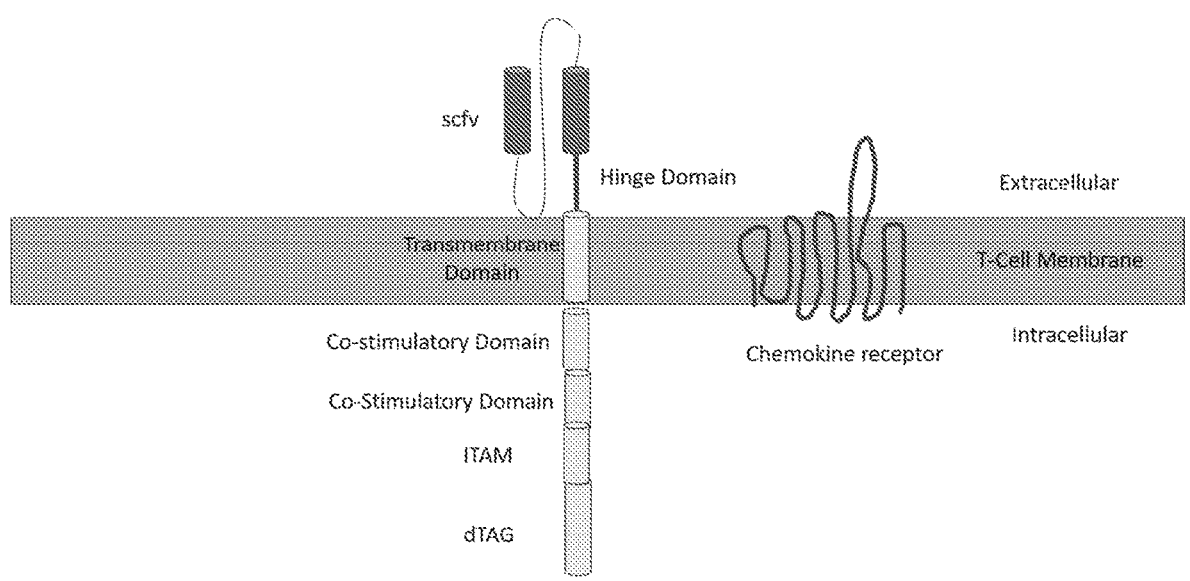
FIG. 3F is a schematic of a self-driving CAR which co-expresses a CAR incorporating a TAG and a chemokine receptor which binds to a tumor ligand.
Figure 3G:
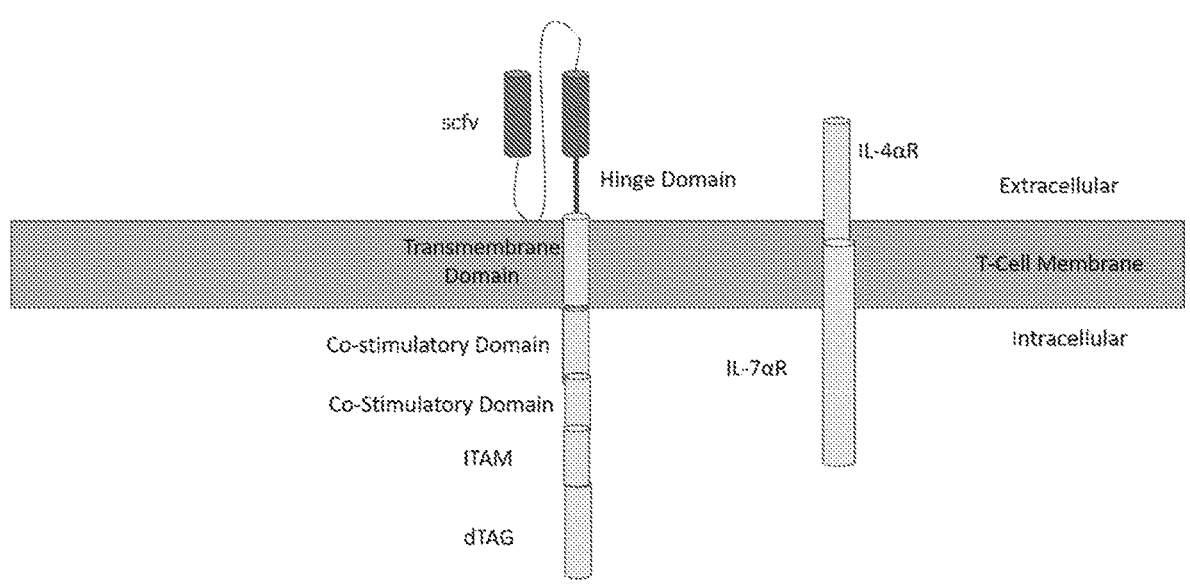
FIG. 3G is a schematic of an exemplary Armored CAR strategy, wherein a CAR incorporating a dTAG is co-expressed with a IL-4αR/IL-7αR construct that further activates the T-cell upon binding with tumor expressed cytokine IL-4.
Figure 3H:
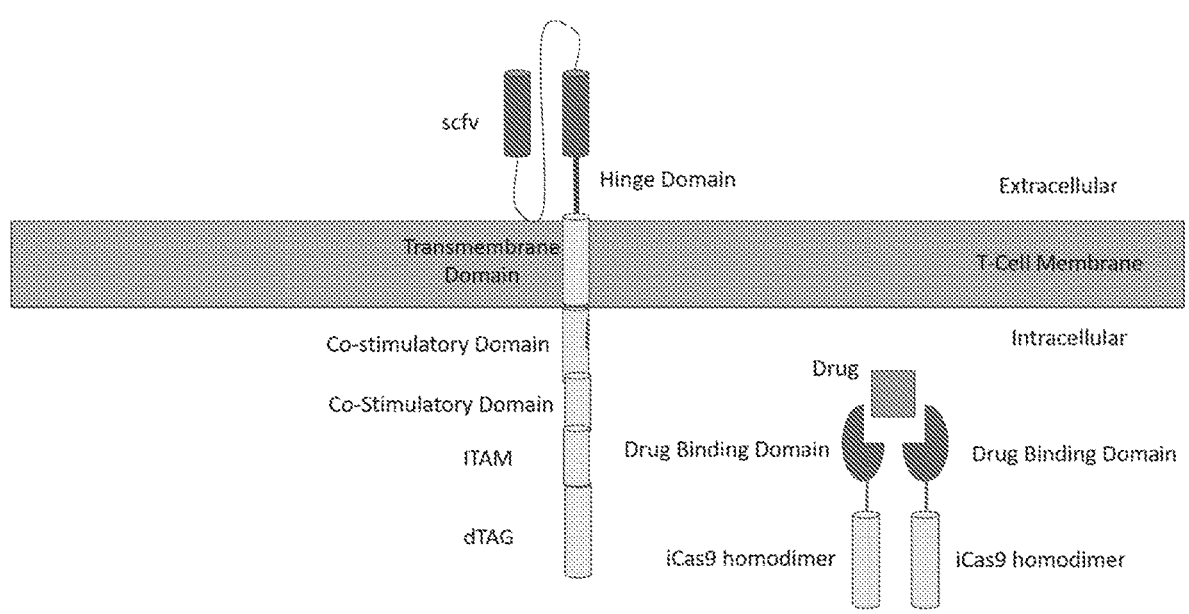
FIG. 3H is a schematic of an exemplary suicide gene strategy, wherein the cell expressing the CAR also expresses a suicide gene.
Figure 3I:
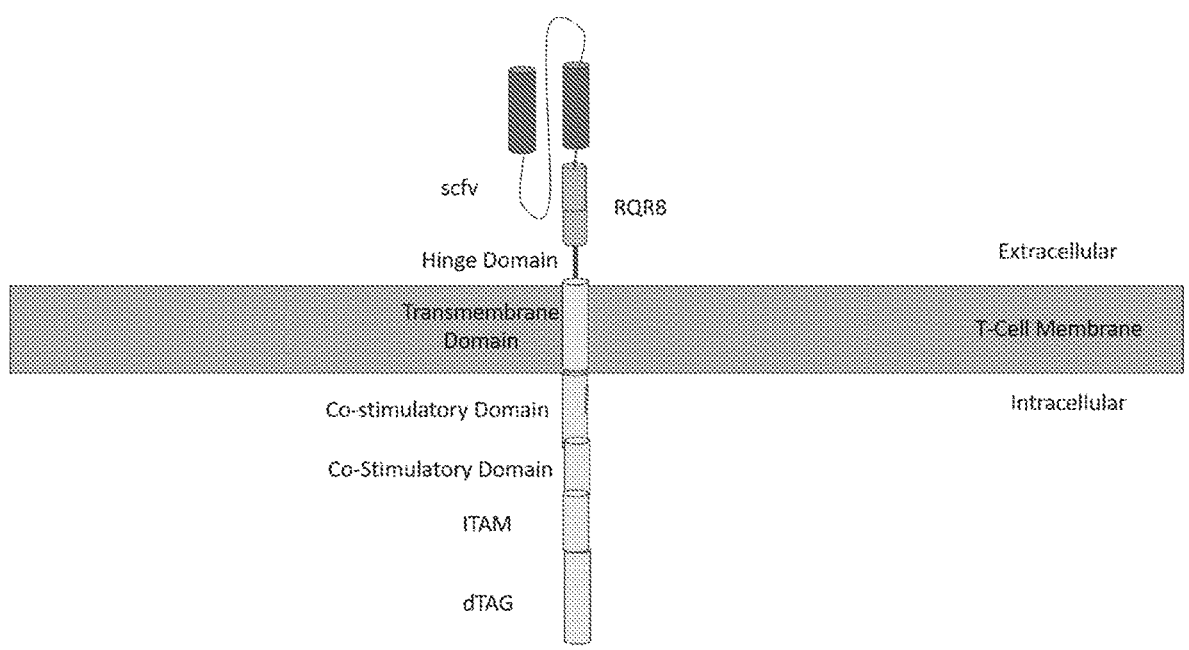
FIG. 3I is a schematic of an exemplary strategy wherein the dTAG can be incorporated into a CAR for use in a cell also expressing a ligand capable of binding to a monoclonal antibody, for example a fusion of CD34 and CD20 epitopes (RQR8) which binds to rituximab (monoclonal CD20 antibody).
Figure 3J:
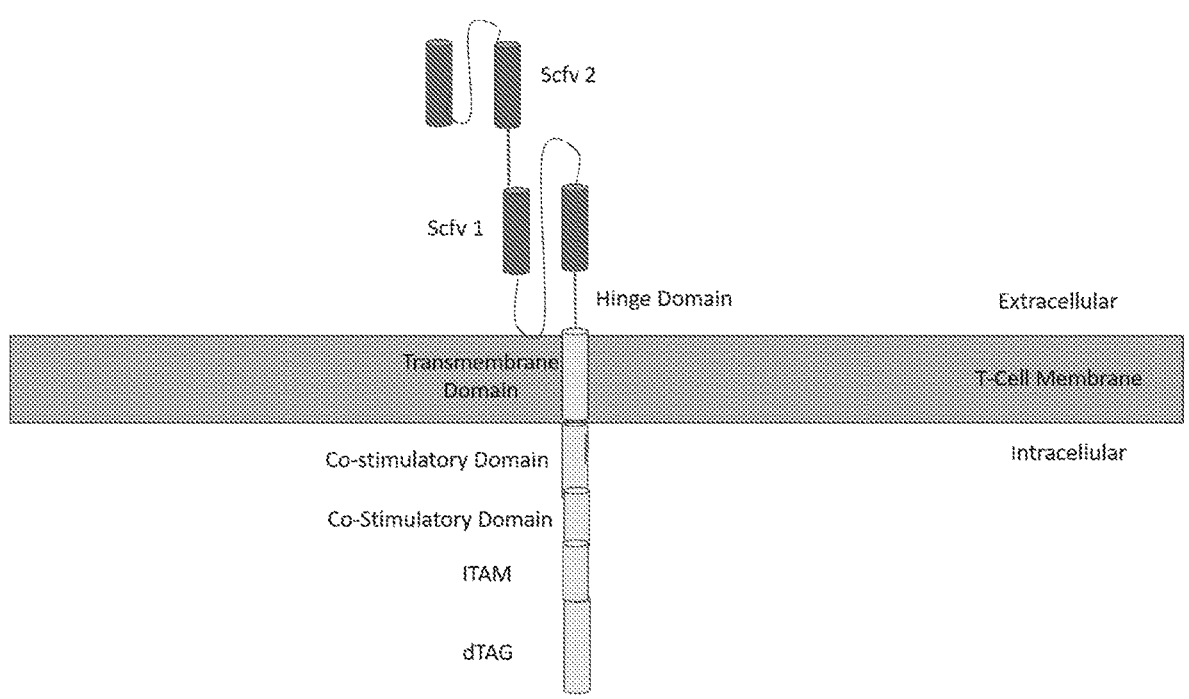
FIG. 3J is a schematic of an exemplary strategy wherein the dTAG is incorporated into a CAR construct having two binding domains (a Tandem CAR), wherein the CAR cell is only activated when target cells co-express both targets.
Figure 3K:
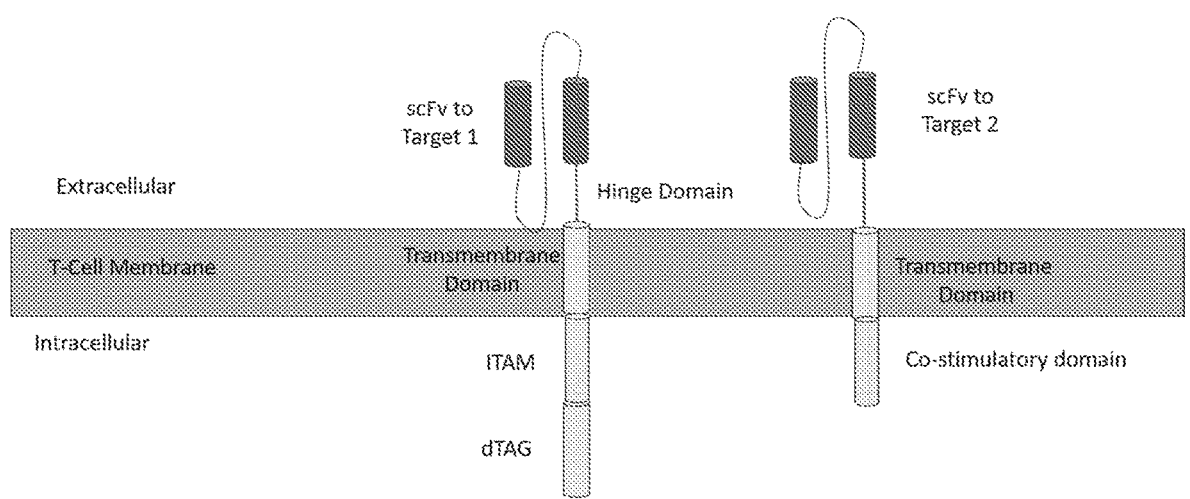
FIG. 3K is a schematic of an exemplary strategy wherein the dTAG can be incorporated into one or more CAR constructs expressed in a cell, for example, in a dual target strategy wherein the cell expresses two separate CARs with different ligand binding targets; one CAR includes only co-stimulatory domains while the other CAR includes only an ITAM. In such a strategy, the dTAG can be incorporated on either one of the CARs, or both CARs.
Figure 3L:
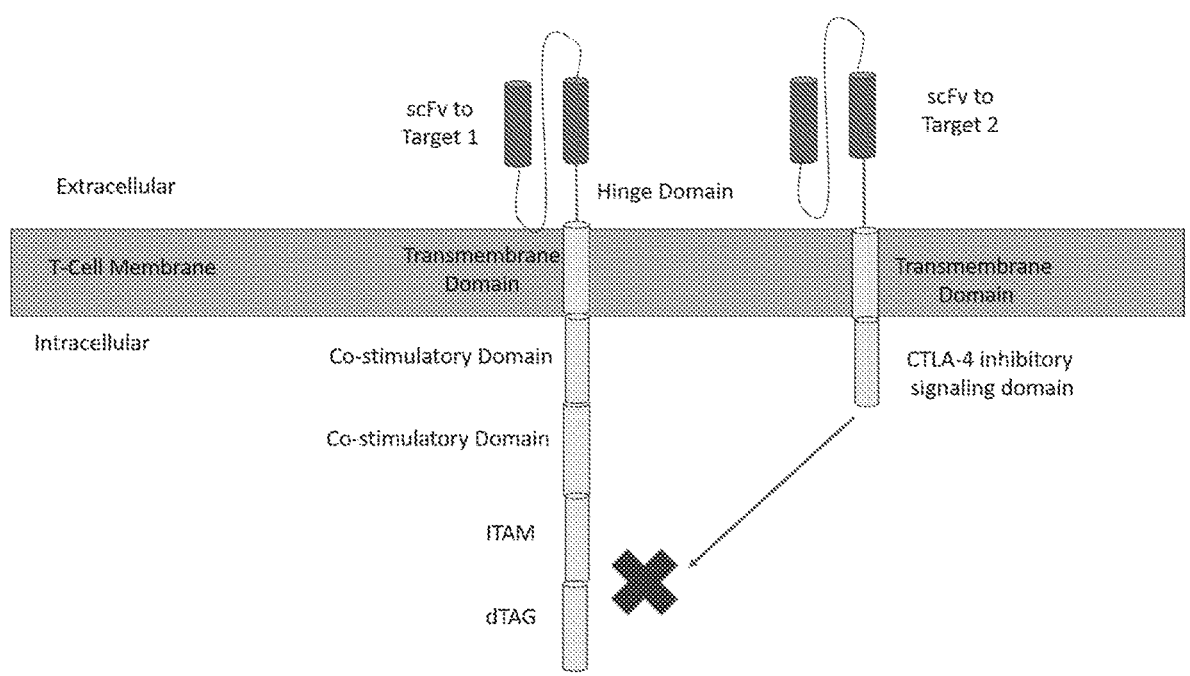
FIG. 3L is a schematic of an exemplary strategy wherein the dTAG is incorporated into one or more CAR constructs expressed in a cell, for example, wherein one CAR comprises an inhibitory domain that is activated upon binding a ligand, for example on a normal cell, and a second CAR directed to a tumor target. This type of strategy, often referred to as inhibitory CAR or iCAR.
Figure 3M:
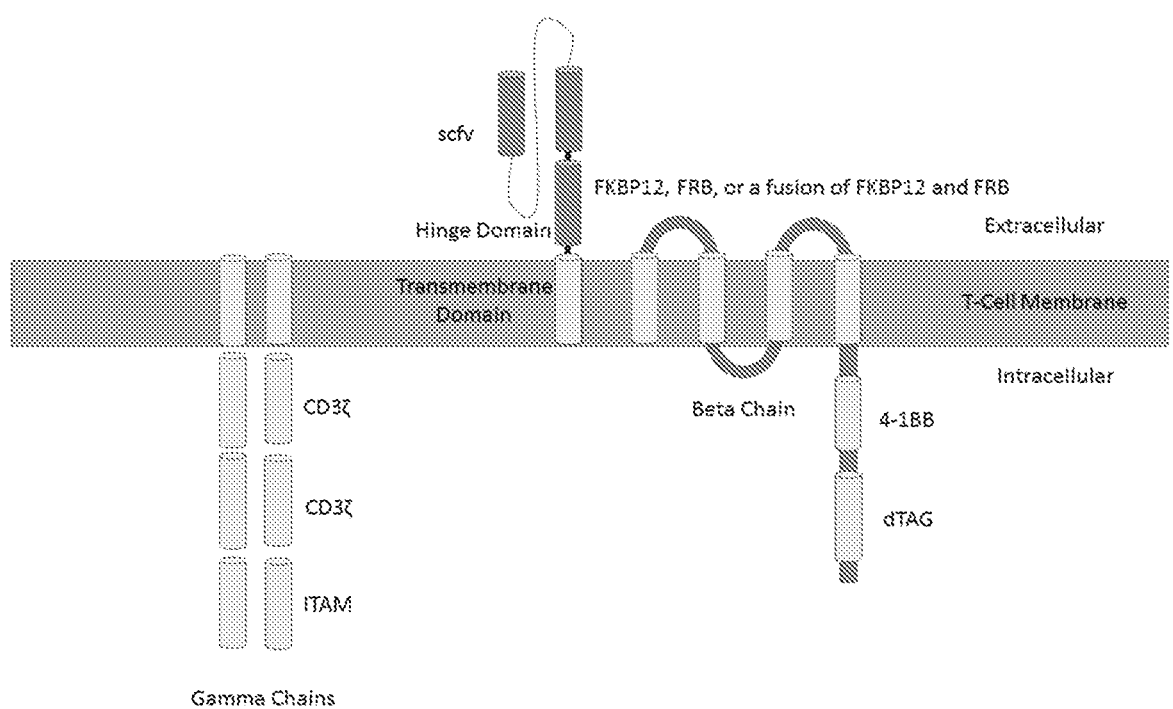
FIG. 3M is a schematic of an exemplary strategy wherein the dTAG is integrated into a multi chain CAR (mcCAR) where either the FRB protein, the FKB12 protein, or a fusion of the FRB and FKB12 have been inserted between the hinge and scFv domains. This engineered protein can then be manipulated by adding a small molecule, for example, rapamycin or tacrolimus. Once the small molecule binds, this induces a conformational change that causes the protein to move from an "off-state," or inactive state, to an "on-state." The dTAG can be incorporated into either the gamma chains or the beta chains. mCAR mimics the complexity of the T-cell receptor native architecture.

In one embodiment, a method is provided that includes at least the steps of:
(i) administering to a patient with a disorder of diseased cells an immune effector cell that can recognize and bind to the diseased cells, wherein the immune effector cell has been transformed to express a CAR having at least a sequence targeting a diseased cell surface antigen and an amino acid sequence that can be recognized by and bound to a dTAG Targeting Ligand of a heterobifunctional compound to form a CAR immune effector cell; and,
(ii) administering to the patient, as needed, a heterobifunctional compound which binds to a) the dTAG and b) a ubiquitin ligase; in a manner that brings the dTAG (and thus the immune effector cell) into proximity of the ubiquitin ligase, such that the CAR is ubiquitinated, and then degraded by the proteasome.

In one embodiment, a method is provided that includes at least the steps of:

administering to a patient as needed, a heterobifunctional compound;

wherein the patient has a disorder of diseased cells that can be treated by increasing the ability of an immune effector cell, for example a T-cell, to recognize and bind to the diseased cells;

wherein the patient has previously been administered allogeneic or autologous immune effector cells, for example, CAR T-cells, which have been transformed ex vivo by inserting a gene encoding a CAR having at least a sequence targeting a diseased cell surface antigen and an amino acid sequence that can be recognized by and bound to a dTAG Targeting Ligand of a heterobifunctional compound to form a CAR T-cell;

wherein the heterobifunctional compound is capable of binding to a) the dTAG and b) a ubiquitin ligase in a manner that brings the dTAG (and thus the CAR) into proximity of the ubiquitin ligase, such that the CAR is ubiquitinated, and then degraded by the proteasome.

In one embodiment, a method is provided that includes at least the steps of:

(i) administering to the patient allogeneic CAR T-cells; and then (ii) administering to the patient, as needed, a heterobifunctional compound which binds to a) the dTAG and b) a ubiquitin ligase; in a manner that brings the dTAG (and thus the CAR T-cell) into proximity of the ubiquitin ligase, such that the CAR is ubiquitinated, and then degraded by the proteasome.

In one embodiment, a method is provided that includes at least the steps of:

(i) administering to the patient an immune effector CAR cell, wherein the CAR cell includes a CAR and a second polynucleotide including one or more signaling domains capable of activating the immune effector cell in concert with the CAR, and wherein a dTAG is incorporated in either the CAR or second polypeptide; and then (iv) administering to the patient, as needed, a heterobifunctional compound which binds to a) the dTAG and b) a ubiquitin ligase; in a manner that brings the dTAG (and thus the CAR or second polypeptide) into proximity of the ubiquitin ligase, such that the CAR or second polypeptide is ubiquitinated, and then degraded by the proteasome.

The invention includes compositions and methods for mediating CAR immune effector cell, for example CAR T-cell, stimulation through the incorporation of a heterobifunctional compound targeted protein or heterobifunctional compound tag, collectively referred to as a dTAG, within a synthetic chimeric antigen receptor (CAR) construct that allows for reversible targeted protein degradation using a heterobifunctional compound. The CARs of the invention are useful in treating cancer including but not limited to hematologic malignancies and solid tumors. The present invention includes a strategy of adoptive cell transfer of T-cells transduced to express a chimeric antigen receptor (CAR) having a dTAG that is capable of being bound by a heterobifunctional compound, which, upon contact with the heterobifunctional compound, is degraded by the ubiquitin proteasomal pathway.

CARs are molecules that combine antibody-based specificity for a desired antigen (e.g., tumor antigen) with a T-cell receptor-activating intracellular domain to generate a chimeric protein that exhibits a specific anti-tumor cellular immune activity.

The present invention relates generally to the use of T-cells genetically modified to stably express a desired CAR having a dTAG. T-cells expressing these CARs are referred to herein as CAR T-cells or CAR modified T-cells. Preferably, the cell can be genetically modified to stably express an antibody binding domain on its surface, conferring novel antigen specificity that is WIC independent. In some instances, the T-cell is genetically modified to stably express a CAR that combines an antigen recognition domain of a specific antibody with an intracellular domain having a dTAG in a single chimeric protein.

In one embodiment, the CAR of the invention includes an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In one embodiment, the transmembrane domain is the CD8α hinge domain.

With respect to the cytoplasmic domain, the CAR of the invention is designed to include at least one signaling domain and a heterobifunctional compound targeted protein (dTAG). The heterobifunctional compound targeted protein of the CAR is any amino acid sequence to which a heterobifunctional compound can be bound, leading to the degradation of the CAR when in contact with the heterobifunctional compound. Preferably, the dTAG should not interfere with the function of the CAR. In one embodiment, the dTAG is a non-endogenous peptide, leading to heterobifunctional compound selectivity and allowing for the avoidance of off target effects upon administration of the heterobifunctional compound. In one embodiment, the dTAG is an amino acid sequence derived from an endogenous protein which has been modified so that the heterobifunctional compound binds only to the modified amino acid sequence and not the endogenously expressed protein.

The signaling domain can be any suitable signaling domain capable of activating the T-cell, for example, CD3, CD28, 4-1BB, OX40 (CD134), CD27, ICOS, DAP-10, or DAP-12 signaling domain, which can be by itself or be combined with any other desired cytoplasmic domain(s) useful in the context of the CAR of the invention. In one embodiment, the cytoplasmic domain of the CAR can be designed to further comprise a second signaling domain, for example, the signaling domain of CD3-zeta, CD28, 4-1BB, OX40 (CD134), CD27, ICOS, DAP-10, and/or DAP-12 signaling domain, or any combination thereof. For example, the cytoplasmic domain of the CAR can include but is not limited to CD3-zeta, 4-1BB, and/or CD28 signaling modules and combinations thereof.

The generation of CAR T-cells is known in the art. For example, see Wang et al, "Clinical manufacturing of CAR T cells: foundation of a promising therapy," Oncolytics (2016) 3:1-7 (and incorporated herein). In general, the CAR T-cells of the invention can be generated by introducing, for example, a lentiviral vector including a desired CAR, for example a CAR comprising anti-CD19, CD8α hinge and transmembrane domain, human CD28 and CD3zeta signaling domains, and a FKBP* dTAG into the cells. The CAR T-cells of the invention are able to replicate in vivo resulting in long-term persistence that can lead to sustained tumor control, and are subject to modulation of activation via administration of a heterobifunctional compound.

In one embodiment, genetically modified T-cells expressing a CAR for the treatment of a patient having cancer or at risk of having cancer are administered using lymphocyte infusion. Autologous lymphocyte infusion is used in the treatment. Autologous PBMCs are collected from a patient in need of treatment and T-cells are activated and expanded using the methods described herein and known in the art and then infused back into the patient. Alternatively, an allogeneic immune effector cell, for example a T-cell, can be utilized.

In yet another embodiment, the treatment of a patient at risk of developing CLL is provided. The invention also includes treating a malignancy or an autoimmune disease in which chemotherapy and/or immunotherapy in a patient results in significant immunosuppression in the patient, thereby increasing the risk of the patient of developing CLL.

The invention includes using CAR T-cells that express a CAR containing a dTAG. The CAR T-cells of the invention can undergo robust in vivo CAR T-cell expansion and can establish targeted antigen-specific memory cells that persist at high levels for an extended amount of time in blood and bone marrow. In some instances, the CAR T-cells of the invention infused into a patient can be modulated by administering to the subject a heterobifunctional compound that is capable of binding the dTAG on the CAR, resulting in degradation of the dTAG and a down regulation of the CAR T-cell activation without destroying the CAR T-cell.

Terminology

Unless defined otherwise, all technical and scientific terms used herein have the same meaning as commonly understood by one of ordinary skill in the art. Although any methods and materials similar or equivalent to those described herein can be used in the practice for testing of the present invention, typical materials and methods are described herein.

It is also to be understood that the terminology used herein is for the purpose of describing particular embodiments only, and is not intended to be limiting.

As used herein, a "chimeric antigen receptor (CAR)" means a fused protein comprising an extracellular domain capable of binding to an antigen, a transmembrane domain, and at least one intracellular signaling domain. The "chimeric antigen receptor (CAR)" is sometimes called a "chimeric receptor", a "T-body", or a "chimeric immune receptor (CIR)." The "extracellular ligand binding domain" means any oligopeptide or polypeptide that can bind to another protein. The "intracellular signaling domain" or "cytoplasmic signaling domain" means any oligopeptide or polypeptide known to function as a domain that transmits a signal to cause activation or inhibition of a biological process in a cell.

As used herein, a "tumor antigen" means a biological molecule having antigenicity, expression of which is associated with a neoplastic cell. The tumor antigens targeted in the present invention include a tumor specific antigen (an antigen which is present only in tumor cells and is not found in other normal cells), and a tumor-associated antigen (an antigen which is also present in other organs and tissues or heterogeneous and allogeneic normal cells, or an antigen which is expressed on the way of development and differentiation).

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing a scFv are known, and include methods described in U.S. Pat. No. 4,694,778, *Science,* 242 (1988):423-442, *Nature* 334 (1989):54454, and *Science* 240 (1988):1038-1041.

As used herein, a "domain" means one region in a polypeptide which is folded into a particular structure independently of other regions.

"Activation", as used herein, refers to the state of an immune effector cell, for example a T-cell, that has been sufficiently stimulated to induce detectable cellular proliferation. Activation can also be associated with induced cytokine production, and detectable effector functions. The term "activated T-cells" refers to, among other things, T-cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies (Harlow et al., "Using Antibodies: A Laboratory Manual", Cold Spring Harbor Laboratory Press, N Y (1999); Harlow et al., "Antibodies: A Laboratory Manual", Cold Spring Harbor, N.Y. (1989); Houston et al., *Proc. Natl. Acad. Sci.* 85 (1988):5879-5883; and Bird et al., *Science* 242 (1988):423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

The term "antigen" or "Ag" as used herein is defined as a molecule that can be targeted by an antibody or antibody fragment thereof.

As used herein, the term "autologous" is meant to refer to any material derived from the same individual to which it is later to be re-introduced into the individual. As used herein, the term "allogeneic" is meant to refer to any material derived from a different individual than the subject to which it is later introduced into the individual.

"Co-stimulatory ligand," as the term is used herein, includes a molecule on an antigen presenting cell (e.g., an APC, dendritic cell, B cell, and the like) that specifically binds a cognate co-stimulatory molecule on a T-cell, thereby providing a signal which, in addition to the primary signal provided by, for instance, binding of a TCR/CD3 complex with an MHC molecule loaded with peptide, mediates a T-cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T-cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue, or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host T-cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

A "co-stimulatory molecule" refers to the cognate binding partner on a T-cell that specifically binds with a co-stimulatory ligand, thereby mediating a co-stimulatory response by the T-cell, such as, but not limited to, proliferation. Co-stimulatory molecules include, but are not limited to an MHC class I molecule, BTLA and a Toll ligand receptor.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host T-cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

A "co-stimulatory signal", as used herein, refers to a signal, which in combination with a primary signal, such as TCR/CD3 ligation, leads to T-cell proliferation, activation, and/or upregulation or downregulation of key molecules.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "stimulation," is meant a primary response induced by binding of a stimulatory molecule (e.g., a TCR/CD3 complex or CAR) with its cognate ligand thereby mediating a signal transduction event, such as, but not limited to, signal transduction via, for example, the TCR/CD3 or CD3ζ complex. Stimulation can mediate T-cell proliferation, activation, and/or upregulation or downregulation of key molecules, and the like.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into, for example, the host T-cell. A "transfected" or "transformed" or "transduced" cell is one which has been transfected, transformed or transduced with exogenous nucleic acid. The cell includes the primary subject T-cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, a "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., (1985):1418.

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, including but not limited to adverse immune responses associated with any CAR T-cell cancer treatment. Typically, the host is a human. A "patient" or "host" or "subject" also refers to for example, a mammal, primate (e.g., human), cows, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

Chimeric Antigen Receptors (CARs)

The CARs of the present invention are characterized in that they include an extracellular ligand binding domain capable of binding to an antigen, a transmembrane domain, and an intracellular domain in this order from the N-terminal side, wherein the intracellular domain includes at least one signaling domain and a dTAG. Alternatively, the CAR can be part of a complex wherein a second polypeptide is capable of interacting with the CAR for immune effector cell activation. As contemplated herein, the dTAG can be incorporated into the CAR and/or the second polypeptide.

(a) Extracellular Domain

The CARs of the invention include an extracellular target-specific ligand binding domain, for example an antigen binding moiety. The choice of moiety depends on the type and number of ligands that define the surface of a target cell. For example, the extracellular ligand binding domain may be chosen to recognize a ligand that acts as a cell surface marker on target cells associated with a particular disease state. Thus examples of cell surface markers that may act as ligands for the extracellular ligand binding domain in the CARs of the present invention include those associated with viral, bacterial and parasitic infections, autoimmune disease, and cancer cells.

In one embodiment, the CARs of the invention can be engineered to target a tumor antigen of interest by way of engineering a desired antigen binding moiety that specifically binds to an antigen on a tumor cell. In the context of the present invention, tumor antigen refers to antigens that are common to specific types of cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, mesothelin, α-Folate receptor, CAIX, EGP-2, EGP-40, IL13R-a2, KDR, kappa-light chain, LeY, L1 cell adhesion molecule, murine CMV, NKG2D ligands, GD2, GD3, and VEGF-R2.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2, Erb-B3, Erb-B4. Yet another group of target antigens are oncofetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations, such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In an embodiment, the antigen binding moiety portion of the CAR targets an antigen that includes but is not limited to CD19, CD20, CD30, CD44, CD22, ROR1, Mesothelin, CD33/IL3Ra, c-Met, PSMA, Glycolipid F77, EGFRvIII, GD-2, MY-ESO-1 TCR, MAGE A3 TCR, and the like.

In one embodiment, the antigen binding moiety portion of the CAR targets a particular cell surface molecule on a cell, wherein the cell surface molecule is associated with a particular type of cell, for example a cluster of differentiation molecule.

Depending on the desired antigen to be targeted, the CAR of the invention can be engineered to include the appropriate antigen bind moiety that is specific to the desired antigen target. For example, if CD19 is the desired antigen that is to be targeted, an antibody or antibody fragment, for example a scFv for CD19 can be used as the antigen bind moiety for incorporation into the CAR of the invention. In one embodiment, the antigen binding domain is comprised of a scFv. Single chain antibodies refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 341:544-546; Skerra et al. (1988) Science 240:1038-1041.

In one embodiment, the extracellular ligand binding domain binds a label or tag, for example biotin or fluorescein isothiocyanate, wherein biotin or fluorescein isothiocyanate is bound to an antibody capable of binding a molecule on the surface of a tumor cell.

In one embodiment, the extracellular ligand binding domain binds a marker associated with a particular cell or disease state, for example IL13R. In one embodiment, the extracellular ligand binding domain binds to a cluster of differentiation molecule associated with a particular cell.

(b) Transmembrane Domain

The CARs of the present invention can be designed to include a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or GITR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker In one embodiment, the transmembrane domain in the CAR of the invention is derived from the CD8 transmembrane domain. In some instances, the transmembrane domain of the CAR of the invention comprises the CD8α hinge domain.

Further, in the CAR of the present invention, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR of the present invention.

(c) Intracellular Signaling Domain

The intracellular signaling domain, or cytoplasmic signaling domain, used interchangeably herein, of the CAR of the invention is responsible for activation of at least one of the normal effector functions of the immune cell in which the CAR has been placed. The term "effector function" refers to a specialized function of a cell. Effector function of a T-cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T-cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone may not be sufficient for full activation of the T-cell and that a secondary or co-stimulatory signal may also be required. Thus, T-cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. In one embodiment, the cytoplasmic signaling molecule in the CAR of the invention comprises a cytoplasmic signaling sequence derived from CD3 zeta.

The cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, any of the costimulatory elements known in the art as useful in the construction of CARs are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB. In some embodiments, the intracellular signaling domain comprises a chimeric CD28 and OX40 co-stimulatory domain. In some embodiments, the intracellular signaling domain comprises a chimeric CD27 co-stimulatory domain. In some embodiments, the intracellular signaling domain comprises a chimeric CD27 and DAP10 co-stimulatory domain.

(d) Heterobifunctional Compound Targeted Protein (dTAG)

As contemplated herein, the CAR of the present invention has a heterobifunctional compound targeted protein (dTAG) that locates in the cytoplasm. The dTAG of the CAR is any amino acid sequence to which a heterobifunctional compound can be bound, leading to the ubiquitination and degradation of the CAR when in contact with the heterobifunctional compound. Preferably, the dTAG should not interfere with the function of the CAR. In one embodiment, the dTAG is a non-endogenous peptide, leading to heterobifunctional compound selectivity and minimizing off target effects that might occur if a heterobifunctional compound targets an endogenous protein. In one embodiment, the dTAG is an amino acid sequence derived from an endogenous protein which has been modified so that the heterobifunctional compound binds only to the modified amino acid sequence and not the endogenously expressed protein. In one embodiment, the dTAG is an endogenously expressed protein. Any amino acid sequence domain that can be bound by a ligand for use in a heterobifunctional compound can be used as a dTAG as contemplated herewith.

In particular embodiments, the dTAG for use in the present invention include, but are not limited to, an amino acid sequence derived from an endogenously expressed protein such as FK506 binding protein-12 (FKBP12), bromodomain-containing protein 4 (BRD4), CREB binding protein (CREBBP), and transcriptional activator BRG1 (SMARCA4), or a variant thereof. As contemplated herein, "variant" means any variant comprising a substitution, deletion, or addition of one or a few to plural amino acids, provided that the variant substantially retains the same function as the original sequence, which in this case is providing a ligand for a heterobifunctional compound. In other embodiments, a dTAG for use in the present invention may include, for example, a hormone receptor e.g. estrogen-receptor protein, androgen receptor protein, retinoid x receptor (RXR) protein, and dihydrofolate reductase (DHFR), including bacterial DHFR, bacterial dehydrogenase, and variants.

Some embodiments of dTAGs can be, but are not limited to, those derived from Hsp90 inhibitors, kinase inhibitors, MDM2 inhibitors, compounds targeting Human BET Bromodomain-containing proteins, compounds targeting cytosolic signaling protein FKBP12, HDAC inhibitors, human lysine methyltransferase inhibitors, angiogenesis inhibitors, immunosuppressive compounds, and compounds targeting the aryl hydrocarbon receptor (AHR).

In certain embodiments, the dTAG is derived from, a kinase, a BET bromodomain-containing protein, a cytosolic signaling protein (e.g., FKBP12), a nuclear protein, a histone deacetylase, a lysine methyltransferase, a protein regulating angiogenesis, a protein regulating immune response, an aryl hydrocarbon receptor (AHR), an estrogen receptor, an androgen receptor, a glucocorticoid receptor, or a transcription factor (e.g., SMARCA4, SMARCA2, TRIM24).

In certain embodiments, the dTAG is derived from a kinase, for example, but not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70), a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIPS, RSK1, RSK2, SGK2, SGK3, SIK1, STK33, TAO1, TAO2, TGF-beta, TLK2, TSSK1, TSSK2, ULK1, or ULK2), a cyclin dependent kinase (e.g., Cdk1-Cdk11), and a leucine-rich repeat kinase (e.g., LRRK2).

In certain embodiments, the dTAG is derived from a BET bromodomain-containing protein, for example, but not limited to, ASH1L, ATAD2, BAZ1A, BAZ1B, BAZ2A, BAZ2B, BRD1, BRD2, BRD3, BRD4, BRD5, BRD6, BRD7, BRD8, BRD9, BRD10, BRDT, BRPF1, BRPF3, BRWD3, CECR2, CREBBP, EP300, FALZ, GCN5L2, KIAA1240, LOC93349, MLL, PB1, PCAF, PHIP, PRKCBP1, SMARCA2, SMARCA4, SP100, SP110, SP140, TAF1, TAF1L, TIF1a, TRIM28, TRIM33, TRIM66, WDR9, ZMYND11, and MLL4. In certain embodiments, a BET bromodomain-containing protein is BRD4.

In certain embodiments, the dTAG is derived from, but not limited to, 7,8-dihydro-8-oxoguanin triphosphatase, AFAD, Arachidonate 5-lipoxygenase activating protein, apolipoprotein, baculoviral IAP repeat-containing protein 2, Bcl-2, Bcl-xL, E3 ligase XIAP, fatty acid binding protein from adipocytes 4 (FABP4), GTPase k-RAS, HDAC6, hematopoietic prostaglandin D synthase, lactoglutathione lyase, Mcl-1, PA2GA, peptidyl-prolyl cis-trans isomerase NIMA-interacting 1, poly-ADP-ribose polymerase 14, poly-ADP-ribose polymerase 15, prosaposin, prostaglandin E synthase, retinal rod rhodopsin-sensitive cGMP 315-cyclic phosphodiesterase subunit delta, S100-A7, Src, Sumo-conjugating enzyme UBC9, superoxide dismutase, tankyrase 1, or tankyrase 2.

In certain embodiments, the dTAG is derived from a nuclear protein including, but not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In a particular embodiment, the dTAG has an amino acid sequence derived from BRD2 ((Universal Protein Resource Knowledge Base (UniProtKB)—P25440 (BRD2 HUMAN) incorporated herein by reference), BRD3 (UniProtKB—Q15059 (BRD3 HUMAN) incorporated herein by reference), BRD4 (UniProtKB—O60885 (BRD4 HUMAN) incorporated herein by reference), or BRDT (UniProtKB—Q58F21 (BRDT_HUMAN) incorporated herein by reference) (see Baud et al., "A bump-and-hole approach to engineer controlled selectivity of BET bromodomains chemical probes", *Science* 346(6209) (2014):638-641; and Baud et al., "New Synthetic Routes to Triazolo-benzodiazepine Analogues: Expanding the Scope of the Bump-and-Hole Approach for Selective Bromo and Extra-Terminal (BET) Bromodomain Inhibition", *JMC* 59 (2016):1492-1500, both incorporated herein by reference). In certain embodiments, the one or more mutations of BRD2 include a mutation of the Tryptophan (W) at amino acid position 97, a mutation of the Valine (V) at amino acid position 103, a mutation of the Leucine (L) at amino acid position 110, a mutation of the W at amino acid position 370, a mutation of the V at amino acid position 376, or a mutation of the L at amino acid position 381. In certain embodiments, the one or more mutations of BRD3 include a mutation of the W at amino acid position 57, a mutation of the V at amino acid position 63, a mutation of the L at amino acid position 70, a mutation of the W at amino acid position 332, a mutation of the V at amino acid position 338, or a mutation of the L at amino acid position 345. In certain embodiments, the one or more mutations of BRD4 include a mutation of the W at amino acid position 81, a mutation of the V at amino acid position 87, a mutation of the L at amino acid position 94, a mutation of the W at amino acid position 374, a mutation of the V at amino acid position 380, or a mutation of the L at amino acid position 387. In certain embodiments, the one or more mutations of BRDT include a mutation of the W at amino acid position 50, a mutation of the V at amino acid position 56, a mutation of the L at amino acid position 63, a mutation of the W at amino acid position 293, a mutation of the V at amino acid position 299, or a mutation of the L at amino acid position 306.

In certain embodiments, the dTAG is derived from a kinase inhibitor, a BET bromodomain-containing protein inhibitor, cytosolic signaling protein FKBP12 ligand, an HDAC inhibitor, a lysine methyltransferase inhibitor, an angiogenesis inhibitor, an immunosuppressive compound, and an aryl hydrocarbon receptor (AHR) inhibitor.

In a particular embodiment, the dTAG is derived from cytosolic signaling protein FKBP12. In certain embodiments, the dTAG is a modified or mutant cytosolic signaling protein FKBP12. In certain embodiments, the modified or mutant cytosolic signaling protein FKBP12 contains one or more mutations that create an enlarged binding pocket for FKBP12 ligands. In certain embodiments, the one or more mutations include a mutation of the phenylalanine (F) at amino acid position 36 to valine (V) (F36V) (as counted without the methionine start codon) (referred to as FKBP12* or FKBP*, used interchangeably herein) (see Clackson et al., "Redesigning an FKBP-ligand interface to generate chemical dimerizers with novel specificity", *PNAS* 95 (1998):10437-10442, incorporated herein by reference).

In a particular embodiment, the dTAG has an amino acid sequence derived from an FKBP12 protein (UniProtKB—P62942 (FKB1A_HUMAN), incorporated herein by reference), or variant thereof. In one embodiment, the dTAG is derived from the amino acid sequence:

```
                                          (SEQ. ID. NO.: 1)
GVQVETISPGDGRTFPKRGQTCVVHYTGMLEDGKKFDSSRDRNKPFKFML

GKQEVIRGWEEGVAQMSVGQRAKLTISPDYAYGATGHPGIIPPHATLVFD

VELLKLE.
```

In one embodiment, the dTAG is a FKBP12 derived amino acid sequence with a mutation of the phenylalanine (F) at amino acid position 36 (as counted without the methionine) to valine (V) (F36V) (referred to as FKBP12* or FKBP*, used interchangeably herein), and has the amino acid sequence:

```
                                          (SEQ. ID. NO.: 2)
GVQVETISPGDGRTFPKRGQTCVVHYTGMLEDGKKFDSSRDRNKPFKFML

GKQEVIRGWEEGVAQMSVGQRAKLTISPDYAYGATGHPGIIPPHATLVFD

VELLKLE.
```

In one embodiment, the dTAG has an amino acid sequence derived from a BRD4 protein (UniProtKB—O60885 (BRD4 HUMAN) incorporated herein by reference), or variant thereof. In one embodiment, the dTAG is derived from the amino acid sequence:

```
                                          (SEQ. ID. NO.: 3)
MSAESGPGTRLRNLPVMGDGLETSQMSTTQAQAQPQPANAASTNPPPPET

SNPNKPKRQTNQLQYLLRVVLKTLWKHQFAWPFQQPVDAVKLNLPDYYKI

IKTPMDMGTIKKRLENNYYWNAQECIQDFNTMFTNCYIYNKPGDDIVLMA

EALEKLFLQKINELPTEETEIMIVQAKGRGRGRKETGTAKPGVSTVPNTT

QASTPPQTQTPQPNPPPVQATPHPFPAVTPDLIVQTPVMTVVPPQPLQTP

PPVPPQPQPPPAPAPQPVQSHPPIIAATPQPVKTKKGVKRKADTTTPTTI

DPIHEPPSLPPEPKTTKLGQRRESSRPVKPPKKDVPDSQQHPAPEKSSKV

SEQLKCCSGILKEMFAKKHAAYAWPFYKPVDVEALGLHDYCDIIKHPMDM

STIKSKLEAREYRDAQEFGADVRLMFSNCYKYNPPDHEVVAMARKLQDVF

EMRFAKMPDEPEEPVVAVSSPAVPPPTKVVAPPSSSDSSSDSSSDSDSST

DDSEEERAQRLAELQEQLKAVHEQLAALSQPQQNKPKKKEKDKKEKKKEK

HKRKEEVEENKKSKAKEPPPKKTKKNNSSNSNVSKKEPAPMKSKPPPTYE

SEEEDKCKPMSYEEKRQLSLDINKLPGEKLGRVVHIIQSREPSLKNSNPD

EIEIDFETLKPSTLRELERYVTSCLRKKRKPQAEKVDVIAGSSKMKGFSS

SESESSSESSSSDSEDSETEMAPKSKKKGHPGREQKKHHHHHHQQMQQAP

APVPQQPPPPPQQPPPPPPQQQQQPPPPPPPPSMPQQAAPAMKSSPPPF

IATQVPVLEPQLPGSVFDPIGHFTQPILHLPQPELPPHLPQPPEHSTPPH

LNQHAVVSPPALHNALPQQPSRPSNRAAALPPKPARPPAVSPALTQTPLL

PQPPMAQPPQVLLEDEEPPAPPLTSMQMQLYLQQLQKVQPPTPLLPSVKV

QSQPPPPLPPPPHPSVQQQLQQQPPPPPPPQPQPPPQQQHQPPPRPVHLQ

PMQFSTHIQQPPPPQGQQPPHPPPGQQPPPPQPAKPQQVIQHHHSPRHHK

SDPYSTGHLREAPSPLMIHSPQMSQFQSLTHQSPPQQNVQPKKQELRAAS

VVQPQPLVVVKEEKIHSPIIRSEPFSPSLRPEPPKHPESIKAPVHLPQRP

EMKPVDVGRPVIRPPEQNAPPPGAPDKDKQKQEPKTPVAPKKDLKIKNMG

SWASLVQKHPTTPSSTAKSSSDSFEQFRRAAREKEEREKALKAQAEHAEK

EKERLRQERMRSREDEDALEQARRAHEEARRRQEQQQQQRQEQQQQQQQQ

AAAVAAAATPQAQSSQPQSMLDQQRELARKREQERRRREAMAATIDMNFQ

SDLLSIFEENLF.
```

In one embodiment, the dTAG has an amino acid sequence derived from a BRD4 protein having the sequence:

```
                                          (SEQ. ID. NO.: 95)
NPPPPETSNPNKPKRQTNQLQYLLRVVLKTLWKHQFAWPFQQPVDAVKLN

LPDYYKIIKTPMDMGTIKKRLENNYYWNAQECIQDFNTMFTNCYIYNKPG

DDIVLMAEALEKLFLQKINELPTEE.
```

In one embodiment, the dTAG is derived from amino acid 75-147 of SEQ. ID. NO.: 3.

In one embodiment, the dTAG has an amino acid sequence derived from a ASH1L protein (UniProtKB—Q9NR48 (ASH1L_HUMAN) incorporated herein by reference), or variant thereof. In one embodiment, the dTAG is derived from amino acid 2463-2533 of Q9NR48:

(SEQ. ID. NO.: 96)
SRQALAAPLLNLPPKKKNADYYEKISDPLDLITIEKQILTGYYKTVEAFD

ADMLKVFRNAEKYYGRKSPVG.

In one embodiment, the dTAG has an amino acid sequence derived from a ATAD2 protein (UniProtKB—Q6PL18 (ATAD2_HUMAN) incorporated herein by reference), or variant thereof. In one embodiment, the dTAG is derived from amino acid 1001-1071 of Q6P18.

(SEQ. ID. NO.: 97)
AIDKRFRVFTKPVDPDEVPDYVTVIKQPMDLSSVISKIDLHKYLTVKDYL

RDIDLICSNALEYNPDRDPG.

In one embodiment, the dTAG has an amino acid sequence derived from a BAZ1A protein (UniProtKB—Q9NRL2 (BAZ1A_HUMAN) incorporated herein by reference), or variant thereof. In one embodiment, the dTAG is derived from amino acid 1446-1516 of Q9NRL2:

(SEQ. ID. NO.: 98)
VRHDDSWPFLKLVSKIQVPDYYDIIKKPIALNIIREKVNKCEYKLASEFI

DDIELMFSNCFEYNPRNTSEA.

In one embodiment, the dTAG has an amino acid sequence derived from a BAZ1B protein (UniProtKB—Q9UIG0 (BAZ1B_HUMAN) incorporated herein by reference), or variant thereof. In one embodiment, the dTAG is derived from amino acid 1356-1426 of Q9UIG0 (SEQ. ID. NO.: 99)
VKYRFSWPFREPVTRDEAEDYYD-
VITHPMDFQTVQNKCSCGSYRSVQEFLTDMKQVFT
NAEVYNCRGSHVL.

In one embodiment, the dTAG has an amino acid sequence derived from a BAZ2A protein (UniProtKB—Q9UIF9 (BAZ2A_HUMAN) incorporated herein by reference), or variant thereof. In one embodiment, the dTAG is derived from amino acid 1810-1880 of Q9UIF9:

(SEQ. ID. NO.: 100)
ESHDAAWPFLEPVNPRLVSGYRRIIKNPMDFSTMRERLLRGGYTSSEEFA

ADALLVFDNCQTFNEDDSEVG.

In one embodiment, the dTAG has an amino acid sequence derived from a BAZ2B protein (UniProtKB—Q9UIF8 (BAZ2B_HUMAN) incorporated herein by reference), or variant thereof. In one embodiment, the dTAG is derived from amino acid 2077-2147 of Q9UIF8:

(SEQ. ID. NO.: 101)
ETHEDAWPFLLPVNLKLVPGYKKVIKKPMDFSTIREKLSSGQYPNLETFA

LDVRLVFDNCETFNEDDSDIG.

In one embodiment, the dTAG has an amino acid sequence derived from a BRD1 protein (UniProtKB—O95696 (BRD1_HUMAN) incorporated herein by reference), or variant thereof. In one embodiment, the dTAG is derived from amino acid 579-649 of O95696:

(SEQ. ID. NO.: 102)
QDKDPARIFAQPVSLKEVPDYLDHIKHPMDFATMRKRLEAQGYKNLHEFE

EDFDLIIDNCMKYNARDTVFY.

In one embodiment, the dTAG has an amino acid sequence derived from a BRD2 protein (UniProtKB—P25440 (BRD2_HUMAN) incorporated herein by reference), or variant thereof. In one embodiment, the dTAG is derived from the amino acid sequence:

(SEQ. ID. NO.: 27)
MLQNVTPHNKLPGEGNAGLLGLGPEAAAPGKRIRKPSLLYEGFESPTMAS

VPALQLTPANPPPPEVSNPKKPGRVTNQLQYLHKVVMKALWKHQFAWPFR

QPVDAVKLGLPDYHKIIKQPMDMGTIKRRLENNYYWAASECMQDFNTMFT

NCYIYNKPTDDIVLMAQTLEKIFLQKVASMPQEEQELVVTIPKNSHKKGA

KLAALQGSVTSAHQVPAVSSVSHTALYTPPPEIPTTVLNIPHPSVISSPL

LKSLHSAGPPLLAVTAAPPAQPLAKKKGVKRKADTTTPTPTAILAPGSPA

SPPGSLEPKAARLPPMRRESGRPIKPPRKDLPDSQQQHQSSKKGKLSEQL

KHCNGILKELLSKKHAAYAWPFYKPVDASALGLHDYHDIIKHPMDLSTVK

RKMENRDYRDAQEFAADVRLMFSNCYKYNPPDHDVVAMARKLQDVFEFRY

AKMPDEPLEPGPLPVSTAMPPGLAKSSSESSSEESSSESSSEEEEEDEE

DEEEEESESSDSEEERAHRLAELQEQLRAVHEQLAALSQGPISKPKRKRE

KKEKKKKRKAEKHRGRAGADEDDKGPRAPRPPQPKKSKKASGSGGGSAAL

GPSGFGPSGGSGTKLPKKATKTAPPALPTGYDSEEEEESRPMSYDEKRQL

SLDINKLPGEKLGRVVHIIQAREPSLRDSNPEEIEIDFETLKPSTLRELE

RYVLSCLRKKPRKPYTIKKPVGKTKEELALEKKRELEKRLQDVSGQLNST

KKPPPKKANEKTESSSAQQVAVSRLSASSSSSDSSSSSSSSSSDTSDSDS

G.

In one embodiment, the dTAG is derived from amino acid 91-163 or 364-436 of SEQ. ID. NO.: 27.

In one embodiment, the dTAG has an amino acid sequence derived from a BRD3 protein (UniProtKB—Q15059 (BRD3 HUMAN) incorporated herein by reference), or variant thereof. In one embodiment, the dTAG is derived from the amino acid sequence:

(SEQ. ID. NO.: 28)
MSTATTVAPAGIPATPGPVNPPPPEVSNPSKPGRKTNQLQYMQNVVVKTL

WKHQFAWPFYQPVDAIKLNLPDYHKIIKNPMDMGTIKKRLENNYYWSASE

CMQDFNTMFTNCYIYNKPTDDIVLMAQALEKIFLQKVAQMPQEEVELLPP

APKGKGRKPAAGAQSAGTQQVAAVSSVSPATPFQSVPPTVSQTPVIAATP

VPTITANVTSVPVPPAAAPPPPATPIVPVVPPTPPVVKKKGVKRKADTTT

PTTSAITASRSESPPPLSDPKQAKVVARRESGGRPIKPPKKDLEDGEVPQ

HAGKKGKLSEHLRYCDSILREMLSKKHAAYAWPFYKPVDAEALELHDYHD

IIKHPMDLSTVKRKMDGREYPDAQGFAADVRLMFSNCYKYNPPDHEVVAM

ARKLQDVFEMRFAKMPDEPVEAPALPAPAAPMVSKGAESSRSSEESSSDS

GSSDSEEERATRLAELQEQLKAVHEQLAALSQAPVNKPKKKKEKKEKEKK

KKDKEKEKEKHKVKAEEEKKAKVAPPAKQAQQKKAPAKKANSTTTAGRQL

KKGGKQASASYDSEEEEEGLPMSYDEKRQLSLDINRLPGEKLGRVVHIIQ

SREPSLRDSNPDEIEIDFETLKPTTLRELERYVKSCLQKKQRKPFSASGK

KQAAKSKEELAQEKKKELEKRLQDVSGQLSSSKKPARKEKPGSAPSGGPS

RLSSSSSSESGSSSSSGSSSDSSDSE.

In one embodiment, the dTAG is derived from amino acid 51-123 or 326-398 of SEQ. ID. NO.: 28.

In one embodiment, the dTAG has an amino acid sequence derived from a BRD7 protein (UniProtKB—Q9NPI1 (BRD7_HUMAN) incorporated herein by reference), or variant thereof. In one embodiment, the dTAG is derived from amino acid 148-218 of Q9NP11 (SEQ. ID. NO.: 103):

```
                                     (SEQ. ID. NO.: 103)
QRKDPSAFFSFPVTDFIAPGYSMIIKHPMDFSTMKEKIKNNDYQSIEELK

DNFKLMCTNAMIYNKPETIYY.
```

In one embodiment, the dTAG has an amino acid sequence derived from a BRD8 protein (UniProtKB—Q9H0E9 (BRD8_HUMAN) incorporated herein by reference), or variant thereof. In one embodiment, the dTAG is derived from amino acid 724-794 or 1120-1190 of Q9H0E9:

```
                                     (SEQ. ID. NO.: 104)
ANHRYANVFLQPVTDDIAPGYHSIVQRPMDLSTIKKNIENGLIRSTAEFQ

RDIMLMFQNAVMYNSSDHDVY;

(SEQ. ID. NO.: 105)
ASHRFSSPFLKPVSERQAPGYKDVVKRPMDLTSLKRNLSKGRIRTMAQFL

RDLMLMFQNAVMYNDSDHHVY.
```

In one embodiment, the dTAG has an amino acid sequence derived from a BRD9 protein (UniProtKB—Q9H8M2 (BRD9_HUMAN) incorporated herein by reference), or variant thereof. In one embodiment, the dTAG is derived from amino acid 153-223 of Q9H8M2 (SEQ. ID. NO.: 106):

```
QRKDPHGFFAFPVTDAIAPGYSMIIKHPMDFGTMKDKIVANEYKSVTEFK

ADFKLMCDNAMTYNRPDTVYY.
```

In one embodiment, the dTAG has an amino acid sequence derived from a BRDT protein (UniProtKB—Q58F21 (BRDT_HUMAN) incorporated herein by reference), or variant thereof. In one embodiment, the dTAG is derived from the amino acid sequence:

```
                                      (SEQ. ID. NO.: 29)
MSLPSRQTAIIVNPPPPEYINTKKNGRLTNQLQYLQKVVLKDLWKHSFSW

PFQRPVDAVKLQLPDYYTIIKNPMDLNTIKKRLENKYYAKASECIEDFNT

MFSNCYLYNKPGDDIVLMAQALEKLFMQKLSQMPQEEQVVGVKERIKKGT

QQNIAVSSAKEKSSPSATEKVFKQQEIPSVFPKTSISPLNVVQGASVNSS

SQTAAQVTKGVKRKADTTTPATSAVKASSEFSPTFTEKSVALPPIKENMP

KNVLPDSQQQYNVVKTVKVTEQLRHCSEILKEMLAKKHFSYAWPFYNPVD

VNALGLHNYYDVVKNPMDLGTIKEKMDNQEYKDAYKFAADVRLMFMNCYK

YNPPDHEVVTMARMLQDVFETHFSKIPIEPVESMPLCYIKTDITETTGRE

NTNEASSEGNSSDDSEDERVKRLAKLQEQLKAVHQQLQVLSQVPFRKLNK

KKEKSKKEKKKEKVNNSNENPRKMCEQMRLKEKSKRNQPKKRKQQFIGLK

SEDEDNAKPMNYDEKRQLSLNINKLPGDKLGRVVHIIQSREPSLSNSNPD

EIEIDFETLKASTLRELEKYVSACLRKRPLKPPAKKIMMSKEELHSQKKQ

ELEKRLLDVNNQLNSRKRQTKSDKTQPSKAVENVSRLSESSSSSSSSSES

ESSSSDLSSSDSSDSESEMFPKFTEVKPNDSPSKENVKKMKNECIPPEGR

TGVTQIGYCVQDTTSANTTLVHQTTPSHVMPPNHHQLAFNYQELEHLQTV

KNISPLQILPPSGDSEQLSNGITVMHPGSDSDTTMLESECQAPVQKDIKI

KNADSWKSLGKPVKPSGVMKSSDELFNQFRKAAIEKEVKARTQELIRKHL

EQNTKELKASQENQRDLGNGLTVESFSNKIQNKCSGEEQKEHQQSSEAQD

KSKLWLLKDRDLARQKEQERRRREAMVGTIDMTLQSDIMTMFENNFD.
```

In one embodiment, the dTAG is derived from amino acid 44-116 or 287-359 of SEQ. ID. NO.: 29:

```
                                     (SEQ. ID. NO.: 107)
WKHSFSWPFQRPVDAVKLQLPDYYTIIKNPMDLNTIKKRL50KYYAKASE

CIEDFNTMFSNCYLYNKPGDDIV;

(SEQ. ID. NO.: 108)
KHFSYAWPFYNPVDVNALGLHNYYDVVKNPMDLGTIKEKMDNQEYKDAYK

FAADVRLMFMNCYKYNPPDHEV.
```

In one embodiment, the dTAG has an amino acid sequence derived from a BRPF1 protein (UniProtKB—P55201 (BRPF1_HUMAN) incorporated herein by reference), or variant thereof. In one embodiment, the dTAG is derived from amino acid 645-715 of P55201 (SEQ. ID. NO.: 109):

```
QEKDTGNIFSEPVPLSEVPDYLDHIKKPMDFFTMKQNLEAYRYLNFDDFE

EDFNLIVSNCLKYNAKDTIFY.
```

In one embodiment, the dTAG has an amino acid sequence derived from a BRPF3 protein (UniProtKB—Q9ULD4 (BRPF3_HUMAN) incorporated herein by reference), or variant thereof. In one embodiment, the dTAG is derived from amino acid 606-676 of Q9ULD4 (SEQ. ID. NO.: 110)

```
QEKDPAHIFAEPVNLSEVPDYLEFISKPMDFSTMRRKLESHLYRTLEEFE

EDFNLIVTNCMKYNAKDTIFH.
```

In one embodiment, the dTAG has an amino acid sequence derived from a BRWD3 protein (UniProtKB—Q6RI45 (BRWD3_HUMAN) incorporated herein by reference), or variant thereof. In one embodiment, the dTAG is derived from amino acid 1158-1228 or 1317-1412 of Q6RI45:

```
                                     (SEQ. ID. NO.: 111)
LSLDFASPFAVPVDLSAYPLYCTVVAYPTDLNTIRRRLENRFYRRISALM

WEVRYIEHNARTFNEPDSPIV;
```

```
                                             (SEQ. ID. NO.: 112)
YEREDSEPFRQPADLLSYPGHQEQEGESSESVVPERQQDSSLSEDYQDVI

DTPVDFSTVKETLEAGNYGSPLEFYKDVRQIFNNSKAYTSNKKSRI.
```

In one embodiment, the dTAG has an amino acid sequence derived from a CECR2 protein (UniProtKB—Q9BXF3 (CECR2_HUMAN) incorporated herein by reference), or variant thereof. In one embodiment, the dTAG is derived from amino acid 451-521 of Q9BXF3:

```
                                             (SEQ. ID. NO.: 113)
KAHKDSWPFLEPVDESYAPNYYQIIKAPMDISSMEKKLNGGLYCTKEEFV

NDMKTMFRNCRKYNGESSEYT.
```

In one embodiment, the dTAG has an amino acid sequence derived from a CREBBP protein (UniProtKB—Q92793 (CBP_HUMAN) incorporated herein by reference), or variant thereof. In one embodiment, the dTAG is derived from amino acid 1103-1175 of Q92793.

In one embodiment, the dTAG has an amino acid sequence derived from an EP300 protein (UniProtKB—Q09472 (EP300_HUMAN) incorporated herein by reference), or variant thereof. In one embodiment, the dTAG is derived from amino acid 1067-1139 of Q09472.

In one embodiment, the dTAG has an amino acid sequence derived from a FALZ protein (UniProtKB—Q12830 (BPTF_HUMAN) incorporated herein by reference), or variant thereof. In one embodiment, the dTAG is derived from amino acid 2944-3014 of Q12830.

In one embodiment, the dTAG has an amino acid sequence derived from a GCN5L2 protein (UniProtKB—Q92830 (KAT2A_HUMAN) incorporated herein by reference), or variant thereof. In one embodiment, the dTAG is derived from amino acid 745-815 of Q92830.

In one embodiment, the dTAG has an amino acid sequence derived from a KIAA1240 protein (UniProtKB—Q9ULI0 (ATD2B_HUMAN) incorporated herein by reference), or variant thereof. In one embodiment, the dTAG is derived from amino acid 975-1045 of Q9ULI0.

In one embodiment, the dTAG has an amino acid sequence derived from a LOC93349 protein (UniProtKB—Q13342 (SP140_HUMAN) incorporated herein by reference), or variant thereof. In one embodiment, the dTAG is derived from amino acid 796-829 of Q13342.

In one embodiment, the dTAG has an amino acid sequence derived from a MLL protein (UniProtKB—Q03164 (KMT2A_HUMAN) incorporated herein by reference), or variant thereof. In one embodiment, the dTAG is derived from amino acid 1703-1748 of Q03164.

In one embodiment, the dTAG has an amino acid sequence derived from a PB1 protein (UniProtKB—Q86U86 (PB1_HUMAN) incorporated herein by reference), or variant thereof. In one embodiment, the dTAG is derived from amino acid 63-134, 200-270, 400-470, 538-608, 676-746, or 792-862 of Q86U86.

In one embodiment, the dTAG has an amino acid sequence derived from a PCAF protein (UniProtKB—Q92831 (KAT2B_HUMAN) incorporated herein by reference), or variant thereof. In one embodiment, the dTAG is derived from amino acid 740-810 of Q92831.

In one embodiment, the dTAG has an amino acid sequence derived from a PHIP protein (UniProtKB—Q8WWQ0 (PHIP_HUMAN) incorporated herein by reference), or variant thereof. In one embodiment, the dTAG is derived from amino acid 1176-1246 or 1333-1403 of Q8WWQ0.

In one embodiment, the dTAG has an amino acid sequence derived from a PRKCBP1 protein (UniProtKB—Q9ULU4 (PKCB1_HUMAN) incorporated herein by reference), or variant thereof. In one embodiment, the dTAG is derived from amino acid 165-235 of Q9ULU4.

In one embodiment, the dTAG has an amino acid sequence derived from a SMARCA2 protein (UniProtKB—P51531 (SMCA2_HUMAN) incorporated herein by reference), or variant thereof. In one embodiment, the dTAG is derived from amino acid 1419-1489 of P51531.

In one embodiment, the dTAG has an amino acid sequence derived from a SMARCA4 protein (UniProtKB—P51532 (SMCA4_HUMAN) incorporated herein by reference), or variant thereof. In one embodiment, the dTAG is derived from amino acid 1477-1547 of P51532.

In one embodiment, the dTAG has an amino acid sequence derived from a SP100 protein (UniProtKB—P23497 (SP100_HUMAN) incorporated herein by reference), or variant thereof. In one embodiment, the dTAG is derived from amino acid 761-876 of P23497.

In one embodiment, the dTAG has an amino acid sequence derived from a SP110 protein (UniProtKB—Q9HB58 (SP110_HUMAN) incorporated herein by reference), or variant thereof. In one embodiment, the dTAG is derived from amino acid 581-676 of Q9HB58.

In one embodiment, the dTAG has an amino acid sequence derived from a SP140 protein (UniProtKB—Q13342 (SP140_HUMAN) incorporated herein by reference), or variant thereof. In one embodiment, the dTAG is derived from amino acid 796-829 of Q13342.

In one embodiment, the dTAG has an amino acid sequence derived from a TAF1 protein (UniProtKB—P21675 (TAF1_HUMAN) incorporated herein by reference), or variant thereof. In one embodiment, the dTAG is derived from amino acid 1397-1467 or 1520-1590 of P21675.

In one embodiment, the dTAG has an amino acid sequence derived from a TAF1L protein (UniProtKB—Q8IZX4 (TAF1L_HUMAN) incorporated herein by reference), or variant thereof. In one embodiment, the dTAG is derived from amino acid 1416-1486 or 1539-1609 of Q8IZX4.

In one embodiment, the dTAG has an amino acid sequence derived from a TIF1A protein (UniProtKB—O15164 (TIF1A_HUMAN) incorporated herein by reference), or variant thereof. In one embodiment, the dTAG is derived from amino acid 932-987 of O15164.

In one embodiment, the dTAG has an amino acid sequence derived from a TRIM28 protein (UniProtKB—Q13263 (TIF1B_HUMAN) incorporated herein by reference), or variant thereof. In one embodiment, the dTAG is derived from amino acid 697-801 of Q13263.

In one embodiment, the dTAG has an amino acid sequence derived from a TRIM33 protein (UniProtKB—Q9UPN9 (TRI33_HUMAN) incorporated herein by reference), or variant thereof. In one embodiment, the dTAG is derived from amino acid 974-1046 of Q9UPN9.

In one embodiment, the dTAG has an amino acid sequence derived from a TRIM66 protein (UniProtKB—O15016 (TRI66_HUMAN) incorporated herein by reference), or variant thereof. In one embodiment, the dTAG is derived from amino acid 1056-1128 of O15016.

In one embodiment, the dTAG has an amino acid sequence derived from a WDR9 protein (UniProtKB—

Q9NSI6 (BRWD1_HUMAN) incorporated herein by reference), or variant thereof. In one embodiment, the dTAG is derived from amino acid 1177-1247 or 1330-1400 of Q9NSI6.

In one embodiment, the dTAG has an amino acid sequence derived from a ZMYND11 protein (UniProtKB—Q15326 (ZMY11_HUMAN) incorporated herein by reference), or variant thereof. In one embodiment, the dTAG is derived from amino acid 168-238 of Q15326.

In one embodiment, the dTAG has an amino acid sequence derived from a MLL4 protein (UniProtKB—Q9UMN6 (KMT2B_HUMAN) incorporated herein by reference), or variant thereof. In one embodiment, the dTAG is derived from amino acid 1395-1509 of Q9UMN6.

In one embodiment, the dTAG has an amino acid sequence derived from an estrogen receptor, human (UniProtKB—P03372-1, incorporated herein by reference), or a variant thereof. In one embodiment, the dTAG is derived from the amino acid sequence:

(SEQ. ID. NO.: 4)
MTMTLHTKASGMALLHQIQGNELEPLNRPQLKIPLERPLGEVYLDSSKPA

VYNYPEGAAYEFNAAAAANAQVYGQTGLPYGPGSEAAAFGSNGLGGFPPL

NSVSPSPLMLLHPPPQLSPFLQPHGQQVPYYLENEPSGYTVREAGPPAFY

RPNSDNRRQGGRERLASTNDKGSMAMESAKETRYCAVCNDYASGYHYGVW

SCEGCKAFFKRSIQGHNDYMCPATNQCTIDKNRRKSCQACRLRKCYEVGM

MKGGIRKDRRGGRMLKHKRQRDDGEGRGEVGSAGDMRAANLWPSPLMIKR

SKKNSLALSLTADQMVSALLDAEPPILYSEYDPTRPFSEASMMGLLTNLA

DRELVHMINWAKRVPGFVDLTLHDQVHLLECAWLEILMIGLVWRSMEHPG

KLLFAPNLLLDRNQGKCVEGMVEIFDMLLATSSRFRMMNLQGEEFVCLKS

IILLNSGVYTFLSSTLKSLEEKDHIHRVLDKITDTLIHLMAKAGLTLQQQ

HQRLAQLLLILSHIRHMSNKGMEHLYSMKCKNVVPLYDLLLEMLDAHRLH

APTSRGGASVEETDQSHLATAGSTSSHSLQKYYITGEAEGFPATV.

In one embodiment, the dTAG has an amino acid sequence derived from an estrogen receptor ligand-binding domain, or a variant thereof. In one embodiment, the dTAG is derived from the amino acid sequence:

(SEQ. ID. NO.: 5)
SLALSLTADQMVSALLDAEPPILYSEYDPTRPFSEASMMGLLTNLADREL

VHMINWAKRVPGFVDLTLHDQVHLLECAWLEILMIGLVWRSMEHPGKLLF

APNLLLDRNQGKCVEGMVEIFDMLLATSSRFRMMNLQGEEFVCLKSIILL

NSGVYTFLSSTLKSLEEKDHIHRVLDKITDTLIHLMAKAGLTLQQQHQRL

AQLLLILSHIRHMSNKGMEHLYSMKCKNVVPLYDLLLEMLDAHRL.

In one embodiment, the dTAG has an amino acid sequence derived from an androgen receptor, UniProtKB—P10275 (ANDR_HUMAN) incorporated herein by reference, or a variant thereof. In one embodiment, the dTAG is derived from the amino acid sequence:

(SEQ. ID. NO.: 6)
MEVQLGLGRVYPRPPSKTYRGAFQNLFQSVREVIQNPGPRHPEAASAAPP

GASLLLLQQQQQQQQQQQQQQQQQQQQQQQQETSPRQQQQQQGEDGSPQAH

RRGPTGYLVLDEEQQPSQPQSALECHPERGCVPEPGAAVAASKGLPQQLP

APPDEDDSAAPSTLSLLGPTFPGLSSCSADLKDILSEASTMQLLQQQQQE

AVSEGSSSGRAREASGAPTSSKDNYLGGTSTISDNAKELCKAVSVSMGLG

VEALEHLSPGEQLRGDCMYAPLLGVPPAVRPTPCAPLAECKGSLLDDSAG

KSTEDTAEYSPFKGGYTKGLEGESLGCSGSAAAGSSGTLELPSTLSLYKS

GALDEAAAYQSRDYYNFPLALAGPPPPPPPPHPHARIKLENPLDYGSAWA

AAAAQCRYGDLASLHGAGAAGPGSGSPSAAASSSWHTLFTAEEGQLYGPC

GGGGGGGGGGGGGGGGGGGGGGEAGAVAPYGYTRPPQGLAGQESDFTAP

DVWYPGGMVSRVPYPSPTCVKSEMGPWMDSYSGPYGDMRLETARDHVLPI

DYYFPPQKTCLICGDEASGCHYGALTCGSCKVFFKRAAEGKQKYLCASRN

DCTIDKFRRKNCPSCRLRKCYEAGMTLGARKLKKLGNLKLQEEGEASSTT

SPTEETTQKLTVSHIEGYECQPIFLNVLEAIEPGVVCAGHDNNQPDSFAA

LLSSLNELGERQLVHVVKWAKALPGFRNLHVDDQMAVIQYSWMGLMVFAM

GWRSFTNVNSRMLYFAPDLVFNEYRMHKSRMYSQCVRMRHLSQEFGWLQI

TPQEFLCMKALLLFSIIPVDGLKNQKFFDELRMNYIKELDRIIACKRKNP

TSCSRRFYQLTKLLDSVQPIARELHQFTFDLLIKSHMVSVDFPEMMAEII

SVQVPKILSGKVKPIYFHTQ.

In one embodiment, the dTAG has an amino acid sequence derived from an androgen receptor ligand-binding domain, or a variant thereof. In one embodiment, the dTAG is derived from the amino acid sequence:

(SEQ. ID. NO.: 24)
DNNQPDSFAALLSSLNELGERQLVHVVKWAKALPGFRNLHVDDQMAVIQY

SWMGLMVFAMGWRSFTNVNSRMLYFAPDLVFNEYRMHKSRMYSQCVRMRH

LSQEFGWLQITPQEFLCMKALLLFSIIPVDGLKNQKFFDELRMNYIKELD

RIIACKRKNPTSCSRRFYQLTKLLDSVQPIARELHQFTFDLLIKSHMVSV

DFPEMMAEIISVQVPKILSGKVKPIYFHT.

In one embodiment, the dTAG has an amino acid sequence derived from a Retinoic Receptor, (UniProtKB—P19793) (RXRA_HUMAN) (incorporated herein by reference), or a variant thereof. In one embodiment, the dTAG is derived from the amino acid sequence:

(SEQ. ID. NO.: 7)
MDTKHFLPLDFSTQVNSSLTSPTGRGSMAAPSLHPSLGPGIGSPGQLHSP

ISTLSSPINGMGPPFSVISSPMGPHSMSVPTTPTLGFSTGSPQLSSPMNP

VSSSEDIKPPLGLNGVLKVPAHPSGNMASFTKHICAICGDRSSGKHYGVY

SCEGCKGFFKRTVRKDLTYTCRDNKDCLIDKRQRNRCQYCRYQKCLAMGM

KREAVQEERQRGKDRNENEVESTSSANEDMPVERILEAELAVEPKTETYV

EANMGLNPSSPNDPVTNICQAADKQLFTLVEWAKRIPHFSELPLDDQVIL

LRAGWNELLIASFSHRSIAVKDGILLATGLHVHRNSAHSAGVGAIFDRVL

TELVSKMRDMQMDKTELGCLRAIVLFNPDSKGLSNPAEVEALREKVYASL

EAYCKHKYPEQPGRFAKLLLRLPALRSIGLKCLEHLFFFKLIGDTPIDTF

LMEMLEAPHQMT.

In one embodiment, the dTAG has an amino acid sequence derived from a Retinoic Receptor ligand-binding domain, or a variant thereof. In one embodiment, the dTAG is derived from the amino acid sequence:

(SEQ. ID. NO.: 25)
SANEDMPVERILEAELAVEPKTETYVEANMGLNPSSPNDPVTNICQAADK

QLFTLVEWAKRIPHFSELPLDDQVILLRAGWNELLIASFSHRSIAVKDGI

LLATGLHVHRNSAHSAGVGAIFDRVLTELVSKMRDMQMDKTELGCLRAIV

LFNPDSKGLSNPAEVEALREKVYASLEAYCKHKYPEQPGRFAKLLLRLPA

LRSIGLKCLEHLFFFKLIGDTPIDTFLMEMLEAPHQMT.

In one embodiment, the dTAG has an amino acid sequence derived from a DHFR, E. coli, UniProtKB—Q79DQ2 (Q79DQ2_ECOLX) incorporated herein by reference, or a variant thereof. In one embodiment, the dTAG is derived from the amino acid sequence:

(SEQ. ID. NO.: 8)
MNSESVRIYLVAAMGANRVIGNGPNIPWKIPGEQKIFRRLTEGKVVVMGR

KTFESIGKPLPNRHTLVISRQANYRATGCVVVSTLSHAIALASELGNELY

VAGGAEIYTLALPHAHGVFLSEVHQTFEGDAFFPMLNETEFELVSTETIQ

AVIPYTHSVYARRNG.

In one embodiment, the dTAG has an amino acid sequence derived from a bacterial dehalogenase, or variant thereof. In one embodiment, the dTAG is derived from the amino acid sequence:

(SEQ. ID. NO.: 9)
MAEIGTGFPFDPHYVEVLGERMHYVDVGPRDGTPVLFLHGNPTSSYVWRN

IIPHVAPTHRCIAPDLIGMGKSDKPDLGYFFDDHVRFMDAFIEALGLEEV

VLVIHDWGSALGFHWAKRNPERVKGIAFMEFIRPIPTWDEWPEFARETFQ

AFRTTDVGRKLIIDQNVFIEGTLPMGVVRPLTEVEMDHYREPFLNPVDRE

PLWRFPNELPIAGEPANIVALVEEYMDWLHQSPVPKLLFWGTPGVLIPPA

EAARLAKSLPNCKAVDIGPGLNLLQEDNPDLIGSEIARWLSTLEISG.

In one embodiment, the dTAG has an amino acid sequence derived from the N-terminus of MDM2, or variants thereof. In one embodiment, the dTAG is derived from the amino acid sequence:

(SEQ. ID. NO.: 26)
MCNTNMSVPTDGAVTTSQIPASEQETLVRPKPLLLKLLKSVGAQKDTYTM

KEVLFYLGQYIMTKRLYDEKQQHIVYCSNDLLGDLFGVPSFSVKEHRKIY

TMIYRNLVVV.

In one embodiment, the dTAG has an amino acid sequence derived from apoptosis regulator Bcl-xL protein, UniProtKB—Q07817 (B2CL1_HUMAN) incorporated herein by reference, or a variant thereof. In one embodiment, the dTAG is derived from the amino acid sequence:

(SEQ. ID. NO.: 30)
MSQSNRELVVDFLSYKLSQKGYSWSQFSDVEENRTEAPEGTESEMETPSA

INGNPSWHLADSPAVNGATGHSSSLDAREVIPMAAVKQALREAGDEFELR

YRRAFSDLTSQLHITPGTAYQSFEQVVNELFRDGVNWGRIVAFFSFGGAL

CVESVDKEMQVLVSRIAAWMATYLNDHLEPWIQENGGWDTFVELYGNNAA

AESRKGQERFNRWFLTGMTVAGVVLLGSLFSRK.

In one embodiment, the dTAG has an amino acid sequence derived from the CD209 antigen, UniProtKB—Q9NNX6 (CD209_HUMAN) incorporated herein by reference, or a variant thereof. In one embodiment, the dTAG is derived from the amino acid sequence:

(SEQ. ID. NO.: 31)
MSDSKEPRLQQLGLLEEEQLRGLGFRQTRGYKSLAGCLGHGPLVLQLLSF

TLLAGLLVQVSKVPSSISQEQSRQDAIYQNLTQLKAAVGELSEKSKLQEI

YQELTQLKAAVGELPEKSKLQEIYQELTRLKAAVGELPEKSKLQEIYQEL

TWLKAAVGELPEKSKMQEIYQELTRLKAAVGELPEKSKQQEIYQELTRLK

AAVGELPEKSKQQEIYQELTRLKAAVGELPEKSKQQEIYQELTQLKAAVE

RLCHPCPWEWTFFQGNCYFMSNSQRNWHDSITACKEVGAQLVVIKSAEEQ

NFLQLQSSRSNRFTWMGLSDLNQEGTWQWVDGSPLLPSFKQYWNRGEPNN

VGEEDCAEFSGNGWNDDKCNLAKFWICKKSAASCSRDEEQFLSPAPATPN

PPPA.

In one embodiment, the dTAG has an amino acid sequence derived from E3 ligase XIAP, UniProtKB—P98170 (XIAP_HUMAN) incorporated herein by reference, or a variant thereof. In one embodiment, the dTAG is derived from the amino acid sequence:

(SEQ. ID. NO.: 32)
MTFNSFEGSKTCVPADINKEEEFVEEFNRLKTFANFPSGSPVSASTLARA

GFLYTGEGDTVRCFSCHAAVDRWQYGDSAVGRHRKVSPNCRFINGFYLEN

SATQSTNSGIQNGQYKVENYLGSRDHFALDRPSETHADYLLRTGQVVDIS

DTIYPRNPAMYSEEARLKSFQNWPDYAHLTPRELASAGLYYTGIGDQVQC

FCCGGKLKNWEPCDRAWSEHRRHFPNCFFVLGRNLNIRSESDAVSSDRNF

PNSTNLPRNPSMADYEARIFTFGTWIYSVNKEQLARAGFYALGEGDKVKC

FHCGGGLTDWKPSEDPWEQHAKWYPGCKYLLEQKGQEYINNIHLTHSLEE

CLVRTTEKTPSLTRRIDDTIFQNPMVQEAIRMGFSFKDIKKIMEEKIQIS

GSNYKSLEVLVADLVNAQKDSMQDESSQTSLQKEISTEEQLRRLQEEKLC

KICMDRNIAIVFVPCGHLVTCKQCAEAVDKCPMCYTVITFKQKIFMS.

In one embodiment, the dTAG has an amino acid sequence derived from baculoviral IAP repeat-containing protein 2, UniProtKB—Q13490 (BIRC2_HUMAN) incorporated herein by reference, or a variant thereof. In one embodiment, the dTAG is derived from the amino acid sequence:

(SEQ. ID. NO.: 33)
MHKTASQRLFPGPSYQNIKSIMEDSTILSDWTNSNKQKMKYDFSCELYRM

STYSTFPAGVPVSERSLARAGFYYTGVNDKVKCFCCGLMLDNWKLGDSPI

QKHKQLYPSCSFIQNLVSASLGSTSKNTSPMRNSFAHSLSPTLEHSSLFS

GSYSSLSPNPLNSRAVEDISSSRTNPYSYAMSTEEARFLTYHMWPLTFLS

PSELARAGFYYIGPGDRVACFACGGKLSNWEPKDDAMSEHRRHFPNCPFL

ENSLETLRFSISNLSMQTHAARMRTFMYWPSSVPVQPEQLASAGFYYVGR

NDDVKCFCCDGGLRCWESGDDPWVEHAKWFPRCEFLIRMKGQEFVDEIQG

RYPHLLEQLLSTSDTTGEENADPPIIHFGPGESSSEDAVMMNTPVVKSAL

EMGFNRDLVKQTVQSKILTTGENYKTVNDIVSALLNAEDEKREEEKEKQA

EEMASDDLSLIRKNRMALFQQLTCVLPILDNLLKANVINKQEHDIIKQKT

QIPLQARELIDTILVKGNAAANIFKNCLKEIDSTLYKNLFVDKNMKYIPT

EDVSGLSLEEQLRRLQEERTCKVCMDKEVSVVFIPCGHLVVCQECAPSLR

KCPICRGIIKGTVRTFLS.

In one embodiment, the dTAG has an amino acid sequence derived from hematopoietic prostaglandin D synthase, UniProtKB—O60760 (HPGDS_HUMAN) incorporated herein by reference, or a variant thereof. In one embodiment, the dTAG is derived from the amino acid sequence:

(SEQ. ID. NO.: 34)
MPNYKLTYFNMRGRAEIIRYIFAYLDIQYEDHRIEQADWPEIKSTLPFGK

IPILEVDGLTLHQSLAIARYLTKNTDLAGNTEMEQCHVDAIVDTLDDFMS

CFPWAEKKQDVKEQMFNELLTYNAPHLMQDLDTYLGGREWLIGNSVTWAD

FYWEICSTTLLVFKPDLLDNHPRLVTLRKKVQAIPAVANWIKRRPQTKL.

In one embodiment, the dTAG has an amino acid sequence derived from GTPase k-RAS, UniProtKB—P01116 (RASK_HUMAN) incorporated herein by reference, or a variant thereof. In one embodiment, the dTAG is derived from the amino acid sequence:

(SEQ. ID. NO.: 35)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

RVEDAFYTLVREIRQYRLKKISKEEKTPGCVKIKKCIIM.

In one embodiment, the dTAG has an amino acid sequence derived from Poly-ADP-ribose polymerase 15, UniProtKB—Q460N3 (PAR15_HUMAN) incorporated herein by reference, or a variant thereof. In one embodiment, the dTAG is derived from the amino acid sequence:

(SEQ. ID. NO.: 36)
MAAPGPLPAAALSPGAPTPRELMHGVAGVTSRAGRDREAGSVLPAGNRGA

RKASRRSSSRSMSRDNKFSKKDCLSIRNVVASIQTKEGLNLKLISGDVLY

IWADVIVNSVPMNLQLGGGPLSRAFLQKAGPMLQKELDDRRRETEEKVGN

IFMTSGCNLDCKAVLHAVAPYWNNGAETSWQIMANIIKKCLTTVEVLSFS

SITFPMIGTGSLQFPKAVFAKLILSEVFEYSSSTRPITSPLQEVHFLVYT

NDDEGCQAFLDEFTNWSRINPNKARIPMAGDTQGVVGTVSKPCFTAYEMK

IGAITFQVATGDIATEQVDVIVNSTARTFNRKSGVSRAILEGAGQAVESE

CAVLAAQPHRDFIITPGGCLKCKIIIHVPGGKDVRKTVTSVLEECEQRKY

TSVSLPAIGTGNAGKNPITVADNIIDAIVDFSSQHSTPSLKTVKVVIFQP

ELLNIFYDSMKKRDLSASLNFQSTFSMTTCNLPEHWTDMNHQLFCMVQLE

PGQSEYNTIKDKFTRTCSSYAIEKIERIQNAFLWQSYQVKKRQMDIKNDH

KNNERLLFHGTDADSVPYVNQHGFNRSCAGKNAVSYGKGTYFAVDASYSA

KDTYSKPDSNGRKHMYVVRVLTGVFTKGRAGLVTPPPKNPHNPTDLFDSV

TNNTRSPKLFVVFFDNQAYPEYLITFTA.

In one embodiment, the dTAG has an amino acid sequence derived from Poly-ADP-ribose polymerase 14, UniProtKB—Q460N5 (PAR14_HUMAN) incorporated herein by reference, or a variant thereof. In one embodiment, the dTAG is derived from the amino acid sequence:

(SEQ. ID. NO.: 37)
MAVPGSFPLLVEGSWGPDPPKNLNTKLQMYFQSPKRSGGGECEVRQDPRS

PSRFLVFFYPEDVRQKVLERKNHELVWQGKGTFKLTVQLPATPDEIDHVF

EEELLTKESKTKEDVKEPDVSEELDTKLPLDGGLDKMEDIPEECENISSL

VAFENLKANVTDIMLILLVENISGLSNDDFQVEIIRDFDVAVVTFQKHID

TIRFVDDCTKHHSIKQLQLSPRLLEVTNTIRVENLPPGADDYSLKLFFEN

PYNGGGRVANVEYFPEESSALIEFFDRKVLDTIMATKLDFNKMPLSVFPY

YASLGTALYGKEKPLIKLPAPFEESLDLPLWKFLQKKNHLIEEINDEMRR

CHCELTWSQLSGKVTIRPAATLVNEGRPRIKTWQADTSTTLSSIRSKYKV

NPIKVDPTMWDTIKNDVKDDRILIEFDTLKEMVILAGKSEDVQSIEVQVR

ELIESTTQKIKREEQSLKEKMIISPGRYFLLCHSSLLDHLLTECPEIEIC

YDRVTQHLCLKGPSADVYKAKCEIQEKVYTMAQKNIQVSPEIFQFLQQVN

WKEFSKCLFIAQKILALYELEGTTVLLTSCSSEALLEAEKQMLSALNYKR

IEVENKEVLHGKKWKGLTHNLLKKQNSSPNTVIINELTSETTAEVIITGC

VKEVNETYKLLFNFVEQNMKIERLVEVKPSLVIDYLKTEKKLFWPKIKKV

NVQVSFNPENKQKGILLTGSKTEVLKAVDIVKQVWDSVCVKSVHTDKPGA

KQFFQDKARFYQSEIKRLFGCYIELQENEVMKEGGSPAGQKCFSRTVLAP

GVVLIVQQGDLARLPVDVVVNASNEDLKHYGGLAAALSKAAGPELQADCD

QIVKREGRLLPGNATISKAGKLPYHHVIHAVGPRWSGYEAPRCVYLLRRA

VQLSLCLAEKYKYRSIAIPAISSGVFGFPLGRCVETIVSAIKENFQFKKD

GHCLKEIYLVDVSEKTVEAFAEAVKTVFKATLPDTAAPPGLPPAAAGPGK

TSWEKGSLVSPGGLQMLLVKEGVQNAKTDVVVNSVPLDLVLSRGPLSKSL

LEKAGPELQEELDTVGQGVAVSMGTVLKTSSWNLDCRYVLHVVAPEWRNG

STSSLKIMEDIIRECMEITESLSLKSIAFPAIGTGNLGFPKNIFAELIIS

EVFKFSSKNQLKTLQEVHFLLHPSDHENIQAFSDEFARRANGNLVSDKIP

KAKDTQGFYGTVSSPDSGVYEMKIGSIIFQVASGDITKEEADVIVNSTSN

SFNLKAGVSKAILECAGQNVERECSQQAQQRKNDYIITGGGFLRCKNIIH

VIGGNDVKSSVSSVLQECEKKNYSSICLPAIGTGNAKQHPDKVAEAIIDA

IEDFVQKGSAQSVKKVKVVIFLPQVLDVFYANMKKREGTQLSSQQSVMSK

LASFLGFSKQSPQKKNHLVLEKKTESATFRVCGENVTCVEYAISWLQDLI

EKEQCPYTSEDECIKDFDEKEYQELNELQKKLNINISLDHKRPLIKVLGI

SRDVMQARDEIEAMIKRVRLAKEQESRADCISEFIEWQYNDNNTSHCFNK

MTNLKLEDARREKKKTVDVKINHRHYTVNLNTYTATDTKGHSLSVQRLTK

SKVDIPAHWSDMKQQNFCVVELLPSDPEYNTVASKFNQTCSHFRIEKIER

IQNPDLWNSYQAKKKTMDAKNGQTMNEKQLFHGTDAGSVPHVNRNGFNRS

YAGKNAVAYGKGTYFAVNANYSANDTYSRPDANGRKHVYYVRVLTGIYTH

GNHSLIVPPSKNPQNPTDLYDTVTDNVHHPSLFVAFYDYQAYPEYLITFR

K.

In one embodiment, the dTAG has an amino acid sequence derived from superoxide dismutase, UniProtKB—P00441 (SODC_HUMAN) incorporated herein by reference, or a variant thereof. In one embodiment, the dTAG is derived from the amino acid sequence:

(SEQ. ID. NO.: 38)
MATKAVCVLKGDGPVQGIINFEQKESNGPVKVWGSIKGLTEGLHGFHVHE

FGDNTAGCTSAGPHFNPLSRKHGGPKDEERHVGDLGNVTADKDGVADVSI

EDSVISLSGDHCIIGRTLVVHEKADDLGKGGNEESTKTGNAGSRLACGVI

GIAQ.

In one embodiment, the dTAG has an amino acid sequence derived from retinal rod rhodopsin-sensitive cGMP 3',5'-cyclic phosphodiesterase subunit delta, UniProtKB—O43924 (PDE6D_HUMAN) incorporated herein by reference, or a variant thereof. In one embodiment, the dTAG is derived from the amino acid sequence:

(SEQ. ID. NO.: 39)
MSAKDERAREILRGFKLNWMNLRDAETGKILWQGTEDLSVPGVEHEARVP

KKILKCKAVSRELNFSSTEQMEKFRLEQKVYFKGQCLEEWFFEFGFVIPN

STNTWQSLIEAAPESQMMPASVLTGNVIIETKFFDDDLLVSTSRVRLFY

V.

In one embodiment, the dTAG has an amino acid sequence derived from induced myeloid leukemia cell differentiation protein Mcl-1, UniProtKB—Q07820 (MCL1_HUMAN) incorporated herein by reference, or a variant thereof. In one embodiment, the dTAG is derived from the amino acid sequence:

(SEQ. ID. NO.: 40)
MFGLKRNAVIGLNLYCGGAGLGAGSGGATRPGGRLLATEKEASARREIGG

GEAGAVIGGSAGASPPSTLTPDSRRVARPPPIGAEVPDVTATPARLLFFA

PTRRAAPLEEMEAPAADAIMSPEEELDGYEPEPLGKRPAVLPLLELVGES

GNNTSTDGSLPSTPPPAEEEEDELYRQSLEIISRYLREQATGAKDTKPMG

RSGATSRKALETLRRVGDGVQRNHETAFQGMLRKLDIKNEDDVKSLSRVM

IHVFSDGVTNWGRIVTLISFGAFVAKHLKTINQESCIEPLAESITDVLVR

TKRDWLVKQRGWDGFVEFFHVEDLEGGIRNVLLAFAGVAGVGAGLAYLI

R.

In one embodiment, the dTAG has an amino acid sequence derived from apoptosis regulator Bcl-2, UniProtKB—Q07820 (BCL2_HUMAN) incorporated herein by reference, or a variant thereof. In one embodiment, the dTAG is derived from the amino acid sequence:

(SEQ. ID. NO.: 41)
MAHAGRTGYDNREIVMKYIHYKLSQRGYEWDAGDVGAAPPGAAPAPGIFS

SQPGHTPHPAASRDPVARTSPLQTPAAPGAAAGPALSPVPPVVHLTLRQA

GDDFSRRYRRDFAEMSSQLHLTPFTARGRFATVVEELFRDGVNWGRIVAF

FEFGGVMCVESVNREMSPLVDNIALWMTEYLNRHLHTWIQDNGGWDAFVE

LYGPSMRPLFDFSWLSLKTLLSLALVGACITLGAYLGHK.

In one embodiment, the dTAG has an amino acid sequence derived from peptidyl-prolyl cis-trans isomerase NIMA-interacting 1, UniProtKB—Q13526 (PIN1_HUMAN) incorporated herein by reference, or a variant thereof. In one embodiment, the dTAG is derived from the amino acid sequence:

(SEQ. ID. NO.: 42)
MADEEKLPPGWEKRMSRSSGRVYYFNHITNASQWERPSGNSSSGGKNGQG

EPARVRCSHLLVKHSQSRRPSSWRQEKITRTKEEALELINGYIQKIKSGE

EDFESLASQFSDCSSAKARGDLGAFSRGQMQKPFEDASFALRTGEMSGPV

FTDSGIHIILRTE.

In one embodiment, the dTAG has an amino acid sequence derived from tankyrase 1, UniProtKB—O95271 (TNKS1_HUMAN) incorporated herein by reference, or a variant thereof. In one embodiment, the dTAG is derived from the amino acid sequence (SEQ. ID. NO.: 43)
MAASRRSQHHHHHHQQQLQPAPGASAPPPPPPPPLSPGLAPGTTPASPTA

SGLAPFASPRHGLALPEGDGSRDPPDRPRSPDPVDGTSCCSTTSTICTVA

AAPVVPAVSTSSAAGVAPNPAGSGSNNSPSSSSSPTSSSSSSPSSPGSSL

AESPEAAGVSSTAPLGPGAAGPGTGVPAVSGALRELLEACRNGDVSRVKR

LVDAANVNAKDMAGRKSSPLHFAAGFGRKDVVEHLLQMGANVHARDDGGL

IPLHNACSFGHAEVVSLLLCQGADPNARDNWNYTPLHEAAIKGKIDVCIV

LLQHGADPNIRNTDGKSALDLADPSAKAVLTGEYKKDELLEAARSGNEEK

LMALLTPLNVNCHASDGRKSTPLHLAAGYNRVRIVQLLLQHGADVHAKDK

GGLVPLHNACSYGHYEVTELLLLKHGACVNAMDLWQFTPLHEAASKNRVEV

CSLLLSHGADPTLVNCHGKSAVDMAPTPELRERLTYEFKGHSLLQAAREA

DLAKVKKTLALEIINFKQPQSHETALHCAVASLHPKRKQVTELLLRKGAN

VNEKNKDFMTPLHVAAERAHNDVMEVLHKHGAKMNALDTLGQTALHRAAL

AGHLQTCRLLLSYGSDPSIISLQGFTAAQMGNEAVQQILSESTPIRTSDV

DYRLLEASKAGDLETVKQLCSSQNVNCRDLEGRHSTPLHFAAGYNRVSVV

```
EYLLHHGADVHAKDKGGLVPLHNACSYGHYEVAELLVRHGASVNVADLWK

FTPLHEAAAKGKYEICKLLLKHGADPTKKNRDGNTPLDLVKEGDTDIQDL

LRGDAALLDAAKKGCLARVQKLCTPENINCRDTQGRNSTPLHLAAGYNNL

EVAEYLLEHGADVNAQDKGGLIPLHNAASYGHVDIAALLIKYNTCVNATD

KWAFTPLHEAAQKGRTQLCALLLAHGADPTMKNQEGQTPLDLATADDIRA

LLIDAMPPEALPTCFKPQATVVSASLISPASTPSCLSAASSIDNLTGPLA

ELAVGGASNAGDGAAGTERKEGEVAGLDMNISQFLKSLGLEHLRDIFETE

QITLDVLADMGHEELKEIGINAYGHRHKLIKGVERLLGGQQGTNPYLTFH

CVNQGTILLDLAPEDKEYQSVEEEMQSTIREHRDGGNAGGIFNRYNVIRI

QKVVNKKLRERFCHRQKEVSEEENHNHHNERMLFHGSPFINAIIHKGFDER

HAYIGGMFGAGIYFAENSSKSNQYVYGIGGGTGCPTHKDRSCYICHRQML

FCRVTLGKSFLQFSTMKMAHAPPGHHSVIGRPSVNGLAYAEYVIYRGEQA

YPEYLITYQIMKPEAPSQTATAAEQKT.
```

In one embodiment, the dTAG has an amino acid sequence derived from tankyrase 2, UniProtKB—Q9H2K2 (TNKS2_HUMAN) incorporated herein by reference, or a variant thereof. In one embodiment, the dTAG is derived from the amino acid sequence:

```
                                      (SEQ. ID. NO.: 44)
MSGRRCAGGGAACASAAAEAVEPAARELFEACRNGDVERVKRLVTPEKVN

SRDTAGRKSTPLHFAAGFGRKDVVEYLLQNGANVQARDDGGLIPLHNACS

FGHAEVVNLLLRHGADPNARDNWNYTPLHEAAIKGKIDVCIVLLQHGAEP

TIRNTDGRTALDLADPSAKAVLTGEYKKDELLESARSGNEEKMMALLTPL

NVNCHASDGRKSTPLHLAAGYNRVKIVQLLLQHGADVHAKDKGDLVPLHN

ACSYGHYEVTELLVKHGACVNAMDLWQFTPLHEAASKNRVEVCSLLLSYG

ADPTLLNCHNKSAIDLAPTPQLKERLAYEFKGHSLLQAAREADVTRIKKH

LSLEMVNFKHPQTHETALHCAAASPYPKRKQICELLLRKGANINEKTKEF

LTPLHVASEKAHNDVVEVVVKHEAKVNALDNLGQTSLHRAAYCGHLQTCR

LLLSYGCDPNIISLQGFTALQMGNENVQQLLQEGISLGNSEADRQLLEAA

KAGDVETVKKLCTVQSVNCRDIEGRQSTPLHFAAGYNRVSVVEYLLQHGA

DVHAKDKGGLVPLHNACSYGHYEVAELLVKHGAVVNVADLWKFTPLHEAA

AKGKYEICKLLLQHGADPTKKNRDGNTPLDLVKDGDTDIQDLLRGDAALL

DAAKKGCLARVKKLSSPDNVNCRDTQGRHSTPLHLAAGYNNLEVAEYLLQ

HGADVNAQDKGGLIPLHNAASYGHVDVAALLIKYNACVNATDKWAFTPLH

EAAQKGRTQLCALLLAHGADPTLKNQEGQTPLDLVSADDVSALLTAAMPP

SALPSCYKPQVLNGVRSPGATADALSSGPSSPSSLSAASSLDNLSGSFSE

LSSVVSSSGTEGASSLEKKEVPGVDFSITQFVRNLGLEHLMDIFEREQIT

LDVLVEMGHKELKEIGINAYGHRHKLIKGVERLISGQQGLNPYLTLNTSG

SGTILIDLSPDDKEFQSVEEEMQSTVREHRDGGHAGGIFNRYNILKIQKV

CNKKLWERYTHRRKEVSEENHNHANERMLFHGSPFVNAIIHKGFDERHAY

IGGMFGAGIYFAENSSKSNQYVYGIGGGTGCPVHKDRSCYICHRQLLFCR

VTLGKSFLQFSAMKMAHSPPGHHSVTGRPSVNGLALAEYVIYRGEQAYPE

YLITYQIMRPEGMVDG.
```

In one embodiment, the dTAG has an amino acid sequence derived from 7,8-dihydro-8-oxoguanin triphosphatase, UniProtKB—P36639 (8ODP_HUMAN) incorporated herein by reference, or a variant thereof. In one embodiment, the dTAG is derived from the amino acid sequence:

```
                                      (SEQ. ID. NO.: 45)
MYWSNQITRRLGERVQGFMSGISPQQMGEPEGSWSGKNPGTMGASRLYTL

VLVLQPQRVLLGMKKRGFGAGRWNGFGGKVQEGETIEDGARRELQEESGL

TVDALHKVGQIVFEFVGEPELMDVHVFCTDSIQGTPVESDEMRPCWFQLD

QIPFKDMWPDDSYWFPLLLQKKKFHGYFKFQGQDTILDYTLREVDTV.
```

In one embodiment, the dTAG has an amino acid sequence derived from Proto-oncogene tyrosine protein kinase Src, UniProtKB—P12931 (SRC_HUMAN) incorporated herein by reference, or a variant thereof. In one embodiment, the dTAG is derived from the amino acid sequence:

```
                                      (SEQ. ID. NO.: 46)
MGSNKSKPKDASQRRRSLEPAENVHGAGGGAFPASQTPSKPASADGHRGP

SAAFAPAAAEPKLFGGFNSSDTVTSPQRAGPLAGGVTTFVALYDYESRTE

TDLSFKKGERLQIVNNTEGDWWLAHSLSTGQTGYIPSNYVAPSDSIQAEE

WYFGKITRRESERLLLNAENPRGTFLVRESETTKGAYCLSVSDFDNAKGL

NVKHYKIRKLDSGGFYITSRTQFNSLQQLVAYYSKHADGLCHRLTTVCPT

SKPQTQGLAKDAWEIPRESLRLEVKLGQGCFGEVWMGTWNGTTRVAIKTL

KPGTMSPEAFLQEAQVMKKLRHEKLVQLYAVVSEEPIYIVTEYMSKGSLL

DFLKGETGKYLRLPQLVDMAAQIASGMAYVERMNYVHRDLRAANILVGEN

LVCKVADFGLARLIEDNEYTARQGAKFPIKWTAPEAALYGRFTIKSDVWS

FGILLTELTTKGRVPYPGMVNREVLDQVERGYRMPCPPECPESLHDLMCQ

CWRKEPEERPTFEYLQAFLEDYFTSTEPQYQPGENL.
```

In one embodiment, the dTAG includes a substitution of Threonine (T) with Glycine (G) or Alanine (A) at amino acid position 341. In one embodiment, the dTAG is an amino acid sequence derived from, or a fragment thereof, of SEQ. ID. NO.: 114.

```
LRLEVKLGQGCFGEVWMGTWNGTTRVAIKTLKPGTMSPEAFLQEAQVMKK

LRHEKLVQLYAVVSEEPIYIVTEYGSKGSLLDFLKGETGKYLRLPQLVDM

AAQIASGMAYVERMNYVHRDLRAANILVGENLVCKVADFGLARLIEDNEY

TARQGAKFPIKWTAPEAALYGRFTIKSDVWSFGILLTELTTKGRVPYPGM

VNREVLDQVERGYRMPCPPECPESLHDLMCQCWRKEPEERPTFEYLQAFL

EDYF.
```

In one embodiment, the dTAG is an amino acid sequence derived from, or a fragment thereof, of SEQ. ID. NO.: 115.

LRLEVKLGQGCFGEVWMGTWNGTTRVAIKTLKPGTMSPEAFLQEAQVMKK

LRHEKLVQLYAVVSEEPIYIVTEYASKGSLLDFLKGETGKYLRLPQLVDM

AAQIASGMAYVERMNYVHRDLRAANILVGENLVCKVADFGLARLIEDNEY

TARQGAKFPIKWTAPEAALYGRFTIKSDVWSFGILLTELTTKGRVPYPGM

VNREVLDQVERGYRMPCPPECPESLHDLMCQCWRKEPEERPTFEYLQAFL

EDYF.

In one embodiment, the dTAG has an amino acid sequence derived from prostaglandin E synthase, UniProtKB—O14684 (PTGES_HUMAN) incorporated herein by reference, or a variant thereof. In one embodiment, the dTAG is derived from the amino acid sequence:

(SEQ. ID. NO.: 47)
MPAHSLVMSSPALPAFLLCSTLLVIKMYVVAIITGQVRLRKKAFANPEDA

LRHGGPQYCRSDPDVERCLRAHRNDMETIYPFLFLGFVYSFLGPNPFVAW

MHFLVFLVGRVAHTVAYLGKLRAPIRSVTYTLAQLPCASMALQILWEAAR

HL.

In one embodiment, the dTAG has an amino acid sequence derived from Arachidonate 5-lipoxygenase activating protein, UniProtKB—P20292 (AL5AP_HUMAN) incorporated herein by reference, or a variant thereof. In one embodiment, the dTAG is derived from the amino acid sequence:

(SEQ. ID. NO.: 48)
MDQETVGNVVLLAIVTLISVVQNGFFAHKVEHESRTQNGRSFQRTGTLAF

ERVYTANQNCVDAYPTFLAVLWSAGLLCSQVPAAFAGLMYLFVRQKYFVG

YLGERTQSTPGYIFGKRIILFLFLMSVAGIFNYYLIFFFGSDFENYIKTI

STTISPLLLIP.

In one embodiment, the dTAG has an amino acid sequence derived from fatty acid binding protein from adipocyte, UniProtKB—P15090 (FABP4_HUMAN) incorporated herein by reference, or a variant thereof. In one embodiment, the dTAG is derived from the amino acid sequence:

(SEQ. ID. NO.: 49)
MCDAFVGTWKLVSSENFDDYMKEVGVGFATRKVAGMAKPNMIISVNGDVI

TIKSESTFKNTEISFILGQEFDEVTADDRKVKSTITLDGGVLVHVQKWDG

KSTTIKRKREDDKLVVECVMKGVTSTRVYERA.

In one embodiment, the dTAG has an amino acid sequence derived from PH-interacting protein, UniProtKB—Q8WWQ0 (PHIP_HUMAN) incorporated herein by reference, or a variant thereof. In one embodiment, the dTAG is derived from the amino acid sequence:

(SEQ. ID. NO.: 50)
MSCERKGLSELRSELYFLIARFLEDGPCQQAAQVLIREVAEKELLPRRTD

WTGKEHPRTYQNLVKYYRHLAPDHLLQICHRLGPLLEQEIPQSVPGVQTL

LGAGRQSLLRTNKSCKHVVWKGSALAALHCGRPPESPVNYGSPPSIADTL

FSRKLNGKYRLERLVPTAVYQHMKMHKRILGHLSSVYCVTFDRTGRRIFT

GSDDCLVKIWATDDGRLLATLRGHAAEISDMAVNYENTMIAAGSCDKMIR

VWCLRTCAPLAVLQGHSASITSLQFSPLCSGSKRYLSSTGADGTICFWLW

DAGTLKINPRPAKFTERPRPGVQMICSSFSAGGMFLATGSTDHIIRVYFF

GSGQPEKISELEFHTDKVDSIQFSNTSNRFVSGSRDGTARIWQFKRREWK

SILLDMATRPAGQNLQGIEDKITKMKVTMVAWDRHDNTVITAVNNMTLKV

WNSYTGQLIHVLMGHEDEVFVLEPHPFDPRVLFSAGHDGNVIVWDLARGV

KIRSYFNMIEGQGHGAVFDCKCSPDGQHFACTDSHGHLLIFGFGSSSKYD

KIADQMFFHSDYRPLIRDANNFVLDEQTQQAPHLMPPPFLVDVDGNPHPS

RYQRLVPGRENCREEQLIPQMGVTSSGLNQVLSQQANQEISPLDSMIQRL

QQEQDLRRSGEAVISNTSRLSRGSISSTSEVHSPPNVGLRRSGQIEGVRQ

MHSNAPRSEIATERDLVAWSRRVVVPELSAGVASRQEEWRTAKGEEEIKT

YRSEEKRKHLTVPKENKIPTVSKNHAHEHFLDLGESKKQQTNQHNYRTRS

ALEETPRPSEEIENGSSSSDEGEVVAVSGGTSEEEERAWHSDGSSSDYSS

DYSDWTADAGINLQPPKKVPKNKTKKAESSSDEEEESEKQKQKQIKKEKK

KVNEEKDGPISPKKKKPKERKQKRLAVGELTENGLTLEEWLPSTWITDTI

PRRCPFVPQMGDEVYYFRQGHEAYVEMARKNKIYSINPKKQPWHKMELRE

QELMKIVGIKYEVGLPTLCCLKLAFLDPDTGKLTGGSFTMKYHDMPDVID

FLVLRQQFDDAKYRRWNIGDRFRSVIDDAWWFGTIESQEPLQLEYPDSLF

QCYNVCWDNGDTEKMSPWDMELIPNNAVFPEELGTSVPLTDGECRSLIYK

PLDGEWGTNPRDEECERIVAGINQLMTLDIASAFVAPVDLQAYPMYCTVV

AYPTDLSTIKQRLENRFYRRVSSLMWEVRYIEHNTRTFNEPGSPIVKSAK

FVTDLLLHFIKDQTCYNIIPLYNSMKKKVLSDSEDEEKDADVPGTSTRKR

KDHQPRRRLRNRAQSYDIQAWKKQCEELLNLIFQCEDSEPFRQPVDLLEY

PDYRDIIDTPMDFATVRETLEAGNYESPMELCKDVRLIFSNSKAYTPSKR

SRIYSMSLRLSAFFEEHISSVLSDYKSALRFHKRNTITKRRKKRNRSSSV

SSSAASSPERKKRILKPQLKSESSTSAFSTPTRSIPPRHNAAQINGKTES

SSVVRTRSNRVVVDPVVTEQPSTSSAAKTFITKANASAIPGKTILENSVK

HSKALNTLSSPGQSSFSHGTRNNSAKENMEKEKPVKRKMKSSVLPKASTL

SKSSAVIEQGDCKNNALVPGTIQVNGHGGQPSKLVKRGPGRKPKVEVNTN

SGEIIHKKRGRKPKKLQYAKPEDLEQNNVHPIRDEVLPSSTCNFLSETNN

VKEDLLQKKNRGGRKPKRKMKTQKLDADLLVPASVKVLRRSNRKKIDDPI

DEEEEFEELKGSEPHMRTRNQGRRTAFYNEDDSEEEQRQLLFEDTSLTFG

TSSRGRVRKLTEKAKANLIGW.

In one embodiment, the dTAG has an amino acid sequence derived from SUMO-conjugating enzyme UBC9, UniProtKB—P63279 (UBC9_HUMAN) incorporated herein by reference, or a variant thereof. In one embodiment, the dTAG is derived from the amino acid sequence:

(SEQ. ID. NO.: 51)
MSGIALSRLAQERKAWRKDHPFGFVAVPTKNPDGTMNLMNWECAIPGKKG

TPWEGGLFKLRMLFKDDYPSSPPKCKFEPPLFHPNVYPSGTVCLSILEED

KDWRPAITIKQILLGIQELLNEPNIQDPAQAEAYTIYCQNRVEYEKRVRA

QAKKFAPS.

In one embodiment, the dTAG has an amino acid sequence derived from Protein S100-A7, UniProtKB—P31151 (S10A7_HUMAN) incorporated herein by reference, or a variant thereof. In one embodiment, the dTAG is derived from the amino acid sequence:

(SEQ. ID. NO.: 52)
MSNTQAERSIIGMIDMFHKYTRRDDKIEKPSLLTMMKENFPNFLSACDKK

GTNYLADVFEKKDKNEDKKIDFSEFLSLLGDIATDYHKQSHGAAPCSGGS

Q.

In one embodiment, the dTAG has an amino acid sequence derived from phospholipase A2, membrane associated, UniProtKB—P14555 (PA2GA_HUMAN) incorporated herein by reference, or a variant thereof. In one embodiment, the dTAG is derived from the amino acid sequence:

(SEQ. ID. NO.: 53)
MKTLLLLAVIMIFGLLQAHGNLVNFHRMIKLTTGKEAALSYGFYGCHCGV

GGRGSPKDATDRCCVTHDCCYKRLEKRGCGTKFLSYKFSNSGSRITCAKQ

DSCRSQLCECDKAAATCFARNKTTYNKKYQYYSNKHCRGSTPRC.

In one embodiment, the dTAG has an amino acid sequence derived from histone deacetylase 6, UniProtKB—Q9UBN7 (HDAC6_HUMAN) incorporated herein by reference, or a variant thereof. In one embodiment, the dTAG is derived from the amino acid sequence:

(SEQ. ID. NO.: 54)
MTSTGQDSTTTRQRRSRQNPQSPPQDSSVTSKRNIKKGAVPRSIPNLAEV

KKKGKMKKLGQAMEEDLIVGLQGMDLNLEAEALAGTGLVLDEQLNEFHCL

WDDSFPEGPERLHAIKEQLIQEGLLDRCVSFQARFAEKEELMLVHSLEYI

DLMETTQYMNEGELRVLADTYDSVYLHPNSYSCACLASGSVLRLVDAVLG

AEIRNGMAIIRPPGHHAQHSLMDGYCMFNHVAVAARYAQQKHRIRRVLIV

DWDVHHGQGTQFTFDQDPSVLYFSIHRYEQGRFWPHLKASNWSTTGFGQG

QGYTINVPWNQVGMRDADYIAAFLHVLLPVALEFQPQLVLVAAGFDALQG

DPKGEMAATPAGFAQLTHLLMGLAGGKLILSLEGGYNLRALAEGVSASLH

TLLGDPCPMLESPGAPCRSAQASVSCALEALEPFWEVLVRSTETVERDNM

EEDNVEESEEEGPWEPPVLPILTWPVLQSRTGLVYDQNMMNHCNLWDSHH

PEVPQRILRIMCRLEELGLAGRCLTLTPRPATEAELLTCHSAEYVGHLRA

TEKMKTRELHRESSNFDSIYICPSTFACAQLATGAACRLVEAVLSGEVLN

GAAVVRPPGHHAEQDAACGFCFFNSVAVAARHAQTISGHALRILIVDWDV

HHGNGTQHMFEDDPSVLYVSLHRYDHGTFFPMGDEGASSQIGRAAGTGFT

VNVAWNGPRMGDADYLAAWHRLVLPIAYEFNPELVLVSAGFDAARGDPLG

GCQVSPEGYAHLTHLLMGLASGRIILILEGGYNLTSISESMAACTRSLLG

DPPPLLTLPRPPLSGALASITETIQVHRRYWRSLRVMKVEDREGPSSSKL

VTKKAPQPAKPRLAERMTTREKKVLEAGMGKVTSASFGEESTPGQTNSET

AVVALTQDQPSEAATGGATLAQTISEAAIGGAMLGQTTSEEAVGGATPDQ

TTSEETVGGAILDQTTSEDAVGGATLGQTTSEEAVGGATLAQTTSEAAME

GATLDQTTSEEAPGGTELIQTPLASSTDHQTPPTSPVQGTTPQISPSTLI

GSLRTLELGSESQGASESQAPGEENLLGEAAGGQDMADSMLMQGSRGLTD

QAIFYAVTPLPWCPHLVAVCPIPAAGLDVTQPCGDCGTIQENWVCLSCYQ

VYCGRYINGHMLQHHGNSGHPLVLSYIDLSAWCYYCQAYVHHQALLDVKN

IAHQNKFGEDMPHPH.

In one embodiment, the dTAG has an amino acid sequence derived from prosaposin, UniProtKB—P07602 (SAP_HUMAN) incorporated herein by reference, or a variant thereof. In one embodiment, the dTAG is derived from the amino acid sequence:

(SEQ. ID. NO.: 55)
MYALFLLASLLGAALAGPVLGLKECTRGSAVWCQNVKTASDCGAVKHCLQ

TVWNKPTVKSLPCDICKDVVTAAGDMLKDNATEEEILVYLEKTCDWLPKP

NMSASCKEIVDSYLPVILDIIKGEMSRPGEVCSALNLCESLQKHLAELNH

QKQLESNKIPELDMTEVVAPFMANIPLLLYPQDGPRSKPQPKDNGDVCQD

CIQMVTDIQTAVRTNSTFVQALVEHVKEECDRLGPGMADICKNYISQYSE

IAIQMMMHMQPKEICALVGFCDEVKEMPMQTLVPAKVASKNVIPALELVE

PIKKHEVPAKSDVYCEVCEFLVKEVTKLIDNNKTEKEILDAFDKMCSKLP

KSLSEECQEVVDTYGSSILSILLEEVSPELVCSMLHLCSGTRLPALTVHV

TQPKDGGFCEVCKKLVGYLDRNLEKNSTKQEILAALEKGCSFLPDPYQKQ

CDQFVAEYEPVLIEILVEVMDPSFVCLKIGACPSAHKPLLGTEKCIWGPS

YWCQNTETAAQCNAVEHCKRHVWN.

In one embodiment, the dTAG has an amino acid sequence derived from apolipoprotein a, UniProtKB—P08519 (APOA_HUMAN) incorporated herein by reference, or a variant thereof. In one embodiment, the dTAG is derived from the amino acid sequence:

(SEQ. ID. NO.: 56)
MEHKEVVLLLLLFLKSAAPEQSHVVQDCYHGDGQSYRGTYSTTVTGRTCQ

AWSSMTPHQHNRTTENYPNAGLIMNYCRNPDAVAAPYCYTRDPGVRWEYC

NLTQCSDAEGTAVAPPTVTPVPSLEAPSEQAPTEQRPGVQECYHGNGQSY

RGTYSTTVTGRTCQAWSSMTPHSHSRTPEYYPNAGLIMNYCRNPDAVAAP

YCYTRDPGVRWEYCNLTQCSDAEGTAVAPPTVTPVPSLEAPSEQAPTEQR

PGVQECYHGNGQSYRGTYSTTVTGRTCQAWSSMTPHSHSRTPEYYPNAGL

IMNYCRNPDAVAAPYCYTRDPGVRWEYCNLTQCSDAEGTAVAPPTVTPVP

SLEAPSEQAPTEQRPGVQECYHGNGQSYRGTYSTTVTGRTCQAWSSMTPH

SHSRTPEYYPNAGLIMNYCRNPDAVAAPYCYTRDPGVRWEYCNLTQCSDA

EGTAVAPPTVTPVPSLEAPSEQAPTEQRPGVQECYHGNGQSYRGTYSTTV

TGRTCQAWSSMTPHSHSRTPEYYPNAGLIMNYCRNPDAVAAPYCYTRDPG

VRWEYCNLTQCSDAEGTAVAPPTVTPVPSLEAPSEQAPTEQRPGVQECYH

-continued

GNGQSYRGTYSTTVTGRTCQAWSSMTPHSHSRTPEYYPNAGLIMNYCRNP
DAVAAPYCYTRDPGVRWEYCNLTQCSDAEGTAVAPPTVTPVPSLEAPSEQ
APTEQRPGVQECYHGNGQSYRGTYSTTVTGRTCQAWSSMTPHSHSRTPEY
YPNAGLIMNYCRNPDAVAAPYCYTRDPGVRWEYCNLTQCSDAEGTAVAPP
TVTPVPSLEAPSEQAPTEQRPGVQECYHGNGQSYRGTYSTTVTGRTCQAW
SSMTPHSHSRTPEYYPNAGLIMNYCRNPDAVAAPYCYTRDPGVRWEYCNL
TQCSDAEGTAVAPPTVTPVPSLEAPSEQAPTEQRPGVQECYHGNGQSYRG
TYSTTVTGRTCQAWSSMTPHSHSRTPEYYPNAGLIMNYCRNPDAVAAPYC
YTRDPGVRWEYCNLTQCSDAEGTAVAPPTVTPVPSLEAPSEQAPTEQRPG
VQECYHGNGQSYRGTYSTTVTGRTCQAWSSMTPHSHSRTPEYYPNAGLIM
NYCRNPDAVAAPYCYTRDPGVRWEYCNLTQCSDAEGTAVAPPTVTPVPSL
EAPSEQAPTEQRPGVQECYHGNGQSYRGTYSTTVTGRTCQAWSSMTPHSH
SRTPEYYPNAGLIMNYCRNPDAVAAPYCYTRDPGVRWEYCNLTQCSDAEG
TAVAPPTVTPVPSLEAPSEQAPTEQRPGVQECYHGNGQSYRGTYSTTVTG
RTCQAWSSMTPHSHSRTPEYYPNAGLIMNYCRNPDAVAAPYCYTRDPGVR
WEYCNLTQCSDAEGTAVAPPTVTPVPSLEAPSEQAPTEQRPGVQECYHGN
GQSYRGTYSTTVTGRTCQAWSSMTPHSHSRTPEYYPNAGLIMNYCRNPDA
VAAPYCYTRDPGVRWEYCNLTQCSDAEGTAVAPPTVTPVPSLEAPSEQAP
TEQRPGVQECYHGNGQSYRGTYSTTVTGRTCQAWSSMTPHSHSRTPEYYP
NAGLIMNYCRNPDAVAAPYCYTRDPGVRWEYCNLTQCSDAEGTAVAPPTV
TPVPSLEAPSEQAPTEQRPGVQECYHGNGQSYRGTYSTTVTGRTCQAWSS
MTPHSHSRTPEYYPNAGLIMNYCRNPDAVAAPYCYTRDPGVRWEYCNLTQ
CSDAEGTAVAPPTVTPVPSLEAPSEQAPTEQRPGVQECYHGNGQSYRGTY
STTVTGRTCQAWSSMTPHSHSRTPEYYPNAGLIMNYCRNPDAVAAPYCYT
PGVRWEYCNLTQCSDAEGTAVAPPTVTPVPSLEAPSEQAPTEQRPGVQEC
YHGNGQSYRGSYRGTYSTTVTGRTCQAWSSMTPHSHSRTPEYYPNAGLIM
NYCRNPDAVAAPYCYTRDPGVRWEYCNLTQCSDAEGTAVAPPTVTPVPSL
EAPSEQAPTEQRPGVQECYHGNGQSYRGTYSTTVTGRTCQAWSSMTPHSH
SRTPEYYPNAGLIMNYCRNPDAVAAPYCYTRDPGVRWEYCNLTQCSDAEG
TAVAPPTVTPVPSLEAPSEQAPTEQRPGVQECYHGNGQSYRGTYSTTVTG
RTCQAWSSMTPHSHSRTPEYYPNAGLIMNYCRNPDAVAAPYCYTRDPGVR
WEYCNLTQCSDAEGTAVAPPTVTPVPSLEAPSEQAPTEQRPGVQECYHGN
GQSYRGTYSTTVTGRTCQAWSSMTPHSHSRTPEYYPNAGLIMNYCRNPDA
VAAPYCYTRDPGVRWEYCNLTQCSDAEGTAVAPPTVTPVPSLEAPSEQAP
TEQRPGVQECYHGNGQSYRGTYSTTVTGRTCQAWSSMTPHSHSRTPEYYP
NAGLIMNYCRNPDAVAAPYCYTRDPGVRWEYCNLTQCSDAEGTAVAPPTV
TPVPSLEAPSEQAPTEQRPGVQECYHGNGQSYRGTYSTTVTGRTCQAWSS
MTPHSHSRTPEYYPNAGLIMNYCRNPDAVAAPYCYTRDPGVRWEYCNLTQ
CSDAEGTAVAPPTVTPVPSLEAPSEQAPTEQRPGVQECYHGNGQSYRGTY
STTVTGRTCQAWSSMTPHSHSRTPEYYPNAGLIMNYCRNPDAVAAPYCYT
RDPGVRWEYCNLTQCSDAEGTAVAPPTVTPVPSLEAPSEQAPTEQRPGVQ

-continued

ECYHGNGQSYRGTYSTTVTGRTCQAWSSMTPHSHSRTPEYYPNAGLIMNY
CRNPDAVAAPYCYTRDPGVRWEYCNLTQCSDAEGTAVAPPTVTPVPSLEA
PSEQAPTEQRPGVQECYHGNGQSYRGTYSTTVTGRTCQAWSSMTPHSHSR
TPEYYPNAGLIMNYCRNPDAVAAPYCYTRDPGVRWEYCNLTQCSDAEGTA
VAPPTVTPVPSLEAPSEQAPTEQRPGVQECYHGNGQSYRGTYSTTVTGRT
CQAWSSMTPHSHSRTPEYYPNAGLIMNYCRNPDAVAAPYCYTRDPGVRWE
YCNLTQCSDAEGTAVAPPTVTPVPSLEAPSEQAPTEQRPGVQECYHGNGQ
SYRGTYSTTVTGRTCQAWSSMTPHSHSRTPEYYPNAGLIMNYCRNPDAVA
APYCYTRDPGVRWEYCNLTQCSDAEGTAVAPPTVTPVPSLEAPSEQAPTE
QRPGVQECYHGNGQSYRGTYSTTVTGRTCQAWSSMTPHSHSRTPEYYPNA
GLIMNYCRNPDAVAAPYCYTRDPGVRWEYCNLTQCSDAEGTAVAPPTVTP
VPSLEAPSEQAPTEQRPGVQECYHGNGQSYRGTYSTTVTGRTCQAWSSMT
PHSHSRTPEYYPNAGLIMNYCRNPDAVAAPYCYTRDPGVRWEYCNLTQCS
DAEGTAVAPPTVTTVTPVPSLEAPSEQAPTEQRPGVQECYHGNGQSYRGT
YSTTVTGRTCQAWSSMTPHSHSRTPEYYPNAGLIMNYCRNPDAVAAPYCY
TRDPGVRWEYCNLTQCSDAEGTAVAPPTVTPVPSLEAPSEQAPTEQRPGV
QECYHGNGQSYRGTYSTTVTGRTCQAWSSMTPHSHSRTPEYYPNAGLIMN
YCRNPDAVAAPYCYTRDPGVRWEYCNLTQCSDAEGTAVAPPTVTPVPSLE
APSEQAPTEQRPGVQECYHGNGQSYRGTYSTTVTGRTCQAWSSMTPHSHS
RTPEYYPNAGLIMNYCRNPDPVAAPYCYTRDPSVRWEYCNLTQCSDAEGT
AVAPPTITPIPSLEAPSEQAPTEQRPGVQECYHGNGQSYQGTYFITVTGR
TCQAWSSMTPHSHSRTPAYYPNAGLIKNYCRNPDPVAAPWCYTTDPSVRW
EYCNLTRCSDAEWTAFVPPNVILAPSLEAFFEQALTEETPGVQDCYYHYG
QSYRGTYSTTVTGRTCQAWSSMTPHQHSRTPENYPNAGLTRNYCRNPDAE
IRPWCYTMDPSVRWEYCNLTQCLVTESSVLATLTVVPDPSTEASSEEAPT
EQSPGVQDCYHGDGQSYRGSFSTTVTGRTCQSWSSMTPHWHQRTTEYYPN
GGLTRNYCRNPDAEISPWCYTMDPNVRWEYCNLTQCPVTESSVLATSTAV
SEQAPTEQSPTVQDCYHGDGQSYRGSFSTTVTGRTCQSWSSMTPHWHQRT
TEYYPNGGLTRNYCRNPDAEIRPWCYTMDPSVRWEYCNLTQCPVMESTLL
TTPTVVPVPSTELPSEEAPTENSTGVQDCYRGDGQSYRGTLSTTITGRTC
QSWSSMTPHWHRRIPLYYPNAGLTRNYCRNPDAEIRPWCYTMDPSVRWEY
CNLTRCPVTESSVLTTPTVAPVPSTEAPSEQAPPEKSPVVQDCYHGDGRS
YRGISSTTVTGRTCQSWSSMIPHWHQRTPENYPNAGLTENYCRNPDSGKQ
PWCYTTDPCVRWEYCNLTQCSETESGVLETPTVVPVPSMEAHSEAAPTEQ
TPVVRQCYHGNGQSYRGTFSTTVTGRTCQSWSSMTPHRHQRTPENYPNDG
LTMNYCRNPDADTGPWCFTMDPSIRWEYCNLTRCSDTEGTVVAPPTVIQV
PSLGPPSEQDCMFGNGKGYRGKKATTVTGTPCQEWAAQEPHRHSTFIPGT
NKWAGLEKNYCRNPDGDINGPWCYTMNPRKLFDYCDIPLCASSSFDCGKP
QVEPKKCPGSIVGGCVAHPHSWPWQVSLRTRFGKHFCGGTLISPEWVLTA
AHCLKKSSRPSSYKVILGAHQEVNLESHVQEIEVSRLFLEPTQADIALLK

```
LSRPAVITDKVMPACLPSPDYMVTARTECYITGWGETQGTFGTGLLKEAQ

LLVIENEVCNHYKYICAEHLARGTDSCQGDSGGPLVCFEKDKYILQGVTS

WGLGCARPNKPGVYARVSRFVTWIEGMMRNN.
```

In one embodiment, the dTAG has an amino acid sequence derived from lactoglutathione lyase, UniProtKB—Q04760 (LGUL_HUMAN) incorporated herein by reference, or a variant thereof. In one embodiment, the dTAG is derived from the amino acid sequence:

```
                                        (SEQ. ID. NO.: 57)
MAEPQPPSGGLTDEAALSCCSDADPSTKDFLLQQTMLRVKDPKKSLDFY

TRVLGMTLIQKCDFPIMKFSLYFLAYEDKNDIPKEKDEKIAWALSRKAT

LELTHNWGTEDDETQSYHNGNSDPRGFGHIGIAVPDVYSACKRFEELGV

KFVKKPDDGKMKGLAFIQDPDGYWIEILNPNKMATLM.
```

In one embodiment, the dTAG has an amino acid sequence derived from protein afadin, UniProtKB—P55196 (AFAD_HUMAN) incorporated herein by reference, or a variant thereof. In one embodiment, the dTAG is derived from the amino acid sequence:

```
                                        (SEQ. ID. NO.: 58)
MSAGGRDEERRKLADIIHHWNANRLDLFEISQPTEDLEFHGVMRFYFQDK

AAGNFATKCIRVSSTATTQDVIETLAEKFRPDMRMLSSPKYSLYEVHVSG

ERRLDIDEKPLVVQLNWNKDDREGRFVLKNENDAIPPKKAQSNGPEKQEK

EGVIQNFKRTLSKKEKKEKKKREKEALRQASDKDDRPFQGEDVENSRLAA

EVYKDMPETSFTRTISNPEVVMKRRRQQKLEKRMQEFRSSDGRPDSGGTL

RIYADSLKPNIPYKTILLSTTDPADFAVAEALEKYGLEKENPKDYCIARV

MLPPGAQHSDEKGAKEIILDDDECPLQIFREWPSDKGILVFQLKRRPPDH

IPKKTKKHLEGKTPKGKERADGSGYGSTLPPEKLPYLVELSPGRRNHFAY

YNYHTYEDGSDSRDKPKLYRLQLSVTEVGTEKLDDNSIQLFGPGIQPHHC

DLTNMDGVVTVTPRSMDAETYVEGQRISETTMLQSGMKVQFGASHVFKFV

DPSQDHALAKRSVDGGLMVKGPRHKPGIVQETTFDLGGDIHSGTALPTSK

STTRLDSDRVSSASSTAERGMVKPMIRVEQQPDYRRQESRTQDASGPELI

LPASIEFRESSEDSFLSAIINYTNSSTVHFKLSPTYVLYMACRYVLSNQY

RPDISPTERTHKVIAVVNKMVSMMEGVIQKQKNIAGALAFWMANASELLN

FIKQDRDLSRITLDAQDVLAHLVQMAFKYLVHCLQSELNNYMPAFLDDPE

ENSLQRPKIDDVLHTLTGAMSLLRRCRVNAALTIQLFSQLFHFINMWLFN

RLVTDPDSGLCSHYWGAIIRQQLGHIEAWAEKQGLELAADCHLSRIVQAT

TLLTMDKYAPDDIPNINSTCFKLNSLQLQALLQNYHCAPDEPFIPTDLIE

NVVTVAENTADELARSDGREVQLEEDPDLQLPFLLPEDGYSCDVVRNIPN

GLQEFLDPLCQRGFCRLIPHTRSPGTWTIYFEGADYESHLLRENTELAQP

LRKEPEIITVTLKKQNGMGLSIVAAKGAGQDKLGIYVKSVVKGGAADVDG

RLAAGDQLLSVDGRSLVGLSQERAAELMTRTSSVVTLEVAKQGAIYHGLA

TLLNQPSPMMQRISDRRGSGKPRPKSEGFELYNNSTQNGSPESPQLPWAE

YSEPKKLPGDDRLMKNRADHRSSPNVANQPPSPGGKSAYASGTTAKITSV

STGNLCTEEQTPPPRPEAYPIPTQTYTREYFTFPASKSQDRMAPPQNQWP

NYEEKPHMHTDSNHSSIAIQRVTRSQEELREDKAYQLERHRIEAAMDRKS

DSDMWINQSSSLDSSTSSQEHLNHSSKSVTPASTLTKSGPGRWKTPAAIP

ATPVAVSQPIRTDLPPPPPPPPVHYAGDFDGMSMDLPLPPPPSANQIGLP

SAQVAAAERRKREEHQRWYEKEKARLEEERERKRREQERKLGQMRTQSLN

PAPFSPLTAQQMKPEKPSTLQRPQETVIRELQPQQQPRTIERRDLQYITV

SKEELSSGDSLSPDPWKRDAKEKLEKQQQMHIVDMLSKEIQELQSKPDRS

AEESDRLRKLMLEWQFQKRLQESKQKDEDDEEEEDDVDTMLIMQRLEAE

RRARLQDEERRRQQQLEEMRKREAEDRARQEEERRRQEEERTKRDAEEKR

RQEEGYYSRLEAERRRQHDEAARRLLEPEAPGLCRPPLPRDYEPPSPSPA

PGAPPPPPQRNASYLKTQVLSPDSLFTAKFVAYNEEEEEEDCSLAGPNSY

PGSTGAAVGAHDACRDAKEKRSKSQDADSPGSSGAPENLTFKERQRLFSQ

GQDVSNKVKASRKLTELENELNTK.
```

In one embodiment, the dTAG has an amino acid sequence derived from epidermal growth factor receptor (EGFR, UniProtKB P00533 (EGFR_HUMAN) incorporated herein by reference, or a variant thereof. In one embodiment, the dTAG is derived from, includes, or is the amino acid sequence:

```
(L858R)
(SEQ. ID. NO.: 59):
GEAPNQALLRILKETEFKKIKVLGSGAFGTVYKGLWIPEGEKVKIPVAIK

ELREATSPKANKEILDEAYVMASVDNPHVCRLLGICLTSTVQLITQLMPF

GCLLDYVREHKDNIGSQYLLNWCVQIAKGMNYLEDRRLVHRDLAARNVLV

KTPQHVKITDFGRAKLLGAEEKEYHAEGGKVPIKWMALESILHRIYTHQS

DVWSYGVTVWELMTFGSKPYDGIPASEISSILEKGERLPQPPICTIDVYM

IMVKCWMIDADSRPKFRELIIEFSKMARDPQRYLVIQGDERMHLPSPTDS

NFYRALMDEEDMDDVVDADEYLIPQQG.
```

In one embodiment, the dTAG is derived from, includes, or is the amino acid sequence: (SEQ. ID. NO.: 60): (T790M) GEAPNQALLRILKETEFK-KIKVLGSGAFGTVYKGLWIPEGEKVKIPVAIKEL-REATSPKA NKEILDEAYVMASVDNPHVCRLLGICLT-STVQLIMQLMPFGCLLDYVREHKDINIGSQYL LNWCVQIAKGMNYLEDRRLVHRD-LAARNVKKTPQHVKITDFGRAKLLGAEEKEYHA EGGKVPIKWMALE-SILHRIYTHQSDVWSYGVFVWELMTFGSKPYDGIPA-SEISSILEKGE RLPQPPICTIDVYMIIMVKCWMI-DADSRPKFRELIIEFSKMARDPQRYLVIQGDERMHLP S PTDSNFYRALMDEEDMDDVVDADEYLIPQQG. In one embodiment, SEQ. ID. NO.: 60 has a Leucine at position 163.

In one embodiment, the dTAG is derived from, includes, or is the amino acid sequence: (SEQ. ID. NO.: 61): (C797S) GEAPNQALLRILKETEFK-KIKVLGSGAFGTVYKGLWIPEGEKVKIPVAIKEL-REATSPKA NKEILDEAYVMASVDNPHVCRLLGICLT-STVQLIMQLMPFGSLLDYVREHKDNIGSQYL LNWCVQIAKGMNYLEDRRLVHRD-LAARNVLKTPQHVKITDFGRAKLLGAEEKEYHA EGGKVPIKWMALESIL- EIRTYTHQSDVWSYGVTVWELMITGSKPYDGIPA-SEISSILEKGE RLPQPPICTIDVYMIMVKCWMI-DADSRPKFRELIIEFSKMARDPQRYLVIQGDERMHLPS PTDSNFYRALMDEEDMDDVVDADEYLIPQQG. In one embodiment, SEQ. ID. NO.: 61 has a Leucine at position 163. In one embodiment, SEQ. ID, NO.: 61 has a Threonine at position 95. In one embodiment, SEQ. ID. NO.: 61 has a Leucine at position 163 and a Threonine at position 95.

In one embodiment, the dTAG is derived from, includes, or is the amino acid sequence: (SEQ. ID. NO.: 62): (C790G) GEAPNQALLRILKETEFK-KIKVLGSGAFGTVYKGLWIPEGEKIPVAIKELREAT-SPKA NKEILDEAYVMASVDNPHVCRLLGICLT-STVQLIMQLMPFGCGLDYVREHKDNIGSQYL LNWCVQIAKGMNYLEDRRLVHRD-LAARNVLVKTPQHVKITDFGRAKLLGAEEKEYHA EGGKVPIKWMALE-SILHRIYTHQSDVWSYGVTVWELMTFGSKPYDGIPA-SEISSILEKGE RLPQPPICTIDVYMIMVKCWMI-DADSRPKFRELIIEFSKMARDPQRYLVIQGDERMHLPS PTDSNFYRALMDEEDMDDVVDADEYLIPQQG. In one embodiment, SEQ. ID. NO.: 62 has a Leucine at position 163. In one embodiment, SEQ. ID. NO.: 62 has a Threonine at position 95. In one embodiment, SEQ. ID NO.: 62 has a Leucine at position 163 and a Threonine at position 95.

In one embodiment, the dTAG has an amino acid sequence derived from epidermal growth factor receptor (BCR-ABL, or a variant thereof. In one embodiment, the dTAG is derived from, includes, or is the amino acid sequence: (SEQ. ID. NO.: 63): (T315I) SPNYDKWEMERTDITMKHKLGGGQY-GEVYEGVWKKY SLTVAVKTLKEDTMEVEEFL KEAAVMKEIKEIPNLVQLLGVCTREPPFYIIIEFMTYG-NLLDYLRECNRQEVNAVVLLYM ATQISSAMEY-LEKKNFIHRDLAARNCLVGENHLVK-VADFGLSRLMTGDTYTAHAGAKF PIKWTAPESLAYNKFSIKSDVWAFGVLLWEI-ATYGMSPYPGIDLSQVYELLEKDYRMER PEGC-PEKVYELMRACWQWNPSDRPS-FAEIHQAFETMFQES. In one embodiment, SEQ. ID. NO.: 63 has a Threonine at position 87.

In one embodiment, the dTAG has an amino acid sequence derived from BCR-ABL (BCR-ABL) or a variant thereof. In one embodiment, the dTAG is derived from, includes, or is the amino acid sequence:

(SEQ. ID. NO.: 64):
SPNYDKWEMERTDITMKHKLGGGQYGEVYEGVWKKYSLTVAVKTLKEDTM

EVEEFLKEAAVMKEIKHPNLVQLLGVCTREPPFYIITEFMTYGNLLDYLR

ECNRQEVNAVVLLYMATQISSAMEYLEKKNFIHRDLAARNCLVGENHLVK

VADFGLSRLMTGDTYTAHAGAKFPIKWTAPESLAYNKFSIKSDVWAFGVL

LWEIATYGMSPYPGIDLSQVYELLEKDYRMERPEGCPEKVYELMRACWQW

NPSDRPSFAEIHQAFETMFQES.

In one embodiment, the dTAG has an amino acid sequence derived from ALK (ALK, UniProtKB Q9UM73 (ALK_HUMAN) incorporated herein by reference, or a variant thereof. In one embodiment, the dTAG is derived from, includes, or is the amino acid sequence: (SEQ. ID. NO.: 65) (L1196M):
ELQSPEYKLSKLRTSTIMTDYNPNYCFAGKTSSIS-DLKEVPRKNITLIRGLGHGAFGEVYE GQVSGMPND-PSPLQVAVKTLPEVCSEQDELDFLMEALI-ISKFNHQNIVRCIGVSLQSLPRF IMLELMAGGDLKSFLRETRPRPSQPSSLAMLDLLH-VARDIACGCQYLEENHFIHRDIAAR NCLLTCPGPGR-VAKIGDFGMARDIYRAGYYRKGGCAMLPVKWMP-PEAFMEGIFTSKTD TWSFGVLLWEIFSLGYMPYPSKSNQEVLEFVTSG-GRMDPPKNCPGPVYRIIVITQCWQHQ PEDRPN-FAIILERIEYCTQDPDVINTALPIEYGPLVEEEEK. In one embodiment, SEQ. ID. NO.: 65 has a Leucine at position 136.

In one embodiment, the dTAG has an amino acid sequence derived from JAK2 (JAK2, UniProtKB O60674 (JAK2_HUMAN) incorporated herein by reference, or a variant thereof. In one embodiment, the dTAG is derived from, includes, or is the amino acid sequence: (SEQ. ID. NO.: 66) (V617F):
VFHKIRNEDLIFNESLGQGTFTKIFKGVR-REVGDYGQLHETEVLLKVLDKAHRNYSESFF EAASMMSKLSHKHLVLNYGVCFCGDENIL-VQEFVKFGSLDTYLKKNKNCINILWKLEV AKQLAW-AMHFLEENTLIHGNVCAKNILLI-REEDRKTGNPPFIKLSDPGISITVLPKDILQE RIPWVPPECIENPKNLNLATDKWSFGTTLWE-ICSGGDKPLSALDSQRKLQFYEDRHQLP APKAAEL-ANLINNCMDYEPDHRPSFRAIIRDLNSLFTPD. In one embodiment, SEQ. ID. NO.: 66 has a valine at position 82.

In one embodiment, the dTAG has an amino acid sequence derived from BRAF (BRAF, UniProtKB P15056 (BRAF_HUMAN) incorporated herein by reference, or a variant thereof. In one embodiment, the dTAG is derived from, includes, or is the amino acid sequence: (SEQ. ID. NO.: 67) (V600E):
DWEIPDGQITVGQRIGSGSFGTVYKGKWHGDVA-VKMLNVTAPTPQQLQAFKNEVGVL RKTRHVNILL-FMGYSTAPQLAIVTQWCEGSSLYHHLHA-SETKFEMKKLIDIARQTARGM DYLHAKSIIHRDLKSNNIFL-HEDNTVKIGDFGLATEKSRWSGSHQFEQLSGSILW-MAPEV IRMQDSNPYSFQSDVYAFGIVLY-ELMTGQLPYSNINNRDQIIEMVGRGSLSPDLSKVRSN CPKRMKRLMAECLKKKRDERPSFPRILAEIEELARE.

In one embodiment, SEQ. ID. NO.: 67 has a Valine at position 152. In one embodiment, SEQ. ID. NO. 67 has a Tyrosine at position 153. In one embodiment, SEQ. ID. NO.: 67 has a Valine at position 152. In one embodiment, SEQ. ID. NO. 67 has a Lysine at position 153. In one embodiment, SEQ. ID. NO.: 67 has a Valine at position 152 and a Lysine at position 153.

In one embodiment, the dTAG has an amino acid sequence derived from a LRRK2 protein (UniProtKB—Q5S007 (LRRK2_HUMAN) incorporated herein by reference), or variant thereof. In one embodiment, the dTAG is derived from LRRK2 amino acid 1328 to 1511. In one embodiment, the dTAG is derived from LRRK2 amino acid 1328 to 1511, wherein amino acid 1441 is Cysteine In one embodiment, the dTAG has an amino acid sequence derived from a PDGFRα protein (UniProtKB—P09619 (PDGFR_HUMAN) incorporated herein by reference), or variant thereof. In one embodiment, the dTAG is derived from amino acid 600 to 692 of P09619. In one embodiment, the dTAG is derived from amino acid 600 to 692 of P09619, wherein amino acid 674 is Isoleucine.

In one embodiment, the dTAG has an amino acid sequence derived from a RET protein (UniProtKB—P07949 (RET_HUMAN) incorporated herein by reference), or variant thereof. In one embodiment, the dTAG is derived from amino acid 724 to 1016 of P07949. In one embodiment, the dTAG is derived from amino acid 724 to 1016 of P07949, wherein amino acid 691 is Serine. In one embodiment, the dTAG is derived from amino acid 724 to 1016 of P07949, wherein amino acid 749 is Threonine. In one embodiment, the dTAG is derived from amino acid 724 to 1016 of P07949, wherein amino acid 762 is Glutamine. In one embodiment, the dTAG is derived from amino acid 724 to 1016 of P07949, wherein amino acid 791 is Phenylalanine. In one embodiment, the dTAG is derived from amino acid 724 to 1016 of P07949, wherein amino acid 804 is Methionine. In one embodiment, the dTAG is derived from amino acid 724 to 1016 of P07949, wherein amino acid 918 is Threonine.

In one embodiment, the dTAG has an amino acid sequence derived from a JAK3 protein (UniProtKB—P52333 (JAK3_HUMAN) incorporated herein by reference), or variant thereof.

In one embodiment, the dTAG has an amino acid sequence derived from a ABL protein (UniProtKB—P00519 (ABL_HUMAN) incorporated herein by reference), or variant thereof.

In one embodiment, the dTAG has an amino acid sequence derived from a MEK1 protein (UniProtKB—Q02750 (MP2K1_HUMAN) incorporated herein by reference), or variant thereof.

In one embodiment, the dTAG has an amino acid sequence derived from a KIT protein (UniProtKB—P10721 (KIT_HUMAN) incorporated herein by reference), or variant thereof.

In one embodiment, the dTAG has an amino acid sequence derived from a KIT protein (UniProtKB—P10721 (KIT_HUMAN) incorporated herein by reference), or variant thereof.

In one embodiment, the dTAG has an amino acid sequence derived from a HIV reverse transcriptase protein (UniProtKB—P04585 (POL_HV1H2) incorporated herein by reference), or variant thereof.

In one embodiment, the dTAG has an amino acid sequence derived from a HIV integrase protein (UniProtKB—Q76353 (Q76353_9HIV1)) incorporated herein by reference), or variant thereof.

Heterobifunctional compounds capable of binding to the amino acid sequences, or a fragment thereof, described above can be generated using the dTAG Targeting Ligand described in Table T. In one embodiment, the CAR contains a dTAG derived from an amino acid sequence described above, or a fragment thereof, and is degraded by administering to the subject a heterobifunctional compound comprising a dTAG Targeting Ligand described in Table T. In one embodiment, the CAR contains a dTAG derived from an amino acid sequence described above, or a fragment thereof, and is degraded by administering to the subject its corresponding heterobifunctional compound, which is capable of binding to the to the dTAG described in the CAR, for example a heterobifunctional compound described in FIG. 50, FIG. 51, FIG. 52, FIG. 53, or FIG. 54, or any other heterobifunctional compound described herein.

Nucleic Acid Encoding CAR

The present invention provides a nucleic acid encoding a CAR or a costimulatory polypeptide including a dTAG as described herein. The nucleic acid encoding the CAR or costimulatory polypeptide can be easily prepared from an amino acid sequence of the specified CAR by a conventional method. A base sequence encoding an amino acid sequence can be readily obtained from, for example, the aforementioned amino acid sequences or publicly available references sequences, for example, NCBI RefSeq IDs or accession numbers of GenBank, for an amino acid sequence of each domain, and the nucleic acid of the present invention can be prepared using a standard molecular biological and/or chemical procedure. RefSeq IDs for commonly used CAR domains are known in the art, for example, U.S. Pat. No. 9,175,308 (which are incorporated herein by reference) discloses a number of specific amino acid sequences particularly used as CAR transmembrane and intracellular signaling domains. As one example, based on the base sequence, a nucleic acid can be synthesized, and the nucleic acid of the present invention can be prepared by combining DNA fragments which are obtained from a cDNA library using a polymerase chain reaction (PCR).

The nucleic acids of the present invention can be linked to another nucleic acid so as to be expressed under control of a suitable promoter. Examples of the promoter include a promoter that constitutively promotes the expression of a gene, a promoter that induces the expression of a gene by the action of a drug or the like (e.g. tetracycline or doxorubicin). The nucleic acid of the present invention can be also linked to, in order to attain efficient transcription of the nucleic acid, other regulatory elements that cooperate with a promoter or a transcription initiation site, for example, a nucleic acid comprising an enhancer sequence or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The present invention contemplates a composition comprising the nucleic acid of the present invention as an active ingredient, together with a pharmaceutically acceptable excipient. Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. An adjuvant such as a wetting agent or an emulsifier, and a pH buffering agent can also be used. As the pharmaceutically acceptable excipients, excipients described in *Remington's Pharmaceutical Sciences* (Mack Pub. Co., N.J. (1991)) (which is incorporated herein by reference) can be appropriately used. The composition of the present invention can be formulated into a known form suitable for parenteral administration, for example, injection or infusion. Further, the composition of the present invention may comprise formulation additives such as a suspending agent, a preservative, a stabilizer and/or a dispersant, and a preservation agent for extending a validity term during storage. The composition may be in a dry form for reconstitution with an appropriate sterile liquid prior to use. For fine particle-mediated administration, a particle such as a gold particle of a microscopic size can be coated with a DNA.

When the nucleic acid of the present invention is introduced into a cell ex vivo, the nucleic acid of the present invention may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful as described later. Particularly, a composition in a form suitable for administration to a living body which contains the nucleic acid of present invention carried by a suitable vector is suitable for in vivo gene therapy.

A composition that includes the nucleic acid of the present invention as an active ingredient can be administered for treatment of, for example, a cancer [blood cancer (leukemia), solid tumor etc.], an inflammatory disease/autoimmune disease (asthma, eczema), hepatitis, or an infectious disease the cause of which is a virus such as influenza and HIV, a bacterium, or a fungus, for example, a disease such as tuberculosis, MRSA, VRE, or deep mycosis, depending on an antigen to which a CAR encoded by the nucleic acid binds. A composition comprising the nucleic acid of the present invention as an active ingredient can be administered, by any desired route, including but not limited to, intradermally, intramuscularly, subcutaneously, intraperitoneally, intranasally, intraarterially, intravenously, intratumorally, or into an afferent lymph vessel, by parenteral administration, for example, by injection or infusion, although the administration route is not particularly limited.

Immune Effector Cells Expressing CARs

Immune effector cells expressing the CAR or costimulatory polypeptide of the present invention can be engineered by introducing the nucleic acid encoding a CAR or costimulatory polypeptide described above into a cell. In one embodiment, the step is carried out ex vivo. For example, a cell can be transformed ex vivo with a virus vector or a non-virus vector carrying the nucleic acid of the present invention to produce a cell expressing the CAR or costimulatory polypeptide of the present invention.

The nucleic acid encoding the CAR or costimulatory polypeptide of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. Preferably, a virus vector lacking the replicating ability so as not to self-replicate in an infected cell is preferably used.

In addition, a non-virus vector can also be used in the present invention in combination with a liposome and a condensing agent such as a cationic lipid as described in WO 96/10038, WO 97/18185, WO 97/25329, WO 97/30170, and WO 97/31934 (which are incorporated herein by reference). The nucleic acid of the present invention can be also introduced into a cell by calcium phosphate transduction, DEAE-dextran, electroporation, or particle bombardment.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+en-vAm-12 (U.S. Pat. No. 5,278,056), and Psi-Crip (PNAS 85 (1988):6460-6464). A retrovirus particle can also be prepared using a 293 cell or a 293T-cell having high transfection efficiency. Many kinds of retrovirus vectors produced based on retroviruses and packaging cells that can be used for packaging of the retrovirus vectors are widely commercially available from many companies.

In the step of introducing a nucleic acid into a cell, a functional substance for improving the introduction efficiency can also be used (e.g. WO 95/26200 and WO 00/01836 (which are incorporated herein by reference)). Examples of the substance for improving the introduction efficiency include a substance having ability to bind to a virus vector, for example, fibronectin and a fibronectin fragment. Preferably, a fibronectin fragment having a heparin binding site, for example, a fragment commercially available as RetroNetcin (registered trademark, CH-296, manufactured by TAKARA BIC INC.) can be used. Also, polybrene which is a synthetic polycation having an effect of improving the efficiency of infection of a retrovirus into a cell, a fibroblast growth factor, V type collagen, polylysine or DEAE-dextran can be used.

In one aspect of the present invention, the functional substance can be used in a state of being immobilized on a suitable solid phase, for example, a container used for cell culture (plate, petri dish, flask or bag) or a carrier (microbeads etc.).

In order to assess the expression of a CAR polypeptide or portion thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the hosT-cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

The cell expressing the CAR of the present invention is a cell in which the nucleic acid encoding a CAR described above is introduced and expressed by the cell. The cell of the present invention binds to a specific antigen via the CAR, and then a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage. In order to confirm the presence of the recombinant DNA sequence in the cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

An immune effector cell such as lymphocytes including but not limited to cytotoxic lymphocytes, T-cells, cytotoxic T-cells, T helper cells, Th17 T-cells, natural killer (NK) cells, natural killer T (NKT) cells, mast cells, dendritic cells, killer dendritic cells, or B cells derived from a mammal, for example, a human cell, or a cell derived from a non-human mammal such as a monkey, a mouse, a rat, a pig, a horse, or a dog can be used. For example, a cell collected, isolated, purified or induced from a body fluid, a tissue or an organ such as blood (peripheral blood, umbilical cord blood etc.) or bone marrow can be used. A peripheral blood mononuclear cell (PBMC), an immune cell (a dendritic cell, a B cell, a hematopoietic stem cell, a macrophage, a monocyte, a NK cell or a hematopoietic cell (a neutrophil, a basophil)), an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. In the present invention, particularly, use of a T-cell, a precursor cell of a T-cell (a hematopoietic stem cell, a lymphocyte precursor cell etc.) or a cell population containing them is preferable. Examples of the T-cell include a CD8-positive T-cell, a CD4-positive T-cell, a regulatory T-cell, a cytotoxic T-cell, and a tumor infiltrating lymphocyte. The cell population containing a T-cell and a precursor cell of a T-cell includes a PBMC. The aforementioned cells may be collected from a living body, obtained by expansion culture of a cell collected from a living body, or established as a cell strain. When transplantation of the produced CAR-expressing cell or a cell differentiated from the produced CAR-expressing cell into a living body is desired, it is preferable to introduce the nucleic acid into a cell collected from the living body itself or a conspecific living body thereof.

In one embodiment, the CAR expressing cell is a T-cell isolated from a subject for autologous therapy. Typically, prior to expansion and genetic modification of the T-cells of the invention, a source of T-cells is obtained from a subject. T-cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T-cell lines available in the art, may be used. In certain embodiments of the present invention, T-cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T-cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium may lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In another embodiment, T-cells are isolated from peripheral blood lymphocytes by lysing the red blood cells and depleting the monocytes, for example, by centrifugation through a PERCOLL™ gradient or by counterflow centrifugal elutriation. A specific subpopulation of T-cells, such as CD3+, CD28+, CD4+, CD8+, CD45RA+, and CD45RO+ T-cells, can be further isolated by positive or negative selection techniques. For example, in one embodiment, T-cells are isolated by incubation with anti-CD3/anti-CD28 (i.e., 3×28)-conjugated beads, such as DYNABEADS® M-450 CD3/CD28 T, for a time period sufficient for positive selection of the desired T-cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T-cells from patients with leukemia, use of longer incubation times, such as 24 hours, can increase cell yield. Longer incubation times may be used to isolate T-cells in any situation where there are few T-cells as compared to other cell types, such in isolating tumor infiltrating lymphocytes (TIL) from tumor tissue or from immune-compromised individuals. Further, use of longer incubation times can increase the efficiency of capture of CD8+ T-cells. Thus, by simply shortening or lengthening the time T-cells are allowed to bind to the CD3/CD28 beads and/or by increasing or decreasing the ratio of beads to T-cells (as described further herein), subpopulations of T-cells can be preferentially selected for or against at culture initiation or at other time points during the process. Additionally, by increasing or decreasing the ratio of anti-CD3 and/or anti-CD28 antibodies on the beads or other surface, subpopulations of T-cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T-cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T-cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T-cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T-cells that normally have weaker CD28 expression.

In a related embodiment, it may be desirable to use lower concentrations of cells. By significantly diluting the mixture of T-cells and surface (e.g., particles such as beads), interactions between the particles and cells is minimized. This selects for cells that express high amounts of desired antigens to be bound to the particles. For example, CD4+ T-cells express higher levels of CD28 and are more efficiently captured than CD8+ T-cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T-cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also, contemplated in the context of the invention is the collection of blood samples or apheresis product from a subject at a time period prior to when the expanded cells as described herein might be needed. As such, the source of the cells to be expanded can be collected at any time point necessary, and desired cells, such as T-cells, isolated and frozen for later use in T-cell therapy for any number of diseases or conditions that would benefit from T-cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T-cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66 (1991):807-815; Henderson et al., *Immun* 73 (1991):316-321; Bierer et al., *Curr. Opin. Immun* 5 (1993):763-773). In a further embodiment, the cells are isolated for a patient and frozen for later use in conjunction with (e.g., before, simultaneously or following) bone marrow or stem cell transplantation, T-cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T-cells are obtained from a patient directly following treatment. In this regard, it has been observed that following certain cancer treatments, in particular treatments with drugs that damage the immune system, shortly after treatment during the period when patients would normally be recovering from the treatment, the quality of T-cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T-cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T-cells, B cells, dendritic cells, and other cells of the immune system.

Whether prior to or after genetic modification of the T-cells to express a desirable CAR, the T-cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T-cells of the invention are expanded by contact with a surface having attached thereto an agent that stimulates a CD3/TCR complex associated signal and a ligand that stimulates a co-stimulatory molecule on the surface of the T-cells. In particular, T-cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berge et al., *Transplant Proc.* 30(8) (1998):3975-3977; Haanen et al., *J. Exp. Med.* 190(9) (1999):1319-1328, 1999; and Garland et al., *J. Immunol Meth.* 227(1-2) (1999):53-63).

In certain embodiments, the primary stimulatory signal and the co-stimulatory signal for the T-cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T-cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T-cell expansion and T-cell growth is used. In certain aspects of the present invention, a ratio of anti CD3:CD28 antibodies bound to the beads is used such that an increase in T-cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T-cells or other target cells. As those of ordinary skill in the art can readily appreciate, the ratio of particles to cells may depend on particle size relative to the target cell. For example, small sized beads could only bind a few cells, while larger beads could bind many. In certain embodiments, the ratio of cells to particles ranges from 1:100 to 100:1 and any integer values in-between and in further embodiments the ratio comprises 1:9 to 9:1 and any integer values in between, can also be used to stimulate T-cells. The ratio of anti-CD3- and anti-CD28-coupled particles to T-cells that result in T-cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T-cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T-cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T-cells. In one embodiment, the cells (for example, 104 to 109 T-cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T-cells. Such populations of cells may have therapeutic value and would be desirable to obtain in certain embodiments. For example, using high concentration of cells allows more efficient selection of CD8+ T-cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T-cells are cultured together for about eight days. In another embodiment, the beads and T-cells are cultured together for 2-3 days. Several cycles of stimulation may also be desired such that culture time of T-cells can be 60 days or more. Conditions appropriate for T-cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T-cells. Antibiotics, e.g., penicillin and streptomycin, are included only in experimental cultures, not in cultures of cells that are to be infused into a subject. The T-cells are maintained under conditions necessary to support growth, for example, an appropriate temperature (e.g., 37° C.) and atmosphere (e.g., air plus 5% CO2).

T-cells that have been exposed to varied stimulation times may exhibit different characteristics. For example, typical blood or apheresed peripheral blood mononuclear cell products have a helper T-cell population (TH, CD4+) that is greater than the cytotoxic or suppressor T-cell population (TC, CD8+). Ex vivo expansion of T-cells by stimulating CD3 and CD28 receptors produces a population of T-cells that prior to about days 8-9 consists predominately of TH cells, while after about days 8-9, the population of T-cells comprises an increasingly greater population of TC cells. Depending on the purpose of treatment, infusing a subject with a T-cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T-cell product for specific purposes.

Use of CAR Expressing Cells for Treatment of Disease

The cell expressing the CAR, and in certain embodiments a costimulatory polypeptide, can be used as a therapeutic agent for a disease. The therapeutic agent can be the cell expressing the CAR as an active ingredient, and may further include a suitable excipient. Examples of the excipient include the aforementioned pharmaceutically acceptable excipients for the composition includes the nucleic acid of the present invention as an active ingredient, various cell culture media, and isotonic sodium chloride. The disease against which the cell expressing the CAR is administered is not limited as long as the disease shows sensitivity to the cell. Examples of the disease include a cancer (blood cancer (leukemia), solid tumor etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis. The cell expressing the CAR of the present invention that binds to an antigen possessed by a cell that is desired to be decreased or eliminated for treatment of the aforementioned diseases, that is, a tumor antigen, a viral antigen, a bacterial antigen or the like is administered for treatment of these diseases. The cell of the present invention can also be utilized for prevention of an infectious disease after bone marrow transplantation or exposure to radiation, donor lymphocyte transfusion for the purpose of remission of recurrent leukemia, and the like. The therapeutic agent comprising the cell expressing the CAR as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

In a particular embodiment, the CAR expressing cell is an autologous T-cell from a subject with cancer. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Other hematological cancers include T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, the CAR expressing cells can be used in an effective amount to treat a host, for example a human, with a lymphoma or lymphocytic or myelocytic proliferation disorder or abnormality. For example, the CAR expressing cells as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, a CAR expressing cells disclosed herein can be used in an effective amount to treat a host, for example a human, with a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

Alternatively, a CAR expressing cells disclosed herein can be used in an effective amount to treat a host, for example a human with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T-cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In one embodiment, CAR expressing cells disclosed herein can be used in an effective amount to treat a host, for example a human with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CIVIL); juvenile myelomonocytic leukemia (JMML); hairy cell leukemia (HCL); acute promyelocytic leukemia (a subtype of AML); large granular lymphocytic leukemia; or Adult T-cell chronic leukemia. In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In one embodiment, a CAR expressing cell disclosed herein can be used in an effective amount to treat a host, for example a human with a solid tumor. Examples include, but are not limited to, but are not limited to: estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, adenocarcinoma of the colon, adenocarcinoma of the rectum, central nervous system germ cell tumors, teratomas, estrogen receptor-negative breast cancer, estrogen receptor-positive breast cancer, familial testicular germ cell tumors, HER2-negative breast cancer, HER2-positive breast cancer, male breast cancer, ovarian immature teratomas, ovarian mature teratoma, ovarian monodermal and highly specialized teratomas, progesterone receptor-negative breast cancer, progesterone receptor-positive breast cancer, recurrent breast cancer, recurrent colon cancer, recurrent extragonadal germ cell tumors, recurrent extragonadal non-seminomatous germ cell tumor, recurrent extragonadal seminomas, recurrent malignant testicular germ cell tumors, recurrent melanomas, recurrent ovarian germ cell tumors, recurrent rectal cancer, stage III extragonadal non-seminomatous germ cell tumors, stage III extragonadal seminomas, stage III malignant testicular germ cell tumors, stage III ovarian germ cell tumors, stage IV breast cancers, stage IV colon cancers, stage IV extragonadal non-seminomatous germ cell tumors, stage IV extragonadal seminoma, stage IV melanomas, stage IV ovarian germ cell tumors, stage IV rectal cancers, testicular immature teratomas, testicular mature teratomas, estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, metastatic colorectal cancer, metastatic melanoma, or cisplatin-refractory, unresectable germ cell tumors, carcinoma, sarcoma, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, fibrosarcoma, myxosarcoma, chondrosarcoma, osteosarcoma, chordoma, malignant fibrous histiocytoma, hemangiosarcoma, angiosarcoma, lymphangiosarcoma. Mesothelioma, leiomyosarcoma, rhabdomyosarcoma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, IsleT-cell carcinoma, malignant carcinoid, malignant paraganglioma, melanoma, Merkel cell neoplasm, cystosarcoma phylloide, salivary cancers, thymic carcinomas, bladder cancer, and Wilms tumor, a blood disorder or a hematologic malignancy, including, but not limited to, myeloid disorder, lymphoid disorder, leukemia, lymphoma, myelodysplastic syndrome (MDS), myeloproliferative disease (MPD), masT-cell disorder, and myeloma (e.g., multiple myeloma).

In another embodiment, a CAR expressing cell disclosed herein can be used in an effective amount to treat a host, for example a human with an autoimmune disorder. Examples include, but are not limited to: Acute disseminated encephalomyelitis (ADEM); Addison's disease; Agammaglobulinemia; Alopecia areata; Amyotrophic lateral sclerosis (Also Lou Gehrig's disease; Motor Neuron Disease); Ankylosing Spondylitis; Antiphospholipid syndrome; Antisynthetase syndrome; Atopic allergy; Atopic dermatitis; Autoimmune aplastic anemia; Autoimmune arthritis; Autoimmune cardiomyopathy; Autoimmune enteropathy; Autoimmune granulocytopenia; Autoimmune hemolytic anemia; Autoimmune hepatitis; Autoimmune hypoparathyroidism; Autoimmune inner ear disease; Autoimmune lymphoproliferative syndrome; Autoimmune myocarditis; Autoimmune pancreatitis; Autoimmune peripheral neuropathy; Autoimmune ovarian failure; Autoimmune polyendocrine syndrome; Autoimmune progesterone dermatitis; Autoimmune thrombocytopenic purpura; Autoimmune thyroid disorders; Autoimmune urticarial; Autoimmune uveitis; Autoimmune vasculitis; Balo disease/Balo concentric sclerosis; Behcet's disease; Berger's disease; Bickerstaff's encephalitis; Blau syndrome; Bullous pemphigoid; Cancer; Castleman's disease; Celiac disease; Chagas disease; Chronic inflammatory demyelinating polyneuropathy; Chronic inflammatory demyelinating polyneuropathy; Chronic obstructive pulmonary disease; Chronic recurrent multifocal osteomyelitis; Churg-Strauss syndrome; Cicatricial pemphigoid; Cogan syndrome; Cold agglutinin disease; Complement component 2 deficiency; Contact dermatitis; Cranial arteritis; CREST syndrome; Crohn's disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Discoid lupus erythematosus; Dressler's syndrome; Drug-induced lupus; Eczema; Endometriosis; Enthesitis-related arthritis; Eosinophilic fasciitis; Eosinophilic gastroenteritis; Eosinophilic pneumonia; Epidermolysis bullosa acquisita; Erythema nodosum; Erythroblastosis fetalis; Essential mixed cryoglobulinemia; Evan's syndrome; Extrinsic and intrinsic reactive airways disease (asthma); Fibrodysplasia ossificans progressive; Fibrosing alveolitis (or Idiopathic pulmonary fibrosis); Gastritis; Gastrointestinal pemphigoid; Glomerulonephritis; Goodpasture's syndrome; Graves' disease; Guillain-Barre syndrome (GBS); Hashimoto's encephalopathy; Hashimoto's thyroiditis; Hemolytic anemia; Henoch-Schonlein purpura; Herpes gestationis (Gestational Pemphigoid); Hidradenitis suppurativa; Hughes-Stovin syndrome; Hypogammaglobulinemia; Idiopathic inflammatory demyelinating diseases; Idiopathic pulmonary fibrosis; Idiopathic thrombocytopenic purpura; IgA nephropathy; Immune glomerulonephritis; Immune nephritis; Immune pneumonitis; Inclusion body myositis; inflammatory bowel disease; Interstitial cystitis; Juvenile idiopathic arthritis aka Juvenile rheumatoid arthritis; Kawasaki's disease; Lambert-Eaton myasthenic syndrome; Leukocytoclastic vasculitis; Lichen planus; Lichen sclerosus; Linear IgA disease (LAD); Lupoid hepatitis aka Autoimmune hepatitis; Lupus erythematosus; Majeed syndrome; microscopic polyangiitis; Miller-Fisher syndrome; mixed connective tissue disease; Morphea; Mucha-Habermann disease aka Pityriasis lichenoides et varioliformis acuta; Multiple sclerosis; Myasthenia gravis; Myositis; Meniere's disease; Narcolepsy; Neuromyelitis optica (also Devic's disease); Neuromyotonia; Occular cicatricial pemphigoid; Opsoclonus myoclonus syndrome; Ord's thyroiditis; Palindromic rheumatism; PANDAS (pediatric autoimmune neuropsychiatric disorders associated with *streptococcus*); Paraneoplastic cerebellar degeneration; Paroxysmal nocturnal hemoglobinuria (PNH); Parry Romberg syndrome; Pars planitis; Parsonage-Turner syndrome; Pemphigus vulgaris; Perivenous encephalomyelitis; Pernicious anaemia; POEMS syndrome; Polyarteritis nodosa; Polymyalgia rheumatic; Polymyositis; Primary biliary cirrhosis; Primary sclerosing cholangitis; Progressive inflammatory neuropathy; Psoriasis; Psoriatic arthritis; pure red cell aplasia; Pyoderma gangrenosum; Rasmussen's encephalitis; Raynaud phenomenon; Reiter's syndrome; relapsing polychondritis; restless leg syndrome; retroperitoneal fibrosis; rheumatic fever; rheumatoid arthritis; Sarcoidosis; Schizophrenia; Schmidt syndrome; Schnitzler syndrome; Scleritis; Scleroderma; Sclerosing cholangitis; serum sickness; Sjögren's syndrome; Spondyloarthropathy; Stiff person syndrome; Still's disease; Subacute bacterial endocarditis (SBE); Susac's syndrome; Sweet's syndrome; Sydenham chorea; sympathetic ophthalmia; systemic lupus erythematosus; Takayasu's arteritis; temporal arteritis (also known as "gianT-cell arteritis"); thrombocytopenia; Tolosa-Hunt syndrome; transverse myelitis; ulcerative colitis; undifferentiated connective tissue disease; undifferentiated spondyloarthropathy; urticarial vasculitis; vasculitis; vitiligo; viral diseases such as Epstein Barr Virus (EBV), Hepatitis B, Hepatitis C, HIV, HTLV 1, Varicella-Zoster Virus (VZV) and Human Papilloma Virus (HPV); or Wegener's granulomatosis. In some embodiments, the autoimmune disease is an allergic condition, including those from asthma, food allergies, atopic dermatitis, and rhinitis.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen binding moiety portion of the CAR of the invention is designed to treat a particular cancer. For example, a CAR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In another embodiment, the CAR can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, the CAR can be designed to target mesothelin to treat mesothelioma, pancreatic cancer, ovarian cancer, and the like.

In one embodiment, the CAR can be designed to target CD33/IL3Ra to treat acute myelogenous leukemia and the like.

In one embodiment, the CAR can be designed to target CD30 to treat lymphoma, for example Hodgkin lymphoma, and the like.

In one embodiment, the CAR can be designed to target c-Met to treat triple negative breast cancer, non-small cell lung cancer, and the like.

In one embodiment, the CAR can be designed to target PSMA to treat prostate cancer and the like.

In one embodiment, the CAR can be designed to target Glycolipid F77 to treat prostate cancer and the like.

In one embodiment, the CAR can be designed to target EGFRvIII to treat gliobastoma and the like.

In one embodiment, the CAR can be designed to target GD-2 to treat neuroblastoma, melanoma, and the like.

In one embodiment, the CAR can be designed to target NY-ESO-1 TCR to treat myeloma, sarcoma, melanoma, and the like.

In one embodiment, the CAR can be designed to target MAGE A3 TCR to treat myeloma, sarcoma, melanoma, and the like.

In one embodiment, the CAR can be designed to target CEA to treatcolorectal cancer and the like.

In one embodiment, the CAR can be designed to target erb-B2, erb-B3, and/or erb-B4 to treat breast cancer, and the like.

In one embodiment, the CAR can be designed to target IL-13R-a2 to treat glioma, glioblastoma, or medulloblastoma, and the like.

In one embodiment, the CAR can be designed to target BMCA to treat multiple myeloma.

In one embodiment, the CAR can be designed to target MTH1 to treat multiple myeloma.

However, the invention should not be construed to be limited to solely to the antigen targets and diseases disclosed herein. Rather, the invention should be construed to include any antigenic or ligand target that is associated with a disease where a CAR having a dTAG can be used to treat the disease.

The CAR-expressing cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

The CAR-expressing cells of the present invention can be administered either alone, or as a pharmaceutical composition in combination with diluents and/or with other components such as IL-2 or other cytokines or cell populations. Briefly, pharmaceutical compositions of the present invention may comprise a target T-cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of CAR expressing cells of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T-cells described herein may be administered at a dosage of $10^4$ to $10^9$ cells/kg body weight, preferably $10^5$ to $10^6$ cells/kg body weight, including all integer values within those ranges. T-cell compositions may also be administered multiple times at these dosages. The cells can be administered by using infusion techniques that are commonly known in immunotherapy (see, e.g., Rosenberg et al., *New Eng. J. of Med.* 319 (1988):1676). The optimal dosage and treatment regime for a particular patient can readily be determined by one skilled in the art of medicine by monitoring the patient for signs of disease and adjusting the treatment accordingly.

The administration of the CAR expressing cells may be carried out in any convenient manner, including by aerosol inhalation, injection, ingestion, transfusion, implantation or transplantation. The CAR expressing cells described herein may be administered to a patient subcutaneously, intradermally, intratumorally, intranodally, intramedullary, intramuscularly, by intravenous (i.v.) injection, or intraperitoneally. In one embodiment, the CAR expressing cells of the present invention are administered to a patient by intradermal or subcutaneous injection. In another embodiment, the CAR expressing cells of the present invention are preferably administered by i.v. injection. The CAR expressing cells may be injected directly into a tumor, lymph node, or site of infection.

The dosage of the above treatments to be administered to a patient will vary with the precise nature of the condition being treated and the recipient of the treatment. The scaling of dosages for human administration can be performed according to art-accepted practices.

Heterobifunctional Compounds

As described above, the CARs of the present invention include an intracellular heterobifunctional compound binding moiety or domain that provides a ligand for a targeting heterobifunctional compound. By including a dTAG in the CAR construct, the CAR as expressed by the CAR expressing cells can be readily and rapidly degraded upon exposure to a heterobifunctional compound, which utilizes the ubiquitin proteasomal pathway to degrade the CAR. In this way, administering a heterobifunctional compound targeting a specific dTAG within a CAR allows for the modulation of the activation of the CAR expressing cell, as degradation of the CAR or a portion thereof within the CAR expressing cell prohibits activation signaling from occurring. This strategy can be utilized to modulate the activation of the CAR expressing cell, for example, to lessen the activation of the CAR expressing cell in order to reduce adverse inflammatory responses. Furthermore, by utilizing a heterobifunctional compound strategy, the CAR expressing cell is spared.

Strategies harnessing the ubiquitin proteasome pathway (UPP) to selectively target and degrade proteins have been employed for post-translational control of protein function. Heterobifunctional compounds, are composed of a target protein-binding ligand and an E3 ubiquitin ligase ligand. Heterobifunctional compounds, are capable of induced proteasome-mediated degradation of selected proteins via their recruitment to E3 ubiquitin ligase and subsequent ubiquitination. These drug-like molecules offer the possibility of reversible, dose-responsive, tunable, temporal control over protein levels. An early description of such compounds was provided in U.S. Pat. No. 7,041,298, titled "Proteolysis Targeting Chimeric Pharmaceutical," filed in September 2000 by Deshales et al. and granted in May 2006. The publication by Sakamoto et al. (PNAS 98(15) (2001): 8554-8559), titled "PROTACS: Chimeric Molecules that Target Proteins to the Skp 1-Cullin F Box Complex for Ubiquitination and Degradation," describes a heterobifunctional compound consisting of a small molecule binder of MAP-AP-2 linked to a peptide capable of binding the F-box protein β-TRCP, the disclosure of which is also provided in U.S. Pat. No. 7,041,298. The publication by Sakamoto et al. (*Molecular and Cellular Proteomics* 2 (2003):1350-1358), titled "Development of PROTACS to Target Cancer-promoting Proteins for Ubiquitination and Degradation," describes an analogous heterobifunctional compound (PROTAC2) that instead of degrading MAP-AP-2 degrades estrogen and androgen receptors. The publication by Schneekloth et al. (*JACS* 126 (2004):3748-3754), titled "Chemical Genetic Control of Protein Levels: Selective in vivo Targeted Degradation," describes an analogous heterobifunctional compound (PROTAC3) that targets the FK506 binding protein (FKBP12) and shows both PROTAC2 and PROTAC3 hit their respective targets with green fluorescent protein (GFP) imaging. The publication by Schneekloth et al. (*Chem-*

BioChem 6 (2005)40-46) titled "Chemical Approaches to Controlling Intracellular Protein Degradation" described the state of the field at the time, using the technology. The publication by Schneekloth et al. (*BMCL* 18(22) (2008): 5904-5908), titled "Targeted Intracellular Protein Degradation Induced by a Small Molecule: En Route to Chemical Proteomics," describes a heterobifunctional compound that consist of two small molecules linked by PEG that in vivo degrades the androgen receptor by concurrently binding the androgen receptor and Ubiquitin E3 ligase. WO 2013/170147 to Crews et al., titled "Compounds Useful for Promoting Protein Degradation and Methods Using Same," describes compounds comprising a protein degradation moiety covalently bound to a linker, wherein the C log P of the compound is equal to or higher than 1.5. A review of the foregoing publications by Buckley et al. (*Angew. Chem. Int. Ed.* 53 (2014):2312-2330) is titled "Small-Molecule Control of Intracellular Protein Levels through Modulation of the Ubiquitin Proteasome System." WO 2015/160845 assigned to Arvinas Inc., titled "Imide Based Modulators of Proteolysis and Associated methods of Use," describes the use of Degron technology with thalidomide to utilize cereblon as the E3 ligase protein. The following publication by J. Lu et al. (*Chemistry and Biol.* 22(6) (2015):755-763), titled "Hijacking the E3 Ubiquitin Ligase Cereblon to efficiently Target BDR4," similarly describes thalidomide based compounds useful for degrading BDR4. Additional publications describing this technology include Bondeson et al. (*Nature Chemical Biology* 11 (2015):611-617), Gustafson et al. (*Angew. Chem. Int. Ed.* 54 (2015):9659-9662), Buckley et al. (*ACS Chem. Bio.* 10 (2015):1831-1837), U.S. 2016/0058872 assigned to Arvinas Inc. titled "Imide Based Modulators of Proteolysis and Associated Methods of Use", U.S. 2016/0045607 assigned to Arvinas Inc. titled "Estrogen-related Receptor Alpha Based PROTAC Compounds and Associated Methods of Use", U.S. 2014/0356322 assigned to Yale University, GlaxoSmithKline, and Cambridge Enterprise Limited University of Cambridge titled "Compounds and Methods for the Enhanced Degradation of Targeted Proteins & Other Polypeptides by an E3 Ubiquitin Ligase", Lai et al. (*Angew. Chem. Int. Ed.* 55 (2016):807-810), Toure et al. (*Angew. Chem. Int. Ed.* 55 (2016):1966-1973), and US 2016/0176916 assigned to Dana Farber Cancer Institute titled "Methods to Induce Targeted Protein Degradation Through Bifunctional Molecules."

Other descriptions of targeted protein degradation technology include Itoh et al. (*JACS* 132(16) (2010):5820-5826), titled "Protein Knockdown Using Methyl Bestatin-Ligand Hybrid Molecules: Design and Synthesis of Inducers of Ubiquitination-Mediated Degradation of Cellular Retinoic Acid-Binding Proteins," which describes a small molecule linked to a peptide that utilizes E3 ubiquitin ligase to degraded retinoic acid-binding proteins, and Winter et al. (*Science* 348 (2015):1376-1381), titled "Phthalimide Conjugation as a Strategy for in vivo Target Protein Degradation," describes thalidomide based targeted protein degradation technology.

Heterobifunctional compounds useful to degrade the CARs or costimulatory polypeptides of the present invention may be any heterobifunctional compound capable of binding to a dTAG within the CAR or costimulatory polypeptide to induce degradation. Heterobifunctional compounds are generally known in the art, for example, see U.S. Pat. No. 7,041,298; Sakamoto et al. (PNAS, 2001, 98(15): 8554-8559); Sakamoto et al. (*Molecular and Cellular Proteomics* 2 (2003)1350-1358); Schneekloth et al. (*JACS* 126 (2004):3748-3754); Schneekloth et al. (*ChemBioChem* 6 (2005):40-46); Schneekloth et al. (*BMCL* 18(22) (2008): 5904-5908); WO 2013/170147; Buckley et al. (*Angew. Chem. Int. Ed.* 53 (2014):2312-2330); WO 2015/160845; Lu et al.(*Chemistry and Biol.* 22(6) (2015):755-763); Bondeson et al. (*Nature Chemical Biology* 11 (2015):611-617); Gustafson et al. (*Angew. Chem. Int. Ed.* 54 (2015):9659-9662); Buckley et al. (*ACS Chem. Bio.* 10 (2015):1831-1837); U.S. 2016/0058872 assigned to Arvinas Inc. titled "Imide Based Modulators of Proteolysis and Associated Methods of Use", U.S. 2016/0045607 assigned to Arvinas Inc. titled "Estrogen-related Receptor Alpha Based PROTAC Compounds and Associated Methods of Use", U.S. 2014/0356322 assigned to Yale University, GlaxoSmithKline, and Cambridge Enterprise Limited University of Cambridge titled "Compounds and Methods for the Enhanced Degradation of Targeted Proteins & Other Polypeptides by an E3 Ubiquitin Ligase", U.S. 2016/0176916 assigned to Dana-Farber Cancer Institute, Inc. titled "Methods to Induce Targeted Protein Degradation Through Bifunctional Molecules", Lai et al. (*Angew. Chem. Int. Ed.* 55 (2016):807-810); Toure et al. (*Angew. Chem. Int. Ed.* 55 (2016):1966-1973); Itoh et al. (*JACS* 132(16) (2010):5820-5826); and Winter et al. (*Science* 348 (2015):1376-1381), each of which is incorporated herein by reference.

In certain aspects of the present invention, the heterobifunctional compounds described herein can be utilized to modulate the activation of a CAR expressing cell of the present invention. In particular, heterobifunctional compounds suitable for use in the present application contain a ligand, e.g., a small molecule ligand (i.e., having a molecular weight of below 2,000, 1,000, 500, or 200 Daltons), such as a thalidomide-like ligand, which is capable of binding to a ubiquitin ligase, such as cereblon, and a moiety that is capable of binding to a target or being bound by a target that allows tagging to occur.

In general, heterobifunctional compounds suitable for use in the present application have the general structure:

Degron-Linker-dTAG Targeting Ligand wherein the Linker is covalently bound to a Degron and a dTAG Targeting Ligand, the Degron is a compound capable of binding to a ubiquitin ligase such as an E3 Ubiquitin Ligase (e.g., cereblon), and the dTAG Targeting Ligand is capable of binding to the dTAG on the CAR. In certain embodiments, the present application utilizes a compound of Formula I or Formula II:

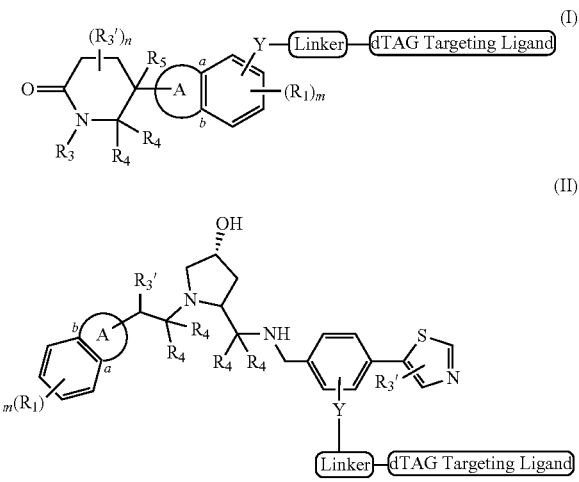

wherein:

the Linker is a group that covalently binds to the dTAG Targeting Ligand and Y; and the dTAG Targeting Ligand is capable of binding to a dTAG target or being bound by a dTAG target that allows tagging to occur.

In certain embodiments, the present application provides a compound of Formula (I), or an enantiomer, diastereomer, stereoisomer, or pharmaceutically acceptable salt thereof, wherein:

wherein:

the Linker is a group that covalently binds to the dTAG Targeting Ligand and Y; and the dTAG Targeting Ligand is capable of binding to or binds to a targeted protein;

and wherein $X_1$, $X_2$, Y, $R_1$, $R_2$, $R_2'$, $R_3$, $R_3'$, $R_4$, $R_5$, m and n are each as defined herein.

In certain embodiments, the present invention uses a compound of Formula III, Formula IV, Formula V, Formula VI, Formula VII, Formula VIII, and Formula IX:

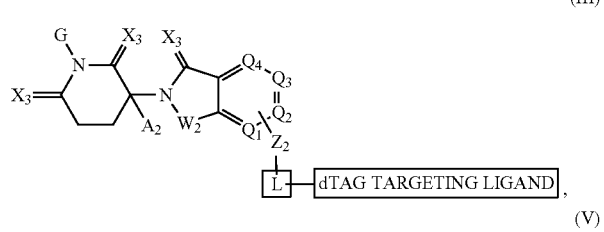

(III)

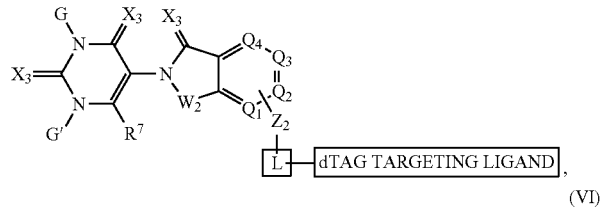

(IV)

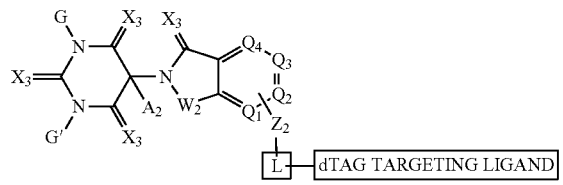

(V)

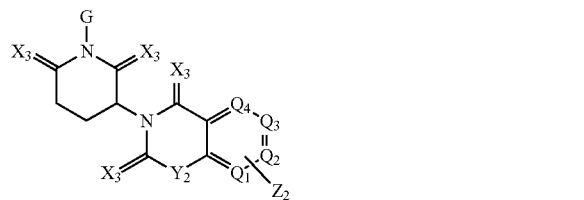

(VI)

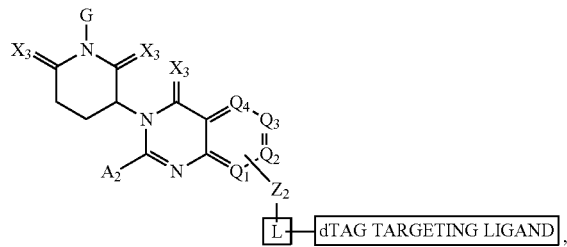

(VII)

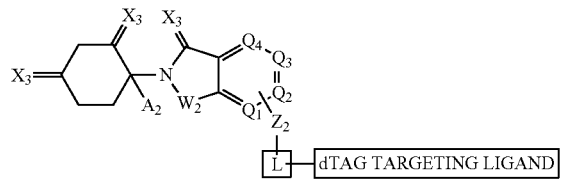

(VIII)

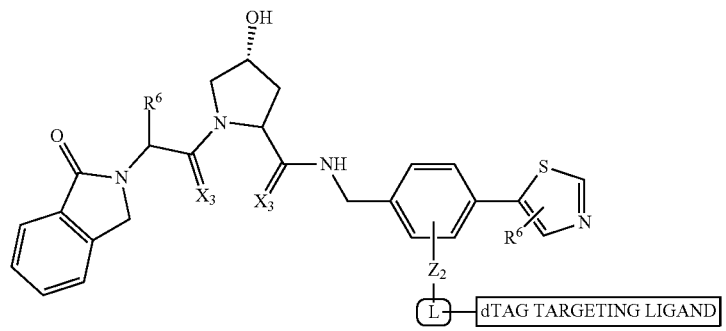

(IX)

the Linker (L) is a group that covalently binds to the dTAG Targeting Ligand and Y; and the dTAG Targeting Ligand is capable of binding to or binds to a dTAG targeted protein;

and wherein X1, X2, Y, $R_1$, $R_2$, $R_2'$, $R_3$, $R_3'$, $R_4$, $R_5$, m and n are each as defined herein.

In certain embodiments, the present application provides a compound of Formula (II), or an enantiomer, diastereomer, stereoisomer, or pharmaceutically acceptable salt thereof, wherein:

the Linker (L) is a group that covalently binds to the dTAG Targeting Ligand and $Z_2$;

the dTAG Targeting Ligand is capable of binding to a target dTAG or being bound by a target dTAG;

$Z_2$ is a bond, alkyl, —O—, —C(O)NR$_2$, —NR$^6$C(O), —NH, or —NR$^6$;

$R^6$ is H, alkyl, —C(O)alkyl, or —C(O)H;

$X_3$ is independently selected from O, S, and CH$_2$,

W₂ is independently selected from the group CH₂, CHR, C=O, SO₂, NH, and N-alkyl;

Y₂ is independently selected from the group NH, N-alkyl, N-aryl, N-hetaryl, N-cycloalkyl, N-heterocyclyl, O, and S;

G and G' are independently selected from the group H, alkyl, OH, CH₂-heterocyclyl optionally substituted with R', and benzyl optionally substituted with R;

Q₁, Q₂, Q₃, and Q₄ are independently selected from CH, N, CR', and N-oxide.

A₂ is independently selected from the group alkyl, cycloalkyl, Cl and F;

R⁷ is selected from: —CONR'R", —OR', —NR'R", —SR', —SO₂R', —SO₂NR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —CF₃, —CN, —NR'SO₂NR'R", —NR'CONR'R", —CONR'COR", —NR'C(=N—CN)NR'R", —C(=N—CN)NR'R", —NR'C(=N—CN)R", —NR'C(=C—NO₂)NR'R", —SO₂NR'COR", —NO₂, —CO₂R', —C(C=N—OR')R", —CR'=CR'R", —CCR', —S(C=O)(C=N—W)R", —SF₅ and —OCF₃

R' and R" are independently selected from a bond, H, alkyl, cycloalkyl, aryl, heteroaryl, heterocyclyl Non-limiting examples of dTAG Targeting Ligands for use in the present invention include:

Dehalogenase targeting ligands such as

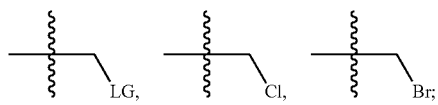

FKBP12 targeting ligands such as

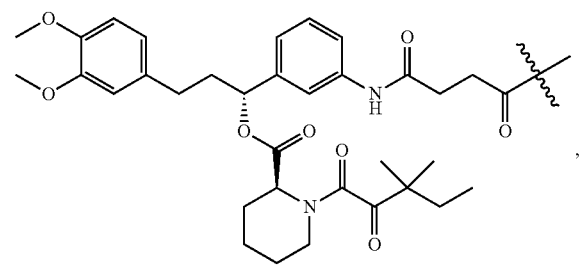

,

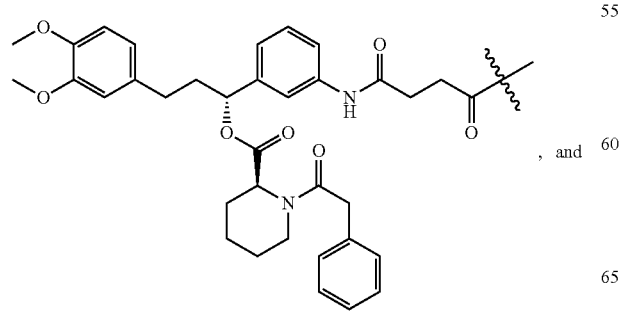

, and

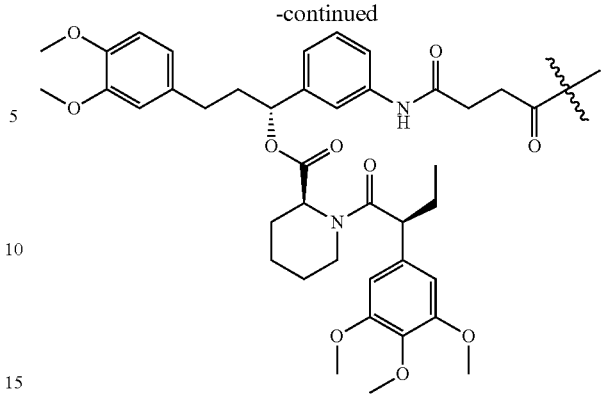

In some embodiments the dTAG Targeting Ligand targets a mutated endogenous target or a non-endogenous target.

Degron

The Degron is a compound moiety that links a dTAG, through the Linker and dTAG Targeting Ligand, to a ubiquitin ligase for proteosomal degradation. In certain embodiments, the Degron is a compound that binds to a ubiquitin ligase. In further embodiments, the Degron is a compound that binds to a E3 Ubiquitin Ligase. In further embodiments, the Degron is a compound that binds to cereblon. In further embodiments, the Degron is a thalidomide or a derivative or analog thereof.

In certain embodiments, the Degron is a moiety of Formula D, Formula D0, or Formula D':

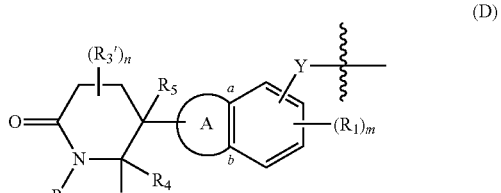
(D)

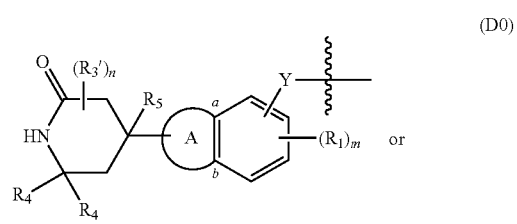
(D0)

or

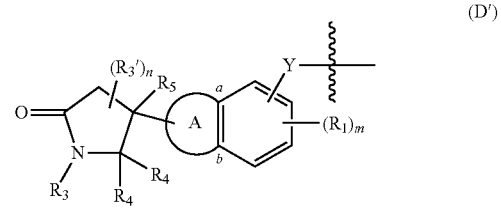
(D')

or an enantiomer, diastereomer, or stereoisomer thereof, wherein:

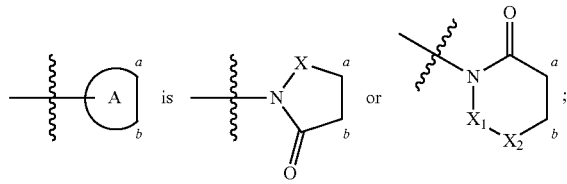

Y is a bond, $(CH_2)_{1-6}$, $(CH_2)_{0-6}$—O, $(CH_2)_{0-6}$—C(O)NR$_2$', $(CH_2)_{0-6}$—NR$_2$'C(O), $(CH_2)_{0-6}$—NH, or $(CH_2)_{0-6}$—NR$_2$;

X is C(O) or C(R$_3$)$_2$;

X$_1$—X$_2$ is C(R$_3$)=N or C(R$_3$)$_2$—C(R$_3$)$_2$;

each R$_1$ is independently halogen, OH, C$_1$-C$_6$ alkyl, or C$_1$-C$_6$ alkoxy;

R$_2$ is C$_1$-C$_6$ alkyl, C(O)—C$_1$-C$_6$ alkyl, or C(O)—C$_3$-C$_6$ cycloalkyl;

R$_2$' is H or C$_1$-C$_6$ alkyl;

each R$_3$ is independently H or C$_1$-C$_3$ alkyl;

each R$_3$' is independently C$_1$-C$_3$ alkyl;

each R$_4$ is independently H or C$_1$-C$_3$ alkyl; or two R$_4$, together with the carbon atom to which they are attached, form C(O), a C$_3$-C$_6$ carbocycle, or a 4-, 5-, or 6-membered heterocycle comprising 1 or 2 heteroatoms selected from N and O;

R$_5$ is H, deuterium, C$_1$-C$_3$ alkyl, F, or Cl;

m is 0, 1, 2 or 3; and n is 0, 1 or 2;

wherein the compound is covalently bonded to another moiety (e.g., a compound, or a Linker) via

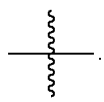

In certain embodiments, the Degron is a moiety of Formula D, wherein

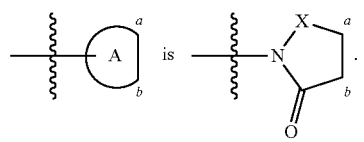

In certain embodiments, the Degron is a moiety of Formula D, wherein

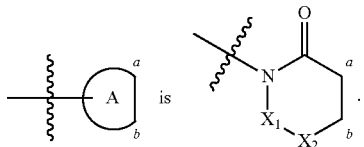

In certain embodiments, the Degron is a moiety of Formula D, wherein X is C(O).

In certain embodiments, the Degron is a moiety of Formula D, wherein X is C(R$_3$)$_2$; and each R$_3$ is H. In certain embodiments, X is C(R$_3$)$_2$; and one of R$_3$ is H, and the other is C$_1$-C$_3$ alkyl selected from methyl, ethyl, and propyl. In certain embodiments, X is C(R$_3$)$_2$; and each R$_3$ is independently selected from methyl, ethyl, and propyl.

In certain embodiments, the Degron is a moiety of Formula D, wherein X$_1$—X$_2$ is C(R$_3$)=N. In certain embodiments, X$_1$—X$_2$ is CH=N. In certain embodiments, X$_1$—X$_2$ is C(R$_3$)=N; and R$_3$ is C$_1$-C$_3$ alkyl selected from methyl, ethyl, and propyl. In certain embodiments, X$_1$—X$_2$ is C(CH$_3$)=N.

In certain embodiments, the Degron is a moiety of Formula D, wherein X$_1$—X$_2$ is C(R$_3$)$_2$—C(R$_3$)$_2$; and each R$_3$ is H. In certain embodiments, X$_1$—X$_2$ is C(R$_3$)$_2$—C(R$_3$)$_2$; and one of R$_3$ is H, and the other three R$_3$ are independently C$_1$-C$_3$ alkyl selected from methyl, ethyl, and propyl. In certain embodiments, X$_1$—X$_2$ is C(R$_3$)$_2$—C(R$_3$)$_2$; and two of the R$_3$ are H, and the other two R$_3$ are independently C$_1$-C$_3$ alkyl selected from methyl, ethyl, and propyl. In certain embodiments, X$_1$—X$_2$ is C(R$_3$)$_2$—C(R$_3$)$_2$; and three of the R$_3$ are H, and the remaining R$_3$ is C$_1$-C$_3$ alkyl selected from methyl, ethyl, and propyl.

In certain embodiments, the Degron is a moiety of Formula D, wherein Y is a bond.

In certain embodiments, the Degron is a moiety of Formula D, wherein Y is $(CH_2)_1$, $(CH_2)_2$, $(CH_2)_3$, $(CH_2)_4$, $(CH_2)_5$, or $(CH_2)_6$. In certain embodiments, Y is $(CH_2)_1$, $(CH_2)_2$, or $(CH_2)_3$. In certain embodiments, Y is $(CH_2)_1$ or $(CH_2)_2$.

In certain embodiments, the Degron is a moiety of Formula D, wherein Y is O, CH$_2$—O, $(CH_2)_2$—O, $(CH_2)_3$—O, $(CH_2)_4$—O, $(CH_2)_5$—O, or $(CH_2)_6$—O. In certain embodiments, Y is O, CH$_2$—O, $(CH_2)_2$—O, or $(CH_2)_3$—O. In certain embodiments, Y is O or CH$_2$—O. In certain embodiments, Y is O.

In certain embodiments, the Degron is a moiety of Formula D, wherein Y is C(O)NR$_2$', CH$_2$—C(O)NR$_2$', $(CH_2)_2$—C(O)NR$_2$', $(CH_2)_3$—C(O)NR$_2$', $(CH_2)_4$—C(O)NR$_2$', $(CH_2)_5$—C(O)NR$_2$', or $(CH_2)_6$—C(O)NR$_2$'. In certain embodiments, Y is C(O)NR$_2$', CH$_2$—C(O)NR$_2$', $(CH_2)_2$—C(O)NR$_2$', or $(CH_2)_3$—C(O)NR$_2$'. In certain embodiments, Y is C(O)NR$_2$' or CH$_2$—C(O)NR$_2$'. In certain embodiments, Y is C(O)NR$_2$'.

In certain embodiments, the Degron is a moiety of Formula D, wherein Y is NR$_2$'C(O), CH$_2$—NR$_2$' C(O), $(CH_2)_2$—NR$_2$' C(O), $(CH_2)_3$—NR$_2$' C(O), $(CH_2)_4$—NR$_2$' C(O), $(CH_2)_5$—NR$_2$' C(O), or $(CH_2)_6$—NR$_2$' C(O). In certain embodiments, Y is NR$_2$'C(O), CH$_2$—NR$_2$'C(O), $(CH_2)_2$—NR$_2$'C(O), or $(CH_2)_3$—NR$_2$'C(O). In certain embodiments, Y is NR$_2$'C(O) or CH$_2$—NR$_2$'C(O). In certain embodiments, Y is NR$_2$' C(O).

In certain embodiments, the Degron is a moiety of Formula D, wherein R$_2$' is H. In certain embodiments, the Degron is a moiety of Formula D, wherein R$_2$' is selected from methyl, ethyl, propyl, butyl, i-butyl, t-butyl, pentyl, i-pentyl, and hexyl. In certain embodiments, R$_2$' is C$_1$-C$_3$ alkyl selected from methyl, ethyl, and propyl.

In certain embodiments, the Degron is a moiety of Formula D, wherein Y is NH, CH$_2$—NH, $(CH_2)_2$—NH, $(CH_2)_3$—NH, $(CH_2)_4$—NH, $(CH_2)_5$—NH, or $(CH_2)_6$—NH. In certain embodiments, Y is NH, CH$_2$—NH, $(CH_2)_2$—NH, or $(CH_2)_3$—NH. In certain embodiments, Y is NH or CH$_2$—NH. In certain embodiments, Y is NH.

In certain embodiments, the Degron is a moiety of Formula D, wherein Y is NR$_2$, CH$_2$—NR$_2$, $(CH_2)_2$—NR$_2$, $(CH_2)_3$—NR$_2$, $(CH_2)_4$—NR$_2$, $(CH_2)_5$—NR$_2$, or $(CH_2)_6$—NR$_2$. In certain embodiments, Y is NR$_2$, CH$_2$—NR$_2$, ($CH_2$)$_2$—$NR_2$, or ($CH_2$)$_3$—$NR_2$. In certain embodiments, Y is $NR_2$ or $CH_2$—$NR_2$. In certain embodiments, Y is $NR_2$.

In certain embodiments, the Degron is a moiety of Formula D, wherein $R_2$ is selected from methyl, ethyl, propyl, butyl, i-butyl, t-butyl, pentyl, i-pentyl, and hexyl. In certain embodiments, $R_2$ is $C_1$-$C_3$ alkyl selected from methyl, ethyl, and propyl.

In certain embodiments, the Degron is a moiety of Formula D, wherein $R_2$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In certain embodiments, $R_2$ is C(O)—$C_1$-$C_3$ alkyl selected from C(O)-methyl, C(O)-ethyl, and C(O)-propyl.

In certain embodiments, the Degron is a moiety of Formula D, wherein $R_2$ is selected from C(O)-cyclopropyl, C(O)-cyclobutyl, C(O)-cyclopentyl, and C(O)-cyclohexyl. In certain embodiments, $R_2$ is C(O)-cyclopropyl.

In certain embodiments, the Degron is a moiety of Formula D, wherein $R_3$ is H.

In certain embodiments, the Degron is a moiety of Formula D, wherein $R_3$ is $C_1$-$C_3$ alkyl selected from methyl, ethyl, and propyl. In certain embodiments, $R_3$ is methyl.

In certain embodiments, the Degron is a moiety of Formula D, wherein n is 0.

In certain embodiments, the Degron is a moiety of Formula D, wherein n is 1.

In certain embodiments, the Degron is a moiety of Formula D, wherein n is 2.

In certain embodiments, the Degron is a moiety of Formula D, wherein each $R_3'$ is independently $C_1$-$C_3$ alkyl selected from methyl, ethyl, and propyl.

In certain embodiments, the Degron is a moiety of Formula D, wherein m is 0.

In certain embodiments, the Degron is a moiety of Formula D, wherein m is 1.

In certain embodiments, the Degron is a moiety of Formula D, wherein m is 2.

In certain embodiments, the Degron is a moiety of Formula D, wherein m is 3.

In certain embodiments, the Degron is a moiety of Formula D, wherein each $R_1$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_6$ alkoxy (e.g., methoxy, ethoxy, propoxy, butoxy, i-butoxy, t-butoxy, and pentoxy). In further embodiments, the Degron is a moiety of Formula D, wherein each $R_1$ is independently selected from F, Cl, OH, methyl, ethyl, propyl, butyl, i-butyl, t-butyl, methoxy, and ethoxy.

In certain embodiments, the Degron is a moiety of Formula D, wherein each $R_4$ is H.

In certain embodiments, the Degron is a moiety of Formula D, wherein one of $R_4$ is H, and the other $R_4$ is $C_1$-$C_3$ alkyl selected from methyl, ethyl, and propyl.

In certain embodiments, the Degron is a moiety of Formula D, wherein each $R_4$ is independently $C_1$-$C_3$ alkyl selected from methyl, ethyl, and propyl.

In certain embodiments, the Degron is a moiety of Formula D, wherein two $R_4$, together with the carbon atom to which they are attached, form C(O).

In certain embodiments, the Degron is a moiety of Formula D, wherein two $R_4$, together with the carbon atom to which they are attached, form cyclopropyl, cyclobutyl, cyclopentyl, or cyclohexyl.

In certain embodiments, the Degron is a moiety of Formula D, wherein two $R_4$, together with the carbon atom to which they are attached, form a 4-, 5-, or 6-membered heterocycle selected from oxetane, azetidine, tetrahydrofuran, pyrrolidine, piperidine, piperazine, and morpholine. In certain embodiments, two $R_4$, together with the carbon atom to which they are attached, form oxetane.

In certain embodiments, the Degron is a moiety of Formula D, wherein $R_5$ is H, deuterium, or $C_1$-$C_3$ alkyl. In further embodiments, $R_5$ is in the (S) or (R) configuration. In further embodiments, $R_5$ is in the (5) configuration. In certain embodiments, the Degron is a moiety of Formula D, wherein the compound comprises a racemic mixture of (S)—$R_5$ and (R)—$R_5$.

In certain embodiments, the Degron is a moiety of Formula D, wherein $R_5$ is H.

In certain embodiments, the Degron is a moiety of Formula D, wherein $R_5$ is deuterium.

In certain embodiments, the Degron is a moiety of Formula D, wherein $R_5$ is $C_1$-$C_3$ alkyl selected from methyl, ethyl, and propyl. In certain embodiments, $R_5$ is methyl.

In certain embodiments, the Degron is a moiety of Formula D, wherein $R_5$ is F or Cl. In further embodiments, $R_5$ is in the (S) or (R) configuration. In further embodiments, $R_5$ is in the (R) configuration. In certain embodiments, the Degron is a moiety of Formula D, wherein the compound comprises a racemic mixture of (S)—$R_5$ and (R)—$R_5$. In certain embodiments, $R_5$ is F.

In certain embodiments, the Degron is selected from the structures in FIG. 42, wherein X is H, deuterium, $C_1$-$C_3$ alkyl, or halogen; and R is the attachment point for the Linker.

Figure 43:
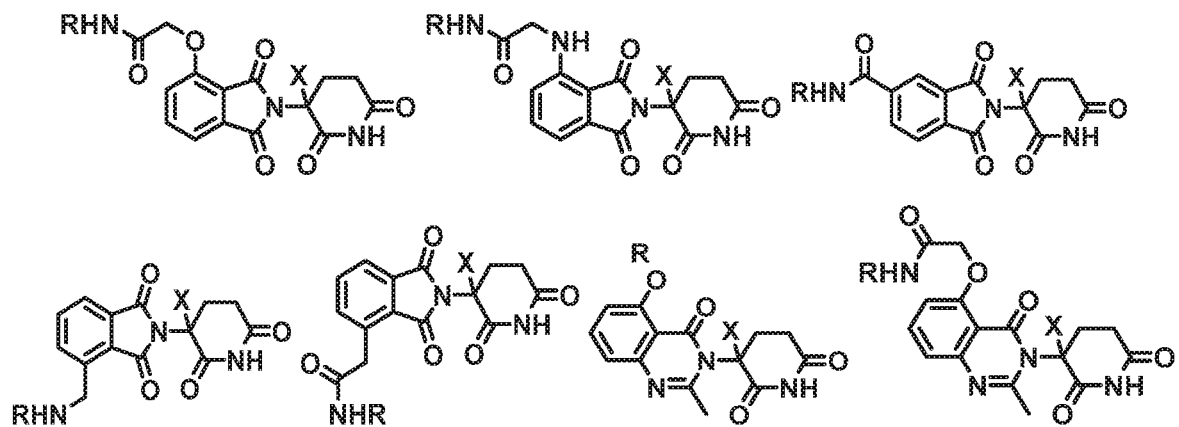
FIG. 43 provides additional examples of Degron moieties for use in the present invention, wherein R is the point of attachment for the Linker and X is as defined herein.

In certain embodiments, the Degron is selected from the structures in FIG. 43.

Figure 44:
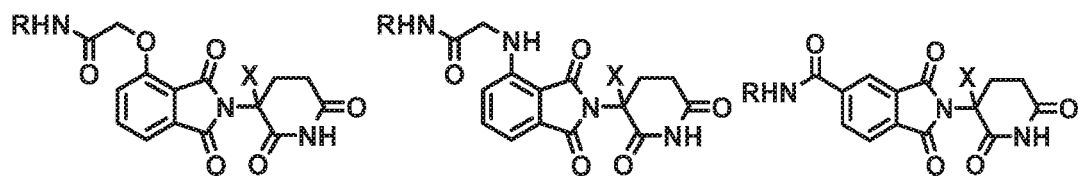
FIG. 44 provides additional examples of Degron moieties for use in the present invention, wherein R is the point of attachment for the Linker and X is as defined herein.

In certain embodiments, the Degron is selected from the structures in FIG. 44.

Linker

The Linker is a bond or a chemical group that links a dTAG Targeting Ligand with a Degron. In certain embodiments the Linker is a carbon chain. In certain embodiments, the carbon chain optionally includes one, two, three, or more heteroatoms selected from N, O, and S. In certain embodiments, the carbon chain comprises only saturated chain carbon atoms. In certain embodiments, the carbon chain optionally comprises two or more unsaturated chain carbon atoms $$(\text{e.g.,} \ C=C \ \text{or} \ C\equiv C).$$

In certain embodiments, one or more chain carbon atoms in the carbon chain are optionally substituted with one or more substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, NH($C_1$-$C_3$ alkyl), N($C_1$-$C_3$ alkyl)$_2$, CN, $C_3$-$C_8$ cycloalkyl, heterocyclyl, phenyl, and heteroaryl).

In certain embodiments, the Linker includes at least 5 chain atoms (e.g., C, O, N, and S). In certain embodiments, the Linker comprises less than 20 chain atoms (e.g., C, O, N, and S). In certain embodiments, the Linker comprises 5, 6, 7, 8, 9, 10, 11, 12, 13, 14, 15, 16, 17, 18, or 19 chain atoms (e.g., C, O, N, and S). In certain embodiments, the Linker comprises 5, 7, 9, 11, 13, 15, 17, or 19 chain atoms (e.g., C, O, N, and S). In certain embodiments, the Linker comprises 5, 7, 9, or 11 chain atoms (e.g., C, O, N, and S). In certain embodiments, the Linker comprises 6, 8, 10, 12, 14, 16, or 18 chain atoms (e.g., C, O, N, and S). In certain embodiments, the Linker comprises 6, 8, 10, or 12 chain atoms (e.g., C, O, N, and S).

In certain embodiments, the Linker is a carbon chain optionally substituted with non-bulky substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, and CN). In certain embodiments, the non-bulky substitution is located on the chain carbon atom proximal to the Degron (i.e., the carbon atom is separated from the carbon atom to which the Degron is bonded by at least 3, 4, or 5 chain atoms in the Linker).

In certain embodiments, the Linker is of Formula L0:

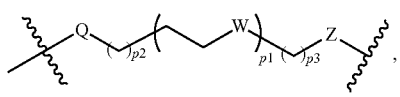
(L0)

or an enantiomer, diastereomer, or stereoisomer thereof, wherein
p1 is an integer selected from 0 to 12;
p2 is an integer selected from 0 to 12;
p3 is an integer selected from 1 to 6;
each W is independently absent, $CH_2$, O, S, NH or $NR_5$;
Z is absent, $CH_2$, O, NH or $NR_5$;
each $R_5$ is independently $C_1$-$C_3$ alkyl; and
Q is absent or —$CH_2C(O)NH$—,
wherein the Linker is covalently bonded to the Degron with the

next to Q, and covalently bonded to the dTAG Targeting Ligand with the

next to Z, and wherein the total number of chain atoms in the Linker is less than 20.

In certain embodiments, the Linker-dTAG Targeting Ligand (TL) has the structure of Formula L1 or L2:

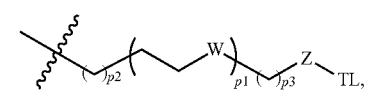
(L1)

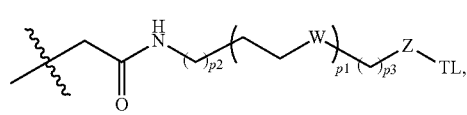
(L2)

or an enantiomer, diastereomer, or stereoisomer thereof, wherein:
p1 is an integer selected from 0 to 12;
p2 is an integer selected from 0 to 12;
p3 is an integer selected from 1 to 6;
each W is independently absent, $CH_2$, O, S, NH or $NR_5$;
Z is absent, $CH_2$, O, NH or $NR_5$;
each $R_5$ is independently $C_1$-$C_3$ alkyl; and
TL is a dTAG Targeting Ligand,
wherein the Linker is covalently bonded to the Degron with

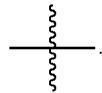

In certain embodiments, p1 is an integer selected from 0 to 10.
In certain embodiments, p1 is an integer selected from 2 to 10.
In certain embodiments, p1 is selected from 1, 2, 3, 4, 5, and 6.
In certain embodiments, p1 is selected from 1, 3, and 5.
In certain embodiments, p1 is selected from 1, 2, and 3.
In certain embodiments, p1 is 3.
In certain embodiments, p2 is an integer selected from 0 to 10.
In certain embodiments, p2 is selected from 0, 1, 2, 3, 4, 5, and 6.
In certain embodiments, p2 is an integer selected from 0 and 1.
In certain embodiments, p3 is an integer selected from 1 to 5.
In certain embodiments, p3 is selected from 2, 3, 4, and 5.
In certain embodiments, p3 is selected from 1, 2, and 3.
In certain embodiments, p3 is selected from 2 and 3.
In certain embodiments, at least one W is $CH_2$.
In certain embodiments, at least one W is O.
In certain embodiments, at least one W is S.
In certain embodiments, at least one W is NH.
In certain embodiments, at least one W is $NR_5$; and $R_5$ is $C_1$-$C_3$ alkyl selected from methyl, ethyl, and propyl.
In certain embodiments, W is O.
In certain embodiments, Z is absent.
In certain embodiments, Z is $CH_2$.
In certain embodiments, Z is O.
In certain embodiments, Z is NH.
In certain embodiments, Z is $NR_5$; and $R_5$ is $C_1$-$C_3$ alkyl selected from methyl, ethyl, and propyl.
In certain embodiments, Z is part of the dTAG Targeting Ligand that is bonded to the Linker, namely, Z is formed from reacting a functional group of the dTAG Targeting Ligand with the Linker.
In certain embodiments, W is $CH_2$, and Z is $CH_2$.
In certain embodiments, W is O, and Z is $CH_2$.
In certain embodiments, W is $CH_2$, and Z is O.
In certain embodiments, W is O, and Z is O.
In certain embodiments, the Linker-dTAG Targeting Ligand has the structure selected from Table L:

TABLE L

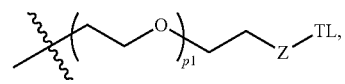

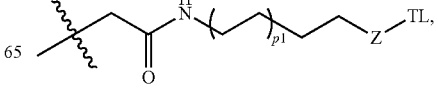

TABLE L-continued

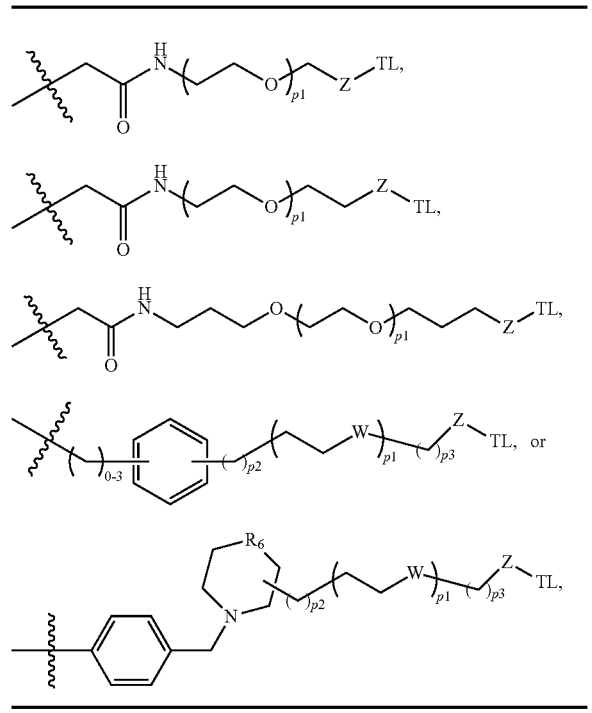

wherein Z, TL, and p1 are each as described above.

Any one of the Degrons described herein can be covalently bound to any one of the Linkers described herein.

In certain embodiments, the present application includes the Degron-Linker (DL) having the following structure:

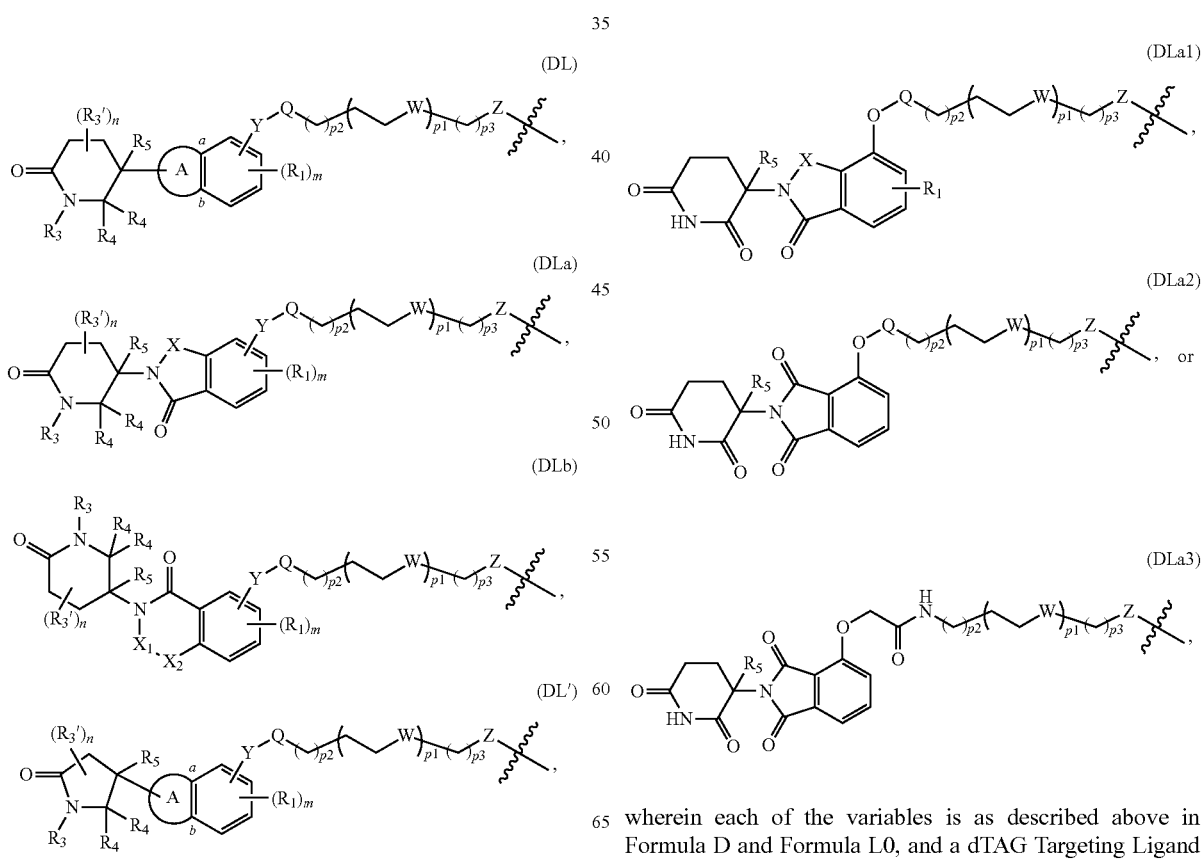

wherein each of the variables is as described above in Formula D0 and Formula L0, and a dTAG Targeting Ligand is covalently bonded to the DL with the next to Z.

In certain embodiments, the present application includes to the Degron-Linker (DL) having the following structure:

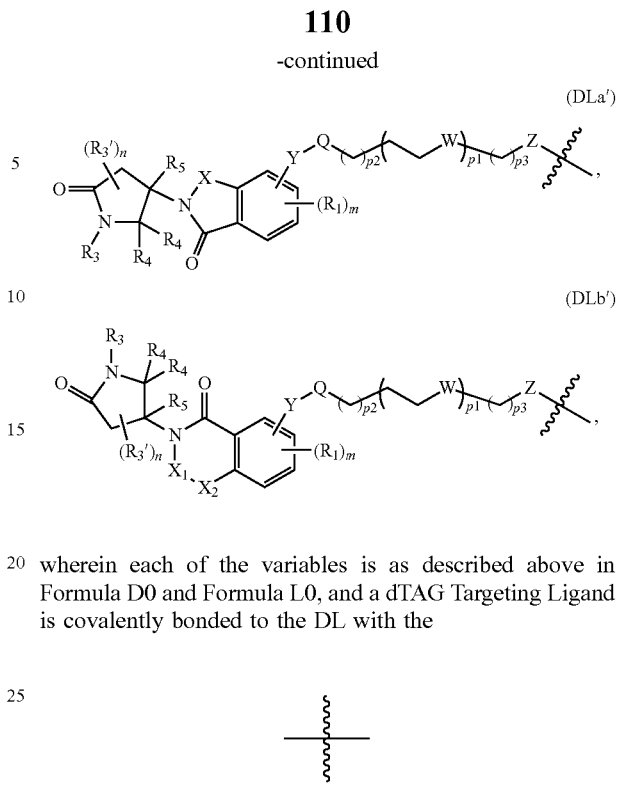

wherein each of the variables is as described above in Formula D and Formula L0, and a dTAG Targeting Ligand is covalently bonded to the DL with the

next to Z.

Some embodiments of the present application relate to a bifunctional compound having the following structure:

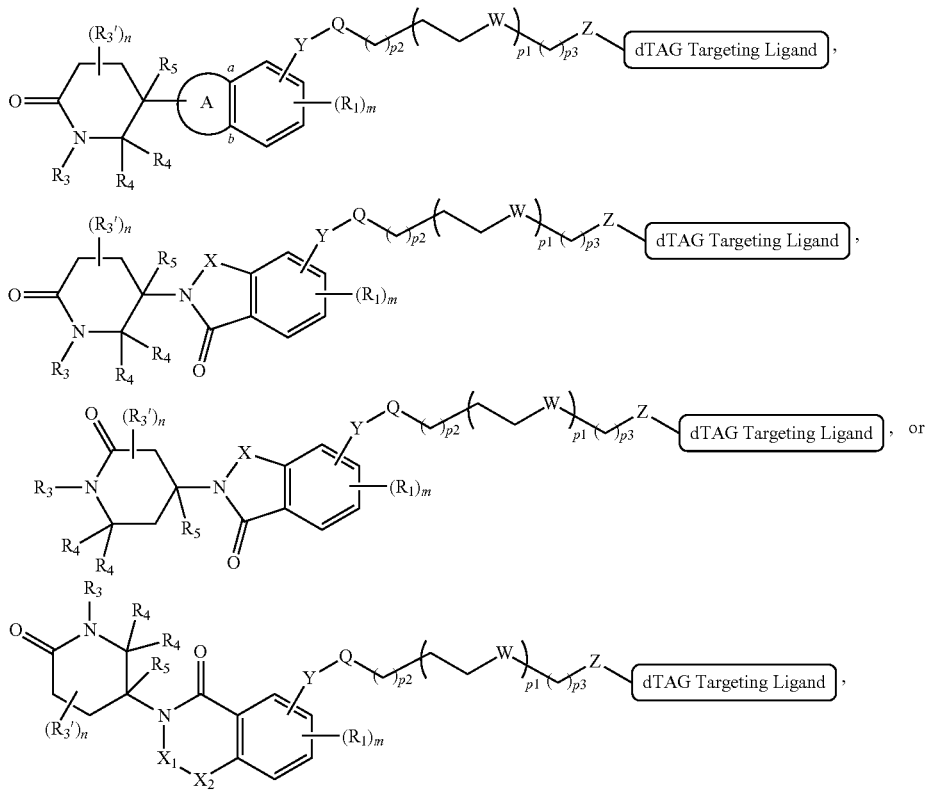

or an enantiomer, diastereomer, or stereoisomer thereof, wherein each of the variables is as described above in Formula D and Formula L0, and the dTAG Targeting Ligand is described herein below.

Further embodiments of the present application relate to a bifunctional compound having the following structure:

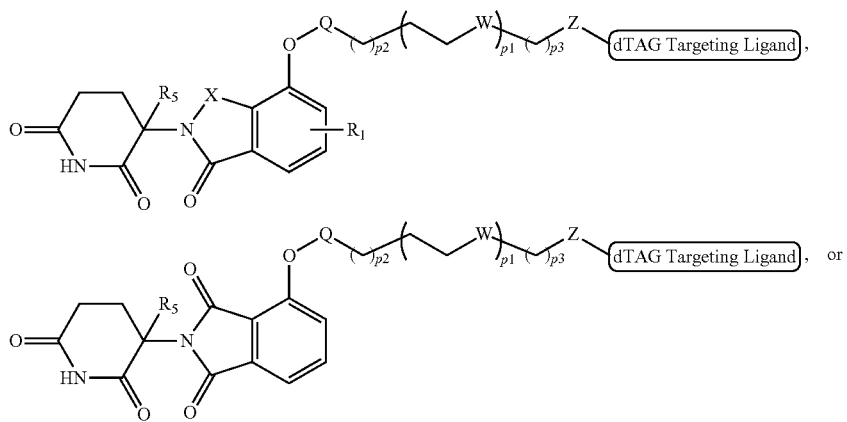

-continued
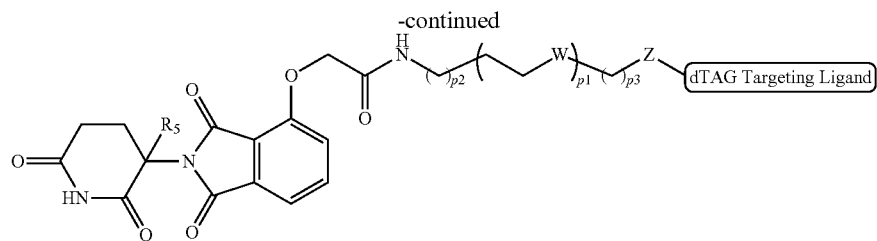
or an enantiomer, diastereomer, or stereoisomer thereof, wherein each of the variables is as described above in Formula D and Formula L0, and the dTAG Targeting Ligand is described herein below.
Certain embodiments of the present application relate to bifunctional compounds having one of the following structures:
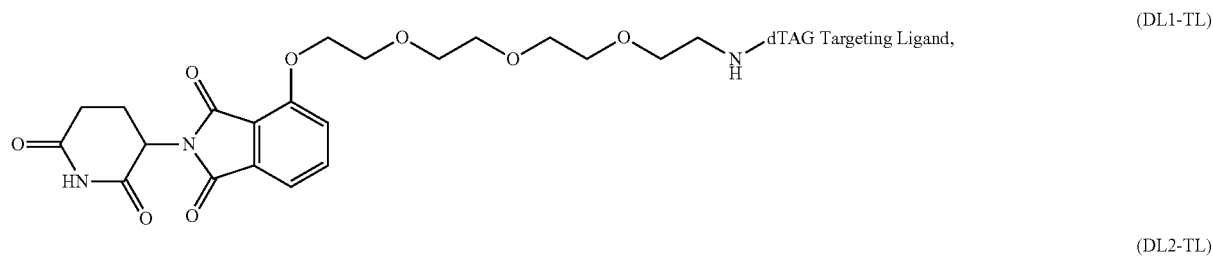
(DL1-TL)
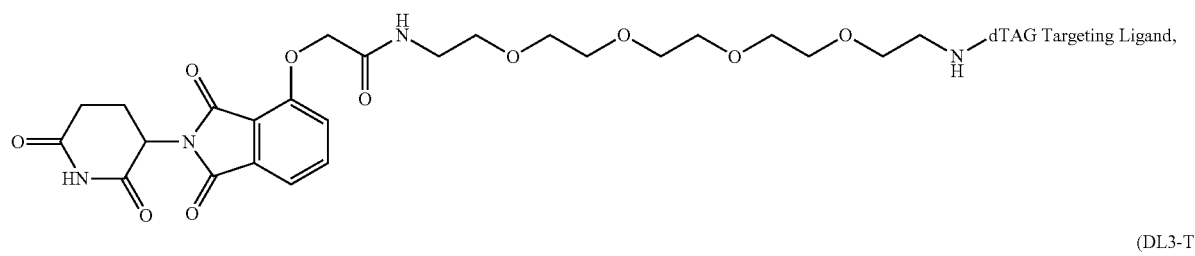
(DL2-TL)
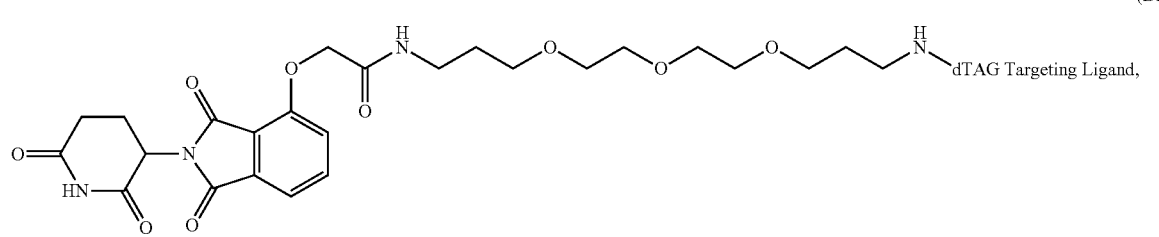
(DL3-TL)
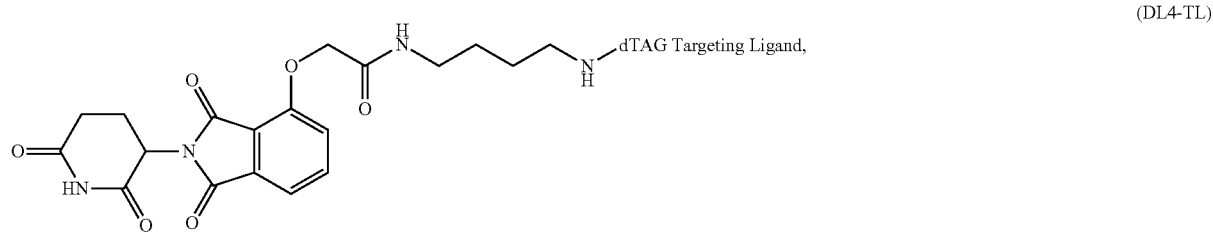
(DL4-TL)
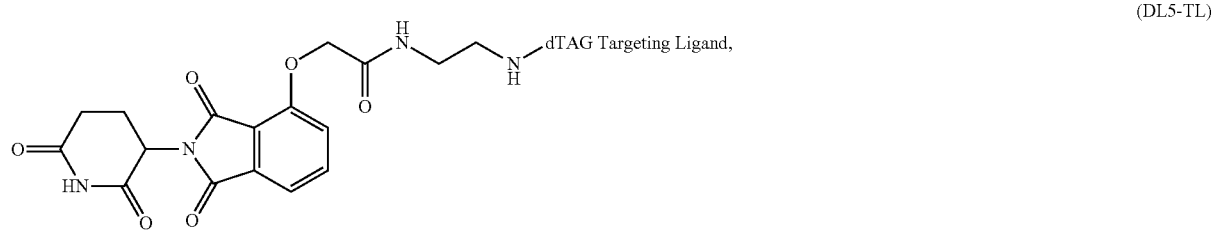
(DL5-TL)

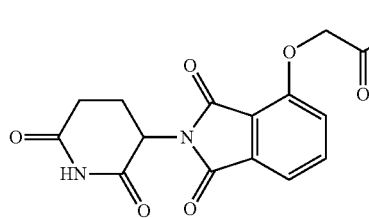

(DL6-TL)

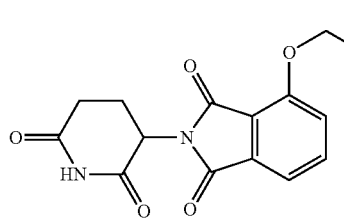

(DL7-TL)

In certain embodiments, the Linker may be a polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In certain embodiments, the Linker is designed and optimized based on SAR (structure-activity relationship) and X-ray crystallography of the dTAG Targeting Ligand with regard to the location of attachment for the Linker.

In certain embodiments, the optimal Linker length and composition vary by target and can be estimated based upon X-ray structures of the original dTAG Targeting Ligand bound to its target. Linker length and composition can be also modified to modulate metabolic stability and pharmacokinetic (PK) and pharmacodynamics (PD) parameters.

In certain embodiments, where the dTAG Targeting Ligand binds multiple targets, selectivity may be achieved by varying Linker length where the ligand binds some of its targets in different binding pockets, e.g., deeper or shallower binding pockets than others.

In an additional embodiment, the heterobifunctional compounds for use in the present invention include a chemical Linker (L). In certain embodiments, the Linker group L is a group comprising one or more covalently connected structural units of A (e.g., $-A_1 \ldots A_q-$), wherein $A_1$ is a group coupled to at least one of a Degron, a dTAG Targeting Ligand, or a combination thereof. In certain embodiments, $A_1$ links a Degron, a dTAG Targeting Ligand, or a combination thereof directly to another Degron, Targeting Ligand, or combination thereof. In other embodiments, $A_1$ links a Degron, a dTAG Targeting Ligand, or a combination thereof indirectly to another Degron, dTAG Targeting Ligand or combination thereof through $A_q$.

In certain embodiments, $A_1$ to $A_q$ are, each independently, a bond, $CR^{L1}R^{L2}$, O, S, SO, $SO_2$, $NR^{L3}$, $SO_2NR^{L3}$, $SONR^{L3}$, $CONR^{L3}$, $NR_{L3}CONR^{L4}$, $NR_{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$, $C_{3-11}$cycloalkyl optionally substituted with 0-6 $R^{L1}$ and/or $R^{L2}$ groups, $C_{3-11}$heterocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently, can be linked to other A groups to form a cycloalkyl and/or heterocyclyl moiety which can be further substituted with 0-4 $R^{L5}$ groups; wherein $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, P(O)($OC_{1-8}$alkyl)($C_{1-8}$alkyl), $P(O)(OC_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl)$CONH(C_{1-8}$alkyl), $N(C_{1-8}$alkyl)$CON(C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl) $SO_2N(C_{1-8}$alkyl$)_2$, NH $SO_2NH(C_{1-8}$alkyl), NH $SO_2N(C_{1-8}$alkyl$)_2$, NH $SO_2NH_2$.

In certain embodiments, q is an integer greater than or equal to 0. In certain embodiments, q is an integer greater than or equal to 1.

In certain embodiments, e.g., where q is greater than 2, $A_q$ is a group which is connected to a Degron, and $A_1$ and $A_q$ are connected via structural units of A (number of such structural units of A: q-2).

In certain embodiments, e.g., where q is 2, $A_q$ is a group which is connected to $A_1$ and to a Degron moiety.

In certain embodiments, e.g., where q is 1, the structure of the Linker group L is $-A_1-$, and $A_1$ is a group which is connected to a Degron moiety and a dTAG Targeting Ligand moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

Figure 45:
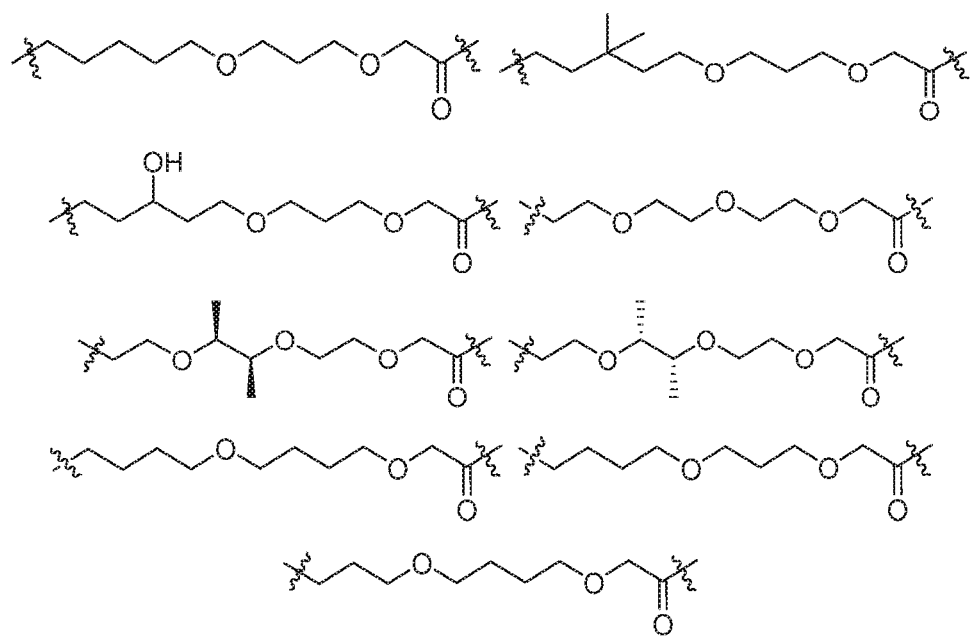
FIG. 45 provides examples of Linker moieties for use in the present invention.

In certain embodiments, the Linker (L) is selected from the structures in FIG. 45.

Figure 46:
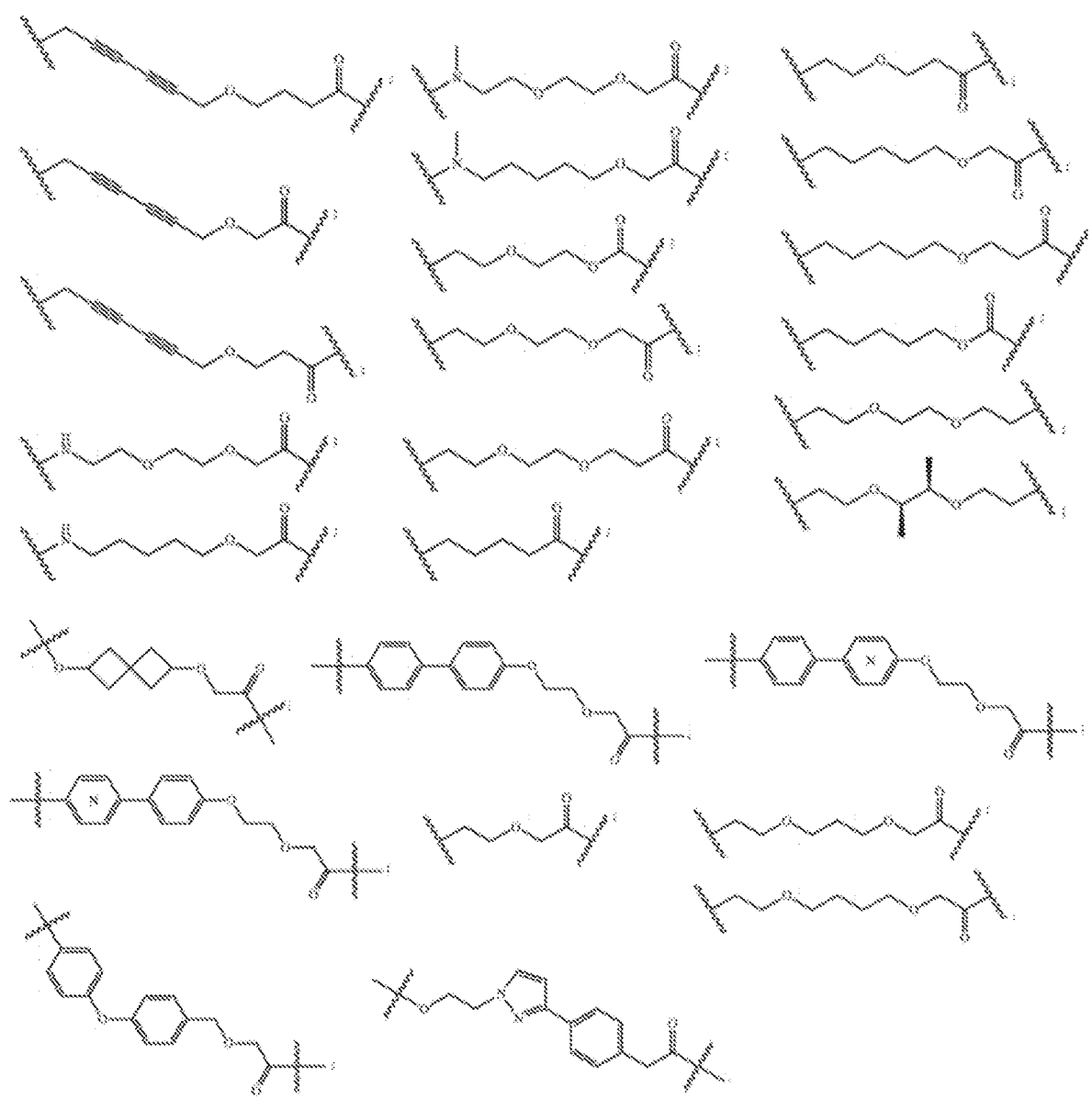
FIG. 46 provides additional examples of Linker moieties for use in the present invention.

In other embodiments the Linker (L) is selected from the structures in FIG. 46, wherein

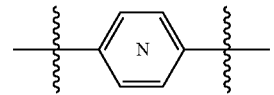

represents

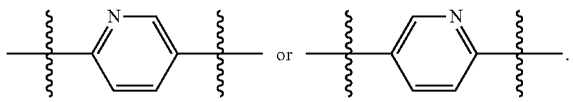 [SMILES: *c1ccc(*)nc1 ; *c1ccc(*)nc1]

In additional embodiments, the Linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interspersed with optionally substituted, O, N, S, P or Si atoms. In certain embodiments, the Linker is substituted with an aryl, phenyl, benzyl, alkyl, alkylene, or heterocycle group. In certain embodiments, the Linker may be asymmetric or symmetrical.

In any of the embodiments of the compounds described herein, the Linker group may be any suitable moiety as described herein. In one embodiment, the Linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

Although the Degron group and dTAG Targeting Ligand group may be covalently linked to the Linker group through any group which is appropriate and stable to the chemistry of the Linker, the Linker is independently covalently bonded to the Degron group and the dTAG Targeting Ligand group preferably through an amide, ester, thioester, keto group, carbamate (urethane), carbon or ether, each of which groups may be inserted anywhere on the Degron group and dTAG Targeting Ligand group to provide maximum binding of the Degron group on the ubiquitin ligase and the dTAG Targeting Ligand group on the target dTAG. (It is noted that in certain aspects where the Degron group targets Ubiquitin Ligase, the target protein for degradation may be the ubiquitin ligase itself). The Linker may be linked to an optionally substituted alkyl, alkylene, alkene or alkyne group, an aryl group or a heterocyclic group on the Degron and/or dTAG Targeting Ligand groups.

Figure 47:
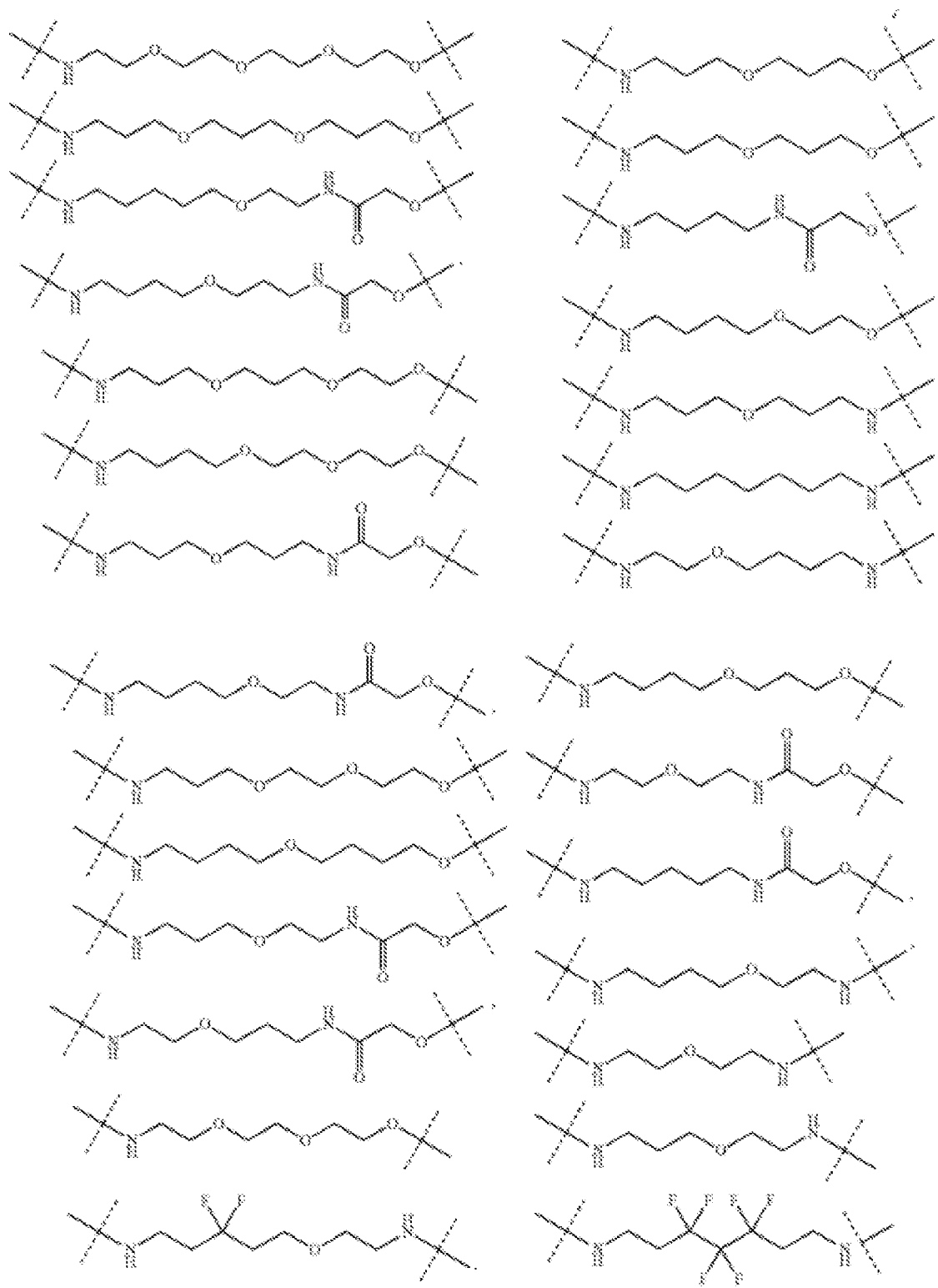
FIG. 47 provides examples of heteroaliphatic Linker moieties for use in the present invention.

In certain embodiments, "L" can be linear chains with linear atoms from 4 to 24, the carbon atom in the linear chain can be substituted with oxygen, nitrogen, amide, fluorinated carbon, etc., such as the structures in FIG. 47.

Figure 48:
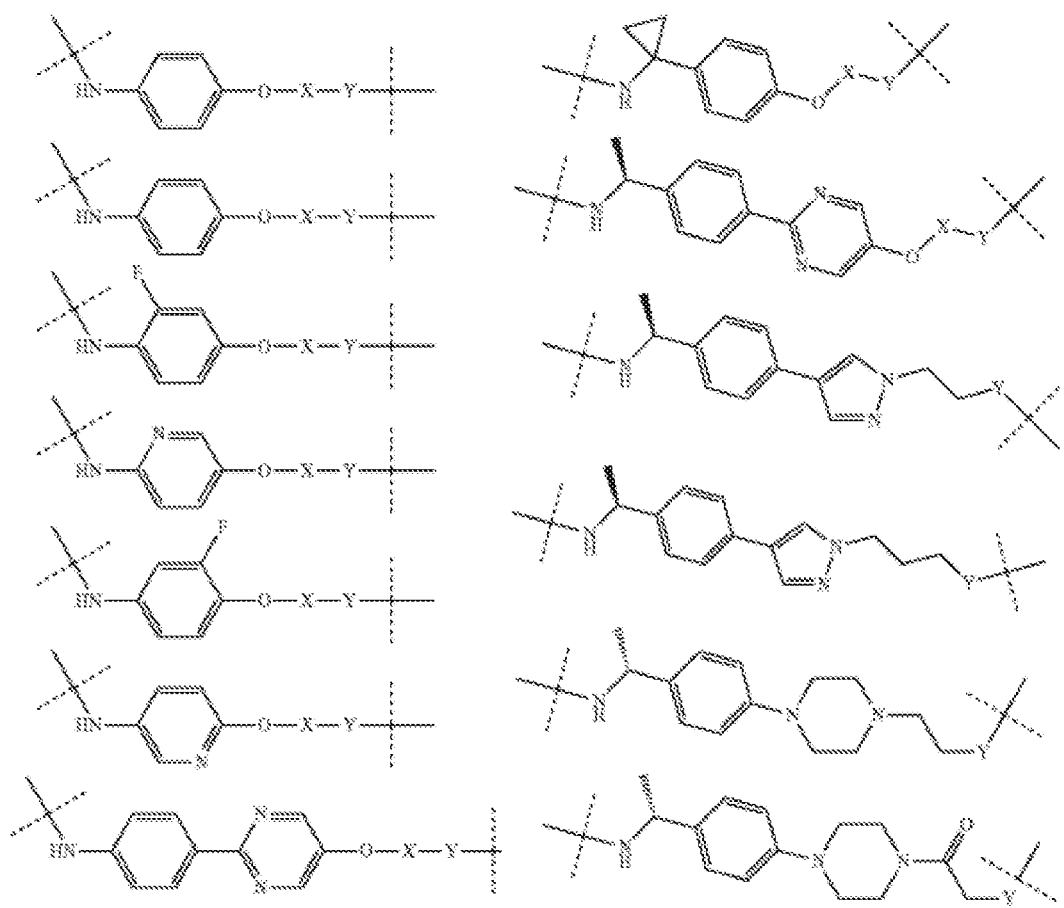
FIG. 48 provides examples of aromatic Linker moieties for use in the present invention.
Figure 49A:
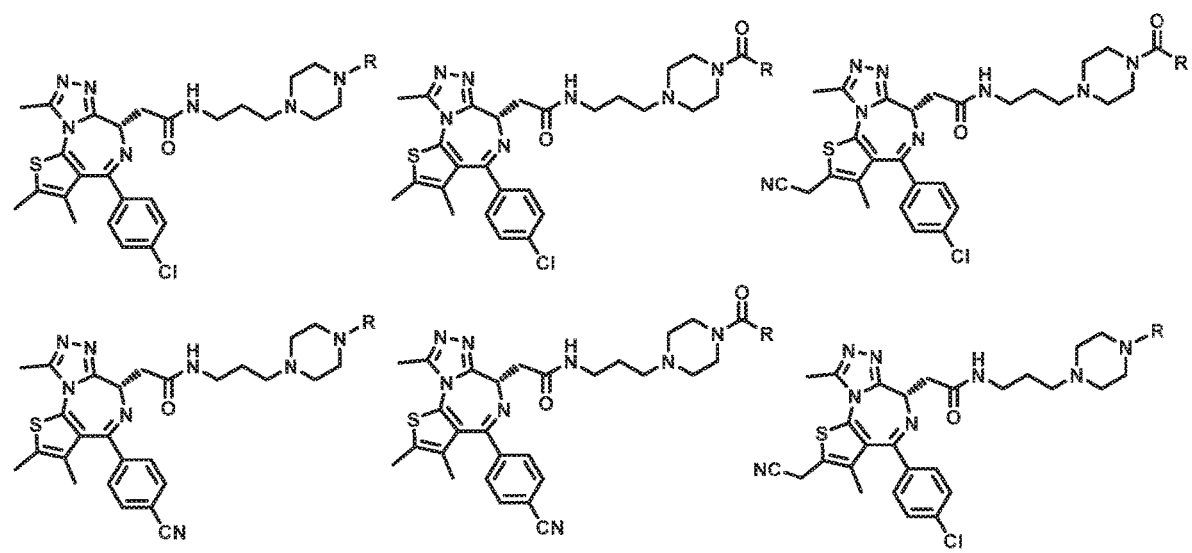
FIG. 49A, FIG. 49B, FIG. 49C, FIG. 49D, FIG. 49E, FIG. 49F, and FIG. 49G provide dTAG Targeting Ligands for use in the present invention, wherein R is the point at which the Linker is attached.
Figure 49B:
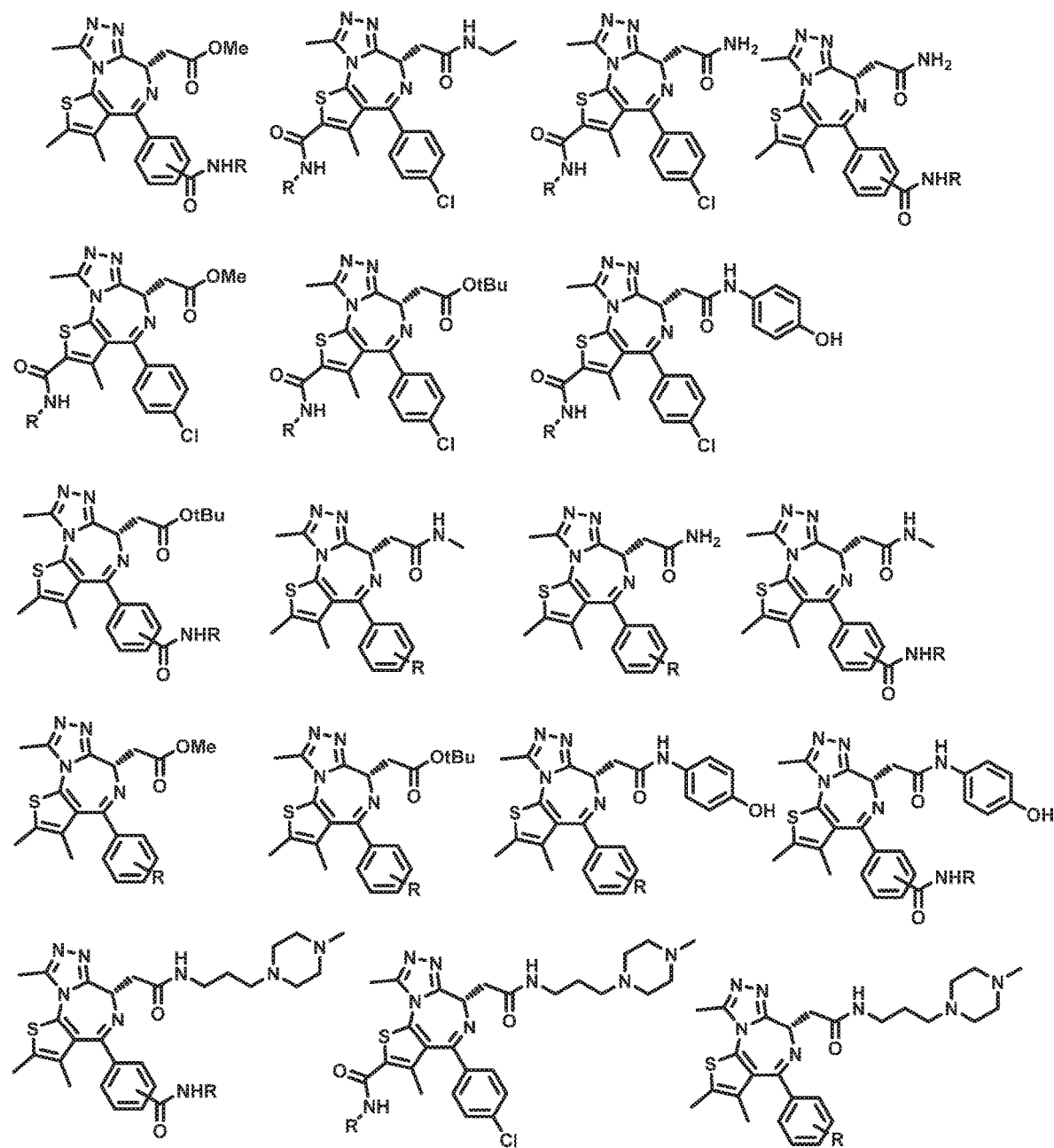
Figure 49C:
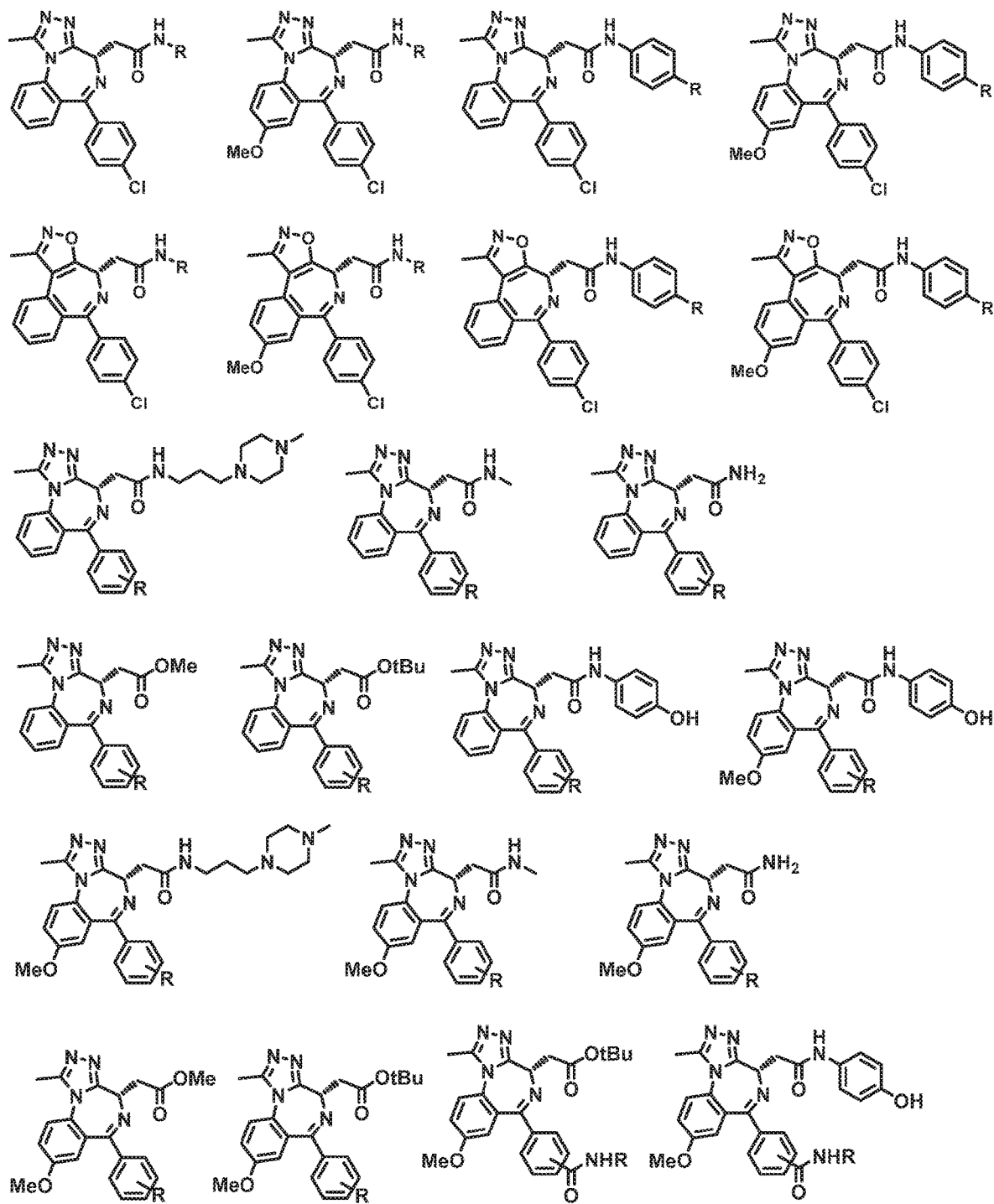
Figure 49D:
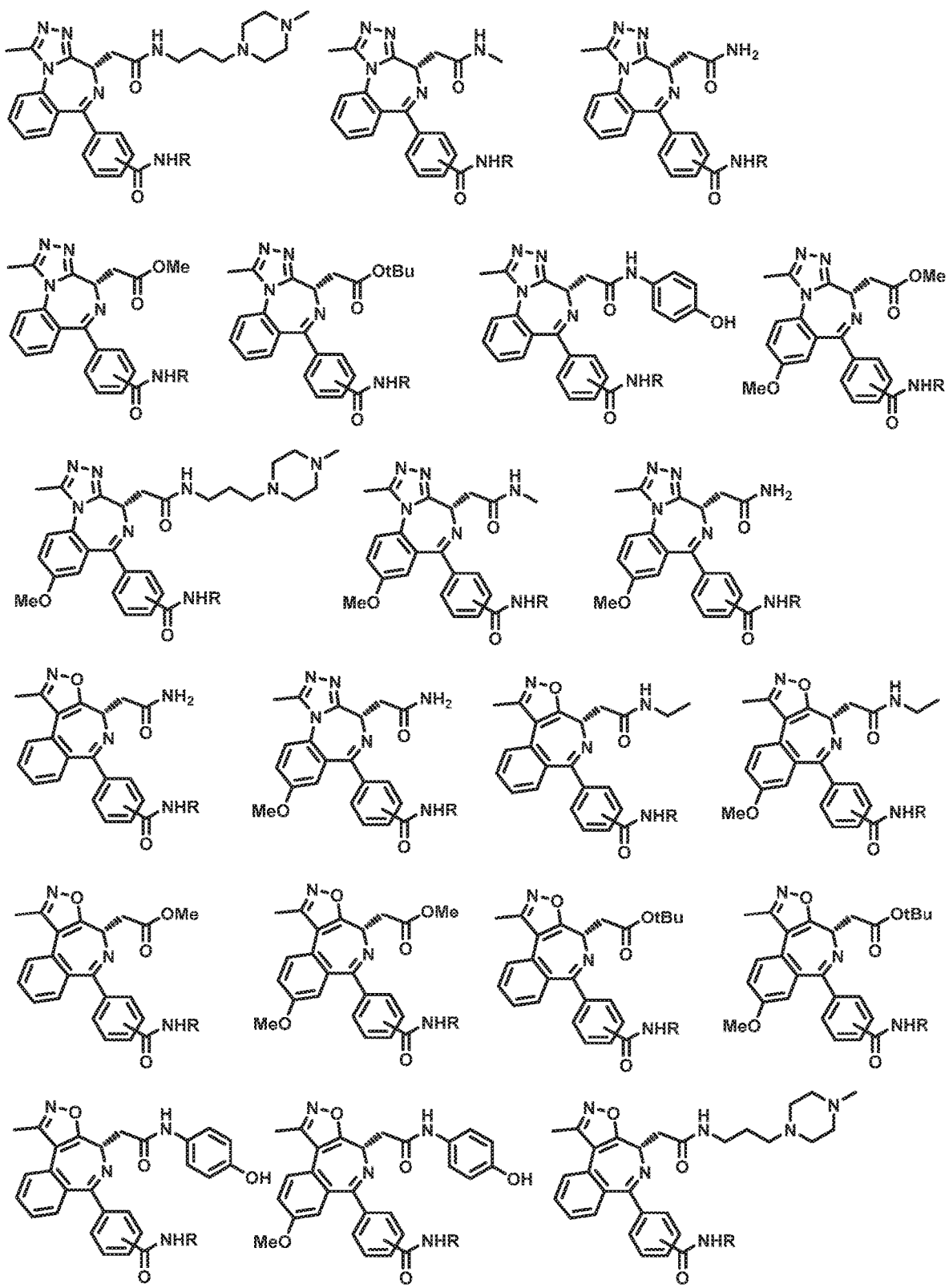
Figure 49E:
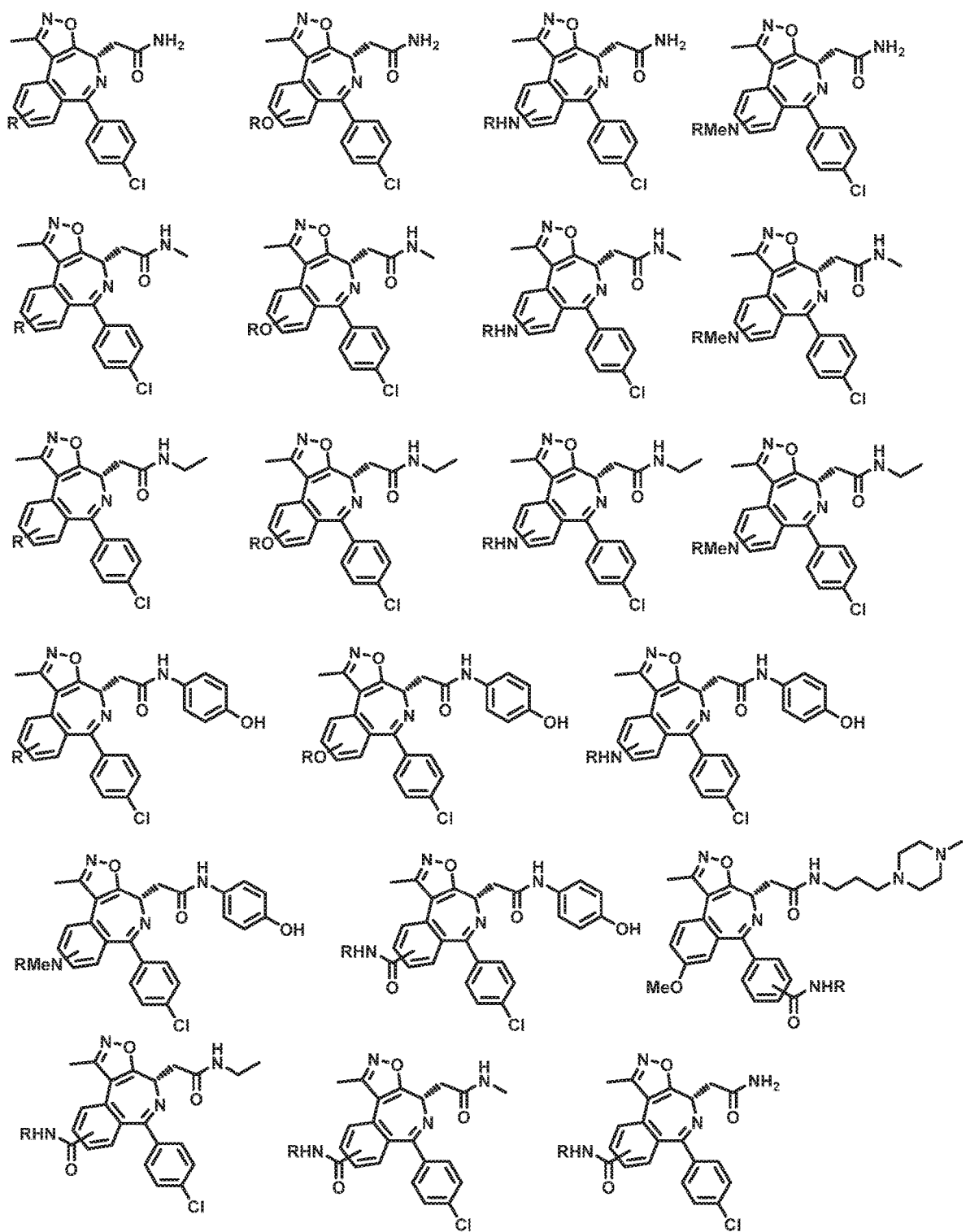
Figure 49F:
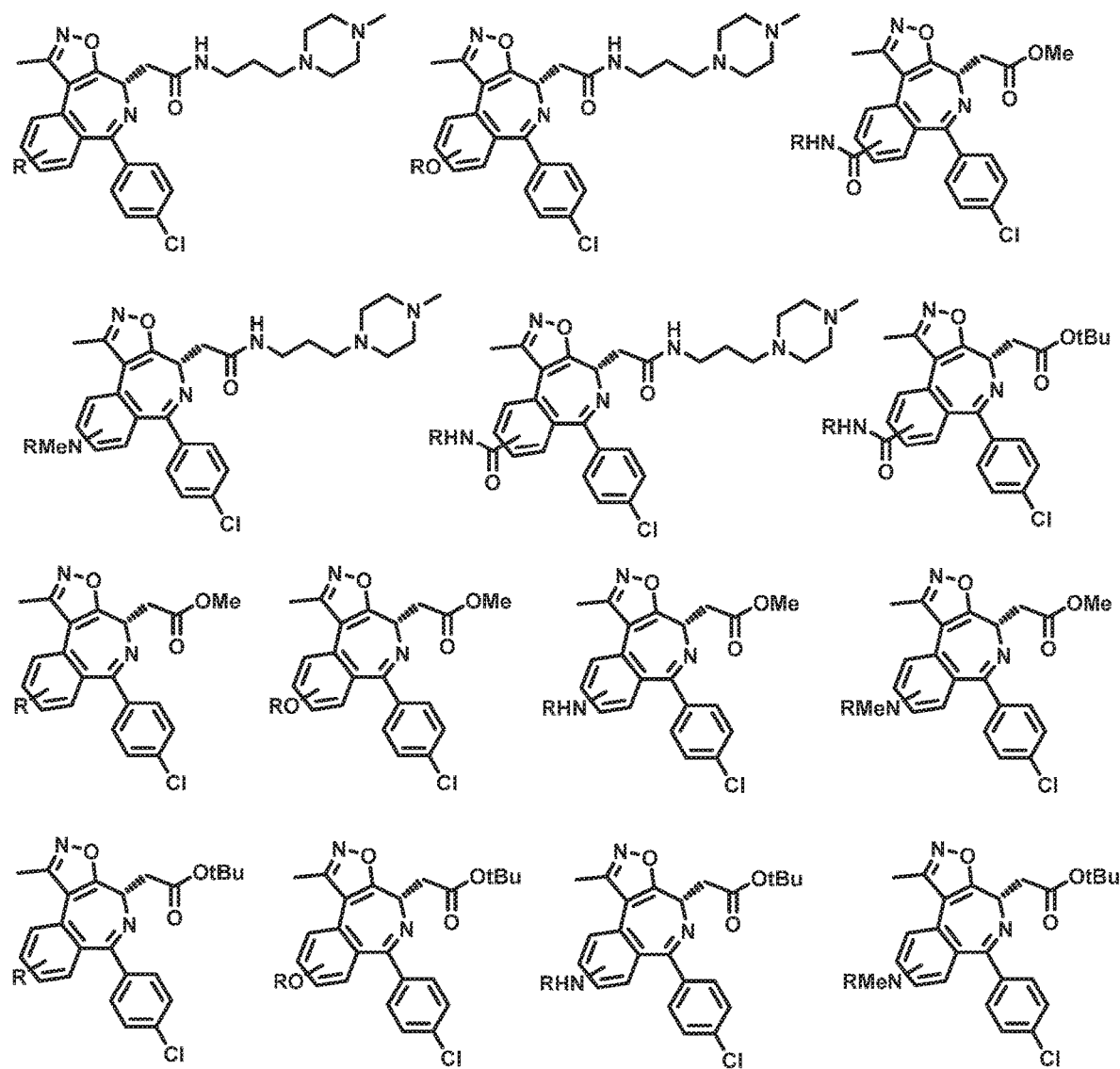
Figure 49G:
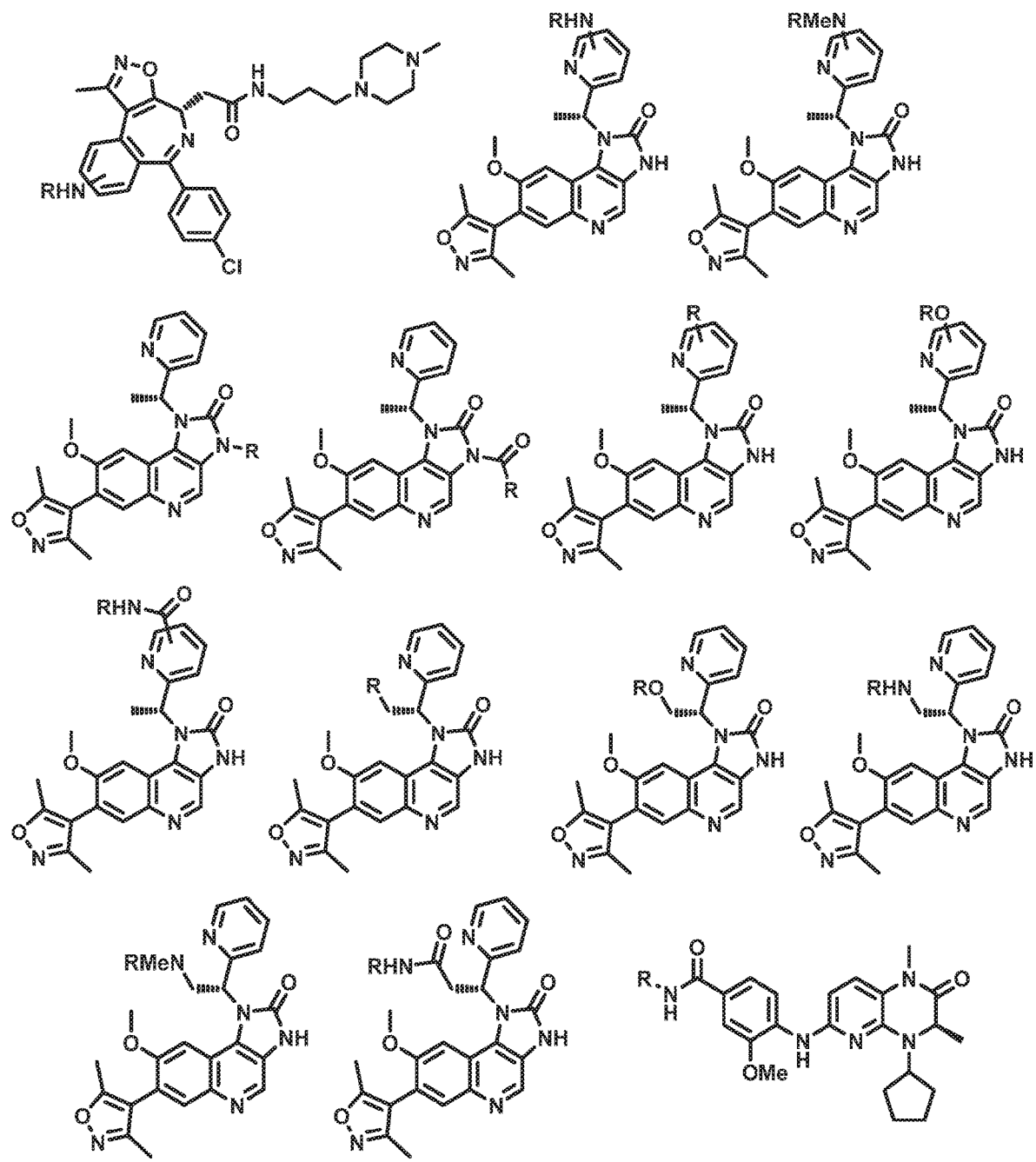
Figure 50A:
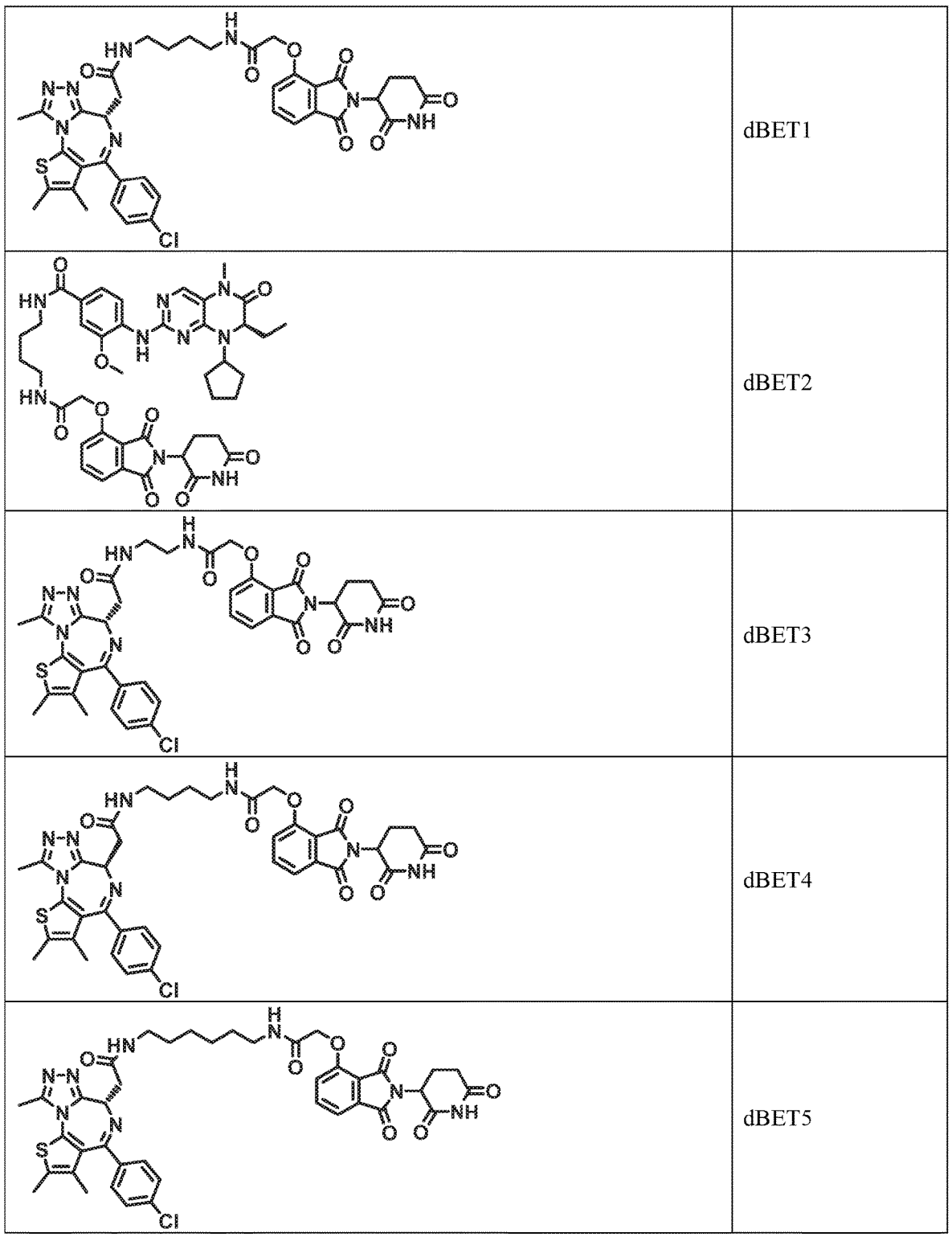
FIG. 50A, FIG. 50B, FIG. 50C, FIG. 50D, FIG. 50E, FIG. 50F, FIG. 50G, and FIG. 50H provide specific heterobifunctional compounds for use in the present invention.
Figure 50B:
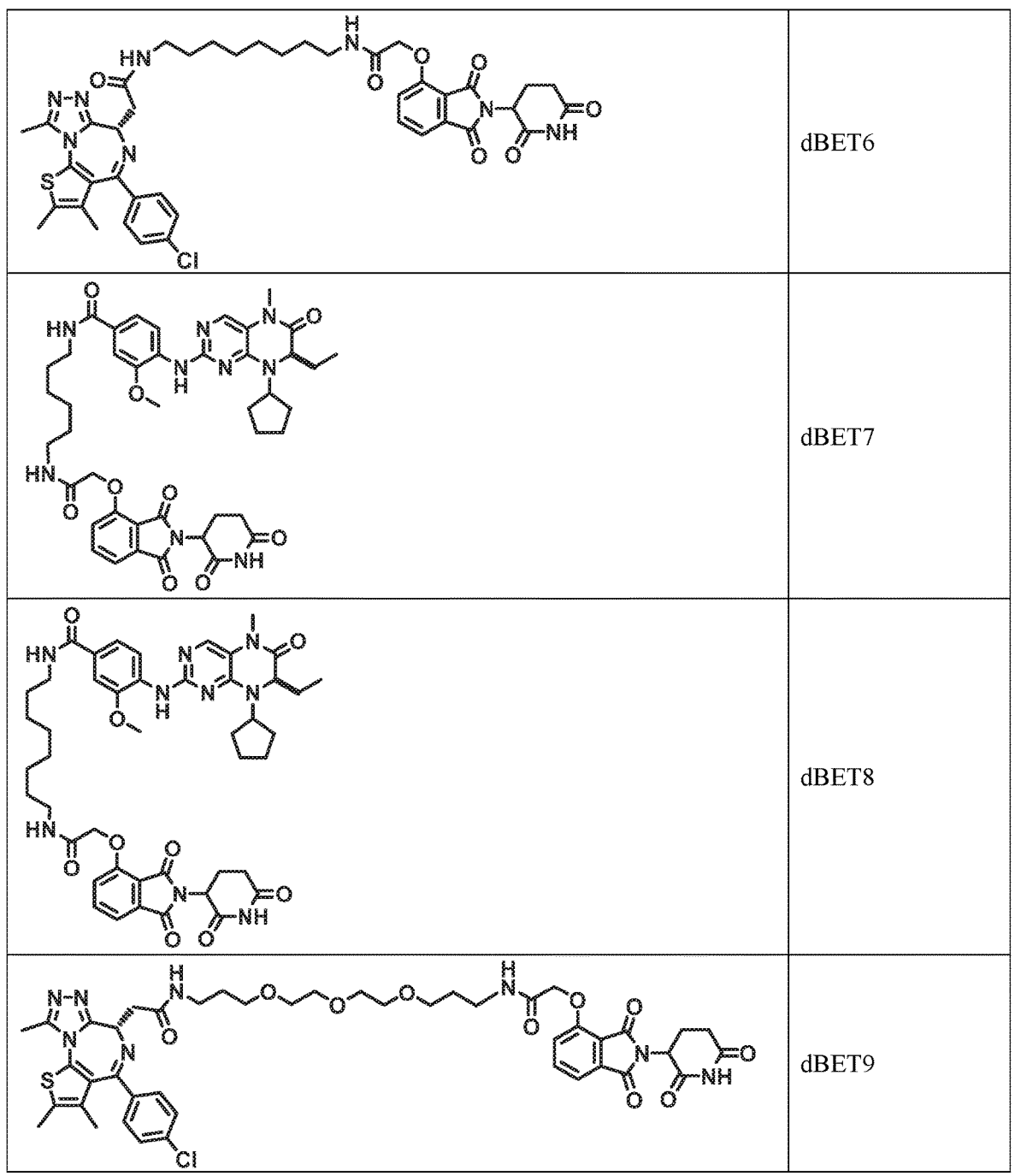
Figure 50C:
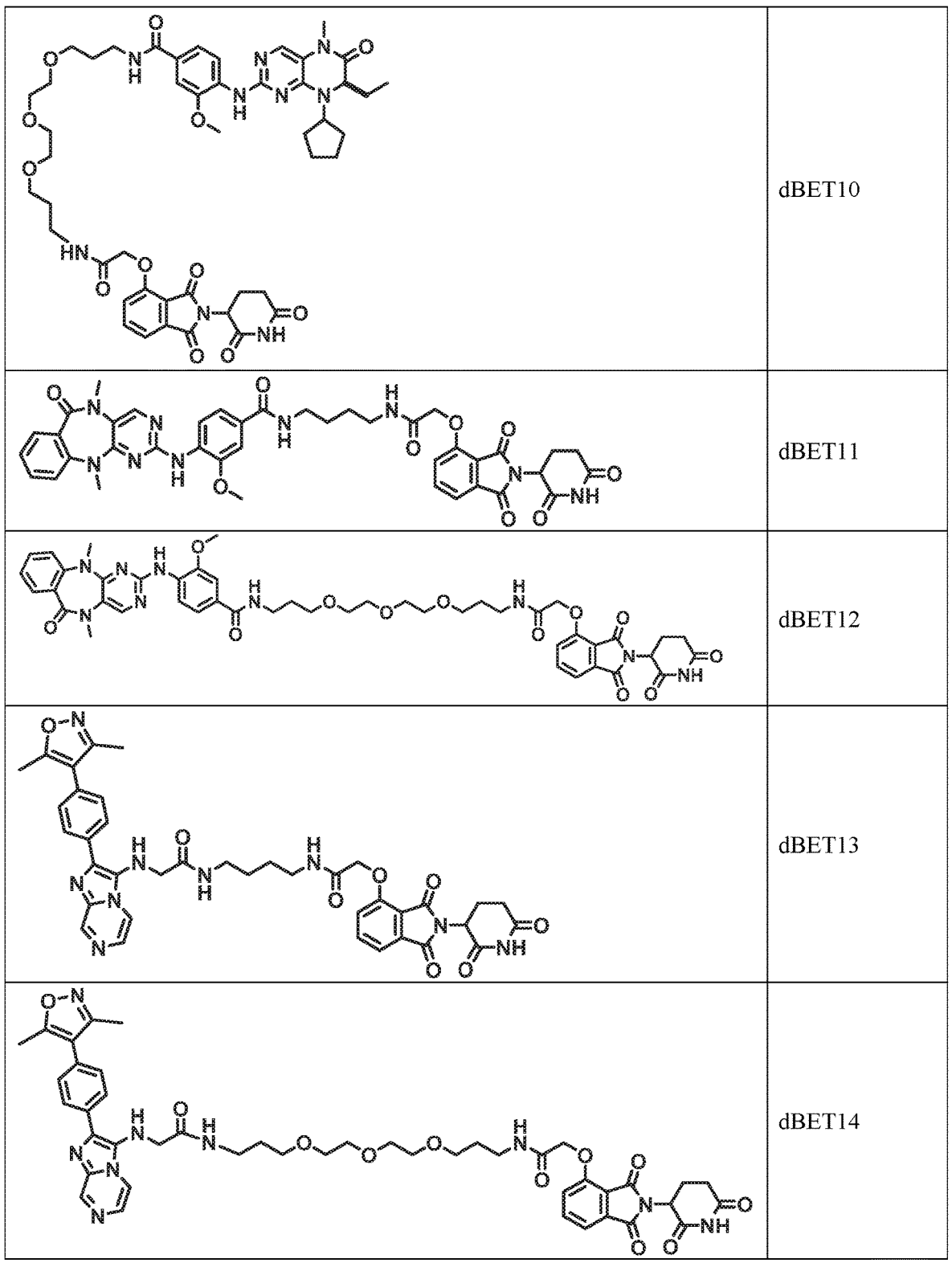
Figure 50D:
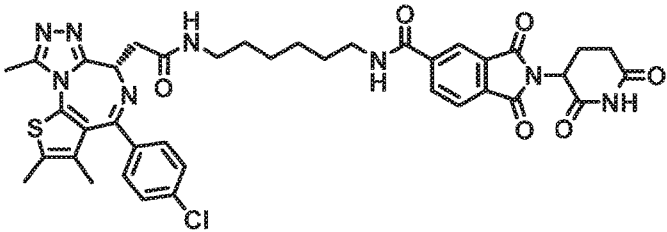
Figure 50D:
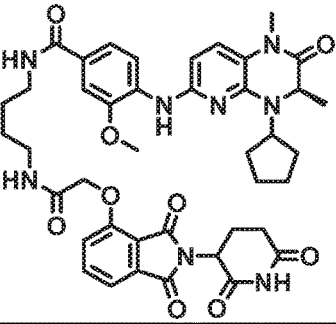
Figure 50D:
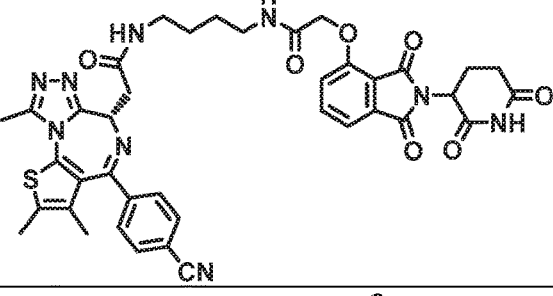
Figure 50D:
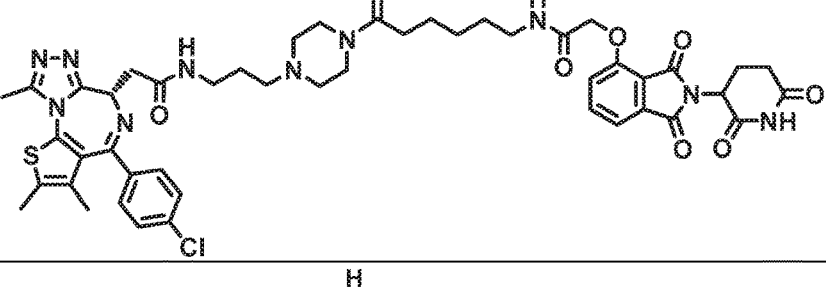
Figure 50D:
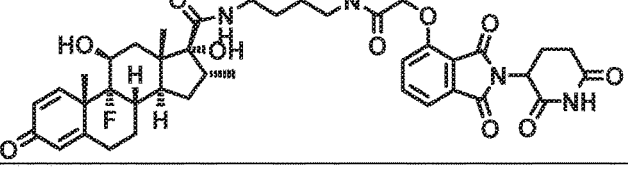
Figure 50D:
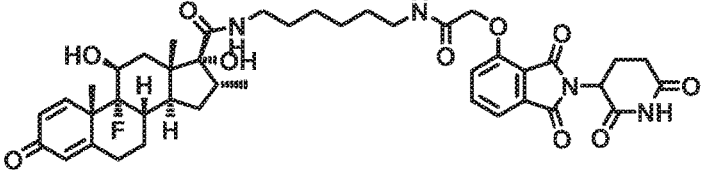
Figure 50E:
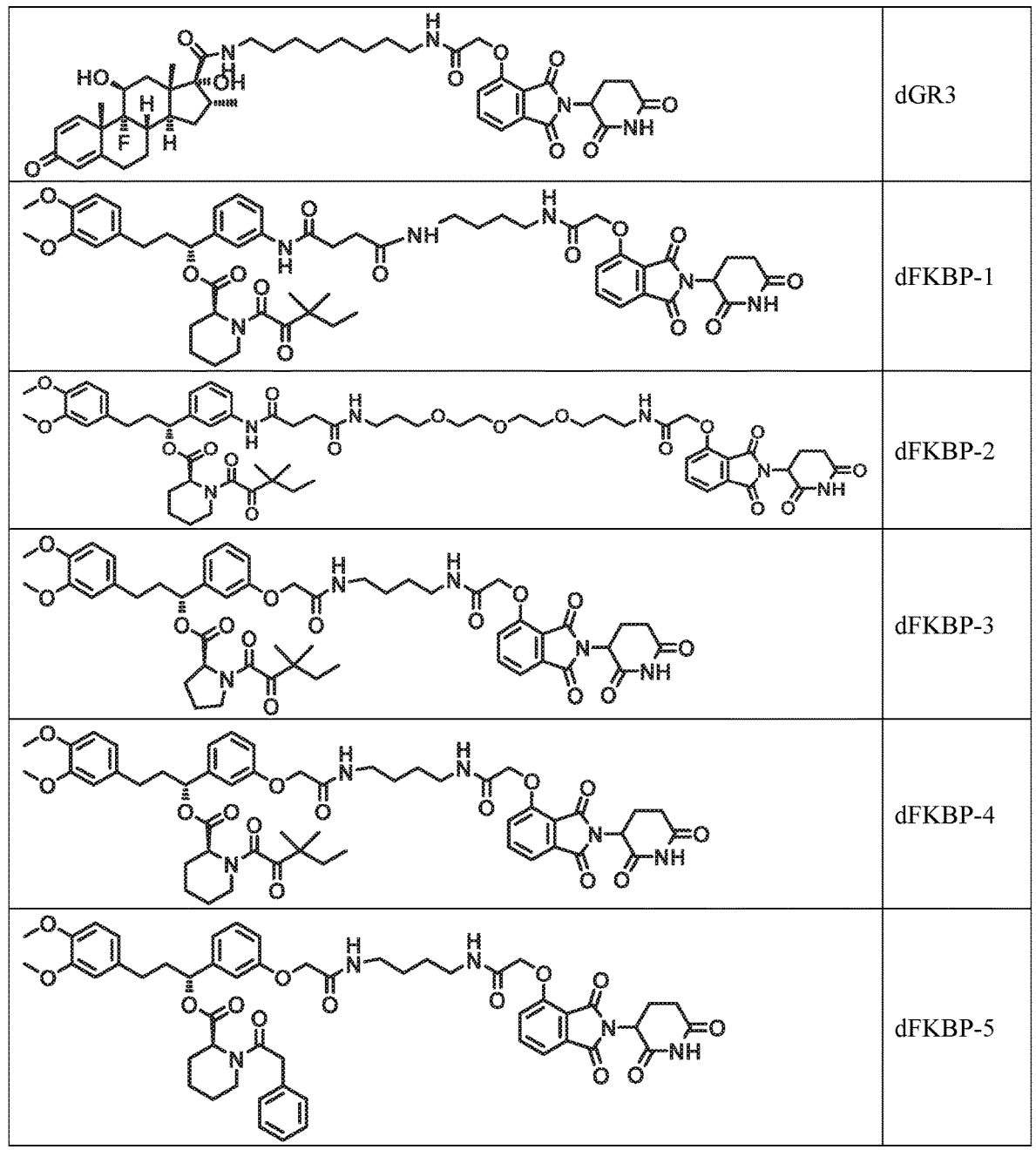
Figure 50F:
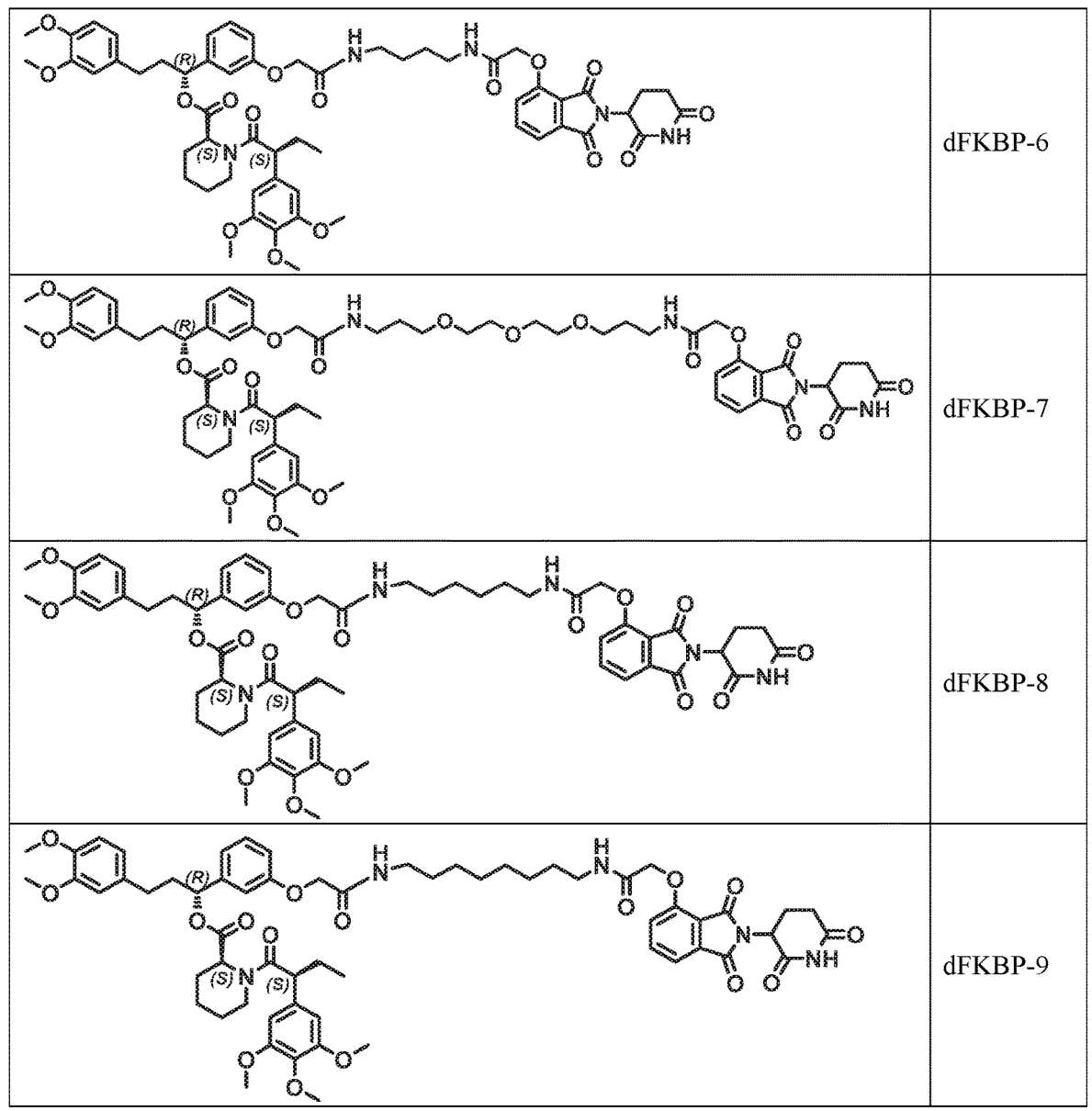
Figure 50G:
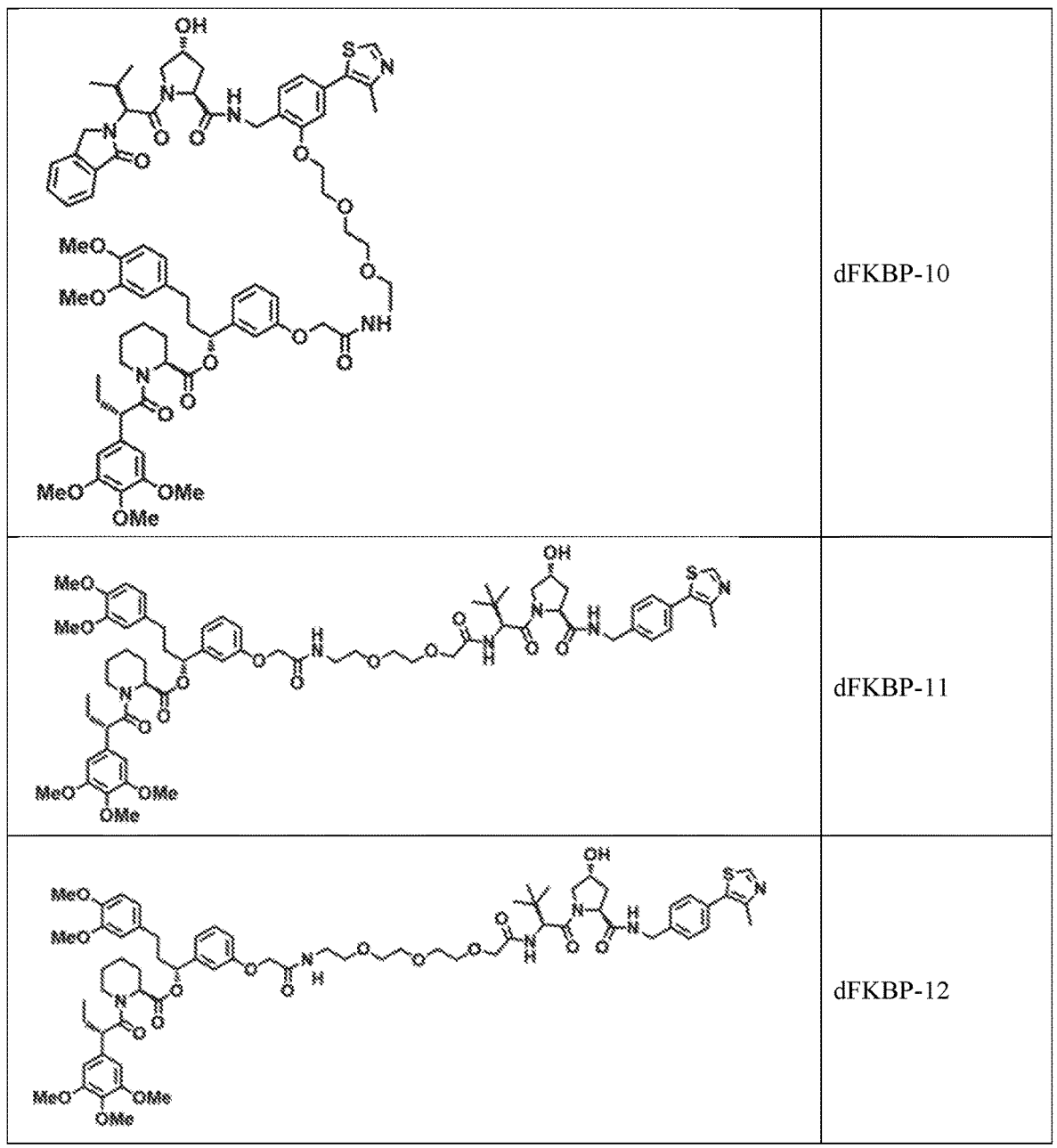
Figure 50H:
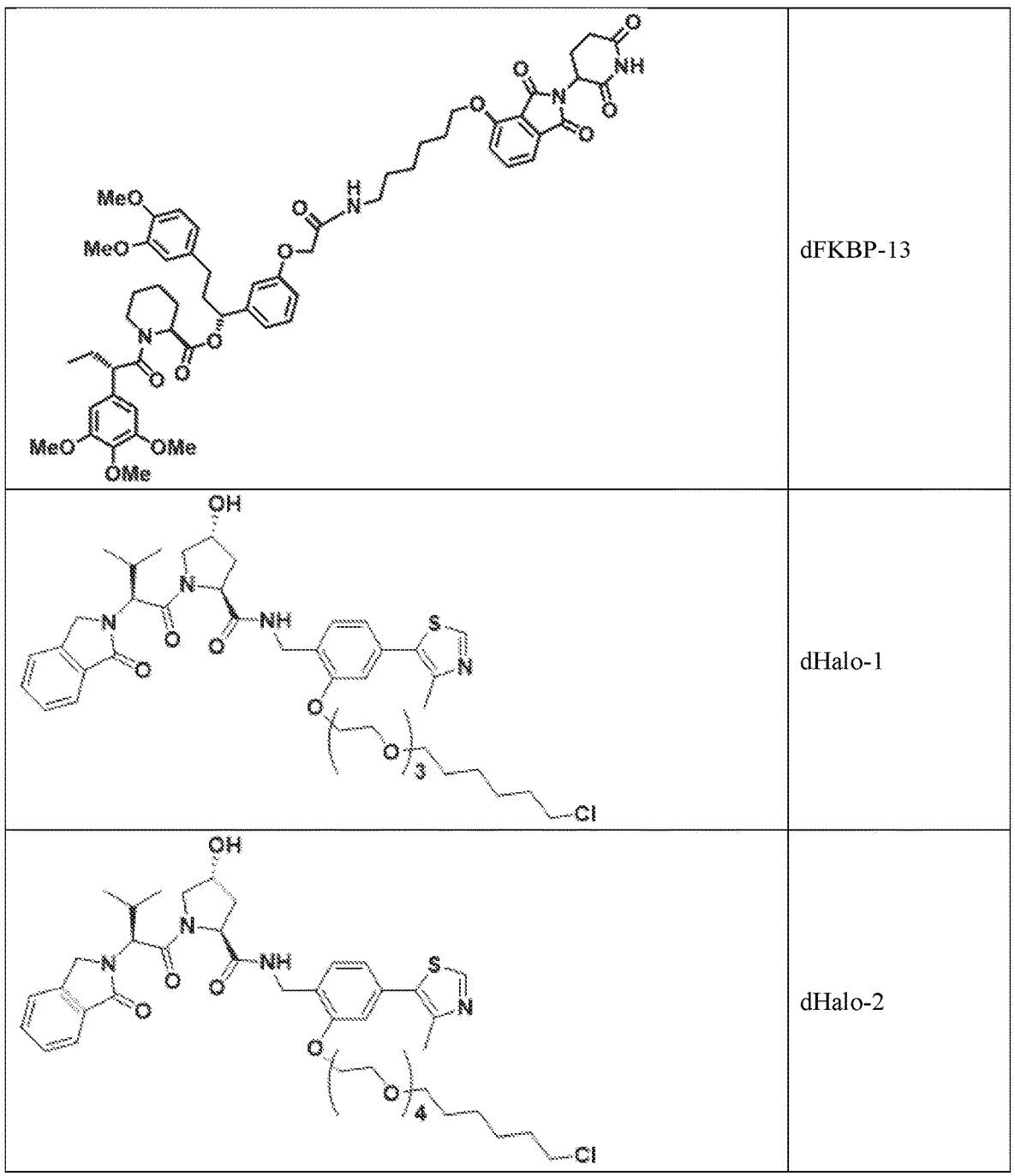
Figure 51A:
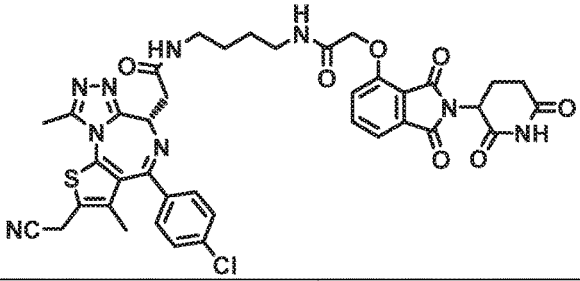
Figure 51A:
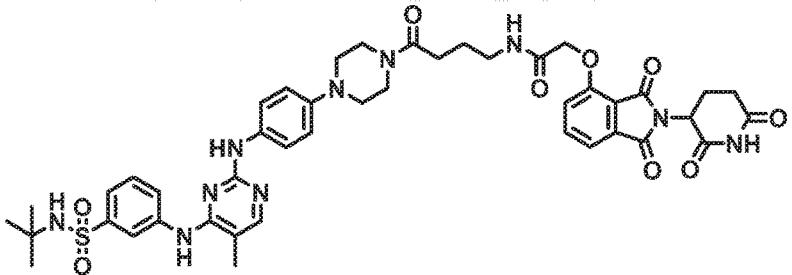
Figure 51A:
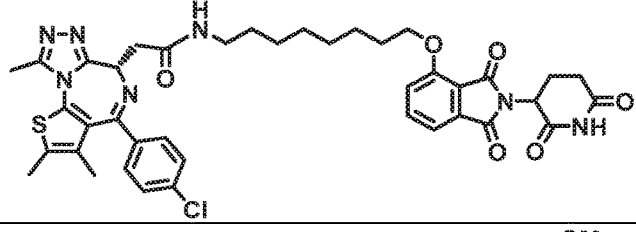
Figure 51A:
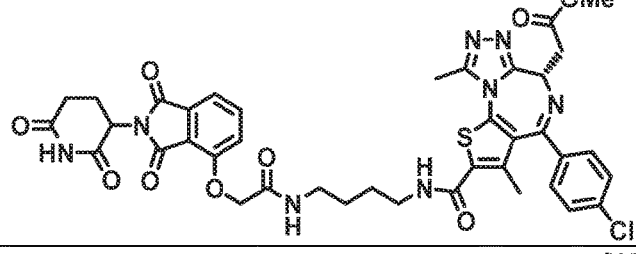
Figure 51A:
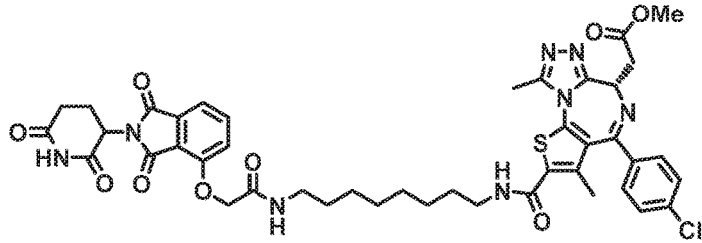
Figure 51C:
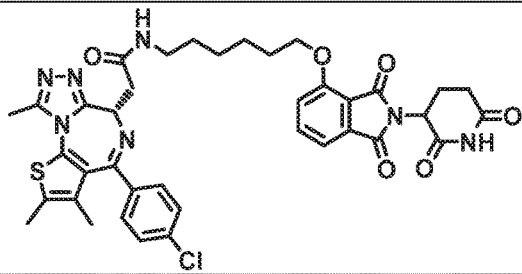
Figure 51C:
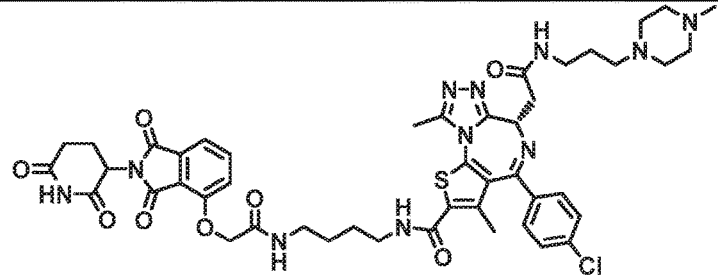
Figure 51C:
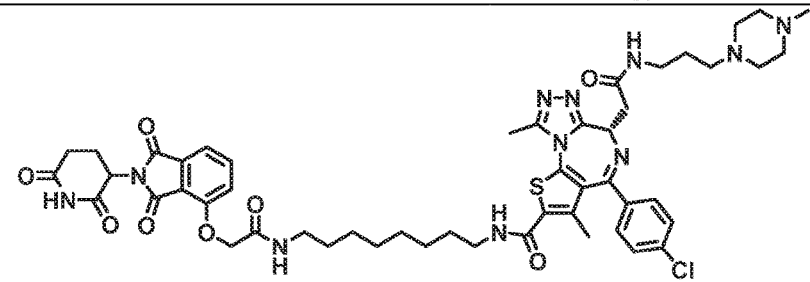
Figure 51C:
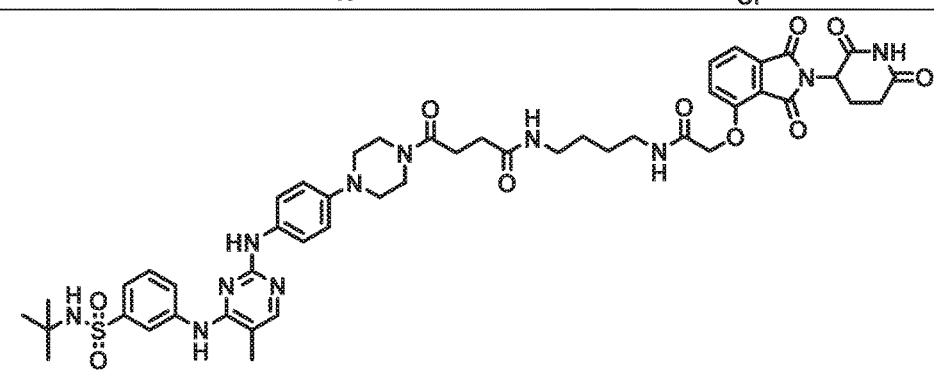
Figure 51C:
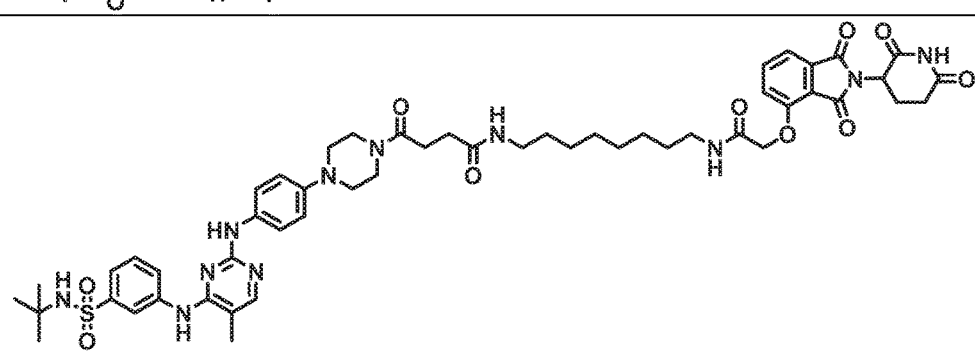
Figure 51D:
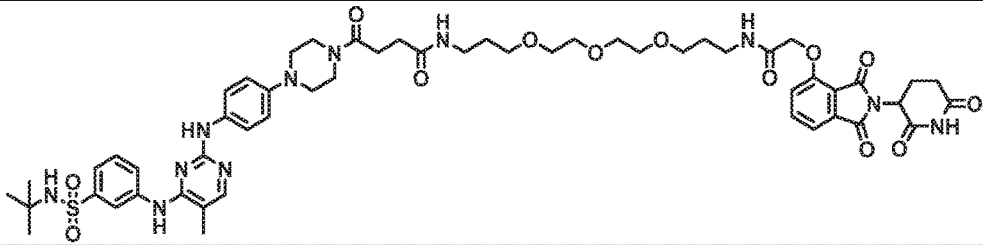
Figure 51D:
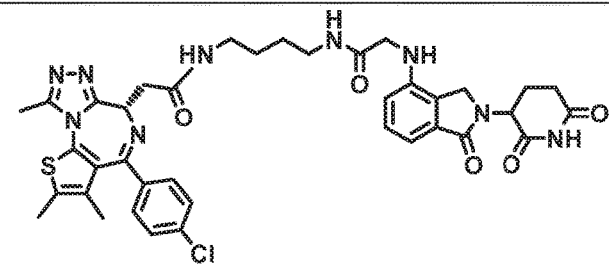
Figure 51D:
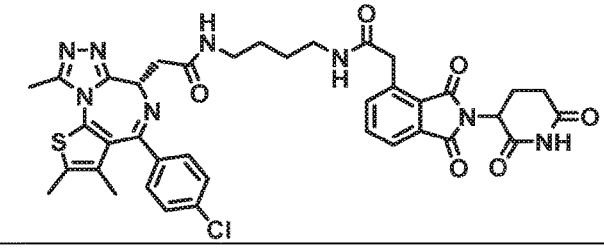
Figure 51D:
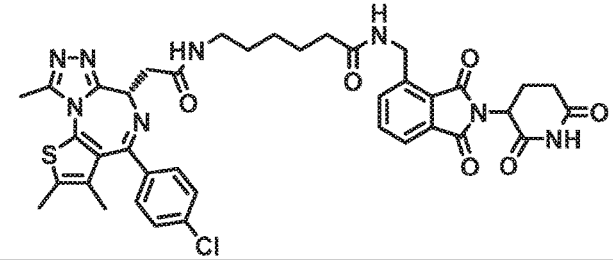
Figure 51D:
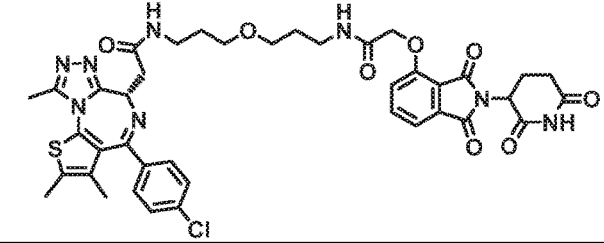
Figure 51D:
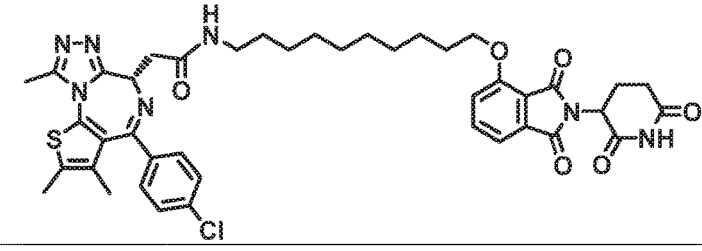
Figure 51E:
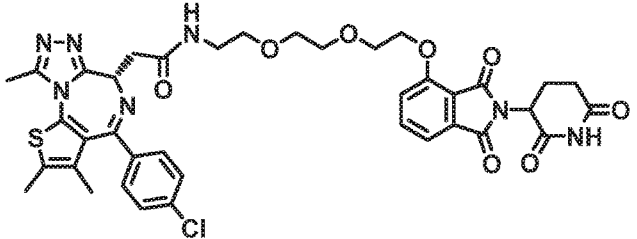
Figure 51E:
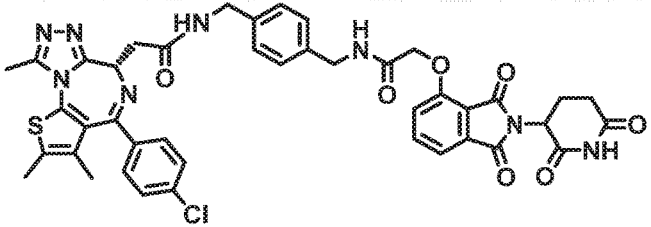
Figure 51E:
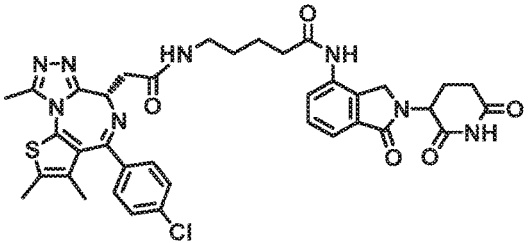
Figure 51E:
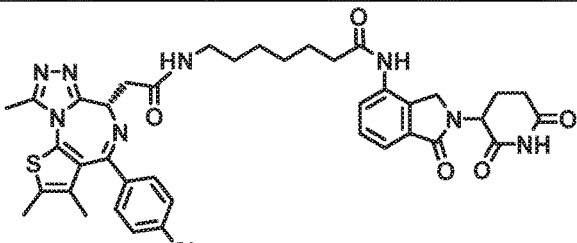
Figure 51E:
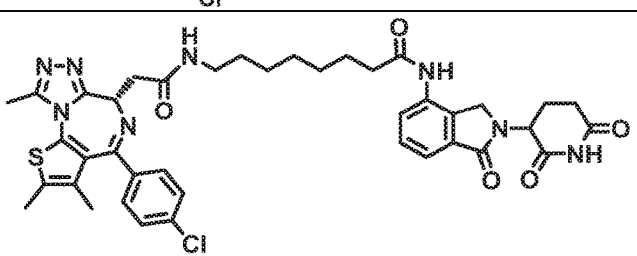
Figure 51G:
Figure 51H:
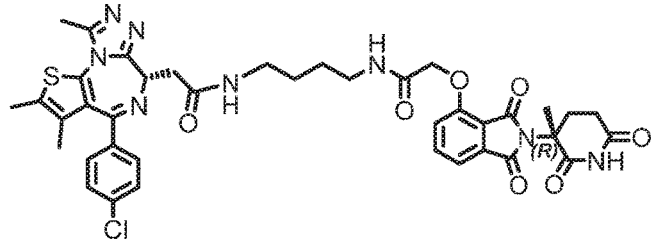
Figure 51I:
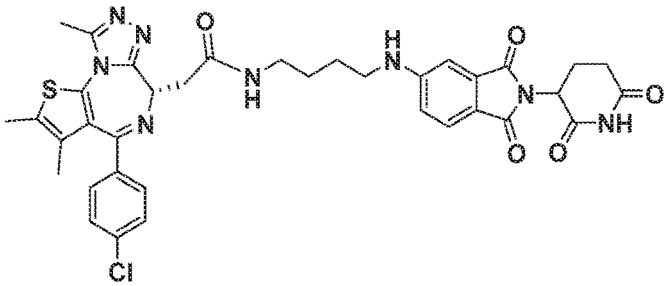
Figure 51I:
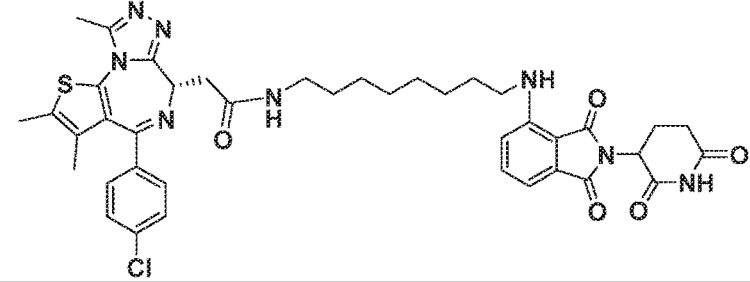
Figure 51I:
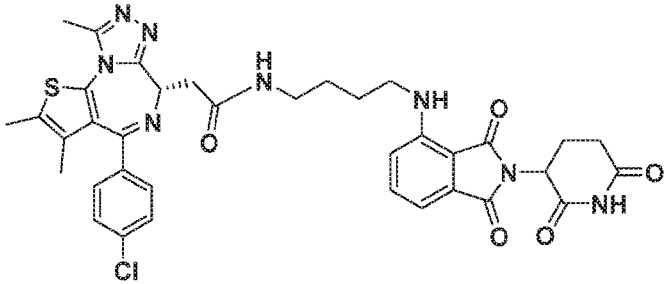
Figure 51I:
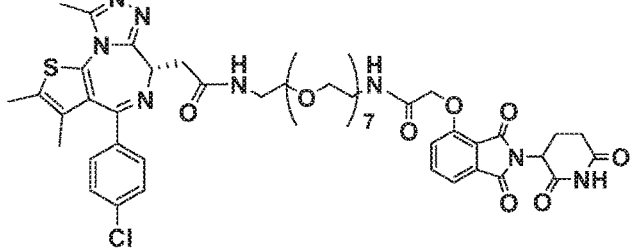
Figure 51I:
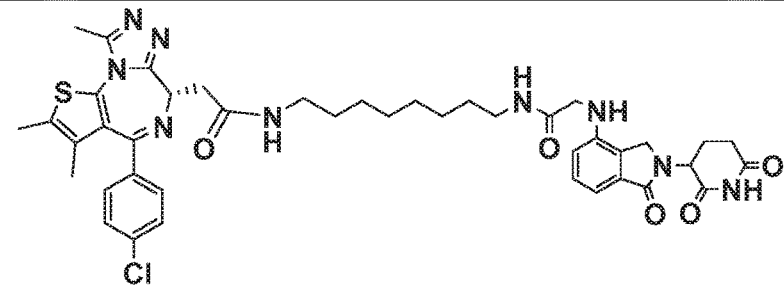
Figure 51J:
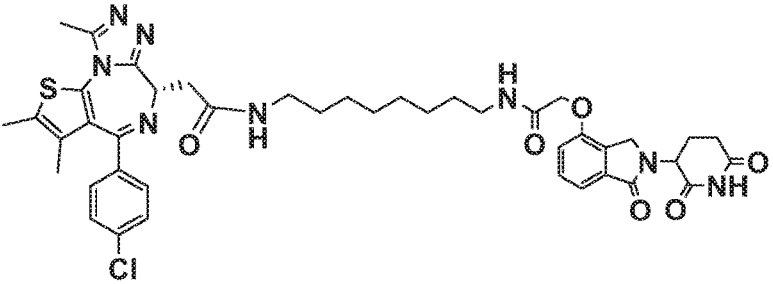
Figure 51K:
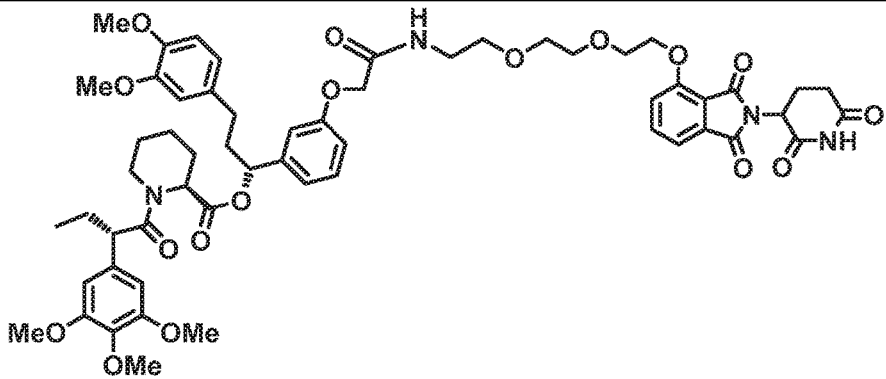
Figure 51K:
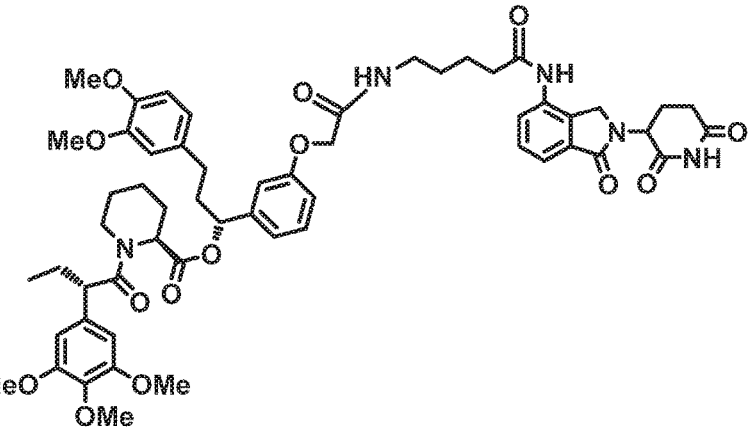
Figure 51K:
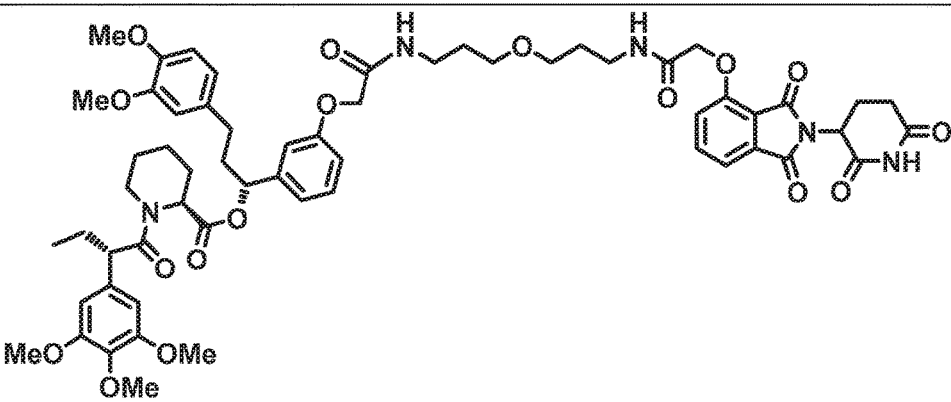
Figure 51L:
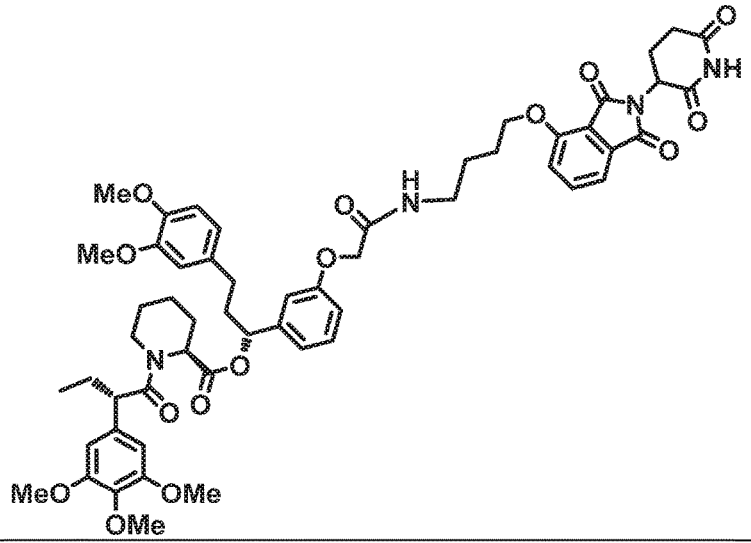
Figure 51L:
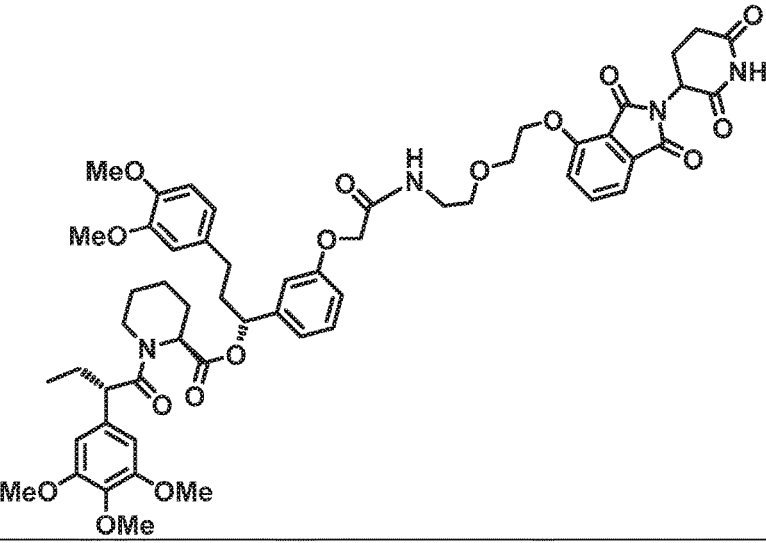
Figure 51L:
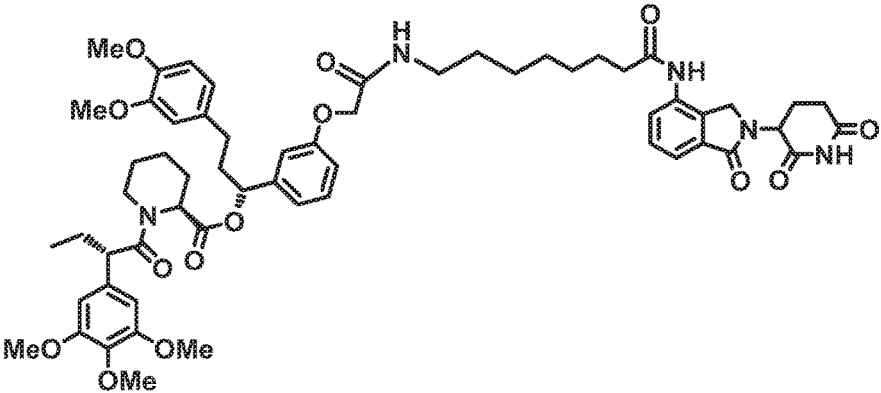
Figure 51M:
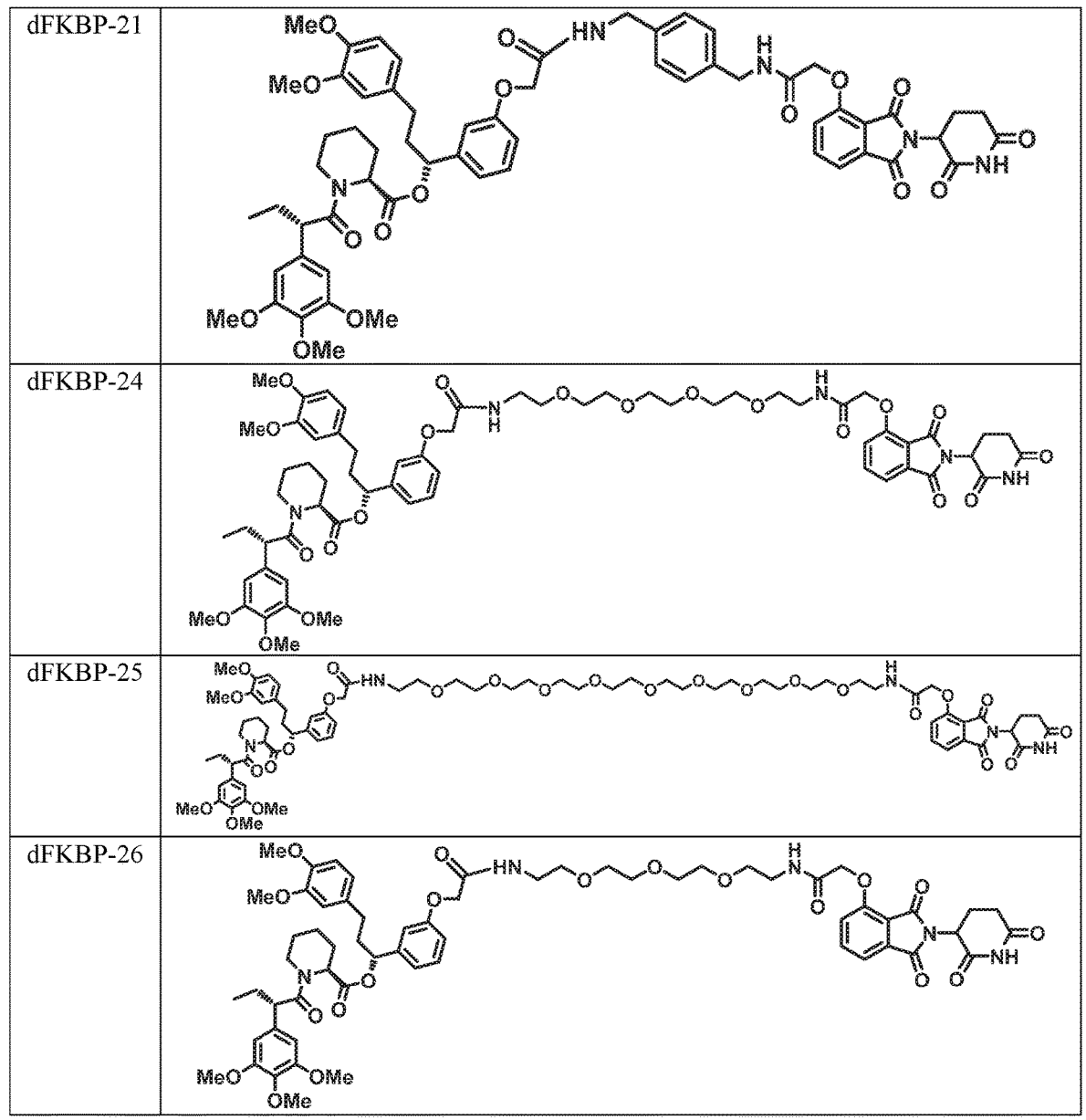
Figure 51N:
Figure 51N:
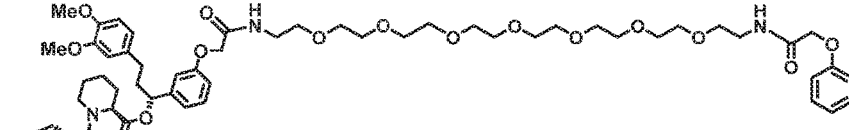
Figure 51N:
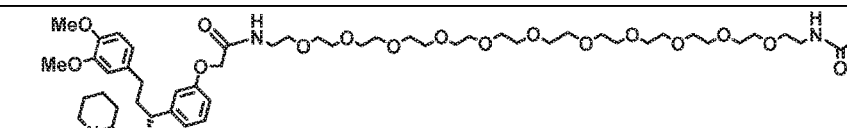
Figure 51N:
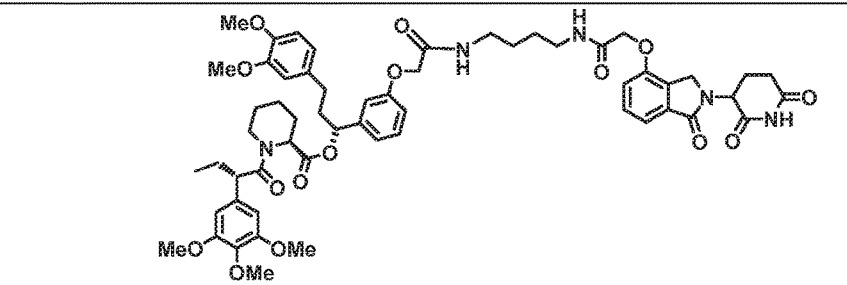
Figure 51N:
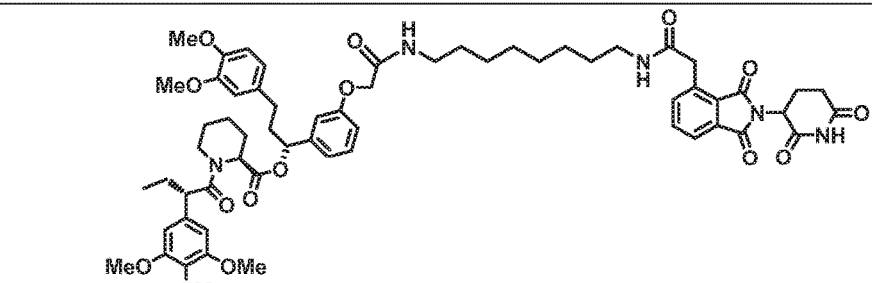
Figure 51O:
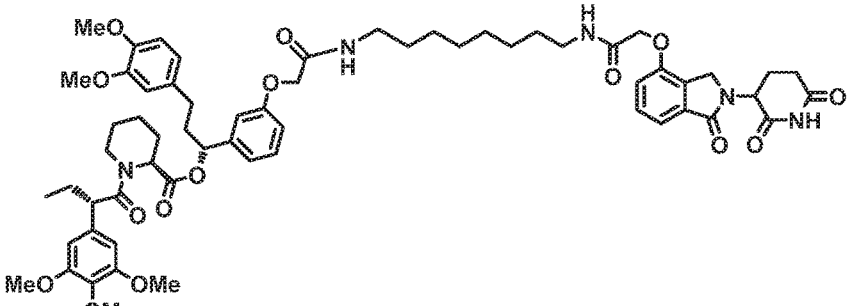
Figure 51O:
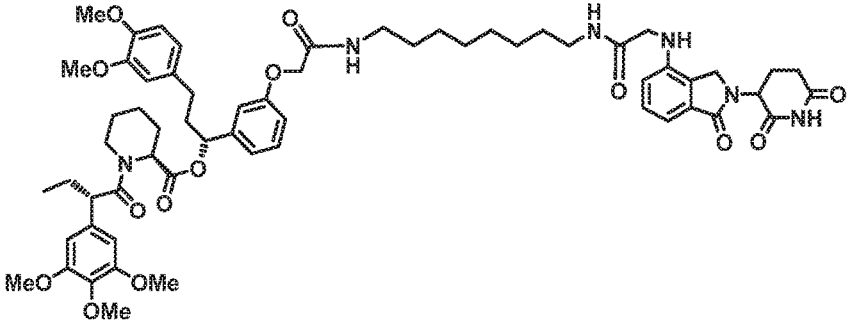
Figure 51O:
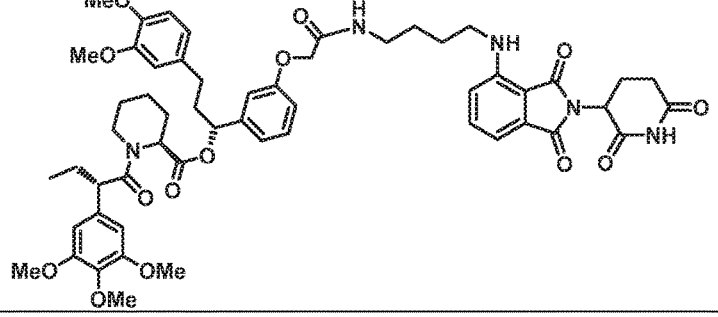
Figure 51O:
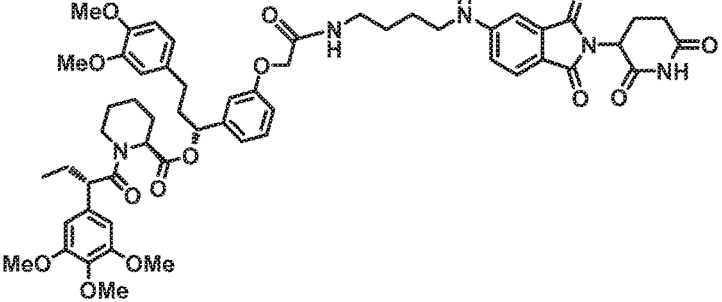
Figure 52A:
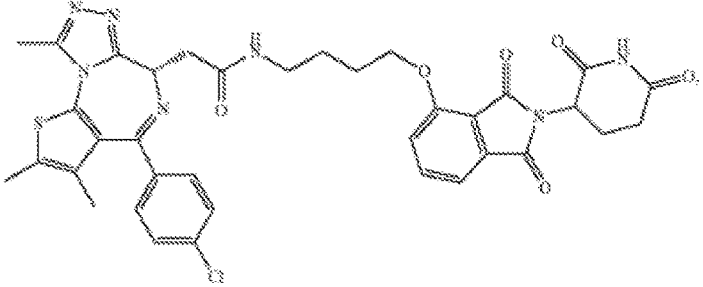
FIG. 52A, FIG. 52B, FIG. 52C, FIG. 52D, FIG. 52E, FIG. 52F, FIG. 52G, FIG. 52H, FIG. 52I, and FIG. 52J provide specific heterobifunctional compounds for use in the present invention.
Figure 52A:
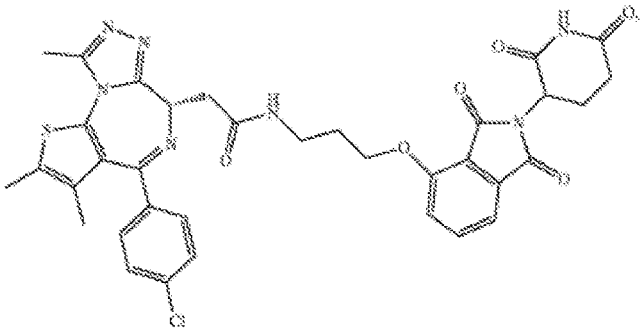
Figure 52A:
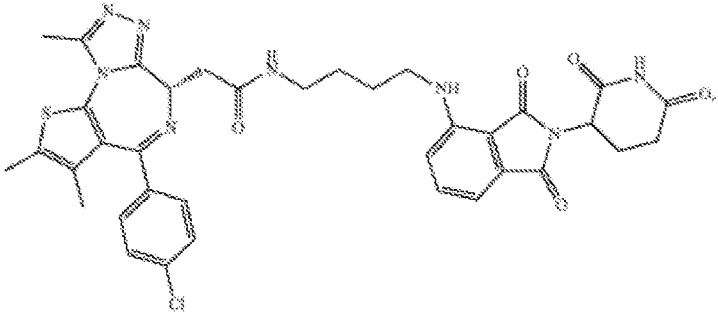
Figure 52A:
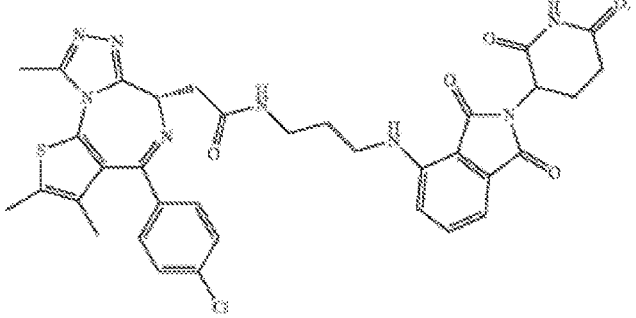
Figure 52B:
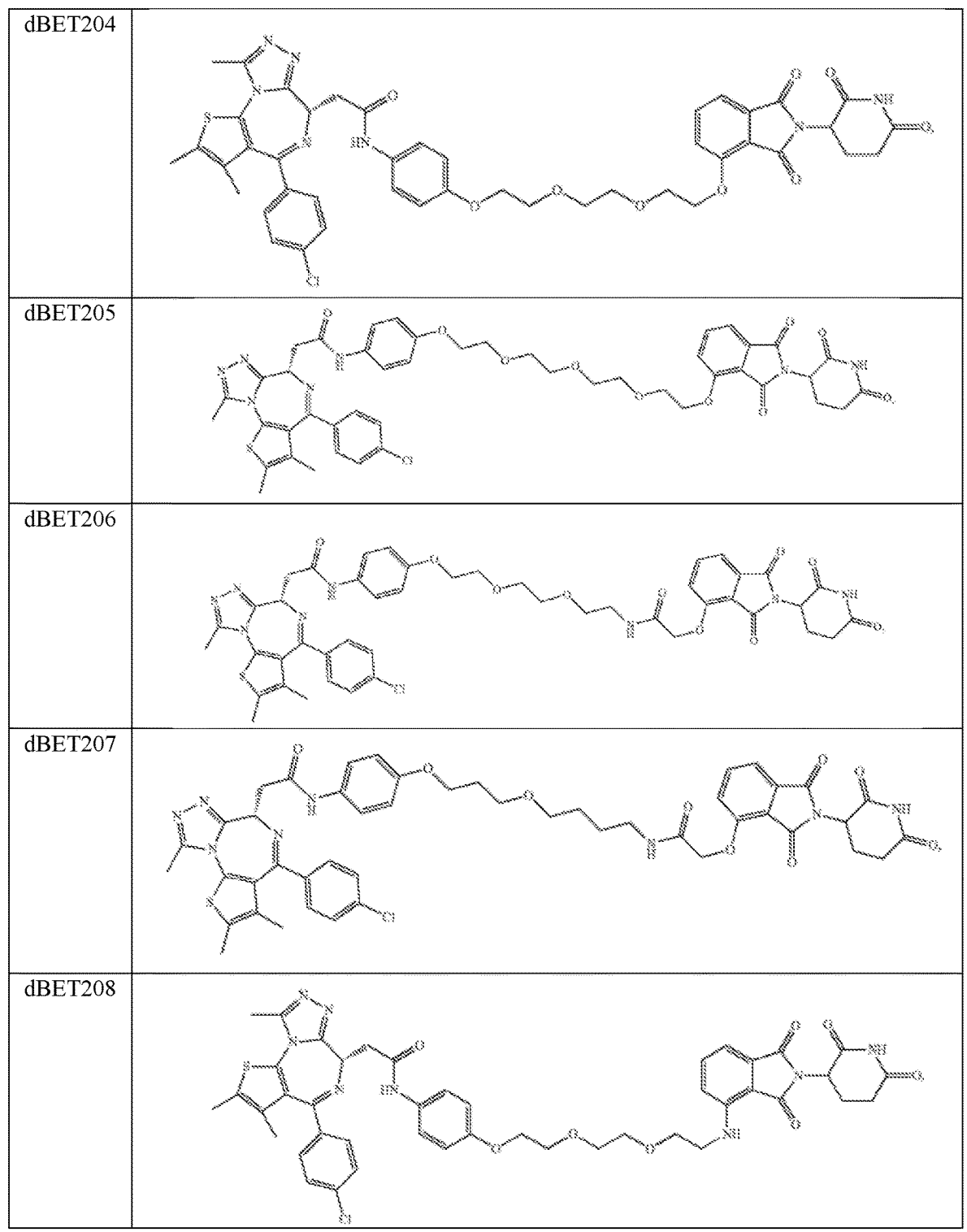
Figure 52C:
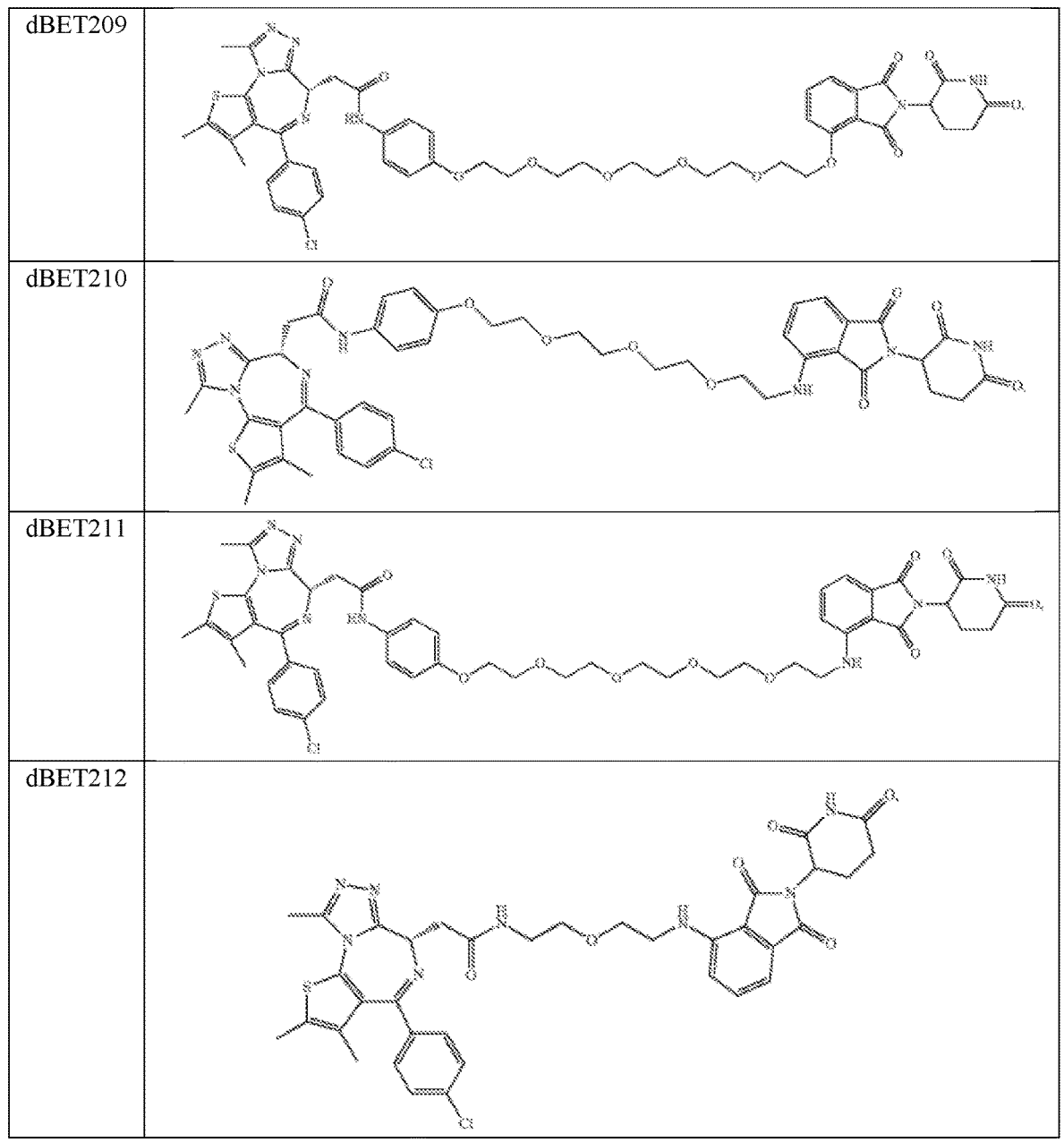
Figure 52D:
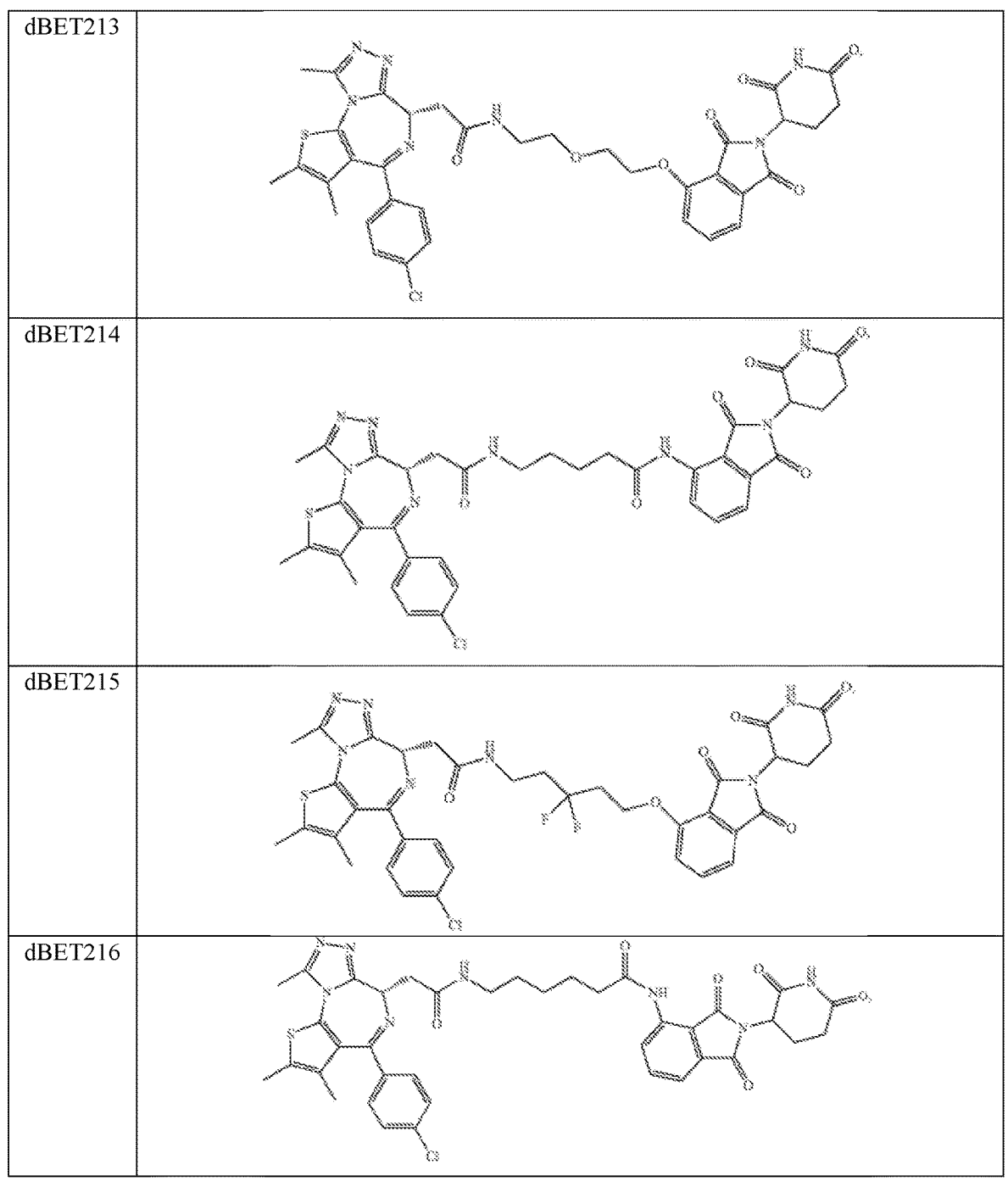
Figure 52E:
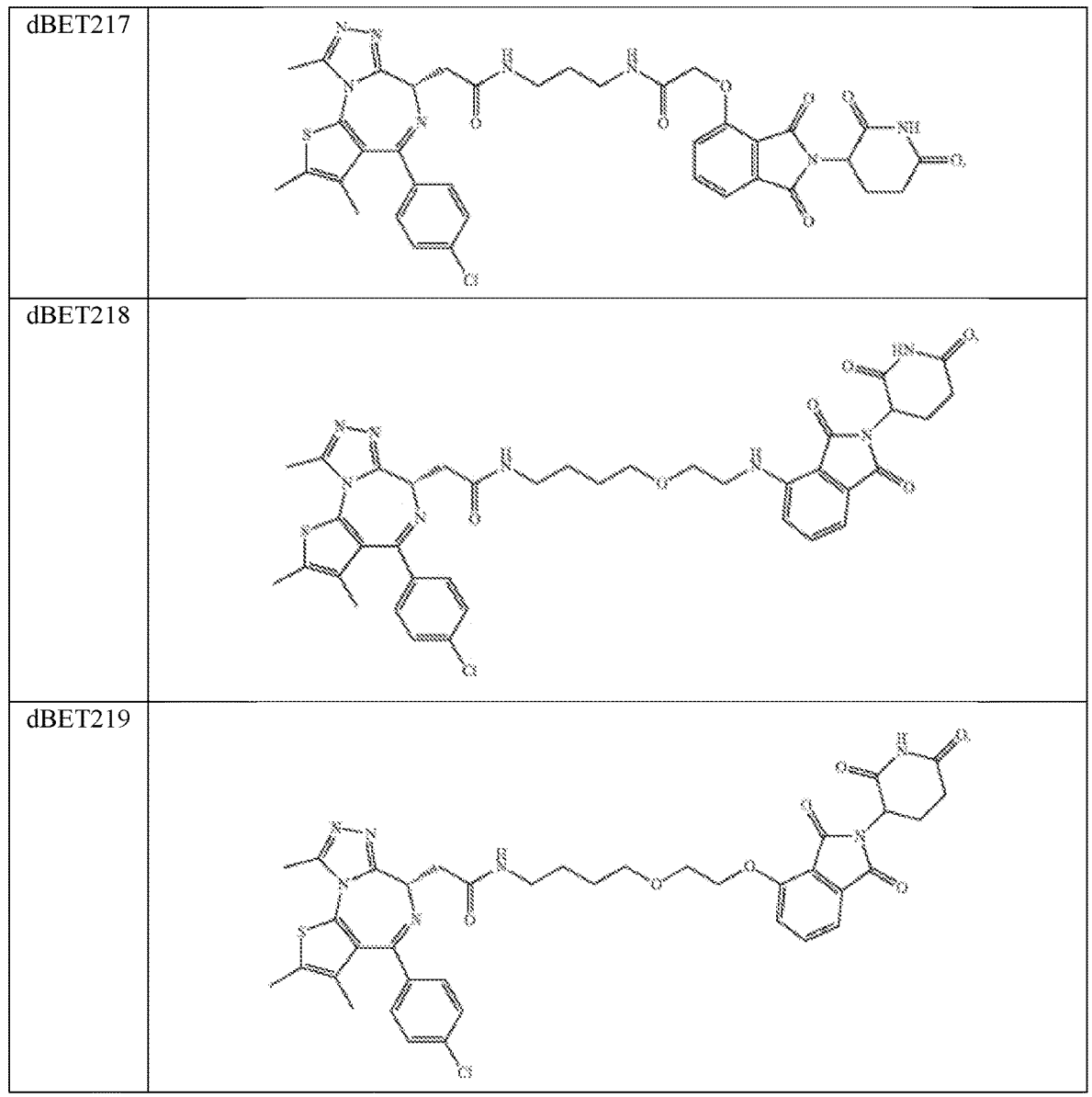
Figure 52F:
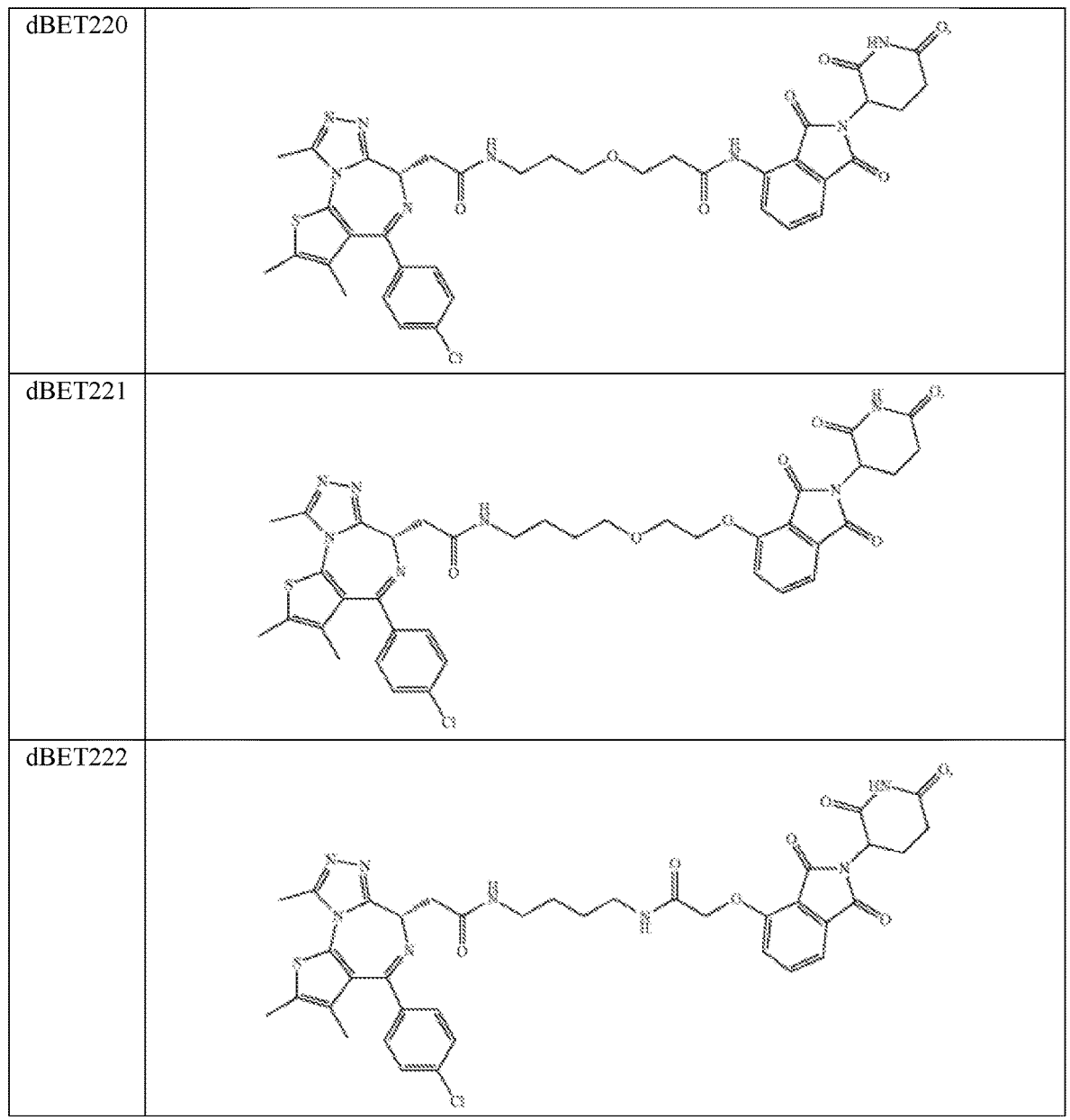
Figure 52G:
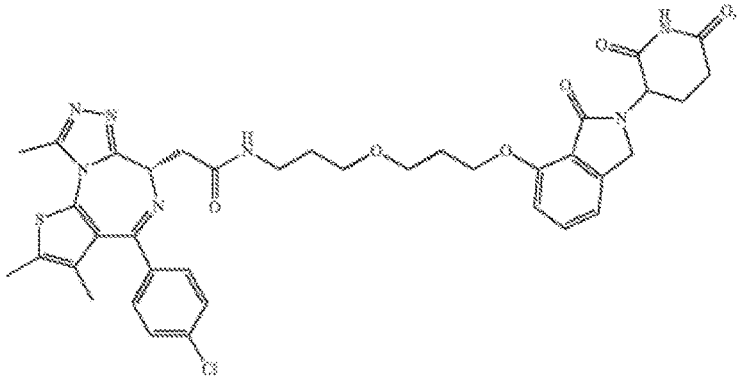
Figure 52G:
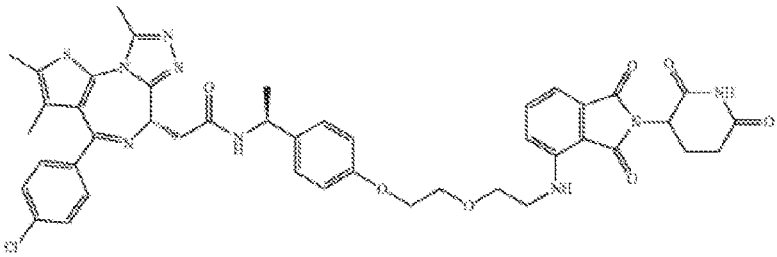
Figure 52G:
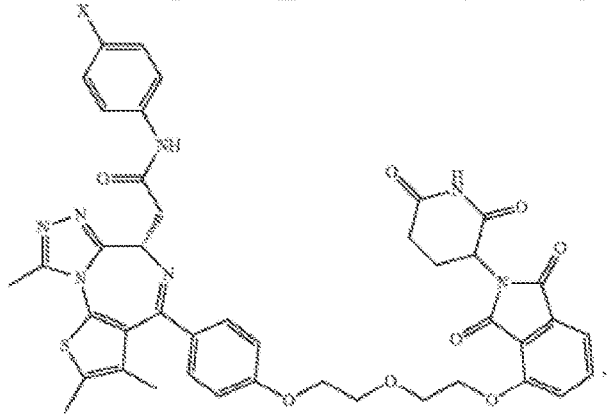
Figure 52G:
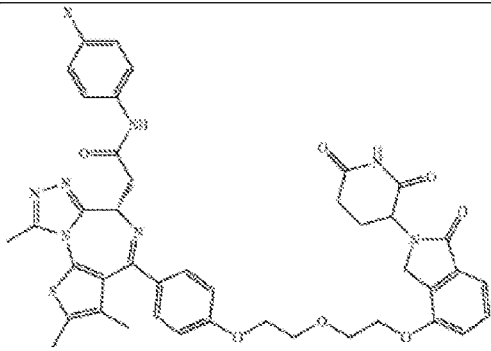
Figure 52H:
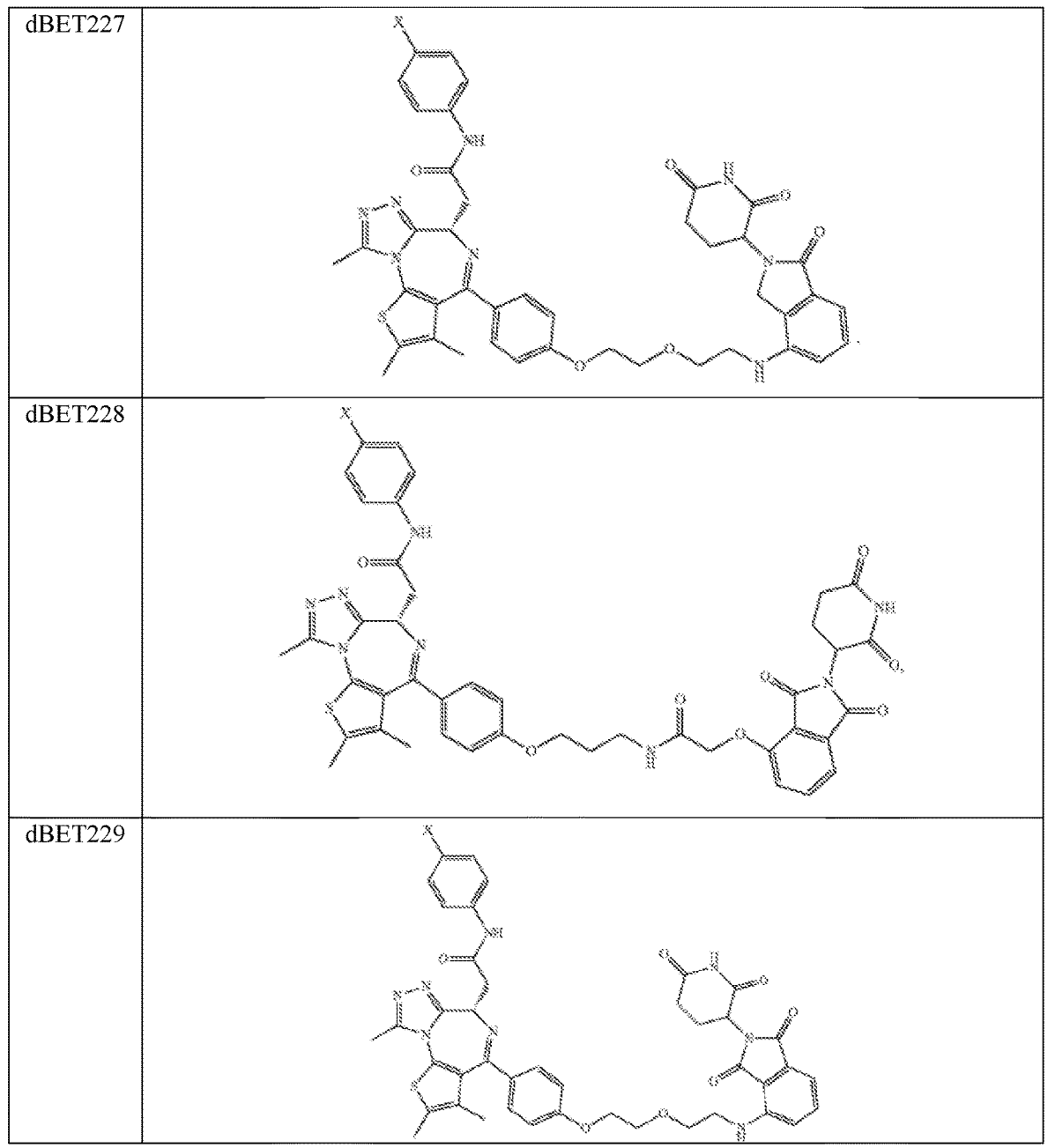
Figure 52I:
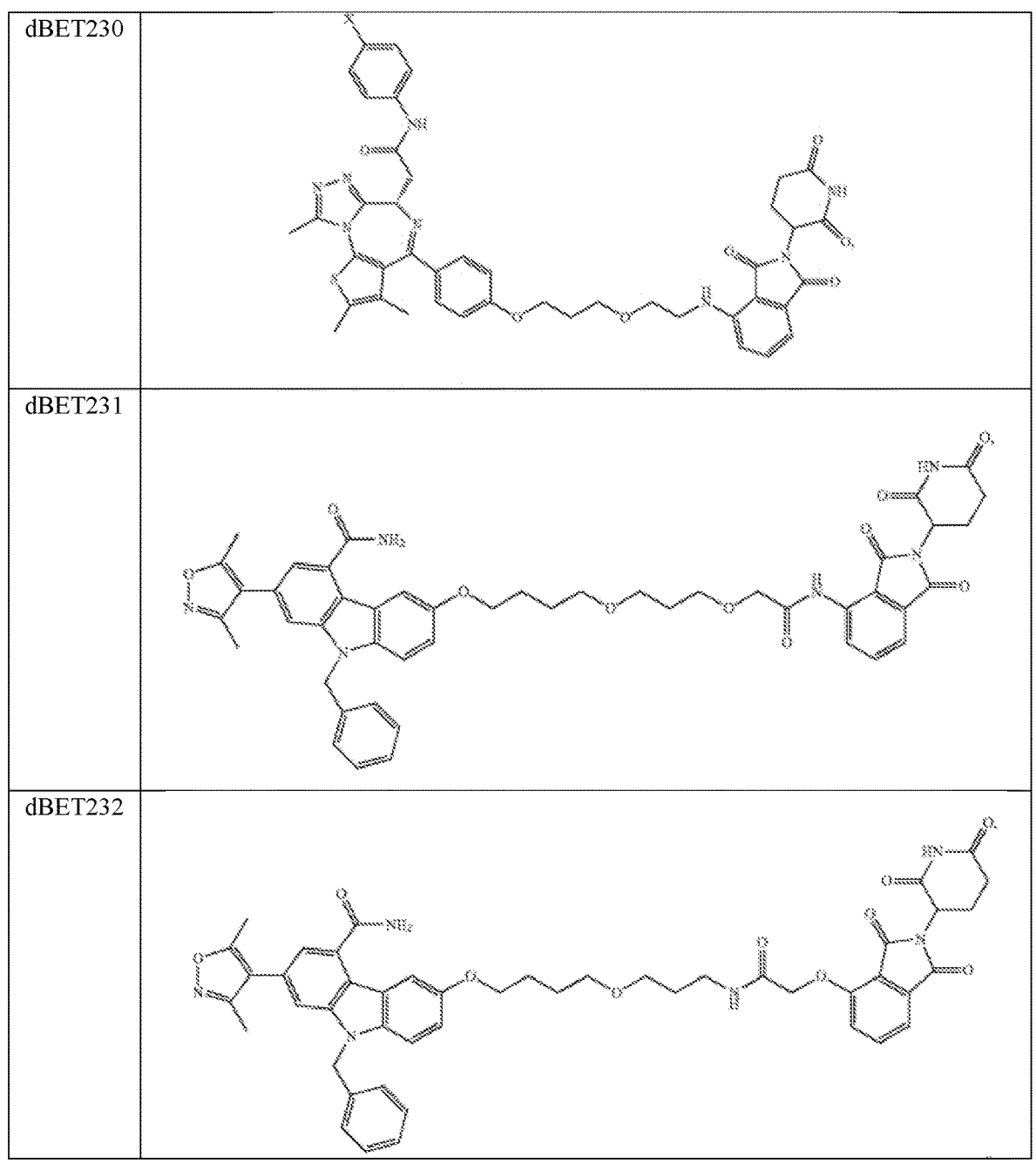
Figure 52J:
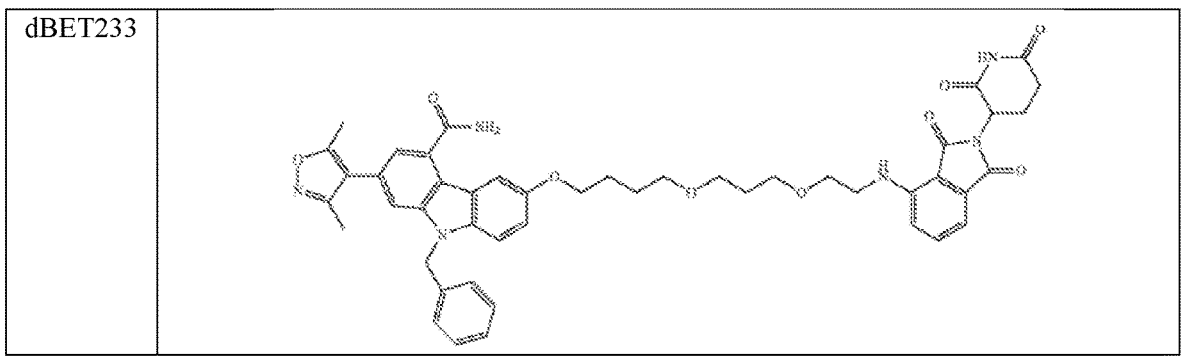
Figure 53B:
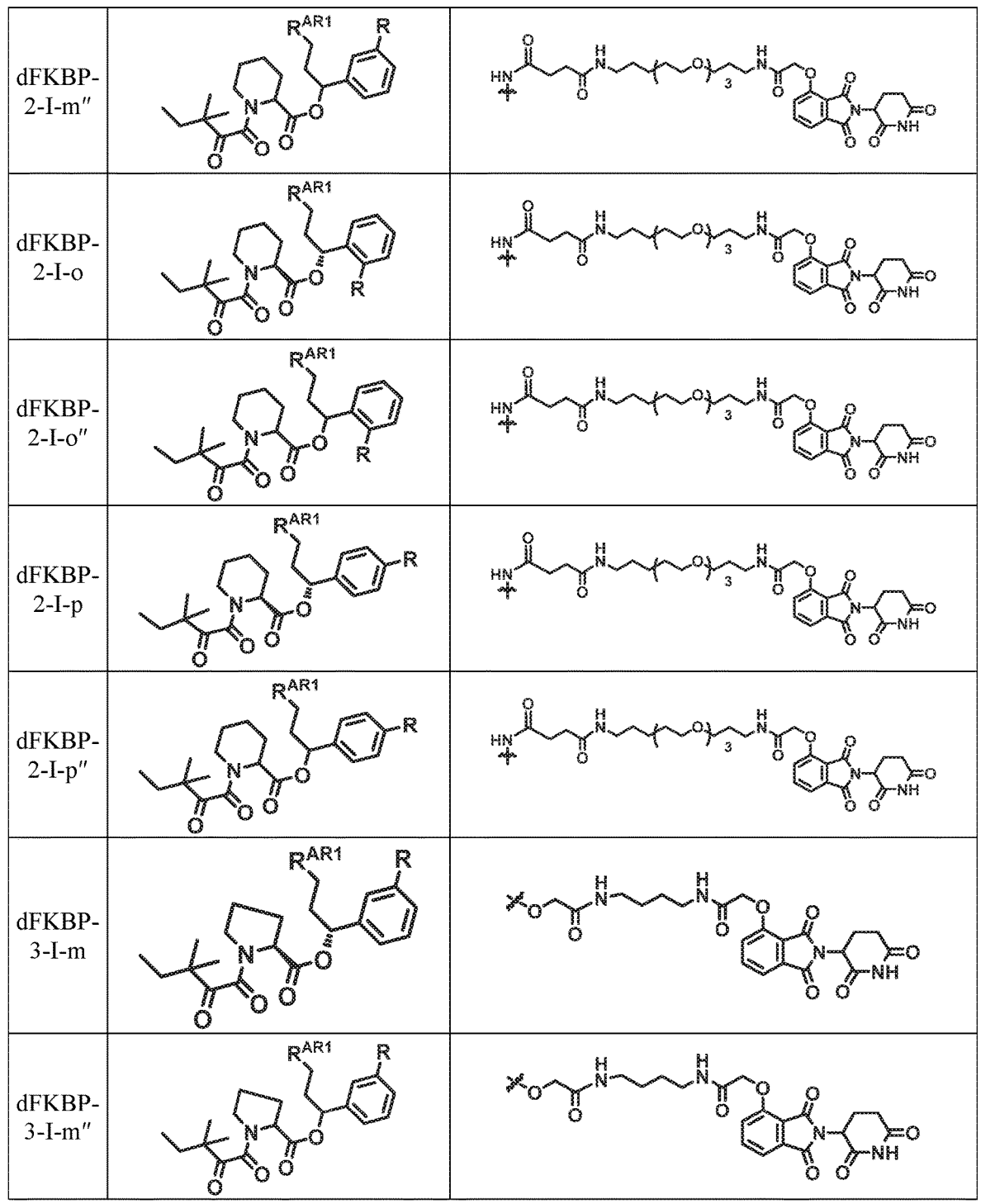
Figure 53C:
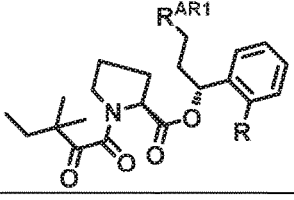
Figure 53C:
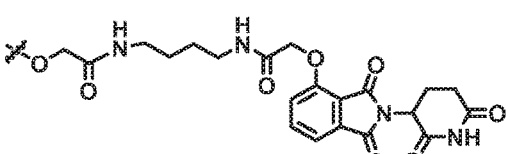
Figure 53C:
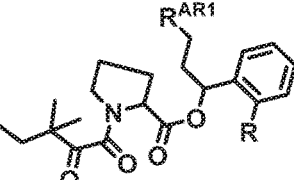
Figure 53C:
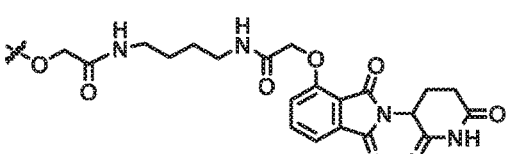
Figure 53C:
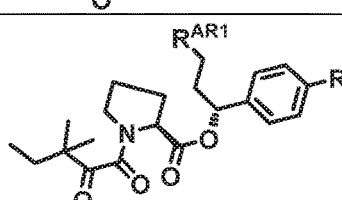
Figure 53C:
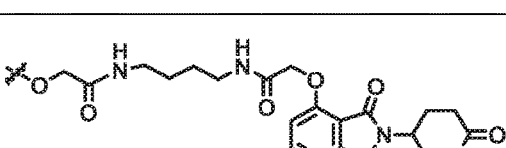
Figure 53C:
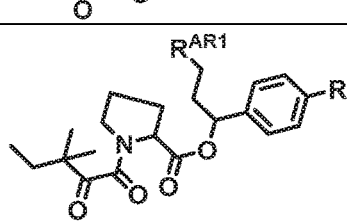
Figure 53C:
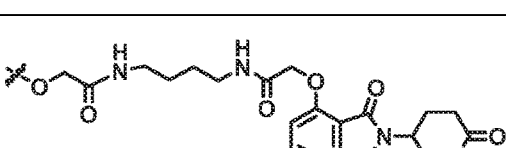
Figure 53C:
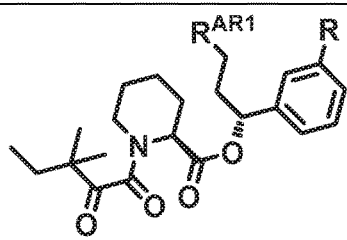
Figure 53C:
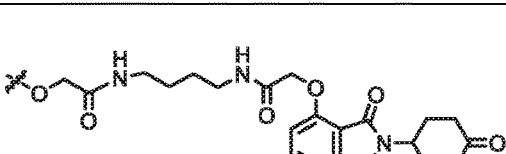
Figure 53C:
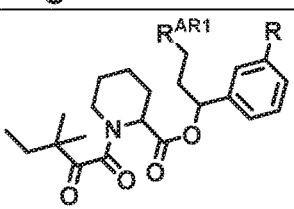
Figure 53C:
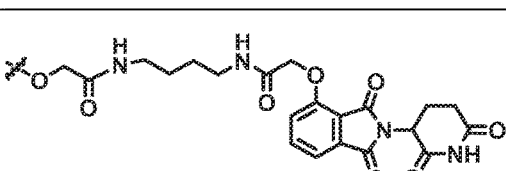
Figure 53C:
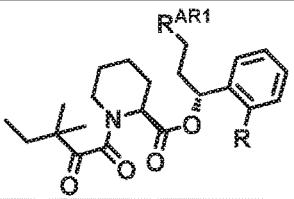
Figure 53C:
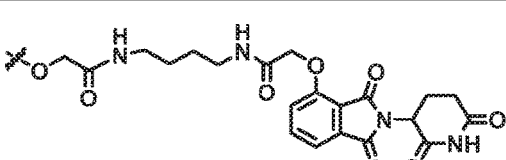
Figure 53D:
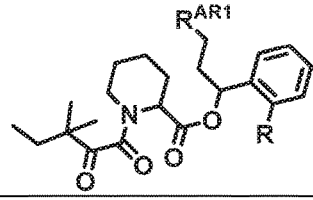
Figure 53D:
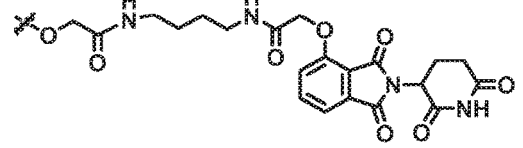
Figure 53D:
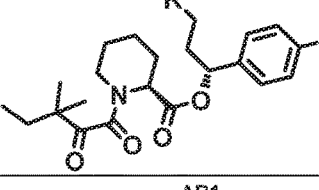
Figure 53D:
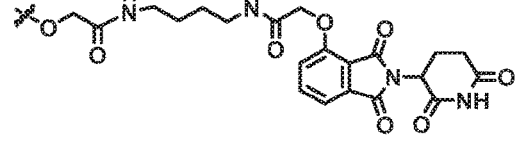
Figure 53D:
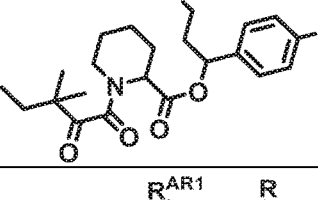
Figure 53D:
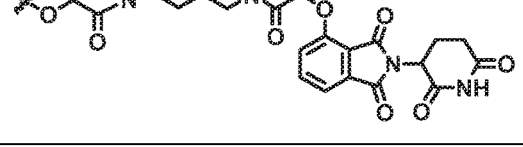
Figure 53D:
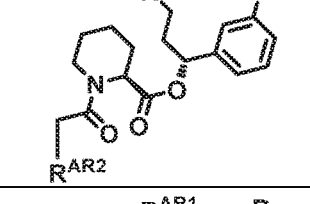
Figure 53D:
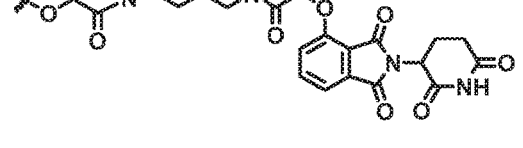
Figure 53D:
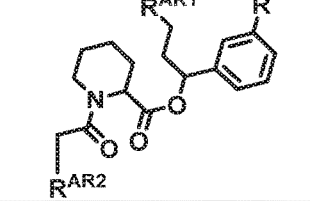
Figure 53D:
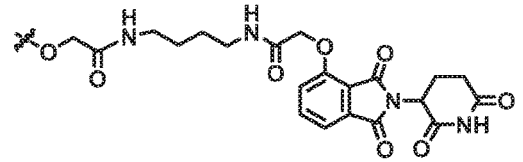
Figure 53D:
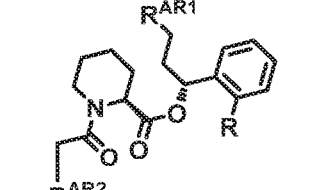
Figure 53D:
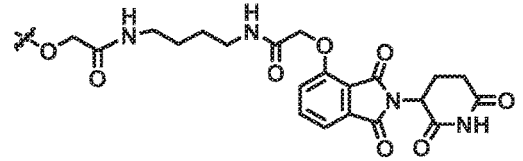
Figure 53D:
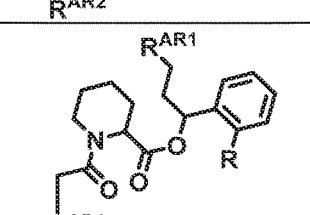
Figure 53D:
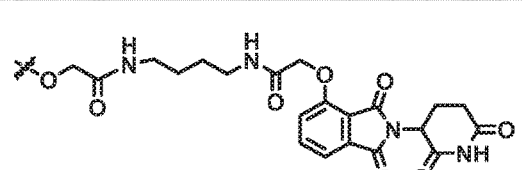
Figure 53H:
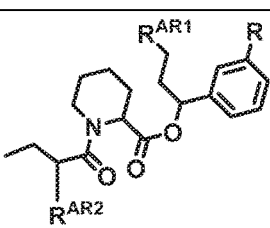
Figure 53I:
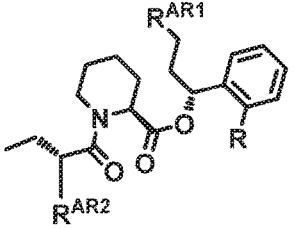
Figure 53I:
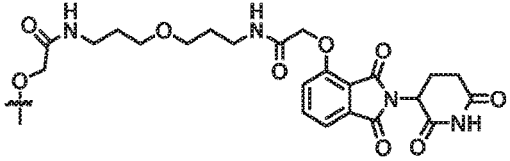
Figure 53I:
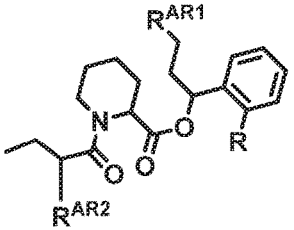
Figure 53I:
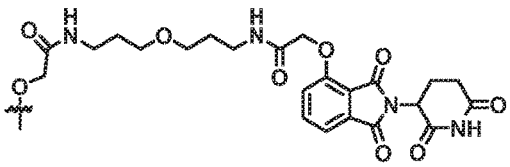
Figure 53I:
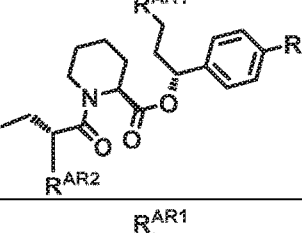
Figure 53I:
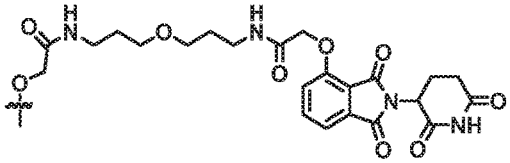
Figure 53I:
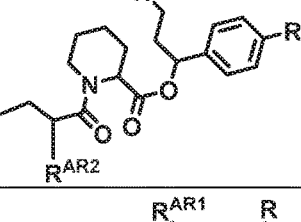
Figure 53I:
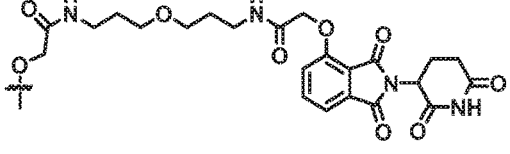
Figure 53I:
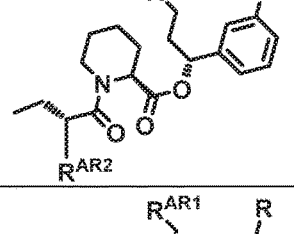
Figure 53I:
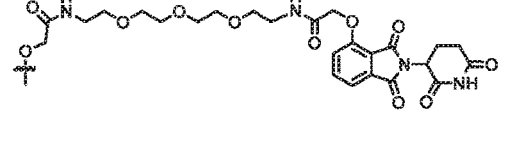
Figure 53I:
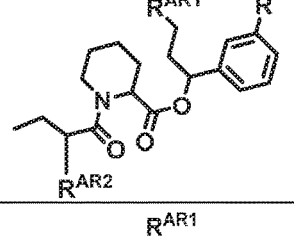
Figure 53I:
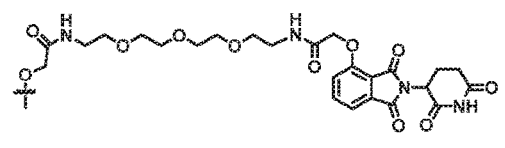
Figure 53I:
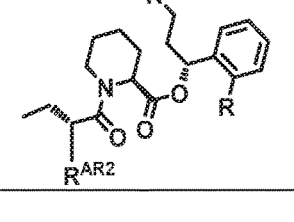
Figure 53I:
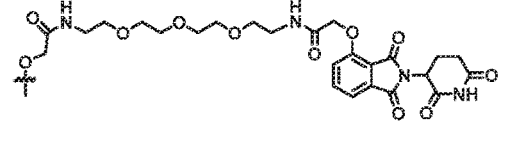
Figure 53J:
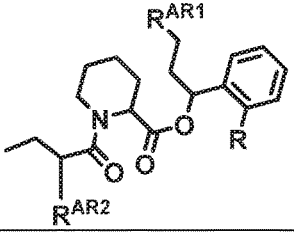
Figure 53J:
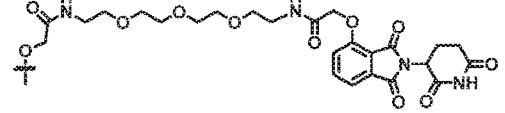
Figure 53J:
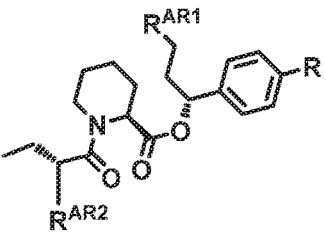
Figure 53J:
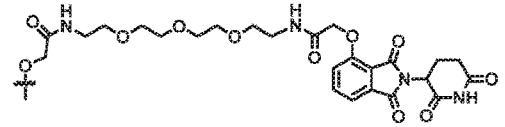
Figure 53J:
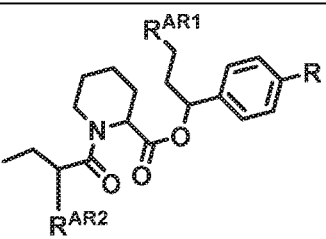
Figure 53J:
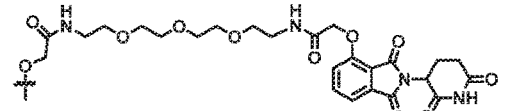
Figure 53J:
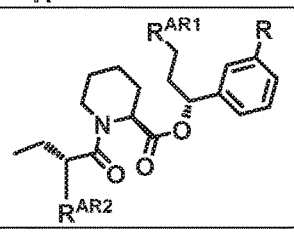
Figure 53J:
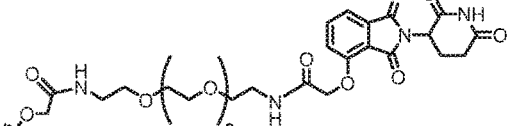
Figure 53J:
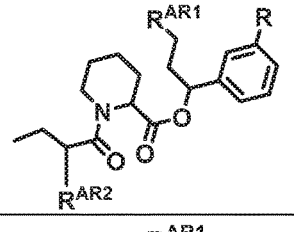
Figure 53J:
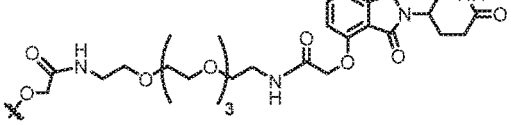
Figure 53J:
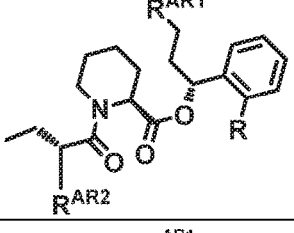
Figure 53J:
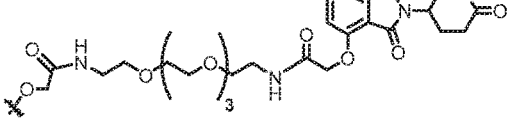
Figure 53J:
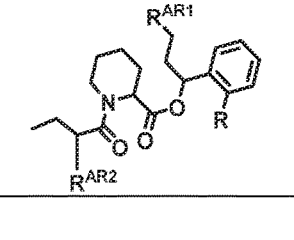
Figure 53J:
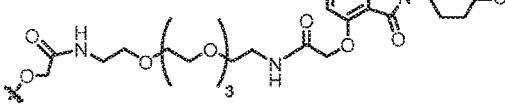
Figure 53K:
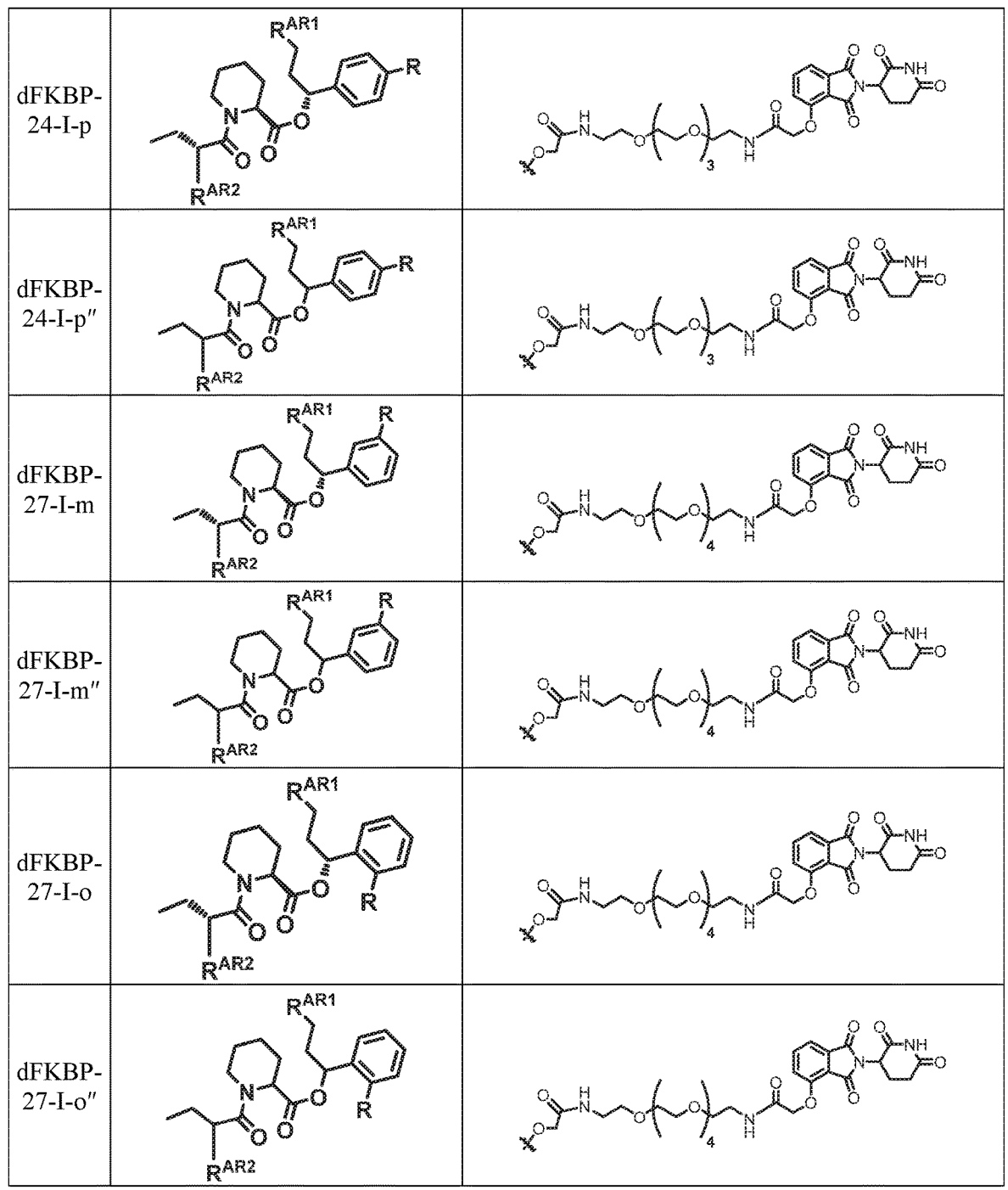
Figure 53L:
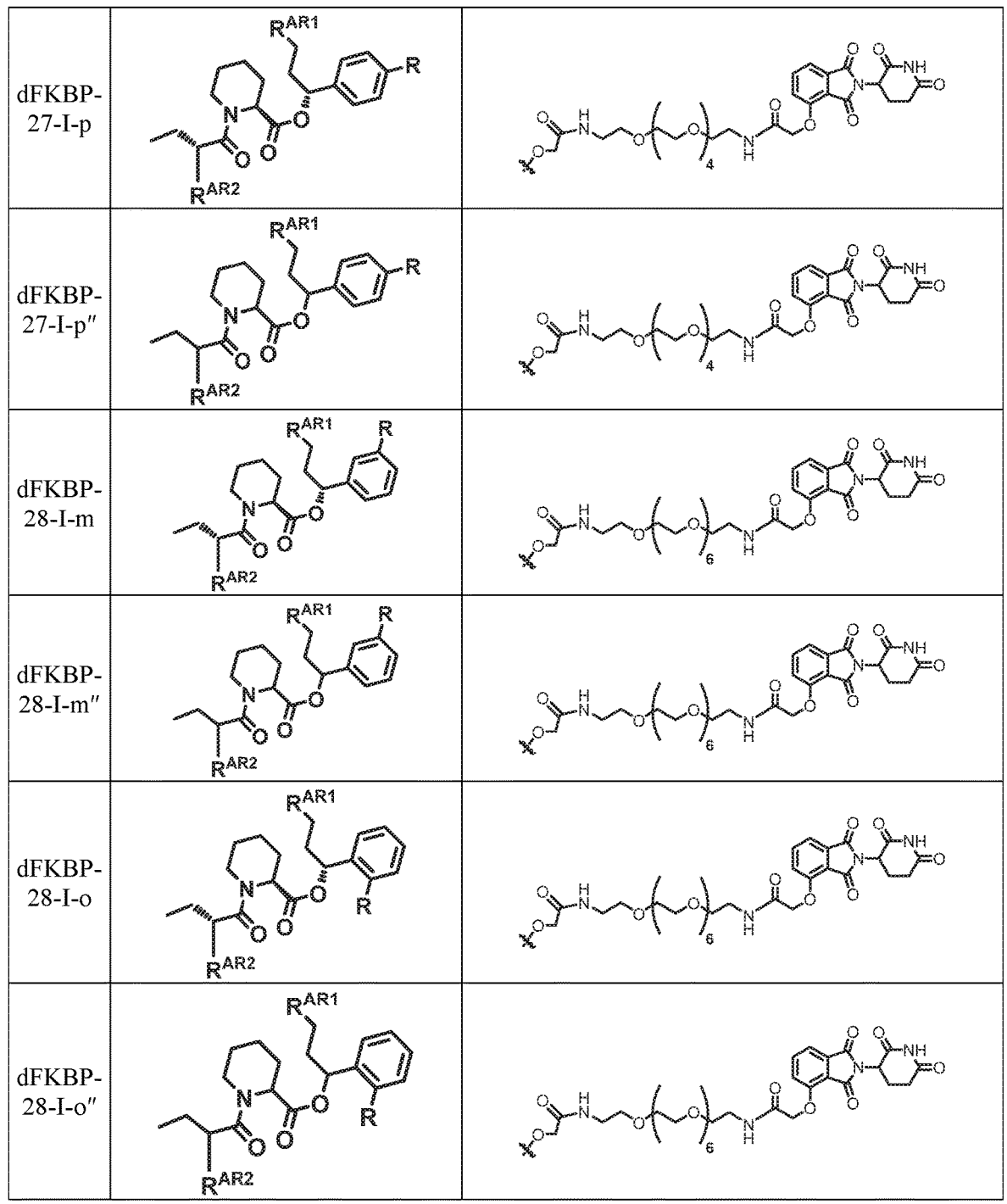
Figure 53M:
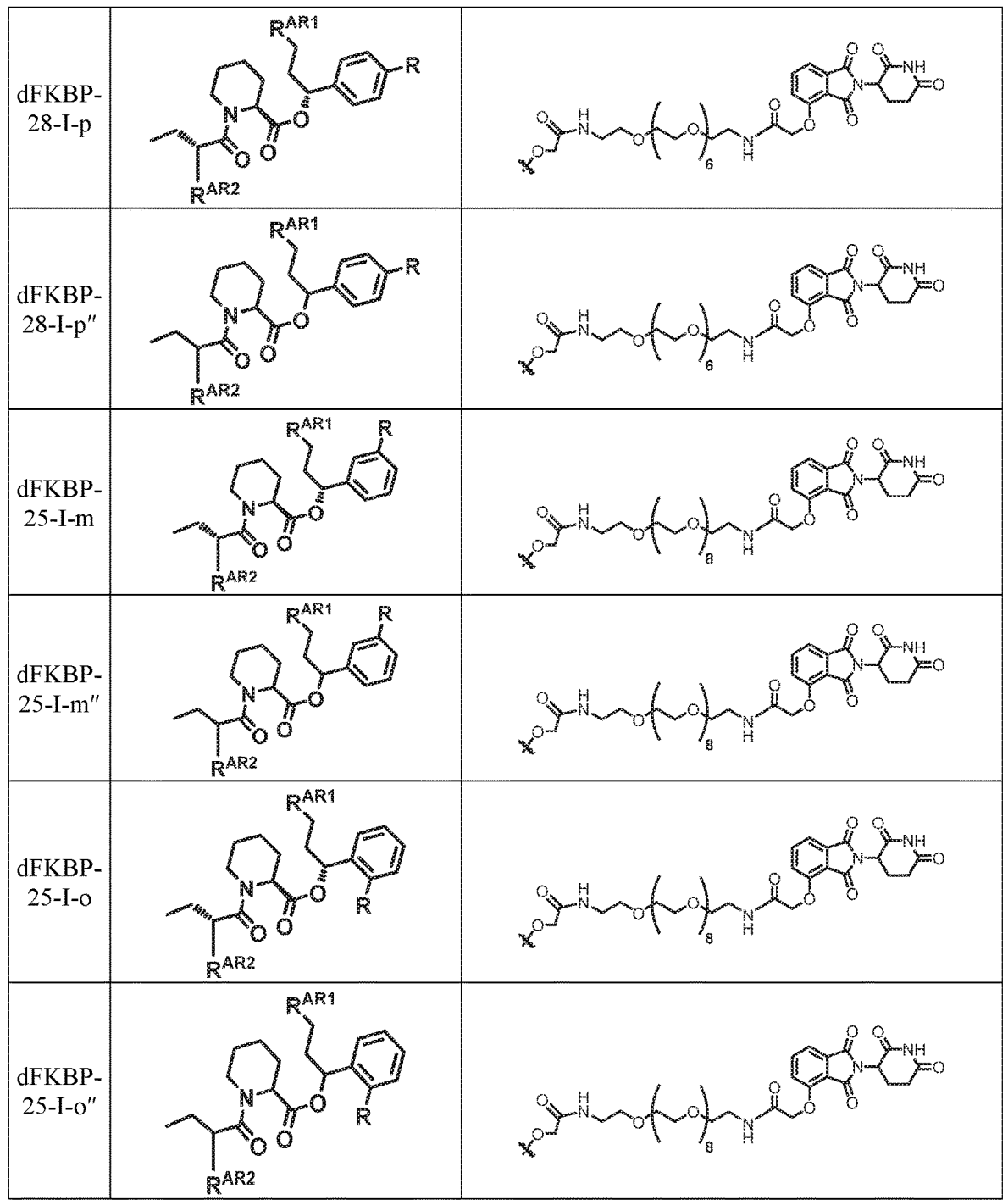
Figure 53N:
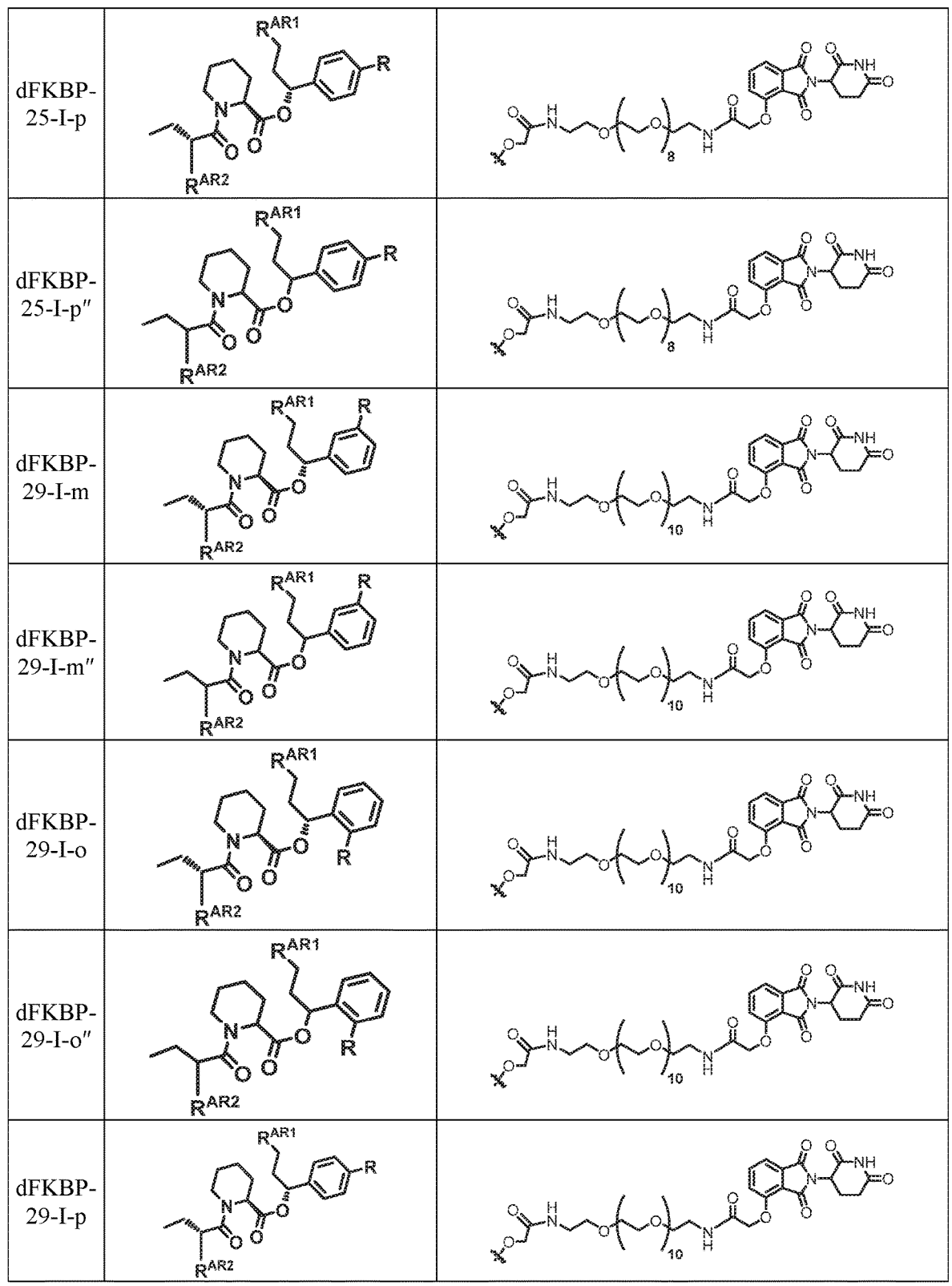
Figure 53O:
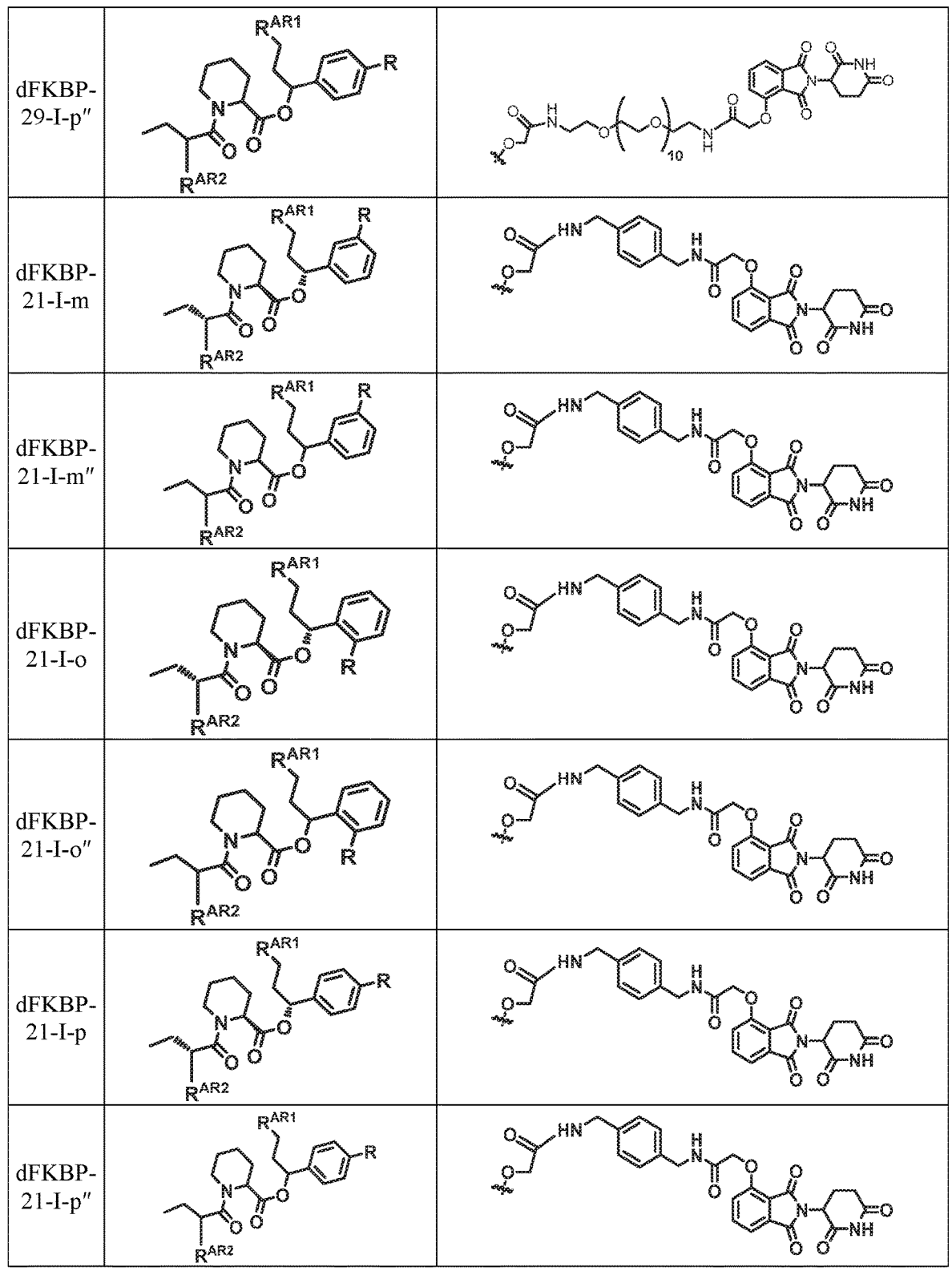
Figure 53P:
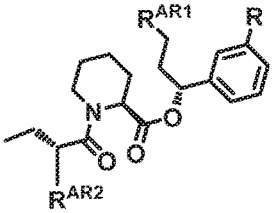
Figure 53P:
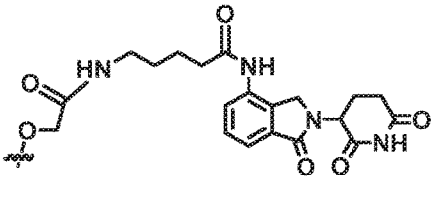
Figure 53P:
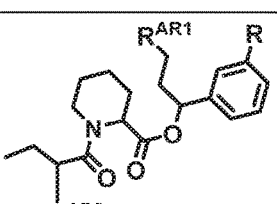
Figure 53P:
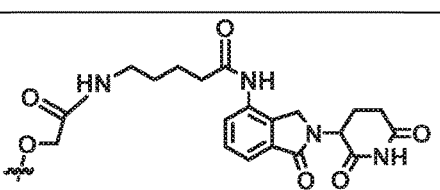
Figure 53P:
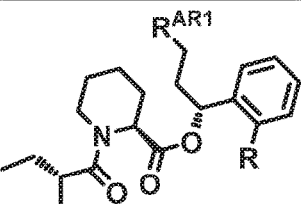
Figure 53P:
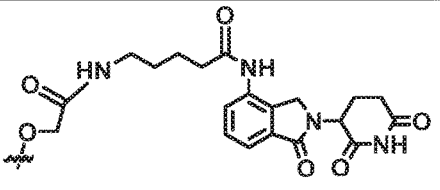
Figure 53P:
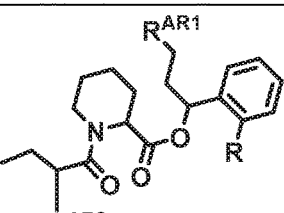
Figure 53P:
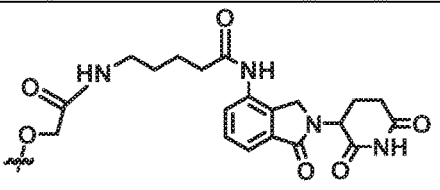
Figure 53P:
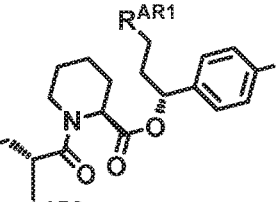
Figure 53P:
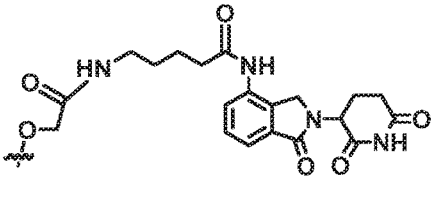
Figure 53Q:
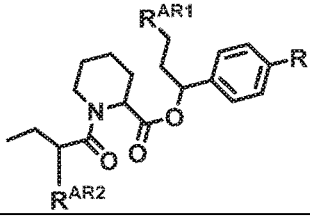
Figure 53Q:
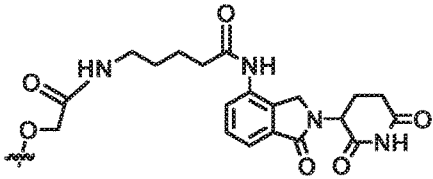
Figure 53Q:
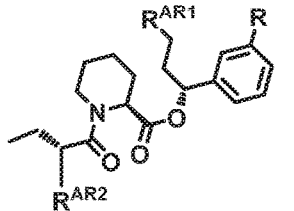
Figure 53Q:
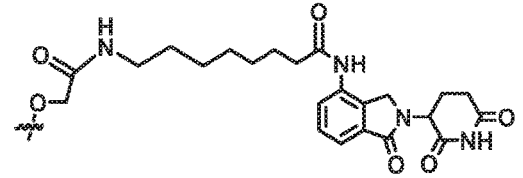
Figure 53Q:
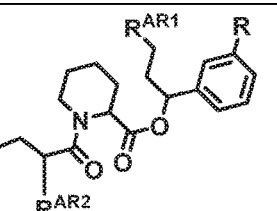
Figure 53Q:
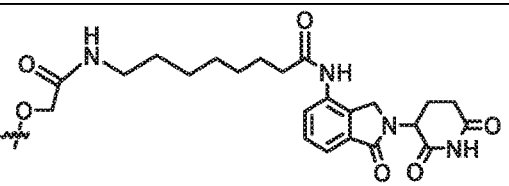
Figure 53Q:
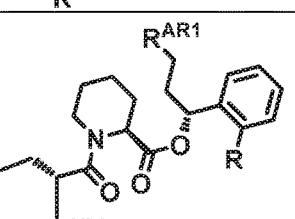
Figure 53Q:
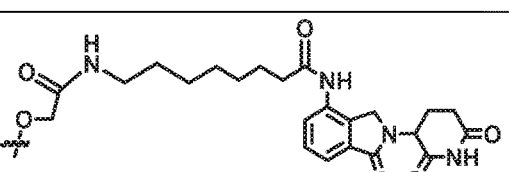
Figure 53Q:
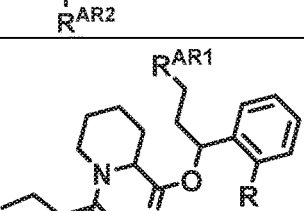
Figure 53Q:
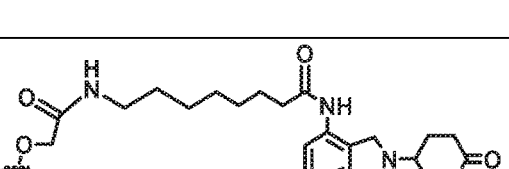
Figure 53Q:
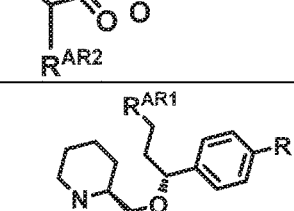
Figure 53Q:
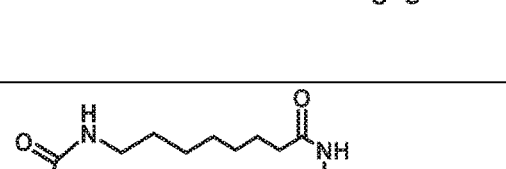
Figure 53Q:
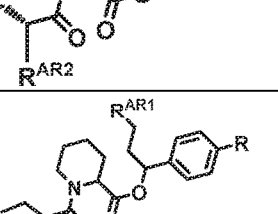
Figure 53Q:
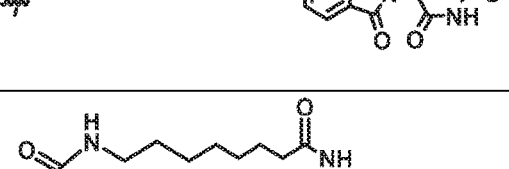
Figure 53R:
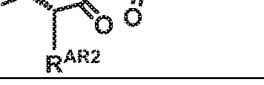
Figure 53R:
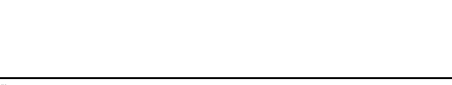
Figure 53R:
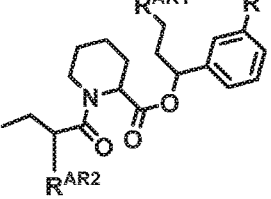
Figure 53R:
Figure 53R:
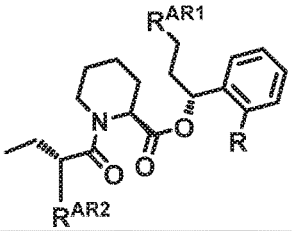
Figure 53R:
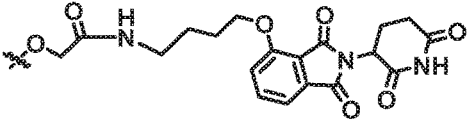
Figure 53R:
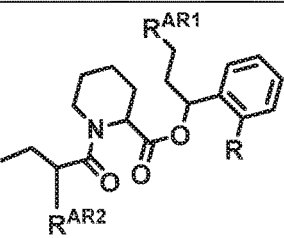
Figure 53R:
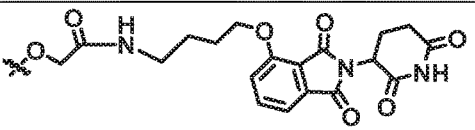
Figure 53R:
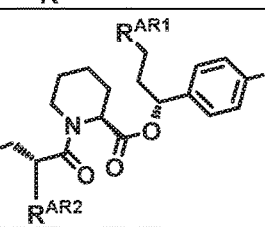
Figure 53R:
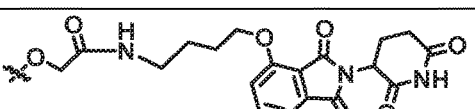
Figure 53R:
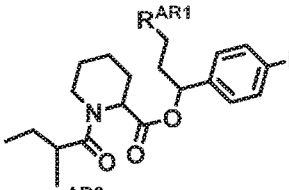
Figure 53R:
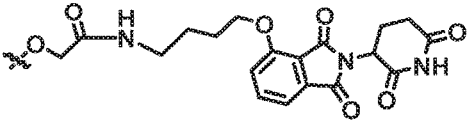
Figure 53T:
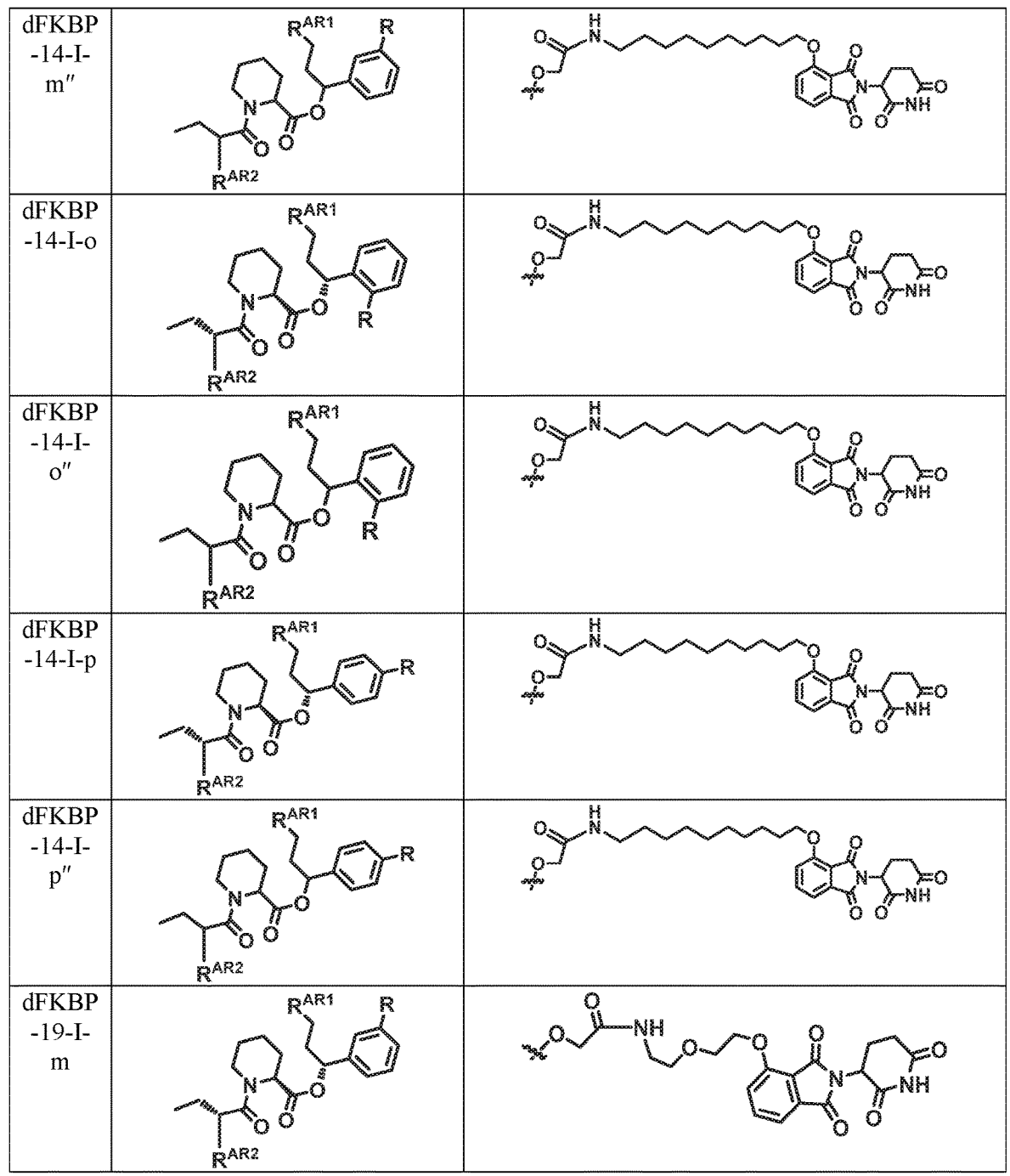
Figure 53U:
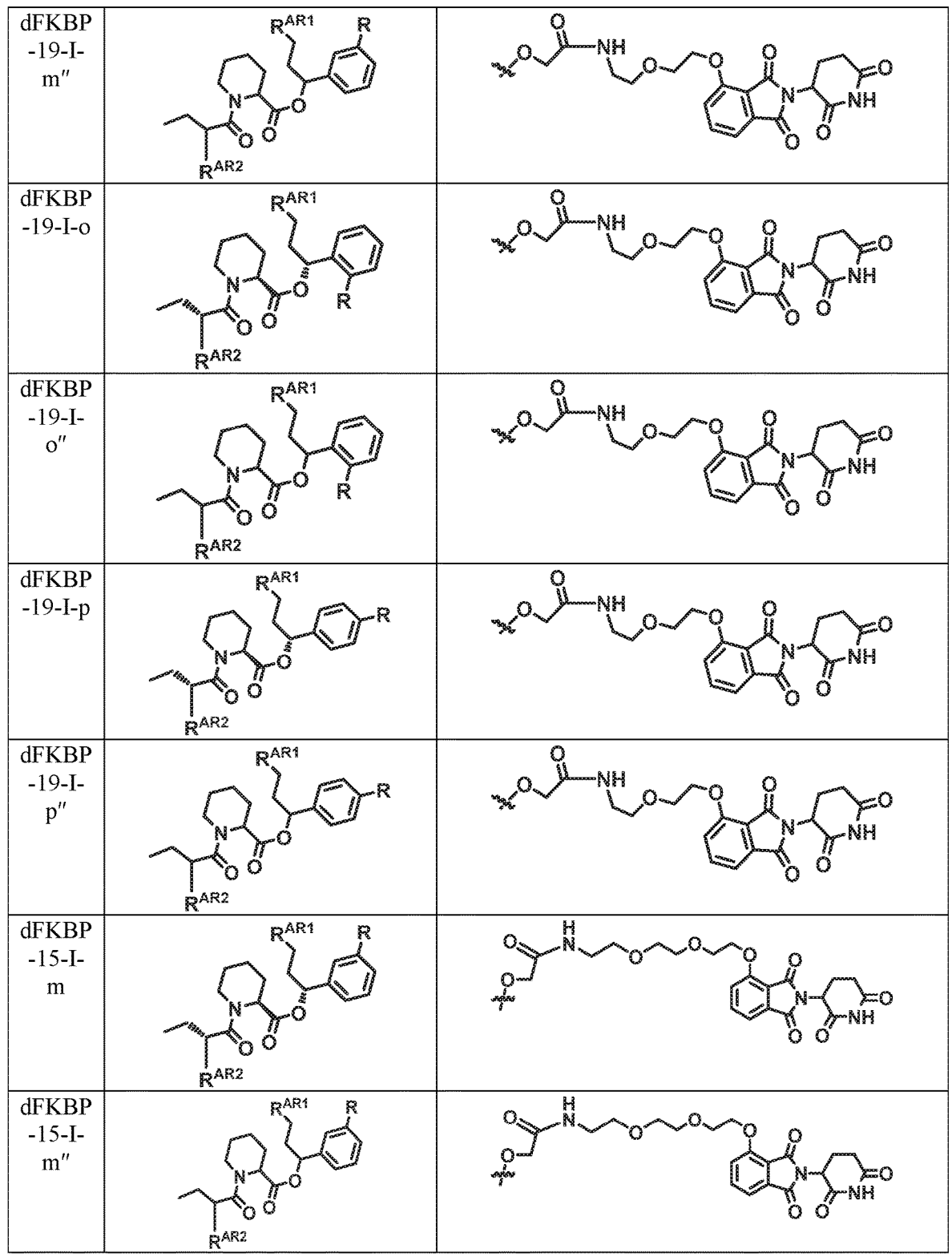
Figure 53W:
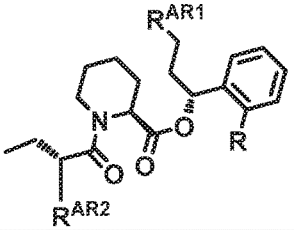
Figure 53W:
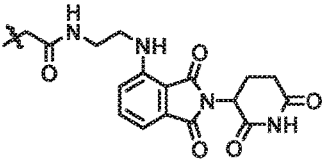
Figure 53W:
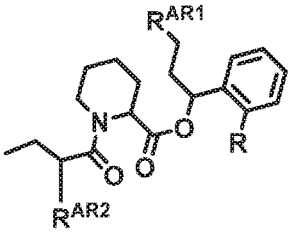
Figure 53W:
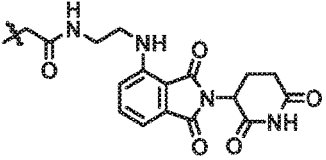
Figure 53W:
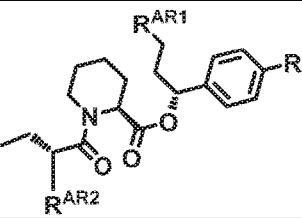
Figure 53W:
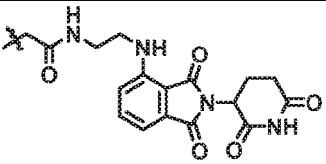
Figure 53W:
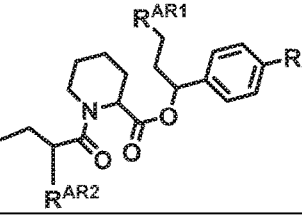
Figure 53W:
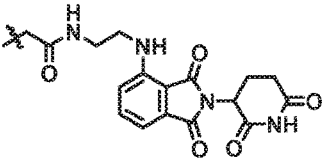
Figure 53W:
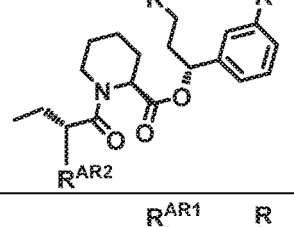
Figure 53W:
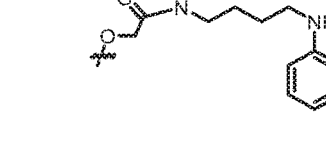
Figure 53W:
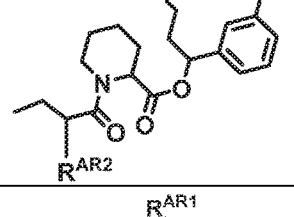
Figure 53W:
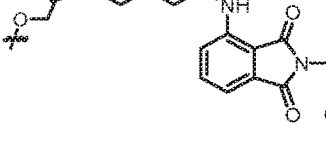
Figure 53W:
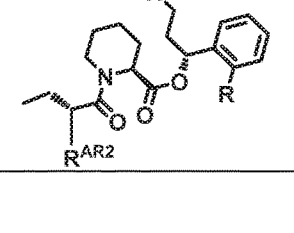
Figure 53W:
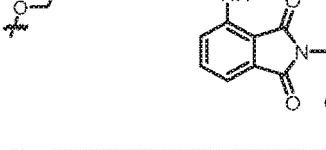
Figure 53X:
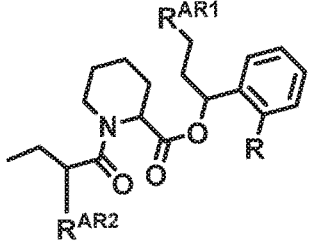
Figure 53X:
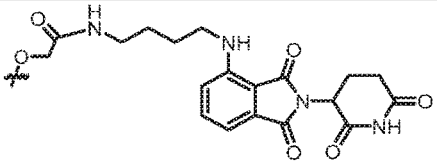
Figure 53X:
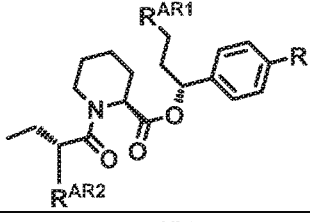
Figure 53X:
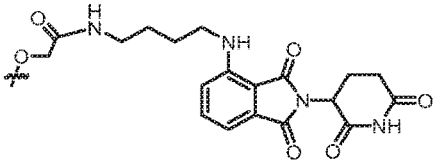
Figure 53X:
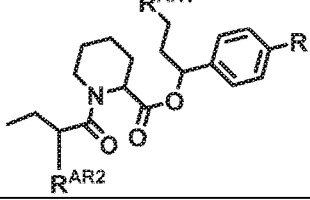
Figure 53X:
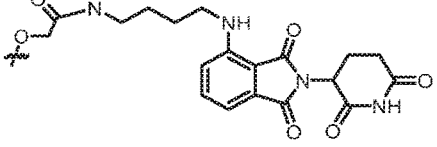
Figure 53X:
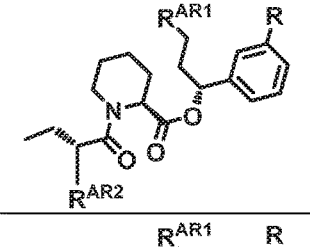
Figure 53X:
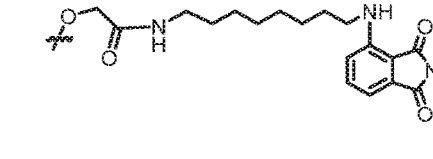
Figure 53X:
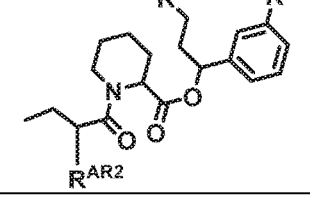
Figure 53X:
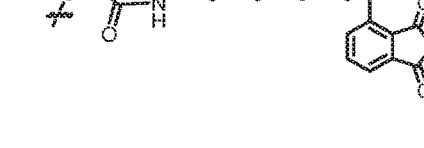
Figure 53X:
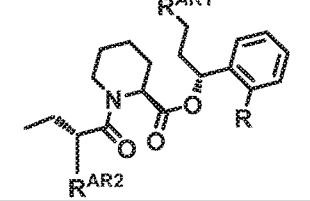
Figure 53X:
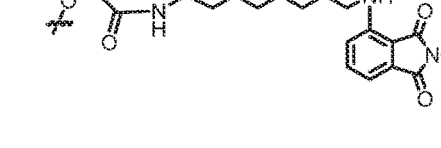
Figure 53X:
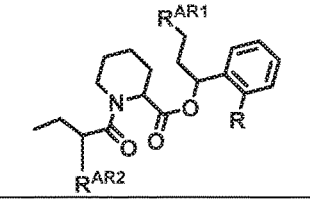
Figure 53X:
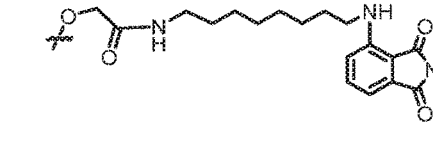
Figure 53Z:
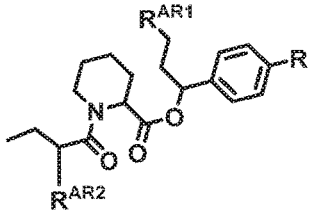
Figure 53Z:
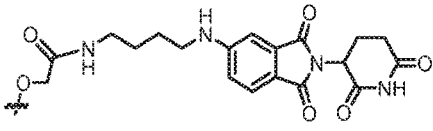
Figure 53Z:
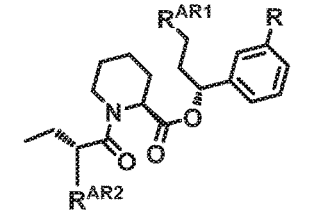
Figure 53Z:
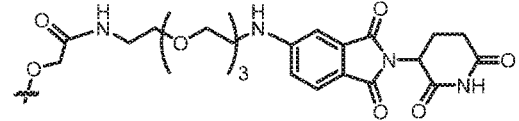
Figure 53Z:
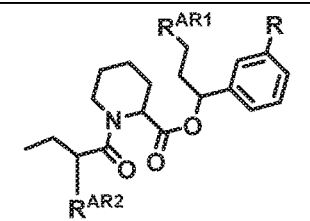
Figure 53Z:
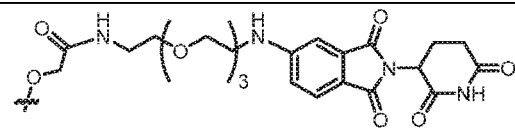
Figure 53Z:
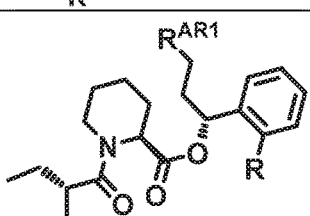
Figure 53Z:
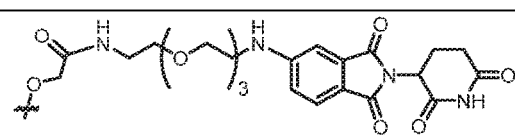
Figure 53Z:
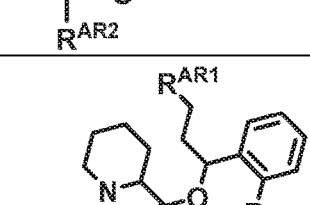
Figure 53Z:
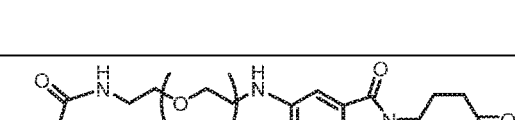
Figure 53Z:
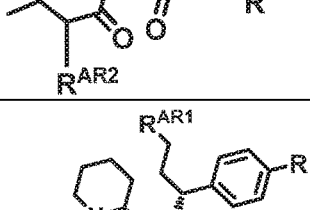
Figure 53Z:
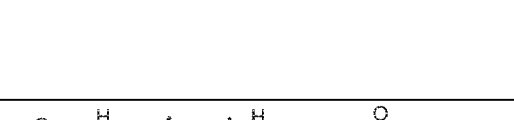
Figure 53Z:
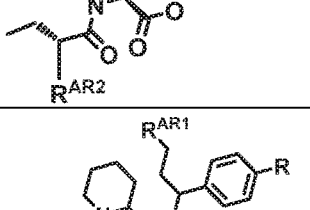
Figure 53Z:
Figure 53A:
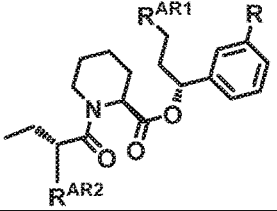
Figure 53A:
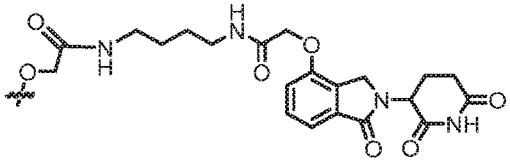
Figure 53A:
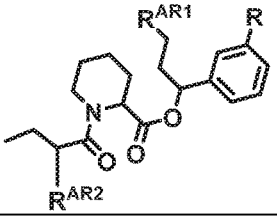
Figure 53A:
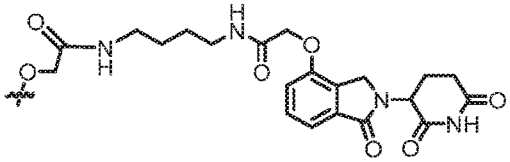
Figure 53A:
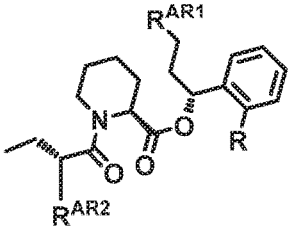
Figure 53A:
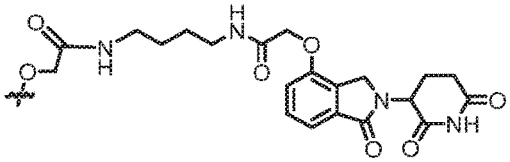
Figure 53A:
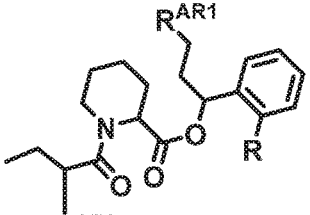
Figure 53A:
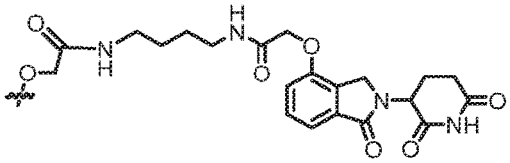
Figure 53A:
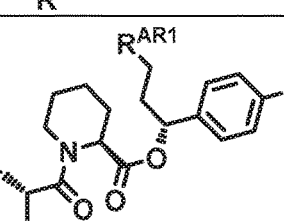
Figure 53A:
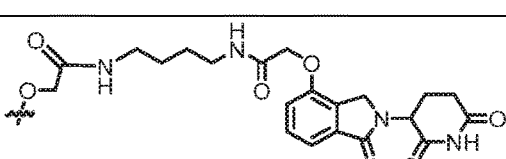
Figure 53A:
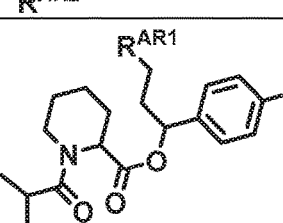
Figure 53A:
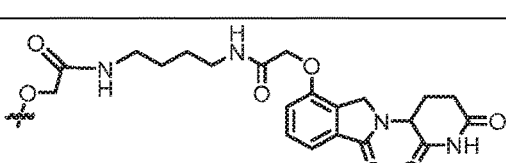
Figure 53B:
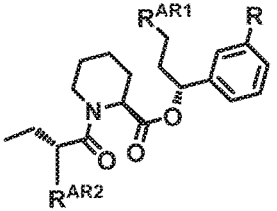
Figure 53B:
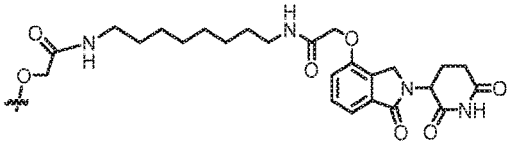
Figure 53B:
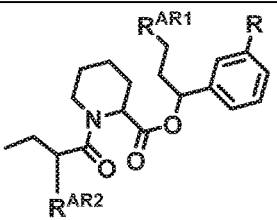
Figure 53B:
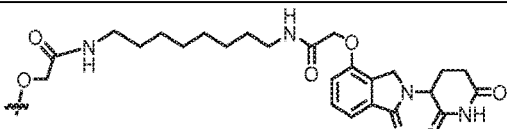
Figure 53B:
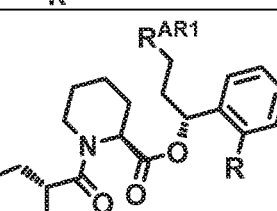
Figure 53B:
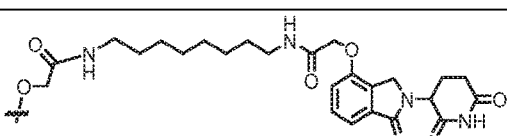
Figure 53B:
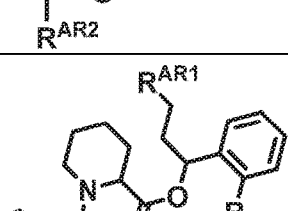
Figure 53B:
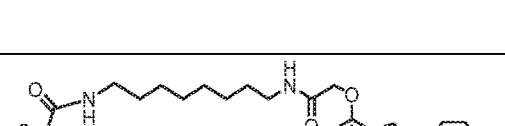
Figure 53B:
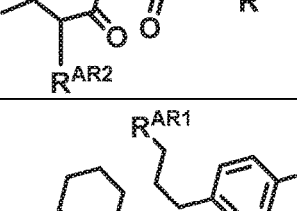
Figure 53B:
Figure 53B:
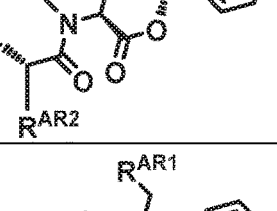
Figure 53B:
Figure 53C:
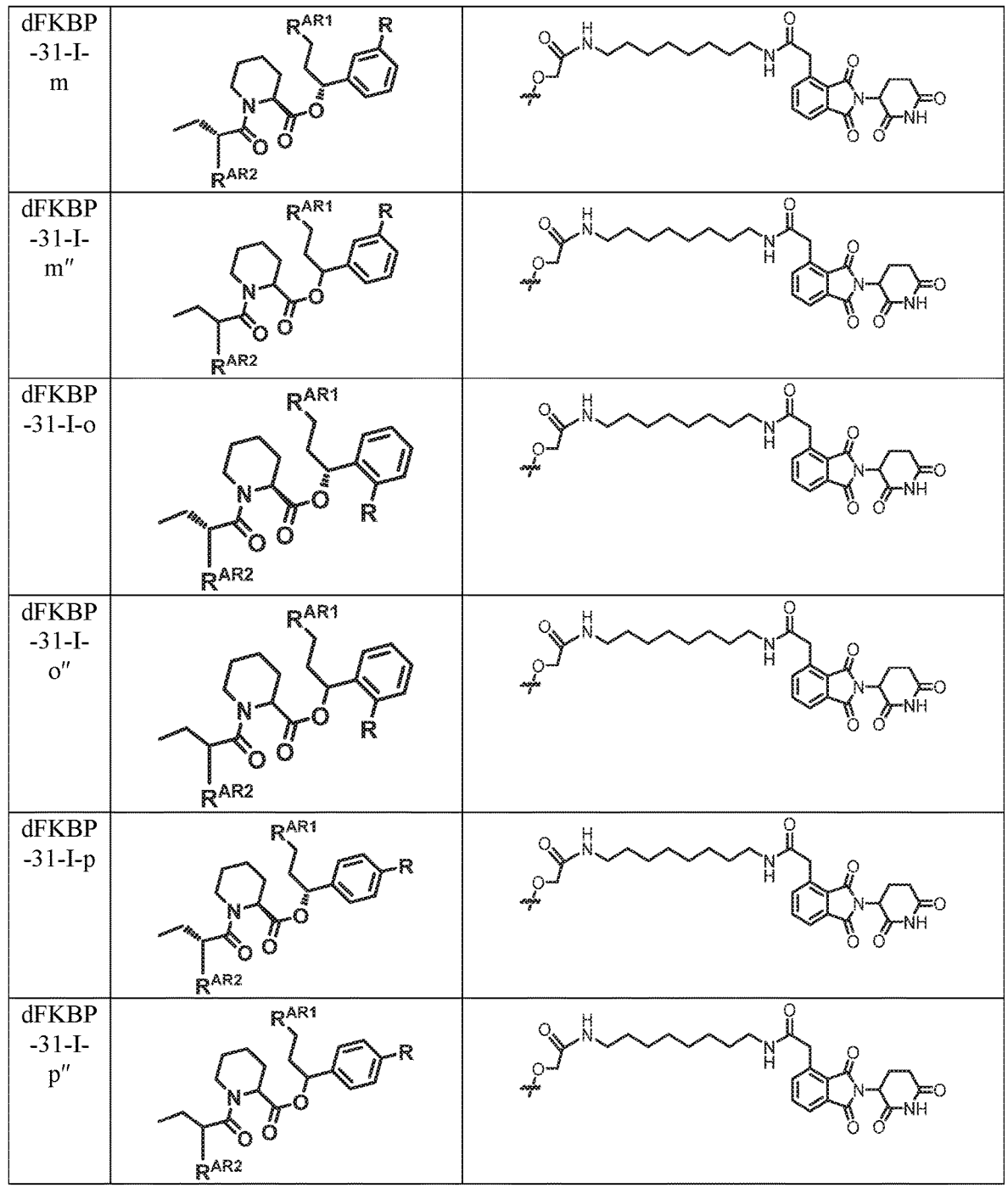
Figure 53D:
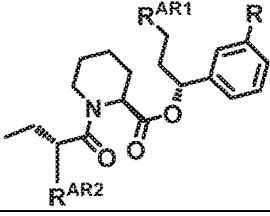
Figure 53D:
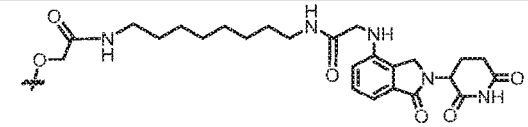
Figure 53D:
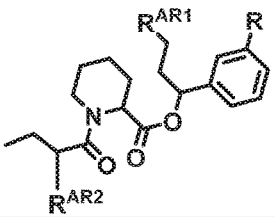
Figure 53D:
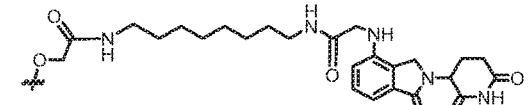
Figure 53D:
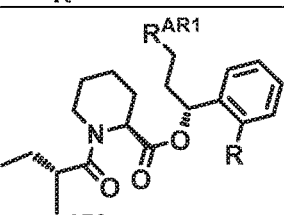
Figure 53D:
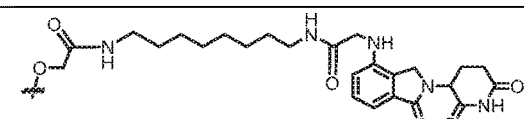
Figure 53D:
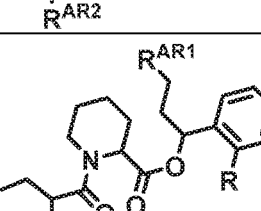
Figure 53D:
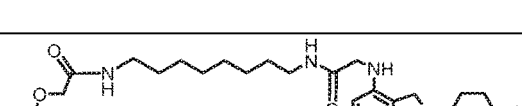
Figure 53D:
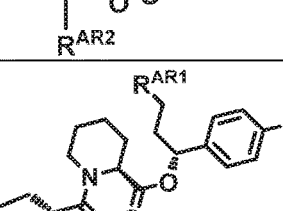
Figure 53D:
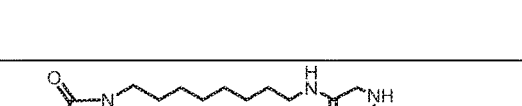
Figure 53D:
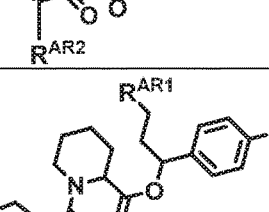
Figure 53D:
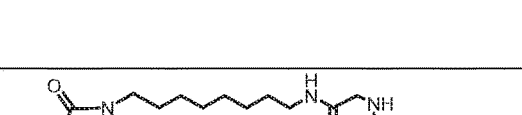
Figure 53D:
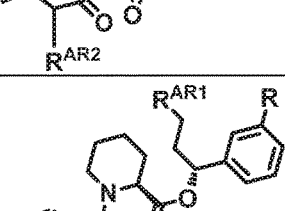
Figure 53D:
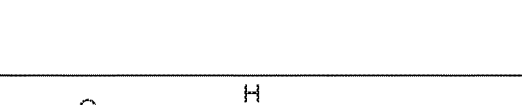
Figure 54A:
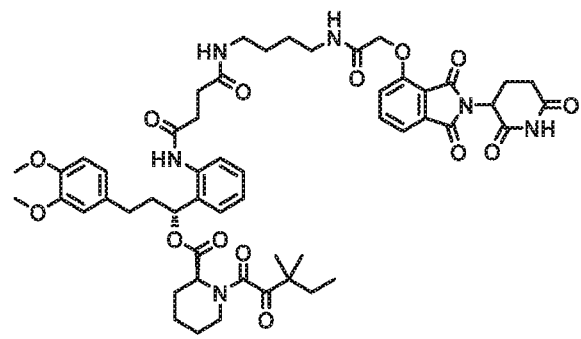
FIG. 54A, FIG. 54B, FIG. 54C, FIG. 54D, FIG. 54E, FIG. 54F, FIG. 54G, FIG. 54H, FIG. 54I, FIG. 54J, FIG. 54K, FIG. 54L, FIG. 54M, FIG. 54N, FIG. 54O, FIG. 54P, FIG. 54Q, FIG. 54R, FIG. 54S, FIG. 54T, FIG. 54U, FIG. 54V, and FIG. 54W provide additional heterobifunctional compounds for use in the present invention.
Figure 54A:
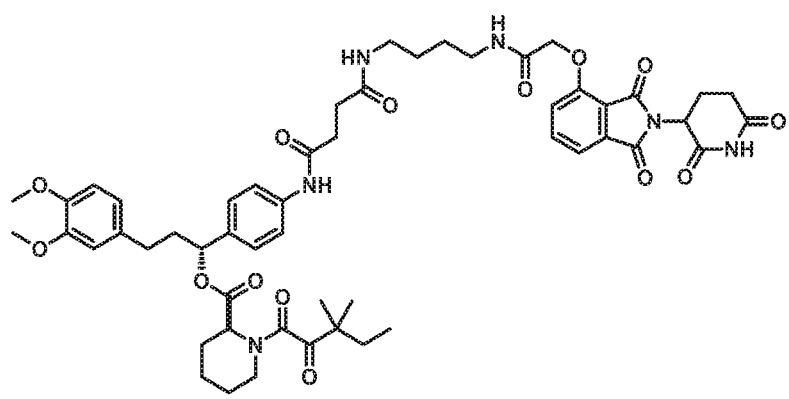
Figure 54A:
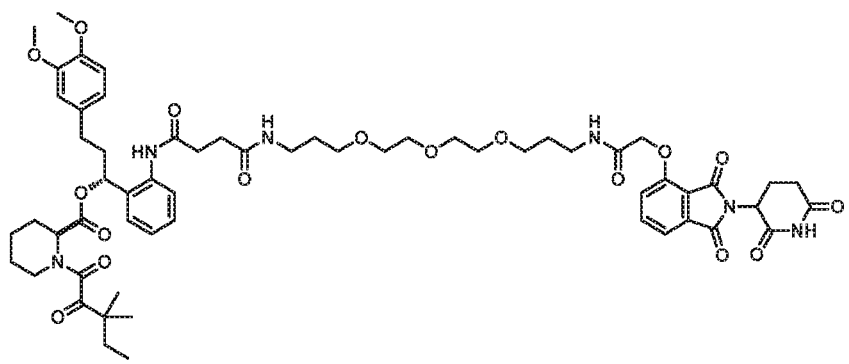
Figure 54B:
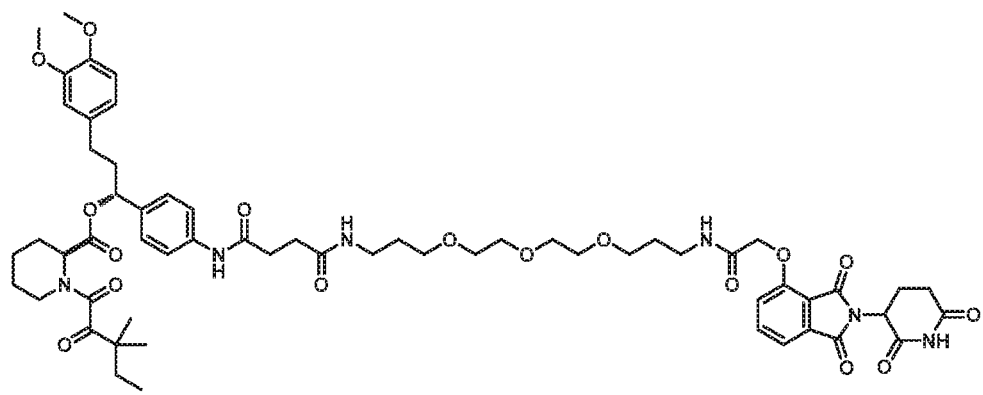
Figure 54B:
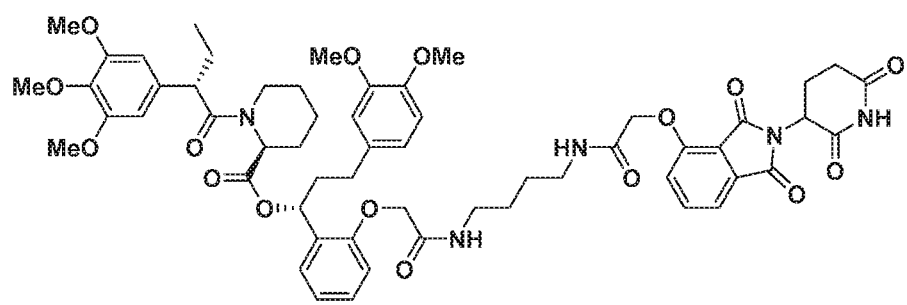
Figure 54B:
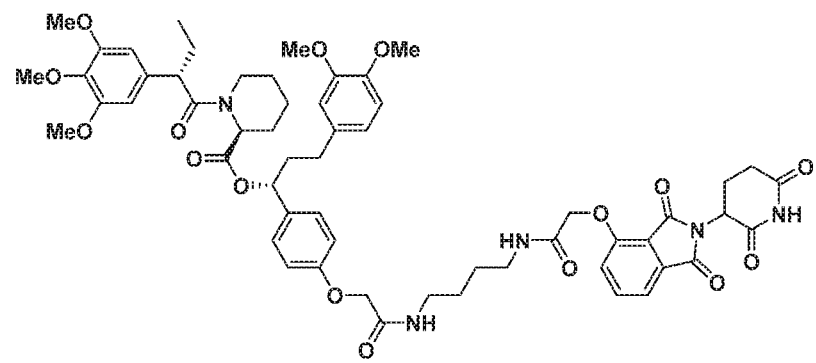
Figure 54B:
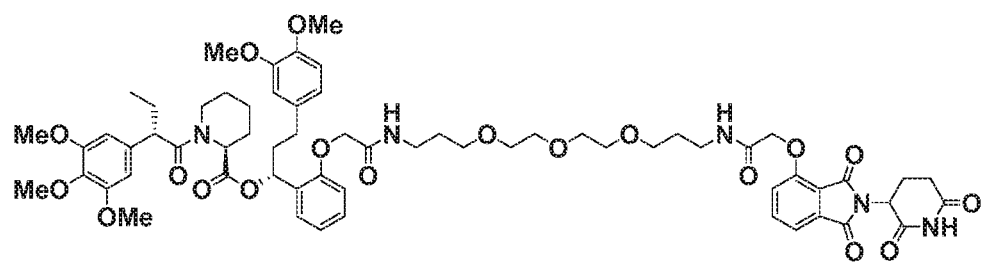
Figure 54C:
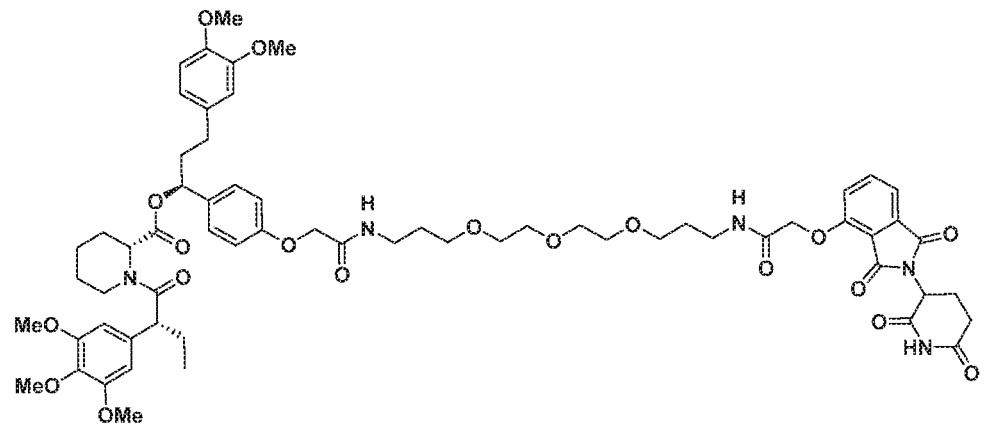
Figure 54C:
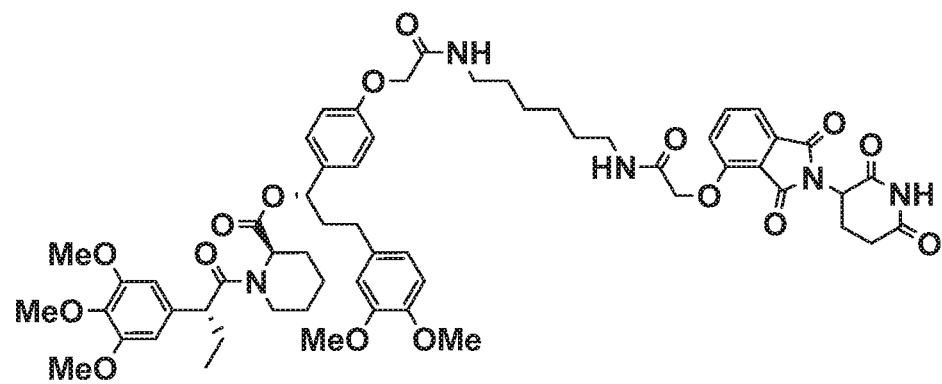
Figure 54C:
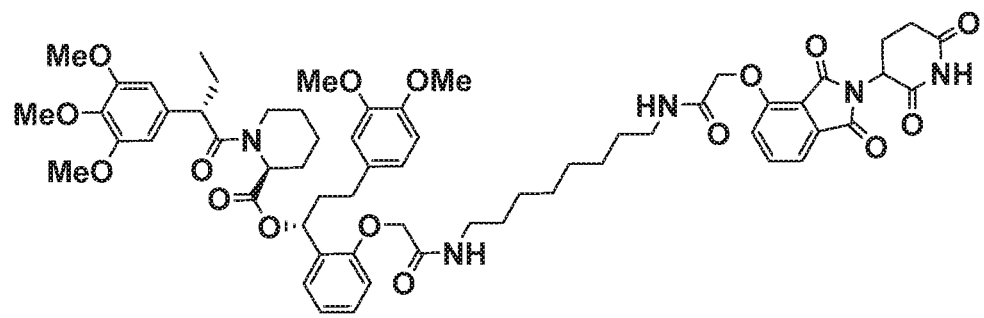
Figure 54D:
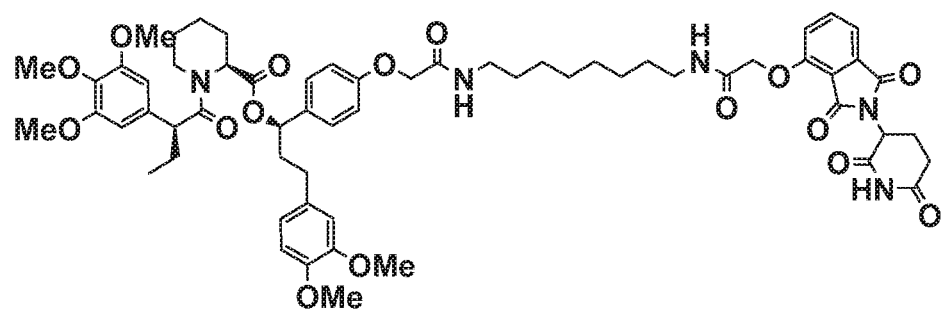
Figure 54D:
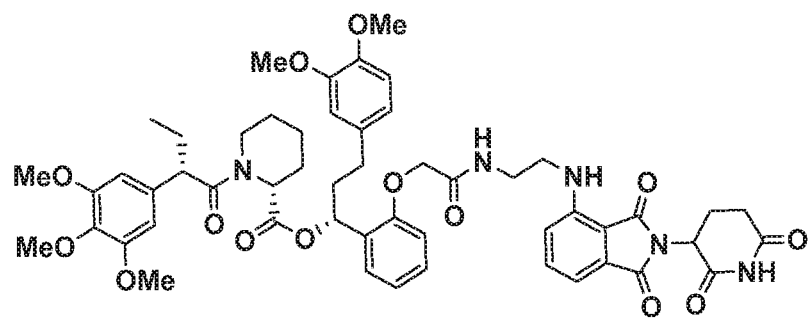
Figure 54D:
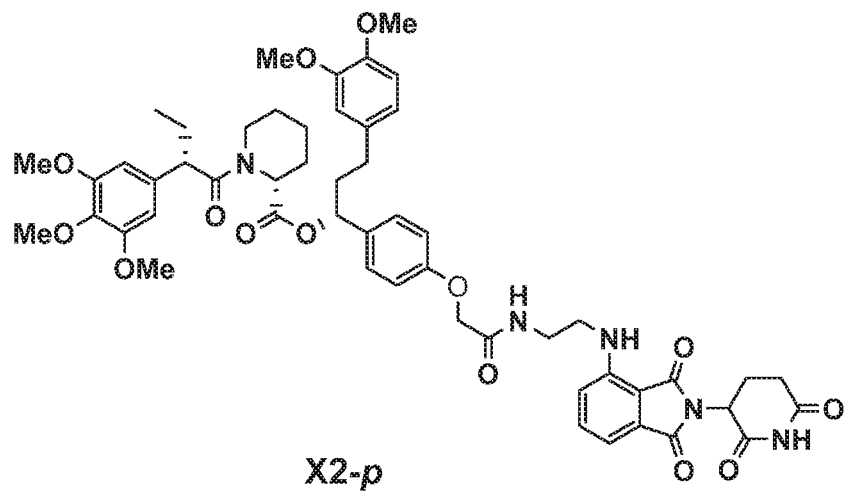
Figure 54E:
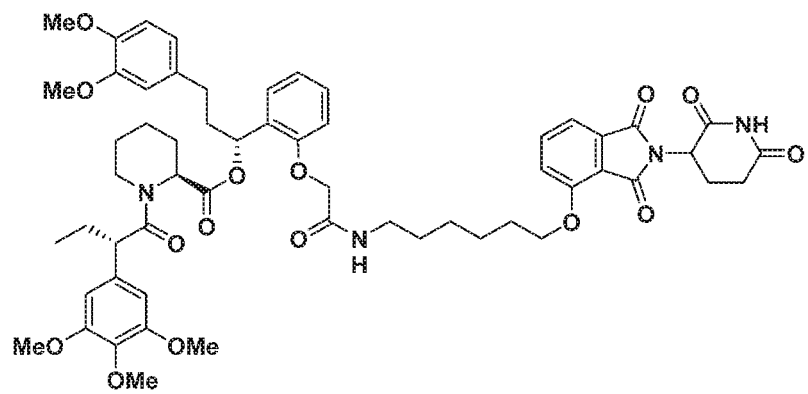
Figure 54E:
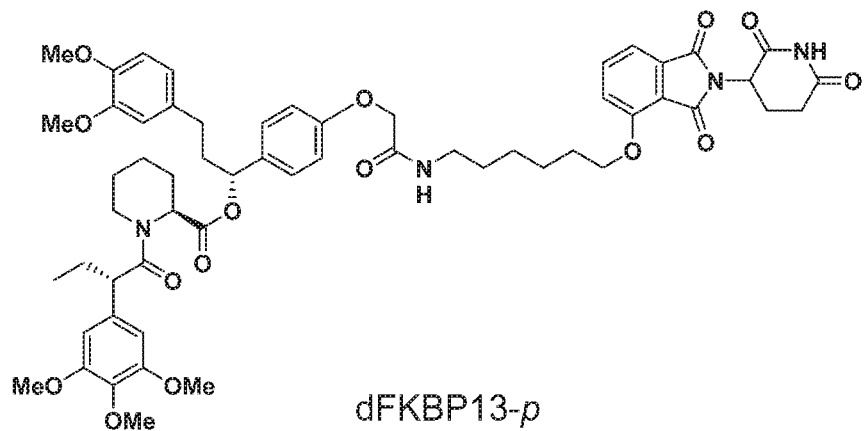
Figure 54E:
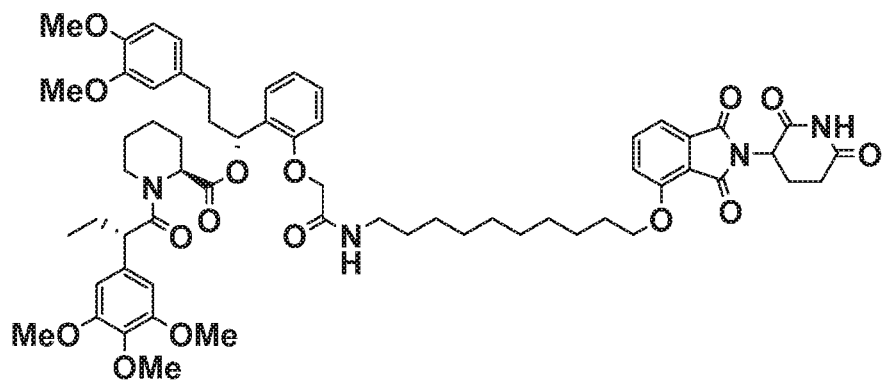
Figure 54F:
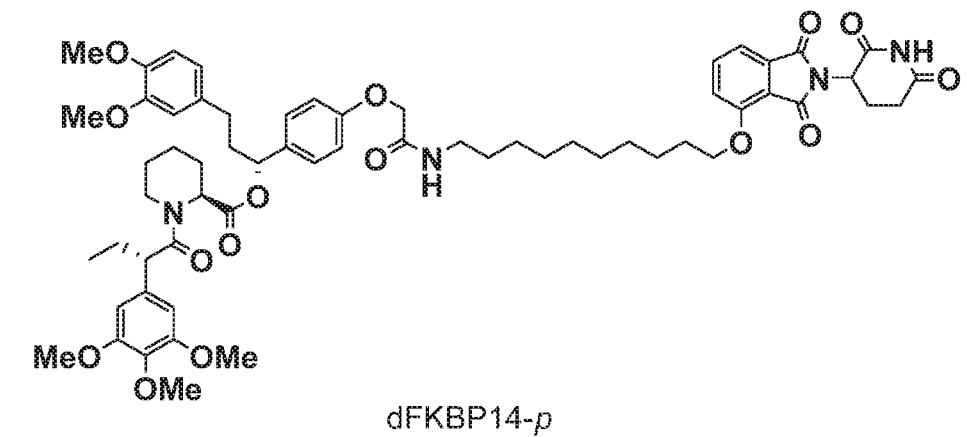
Figure 54F:
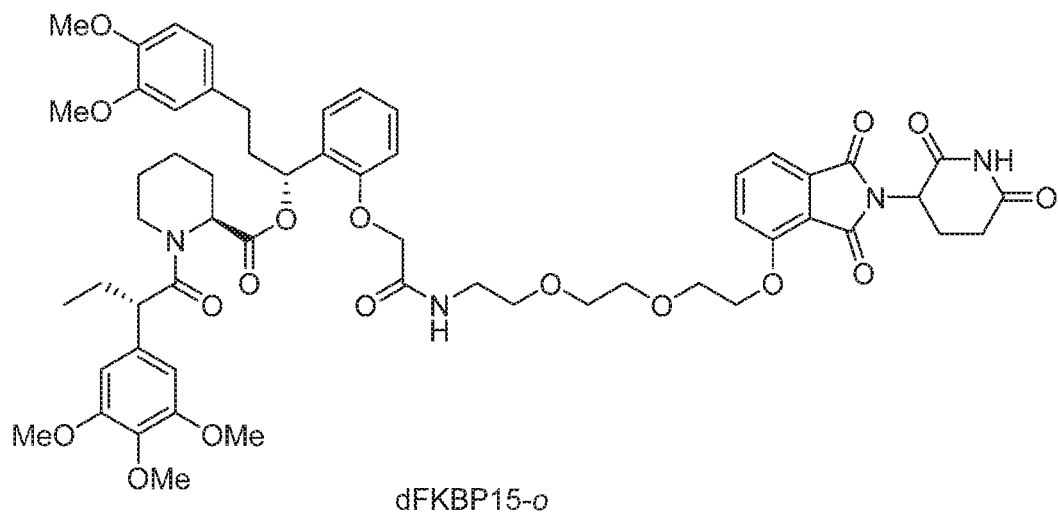
Figure 54F:
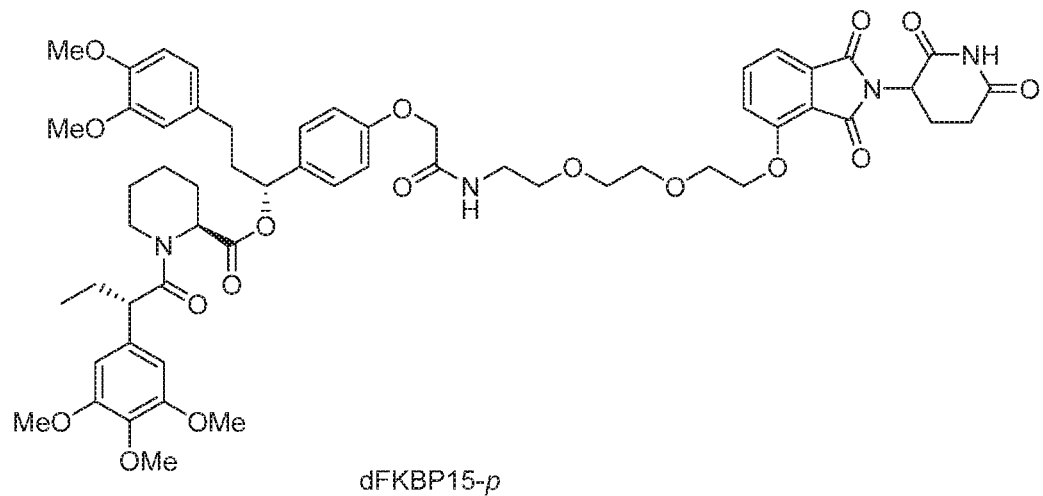
Figure 54G:
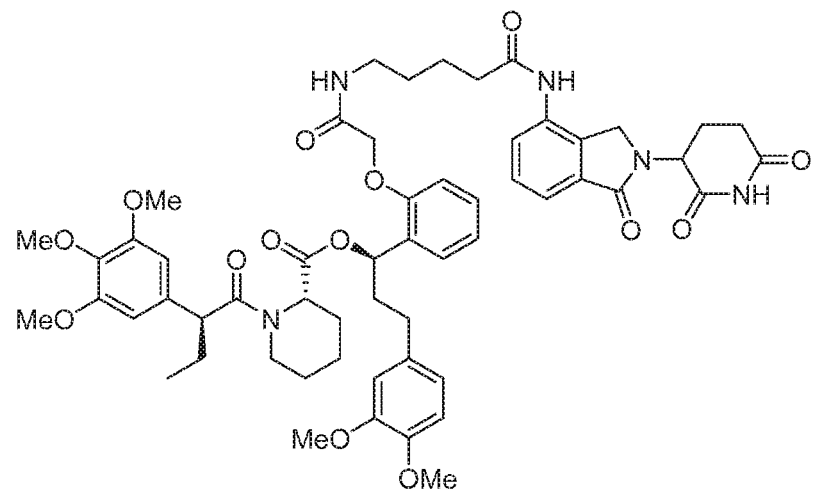
Figure 54G:
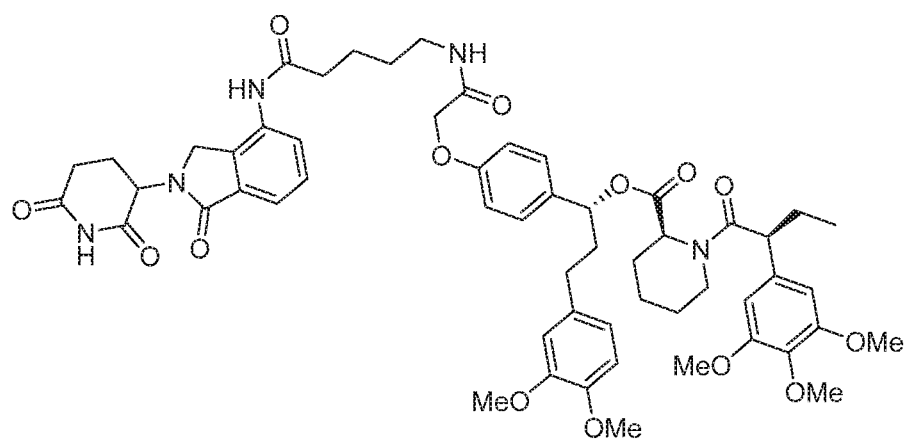
Figure 54G:
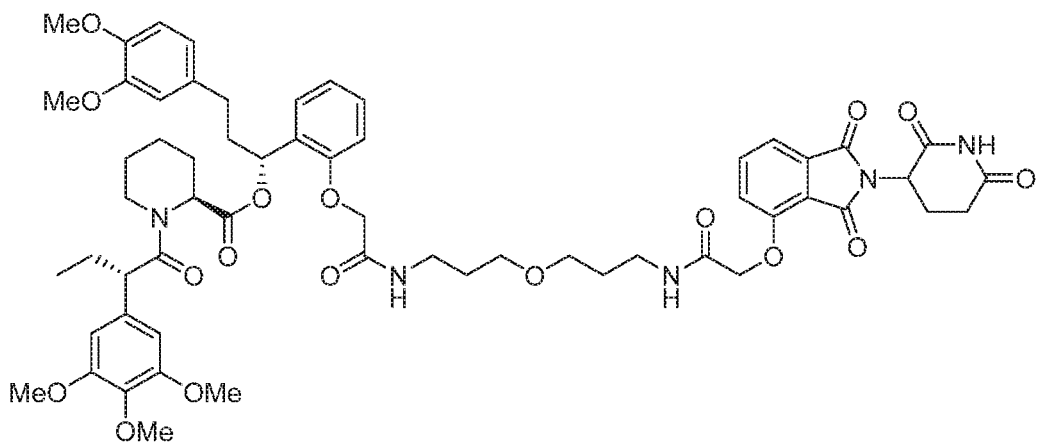
Figure 54H:
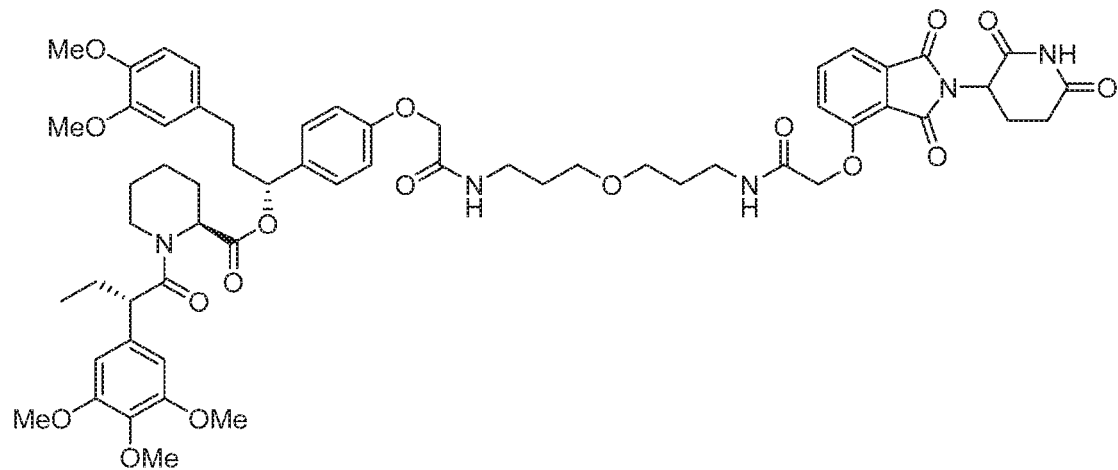
Figure 54H:
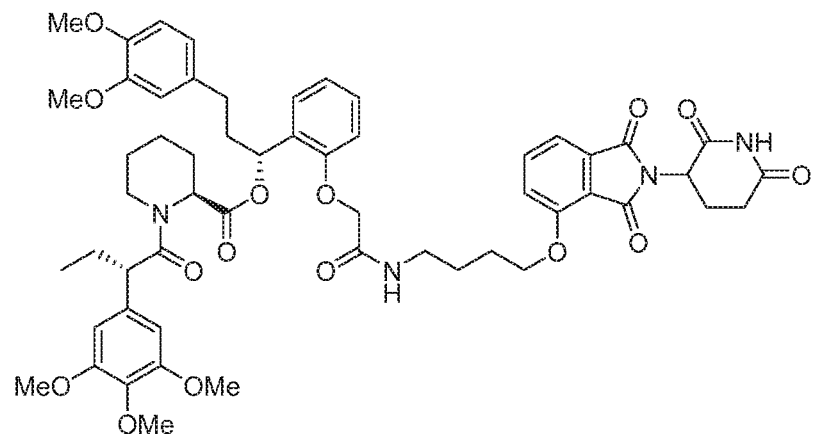
Figure 54H:
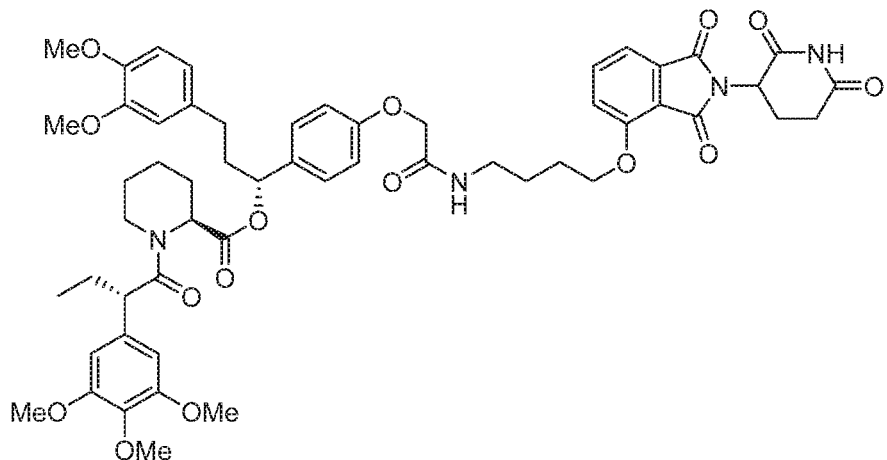
Figure 54I:
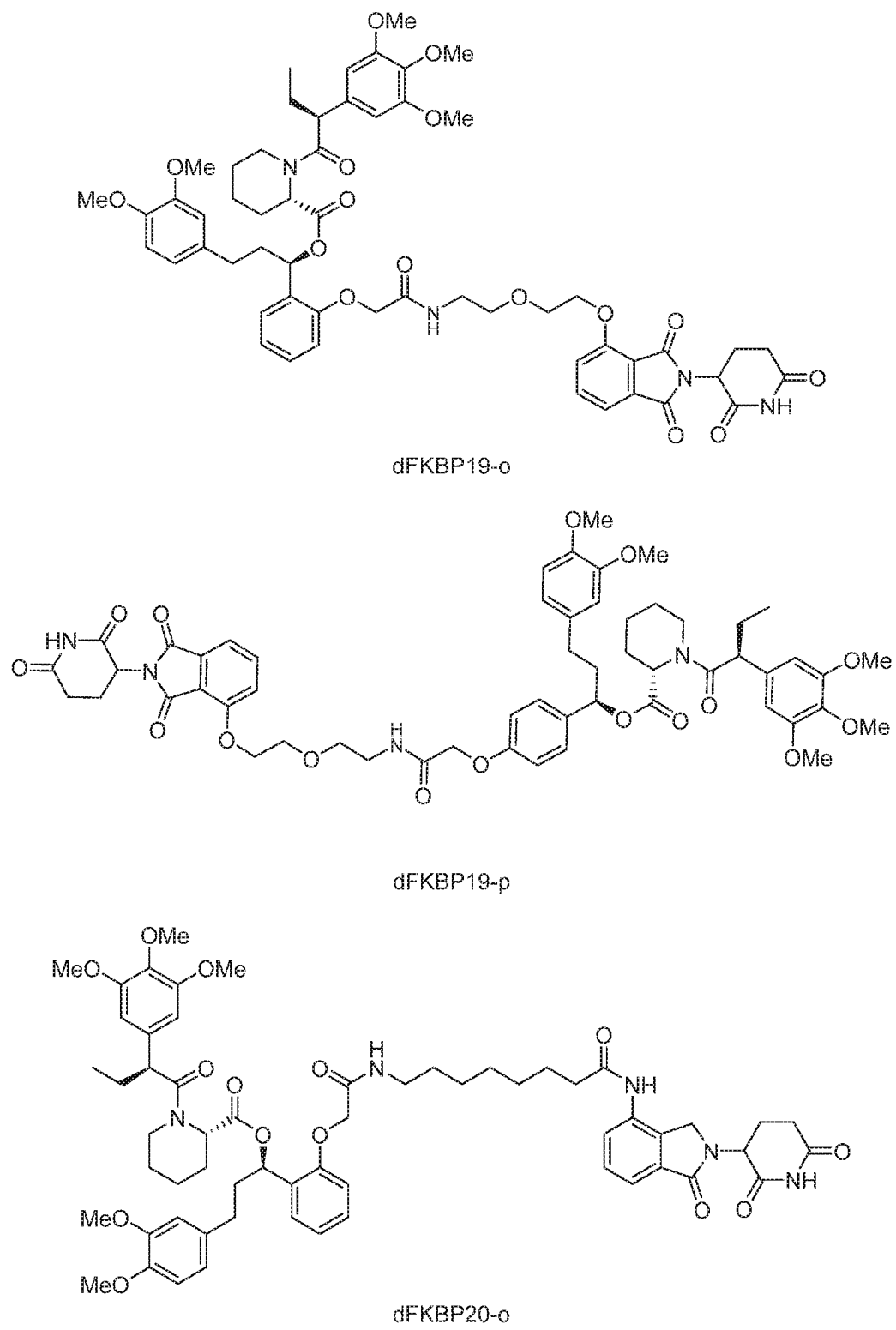
Figure 54J:
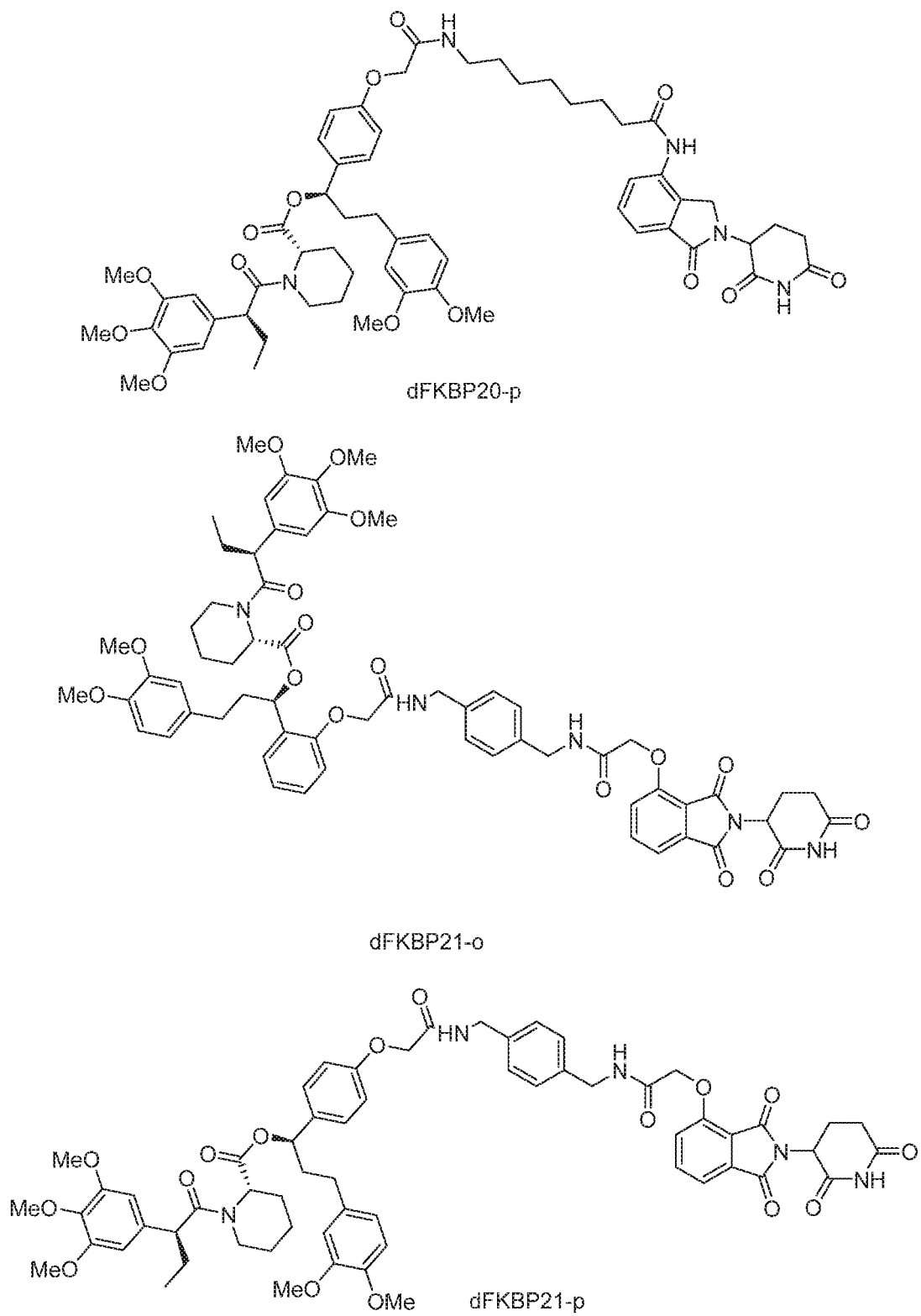
Figure 54K:
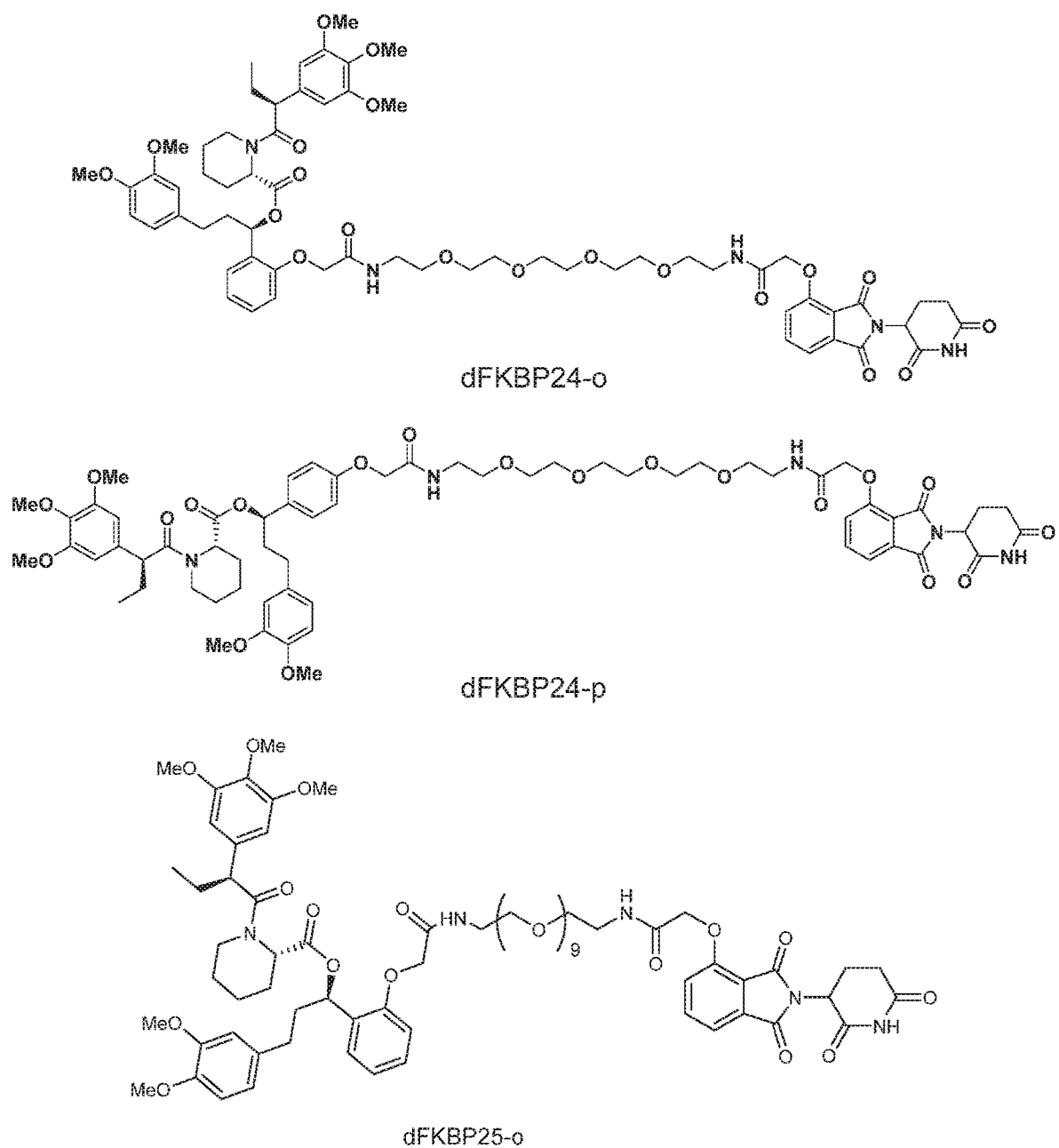
Figure 54L:
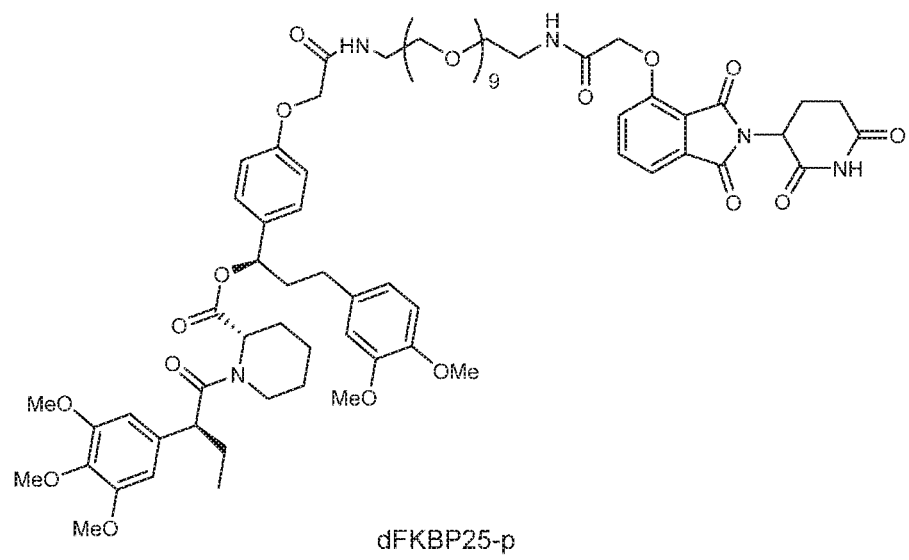
Figure 54L:
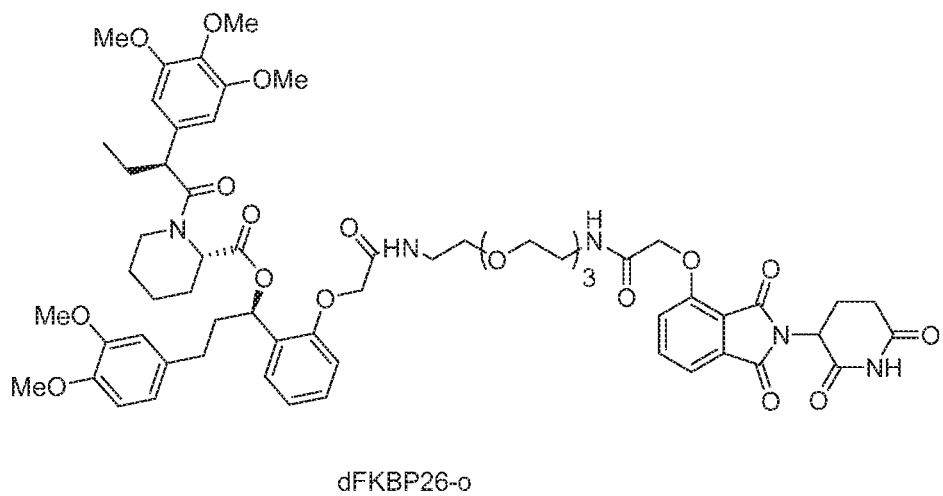
Figure 54L:
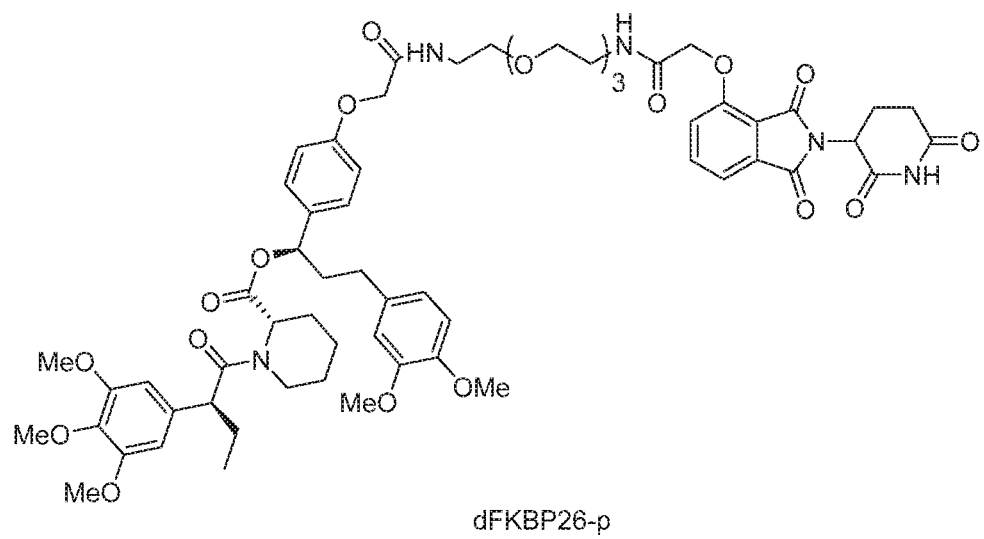
Figure 54M:
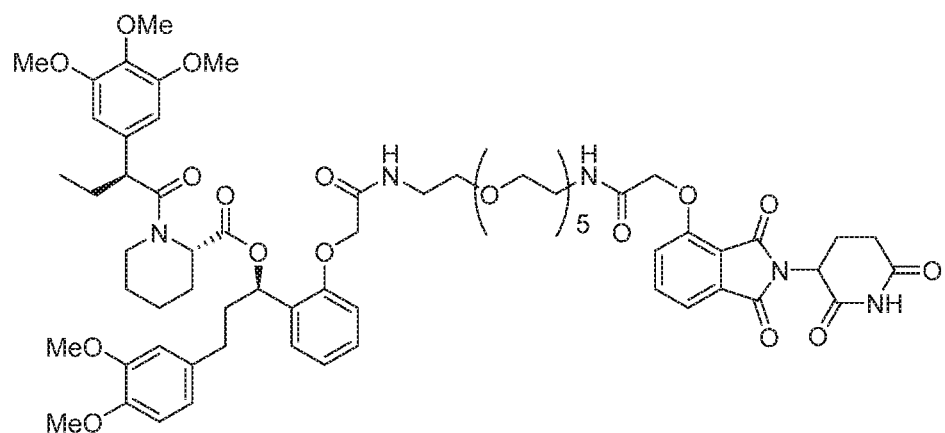
Figure 54M:
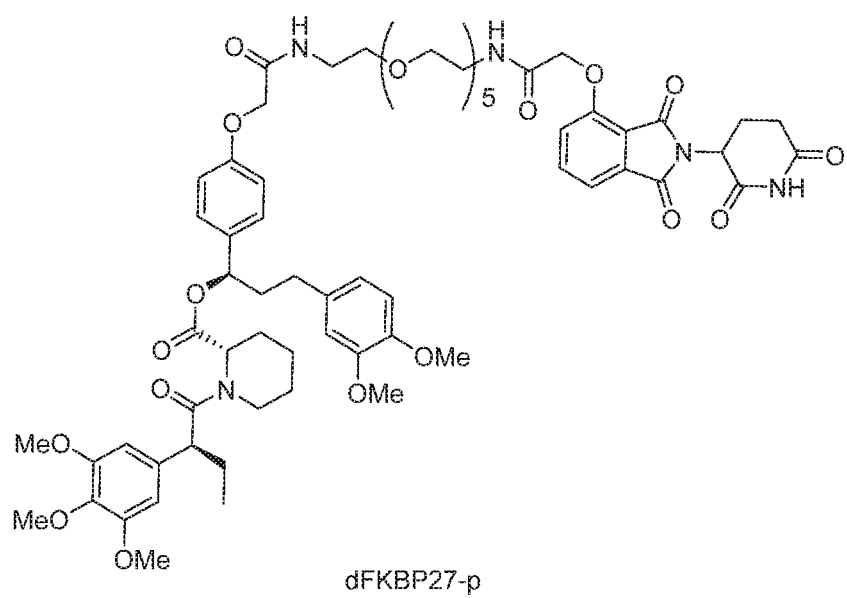
Figure 54M:
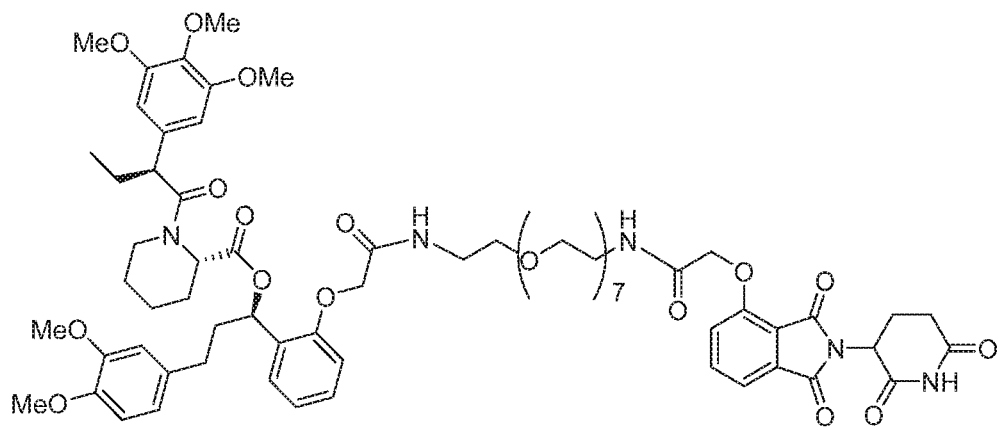
Figure 54N:
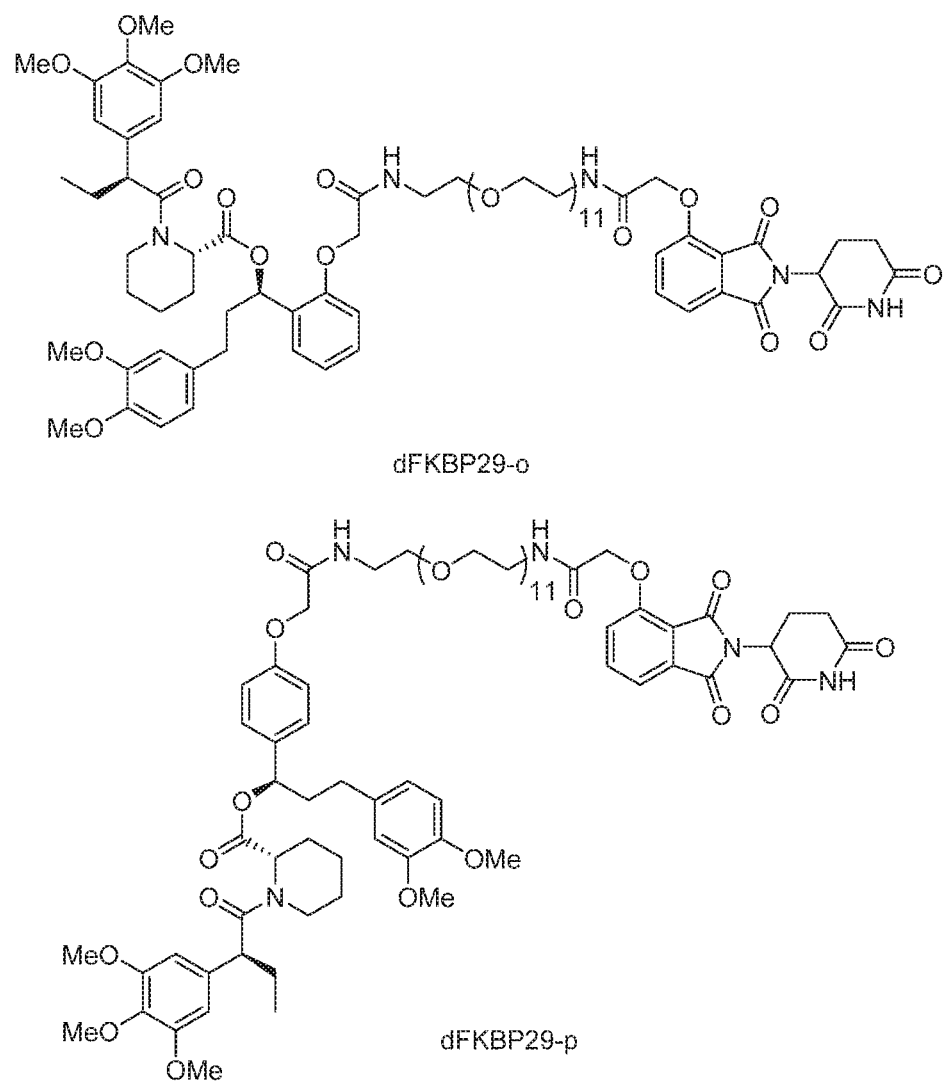
Figure 54O:
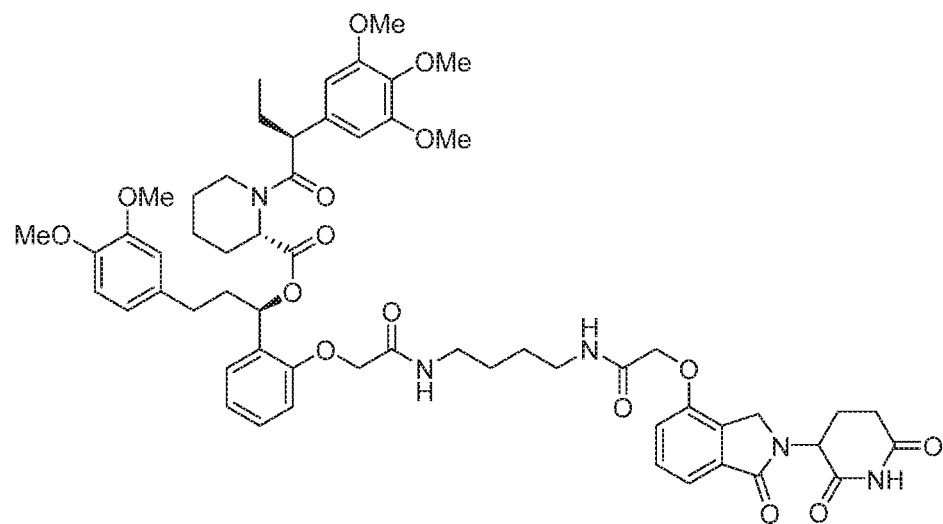
Figure 54O:
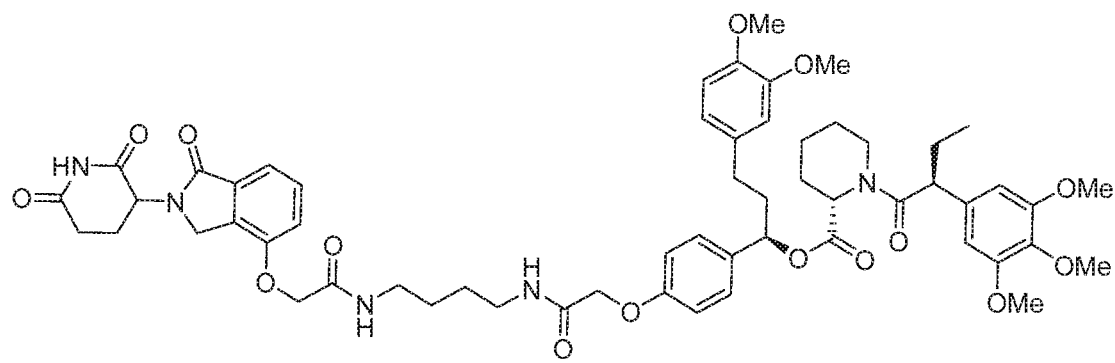
Figure 54O:
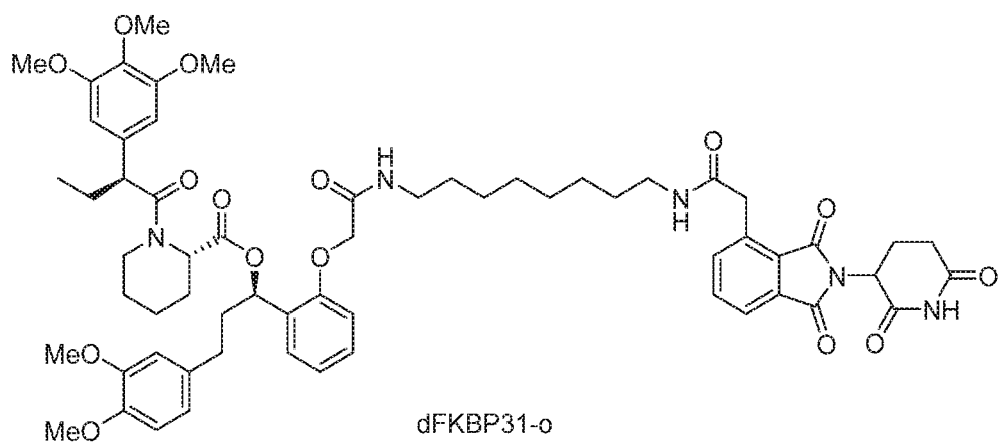
Figure 54P:
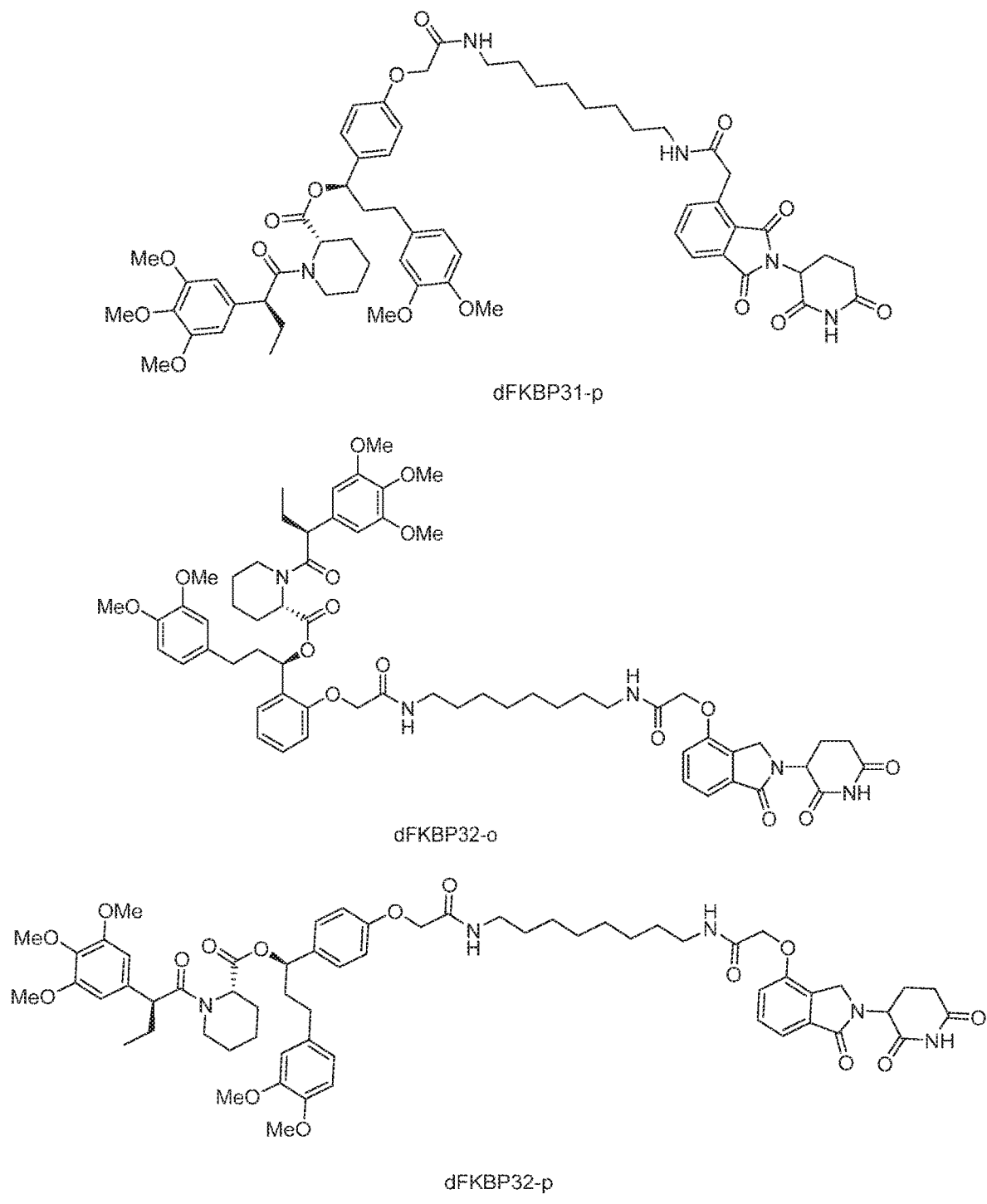
Figure 54Q:
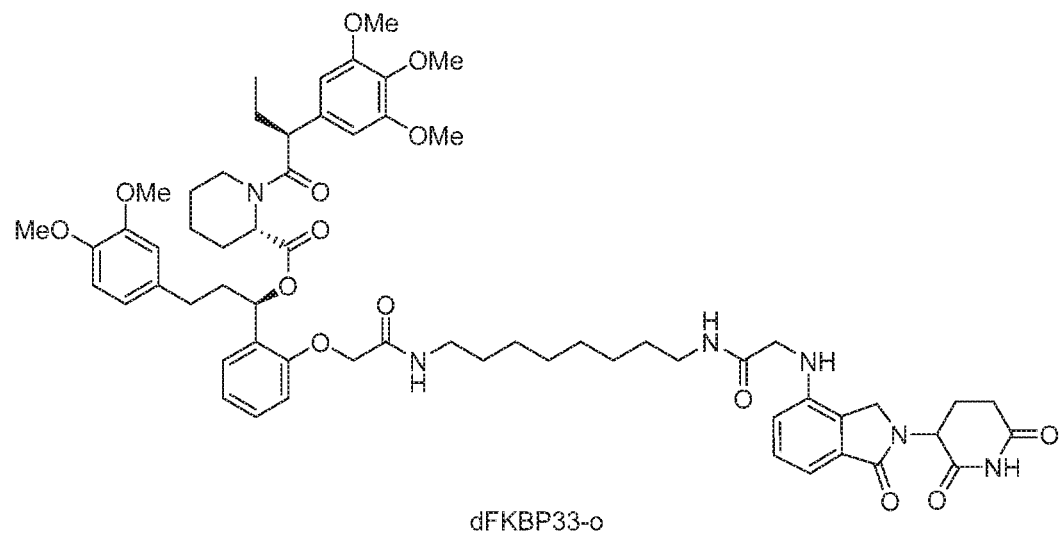
Figure 54Q:
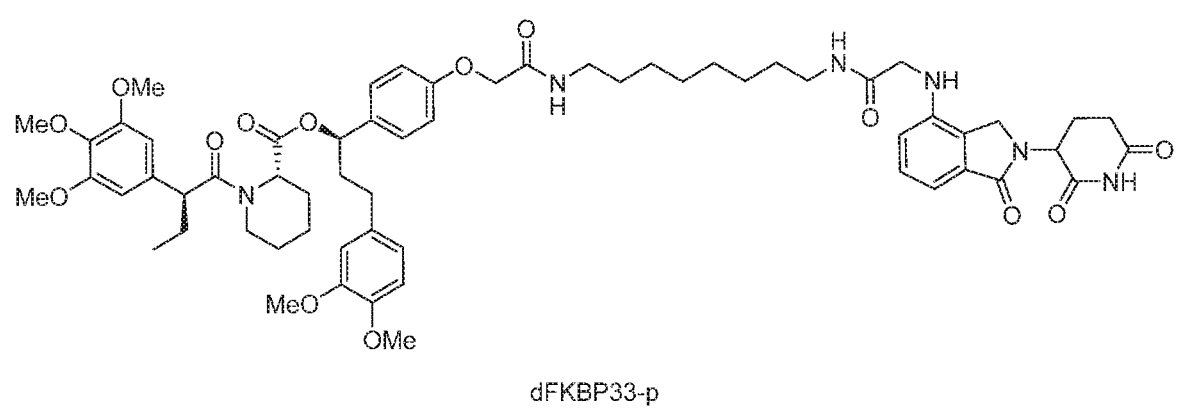
Figure 54Q:
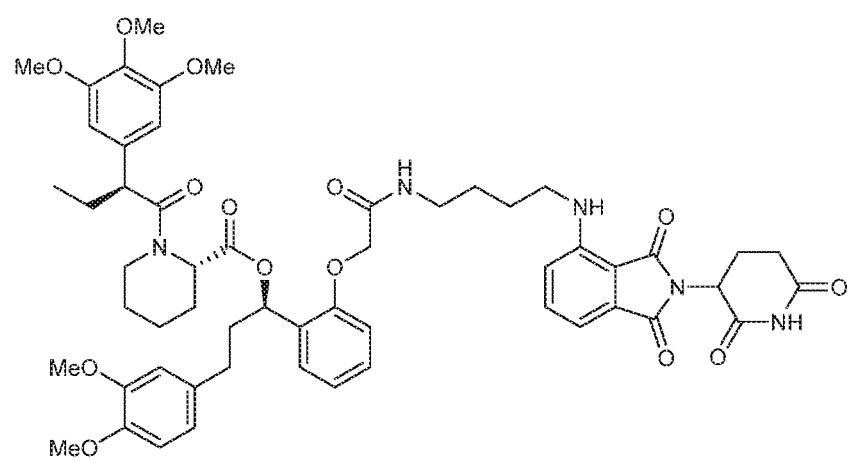
Figure 54R:
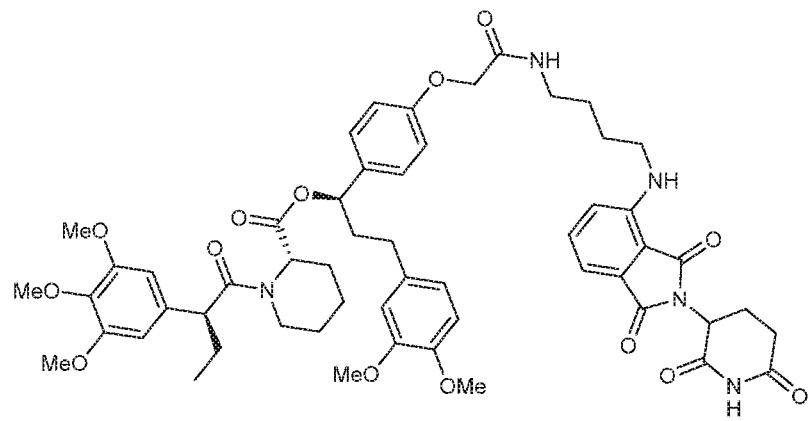
Figure 54R:
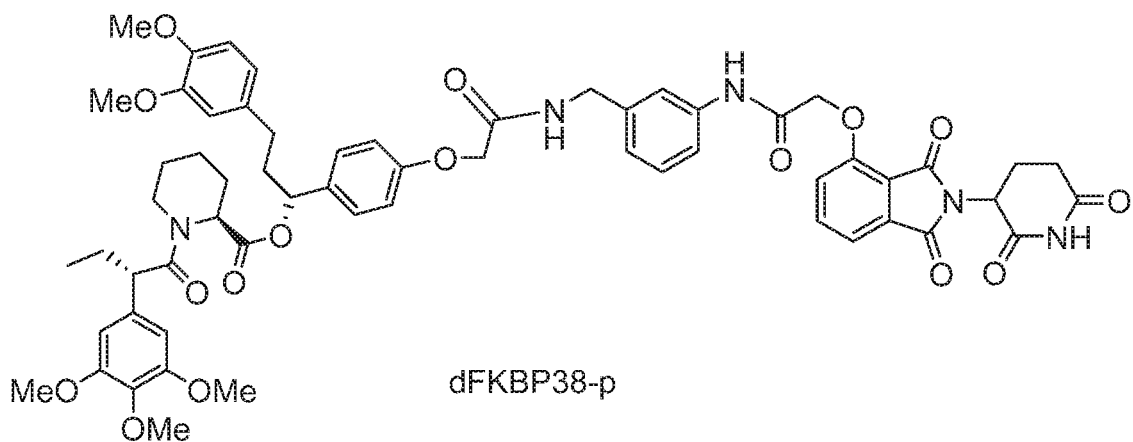
Figure 54R:
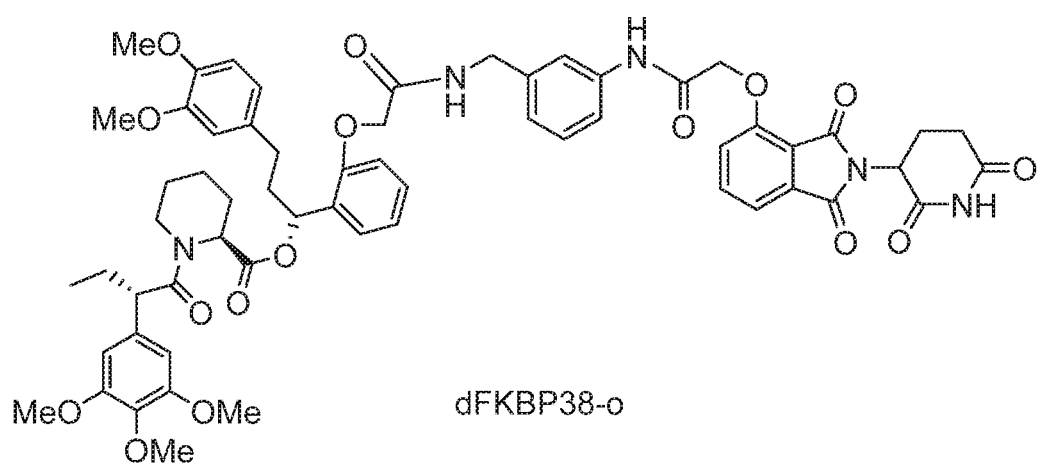
Figure 54S:
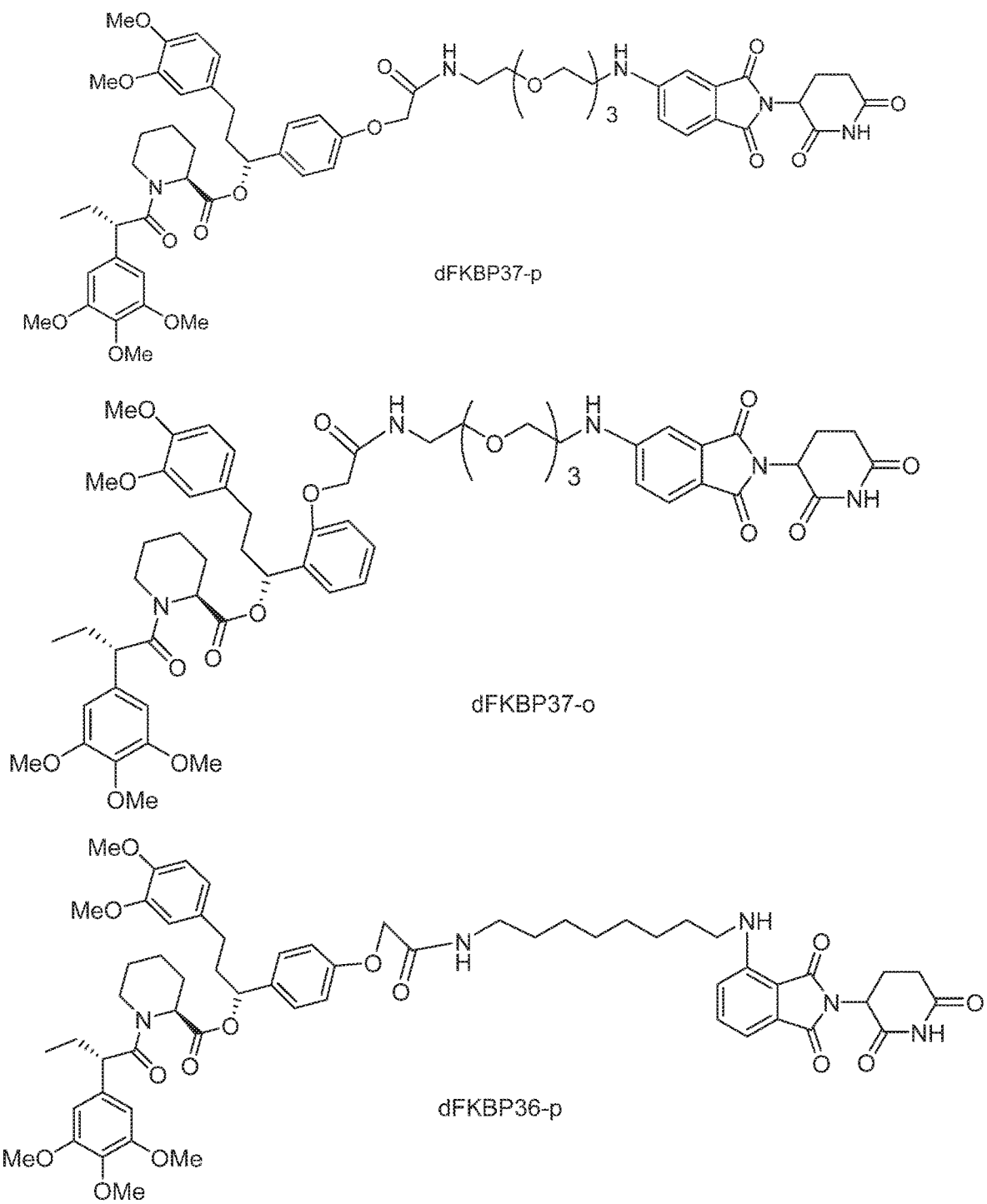
Figure 54T:
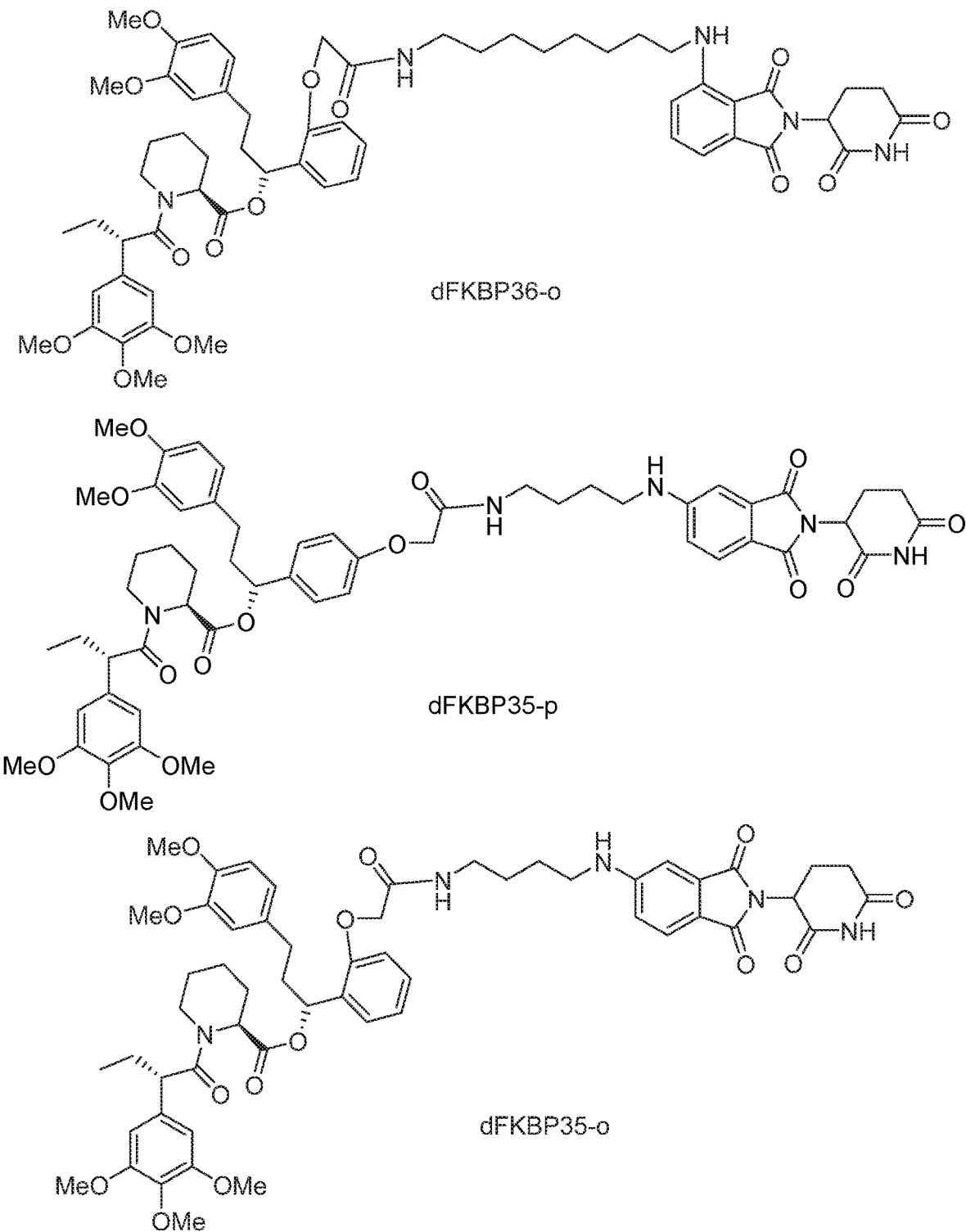
Figure 54U:
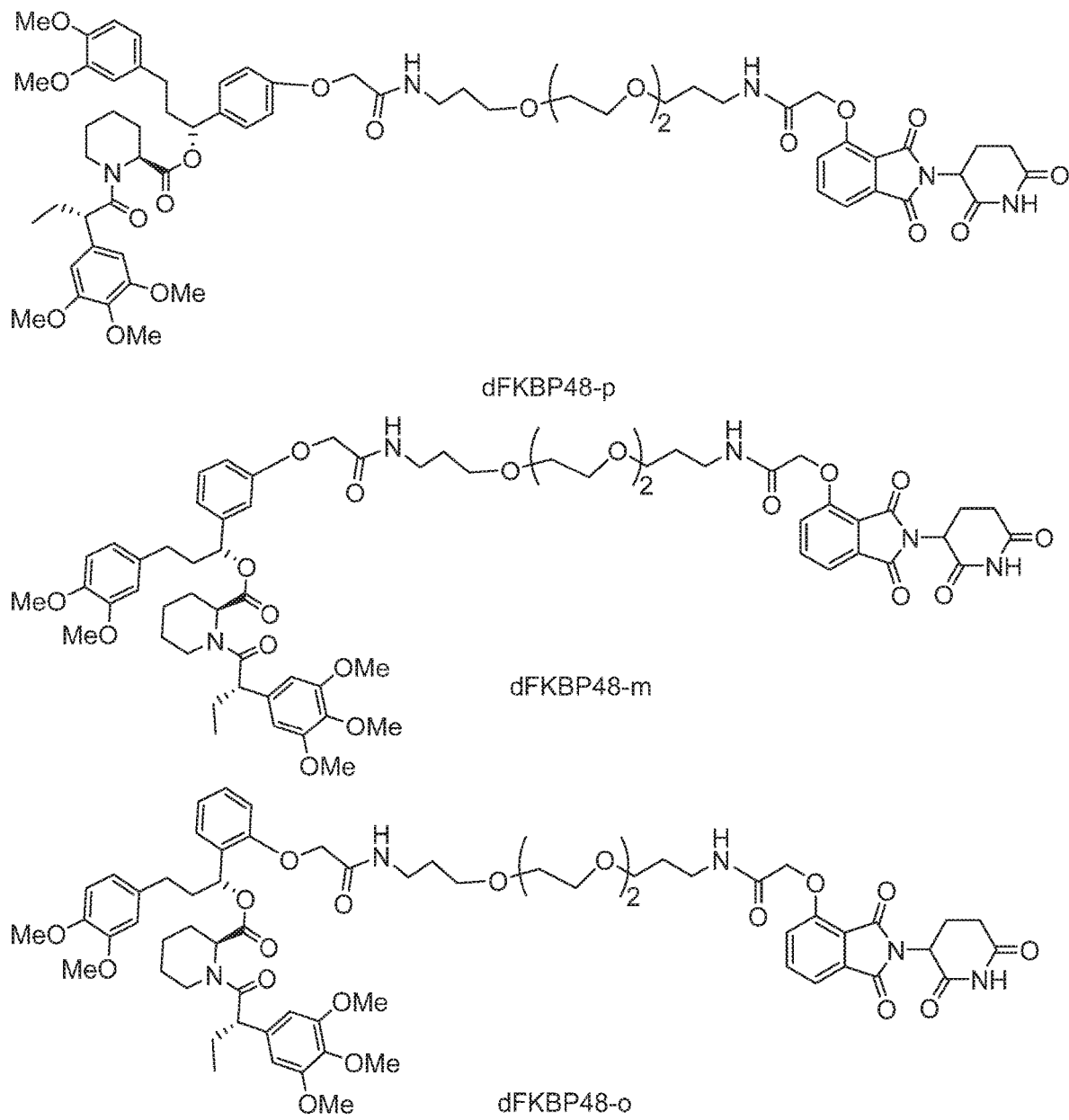
Figure 54V:
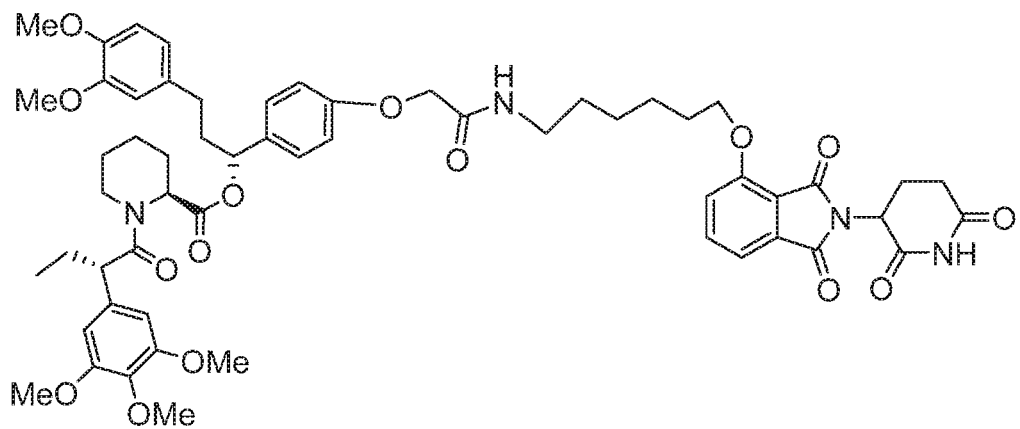
Figure 54V:
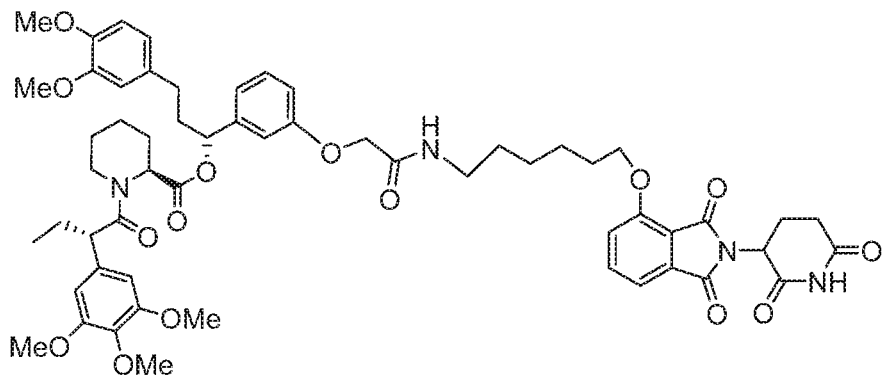
Figure 54V:
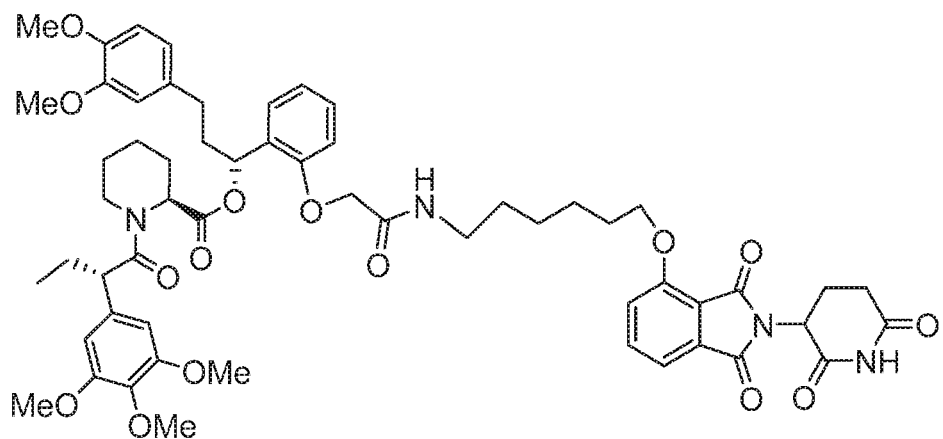
Figure 54W:
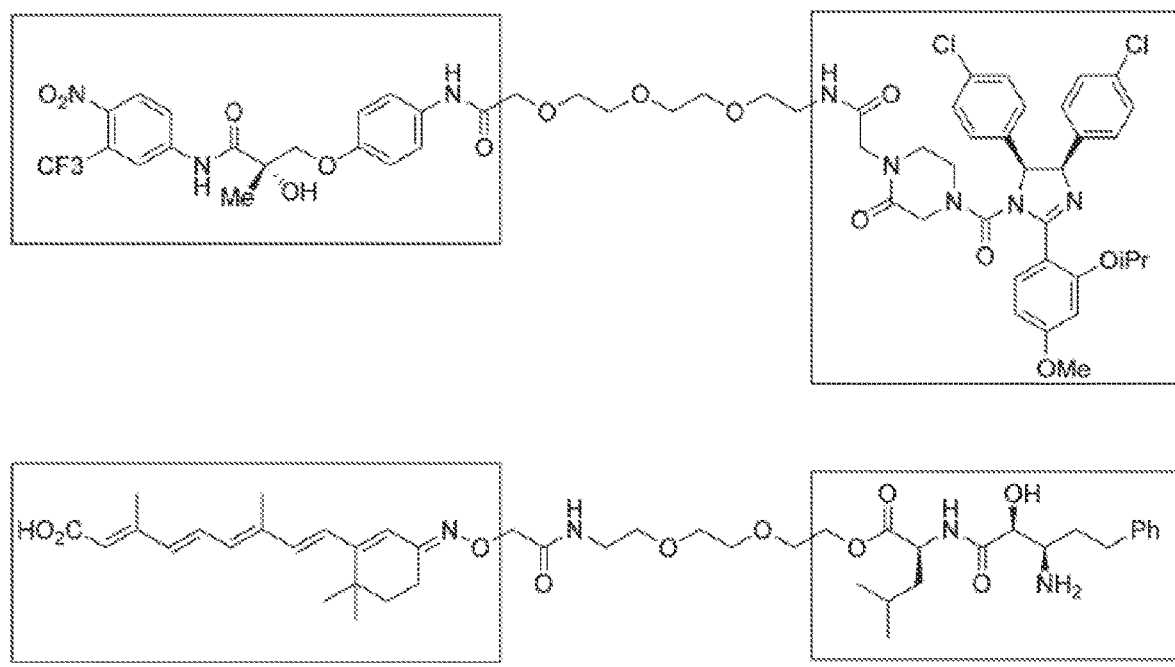

In certain embodiments, "L" can be nonlinear chains, and can be aliphatic or aromatic or heteroaromatic cyclic moieties, some examples of "L" include but not be limited to the structures of FIG. 48, wherein X and Y are independently selected from a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, P(O)$R^{L1}$, P(O)O$R^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently, can be linked to other A groups to form a cycloalkyl and/or heterocyclyl moiety which can be further substituted with 0-4 $R^{L5}$ groups.

dTAG Targeting Ligand

The dTAG Targeting Ligand (TL) is capable of binding to a dTAG or being bound by a dTAG target that allows tagging with ubiquitin to occur;

As contemplated herein, the CARs of the present invention include a heterobifunctional compound targeted protein (dTAG) which locates in the cytoplasm. The heterobifunctional compound targeted protein of the CAR is any amino acid sequence to which a heterobifunctional compound can be bound, leading to the degradation of the CAR when in contact with the heterobifunctional compound. Preferably, the dTAG should not interfere with the function of the CAR. In one embodiment, the dTAG is a non-endogenous peptide, leading to heterobifunctional compound selectivity and allowing for the avoidance of off target effects upon administration of the heterobifunctional compound. In one embodiment, the dTAG is an amino acid sequence derived from an endogenous protein which has been modified so that the heterobifunctional compound binds only to the modified amino acid sequence and not the endogenously expressed protein. In one embodiment, the dTAG is an endogenously expressed protein. Any amino acid sequence domain that can be bound by a ligand for use in a heterobifunctional compound can be used as a dTAG as contemplated herewith.

In particular embodiments, the dTAGs for use in the present invention include, but are not limited to, amino acid sequences derived from endogenously expressed proteins such as FK506 binding protein-12 (FKBP12), bromodomain-containing protein 4 (BRD4), CREB binding protein (CREBBP), and transcriptional activator BRG1 (SMARCA4), or a variant thereof. As contemplated herein, "variant" means any variant such as a substitution, deletion, or addition of one or a few to plural amino acids, provided that the variant substantially retains the same function as the original sequence, which in this case is providing ligand binding for a heterobifunctional compound. In other embodiments, dTAGs for us in the present invention may include, for example, hormone receptors e.g. estrogen-receptor proteins, androgen receptor proteins, retinoid x receptor (RXR) protein, and dihydrofolate reductase (DHFR), including bacterial DHFR, bacterial dehydrogenase, and variants.

In one embodiment the dTAG is a portion of any of the proteins identified herein. For example, the dTAG can be the BD1 domain of BRD4 or the BD2 domain of BRD4. In one embodiment that Targeting Ligands identified herein to target the parent dTAG are instead used to target portion. In one embodiment, the BRD4 Targeting Ligands in Table T can be used to target the BD1 dTAG. In another embodiment, the BRD4 Targeting Ligands in Table T can be used to target the BD2 dTAG.

Some embodiments of the present application include TLs which target dTAGs including, but not limited to, those derived from Hsp90 inhibitors, kinase inhibitors, MDM2 inhibitors, compounds targeting Human BET bromodomain-containing proteins, compounds targeting cytosolic signaling protein FKBP12, HDAC inhibitors, human lysine methyltransferase inhibitors, angiogenesis inhibitors, immunosuppressive compounds, and compounds targeting the aryl hydrocarbon receptor (AHR).

In certain embodiments, the dTAG Targeting Ligand is a compound that is capable of binding to or binds to a dTAG derived from a kinase, a BET bromodomain-containing protein, a cytosolic signaling protein (e.g., FKBP12), a nuclear protein, a histone deacetylase, a lysine methyltransferase, a protein regulating angiogenesis, a protein regulating immune response, an aryl hydrocarbon receptor (AHR), an estrogen receptor, an androgen receptor, a glucocorticoid receptor, or a transcription factor (e.g., SMARCA4, SMARCA2, TRIM24).

In certain embodiments, the dTAG is derived from a kinase to which the dTAG Targeting Ligand is capable of binding or binds including, but not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDG-FRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70), a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIPS, RSK1, RSK2, SGK2, SGK3, SIK1, STK33, TAO1, TAO2, TGF-beta, TLK2, TSSK1, TSSK2, ULK1, or ULK2), a cyclin dependent kinase (e.g., Cdk1-Cdk11), and a leucine-rich repeat kinase (e.g., LRRK2).

In certain embodiments, the dTAG is derived from a BET bromodomain-containing protein to which the dTAG Targeting Ligand is capable of binding or binds including, but not limited to, ASH1L, ATAD2, BAZ1A, BAZ1B, BAZ2A, BAZ2B, BRD1, BRD2, BRD3, BRD4, BRD5, BRD6, BRD7, BRD8, BRD9, BRD10, BRDT, BRPF1, BRPF3, BRWD3, CECR2, CREBBP, EP300, FALZ, GCN5L2, KIAA1240, LOC93349, MLL, PB1, PCAF, PHIP, PRKCBP1, SMARCA2, SMARCA4, SP100, SP110, SP140, TAF1, TAF1L, TIF1a, TRIM28, TRIM33, TRIM66, WDR9, ZMYND11, and MLL4. In certain embodiments, a BET bromodomain-containing protein is BRD4.

In certain embodiments, the dTAG is derived from a nuclear protein to which the dTAG Targeting Ligand is capable of binding or binds including, but not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In certain embodiments, the dTAG Targeting Ligand is selected from a kinase inhibitor, a BET bromodomain-containing protein inhibitor, cytosolic signaling protein FKBP12 ligand, an HDAC inhibitor, a lysine methyltransferase inhibitor, an angiogenesis inhibitor, an immunosuppressive compound, and an aryl hydrocarbon receptor (AHR) inhibitor.

In certain embodiments, the dTAG Targeting Ligand is a SERM (selective estrogen receptor modulator) or SERD (selective estrogen receptor degrader). Non-limiting examples of SERMs and SERDs are provided in WO 2014/191726 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138 assigned to Seragon Pharmaceuticals.

Additional dTAG Targeting Ligands include, for example, any moiety which binds to an endogenous protein (binds to a target dTAG). Illustrative dTAG Targeting Ligands includes the small molecule dTAG Targeting Ligand: Hsp90 inhibitors, kinase inhibitors, HDM2 and MDM2 inhibitors, compounds targeting Human BET bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. Such small molecule target dTAG binding moieties also include pharmaceutically acceptable salts, enantiomers, solvates and polymorphs of these compositions, as well as other small molecules that may target a dTAG of interest.

In some embodiments the dTAG Targeting Ligand is an Ubc9 SUMO E2 ligase 5F6D targeting ligand including but not limited to those described in "Insights Into the Allosteric Inhibition of the SUMO E2 Enzyme Ubc9." by Hewitt, W. M., et. al. (2016) Angew. Chem. Int. Ed. Engl. 55: 5703-5707

In another embodiment the dTAG Targeting Ligand is a Tank1 targeting ligand including but not limited to those described in "Structure of human tankyrase 1 in complex with small-molecule inhibitors PJ34 and XAV939." Kirby, C. A., Cheung, A., Fazal, A., Shultz, M. D., Stams, T, (2012) Acta Crystallogr., Sect. F 68: 115-118; and "Structure-Efficiency Relationship of [1,2,4]Triazol-3-ylamines as Novel Nicotinamide Isosteres that Inhibit Tankyrases." Shultz, M. D., et al. (2013) J. Med. Chem. 56: 7049-7059.

In another embodiment the dTAG Targeting Ligand is a SH2 domain of pp60 Src targeting ligand including but not limited to those described in "Requirements for Specific Binding of Low Affinity Inhibitor Fragments to the SH2 Domain of pp60Src Are Identical to Those for High Affinity Binding of Full Length Inhibitors" Gudrun Lange, et al., J. Med. Chem. 2003, 46, 5184-5195.

In another embodiment the dTAG Targeting Ligand is a Sec7 domain targeting ligand including but not limited to those described in "The Lysosomal Protein Saposin B Binds Chloroquine." Huta, B. P., et al., (2016) Chemmedchem 11: 277.

In another embodiment the dTAG Targeting Ligand is a Saposin-B targeting ligand including but not limited to those described in "The structure of cytomegalovirus immune modulator UL141 highlights structural Ig-fold versatility for receptor binding" I. Nemcovicova and D. M. Zajonc Acta Cryst. (2014). D70, 851-862.

In another embodiment the dTAG Targeting Ligand is a Protein S100-A7 2OWS targeting ligand including but not limited to those described in "2WOS STRUCTURE OF HUMAN S100A7 IN COMPLEX WITH 2, 6 ANS" DOI: 10.2210/pdb2wos/pdb; and "Identification and Characterization of Binding Sites on S100A7, a Participant in Cancer and Inflammation Pathways." Leon, R., Murray, et al., (2009) Biochemistry 48: 10591-10600.

In another embodiment the dTAG Targeting Ligand is a Phospholipase A2 targeting ligand including but not limited to those described in "Structure-based design of the first potent and selective inhibitor of human non-pancreatic secretory phospholipase A2" Schevitz, R. W., et al., Nat. Struct. Biol. 1995, 2, 458-465.

In another embodiment the dTAG Targeting Ligand is a PHIP targeting ligand including but not limited to those described in "A Poised Fragment Library Enables Rapid Synthetic Expansion Yielding the First Reported Inhibitors of PHIP(2), an Atypical Bromodomain" Krojer, T.; et al. Chem. Sci. 2016, 7, 2322-2330.

In another embodiment the dTAG Targeting Ligand is a PDZ targeting ligand including but not limited to those described in "Discovery of Low-Molecular-Weight Ligands for the AF6 PDZ Domain" Mangesh Joshi, et al. Angew. Chem. Int. Ed. 2006, 45, 3790-3795.

In another embodiment the dTAG Targeting Ligand is a PARP15 targeting ligand including but not limited to those described in "Structural Basis for Lack of ADP-ribosyltransferase Activity in Poly(ADP-ribose) Polymerase-13/Zinc Finger Antiviral Protein." Karlberg, T., et al., (2015) J. Biol. Chem. 290: 7336-7344.

In another embodiment the dTAG Targeting Ligand is a PARP14 targeting ligand including but not limited to those described in "Discovery of Ligands for ADP-Ribosyltransferases via Docking-Based Virtual Screening." Andersson, C. D., et al., (2012) J. Med. Chem. 55: 7706-7718; "Family-wide chemical profiling and structural analysis of PARP and tankyrase inhibitors." Wahlberg, E., et al. (2012) Nat. Biotechnol. 30: 283-288; "Discovery of Ligands for ADP-Ribosyltransferases via Docking-Based Virtual Screening. "Andersson, C. D., et al. (2012) J. Med. Chem. 55: 7706-7718.

In another embodiment the dTAG Targeting Ligand is a MTH1 targeting ligand including but not limited to those described in "MTH1 inhibition eradicates cancer by preventing sanitation of the dNTP pool" Helge Gad, et. al. Nature, 2014, 508, 215-221.

In another embodiment the dTAG Targeting Ligand is a mPGES-1 targeting ligand including but not limited to those described in "Crystal Structures of mPGES-1 Inhibitor Complexes Form a Basis for the Rational Design of Potent Analgesic and Anti-Inflammatory Therapeutics." Luz, J. G., et al., (2015) J. Med. Chem. 58: 4727-4737.

In another embodiment the dTAG Targeting Ligand is a FLAP-5-lipoxygenase-activating protein targeting ligand including but not limited to those described in "Crystal structure of inhibitor-bound human 5-lipoxygenase-activating protein." Ferguson, A. D., McKeever, B. M., Xu, S., Wisniewski, D., Miller, D. K., Yamin, T. T., Spencer, R. H., Chu, L., Ujjainwalla, F., Cunningham, B. R., Evans, J. F., Becker, J. W. (2007) Science 317: 510-512.

In another embodiment the dTAG Targeting Ligand is a FA Binding Protein targeting ligand including but not limited to those described in "A Real-World Perspective on Molecular Design." Kuhn, B.; et al. J. Med. Chem. 2016, 59, 4087-4102.

In another embodiment the dTAG Targeting Ligand is a BCL2 targeting ligand including but not limited to those described in "ABT-199, a potent and selective BCL-2 inhibitor, achieves antitumor activity while sparing platelets." Souers, A. J., et al. (2013) NAT. MED. (N.Y.) 19: 202-208.

In another embodiment the dTAG Targeting Ligand is an EGFR targeting ligand. In one embodiment the dTAG Targeting Ligand is selected from erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EA1045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer). The linker can be placed on these Targeting Ligands in any location that does not interfere with the Ligands binding to EGFR. Non-limiting examples of Linker binding locations are provided in Table T below. In one embodiment the EGFR targeting ligand binds the L858R mutant of EGFR. In another embodiment the EGFR targeting ligand binds the T790M mutant of EGFR. In another embodiment the EGFR targeting ligand binds the C797G or C797S mutant of EGFR. In one embodiment the EGFR targeting ligand is selected from erlotinib, gefitinib, afatinib, neratinib, and dacomitinib and binds the L858R mutant of EGFR. In another embodiment the EGFR targeting ligand is selected from osimertinib, rociletinib, olmutinib, naquotinib, nazartinib, PF-06747775, Icotinib, Neratinib, Avitinib, Tarloxotinib, PF-0645998, Tesevatinib, Transtinib, WZ-3146, WZ8040, and CNX-2006 and binds the T790M mutant of EGFR. In another embodiment the EGFR targeting ligand is EA1045 and binds the C797G or C797S mutant of EGFR.

Any protein which can bind to a dTAG Targeting Ligand group and acted on or degraded by a ubiquitin ligase is a target protein according to the present invention. In general, an endogenous target proteins for use as dTAGs may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity.

More specifically, a number of drug targets for human therapeutics represent dTAG targets to which protein target or dTAG Targeting Ligand may be bound and incorporated into compounds according to the present invention. These include proteins which may be used to restore function in numerous polygenic diseases, including for example B7.1 and B7, TINFR1m, TNFR2, NADPH oxidase, BclIBax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyl-transferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets useful as dTAGs include, for example, ecdysone 20-monooxygenase, ion channel of the GABA gated chloride channel, acetylcholinesterase, voltage-sensitive sodium channel protein, calcium release channel, and chloride channels. Still further target proteins for use as dTAGs include Acetyl-CoA carboxylase, adenylosuccinate synthetase, protoporphyrinogen oxidase, and enolpyruvylshikimate-phosphate synthase.

In one embodiment the dTAG and dTAG Targeting Ligand pair are chosen by screening a library of ligands. Such a screening is exemplified in "Kinase Inhibitor Profiling Reveals Unexpected Opportunities to Inhibit Disease-Associated Mutant Kinases" by Duong-Ly et al.; Cell Reports 14, 772-781 Feb. 2, 2016.

Haloalkane dehalogenase enzymes are another target of specific compounds according to the present invention which may be used as dTAGs. Compounds according to the present invention which contain chloroalkane peptide binding moieties ($C_1$-$C_{12}$ often about C2-C10 alkyl halo groups) may be used to inhibit and/or degrade haloalkane dehalogenase enzymes which are used in fusion proteins or related diagnostic proteins as described in PCT/US2012/063401 filed Dec. 6, 2011 and published as WO 2012/078559 on Jun. 14, 2012, the contents of which is incorporated by reference herein.

Non-limiting examples of dTAG Targeting Ligands are shown below in Table T and represent dTAG Targeting Ligands capable of targeting proteins or amino acid sequence useful as dTAGs.

TABLE T

A. BRD dTAG Targeting Ligands:

BRD dTAG Targeting Ligands as used herein include, but are not limited to:

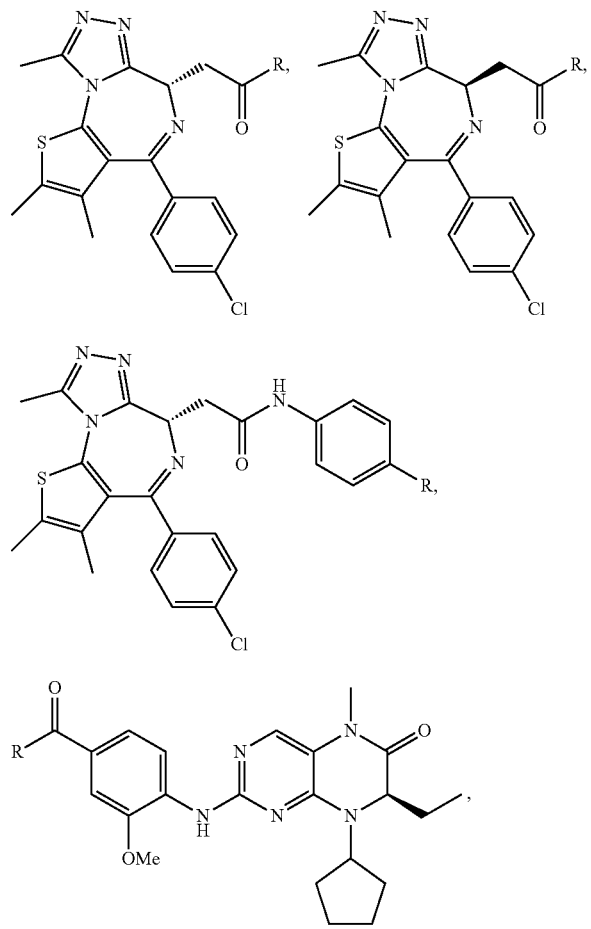

TABLE T-continued
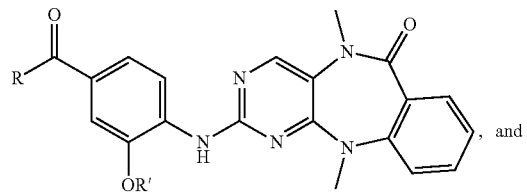
, and
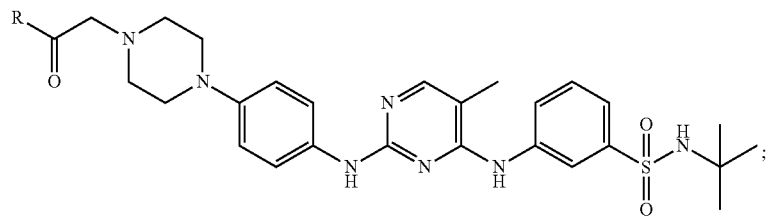
;
wherein:
R is the point at which the Linker is attached; and
R': is methyl or ethyl.
B. CREBBP dTAG Targeting Ligands:
CREBBP dTAG Targeting Ligands as used herein include, but are not limited to:
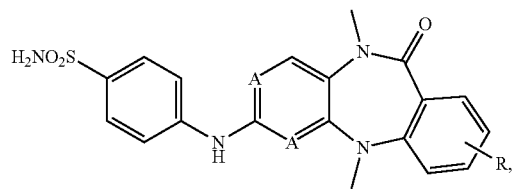
,
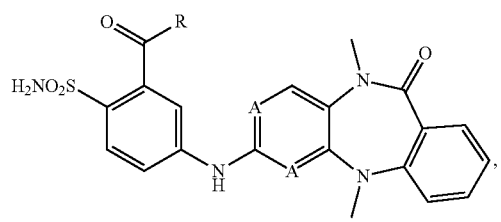
,
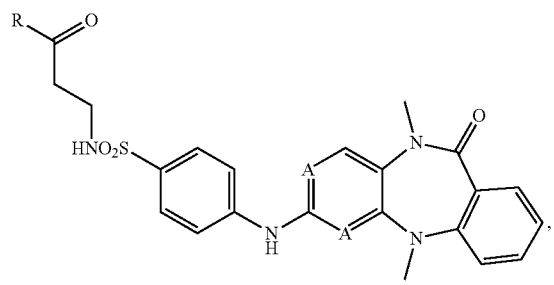
, TABLE T-continued
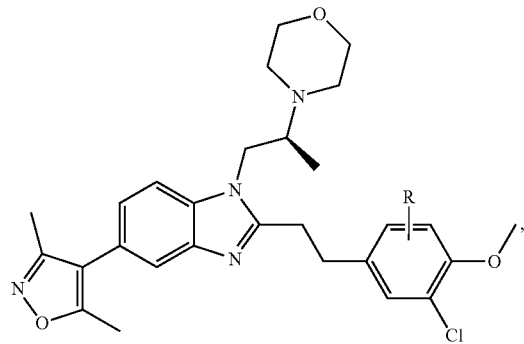
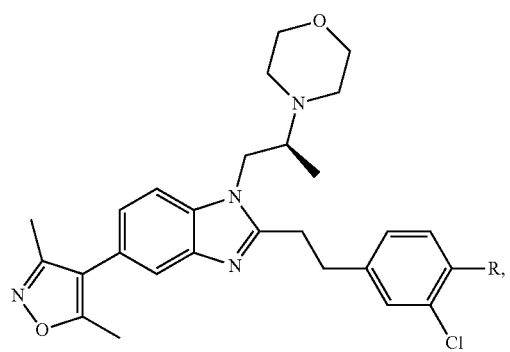
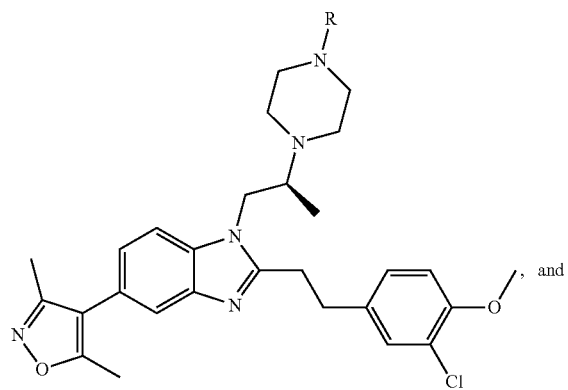

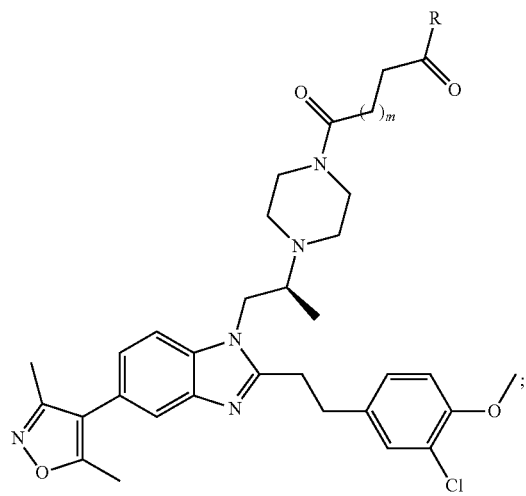
wherein:
R is the point at which the Linker is attached;
A is N or CH; and
m is 0, 1, 2, 3, 4, 5, 6, 7, or 8.
C. SMARCA4, PB1, and/or SMARCA2 dTAG Targeting Ligands:
SMARCA4, PB1, and/or SMARCA2 dTAG Targeting Ligands as used herein include, but are not limited to:
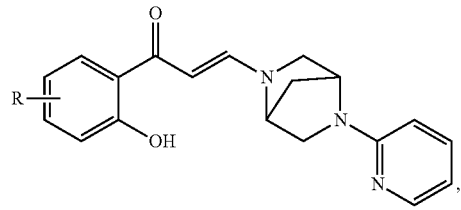
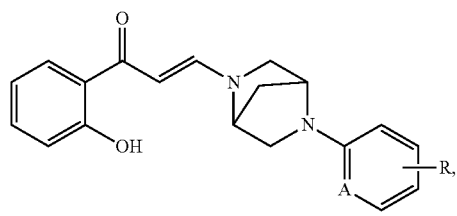
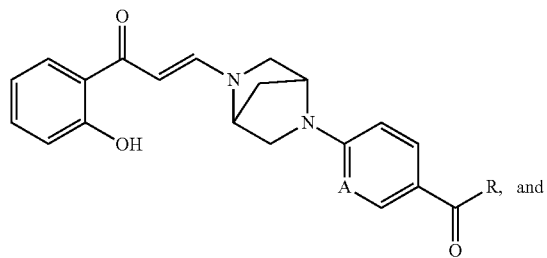

TABLE T-continued
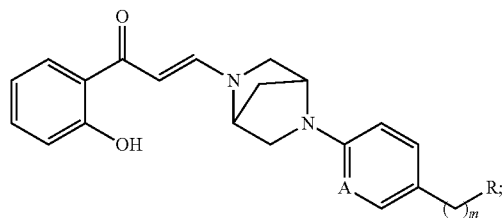
wherein:
R is the point at which the Linker is attached;
A is N or CH; and
m is 0, 1, 2, 3, 4, 5, 6, 7, or 8.
D. TRIM24 and/or BRPF1 dTAG Targeting Ligands:
TRIM24 and/or BRPF1 dTAG Targeting Ligands as used herein include, but are not limited to:
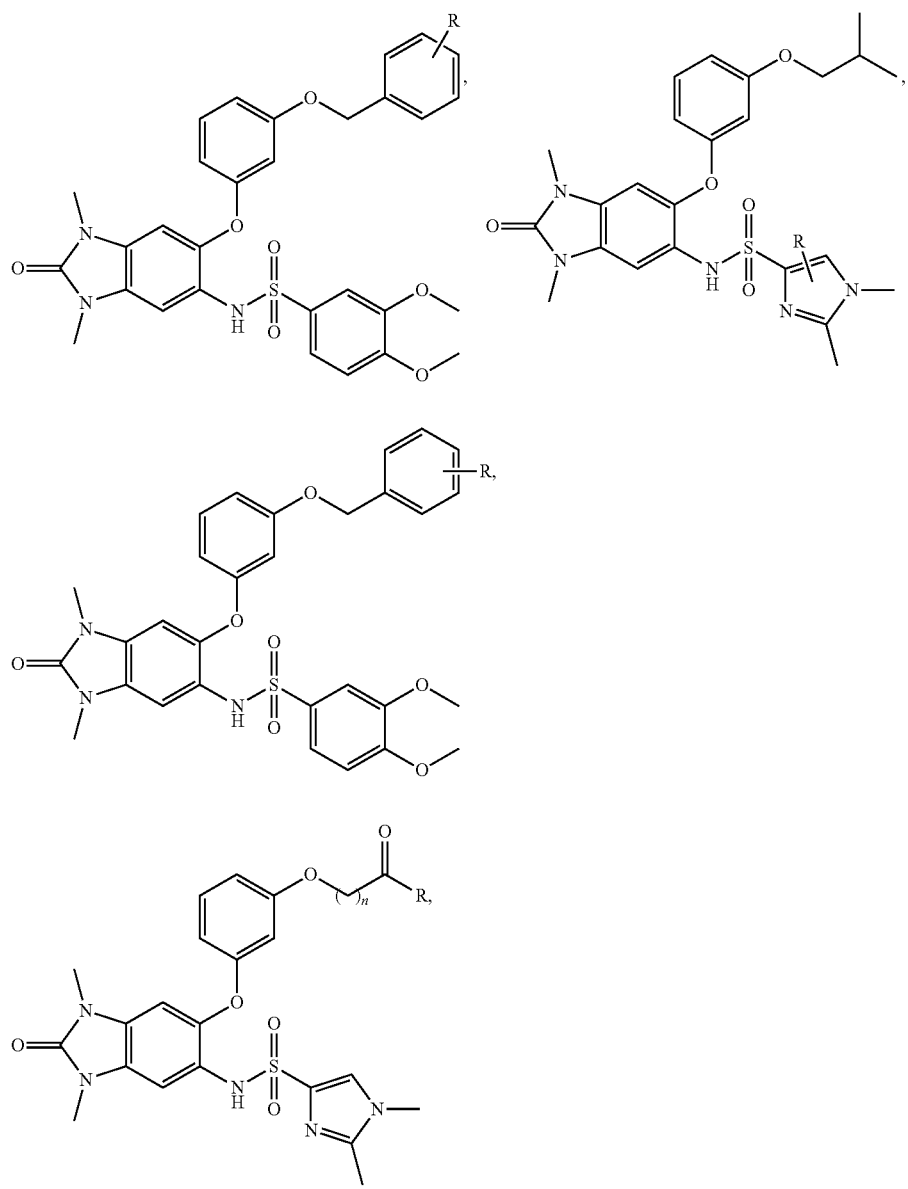

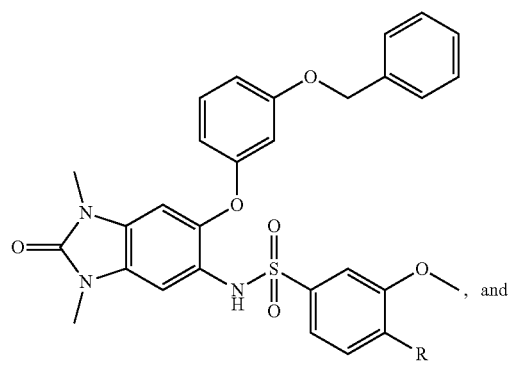
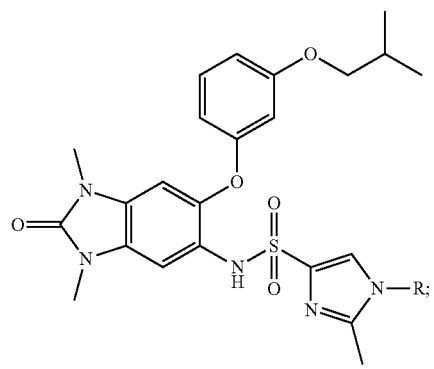
wherein:
R is the point at which the Linker is attached; and
m is 0, 1, 2, 3, 4, 5, 6, 7, or 8.
E. Glucocorticoid Receptor dTAG Targeting Ligand:
Glucocorticoid dTAG Targeting Ligands as used herein include, but are not limited to:
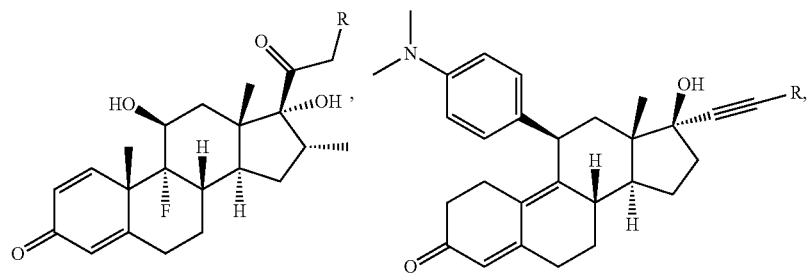
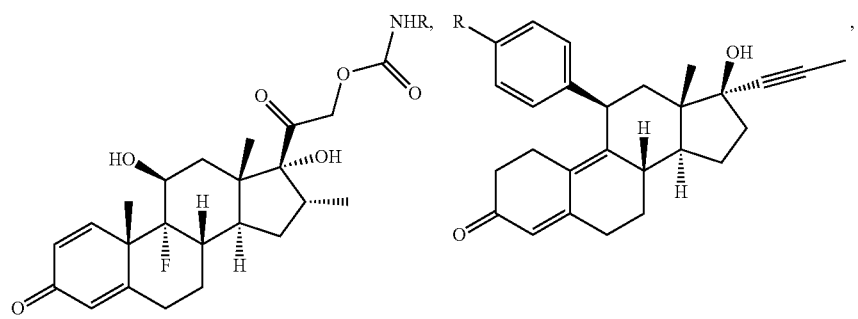

TABLE T-continued
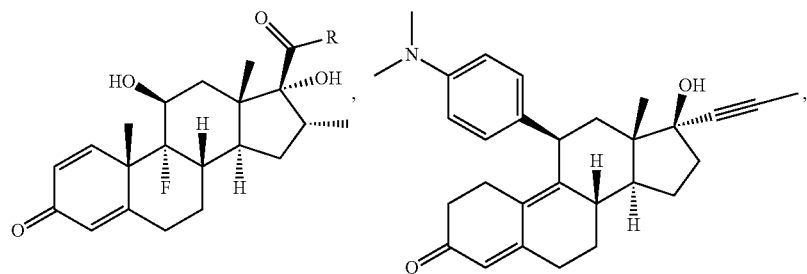
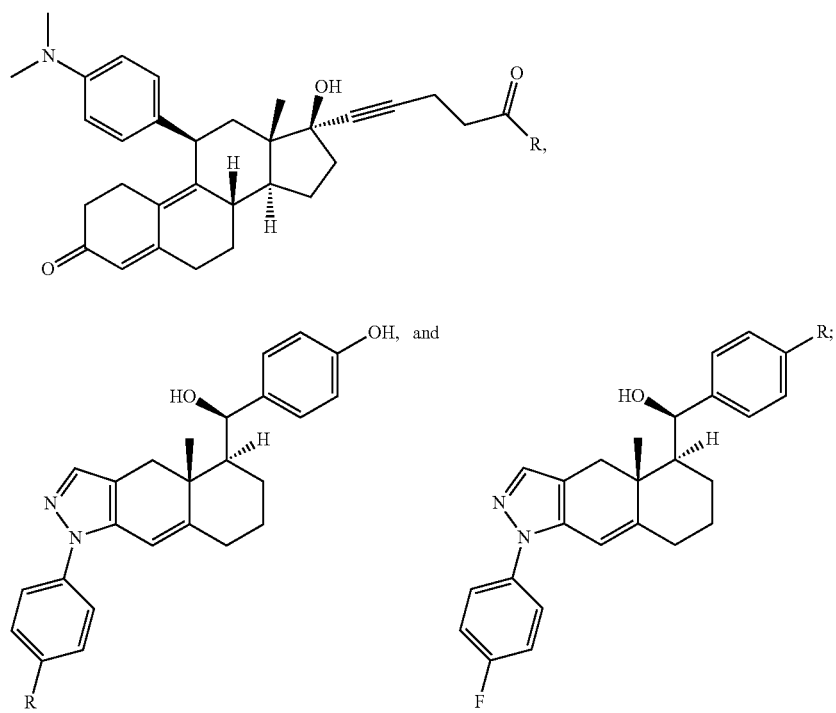
wherein:
R is the point at which the Linker is attached.
F. Estrogen and/or Androgen Receptor dTAG Targeting Ligands:
Estrogen and/or Androgen dTAG Targeting Ligands as used herein include, but are not limited to:
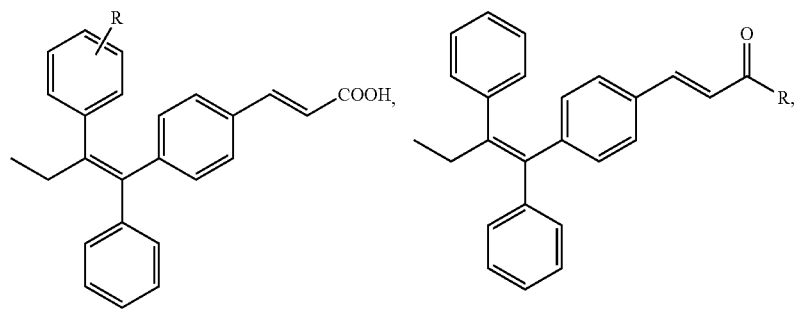

TABLE T-continued
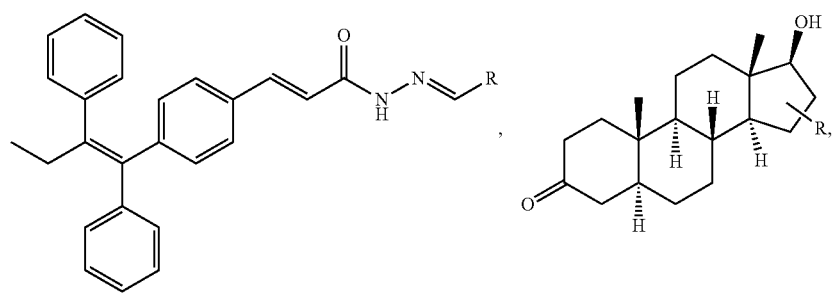
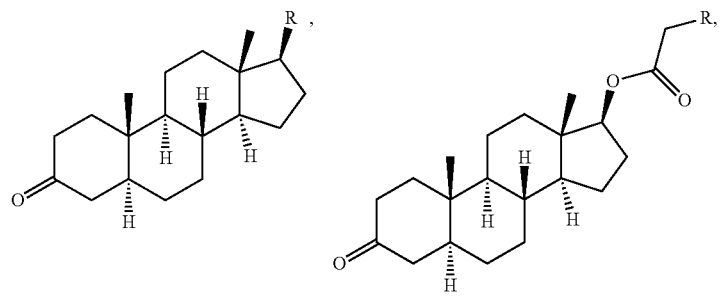
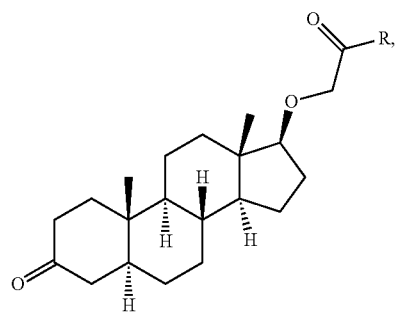
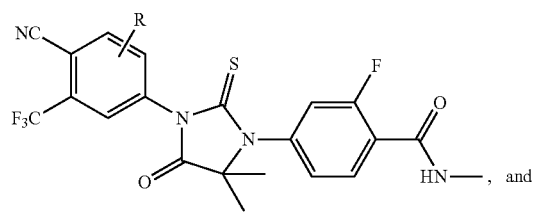
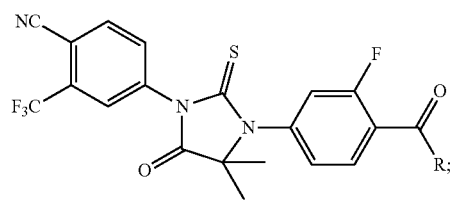
wherein:
R is the point at which the Linker is attached.

G. DOT1L dTAG Targeting Ligands:
DOT1L dTAG Targeting Ligands as used herein include, but are not limited to:
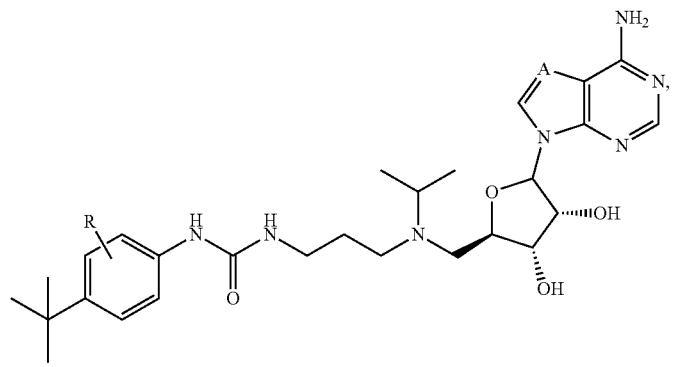
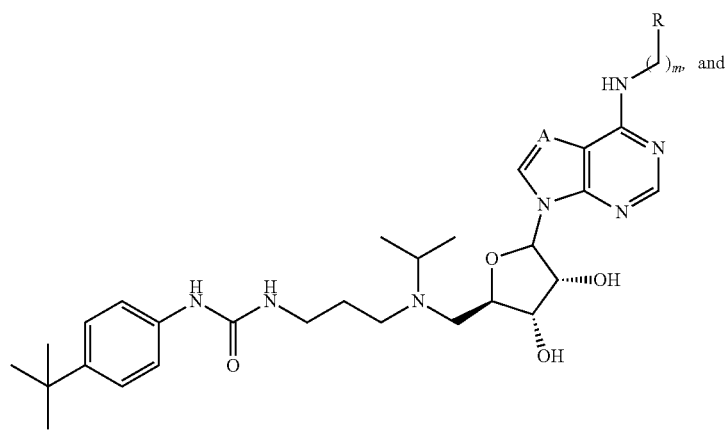
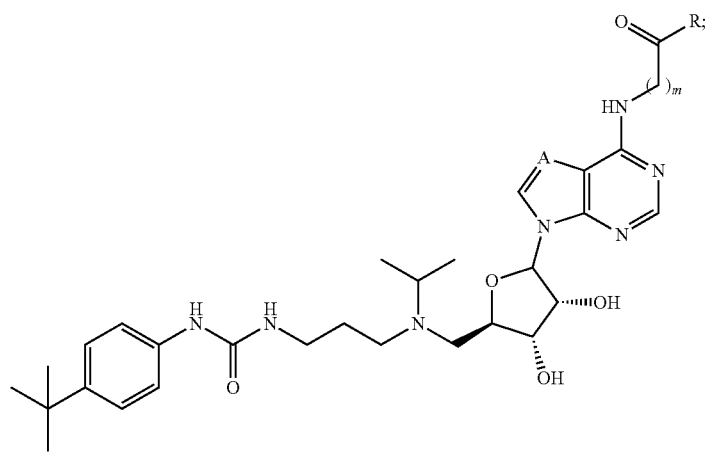
wherein:
R is the point at which the Linker is attached;
A is N or CH; and
m is 0, 1, 2, 3, 4, 5, 6, 7, or 8.

H. Ras dTAG Targeting Ligands:
Ras dTAG Targeting Ligands as used herein include, but are not limited to:
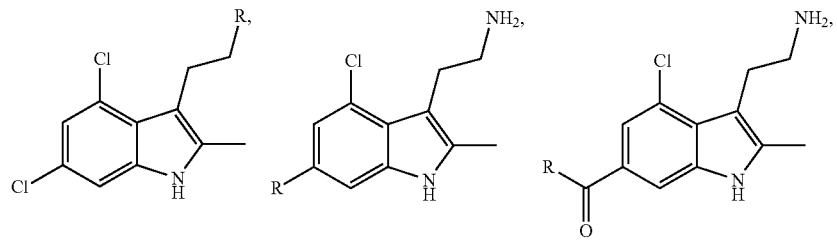
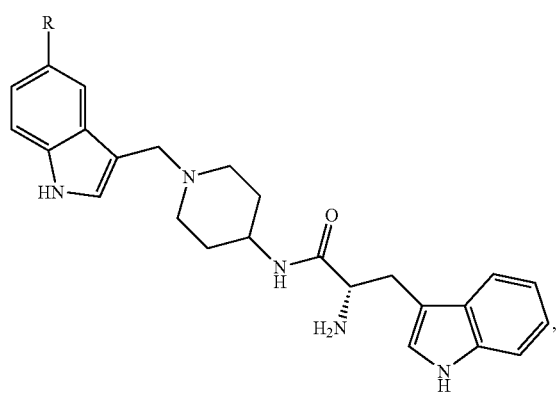
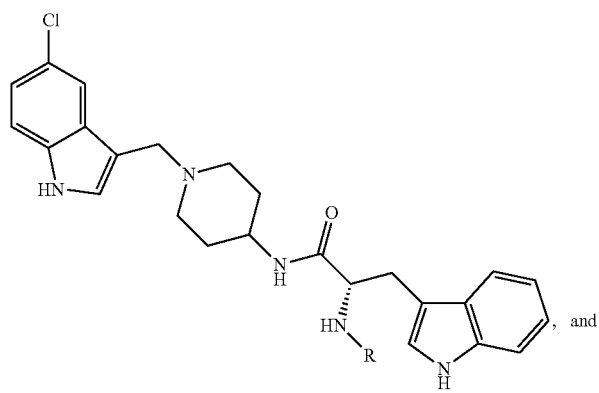, and
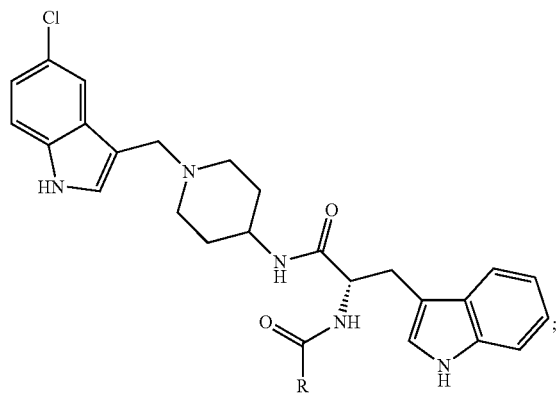;
wherein:
R is the point at which the Linker is attached.

TABLE T-continued
I. RasG12C dTAG Targeting Ligands:
RasG12C dTAG Targeting Ligands as used herein include, but are not limited to:
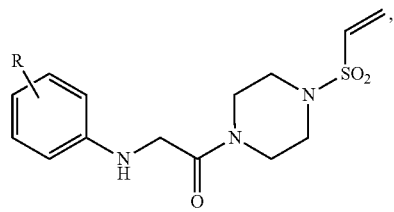
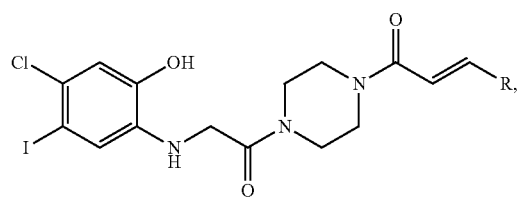
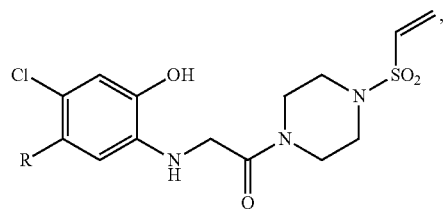
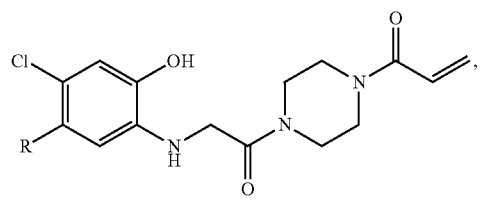
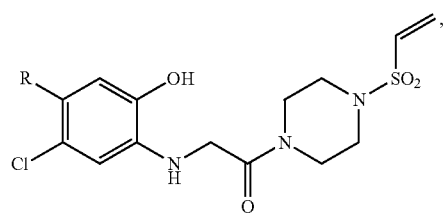
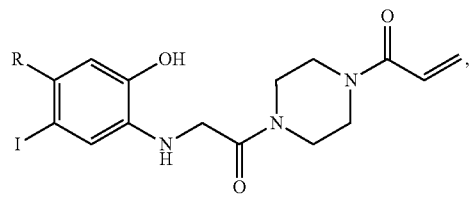
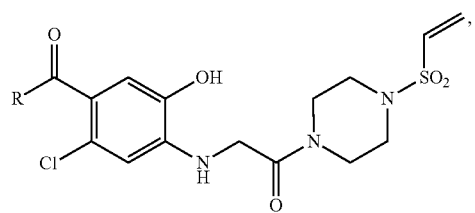

TABLE T-continued
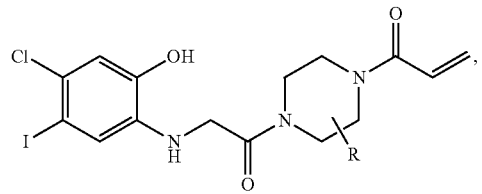
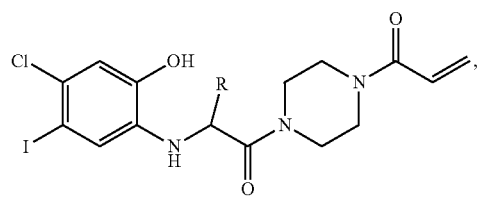
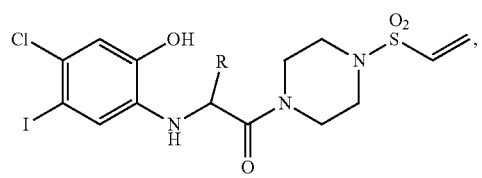
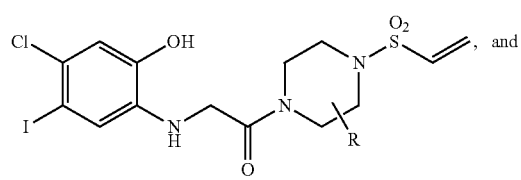
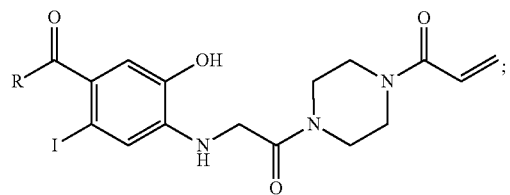
wherein:
R is the point at which the Linker is attached.

TABLE T-continued
J. Her3 dTAG Targeting Ligands:
Her3 dTAG Targeting Ligands as used herein include, but are not limited to:
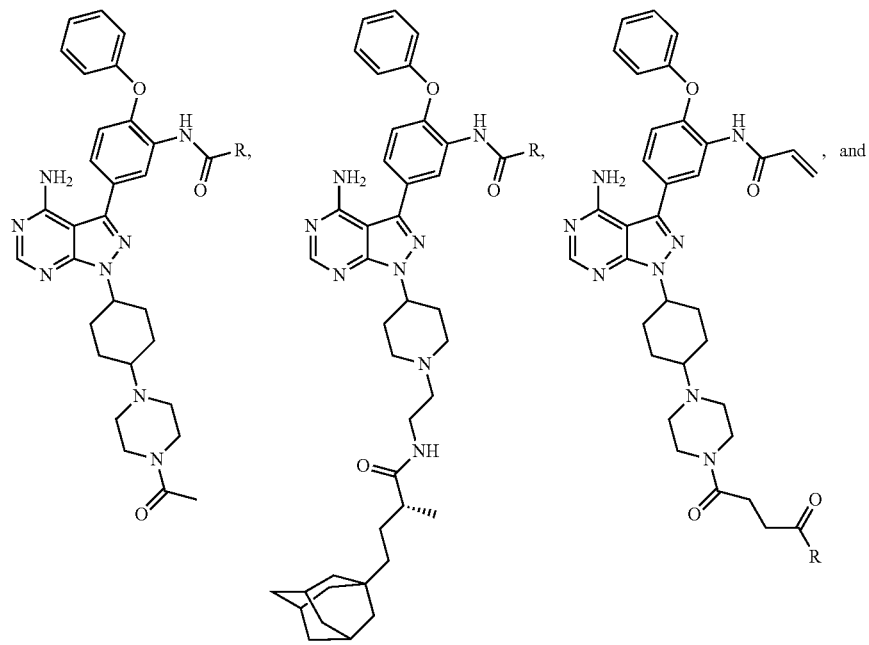
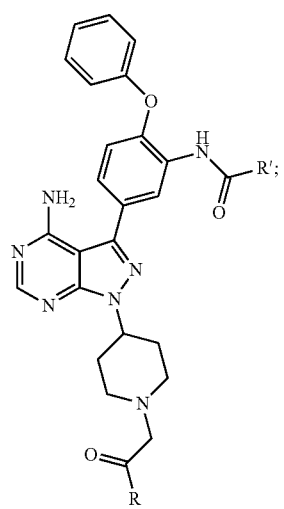
wherein:
R is the point at which the Linker is attached; and
R' is ![structure] or ![structure].

K. Bcl-2 or Bcl-XL dTAG Targeting Ligands:
Bcl-2 or Bcl-XL dTAG Targeting Ligands as used herein include, but are not limited to:
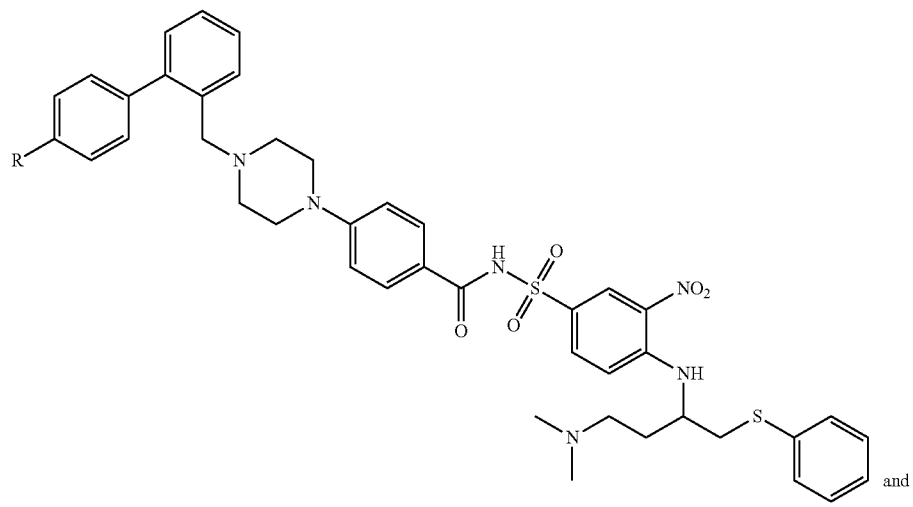
and
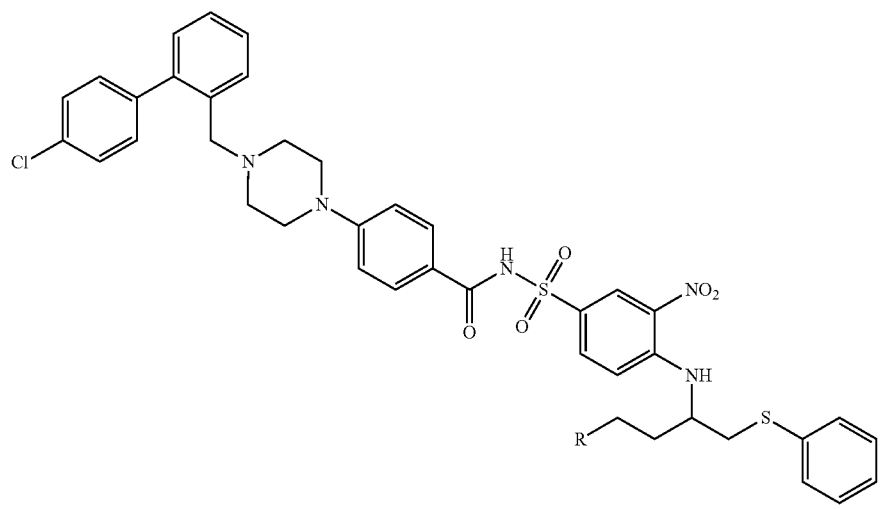
wherein:
R is the point at which the Linker is attached.
L. HDAC dTAG Targeting Ligands:
HDAC dTAG Targeting Ligands as used herein include, but are not limited to:
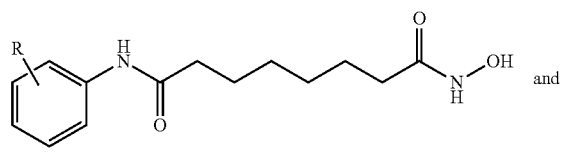
and TABLE T-continued
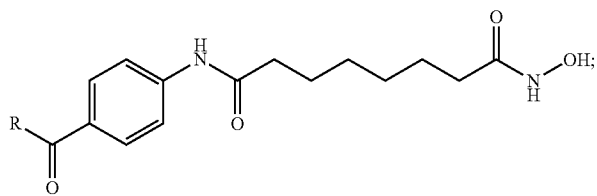
wherein:
R is the point at which the Linker is attached.
M. PPAR-gamma dTAG Targeting Ligands:
PPAR-gamma dTAG Targeting Ligands as used herein include, but are not limited to:
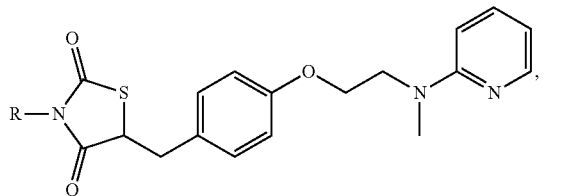
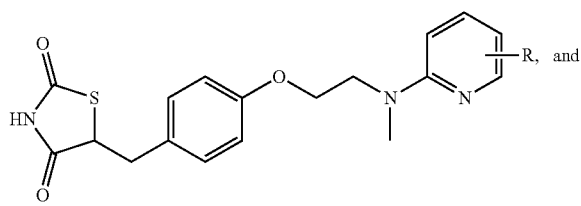
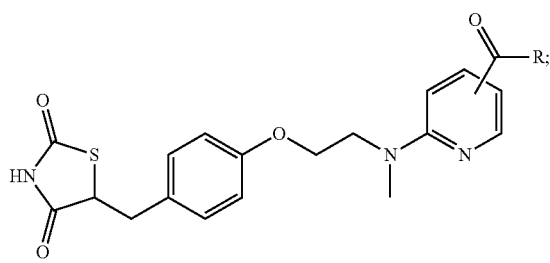
wherein:
R is the point at which the Linker is attached.
N. RXR dTAG Targeting Ligands:
RXR dTAG Targeting Ligands as used herein include, but are not limited to:
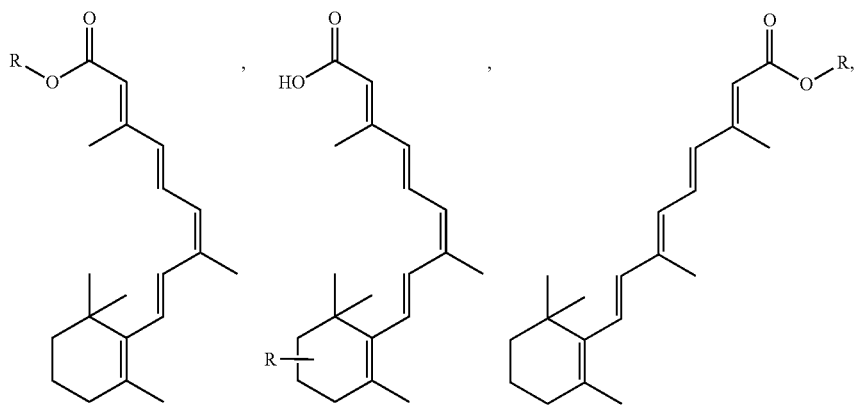

TABLE T-continued
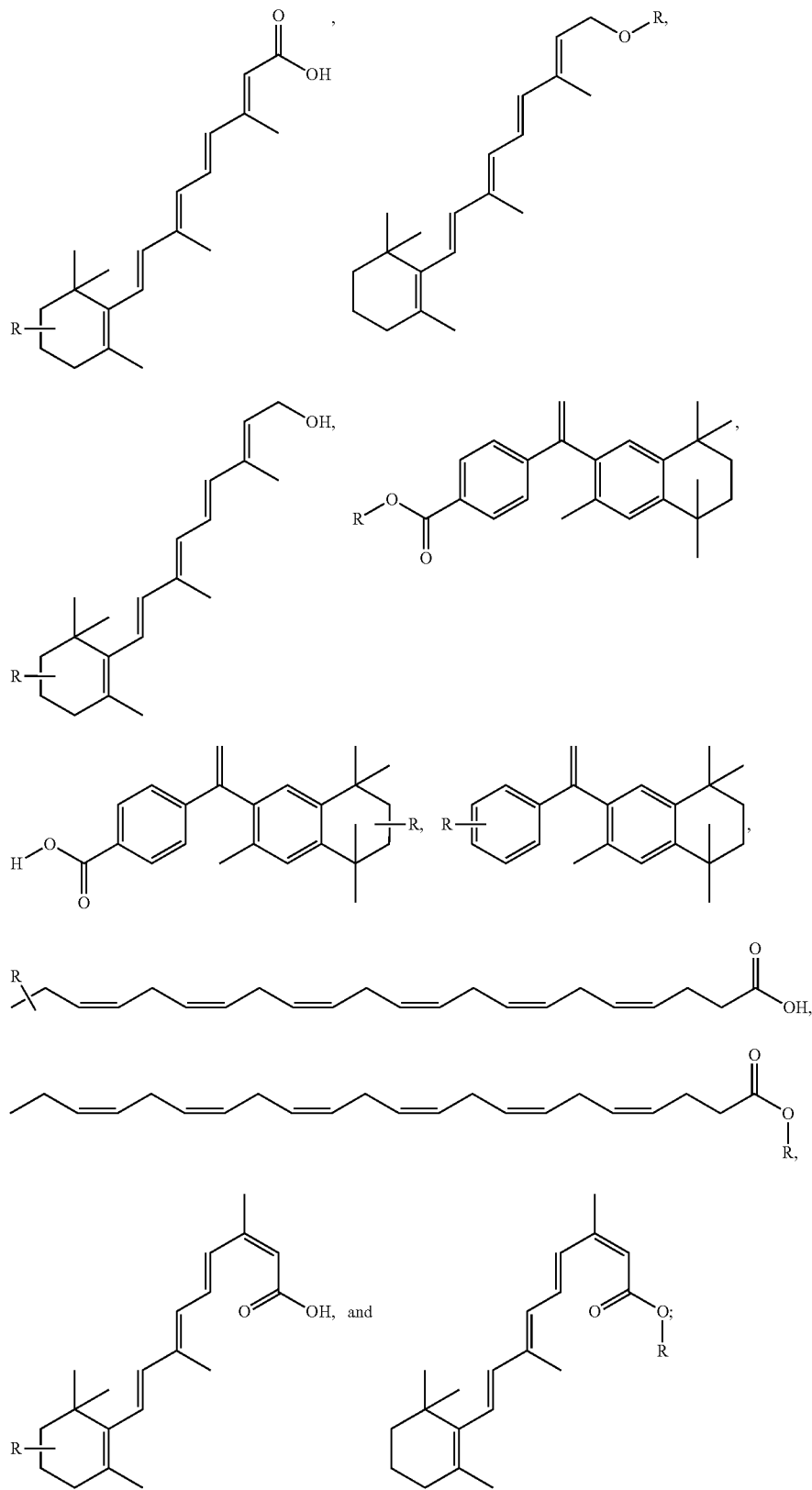
wherein:
R is the point at which the Linker is attached.

TABLE T-continued
O. DHFR dTAG Targeting Ligands:
DHFR dTAG Targeting Ligands as used herein include, but are not limited to:
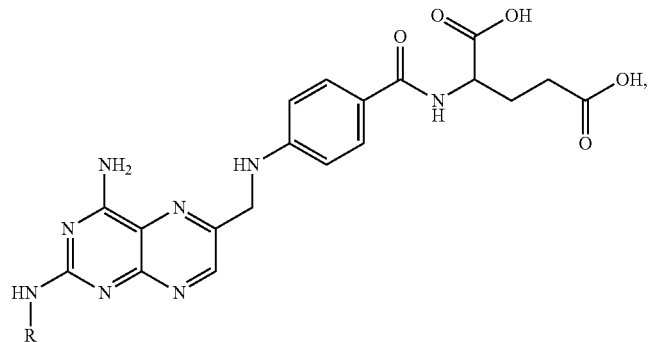
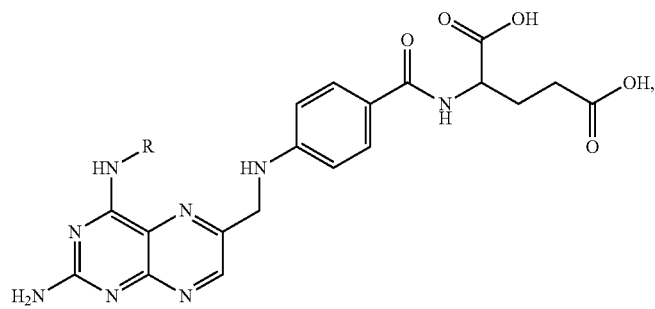
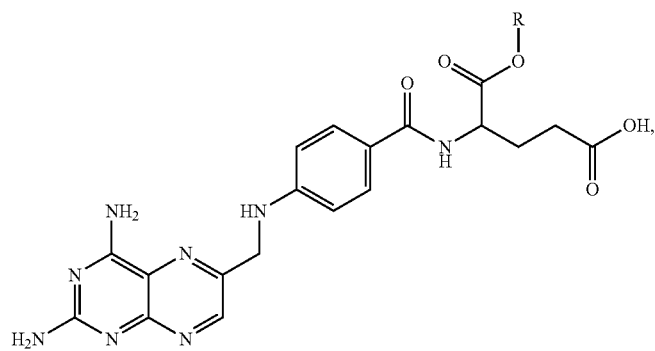
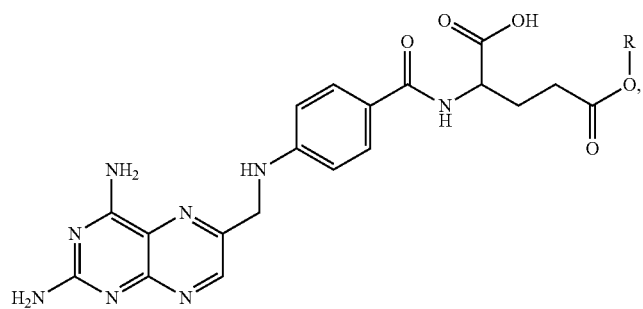

TABLE T-continued
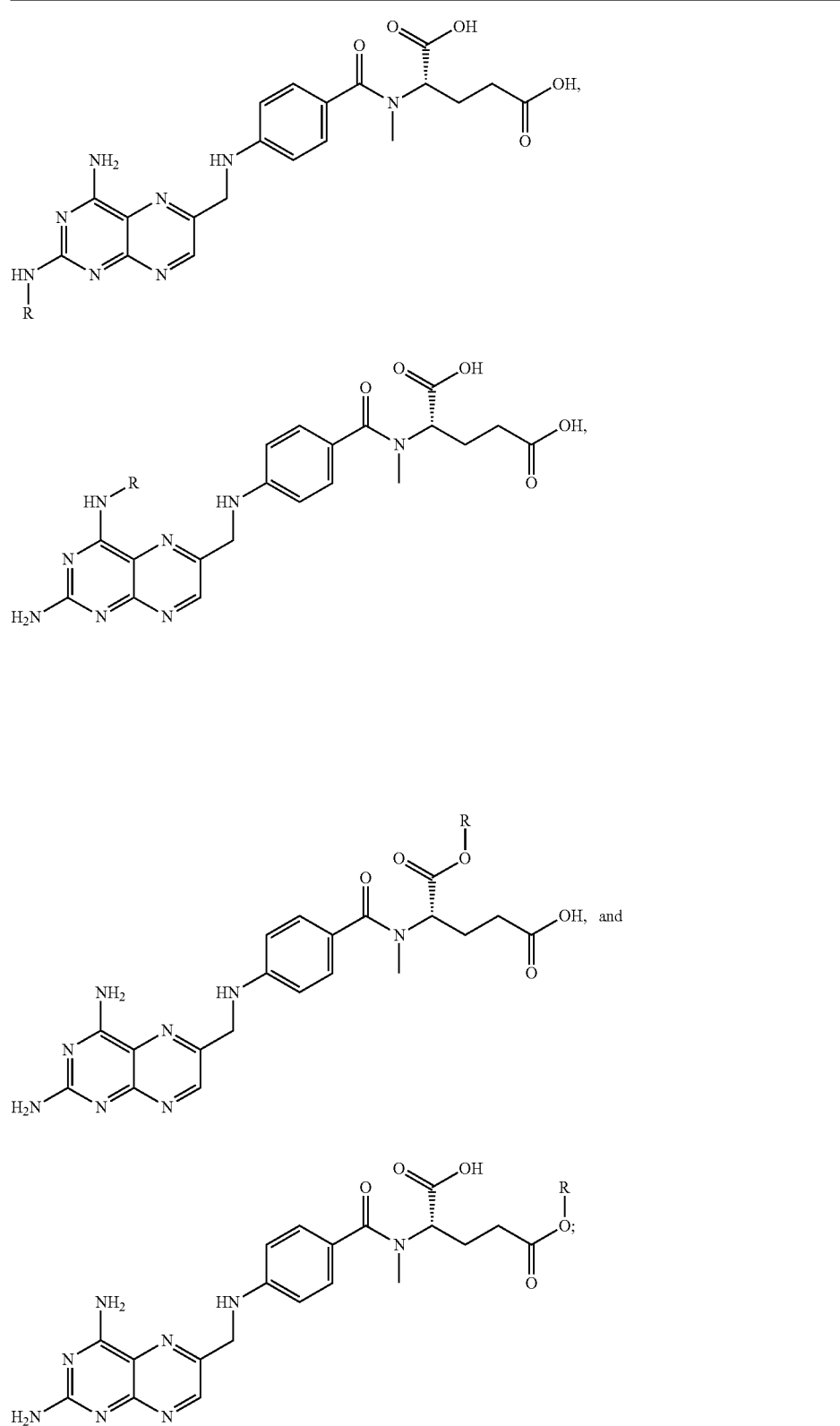
wherein:
R is the point at which the Linker is attached.

TABLE T-continued
P. EGFR dTAG Targeting Ligands:
EGFR dTAG Targeting Ligands as used herein include, but are not limited to:
1. Targeting Ligands that target L858R mutant EGFR, including erlotinib, gefitnib, afatinib, neratinib, and dacomitinib.
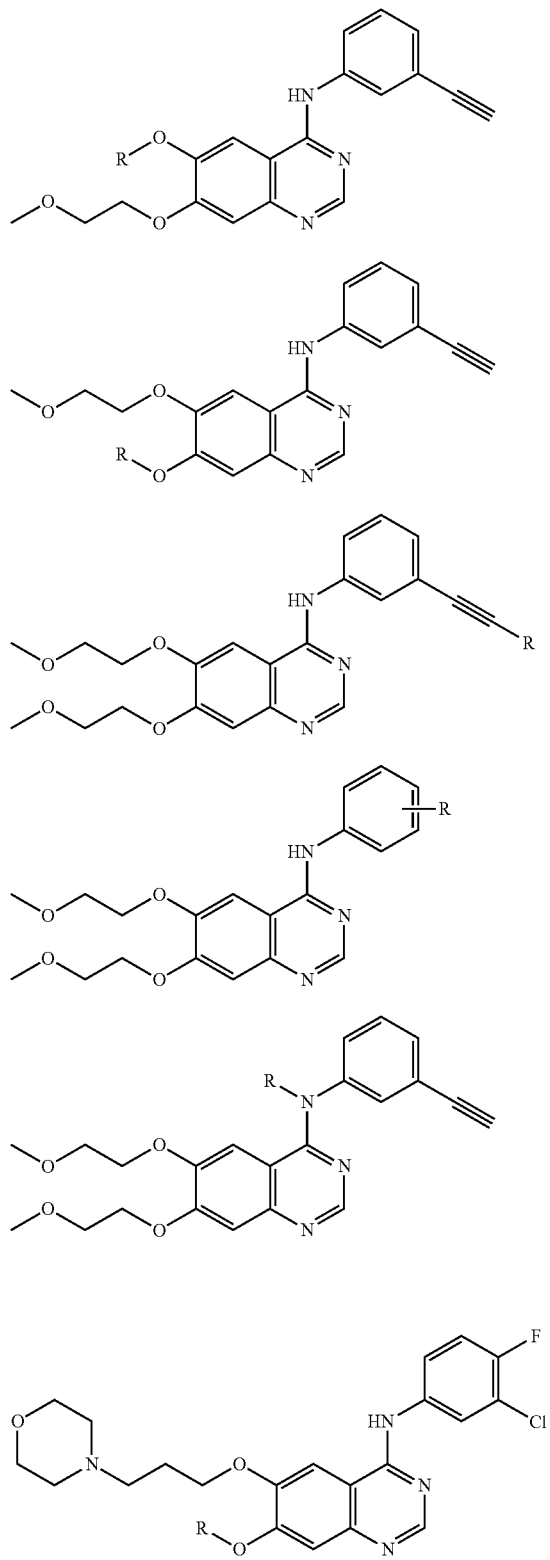

TABLE T-continued
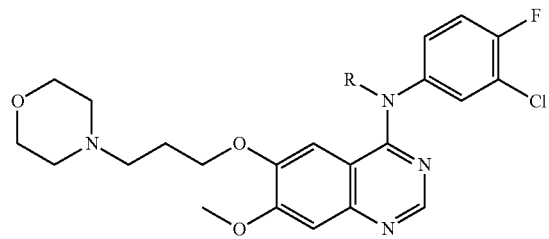
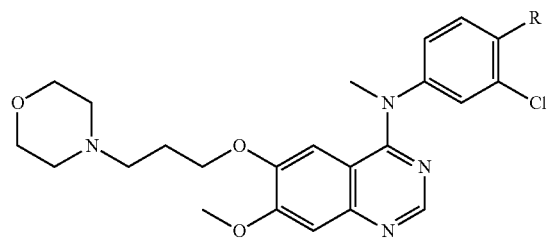
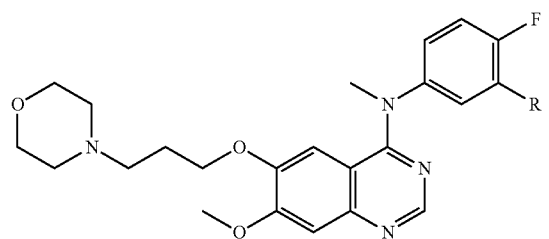
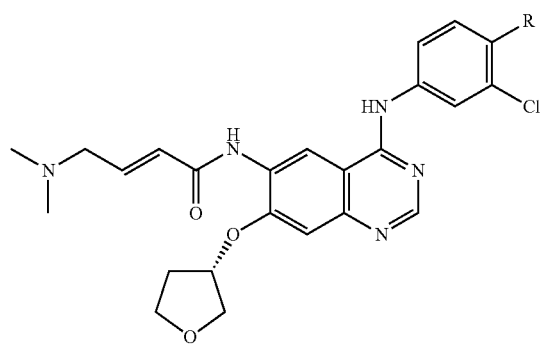
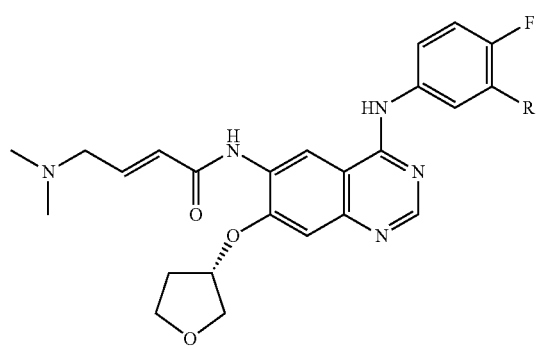

TABLE T-continued
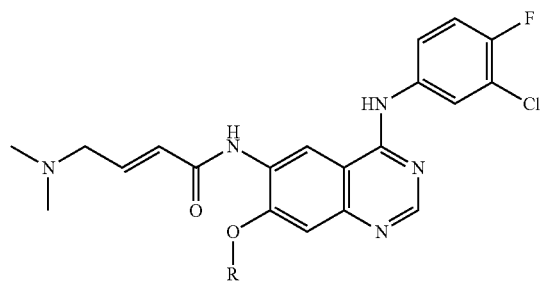
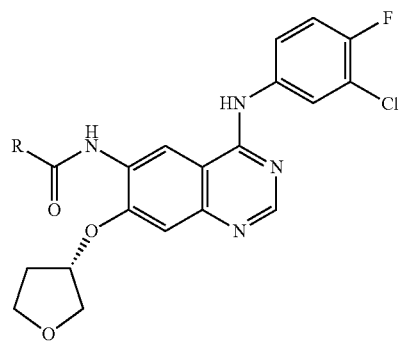
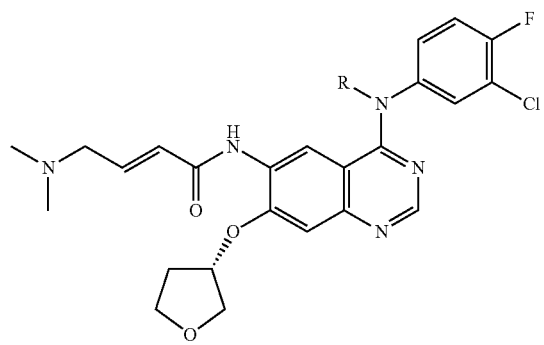
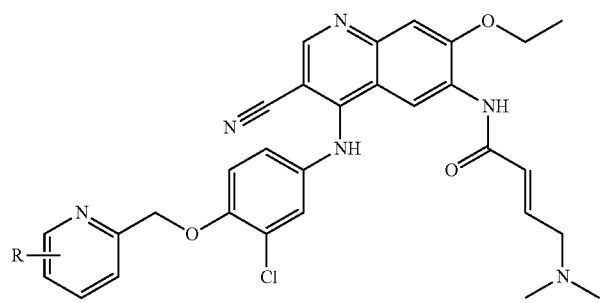
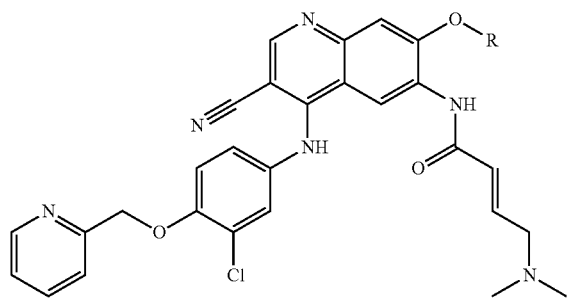

TABLE T-continued
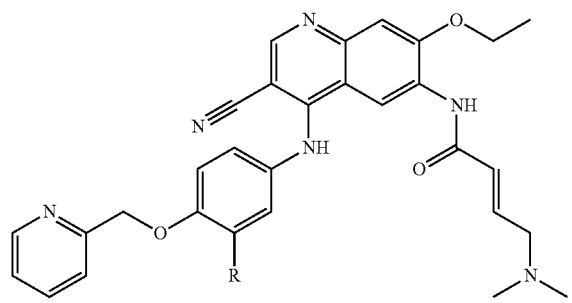
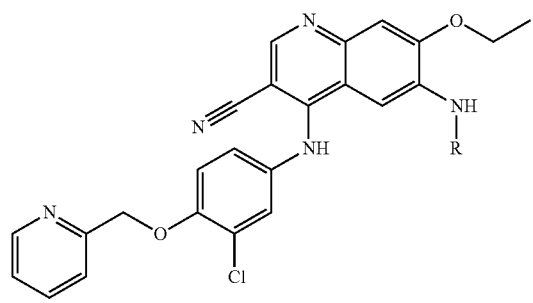
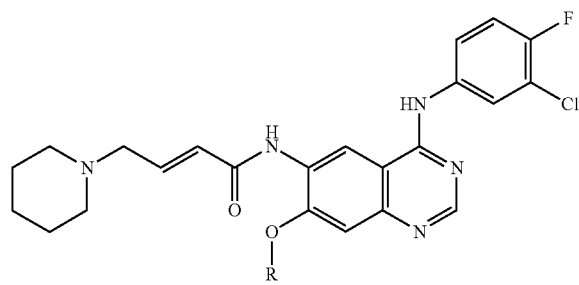
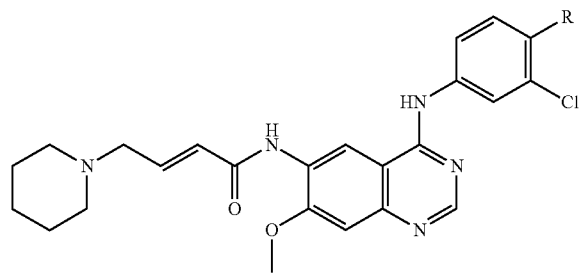
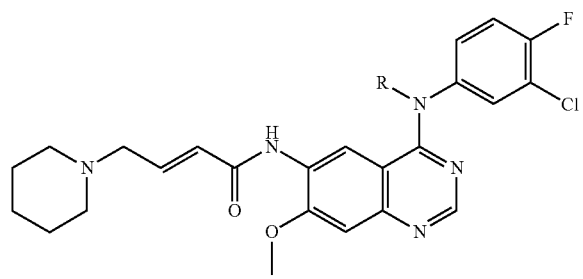

TABLE T-continued
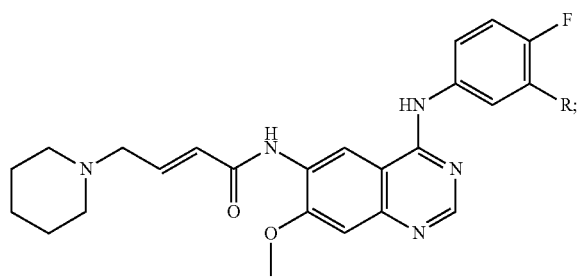
wherein:
R is the point at which the Linker is attached.
2. Targeting Ligands that target T790M mutant EGFR, including osimertinib, rociletinib, olmutinib, naquotinib, nazartinib, PF-06747775, Icotinib, Neratinib, Avitinib, Tarloxotinib, PF-0645998, Tesevatinib, Transtinib, WZ-3146, WZ8040, and CNX-2006:
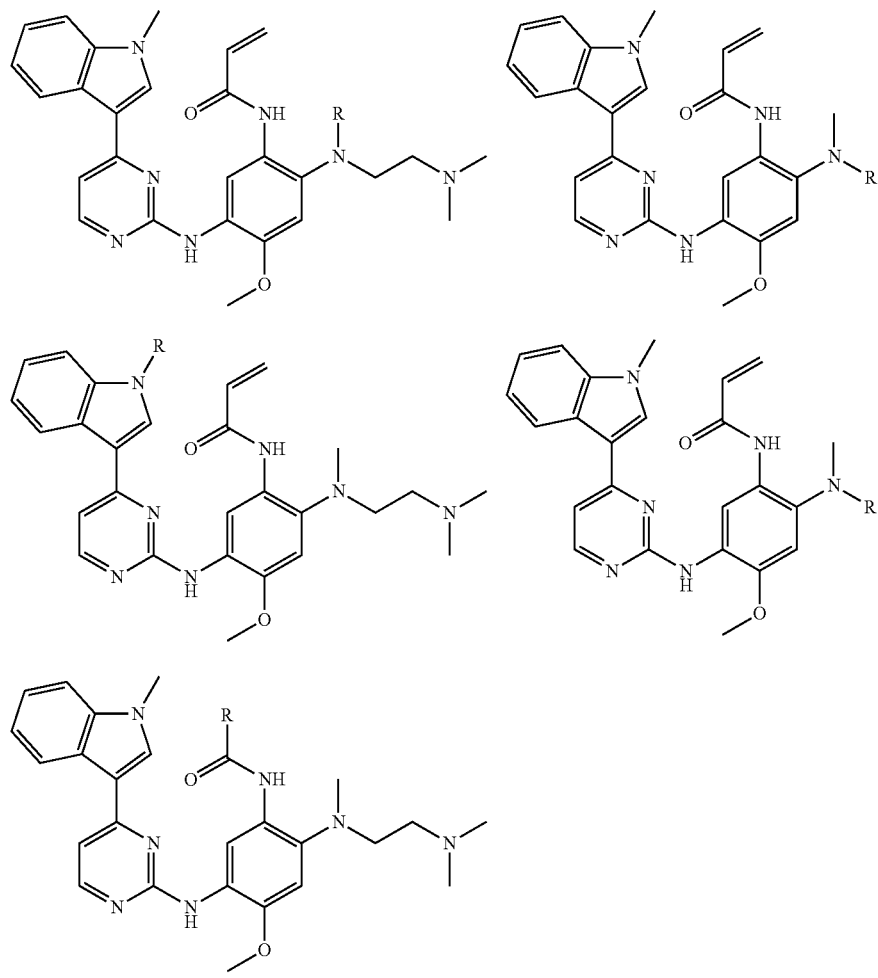
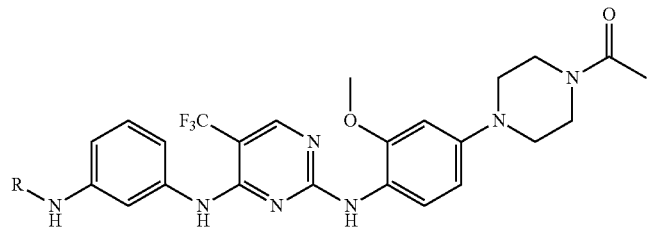

TABLE T-continued
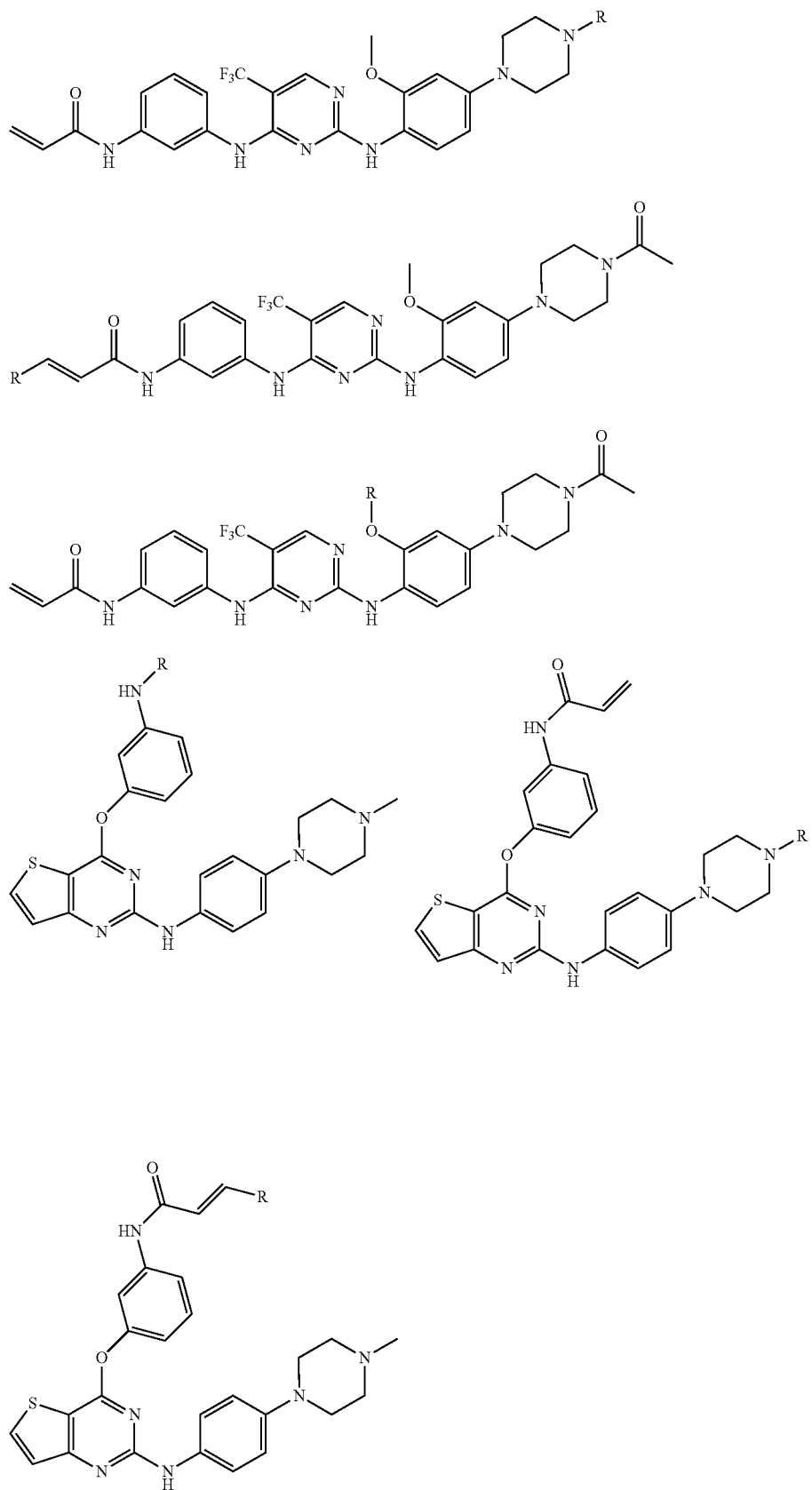

TABLE T-continued
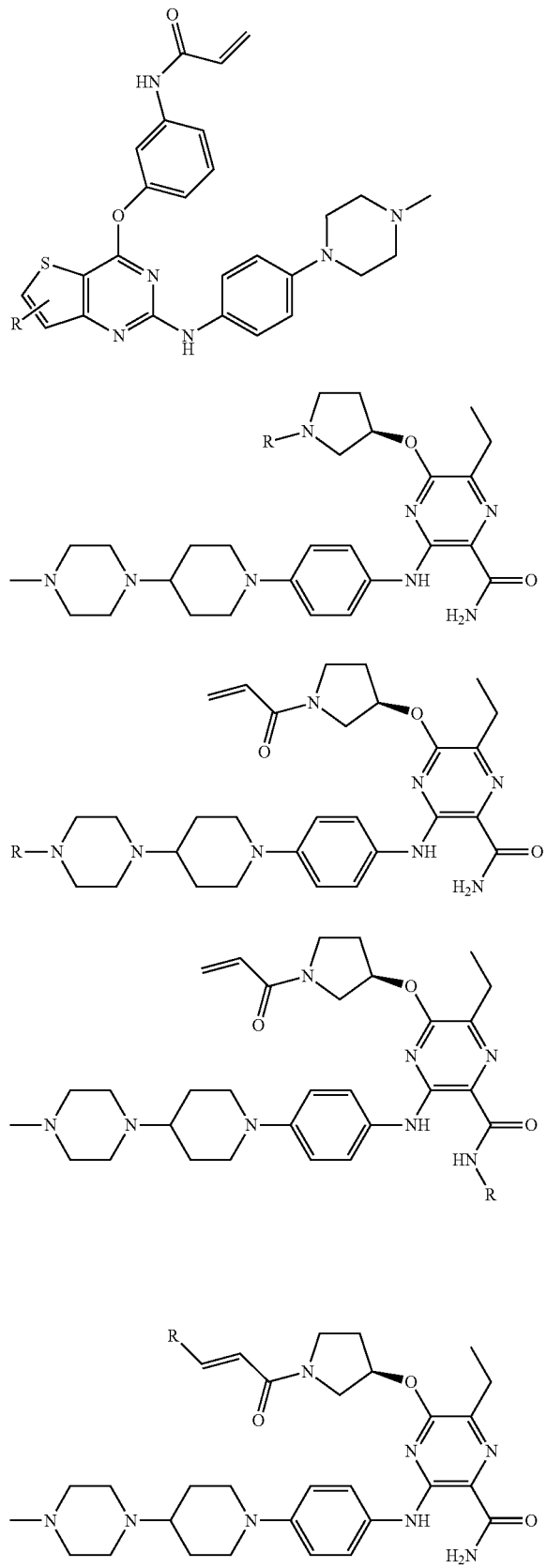

TABLE T-continued
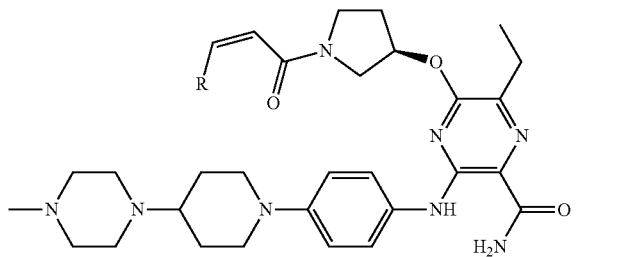
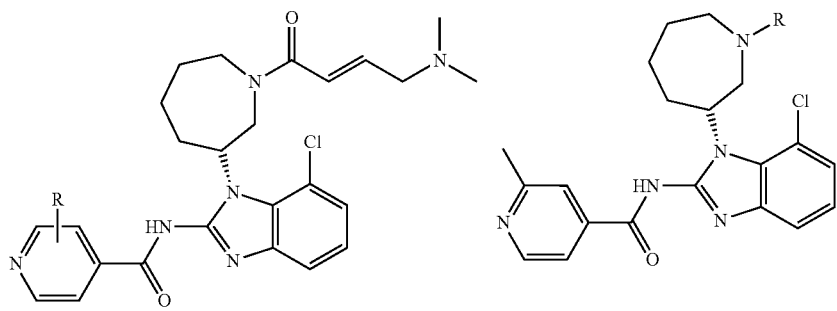
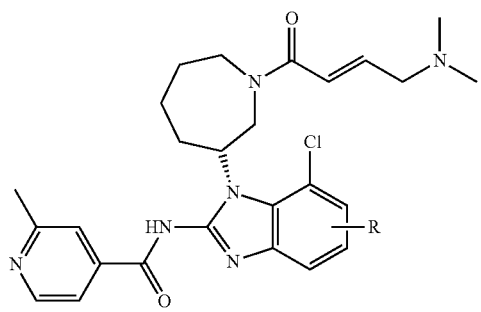
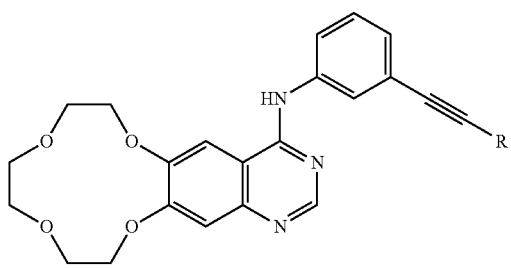
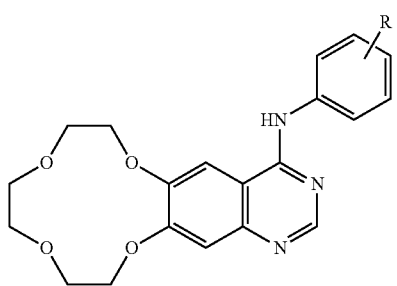

TABLE T-continued
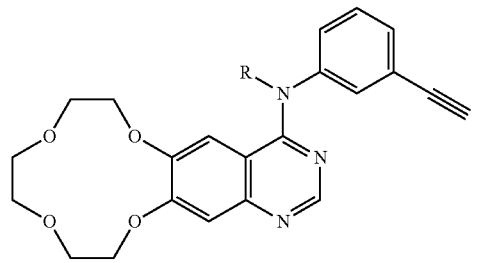
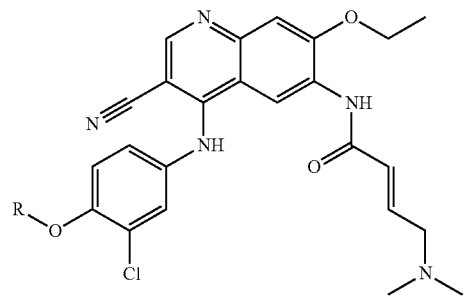
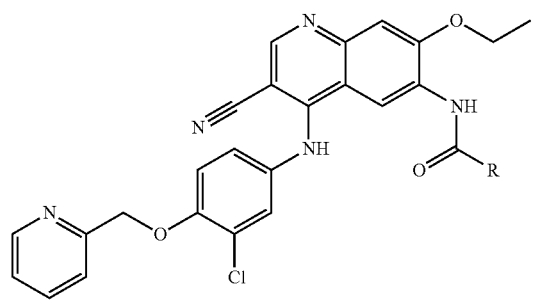
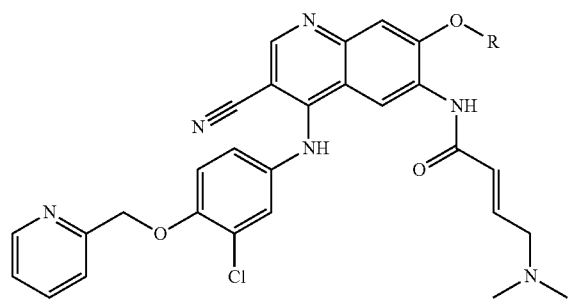
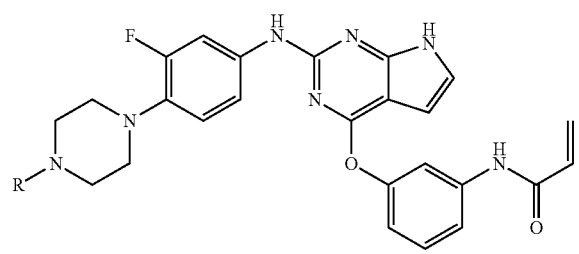

TABLE T-continued
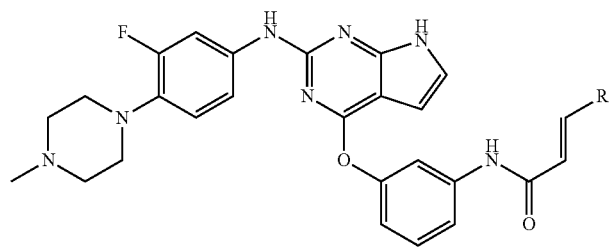
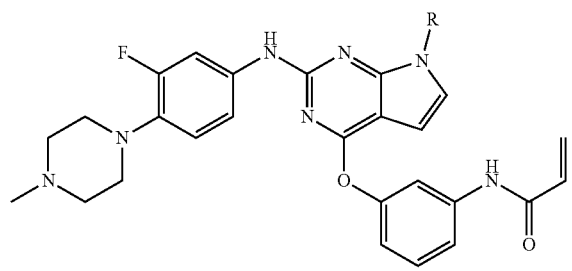
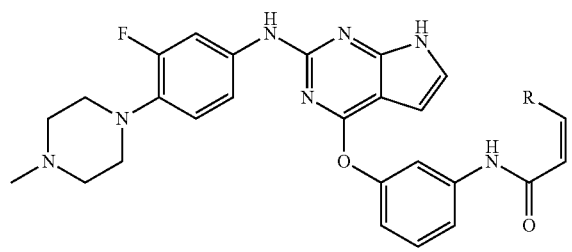
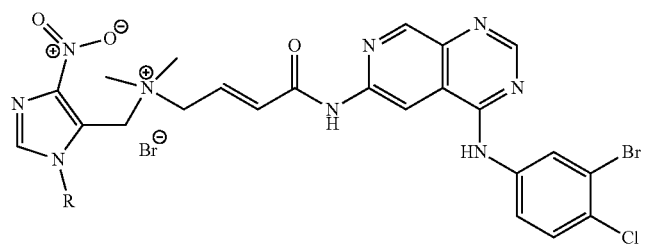
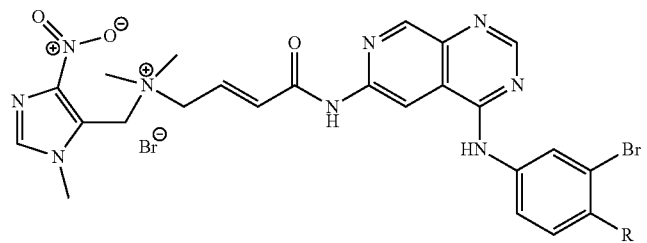
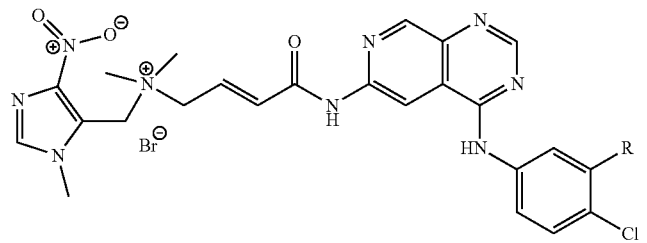

TABLE T-continued
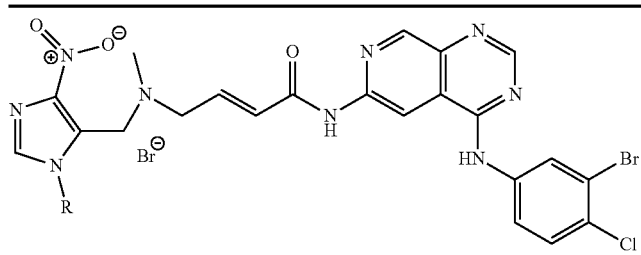
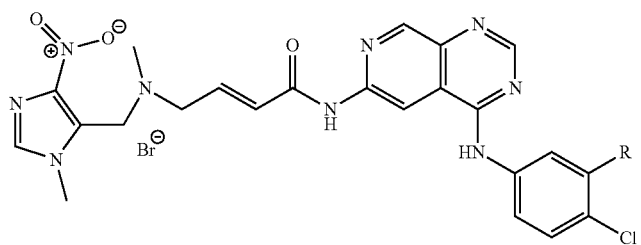
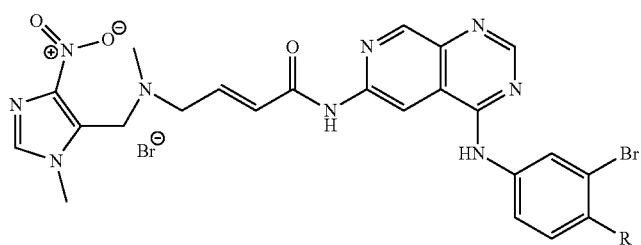
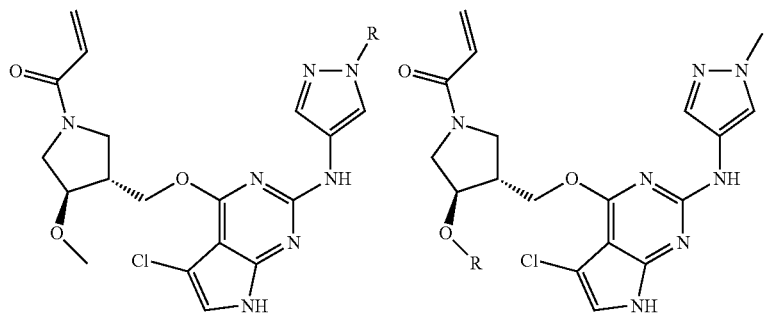
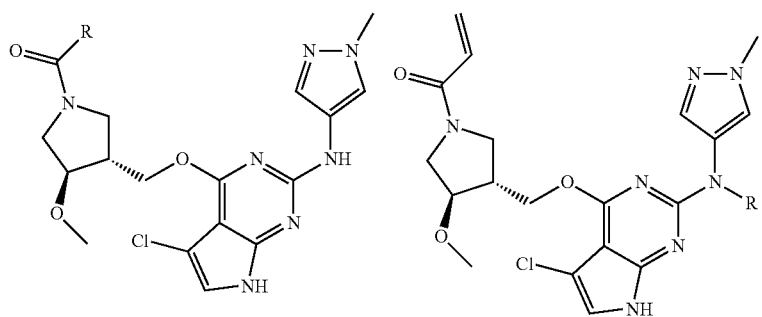

TABLE T-continued
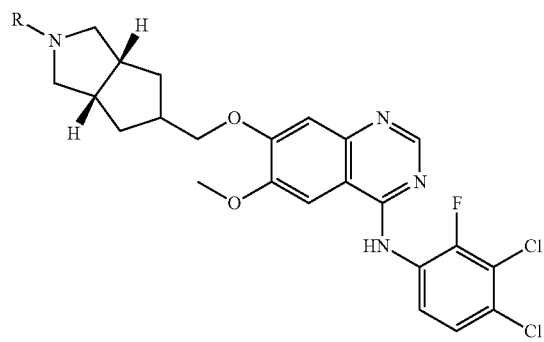
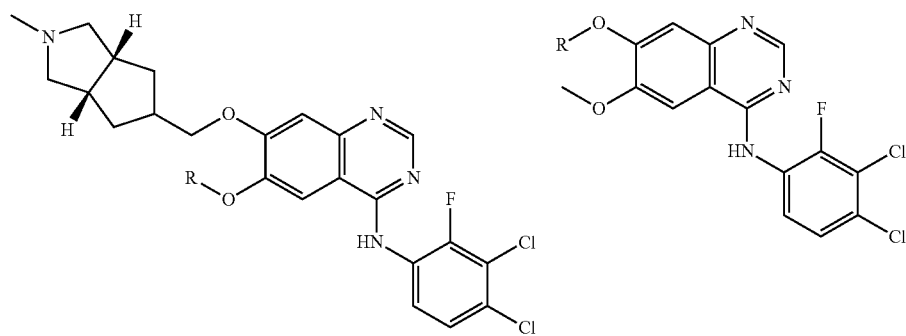
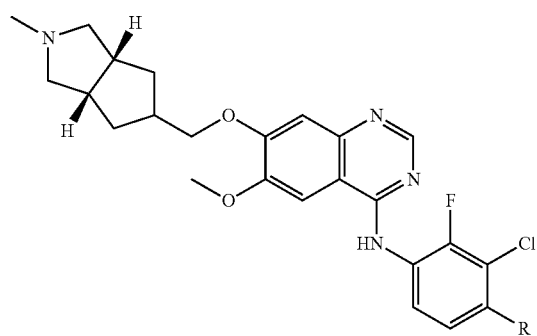
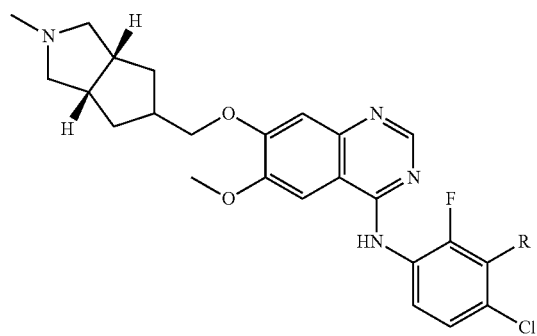

TABLE T-continued
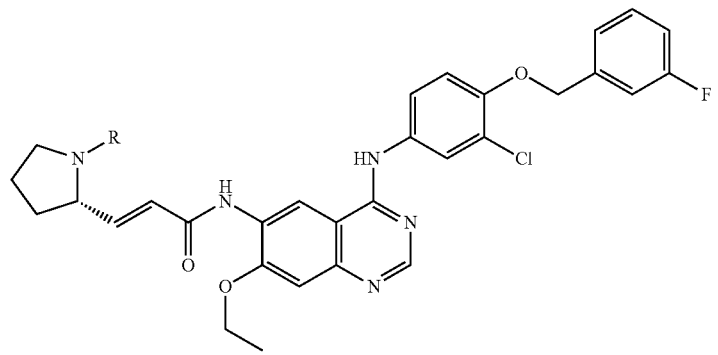
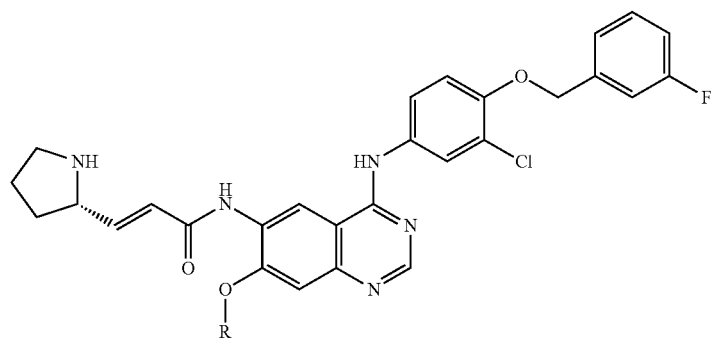
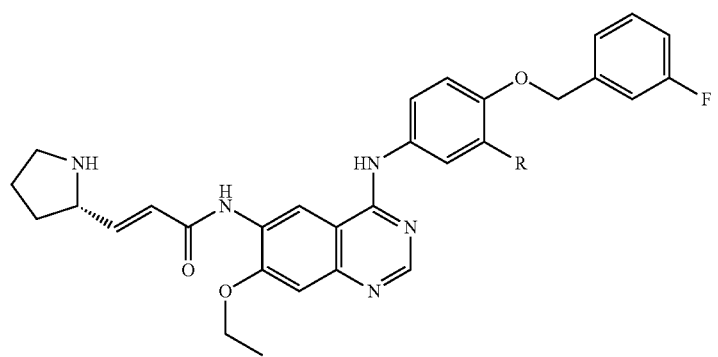
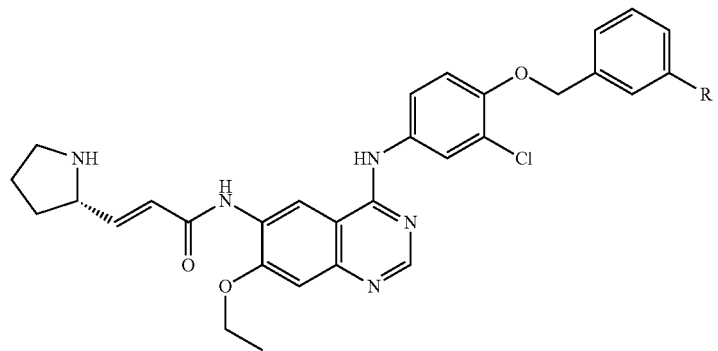

TABLE T-continued
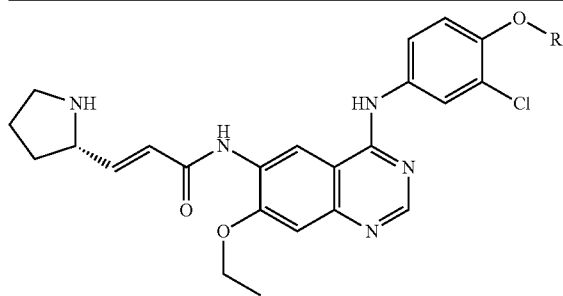
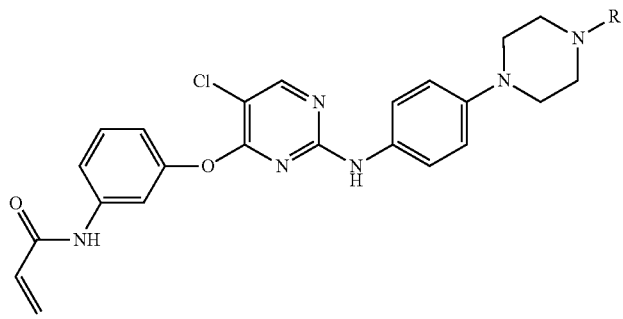
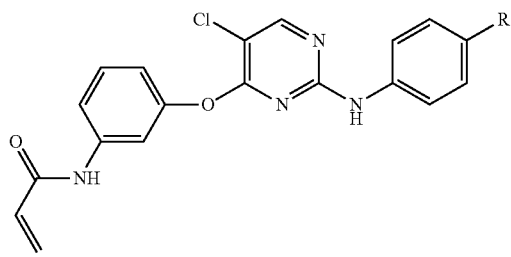
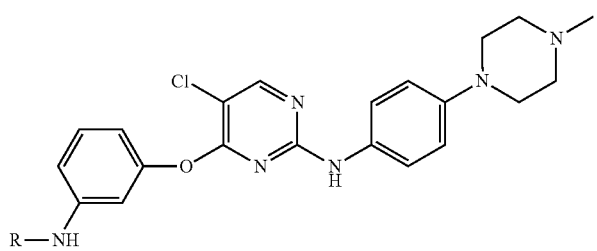
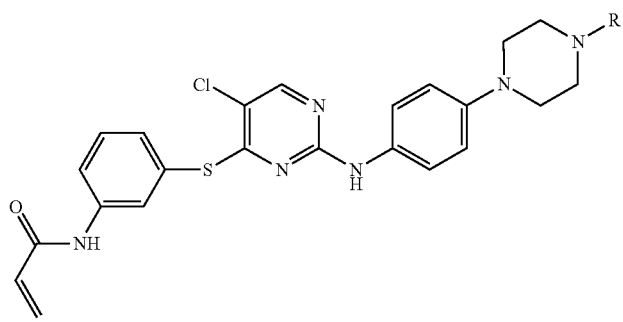

TABLE T-continued
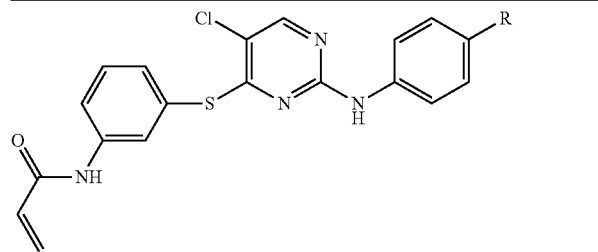
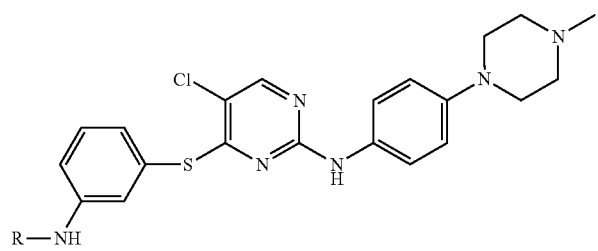
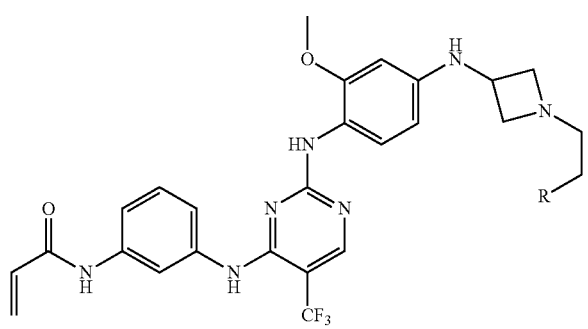
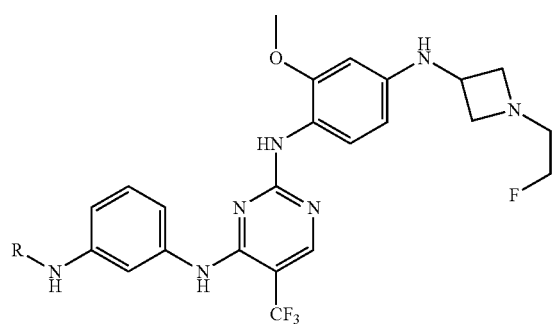
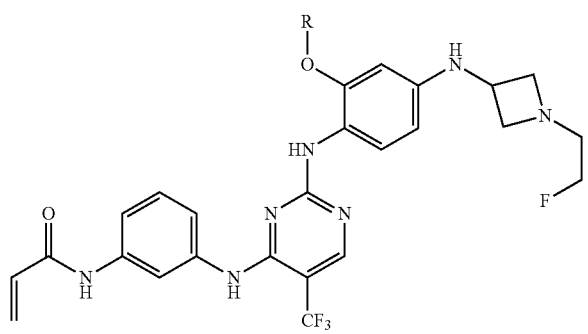

TABLE T-continued

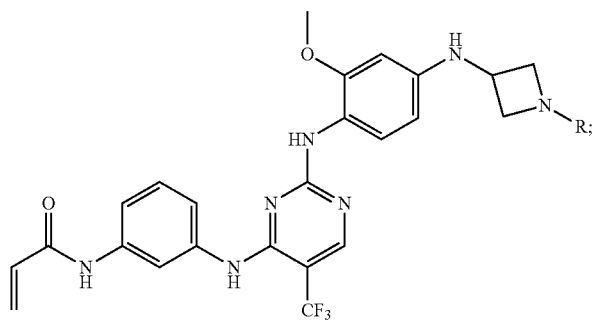

wherein:
R is the point at which the Linker is attached.

3. Targeting Ligands that target C797S mutant EGFR, including EAI045:

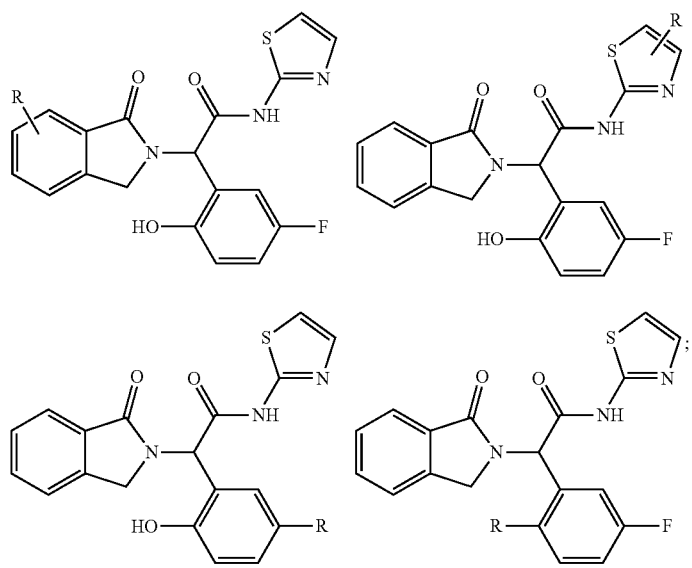

wherein:
R is the point at which the Linker is attached.

Q. BCR-ABL dTAG Targeting Ligands:

BCR-ABL dTAG Targeting Ligands as used herein include, but are not limited to:
1. Targeting Ligands that target T315I mutant BCR-ABL (PDB #3CS9), including Nilotinib and Dasatinib:

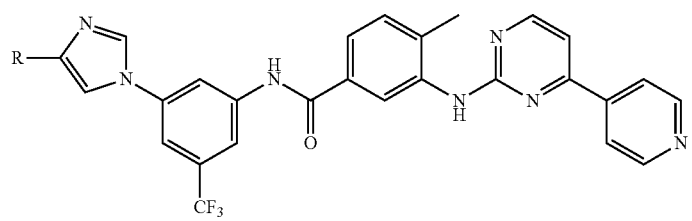

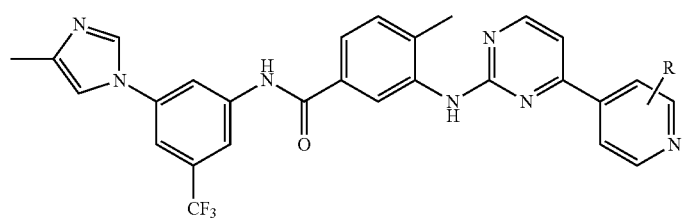

TABLE T-continued
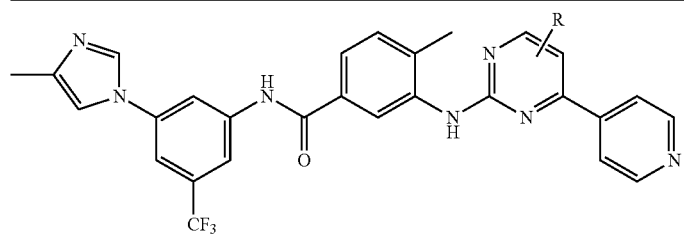
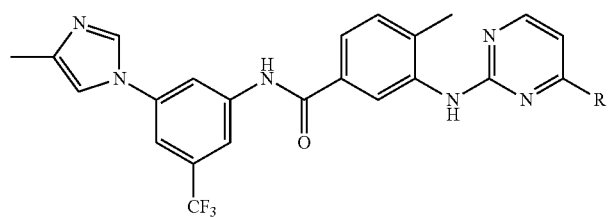
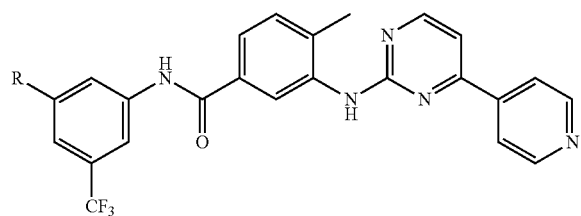
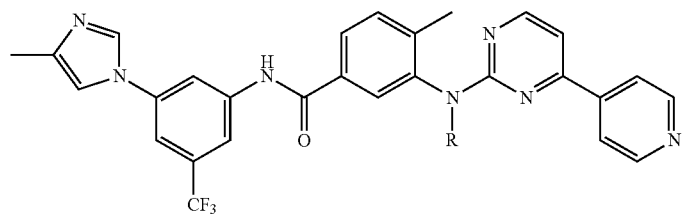
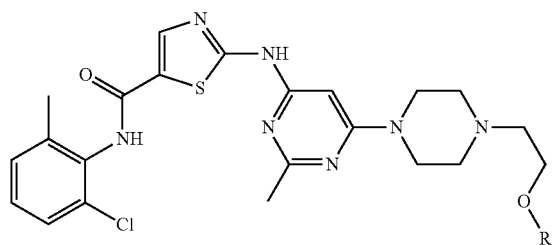
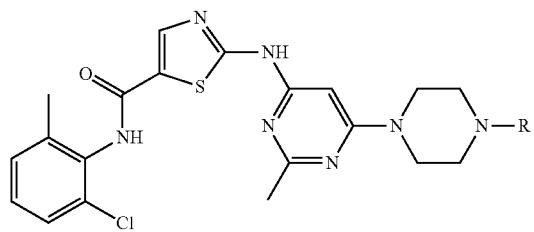
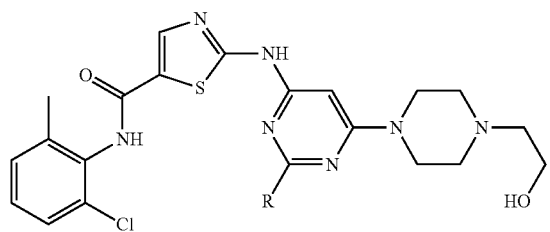

TABLE T-continued
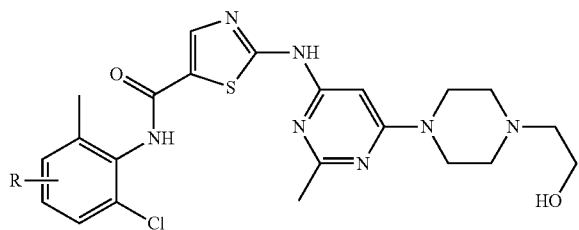
wherein:
R is the point at which the Linker is attached.
2. Targeting Ligands that target BCR-ABL, including Nilotinib, Dasatinib, Ponatinib, and Bosutinib:
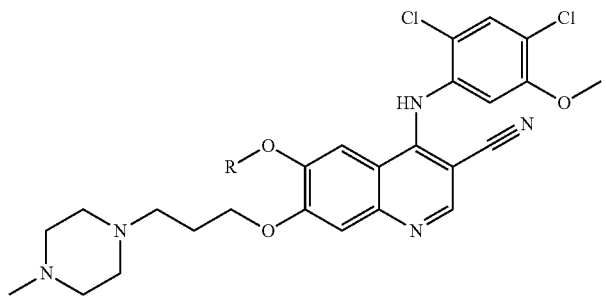
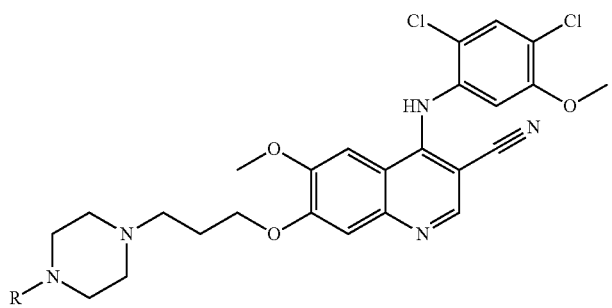
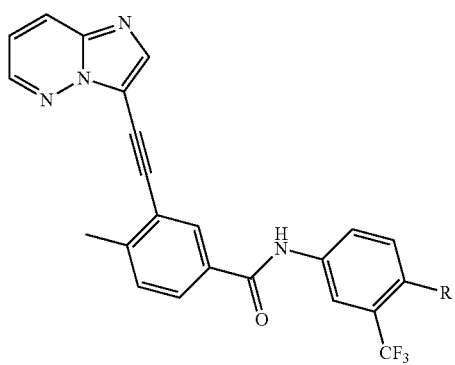

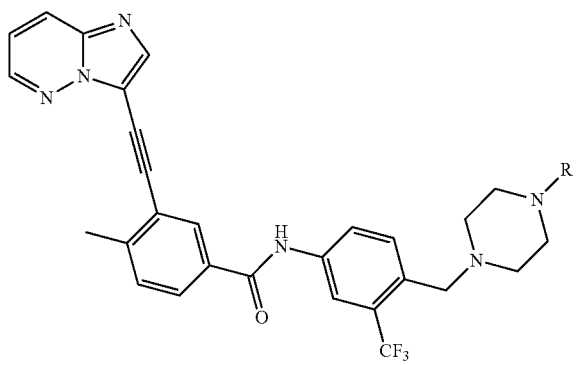
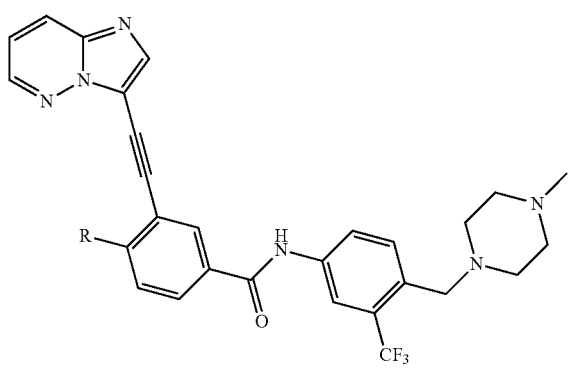
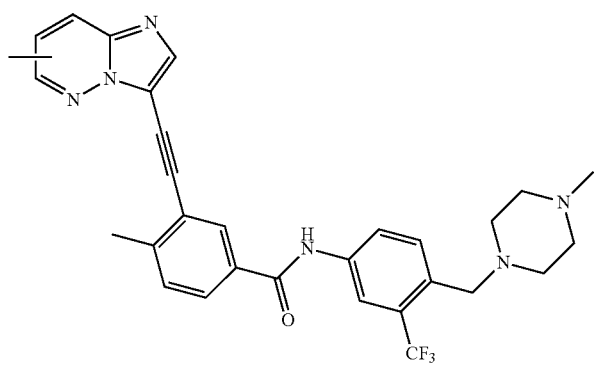
wherein:
R is the point at which the Linker is attached.
R. ALK dTAG Targeting Ligands:
ALK dTAG Targeting Ligands as used herein include, but are not limited to:
1. Targeting Ligands that target L1196M mutant ALK (PDB #4MKC), including Ceritinib:
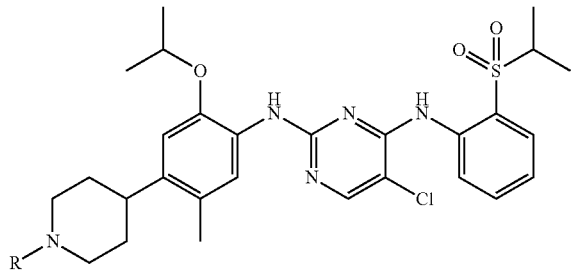

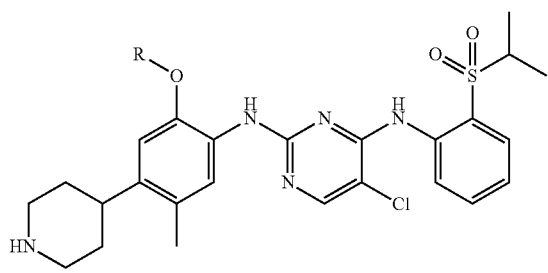
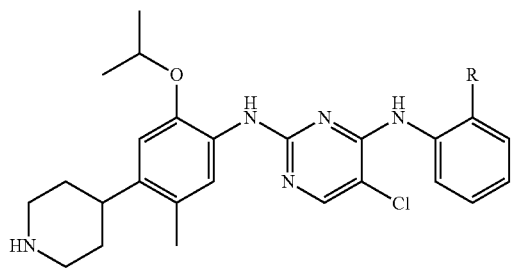
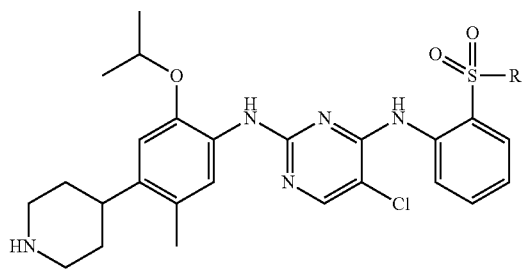
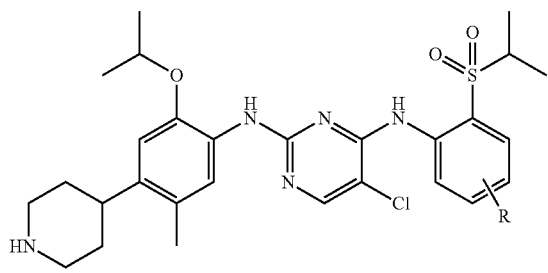
wherein:
R is the point at which the Linker is attached.
S. JAK2 dTAG Targeting Ligands:
JAK2 dTAG Targeting Ligands as used herein include, but are not limited to:
1. Targeting Ligands that target V617F mutant JAK2, including Ruxolitinib:
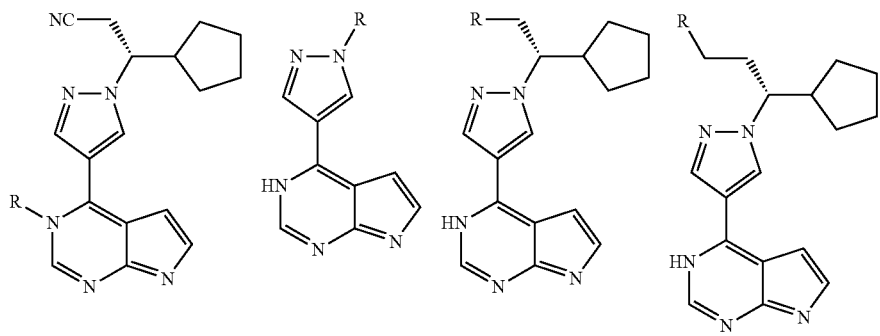

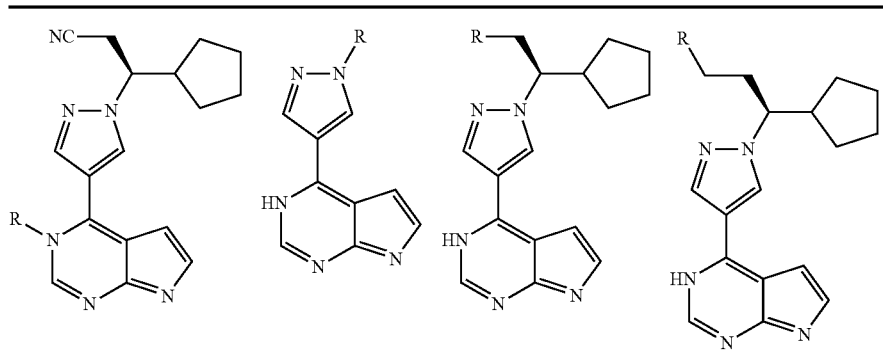
wherein:
R is the point at which the Linker is attached.
T. BRAF dTAG Targeting Ligands:
BRAF dTAG Targeting Ligands as used herein include, but are not limited to:
1. Targeting Ligands that target V600E mutant BRAF (PBD # 3OG7), including Vemurafenib:
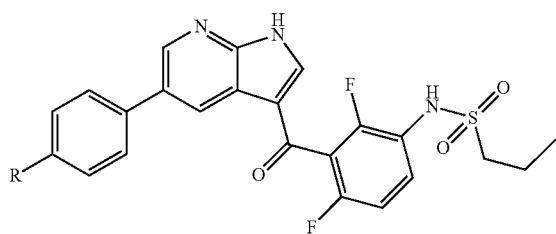
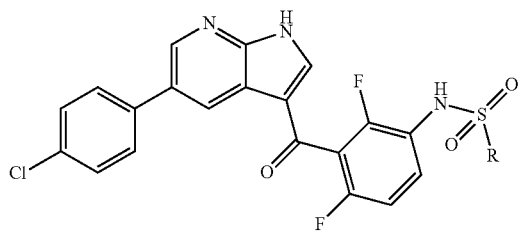
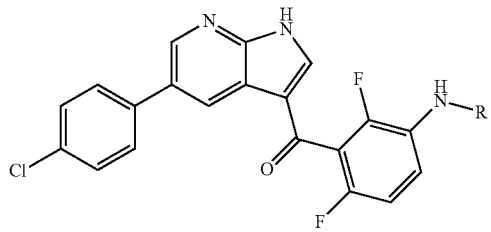
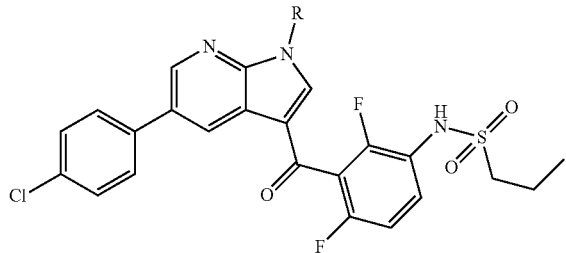

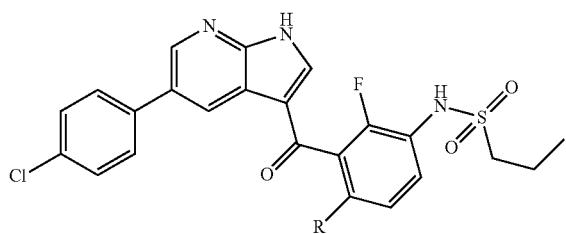
wherein:
R is the point at which the Linker is attached.
2. Targeting Ligands that target BRAF, including Dabrafenib:
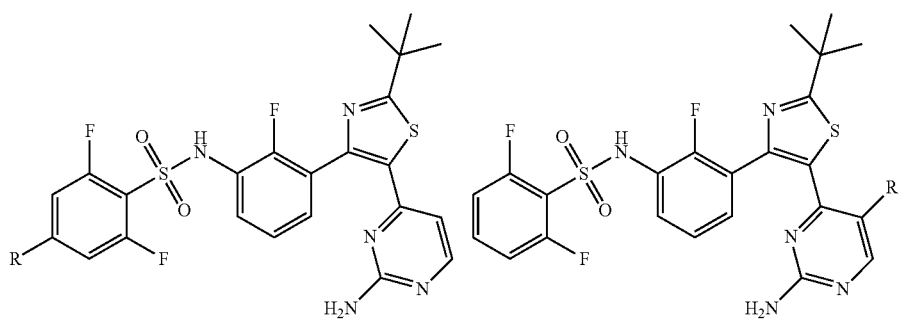
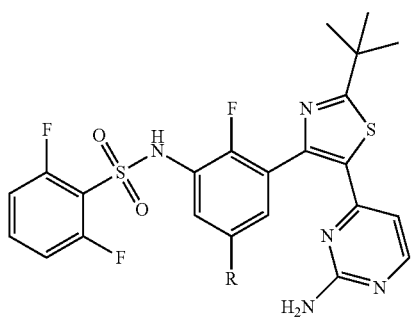
wherein:
R is the point at which the Linker is attached.
U. LRRK2 dTAG Targeting Ligands:
LRRK2 dTAG Targeting Ligands as used herein include, but are not limited to:
1. Targeting Ligands that target R1441C mutant LRRK2, including:
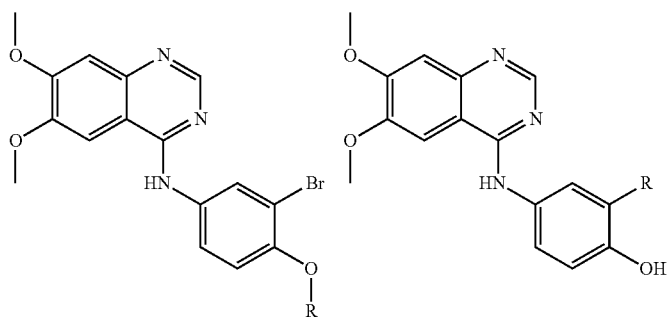

TABLE T-continued
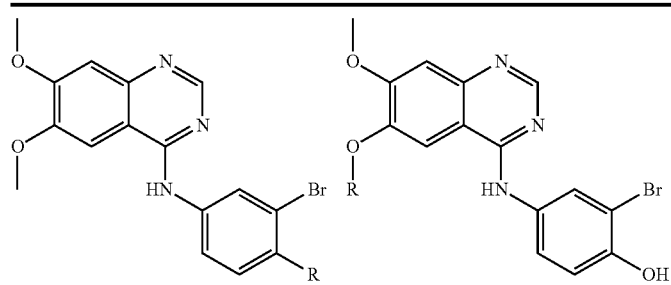
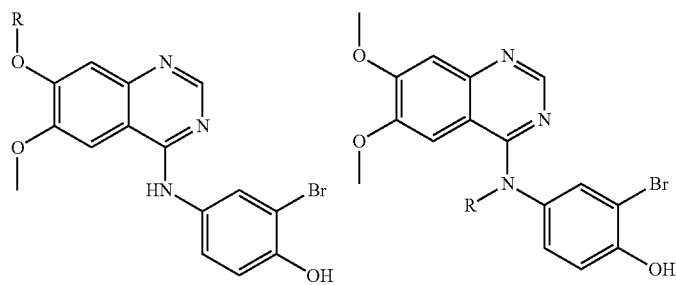
wherein:
R is the point at which the Linker is attached.
2. Targeting Ligands that target G2019S mutant LRRK2, including:
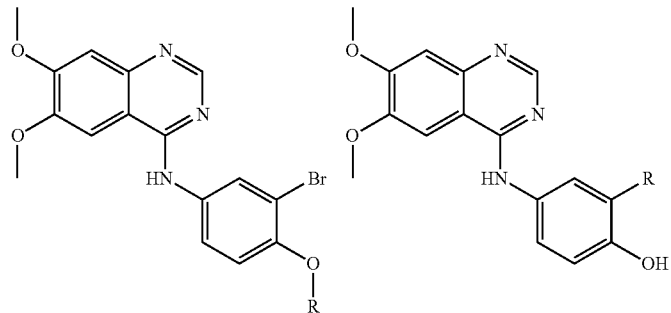
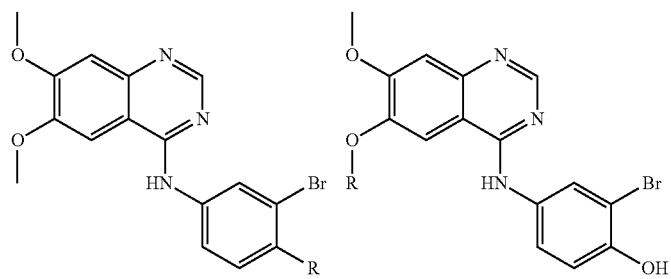
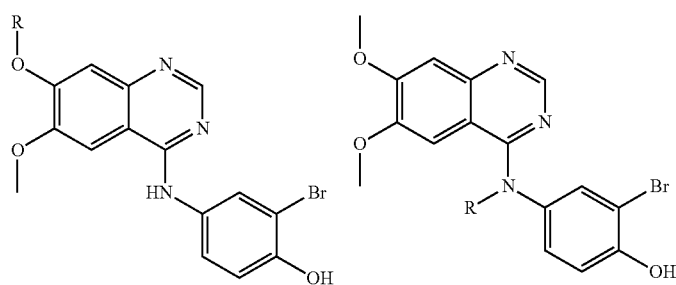
wherein:
R is the point at which the Linker is attached.

TABLE T-continued

3. Targeting Ligands that target I2020T mutant LRRK2, including:

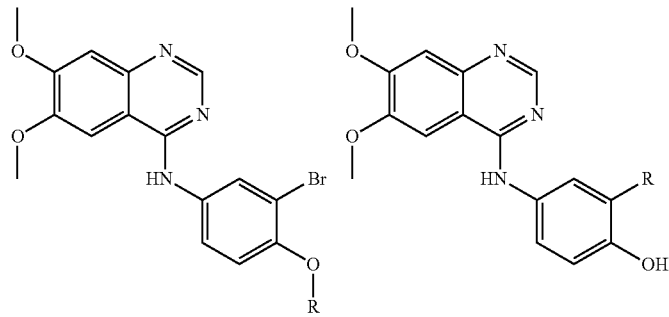

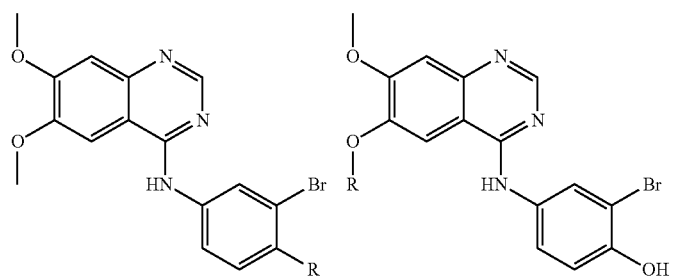

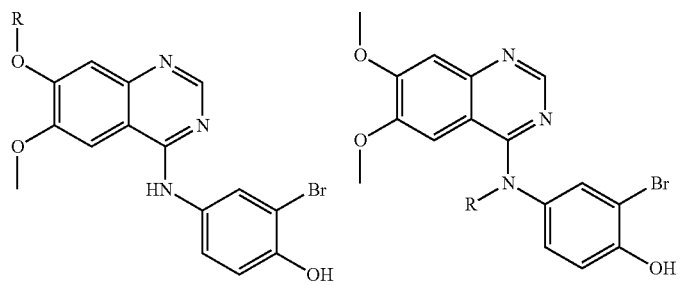

wherein:
R is the point at which the Linker is attached.

V. PDGFRα dTAG Targeting Ligands:

PDGFRα dTAG Targeting Ligands as used herein include, but are not limited to:
1. Targeting Ligands that target T674I mutant PDGFRα, including AG-1478, CHEMBL94431, Dovitinib, erlotinib, gefitinib, imatinib, Janex 1, Pazopanib, PD153035, Sorafenib, Sunitinib, WHI-P180:

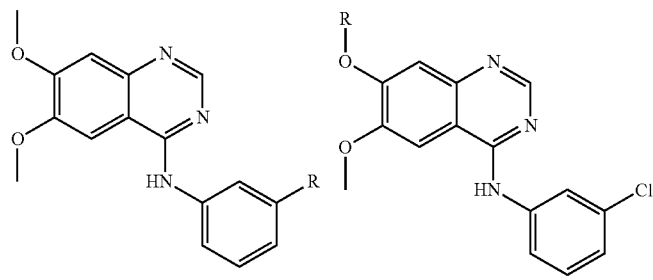

TABLE T-continued
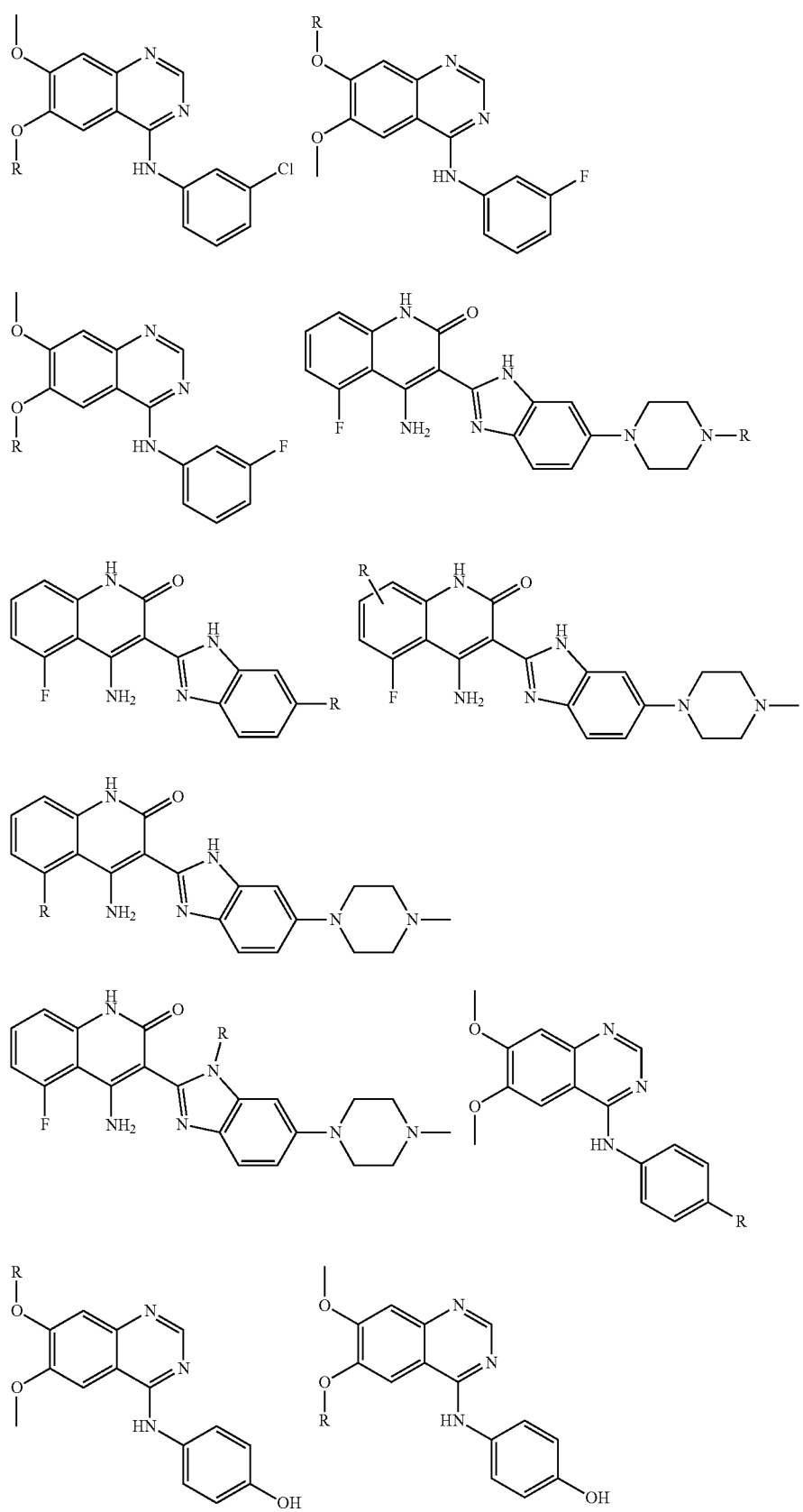

TABLE T-continued
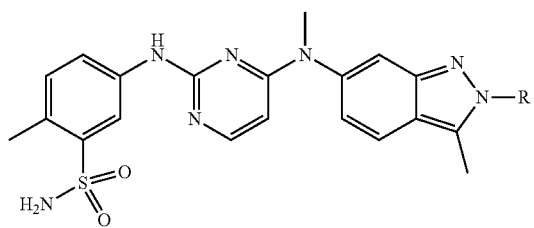
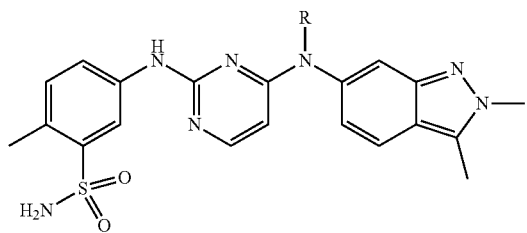
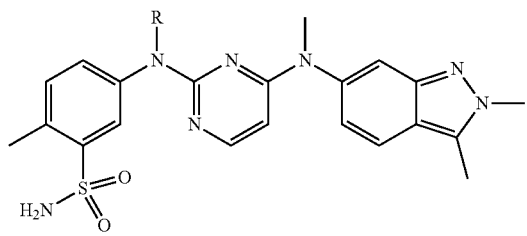
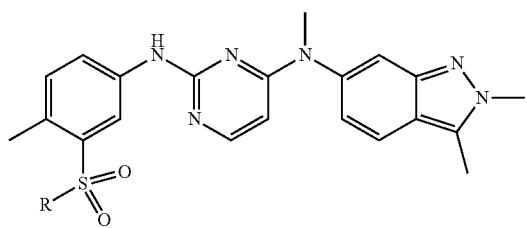
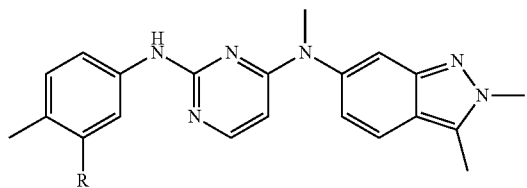
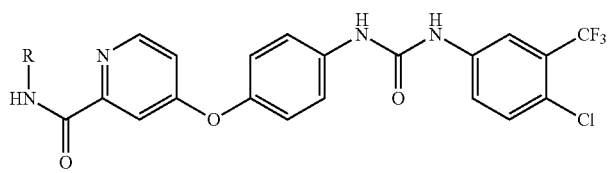
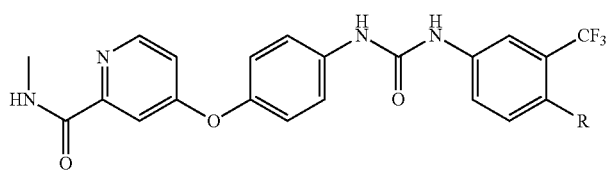

TABLE T-continued
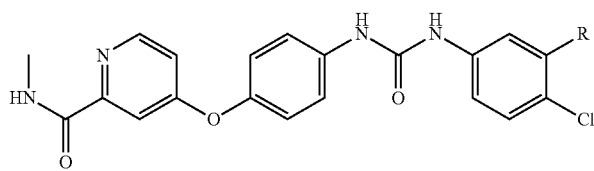
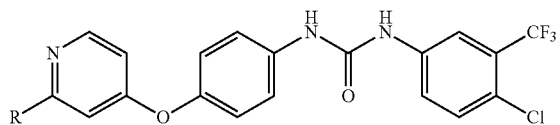
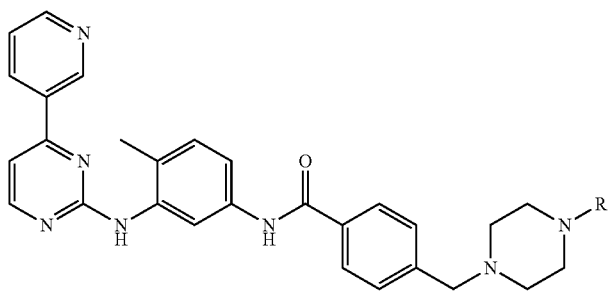
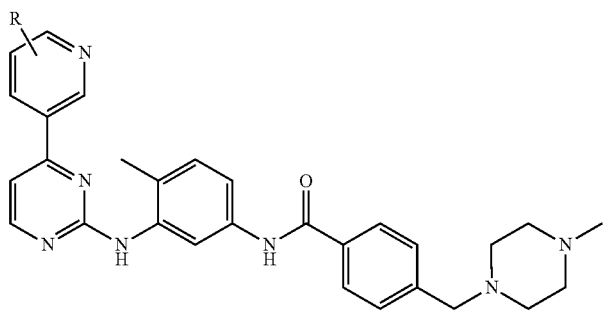
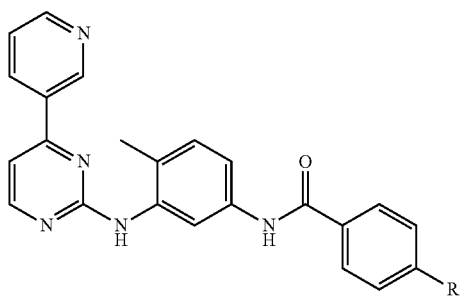
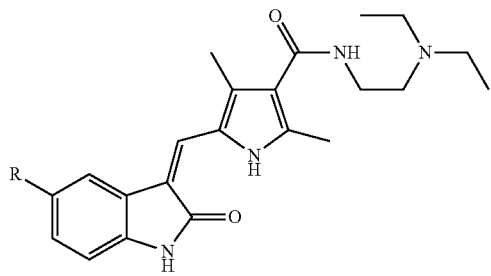

TABLE T-continued
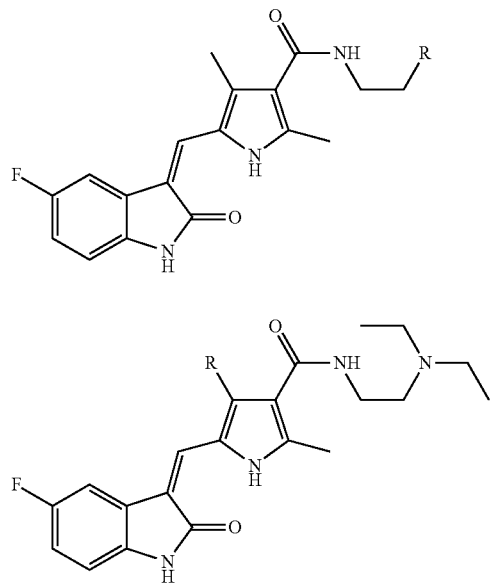
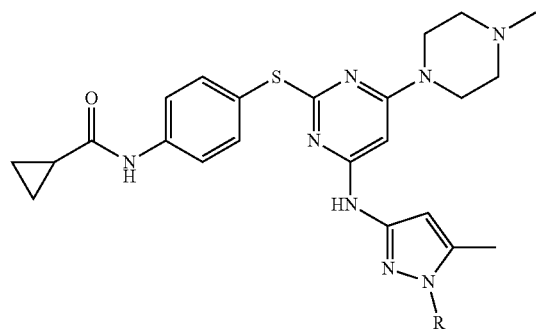
wherein:
R is the point at which the Linker is attached.
W. RET dTAG Targeting Ligands:
RET dTAG Targeting Ligands as used herein include, but are not limited to:
1. Targeting Ligands that target G691S mutant RET, including tozasertib
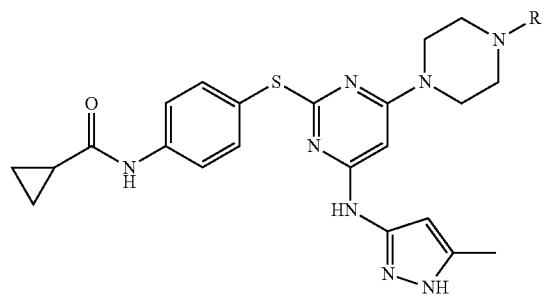

TABLE T-continued
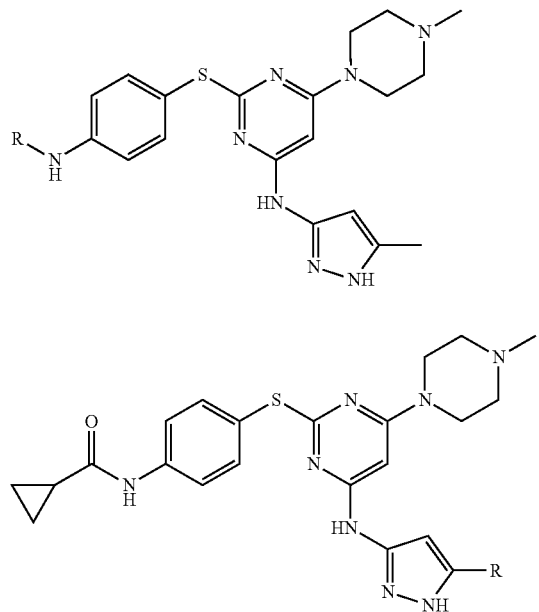
wherein:
R is the point at which the Linker is attached.
2. Targeting Ligands that target R749T mutant RET, including tozasertib
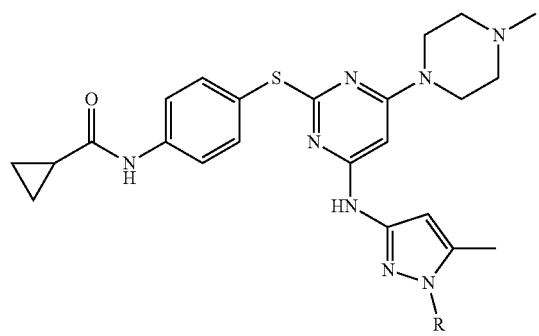
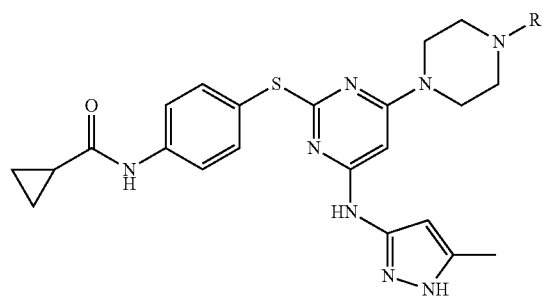

TABLE T-continued
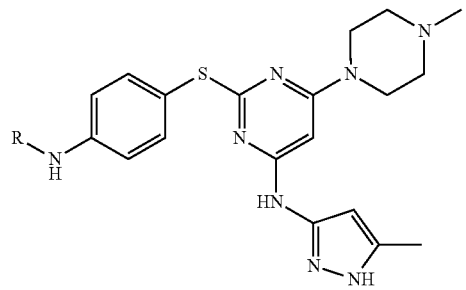
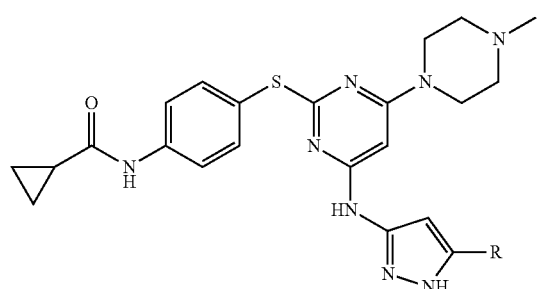
wherein:
R is the point at which the Linker is attached.
3. Targeting Ligands that target E762Q mutant RET, including tozasertib
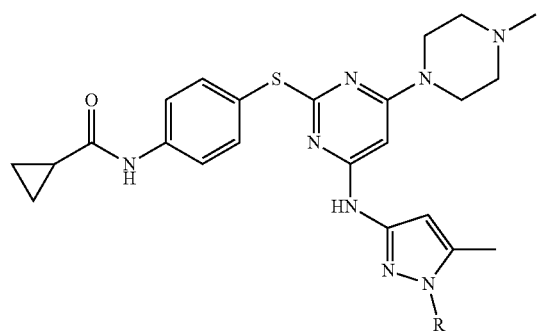
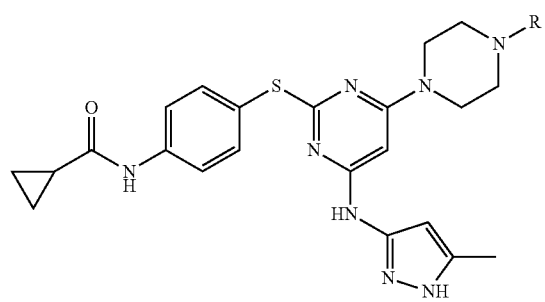

TABLE T-continued
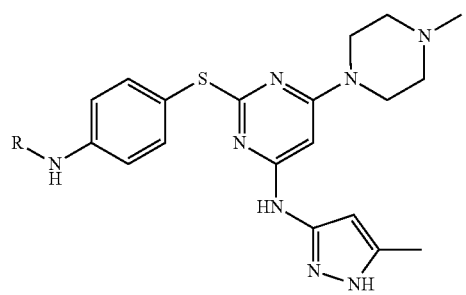
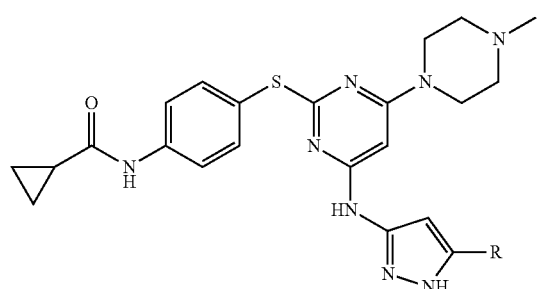
wherein:
R is the point at which the Linker is attached.
4. Targeting Ligands that target Y791F mutant RET, including tozasertib
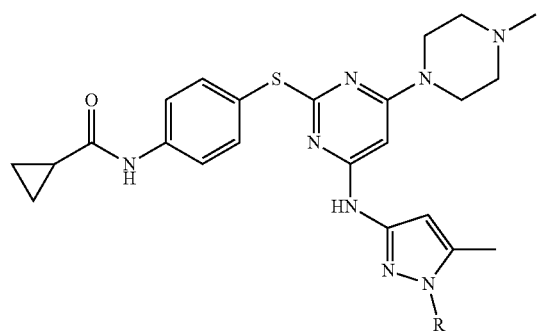
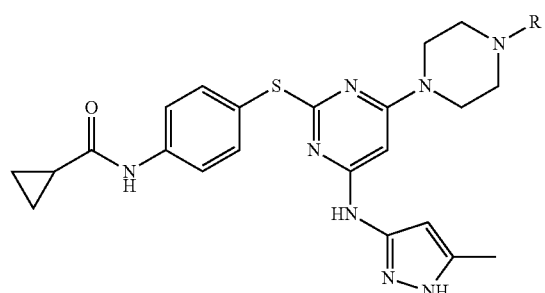

TABLE T-continued
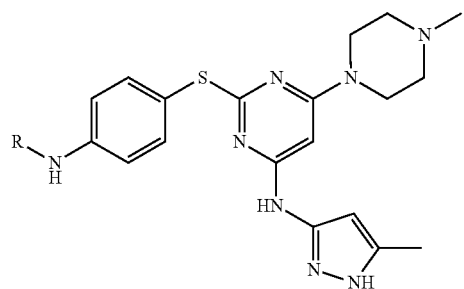
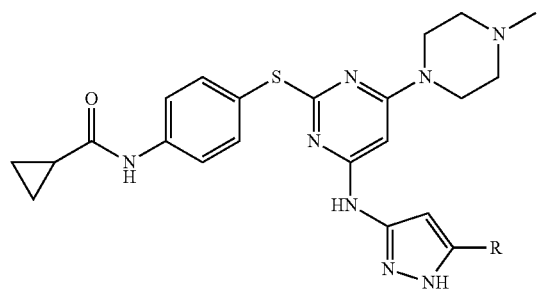
wherein:
R is the point at which the Linker is attached.
5. Targeting Ligands that target V804M mutant RET, including tozasertib
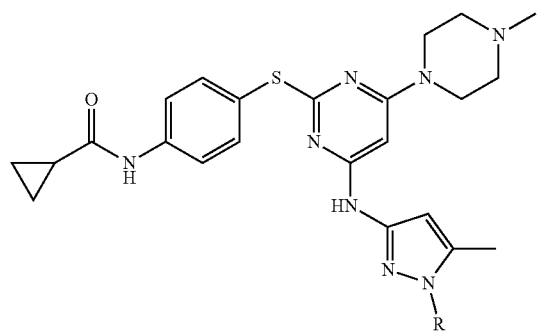
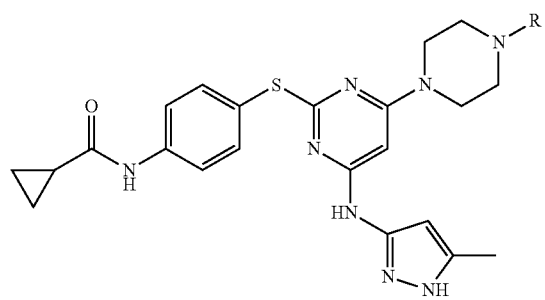

TABLE T-continued
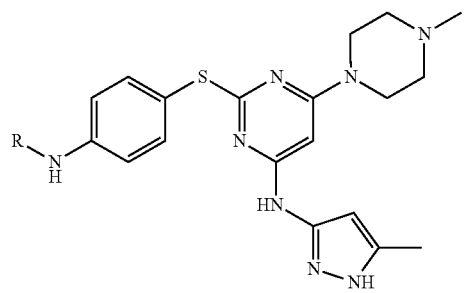
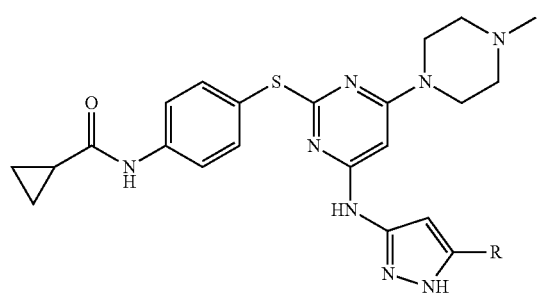
wherein:
R is the point at which the Linker is attached.
6. Targeting Ligands that target M918T mutant RET, including tozasertib
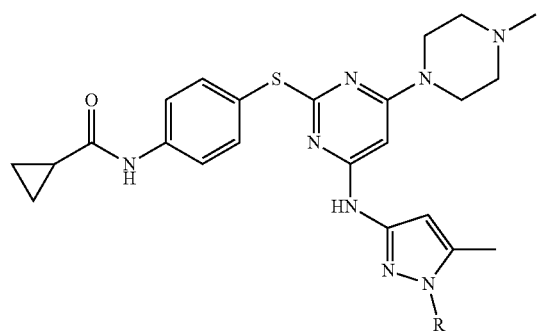
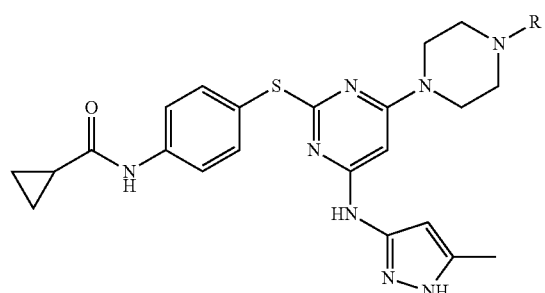

TABLE T-continued

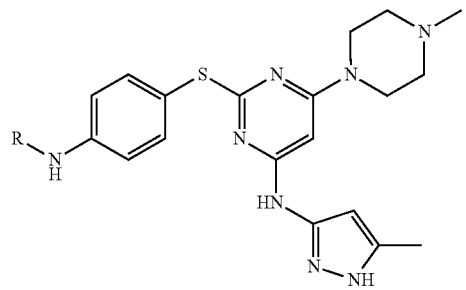

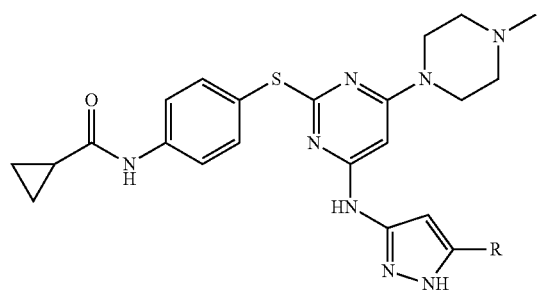

wherein:
R is the point at which the Linker is attached.

X. Heat Shock Protein 90 (HSP90) dTAG Targeting Ligands:

Heat Shock Protein 90 (HSP90) dTAG Targeting Ligands as used herein include, but are not limited to:
1. The HSP90 inhibitors identified in Vallee, et al., "Tricyclic Series of Heat Shock Protein 90 (HSP90) Inhibitors Part I: Discovery of Tricyclic Imidazo[4,5-C]Pyridines as Potent Inhibitors of the HSP90 Molecular Chaperone (2011) J. Med. Chem. 54: 7206, including YKB (N-[4-(3H-imidazo[4,5-C]Pyridin-2-yl)-9H-Fluoren-9-yl]-succinamide):

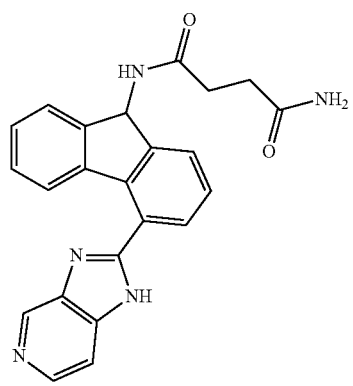 [SMILES: NC(=O)CCC(=O)NC1c2ccccc2-c2c(-c3nc4cnccc4[nH]3)cccc21]

derivatized where a Linker group L or a -(L-DEGRON) group is attached, for example, via the terminal amide group;
2. The HSP90 inhibitor p54 (modified) (8-[(2,4-dimethylphenyl)sulfanyl]-3]pent-4-yn-1-yl-3H-purin-6-amine):

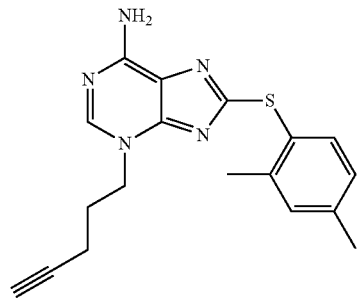 [SMILES: C#CCCCn1cnc(N)c2nc(Sc3ccc(C)cc3C)nc1-2]

derivatized where a Linker group L or a -(L-DEGRON) group is attached, for example, via the terminal acetylene group;
3. The HSP90 inhibitors (modified) identified in Brough, et al., "4,5-Diarylisoxazole HSP90 Chaperone Inhibitors: Potential Therapeutic Agents for the Treatment of Cancer", J. MED. CHEM. vol: 51, page: 196 (2008), including the compound 2GJ (5-[2,4-dihydroxy-5-(1-methylethyl)phenyl]-n-ethyl-4-[4-(morpholin-4-ylmethyl)phenyl]isoxazole-3-carboxamide) having the structure:

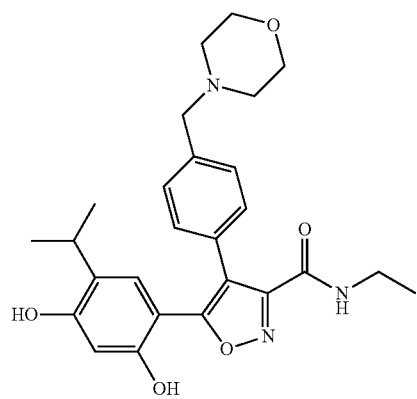 [SMILES: CCNC(=O)c1noc(-c2cc(C(C)C)c(O)cc2O)c1-c1ccc(CN2CCOCC2)cc1]

derivatized, where a Linker group L or a -(L-DEGRON) group is attached, for example, via the amide group (at the amine or at the alkyl group on the amine);
4. The HSP90 inhibitors (modified) identified in Wright, et al., Structure-Activity Relationships in Purine-Based Inhibitor Binding to HSP90 Isoforms, Chem Biol. 2004 June; 11(6): 775-85, including the HSP90 inhibitor PU3 having the structure:

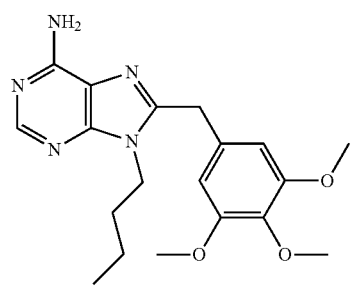 [SMILES: CCCCn1c(Cc2cc(OC)c(OC)c(OC)c2)nc2c(N)ncnc21]

derivatized where a Linker group L or -(L-DEGRON) is attached, for example, via the butyl group; and
5. The HSP90 inhibitor geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")) (derivatized, where a Linker group L or a -(L-DEGRON) group is attached, for example, via the amide group).

Y. Kinase and Phosphatase dTAG Targeting Ligands:

Kinase and Phosphatase dTAG Targeting Ligands as used herein include, but are not limited to:

1. Erlotinib Derivative Tyrosine Kinase Inhibitor:

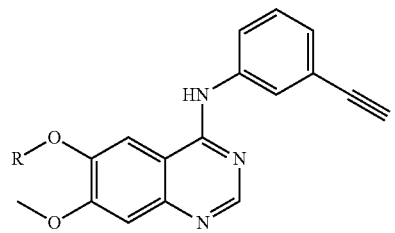

where R is a Linker group L or a -(L-DEGRON) group attached, for example, via the ether group;

2. The kinase inhibitor sunitinib (derivatized):

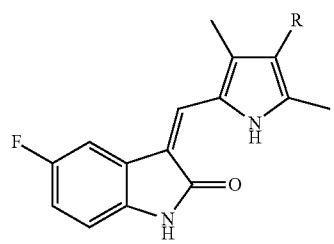

derivatized where R is a Linker group L or a -(L-DEGRON) group attached, for example, to the pyrrole moiety;

3. Kinase Inhibitor sorafenib (derivatized):

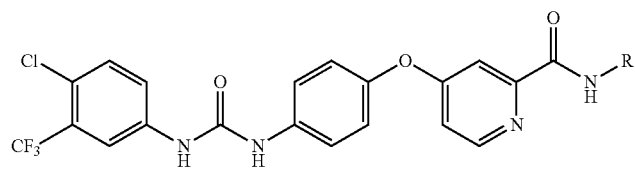

derivatized where R is a Linker group L or a -(L-DEGRON) group attached, for example, to the amide moiety;

4. The kinase inhibitor desatinib (derivatized):

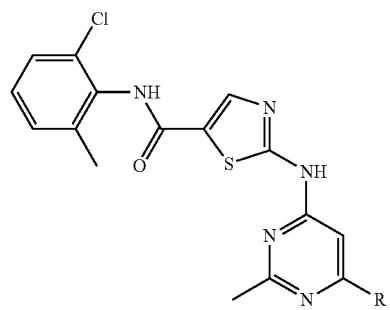

derivatized where R is a Linker group L or a -(L-DEGRON) attached, for example, to the pyrimidine;

5. The kinase inhibitor lapatinib (derivatized):

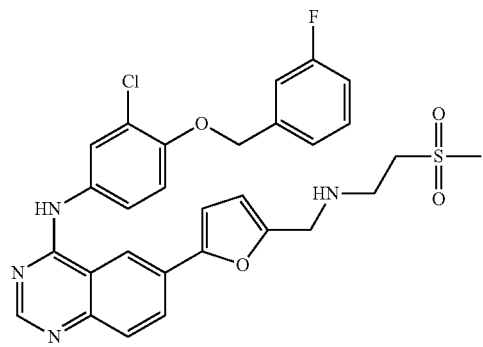 [SMILES: CS(=O)(=O)CCNCc1ccc(-c2ccc3ncnc(Nc4ccc(OCc5cccc(F)c5)c(Cl)c4)c3c2)o1]

derivatized where a Linker group L or a -(L-DEGRON) group is attached, for example, via the terminal methyl of the sulfonyl methyl group;

6. The kinase inhibitor U09-CX-5279 (derivatized):

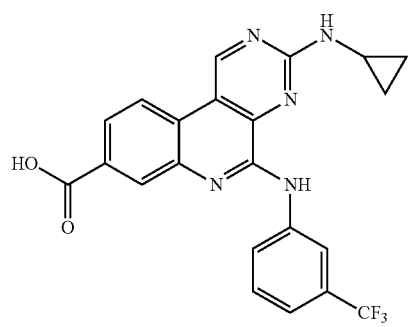 [SMILES: O=C(O)c1ccc2c(c1)nc(Nc1cccc(C(F)(F)F)c1)c1nc(NC3CC3)ncc12]

derivatized where a Linker group L or a -(L-DEGRON) group is attached, for example, via the amine (aniline), carboxylic acid or amine alpha to cyclopropyl group, or cyclopropyl group;

7. The kinase inhibitors identified in Millan, et al., Design and Synthesis of Inhaled P38 Inhibitors for the Treatment of Chronic Obstructive Pulmonary Disease, J. MED. CHEM. vol: 54, page: 7797 (2011), including the kinase inhibitors Y1W and Y1X (Derivatized) having the structures:

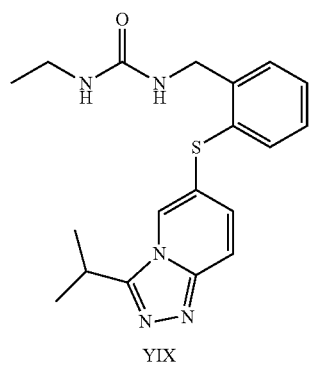 [SMILES: CCNC(=O)NCc1ccccc1Sc1ccc2nnc(C(C)C)n2c1]

Y1X (1-ethyl-3-(2-{[3-(1-methylethyl)[1,2,4]triazolo[4,3-a]pyridine-6-yl]sulfanyl}benzyl)urea, derivatized where a Linker group L or a -(L-DEGRON) group is attached, for example, via the i-propyl group;

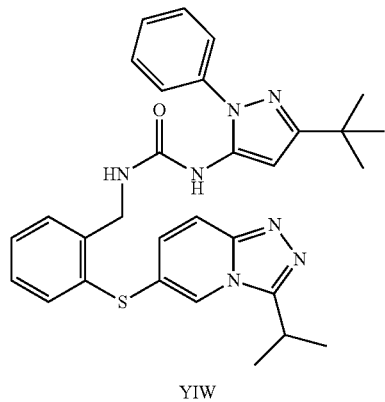 [SMILES: CC(C)c1nnc2ccc(Sc3ccccc3CNC(=O)Nc3cc(C(C)(C)C)nn3-c3ccccc3)cn12]

YIW 1-(3-tert-butyl-1-phenyl-1H-pyrazol-5-yl)-3-(2-{[3-(1-methylethyl)[1,2,4]triazolo[4,3-a]pyridin-6-yl]sulfanyl}benzyl)urea
derivatized where a Linker group L or a -(L-DEGRON) group is attached, for example, preferably via either the i-propyl group or the t-butyl group;
8. The kinase inhibitors identified in Schenkel, et al., Discovery of Potent and Highly Selective Thienopyridine Janus Kinase 2 Inhibitors J. Med. Chem., 2011, 54 (24), pp 8440-8450, including the compounds 6TP and 0TP (Derivatized) having the structures:

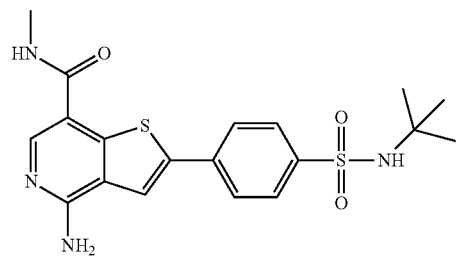

6TP 4-amino-2-[4-(tert-butylsulfamoyl)phenyl]-N-methylthieno[3,2-c]pyridine-7-carboxamide
Thienopyridine 19
derivatized where a Linker group L or a -(L-DEGRON) group is attached, for example, via the terminal methyl group bound to amide moiety;

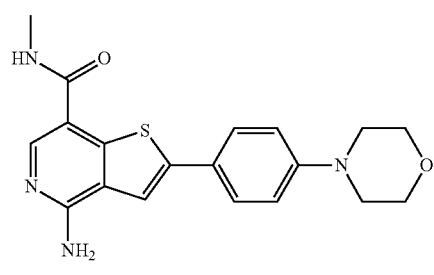

0TP 4-amino-N-methyl-2-[4-(morpholin-4-yl)phenyl]thieno[3,2-c]pyridine-7-carboxamide
Thienopyridine 8
derivatized where a Linker group L or a -(L-DEGRON) group is attached, for example, via the terminal methyl group bound to the amide moiety;

TABLE T-continued

9. The kinase inhibitors identified in Van Eis, et al., "2,6-Naphthyridines as potent and selective inhibitors of the novel protein kinase C isozymes", Biorg. Med. Chem. Lett. 2011 Dec. 15; 21(24): 7367-72, including the kinase inhibitor 07U having the structure:

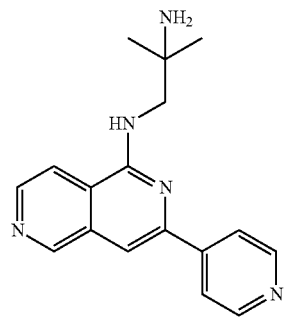

07U 2-methyl-N~1~-[3-(pyridin-4-yl)-2,6-naphthyridin-1-yl]propane-1,2-diamine
derivatized where a Linker group L or a -(L-DEGRON) group is attached, for example, via the secondary amine or terminal amino group;

10. The kinase inhibitors identified in Lountos, et al., "Structural Characterization of Inhibitor Complexes with Checkpoint Kinase 2 (Chk2), a Drug Target for Cancer Therapy", J. STRUCT. BIOL. vol: 176, pag: 292 (2011), including the kinase inhibitor YCF having the structure:

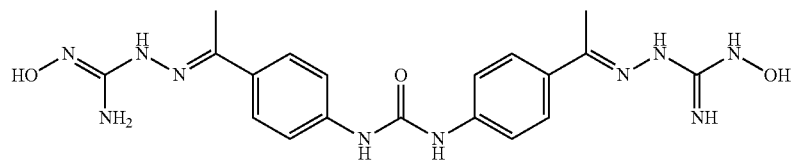 [SMILES: C/C(=N\NC(=N)NO)c1ccc(NC(=O)Nc2ccc(/C(C)=N/N/C(N)=N/O)cc2)cc1]

derivatized where a Linker group L or a -(L-DEGRON) group is attached, for example, via either of the terminal hydroxyl groups;

11. The kinase inhibitors identified in Lountos, et al., "Structural Characterization of Inhibitor Complexes with Checkpoint Kinase 2 (Chk2), a Drug Target for Cancer Therapy", J. STRUCT. BIOL. vol: 176, pag: 292 (2011), including the kinase inhibitors XK9 and NXP (derivatized) having the structures:

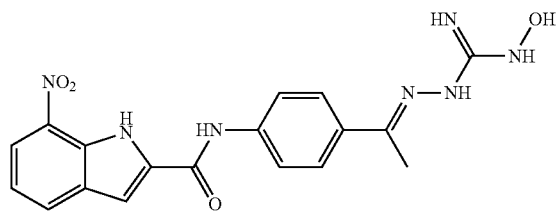

XK9

TABLE T-continued

N-{4-[(1E)-N—(N-hydroxycarbamimidoyl)ethanehydrazonoyl]phenyl}-7-nitro-1H-indole-2-carboxamide

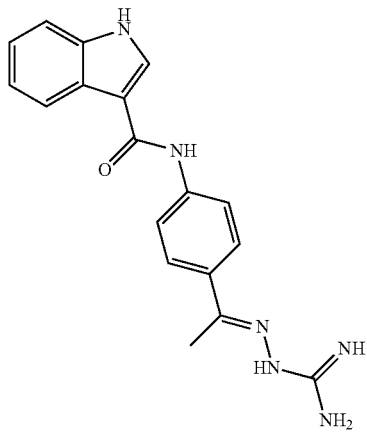

NXP

N-{4-[(1E)-N—CARBAMIMIDOYLETHANEHYDRAZONOYL]PHENYL}-1H-INDOLE-3-CARBOXAMIDE derivatized where a Linker group L or a -(L-DEGRON) group is attached, for example, via the terminal hydroxyl group (XK9) or the hydrazone group (NXP);
12. The kinase inhibitor afatinib (derivatized) (N-[4-[(3-chloro-4-fluorophenyl)amino]-7-[[(3S)-tetrahydro-3-furanyl]oxy]-6-quinazolinyl]-4(dimethylamino)-2-butenamide) (Derivatized where a Linker group L or a -(L-DEGRON) group is attached, for example, via the aliphatic amine group);
13. The kinase inhibitor fostamatinib (derivatized) ([6-({5-fluoro-2-[(3,4,5-trimethoxyphenyl)amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (Derivatized where a Linker group L or a -(L-DEGRON) group is attached, for example, via a methoxy group);
14. The kinase inhibitor gefitinib (derivatized) (N-(3-chloro-4-fluoro-phenyl)-7-methoxy-6-(3-morpholin-4-ylpropoxy)quinazolin-4-amine):

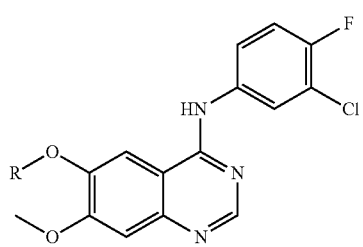

derivatized where a Linker group L or a -(L-DEGRON) group is attached, for example, via a methoxy or ether group;
15. The kinase inhibitor lenvatinib (derivatized) (4-[3-chloro-4-(cyclopropylcarbamoylamino)phenoxy]-7-methoxy-quinoline-6-carboxamide) (derivatized where a Linker group L or a -(L-DEGRON) group is attached, for example, via the cyclopropyl group);
16. The kinase inhibitor vandetanib (derivatized) (N-(4-bromo-2-fluorophenyl)-6-methoxy-7-[(1-methylpiperidin-4-yl)methoxy]quinazolin-4-amine) (derivatized where a Linker group L or a -(L-DEGRON) group is attached, for example, via the methoxy or hydroxyl group);
17. The kinase inhibitor vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide), derivatized where a Linker group L or a -(L-DEGRON) group is attached, for example, via the sulfonyl propyl group;
18. The kinase inhibitor Gleevec (derivatized):

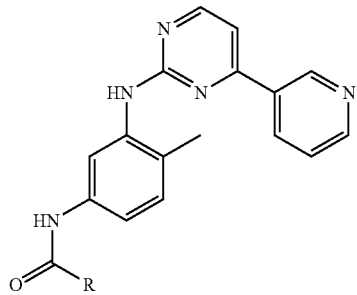

derivatized where R as a Linker group L or a -(L-DEGRON) group is attached, for example, via the amide group or via the aniline amine group;

TABLE T-continued

19. The kinase inhibitor pazopanib (derivatized) (VEGFR3 inhibitor):

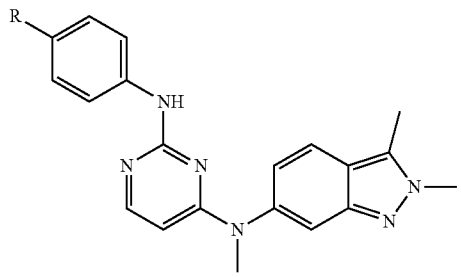

derivatized where R is a Linker group L or a -(L-DEGRON) group attached, for example, to the phenyl moiety or via the aniline amine group;

20. The kinase inhibitor AT-9283 (Derivatized) Aurora Kinase Inhibitor

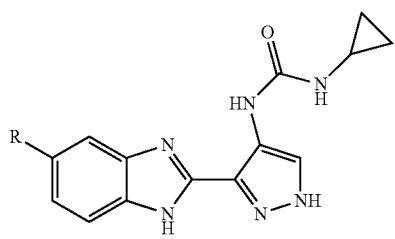

where R is a Linker group L or a -(L-DEGRON) group attached, for example, to the phenyl moiety);

21. The kinase inhibitor TAE684 (derivatized) ALK inhibitor

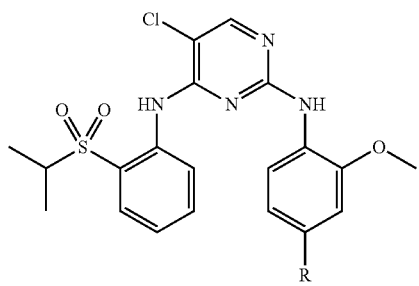

where R is a Linker group L or a -(L-DEGRON) group attached, for example, to the phenyl moiety);

22. The kinase inhibitor nilotanib (derivatized) Abl inhibitor:

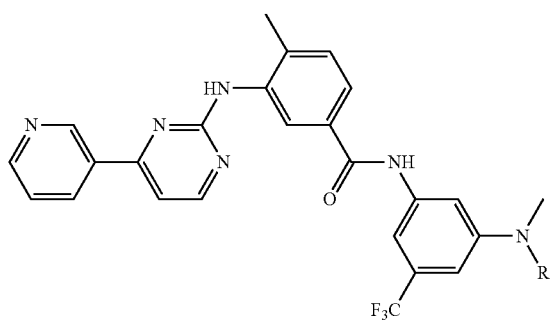

derivatized where R is a Linker group L or a -(L-DEGRON) group attached, for example, to the phenyl moiety or the aniline amine group;

TABLE T-continued

23. Kinase Inhibitor NVP-BSK805 (derivatized) JAK2 Inhibitor

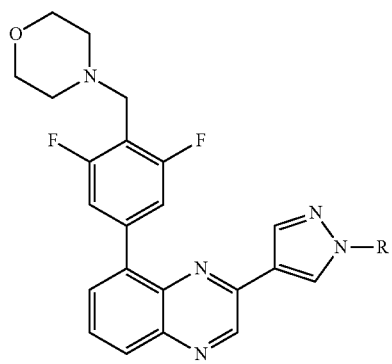

derivatized where R is a Linker group L or a -(L-DEGRON) group attached, for example, to the phenyl moiety or the diazole group;

24. Kinase Inhibitor crizotinib Derivatized Alk Inhibitor

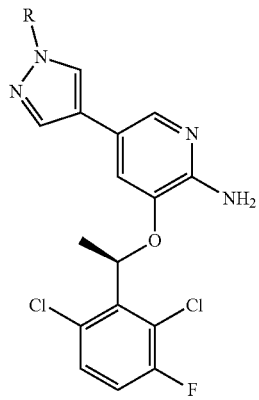

derivatized where R is a Linker group L or a -(L-DEGRON) group attached, for example, to the phenyl moiety or the diazole group;

25. Kinase Inhibitor JNJ FMS (derivatized) Inhibitor

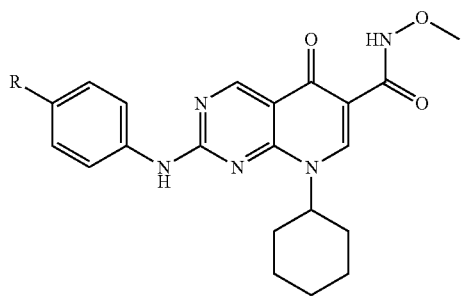

derivatized where R is a Linker group L or a -(L-DEGRON) group attached, for example, to the phenyl moiety;

26. The kinase inhibitor foretinib (derivatized) Met Inhibitor

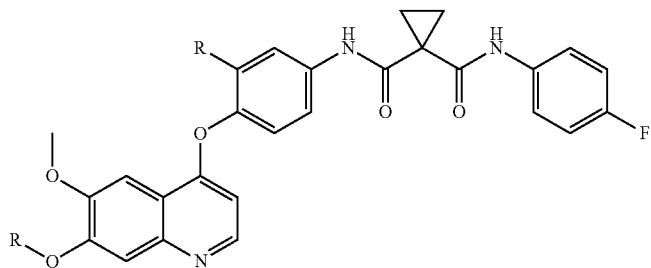

TABLE T-continued derivatized where R is a Linker group L or a -(L-DEGRON) group attached, for example, to the phenyl moiety or a hydroxyl or ether group on the quinoline moiety;

27. The allosteric Protein Tyrosine Phosphatase Inhibitor PTP1B (derivatized):

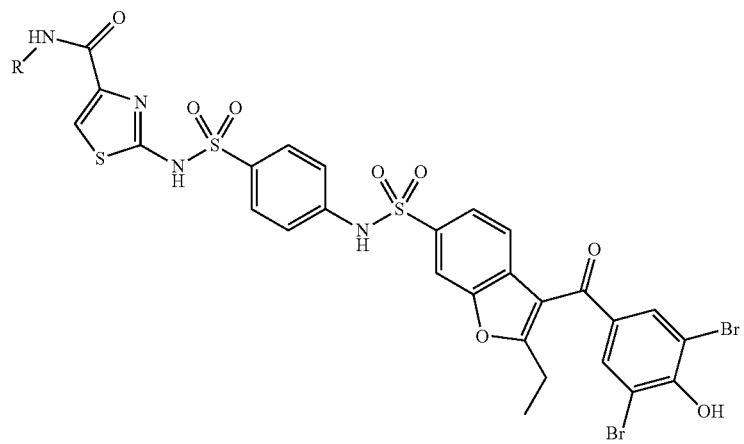

derivatized where a Linker group L or a -(L-DEGRON) group is attached, for example, at R, as indicated;

28. The inhibitor of SHP-2 Domain of Tyrosine Phosphatase (derivatized):

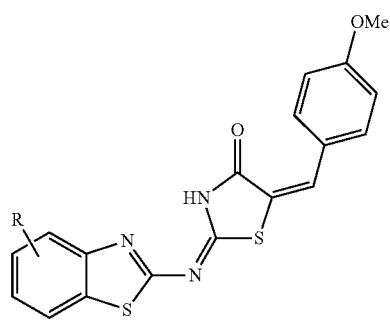

derivatized where a Linker group L or a -(L-DEGRON) group is attached, for example, at R;

29. The inhibitor (derivatized) of BRAF (BRAFV600E)/MEK:

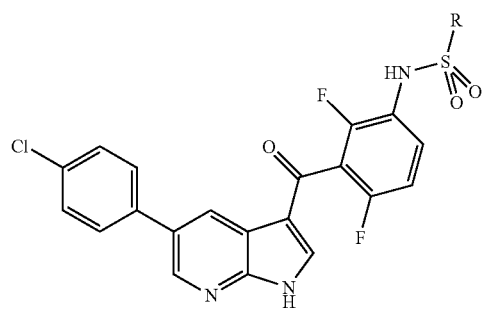

derivatized where a Linker group L or a -(L-DEGRON) group is attached, for example, at R;

30. Inhibitor (derivatized) of Tyrosine Kinase ABL

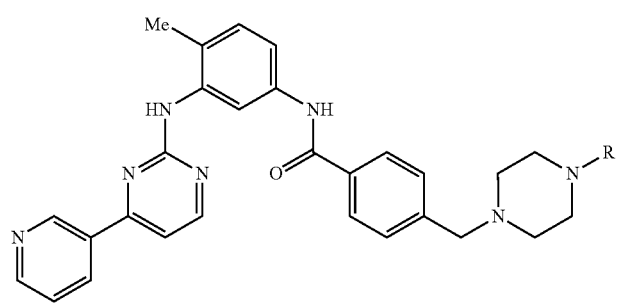

TABLE T-continued derivatized where a Linker group L or a -(L-DEGRON) group is attached, for example, at R;
31. The kinase inhibitor OSI-027 (derivatized) mTORC1/2 inhibitor

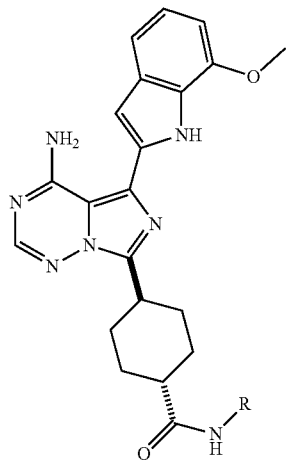

derivatized where a Linker group L or a -(L-DEGRON) group is attached, for example, at R;
32. The kinase inhibitor OSI-930 (derivatized) c-Kit/KDR inhibitor

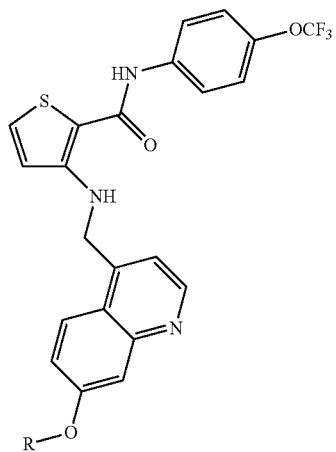

derivatized where a Linker group L or a -(L-DEGRON) group is attached, for example, at R; and
33. The kinase inhibitor OSI-906 (derivatized) IGF1R/IR inhibitor

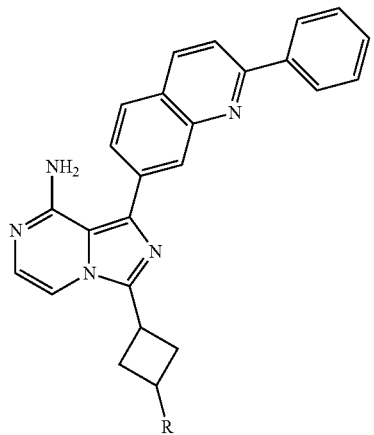

derivatized where a Linker group L or a -(L-DEGRON) group is attached, for example, at R.
Wherein, in any of the embodiments described in sections I-XVII, "R" designates a site for attachment of a Linker group L or a -(L-DEGRON) group on the piperazine moiety.

TABLE T-continued

Z. HDM2 and/or MDM2 dTAG Targeting Ligands:

HDM2 and/or MDM2 dTAG Targeting Ligands as used herein include, but are not limited to:
1. The HDM2/MDM2 inhibitors identified in Vassilev, et al., In vivo activation of the p53 pathway by small-molecule antagonists of MDM2, SCIENCE vol: 303, pag: 844-848 (2004), and Schneekloth, et al., Targeted intracellular protein degradation induced by a small molecule: En route to chemical proteomics, Bioorg. Med. Chem. Lett. 18 (2008) 5904-5908, including (or additionally) the compounds nutlin-3, nutlin-2, and nutlin-1 (derivatized) as described below, as well as all derivatives and analogs thereof:

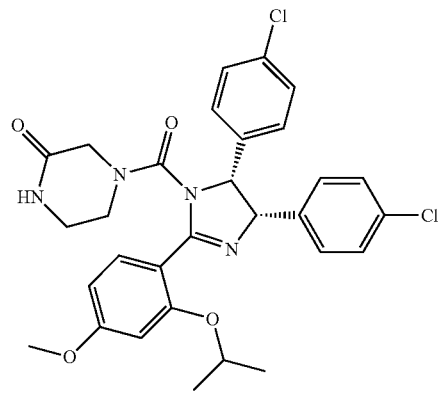 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a Linker group L or a -(L-DEGRON) group is attached, for example, at the methoxy group or as a hydroxyl group);

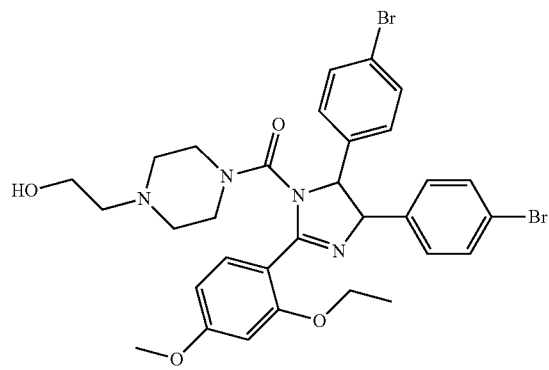 [SMILES: CCOc1cc(OC)ccc1C1=NC(c2ccc(Br)cc2)C(c2ccc(Br)cc2)N1C(=O)N1CCN(CCO)CC1]

(derivatized where a Linker group L or a -(L-DEGRON) group is attached, for example, at the methoxy group or hydroxyl group);

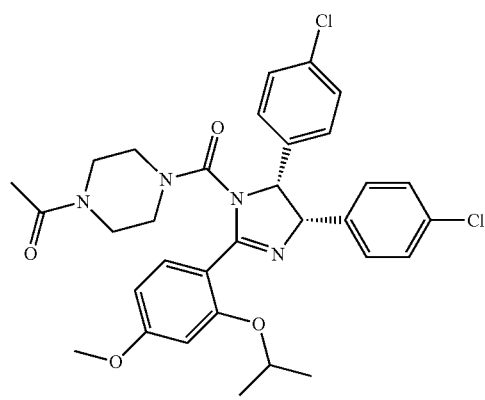 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a Linker group L or a -(L-DEGRON) group is attached, for example, via the methoxy group or as a hydroxyl group); and 2. Trans-4-Iodo-4'-Boranyl-Chalcone

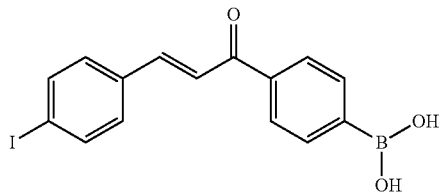 [SMILES: O=C(/C=C/c1ccc(I)cc1)c1ccc(B(O)O)cc1]

(derivatized where a Linker group L or a Linker group L or a -(L-DEGRON) group is attached, for example, via a hydroxy group).

AA. Human BET Bromodomain-Containing Proteins dTAG Targeting Ligands:

In certain embodiments, "dTAG Targeting Ligand" can be ligands binding to Bromo-and Extra-terminal (BET) proteins BRD2, BRD3 and BRD4. Compounds targeting Human BET Bromodomain-containing proteins include, but are not limited to the compounds associated with the targets as described below, where "R" or "Linker" designates a site for Linker group L or a -(L-DEGRON) group attachment, for example:

1. JQ1, Filippakopoulos et al. Selective inhibition of BET bromodomains. Nature (2010):

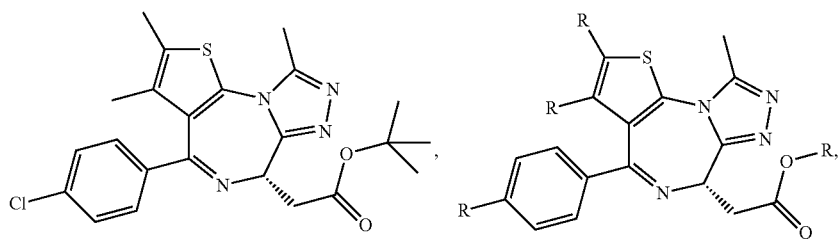

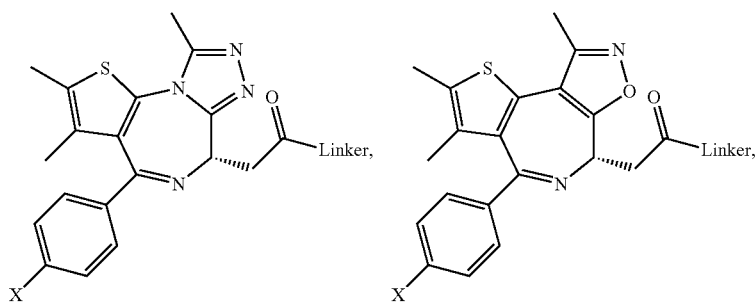

X = Cl, Br, F, H        X = Cl, Br, F, H

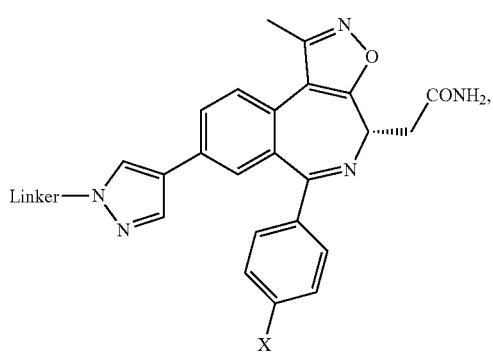

X = Cl, Br, F, H

TABLE T-continued
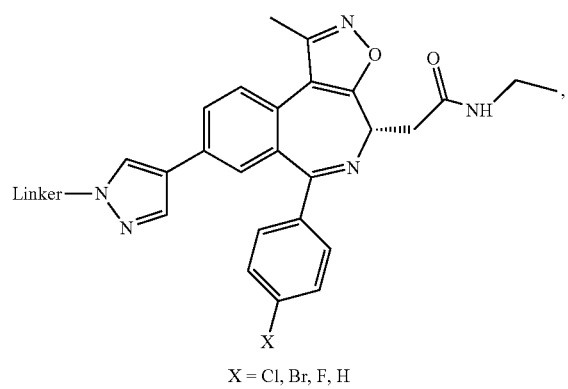
X = Cl, Br, F, H
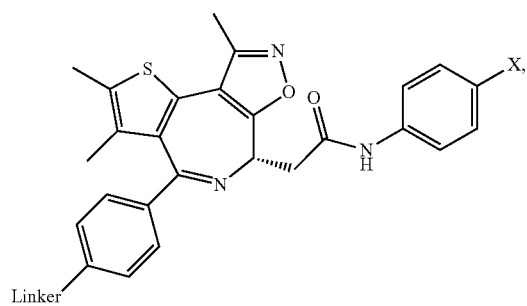
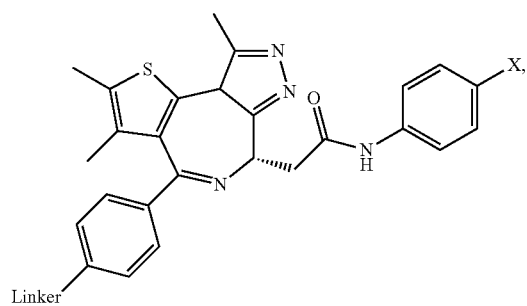
X = H, F
2. I-BET, Nicodeme et al. Suppression of Inflammation by a Synthetic Histone Mimic. Nature (2010). Chung et al. Discovery and Characterization of Small Molecule Inhibitors of the BET Family Bromodomains. J. Med Chem. (2011):
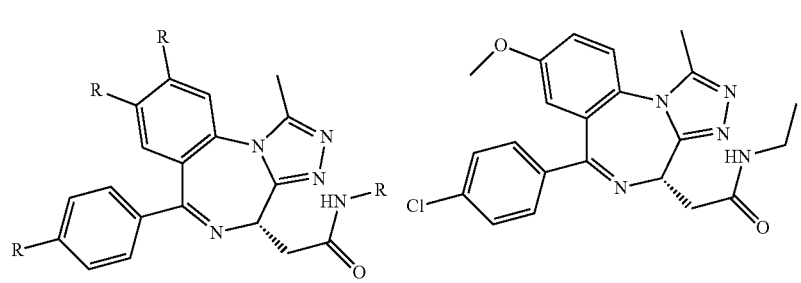

TABLE T-continued
3. Compounds described in Hewings et al. 3,5-Dimethylisoxazoles Act as Acetyl-lysine Bromodomain Ligands. J. Med. Chem. (2011) 54 6761-6770.
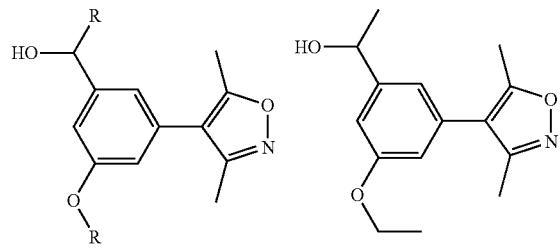
4. I-BET151, Dawson et al. Inhibition of BET Recruitment to Chromatin as an Effective Treatment for MLL-fusion Leukemia. Nature (2011):
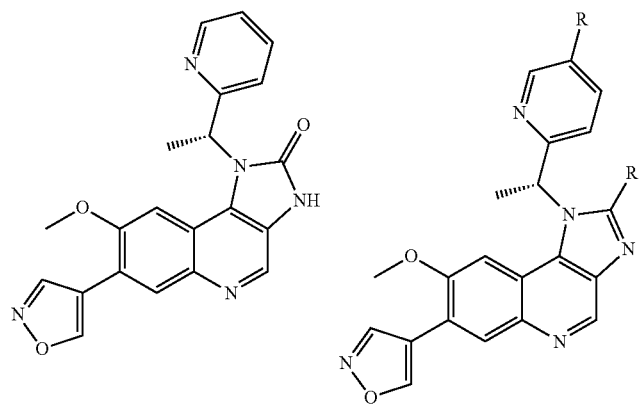
5. Carbazole type (US 2015/0256700)
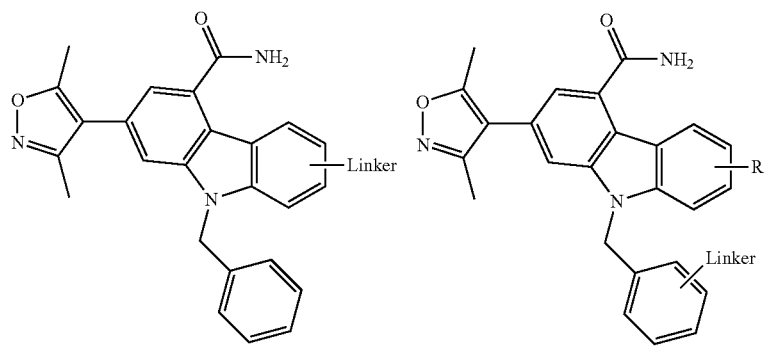
6. Pyrrolopyridone type (US 2015/0148342)
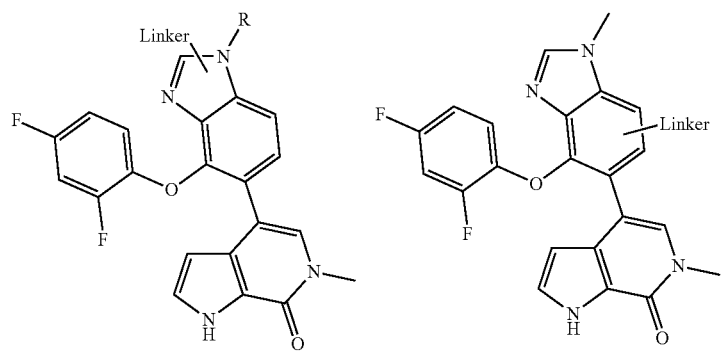

TABLE T-continued
7. Tetrahydroquinoline type (WO 2015/074064)
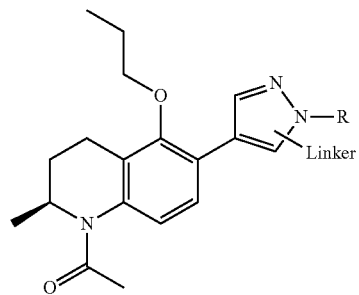
8. Triazolopyrazine type (WO 2015/067770)
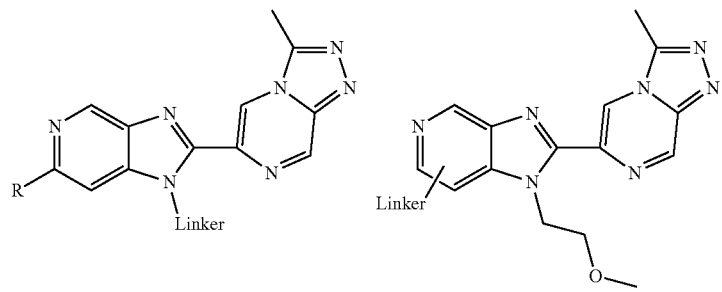
9. Pyridone type (WO 2015/022332)
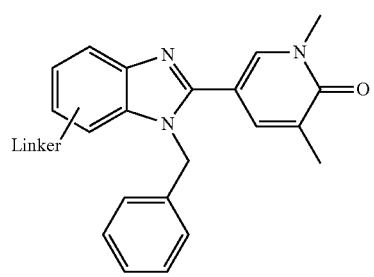
10. Quinazolinone type (WO 2015/015318)
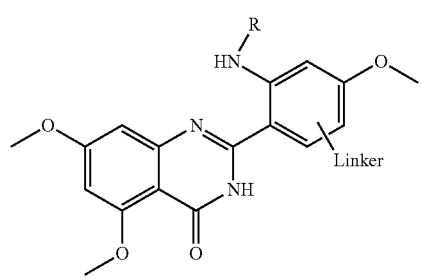

11. Dihydropyridopyrazinone type (WO 2015/011084)

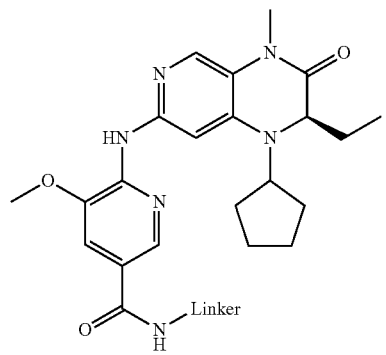

(Where R or L or Linker, in each instance, designates a site for attachment, for example, of a Linker group L or a -(L-DEGRON) group).
BB. HDAC dTAG Targeting Ligands:

HDAC dTAG Targeting Ligands as used herein include, but are not limited to:
1. Finnin, M. S. et al. Structures of Histone Deacetylase Homologue Bound to the TSA and SAHA Inhibitors. Nature 40, 188-193 (1999).

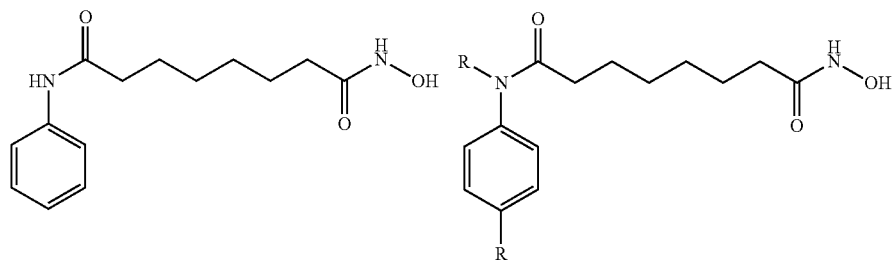

(Derivatized where "R" designates a site for attachment, for example, of a Linker group L or a -(L-DEGRON) group); and
2. Compounds as defined by formula (I) of PCT WO0222577 ("DEACETYLASE INHIBITORS")
(Derivatized where a Linker group L or a -(L-DEGRON) group is attached, for example, via the hydroxyl group);
CC. Human Lysine Methyltransferase dTAG Targeting Ligands:

Human Lysine Methyltransferase dTAG Targeting Ligands as used herein include, but are not limited to:
1. Chang et al. Structural Basis for G9a-Like protein Lysine Methyltransferase Inhibition by BIX-1294. Nat. Struct. Biol. (2009) 16(3) 312.

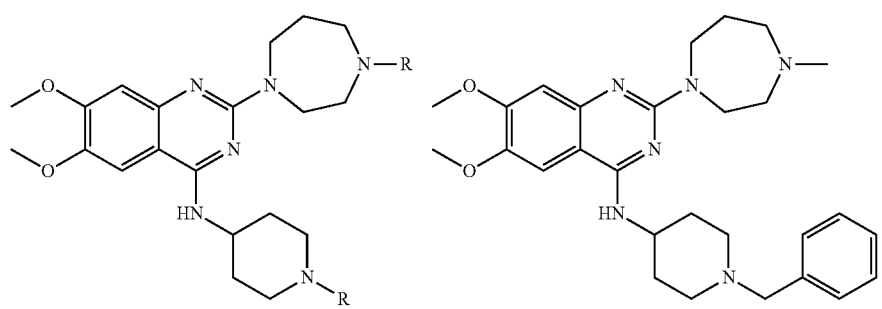

(Derivatized where "R" designates a site for attachment, for example, of a Linker group L or a -(L-DEGRON) group);
2. Liu, F. et al Discovery of a 2,4-Diamino-7-aminoalkoxyquinazoline as a Potent and Selective Inhibitor of Histone Methyltransferase G9a. J. Med. Chem. (2009) 52(24) 7950.

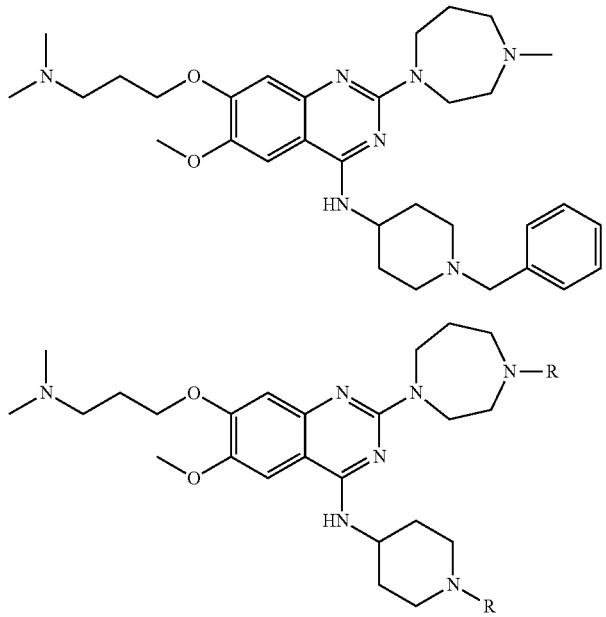

(Derivatized where "R" designates a potential site for attachment, for example, of a Linker group L or a -(L-DEGRON) group);
3. Azacitidine (derivatized) (4-amino-1-(3-D-ribofuranosyl-1,3,5-triazin-2(1H)-one) (Derivatized where a Linker group L or a -(L-DEGRON) group is attached, for example, via the hydroxy or amino groups); and
4. Decitabine (derivatized) (4-amino-1-(2-deoxy-b-D-erythro-pentofuranosyl)-1,3,5-triazin-2(1H)-one) (Derivatized where a Linker group L or a -(L-DEGRON) group is attached, for example, via either of the hydroxy groups or at the amino group).
DD. dTAG targeting ligands organized by functionality
Angiogenesis Inhibitors:

Angiogenesis inhibitors include, but are not limited to:
1. GA-1 (derivatized) and derivatives and analogs thereof, having the structure(s) and binding to Linkers as described in Sakamoto, et al., Development of Protacs to target cancer-promoting proteins for ubiquitination and degradation, Mol Cell Proteomics 2003 December; 2(12): 1350-8;
2. Estradiol (derivatized), which may be bound to a Linker group L or a -(L-DEGRON) group as is generally described in Rodriguez-Gonzalez, et al., Targeting steroid hormone receptors for ubiquitination and degradation in breast and prostate cancer, Oncogene (2008) 27, 7201-7211;
3. Estradiol, testosterone (derivatized) and related derivatives, including but not limited to DHT and derivatives and analogs thereof, having the structure(s) and binding to a Linker group L or a -(L-DEGRON) group as generally described in Sakamoto, et al., Development of Protacs to target cancer-promoting proteins for ubiquitination and degradation, Mol Cell Proteomics 2003 December; 2(12): 1350-8; and
4. Ovalicin, fumagillin (derivatized), and derivatives and analogs thereof, having the structure(s) and binding to a Linker group L or a -(L-DEGRON) group as is generally described in Sakamoto, et al., Protacs: chimeric molecules that target proteins to the Skp1-Cullin-F box complex for ubiquitination and degradation Proc Natl Acad Sci USA. 2001 Jul. 17; 98(15): 8554-9 and U.S. Pat. No. 7,208,157.
Immunosuppressive Compounds:

Immunosuppressive compounds include, but are not limited to:
1. AP21998 (derivatized), having the structure(s) and binding to a Linker group L or a -(L-DEGRON) group as is generally described in Schneekloth, et al., Chemical Genetic Control of Protein Levels: Selective in Vivo Targeted Degradation, J. AM. CHEM. SOC. 2004, 126, 3748-3754;
2. Glucocorticoids (e.g., hydrocortisone, prednisone, prednisolone, and methylprednisolone) (Derivatized where a Linker group L or a -(L-DEGRON) group is to bound, e.g. to any of the hydroxyls) and beclometasone dipropionate (Derivatized where a Linker group or a -(L-DEGRON) is bound, e.g. to a propionate);
3. Methotrexate (Derivatized where a Linker group or a -(L-DEGRON) group can be bound, e.g. to either of the terminal hydroxyls);
4. Ciclosporin (Derivatized where a Linker group or a -(L-DEGRON) group can be bound, e.g. at any of the butyl groups);
5. Tacrolimus (FK-506) and rapamycin (Derivatized where a Linker group L or a -(L-DEGRON) group can be bound, e.g. at one of the methoxy groups); and
6. Actinomycins (Derivatized where a Linker group L or a -(L-DEGRON) group can be bound, e.g. at one of the isopropyl groups).

TABLE T-continued

EE. Aryl Hydrocarbon Receptor (AHR) dTAG Targeting Ligands:

AHR dTAG Targeting Ligands as used herein include, but are not limited to:
1. Apigenin (Derivatized in a way which binds to a Linker group L or a -(L-DEGRON) group as is generally illustrated in Lee, et al., Targeted Degradation of the Aryl Hydrocarbon Receptor by the PROTAC Approach: A Useful Chemical Genetic Tool, Chem Bio Chem Volume 8, Issue 17, pages 2058-2062, Nov. 23, 2007); and
2. SR1 and LGC006 (derivatized such that a Linker group L or a -(L-DEGRON) is bound), as described in Boitano, et al., Aryl Hydrocarbon Receptor Antagonists Promote the Expansion of Human Hematopoietic Stem Cells, Science 10 Sep. 2010: Vol. 329 no. 5997 pp. 1345-1348.

FF. RAF dTAG Targeting Ligands:

RAF dTAG Targeting Ligands as used herein include, but are not limited to:

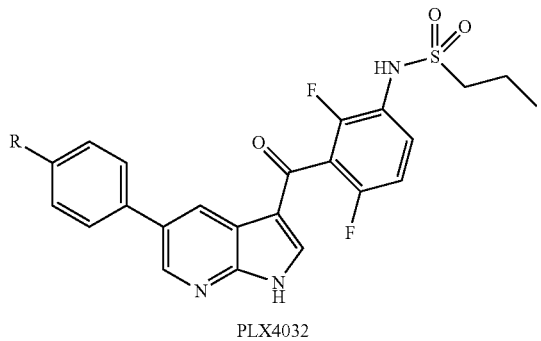

PLX4032

(Derivatized where "R" designates a site for Linker group L or -(L-DEGRON) group attachment, for example).

GG. FKBP dTAG Targeting Ligands:

FKBP dTAG Targeting Ligands as used herein include, but are not limited to:

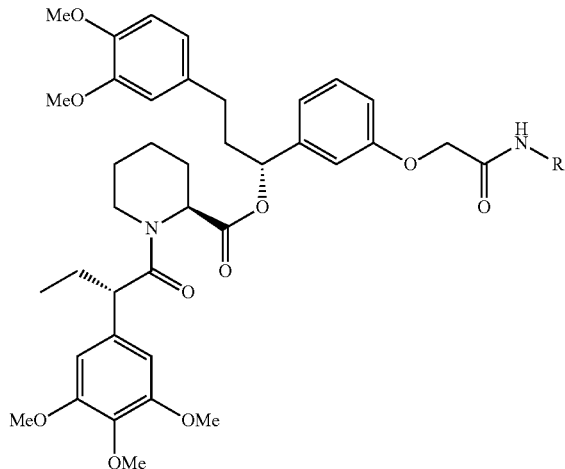

(Derivatized where "R" designates a site for a Linker group L or a -(L-DEGRON) group attachment, for example)

HH. Androgen Receptor (AR) dTAG Targeting Ligands:

AR dTAG Targeting Ligands as used herein include, but are not limited to:
1. RU59063 Ligand (derivatized) of Androgen Receptor

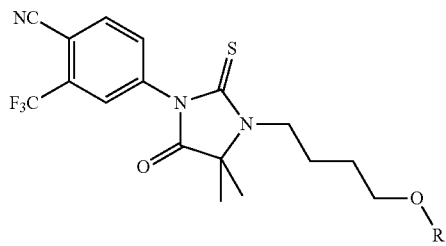

(Derivatized where "R" designates a site for a Linker group L or a -(L-DEGRON) group attachment, for example).

TABLE T-continued

2. SARM Ligand (derivatized) of Androgen Receptor

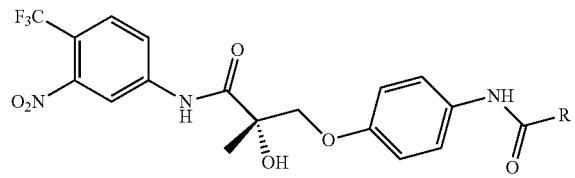

(Derivatized where "R" designates a site for a Linker group L or a -(L-DEGRON) group attachment, for example).

3. Androgen Receptor Ligand DHT (derivatized)

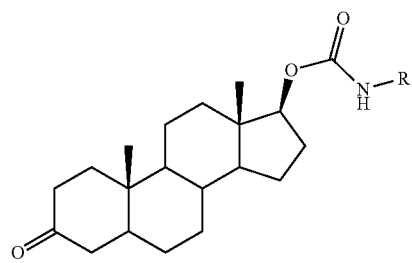

(Derivatized where "R" designates a site for a Linker group L or -(L-DEGRON) group attachment, for example).

4. MDV3100 Ligand (derivatized)

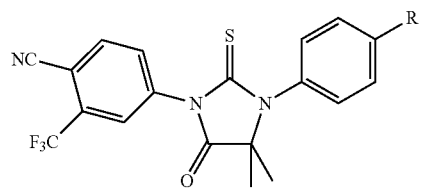

5. ARN-509 Ligand (derivatized)

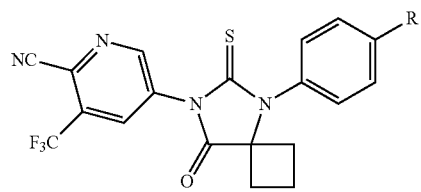

6. Hexahydrobenzisoxazoles

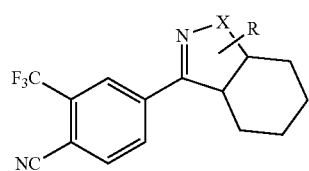

7. Tetramethylcyclobutanes

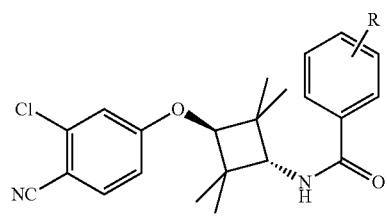

TABLE T-continued

II. Estrogen Receptor (ER) dTAG Targeting Ligands:

ER dTAG Targeting Ligands as used herein include, but are not limited to:
1. Estrogen Receptor Ligand

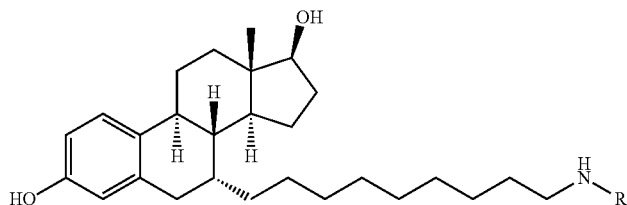

(Derivatized where "R" designates a site for Linker group L or -(L-DEGRON) group attachment).

JJ. Thyroid Hormone Receptor (TR) dTAG Targeting Ligands:

TR dTAG Targeting Ligands as used herein include, but are not limited to:
1. Thyroid Hormone Receptor Ligand (derivatized)

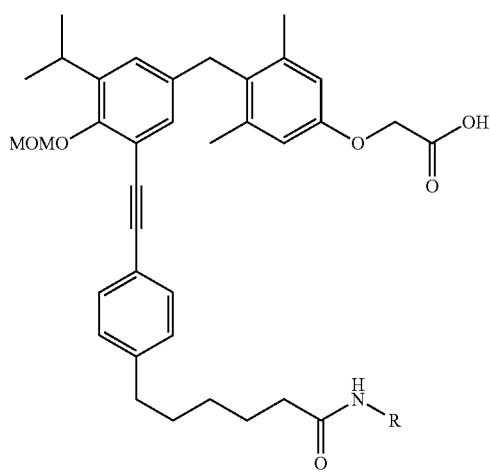

(Derivatized where "R" designates a site for Linker group L or -(L-DEGRON) group attachment and MOMO indicates a methoxymethoxy group).

KK. HIV Protease dTAG Targeting Ligands:

HIV Protease dTAG Targeting Ligands as used herein include, but are not limited to:
1. Inhibitor of HIV Protease (derivatized)

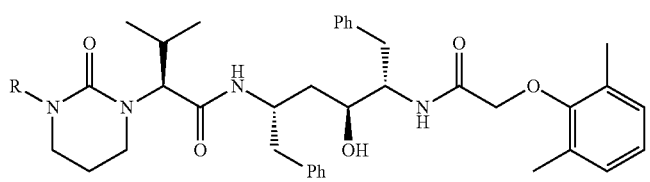

(Derivatized where "R" designates a site for Linker group L or -(L-DEGRON) group attachment). See, J. Med. Chem. 2010, 53, 521-538.

2. Inhibitor of HIV Protease

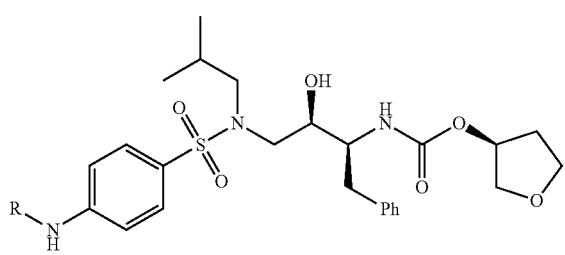

(Derivatized where "R" designates a potential site for Linker group L or -(L-DEGRON) group attachment). See, J. Med. Chem. 2010, 53, 521-538.

LL. HIV Integrase dTAG Targeting Ligands:

HIV Integrase dTAG Targeting Ligands as used herein include, but are not limited to:

1. Inhibitor of HIV Integrase (derivatized)

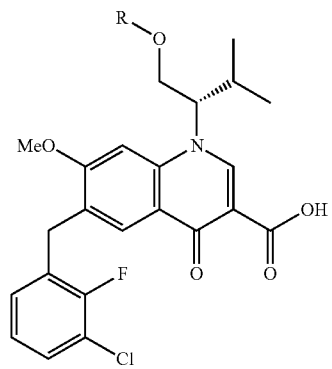

(Derivatized where "R" designates a site for Linker group L or -(L-DEGRON) group attachment). See, J. Med. Chem. 2010, 53, 6466.

2. Inhibitor of HIV Integrase (derivatized)

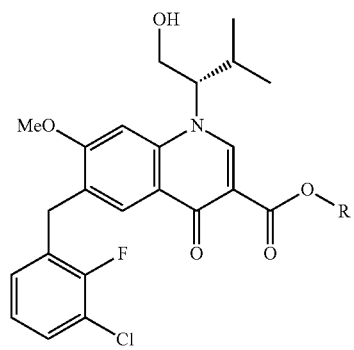

3. Inhibitor of HIV integrase (derivatized)

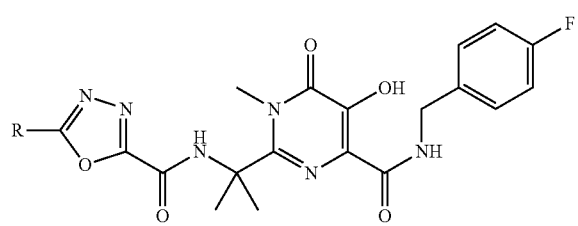

(Derivatized where "R" designates a site for Linker group L or -(L-DEGRON) group attachment). See, J. Med. Chem. 2010, 53, 6466.

MM. HCV Protease dTAG Targeting Ligands:

HCV Protease dTAG Targeting Ligands as used herein include, but are not limited to:
1. Inhibitors of HCV Protease (Derivatized)

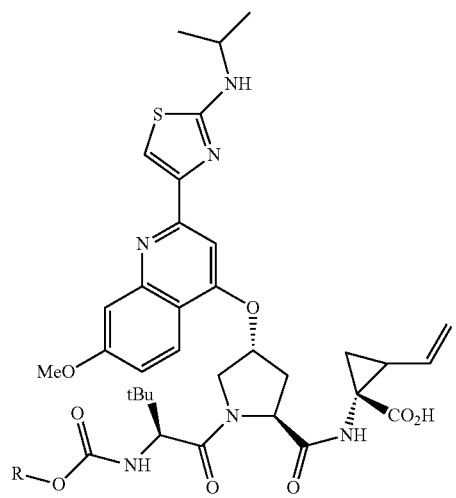

(Derivatized where "R" designates a site for Linker group L or -(L-DEGRON) group attachment).

NN. Acyl-Protein Thioesterase-1 and -2 (APT1 and APT2) dTAG Targeting Ligands:

Acyl-Protein Thioesterase-1 and -2 (APT1 and APT2) dTAG Targeting Ligands as used herein include, but are not limited to:
1. Inhibitor of APT1 and APT2 (Derivatized)

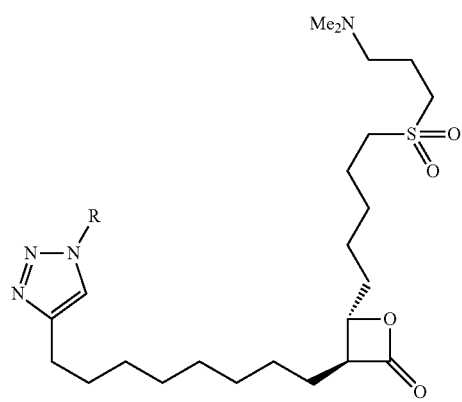

(Derivatized where "R" designates a site for Linker group L or -(L-DEGRON) group attachment). See, Angew. Chem. Int. Ed. 2011, 50, 9838-9842, where L is a Linker group as otherwise described herein and said Degron group is as otherwise described herein such that the Linker binds the Degron group to a dTAG Targeting Ligand group as otherwise described herein.

OO. BCL2 dTAG Targeting Ligands:
BCL2 dTAG Targeting Ligands as used herein include, but are not limited to:
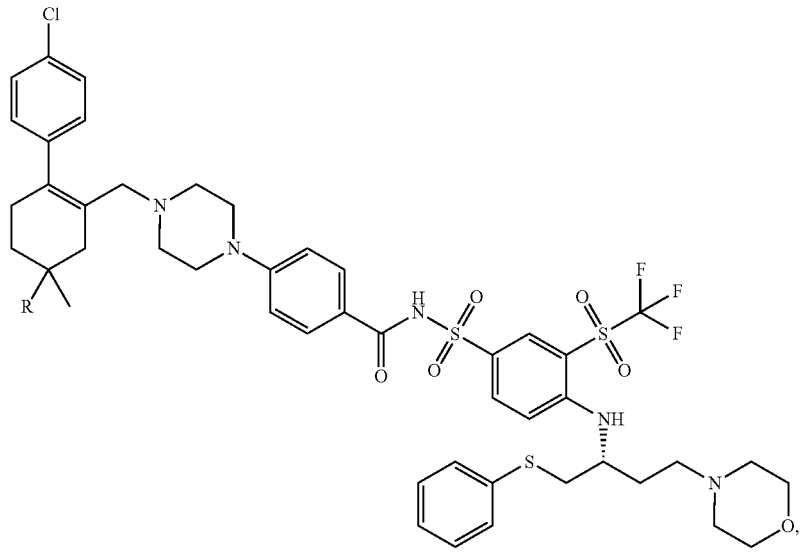
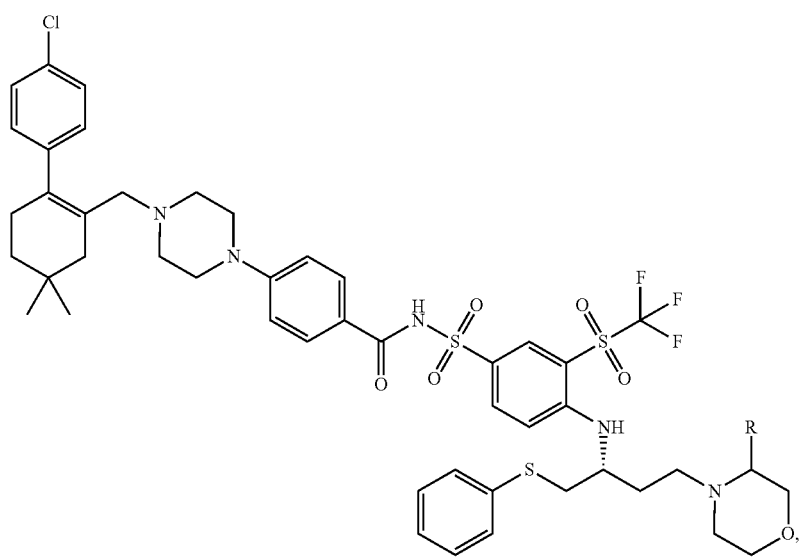

TABLE T-continued
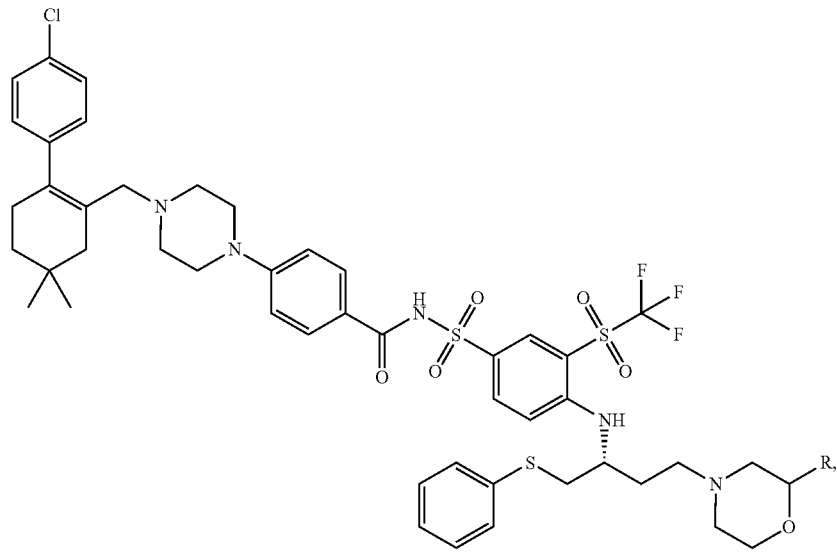
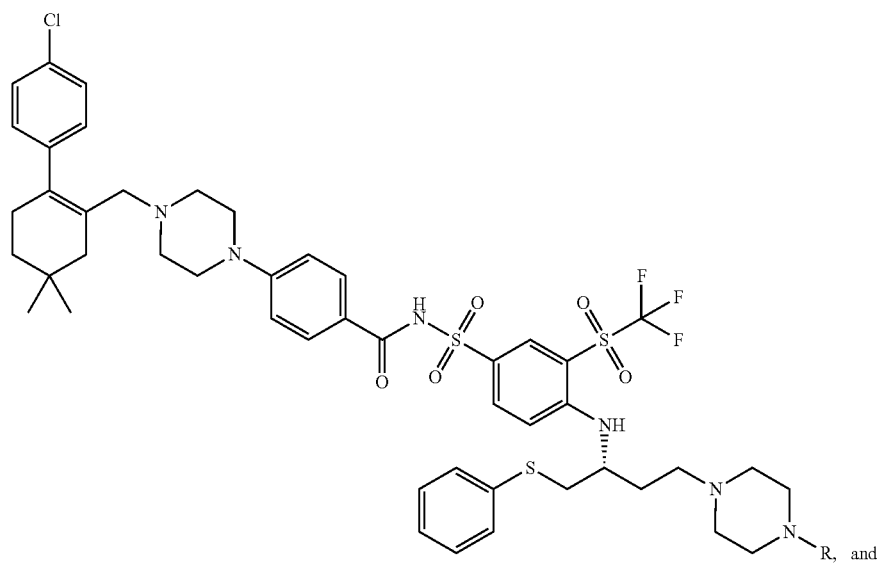

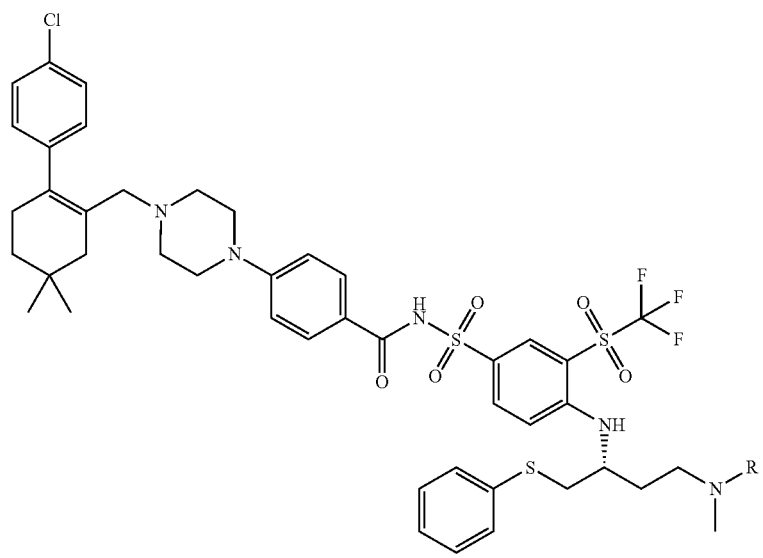
wherein:
R is the point at which the Linker is attached.
PP. BCL-XL dTAG Targeting Ligands:
BCL-XL dTAG Targeting Ligands as used herein include, but are not limited to:
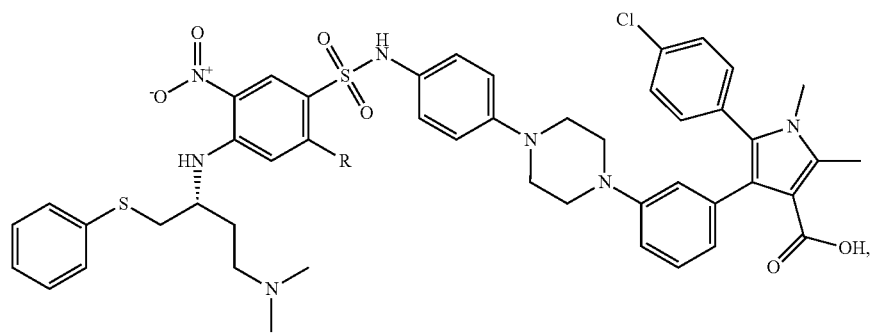
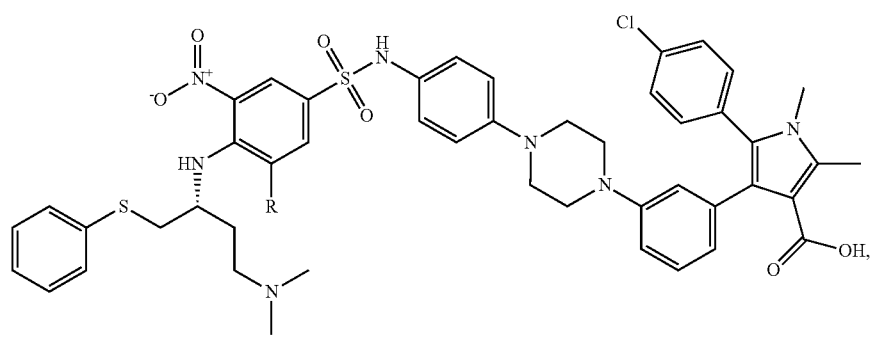

TABLE T-continued
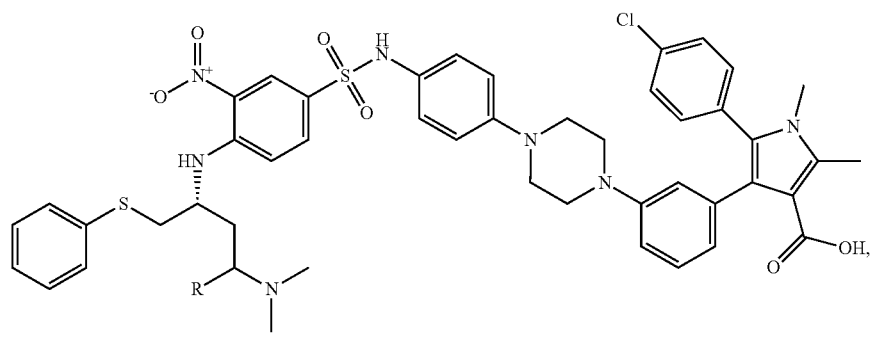
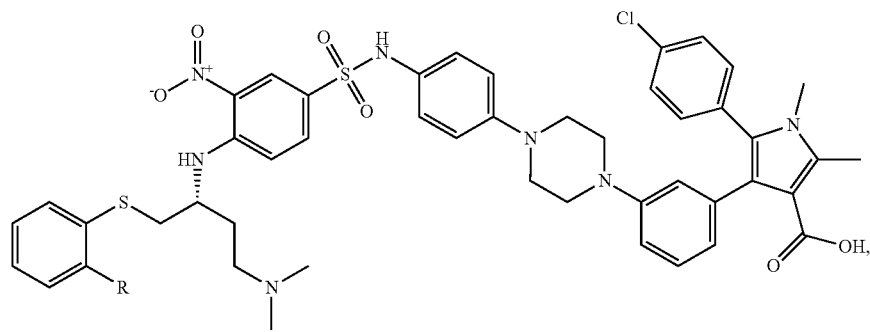
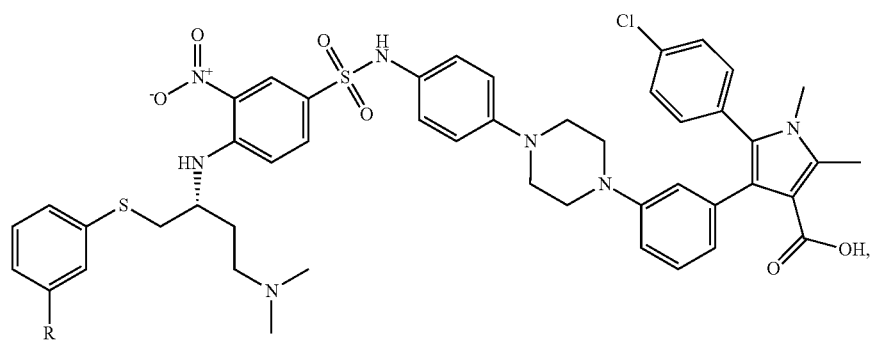
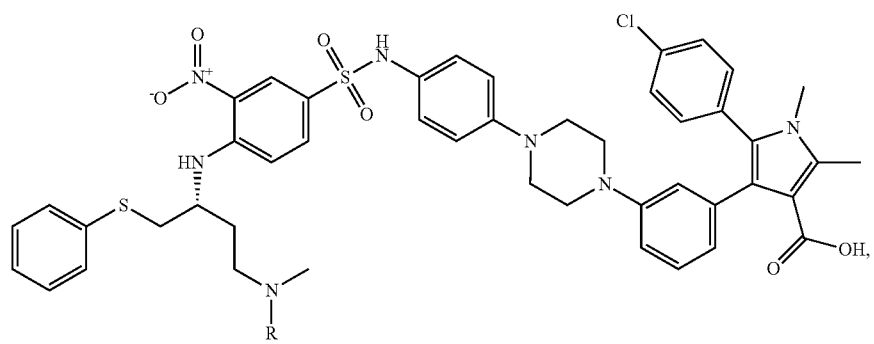

TABLE T-continued
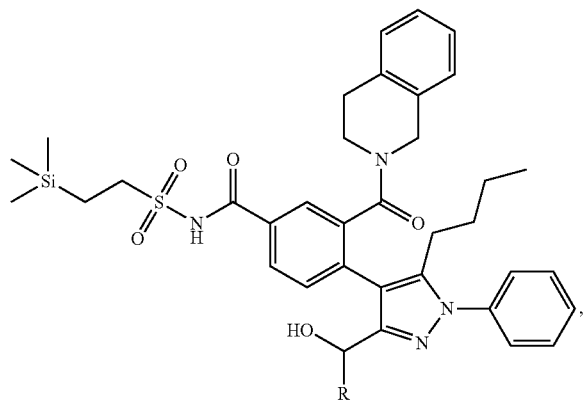
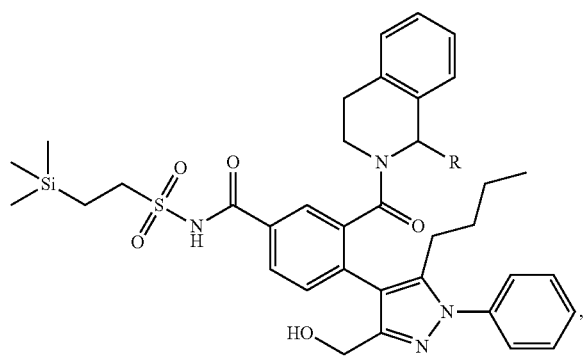
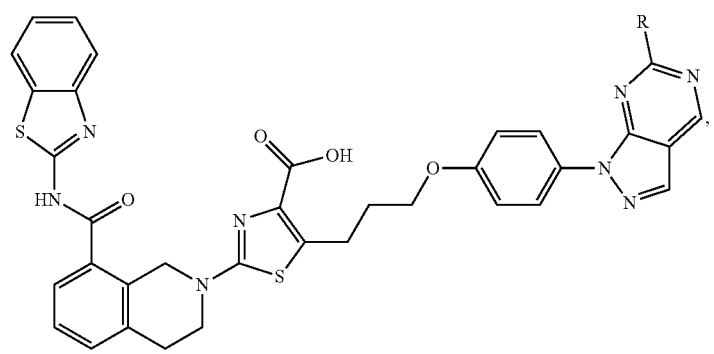
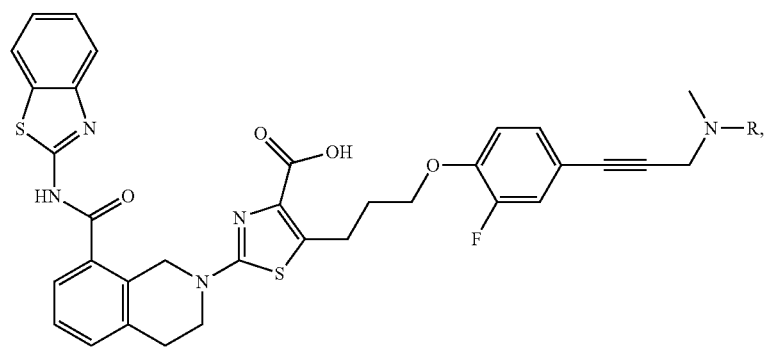

TABLE T-continued
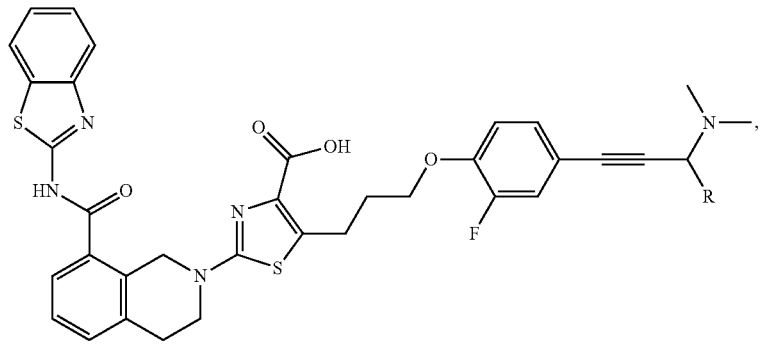
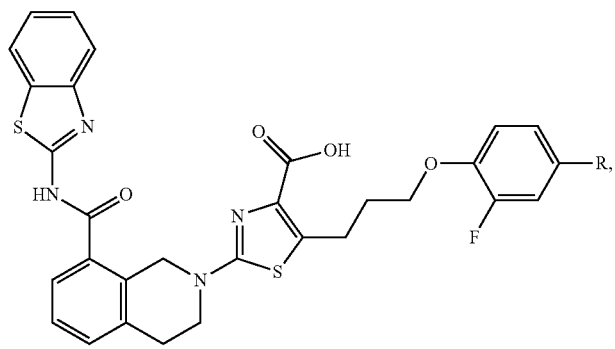
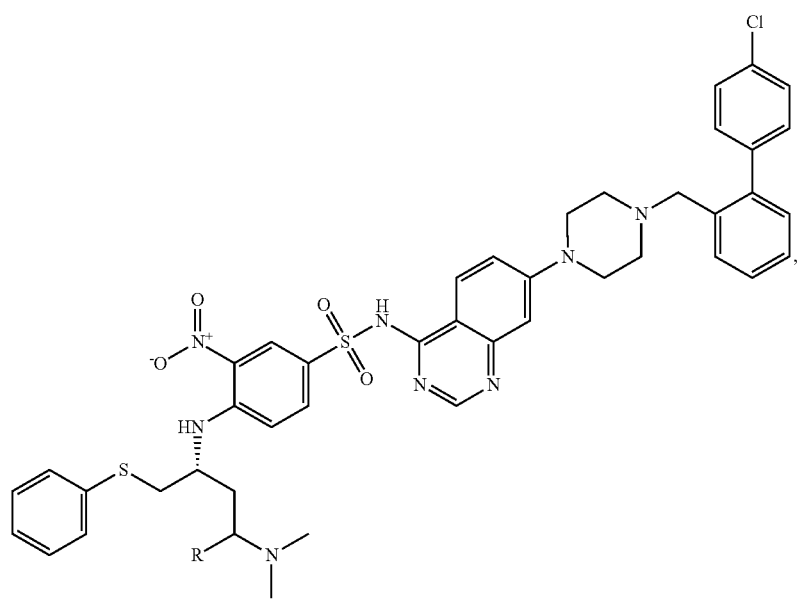

TABLE T-continued
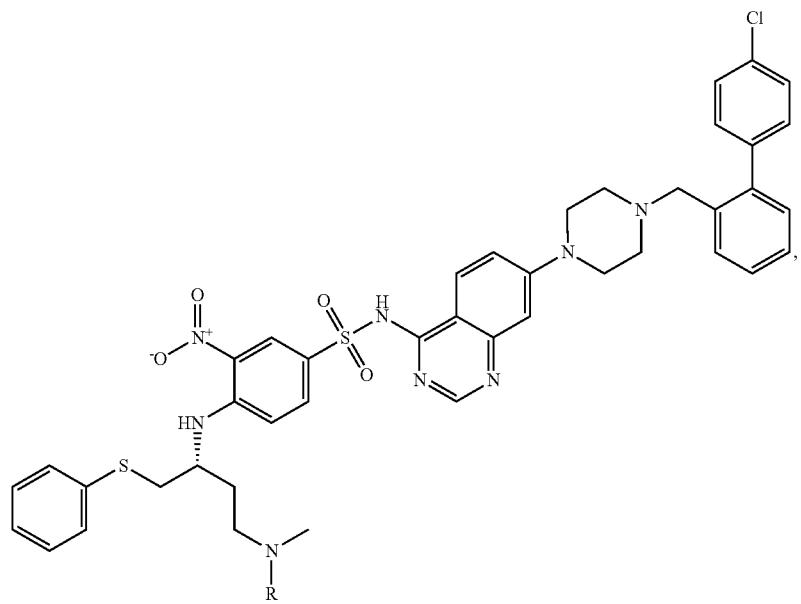
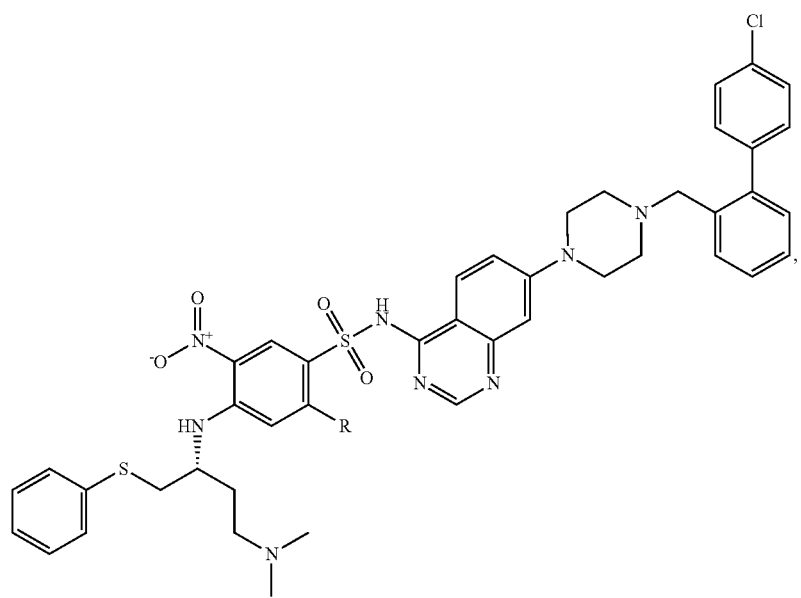

TABLE T-continued
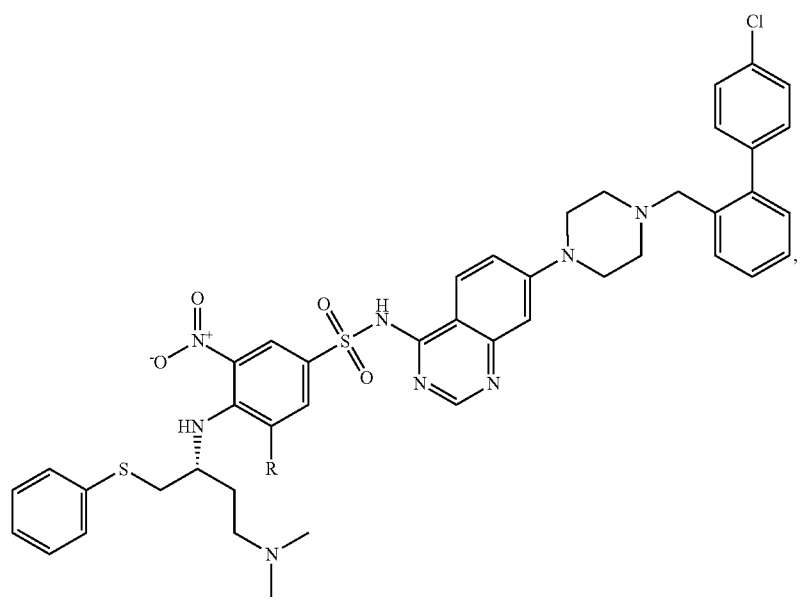
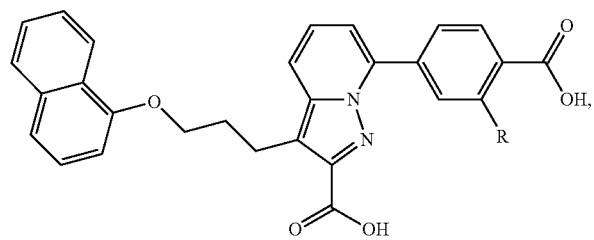
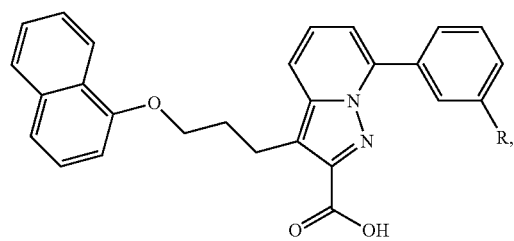
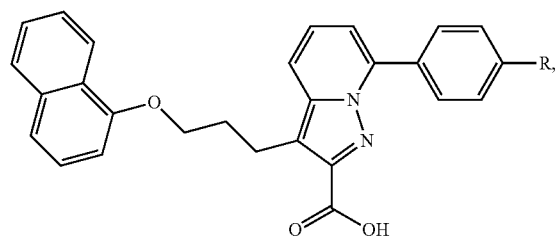

TABLE T-continued
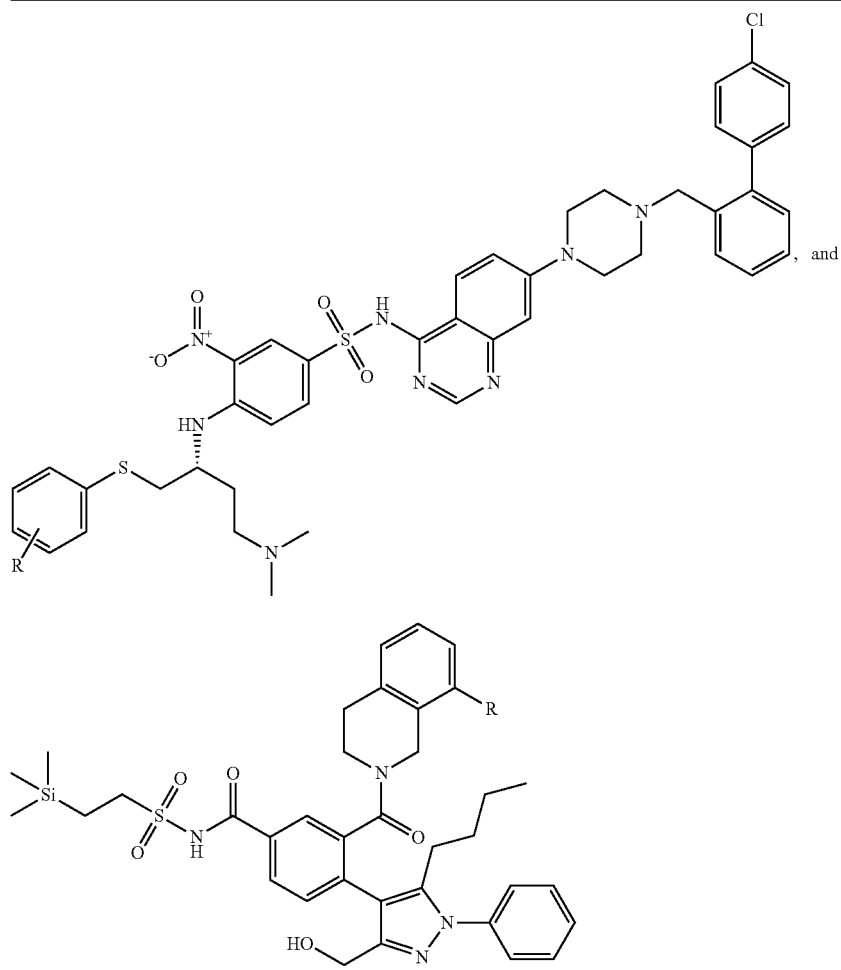
wherein:
R is the point at which the Linker is attached.
QQ. FA Binding Protein dTAG Targeting Ligands:
FA dTAG Targeting Ligands as used herein include, but are not limited to:
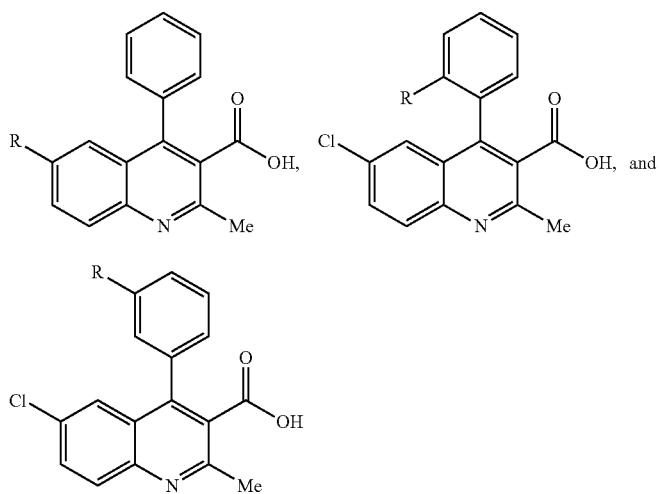
wherein:
R is the point at which the Linker is attached.

TABLE T-continued

RR. FLAP - 5-Lipoxygenase Activating Protein dTAG Targeting Ligands:

FLAP - 5-Lipoxygenase Activating Protein dTAG Targeting Ligands as used herein include, but are not limited to:

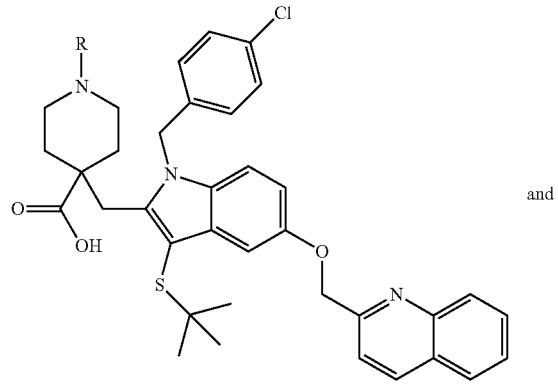 and

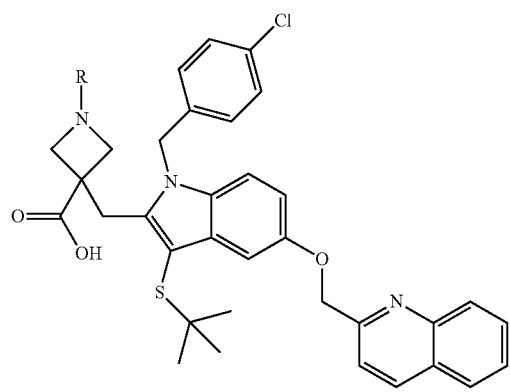

wherein:
R is the point at which the Linker is attached.

SS. HDAC6 Zn Finger Domain dTAG Targeting Ligands:

HDAC6 Zn Finger Domain dTAG Targeting Ligands as used herein include, but are not limited to:

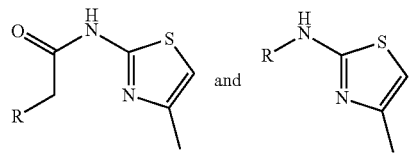

wherein:
R is the point at which the Linker is attached.

TT. Kringle Domain V 4BVV dTAG Targeting Ligands:

Kringle Domain V 4BVV dTAG Targeting used herein include, but are not limited to:

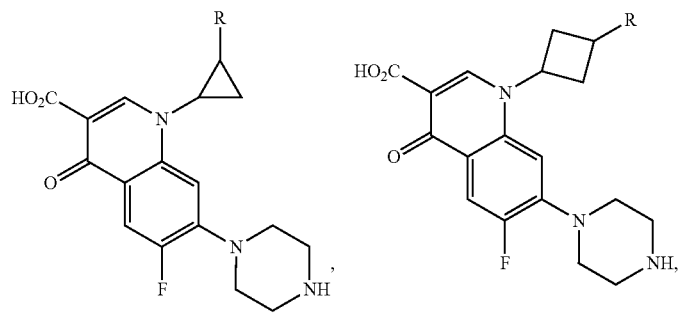

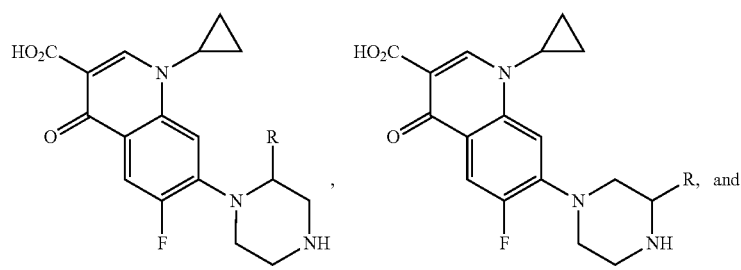
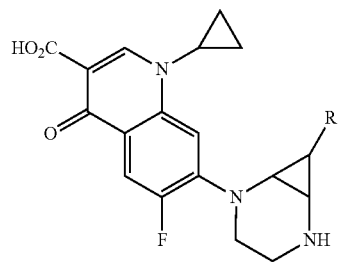
wherein:
R is the point at which the Linker is attached.
UU. Lactoylglutathione Lyase dTAG Targeting Ligands:
Lactoylglutathione Lyase dTAG Targeting Ligands as used herein include, but are not limited to:
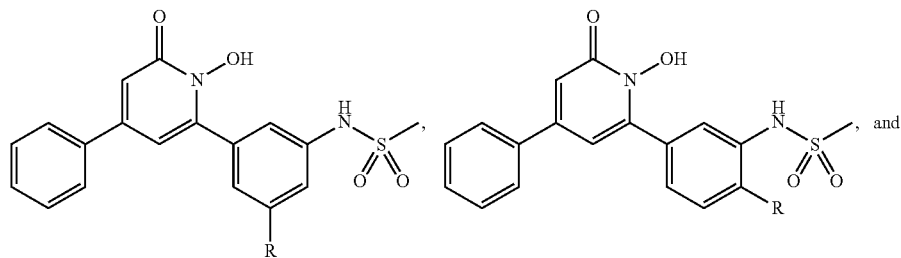
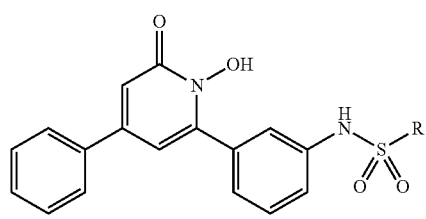
wherein:
R is the point at which the Linker is attached.

TABLE T-continued
VV. mPGES-1 dTAG Targeting Ligands:
mPGES-1 dTAG Targeting Ligands as used herein include, but are not limited to:
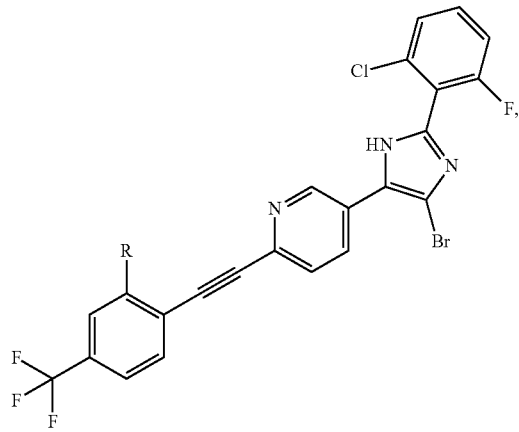
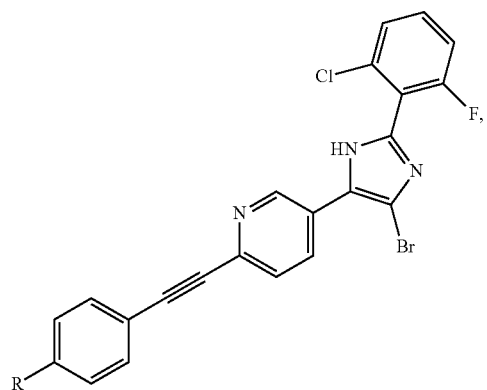
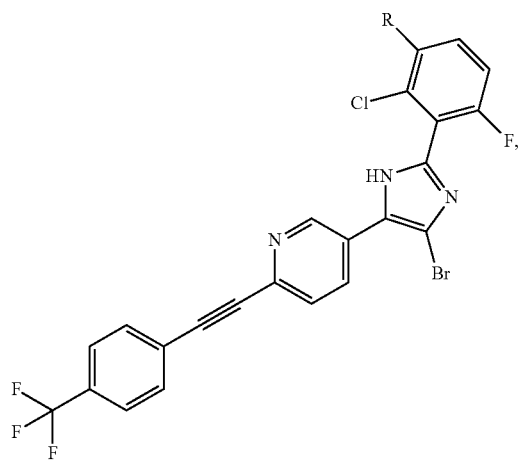

TABLE T-continued
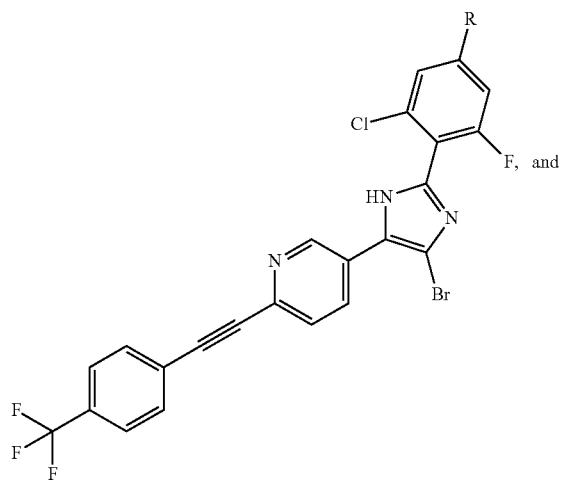
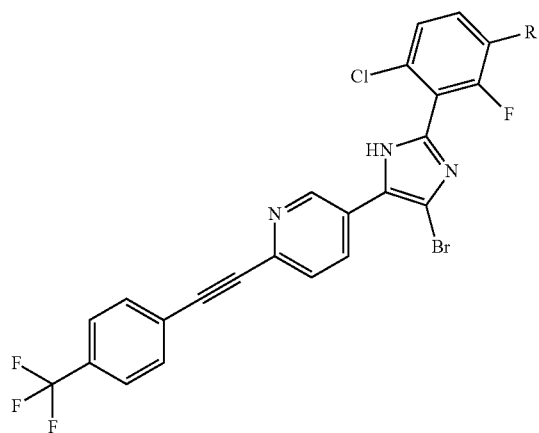
wherein:
R is the point at which the Linker is attached.
WW. MTH1 dTAG Targeting Ligands:
MTH1 dTAG Targeting Ligands as used herein include, but are not limited to:
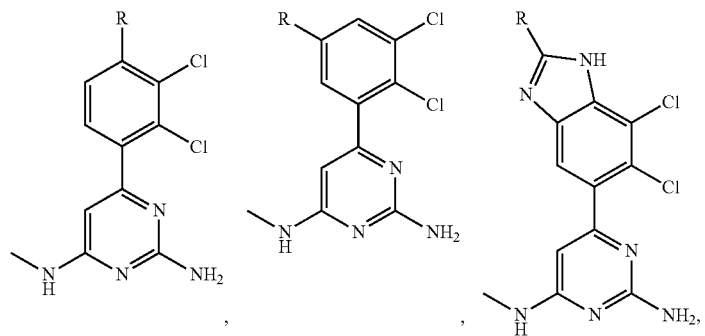

TABLE T-continued
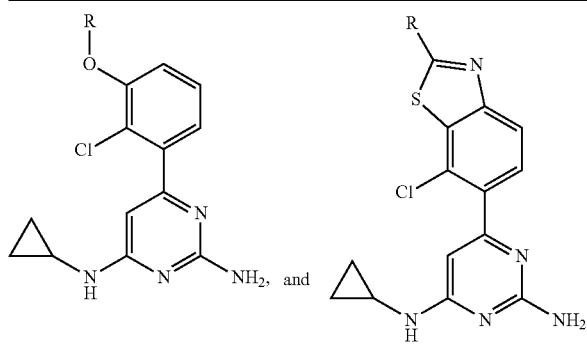
wherein:
R is the point at which the Linker is attached.
XX. PARP14 dTAG Targeting Ligands:
PARP14 dTAG Targeting Ligands as used herein include, but are not limited to:
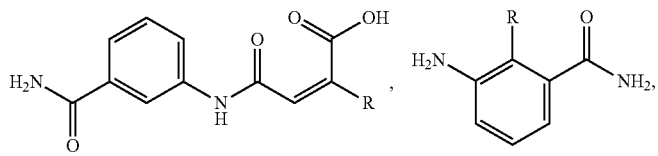
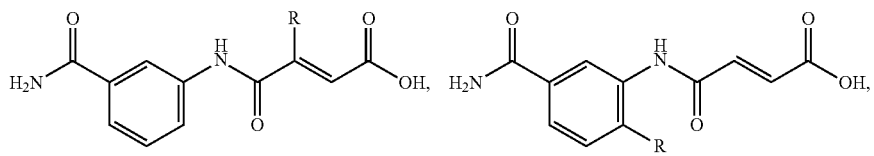
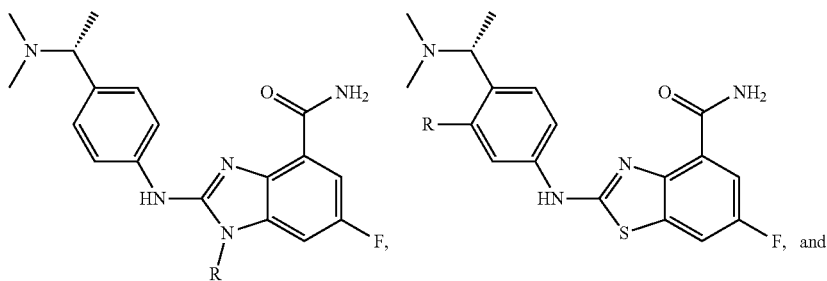
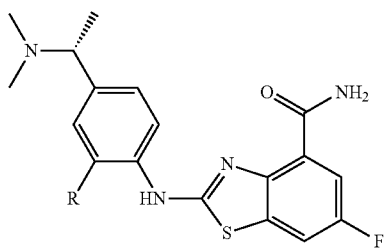
wherein:
R is the point at which the Linker is attached.

TABLE T-continued
YY. PARP15 dTAG Targeting Ligands:
PARP15 dTAG Targeting Ligands as used herein include, but are not limited to:
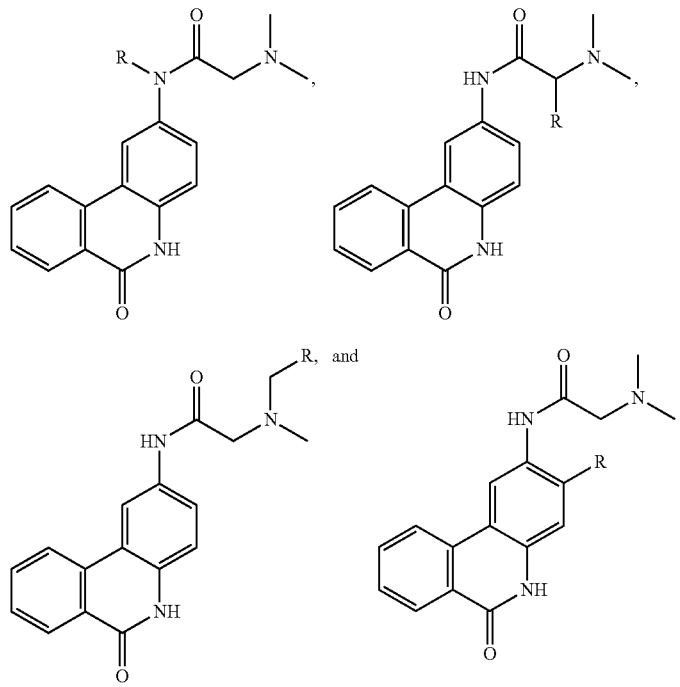
wherein:
R is the point at which the Linker is attached.
ZZ. PDZ domain dTAG Targeting Ligands:
PDZ domain dTAG Targeting Ligands as used herein include, but are not limited to:
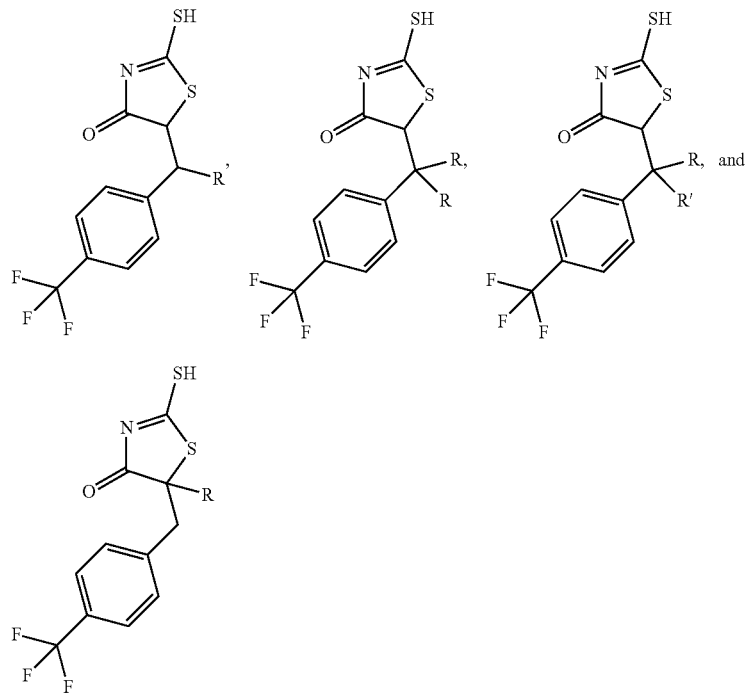
wherein:
R and R' are points at which the Linker(s) are attached.

TABLE T-continued

AAA. PHIP dTAG Targeting Ligands:

PHIP dTAG Targeting Ligands as used herein include, but are not limited to:

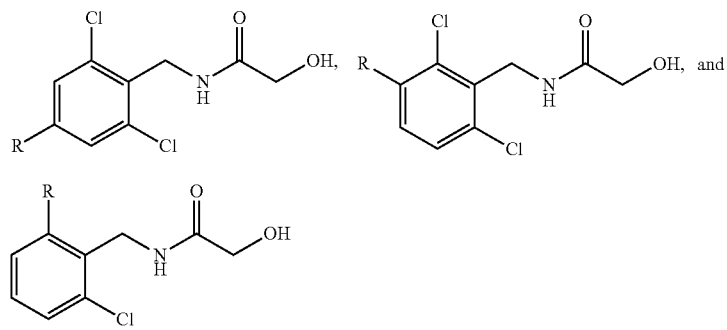

wherein:
R is the point at which the Linker is attached.

BBB. Phospholipase A2 domain dTAG Targeting Ligands:

Phospholipase A2 domain dTAG Targeting Ligands as used herein include, but are not limited to:

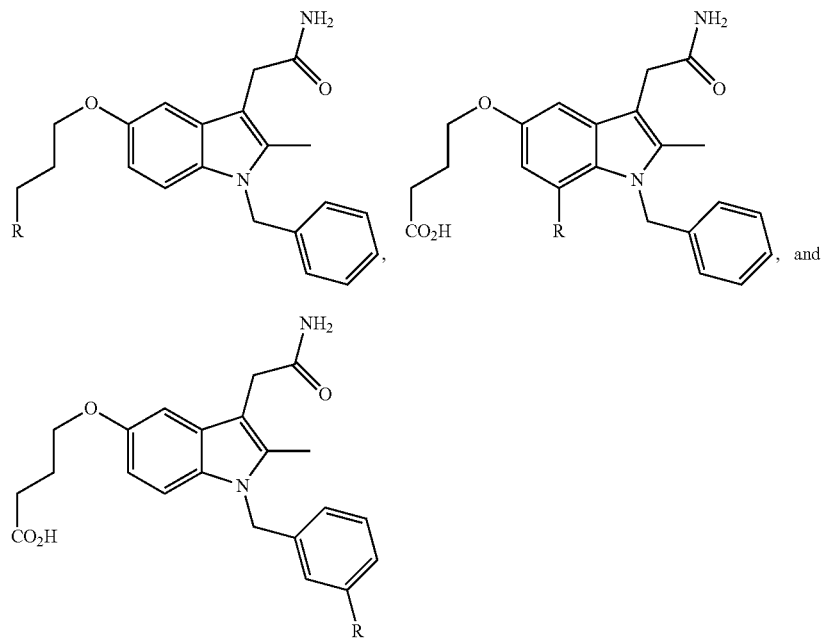

wherein:
R is the point at which the Linker is attached.

CCC. Protein S100-A7 2WOS dTAG Targeting Ligands:

Protein S100-A7 2WOS dTAG Targeting Ligands as used herein include, but are not limited to:

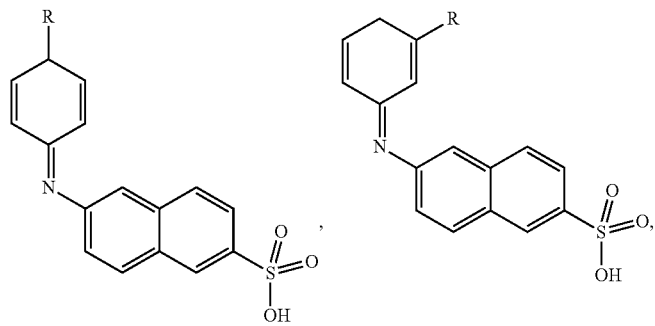

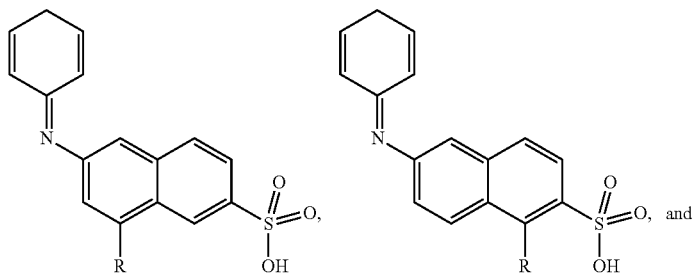
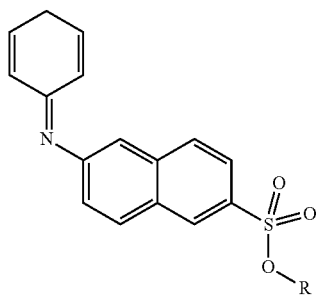
wherein:
R is the point at which the Linker is attached.
DDD. Saposin-B dTAG Targeting Ligands:
Saposin-B dTAG Targeting Ligands as used herein include, but are not limited to:
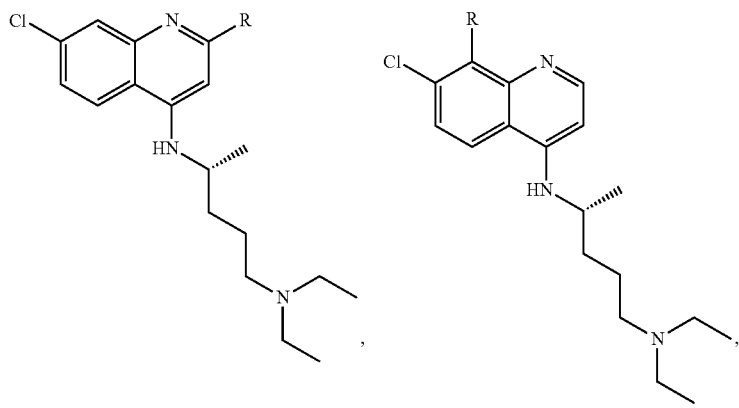
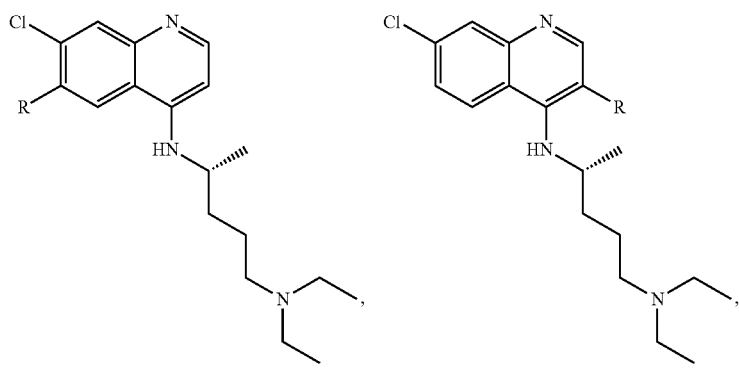

TABLE T-continued
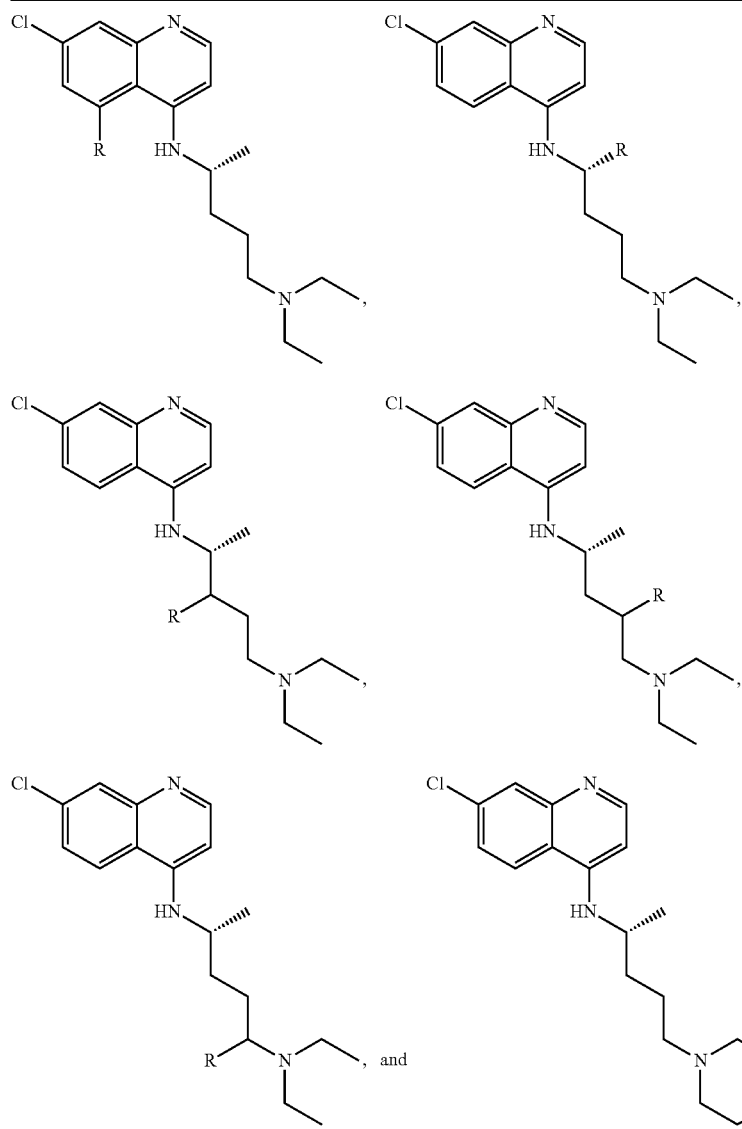
wherein:
R is the point at which the Linker is attached.
EEE. Sec7 dTAG Targeting Ligands:
Sec7 dTAG Targeting Ligands as used herein include, but are not limited to:

TABLE T-continued
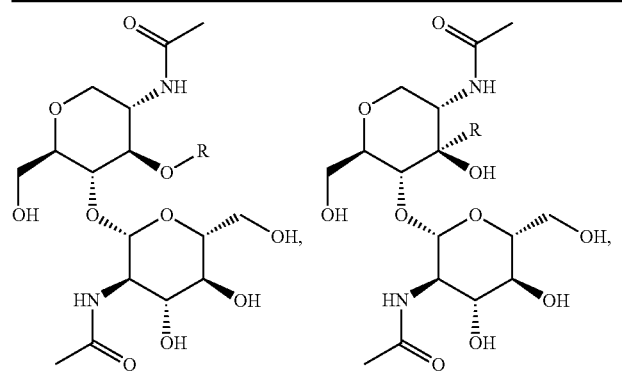
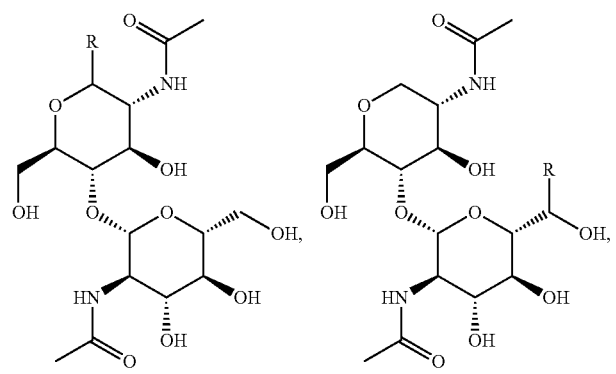
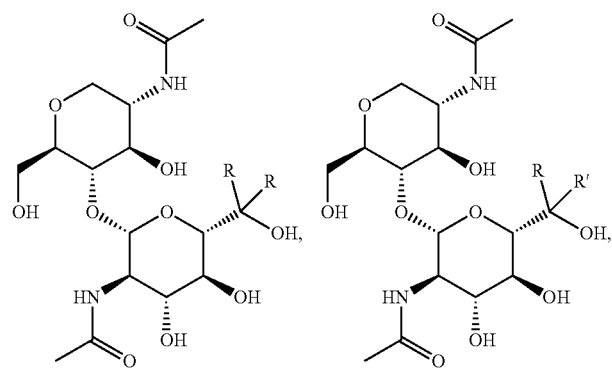
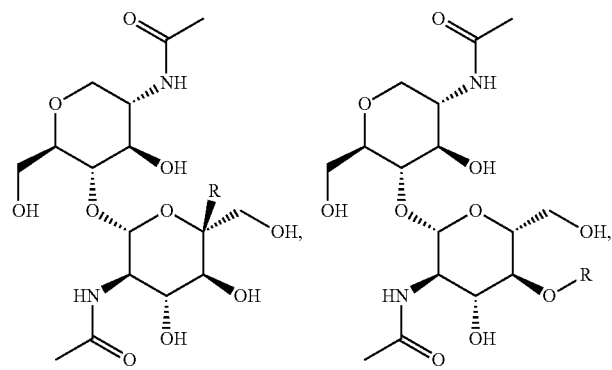

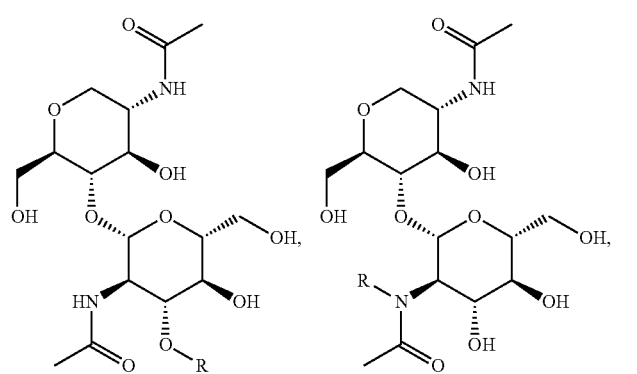
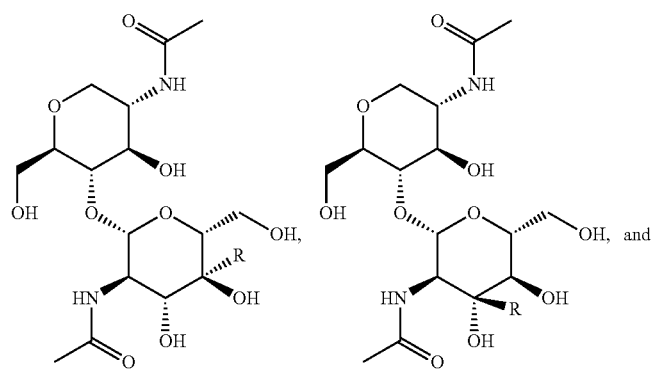
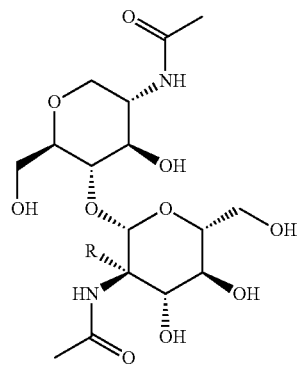
wherein:
R is the point at which the Linker is attached.
FFF. SH2 domain of pp60 Src dTAG Targeting Ligands:
SH2 domain of pp60 Src dTAG Targeting Ligands as used herein include, but are not limited to:
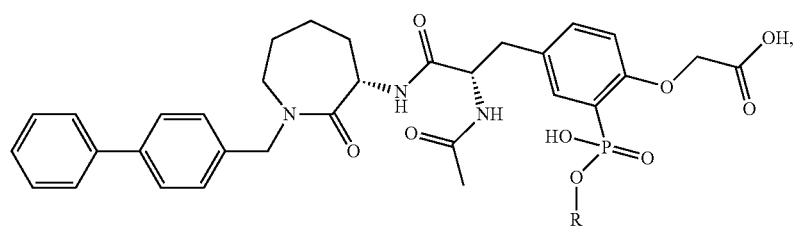

TABLE T-continued
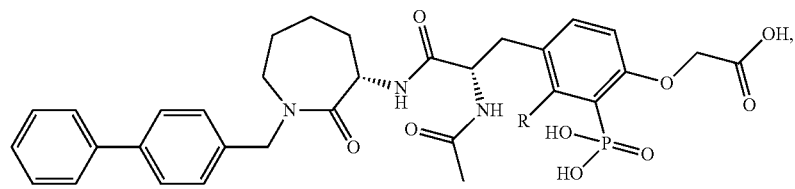
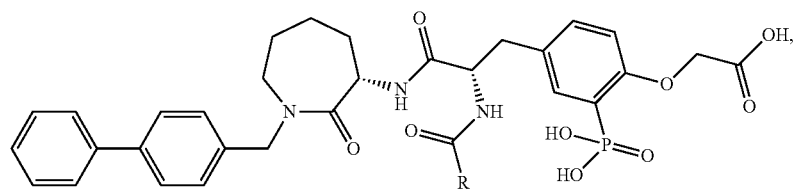
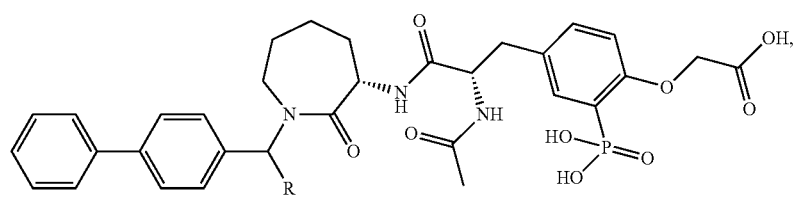
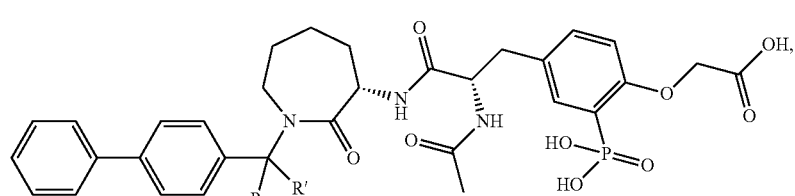
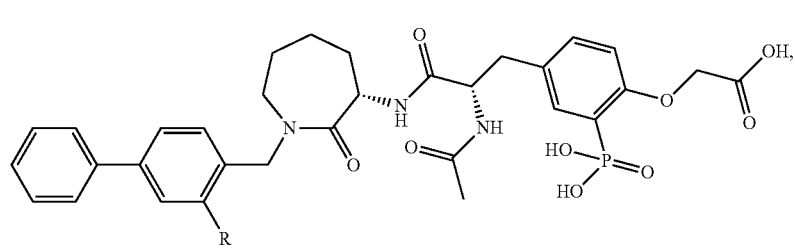
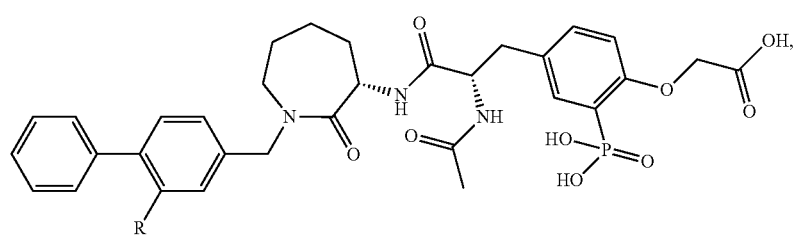
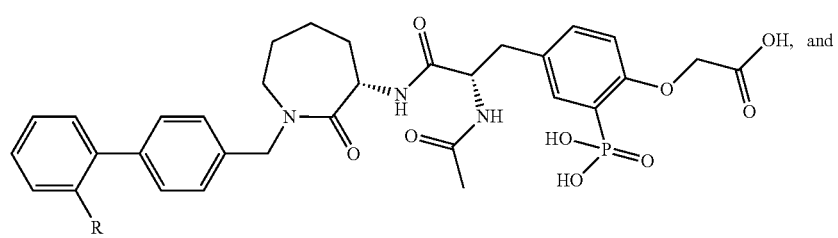

TABLE T-continued
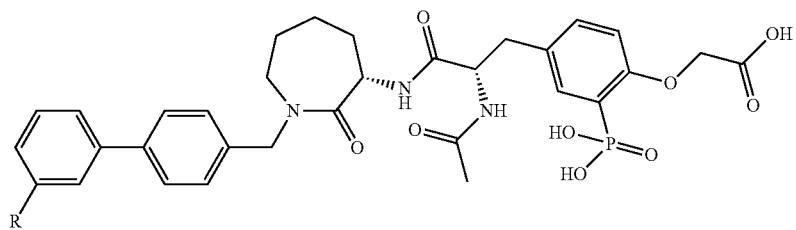
wherein:
R is the point at which the Linker is attached.
GGG. Tank1 dTAG Targeting Ligands:
Tank1 dTAG Targeting Ligands as used herein include, but are not limited to:
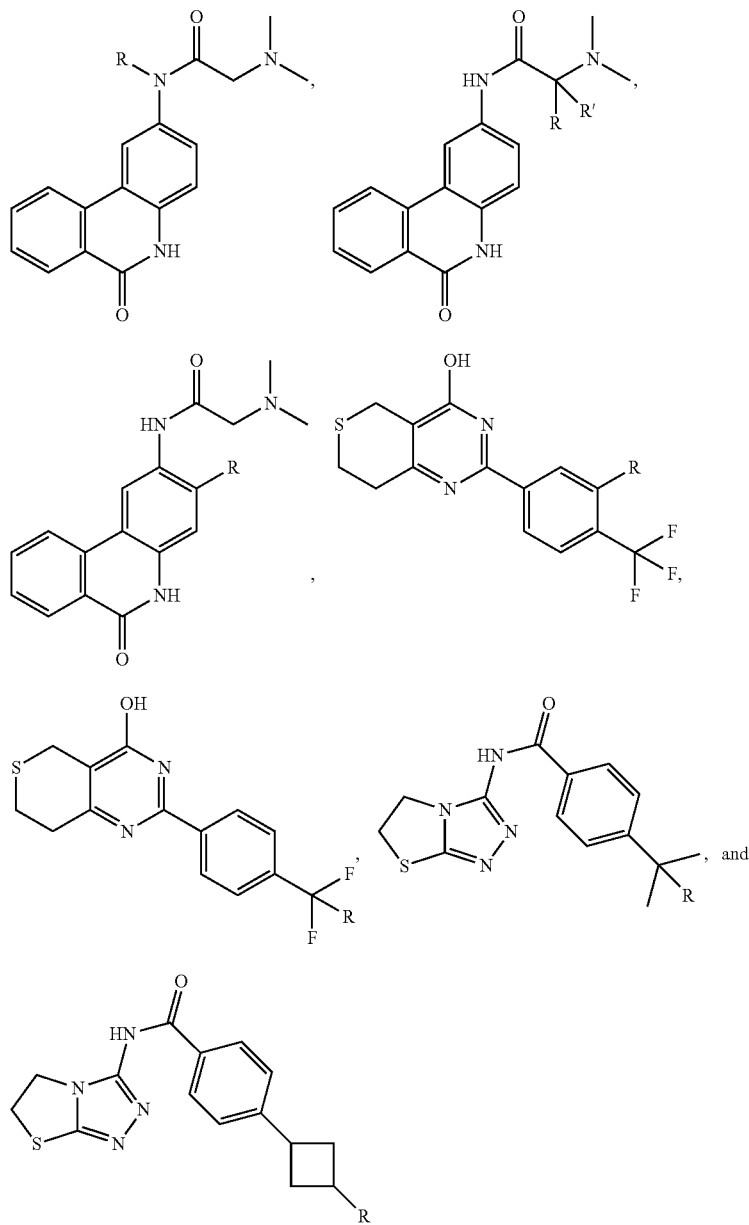
wherein:
R is the point at which the Linker is attached.

HHH. Ubc9 SUMO E2 ligase SF6D dTAG Targeting Ligands:
Ubc9 SUMO E2 ligase SF6D dTAG Targeting Ligands as used herein include, but are not limited to:
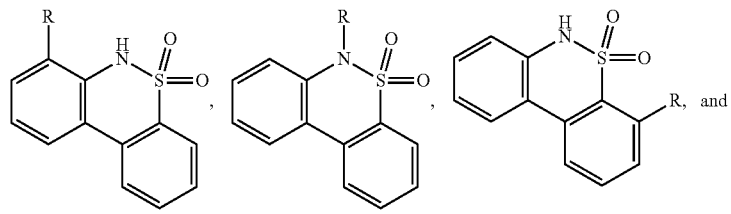, and
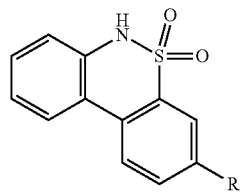
wherein:
R is the point at which the Linker is attached.
III. Src (c-Src) dTAG Targeting Ligands:
Src dTAG Targeting Ligands as used herein include, but are not limited to:
1. Src Targeting Ligands including AP23464:
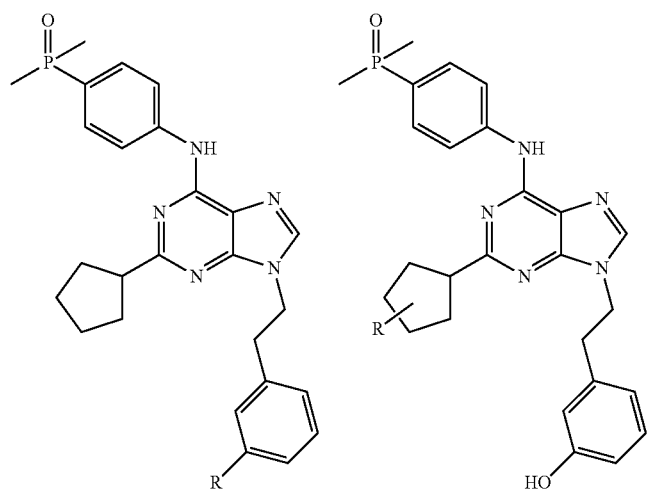

TABLE T-continued
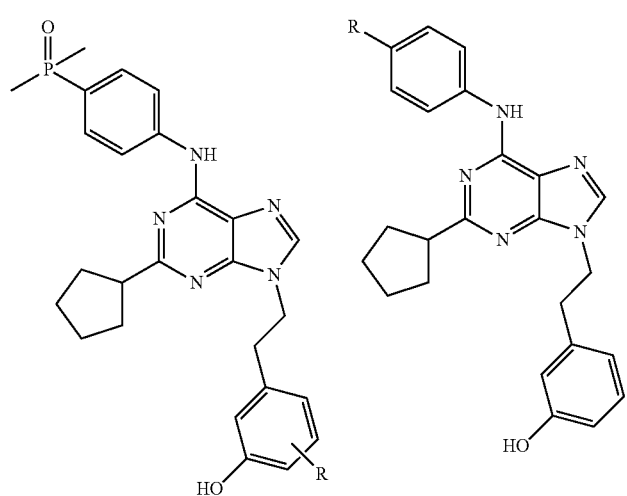
wherein:
R is the point at which the Linker is attached.
2. Src-AS1 and/or Src AS2 Targeting Ligands including:
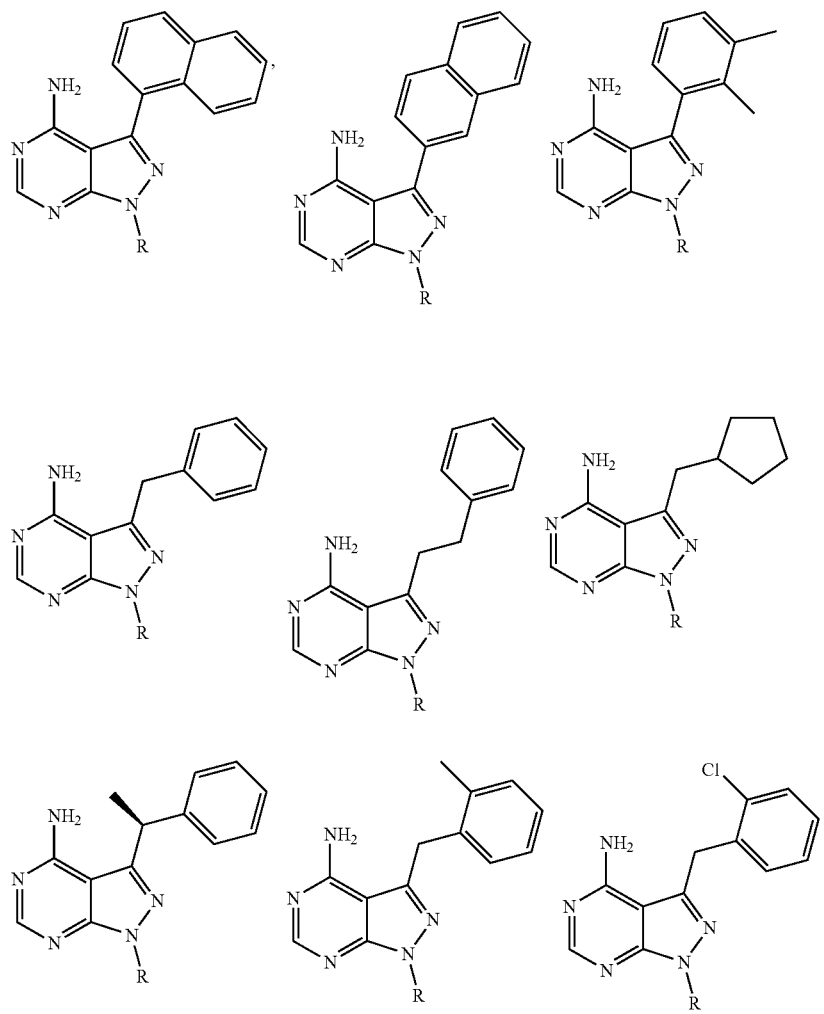

TABLE T-continued
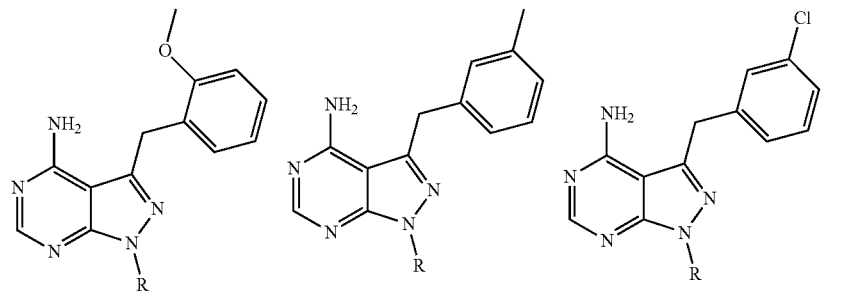
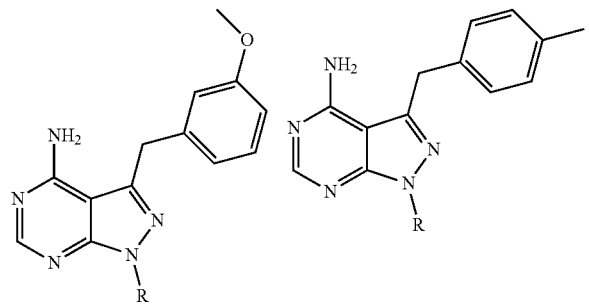
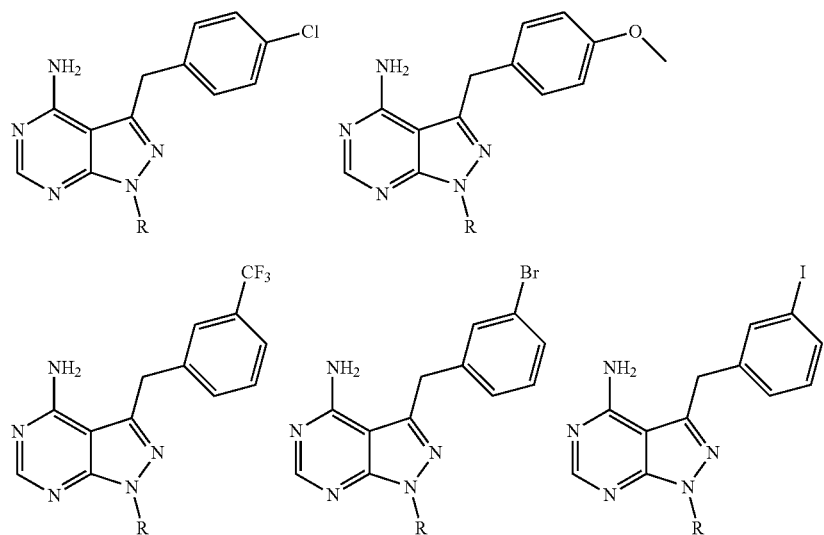
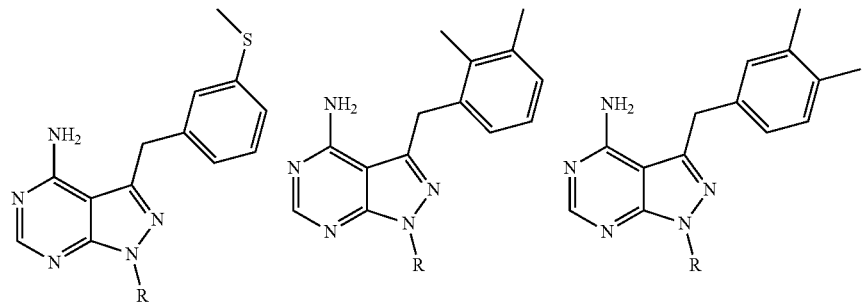

TABLE T-continued
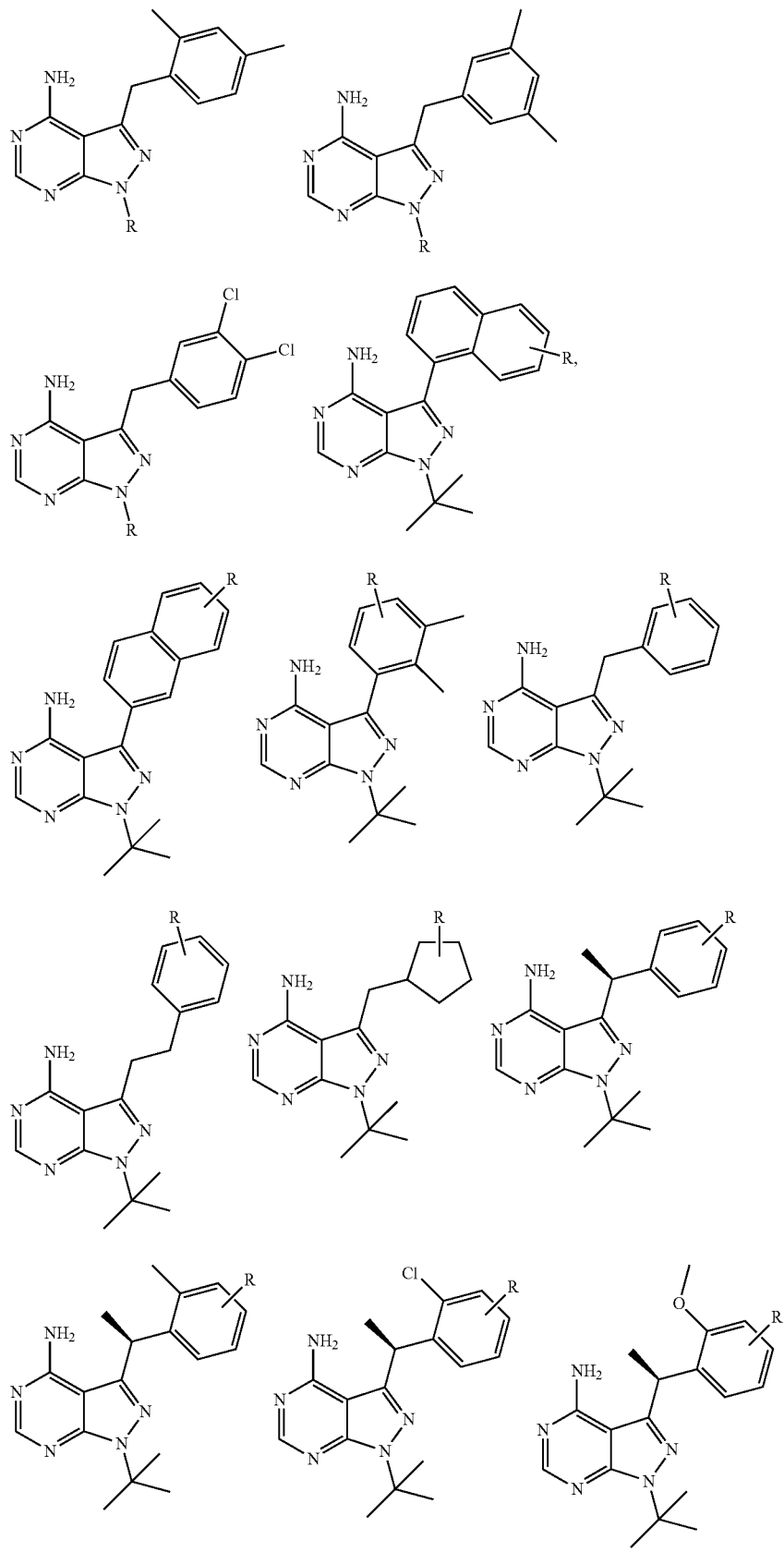

TABLE T-continued
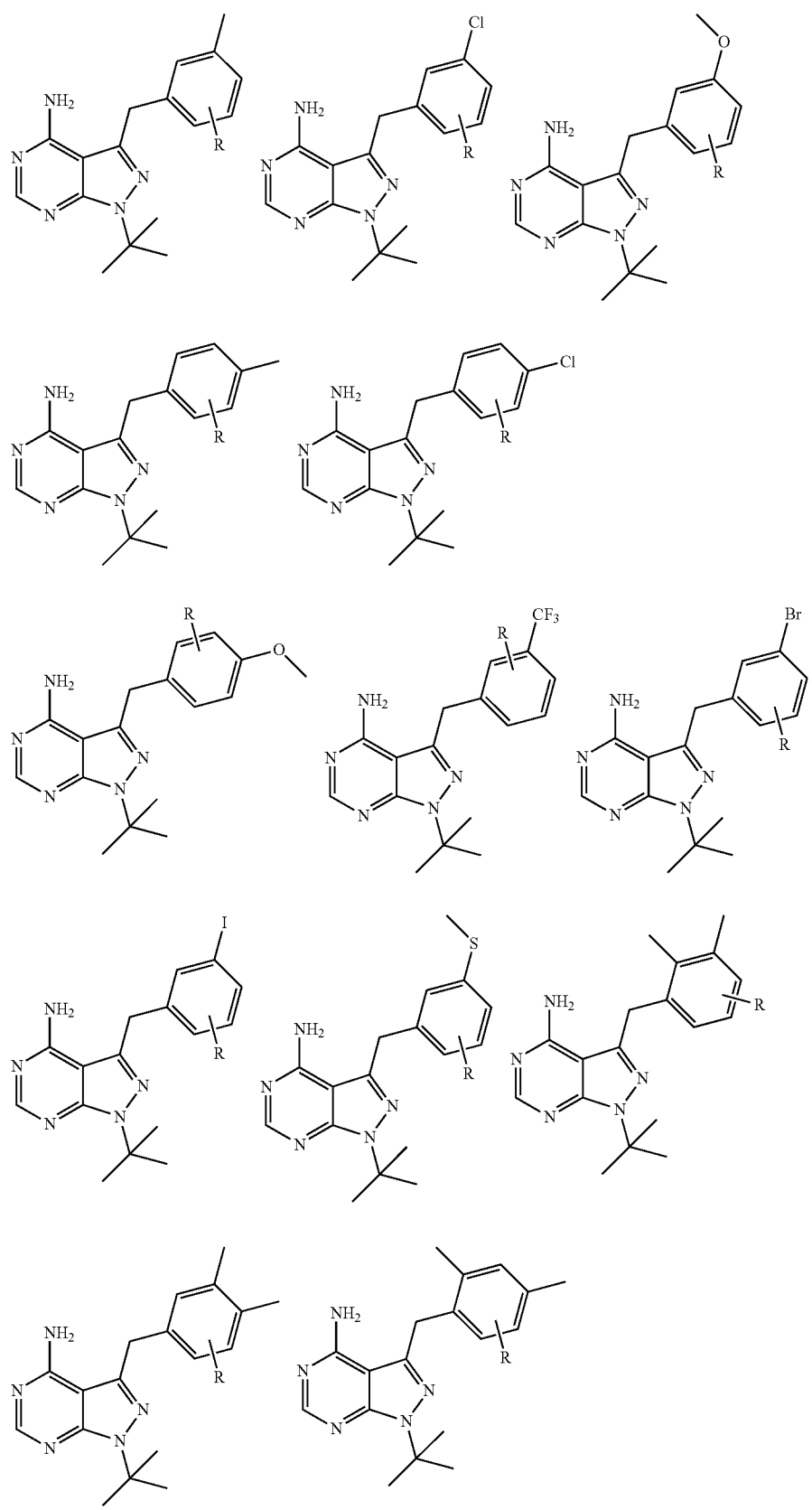

TABLE T-continued
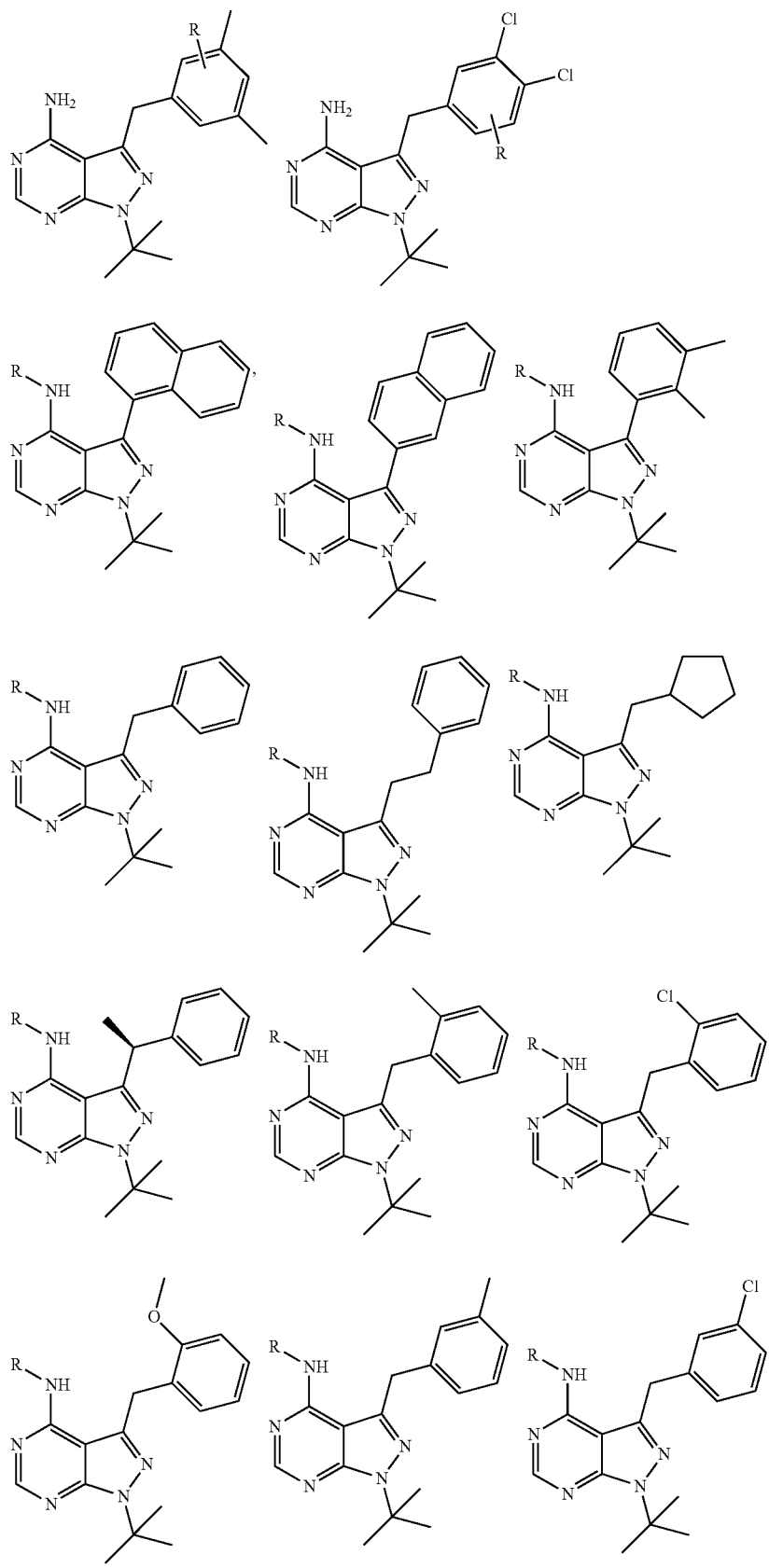

TABLE T-continued
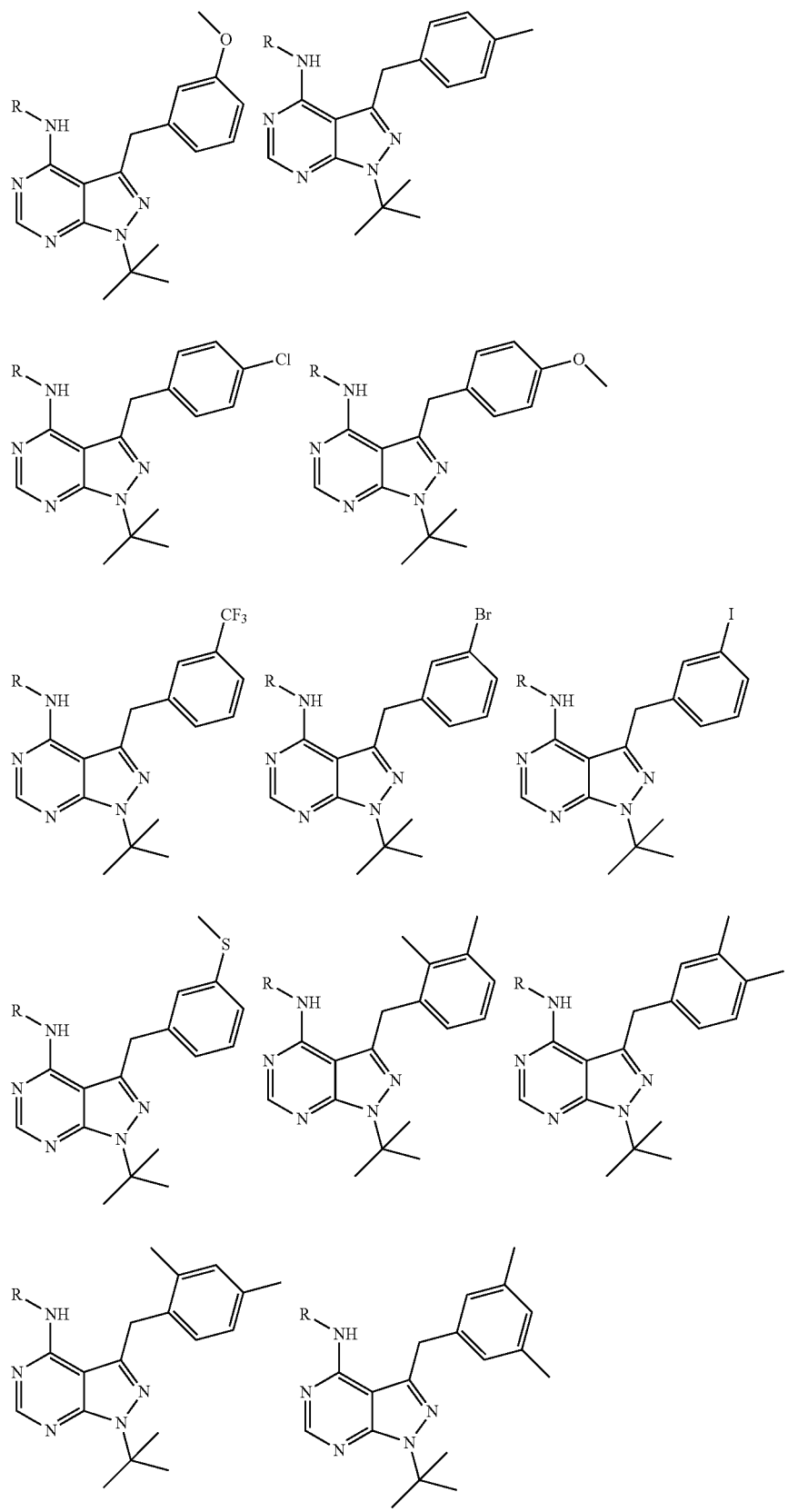

TABLE T-continued

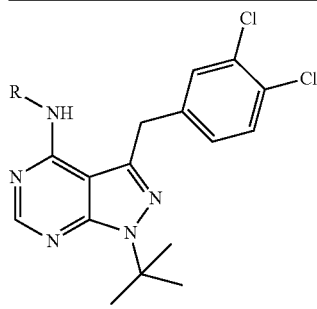

wherein:
R is the point at which the Linker is attached.

JJJ. JAK3 dTAG Targeting Ligands:

JAK3 dTAG Targeting Ligands as used herein include, but are not limited to:
1. Targeting Ligands that target JAK3, including Tofacitinib:

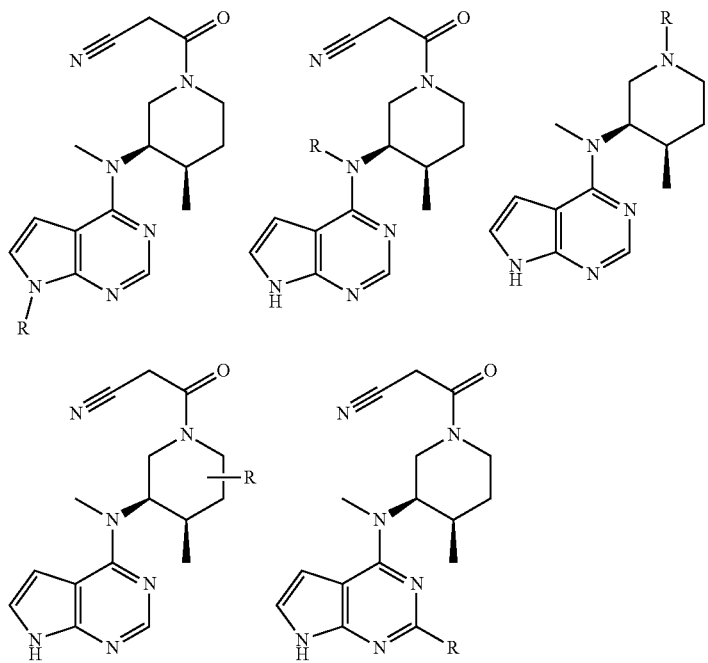

wherein:
R is the point at which the Linker is attached.

KKK. Abl dTAG Targeting Ligands:

Abl dTAG Targeting Ligands as used herein include, but are not limited to:
1. Targeting Ligands that target Abl, including Tofacitinib and Ponatinib:

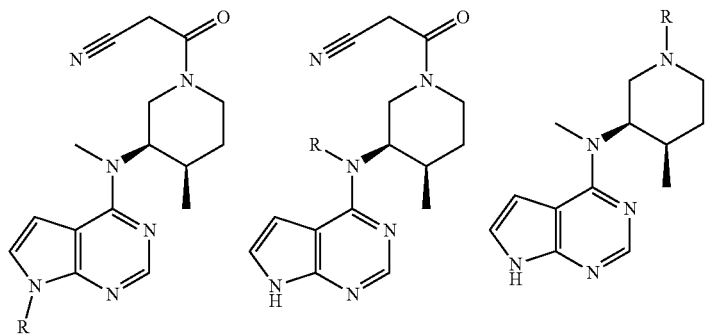

TABLE T-continued
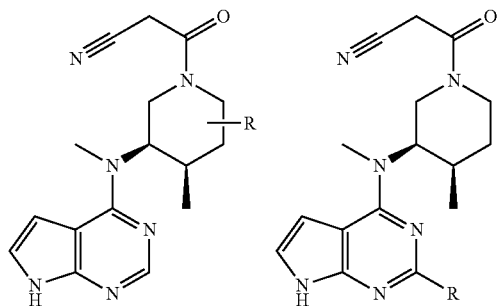
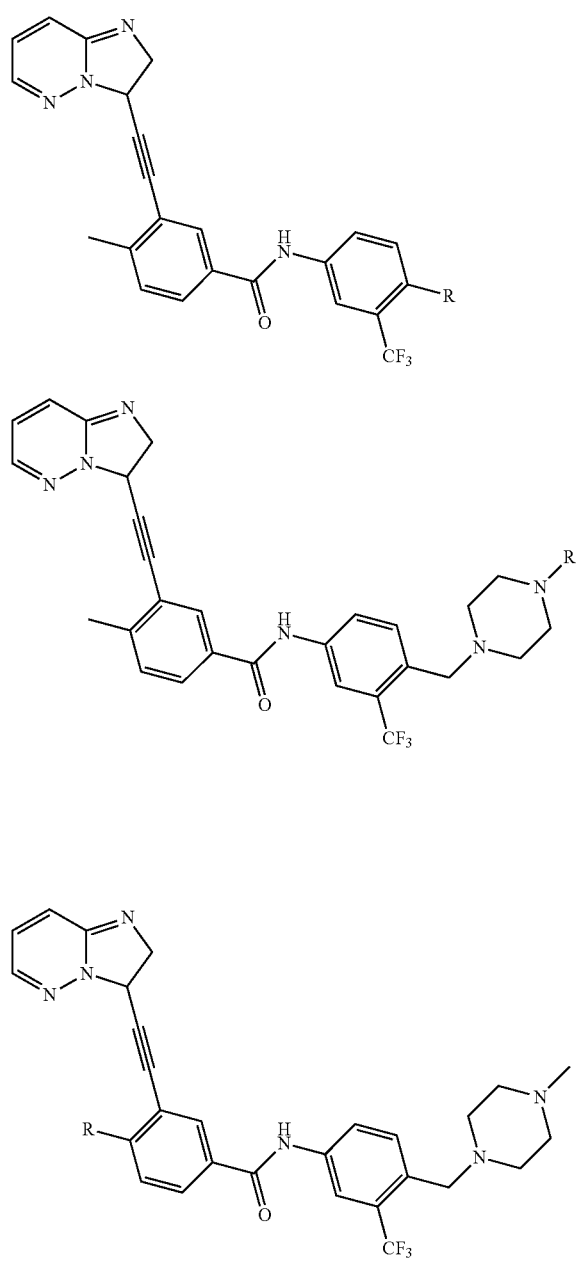

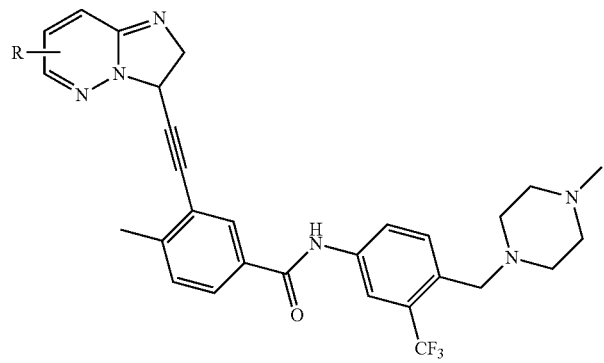
wherein:
R is the point at which the Linker is attached.
LLL. MEK1 dTAG Targeting Ligands:
MEK1 dTAG Targeting Ligands as used herein include, but are not limited to:
1. Targeting Ligands that target MEK1, including PD318088, Trametinib, and G-573:
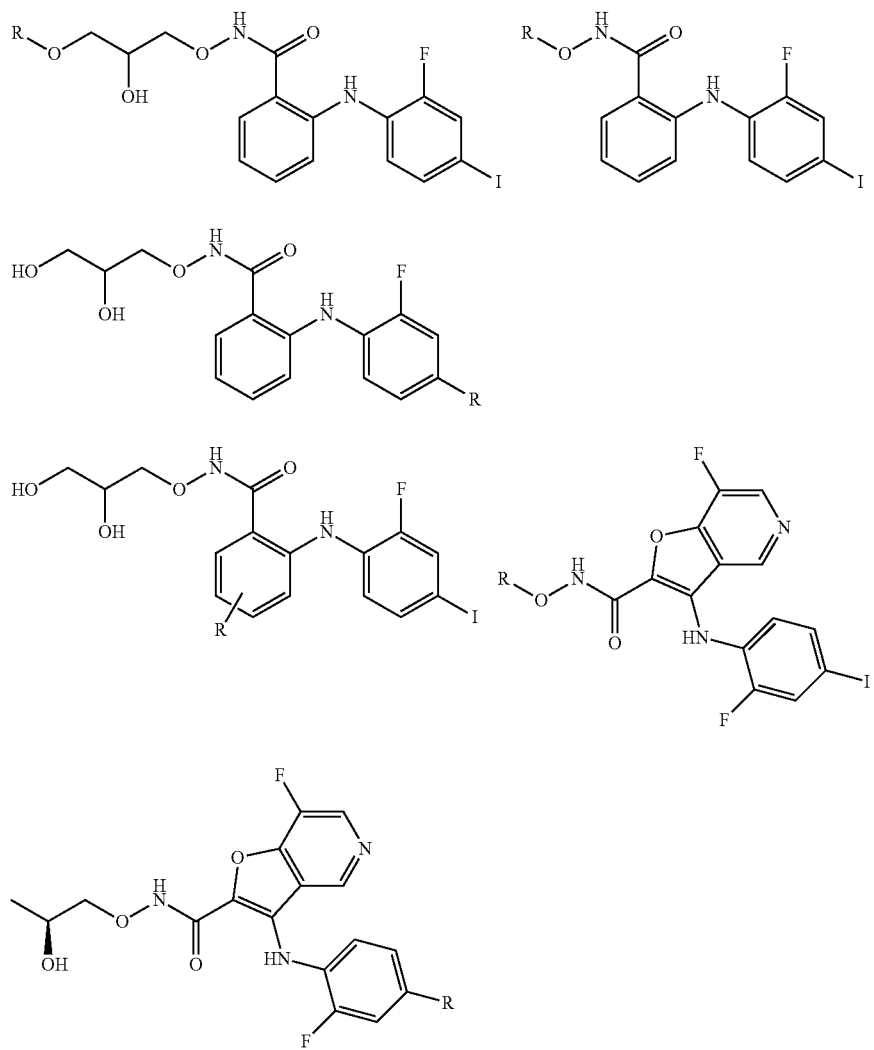

TABLE T-continued
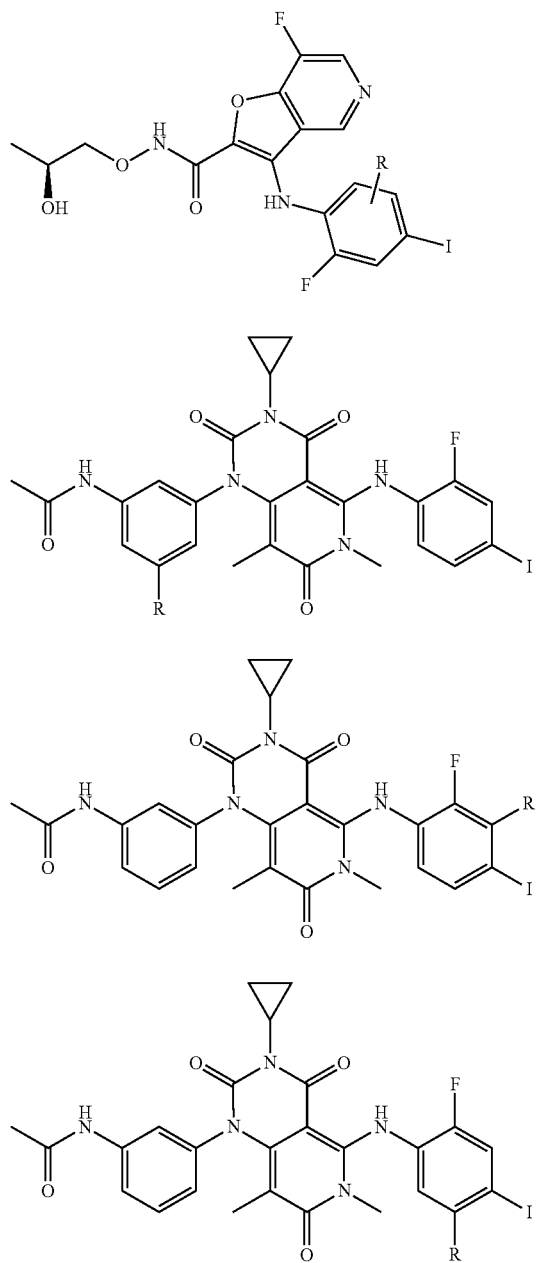
wherein:
R is the point at which the Linker is attached.
MMM. KIT dTAG Targeting Ligands:
KIT dTAG Targeting Ligands as used herein include, but are not limited to:
1. Targeting Ligands that target KIT, including Regorafenib:
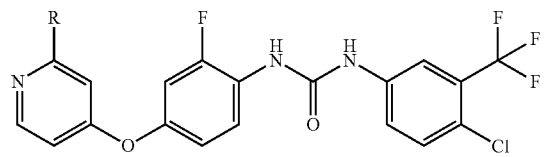

TABLE T-continued

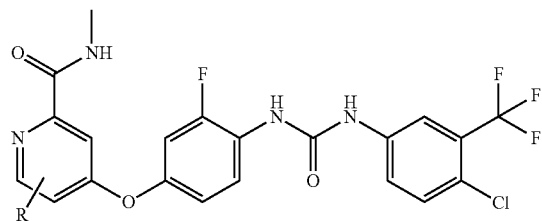

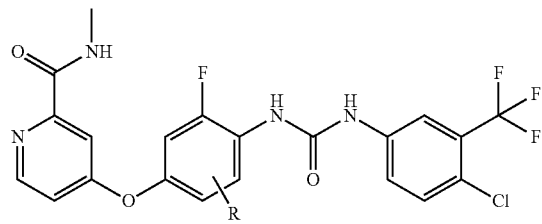

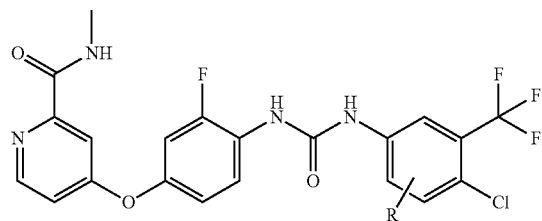

wherein:
R is the point at which the Linker is attached.

NNN. HIV Reverse Transcriptase dTAG Targeting Ligands:

HIV Reverse Transcriptase dTAG Targeting Ligands as used herein include, but are not limited to:
1. Targeting Ligands that target HIV Reverse Transcriptase, including Efavirenz, Tenofovir, Emtricitabine, Ritonavir, Raltegravir, and Atazanavir:

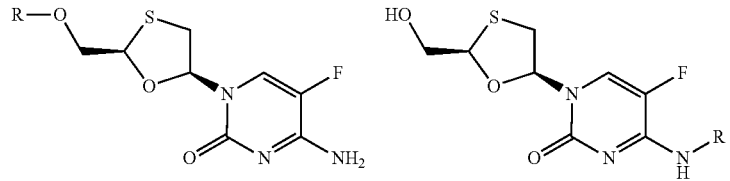

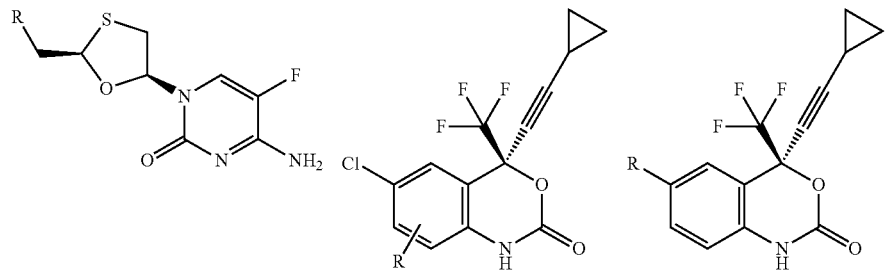

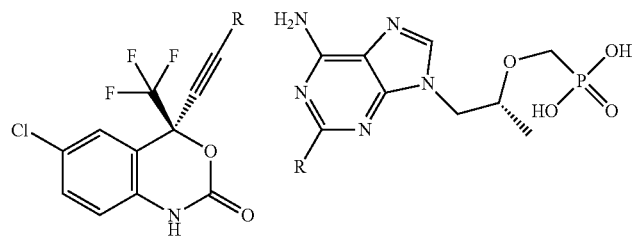

TABLE T-continued
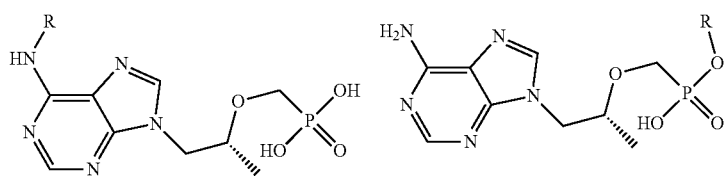
wherein:
R is the point at which the Linker is attached.
OOO. HIV Protease dTAG Targeting Ligands:
HIV Protease dTAG Targeting Ligands as used herein include, but are not limited to:
1. Targeting Ligands that target HIV Protease, including Ritonavir, Raltegravir, and Atazanavir:
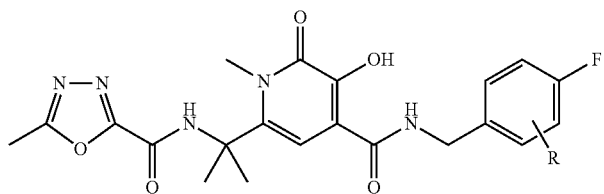
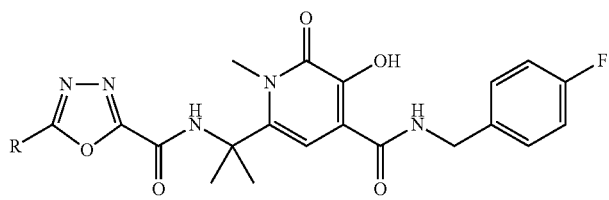
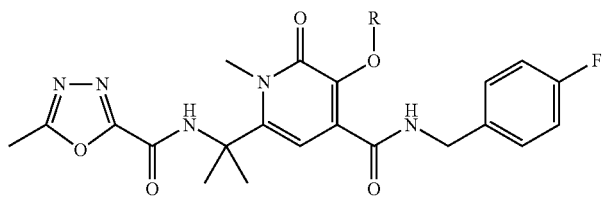
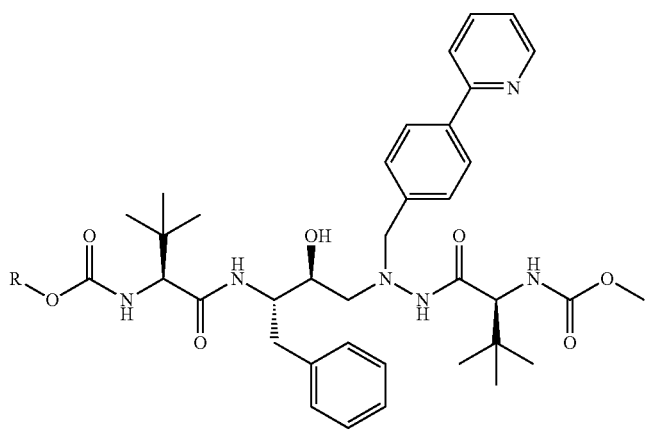

TABLE T-continued
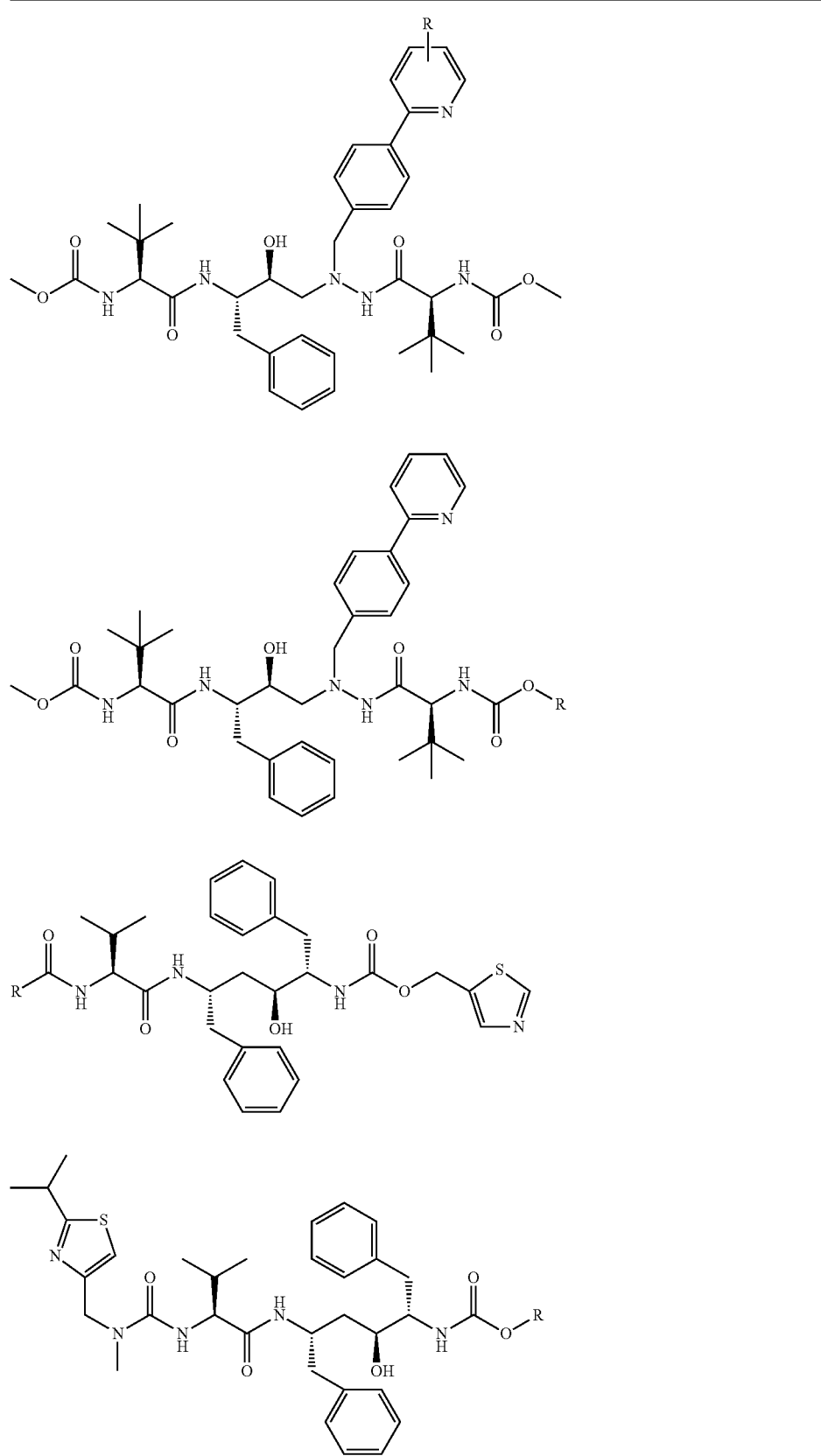

TABLE T-continued

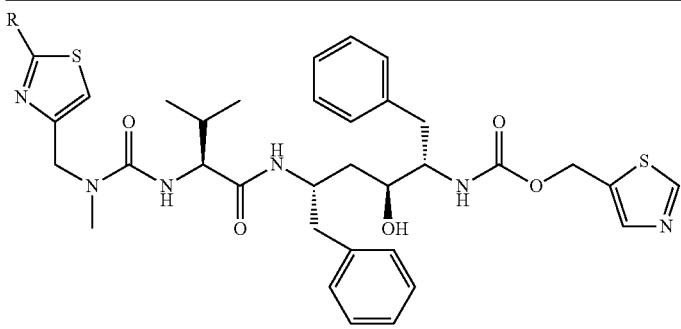

wherein:
R is the point at which the Linker is attached.

In one embodiment any of the above dTAG Targeting Ligands of Table T is used to target any dTAG described herein.

Many dTag targeting ligands are capable of binding to more than one dTAG, for example, Afatinib binds to the EGFR, the ErbB2, and the ErbB4 protein. This allows for dual attack of many proteins, as exemplified in Table Z. In one embodiment, the dTAG targeting ligand is selected from the "dTAG targeting ligand" column in Table Z and the dTAG is selected from the corresponding "dTAG" row.

TABLE Z dTAG Targeting Ligands and corresponding dTAG

| dTAG Targeting Ligand | dTAG |
|---|---|
| Afatinib | EGFR, ErbB2/4 |

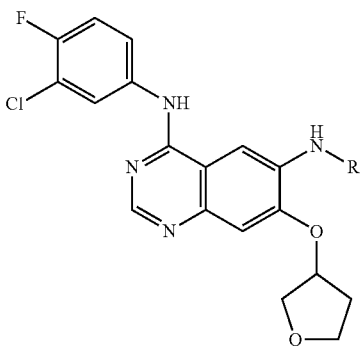
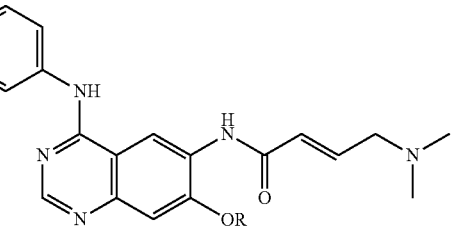
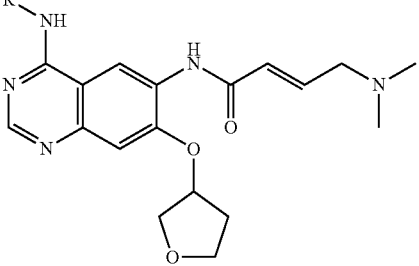

TABLE Z-continued
dTAG Targeting Ligands and corresponding dTAG
| dTAG Targeting Ligand | dTAG |
|---|---|
| 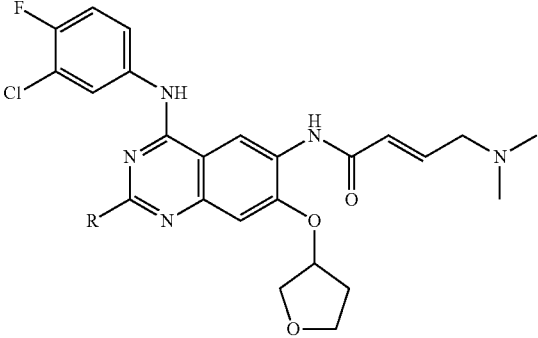<br>Axitinib | VEGFR1/2/3, PDGFRβ, Kit |
| 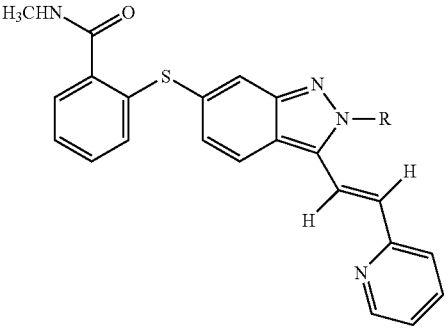<br>Bosutinib | BCR-Abl, Src, Lyn, Hck |
| 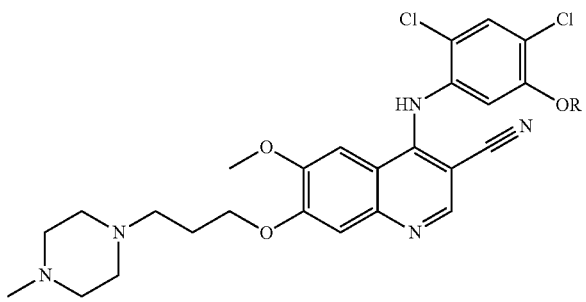 | |

TABLE Z-continued
dTAG Targeting Ligands and corresponding dTAG
| dTAG Targeting Ligand | dTAG |
|---|---|
| 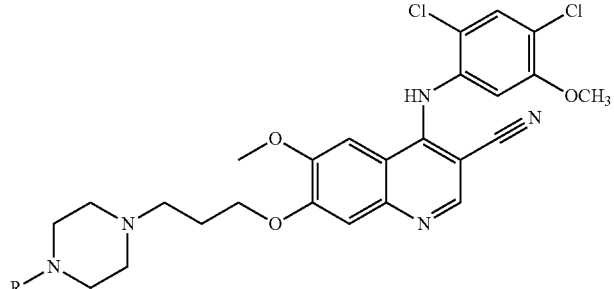 | |
| 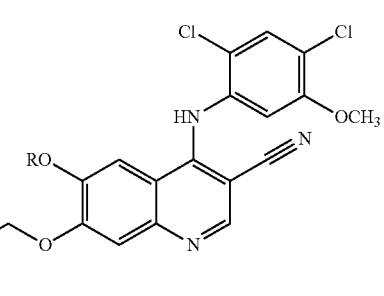<br>Cabozantinib | RET, c-Met, VEGFR1/2/3, Kit, TrkB, Flt3, Axl, Tie2 |
| 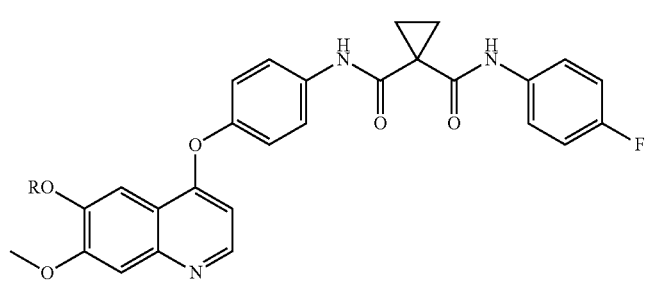 | |
| 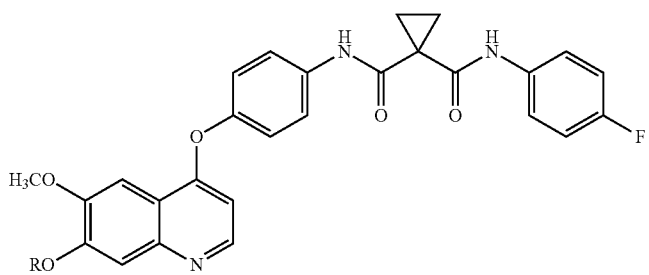 | |
| 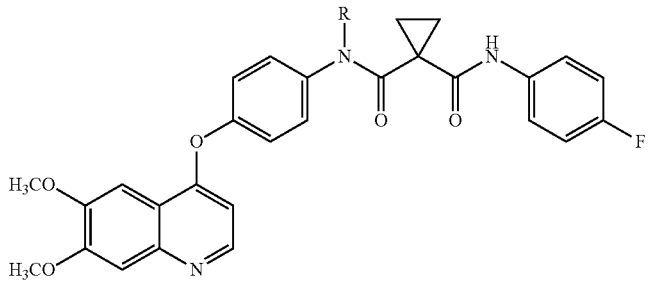 | |

TABLE Z-continued
dTAG Targeting Ligands and corresponding dTAG
| dTAG Targeting Ligand | dTAG |
|---|---|
| 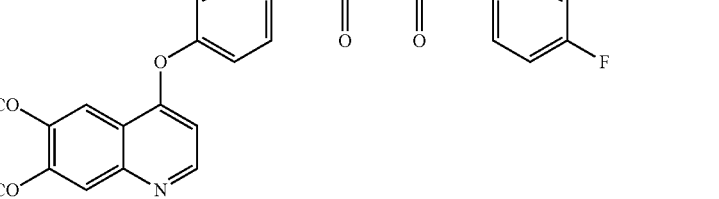<br>Ceritinib | ALK, IGF-1R, InsR, ROS1 |
| 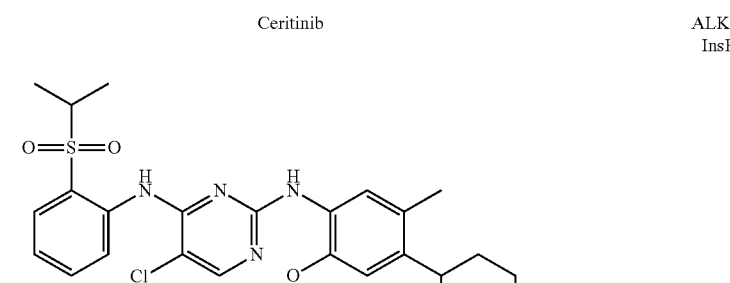<br>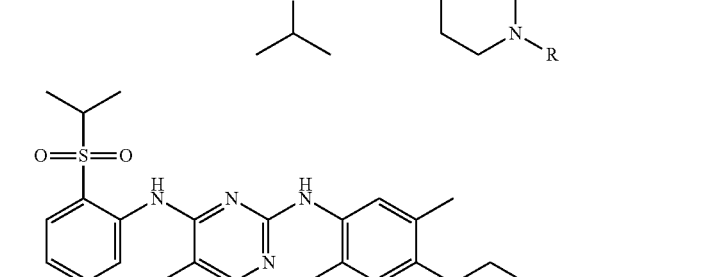<br>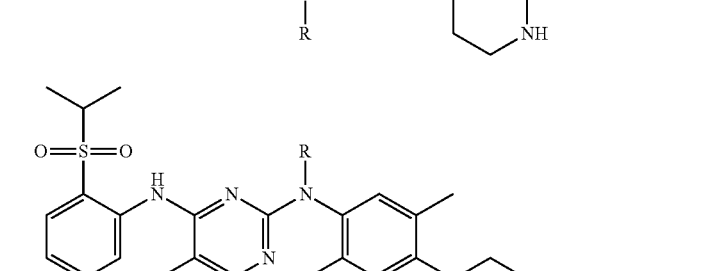<br>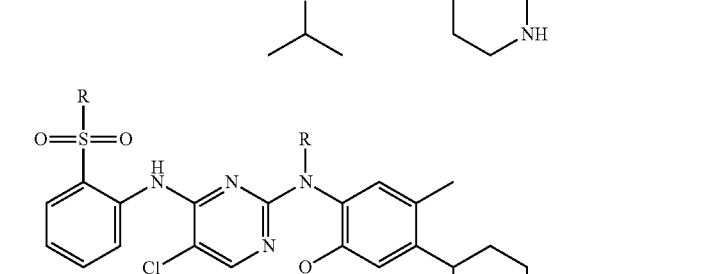<br>Crizotinib | ALK, c-Met, (HGFR), ROS1, MST1R |

TABLE Z-continued
dTAG Targeting Ligands and corresponding dTAG
| dTAG Targeting Ligand | dTAG |
|---|---|
| 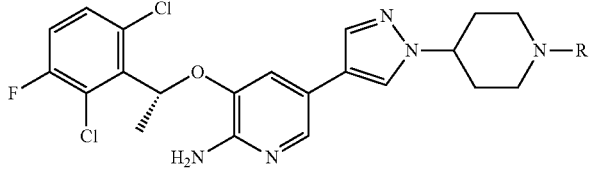 Dabrafenib | B-Raf |
| 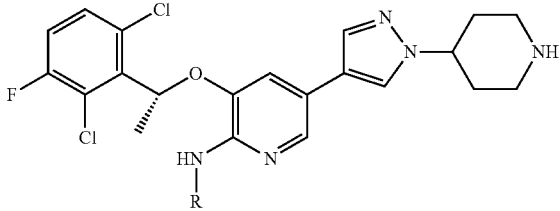 Dasatinib | BCR-Abl, Src, Lck, Lyn, Yes, Fyn, Kit, EphA2, PDGFRβ |
| 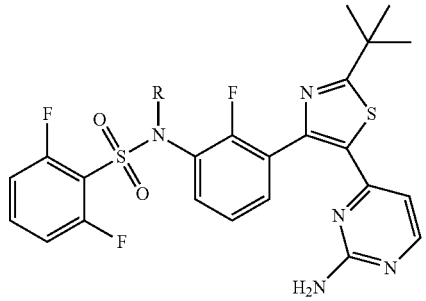 | |

TABLE Z-continued dTAG Targeting Ligands and corresponding dTAG

| dTAG Targeting Ligand | dTAG |
|---|---|
| Erlotinib | EGFR |

TABLE Z-continued dTAG Targeting Ligands and corresponding dTAG

| dTAG Targeting Ligand | dTAG |
|---|---|
| Everolimus | HER2- breast cancer, PNET, RCC, RAML, SEGA |

TABLE Z-continued dTAG Targeting Ligands and corresponding dTAG

| dTAG Targeting Ligand | dTAG |
|---|---|

TABLE Z-continued

| dTAG Targeting Ligands and corresponding dTAG | |
|---|---|
| dTAG Targeting Ligand | dTAG |
| Gefitinib | EGFR, PDGFR |
| Ibrutinib | BTK |
| Imatinib | BCR-Abl, Kit, PDGFR |

TABLE Z-continued dTAG Targeting Ligands and corresponding dTAG

| dTAG Targeting Ligand | dTAG |
|---|---|
| Lapatinib | EGFR, ErbB2 |
| Lenvatinib | VEGFR1/2/3, FGFR1/2/3/4, PDGFRα, Kit, RET |

TABLE Z-continued

| dTAG Targeting Ligands and corresponding dTAG | |
|---|---|
| dTAG Targeting Ligand | dTAG |
| (structure) | |
| (structure) | |
| (structure) | |
| Nilotinib (structure) | BCR-Abl, PDGFR, DDR1 |
| (structure) | |

TABLE Z-continued dTAG Targeting Ligands and corresponding dTAG

| dTAG Targeting Ligand | dTAG |
|---|---|
| Nintedanib | FGFR1/2/3, Flt3, Lck, PDGFRα/β, VEGFR1/2/3 |

TABLE Z-continued
dTAG Targeting Ligands and corresponding dTAG
| dTAG Targeting Ligand | dTAG |
|---|---|
| 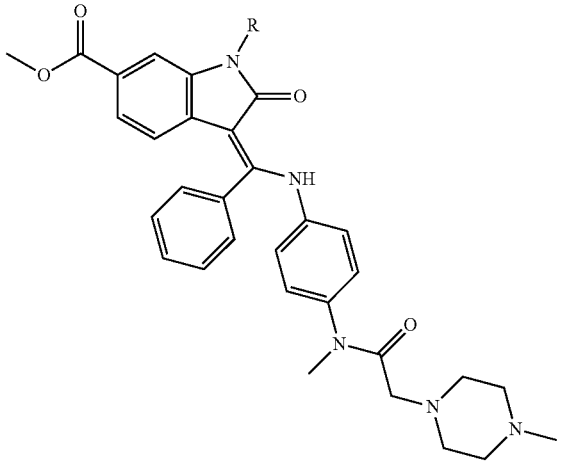 | |
| 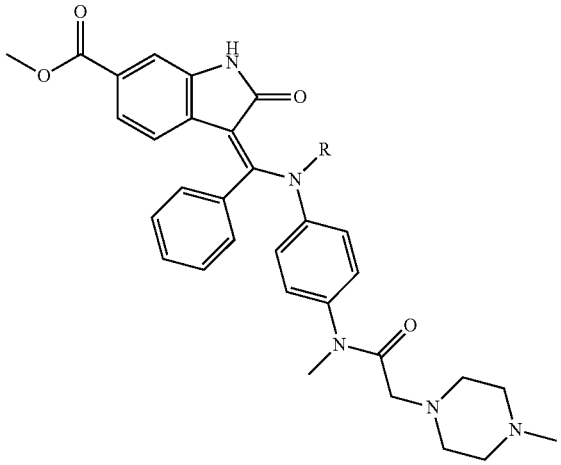 | |
| 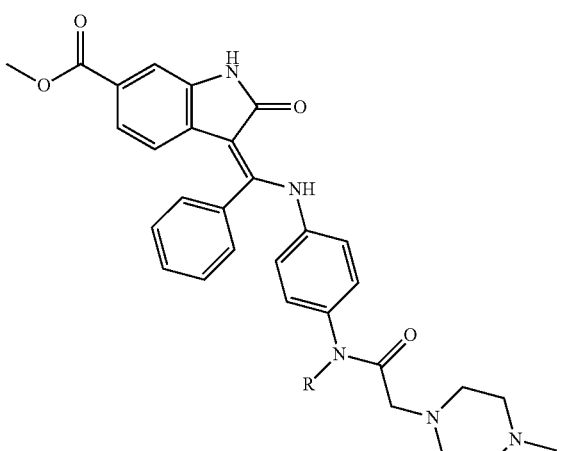 | |

TABLE Z-continued
dTAG Targeting Ligands and corresponding dTAG
| dTAG Targeting Ligand | dTAG |
|---|---|
| 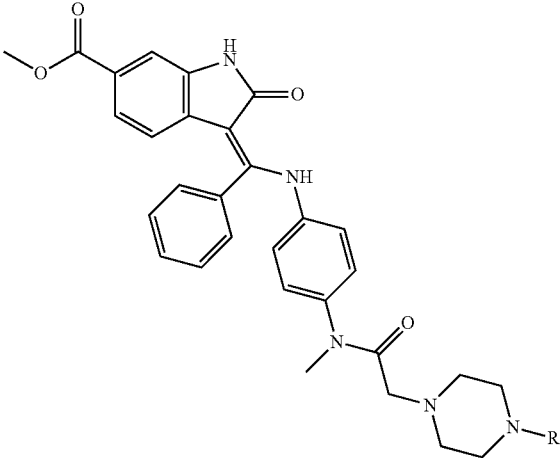 Palbociclib | CDK4/6 |
| 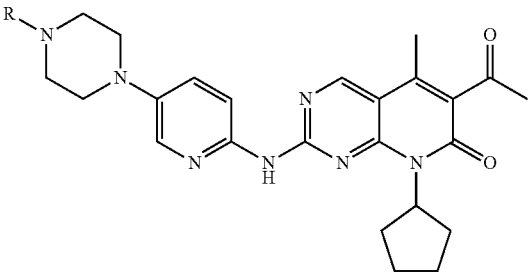 | |
| 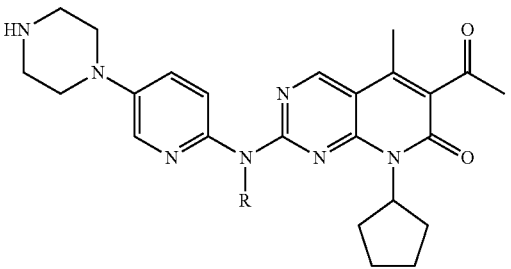 | |
| 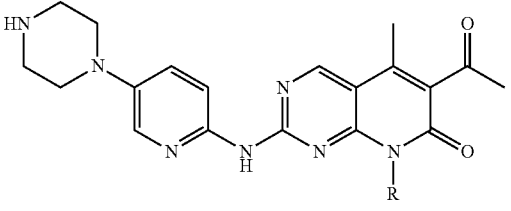 | |
| 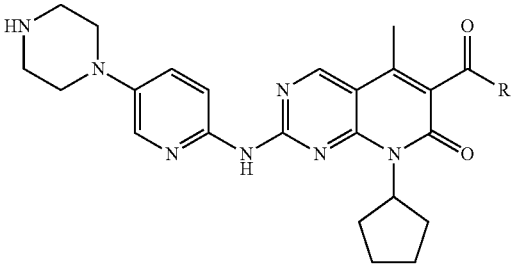 | |

TABLE Z-continued dTAG Targeting Ligands and corresponding dTAG

| dTAG Targeting Ligand | dTAG |
|---|---|
| Pazopanib | VEGFR1/2/3, PDGFRα/β, FGFR1/3, Kit, Lck, Fms, Itk |
| Ponatinib | BCR-Abl, BCR-Abl T3151, VEGFR, PDGFR, FGFR, EphR, Src family kinases, Kit, RET, Tie2, Flt3 |

TABLE Z-continued dTAG Targeting Ligands and corresponding dTAG

| dTAG Targeting Ligand | dTAG |
|---|---|
| Regorafenib | VEGFR1/2/3, BCR-Abl, B-Raf, B-Raf (V600E), Kit, PDGFRα/β, RET, FGFR1/2, Tie2, and Eph2A |
| Ruxolitinib | JAK1/2 |

TABLE Z-continued
dTAG Targeting Ligands and corresponding dTAG
| dTAG Targeting Ligand | dTAG |
|---|---|
| 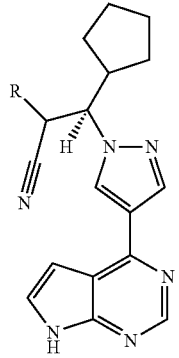 | |
| Sirolimus | FKBP12/mTOR |
| 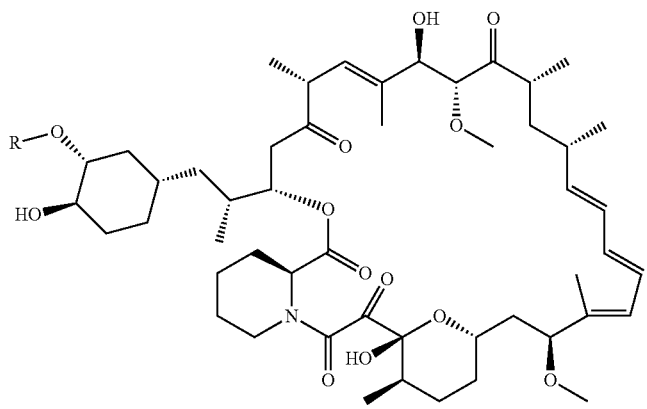 | |
| 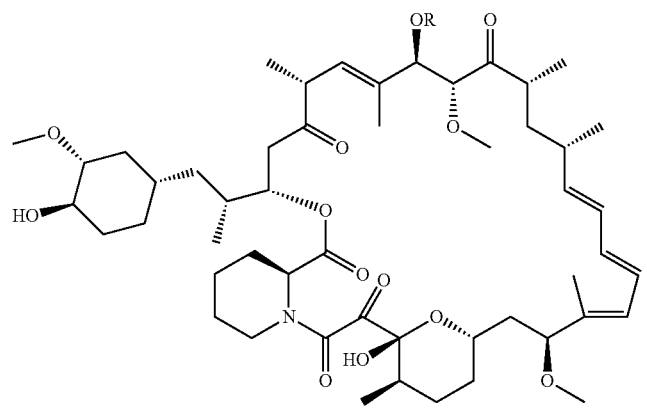 | |

TABLE Z-continued
dTAG Targeting Ligands and corresponding dTAG
| dTAG Targeting Ligand | dTAG |
|---|---|
| 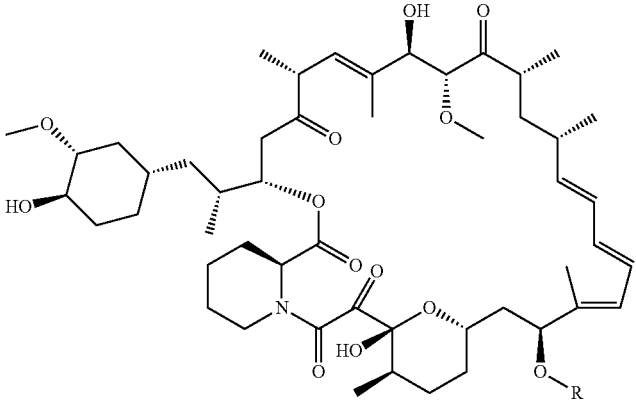 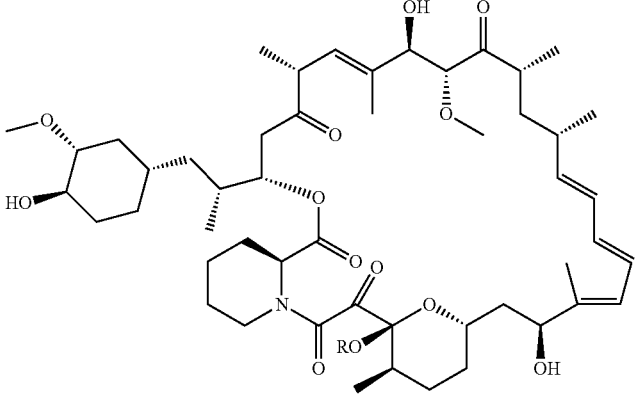 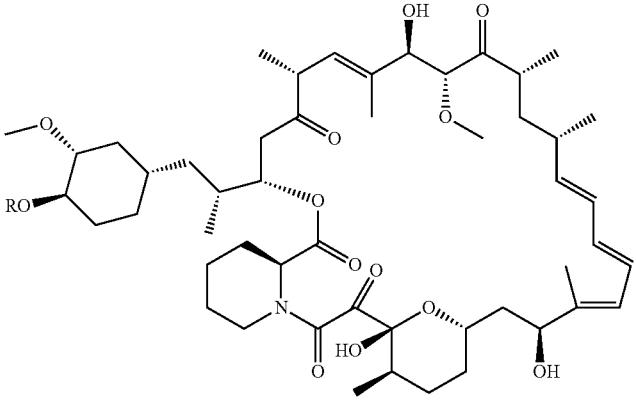 <br> Sorafenib <br> 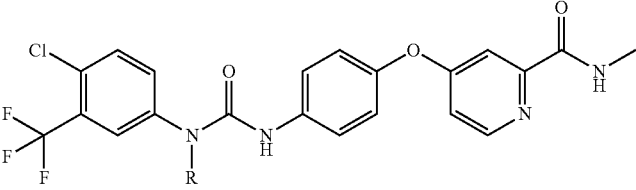 | B-Raf, CDK8, Kit, Flt3, RET, VEGFR1/2/3, PDGFR |

TABLE Z-continued
dTAG Targeting Ligands and corresponding dTAG
| dTAG Targeting Ligand | dTAG |
|---|---|
| 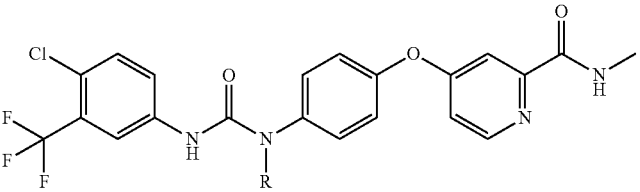 | |
| 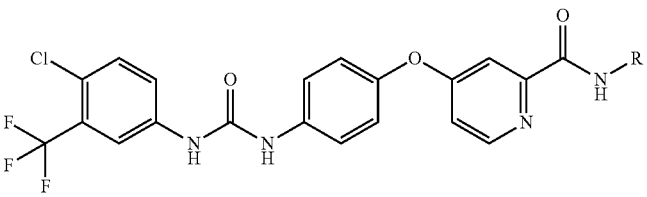 | |
| Sunitinib | PDGFRα/β, VEGFR1/2/3, Kit, Flt3, CSF-1R, RET |
| 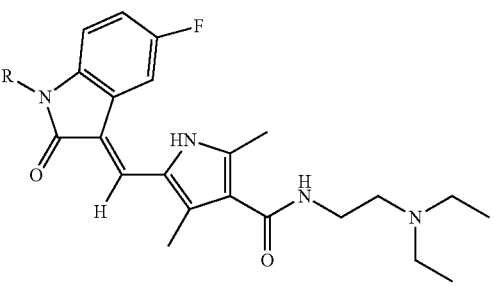 | |
| 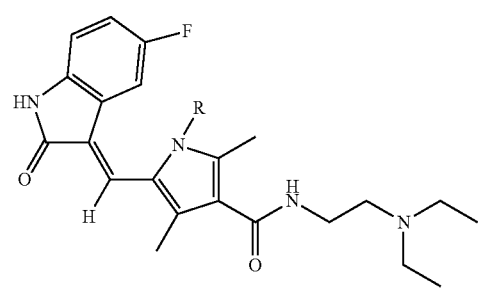 | |
| 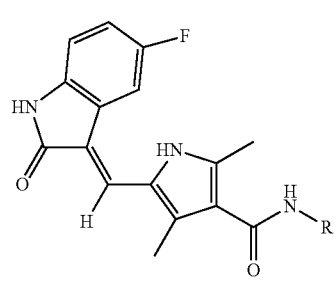 | |

TABLE Z-continued dTAG Targeting Ligands and corresponding dTAG

| dTAG Targeting Ligand | dTAG |
|---|---|
| Temsirolimus | FKBP12/mTOR |

TABLE Z-continued dTAG Targeting Ligands and corresponding dTAG

| dTAG Targeting Ligand | dTAG |
|---|---|
| | |
| Tofacitinib | JAK3 |

TABLE Z-continued dTAG Targeting Ligands and corresponding dTAG

| dTAG Targeting Ligand | dTAG |
|---|---|
| Trametinib | MEK1/2 |

TABLE Z-continued
dTAG Targeting Ligands and corresponding dTAG
| dTAG Targeting Ligand | dTAG |
|---|---|
| 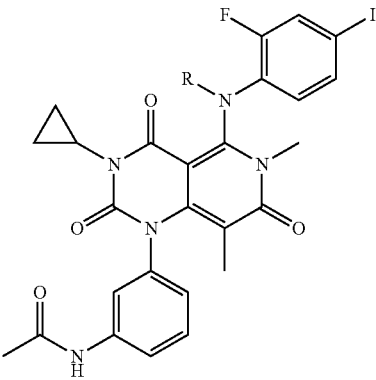 Vandetanib | EGFR, VEGFR, RET, Tie2, Brk, EphR |
| 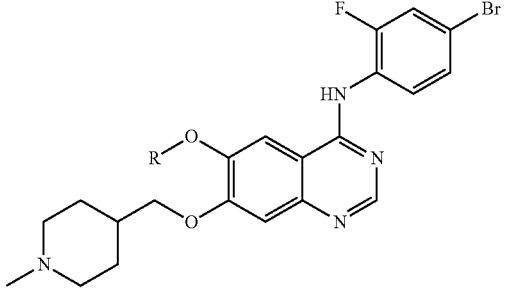 | |
| 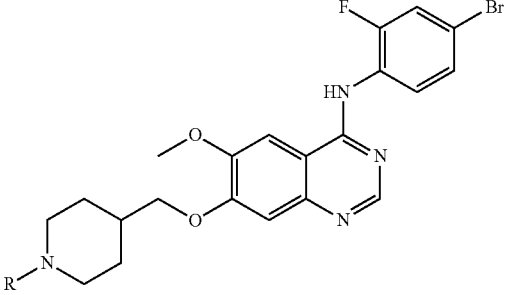 | |
| 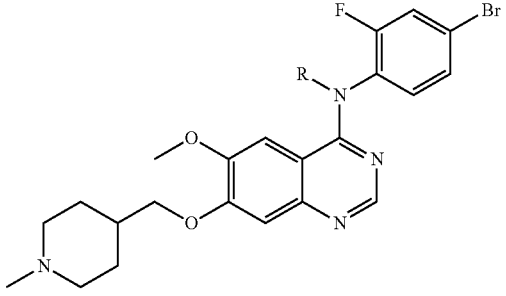 Vemurafenib | A/B/C-Raf and B-Raf (V600E) |

TABLE Z-continued
dTAG Targeting Ligands and corresponding dTAG
| dTAG Targeting Ligand | dTAG |
|---|---|
| 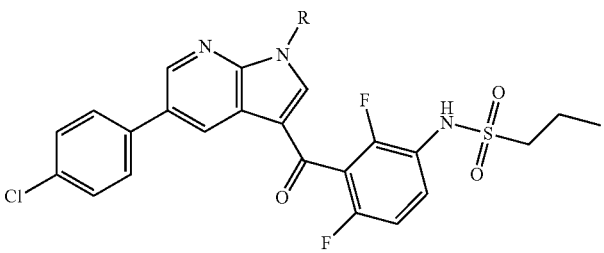 | |
| 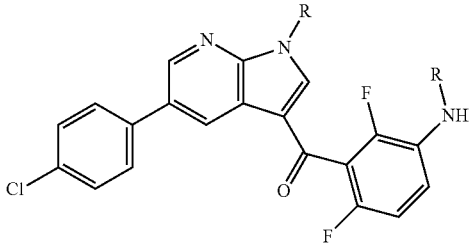 | |
In certain embodiments, the present application includes compounds containing the dTAG Targeting Ligands shown in Table 1.
TABLE 1
dTAG Targeting Ligands 1-6
| Compound | Structure |
|---|---|
| TL1 | 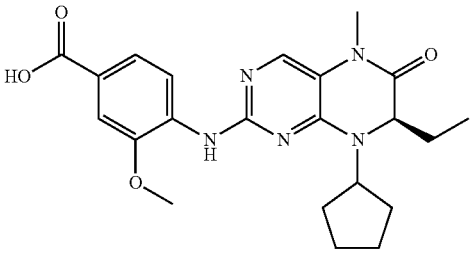 [SMILES: CC[C@@H]1C(=O)N(C)c2cnc(Nc3ccc(C(=O)O)cc3OC)nc2N1C1CCCC1]<br>Ang. Chem. Int'l. Ed. 50, 9378 (2011) |
| TL2 | 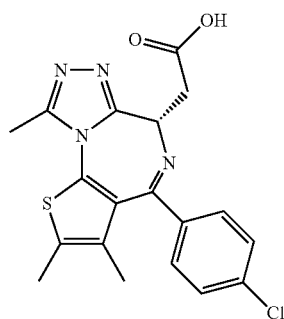 [SMILES: Cc1sc2c(c1C)C(c1ccc(Cl)cc1)=N[C@@H](CC(=O)O)c1nnc(C)n1-2] |

TABLE 1-continued
dTAG Targeting Ligands 1-6
| Compound | Structure |
|---|---|
| TL3 | 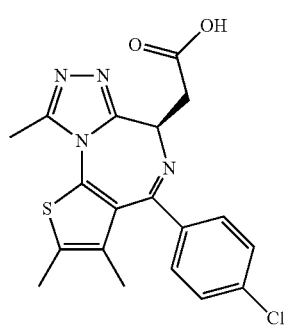 [SMILES: Cc1sc2c(c1C)C(c1ccc(Cl)cc1)=N[C@H](CC(=O)O)c1nnc(C)n1-2] |
| TL4 | 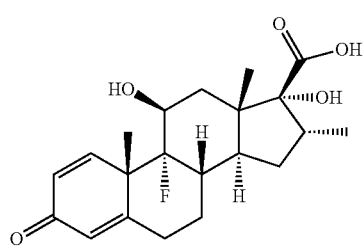 |
| TL5 | 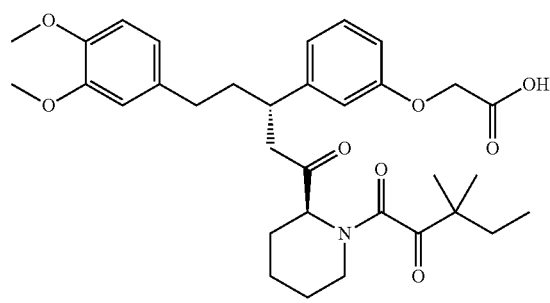 [SMILES: CCC(C)(C)C(=O)C(=O)N1CCCC[C@H]1C(=O)C[C@H](CCc1ccc(OC)c(OC)c1)c1cccc(OCC(=O)O)c1]<br>JACS 115, 9925 (1993) |
| TL6 | 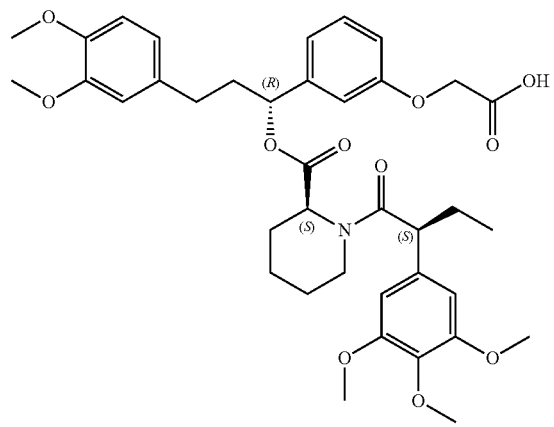 |

TABLE 1-continued dTAG Targeting Ligands 1-6

| Compound | Structure |
|---|---|
| TL7 | 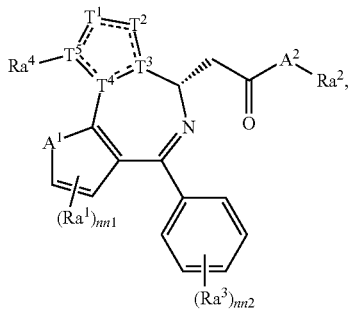 |

In certain embodiments, the dTAG Targeting Ligand is a compound of Formula TL-I:

(TL-1)

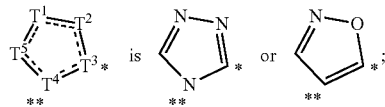

or a pharmaceutically acceptable salt thereof, wherein:

$T^1=T^2$, $T^3$, $T^4$ is triazole or isoxazole;

$A^1$ is S or C=C;
$A^2$ is $NRa^5$ or O;
nn1 is 0, 1, or 2;
each $Ra^1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, $C(O)NRa^5L$, OL, $NRa^5L$, or L;
$Ra^2$ is H, $C_1$-$C_6$ alkyl, $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is optionally substituted with $C_1$-$C_3$ alkyl, L, or C(O)L, and wherein the phenyl is optionally substituted with $C_1$-$C_3$ alkyl, CN, halogen, OH, $C_1$-$C_3$ alkoxy, or L;
nn2 is 0, 1, 2, or 3;
each $Ra^3$ is independently $C_1$-$C_3$ alkyl, $(CH_2)_{0-3}$—CN, $(CH_2)_{0-3}$-halogen, L, or $C(O)NRa^5L$;
$Ra^4$ is $C_1$-$C_3$ alkyl;
$Ra^5$ is H or $C_1$-$C_3$ alkyl; and
L is a Linker,
provided that the compound of Formula TL-I is substituted with only one L.

In certain embodiments, $T^1=T^2$, $T^3$, $T^4$ is triazole.

In certain embodiments, $T^1=T^2$, $T^3$, $T^4$ is isoxazole.

In certain embodiments, $A^1$ is S.
In certain embodiments, $A^1$ is C=C.
In certain embodiments, $A^2$ is $NRa^5$. In further embodiments, $Ra^5$ is H. In other embodiments, $Ra^5$ is $C_1$-$C_3$ alkyl (e.g., methyl, ethyl, propyl, or i-propyl). In further embodiments, $Ra^5$ is methyl.
In certain embodiments, $A^2$ is O.
In certain embodiments, nn1 is 0.
In certain embodiments, nn1 is 1.
In certain embodiments, nn1 is 2.
In certain embodiments, at least one $Ra^1$ is $C_1$-$C_3$ alkyl (e.g., methyl, ethyl, propyl, or i-propyl). In further embodiments, at least one $Ra^1$ is methyl. In further embodiments, two $Ra^1$ are methyl.
In certain embodiments, at least one $Ra^1$ is CN, $(CH_2)$—CN, $(CH_2)_2$—CN, or $(CH_2)_3$—CN. In further embodiments, at least one $Ra^1$ is $(CH_2)$—CN.
In certain embodiments, at least one $Ra^1$ is halogen (e.g., F, Cl, or Br), $(CH_2)$-halogen, $(CH_2)_2$-halogen, or $(CH_2)_3$-halogen. In further embodiments, at least one $Ra^1$ is Cl, $(CH_2)$—Cl, $(CH_2)_2$—Cl, or $(CH_2)_3$—Cl.
In certain embodiments, at least one $Ra^1$ is OH, $(CH_2)$—OH, $(CH_2)_2$—OH, or $(CH_2)_3$—OH.
In certain embodiments, at least one $Ra^1$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra^1$ is methoxy.
In certain embodiments, one $Ra^1$ is $C(O)NRa^5L$. In further embodiments, $Ra^5$ is H. In other embodiments, $Ra^5$ is $C_1$-$C_3$ alkyl (e.g., methyl, ethyl, propyl, or i-propyl).
In certain embodiments, one $Ra^1$ is OL.

In certain embodiments, one $Ra^1$ is $NRa^5L$. In further embodiments, $Ra^5$ is H. In other embodiments, $Ra^5$ is $C_1$-$C_3$ alkyl (e.g., methyl, ethyl, propyl, or i-propyl). In other embodiments, $Ra^5$ is methyl.

In certain embodiments, one $Ra^1$ is L.

In certain embodiments, $Ra^2$ is H.

In certain embodiments, $Ra^2$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra^2$ is methyl, ethyl, or t-butyl.

In certain embodiments, $Ra^2$ is heterocyclyl, $(CH_2)$-heterocyclyl, $(CH_2)_2$-heterocyclyl, or $(CH_2)_3$-heterocyclyl. In further embodiments, $Ra^2$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with $C_1$-$C_3$ alkyl (e.g., methyl, ethyl, propyl, or i-propyl).

In certain embodiments, the heterocyclyl is substituted with C(O)L.

In certain embodiments, the heterocyclyl is substituted with L.

In certain embodiments, $Ra^2$ is phenyl, $(CH_2)$-phenyl, $(CH_2)_2$-phenyl, or $(CH_2)_3$-phenyl. In further embodiments, $Ra^2$ is phenyl.

In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, the phenyl is substituted with L.

In certain embodiments, $Ra^2$ is L.

In certain embodiments, nn2 is 0.

In certain embodiments, nn2 is 1.

In certain embodiments, nn2 is 2.

In certain embodiments, nn2 is 3.

In certain embodiments, at least one $Ra^3$ is $C_1$-$C_3$ alkyl (e.g., methyl, ethyl, propyl, or i-propyl). In further embodiments, at least one $Ra^3$ is methyl.

In certain embodiments, at least one $Ra^3$ is CN, $(CH_2)$—CN, $(CH_2)_2$—CN, or $(CH_2)_3$—CN. In further embodiments, at least one $Ra^3$ is CN.

In certain embodiments, at least one $Ra^3$ is halogen (e.g., F, Cl, or Br), $(CH_2)$-halogen, $(CH_2)_2$-halogen, or $(CH_2)_3$-halogen. In further embodiments, at least one $Ra^3$ is Cl, $(CH_2)$—Cl, $(CH_2)_2$—Cl, or $(CH_2)_3$—Cl. In further embodiments, at least one $Ra^3$ is Cl.

In certain embodiments, one $Ra^3$ is L.

In certain embodiments, one $Ra^3$ is $C(O)NRa^5L$. In further embodiments, $Ra^5$ is H. In other embodiments, $Ra^5$ is $C_1$-$C_3$ alkyl (e.g., methyl, ethyl, propyl, or i-propyl).

In certain embodiments, $Ra^4$ is $C_1$-$C_3$ alkyl (e.g., methyl, ethyl, propyl, or i-propyl). In further embodiments, $Ra^4$ is methyl.

In certain embodiments, $Ra^5$ is H.

In certain embodiments, $Ra^5$ is $C_1$-$C_3$ alkyl (e.g., methyl, ethyl, propyl, or i-propyl). In further embodiments, $Ra^5$ is methyl.

In certain embodiments,

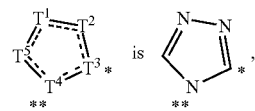

and $A^1$ is S.

In certain embodiments,

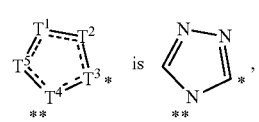

and $A^1$ is C=C.

In certain embodiments,

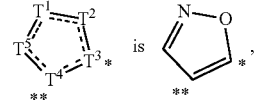

and $A^1$ is C=C.

In certain embodiments, $A^2$ is NH, and $Ra^2$ is $(CH_2)_{0-3}$-heterocyclyl. In further embodiments, $Ra^2$ is $(CH_2)_3$-heterocyclyl. In further embodiments, the heterocyclyl is piperazinyl. In further embodiments, the heterocyclyl is substituted with $C_1$-$C_3$ alkyl, L, or C(O)L.

In certain embodiments, $A^2$ is NH, and $Ra^2$ is $(CH_2)_{0-3}$-phenyl. In further embodiments, $Ra^2$ is phenyl. In further embodiments, the phenyl is substituted with OH or L.

In certain embodiments, $A^2$ is NH, and $Ra^2$ is L.

In certain embodiments, $A^2$ is NH, and $Ra^2$ is H or $C_1$-$C_6$ alkyl. In further embodiments, $Ra^2$ is $C_1$-$C_4$ alkyl.

In certain embodiments, $A^2$ is O, and $Ra^2$ is H or $C_1$-$C_6$ alkyl. In further embodiments, $Ra^2$ is $C_1$-$C_4$ alkyl.

In certain embodiments, a dTAG Targeting Ligand is a compound of Formula TL-I1:

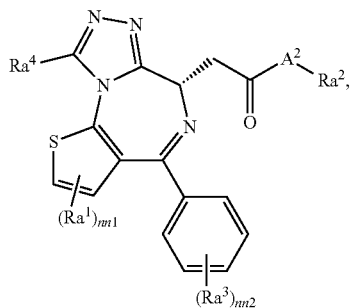

(TL-I1)

or a pharmaceutically acceptable salt thereof, wherein $A^2$, $Ra^1$, $Ra^2$, $Ra^3$, $Ra^4$, $Ra^5$, nn1, and nn2 are each as defined above in Formula TL-I.

Each of $A^2$, $Ra^1$, $Ra^2$, $Ra^3$, $Ra^4$, $Ra^5$, nn1, and nn2 may be selected from the moieties described above in Formula TL-I. Each of the moieties defined for one of $A^2$, $Ra^1$, $Ra^2Ra^3$, $Ra^4Ra^5$, nn1, and nn2, can be combined with any of the moieties defined for the others of $A^2$, $Ra^1$, $Ra^2$, $Ra^3$, $Ra^4$, $Ra^5$, nn1, and nn2, as described above in Formula TL-I.

In certain embodiments, a dTAG Targeting Ligand is a compound of Formula TL-I1a-TL-I1d:

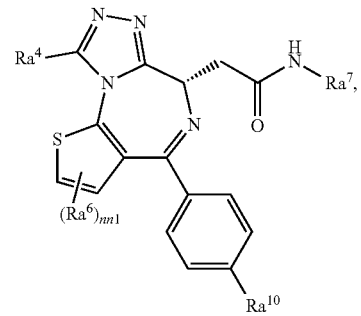
(TL-I1a)

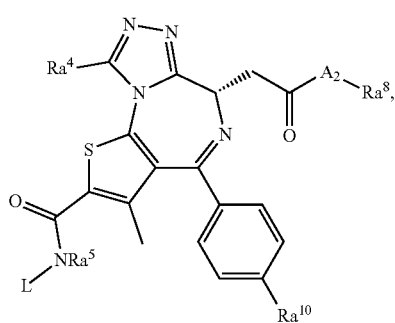
(TL-I1b)

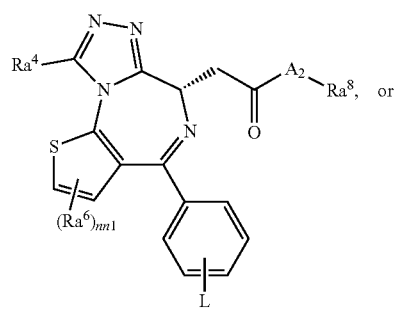
(TL-I1c)

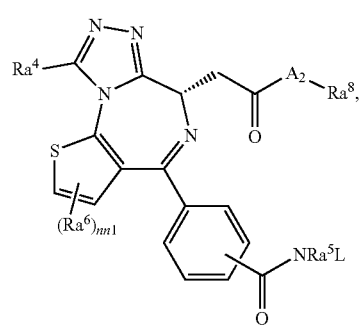
(TL-I1d)

or a pharmaceutically acceptable salt thereof, wherein:

each $Ra^6$ is independently $C_1$-$C_3$ alkyl, $(CH_2)_{0-3}$—CN, $(CH_2)_{0-3}$-halogen, $(CH_2)_{0-3}$—OH, or $(CH_2)_{0-3}$—$C_1$-$C_3$ alkoxy;

$Ra^7$ is $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is substituted with L or C(O)L, and wherein the phenyl is substituted with L;

$Ra^8$ is H, $C_1$-$C_6$ alkyl, $(CH_2)_{0-3}$-heterocyclyl, or $(CH_2)_{0-3}$-phenyl, wherein the heterocyclyl comprises one saturated 5- or 6-membered ring and 1-2 heteroatoms selected from N, O, and S and is optionally substituted with $C_1$-$C_3$ alkyl, and wherein the phenyl is optionally substituted with $C_1$-$C_3$ alkyl, CN, halogen, OH, or $C_1$-$C_3$ alkoxy;

$Ra^{10}$ is $C_1$-$C_3$ alkyl, $(CH_2)_{0-3}$—CN, or $(CH_2)_{0-3}$-halogen; and $A^2$, $Ra^4$, $Ra^5$, nn1, and L are each as defined above in Formula TL-I.

In certain embodiments, nn1 is 0.
In certain embodiments, nn1 is 1.
In certain embodiments, nn1 is 2.
In certain embodiments, at least one $Ra^6$ is $C_1$-$C_3$ alkyl (e.g., methyl, ethyl, propyl, or i-propyl). In further embodiments, at least one $Ra^6$ is methyl. In further embodiments, two $Ra^6$ are methyl.

In certain embodiments, at least one $Ra^6$ is CN, $(CH_2)$—CN, $(CH_2)_2$—CN, or $(CH_2)_3$—CN. In further embodiments, at least one $Ra^6$ is $(CH_2)$—CN.

In certain embodiments, at least one $Ra^6$ is halogen (e.g., F, Cl, or Br), $(CH_2)$-halogen, $(CH_2)_2$-halogen, or $(CH_2)_3$-halogen. In further embodiments, at least one $Ra^6$ is Cl, $(CH_2)$—Cl, $(CH_2)_2$—Cl, or $(CH_2)_3$—Cl.

In certain embodiments, at least one $Ra^6$ is OH, $(CH_2)$—OH, $(CH_2)_2$—OH, or $(CH_2)_3$—OH.

In certain embodiments, at least one $Ra^6$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra^6$ is methoxy.

In certain embodiments, $Ra^7$ is heterocyclyl, $(CH_2)$-heterocyclyl, $(CH_2)_2$-heterocyclyl, or $(CH_2)_3$-heterocyclyl. In further embodiments, $Ra^7$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with C(O)L.

In certain embodiments, the heterocyclyl is substituted with L.

In certain embodiments, $Ra^7$ is phenyl, $(CH_2)$-phenyl, $(CH_2)_2$-phenyl, or $(CH_2)_3$-phenyl. In further embodiments, $Ra^7$ is phenyl.

In certain embodiments, $Ra^7$ is L.
In certain embodiments, $Ra^8$ is H.
In certain embodiments, $Ra^8$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra^8$ is methyl, ethyl, or t-butyl.

In certain embodiments, $Ra^8$ is heterocyclyl, $(CH_2)$-heterocyclyl, $(CH_2)_2$-heterocyclyl, or $(CH_2)_3$-heterocyclyl. In further embodiments, $Ra^8$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with $C_1$-$C_3$ alkyl (e.g., methyl, ethyl, propyl, or i-propyl).

In certain embodiments, $Ra^8$ is phenyl, $(CH_2)$-phenyl, $(CH_2)_2$-phenyl, or $(CH_2)_3$-phenyl. In further embodiments, $Ra^8$ is phenyl.

In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, $Ra^{10}$ is $C_1$-$C_3$ alkyl (e.g., methyl, ethyl, propyl, or i-propyl).

In certain embodiments, $Ra^{10}$ is CN, $(CH_2)$—CN, $(CH_2)_2$—CN, or $(CH_2)_3$—CN.

In certain embodiments, $Ra^{10}$ is halogen (e.g., F, Cl, or Br), $(CH_2)$-halogen, $(CH_2)_2$-halogen, or $(CH_2)_3$-halogen. In further embodiments, $Ra^{10}$ is Cl, $(CH_2)$—Cl, $(CH_2)_2$—Cl, or $(CH_2)_3$—Cl. In further embodiments, $Ra^{10}$ is Cl.

Each of $A^2$, $Ra^4$, $Ra^5$, and nn1 may be selected from the moieties described above in Formula TL-I. Each of the moieties defined for one of $A^2$, $Ra^4$, $Ra^5$, $Ra^6$, $Ra^7$, $Ra^8$, $Ra^{10}$, and nn1, can be combined with any of the moieties defined for the others of $A^2$, $Ra^4$, $Ra^5$, $Ra^6$, $Ra^7$, $Ra^8$, $Ra^{10}$, and nn1, as described above and in Formula TL-I.

In certain embodiments, a dTAG Targeting Ligand is a compound of Formula TL-I2:

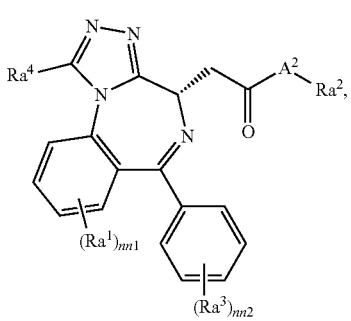

(TL-I2)

or a pharmaceutically acceptable salt thereof, wherein $A^2$, $Ra^1$, $Ra^2$, $Ra^3$, $Ra^4$, $Ra^5$, nn1, and nn2 are each as defined above in Formula TL-I.

Each of $A^2$, $Ra^1$, $Ra^2$, $Ra^3$, $Ra^4$, $Ra^5$, nn1, and nn2 may be selected from the moieties described above in Formula TL-I. Each of the moieties defined for one of $A^2$, $Ra^1 Ra^2 Ra^3 Ra^4$, $Ra^5$, nn1, and nn2, can be combined with any of the moieties defined for the others of $A^2$, $Ra^1$, $Ra^2$, $Ra^3$, $Ra^4$, $Ra^5$, nn1, and nn2, as described above in Formula TL-I.

In certain embodiments, a dTAG Targeting Ligand is a compound of Formula TL-I2a-TL-I2c:

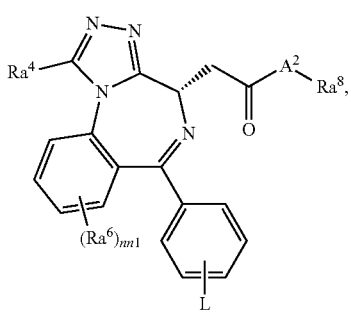

(TL-I2a)

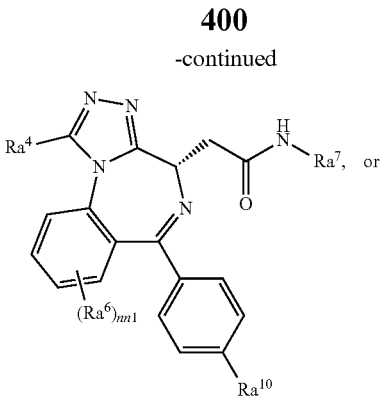

(TL-I2b)

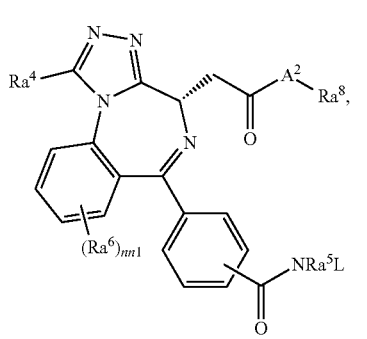

(TL-I2c)

or a pharmaceutically acceptable salt thereof, wherein $A^2$, $Ra^4$, $Ra^5$, nn1, and L are each as defined above in Formula TL-I, and $Ra^6$, $Ra^7$, $Ra^8$, and $Ra^{10}$ are each as defined above in Formula TL-I1a-TL-I1d.

Each of $A^2$, $Ra^4$, $Ra^5$, and nn1 may be selected from the moieties described above in Formula TL-I, and each of $Ra^6$, $Ra^7$, $Ra^8$, and $Ra^{10}$ may be selected from the moieties described above in Formula TL-I1a-TL-I1d. Each of the moieties defined for one of $A^2$, $Ra^4$, $Ra^5$, $Ra^6$, $Ra^7$, $Ra^8$, $Ra^{10}$, and nn1, can be combined with any of the moieties defined for the others of $A^2$, $Ra^4$, $Ra^5$, $Ra^6$, $Ra^7$, $Ra^8$, $Ra^{10}$, and nn1, as described above in Formula TL-I and TL-I1a-TL-I1d.

In certain embodiments, a dTAG Targeting Ligand is a compound of Formula TL-I3:

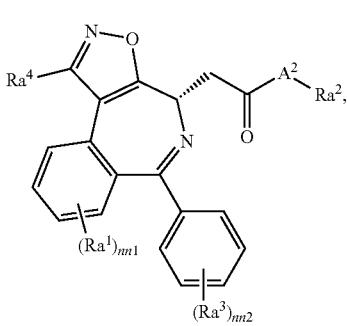

(TL-I3)

or a pharmaceutically acceptable salt thereof.

$A^2$, $Ra^1$, $Ra^2$, $Ra^3$, $Ra^4$, $Ra^5$, nn1, and nn2 are each as defined above in Formula TL-I. Each of $A^2$, $Ra^1$, $Ra^2$, $Ra^3$, $Ra^4$, $Ra^5$, nn1, and nn2 may be selected from the moieties described above in Formula TL-I. Each of the moieties defined for one of $A^2$, $Ra^1$, $Ra^2$, $Ra^3$, $Ra^4$, $Ra^5$, nn1, and nn2, can be combined with any of the moieties defined for the others of $A^2$, $Ra^1$, $Ra^2$, $Ra^3$, $Ra^4$, $Ra^5$, nn1, and nn2, as described above in Formula TL-I.

In certain embodiments, a dTAG Targeting Ligand is a compound of Formula TL-I3a-TL-I3c:

(TL-I3a)

(TL-I3b)

(TL-I3c)

or a pharmaceutically acceptable salt thereof, wherein:
Ra$^9$ is C(O)NRa$^5$L, OL, NRa$^5$L, or L;
A$^2$, Ra$^4$, Ra$^5$, nn1, and L are each as defined above in Formula TL-I; and
Ra$^6$, Ra$^7$, Ra$^8$, and Ra$^{10}$ are each as defined above in Formula TL-I1a-TL-I1d.

In certain embodiments, Ra$^9$ is C(O)NRa$^5$L. In further embodiments, Ra$^5$ is H. In other embodiments, Ra$^5$ is C$_1$-C$_3$ alkyl (e.g., methyl, ethyl, propyl, or i-propyl).

In certain embodiments, Ra$^9$ is OL.

In certain embodiments, Ra$^9$ is NRa$^5$L. In further embodiments, Ra$^5$ is H. In other embodiments, Ra$^5$ is C$_1$-C$_3$ alkyl (e.g., methyl, ethyl, propyl, or i-propyl). In other embodiments, Ras is methyl.

In certain embodiments, Ra$^9$ is L.

Each of A$^2$, Ra$^4$, Ra$^5$, and nn1 may be selected from the moieties described above in Formula TL-I, and each of Ra$^6$, Ra$^7$, Ra$^8$, and Ra$^{10}$ may be selected from the moieties described above in Formula TL-I1a-TL-I1d. Each of the moieties defined for one of A$^2$, Ra$^4$, Ra$^5$, Ra$^6$, Ra$^7$, Ra$^8$, Ra$^9$, Ra$^{10}$, and nn1, can be combined with any of the moieties defined for the others of A$^2$, Ra$^4$, Ra$^5$, Ra$^6$, Ra$^7$, Ra$^8$, Ra$^9$, Ra$^{10}$, and nn1, as described above and in Formula TL-I and TL-I1a-TL-I1d.

In certain embodiments, a dTAG Targeting Ligand is a compound of Formula TL-VI:

(TL-VI)

or a pharmaceutically acceptable salt thereof, wherein:
R$^{f1}$ is C(O)NR$^{f2}$L, OL, NR$^{f2}$L, or L;
R$^{f2}$ is independently H or C$_1$-C$_3$ alkyl; and
L is a Linker.

In certain embodiments, R$^{f1}$ is C(O)NR$^{f2}$L. In further embodiments, R$^{f2}$ is H. In other embodiments, R$^{f2}$ is C$_1$-C$_3$ alkyl (e.g., methyl, ethyl, propyl, or i-propyl).

In certain embodiments, R$^{f1}$ is OL.

In certain embodiments, R$^{f1}$ is NR$^{f2}$L. In further embodiments, R$^{f2}$ is H. In other embodiments, R$^{f2}$ is C$_1$-C$_3$ alkyl (e.g., methyl, ethyl, propyl, or i-propyl). In other embodiments, R$^{f2}$ is methyl.

In certain embodiments, R$^{f1}$ is L.

In certain embodiments, a dTAG Targeting Ligand is a compound of Formula TL-VII:

(TL-VII)

or a pharmaceutically acceptable salt thereof, wherein:
T$^7$ is CH$_2$ or CH$_2$CH$_2$;
Rg$^1$ is C(O)Rg$^5$ or (CH$_2$)$_{1-3}$Rg$^6$;
nn10 is 0, 1, 2, or 3;
nn11 is 0, 1, 2, or 3;
each Rg$^2$ is independently C$_1$-C$_3$ alkyl, C$_1$-C$_3$ alkoxy, CN, or halogen;
Rg$^3$ is C(O)NRg$^4$L, OL, NRg$^4$L, L, O—(CH$_2$)$_{1-3}$—C(O)NRg$^4$L, or NHC(O)—(CH$_2$)$_{1-3}$—C(O)NRg$^4$L;
Rg$^4$ is H or C$_1$-C$_3$ alkyl;
Rg$^5$ is C$_1$-C$_6$ alkyl;
Rg$^6$ is phenyl optionally substituted with C$_1$-C$_3$ alkyl, C$_1$-C$_3$ alkoxy, CN, or halogen; and
L is a Linker.

In certain embodiments, T$^7$ is CH$_2$.
In certain embodiments, T$^7$ is CH$_2$CH$_2$.
In certain embodiments, Rg$^1$ is C(O)Rg$^5$.
In certain embodiments, Rg$^1$ is (CH$_2$)-Rg$^6$, (CH$_2$)$_2$-Rg$^6$, or (CH$_2$)$_3$-Rg$^6$.
In certain embodiments, Rg$^5$ is straight-chain C$_1$-C$_6$ or branched C$_3$-C$_6$ alkyl (e.g., methyl, ethyl, propyl, i-propyl, butyl, i-butyl, t-butyl, pentyl, or hexyl).

In certain embodiments, $Rg^6$ is unsubstituted phenyl.

In certain embodiments, $Rg^6$ is phenyl substituted with one, two, three, or more substituents independently selected from $C_1$-$C_3$ alkyl (e.g., methyl, ethyl, propyl, or i-propyl), $C_1$-$C_3$ alkoxy (e.g., methoxy, ethoxy, or propoxy), CN, and halogen (e.g., F, Cl, or Br).

In certain embodiments, nn10 is 0.
In certain embodiments, nn10 is 1.
In certain embodiments, nn10 is 2.
In certain embodiments, nn10 is 3.
In certain embodiments, nn11 is 0.
In certain embodiments, nn11 is 1.
In certain embodiments, nn11 is 2.
In certain embodiments, nn11 is 3.

In certain embodiments, at least one $Rg^2$ is $C_1$-$C_3$ alkyl (e.g., methyl, ethyl, propyl, or i-propyl). In further embodiments, at least one $Rg^2$ is methyl.

In certain embodiments, at least one $Rg^2$ is $C_1$-$C_3$ alkoxy (e.g., methoxy, ethoxy, or propoxy). In further embodiments, at least one $Rg^2$ is methoxy.

In certain embodiments, at least one $Rg^2$ is CN.

In certain embodiments, at least one $Rg^2$ is halogen (e.g., F, Cl, or Br).

In certain embodiments, $Rg^3$ is $C(O)NRg^4L$. In further embodiments, $Rg^4$ is H. In other embodiments, $Rg^4$ is $C_1$-$C_3$ alkyl (e.g., methyl, ethyl, propyl, or i-propyl).

In certain embodiments, $Rg^3$ is OL.

In certain embodiments, $Rg^3$ is $NRg^4L$. In further embodiments, $Rg^4$ is H. In other embodiments, $Rg^4$ is $C_1$-$C_3$ alkyl (e.g., methyl, ethyl, propyl, or i-propyl). In other embodiments, $Rg^4$ is methyl.

In certain embodiments, $Rg^3$ is L.

In certain embodiments, $Rg^3$ is O—(CH$_2$)—C(O)NRg$^4$L, O—(CH$_2$)$_2$—C(O)NRg$^4$L, or O—(CH$_2$)$_3$—C(O)NRg$^4$L. In further embodiments, $Rg^3$ is O—(CH$_2$)—C(O)NRg$^4$L. In further embodiments, $Rg^4$ is H. In other embodiments, $Rg^4$ is $C_1$-$C_3$ alkyl (e.g., methyl, ethyl, propyl, or i-propyl).

In certain embodiments, $Rg^3$ is NHC(O)—(CH$_2$)—C(O)NRg$^4$L, NHC(O)—(CH$_2$)$_2$—C(O)NRg$^4$L, or NHC(O)—(CH$_2$)$_3$—C(O)NRg$^4$L. In further embodiments, $Rg^3$ is NHC(O)—(CH$_2$)—C(O)NRg$^4$L, NHC(O)—(CH$_2$)$_2$—C(O)NRg$^4$L. In further embodiments, $Rg^3$ is NHC(O)—(CH$_2$)$_2$—C(O)NRg$^4$L. In further embodiments, $Rg^4$ is H. In other embodiments, $Rg^4$ is $C_1$-$C_3$ alkyl (e.g., methyl, ethyl, propyl, or i-propyl).

In certain embodiments, the dTAG Targeting Ligand is selected from the structures of FIG. 49, wherein R is the point at which the Linker is attached.

In certain embodiments, the dTAG Targeting Ligands or targets are chosen based on existence (known dTAG binding moieties) and ability to develop potent and selective ligands with functional positions that can accommodate a Linker. Some embodiments relate to dTAG Targeting Ligands with less selectivity, which may benefit from degradation coupled with proteomics as a measure of compound selectivity or target ID.

Some embodiments of the present application relate to degradation or loss of 30% to 100% of the CAR. Certain embodiments relate to the loss of 50-100% of the CAR. Other embodiments relate to the loss of 75-95% of the CAR.

Non-limiting examples of heterobifunctional compounds for use in the present invention include:

FIG. 50 provides specific compounds for use in the present invention.

FIG. 51, provides specific compounds for use in the present invention, wherein X in the above structures is a halogen chosen from F, Cl, Br, and I.

FIG. 52, provides specific compounds for use in the present invention.

FIG. 53, provides specific compounds for use in the present invention, wherein:

$R^{AR1}$ is selected from:

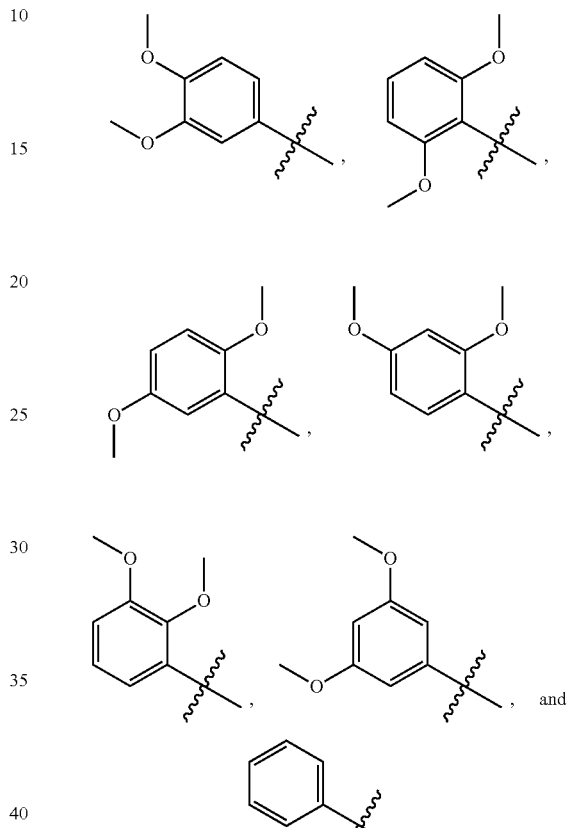

and $R^{AR2}$ is selected from:

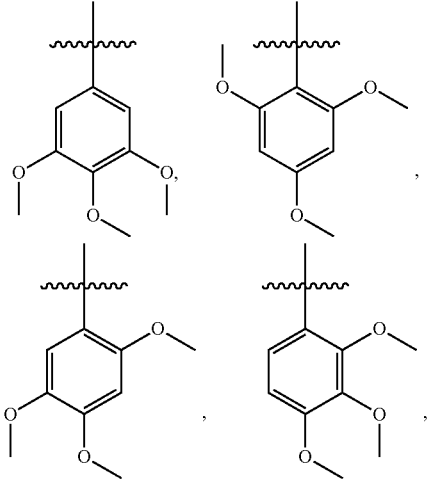

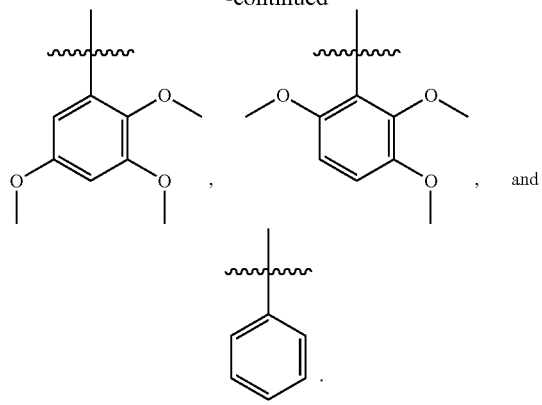

Additional compounds for use in the present invention include the structures of FIG. 54.

Some of the foregoing heterobifunctional compounds include one or more asymmetric centers, and thus can exist in various isomeric forms, e.g., stereoisomers and/or diastereomers. Thus, compounds and pharmaceutical compositions thereof may be in the form of an individual enantiomer, diastereomer, or geometric isomer, or may be in the form of a mixture of stereoisomers. In certain embodiments, the compounds of the application are enantiopure compounds. In certain other embodiments, mixtures of stereoisomers or diastereomers are provided.

Furthermore, certain heterobifunctional compounds, as described herein may have one or more double bonds that can exist as either the Z or E isomer, unless otherwise indicated. The application additionally encompasses the compounds as individual isomers substantially free of other isomers and alternatively, as mixtures of various isomers, e.g., racemic mixtures of stereoisomers. In addition to the above-mentioned compounds per se, this application also encompasses pharmaceutically acceptable derivatives of these heterobifunctional compounds and compositions comprising one or more compounds of the application and one or more pharmaceutically acceptable excipients or additives.

Heterobifunctional compounds of the application may be prepared by crystallization of the compound under different conditions and may exist as one or a combination of polymorphs of the compound forming part of this application. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present application encompasses heterobifunctional compounds, their derivatives, their tautomeric forms, their stereoisomers, their polymorphs, their pharmaceutically acceptable salts their pharmaceutically acceptable solvates and pharmaceutically acceptable compositions containing them.

General Synthesis of the Heterobifunctional Compounds

The heterobifunctional compounds described herein can be prepared by methods known by those skilled in the art. In one non-limiting example the disclosed heterobifunctional compounds can be made by the following schemes.

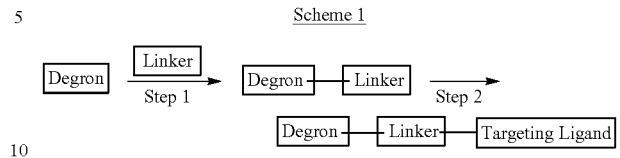

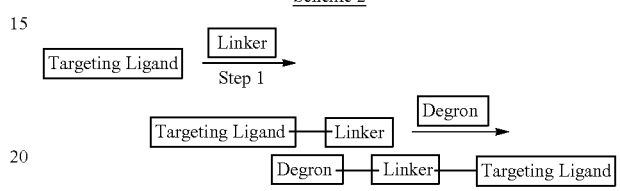

As shown in Scheme 1 heterobifunctional compounds for use in the present invention can be prepared by chemically combining a Degron and a Linker followed by subsequent addition of a dTAG Targeting Ligand. Similarly, in Scheme 2 heterobifunctional compounds for use in the present invention are prepared by chemically combing a dTAG Targeting Ligand and Linker first, followed by subsequent addition of a Degron. As illustrated in the above and following schemes, heterobifunctional compounds for use in the present invention can readily be synthesized by one skilled in the art in a variety of methods and chemical reactions.

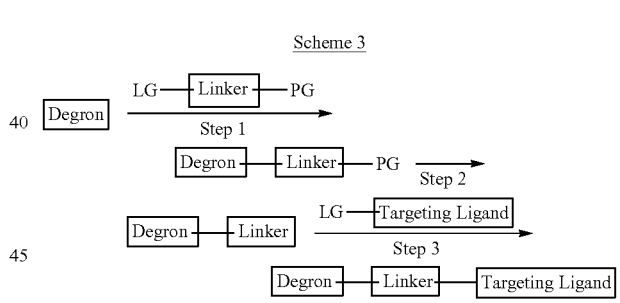

Scheme 3: In Step 1, a nucleophilic Degron displaces a leaving group on the Linker to make a Degron Linker fragment. In Step 2, the protecting group is removed by methods known in the art to free a nucleophilic site on the linker. In Step 3, the nucleophilic Degron Linker fragment displaces a leaving group on the dTAG Targeting Ligand to form a compound for use in the present invention. In an alternative embodiment Step 1 and/or Step 2 is accomplished by a coupling reaction instead of a nucleophilic attack.

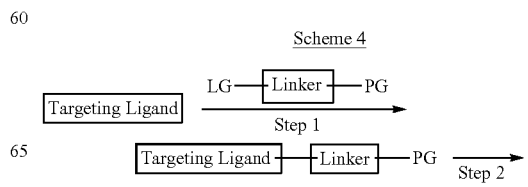

407

-continued

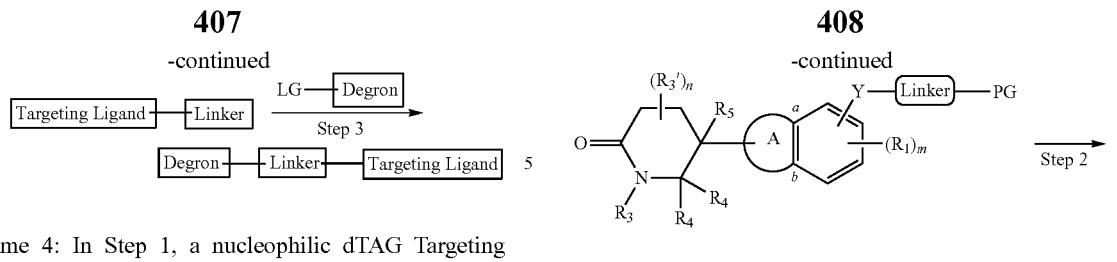

Scheme 4: In Step 1, a nucleophilic dTAG Targeting Ligand displaces a leaving group on the Linker to make a dTAG Targeting Ligand Linker fragment. In Step 2, the protecting group is removed by methods known in the art to free a nucleophilic site on the linker. In Step 3, the nucleophilic dTAG Targeting Ligand Linker fragment displaces a leaving group on the Degron to form a compound for use in the present invention. In an alternative embodiment Step 1 and/or Step 2 is accomplished by a coupling reaction instead of a nucleophilic attack.

Scheme 5

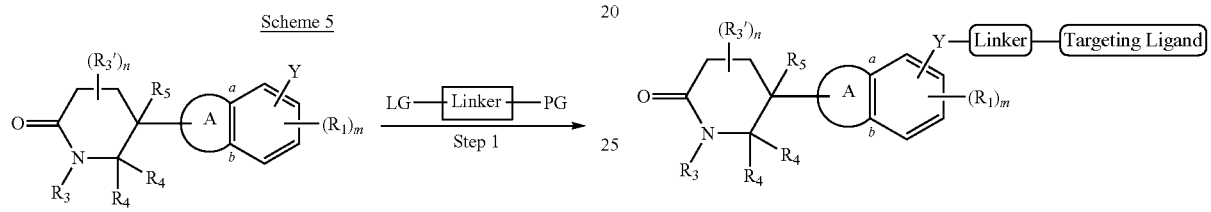

408

-continued

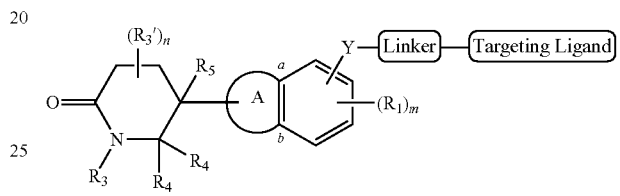

Scheme 6

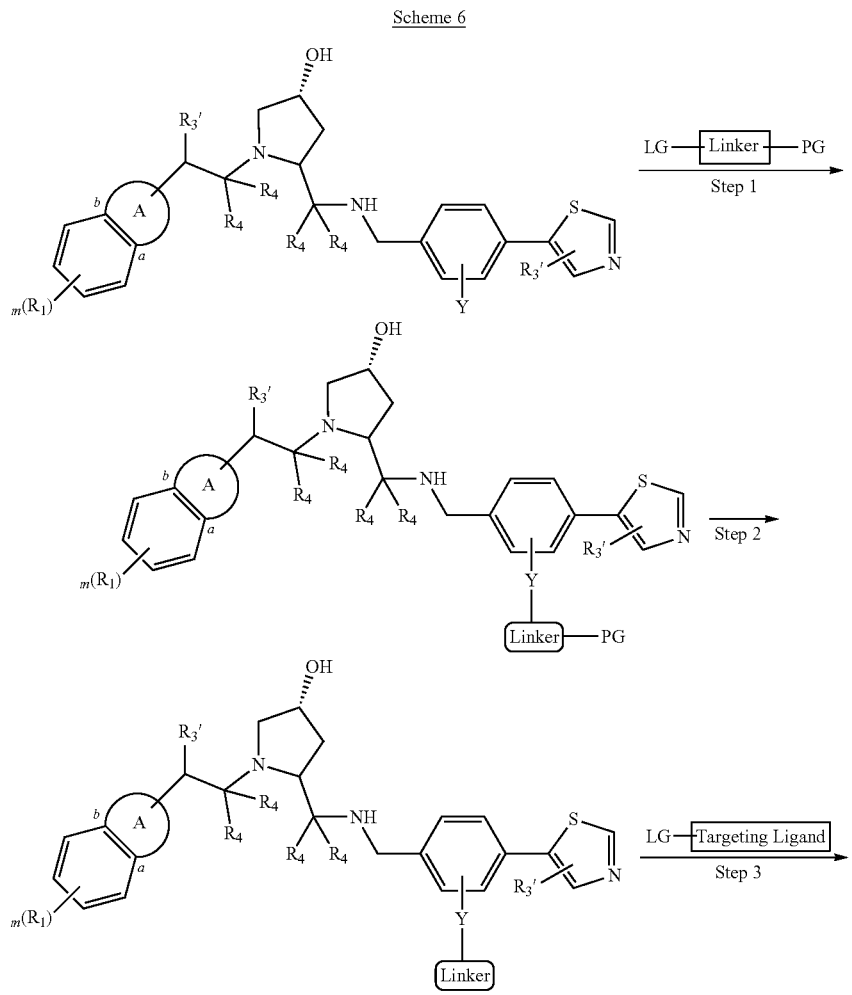

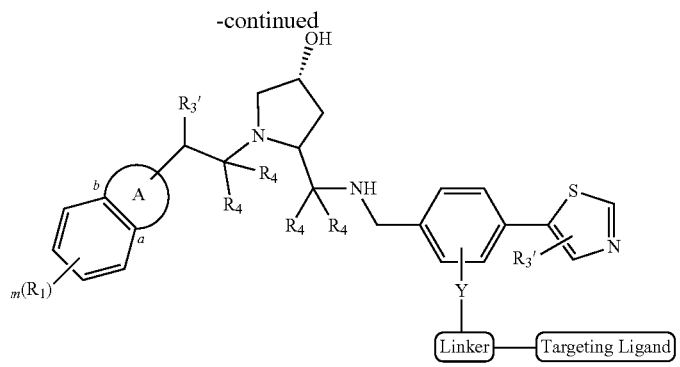

Scheme 5 and Scheme 6: In Step 1, a nucleophilic Degron displaces a leaving group on the Linker to make a Degron Linker fragment. In Step 2, the protecting group is removed by methods known in the art to free a nucleophilic site on the Linker. In Step 3, the nucleophilic Degron Linker fragment displaces a leaving group on the dTAG Targeting Ligand to form a compound of Formula I or Formula II. In an alternative embodiment Step 1 and/or Step 2 is accomplished by a coupling reaction instead of a nucleophilic attack.

Scheme 7

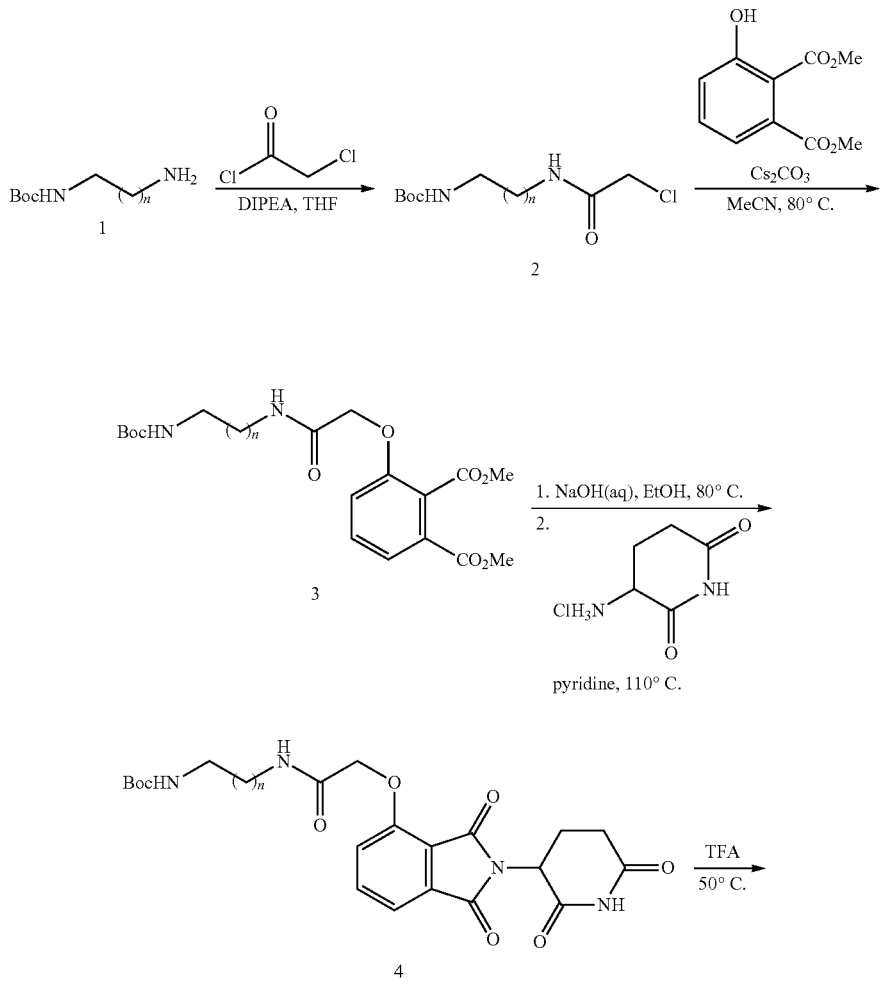

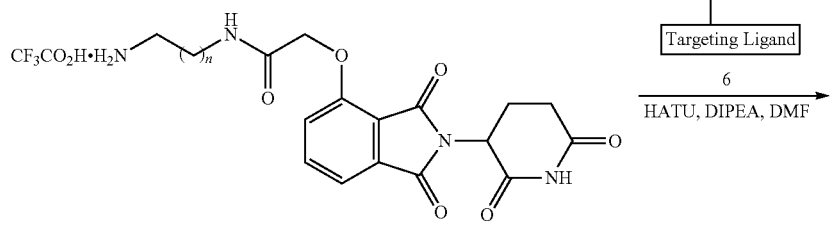

(reagent synthesized as in Fischer et al, Nature, 2014, doi:10.1038/nature 13527)
5

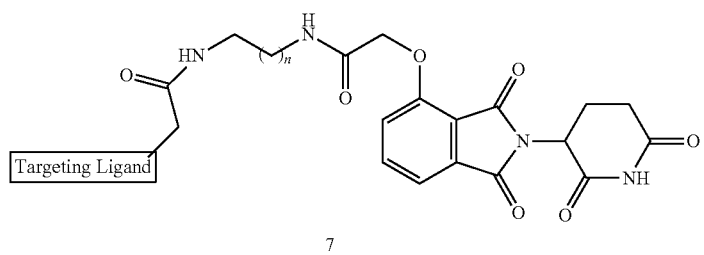

7 a) reacting tert-Butyl (2-aminoethyl)carbamate or its analog (e.g., n=1-20) (1) or its analog (e.g., n=1-20) with chloroacetyl chloride under suitable conditions to generate tert-butyl (2-(2-chloroacetamido)ethyl)carbamate or its analog (e.g., n=1-20) (2);

b) reacting tert-butyl (2-(2-chloroacetamido)ethyl)carbamate or its analog (2) with dimethyl 3-hydroxyphthalate under suitable conditions to provide dimethyl 3-(2-((2-((tert-butoxycarbonyl)amino)ethyl)amino)-2-oxoethoxy)phthalate or its analog (3);

c) reacting dimethyl 3-(2-((2-((tert-butoxycarbonyl)amino)ethyl)amino)-2-oxoethoxy)phthalate or its analog (3) with strong base, followed by 3-aminopiperidine-2,6-dione hydrochloride to generate tert-butyl (2-(2-((2-(2,6-dioxopiperidin-3-yl)-1,3-dioxoisoindolin-4-yl)oxy)acetamido)ethyl)carbamate or its analog (4);

d) deprotecting compound (4) to provide diaminoethyl-acetyl-O-thalidomide trifluoroacetate or its analog (5)

e) reacting compound (5) with an acid derivative of a dTAG Targeting Ligand (compound (6)) under suitable conditions to yield a bifunctional compound (7).

In certain embodiments, the methods described above are carried out in solution phase. In certain other embodiments, the methods described above are carried out on a solid phase. In certain embodiments, the synthetic method is amenable to high-throughput techniques or to techniques commonly used in combinatorial chemistry.

Representative Synthesis of the Heterobifunctional Compounds

Unless otherwise indicated, starting materials are either commercially available or readily accessible through laboratory synthesis by anyone reasonably familiar with the art. Described generally below, are procedures and general guidance for the synthesis of compounds as described generally and in subclasses and species herein.

Synthetic Example 1': Synthesis of IMiD Derivatives and Degrons

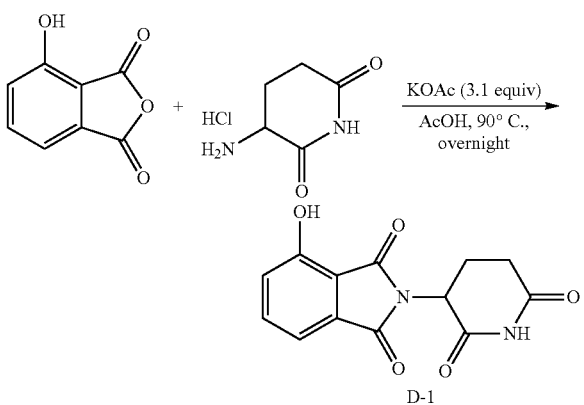

General Procedure I: IMiD Condensation 2-(2,6-dioxopiperidin-3-yl)-4-hydroxyisoindoline-1,3-dione (D-1

In a 20 mL glass vial, a mixture of 3-hydroxyphthalic anhydride (500 mg, 3.05 mmol, 1 equiv), potassium acetate (927 mg, 9.44 mmol, 3.1 equiv) and 3-aminopiperidine-2,6-dione hydrochloride (552 mg, 3.35 mmol, 1.1 equiv) in acetic acid (10.2 mL, 0.3 M) was heated to 90° C. overnight. The black reaction mixture was cooled to room temperature and diluted to 20 mL with water, and subsequently cooled on ice for 30 min. The resulting slurry was transferred to a 50 mL Falcon tube, which was centrifuged at 3500 rpm for 5 min. The supernatant was discarded and the black solid was transferred to a 250 mL RBF with methanol and concentrated in vacuo. The residue was purified by flash column chromatography on silica gel ($CH_2C_2$:MeOH (9:1)) to afford the title compound as a white solid (619 mg, 74%). $^1H$ NMR (400 MHz, DMSO-$d_6$) δ 11.07 (s, 1H), 7.65 (dd, J=8.4, 6.8 Hz, 1H), 7.31 (d, J=6.8 Hz, 1H), 7.24 (d, J=8.4 Hz, 1H), 5.06 (dd, J=12.8, 5.4 Hz, 1H), 2.94-2.82 (m, 1H), 2.64-2.43 (m, 2H), 2.08-1.97 (m, 1H); MS (ESI) calcd for $C_{13}H_{11}N_2O_5$ [M+H]$^+$ 275.07, found 275.26.

2-(2,6-dioxopiperidin-3-yl)-4-nitroisoindoline-1,3-dione (D-10

General procedure I was followed using 3-nitrophthalic anhydride (300 mg, 1.55 mmol, 1 equiv), potassium acetate (473 mg, 4.82 mmol, 3.1 equiv) and 3-aminopiperidine-2,6-dione hydrochloride (281 mg, 1.71 mmol, 1.1 equiv) to afford the title compound as a light yellow solid (280 mg, 59%) following purification by flash column chromatography on silica gel ($CH_2Cl_2$:MeOH (9:1)). $^1H$ NMR (500 MHz, DMSO-$d_6$) δ 11.17 (s, 1H), 8.35 (d, J=8.1 Hz, 1H), 8.24 (d, J=7.5 Hz, 1H), 8.14-8.10 (m, 1H), 5.20 (dd, J=12.9, 5.5 Hz, 1H), 2.93-2.84 (m, 1H), 2.64-2.45 (m, 2H), 2.11-2.04 (m, 1H); MS (ESI) calcd for $C_{13}H_{10}N_3O_6$ [M+H]$^+$ 304.06, found 304.19.

2-(2,6-dioxopiperidin-3-yl)-5-nitroisoindoline-1,3-dione (D-2

General procedure I was followed using 4-nitrophthalic anhydride (300 mg, 1.55 mmol), potassium acetate (473 mg, 4.82 mmol) and 3-aminopiperidine-2,6-dione hydrochloride (281 mg, 1.71 mmol) to afford the title compound as a white solid (409 mg, 87%) following purification by flash column chromatography on silica gel ($CH_2Cl_2$:MeOH (30:1)). $^1H$ NMR (500 MHz, DMSO-$d_6$) δ 11.18 (s, 1H), 8.68 (dd, J=8.1, 1.9 Hz, 1H), 8.56 (d, J=1.9 Hz, 1H), 8.19 (d, J=8.1 Hz, 1H), 5.24 (dd, J=12.9, 5.4 Hz, 1H), 2.90 (ddd, J=17.2, 13.9, 5.5 Hz, 1H), 2.69-2.48 (m, 2H), 2.14-2.05 (m, 1H); MS (ESI) calcd for $C_{13}H_{10}N_3O_6$ [M+H]$^+$ 304.06, found 304.19.

2-(2,6-dioxopiperidin-3-yl)isoindoline-1,3-dione (D-6

General procedure I was followed using phthalic anhydride (155 mg, 1.05 mmol), potassium acetate (318 mg, 3.24 mmol) and 3-aminopiperidine-2,6-dione hydrochloride (189 mg, 1.15 mmol) to afford the title compound as a white solid (235 mg, 87%) following purification by flash column chromatography on silica gel ($CH_2Cl_2$:MeOH (15:1)). $^1H$ NMR (500 MHz, DMSO-$d_6$) δ 11.13 (s, 1H), 8.00-7.76 (m, 4H), 5.16 (dd, J=12.8, 5.4 Hz, 1H), 2.89 (ddd, J=16.8, 13.7, 5.4 Hz, 1H), 2.65-2.42 (m, 2H), 2.12-1.99 (m, 1H); MS (ESI) calcd for $C_{13}H_{11}N_2O_4$ [M+H]$^+$ 259.07, found 259.23.

2-(2,5-dioxopyrrolidin-3-yl)isoindoline-1,3-dione (D-7

General procedure I was followed using phthalic anhydride (90 mg, 0.608 mmol), potassium acetate (185 mg, 1.88 mmol) and 3-aminopyrrolidine-2,5-dione hydrochloride (101 mg, 0.668 mmol) to afford the title compound as a white solid (95 mg, 64%) following purification by flash column chromatography on silica gel ($CH_2Cl_2$:MeOH (14:1)). MS (ESI) calcd for $C_{12}H_9N_2O_4$ [M+H]$^+$ 245.06, found 245.26.

2-(2,6-dioxopiperidin-3-yl)-1,3-dioxoisoindoline-5-carboxylic acid (D-13

General procedure I was followed using 1,2,4-benzenetricarboxylic anhydride (200 mg, 1.04 mmol), potassium acetate (317 mg, 3.23 mmol) and 3-aminopiperidine-2,6-dione hydrochloride (188 mg, 1.15 mmol) to afford the title compound as a white solid (178 mg, 57%) following purification by flash column chromatography on silica gel ($CH_2Cl_2$:MeOH (9:1)). MS (ESI) calcd for $C_{14}H_{11}N_2O_6$ [M+H]$^+$ 303.06, found 303.24.

2-(2,6-dioxopiperidin-3-yl)-4-fluoroisoindoline-1,3-dione (D-14

General procedure I was followed using 3-fluorophthalic anhydride (200 mg, 1.20 mmol), potassium acetate (366 mg, 3.73 mmol) and 3-aminopiperidine-2,6-dione hydrochloride (218 mg, 1.32 mmol) to afford the title compound as a white solid (288 mg, 86%) following purification by flash column chromatography on silica gel ($CH_2Cl_2$:MeOH (50:1)). $^1H$ NMR (500 MHz, DMSO-$d_6$) δ 11.15 (s, 1H), 7.96 (ddd, J=8.3, 7.3, 4.5 Hz, 1H), 7.82-7.71 (m, 2H), 5.17 (dd, J=13.0, 5.4 Hz, 1H), 2.90 (ddd, J=17.1, 13.9, 5.4 Hz, 1H), 2.65-2.47 (m, 2H), 2.10-2.04 (m, 1H), MS (ESI) calcd for $C_{13}H_{10}FN_2O_4$ [M+H]$^+$ 277.06, found 277.25.

2-(2,6-dioxopiperidin-3-yl)-4-methylisoindoline-1,3-dione (D-19

General procedure I was followed using 3-methylphthalic anhydride (150 mg, 0.925 mmol), potassium acetate (281 mg, 2.87 mmol) and 3-aminopiperidine-2,6-dione hydrochloride (167 mg, 1.02 mmol) to afford the title compound as a white solid (168 mg, 67%) following purification by flash column chromatography on silica gel ($CH_2Cl_2$:MeOH (15:1)). MS (ESI) calcd for $C_{14}H_{13}N_2O_4$ [M+H]$^+$ 273.09, found 273.24.

2-(2,6-dioxopiperidin-3-yl)-5-fluoroisoindoline-1,3-dione (D-24

General procedure I was followed using 4-fluorophthalic anhydride (200 mg, 1.20 mmol), potassium acetate (366 mg, 3.73 mmol) and 3-aminopiperidine-2,6-dione hydrochloride (218 mg, 1.32 mmol) to afford the title compound as a white solid (254 mg, 76%) following purification by flash column chromatography on silica gel ($CH_2Cl_2$:MeOH (15:1)). MS (ESI) calcd for $C_{13}H_{10}FN_2O_4$ [M+H]$^+$ 277.06, found 277.24.

2-(2,6-dioxopiperidin-4-yl)isoindoline-1,3-dione (D-43

General procedure I was followed using phthalic anhydride (60 mg, 0.311 mmol), potassium acetate (95 mg, 0.963 mmol) and 4-aminopiperidine-2,6-dione hydrochloride (56 mg, 0.342 mmol) to afford the title compound as a white solid (40 mg, 43%) following purification by flash column chromatography on silica gel ($CH_2Cl_2$:MeOH (9:1)). MS (ESI) calcd for $C_{13}H_{11}N_2O_4$ [M+H]$^+$ 259.07, found 259.18.

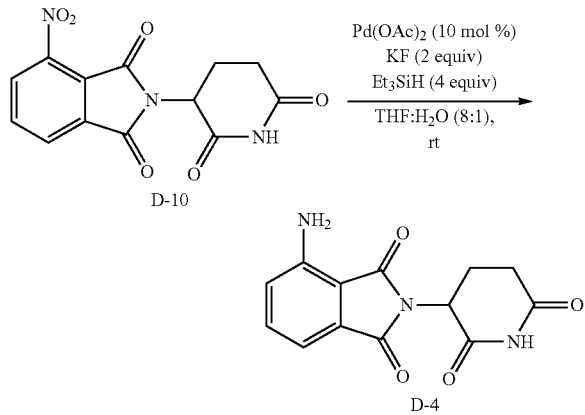

General Procedure II: Reduction of Aromatic Nitro Groups

4-amino-2-(2,6-dioxopiperidin-3-yl)isoindoline-1,3-dione (D-4

A solution of 2-(2,6-dioxopiperidin-3-yl)-4-nitroisoindoline-1,3-dione (173 mg, 0.854 mmol), Pd(OAc)$_2$ (12.8 mg, 0.0854 mmol, 10 mol %) and potassium fluoride (66 mg, 1.71 mmol, 2 equiv) in THF:water (8:1) (5.7 mL, 0.1 M) was stirred at room temperature. Triethylsilane (365 μL, 3.41 mmol, 4 equiv) was added slowly, and the resulting black solution was stirred at room temperature for 1 hour. The reaction mixture was filtered through a pad of celite, which was washed excessively with ethyl acetate. The filtrate was concentrated in vacuo and the residue was purified by flash column chromatography on silica gel ($CH_2Cl_2$:MeOH (7:1)) to afford the title compound as a yellow powder (72 mg, 46%). $^1$H NMR (500 MHz, DMSO-d$_6$) δ 11.08 (s, 1H), 7.47 (dd, J=8.5, 7.0 Hz, 1H), 7.06-6.95 (m, 1H), 6.59-6.44 (m, 1H), 5.04 (dd, J=12.7, 5.4 Hz, 1H), 2.93-2.82 (m, 1H), 2.64-2.45 (m, 2H), 2.05-1.98 (m, 1H); MS (ESI) calcd for $C_{13}H_{11}N_3O_4$ [M+H]$^+$ 274.08, found 274.23.

2-(2,6-dioxopiperidin-3-yl)-5-nitroisoindoline-1,3-dione (D-8

General procedure II was followed using 2-(2,6-dioxopiperidin-3-yl)-5-nitroisoindoline-1,3-dione (100 mg, 0.330 mmol), Pd(OAc)$_2$ (7.4 mg, 0.033 mmol), potassium fluoride (38 mg, 0.660 mmol) and triethylsilane (211 μL, 1.32 mmol to afford the title compound as a yellow solid (33 mg, 37%) following purification by flash column chromatography on silica gel ($CH_2Cl_2$:MeOH (9:1)). $^1$H NMR (500 MHz, DMSO-d$_6$) δ 11.05 (s, 1H), 7.52 (d, J=8.2 Hz, 1H), 6.94 (d, J=2.0 Hz, 1H), 6.83 (dd, J=8.2, 2.0 Hz, 1H), 6.55 (s, 2H), 5.01 (dd, J=12.8, 5.4 Hz, 1H), 2.86 (ddd, J=16.9, 13.9, 5.5 Hz, 1H), 2.68-2.43 (m, 2H), 2.03-1.93 (m, 1H); MS (ESI) calcd for $C_{13}H_{12}N_3O_4$ [M+H]$^+$ 274.08, found 274.59.

4-amino-2-(1-benzyl-2,6-dioxopiperidin-3-yl)isoindoline-1,3-dione (D-12

General procedure II was followed using 2-(1-benzyl-2,6-dioxopiperidin-3-yl)-4-nitroisoindoline-1,3-dione (48 mg, 0.122 mmol), Pd(OAc)$_2$ (2.7 mg, 0.0122 mmol), potassium fluoride (14 mg, 0.244 mmol) and triethylsilane (78 μL, 0.488 mmol to afford the title compound as a yellow solid (7 mg, 16%) following purification by flash column chromatography on silica gel (0 to 100% EtOAc in hexanes). MS (ESI) calcd for $C_{20}H_{18}N_3O_4$ [M+H]$^+$ 364.13, found 364.34.

3-(5-amino-2-methyl-4-oxoquinazolin-3(4H)-yl)piperidine-2,6-dione (D-17

General procedure II was followed using 3-(2-methyl-5-nitro-4-oxoquinazolin-3(4H)-yl)piperidine-2,6-dione (21 mg, 0.0664 mmol), Pd(OAc)$_2$ (1.5 mg, 0.0066 mmol), potassium fluoride (7.7 mg, 0.133 mmol) and triethylsilane (42 μL, 0.266 mmol to afford the title compound as a white solid (7 mg, 37%) following purification by preparative HPLC. MS (ESI) calcd for $C_{14}H_{15}N_4O_3$ [M+H]$^+$ 287.11, found 287.30.

3-(7-amino-1-oxoisoindolin-2-yl)piperidine-2,6-dione (D-41

General procedure II was followed using 3-(7-nitro-1-oxoisoindolin-2-yl)piperidine-2,6-dione (11 mg, 0.038 mmol), Pd(OAc)$_2$ (0.9 mg, 0.0038 mmol), potassium fluoride (4.4 mg, 0.076 mmol) and triethylsilane (24 μL, 0.152 mmol to afford the title compound as a yellow solid (2 mg, 21%) following purification by flash column chromatography on silica gel (0 to 10% MeOH in $CH_2Cl_2$). MS (ESI) calcd for $C_{13}H_{14}N_3O_3$ [M+H]$^+$ 260.10, found 260.52.

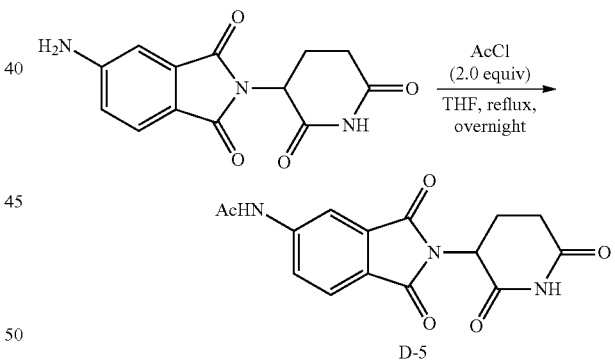

General Procedure III: Acylation of Anilines

N-(2-(2,6-dioxopiperidin-3-yl)-1,3-dioxoisoindolin-5-yl)acetamide (D-5

In a 4 mL glass vial, a mixture of 5-amino-2-(2,6-dioxopiperidin-3-yl)isoindoline-1,3-dione (30 mg, 0.110 mmol, 1 equiv) and acetyl chloride (26 μL, 0.220 mmol, 2 equiv) in THF (1.8 mL, 0.1 M) was heated to reflux overnight. The reaction mixture was filtered, and the filter cake was washed with Et$_2$O to give the title compound as a white solid (27 mg, 47%), that was used without further purification. $^1$H NMR (500 MHz, DMSO-d$_6$) δ 11.11 (s, 1H), 10.63 (s, 1H), 8.24 (d, J=1.5 Hz, 1H), 7.91-7.83 (m, 2H), 5.11 (dd, J=12.8, 5.4 Hz, 1H), 2.88 (ddd, J=17.0, 13.8, 5.4 Hz, 1H), 2.63-2.46 (m, 2H), 2.13 (s, 3H), 2.09-2.00 (m, 1H); MS (ESI) calcd for $C_{15}H_{14}N_3O_5$ [M+H]$^+$ 316.09, found 316.23.

N-(2-(2,6-dioxopiperidin-3-yl)-1,3-dioxoisoindolin-4-yl)acetamide (D-3

General procedure III was followed using 4-amino-2-(2,6-dioxopiperidin-3-yl)isoindoline-1,3-dione (50 mg, 0.183 mmol) and acetyl chloride (26 μL, 0.366 mmol) to afford the title compound as a white solid (10 mg, 17%). $^1$H NMR (500 MHz, DMSO-d$_6$) δ 11.14 (s, 1H), 9.73 (s, 1H), 8.44 (d, J=8.4 Hz, 1H), 7.83 (dd, J=8.4, 7.3 Hz, 1H), 7.62 (d, J=7.2 Hz, 1H), 5.14 (dd, J=12.9, 5.4 Hz, 1H), 2.90 (ddd, J=17.1, 13.9, 5.4 Hz, 1H), 2.66-2.45 (m, 2H), 2.19 (s, 3H), 2.14-2.00 (m, 1H); MS (ESI) calcd for $C_{15}H_{14}N_3O_5$ [M+H]$^+$ 316.09, found 316.27.

2-chloro-N-(2-(2,6-dioxopiperidin-3-yl)-1,3-dioxoisoindolin-5-yl)acetamide (D-32

General procedure III was followed using 5-amino-2-(2,6-dioxopiperidin-3-yl)isoindoline-1,3-dione (10 mg, 0.0366 mmol) and chloroacetyl chloride (6 μL, 0.0732 mmol) to afford the title compound as a white solid (7.1 mg, 55%). MS (ESI) calcd for $C_{15}H_{13}ClN_3O_5$ [M+H]$^+$ 350.05, found 350.23.

2-chloro-N-(2-(2,6-dioxopiperidin-3-yl)-1-oxoisoindolin-4-yl)acetamide (D-34

General procedure III was followed using 3-(4-amino-1-oxoisoindolin-2-yl)piperidine-2,6-dione (20 mg, 0.0771 mmol) and chloroacetyl chloride (12 μL, 0.154 mmol) to afford the title compound as a white solid (14.9 mg, 56%). $^1$H NMR (500 MHz, DMSO-d$_6$) δ 11.02 (s, 1H), 10.20 (s, 1H), 7.81 (dd, J=7.7, 1.3 Hz, 1H), 7.65-7.47 (m, 2H), 5.16 (dd, J=13.3, 5.1 Hz, 1H), 4.45-4.34 (m, 2H), 4.33 (s, 2H), 3.00-2.85 (m, 1H), 2.68-2.56 (m, 1H), 2.41-2.28 (m, 1H), 2.09-1.97 (m, 1H); MS (ESI) calcd for $C_{15}H_{15}ClN_3O_4$ [M+H]$^+$ 336.07, found 336.31.

N-(2-(2,6-dioxopiperidin-3-yl)-1-oxoisoindolin-4-yl)acrylamide (D-35

General procedure III was followed using 3-(4-amino-1-oxoisoindolin-2-yl)piperidine-2,6-dione (20 mg, 0.0771 mmol) and acryloyl chloride (13 μL, 0.154 mmol) to afford the title compound as a white solid (18 mg, 76%). $^1$H NMR (500 MHz, DMSO-d$_6$) δ 15.77 (s, 1H), 14.81 (s, 1H), 12.65 (dd, J=7.4, 1.6 Hz, 1H), 12.37-12.18 (m, 2H), 11.28 (dd, J=17.0, 10.2 Hz, 1H), 11.06 (dd, J=17.0, 1.9 Hz, 1H), 10.57 (dd, J=10.2, 1.9 Hz, 1H), 9.91 (dd, J=13.3, 5.1 Hz, 1H), 9.24-9.05 (m, 2H), 7.67 (ddd, J=17.2, 13.7, 5.5 Hz, 1H), 7.36 (dt, J=17.3, 3.8 Hz, 1H), 7.20-7.03 (m, 1H), 6.83-6.72 (m, 1H); MS (ESI) calcd for $C_{16}H_{16}N_3O_4$ [M+H]$^+$ 314.11, found 314.24.

N-(2-(2,6-dioxopiperidin-3-yl)-1,3-dioxoisoindolin-5-yl)acrylamide (D-36

General procedure III was followed using 5-amino-2-(2,6-dioxopiperidin-3-yl)isoindoline-1,3-dione (10 mg, 0.0366 mmol) and acryloyl chloride (6 μL, 0.0732 mmol) to afford the title compound as a white solid (8.8 mg, 73%). $^1$H NMR (500 MHz, DMSO-d$_6$) δ 11.12 (s, 1H), 10.83 (s, 1H), 8.33 (d, J=1.8 Hz, 1H), 7.99 (dd, J=8.2, 1.9 Hz, 1H), 7.90 (d, J=8.2 Hz, 1H), 6.48 (dd, J=17.0, 10.1 Hz, 1H), 6.36 (dd, J=17.0, 1.9 Hz, 1H), 5.88 (dd, J=10.0, 1.9 Hz, 1H), 5.13 (dd, J=12.8, 5.5 Hz, 1H), 2.95-2.84 (m, 1H), 2.67-2.46 (m, 2H), 2.09-2.01 (m, 1H); MS (ESI) calcd for $C_{16}H_{14}N_3O_5$ [M+H]$^+$ 328.09, found 328.23.

N-(2-(2,6-dioxopiperidin-3-yl)-1-oxoisoindolin-4-yl)acetamide (D-37

General procedure III was followed using 3-(4-amino-1-oxoisoindolin-2-yl)piperidine-2,6-dione (20 mg, 0.0771 mmol) and acetyl chloride (11 μL, 0.154 mmol) to afford the title compound as a white solid (17 mg, 71%). MS (ESI) calcd for $C_{15}H_{16}N_3O_4$ [M+H]$^+$ 302.11, found 301.99.

N-(2-(2,6-dioxopiperidin-3-yl)-1-oxoisoindolin-4-yl)cyclopropanecarboxamide (D-38

General procedure III was followed using 3-(4-amino-1-oxoisoindolin-2-yl)piperidine-2,6-dione (20 mg, 0.0771 mmol) and cyclopropanecarbonyl chloride (14 μL, 0.154 mmol) to afford the title compound as a white solid (19 mg, 75%). $^1$H NMR (500 MHz, DMSO-d$_6$) δ 11.01 (s, 1H), 10.06 (s, 1H), 7.84 (dd, J=7.2, 1.9 Hz, 1H), 7.66-7.38 (m, 2H), 5.14 (dd, J=13.3, 5.1 Hz, 1H), 4.52-4.30 (m, 2H), 2.92 (ddd, J=17.3, 13.6, 5.4 Hz, 1H), 2.64-2.54 (m, 1H), 2.45-2.27 (m, 1H), 2.08-1.95 (m, 1H), 1.93-1.83 (m, 1H), 0.90-0.75 (m, 4H); MS (ESI) calcd for $C_{17}H_{18}N_3O_4$ [M+H]$^+$ 328.13, found 328.00.

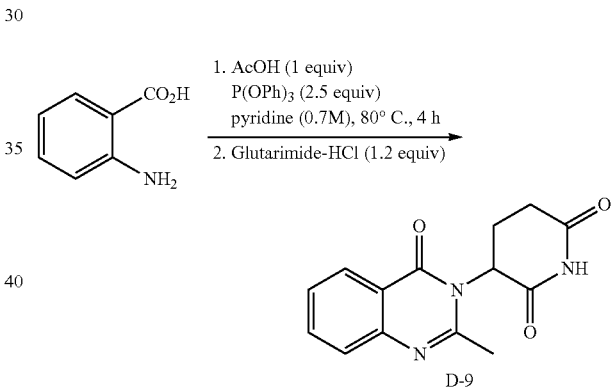

General Procedure IV: Quinazolinone Condensation

3-(2-methyl-4-oxoquinazolin-3(4H)-yl)piperidine-2,6-dione (D-9

In a 20 mL glass vial, anthranilic acid (100 mg, 0.729 mmol, 1 equiv), acetic acid (42 μL, 0.729 mmol, 1 equiv) and P(OPh)$_3$ (479 μL, 1.82 mmol, 2.5 equiv) in pyridine (1.0 uL, 0.7 M) was heated to 90° C. After 4 hours, the reaction mixture was cooled to room temperature and 3-aminopiperidine-2,6-dione hydrochloride (144 mg, 0.875 mmol, 1.2 equiv) was added. The reaction mixture was reheated to 90° C. for 1.5 h, whereupon it was stirred at room temperature overnight. The reaction mixture was taken up in EtOAc (15 mL) and water (15 mL). The organic layer was washed with brine (2×25 mL), dried over Na$_2$SO$_4$ and concentrated in vacuo. The residue was purified by flash column chromatography on silica gel (0-5% MeOH in CH$_2$Cl$_2$) to afford the title compound as a white solid (79 mg, 40%). $^1$H NMR (500 MHz, DMSO-d$_6$) δ 11.03 (s, 1H), 8.03 (dd, J=7.9, 1.5 Hz, 1H), 7.82 (ddd, J=8.5, 7.1, 1.6 Hz, 1H), 7.62 (dd, J=8.3, 1.1 Hz, 1H), 7.50 (ddd, J=8.1, 7.1, 1.1 Hz, 1H), 5.27 (dd, J=11.5, 5.7 Hz, 1H), 2.92-2.78 (m, 1H), 2.73-2.56 (m, 5H), 2.26-2.06 (m, 1H); MS (ESI) calcd for $C_{14}H_{14}N_3O_3$ [M+H]$^+$ 272.10, found 272.33.

3-(2-methyl-4-oxoquinazolin-3(4H)-yl)pyrrolidine-2,5-dione (D-11

General procedure IV was followed using anthranilic acid (200 mg, 1.46 mmol), acetic acid (84 µL, 1.46 mmol), P(OPh)$_3$ (959 µL, 3.65 mmol) and 3-aminopyrrolidine-2,5-dione hydrochloride (263 mg, 1.75 mmol) to afford the title compound as a white solid (25 mg, 7%) following purification by flash column chromatography on silica gel (CH$_2$Cl$_2$:MeOH (15:1)). MS (ESI) calcd for $C_{13}H_{12}N_3O_3$ [M+H]$^+$ 258.09, found 258.22.

3-(5-fluoro-2-methyl-4-oxoquinazolin-3(4H)-yl) piperidine-2,6-dione (D-66

General procedure IV was followed using 6-fluoro anthranilic acid (100 mg, 0.645 mmol), acetic acid (37 µL, 0.644 mmol), P(OPh)$_3$ (424 µL, 1.61 mmol) and 3-aminopiperidine-2,6-dione hydrochloride (127 mg, 0.774 mmol) to afford the title compound as a white solid (70 mg, 38%) following purification by flash column chromatography on silica gel (0-10% MeOH in CH$_2$Cl$_2$). $^1$H NMR (500 MHz, DMSO-d$_6$) δ 11.03 (s, 1H), 7.84-7.76 (m, 1H), 7.44 (dd, J=8.2, 1.0 Hz, 1H), 7.25 (ddd, J=11.1, 8.2, 1.0 Hz, 1H), 5.24 (dd, J=11.3, 5.7 Hz, 1H), 2.90-2.75 (m, 1H), 2.62 (s, 3H), 2.61-2.56 (m, 2H), 2.20-2.12 (m, 1H); MS (ESI) calcd for $C_{14}H_{13}FN_3O_3$ [M+H]$^+$ 290.09, found 290.27.

3-(2-methyl-5-nitro-4-oxoquinazolin-3(4H)-yl)piperidine-2,6-dione (D-67

General procedure IV was followed using 6-nitroanthranilic acid (100 mg, 0.549 mmol), acetic acid (31 µL, 0.549 mmol), P(OPh)$_3$ (361 µL, 1.37 mmol) and 3-aminopiperidine-2,6-dione hydrochloride (108 mg, 0.659 mmol) to afford the title compound as a white solid (29 mg, 17%) following purification by flash column chromatography on silica gel (0-10% MeOH in CH$_2$Cl$_2$). MS (ESI) calcd for $C_{14}H_{13}N_4O_5$ [M+H]$^+$ 317.09, found 317.58.

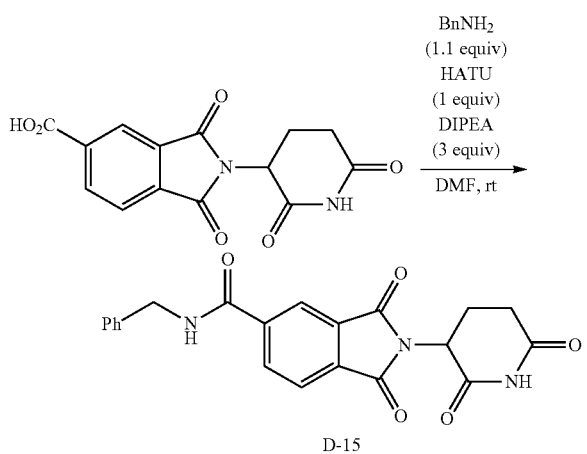

D-15

General Procedure V: Amide Coupling

N-benzyl-2-(2,6-dioxopiperidin-3-yl)-1,3-dioxoisoindoline-5-carboxamide (D-15

In a 4 mL glass vial, 2-(2,6-dioxopiperidin-3-yl)-1,3-dioxoisoindoline-5-carboxylic acid (10 mg, 0.033 mmol, 1 equiv), HATU (13 mg, 0.033 mmol, 1 equiv), DIPEA (17 µL, 0.099 mmol, 3 equiv) and benzyl amine (4 µL, 0.036 mmol, 1.1 equiv) in DMF (331 µL, 0.1 M) was stirred at room temperature overnight. The reaction mixture was diluted with MeOH to 4 mL, filtered and then purified by preparative HPLC to afford the title compound as a white solid (6 mg, 46%). MS (ESI) calcd for $C_{21}H_{18}N_3O_5$ [M+H]$^+$ 392.12, found 392.33.

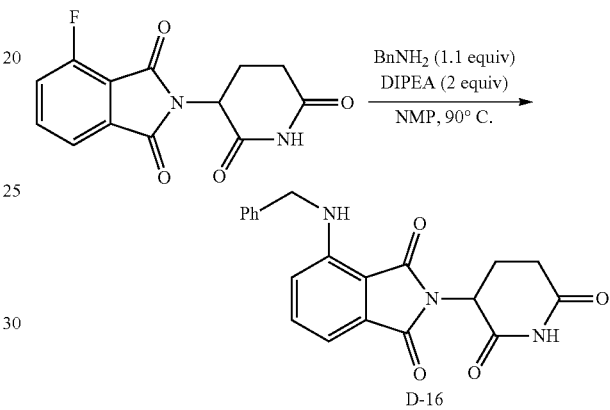

D-16

General Procedure VI: Nucleophilic Aromatic Substitution

4-(benzylamino)-2-(2,6-dioxopiperidin-3-yl)isoindoline-1,3-dione (D-16

In a 4 mL glass vial, 2-(2,6-dioxopiperidin-3-yl)-4-fluoroisoindoline-1,3-dione (10 mg, 0.036 mmol, 1 equiv), benzyl amine (4.4 µL, 0.040 mmol, 1.1 equiv) and DIPEA (13 µL, 0.072 mmol, 2 equiv) in NMP (362 µL, 0.1 M) was heated to 90° C. overnight. The reaction mixture was cooled to room temperature and taken up in EtOAc (15 mL). The organic layer was washed with NaHCO$_3$ (aq) (15 mL), water (15 mL) and brine (3×15 mL), and subsequently dried over Na$_2$SO$_4$ and concentrated in vacuo. The residue was purified by flash column chromatography on silica gel (0-100% EtOAc in hexanes) to afford the title compound as a yellow film (5 mg, 38%). $^1$H NMR (500 MHz, Chloroform-d) δ 8.10 (s, 1H), 7.44 (dd, J=8.5, 7.1 Hz, 1H), 7.40-7.25 (m, 5H), 7.12 (d, J=7.1 Hz, 1H), 6.84 (d, J=8.5 Hz, 1H), 6.71 (t, J=5.9 Hz, 1H), 4.93 (dd, J=12.3, 5.3 Hz, 1H), 4.51 (d, J=5.9 Hz, 2H), 2.93-2.66 (m, 3H), 2.21-2.07 (m, 1H); MS (ESI) calcd for $C_{20}H_{18}N_3O_4$ [M+H]$^+$ 364.13, found 364.31.

2-(2,6-dioxopiperidin-3-yl)-4-(isopropylamino)isoindoline-1,3-dione (D-18

General procedure VI was followed using 2-(2,6-dioxopiperidin-3-yl)-4-fluoroisoindoline-1,3-dione (30 mg, 0.109 mmol), isopropylamine (10 µL, 0.119 mmol) and DIPEA (21 µL, 0.119 mmol) to afford the title compound as a yellow film (11 mg, 32%) following purification by flash column chromatography on silica gel (0-100% EtOAc in hexanes). MS (ESI) calcd for $C_{16}H_{18}N_3O_4$ [M+H]$^+$ 316.13, found 316.65.

4-(diethylamino)-2-(2,6-dioxopiperidin-3-yl)isoindoline-1,3-dione (D-21)

General procedure VI was followed using 2-(2,6-dioxopiperidin-3-yl)-4-fluoroisoindoline-1,3-dione (30 mg, 0.109 mmol), diethylamine (11 µL, 0.130 mmol) and DIPEA (32 µL, 0.181 mmol) to afford the title compound as a yellow film (28 mg, 97%) following purification by flash column chromatography on silica gel (0-100% EtOAc in hexanes). MS (ESI) calcd for $C_{17}H_{20}N_3O_4$ [M+H]$^+$ 330.14, found 330.62.

5-(benzylamino)-2-(2,6-dioxopiperidin-3-yl)isoindoline-1,3-dione (D-25)

General procedure VI was followed using 2-(2,6-dioxopiperidin-3-yl)-5-fluoroisoindoline-1,3-dione (30 mg, 0.109 mmol), benzyl amine (13 µL, 0.119 mmol) and DIPEA (38 µL, 0.217 mmol) to afford the title compound as a yellow film (6 mg, 15%) following purification by flash column chromatography on silica gel (0-100% EtOAc in hexanes). MS (ESI) calcd for $C_{20}H_{18}N_3O_4$ [M+H]$^+$ 364.13, found 364.34.

2-(2,6-dioxopiperidin-3-yl)-5-(isopropylamino)isoindoline-1,3-dione (D-26)

General procedure VI was followed using 2-(2,6-dioxopiperidin-3-yl)-5-fluoroisoindoline-1,3-dione (30 mg, 0.109 mmol), isopropyl amine (11 µL, 0.130 mmol) and DIPEA (38 µL, 0.217 mmol) to afford the title compound as a yellow film (6 mg, 17%) following purification by flash column chromatography on silica gel (0-100% EtOAc in hexanes). $^1$H NMR (500 MHz, Chloroform-d) δ 8.00 (s, 1H), 7.53 (d, J=8.3 Hz, 1H), 6.87 (d, J=2.1 Hz, 1H), 6.64 (dd, J=8.3, 2.2 Hz, 1H), 4.86 (dd, J=12.3, 5.4 Hz, 1H), 4.30 (d, J=7.8 Hz, 1H), 2.86-2.58 (m, 3H), 2.12-2.01 (m, 1H), 1.26-1.15 (m, 6H); MS (ESI) calcd for $C_{16}H_{18}N_3O_4$ [M+H]$^+$ 316.13, found 316.30.

5-(diethylamino)-2-(2,6-dioxopiperidin-3-yl)isoindoline-1,3-dione (D-27)

General procedure VI was followed using 2-(2,6-dioxopiperidin-3-yl)-5-fluoroisoindoline-1,3-dione (30 mg, 0.109 mmol), diethylamine (14 µL, 0.130 mmol) and DIPEA (38 µL, 0.217 mmol) to afford the title compound as a yellow film (6 mg, 31%) following purification by flash column chromatography on silica gel (0-100% EtOAc in hexanes). $^1$H NMR (500 MHz, Chloroform-d) δ 8.08 (s, 1H), 7.57 (d, J=8.6 Hz, 1H), 6.98 (d, J=2.4 Hz, 1H), 6.72 (dd, J=8.7, 2.4 Hz, 1H), 4.90-4.80 (m, 1H), 3.40 (q, J=7.1 Hz, 4H), 2.89-2.61 (m, 3H), 2.11-2.01 (m, 1H), 1.16 (t, J=7.1 Hz, 6H); MS (ESI) calcd for $C_{17}H_{20}N_3O_4$ [M+H]$^+$ 330.14, found 330.69.

2-(2,6-dioxopiperidin-3-yl)-5-((furan-2-ylmethyl)amino)isoindoline-1,3-dione (D-28)

General procedure VI was followed using 2-(2,6-dioxopiperidin-3-yl)-5-fluoroisoindoline-1,3-dione (50 mg, 0.181 mmol), furfurylamine (18 µL, 0.199 mmol) and DIPEA (63 µL, 0.362 mmol) to afford the title compound as a yellow film (8 mg, 13%) following purification by flash column chromatography on silica gel (0-5% MeOH in $CH_2Cl_2$). MS (ESI) calcd for $C_{18}H_{16}N_3O_4$ [M+H]$^+$ 354.11, found 354.25.

tert-butyl (2-((2-(2,6-dioxopiperidin-3-yl)-1,3-dioxoisoindolin-4-yl)amino)ethyl)carbamate (D-29)

General procedure VI was followed using 2-(2,6-dioxopiperidin-3-yl)-4-fluoroisoindoline-1,3-dione (50 mg, 0.181 mmol), 1-Boc-ethylendiamine (32 mg, 0.199 mmol) and DIPEA (63 µL, 0.362 mmol) to afford the title compound as a yellow film (31 mg, 41%) following purification by flash column chromatography on silica gel (0-10% MeOH in $CH_2Cl_2$). $^1$H NMR (500 MHz, CDCl$_3$) δ 8.08 (bs, 1H), 7.50 (dd, J=8.5, 7.1 Hz, 1H), 7.12 (d, J=7.1 Hz, 1H), 6.98 (d, J=8.5 Hz, 1H), 6.39 (t, J=6.1 Hz, 1H), 4.96-4.87 (m, 1H), 4.83 (bs, 1H), 3.50-3.41 (m, 2H), 3.41-3.35 (m, 2H), 2.92-2.66 (m, 3H), 2.16-2.09 (m, 1H), 1.45 (s, 9H); MS (ESI) calcd for $C_{20}H_{25}N_4O_6$ [M+H]$^+$ 417.18, found 417.58.

Tert-butyl (2-((2-(2,6-dioxopiperidin-3-yl)-1,3-dioxoisoindolin-5-yl)amino)ethyl)carbamate (D-30)

General procedure VI was followed using 2-(2,6-dioxopiperidin-3-yl)-5-fluoroisoindoline-1,3-dione (50 mg, 0.181 mmol), 1-Boc-ethylendiamine (32 mg, 0.199 mmol) and DIPEA (63 µL, 0.362 mmol) to afford the title compound as a yellow film (22 mg, 29%) following purification by flash column chromatography on silica gel (0-10% MeOH in $CH_2Cl_2$). MS (ESI) calcd for $C_{20}H_{25}N_4O_6$ [M+H]$^+$ 417.18, found 417.32.

2-(2,6-dioxopiperidin-3-yl)-4-((furan-2-ylmethyl)amino)isoindoline-1,3-dione (D-31)

General procedure VI was followed using 2-(2,6-dioxopiperidin-3-yl)-4-fluoroisoindoline-1,3-dione (19.5 mg, 0.0706 mmol), furfurylamine (7 µL, 0.078 mmol) and DIPEA (25 µL, 0.141 mmol) to afford the title compound as a yellow film (19 mg, 76%) following purification by flash column chromatography on silica gel (0-2.5% MeOH in $CH_2Cl_2$). MS (ESI) calcd for $C_{18}H_{16}N_3O_4$ [M+H]$^+$ 354.11, found 354.27.

3-(5-(benzylamino)-2-methyl-4-oxoquinazolin-3(4H)-yl)piperidine-2,6-dione (D-39)

With the exception that the reaction mixture was heated to 170° C. instead of 90° C., general procedure VI was followed using 3-(5-fluoro-2-methyl-4-oxoquinazolin-3(4H)-yl)piperidine-2,6-dione (30 mg, 0.104 mmol), benzylamine (13 µL, 0.114 mmol) and DIPEA (36 µL, 0.207 mmol) to afford the title compound as a white solid (15 mg, 38%) following purification by flash column chromatography on silica gel (0-10% MeOH in $CH_2Cl_2$). $^1$H NMR (500 MHz, Chloroform-d) δ 8.73 (t, J=5.7 Hz, 1H), 8.39 (s, 1H), 7.41 (t, J=8.1 Hz, 1H), 7.39-7.19 (m, 5H), 6.77 (d, J=7.7 Hz, 1H), 6.41 (d, J=8.3 Hz, 1H), 4.67 (dd, J=11.5, 5.9 Hz, 1H), 4.43 (d, J=5.7 Hz, 2H), 3.03-2.79 (m, 2H), 2.72-2.61 (m, 1H), 2.60 (s, 3H), 2.15-2.07 (m, 1H); MS (ESI) calcd for $C_{21}H_{21}N_4O_3$ [M+H]$^+$ 377.16, found 377.02.

3-(5-(isopropylamino)-2-methyl-4-oxoquinazolin-3(4H)-yl)piperidine-2,6-dione (D-40)

With the exception that the reaction mixture was heated to 170° C. instead of 90° C., general procedure VI was followed using 3-(5-fluoro-2-methyl-4-oxoquinazolin-3(4H)- yl)piperidine-2,6-dione (30 mg, 0.104 mmol), isopropylamine (10 µL, 0.114 mmol) and DIPEA (36 µL, 0.207 mmol) to afford the title compound as a white solid (5 mg, 15%) following purification by flash column chromatography on silica gel (0-10% MeOH in $CH_2Cl_2$). $^1H$ NMR (500 MHz, Chloroform-d) δ 8.31 (s, 1H), 8.21 (d, J=7.2 Hz, 1H), 7.50-7.37 (m, 1H), 6.70 (dd, J=7.9, 0.9 Hz, 1H), 6.47 (d, J=8.4 Hz, 1H), 4.65 (dd, J=11.4, 5.9 Hz, 1H), 3.69-3.56 (m, 1H), 3.03-2.80 (m, 3H), 2.58 (s, 3H), 2.14-2.03 (m, 1H), 1.27 (d, J=2.7 Hz, 3H), 1.26 (d, J=2.7 Hz, 3H); MS (ESI) calcd for $C_{17}H_{21}N_4O_3$ [M+H]$^+$ 329.16, found 329.97.

2-(2,6-dioxopiperidin-3-yl)-4-((2-hydroxyethyl)amino)isoindoline-1,3-dione (D-68

General procedure VI was followed using 2-(2,6-dioxopiperidin-3-yl)-4-fluoroisoindoline-1,3-dione (30 mg, 0.109 mmol), aminoethanol (7 µL, 0.119 mmol) and DIPEA (38 µL, 0.217 mmol) to afford the title compound as a yellow film (6 mg, 18%) following purification by flash column chromatography on silica gel (0-5% MeOH in $CH_2Cl_2$). $^1H$ NMR (500 MHz, Chloroform-d) δ 8.26 (s, 1H), 7.50 (dd, J=8.5, 7.1 Hz, 1H), 7.12 (d, J=7.0 Hz, 1H), 6.95 (d, J=8.5 Hz, 1H), 6.50 (t, J=5.9 Hz, 1H), 4.97-4.85 (m, 1H), 3.94-3.79 (m, 2H), 3.47 (q, J=5.5 Hz, 2H), 3.03-2.68 (m, 3H), 2.19-2.04 (m, 1H); MS (ESI) calcd for $C_{15}H_{16}N_3O_5$ [M+H]$^+$ 318.11, found 318.22.

4-(cyclopropylamino)-2-(2,6-dioxopiperidin-3-yl)isoindoline-1,3-dione (D47)

General procedure VI was followed using 2-(2,6-dioxopiperidin-3-yl)-4-fluoroisoindoline-1,3-dione (20 mg, 0.0724 mmol), cyclopropylamine (6 µL, 0.080 mmol) and DIPEA (25 µL, 0.141 mmol) to afford the title compound as a yellow film (16 mg, 70%) following purification by flash column chromatography on silica gel (0-5% MeOH in $CH_2Cl_2$). $^1H$ NMR (500 MHz, Chloroform-d) δ 8.05 (s, 1H), 7.53 (dd, J=8.5, 7.1 Hz, 1H), 7.33-7.21 (m, 1H), 7.15 (dd, J=7.1, 0.7 Hz, 1H), 6.44 (bs, 1H), 4.95-4.85 (m, 1H), 2.98-2.66 (m, 3H), 2.62-2.50 (m, 1H), 2.19-2.06 (m, 1H), 0.92-0.78 (m, 2H), 0.67-0.56 (m, 2H); MS (ESI) calcd for $C_{16}H_{16}N_3O_4$ [M+H]$^+$ 314.11, found 314.54.

4-((2-(1H-indol-3-yl)ethyl)amino)-2-(2,6-dioxopiperidin-3-yl)isoindoline-1,3-dione (D-48

General procedure VI was followed using 2-(2,6-dioxopiperidin-3-yl)-4-fluoroisoindoline-1,3-dione (20 mg, 0.0724 mmol), tryptamine (13 mg, 0.080 mmol) and DIPEA (25 µL, 0.144 mmol) to afford the title compound as a yellow film (10 mg, 33%) following purification by flash column chromatography on silica gel (0-10% MeOH in $CH_2Cl_2$). $^1H$ NMR (500 MHz, Chloroform-d) δ 8.14 (s, 1H), 8.11 (s, 1H), 7.65-7.55 (m, 1H), 7.45 (dd, J=8.6, 7.1 Hz, 1H), 7.37 (dt, J=8.2, 0.9 Hz, 1H), 7.21 (ddd, J=8.2, 7.0, 1.2 Hz, 1H), 7.16-7.04 (m, 3H), 6.88 (d, J=8.5 Hz, 1H), 6.34 (t, J=5.6 Hz, 1H), 4.89 (dd, J=12.4, 5.4 Hz, 1H), 3.59 (td, J=6.8, 5.5 Hz, 2H), 3.19-3.03 (m, 2H), 2.93-2.64 (m, 3H), 2.14-2.04 (m, 1H); MS (ESI) calcd for $C_{23}H_{21}N_4O_4$ [M+H]$^+$ 417.16, found 417.26.

2-(2,6-dioxopiperidin-3-yl)-4-((4-hydroxyphenethyl)amino)isoindoline-1,3-dione (D-49

General procedure VI was followed using 2-(2,6-dioxopiperidin-3-yl)-4-fluoroisoindoline-1,3-dione (20 mg, 0.0724 mmol), tyramine (11 mg, 0.080 mmol) and DIPEA (25 µL, 0.144 mmol) to afford the title compound as a yellow film (15 mg, 54%) following purification by flash column chromatography on silica gel (0-5% MeOH in $CH_2Cl_2$). $^1H$ NMR (500 MHz, Chloroform-d) δ 8.20 (s, 1H), 7.51 (dd, J=8.5, 7.1 Hz, 1H), 7.17-7.08 (m, 2H), 6.90 (d, J=8.5 Hz, 1H), 6.85-6.72 (m, 2H), 4.95-4.90 (m, 1H), 3.52-3.46 (m, 2H), 2.97-2.87 (m, 2H), 2.86-2.72 (m, 2H), 2.21-2.09 (m, 1H); MS (ESI) calcd for $C_{21}H_{20}N_3O_5$ [M+H]$^+$ 394.14, found 394.25.

4-((2-(1H-imidazol-2-yl)ethyl)amino)-2-(2,6-dioxopiperidin-3-yl)isoindoline-1,3-dione (D-50

General procedure VI was followed using 2-(2,6-dioxopiperidin-3-yl)-4-fluoroisoindoline-1,3-dione (20 mg, 0.0724 mmol), histamine (15 mg, 0.080 mmol) and DIPEA (25 µL, 0.144 mmol) to afford the title compound as a yellow film (5 mg, 19%) following purification by flash column chromatography on silica gel (0-10% MeOH in $CH_2Cl_2$). $^1H$ NMR (500 MHz, Chloroform-d) δ 8.19 (s, 1H), 7.61 (d, J=1.2 Hz, 1H), 7.47 (dd, J=8.5, 7.1 Hz, 1H), 7.07 (d, J=6.9 Hz, 1H), 6.96-6.83 (m, 2H), 6.39 (t, J=5.7 Hz, 1H), 4.97-4.79 (m, 1H), 3.59 (q, J=6.5 Hz, 2H), 2.95 (t, J=6.6 Hz, 2H), 2.92-2.62 (m, 2H), 2.16-2.04 (m, 1H); MS (ESI) calcd for $C_{18}H_{18}N_5O_4$ [M+H]$^+$ 368.14, found 368.47.

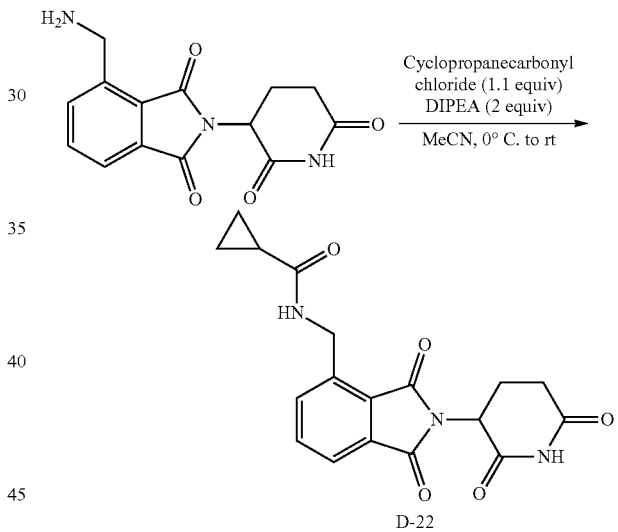

D-22

General Procedure VII: Acylation of Primary Amines

N-((2-(2,6-dioxopiperidin-3-yl)-1,3-dioxoisoindolin-4-yl)methyl)cyclopropanecarboxamide (D-22

In a 4 mL glass vial, 4-(aminomethyl)-2-(2,6-dioxopiperidin-3-yl)isoindoline-1,3-dione (25 mg, 0.087 mmol, 1 equiv) and DIPEA (30 µL, 0.174 mmol, 2 equiv) in MeCN (250 µL, 0.35 M) was cooled to 0° C. Cyclopropanecarbonyl chloride (8.7 µL, 0.096 mmol) was added slowly and the reaction mixture was stirred at room temperature overnight. The product was isolated by filtration to afford the title compound as a white solid (4.8 mg, 15%), that was used without further purification. MS (ESI) calcd for $C_{18}H_{18}N_3O_5$ [M+H]$^+$ 356.12, found 356.32.

N-((2-(2,6-dioxopiperidin-3-yl)-1,3-dioxoisoindolin-4-yl)methyl)acetamide (D-23

General procedure VII was followed using 4-(aminomethyl)-2-(2,6-dioxopiperidin-3-yl)isoindoline-1,3-dione (25 mg, 0.087 mmol), DIPEA (30 μL, 0.174 mmol) and acetyl chloride (7 μL, 0.096 mmol) to afford the title compound as a white solid (4.5 mg, 16%). $^1$H NMR (500 MHz, DMSO-d$_6$) δ 11.13 (s, 1H), 8.47 (t, J=6.0 Hz, 1H), 7.88-7.76 (m, 2H), 7.70 (dt, J=7.3, 1.1 Hz, 1H), 5.15 (dd, J=12.7, 5.4 Hz, 1H), 4.69 (d, J=6.0 Hz, 2H), 2.90 (ddd, J=16.8, 13.8, 5.4 Hz, 1H), 2.64-2.44 (m, 2H), 2.15-2.01 (m, 1H), 1.92 (s, 3H); MS (ESI) calcd for $C_{16}H_{16}N_3O_5$ [M+H]$^+$ 330.11, found 330.05.

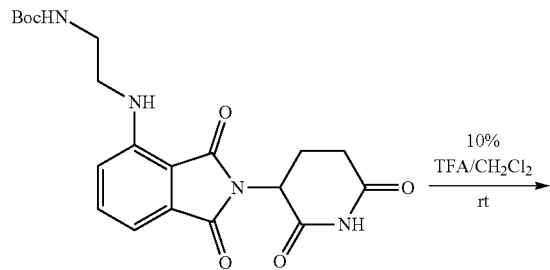

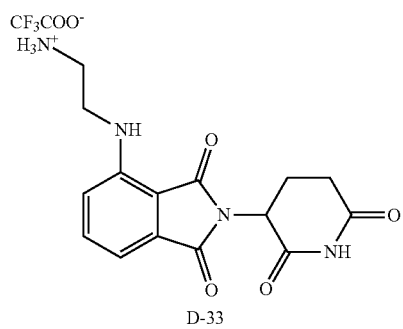

2-((2-(2,6-dioxopiperidin-3-yl)-1,3-dioxoisoindolin-4-yl)amino)ethan-1-aminium 2,2,2-trifluoroacetate (D-33

A stirred solution of tert-butyl (2-((2-(2,6-dioxopiperidin-3-yl)-1,3-dioxoisoindolin-4-yl)amino)ethyl)carbamate (205 mg, 0.492 mmol, 1 equiv) in dichloromethane (2.25 mL) was added trifluoroacetic acid (0.250 mL). The reaction mixture was stirred at room temperature for 4 h, whereupon the volatiles were removed in vacuo. The title compound was obtained as a yellow solid (226 mg, >95%), that was used without further purification. $^1$H NMR (500 MHz, MeOD) δ 7.64 (d, J=1.4 Hz, 1H), 7.27-7.05 (m, 2H), 5.10 (dd, J=12.5, 5.5 Hz, 1H), 3.70 (t, J=6.0 Hz, 2H), 3.50-3.42 (m, 2H), 3.22 (t, J=6.0 Hz, 1H), 2.93-2.85 (m, 1H), 2.80-2.69 (m, 2H), 2.17-2.10 (m, 1H); MS (ESI) calcd for $C_{15}H_{17}N_4O_4$ [M+H]$^+$ 317.12, found 317.53.

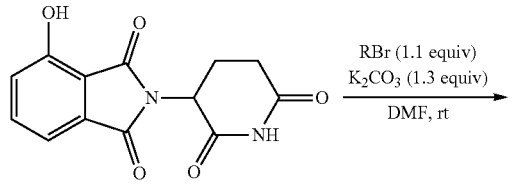

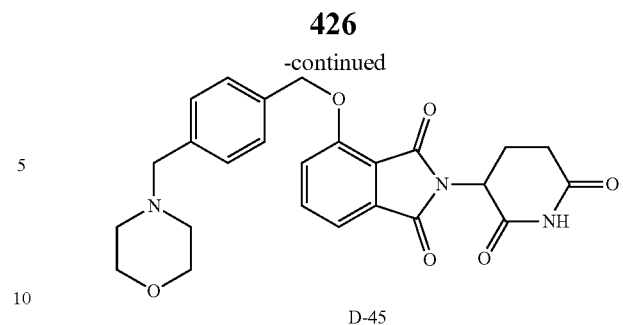

General Procedure VIII: Phenol Alkylation 2-(2,6-dioxopiperidin-3-yl)-4-((4-(morpholinomethyl)benzyl)oxy)isoindoline-1,3-dione (D-45

In a 4 mL glass vial, 2-(2,6-dioxopiperidin-3-yl)-4-hydroxyisoindoline-1,3-dione (30 mg, 0.109 mmol, 1 equiv) and K$_2$CO$_3$ (15 mg, 0.109 mmol, 1 equiv) in DMF (365 μL, 0.3 M) was stirred at room temperature. 4-(4-(bromomethyl)benzyl)morpholine (30 mg, 0.109 mmol, 1 equiv) in DMF (200 μL) was added and the reaction mixture was stirred at room temperature for 4 days. The reaction mixture was taken up in water (15 mL) and EtOAc (15 mL), and the organic layer was washed with brine (3×15 mL), dried over Na$_2$SO$_4$ and concentrated in vacuo. The residue was purified by flash column chromatography on silica gel (0 to 10% MeOH in CH$_2$Cl$_2$) to afford the title compound as a white solid (20 mg, 40%). $^1$H NMR (500 MHz, DMSO-d$_6$) δ 11.10 (s, 1H), 7.82 (dd, J=8.5, 7.2 Hz, 1H), 7.60 (d, J=8.5 Hz, 1H), 7.50-7.42 (m, 3H), 7.35 (d, J=8.1 Hz, 2H), 5.35 (s, 2H), 5.09 (dd, J=12.8, 5.5 Hz, 1H), 3.64-3.51 (m, 4H), 3.46 (s, 2H), 2.88 (ddd, J=17.0, 14.1, 5.4 Hz, 1H), 2.63-2.47 (m, 2H), 2.38-2.31 (m, 4H), 2.07-1.99 (m, 1H); MS (ESI) calcd for $C_{25}H_{26}N_3O_6$ [M+H]$^+$ 464.18, found 464.00.

4-(benzyloxy)-2-(2,6-dioxopiperidin-3-yl)isoindoline-1,3-dione (D-46

General procedure VIII was followed using 2-(2,6-dioxopiperidin-3-yl)-4-hydroxyisoindoline-1,3-dione (30 mg, 0.109 mmol), K$_2$CO$_3$ (15 mg, 0.109 mmol) and benzyl bromide (8 μL, 0109 mmol) to afford the title compound as a white solid (8 mg, 20%) after purification by flash column chromatography on silica gel (0 to 10% MeOH in CH$_2$Cl$_2$). $^1$H NMR (500 MHz, DMSO-d$_6$) δ 11.10 (s, 1H), 7.83 (dd, J=8.5, 7.3 Hz, 1H), 7.60 (d, J=8.5 Hz, 1H), 7.53-7.50 (m, 2H), 7.47 (d, J=7.2 Hz, 1H), 7.45-7.39 (m, 2H), 7.38-7.32 (m, 1H), 5.38 (s, 2H), 5.09 (dd, J=12.8, 5.5 Hz, 1H), 2.88 (ddd, J=16.9, 13.8, 5.5 Hz, 1H), 2.64-2.46 (m, 2H), 2.07-1.99 (m, 1H); MS (ESI) calcd for $C_{20}H_{17}N_2O_5$ [M+H]$^+$ 365.11, found 365.21.

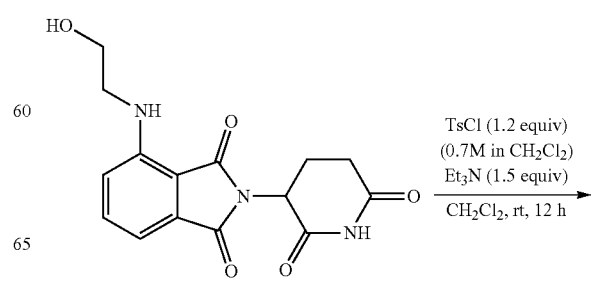

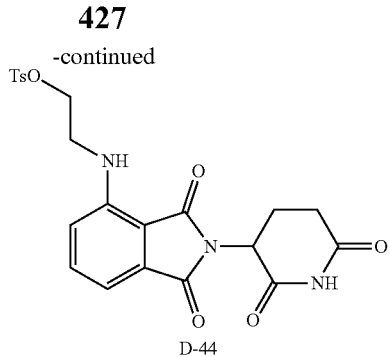

D-44

2-((2-(2,6-dioxopiperidin-3-yl)-1,3-dioxoisoindolin-4-yl)amino)ethyl 4-methylbenzene-sulfonate (D-44

In a 4 mL glass vial, 2-(2,6-dioxopiperidin-3-yl)-4-((2-hydroxyethyl)amino)isoindoline-1,3-dione (7 mg, 0.0221 mmol, 1 equiv) and Et$_3$N (3 µL, 0.033 mmol, 1.5 equiv) in CH$_2$Cl$_2$ (200 µL) was stirred at room temperature. Tosyl chloride (6 mg, 0.026 mmol, 1.2 equiv) in CH$_2$Cl$_2$ (100 µL) was added, and the reaction mixture was stirred at room temperature overnight. The reaction mixture was concentrated in vacuo and the residue was purified by flash column chromatography on silica gel (0-10% MeOH in CH$_2$Cl$_2$) to afford the title compound as a white solid (4 mg, 40%). $^1$H NMR (500 MHz, DMSO-d$_6$) δ 11.13 (s, 1H), 7.64-7.59 (m, 2H), 7.46 (dd, J=8.6, 7.1 Hz, 1H), 7.33-7.27 (m, 2H), 7.04-6.93 (m, 2H), 6.58 (t, J=6.4 Hz, 1H), 5.09 (dd, J=12.7, 5.4 Hz, 1H), 4.15 (t, J=5.1 Hz, 2H), 3.65-3.52 (m, 2H), 2.97-2.83 (m, 1H), 2.67-2.46 (m, 2H), 2.27 (s, 3H), 2.12-2.02 (m, 1H); MS (ESI) calcd for C$_{22}$H$_{22}$N$_3$O$_7$S [M+H]$^+$ 472.12, found 472.39.

(R)-4-hydroxy-2-(3-methyl-2,6-dioxopiperidin-3-yl)isoindoline-1,3-dione (D-52

Hydroxyisobenzofuran-1,3-dione (147.08 mg, 0.896 mmol, 1 eq) was added to (R)-3-amino-3-methylpiperidine-2,6-dione hydrochloric acid (127.32 mg, 0.896 mmol, 1 eq). Pyridine (3.584 ml, 0.25 M) was then added to the mixture and it was stirred at 110° C. for 17 hours. The mixture was diluted with methanol and was condensed under reduced pressure. The crude material was purified by column chromatography (ISCO, 24 g silica column, 0 to 10% MeOH/DCM 25 minute gradient) to give a white oil (110.9 mg, 42.63% yield). $^1$H NMR (400 MHz, DMSO-d$_6$) δ 10.95 (s, 1H), 7.61 (dd, J=8.4, 7.2 Hz, 1H), 7.27-7.14 (m, 2H), 2.73-2.63 (m, 1H), 2.57-2.51 (m, 1H), 2.04-1.97 (m, 1H), 1.86 (s, 3H).
LCMS 289 (M+H).

(S)-4-hydroxy-2-(3-methyl-2,6-dioxopiperidin-3-yl)isoindoline-1,3-dione (D-53

4-hydroxyisobenzofuran-1,3-dione (148.99 mg, 0.907 mmol, 1 eq) was added to (S)-3-amino-3-methylpiperidine-2,6-dione hydrochloric acid (128.97 mg, 0.907 mmol, 1 eq). Pyridine (3.628 ml, 0.25 M) was then added to the mixture and it was stirred at 110° C. for 17 hours. The mixture was diluted with methanol and was condensed under reduced pressure. The crude material was purified by column chromatography (ISCO, 24 g silica column, 0 to 10% MeOH/DCM 25 minute gradient) to give a white oil (150 mg, 57.4% yield). $^1$H NMR (400 MHz, DMSO-d$_6$) δ 10.95 (s, 1H), 7.62 (dd, J=8.4, 7.2 Hz, 1H), 7.27-7.16 (m, 2H), 2.75-2.62 (m, 1H), 2.55 (dd, J=14.0, 4.3 Hz, 1H), 2.05-1.96 (m, 1H), 1.86 (s, 3H). LCMS 289 (M+H).

(S)-2-((2-(3-methyl-2,6-dioxopiperidin-3-yl)-1,3-dioxoisoindolin-4-yl)oxy)acetic Acid (D-55

TFA (0.63 ml, 0.1 M) was added to tert-butyl (S)-2-((2-(3-methyl-2,6-dioxopiperidin-3-yl)-1,3-dioxoisoindolin-4-yl)oxy)acetate (25.4 mg, 0.063 mmol, 1 eq) and the mixture was stirred at 50° C. for an hour. The mixture was then diluted with methanol and condensed under reduced pressure to give a white powder (20.5 mg, 93.9% yield) that was carried forward without further purification. $^1$H NMR (500 MHz, Methanol-d$_4$) δ 7.81-7.75 (m, 1H), 7.50 (d, J=7.3 Hz, 1H), 7.45 (d, J=8.6 Hz, 2H), 7.43-7.37 (m, 3H), 5.09 (dd, J=12.8, 5.5 Hz, 1H), 4.76 (s, 2H), 4.63 (dd, J=9.1, 5.2 Hz, 1H), 3.66-3.55 (m, 30H), 3.51-3.41 (m, 5H), 2.90-2.83 (m, 1H), 2.79-2.71 (m, 2H), 2.69 (s, 3H), 2.43 (s, 3H), 2.14 (ddt, J=10.5, 5.5, 3.2 Hz, 1H), 1.69 (s, 3H). LCMS 347 (M+H).

(R)-2-((2-(3-methyl-2,6-dioxopiperidin-3-yl)-1,3-dioxoisoindolin-4-yl)oxy)acetic acid (D-54

TFA (1.78 ml, 0.1 M) was added to tert-butyl (R)-2-((2-(3-methyl-2,6-dioxopiperidin-3-yl)-1,3-dioxoisoindolin-4-yl)oxy)acetate (71.3 mg, 0.178 mmol, 1 eq) and the mixture was stirred at 50° C. for an hour. The mixture was then diluted with methanol and condensed under reduced pressure to give a white powder (47.2 mg, 76.63% yield) that was carried forward without further purification. $^1$H NMR (400 MHz, Methanol-d$_4$) δ 7.72 (ddd, J=8.5, 7.3, 5.0 Hz, 1H), 7.46-7.42 (m, 1H), 7.30 (dd, J=8.6, 4.5 Hz, 1H), 4.94 (d, J=5.3 Hz, 2H), 2.81-2.56 (m, 2H), 2.24-2.07 (m, 1H), 2.00 (s, 2H), 0.90 (t, J=6.5 Hz, 2H). LCMS 347 (M+H).

4,7-dichloro-2-(2,6-dioxopiperidin-3-yl)isoindoline-1,3-dione (D-51

4,7-dichloroisobenzofuran-1,3-dione (434.6 mg, 2.002 mmol, 1 eq) was added to 3-aminopiperidine-2,6-dione hydrochloric acid (362.6 mg, 2.203 mmol, 1.1 eq). Potassium acetate (609.07 mg, 6.206 mmol, 3.1 eq) and acetic acid (6.67 ml, 0.3 M) were then added to the mixture and it was stirred at 90° C. for 18 hours. The mixture was cooled down to room temperature, diluted with DI water and centrifuged for 5 minutes. The precipitate was diluted with methanol and was condensed under reduced pressure. The crude material was purified by column chromatography (ISCO, 12 g silica column, 0 to 10% MeOH/DCM 25 minute gradient) to give a white powder (160.4 mg, 24.5% yield). $^1$H NMR (500 MHz, DMSO-d$_6$) δ 11.15 (s, 1H), 7.91 (s, 2H), 5.17 (dd, J=12.9, 5.4 Hz, 1H), 2.88 (ddd, J=17.2, 13.9, 5.4 Hz, 1H), 2.68-2.54 (m, 1H), 2.05 (ddd, J=10.5, 5.4, 2.7 Hz, 1H). LCMS 328 (M+H).

Synthetic Example 1: Synthesis of dBET1

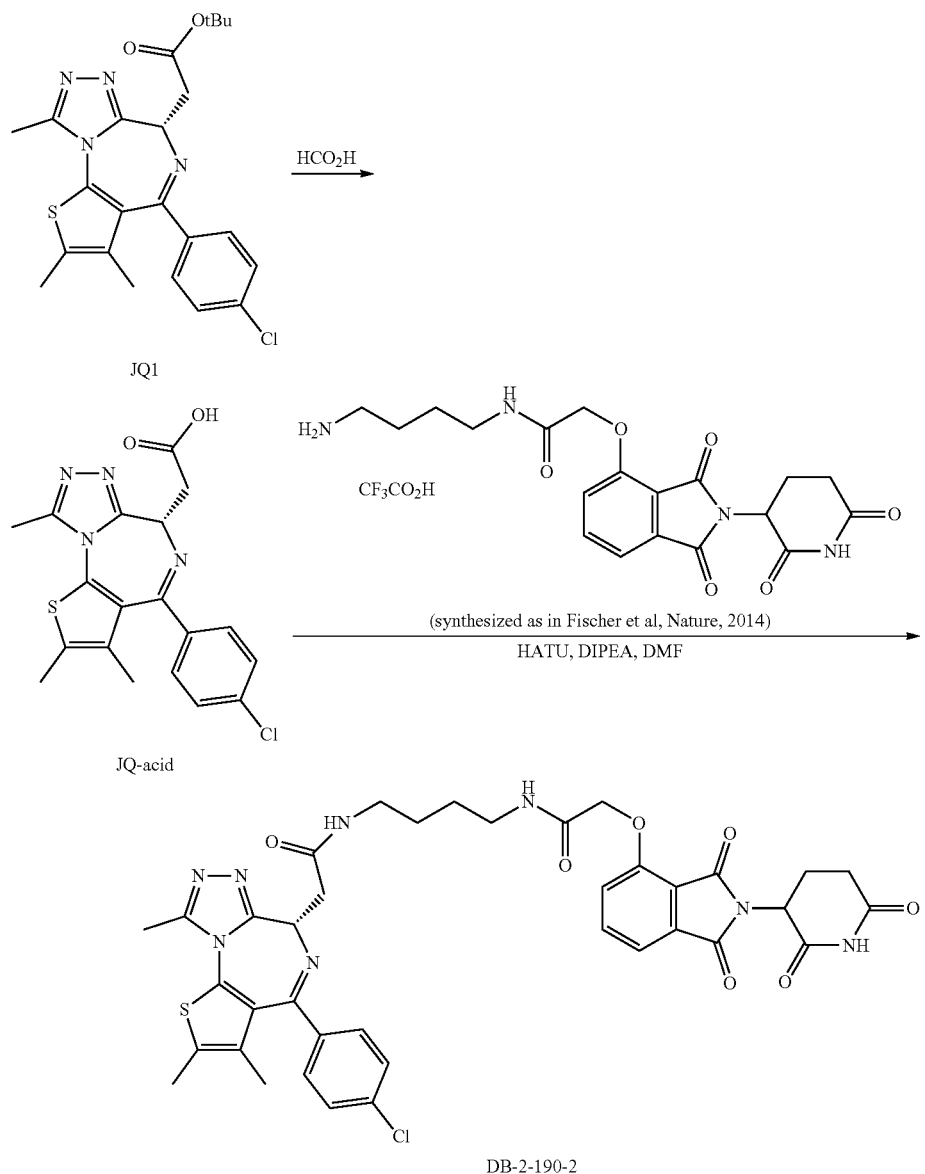

(1) Synthesis of JQ-Acid

JQ1 (1.0 g, 2.19 mmol, 1 eq) was dissolved in formic acid (11 mL, 0.2 M) at room temperature and stirred for 75 hours. The mixture was concentrated under reduced pressure to give a yellow solid (0.99 g, quant yield) that was used without purification. $^1$H NMR (400 MHz, Methanol-$d_4$) δ 7.50-7.36 (m, 4H), 4.59 (t, J=7.1 Hz, 1H), 3.51 (d, J=7.1 Hz, 2H), 2.70 (s, 3H), 2.45 (s, 3H), 1.71 (s, 3H). LCMS 401.33 (M+H).

N-(4-aminobutyl)-2-((2-(2,6-dioxopiperidin-3-yl)-1,3-di-oxoisoindolin-4-yl)oxy)acetamidetrifluoroacetate was synthesized according to the previously published procedure (Fischer et al., Nature 512 (2014):49).

(2) Synthesis of dBET1

JQ-acid (11.3 mg, 0.0281 mmol, 1 eq) and N-(4-aminobutyl)-2-((2-(2,6-dioxopiperidin-3-yl)-1,3-dioxoisoindolin-4-yl)oxy)acetamide trifluoroacetate (14.5 mg, 0.0281 mmol, 1 eq) were dissolved in DMF (0.28 mL, 0.1 M) at room temperature. DIPEA (14.7 microliters, 0.0843 mmol, 3 eq) and HATU (10.7 mg, 0.0281 mmol, 1 eq) were then added and the mixture was stirred for 19 hours. The mixture was then purified by preparative HPLC to give dBET1 as a yellow solid (15.90 mg, 0.0202 mmol, 72%). $^1$H NMR (400 MHz, Methanol-$d_4$) δ 7.77 (dd, J=8.3, 7.5 Hz, 1H), 7.49 (d, J=7.3 Hz, 1H), 7.47-7.37 (m, 5H), 5.07 (dd, J=12.5, 5.4 Hz, 1H), 4.74 (s, 2H), 4.69 (dd, J=8.7, 5.5 Hz, 1H), 3.43-3.32 (m, 3H), 3.29-3.25 (m, 2H), 2.87-2.62 (m, 7H), 2.43 (s, 3H), 2.13-2.04 (m, 1H), 1.72-1.58 (m, 7H). $^{13}$C NMR (100 MHz, cd$_3$od) δ 174.41, 172.33, 171.27, 171.25, 169.87, 168.22, 167.76, 166.73, 166.70, 156.26, 138.40, 138.23, 137.44, 134.83, 133.92, 133.40, 132.30, 132.28, 131.97, 131.50, 129.87, 121.85, 119.31, 118.00, 69.53, 54.90, 50.54, 40.09, 39.83, 38.40, 32.12, 27.74, 27.65, 23.61, 14.42, 12.97, 11.57. LCMS 785.44 (M+H).

Synthetic Example 2: Synthesis of dBET4

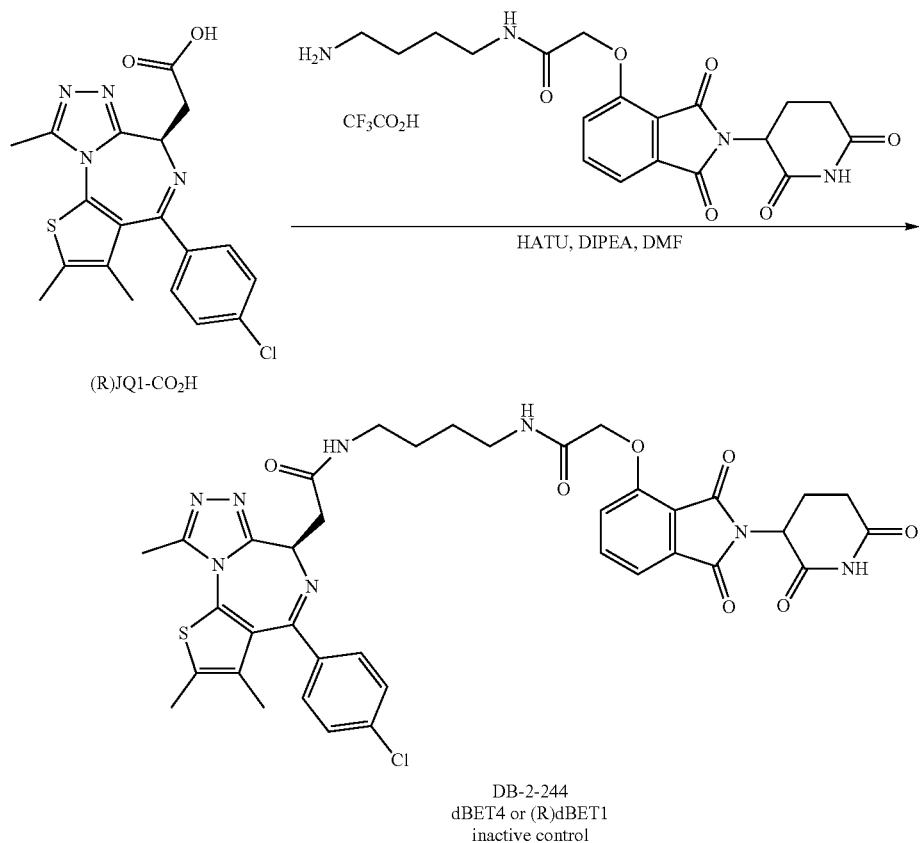

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.438 mL, 0.0438 mmol 1.2 eq) was added to (R)-JQ-acid (prepared from (R)-JQ1 in an analogous method to JQ-acid) (14.63 mg, 0.0365 mmol, 1 eq) at room temperature. DIPEA (19.1 microliters, 0.1095 mmol, 3 eq) and HATU (15.3 mg, 0.0402 mmol, 1.1 eq) were added and the mixture was stirred for 24 hours, then diluted with MeOH and concentrated under reduced pressure. The crude material was purified by preparative HPLC to give a yellow solid (20.64 mg, 0.0263 mmol, 72%). $^1$H NMR (400 MHz, Methanol-$d_4$) δ 7.79 (dd, J=8.4, 7.4 Hz, 1H), 7.51 (d, J=7.3 Hz, 1H), 7.47-7.39 (m, 5H), 5.11-5.06 (m, 1H), 4.75 (s, 2H), 4.68 (dd, J=8.8, 5.5 Hz, 1H), 3.47-3.31 (m, 5H), 2.83-2.65 (m, 7H), 2.44 (s, 3H), 2.13-2.06 (m, 1H), 1.68 (s, 3H), 1.67-1.60 (m, 4H). $^{13}$C NMR (100 MHz, cd$_3$od) δ 174.43, 172.40, 171.29, 169.92, 168.24, 167.82, 166.71, 156.31, 153.14, 138.38, 138.24, 137.54, 134.88, 133.86, 133.44, 132.29, 132.00, 131.49, 129.88, 122.46, 121.90, 119.38, 118.02, 69.59, 54.96, 50.55, 40.09, 39.84, 38.45, 32.14, 27.75, 27.65, 23.62, 14.41, 12.96, 11.56. MS 785.48 (M+H).

Synthetic Example 3: Synthesis of dBET3

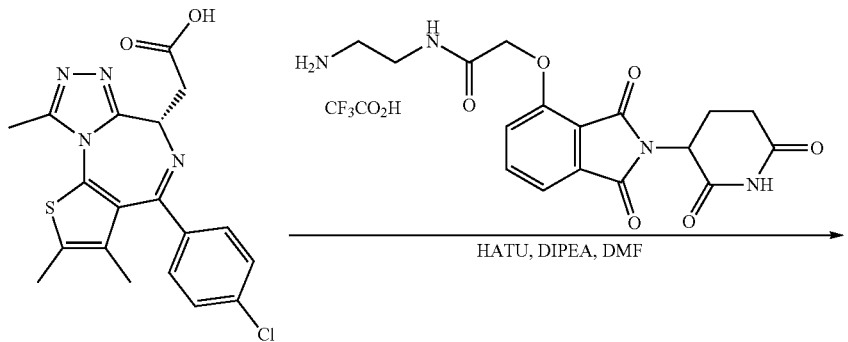

-continued

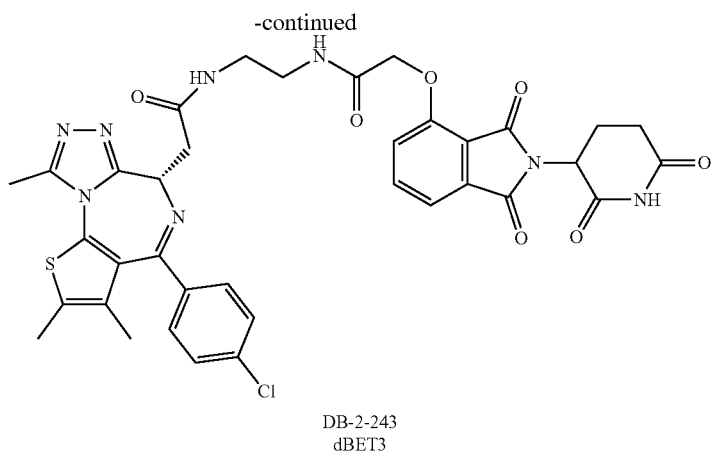

DB-2-243
dBET3

A 0.1 M solution of N-(2-aminoethyl)-2-((2-(2,6-dioxopiperidin-3-yl)-1,3-dioxoisoindolin-4-yl)oxy)acetamide trifluoroacetate in DMF (0.475 mL, 0.0475 mmol, 1.2 eq) was added to JQ-acid (15.86 mg, 0.0396 mmol, 1 eq) at room temperature. DIPEA (20.7 microliters, 0.1188 mmol, 3 eq) and HATU (16.5 mg, 0.0435 mmol, 1.1 eq) were then added and the mixture was stirred for 24 hours, then purified by preparative HPLC to give a yellow solid (22.14 mg, 0.0292 mmol, 74%). $^1$H NMR (400 MHz, Methanol-$d_4$) δ 7.82-7.75 (m, 1H), 7.52-7.32 (m, 6H), 5.04 (dd, J=11.6, 5.5 Hz, 1H), 4.76 (d, J=3.2 Hz, 2H), 4.66 (d, J=6.6 Hz, 1H), 3.58-3.35 (m, 6H), 2.78-2.58 (m, 6H), 2.48-2.41 (m, 3H), 2.11-2.02 (m, 1H), 1.70 (d, J=11.8 Hz, 3H). $^{13}$C NMR (100 MHz, cd$_3$od) δ 174.38, 171.26, 171.19, 170.26, 168.86, 168.21, 167.76, 166.72, 156.27, 153.14, 138.44, 138.36, 138.19, 134.87, 133.71, 132.31, 131.57, 131.51, 129.90, 129.86, 121.81, 119.36, 117.95, 69.48, 54.83, 50.52, 40.09, 39.76, 38.30, 32.09, 23.63, 14.40, 11.61. LCMS 757.41 (M+H).

Synthetic Example 4: Synthesis of dBET5

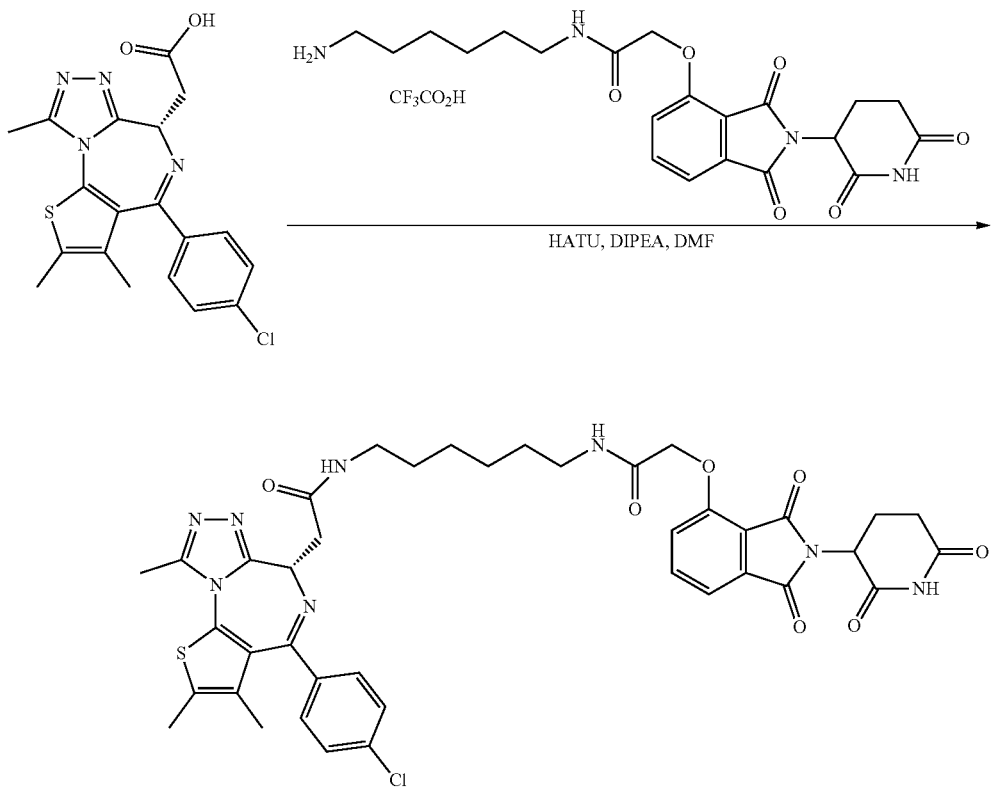

DB-2-264
dBET5

A 0.1M solution of N-(6-aminohexyl)-2-((2-(2,6-dioxopiperidin-3-yl)-1,3-dioxoisoindolin-4-yl)oxy)acetamide trifluoroacetate in DMF (0.247 mL, 0.0247 mmol, 1 eq) was added to JQ-acid (9.9 mg, 0.0247 mmol, 1 eq) at room temperature. DIPEA (12.9 microliters, 0.0741 mmol, 3 eq) and HATU (9.4 mg, 0.0247 mmol, 1 eq) were then added. the mixture was stirred for 21 hours, then diluted with MeOH and concentrated under reduced pressure. The crude material was purified by preparative HPLC to give a yellow solid (13.56 mg, 0.0167 mmol, 67%). $^1$H NMR (400 MHz, Methanol-$d_4$) δ 7.82-7.78 (m, 1H), 7.53 (dd, J=7.3, 2.0 Hz, 1H), 7.49-7.37 (m, 5H), 5.10 (dt, J=12.4, 5.3 Hz, 1H), 4.76 (s, 2H), 4.70 (dd, J=8.7, 5.5 Hz, 1H), 3.42-3.33 (m, 2H), 3.25 (dt, J=12.3, 6.0 Hz, 3H), 2.87-2.67 (m, 7H), 2.48-2.42 (m, 3H), 2.14-2.09 (m, 1H), 1.69 (d, J=4.8 Hz, 3H), 1.58 (s, 4H), 1.42 (d, J=5.2 Hz, 4H). $^{13}$C NMR (100 MHz, cd$_3$od) δ 174.51, 171.31, 171.26, 169.82, 168.27, 168.26, 167.75, 156.26, 150.46, 138.20, 134.92, 133.92, 133.47, 132.34, 132.01, 131.52, 129.88, 121.69, 119.34, 117.95, 111.42, 69.39, 54.97, 50.56, 40.39, 40.00, 38.40, 32.15, 30.46, 30.16, 27.58, 27.48, 23.64, 14.41, 12.96, 11.55. LCMS 813.38.

Synthetic Example 5: Synthesis of dBET6

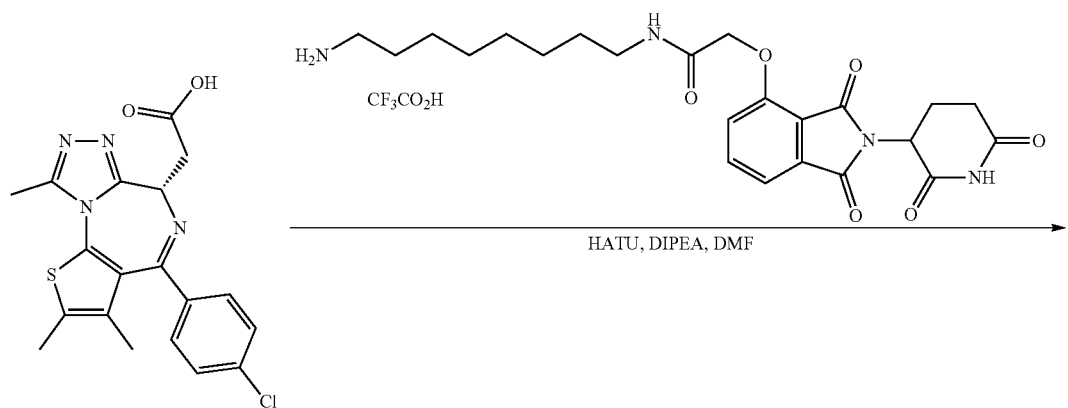

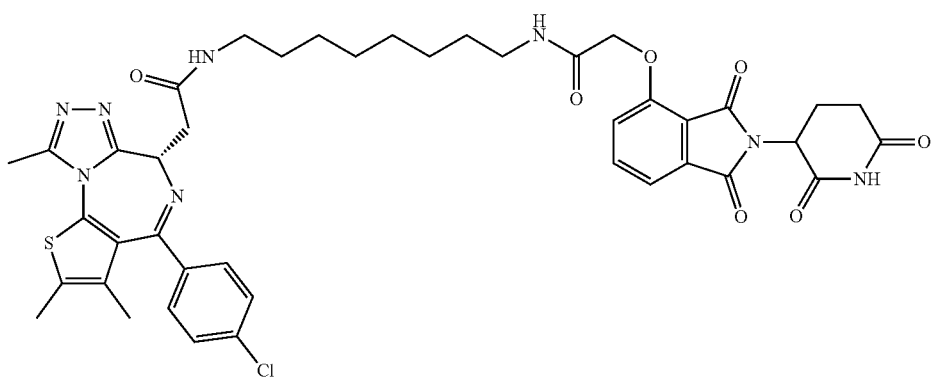

DB-2-270
dBET6

A 0.1M solution of N-(8-aminooctyl)-2-((2-(2,6-dioxopiperidin-3-yl)-1,3-dioxoisoindolin-4-yl)oxy)acetamide trifluoroacetate in DMF (0.191 mL, 0.0191 mmol, 1 eq) was added to JQ-acid (7.66 mg, 0.0191 mmol, 1 eq) at room temperature. DIPEA (10 microliters, 0.0574 mmol, 3 eq) and HATU (7.3 mg, 0.0191 mmol, 1 eq) were added and the mixture was stirred for 22 hours, diluted with MeOH, and concentrated under reduced pressure. The crude material was purified by preparative HPLC to give a cream colored solid. (8.53 mg, 0.0101 mmol, 53%). $^1$H NMR (400 MHz, Methanol-$d_4$) δ 7.80 (dd, J=8.4, 7.4 Hz, 1H), 7.53 (d, J=7.4 Hz, 1H), 7.49-7.36 (m, 5H), 5.10 (dt, J=12.3, 5.3 Hz, 1H), 4.75 (s, 2H), 4.69 (dd, J=8.8, 5.3 Hz, 1H), 3.42 (dd, J=15.0, 8.9 Hz, 1H), 3.30-3.18 (m, 4H), 2.90-2.64 (m, 7H), 2.45 (s, 3H), 2.13 (dtt, J=10.8, 5.2, 2.6 Hz, 1H), 1.71 (d, J=4.4 Hz, 3H), 1.56 (d, J=6.2 Hz, 4H), 1.33 (d, J=17.1 Hz, 8H). $^{13}$C NMR (100 MHz, cd$_3$od) δ 174.50, 172.38, 171.30, 169.81, 168.28, 167.74, 166.64, 156.25, 138.38, 138.20, 137.55, 134.92, 133.88, 133.42, 132.27, 132.02, 131.50, 129.85, 121.66, 119.30, 117.95, 69.37, 55.01, 50.58, 40.51, 40.12, 38.44, 32.18, 30.46, 30.33, 30.27, 30.21, 27.91, 27.81, 23.63, 14.42, 12.96, 11.55. LCMS 841.64 (M+H).

Synthetic Example 6: Synthesis of dBET9

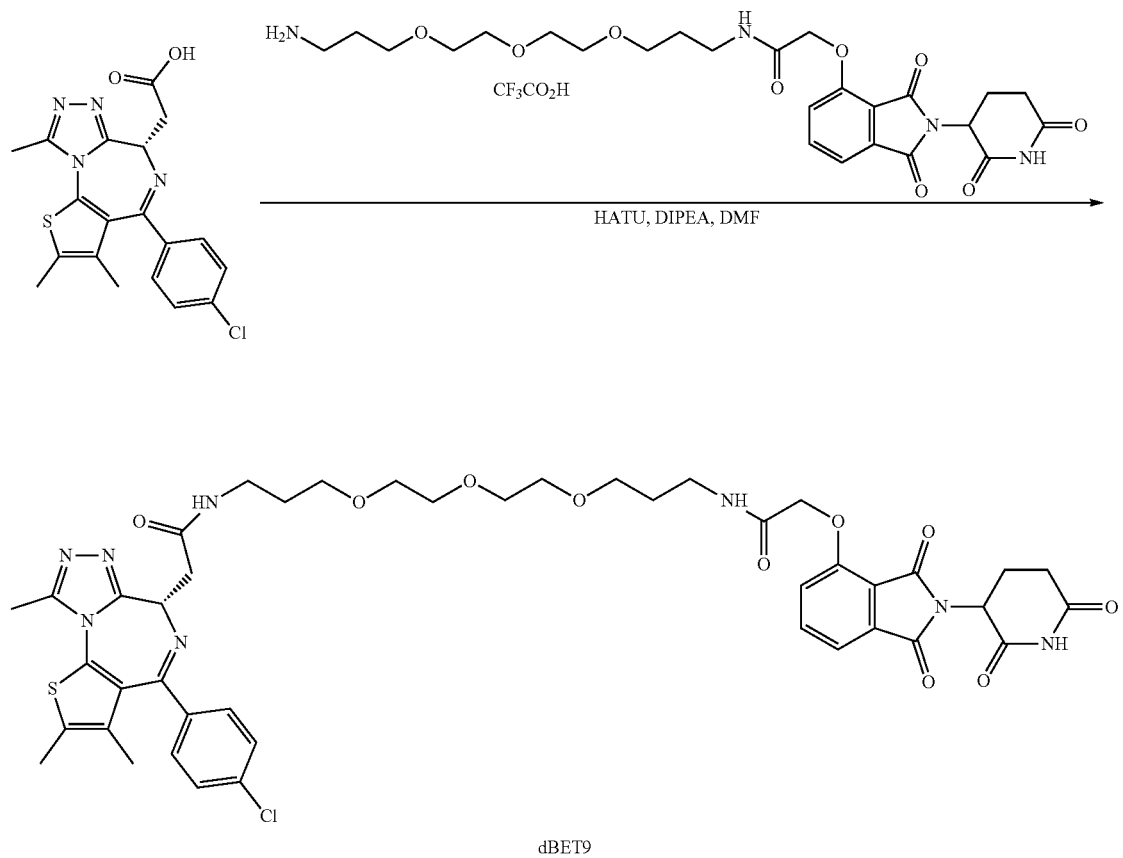 [SMILES: Cc1sc2c(c1C)C(c1ccc(Cl)cc1)=N[C@@H](CC(=O)O)c1nnc(C)n1-2 ; NCCCOCCOCCOCCCNC(=O)COc1cccc2c1C(=O)N(C1CCC(=O)NC1=O)C2=O ; "CF3CO2H" ; Cc1sc2c(c1C)C(c1ccc(Cl)cc1)=N[C@@H](CC(=O)NCCCOCCOCCOCCCNC(=O)COc1cccc3c1C(=O)N(C1CCC(=O)NC1=O)C3=O)c1nnc(C)n1-2]

dBET9

A 0.1M solution of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.321 mL, 0.0321 mmol, 1 eq) was added to JQ-acid (12.87 mg, 0.0321 mmol, 1 eq) at room temperature. DIPEA (16.8 microliters, 0.0963 mmol, 3 eq) and HATU (12.2 mg, 0.0321 mmol, 1 eq) were added and the mixture was stirred for 24 hours, diluted with MeOH, and concentrated under reduced pressure. The crude material was purified by preparative HPLC to give a yellow oil. (16.11 mg, 0.0176 mmol, 55%).

$^1$H NMR (400 MHz, Methanol-$d_4$) δ 7.79 (dd, J=8.4, 7.4 Hz, 1H), 7.52 (d, J=7.2 Hz, 1H), 7.49-7.36 (m, 5H), 5.10 (dd, J=12.5, 5.5 Hz, 1H), 4.78-4.67 (m, 3H), 3.64-3.52 (m, 11H), 3.48-3.32 (m, 6H), 2.94-2.64 (m, 7H), 2.52-2.43 (m, 3H), 2.18-2.08 (m, 1H), 1.81 (p, J=6.3 Hz, 4H), 1.73-1.67 (m, 3H). LCMS 918.45 (M+H).

Synthetic Example 7: Synthesis of dBET17

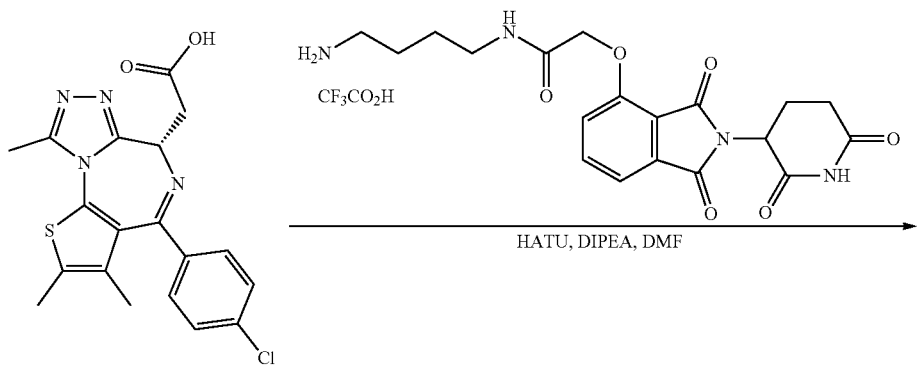

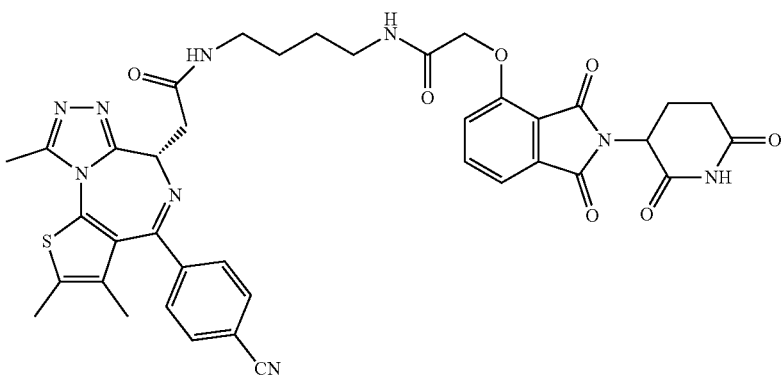

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.281 mL, 0.0281 mmol 1 eq) was added to (S)-2-(4-(4-cyanophenyl)-2,3,9-trimethyl-6H-thieno[3,2-f][1,2,4]triazolo[4,3-a][1,4]diazepin-6-yl)acetic acid (11 mg, 0.0281 mmol, 1 eq) at room temperature. DIPEA (14.7 microliters, 0.0843 mmol, 3 eq) and HATU (10.7 mg, 0.0281 mmol, 1 eq) were added and the mixture was stirred for 24 hours, diluted with EtOAc and washed with saturated sodium bicarbonate, water and brine. The organic layer was dried over sodium sulfate, filtered and condensed. Purification by column chromatography (ISCO, 4 g silica column 0-10% MeOH/DCM) gave a white solid (14.12 mg, 0.0182 mmol, 65%).

$^1$H NMR (400 MHz, Methanol-$d_4$) δ 7.82-7.72 (m, 3H), 7.61 (dd, J=8.5, 2.0 Hz, 2H), 7.51 (d, J=7.9 Hz, 1H), 7.44-7.40 (m, 1H), 5.11-5.05 (m, 1H), 4.76 (s, 2H), 4.66 (dd, J=9.0, 5.1 Hz, 1H), 3.48-3.32 (m, 4H), 3.30-3.23 (m, 1H), 2.87-2.61 (m, 7H), 2.43 (s, 3H), 2.10 (dt, J=10.7, 5.2 Hz, 1H), 1.70-1.59 (m, 7H). $^{13}$C NMR (100 MHz, cd$_3$od) δ 174.42, 172.65, 171.27, 169.92, 168.25, 167.80, 165.88, 156.31, 143.55, 138.24, 134.88, 133.92, 133.50, 133.39, 131.72, 131.46, 130.55, 121.93, 119.39, 119.21, 118.02, 115.17, 69.59, 55.50, 50.55, 40.10, 39.83, 38.86, 32.11, 27.78, 27.67, 23.62, 14.41, 12.91, 11.64. LCMS 776.39 (M+H).

Synthetic Example 8: Synthesis of dBET15

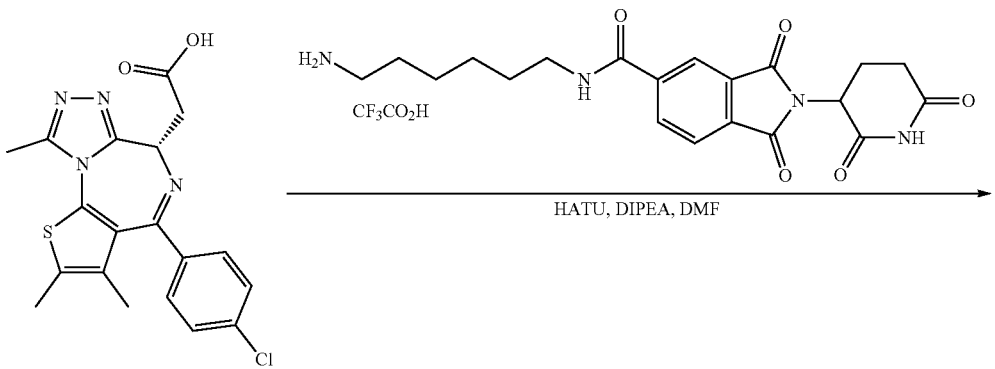

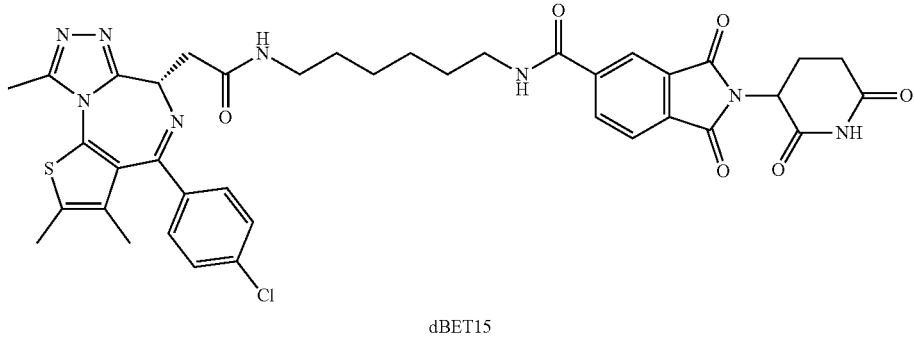

dBET15

N-(6-aminohexyl)-2-(2,6-dioxopiperidin-3-yl)-1,3-dioxoisoindoline-5-carboxamide trifluoroacetate (13.29 mg, 0.258 mmol, 1 eq) and JQ-acid (10.3 mg, 0.0258 mmol, 1 eq) were dissolved in DMF (0.26 mL). DIPEA (13.5 microliters, 0.0775 mmol, 3 eq) was added, followed by HATU (9.8 mg, 0.0258 mmol, 1 eq) and the mixture was stirred at room temperature. After 24 hours, the material was diluted with DCM and purified by column chromatography (ISCO, 0-15% MeOH/DCM) followed by preparative HPLC to give a pale yellow solid (11.44 mg, 0.0146 mmol 57%).

$^1$H NMR (400 MHz, Methanol-d$_4$) δ 8.29-8.23 (m, 2H), 7.93 (dd, J=8.1, 4.2 Hz, 1H), 7.50-7.34 (m, 4H), 5.17-5.11 (m, 1H), 4.75-4.69 (m, 1H), 3.53-3.32 (m, 6H), 3.25 (dd, J=13.8, 6.7 Hz, 1H), 2.90-2.67 (m, 6H), 2.49-2.38 (m, 3H), 2.18-2.10 (m, 1H), 1.64 (d, J=22.4 Hz, 6H), 1.47 (s, 4H). $^{13}$C NMR (100 MHz, cd$_3$od) δ 174.48, 171.17, 168.05, 168.03, 167.99, 167.70, 166.63, 141.81, 138.40, 137.47, 135.09, 134.77, 134.74, 133.96, 133.94, 133.38, 132.24, 132.05, 131.44, 129.85, 124.57, 123.12, 123.09, 54.98, 50.78, 40.88, 40.08, 38.37, 32.13, 30.40, 30.23, 27.34, 27.26, 23.58, 14.40, 12.96, 11.54. LCMS 783.43 (M+H).

Synthetic Example 9: Synthesis of dBET2

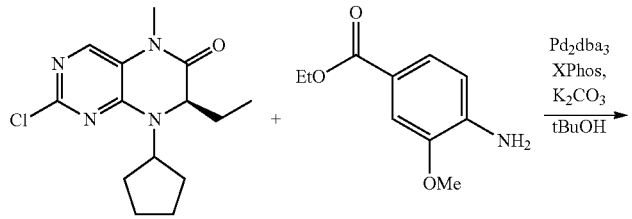

ref: ACIEE, 2011, 50, 9378

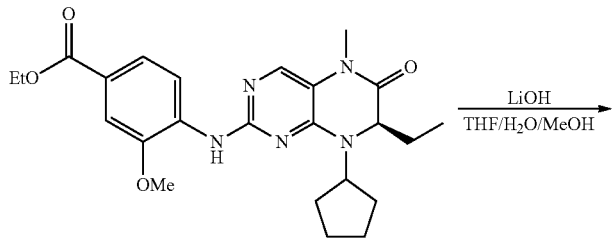

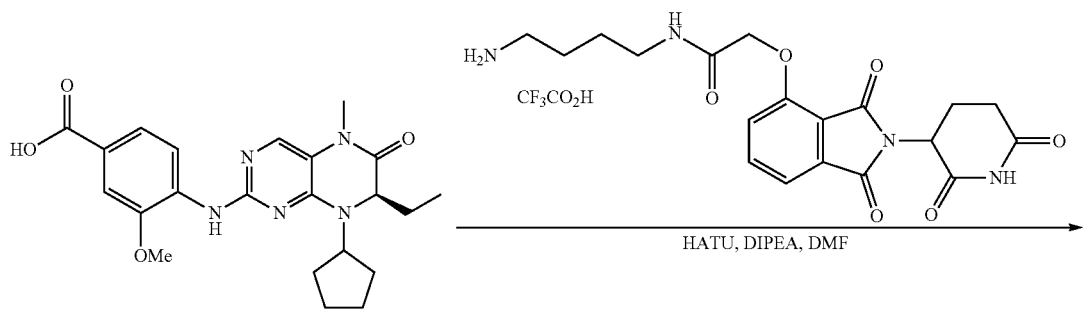

-continued

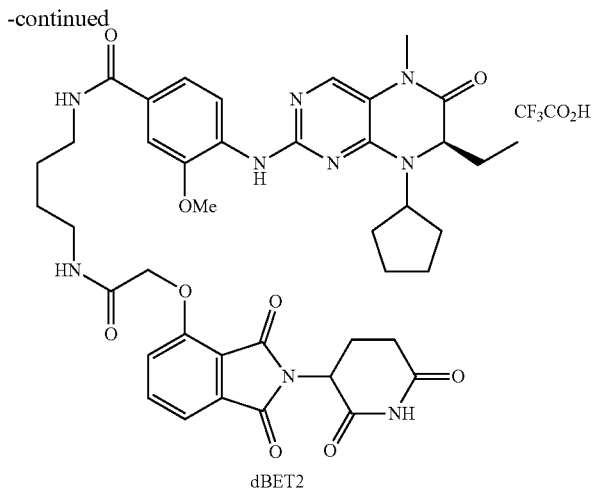

dBET2

(1) Synthesis of (R)-ethyl 4-((8-cyclopentyl-7-ethyl-5-methyl-6-oxo-5,6,7,8-tetrahydropteridin-2-yl)amino)-3-methoxybenzoate

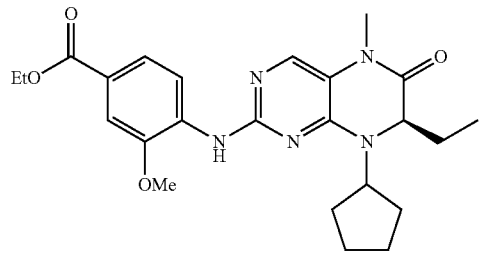 [SMILES: CCOC(=O)c1ccc(Nc2ncc3c(n2)N(C2CCCC2)[C@H](CC)C(=O)N3C)c(OC)c1]

(R)-2-chloro-8-cyclopentyl-7-ethyl-5-methyl-7,8-dihydropteridin-6(5H)-one (44.2 mg, 0.15 mmol, 1 eq), ethyl 4-amino-3-methoxybenzoate (35.1 mg, 0.18 mmol, 1.2 eq), Pd$_2$dba$_3$ (6.9 mg, 0.0075 mmol, 5 mol %), XPhos (10.7 mg, 0.0225 mmol, 15 mol %) and potassium carbonate (82.9 mg, 0.60 mmol, 4 eq) were dissolved in tBuOH (1.5 mL, 0.1 M) and heated to 100° C. After 21 hours, the mixture was cooled to room temperature, filtered through celite, washed with DCM and concentrated under reduced pressure. Purification by column chromatography (ISCO, 4 g silica column, 0-100% EtOAc/hexanes over an 18 minute gradient) gave a yellow oil (52.3 mg, 0.115 mmol, 77%). $^1$H NMR (400 MHz, Chloroform-d) δ 8.57 (d, J=8.5 Hz, 1H), 7.69 (td, J=6.2, 2.9 Hz, 2H), 7.54 (d, J=1.8 Hz, 1H), 4.52 (t, J=7.9 Hz, 1H), 4.37 (q, J=7.1 Hz, 2H), 4.23 (dd, J=7.9, 3.7 Hz, 1H), 3.97 (s, 3H), 3.33 (s, 3H), 2.20-2.12 (m, 1H), 2.03-1.97 (m, 1H), 1.86 (ddd, J=13.9, 7.6, 3.6 Hz, 4H), 1.78-1.65 (m, 4H), 1.40 (t, J=7.1 Hz, 3H), 0.88 (t, J=7.5 Hz, 3H). LCMS 454.32 (M+H).

(2) Synthesis of (R)-4-((8-cyclopentyl-7-ethyl-5-methyl-6-oxo-5,6,7,8-tetrahydropteridin-2-yl)amino)-3-methoxybenzoic Acid

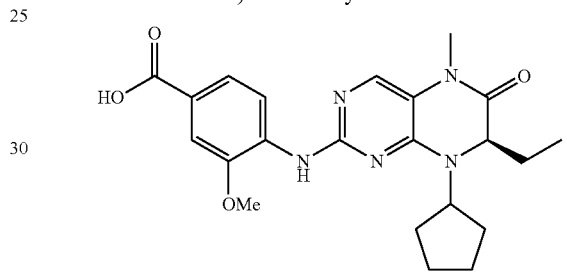

(R)-ethyl 4-((8-cyclopentyl-7-ethyl-5-methyl-6-oxo-5,6,7,8-tetrahydropteridin-2-yl)amino)-3-methoxybenzoate (73.8 mg, 0.163 mmol, 1 eq) and LiOH (11.7 mg, 0.489 mmol, 3 eq) were dissolved in MeOH (0.82 mL) THF (1.63 mL) and water (0.82 mL). After 20 hours, an additional 0.82 mL of water was added and the mixture was stirred for an additional 24 hours before being purified by preparative HPLC to give a cream colored solid (53 mg, 0.125 mmol, 76%). $^1$H NMR (400 MHz, Methanol-d$_4$) δ 7.97 (d, J=8.4 Hz, 1H), 7.67 (dd, J=8.3, 1.6 Hz, 1H), 7.64-7.59 (m, 2H), 4.38 (dd, J=7.0, 3.2 Hz, 1H), 4.36-4.29 (m, 1H), 3.94 (s, 3H), 3.30 (s, 3H), 2.13-1.98 (m, 2H), 1.95-1.87 (m, 2H), 1.87-1.76 (m, 2H), 1.73-1.57 (m, 4H), 0.86 (t, J=7.5 Hz, 3H). $^{13}$C NMR (100 MHz, cd$_3$od) δ 168.67, 163.72, 153.59, 150.74, 150.60, 130.95, 127.88, 125.97, 123.14, 121.68, 116.75, 112.35, 61.76, 61.66, 56.31, 29.40, 29.00, 28.68, 28.21, 23.57, 23.41, 8.69. LCMS 426.45 (M+H).

(3) Synthesis of dBET2

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.183 mL, 0.0183 mmol 1.2 eq) was added to (R)-4-((8-cyclopentyl-7-ethyl-5-methyl-6-oxo-5,6,7,8-tetrahydropteridin-2-yl)amino)-3-methoxybenzoic acid (6.48 mg, 0.0152 mmol, 1 eq) at room temperature. DIPEA (7.9 microliters, 0.0456 mmol, 3 eq) and HATU (6.4 mg, 0.0168 mmol, 1.1 eq) were added and the mixture was stirred for 23 hours, before being purified by preparative HPLC to give a yellow solid (9.44 mg, 0.0102 mmol, 67%). $^1$H NMR (400 MHz, Methanol-d$_4$) δ 7.84-7.77 (m, 2H), 7.58

(d, J=1.8 Hz, 2H), 7.53-7.46 (m, 2H), 7.42 (d, J=8.4 Hz, 1H), 5.11-5.05 (m, 1H), 4.76 (s, 2H), 4.48 (dd, J=6.5, 3.1 Hz, 1H), 4.33-4.24 (m, 1H), 3.95 (s, 3H), 3.49-3.35 (m, 4H), 2.97 (d, J=10.5 Hz, 3H), 2.89-2.65 (m, 5H), 2.17-1.99 (m, 4H), 1.89 (dd, J=14.5, 7.3 Hz, 2H), 1.69-1.54 (m, 6H), 1.36 (dt, J=7.6, 3.9 Hz, 1H), 0.85 (t, J=7.5 Hz, 3H). $^{13}$C NMR (100 MHz, cd$_3$od) δ 176.52, 174.48, 173.05, 171.34, 169.99, 168.91, 168.25, 167.80, 164.58, 156.34, 154.48, 153.10, 150.63, 138.22, 134.89, 133.96, 129.53, 123.93, 121.87, 120.78, 119.36, 117.99, 111.54, 69.55, 63.29, 63.10, 56.68, 50.55, 40.71, 39.86, 32.15, 29.43, 29.26, 28.73, 28.63, 27.81, 27.77, 24.25, 23.63, 8.47. LCMS 810.58 (M+H).

Synthetic Example 10: Synthesis of dBET7

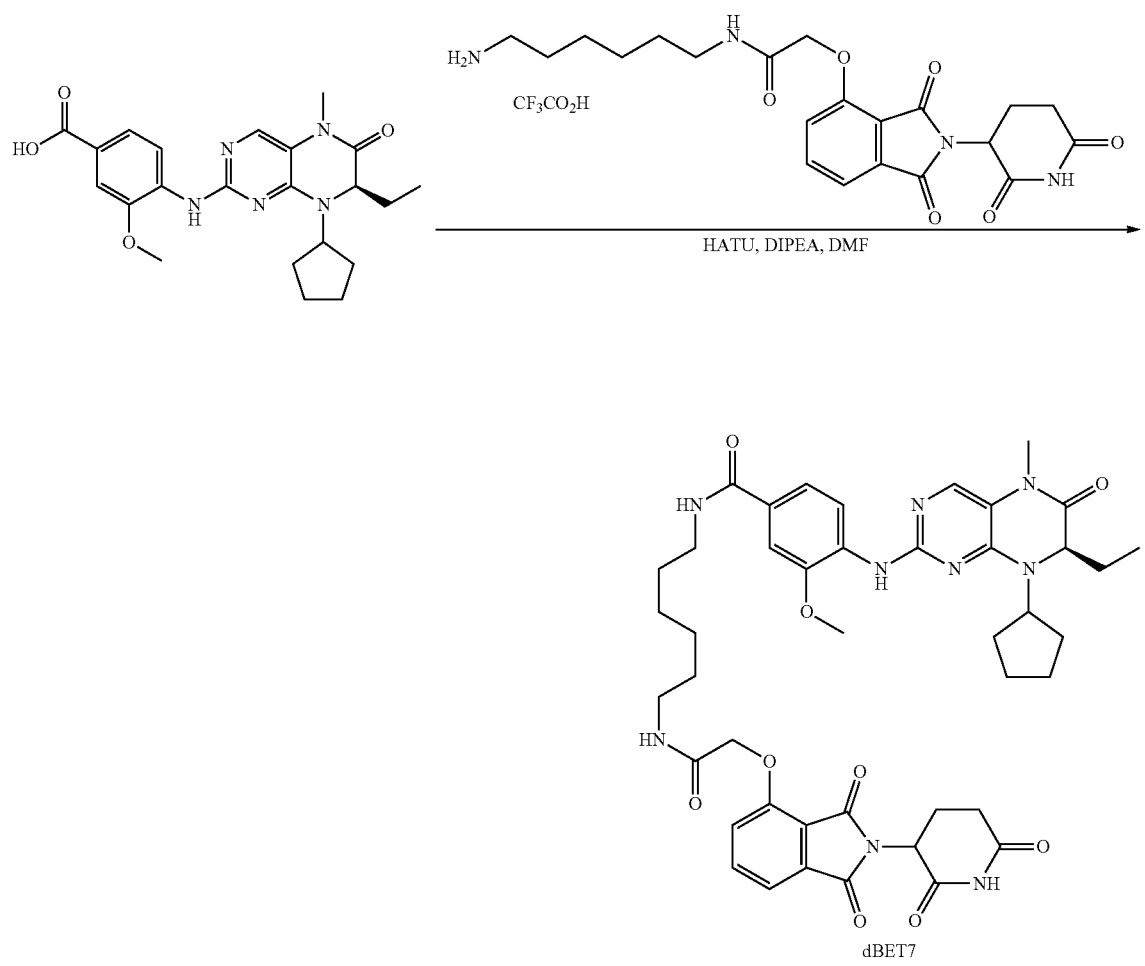

dBET7

A 0.1 M solution N-(6-aminohexyl)-2-((2-(2,6-dioxopiperidin-3-yl)-1,3-dioxoisoindolin-4-yl)oxy)acetamide trifluoroacetate in DMF (0.186 mL, 0.0186 mmol 1 eq) was added to (R)-4-((8-cyclopentyl-7-ethyl-5-methyl-6-oxo-5,6,7,8-tetrahydropteridin-2-yl)amino)-3-methoxybenzoic acid (7.9 mg, 0.0186 mmol, 1 eq) at room temperature. DIPEA (9.7 microliters, 0.0557 mmol, 3 eq) and HATU (7.1 mg, 0.0186 mmol, 1 eq) were added and the mixture was stirred for 19 hours, before being purified by preparative HPLC to give the desired trifluoracetate salt as a yellow solid (13.62 mg, 0.0143 mmol, 77%).

$^1$H NMR (400 MHz, Methanol-d$_4$) δ 7.80 (t, J=8.3 Hz, 2H), 7.61-7.57 (m, 2H), 7.55-7.49 (m, 2H), 7.42 (d, J=8.4 Hz, 1H), 5.13 (dd, J=12.6, 5.5 Hz, 1H), 4.75 (s, 2H), 4.48 (dd, J=6.5, 3.2 Hz, 1H), 4.33-4.24 (m, 1H), 3.97 (s, 3H), 3.40 (t, J=7.1 Hz, 2H), 3.34 (d, J=6.7 Hz, 2H), 3.30 (s, 3H), 2.98 (d, J=8.5 Hz, 1H), 2.89-2.82 (m, 1H), 2.79-2.63 (m, 3H), 2.17-2.00 (m, 4H), 1.91 (dt, J=14.4, 7.1 Hz, 3H), 1.61 (dt, J=13.4, 6.6 Hz, 7H), 1.47-1.41 (m, 3H), 0.86 (t, J=7.5 Hz, 3H). $^{13}$C NMR (100 MHz, cd$_3$od) δ 174.54, 171.37, 169.84, 168.84, 168.27, 167.74, 164.59, 156.26, 154.47, 153.18, 150.69, 138.19, 134.91, 134.05, 129.47, 124.78, 124.01, 121.65, 120.77, 119.29, 117.92, 117.86, 111.55, 69.34, 63.31, 63.13, 56.67, 50.53, 40.97, 39.96, 32.16, 30.42, 30.19, 29.42, 29.26, 28.72, 28.62, 27.65, 27.46, 24.26, 23.65, 8.47. LCMS 838.60 (M+H).

Synthetic Example 11: Synthesis of dBET8

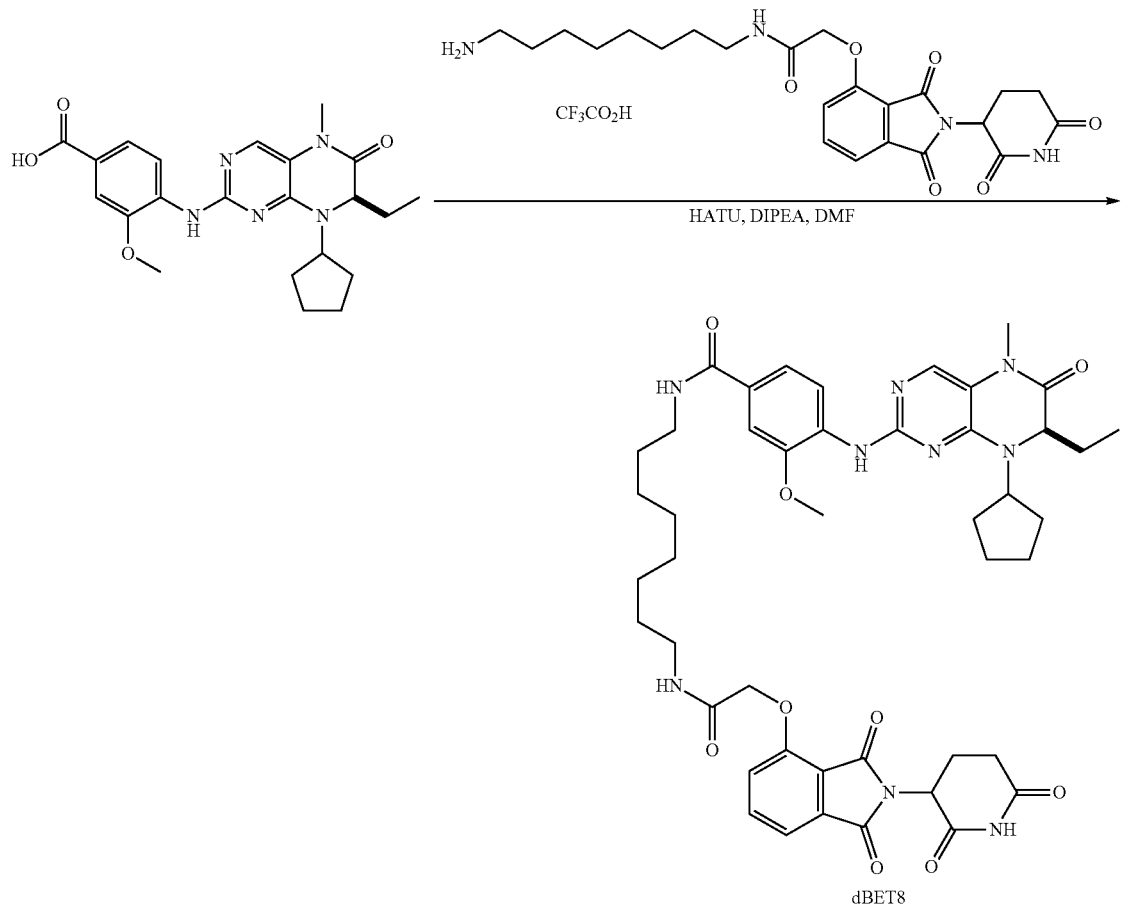

A 0.1 M solution N-(8-aminooctyl)-2-((2-(2,6-dioxopiperidin-3-yl)-1,3-dioxoisoindolin-4-yl)oxy)acetamide trifluoroacetate in DMF (0.186 mL, 0.0186 mmol 1 eq) was added to (R)-4-((8-cyclopentyl-7-ethyl-5-methyl-6-oxo-5,6,7,8-tetrahydropteridin-2-yl)amino)-3-methoxybenzoic acid (7.9 mg, 0.0186 mmol, 1 eq) at room temperature. DIPEA (9.7 microliters, 0.0557 mmol, 3 eq) and HATU (7.1 mg, 0.0186 mmol, 1 eq) were added and the mixture was stirred for 16 hours, before being purified by preparative HPLC to give the desired trifluoracetate salt as an off-white solid (7.15 mg, 0.007296 mmol, 39%).

$^1$H NMR (400 MHz, Methanol-$d_4$) δ 7.83-7.77 (m, 2H), 7.61-7.56 (m, 2H), 7.55-7.50 (m, 2H), 7.42 (d, J=8.5 Hz, 1H), 5.13 (dd, J=12.6, 5.5 Hz, 1H), 4.75 (s, 2H), 4.49 (dd, J=6.6, 3.3 Hz, 1H), 4.33-4.24 (m, 1H), 3.97 (s, 3H), 3.39 (t, J=7.1 Hz, 2H), 3.34-3.32 (m, 2H), 3.30 (s, 3H), 3.01-2.83 (m, 2H), 2.82-2.65 (m, 3H), 2.17-2.01 (m, 4H), 1.91 (dt, J=14.2, 7.4 Hz, 1H), 1.68-1.54 (m, 7H), 1.37 (s, 7H), 0.86 (t, J=7.5 Hz, 3H). $^{13}$C NMR (100 MHz, cd$_3$od) δ 174.52, 171.35, 169.81, 168.85, 168.28, 167.74, 164.58, 156.27, 154.47, 153.89, 150.64, 138.19, 134.93, 134.18, 129.52, 129.41, 124.91, 123.83, 121.67, 120.76, 119.31, 117.95, 117.89, 111.57, 69.37, 63.37, 63.17, 56.67, 50.58, 41.12, 40.12, 32.19, 30.43, 30.28, 30.22, 30.19, 29.40, 29.25, 28.71, 28.62, 27.94, 27.75, 24.29, 23.65, 8.46. LCMS 866.56 (M+H).

Synthetic Example 12: Synthesis of dBET10

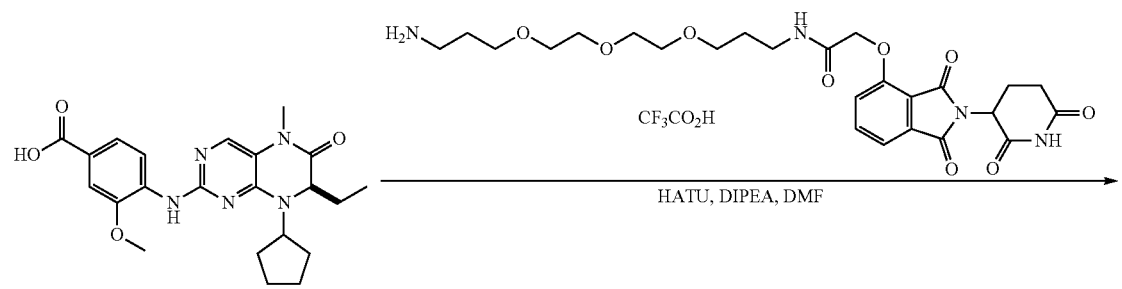

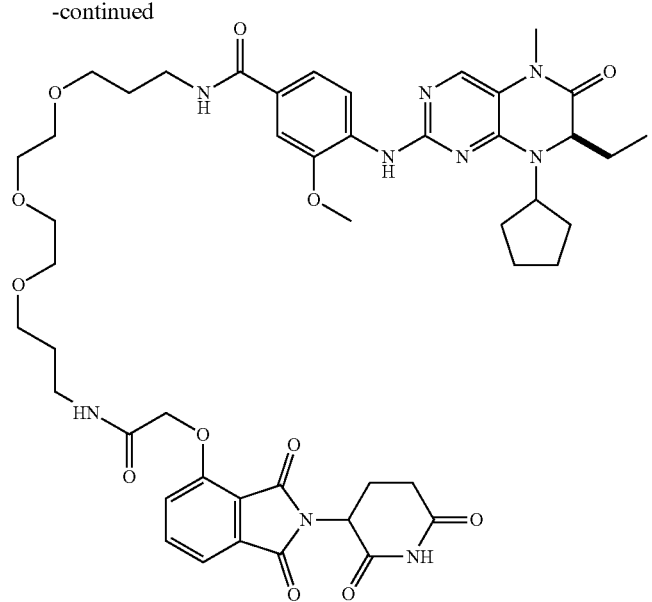

A 0.1 M solution N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.172 mL, 0.0172 mmol 1 eq) was added to (R)-4-((8-cyclopentyl-7-ethyl-5-methyl-6-oxo-5,6,7,8-tetrahydropteridin-2-yl)amino)-3-methoxybenzoic acid (7.3 mg, 0.0172 mmol, 1 eq) at room temperature. DIPEA (9.0 microliters, 0.0515 mmol, 3 eq) and HATU (6.5 mg, 0.0172 mmol, 1 eq) were added and the mixture was stirred for 23 hours, before being purified by preparative HPLC to give the desired trifluoracetate salt as an off-white oil (10.7 mg, 0.0101 mmol, 59%).

$^1$H NMR (400 MHz, Methanol-$d_4$) δ 7.78 (d, J=8.3 Hz, 1H), 7.75 (dd, J=8.4, 7.4 Hz, 1H), 7.56-7.51 (m, 2H), 7.49-7.44 (m, 2H), 7.36 (d, J=8.4 Hz, 1H), 5.08 (dd, J=12.4, 5.4 Hz, 1H), 4.69 (s, 2H), 4.44 (dd, J=6.7, 3.2 Hz, 1H), 4.30-4.21 (m, 1H), 3.92 (s, 3H), 3.59-3.42 (m, 12H), 3.35 (t, J=6.7 Hz, 2H), 3.25 (s, 3H), 2.95-2.64 (m, 5H), 2.13-1.95 (m, 4H), 1.91-1.71 (m, 7H), 1.65-1.48 (m, 4H), 0.81 (t, J=7.5 Hz, 3H). $^{13}$C NMR (100 MHz, cd$_3$od) δ 174.50, 171.35, 169.83, 168.77, 168.25, 167.68, 164.57, 156.26, 154.47, 153.05, 150.59, 138.19, 134.92, 133.89, 129.53, 124.57, 123.98, 121.72, 120.75, 119.26, 117.95, 117.86, 111.54, 71.51, 71.46, 71.28, 71.20, 70.18, 69.65, 69.41, 63.27, 63.07, 56.71, 50.57, 38.84, 37.59, 32.17, 30.41, 30.32, 29.46, 29.26, 28.73, 28.64, 24.27, 23.65, 8.49. LCMS 942.62 (M+H).

Synthetic Example 13: Synthesis of dBET16

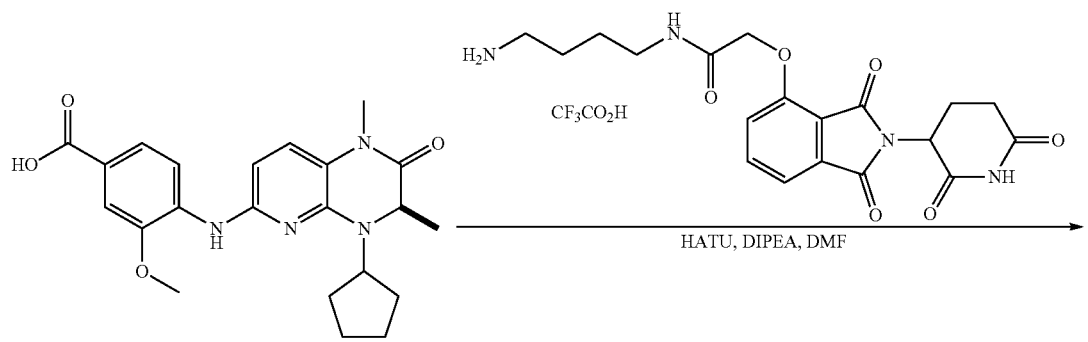

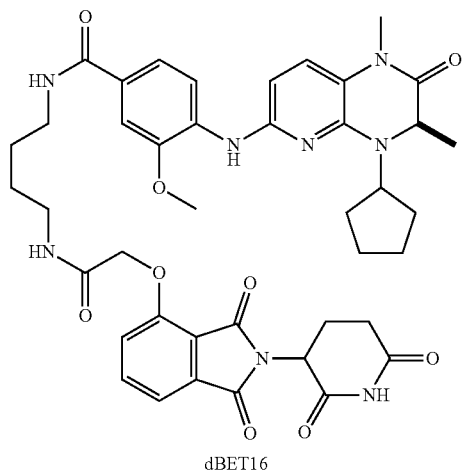

dBET16

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.402 mL, 0.0402 mmol 1 eq) was added (R)-4-((4-cyclopentyl-1,3-dimethyl-2-oxo-1,2,3,4-tetrahydropyrido[2,3-b]pyrazin-6-yl)amino)-3-methoxybenzoic acid (16.55 mg, 0.0402 mmol, 1 eq) at room temperature. DIPEA (21 microliters, 0.1206 mmol, 3 eq) and HATU (15.3 mg, 0.0402 mmol, 1 eq) were added and the mixture was stirred for 21 hours, before being purified by preparative HPLC, followed by column chromatography (ISCO, 12 g NH2-silica column, 0-15% MeOH/DCM, 20 min gradient) to give HPLC to give a brown solid (10.63 mg, 0.0134 mmol, 33%).

$^1$H NMR (400 MHz, Methanol-$d_4$) δ 8.22 (d, J=8.4 Hz, 1H), 7.78 (dd, J=8.4, 7.4 Hz, 1H), 7.73-7.68 (m, 1H), 7.49 (d, J=7.4 Hz, 2H), 7.46-7.39 (m, 2H), 6.98 (d, J=8.8 Hz, 1H), 5.97-5.87 (m, 1H), 5.06 (dd, J=12.6, 5.4 Hz, 1H), 4.76 (s, 2H), 3.98 (s, 3H), 3.61 (s, 2H), 3.44-3.36 (m, 4H), 2.92 (s, 1H), 2.78 (dd, J=14.3, 5.2 Hz, 1H), 2.68 (ddd, J=17.7, 8.2, 4.5 Hz, 2H), 2.36-2.26 (m, 2H), 2.10-1.90 (m, 5H), 1.76-1.62 (m, 6H), 1.31 (d, J=16.0 Hz, 4H). LCMS 795.38 (M+H).

Synthetic Example 14: Synthesis of dBET11

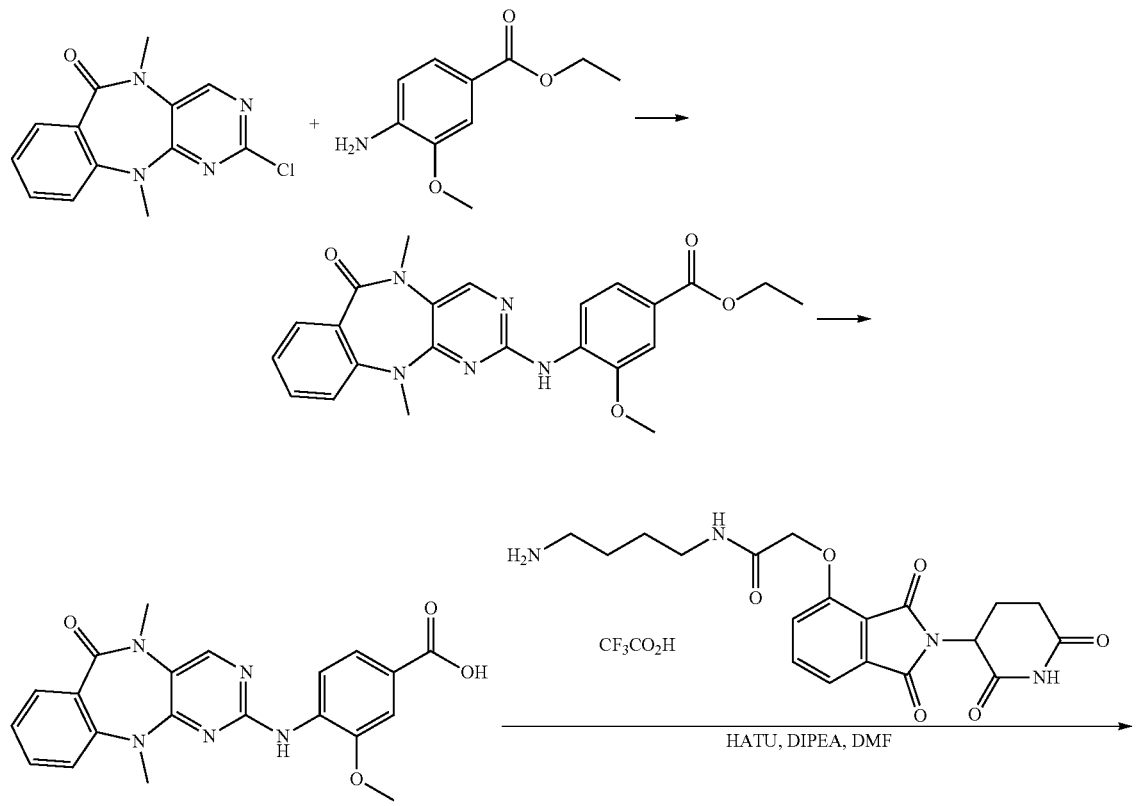

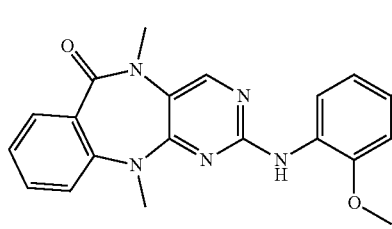 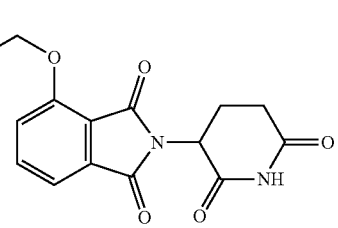

dBET11

(1) Synthesis of Ethyl 4-((5,11-dimethyl-6-oxo-6,11-dihydro-5H-benzo[e]pyrimido[5,4-b][1,4]diazepin-2-yl)amino)-3-methoxybenzoate 2-chloro-5,11-dimethyl-5H-benzo[e]pyrimido[5,4-b][1,4]diazepin-6(11H)-one (82.4 mg, 0.30 mmol, 1 eq), ethyl 4-amino-3-methoxybenzoate (70.3 mg, 0.36 mmol, 1.2 eq) Pd$_2$dba$_3$ (13.7 mg, 0.015 mmol, 5 mol %), XPhos (21.5 mg, 0.045 mmol, 15 mol %) and potassium carbonate (166 mg, 1.2 mmol, 4 eq) were dissolved in tBuOH (3.0 mL) and heated to 100° C. After 17 hours, the mixture was cooled room temperature and filtered through celite. The mixture was purified by column chromatography (ISCO, 12 g silica column, 0-100% EtOAc/hexanes, 19 min gradient) to give an off white solid (64.3 mg, 0.148 mmol, 49%).

$^1$H NMR (400 MHz, 50% cd$_3$od/cdcl$_3$) δ 8.51 (d, J=8.5 Hz, 1H), 8.17 (s, 1H), 7.73 (ddd, J=18.7, 8.1, 1.7 Hz, 2H), 7.52 (d, J=1.8 Hz, 1H), 7.46-7.41 (m, 1H), 7.15-7.10 (m, 2H), 4.34 (q, J=7.1 Hz, 4H), 3.95 (s, 3H), 3.47 (s, 3H), 3.43 (s, 3H), 1.38 (t, J=7.1 Hz, 3H). $^{13}$C NMR (100 MHz, 50% cd$_3$od/cdcl$_3$) δ 169.28, 167.39, 164.29, 155.64, 151.75, 149.73, 147.45, 146.22, 133.88, 133.18, 132.37, 126.44, 124.29, 123.70, 123.36, 122.26, 120.58, 118.05, 116.83, 110.82, 61.34, 56.20, 38.62, 36.25, 14.51. LCMS 434.33 (M+H).

(2) Synthesis of 4-((5,11-dimethyl-6-oxo-6,11-dihydro-5H-benzo[e]pyrimido[5,4-b][1,4]diazepin-2-yl)amino)-3-methoxybenzoic Acid Ethyl 4-((5,11-dimethyl-6-oxo-6,11-dihydro-5H-benzo[e]pyrimido[5,4-b][1,4]diazepin-2-yl)amino)-3-methoxybenzoate (108.9 mg, 0.251 mmol, 1 eq) and LiOH (18 mg) were dissolved in THF (2.5 mL) and water (1.25 mL). After 24 hours, MeOH (0.63 mL) was added to improved solubility) and stirred for an additional 24 hours before being diluted with MeOH and purified by preparative HPLC to give a light yellow solid (41.31 mg).

$^1$H NMR (400 MHz, Methanol-d$_4$) δ 8.51 (d, J=8.5 Hz, 1H), 8.22 (s, 1H), 7.73 (ddd, J=11.8, 8.1, 1.7 Hz, 2H), 7.57 (d, J=1.8 Hz, 1H), 7.49-7.44 (m, 1H), 7.19-7.11 (m, 2H), 3.97 (s, 3H), 3.48 (s, 3H), 3.45 (s, 3H). LCMS 406.32 (M+H).

(3) Synthesis of dBET11

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.190 mL, 0.0190 mmol 1 eq) was added to 4-((5,11-dimethyl-6-oxo-6,11-dihydro-5H-benzo[e]pyrimido[5,4-b][1,4]diazepin-2-yl)amino)-3-methoxybenzoic acid (7.71 mg, 0.0190 mmol, 1 eq) at room temperature. DIPEA (9.9 microliters, 0.0571 mmol, 3 eq) and HATU (7.2 mg, 0.0190 mmol, 1 eq) were added and the mixture was stirred for 22 hours, before being purified by preparative HPLC to give HPLC to give the desired trifluoracetate salt as a cream colored solid (6.72 mg, 0.00744 mmol, 39%).

$^1$H NMR (400 MHz, Methanol-d$_4$) δ 8.46 (d, J=8.3 Hz, 1H), 8.21 (s, 1H), 7.79-7.73 (m, 2H), 7.52 (d, J=7.1 Hz, 1H), 7.50-7.43 (m, 3H), 7.33 (d, J=8.2 Hz, 1H), 7.15 (dd, J=7.7, 5.9 Hz, 2H), 4.98 (dd, J=12.0, 5.5 Hz, 1H), 4.69 (s, 2H), 3.97 (s, 3H), 3.49 (s, 3H), 3.46-3.34 (m, 7H), 2.81-2.67 (m, 3H), 2.13-2.08 (m, 1H), 1.69 (dt, J=6.6, 3.5 Hz, 4H). $^{13}$C NMR (100 MHz, cd$_3$od) δ 173.40, 170.10, 169.68, 169.00, 168.85, 167.60, 167.15, 164.77, 156.01, 155.42, 151.83, 150.03, 148.21, 137.82, 134.12, 133.48, 132.58, 132.52, 128.11, 126.72, 124.54, 122.33, 121.06, 120.63, 118.77, 118.38, 117.94, 117.62, 109.67, 68.90, 56.33, 49.96, 40.16, 39.48, 38.72, 36.34, 31.82, 27.24, 23.16. LCMS 790.48 (M+H).

Synthetic Example 15: Synthesis of dBET12

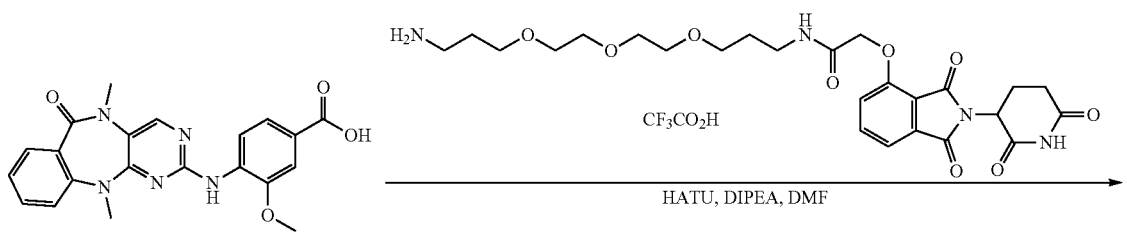

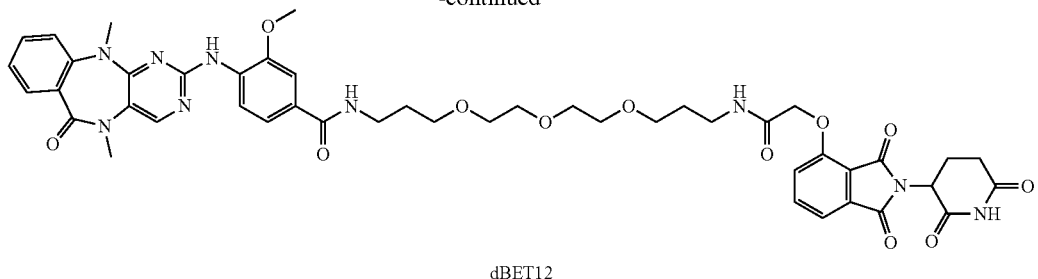

dBET12

A 0.1 M solution N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.186 mL, 0.0186 mmol 1 eq) was added to 4-((5,11-dimethyl-6-oxo-6,11-dihydro-5H-benzo[e]pyrimido[5,4-b][1,4]diazepin-2-yl)amino)-3-methoxybenzoic acid (7.53 mg, 0.0186 mmol, 1 eq) at room temperature. DIPEA (9.7 microliters, 0.0557 mmol, 3 eq) and HATU (7.1 mg, 0.0186 mmol, 1 eq) were added and the mixture was stirred for 22 hours, before being purified by preparative HPLC to give HPLC to give the desired trifluoracetate salt as a cream colored solid (7.50 mg, 0.00724 mmol, 39%).

$^1$H NMR (400 MHz, Methanol-$d_4$) δ 8.46 (d, J=8.9 Hz, 1H), 8.21 (s, 1H), 7.73 (dd, J=15.2, 7.8 Hz, 2H), 7.50-7.42 (m, 3H), 7.28 (d, J=8.5 Hz, 1H), 7.15 (t, J=7.7 Hz, 2H), 5.01 (dd, J=11.8, 5.8 Hz, 1H), 4.68 (s, 2H), 3.97 (s, 3H), 3.67-3.58 (m, 7H), 3.58-3.43 (m, 10H), 3.39 (t, J=6.8 Hz, 2H), 3.35 (s, 2H), 2.97 (s, 1H), 2.84-2.70 (m, 3H), 2.16-2.07 (m, 1H), 1.93-1.76 (m, 4H). LCMS 922.57 (M+H).

Synthetic Example 16: Synthesis of dBET13

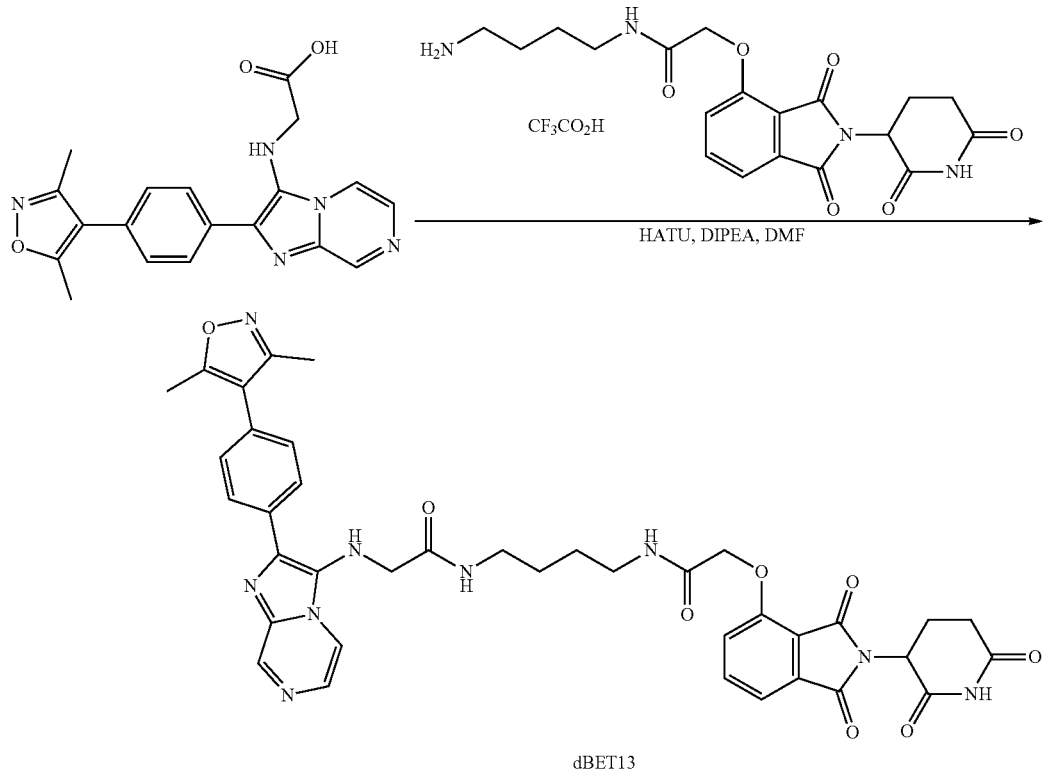

dBET13

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.501 mL, 0.0501 mmol 1 eq) was added to 2-((2-(4-(3,5-dimethylisoxazol-4-yl)phenyl)imidazo[1,2-c]pyrazin-3-yl)amino)acetic acid (synthesized as in McKeown et al, J. Med. Chem, 2014, 57, 9019) (18.22 mg, 0.0501 mmol, 1 eq) at room temperature. DIPEA (26.3 microliters, 0.150 mmol, 3 eq) and HATU (19.0 mg, 0.0501 mmol, 1 eq) were added and the mixture was stirred for 21 hours, before being purified by preparative HPLC to give HPLC to give the desired trifluoracetate salt as a dark yellow oil (29.66 mg, 0.0344 mmol, 69%). $^1$H NMR (400 MHz, Methanol-$d_4$) δ 9.09 (s, 1H), 8.65 (d, J=5.2 Hz, 1H), 8.14-8.06 (m, 2H), 7.94-7.88 (m, 1H), 7.80-7.74 (m, 1H), 7.59-7.47 (m, 3H), 7.40 (dd, J=8.4, 4.7 Hz, 1H), 5.11-5.06 (m, 1H), 4.72 (d, J=9.8 Hz, 2H), 3.90 (s, 2H), 3.25-3.22 (m, 1H), 3.12 (t, J=6.4 Hz, 1H), 2.96 (s, 2H), 2.89-2.79 (m, 1H), 2.76-2.62 (m, 2H), 2.48-2.42 (m, 3H), 2.29 (s, 3H), 2.10 (ddq, J=10.2, 5.3, 2.7 Hz, 1H), 1.49-1.45 (m, 2H), 1.37 (dd, J=6.7, 3.6 Hz, 2H). $^{13}$C NMR (100 MHz, $cd_3od$) δ 174.45, 171.98, 171.35, 169.88, 168.17, 167.85, 167.40, 159.88, 156.28, 141.82, 138.26, 135.85, 134.82, 133.09, 132.06, 130.75, 129.67, 122.07, 121.94, 119.30, 118.98, 118.06, 117.24, 69.56, 50.56, 40.05, 39.73, 32.13, 27.53, 23.62, 18.71, 17.28, 11.64, 10.85. LCMS 748.49 (M+H).

Synthetic Example 17: Synthesis of dBET14

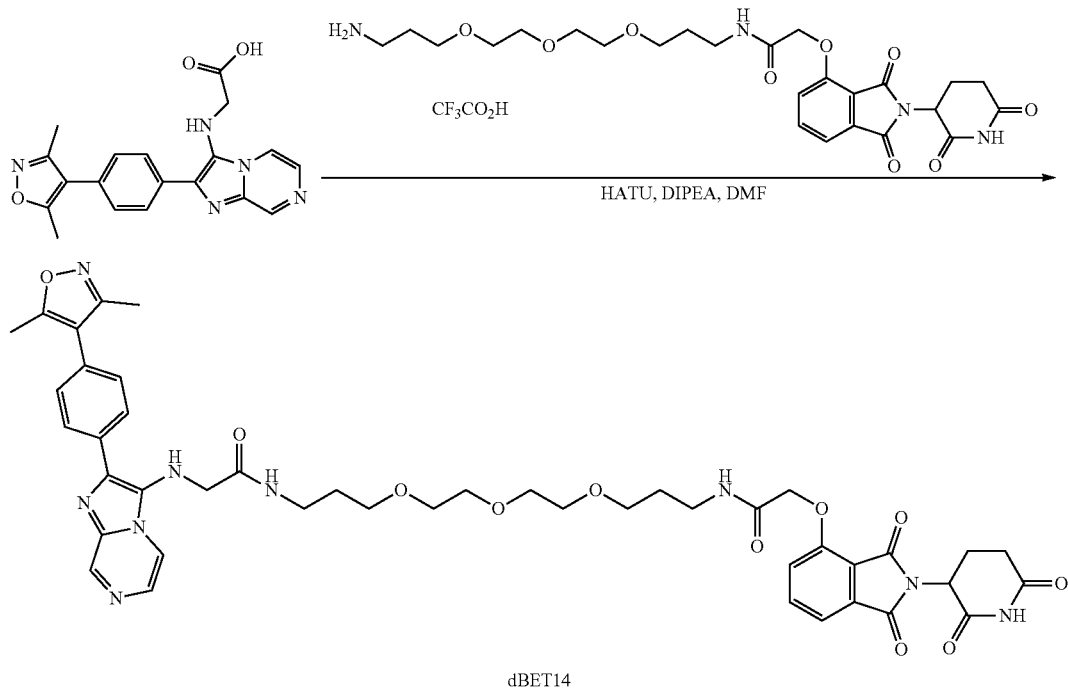

dBET14

A 0.1 M solution N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.510 mL, 0.0510 mmol 1 eq) was added to 2-((2-(4-(3,5-dimethylisoxazol-4-yl)phenyl)imidazo[1,2-a]pyrazin-3-yl)amino)acetic acid (synthesized as in McKeown et al, J. Med. Chem, 2014, 57, 9019) (18.52 mg, 0.0510 mmol, 1 eq) at room temperature. DIPEA (26.6 microliters, 0.153 mmol, 3 eq) and HATU (19.4 mg, 0.0510 mmol, 1 eq) were added and the mixture was stirred for 22 hours, before being purified by preparative HPLC to give HPLC to give the desired trifluoracetate salt as a dark yellow oil (32.63 mg, 0.0328 mmol, 64%). $^1$H NMR (400 MHz, Methanol-$d_4$) δ 9.09 (s, 1H), 8.66 (d, J=5.4 Hz, 1H), 8.17-8.08 (m, 2H), 7.92 (d, J=5.6 Hz, 1H), 7.77 (dd, J=8.4, 7.4 Hz, 1H), 7.60-7.47 (m, 3H), 7.39 (d, J=8.4 Hz, 1H), 5.09 (dd, J=12.4, 5.5 Hz, 1H), 4.71 (s, 2H), 3.91 (s, 2H), 3.62-3.46 (m, 10H), 3.38 (dt, J=16.0, 6.4 Hz, 3H), 3.18 (t, J=6.8 Hz, 2H), 2.97 (s, 1H), 2.89-2.81 (m, 1H), 2.78-2.66 (m, 2H), 2.47 (s, 3H), 2.31 (s, 3H), 2.16-2.08 (m, 1H), 1.79 (dt, J=12.8, 6.5 Hz, 2H), 1.64 (t, J=6.3 Hz, 2H). $^{13}$C NMR (100 MHz, $cd_3od$) δ 174.48, 171.88, 171.34, 169.80, 168.22, 167.69, 167.42, 159.87, 156.24, 141.87, 138.21, 135.89, 134.88, 133.13, 132.04, 130.76, 129.67, 122.08, 121.69, 119.20, 117.94, 117.23, 71.44, 71.22, 71.10, 69.92, 69.62, 69.38, 50.57, 49.64, 38.11, 37.55, 32.16, 30.30, 30.20, 23.63, 11.67, 10.88. LCMS 880.46 (M+H).

Synthetic Example 18: Synthesis of dBET18
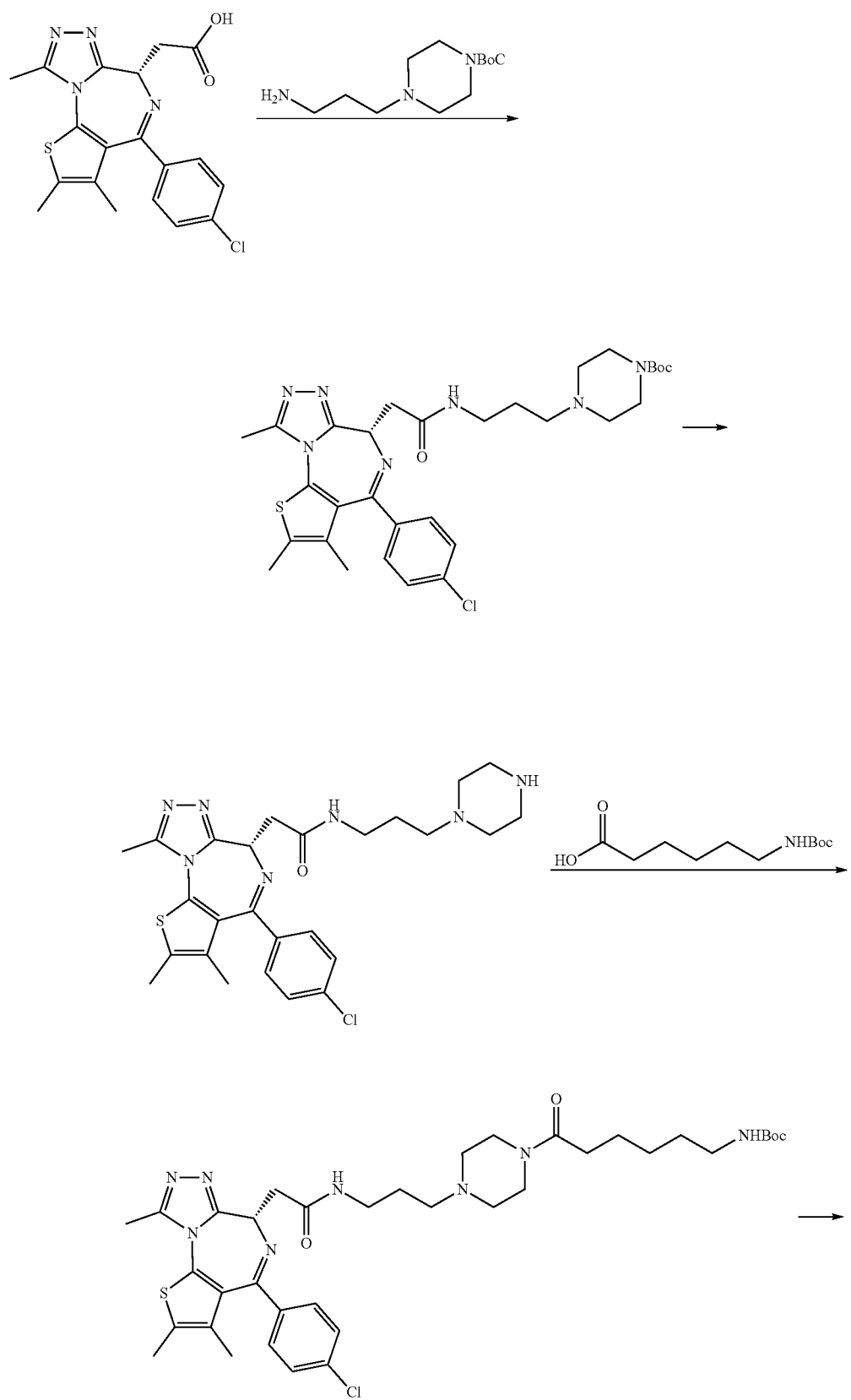

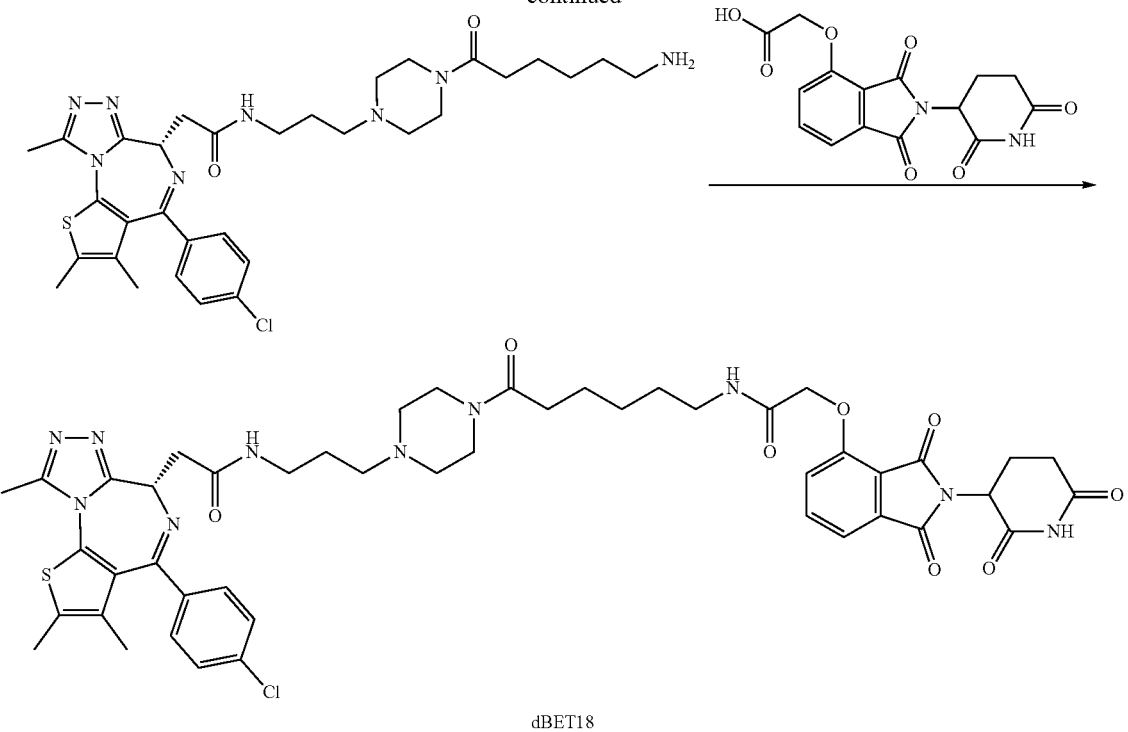

dBET18

(1) Synthesis of (S)-Tert-butyl 4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazine-1-carboxylate JQ-acid (176.6 mg, 0.441 mmol, 1 eq) was dissolved in DMF (4.4 mL) at room temperature. HATU (176 mg, 0.463 mmol, 1.05 eq) was added, followed by DIPEA (0.23 mL, 1.32 mmol, 3 eq). After 10 minutes, tert-butyl 4-(3-aminopropyl)piperazine-1-carboxylate (118 mg, 0.485 mmol, 1.1 eq) was added as a solution in DMF (0.44 mL). After 24 hours, the mixture was diluted with half saturated sodium bicarbonate and extracted twice with DCM and once with EtOAc. The combined organic layer was dried over sodium sulfate, filtered and condensed. Purification by column chromatography (ISCO, 24 g silica column, 0-15% MeOH/DCM, 23 minute gradient) gave a yellow oil (325.5 mg, quant yield)

$^1$H NMR (400 MHz, Chloroform-d) δ 7.67 (t, J=5.3 Hz, 1H), 7.41-7.28 (m, 4H), 4.58 (dd, J=7.5, 5.9 Hz, 1H), 3.52-3.23 (m, 8H), 2.63 (s, 9H), 2.37 (s, 3H), 1.80-1.69 (m, 2H), 1.64 (s, 3H), 1.42 (s, 9H). $^{13}$C NMR (100 MHz, cdcl$_3$) δ 171.41, 164.35, 155.62, 154.45, 150.20, 136.92, 136.64, 132.19, 131.14, 130.98, 130.42, 129.98, 128.80, 80.24, 56.11, 54.32, 52.70, 38.96, 37.85, 28.42, 25.17, 14.43, 13.16, 11.82. LCMS 626.36 (M+H).

(2) Synthesis of (S)-2-(4-(4-chlorophenyl)-2,3,9-trimethyl-6H-thieno[3,2-f][1,2,4]triazolo[4,3-a][1,4]diazepin-6-yl)-N-(3-(piperazin-1-yl)propyl)acetamide (S)-tert-butyl 4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazine-1-carboxylate (325.5 mg) was dissolved in DCM (5 mL) and MeOH (0.5 mL). A solution of 4M HCl in dioxane (1 mL) was added and the mixture was stirred for 16 hours, then concentrated under a stream of nitrogen to give a yellow solid (231.8 mg) which was used without further purification.

$^1$H NMR (400 MHz, Methanol-d$_4$) δ 7.64-7.53 (m, 4H), 5.05 (t, J=7.1 Hz, 1H), 3.81-3.66 (m, 6H), 3.62-3.33 (m, 9H), 3.30 (p, J=1.6 Hz, 1H), 2.94 (s, 3H), 2.51 (s, 3H), 2.09 (dq, J=11.8, 6.1 Hz, 2H), 1.72 (s, 3H). $^{13}$C NMR (100 MHz, cd$_3$od) δ 171.78, 169.38, 155.83, 154.03, 152.14, 140.55, 136.33, 134.58, 134.53, 133.33, 132.73, 130.89, 130.38, 56.07, 53.54, 41.96, 37.22, 36.23, 25.11, 14.48, 13.14, 11.68. LCMS 526.29 (M+H).

(3) Synthesis of (S)-tert-butyl (6-(4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazin-1-yl)-6-oxohexyl)carbamate (S)-2-(4-(4-chlorophenyl)-2,3,9-trimethyl-6H-thieno[3,2-f][1,2,4]triazolo[4,3-a][1,4]diazepin-6-yl)-N-(3-(piperazin-1-yl)propyl)acetamide (62.1 mg) and 6-((tert-butoxycarbonyl)amino)hexanoic acid (24.0 mg, 0.1037 mmol, 1 eq) were dissolved in DMF (1 mL). DIPEA (72.2 microliters, 0.4147 mmol, 4 eq) was added, followed by HATU (39.4 mg, 0.1037 mmol, 1 eq) and the mixture was stirred for 25 hours. The mixture was diluted with half saturated sodium bicarbonate and extracted three times with DCM. The combined organic layer was dried over sodium sulfate, filtered and condensed. Purification by column chromatography (ISCO, 4 g silica column, 0-15% MeOH/DCM, 15 minute gradient) gave a yellow oil (71.75 mg, 0.0970 mmol, 94%).

$^1$H NMR (400 MHz, Chloroform-d) δ 7.61 (s, 1H), 7.43-7.28 (m, 4H), 4.63 (s, 1H), 4.61-4.56 (m, 1H), 3.82-3.21 (m, 10H), 3.11-3.01 (m, 2H), 2.61 (d, J=24.3 Hz, 9H), 2.38 (s, 3H), 2.28 (t, J=7.4 Hz, 2H), 1.73 (dq, J=13.8, 7.4 Hz, 2H), 1.63-1.55 (m, 2H), 1.53-1.24 (m, 14H). $^{13}$C NMR (100

MHz, cdcl$_3$) δ 171.63, 171.11, 164.34, 156.17, 155.66, 150.21, 136.96, 136.72, 132.25, 131.14, 131.01, 130.47, 130.00, 128.85, 79.11, 56.42, 54.46, 53.06, 52.82, 45.04, 41.02, 40.47, 39.29, 38.33, 33.00, 29.90, 28.54, 26.60, 25.29, 24.86, 14.47, 13.20, 11.86. LCMS 739.37 (M+H).

(4) Synthesis of (S)—N-(3-(4-(6-aminohexanoyl) piperazin-1-yl)propyl)-2-(4-(4-chlorophenyl)-2,3,9-trimethyl-6H-thieno[3,2-f][1,2,4]triazolo[4,3-a][1,4] diazepin-6-yl)acetamide (S)-tert-butyl (6-(4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazin-1-yl)-6-oxohexyl)carbamate (71.75 mg, 0.0970 mmol, 1 eq) was dissolved in DCM (2 mL) and MeOH (0.2 mL). A solution of 4M HCl in dioxane (0.49 mL) was added and the mixture was stirred for 2 hours, then concentrated under a stream of nitrogen, followed by vacuum to give a yellow foam (59.8 mg, 0.0840 mmol, 87%).

$^1$H NMR (400 MHz, Methanol-d$_4$) δ 7.68-7.53 (m, 4H), 5.04 (d, J=6.6 Hz, 1H), 4.66 (d, J=13.6 Hz, 1H), 4.23 (d, J=13.6 Hz, 1H), 3.63-3.34 (m, 7H), 3.29-3.00 (m, 5H), 2.95 (d, J=6.0 Hz, 5H), 2.51 (d, J=9.2 Hz, 5H), 2.08 (s, 2H), 1.77-1.62 (m, 7H), 1.45 (dt, J=15.3, 8.6 Hz, 2H). $^{13}$C NMR (100 MHz, cd$_3$od) δ 173.77, 171.84, 169.35, 155.85, 153.99, 140.56, 136.40, 134.58, 133.35, 132.70, 130.39, 55.83, 53.57, 52.92, 52.70, 43.57, 40.55, 39.67, 37.33, 36.25, 33.17, 28.26, 26.94, 25.33, 25.26, 14.49, 13.15, 11.65. LCMS 639.35 (M+H).

(5) Synthesis of dBET18

(S)—N-(3-(4-(6-aminohexanoyl)piperazin-1-yl)propyl)-2-(4-(4-chlorophenyl)-2,3,9-trimethyl-6H-thieno[3,2-f][1,2,4]triazolo[4,3-a][1,4]diazepin-6-yl)acetamide dihydrochloride (20.0 mg, 0.0281 mmol, 1 eq) and 2-((2-(2,6-dioxopiperidin-3-yl)-1,3-dioxoisoindolin-4-yl)oxy)acetic acid (9.32 mg, 0.0281 mmol, 1 eq) were dissolved in DMF (0.281 mL). DIPEA (19.6 microliters, 0.1124 mmol, 4 eq) was added, followed by HATU (10.7 mg, 0.0281 mmol, 1 eq). After 24 hours, the mixture was diluted with MeOH and purified by preparative HPLC to give the desired trifluoracetate salt.

$^1$H NMR (400 MHz, Methanol-d$_4$) δ 7.83-7.79 (m, 1H), 7.54 (d, J=7.1 Hz, 1H), 7.45 (q, J=8.8 Hz, 5H), 5.12 (dd, J=12.5, 5.4 Hz, 1H), 4.76 (s, 2H), 4.68 (t, J=7.3 Hz, 1H), 3.59-3.32 (m, 8H), 3.28-3.18 (m, 4H), 2.87 (ddd, J=19.0, 14.7, 5.3 Hz, 2H), 2.80-2.65 (m, 6H), 2.44 (d, J=6.8 Hz, 5H), 2.33-2.25 (m, 1H), 2.14 (dd, J=9.8, 4.9 Hz, 1H), 2.06-1.89 (m, 3H), 1.70 (s, 3H), 1.61 (dq, J=14.4, 7.3, 6.9 Hz, 4H), 1.45-1.37 (m, 2H). $^{13}$C NMR (100 MHz, cd$_3$od) δ 174.52, 173.97, 173.69, 171.44, 169.88, 168.26, 167.83, 166.72, 156.36, 138.28, 137.84, 134.89, 133.52, 132.12, 131.83, 131.38, 129.89, 121.87, 119.32, 118.01, 69.52, 55.64, 55.03, 52.79, 50.58, 43.69, 39.77, 38.57, 36.89, 33.47, 32.16, 29.93, 27.34, 25.76, 25.45, 23.63, 14.39, 12.94, 11.66. LCMS 953.43 (M+H).

Synthetic Example 19: Synthesis of dBET19

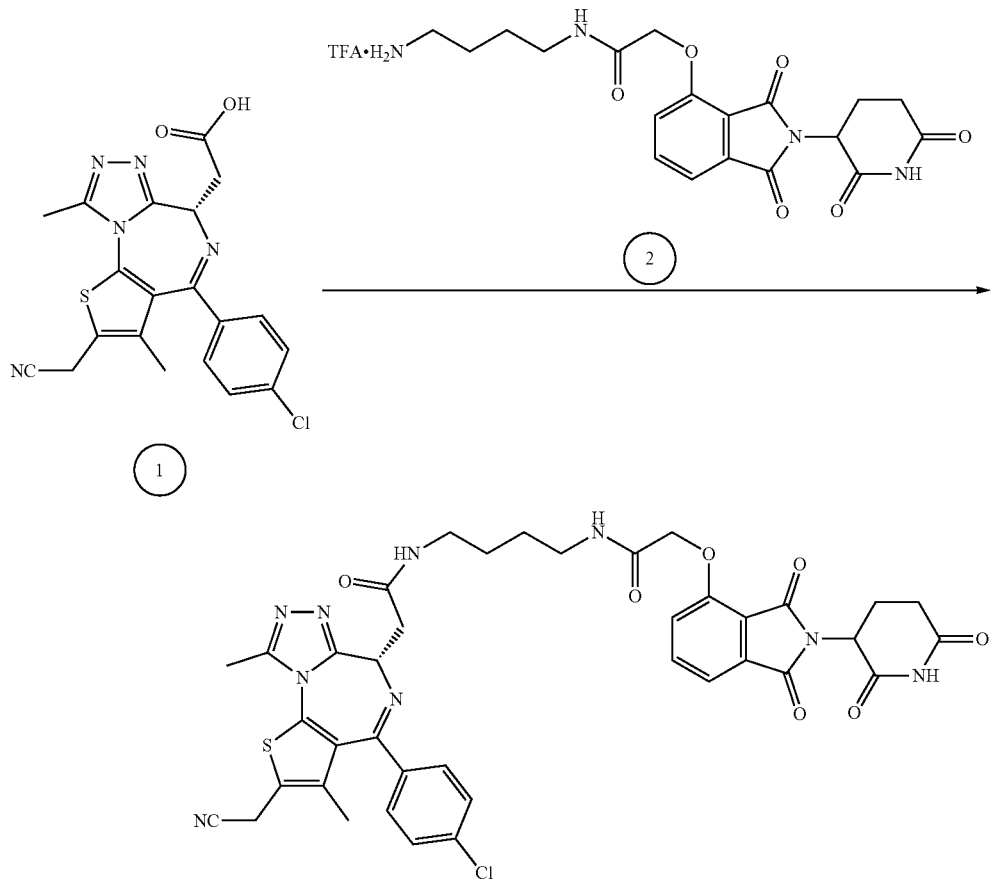

dBET19

A 0.1 M solution of N-(4-aminobutyl)-2-((2-(2,6-dioxopiperidin-3-yl)-1,3-dioxoisoindolin-4-yl)oxy)acetamide trifluoroacetate in DMF (235 microliters, 0.0235 mmol, 1 eq) was added to (S)-2-(4-(4-chlorophenyl)-2-(cyanomethyl)-3,9-dimethyl-6H-thieno[3,2-f][1,2,4]triazolo[4,3-a][1,4]diazepin-6-yl)acetic acid (10 mg, 0.0235 mmol, 1 eq) at room temperature. DIPEA (12.3 microliters, 0.0704 mmol, 3 eq) and HATU (8.9 mg, 0.0235 mmol, 1 eq) were added and the mixture was stirred for 18.5 hours. The mixture was then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a white solid (12.96 mg, 0.0160 mmol, 68%). $^1$H NMR (400 MHz, Chloroform-d) δ 7.80 (dd, J=8.4, 7.4 Hz, 1H), 7.55-7.37 (m, 6H), 5.14-5.06 (m, 1H), 4.77 (d, J=1.5 Hz, 2H), 4.64 (dd, J=8.0, 5.6 Hz, 1H), 3.45-3.32 (m, 5H), 3.29-3.21 (m, 2H), 2.83-2.66 (m, 6H), 2.58 (s, 3H), 2.14-2.06 (m, 1H), 1.71-1.57 (m, 4H). LCMS 810.30, M+H).

Synthetic Example 20: Synthesis of dBET20

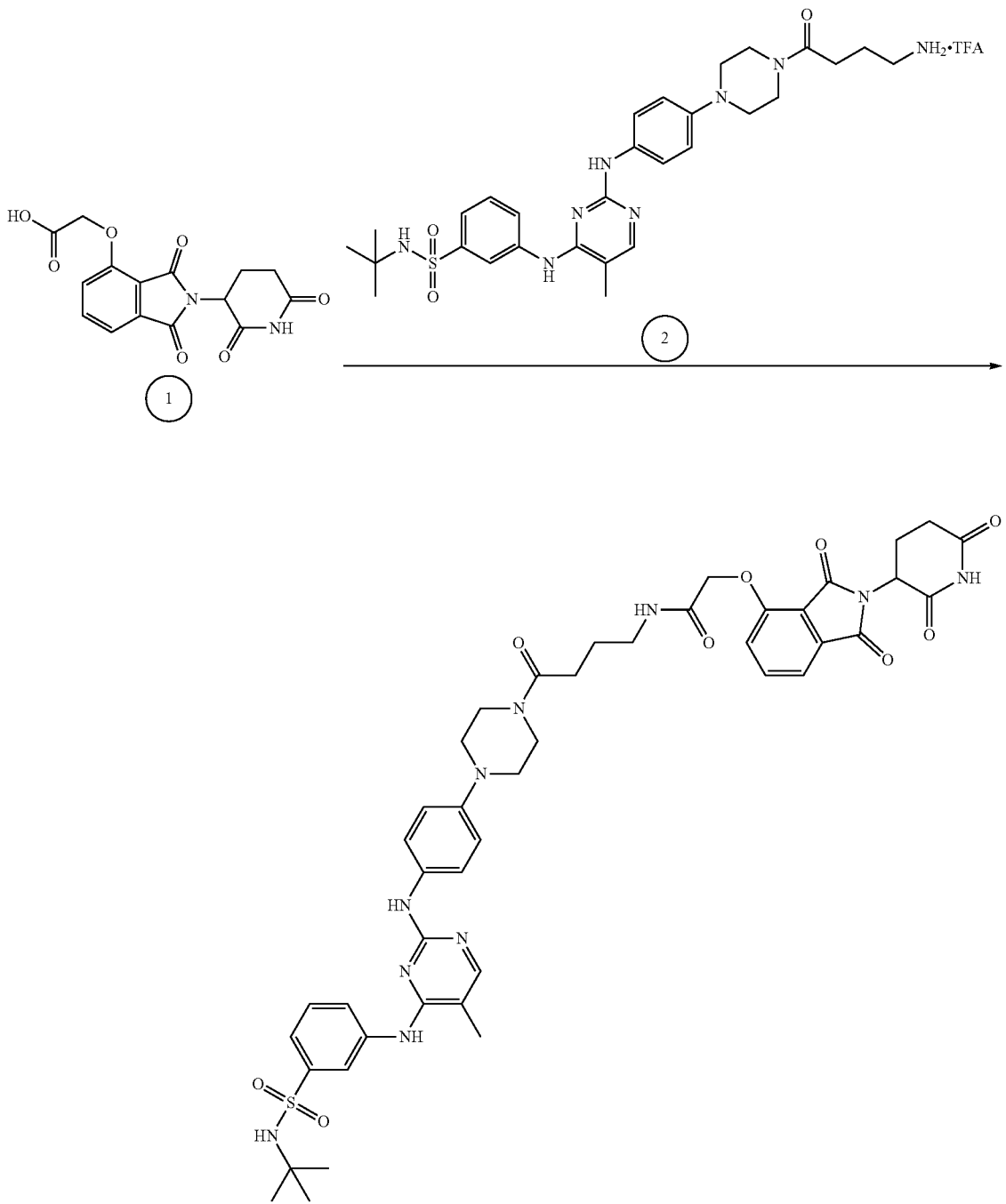

dBET20

3-((2-((4-(4-(4-aminobutanoyl)piperazin-1-yl)phenyl)amino)-5-methylpyrimidin-4-yl)amino)-N-(tert-butyl)benzenesulfonamide trifluoroacetate (7.41 mg, 0.0107 mmol, 1 eq) and 2-((2-(2,6-dioxopiperidin-3-yl)-1,3-dioxoisoindolin-4-yl)oxy)acetic acid (3.6 mg, 0.0107 mmol, 1 eq) were dissolved in DMF (214 microliters, 0.05M) at room temperature. DIPEA (5.6 microliters, 0.0321 mmol, 3 eq) and HATU (4.1 mg, 0.0107 mmol, 1 eq) were added. After 22.5 hours, the mixture was diluted with MeOH and purified by preparative HPLC to give the desired product as a brown residue (6.27 mg, 0.00701 mmol, 65%). $^1$H NMR (500 MHz, Methanol-$d_4$) δ 8.06 (s, 1H), 7.84-7.75 (m, 3H), 7.65 (s, 1H), 7.55 (t, J=7.8 Hz, 2H), 7.45 (d, J=8.4 Hz, 1H), 7.25-7.20 (m, 2H), 6.99 (d, J=8.8 Hz, 2H), 5.11 (dd, J=12.5, 5.4 Hz, 1H), 4.78 (s, 2H), 3.79-3.66 (m, 4H), 3.40 (t, J=6.6 Hz, 2H), 3.24-3.13 (m, 4H), 2.82-2.68 (m, 3H), 2.52 (t, J=7.4 Hz, 2H), 2.24-2.19 (m, 3H), 2.12 (dd, J=10.2, 5.1 Hz, 1H), 1.92 (dd, J=13.4, 6.4 Hz, 2H), 1.18 (s, 9H). LCMS 895.63 (M+H).

Synthetic Example 21: Synthesis of dBET21

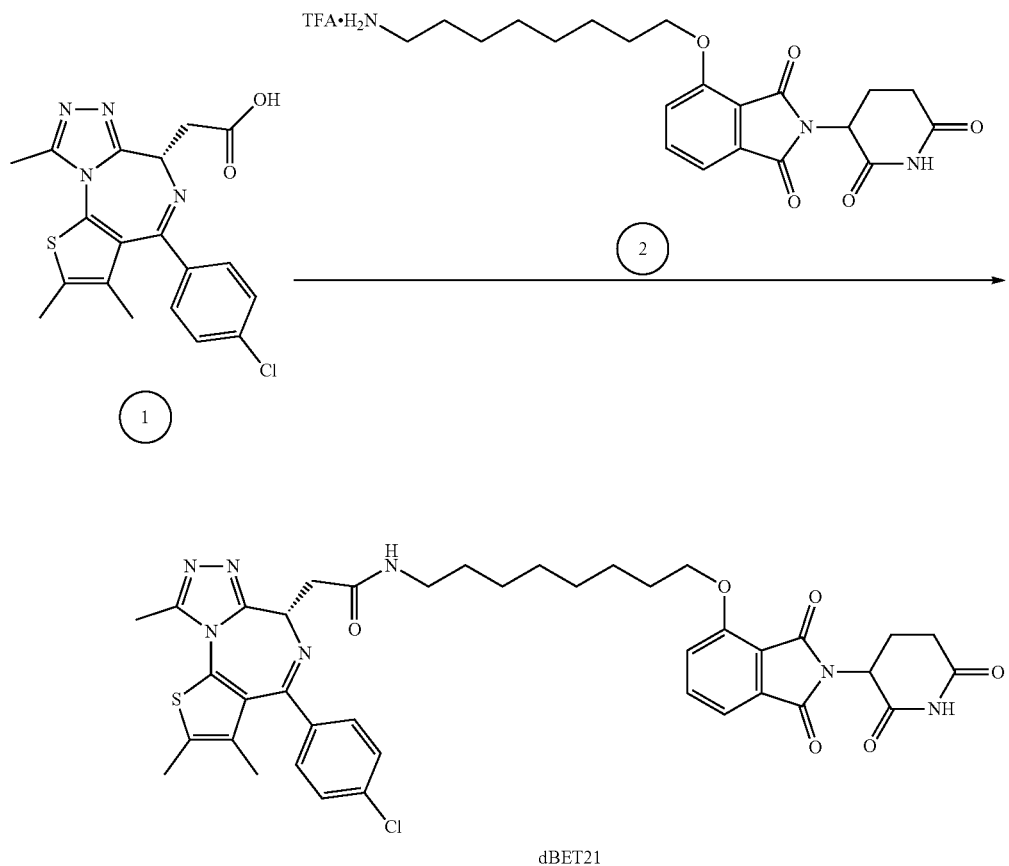

dBET21

A 0.1 M solution of 4-((10-aminodecyl)oxy)-2-(2,6-dioxopiperidin-3-yl)isoindoline-1,3-dione trifluoroacetate in DMF (232 microliters, 0.0232 mmol, 1 eq) was added to JQ-acid (9.3 mg, 0.0232 mmol, 1 eq) at room temperature. DIPEA (12.1 microliters, 0.0696 mmol, 3 eq) and HATU (8.8 mg, 0.0232 mmol, 1 eq) were added and the mixture was stirred for 18 hours. The mixture was then diluted with EtOAc and washed with saturated sodium bicarbonate, water and brine. The organic layer was dried over sodium sulfate, filtered and concentrated under reduced pressure. Purification by preparative HPLC followed by column chromatography (ISCO, 4 g silica column, 0-10% MeOH/DCM, 25 minute gradient) gave the desired product as an off-white residue (1.84 mg, 0.00235 mmol, 10%). $^1$H NMR (500 MHz, Methanol-$d_4$) δ 7.77-7.73 (m, 1H), 7.50-7.33 (m, 6H), 5.09 (dd, J=12.5, 5.5 Hz, 1H), 4.62 (s, 1H), 4.21 (t, J=6.4 Hz, 2H), 3.36 (s, 2H), 2.87-2.67 (m, 6H), 2.44 (s, 3H), 1.88-1.82 (m, 2H), 1.70 (s, 3H), 1.58 (s, 4H), 1.29 (s, 8H). LCMS 784.51 (M+H).

Synthetic Example 22: Synthesis of dBET22

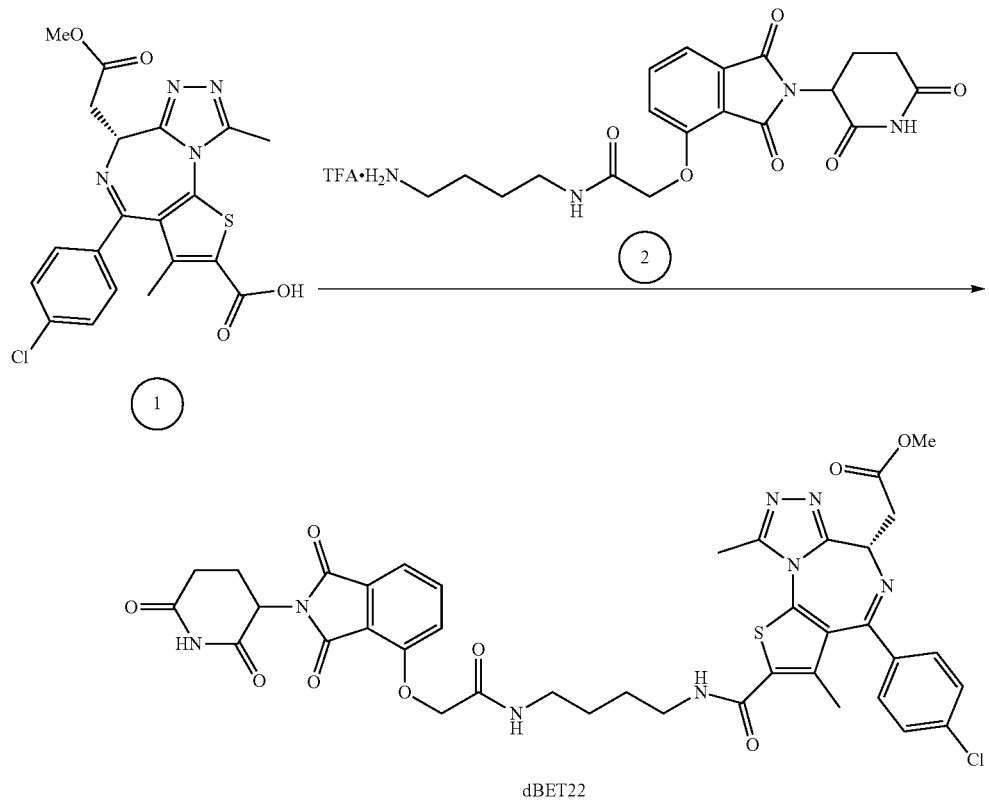

dBET22

A 0.1 M solution of N-(4-aminobutyl)-2-((2-(2,6-dioxopiperidin-3-yl)-1,3-dioxoisoindolin-4-yl)oxy)acetamide trifluoroacetate in DMF (247 microliters, 0.0247 mmol, 1 eq) was added to (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (10.98 mg, 0.0247 mmol, 1 eq) at room temperature. DIPEA (12.9 microliters, 0.0740 mmol, 3 eq) and HATU (9.4 mg, 0.0247 mmol, 1 eq) were added. The mixture was then stirred for 21 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a white solid (9.79 mg, 0.0118 mmol, 48%). $^1$H NMR (400 MHz, Methanol-$d_4$) δ 7.80 (dd, J=8.4, 7.4 Hz, 1H), 7.51 (dd, J=7.1, 1.5 Hz, 1H), 7.48-7.34 (m, 5H), 5.11 (ddd, J=12.4, 5.4, 3.5 Hz, 1H), 4.76 (s, 2H), 4.69 (td, J=7.2, 1.4 Hz, 1H), 3.76 (s, 3H), 3.55 (d, J=7.2 Hz, 2H), 3.48-3.33 (m, 4H), 2.93-2.82 (m, 1H), 2.78-2.64 (m, 5H), 2.14-2.07 (m, 1H), 1.96 (d, J=0.9 Hz, 3H), 1.66 (s, 4H). LCMS 829.39 (M+H).

Synthetic Example 23: Synthesis of dBET23

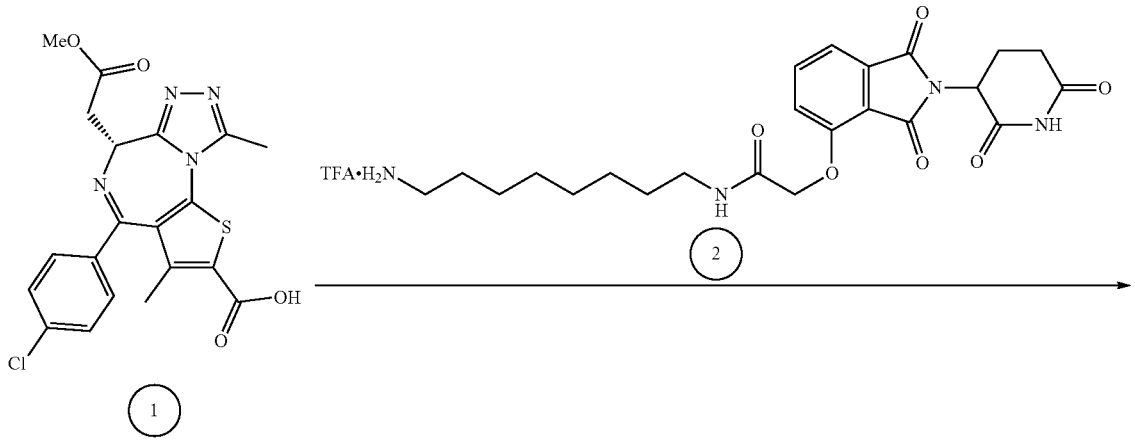

-continued

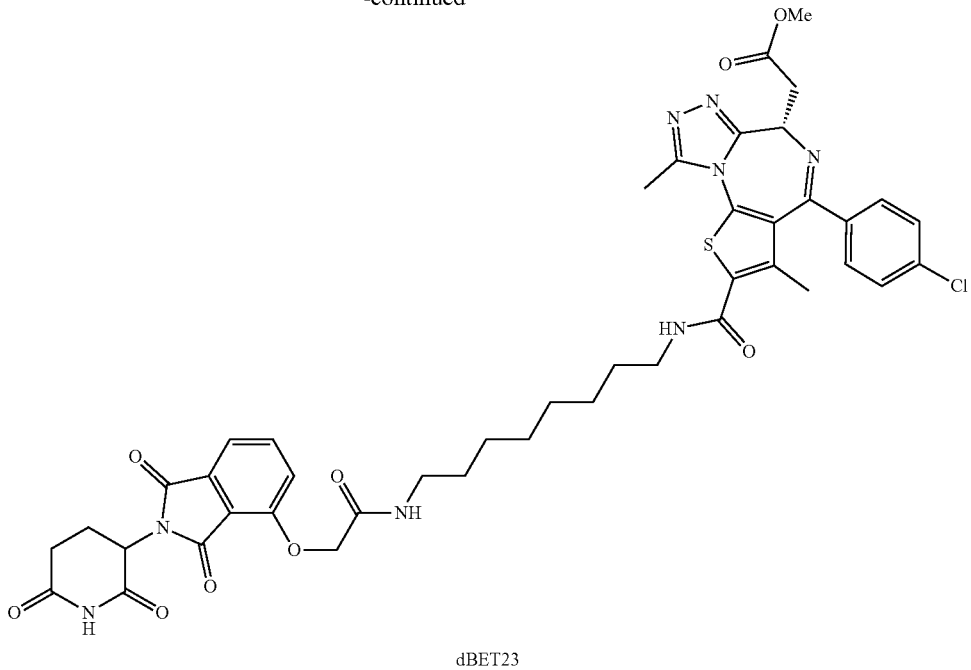

dBET23

A 0.1 M solution of N-(8-aminooctyl)-2-((2-(2,6-dioxopiperidin-3-yl)-1,3-dioxoisoindolin-4-yl)oxy)acetamide trifluoroacetate in DMF (220 microliters, 0.0220 mmol, 1 eq) was added to (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (9.87 mg, 0.0220 mmol, 1 eq) at room temperature. DIPEA (11.5 microliters, 0.0660 mmol, 3 eq) and HATU (8.4 mg, 0.0220 mmol, 1 eq) were added. The mixture was then stirred for 21 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a white solid (8.84 mg, 0.00998 mmol, 45%). $^1$H NMR (400 MHz, Methanol-$d_4$) δ 7.81 (dd, J=8.4, 7.4 Hz, 1H), 7.53 (d, J=7.3 Hz, 1H), 7.50-7.39 (m, 5H), 5.12 (dd, J=12.6, 5.4 Hz, 1H), 4.75 (s, 2H), 4.68 (t, J=7.2 Hz, 1H), 3.76 (s, 3H), 3.54 (d, J=7.2 Hz, 2H), 3.39-3.32 (m, 3H), 3.29 (s, 1H), 2.90-2.83 (m, 1H), 2.79-2.68 (m, 5H), 2.14 (dd, J=8.9, 3.7 Hz, 1H), 1.99 (s, 3H), 1.65-1.53 (m, 4H), 1.36 (d, J=6.5 Hz, 8H). LCMS 885.47 (M+H).

Synthetic Example 24: Synthesis of dBET24

Step 1: Synthesis of Tert-butyl (2-(2-(2-(2-((2-(2,6-dioxopiperidin-3-yl)-1,3-dioxoisoindolin-4-yl)oxy)acetamido)ethoxy)ethoxy)ethyl)carbamate 2-((2-(2,6-dioxopiperidin-3-yl)-1,3-dioxoisoindolin-4-yl)oxy)acetic acid (200 mg, 0.602 mmol, 1 eq) was dissolved in DMF (6.0 mL, 0.1M). HATU (228.9 mg, 0.602 mmol, 1 eq), DIPEA (0.315 mL, 1.81 mmol, 3 eq) and N-Boc-2,2'-(ethylenedioxy)diethylamine (0.143 mL, 0.602 mmol, 1 eq) were added sequentially. After 6 hours, additional HATU (114 mg, 0.30 mmol, 0.5 eq) were added to ensure completeness of reaction. After an additional 24 hours, the mixture was diluted with EtOAc, and washed with saturated sodium bicarbonate, water and twice with brine. The combined organic layer was dried over sodium sulfate, filtered and concentrated under reduced pressure. Purification by column chromatography (ISCO, 12 g silica column, 0-15% MeOH/DCM, 15 minute gradient) gave the desired product as a yellow oil (0.25 g, 0.44 mmol, 74%). $^1$H NMR (400 MHz, Methanol-$d_4$) δ 7.82-7.75 (m, 1H), 7.51 (d, J=7.4 Hz, 1H), 7.41 (d, J=8.5 Hz, 1H), 5.13 (dd, J=12.4, 5.5 Hz, 1H), 4.76 (s, 2H), 3.66-3.58 (m, 6H), 3.53-3.45 (m, 4H), 3.19 (t, J=5.6 Hz, 2H), 2.95-2.83 (m, 1H), 2.80-2.67 (m, 2H), 2.19-2.12 (m, 1H), 1.41 (s, 9H). LCMS 563.34 (M+H).

Step 2: Synthesis of N-(2-(2-(2-aminoethoxy)ethoxy)ethyl)-2-((2-(2,6-dioxopiperidin-3-yl)-1,3-dioxoisoindolin-4-yl)oxy)acetamide Trifluoroacetate tert-butyl (2-(2-(2-(2-((2-(2,6-dioxopiperidin-3-yl)-1,3-dioxoisoindolin-4-yl)oxy)acetamido)ethoxy)ethoxy)ethyl) carbamate (0.25 g, 0.44 mmol, 1 eq) was dissolved in TFA (4.5 mL) and heated to 50° C. After 3 hours, the mixture was cooled to room temperature, diluted with MeOH, and concentrated under reduced pressure. Purification by preparative HPLC gave the desired product as a tan solid (0.197 g, 0.342 mmol, 77%). $^1$H NMR (400 MHz, Methanol-$d_4$) δ 7.81 (ddd, J=8.4, 7.4, 1.1 Hz, 1H), 7.55-7.50 (m, 1H), 7.43 (d, J=8.5 Hz, 1H), 5.13 (dd, J=12.7, 5.5 Hz, 1H), 4.78 (s, 2H), 3.74-3.66 (m, 6H), 3.64 (t, J=5.4 Hz, 2H), 3.52 (t, J=5.3 Hz, 2H), 3.14-3.08 (m, 2H), 2.89 (ddd, J=17.5, 13.9, 5.2 Hz, 1H), 2.80-2.66 (m, 2H), 2.16 (dtd, J=13.0, 5.7, 2.7 Hz, 1H). LCMS 463.36 (M+H).

Step 2: Synthesis of dBET24

A 0.1 M solution of N-(2-(2-(2-aminoethoxy)ethoxy)ethyl)-2-((2-(2,6-dioxopiperidin-3-yl)-1,3-dioxoisoindolin-4-yl)oxy)acetamide trifluoroacetate in DMF (0.324 mL, 0.0324 mmol, 1 eq) was added to JQ-acid (13.0 mg, 0.324 mmol, 1 eq). DIPEA 16.9 microliters, 0.0972 mmol, 3 eq) and HATU (12.3 mg, 0.0324 mmol, 1 eq) were then added and the mixture was stirred for 18 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as an off-white solid (20.0 mg, 0.0236 mmol, 73%). $^1$H NMR (400 MHz, Methanol-$d_4$) δ 7.77-7.72 (m, 1H), 7.49 (d, J=7.4 Hz, 1H), 7.45-7.35 (m, 5H), 5.09 (ddd, J=12.3, 5.4, 3.7 Hz, 1H), 4.76 (s, 2H), 4.60 (dd, J=8.9, 5.3 Hz, 1H), 3.68-3.62 (m, 6H), 3.59 (t, J=5.6 Hz, 2H), 3.54-3.48 (m, 2H), 3.47-3.35 (m, 4H), 2.84 (ddd, J=19.4, 9.9, 4.6 Hz, 1H), 2.77-2.69 (m, 2H), 2.68 (d, J=1.8 Hz, 3H), 2.43 (s, 3H), 2.12 (dt, J=9.8, 5.3 Hz, 1H), 1.68 (s, 3H). LCMS 845.39 (M+H).

Synthetic Example 25: Synthesis of dBET25

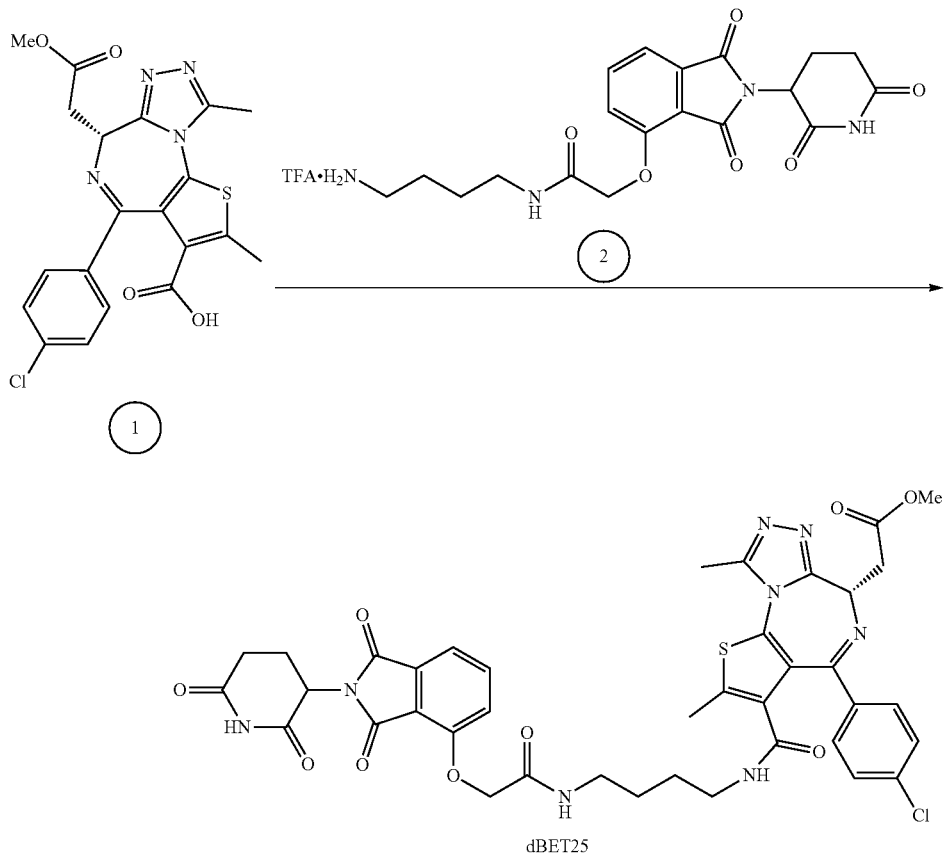

A 0.1 M solution of N-(4-aminobutyl)-2-((2-(2,6-dioxopiperidin-3-yl)-1,3-dioxoisoindolin-4-yl)oxy)acetamide trifluoroacetate in DMF (183 microliters, 0.0183 mmol, 1 eq) was added to (S)-4-(4-chlorophenyl)-6-(2-methoxy-2-oxoethyl)-2,9-dimethyl-6H-thieno[3,2-f][1,2,4]triazolo[4,3-a][1,4]diazepine-3-carboxylic acid (8.16 mg, 0.0183 mmol, 1 eq) at room temperature. DIPEA (9.6 microliters, 0.0550 mmol, 3 eq) and HATU (7.0 mg, 0.0183 mmol, 1 eq) were added. The mixture was then stirred for 23 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a yellow solid (4.39 mg, 0.00529 mmol, 29%). $^1$H NMR (400 MHz, Methanol-$d_4$) δ 7.82 (dd, J=8.4, 7.4 Hz, 1H), 7.55 (d, J=7.3 Hz, 1H), 7.45 (d, J=8.2 Hz, 1H), 7.43-7.31 (m, 4H), 5.16-5.10 (m, 1H), 4.77 (d, J=1.5 Hz, 2H), 4.56 (s, 1H), 3.74 (d, J=1.8 Hz, 3H), 3.66-3.60 (m, 4H), 3.50 (dd, J=16.5, 7.3 Hz, 1H), 3.37-3.32 (m, 1H), 3.28 (s, 3H), 2.85 (t, J=7.2 Hz, 2H), 2.75 (d, J=7.8 Hz, 1H), 2.71 (d, J=0.9 Hz, 3H), 2.59 (d, J=1.0 Hz, 3H), 2.18-2.10 (m, 1H), 1.36-1.24 (m, 4H). LCMS 829.38 (M+H).

Synthetic Example 26: Synthesis of dBET26

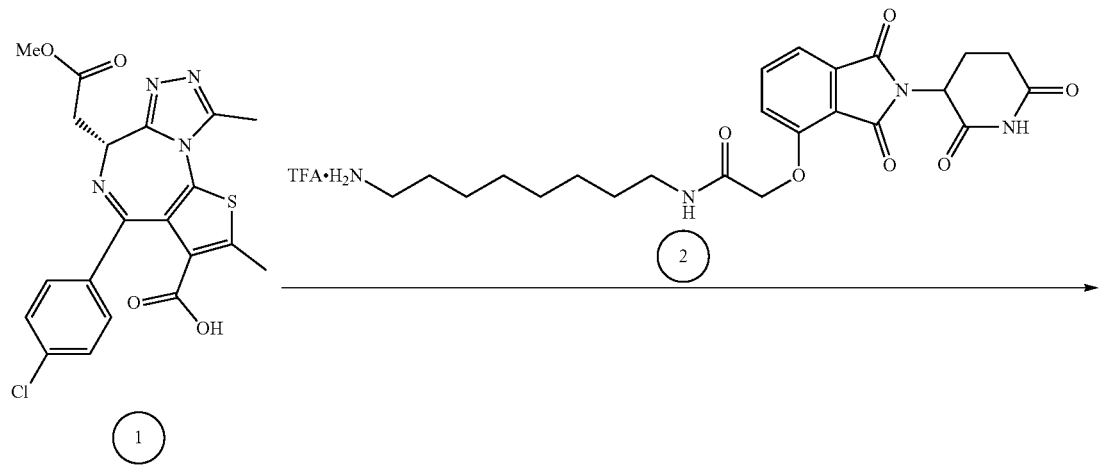

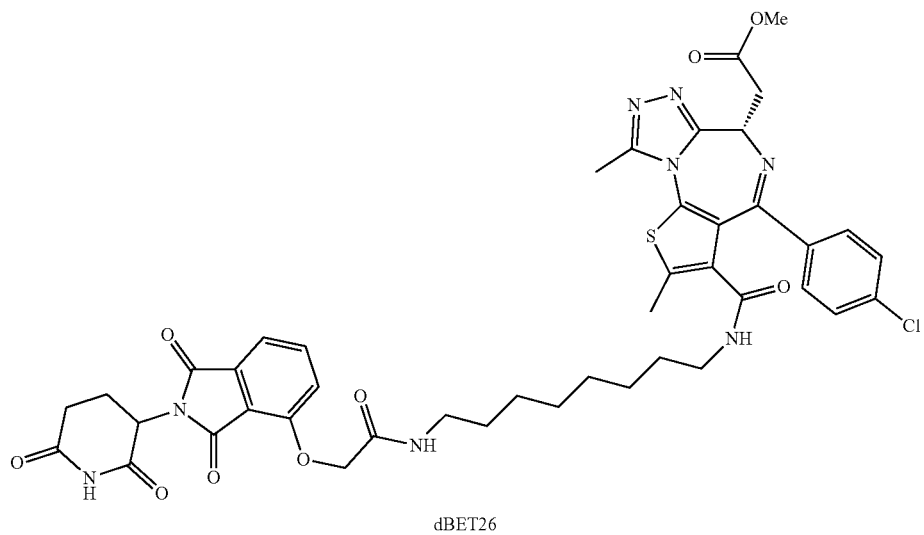

dBET26

A 0.1 M solution of N-(8-aminooctyl)-2-((2-(2,6-dioxopiperidin-3-yl)-1,3-dioxoisoindolin-4-yl)oxy)acetamide trifluoroacetate in DMF (186 microliters, 0.0186 mmol, 1 eq) was added to (S)-4-(4-chlorophenyl)-6-(2-methoxy-2-oxoethyl)-2,9-dimethyl-6H-thieno[3,2-f][1,2,4]triazolo[4,3-a][1,4]diazepine-3-carboxylic acid (8.26 mg, 0.0186 mmol, 1 eq) at room temperature. DIPEA (9.7 microliters, 0.0557 mmol, 3 eq) and HATU (7.1 mg, 0.0186 mmol, 1 eq) were added. The mixture was then stirred for 23 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a cream colored solid (6.34 mg, 0.00716 mmol, 38%). $^1$H NMR (400 MHz, Methanol-$d_4$) δ 7.83-7.78 (m, 1H), 7.53 (dd, J=7.3, 2.2 Hz, 1H), 7.45-7.38 (m, 3H), 7.32 (dd, J=8.5, 1.3 Hz, 2H), 5.16-5.08 (m, 1H), 4.76 (s, 2H), 4.56 (s, 1H), 3.75 (s, 3H), 3.66 (dd, J=15.9, 8.7 Hz, 1H), 3.50 (dd, J=16.9, 6.9 Hz, 1H), 3.32 (d, J=2.8 Hz, 4H), 2.84-2.74 (m, 3H), 2.70 (d, J=1.1 Hz, 3H), 2.66-2.54 (m, 3H), 2.14 (d, J=5.3 Hz, 1H), 1.62-1.22 (m, 12H). LCMS 885.48 (M+H).

Synthetic Example 27: Synthesis of dBET27

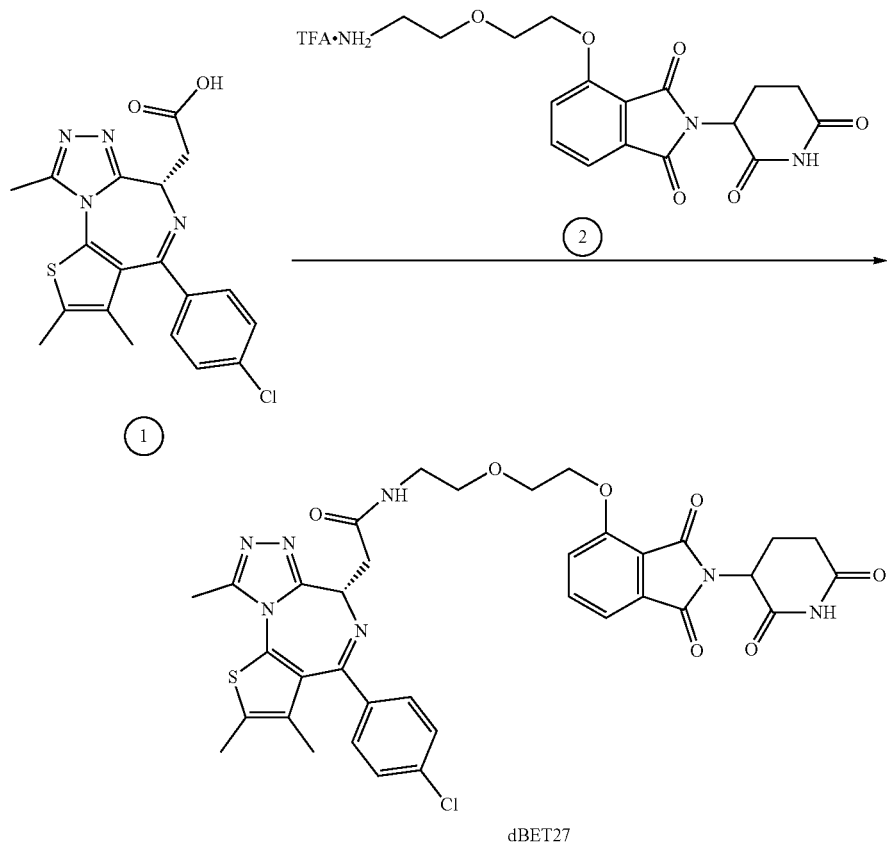

A 0.1 M solution of 4-(2-(2-aminoethoxy)ethoxy)-2-(2,6-dioxopiperidin-3-yl)isoindoline-1,3-dione trifluoroacetate in DMF (257 microliters, 0.0257 mmol, 1 eq) was added to JQ-acid (10.3 mg, 0.0257 mmol, 1 eq). DIPEA (13.4 microliters, 0.0771 mmol, 3 eq) and HATU (9.8 mg, 0.0257 mmol, 1 eq) were then added and the mixture was stirred for 18 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as a white solid (14.53 mg, 0.0195 mmol, 76%). $^1$H NMR (400 MHz, Methanol-$d_4$) δ 7.75 (ddd, J=8.5, 7.3, 1.3 Hz, 1H), 7.47-7.30 (m, 6H), 5.00 (ddd, J=25.4, 12.2, 5.2 Hz, 1H), 4.61 (td, J=9.4, 5.0 Hz, 1H), 4.36 (q, J=4.8 Hz, 2H), 3.96-3.89 (m, 2H), 3.74 (q, J=5.6 Hz, 2H), 3.53-3.41 (m, 3H), 3.30-3.24 (m, 1H), 2.78-2.53 (m, 6H), 2.41 (d, J=3.9 Hz, 3H), 2.09-1.98 (m, 1H), 1.67 (d, J=5.0 Hz, 3H).

Synthetic Example 28: Synthesis of dBET28

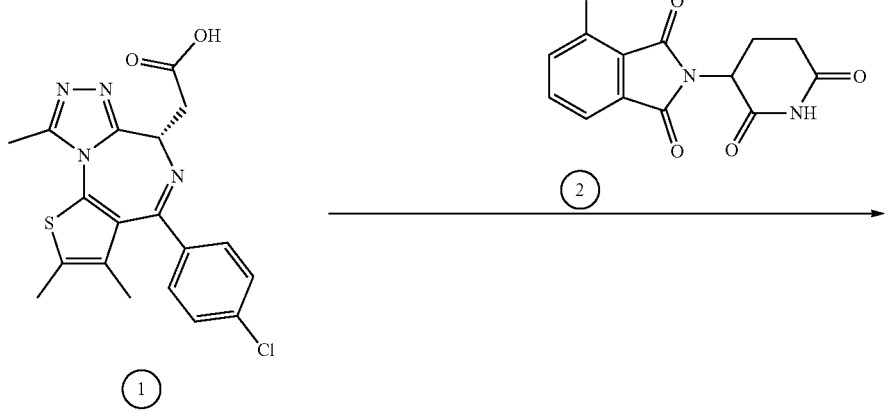

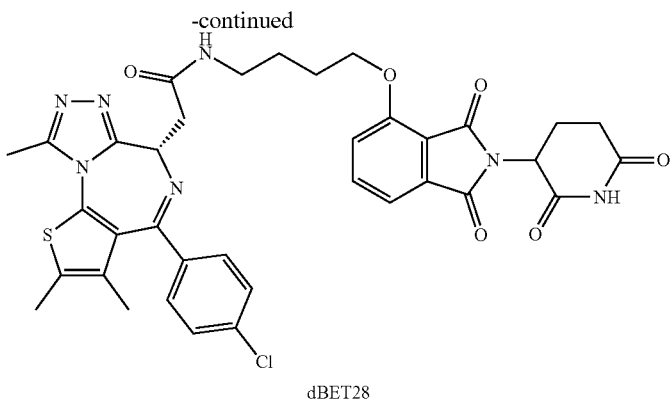

dBET28

A 0.1 M solution of 4-(4-aminobutoxy)-2-(2,6-dioxopiperidin-3-yl)isoindoline-1,3-dione trifluoroacetate in DMF (202 microliters, 0.0202 mmol, 1 eq) was added to JQ-acid (8.1 mg, 0.0202 mmol, 1 eq). DIPEA (10.6 microliters, 0.0606 mmol, 3 eq) and HATU (7.7 mg, 0.0202 mmol, 1 eq) were then added and the mixture was stirred for 18.5 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as a cream colored solid (10.46 mg, 0.0144 mmol, 71%). $^1$H NMR (400 MHz, Methanol-$d_4$) δ 7.76 (t, J=7.5 Hz, 1H), 7.43 (td, J=6.5, 2.5 Hz, 4H), 7.34 (t, J=8.8 Hz, 2H), 5.08-4.98 (m, 1H), 4.64 (td, J=9.1, 5.0 Hz, 1H), 4.26 (t, J=5.3 Hz, 2H), 3.57-3.32 (m, 4H), 2.84-2.59 (m, 6H), 2.45-2.37 (m, 3H), 2.08-2.01 (m, 1H), 2.00-1.91 (m, 2H), 1.82 (dq, J=13.8, 6.9 Hz, 2H), 1.68 (d, J=11.7 Hz, 3H). LCMS 728.38 (M+H).

Synthetic Example 29: Synthesis of dBET29

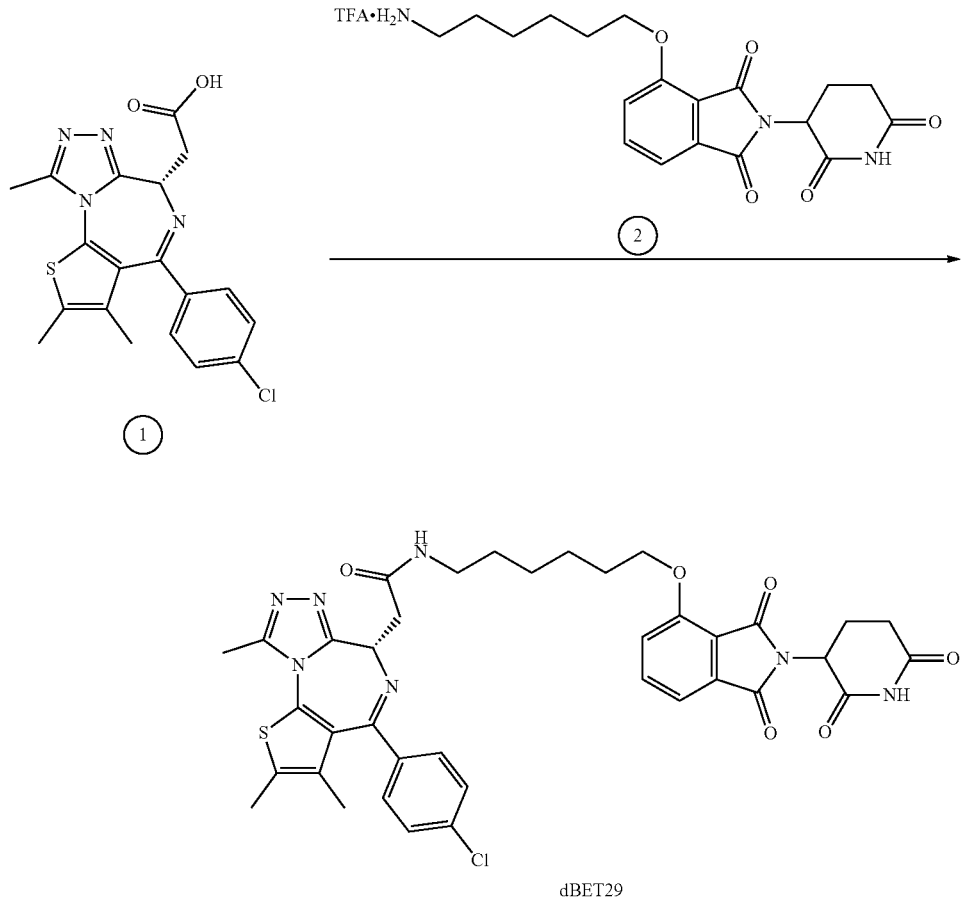

dBET29

A 0.1 M solution of 4-((6-aminohexyl)oxy)-2-(2,6-dioxopiperidin-3-yl)isoindoline-1,3-dione in DMF (205 microliters, 0.0205 mmol, 1 eq) was added to JQ-acid (8.2 mg, 0.0205 mmol, 1 eq). DIPEA (10.7 microliters, 0.0614 mmol, 3 eq) and HATU (7.8 mg, 0.0205 mmol, 1 eq) were then added and the mixture was stirred for 19 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as a white solid (8.04 mg, 0.0106 mmol, 52%). $^1$H NMR (400 MHz, Methanol-$d_4$) δ 7.75-7.71 (m, 1H), 7.51-7.34 (m, 6H), 5.07 (ddd, J=12.1, 5.4, 2.4 Hz, 1H), 4.62 (dd, J=9.0, 5.2 Hz, 1H), 4.22 (t, J=6.4 Hz, 2H), 3.44-3.32 (m, 2H), 3.29-3.21 (m, 2H), 2.88-2.65 (m, 6H), 2.43 (s, 3H), 2.13-2.06 (m, 1H), 1.86 (dt, J=13.9, 6.7 Hz, 2H), 1.68 (s, 3H), 1.59 (dq, J=14.2, 7.0 Hz, 4H), 1.54-1.45 (m, 2H). LCMS 756.40 (M+H).

Synthetic Example 30: Synthesis of dBET30

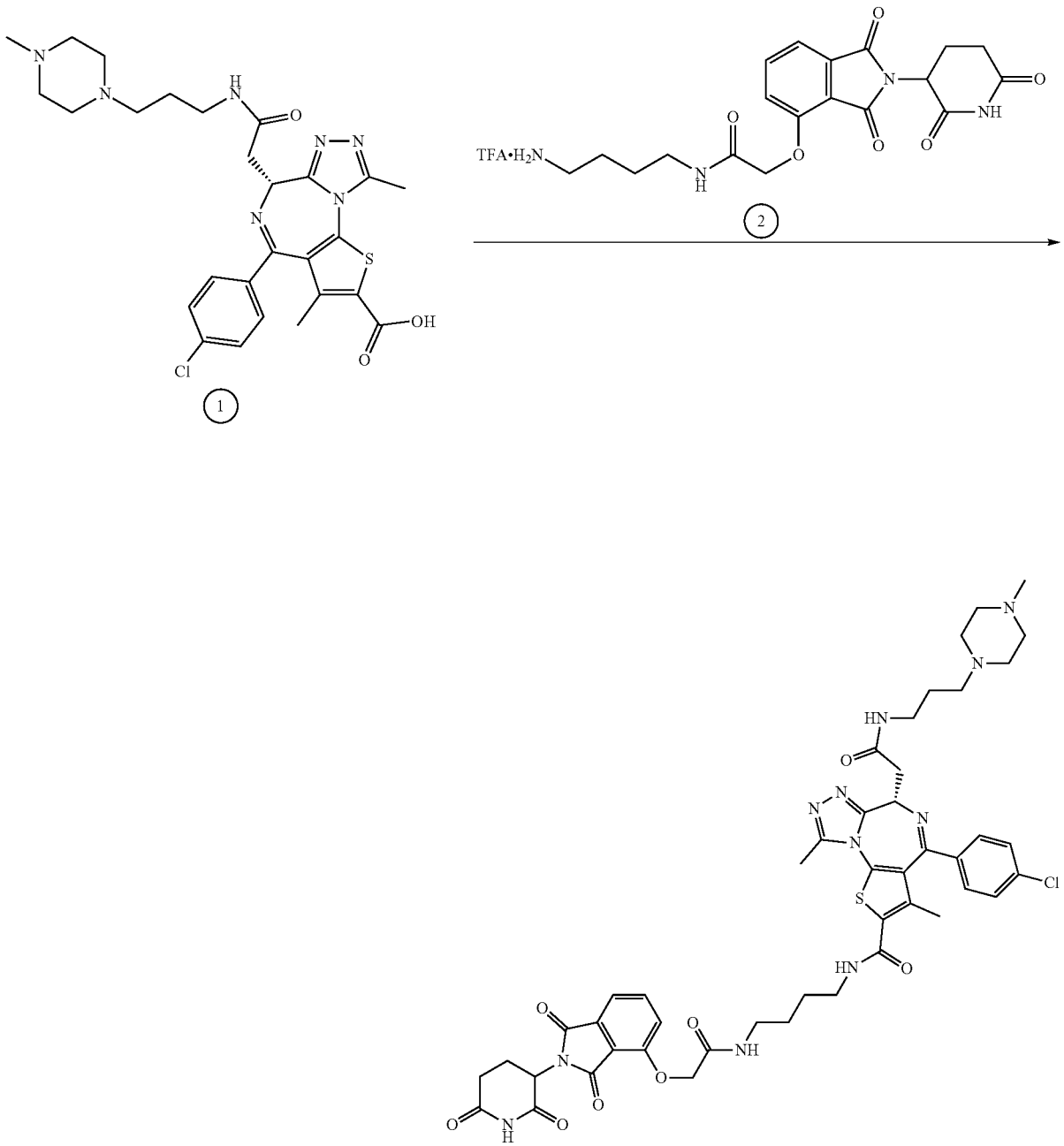

dBET30

A 0.1 M solution of N-(4-aminobutyl)-2-((2-(2,6-dioxopiperidin-3-yl)-1,3-dioxoisoindolin-4-yl)oxy)acetamide trifluoroacetate in DMF (163 microliters, 0.0163 mmol, 1 eq) was added to (S)-4-(4-chlorophenyl)-3,9-dimethyl-6-(2-((3-(4-methylpiperazin-1-yl)propyl)amino)-2-oxoethyl)-6H-thieno[3,2-f][1,2,4]triazolo[4,3-a][1,4]diazepine-2-carboxylic acid (9.31 mg, 0.0163 mmol, 1 eq) at room temperature. DIPEA (8.5 microliters, 0.0490 mmol, 3 eq) and HATU (6.2 mg, 0.0163 mmol, 1 eq) were added. The mixture was then stirred for 23.5 hours, then purified by preparative HPLC to give the desired product as a yellow oil (11.48 mg, 0.0107 mmol, 66%). $^1$H NMR (400 MHz, Methanol-$d_4$) δ 7.82-7.78 (m, 1H), 7.54-7.35 (m, 6H), 5.09 (td, J=12.7, 5.4 Hz, 1H), 4.77-4.70 (m, 3H), 3.56-3.31 (m, 12H), 3.23 (dd, J=8.0, 6.0 Hz, 3H), 3.05 (d, J=3.2 Hz, 2H), 2.93-2.81 (m, 5H), 2.78-2.63 (m, 5H), 2.15-2.05 (m, 2H), 1.96-1.86 (m, 4H), 1.68 (s, 4H). LCMS 954.55 (M+H).

Synthetic Example 31: Synthesis of dBET31

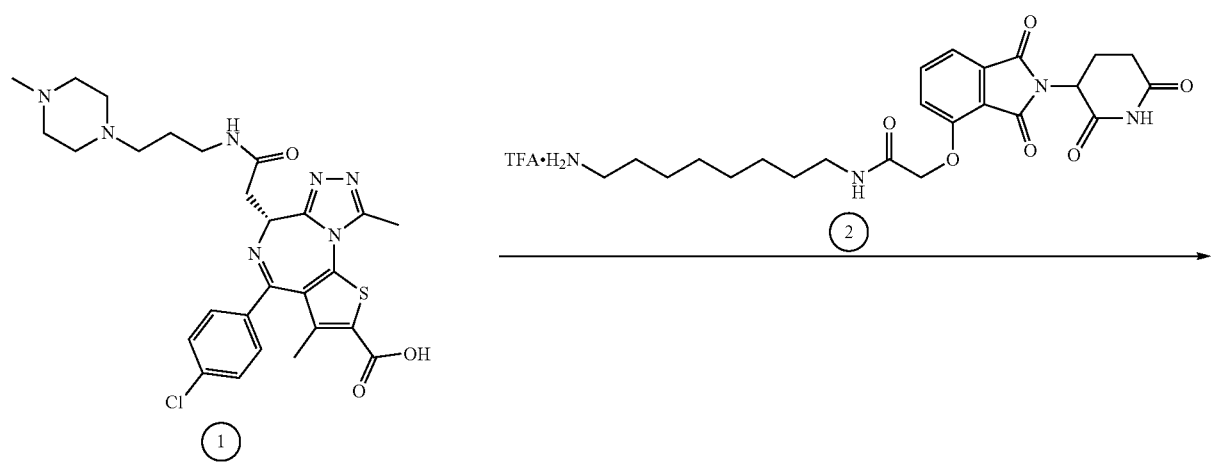

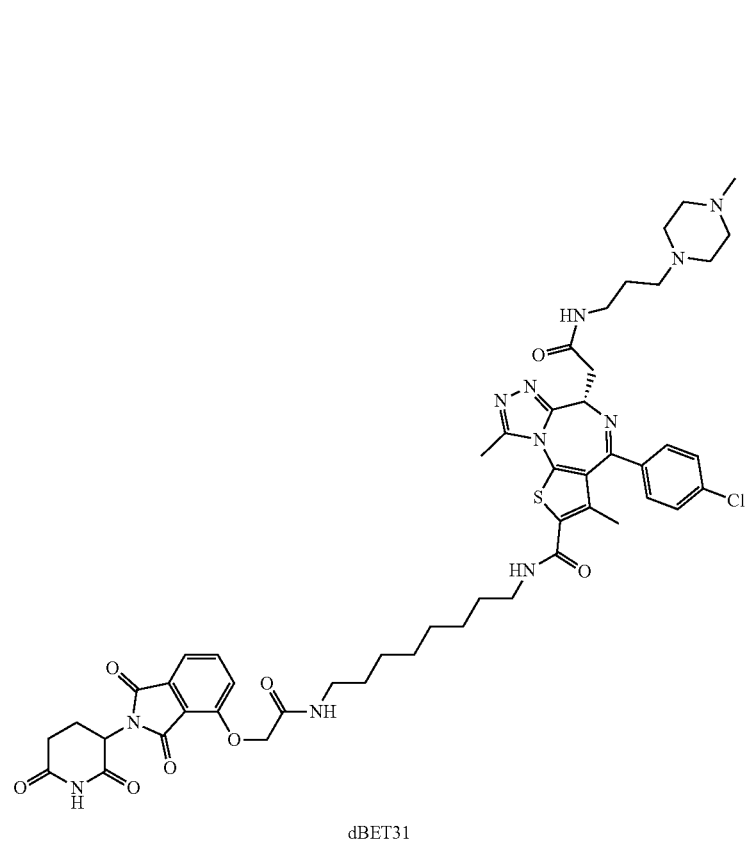

dBET31

A 0.1 M solution of N-(8-aminooctyl)-2-((2-(2,6-dioxopiperidin-3-yl)-1,3-dioxoisoindolin-4-yl)oxy)acetamide trifluoroacetate in DMF (153 microliters, 0.0153 mmol, 1 eq) was added to (S)-4-(4-chlorophenyl)-3,9-dimethyl-6-(2-((3-(4-methylpiperazin-1-yl)propyl)amino)-2-oxoethyl)-6H-thieno[3,2-f][1,2,4]triazolo[4,3-a][1,4]diazepine-2-carboxylic acid (8.7 mg, 0.0153 mmol, 1 eq) at room temperature. DIPEA (7.9 microliters, 0.0458 mmol, 3 eq) and HATU (5.8 mg, 0.0153 mmol, 1 eq) were added. The mixture was then stirred for 25 hours, then purified by preparative HPLC to give the desired product as a nice brown (not like poop brown, kind of like brick) oil (9.52 mg, 0.00847 mmol, 55%). ¹H NMR (400 MHz, Methanol-$d_4$) δ 7.81 (dd, J=8.4, 7.4 Hz, 1H), 7.59-7.40 (m, 6H), 5.12 (dd, J=12.5, 5.4 Hz, 1H), 4.75 (s, 2H), 4.71 (t, J=7.4 Hz, 1H), 3.53-3.34 (m, 8H), 3.29-3.11 (m, 6H), 3.03-2.61 (m, 13H), 2.15 (s, 1H), 2.01-1.84 (m, 5H), 1.59 (s, 4H), 1.37 (s, 8H). LCMS 1010.62 (M+H).

Synthetic Example 32: Synthesis of dBET32

A 0.1 M solution of N-(4-aminobutyl)-2-((2-(2,6-dioxopiperidin-3-yl)-1,3-dioxoisoindolin-4-yl)oxy)acetamide trifluoroacetate in DMF (180 microliters, 0.0180 mmol, 1 eq) was added to 4-(4-(4-((4-((3-(N-(tert-butyl)sulfamoyl)phenyl)amino)-5-methylpyrimidin-2-yl)amino)phenyl)piperazin-1-yl)-4-oxobutanoic acid (10.7 mg, 0.0180 mmol, 1 eq) at room temperature. DIPEA (9.4 microliters, 0.0539 mmol, 3 eq) and HATU (6.8 mg, 0.0180 mmol, 1 eq) were added and the mixture was stirred for 19 hours. The mixture was then diluted with methanol and purified by preparative HPLC to give the desired product as a brown oil (4.40 mg, 0.00449 mmol, 25%). ¹H NMR (500 MHz, Methanol-$d_4$) δ 8.08 (d, J=13.6 Hz, 1H), 7.84-7.76 (m, 3H), 7.63 (s, 1H), 7.57-7.51 (m, 2H), 7.41 (d, J=8.4 Hz, 1H), 7.22 (td, J=6.7, 2.2 Hz, 2H), 7.03-6.97 (m, 2H), 5.14 (dd, J=12.5, 5.5 Hz, 1H), 4.76 (d, J=16.8 Hz, 2H), 3.72 (dt, J=10.0, 5.2 Hz, 4H), 3.34-3.33 (m, 1H), 3.23-3.12 (m, 5H), 2.97 (dd, J=8.8, 4.0 Hz, 3H), 2.80-2.69 (m, 4H), 2.64 (dd, J=7.6, 5.5 Hz, 1H), 2.50 (t, J=6.8 Hz, 1H), 2.22 (dd, J=2.4, 0.9 Hz, 3H), 2.17-2.11 (m, 1H), 1.67-1.52 (m, 4H), 1.18 (d, J=0.8 Hz, 9H). LCMS 980.64 (M+H).

Synthetic Example 33: Synthesis of dBET33
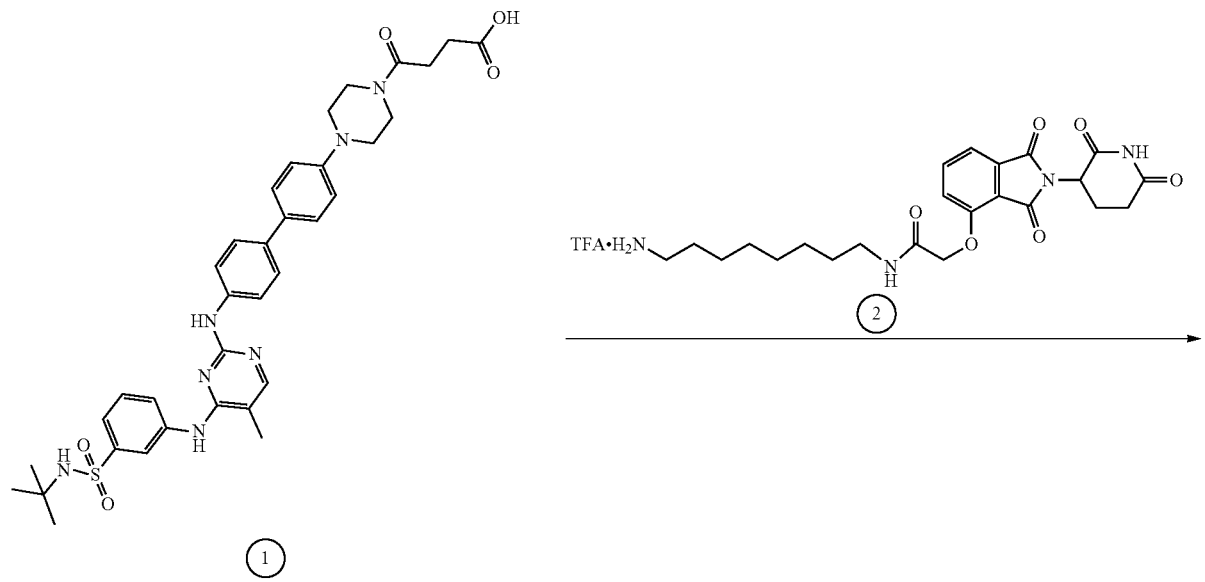
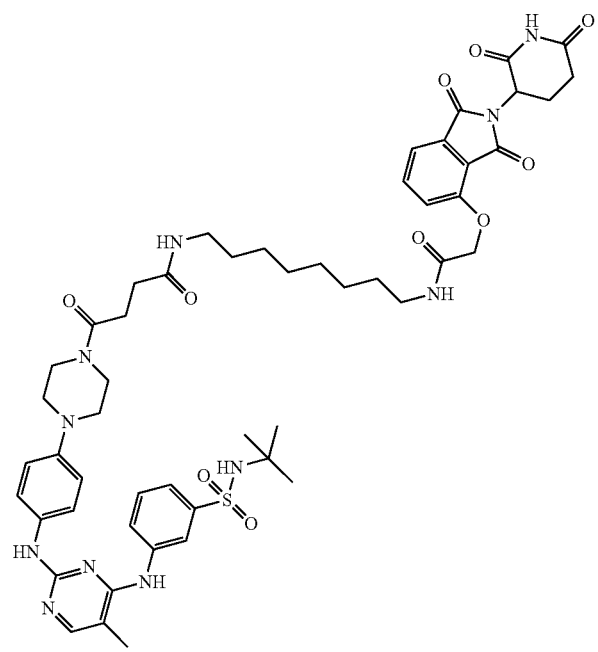
dBET33

A 0.1 M solution of N-(8-aminooctyl)-2-((2-(2,6-dioxopiperidin-3-yl)-1,3-dioxoisoindolin-4-yl)oxy)acetamide trifluoroacetate in DMF (188 microliters, 0.0188 mmol, 1 eq) was added to 4-(4-(4-(((4-((3-(N-(tert-butyl)sulfamoyl)phenyl)amino)-5-methylpyrimidin-2-yl)amino)phenyl)piperazin-1-yl)-4-oxobutanoic acid (10.8 mg, 0.0188 mmol, 1 eq) at room temperature. DIPEA (9.8 microliters, 0.0564 mmol, 3 eq) and HATU (7.1 mg, 0.0188 mmol, 1 eq) were added and the mixture was stirred for 23 hours. The mixture was then diluted with methanol and purified by preparative HPLC to give the desired product as a brown residue (7.41 mg, 0.00715 mmol, 38%). $^1$H NMR (500 MHz, Methanol-$d_4$) δ 8.06 (s, 1H), 7.80 (ddd, J=10.5, 7.6, 3.2 Hz, 3H), 7.65 (d, J=4.5 Hz, 1H), 7.57-7.51 (m, 2H), 7.41 (dd, J=8.4, 2.9 Hz, 1H), 7.25 (td, J=6.7, 2.9 Hz, 2H), 7.02 (t, J=8.0 Hz, 2H), 5.16-5.09 (m, 1H), 4.75 (d, J=9.5 Hz, 2H), 3.76 (dq, J=16.0, 5.3 Hz, 4H), 3.29-3.12 (m, 7H), 3.00-2.67 (m, 7H), 2.51 (t, J=6.8 Hz, 1H), 2.22 (d, J=3.1 Hz, 3H), 2.13 (dtd, J=10.4, 5.7, 3.1 Hz, 1H), 1.59-1.52 (m, 2H), 1.51-1.43 (m, 2H), 1.32 (t, J=16.6 Hz, 8H), 1.18 (d, J=1.3 Hz, 9H). LCMS 1036.69 (M+H).

Synthetic Example 34: Synthesis of dBET34

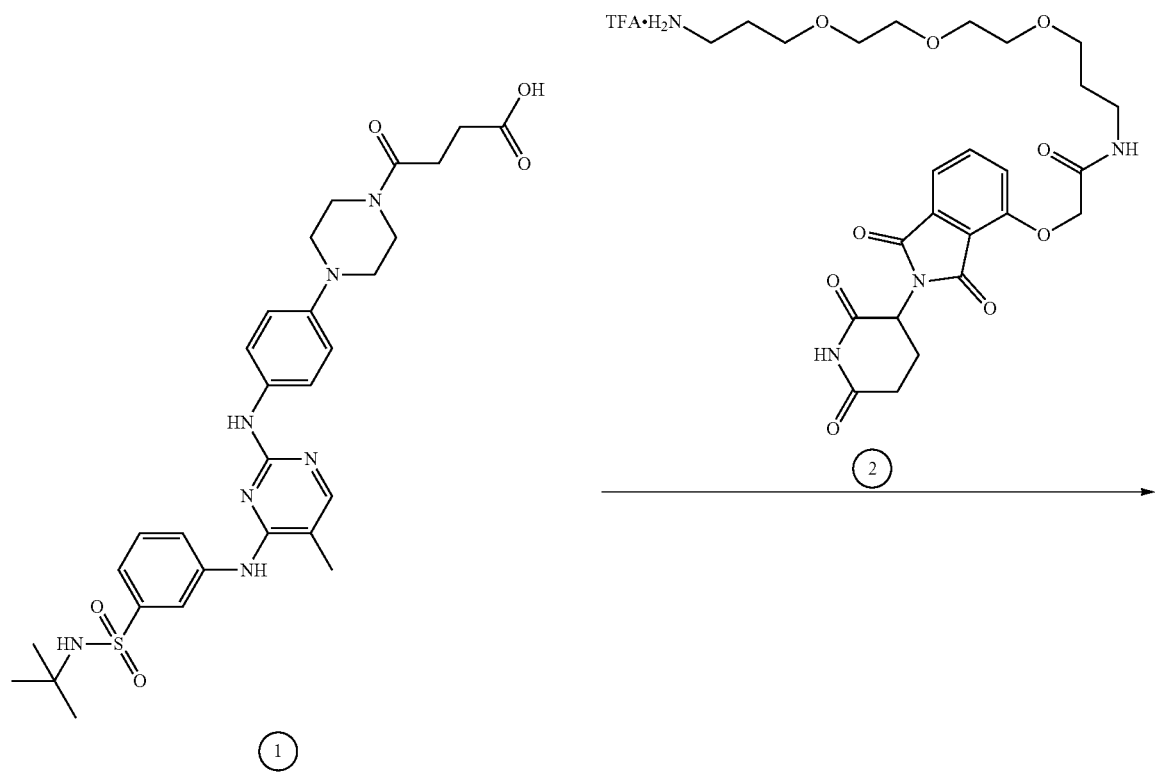

-continued

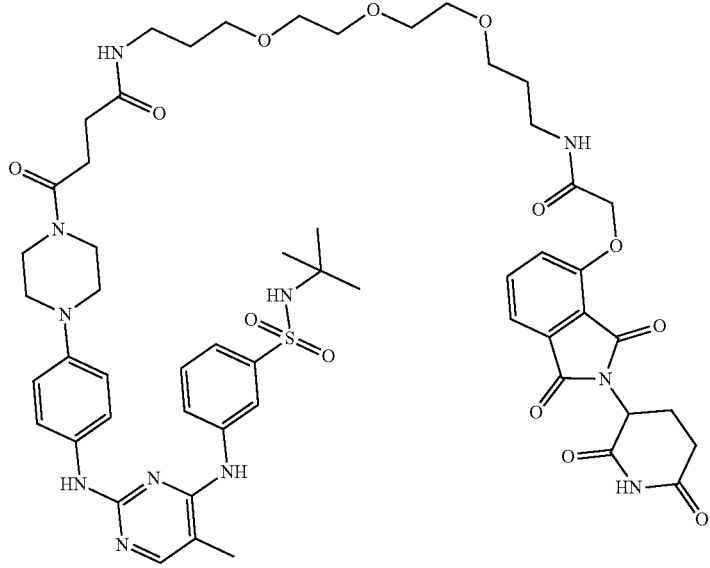

dBET34

A 0.1 M solution of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (173 microliters, 0.0173 mmol, 1 eq) was added to 4-(4-(4-((4-((3-(N-(tert-butyl)sulfamoyl)phenyl)amino)-5-methylpyrimidin-2-yl)amino)phenyl)piperazin-1-yl)-4-oxobutanoic acid (10.3 mg, 0.0173 mmol, 1 eq) at room temperature. DIPEA (9.0 microliters, 0.0519 mmol, 3 eq) and HATU (6.6 mg, 0.0173 mmol, 1 eq) were added and the mixture was stirred for 25 hours. The mixture was then diluted with methanol and purified by preparative HPLC to give the desired product as a brown residue (7.99 mg, 0.00718 mmol, 42%). $^1$H NMR (500 MHz, Methanol-$d_4$) δ 8.06 (s, 1H), 7.83-7.76 (m, 3H), 7.65 (s, 1H), 7.58-7.50 (m, 2H), 7.43 (dd, J=17.7, 8.4 Hz, 1H), 7.27-7.21 (m, 2H), 7.02 (t, J=8.0 Hz, 2H), 5.13 (dt, J=12.7, 5.2 Hz, 1H), 4.76 (d, J=12.4 Hz, 2H), 3.73 (q, J=6.3 Hz, 4H), 3.63-3.49 (m, 10H), 3.41 (q, J=6.6 Hz, 2H), 3.27-3.15 (m, 5H), 3.01-2.81 (m, 4H), 2.79-2.63 (m, 5H), 2.50 (t, J=6.8 Hz, 1H), 2.22 (d, J=2.3 Hz, 3H), 2.17-2.11 (m, 1H), 1.88-1.70 (m, 4H), 1.18 (d, J=1.2 Hz, 9H). LCMS 1112.74 (M+H).

Synthetic Example 35: Synthesis of dBET35

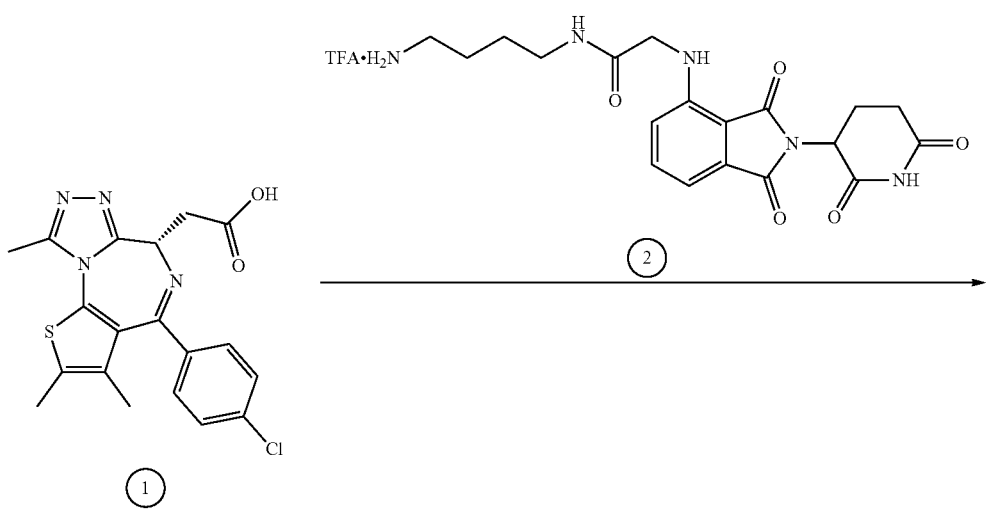

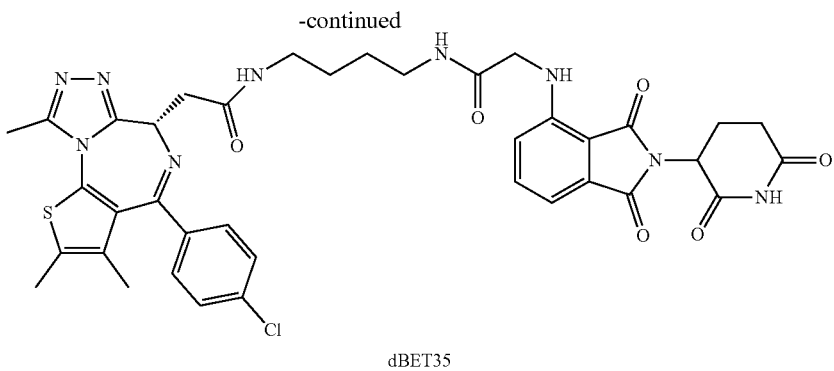

dBET35

A 0.1 M solution of N-(4-aminobutyl)-2-((2-(2,6-dioxopiperidin-3-yl)-1-oxoisoindolin-4-yl)amino)acetamide trifluoroacetate in DMF (185 microliters, 0.0185 mmol, 1 eq) was added to JQ-acid (7.4 mg, 0.0185 mmol, 1 eq). DIPEA (9.6 microliters, 0.0554 mmol, 3 eq) and HATU (7.0 mg, 0.0185 mmol, 1 eq) were then added and the mixture was stirred for 17 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-15% MeOH/DCM, 25 minute gradient) gave the desired product as a white solid (2.71 mg, 0.00351 mmol, 19%). $^1$H NMR (500 MHz, Methanol-$d_4$) δ 7.48-7.37 (m, 4H), 7.34 (t, J=7.8 Hz, 1H), 7.14 (dd, J=7.4, 2.4 Hz, 1H), 6.67 (d, J=8.1 Hz, 1H), 5.14 (td, J=13.5, 5.2 Hz, 1H), 4.66-4.60 (m, 1H), 4.59 (d, J=8.3 Hz, 2H), 4.43-4.31 (m, 2H), 3.88 (s, 2H), 3.25 (dd, J=14.8, 7.1 Hz, 4H), 2.94-2.72 (m, 3H), 2.68 (d, J=4.9 Hz, 3H), 2.49-2.40 (m, 4H), 2.21-2.12 (m, 1H), 1.68 (s, 3H), 1.53 (s, 4H). LCMS 770.51 (M+H).

Synthetic Example 36: Synthesis of dBET36

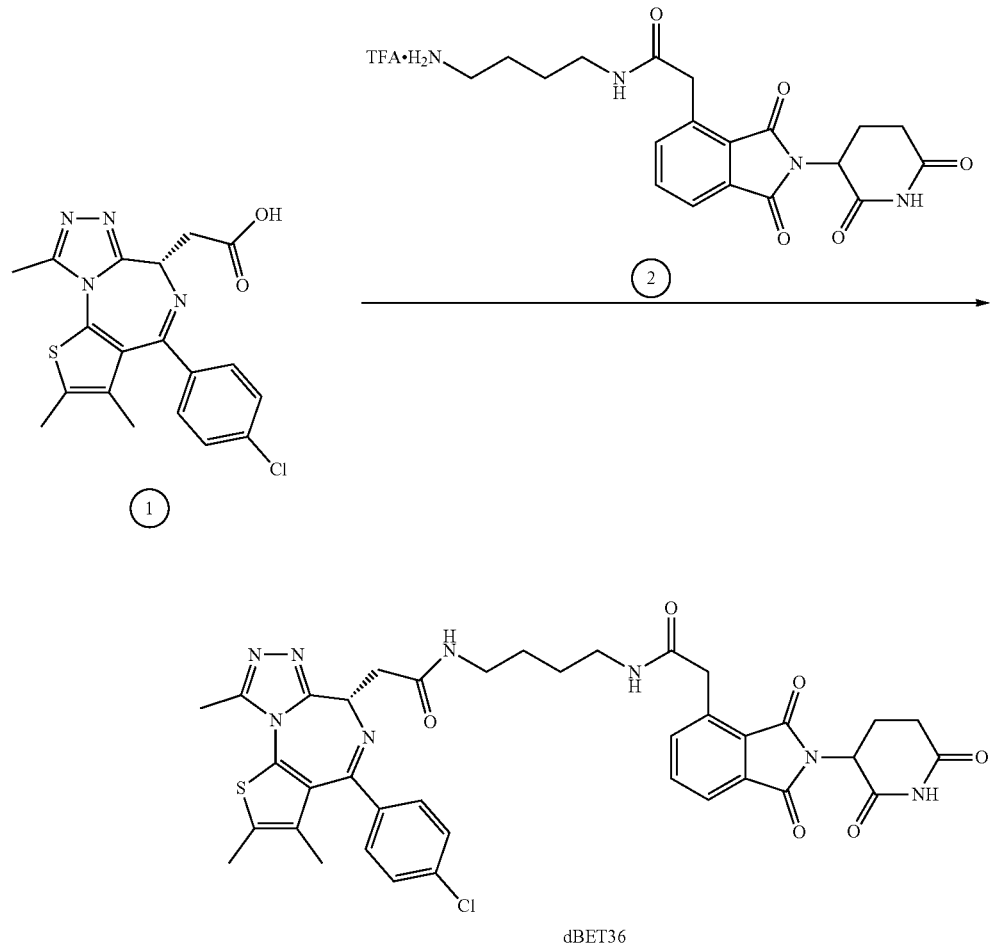

dBET36

A 0.1 M solution of N-(4-aminobutyl)-2-(2-(2,6-dioxopiperidin-3-yl)-1,3-dioxoisoindolin-4-yl)acetamide trifluoroacetate in DMF (222 microliters, 0.0222 mmol, 1 eq) was added to JQ-acid (8.9 mg, 0.0222 mmol, 1 eq). DIPEA (11.6 microliters, 0.0666 mmol, 3 eq) and HATU (8.4 mg, 0.0222 mmol, 1 eq) were then added and the mixture was stirred for 17.5 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-15% MeOH/DCM, 25 minute gradient) gave the desired product as a white solid (12.42 mg, 0.0156 mmol, 70%). $^1$H NMR (500 MHz, Methanol-$d_4$) δ 7.80-7.74 (m, 2H), 7.68 (d, J=6.8 Hz, 1H), 7.42 (q, J=8.7 Hz, 4H), 5.11 (dt, J=12.3, 4.6 Hz, 1H), 4.63 (dd, J=8.8, 5.5 Hz, 1H), 4.10-4.00 (m, 2H), 3.39 (ddd, J=14.9, 8.8, 2.5 Hz, 1H), 3.30-3.21 (m, 5H), 2.88-2.76 (m, 1H), 2.74-2.65 (m, 5H), 2.44 (s, 3H), 2.15-2.08 (m, 1H), 1.69 (s, 3H), 1.63-1.55 (m, 4H). LCMS 769.49 (M+H).

Synthetic Example 37: Synthesis of dBET37

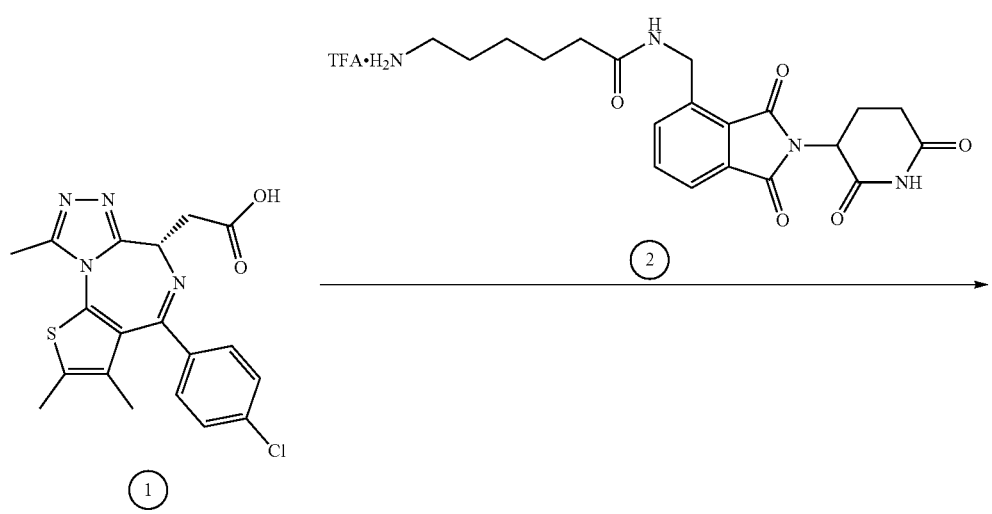

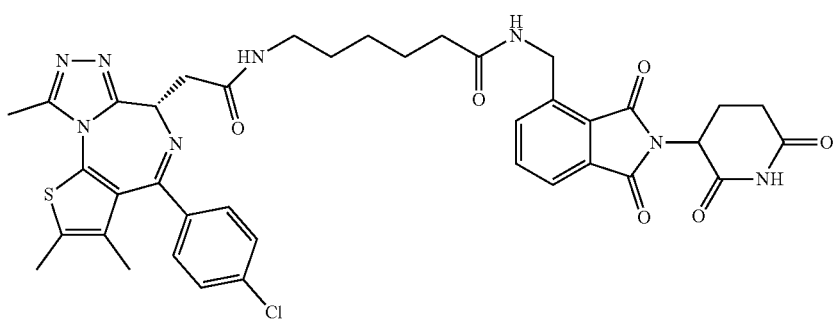

dBET37

A 0.1 M solution of 6-amino-N-((2-(2,6-dioxopiperidin-3-yl)-1,3-dioxoisoindolin-4-yl)methyl)hexanamide trifluoroacetate in DMF (195 microliters, 0.0195 mmol, 1 eq) was added to JQ-acid (7.8 mg, 0.0195 mmol, 1 eq). DIPEA (10.2 microliters, 0.0584 mmol, 3 eq) and HATU (7.4 mg, 0.0195 mmol, 1 eq) were then added and the mixture was stirred for 18 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-15% MeOH/DCM, 25 minute gradient) gave the desired product as a white solid (11.83 mg, 0.0151 mmol, 77%). $^1$H NMR (500 MHz, Methanol-$d_4$) δ 7.78-7.74 (m, 2H), 7.71 (dd, J=5.3, 3.5 Hz, 1H), 7.42 (q, J=8.5 Hz, 4H), 5.13 (dd, J=12.6, 5.5 Hz, 1H), 4.82 (s, 2H), 4.63 (dd, J=8.8, 5.5 Hz, 1H), 3.40 (ddd, J=15.0, 8.8, 1.6 Hz, 1H), 3.30-3.21 (m, 3H), 2.86 (ddd, J=18.4, 14.6, 4.8 Hz, 1H), 2.74 (ddd, J=13.8, 10.1, 2.8 Hz, 2H), 2.69 (s, 3H), 2.44 (s, 3H), 2.30 (t, J=7.4 Hz, 2H), 2.13 (dtd, J=12.9, 4.9, 2.3 Hz, 1H), 1.74-1.64 (m, 5H), 1.59 (p, J=7.0 Hz, 2H), 1.46-1.38 (m, 2H). LCMS 783.47 (M+H).

Synthetic Example 38: Synthesis of dBET38

Step 1: Synthesis of Tert-butyl (3-(3-(2-((2-(2,6-dioxopiperidin-3-yl)-1,3-dioxoisoindolin-4-yl)oxy)acetamido)propoxy)propyl)carbamate tert-butyl (3-(3-aminopropoxy)propyl)carbamate (134.5 mg, 0.579 mmol, 1 eq) was dissolved in DMF (5.79 ml, 0.05 M) then added to 2-((2-(2,6-dioxopiperidin-3-yl)-1,3-dioxoisoindolin-4-yl)oxy)acetic acid (192.38 mg, 0.579 mmol, 1 eq). DIPEA (0.28 ml, 1.74 mmol, 3 eq) and HATU (153.61 mg, 0.579 mmol, 1 eq) were added and the mixture was stirred for 18 hours at room temperature. The mixture was then diluted with EtOAc and washed with saturated sodium bicarbonate, water then brine. The organic layer was dried over sodium sulfate, filtered and condensed to give a yellow oil (157.1 mg). The crude material was purified by column chromatography (ISCO, 12 g silica column, 0 to 15% MeOH/DCM 25 minute gradient) to give a yellow oil (121.3 mg, 0.222 mmol, 38.27%). $^1$H NMR (400 MHz, Methanol-$d_4$) δ 7.78 (dd, J=8.4, 7.4 Hz, 1H), 7.50 (d, J=7.3 Hz, 1H), 7.41 (d, J=8.5 Hz, 1H), 5.13 (dd, J=12.4, 5.5 Hz, 1H), 4.75 (s, 2H), 3.53-3.37 (m, 6H), 3.14-3.07 (m, 2H), 2.94-2.88 (m, 1H), 2.79-2.68 (m, 2H), 2.16 (ddd, J=12.8, 6.6, 2.7 Hz, 1H), 1.81 (p, J=6.4 Hz, 2H), 1.73-1.65 (m, 2H), 1.40 (s, 9H). LCMS 547.6 (M+H).

Step 2: Synthesis of N-(3-(3-aminopropoxy)propyl)-2-((2-(2,6-dioxopiperidin-3-yl)-1,3-dioxoisoindolin-4-yl)oxy)acetamide Trifluoroacetate Salt TFA (2.22 ml, 0.1 M) was added to tert-butyl (3-(3-(2-((2-(2,6-dioxopiperidin-3-yl)-1,3-dioxoisoindolin-4-yl)oxy)acetamido)propoxy)propyl)carbamate (121.3 mg, 0.222 mmol, 1 eq) and the mixture was stirred at 50° C. for 2 hours. The mixture was then dissolved in MeOH and concentrated under reduced pressure to give a brown oil (114.1 mg) that was carried forward without further purification. $^1$H NMR (400 MHz, Methanol-$d_4$) δ 7.81-7.74 (m, 1H), 7.50 (d, J=7.3 Hz, 1H), 7.41 (d, J=8.5 Hz, 1H), 5.12 (dd, J=12.7, 5.5 Hz, 1H), 4.76 (s, 2H), 3.57-3.52 (m, 2H), 3.48 (t, J=5.9 Hz, 2H), 3.40 (t, J=6.6 Hz, 2H), 3.06 (t, J=6.5 Hz, 2H), 2.87 (ddd, J=14.1, 10.1, 7.0 Hz, 1H), 2.79-2.65 (m, 2H), 2.15 (dtd, J=12.8, 5.5, 2.6 Hz, 1H), 1.92 (dt, J=11.7, 5.9 Hz, 2H), 1.81 (p, J=6.3 Hz, 2H). LCMS 447.2 (M+H).

Step 3: Synthesis of dBET38

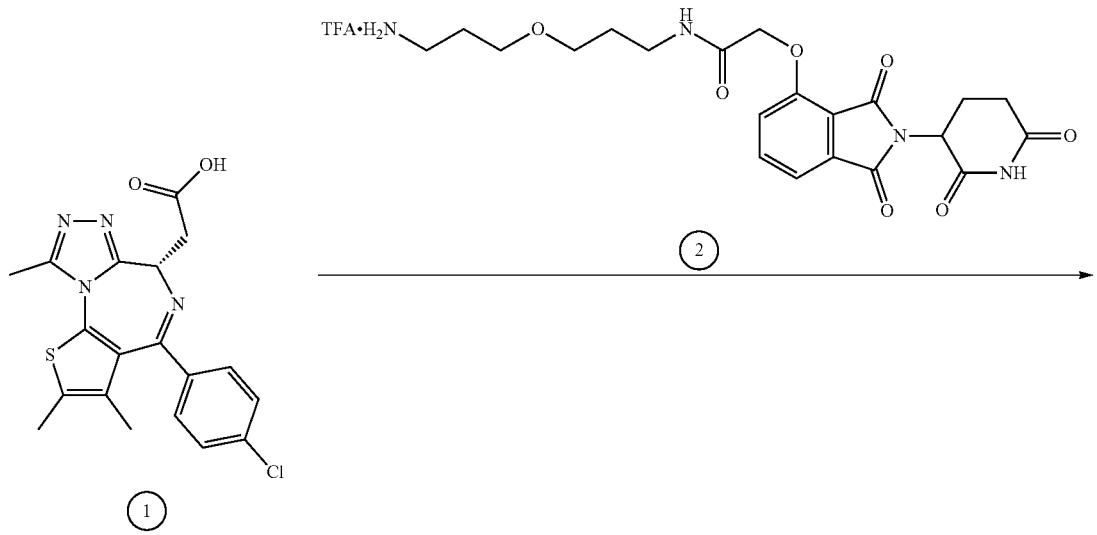

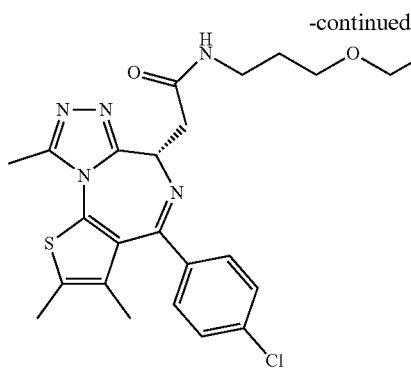
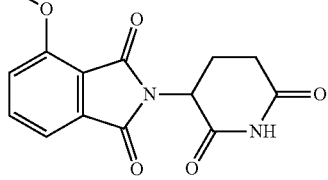

dBET38

A 0.1 M solution of N-(3-(3-aminopropoxy)propyl)-2-((2-(2,6-dioxopiperidin-3-yl)-1,3-dioxoisoindolin-4-yl)oxy)acetamide trifluoroacetate in DMF (0.215 mL, 0.0215 mmol, 1 eq) was added to JQ-acid (8.6 mg, 0.0215 mmol, 1 eq) at room temperature. DIPEA (11.2 microliters, 0.0644 mmol, 3 eq) and HATU (8.2 mg, 0.0215 mmol, 1 eq) were added. After 19 hours, the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-15% MeOH/DCM, 25 minute gradient) gave the desired product as a cream colored solid (10.6 mg, 0.0127 mmol, 59%). $^1$H NMR (500 MHz, Methanol-$d_4$) δ 7.79-7.74 (m, 1H), 7.50 (d, J=8.1 Hz, 1H), 7.46-7.36 (m, 5H), 5.11 (ddd, J=12.4, 5.5, 1.7 Hz, 1H), 4.73 (s, 2H), 4.62 (ddd, J=8.7, 5.4, 1.4 Hz, 1H), 3.50 (q, J=6.3 Hz, 4H), 3.43 (t, J=6.5 Hz, 2H), 3.41-3.32 (m, 3H), 3.29-3.24 (m, 1H), 2.85 (ddd, J=18.3, 14.6, 4.2 Hz, 1H), 2.77-2.65 (m, 5H), 2.43 (s, 3H), 2.17-2.09 (m, 1H), 1.80 (h, J=6.4 Hz, 4H), 1.68 (s, 3H). LCMS 829.32 (M+H).

Synthetic Example 39: Synthesis of dBET39

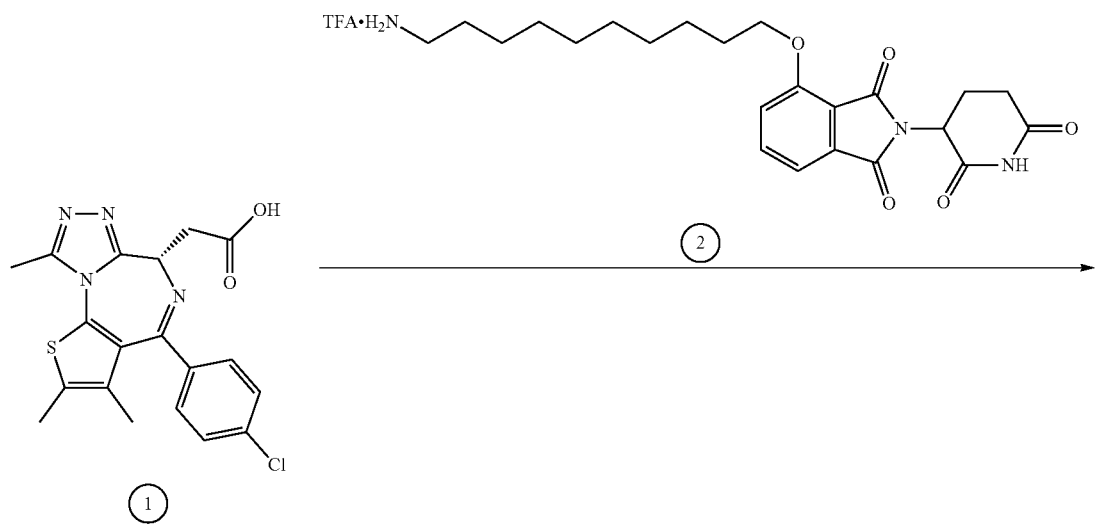

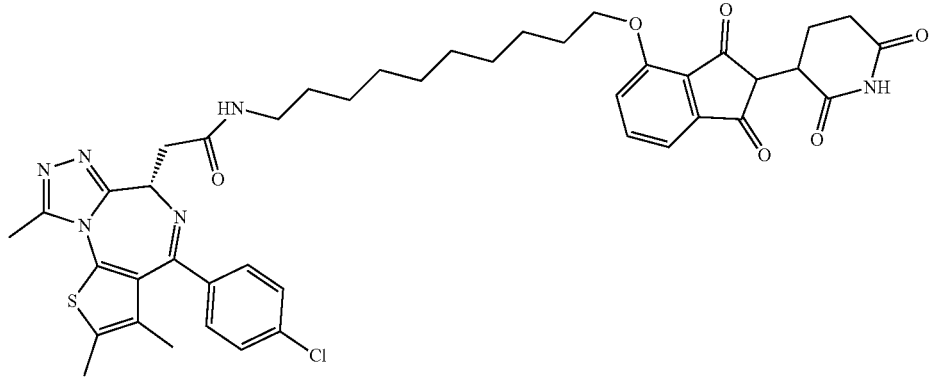

dBET39

A 0.1 M solution of 4-((10-aminodecyl)oxy)-2-(2,6-dioxopiperidin-3-yl)isoindoline-1,3-dione trifluoroacetate in DMF (0.212 mL, 0.0212 mmol, 1 eq) was added to JQ-acid (8.5 mg, 0.0212 mmol, 1 eq) at room temperature. DIPEA (11.1 microliters, 0.0636 mmol, 3 eq) and HATU (8.1 mg, 0.0212 mmol, 1 eq) were added. After 19 hours, the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-15% MeOH/DCM, 25 minute gradient) and preparative HPLC gave the desired product (0.39 mg, 0.00048 mmol, 2.3%). $^1$H NMR (500 MHz, Methanol-$d_4$) δ 7.77-7.73 (m, 1H), 7.56-7.31 (m, 6H), 5.11-5.06 (m, 1H), 4.62 (dd, J=9.2, 5.0 Hz, 1H), 4.58 (s, 2H), 4.21 (t, J=6.3 Hz, 2H), 3.42-3.38 (m, 1H), 3.24-3.20 (m, 1H), 2.90-2.68 (m, 6H), 2.45 (d, J=6.7 Hz, 3H), 2.11 (s, 1H), 1.83 (dd, J=14.7, 6.6 Hz, 2H), 1.70 (s, 3H), 1.61-1.49 (m, 4H), 1.32 (d, J=23.2 Hz, 10H). LCMS 812.60 (M+H).

Synthetic Example 40: Synthesis of dBET40

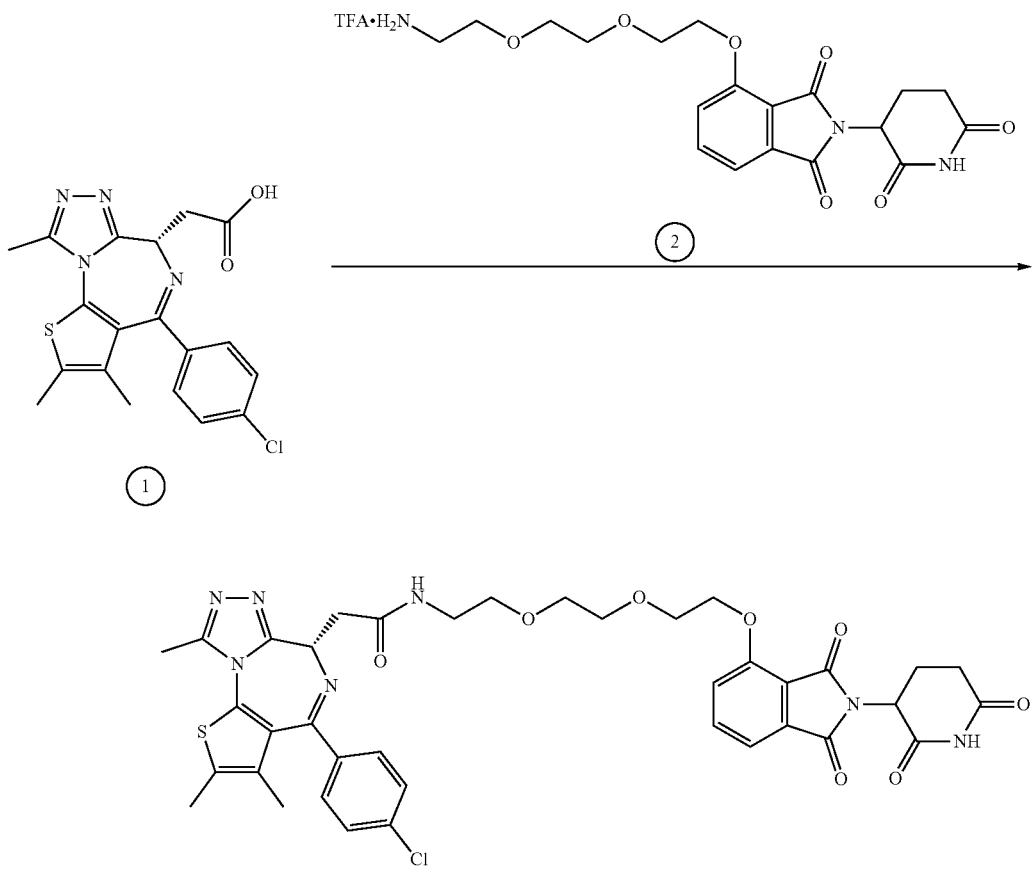

dBET40

A 0.1 M solution of 4-(2-(2-(2-aminoethoxy)ethoxy)ethoxy)-2-(2,6-dioxopiperidin-3-yl)isoindoline-1,3-dione trifluoroacetate in DMF (0.242 mL, 0.0242 mmol, 1 eq) was added to JQ-acid (9.7 mg, 0.0242 mmol, 1 eq) at room temperature. DIPEA (12.6 microliters, 0.0726 mmol, 3 eq) and HATU (9.2 mg, 0.0242 mmol, 1 eq) were added. After 22 hours, the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) and preparative HPLC gave the desired product as a brown oil (4.74 mg, 0.00601 mmol, 25%). $^1$H NMR (500 MHz, Methanol-$d_4$) δ 7.77-7.67 (m, 1H), 7.52-7.36 (m, 5H), 5.09-5.03 (m, 1H), 4.64 (d, J=4.8 Hz, 1H), 4.40-4.32 (m, 2H), 3.97-3.88 (m, 2H), 3.81-3.74 (m, 2H), 3.69-3.60 (m, 5H), 3.55-3.38 (m, 4H), 2.89-2.54 (m, 6H), 2.45 (d, J=5.9 Hz, 3H), 2.11 (s, 1H), 1.70 (d, J=8.6 Hz, 3H). LCMS 788.42 (M+H).

Synthetic Example 41: Synthesis of dBET41

Step 1: Synthesis of Tert-butyl (4-((2-((2-(2,6-dioxopiperidin-3-yl)-1,3-dioxoisoindolin-4-yl)oxy)acetamido)methyl)benzyl)carbamate tert-butyl (4-(aminomethyl)benzyl)carbamate (183.14 mg, 0.755 mmol, 1 eq) was dissolved in DMF (15.1 ml, 0.05 M) and added to 2-((2-(2,6-dioxopiperidin-3-yl)-1,3-dioxoisoindolin-4-yl)oxy)acetic acid (250.90 mg, 0.755 mmol, 1 eq). DIPEA (0.374 ml, 2.265 mmol, 3 eq) and HATU (296.67 mg, 0.755 mmol, 1 eq) were added and the mixture was stirred for 20 hours at room temperature. The mixture was then diluted with EtOAc and washed with saturated sodium bicarbonate, water then brine. The organic layer was dried over sodium sulfate, filtered and condensed to give a light brown oil. The crude material was purified by column chromatography (ISCO, 12 g silica column, 0 to 15% MeOH/DCM 25 minute gradient) to give a light brown oil (373.1 mg, 0.678 mmol, 89.8%). $^1$H NMR (500 MHz, DMSO-$d_6$) δ 11.10 (s, 2H), 8.48 (t, J=5.8 Hz, 1H), 7.80 (dd, J=8.4, 7.3 Hz, 1H), 7.49 (d, J=7.2 Hz, 1H), 7.40 (d, J=8.6 Hz, 1H), 7.26-7.08 (m, 4H), 5.11 (dd, J=12.9, 5.4 Hz, 1H), 4.86 (s, 2H), 4.33 (d, J=3.9 Hz, 2H), 4.09 (d, J=5.3 Hz, 2H), 2.65-2.51 (m, 3H), 2.07-1.99 (m, 1H), 1.38 (s, 9H). LCMS 551.5 (M+H).

Step 2: Synthesis of N-(4-(aminomethyl)benzyl)-2-((2-(2,6-dioxopiperidin-3-yl)-1,3-dioxoisoindolin-4-yl)oxy)acetamide Trifluoracetate Salt TFA (6.77 ml, 0.1 M) was added to tert-butyl (4-((2-((2-(2,6-dioxopiperidin-3-yl)-1,3-dioxoisoindolin-4-yl)oxy)acetamido)methyl)benzyl)carbamate (373.1 mg, 0.677 mmol, 1 eq) and the mixture was stirred at 50° C. for 1.5 hours. The mixture was then dissolved in MeOH and concentrated under reduced pressure to give a brown oil (270.29 mg) that was carried forward without further purification. $^1$H NMR (500 MHz, DMSO-$d_6$) δ 11.11 (s, 1H), 8.55 (t, J=6.2 Hz, 1H), 8.07 (s, 3H), 7.81 (dd, J=8.5, 7.3 Hz, 1H), 7.51 (d, J=7.2 Hz, 1H), 7.40 (dd, J=14.9, 8.3 Hz, 3H), 7.31 (d, J=8.2 Hz, 2H), 5.11 (dd, J=12.9, 5.4 Hz, 1H), 4.87 (s, 2H), 4.37 (d, J=6.1 Hz, 2H), 4.01 (q, J=5.8 Hz, 2H), 2.66-2.51 (m, 3H), 2.07-1.99 (m, 1H). LCMS 451.3 (M+H).

Step 3: Synthesis of dBET41

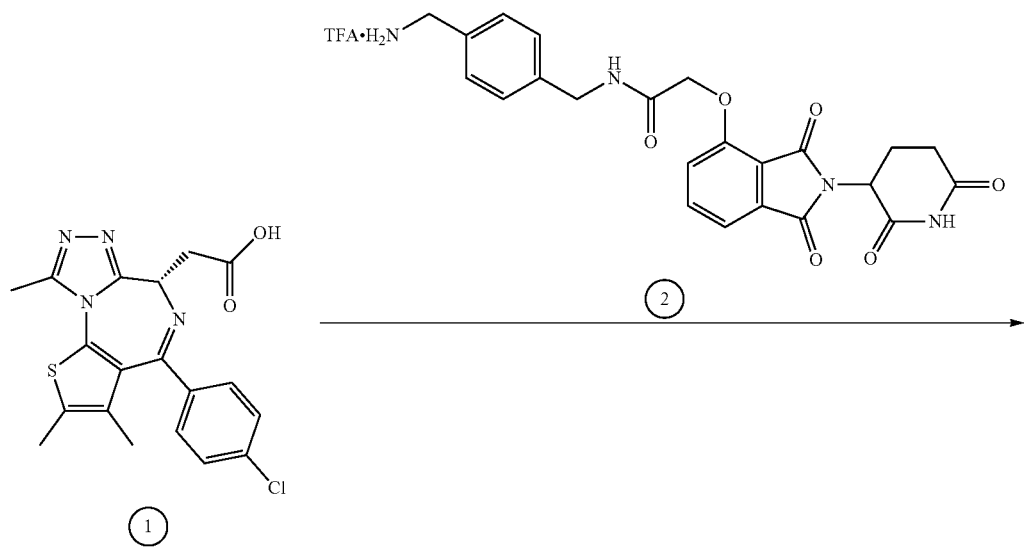

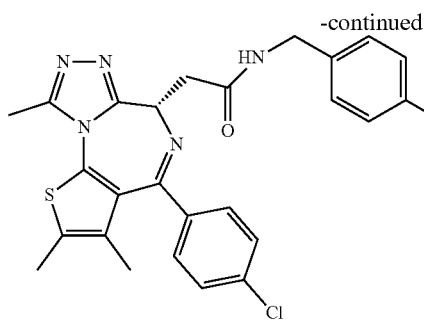 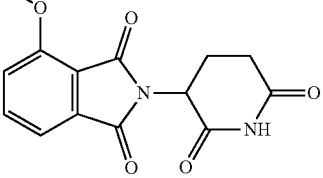

dBET41

A 0.1 M solution of N-(4-(aminomethyl)benzyl)-2-((2-(2,6-dioxopiperidin-3-yl)-1,3-dioxoisoindolin-4-yl)oxy)acetamide trifluoroacetate in DMF (0.237 mL, 0.0237 mmol, 1 eq) was added to JQ-acid (9.5 mg, 0.0237 mmol, 1 eq) at room temperature. After 23 hours, the mixture was diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a cream colored solid (11.8 mg, 0.0142 mmol, 60%). $^1$H NMR (500 MHz, Methanol-$d_4$) δ 7.80-7.75 (m, 1H), 7.51 (dd, J=7.3, 1.5 Hz, 1H), 7.41 (d, J=8.4 Hz, 1H), 7.36 (d, J=2.2 Hz, 4H), 7.34-7.28 (m, 4H), 5.10-5.00 (m, 1H), 4.82 (s, 2H), 4.67-4.64 (m, 1H), 4.61-4.42 (m, 4H), 4.34 (dd, J=14.9, 12.8 Hz, 1H), 3.49 (ddd, J=14.8, 9.5, 5.2 Hz, 1H), 2.83-2.75 (m, 1H), 2.73-2.61 (m, 5H), 2.44-2.39 (m, 3H), 2.06 (ddq, J=9.8, 4.7, 2.6 Hz, 1H), 1.66 (d, J=4.2 Hz, 3H). LCMS 832.92 (M+H).

Synthetic Example 42: Synthesis of dBET42

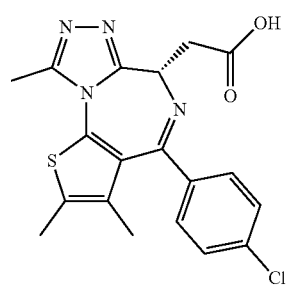 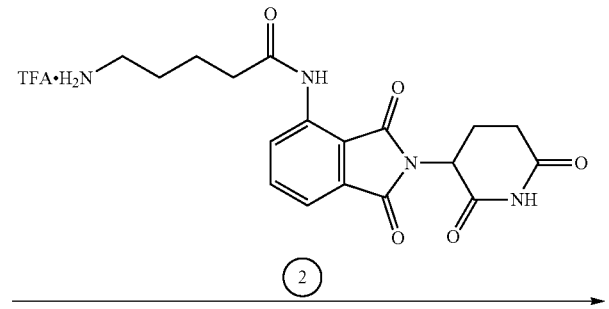

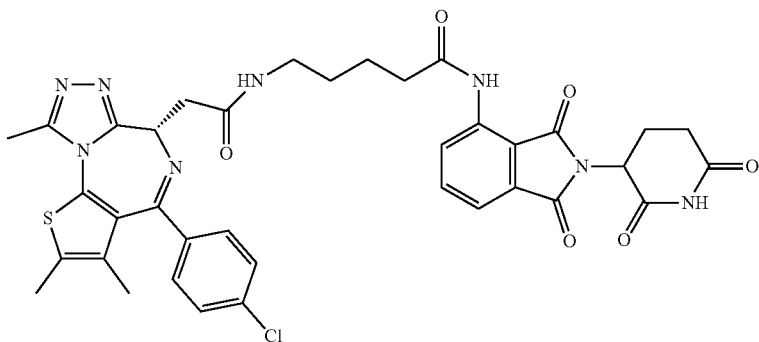

dBET42

A 0.1 M solution of 5-amino-N-(2-(2,6-dioxopiperidin-3-yl)-1-oxoisoindolin-4-yl)pentanamide trifluoroacetate in DMF (222 microliters, 0.0222 mmol, 1 eq) was added to JQ-acid (8.9 mg, 0.0222 mmol, 1 eq). DIPEA (11.6 microliters, 0.0666 mmol, 3 eq) and HATU (8.4 mg, 0.0222 mmol, 1 eq) were then added and the mixture was stirred for 24 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as a white solid (12.23 mg, 0.0165 mmol, 74%). $^1$H NMR (500 MHz, Methanol-$d_4$) δ 7.76-7.71 (m, 1H), 7.66-7.62 (m, 1H), 7.51 (td, J=7.8, 2.5 Hz, 1H), 7.45-7.35 (m, 4H), 5.11 (ddd, J=13.2, 11.3, 5.2 Hz, 1H), 4.63 (ddd, J=8.8, 5.7, 3.2 Hz, 1H), 4.47 (s, 2H), 3.45-3.32 (m, 3H), 3.30-3.27 (m, 1H), 2.90-2.80 (m, 1H), 2.73-2.63 (m, 4H), 2.49 (t, J=7.4 Hz, 2H), 2.46-2.38 (m, 4H), 2.11 (ddtd, J=12.8, 10.5, 5.3, 2.3 Hz, 1H), 1.84-1.75 (m, 2H), 1.66 (dd, J=16.2, 7.6 Hz, 5H). LCMS 741.46 (M+H).

Synthetic Example 43: Synthesis of dBET43

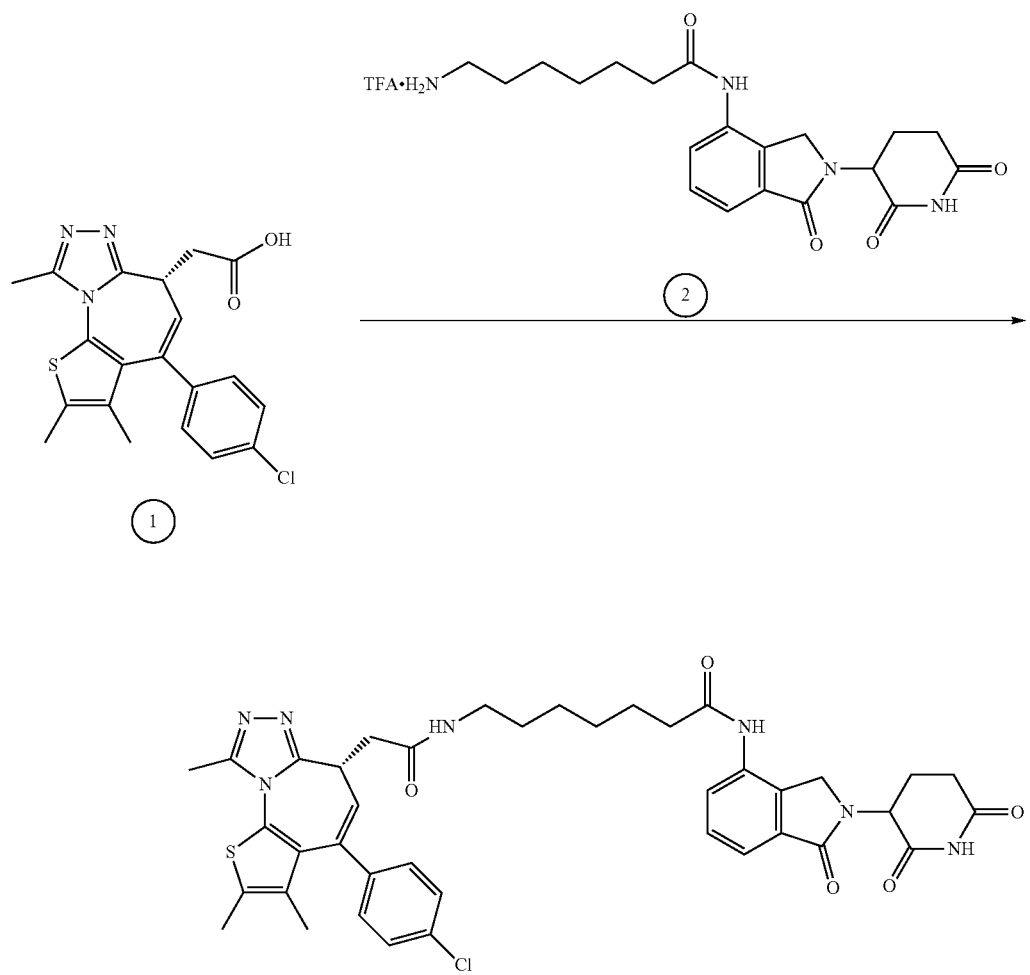

dBET43

A 0.1 M solution of 7-amino-N-(2-(2,6-dioxopiperidin-3-yl)-1-oxoisoindolin-4-yl)heptanamide trifluoroacetate in DMF (227 microliters, 0.0227 mmol, 1 eq) was added to JQ-acid (9.1 mg, 0.0227 mmol, 1 eq). DIPEA (11.9 microliters, 0.0681 mmol, 3 eq) and HATU (8.6 mg, 0.0227 mmol, 1 eq) were then added and the mixture was stirred for 25.5 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as an off-white solid (12.58 mg, 0.0164 mmol, 72%). $^1$H NMR (500 MHz, Methanol-$d_4$) δ 7.71 (d, J=7.9 Hz, 1H), 7.64 (d, J=7.4 Hz, 1H), 7.51 (t, J=7.8 Hz, 1H), 7.46-7.38 (m, 4H), 5.14 (ddd, J=13.3, 5.2, 2.2 Hz, 1H), 4.62 (ddd, J=8.6, 5.6, 2.1 Hz, 1H), 4.49-4.45 (m, 2H), 3.39 (ddd, J=14.9, 8.7, 1.3 Hz, 1H), 3.30-3.24 (m, 3H), 2.93-2.83 (m, 1H), 2.79-2.65 (m, 4H), 2.50-2.40 (m, 6H), 2.16 (ddq, J=9.9, 5.2, 2.6 Hz, 1H), 1.78-1.70 (m, 2H), 1.68 (d, J=2.1 Hz, 3H), 1.63-1.57 (m, 2H), 1.50-1.42 (m, 4H). LCMS 769.55 (M+H).

Synthetic Example 44: Synthesis of dBET44

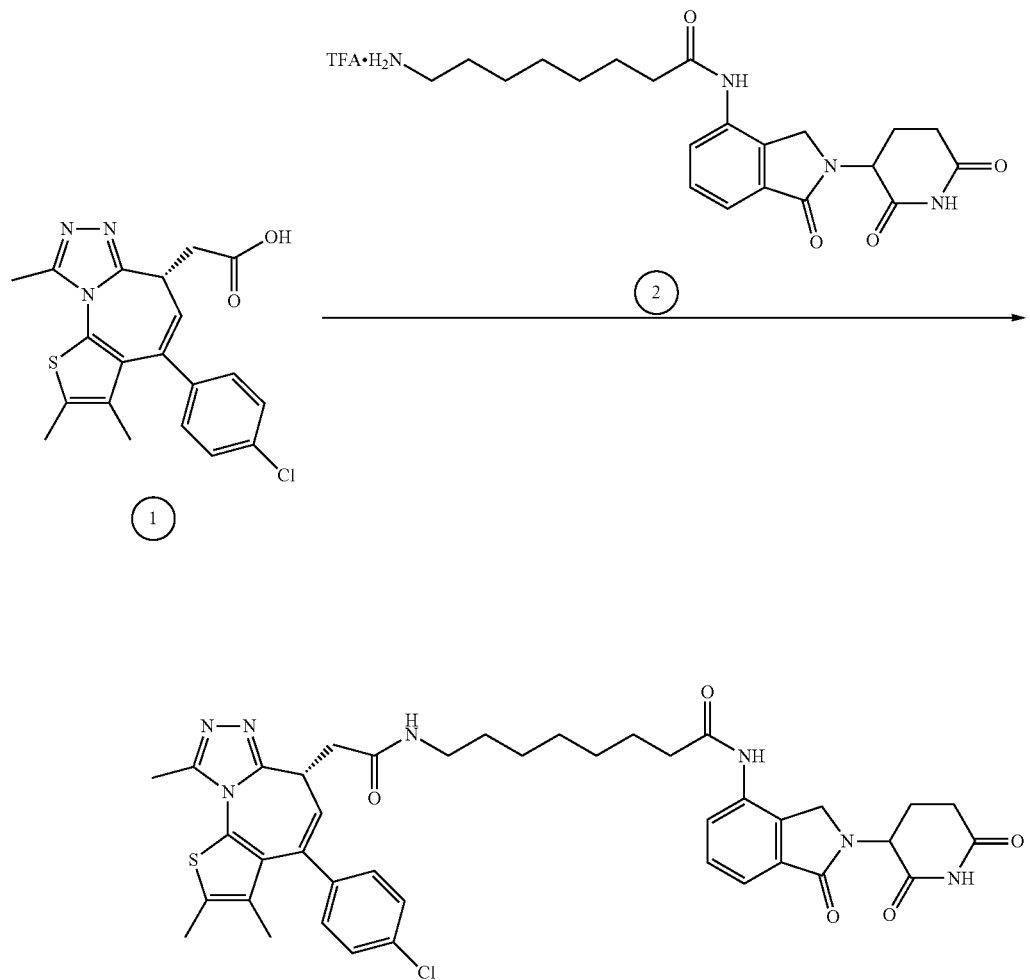

dBET44

A 0.1 M solution of 8-amino-N-(2-(2,6-dioxopiperidin-3-yl)-1-oxoisoindolin-4-yl)octanamide trifluoroacetate in DMF (217 microliters, 0.0217 mmol, 1 eq) was added to JQ-acid (8.7 mg, 0.0217 mmol, 1 eq). DIPEA (11.3 microliters, 0.0651 mmol, 3 eq) and HATU (8.3 mg, 0.0217 mmol, 1 eq) were then added and the mixture was stirred for 20.5 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as an cream colored solid (14.28 mg, 0.0182 mmol, 84%). $^1$H NMR (500 MHz, Methanol-$d_4$) δ 7.72-7.68 (m, 1H), 7.64 (d, J=7.5 Hz, 1H), 7.51 (t, J=7.7 Hz, 1H), 7.46-7.39 (m, 4H), 5.14 (dt, J=13.3, 5.0 Hz, 1H), 4.62 (dd, J=8.8, 5.4 Hz, 1H), 4.48-4.44 (m, 2H), 3.40 (ddd, J=14.9, 8.8, 0.9 Hz, 1H), 3.26 (dt, J=13.2, 6.9 Hz, 3H), 2.88 (ddd, J=18.7, 13.5, 5.4 Hz, 1H), 2.75 (dddd, J=17.6, 7.1, 4.5, 2.4 Hz, 1H), 2.68 (d, J=2.2 Hz, 3H), 2.49-2.39 (m, 6H), 2.17 (ddt, J=9.8, 5.3, 2.3 Hz, 1H), 1.76-1.70 (m, 2H), 1.70-1.67 (m, 3H), 1.61-1.54 (m, 2H), 1.42 (s, 6H). LCMS 783.53 (M+H).

Synthetic Example 45: Synthesis of dBET45

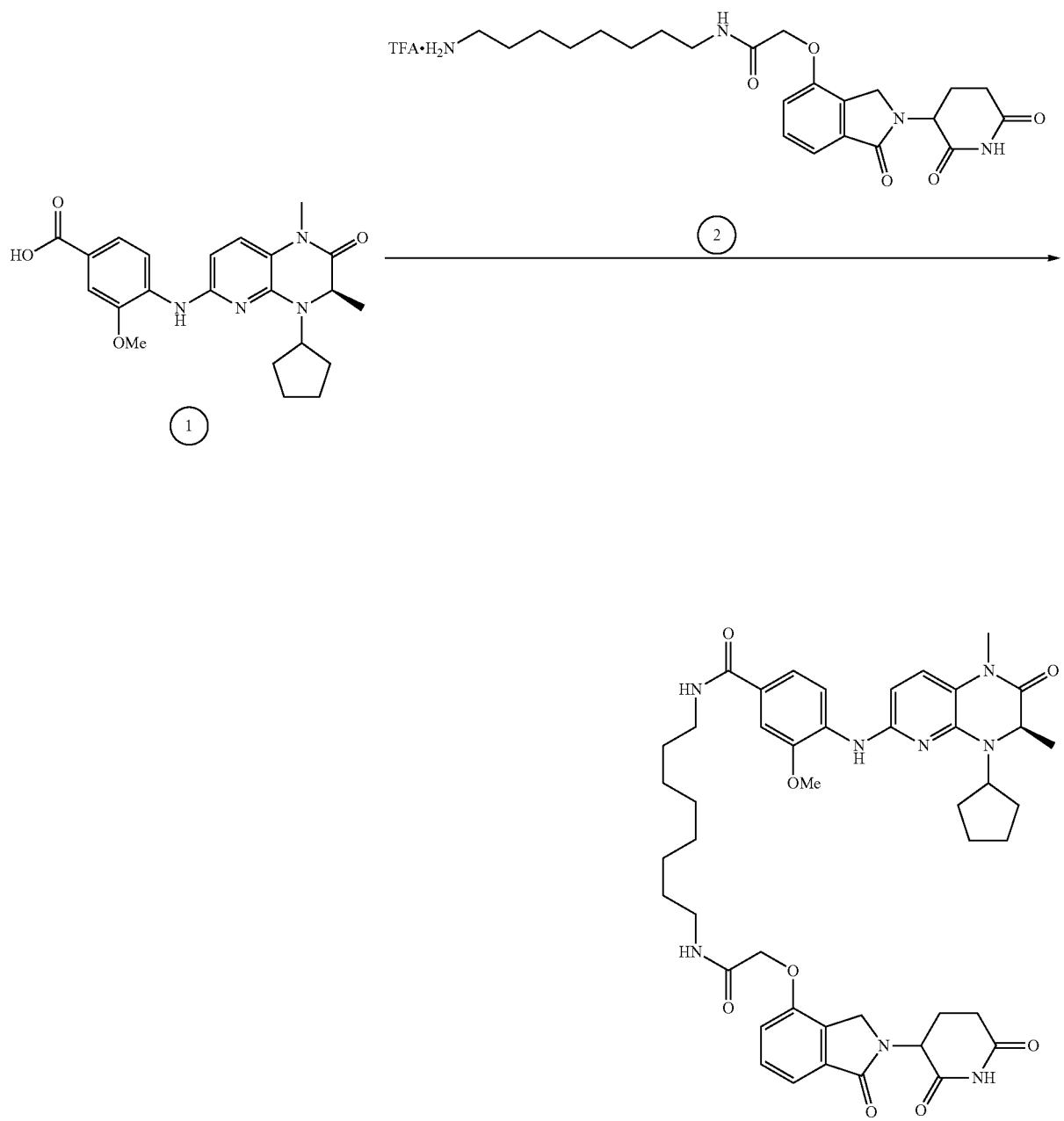

dBET45

A 0.1 M solution of N-(8-aminooctyl)-2-((2-(2,6-dioxopiperidin-3-yl)-1,3-dioxoisoindolin-4-yl)oxy)acetamide trifluoroacetate in DMF (268 microliters, 0.0268 mmol, 1 eq) was added to (R)-4-((4-cyclopentyl-1,3-dimethyl-2-oxo-1,2,3,4-tetrahydropyrido[2,3-b]pyrazin-6-yl)amino)-3-methoxybenzoic acid (11.0 mg, 0.0268 mmol, 1 eq) at room temperature. DIPEA (14.0 microliters, 0.0804 mmol, 3 eq) and HATU (10.2 mg, 0.0268 mmol, 1 eq) were then added and the mixture was stirred for 18.5 hours. The mixture was then diluted with methanol and purified by preparative HPLC to give the desired product as a dark brown solid (10.44 mg, 0.0108 mmol, 40%). $^1$H NMR (500 MHz, Methanol-$d_4$) δ 8.38 (d, J=8.4 Hz, 1H), 7.80-7.75 (m, 1H), 7.55-7.48 (m, 1H), 7.48-7.35 (m, 3H), 7.27 (d, J=8.3 Hz, 1H), 6.45 (d, J=8.2 Hz, 1H), 5.12 (dd, J=12.5, 5.5 Hz, 1H), 4.72 (d, J=5.1 Hz, 2H), 4.53 (s, 1H), 4.28 (d, J=6.8 Hz, 1H), 3.98 (d, J=4.1 Hz, 3H), 3.48-3.33 (m, 4H), 2.90-2.82 (m, 1H), 2.80-2.69 (m, 2H), 2.18-2.01 (m, 4H), 1.88-1.52 (m, 10H), 1.34 (d, J=42.9 Hz, 10H), 1.17 (d, J=6.8 Hz, 3H). LCMS 851.67 (M+H).

Synthetic Example 46: Synthesis of dBET46

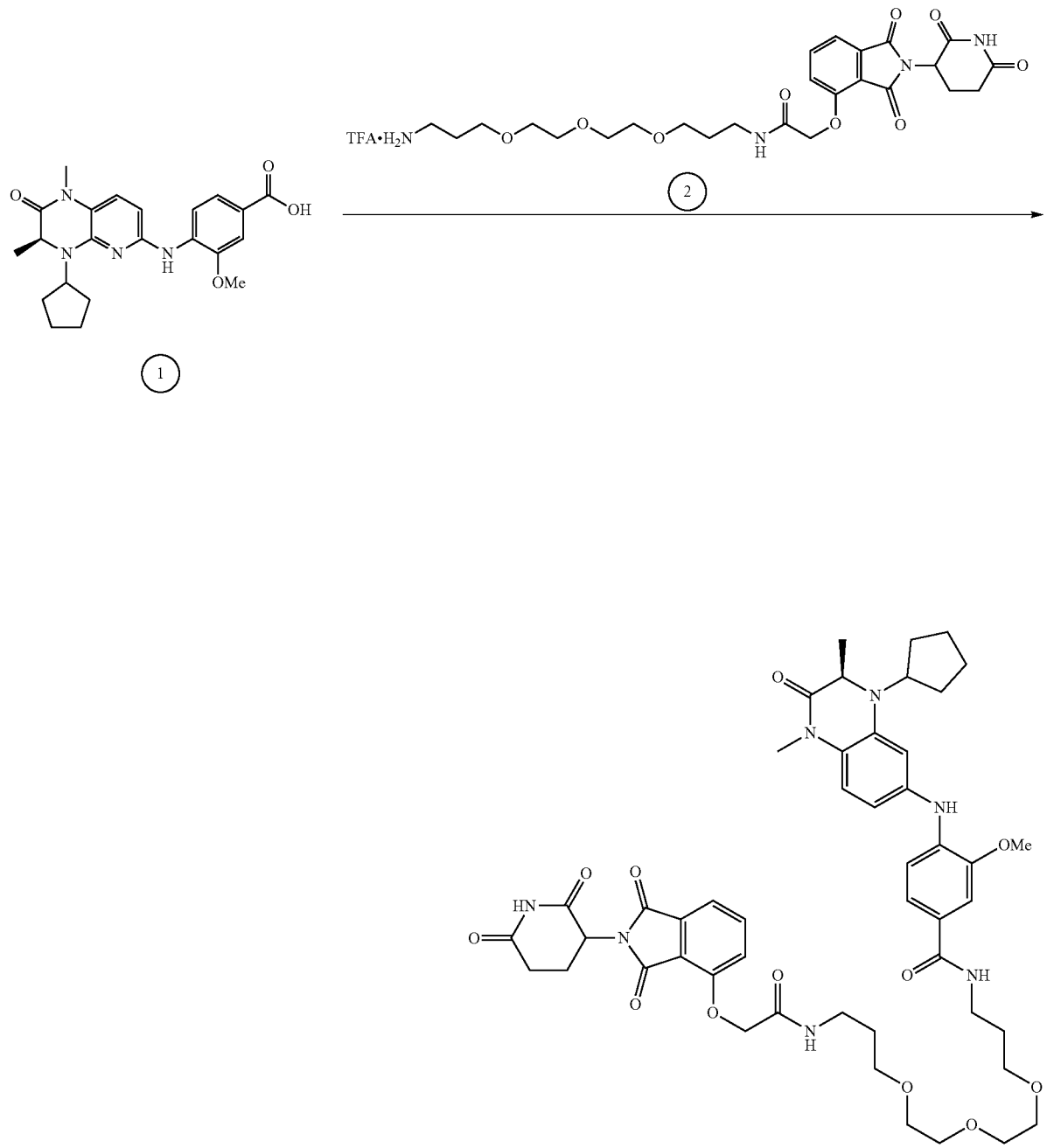

dBET46

A 0.1 M solution of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (256 microliters, 0.0256 mmol, 1 eq) was added to (R)-4-((4-cyclopentyl-1,3-dimethyl-2-oxo-1,2,3,4-tetrahydropyrido[2,3-b]pyrazin-6-yl)amino)-3-methoxybenzoic acid (10.5 mg, 0.0256 mmol, 1 eq) at room temperature. DIPEA (13.4 microliters, 0.0767 mmol, 3 eq) and HATU (9.7 mg, 0.0256 mmol, 1 eq) were then added and the mixture was stirred for 20 hours. The mixture was then diluted with methanol and purified by preparative HPLC to give the desired product as a dark brown solid (13.69 mg, 0.0132 mmol, 51%). $^1$H NMR (500 MHz, Methanol-$d_4$) δ 8.28-8.24 (m, 1H), 7.74-7.71 (m, 1H), 7.49 (dd, J=7.3, 3.7 Hz, 1H), 7.39-7.34 (m, 2H), 7.28-7.25 (m, 1H), 7.14-7.10 (m, 1H), 6.34 (d, J=8.3 Hz, 1H), 5.01-4.97 (m, 1H), 4.62 (s, 2H), 4.25 (q, J=6.7 Hz, 1H), 3.95 (d, J=5.4 Hz, 3H), 3.60 (ddd, J=9.0, 6.1, 1.6 Hz, 8H), 3.53-3.46 (m, 6H), 3.40-3.37 (m, 2H), 2.78 (td, J=11.1, 6.6 Hz, 3H), 2.16-2.00 (m, 4H), 1.84 (ddt, J=33.5, 13.0, 6.4 Hz, 7H), 1.75-1.60 (m, 6H), 1.17 (d, J=6.8 Hz, 3H). LCMS 927.74 (M+H).

Synthetic Example 47: Synthesis of dBET50

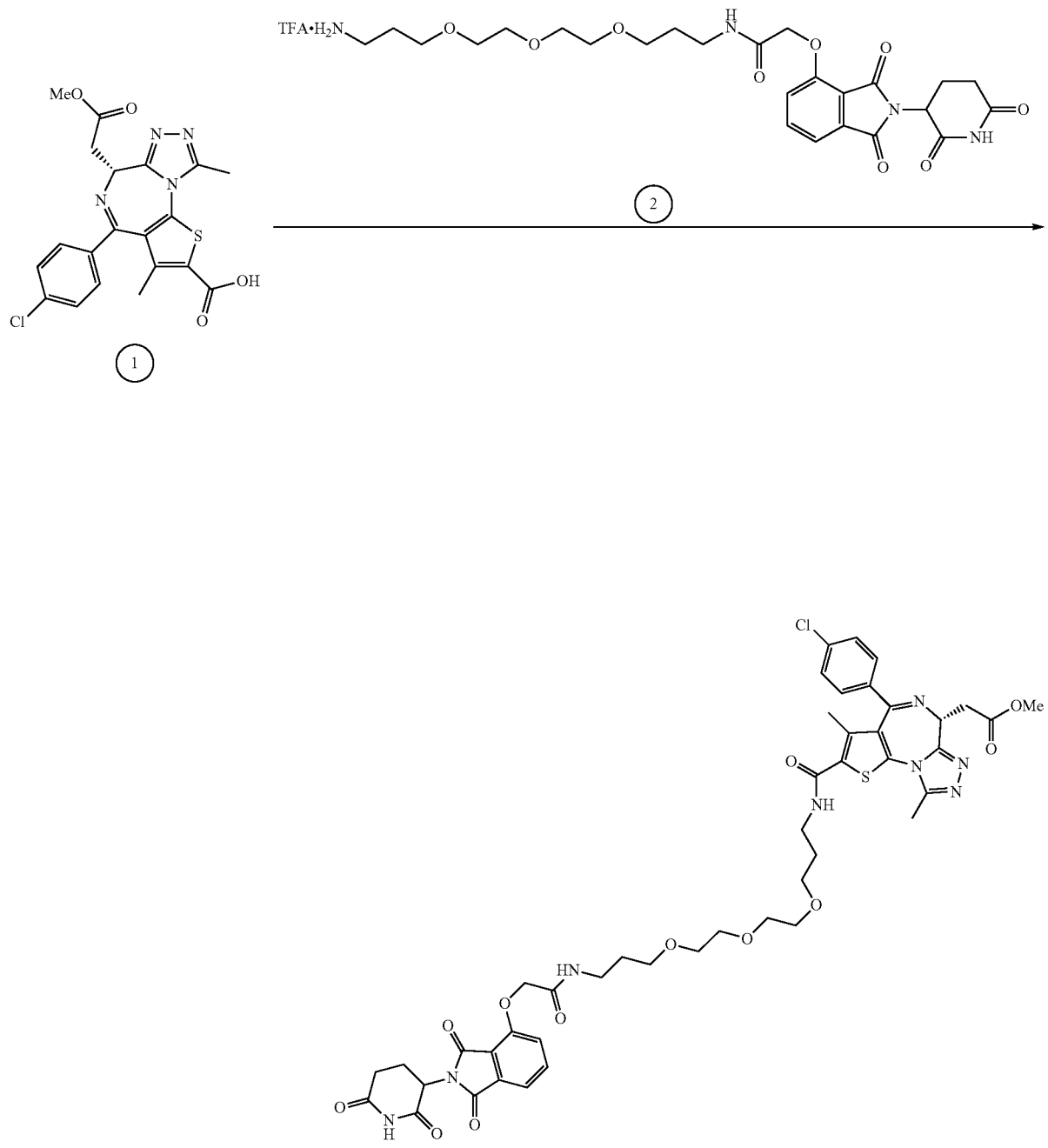

dBET50

A 0.1 M solution of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (200 microliters, 0.0200 mmol, 1 eq) was added to (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (8.9 mg, 0.020 mmol, 1 eq) at room temperature. DIPEA (10.5 microliters, 0.060 mmol, 3 eq) and HATU (7.6 mg, 0.020 mmol, 1 eq) were added. The mixture was then stirred for 17 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a cream colored solid (9.31 mg, 0.00968 mmol, 48%). $^1$H NMR (500 MHz, Methanol-$d_4$) δ 7.82-7.78 (m, 1H), 7.52 (dd, J=7.1, 1.6 Hz, 1H), 7.49-7.40 (m, 5H), 5.10 (ddd, J=12.8, 5.5, 2.9 Hz, 1H), 4.74 (s, 2H), 4.67 (t, J=7.1 Hz, 1H), 3.76 (s, 3H), 3.62-3.50 (m, 14H), 3.49-3.43 (m, 2H), 3.40 (q, J=6.5 Hz, 2H), 2.87 (ddd, J=17.6, 14.0, 5.3 Hz, 1H), 2.79-2.67 (m, 5H), 2.12 (ddq, J=10.3, 5.4, 2.9 Hz, 1H), 2.00 (s, 3H), 1.86 (q, J=6.3 Hz, 2H), 1.80 (p, J=6.4 Hz, 2H). LCMS 961.67 (M+H).

Synthetic Example 48: Synthesis of dBET51

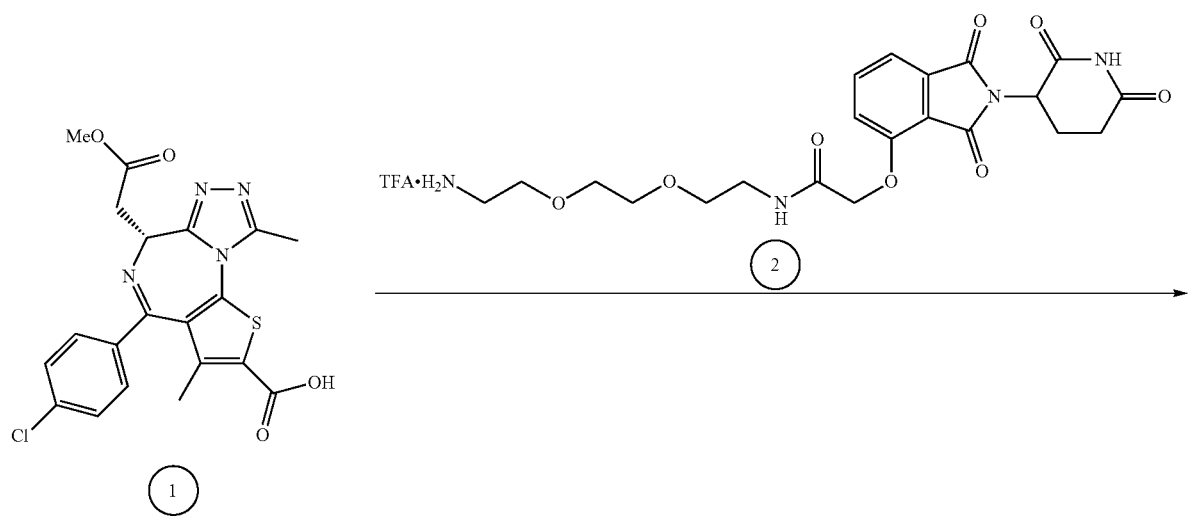

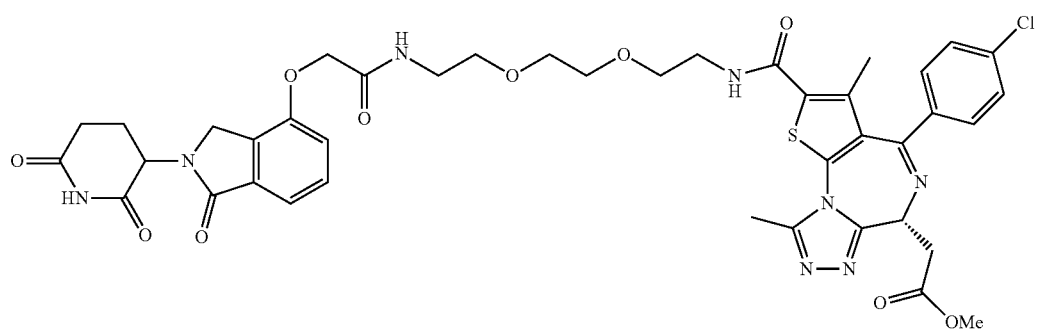

dBET51

A 0.1 M solution of N-(2-(2-(2-aminoethoxy)ethoxy)ethyl)-2-((2-(2,6-dioxopiperidin-3-yl)-1,3-dioxoisoindolin-4-yl)oxy)acetamide trifluoroacetate in DMF (200 microliters, 0.0200 mmol, 1 eq) was added to (S)-4-(4-chlorophenyl)-6-(methoxy-2-oxoethyl)-3,9-dimethyl-6H-thieno[3,2-f][1,2,4]triazolo[4,3-a][1,4]diazepine-2-carboxylic acid (8.9 mg, 0.020 mmol, 1 eq) at room temperature. DIPEA (10.5 microliters, 0.060 mmol, 3 eq) and HATU (7.6 mg, 0.020 mmol, 1 eq) were added. The mixture was then stirred for 17 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as an off-white solid (8.38 mg, 0.00942 mmol, 47%). $^1$H NMR (500 MHz, Methanol-$d_4$) δ 7.80 (dd, J=8.4, 7.4 Hz, 1H), 7.52 (dd, J=7.2, 1.3 Hz, 1H), 7.48-7.38 (m, 5H), 5.08 (ddd, J=12.7, 5.5, 1.6 Hz, 1H), 4.74 (d, J=2.7 Hz, 2H), 4.66 (t, J=7.1 Hz, 1H), 3.75 (d, J=3.0 Hz, 3H), 3.65 (t, J=4.1 Hz, 6H), 3.59 (t, J=5.3 Hz, 2H), 3.57-3.49 (m, 4H), 3.49-3.40 (m, 2H), 2.93-2.84 (m, 1H), 2.78-2.64 (m, 5H), 2.15-2.09 (m, 1H), 2.00 (d, J=0.9 Hz, 3H). LCMS 889.58 (M+H).

Synthetic Example 49: Synthesis of dBET52

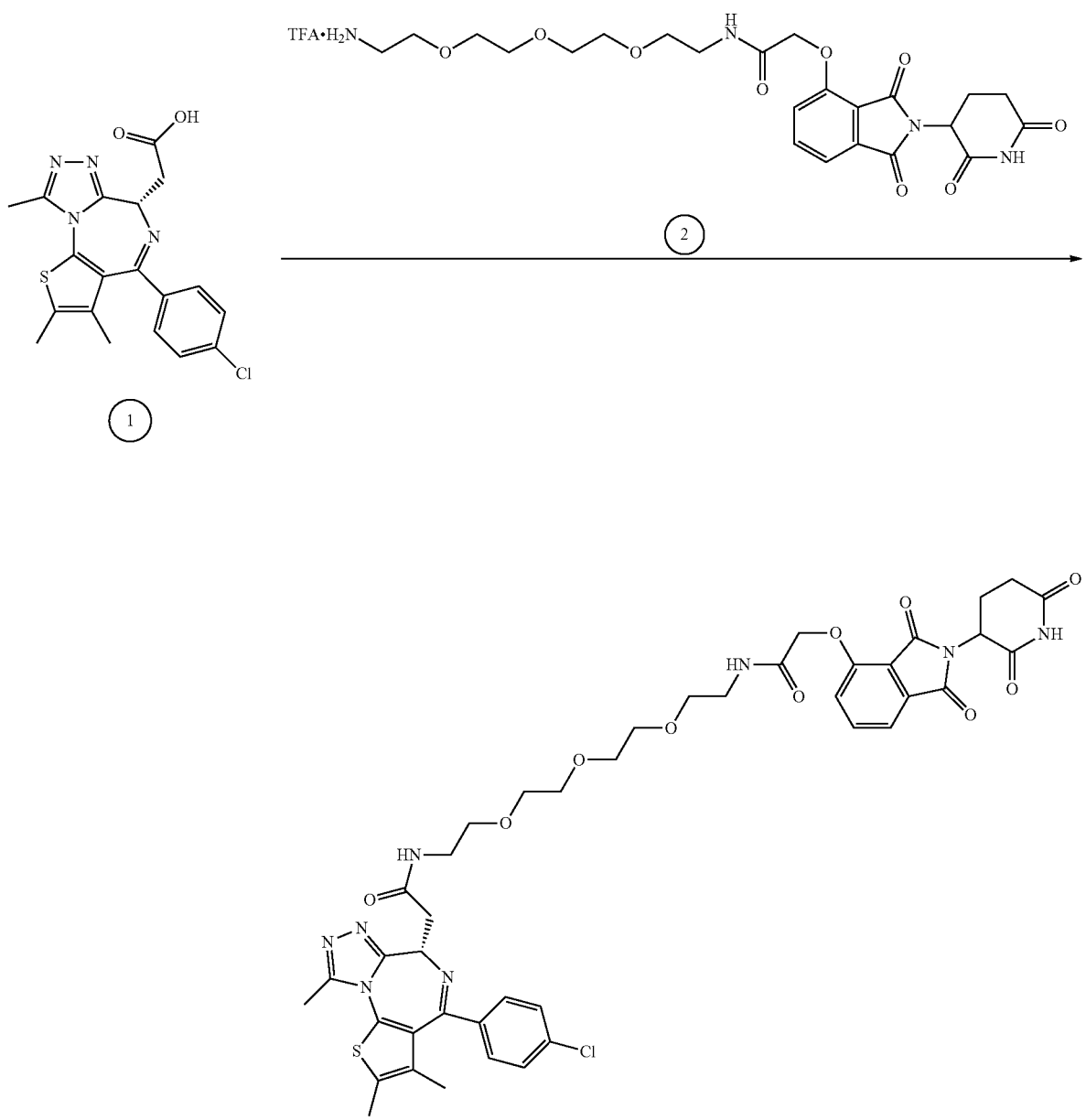

dBET52

A 0.1 M solution of N-(2-(2-(2-(2-aminoethoxy)ethoxy)ethoxy)ethyl)-2-((2-(2,6-dioxopiperidin-3-yl)-1,3-dioxoisoindolin-4-yl)oxy)acetamide trifluoroacetate in DMF (200 microliters, 0.020 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 17.5 hours, the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product as a colorless residue (9.12 mg, 0.01025 mmol, 51%). $^1$H NMR (500 MHz, Methanol-$d_4$) δ 7.77 (t, J=7.9 Hz, 1H), 7.50 (dd, J=7.3, 1.5 Hz, 1H), 7.47-7.36 (m, 5H), 5.09 (ddd, J=13.0, 7.6, 5.5 Hz, 1H), 4.76 (s, 2H), 4.62 (dd, J=9.1, 5.1 Hz, 1H), 3.62 (ddt, J=17.3, 11.2, 6.5 Hz, 12H), 3.52-3.41 (m, 5H), 3.28 (d, J=5.1 Hz, 1H), 2.90-2.81 (m, 1H), 2.79-2.66 (m, 5H), 2.44 (s, 3H), 2.16-2.09 (m, 1H), 1.69 (s, 3H). LCMS 889.38 (M+H).

Synthetic Example 50: Synthesis of dBET53

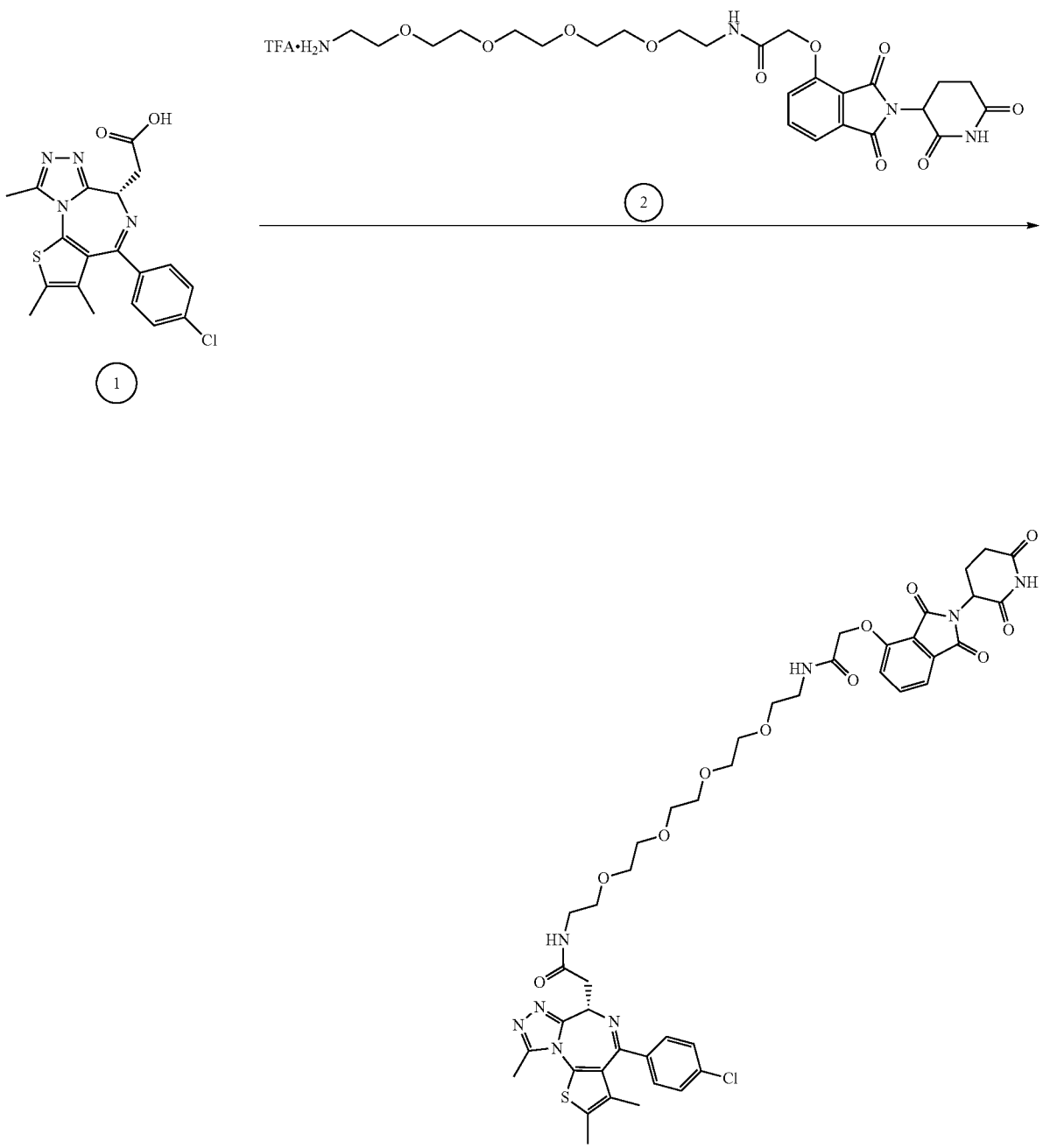

dBET53

A 0.1 M solution of N-(14-amino-3,6,9,12-tetraoxatetradecyl)-2-((2-(2,6-dioxopiperidin-3-yl)-1,3-dioxoisoindolin-4-yl)oxy)acetamide trifluoroacetate in DMF (200 microliters, 0.020 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 17.5 hours, additional HATU (7.6 mg) and DIPEA (10.5 microliters were added) and the mixture was stirred for an additional 5 hours. The mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product (3.66 mg). $^1$H NMR (500 MHz, Methanol-$d_4$) δ 7.79 (dd, J=8.4, 7.4 Hz, 1H), 7.51 (d, J=7.3 Hz, 1H), 7.45 (d, J=7.7 Hz, 2H), 7.43-7.36 (m, 3H), 5.08 (ddd, J=12.7, 5.5, 2.2 Hz, 1H), 4.78-4.74 (m, 2H), 4.62 (dd, J=9.1, 5.1 Hz, 1H), 3.70-3.51 (m, 16H), 3.50-3.41 (m, 5H), 3.27 (dd, J=5.1, 2.3 Hz, 1H), 2.87 (ddt, J=18.2, 9.5, 4.9 Hz, 1H), 2.78-2.66 (m, 5H), 2.44 (s, 3H), 2.16-2.09 (m, 1H), 1.69 (s, 3H). LCMS 933.43 (M+H).

Synthetic Example 51: Synthesis of dBET54

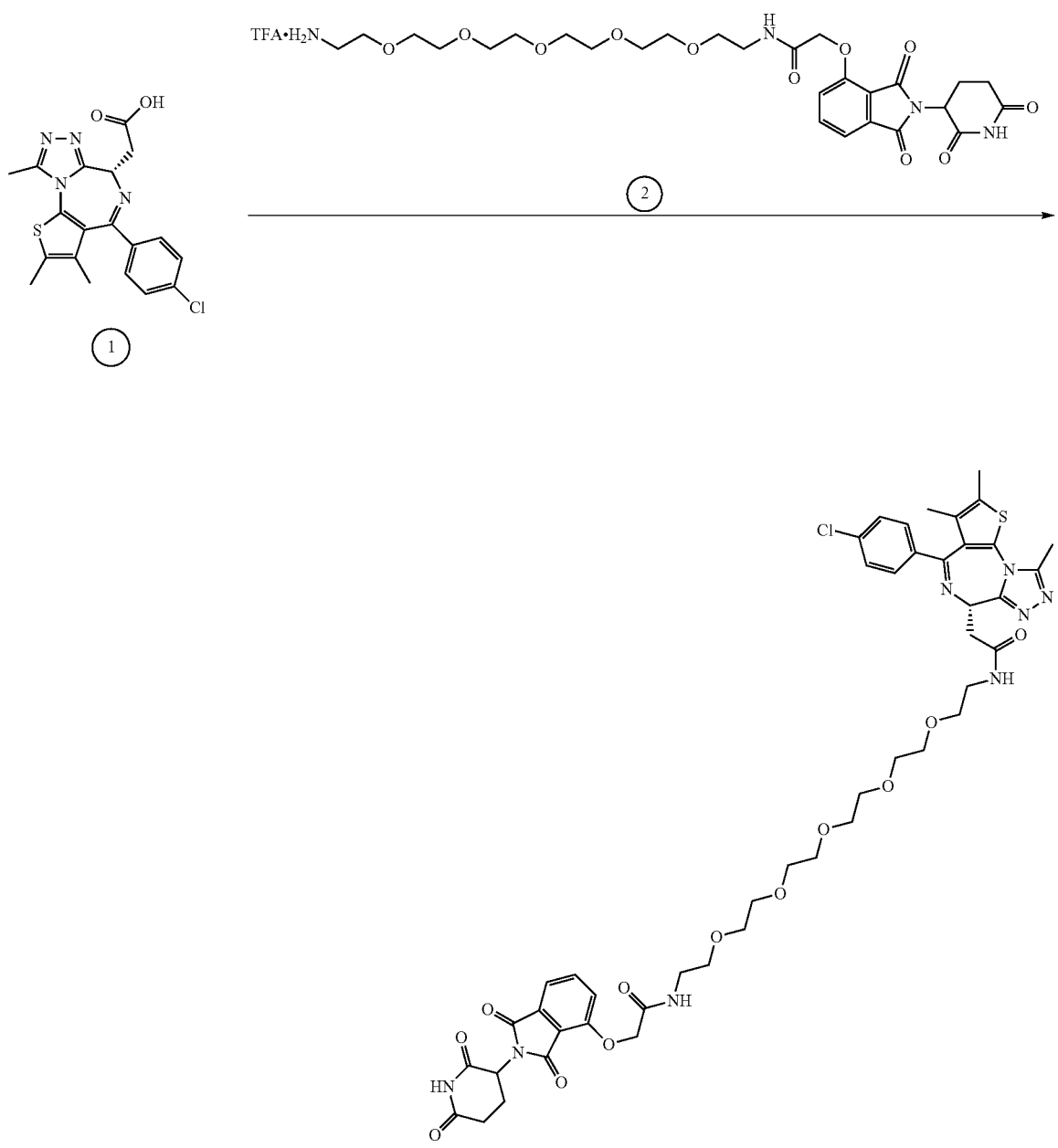

dBET54

A 0.1 M solution of N-(17-amino-3,6,9,12,15-pentaoxaheptadecyl)-2-((2-(2,6-dioxopiperidin-3-yl)-1,3-dioxoisoindolin-4-yl)oxy)acetamide trifluoroacetate in DMF (200 microliters, 0.020 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 16 hours the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product (6.27 mg, 0.00641 mmol, 32%). $^1$H NMR (500 MHz, Methanol-$d_4$) δ 7.81-7.76 (m, 1H), 7.51 (d, J=7.1 Hz, 1H), 7.47-7.38 (m, 5H), 5.09 (dd, J=12.6, 5.5 Hz, 1H), 4.77 (s, 2H), 4.62 (dd, J=8.8, 5.0 Hz, 1H), 3.67-3.55 (m, 20H), 3.46 (ddd, J=20.1, 10.2, 4.7 Hz, 5H), 3.28 (d, J=5.1 Hz, 1H), 2.91-2.83 (m, 1H), 2.78-2.68 (m, 5H), 2.44 (s, 3H), 2.16-2.10 (m, 1H), 1.72-1.66 (m, 3H). LCMS 977.50 (M+H).

Synthetic Example 52: Synthesis of dBET55

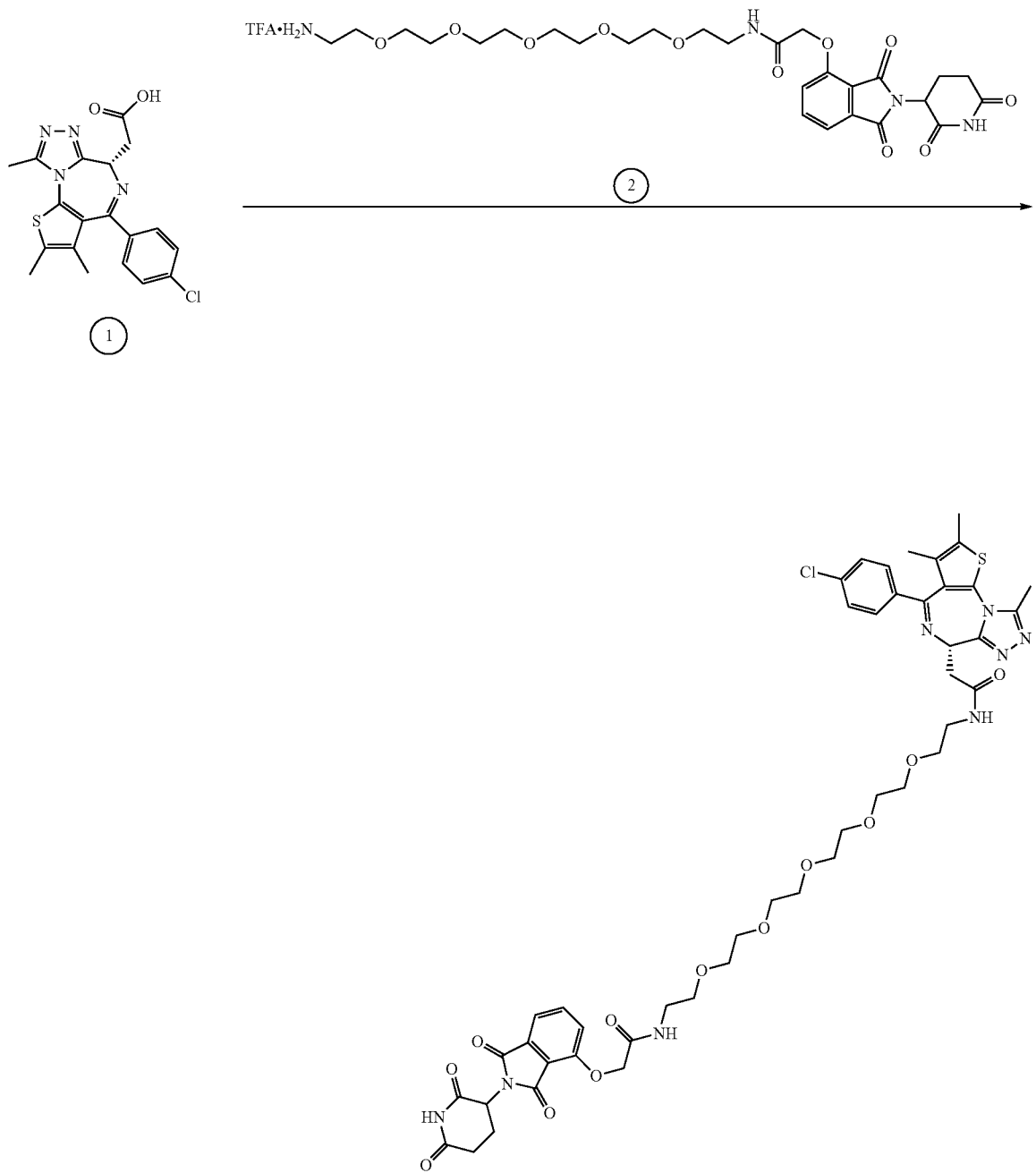

dBET55

A 0.1 M solution of N-(29-amino-3,6,9,12,15,18,21,24,27-nonaoxanonacosyl)-2-((2-(2,6-dioxopiperidin-3-yl)-1,3-dioxoisoindolin-4-yl)oxy)acetamide trifluoroacetate in DMF (200 microliters, 0.020 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 18 hours the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product (10.55 mg, 0.00914 mmol, 46%). $^1$H NMR (500 MHz, Methanol-$d_4$) δ 7.82 (dd, J=8.4, 7.4 Hz, 1H), 7.55 (d, J=7.0 Hz, 1H), 7.49-7.41 (m, 5H), 5.13 (dd, J=12.6, 5.5 Hz, 1H), 4.80 (s, 2H), 4.65 (dd, J=9.1, 5.1 Hz, 1H), 3.68-3.58 (m, 36H), 3.53-3.44 (m, 5H), 2.94-2.86 (m, 1H), 2.81-2.70 (m, 5H), 2.46 (s, 3H), 2.19-2.13 (m, 1H), 1.74-1.69 (m, 3H). LCMS 1153.59 (M+H).

Synthetic Example 53: Synthesis of dBET56

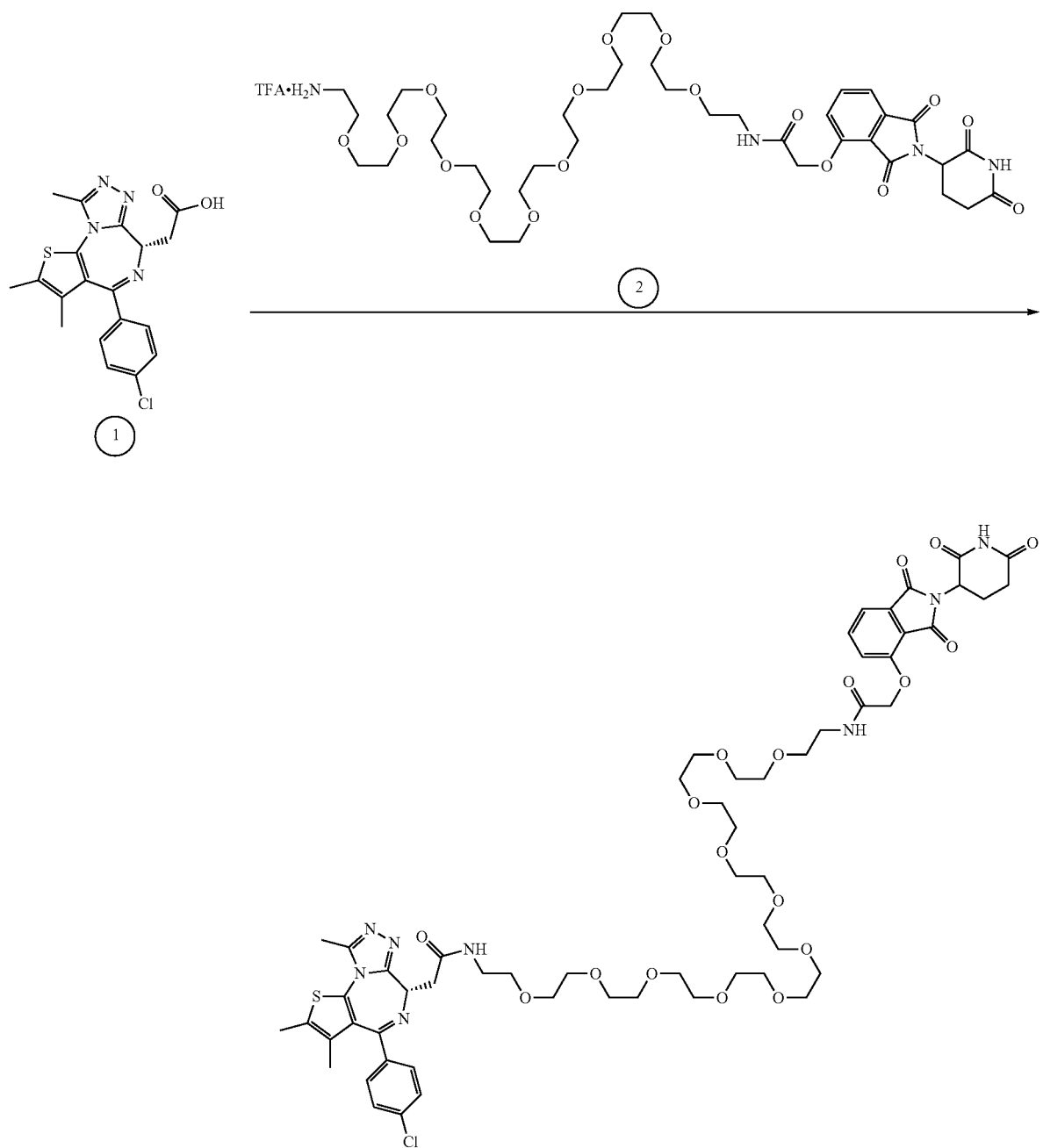

dBET56

A 0.1 M solution of N-(35-amino-3,6,9,12,15,18,21,24,27,30,33-undecaoxapentatriacontyl)-2-((2-(2,6-dioxopiperidin-3-yl)-1,3-dioxoisoindolin-4-yl)oxy)acetamide trifluoroacetate in DMF (200 microliters, 0.020 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 20 hours the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product as an oily residue (9.03 mg, 0.00727 mmol, 36%). $^1$H NMR (500 MHz, Methanol-$d_4$) δ 7.81 (dd, J=8.4, 7.4 Hz, 1H), 7.53 (d, J=7.1 Hz, 1H), 7.50-7.40 (m, 5H), 5.11 (dd, J=12.6, 5.5 Hz, 1H), 4.78 (s, 2H), 4.68 (dd, J=8.6, 5.0 Hz, 1H), 3.69-3.56 (m, 44H), 3.52-3.43 (m, 5H), 3.34 (dd, J=7.9, 3.5 Hz, 1H), 2.88 (ddd, J=18.0, 14.0, 5.2 Hz, 1H), 2.79-2.68 (m, 5H), 2.46 (s, 3H), 2.17-2.12 (m, 1H), 1.71 (s, 3H). LCMS 1241.60 (M+H).

Synthetic Example 54: Synthesis of dBET57

Step 1: Synthesis of 2-(2,6-dioxopiperidin-3-yl)-4-fluoroisoindoline-1,3-dione

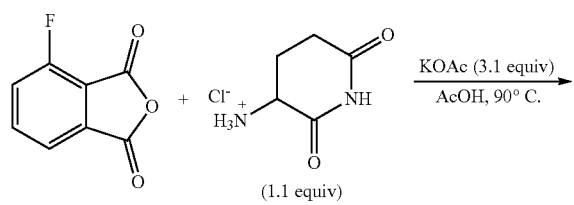

A solution of 4-fluoroisobenzofuran-1,3-dione (200 mg, 1.20 mmol, 1 equiv) in AcOH (4.0 mL, 0.3 M) was added 2,6-dioxopiperidin-3-amine hydrochloride (218 mg, 1.32 mmol, 1.1 equiv) and potassium acetate (366 mg, 3.73 mmol, 3.1 equiv). The reaction mixture was heated to 90° C. overnight, whereupon it was diluted with water to 20 mL and cooled on ice for 30 min. The resulting slurry was filtered, and the black solid was purified by flash column chromatography on silica gel (2% MeOH in CH$_2$Cl$_2$, R$_f$=0.3) to afford the title compound as a white solid (288 mg, 86%). $^1$H NMR (500 MHz, DMSO-$d_6$) δ 11.15 (s, 1H), 7.96 (ddd, J=8.3, 7.3, 4.5 Hz, 1H), 7.82-7.71 (m, 2H), 5.17 (dd, J=13.0, 5.4 Hz, 1H), 2.90 (ddd, J=17.1, 13.9, 5.4 Hz, 1H), 2.65-2.47 (m, 2H), 2.10-2.04 (m, 1H), MS (ESI) calcd for C$_{13}$H$_{10}$FN$_2$O$_4$ [M+H]$^+$ 277.06, found 277.25.

Step 2: Synthesis of Tert-butyl (2-((2-(2,6-dioxopiperidin-3-yl)-1,3-dioxoisoindolin-4-yl)amino)ethyl)carbamate

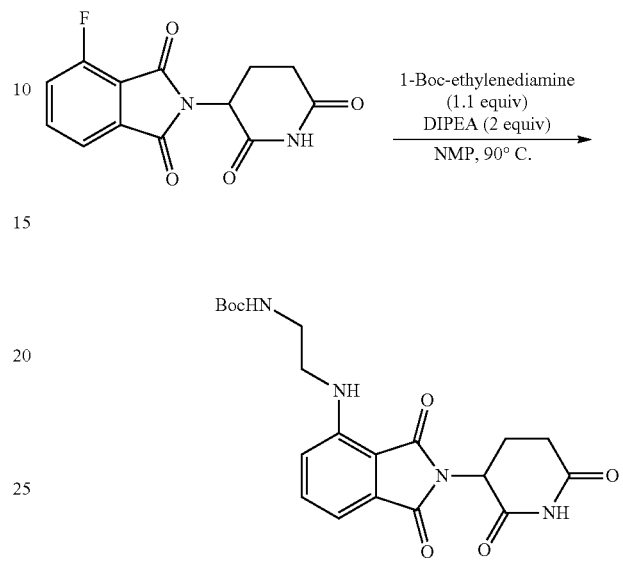

A stirred solution of 2-(2,6-dioxopiperidin-3-yl)-4-fluoroisoindoline-1,3-dione (174 mg, 0.630 mmol, 1 equiv) in DMF (6.3 mL, 0.1 M) was added DIPEA (220 μL, 1.26 mmol, 2 equiv) and 1-Boc-ethylendiamine (110 μL, 0.693 mmol, 1.1 equiv). The reaction mixture was heated to 90° C. overnight, whereupon it was cooled to room temperature and taken up in EtOAc (30 mL) and water (30 mL). The organic layer was washed with brine (3×20 mL), dried over Na$_2$SO$_4$ and concentrated in vacuo. The residue was purified by flash column chromatography on silica gel (0→10% MeOH in CH$_2$Cl$_2$) to give the title compound as a yellow solid (205 mg, 79%). $^1$H NMR (500 MHz, CDCl$_3$) δ 8.08 (bs, 1H), 7.50 (dd, J=8.5, 7.1 Hz, 1H), 7.12 (d, J=7.1 Hz, 1H), 6.98 (d, J=8.5 Hz, 1H), 6.39 (t, J=6.1 Hz, 1H), 4.96-4.87 (m, 1H), 4.83 (bs, 1H), 3.50-3.41 (m, 2H), 3.41-3.35 (m, 2H), 2.92-2.66 (m, 3H), 2.16-2.09 (m, 1H), 1.45 (s, 9H); MS (ESI) calcd for C$_{20}$H$_{25}$N$_4$O$_6$ [M+H]$^+$ 417.18, found 417.58.

Step 3: Synthesis of 2-((2-(2,6-dioxopiperidin-3-yl)-1,3-dioxoisoindolin-4-yl)amino)ethan-1-aminium 2,2,2-trifluoroacetate

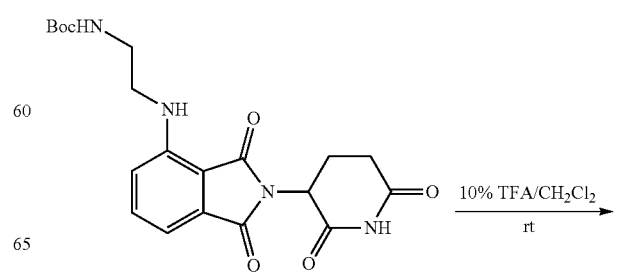

531

-continued

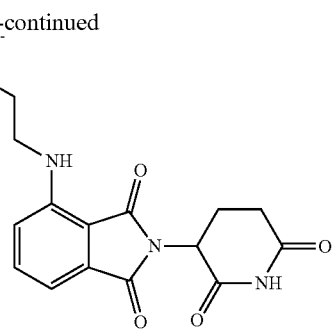

532

-continued

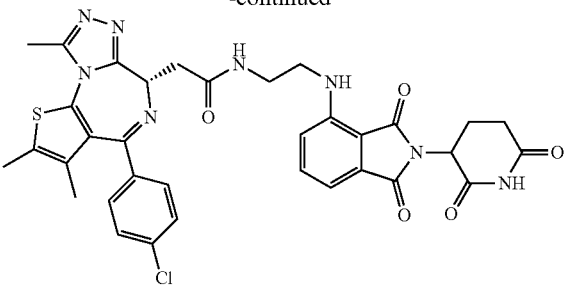

dBET57

A stirred solution of tert-butyl (2-((2-(2-(2,6-dioxopiperidin-3-yl)-1,3-dioxoisoindolin-4-yl)amino)ethyl)carbamate (205 mg, 0.492 mmol, 1 equiv) in dichloromethane (2.25 mL) was added trifluoroacetic acid (0.250 mL). The reaction mixture was stirred at room temperature for 4 h, whereupon the volatiles were removed in vacuo. The title compound was obtained as a yellow solid (226 mg, >95%), that was used without further purification. $^1$H NMR (500 MHz, MeOD) δ 7.64 (d, J=1.4 Hz, 1H), 7.27-7.05 (m, 2H), 5.10 (dd, J=12.5, 5.5 Hz, 1H), 3.70 (t, J=6.0 Hz, 2H), 3.50-3.42 (m, 2H), 3.22 (t, J=6.0 Hz, 1H), 2.93-2.85 (m, 1H), 2.80-2.69 (m, 2H), 2.17-2.10 (m, 1H); MS (ESI) calcd for $C_{15}H_{17}N_4O_4$ [M+H]$^+$ 317.12, found 317.53.

Step 2: Synthesis of dBET57

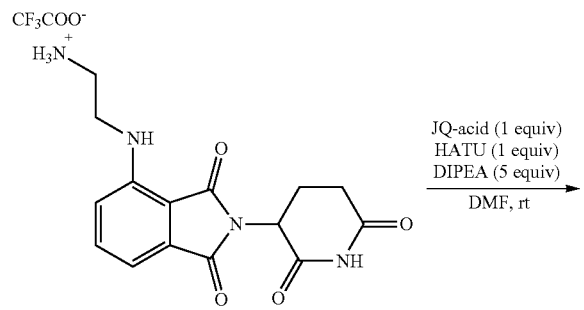

JQ-acid (8.0 mg, 0.0200 mmol, 1 eq) and 2-((2-(2,6-dioxopiperidin-3-yl)-1,3-dioxoisoindolin-4-yl)amino)ethan-1-aminium 2,2,2-trifluoroacetate (8.6 mg, 0.0200 mmol, 1 equiv) were dissolved in DMF (0.200 mL, 0.1 M) at room temperature. DIPEA (17.4 μL, 0.100 mmol, 5 equiv) and HATU (7.59 mg, 0.0200 mmol, 1 equiv) were then added and the mixture was stirred at room temperature overnight. The reaction mixture was taken up in EtOAc (15 mL), and washed with satd. NaHCO$_3$ (aq) (15 mL), water (15 mL) and brine (3×15 mL). The organic layer was dried over Na$_2$SO$_4$ and concentrated in vacuo. The residue was purified by flash column chromatography on silica gel (0→10% MeOH in CH$_2$Cl$_2$, R$_f$=0.3 (10% MeOH in CH$_2$Cl$_2$)) to give the title compound as a bright yellow solid (11.2 mg, 80%). $^1$H NMR (400 MHz, CDCl$_3$) δ 8.49 (bs, 0.6H), 8.39 (bs, 0.4H), 7.51-7.43 (m, 1H), 7.38 (d, J=7.8 Hz, 2H), 7.29 (dd, J=8.8, 1.7 Hz, 2H), 7.07 (dd, J=7.1, 4.9 Hz, 1H), 6.97 (dd, J=8.6, 4.9 Hz, 1H), 6.48 (t, J=5.9 Hz, 1H), 6.40 (t, J=5.8 Hz, 0.6H), 4.91-4.82 (m, 0.4H), 4.65-4.60 (m, 1H), 3.62-3.38 (m, 6H), 2.87-2.64 (m, 3H), 2.63 (s, 3H), 2.40 (s, 6H), 2.12-2.04 (m, 1H), 1.67 (s, 3H), rotamers; MS (ESI) calcd for $C_{34}H_{32}ClN_8O_5S$ [M+H]$^+$ 700.19, found 700.34.

Synthetic Example 55: Synthesis of dGR1

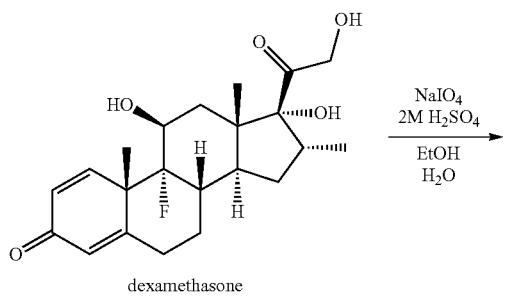

dexamethasone

-continued
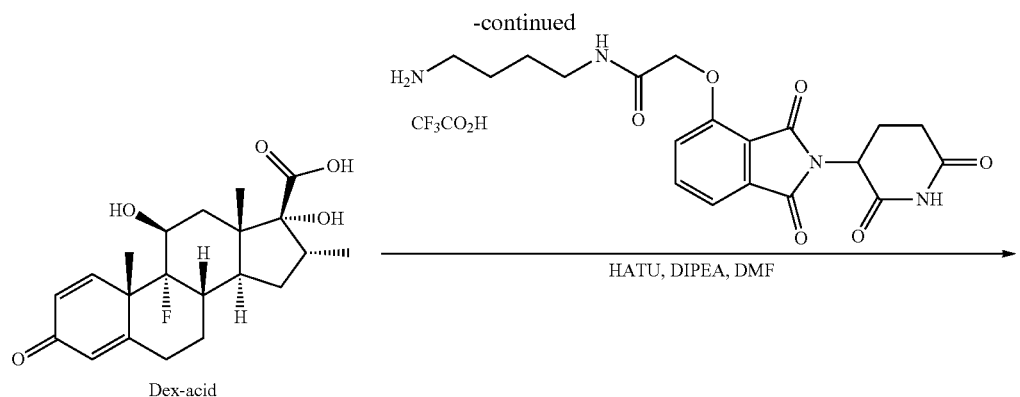
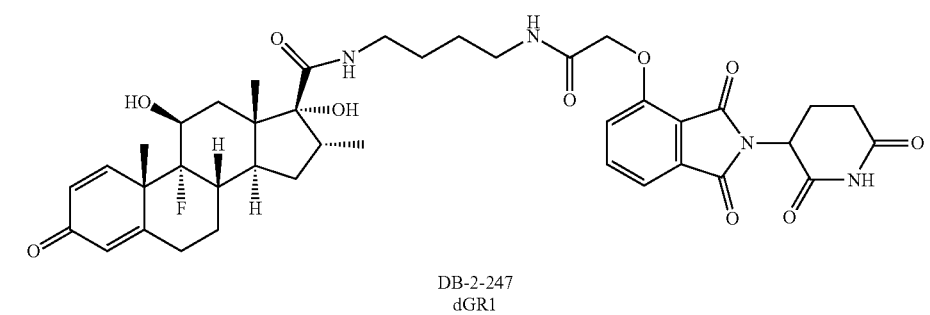
DB-2-247
dGR1
Synthetic Example 56: Synthesis of dGR2
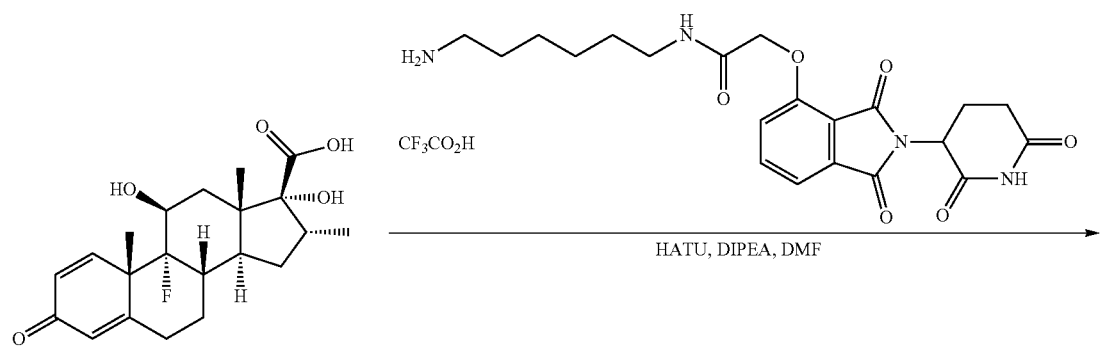
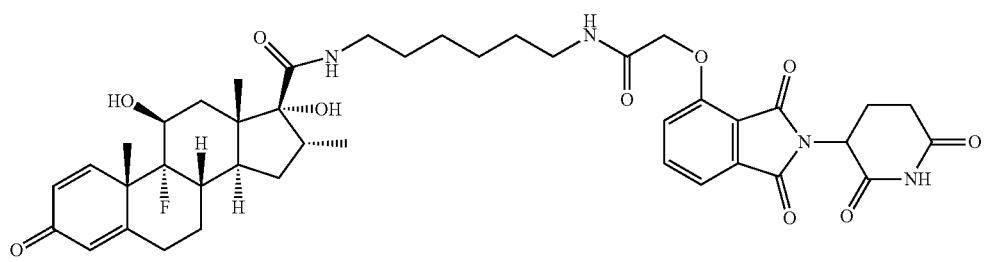
DB-2-265
dGR2

Synthetic Example 57: Synthesis of dGR3
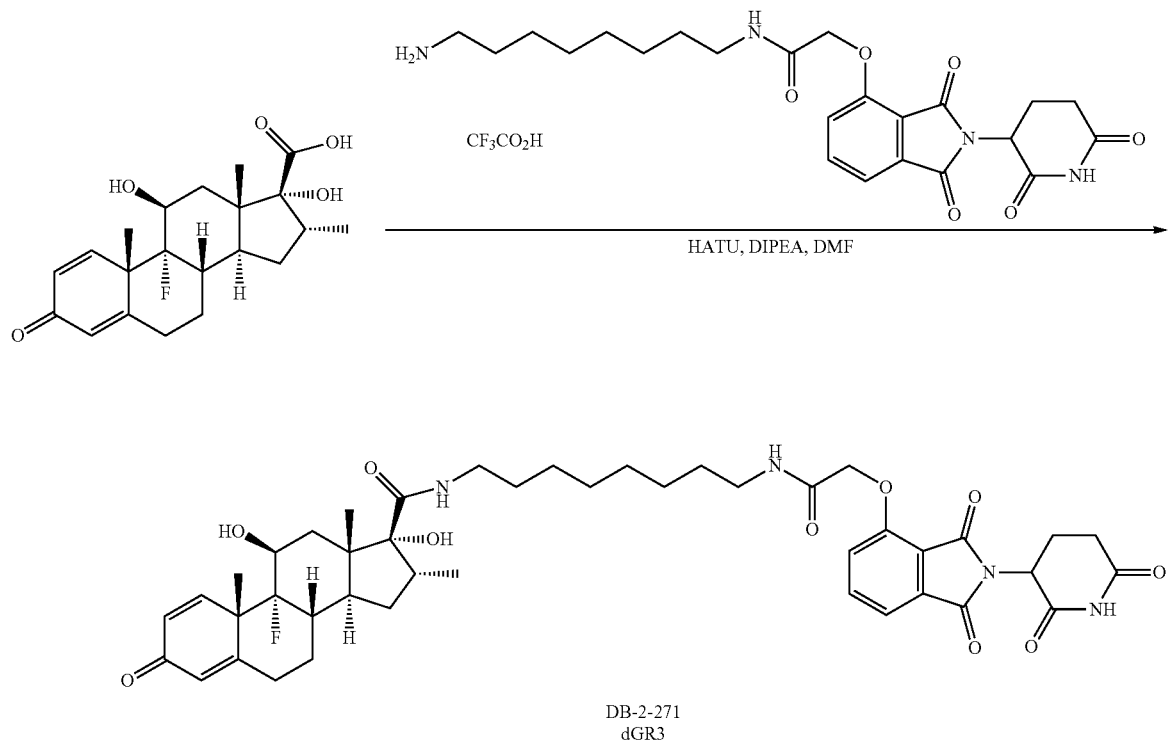
Synthetic Example 58: Synthesis of dFKBP-1
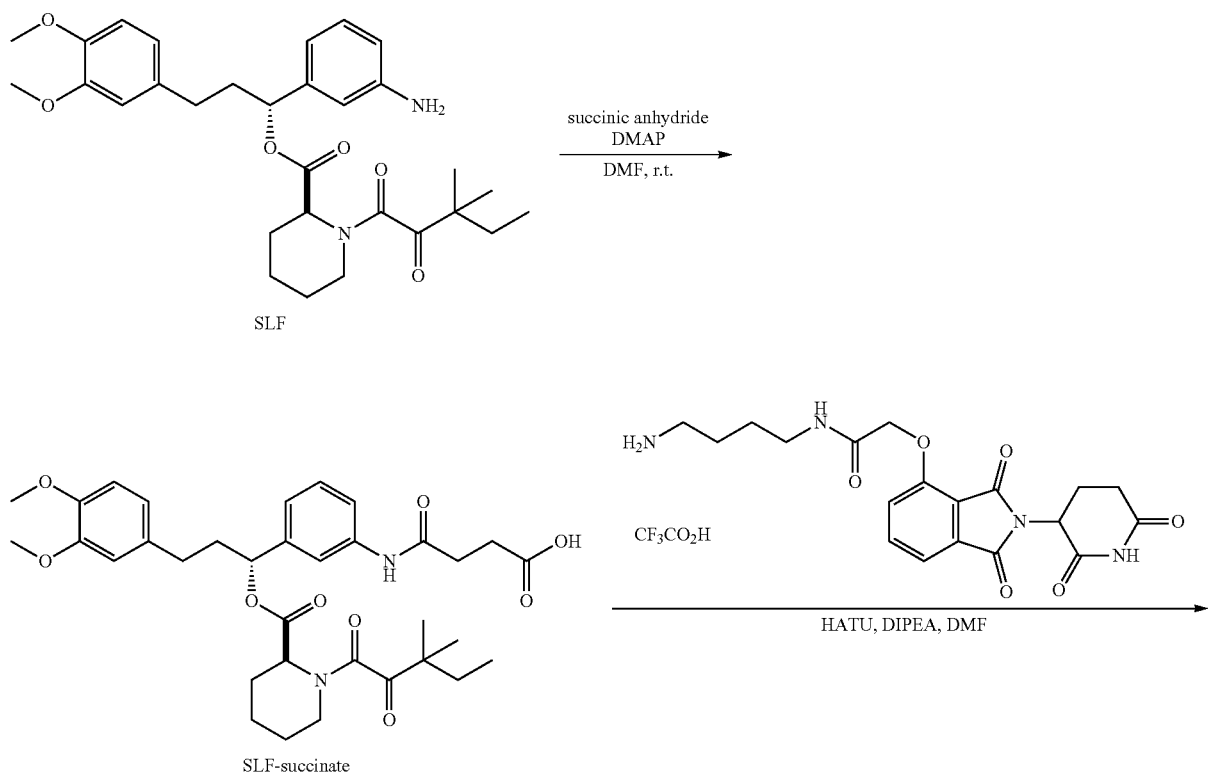

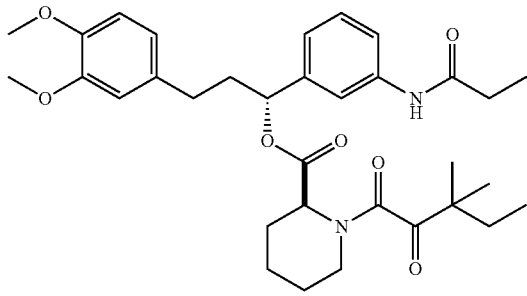

dFKBP-1

(1) Synthesis of SLF-Succinate

SLF (25 mg, 2.5 mL of a 10 mg/mL solution in MeOAc, 0.0477 mmol, 1 eq) was combined with DMF (0.48 mL, 0.1 M) and succinic anhydride (7.2 mg, 0.0715 mmol, 1.5 eq) and stirred at room temperature for 24 hours. Low conversion was observed and the mixture was placed under a stream of $N_2$ to remove the MeOAc. An additional 0.48 mL of DMF was added, along with an additional 7.2 mg succinic anhydride and DMAP (5.8 mg, 0.0477 mmol, 1 eq). The mixture was then stirred for an additional 24 hours before being purified by preparative HPLC to give SLF-succinate as a yellow oil (24.06 mg, 0.0385 mmol, 81%).

$^1$H NMR (400 MHz, Methanol-d4) δ 7.62 (d, J=10.7 Hz, 1H), 7.44 (d, J=8.0 Hz, 1H), 7.26 (td, J=7.9, 2.7 Hz, 1H), 7.07-6.97 (m, 1H), 6.80 (dd, J=8.1, 2.1 Hz, 1H), 6.74-6.66 (m, 2H), 5.73 (dd, J=8.1, 5.5 Hz, 1H), 5.23 (d, J=4.8 Hz, 1H), 3.83 (s, 3H), 3.81 (s, 3H), 3.39-3.29 (m, 4H), 3.21 (td, J=13.2, 3.0 Hz, 1H), 2.68-2.50 (m, 5H), 2.37-2.19 (m, 2H), 2.12-2.02 (m, 1H), 1.79-1.61 (m, 4H), 1.49-1.30 (m, 2H), 1.27-1.05 (m, 6H), 0.82 (dt, J=41.2, 7.5 Hz, 3H). LCMS 624.72 (M+H).

(2) Synthesis of dFKBP-1

N-(4-aminobutyl)-2-((2-(2,6-dioxopiperidin-3-yl)-1,3-dioxoisoindolin-4-yl)oxy)acetamide trifluoroacetate (9.9 mg, 0.0192 mmol, 1 eq) was added to SLF succinate (11.98 mg, 0.0192 mmol, 1 eq) as a solution in 0.192 mL DMF (0.1 M). DIPEA (10.0 microliters, 0.0575 mmol, 3 eq) was added, followed by HATU (7.3 mg, 0.0192 mmol, 1 eq). The mixture was stirred for 17 hours, then diluted with MeOH and purified by preparative HPLC to give dFKBP-1 (7.7 mg, 0.00763 mmol, 40%) as a yellow solid.

$^1$H NMR (400 MHz, Methanol-d4) δ 7.81 (s, 1H), 7.77-7.70 (m, 1H), 7.55-7.49 (m, 2H), 7.26 (dd, J=8.0, 5.3 Hz, 2H), 7.05-6.99 (m, 1H), 6.77 (d, J=8.8 Hz, 1H), 6.66 (d, J=6.8 Hz, 2H), 5.77-5.72 (m, 1H), 5.24 (d, J=4.8 Hz, 1H), 4.99 (dd, J=12.3, 5.7 Hz, 1H), 4.68-4.59 (m, 2H), 3.82 (s, 3H), 3.81 (s, 3H), 3.32 (dt, J=3.3, 1.6 Hz, 4H), 3.26-3.14 (m, 3H), 2.79 (dd, J=18.9, 10.2 Hz, 3H), 2.64-2.48 (m, 5H), 2.34 (d, J=14.4 Hz, 1H), 2.22 (d, J=9.2 Hz, 1H), 2.14-2.02 (m, 2H), 1.78-1.49 (m, 9H), 1.43-1.30 (m, 2H), 1.20-1.04 (m, 6H), 0.90-0.76 (m, 3H). 13C NMR (100 MHz, cd3od) δ 208.51, 173.27, 172.64, 171.63, 169.93, 169.51, 168.04, 167.69, 167.09, 166.71, 154.92, 149.05, 147.48, 140.76, 138.89, 137.48, 133.91, 133.67, 129.36, 122.19, 120.61, 120.54, 119.82, 118.41, 118.12, 117.79, 112.12, 111.76, 68.54, 56.10, 55.98, 51.67, 46.94, 44.57, 39.32, 39.01, 38.23, 32.64, 31.55, 31.43, 26.68, 26.64, 25.08, 23.52, 23.21, 22.85, 21.27, 8.76. LCMS 1009.66 (M+H).

Synthetic Example 59: Synthesis of dFKBP-2

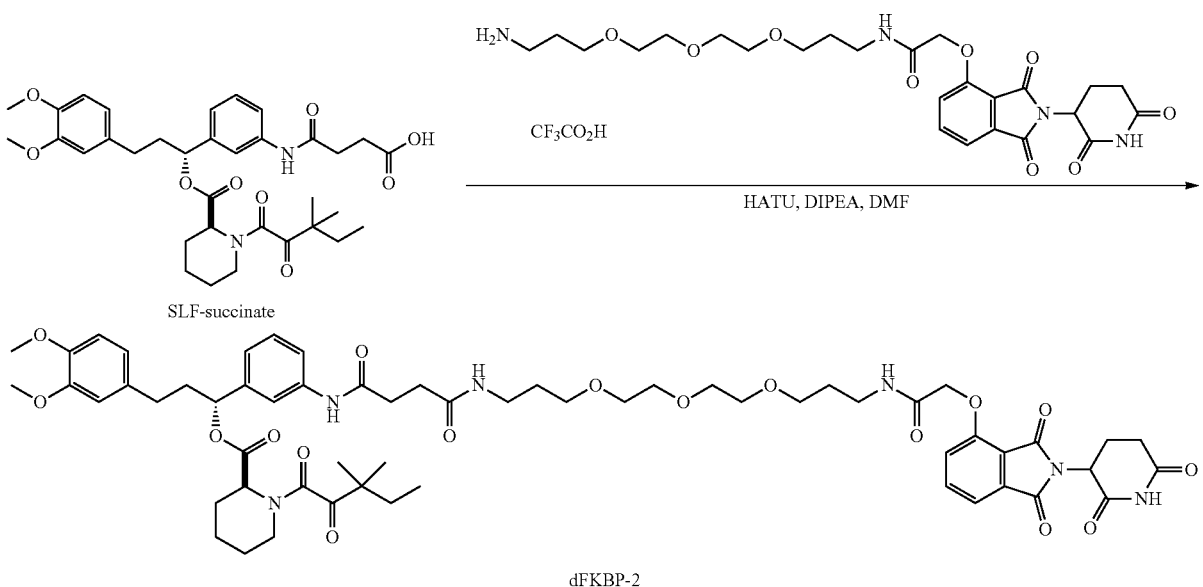

dFKBP-2

(1) Synthesis of Tert-butyl (1-chloro-2-oxo-7,10,13-trioxa-3-azahexadecan-16-yl)carbamate tert-butyl (3-(2-(2-(3-aminopropoxy)ethoxy)ethoxy)propyl)carbamate (1.0 g, 3.12 mmol, 1 eq) was dissolved in THF (31 mL, 0.1 M). DIPEA (0.543 mL, 3.12 mmol, 1 eq) was added and the solution was cooled to 0° C. Chloroacetyl chloride (0.273 mL, 3.43 mmol, 1.1 eq) was added and the mixture was warmed slowly to room temperature. After 24 hours, the mixture was diluted with EtOAc and washed with saturated sodium bicarbonate, water then brine. The organic layer was dried over sodium sulfate, filtered and condensed to give a yellow oil (1.416 g) that was carried forward without further purification.

$^1$H NMR (400 MHz, Chloroform-d) δ 7.24 (s, 1H), 5.00 (s, 1H), 3.98-3.89 (m, 2H), 3.54 (dddt, J=17.0, 11.2, 5.9, 2.2 Hz, 10H), 3.47-3.40 (m, 2H), 3.37-3.31 (m, 2H), 3.17-3.07 (m, 2H), 1.79-1.70 (m, 2H), 1.67 (p, J=6.1 Hz, 2H), 1.35 (s, 9H). $^{13}$C NMR (100 MHz, cdcl3) δ 165.83, 155.97, 78.75, 70.49, 70.47, 70.38, 70.30, 70.14, 69.48, 42.61, 38.62, 38.44, 29.62, 28.59, 28.40. LCMS 397.37 (M+H).

(2) Synthesis of Dimethyl 3-((2,2-dimethyl-4,20-dioxo-3,9,12,15-tetraoxa-5,19-diazahenicosan-21-yl)oxy)phthalate tert-butyl (1-chloro-2-oxo-7,10,13-trioxa-3-azahexadecan-16-yl)carbamate (1.41 g, 3.12 mmol, 1 eq) was dissolved in MeCN (32 mL, 0.1 M). Dimethyl 3-hydroxyphthalate (0.721 g, 3.43 mmol, 1.1 eq) and cesium carbonate (2.80 g, 8.58 mmol, 2.75 eq) were added. The flask was fitted with a reflux condenser and heated to 80° C. for 19 hours. The mixture was cooled to room temperature and diluted water and extracted once with chloroform and twice with EtOAc. The combined organic layers were dried over sodium sulfate, filtered and concentrated under reduced pressure. The crude material was purified by column chromatography (ISCO, 24 g silica column, 0-15% MeOH/DCM 22 minute gradient) to give a yellow oil (1.5892 g, 2.78 mmol, 89% over two steps).

$^1$H NMR (400 MHz, Chloroform-d) δ 7.52 (d, J=7.8 Hz, 1H), 7.35 (t, J=8.1 Hz, 1H), 7.04 (d, J=8.3 Hz, 1H), 7.00 (t, J=5.3 Hz, 1H), 5.06 (s, 1H), 4.46 (s, 2H), 3.83 (s, 3H), 3.78 (s, 3H), 3.47 (ddd, J=14.9, 5.5, 2.8 Hz, 8H), 3.39 (dt, J=9.4, 6.0 Hz, 4H), 3.29 (q, J=6.5 Hz, 2H), 3.09 (d, J=6.0 Hz, 2H), 1.70 (p, J=6.5 Hz, 2H), 1.63 (p, J=6.3 Hz, 2H), 1.31 (s, 9H). $^{13}$C NMR (100 MHz, cdcl3) δ 167.68, 167.36, 165.45, 155.93, 154.41, 130.87, 129.60, 125.01, 123.20, 117.06, 78.60, 70.40, 70.17, 70.06, 69.39, 68.67, 68.25, 52.77, 52.57, 38.38, 36.58, 29.55, 29.20, 28.34. LCMS 571.47 (M+H).

(3) Synthesis of N-(3-(2-(2-(3-aminopropoxy)ethoxy)ethoxy)propyl)-2-((2-(2,6-di oxopiperidin-3-yl)-1,3-dioxoisoindolin-4-yl)oxy)acetamide trifluoroacetate Dimethyl 3-((2,2-dimethyl-4,20-dioxo-3,9,12,15-tetraoxa-5,19-diazahenicosan-21-yl)oxy)phthalate (1.589 g, 2.78 mmol, 1 eq) was dissolved in EtOH (14 mL, 0.2 M). Aqueous 3M NaOH (2.8 mL, 8.34 mmol, 3 eq) was added and the mixture was heated to 80° C. for 22 hours. The mixture was then cooled to room temperature, diluted with 50 mL DCM and 20 mL 0.5 M HCl. The layers were separated and the organic layer was washed with 25 mL water. The aqueous layers were combined and extracted three times with 50 mL chloroform. The combined organic layers were dried over sodium sulfate, filtered and condensed to give 1.53 g of material that was carried forward without further purification. LCMS 553.44.

The resultant material (1.53 g) and 3-aminopiperidine-2,6-dione hydrochloride (0.480 g, 2.92 mmol, 1 eq) were dissolved in pyridine (11.7 mL, 0.25 M) and heated to 110° C. for 17 hours. The mixture was cooled to room temperature and concentrated under reduced pressure to give crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate as a black sludge (3.1491 g) that was carried forward without further purification. LCMS 635.47.

The crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate (3.15 g) was dissolved in TFA (20 mL) and heated to 50° C. for 2.5 hours. The mixture was cooled to room temperature, diluted with MeOH and concentrated under reduced pressure. The material was purified by preparative HPLC to give N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate (1.2438 g, 1.9598 mmol, 71% over 3 steps) as a dark red oil.

$^1$H NMR (400 MHz, Methanol-d4) δ 7.77 (dd, J=8.3, 7.5 Hz, 1H), 7.49 (d, J=7.3 Hz, 1H), 7.40 (d, J=8.5 Hz, 1H), 5.12 (dd, J=12.8, 5.5 Hz, 1H), 4.75 (s, 2H), 3.68-3.51 (m, 12H), 3.40 (t, J=6.8 Hz, 2H), 3.10 (t, J=6.4 Hz, 2H), 2.94-2.68 (m, 3H), 2.16 (dtd, J=12.6, 5.4, 2.5 Hz, 1H), 1.92 (p, J=6.1 Hz, 2H), 1.86-1.77 (m, 2H). $^{13}$C NMR (100 MHz, cd3od) δ 173.17, 169.97, 168.48, 166.87, 166.30, 154.82, 136.89, 133.41, 120.29, 117.67, 116.58, 69.96, 69.68, 69.60, 68.87, 68.12, 67.92, 49.19, 38.62, 36.14, 30.80, 28.92, 26.63, 22.22. LCMS 536.41 (M+H).

(4) Synthesis of dFKBP-2

N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate (12.5 mg, 0.0193 mmol, 1 eq) was added to SLF-succinate (12.08 mg, 0.0193 mmol, 1 eq) as a solution in 0.193 mL in DMF (0.1 M). DIPEA (10.1 microliters, 0.0580 mmol, 3 eq) and HATU (7.3 mg, 0.0193 mmol, 1 eq) were added and the mixture was stirred for 19 hours. The mixture was then diluted with MeOH and purified by preparative HPLC to give dFKBP-2 (9.34 mg, 0.00818 mmol, 42%) as a yellow oil.

$^1$H NMR (400 MHz, 50% MeOD/Chloroform-d) δ 7.76-7.70 (m, 1H), 7.58-7.45 (m, 3H), 7.26 (t, J=8.2 Hz, 2H), 7.05-6.98 (m, 1H), 6.77 (d, J=7.9 Hz, 1H), 6.71-6.63 (m, 2H), 5.73 (dd, J=8.1, 5.6 Hz, 1H), 5.23 (d, J=5.4 Hz, 1H), 5.03-4.95 (m, 1H), 4.64 (s, 2H), 3.82 (s, 3H), 3.80 (s, 3H), 3.62-3.52 (m, 8H), 3.47 (t, J=6.1 Hz, 2H), 3.44-3.33 (m, 3H), 3.27-3.14 (m, 3H), 2.84-2.70 (m, 3H), 2.64-2.47 (m, 6H), 2.34 (d, J=14.1 Hz, 1H), 2.24 (dd, J=14.3, 9.3 Hz, 2H), 2.13-2.00 (m, 2H), 1.83 (p, J=6.3 Hz, 2H), 1.67 (dtd, J=38.4, 16.8, 14.8, 7.0 Hz, 7H), 1.51-1.26 (m, 3H), 1.22-1.05 (m, 6H), 0.80 (dt, J=39.8, 7.5 Hz, 3H). $^{13}$C NMR (100 MHz, cdcl3) δ 208.64, 173.39, 173.01, 171.76, 170.11, 169.62, 168.24, 167.92, 167.36, 166.69, 155.02, 149.23, 147.66, 140.94, 139.18, 137.57, 134.09, 133.91, 129.49, 122.32, 120.75, 120.52, 119.93, 118.42, 117.75, 112.33, 111.98, 70.77, 70.51, 70.40, 69.45, 69.04, 68.48, 56.20, 56.10, 51.88, 47.09, 44.78, 38.40, 37.48, 36.91, 32.80, 32.71, 31.70, 31.59, 31.55, 29.53, 29.30, 26.77, 25.22, 23.63, 23.33, 22.98, 21.43. LCMS 1141.71 (M+H).

Synthetic Example 60: Synthesis of dFKBP-3

A 0.1 M solution of N-(4-aminobutyl)-2-((2-(2,6-dioxopiperidin-3-yl)-1,3-dioxoisoindolin-4-yl)oxy)acetamide trifluoroacetate (0.233 mL, 0.0233 mmol, 1 eq) was added to 2-(3-((R)-3-(3,4-dimethoxyphenyl)-1-(((S)-1-(3,3-dimethyl-2-oxopentanoyl)pyrrolidine-2-carbonyl)oxy)propyl)phenoxy)acetic acid (13.3 mg, 0.0233 mmol, 1 eq). DIPEA (12.2 microliters, 0.0700 mmol, 3 eq) was added, followed by HATU (8.9 mg, 0.0233 mmol, 1 eq). The mixture was stirred for 23 hours, then diluted with MeOH and purified by preparative HPLC to give a white solid (10.72 mg, 0.0112 mmol, 48%).

$^1$H NMR (400 MHz, Methanol-$d_4$) δ 7.79-7.74 (m, 1H), 7.52 (d, J=7.4 Hz, 1H), 7.33 (d, J=8.4 Hz, 1H), 7.26 (t, J=8.1 Hz, 1H), 6.97-6.90 (m, 2H), 6.89-6.84 (m, 1H), 6.79 (dd, J=8.2, 1.9 Hz, 1H), 6.73-6.64 (m, 2H), 5.73-5.65 (m, 1H), 5.07-4.99 (m, 1H), 4.67 (s, 2H), 4.57-4.51 (m, 1H), 4.48 (dd, J=5.7, 2.5 Hz, 2H), 3.82 (d, J=1.9 Hz, 3H), 3.80 (s, 3H), 3.66-3.39 (m, 3H), 2.88-2.48 (m, 6H), 2.42-1.87 (m, 9H), 1.73-1.51 (m, 6H), 1.19-0.92 (m, 6H), 0.75 (dt, J=56.7, 7.5 Hz, 3H). LCMS 954.52 (M+H).

Example 61: Synthesis of dFKBP-4

A 0.1 M solution of N-(4-aminobutyl)-2-((2-(2,6-dioxopiperidin-3-yl)-1,3-dioxoisoindolin-4-yl)oxy)acetamide trifluoroacetate (0.182 mL, 0.0182 mmol, 1 eq) was added to 2-(3-((R)-3-(3,4-dimethoxyphenyl)-1-(((S)-1-(3,3-dimethyl-2-oxopentanoyl)piperidine-2-carbonyl)oxy)propyl)phenoxy)acetic acid (10.6 mg, 0.0182 mmol, 1 eq). DIPEA (9.5 microliters, 0.0545 mmol, 3 eq) was added, followed by HATU (6.9 mg, 0.0182 mmol, 1 eq). The mixture was stirred for 26 hours, then diluted with MeOH and purified by preparative HPLC to give a white solid (9.74 mg, 0.01006 mmol, 55%).

$^1$H NMR (400 MHz, Methanol-$d_4$) δ 7.75 (dd, J=8.3, 7.4 Hz, 1H), 7.53 (d, J=2.3 Hz, 1H), 7.33-7.25 (m, 2H), 7.00-6.84 (m, 3H), 6.79 (dd, J=8.1, 2.5 Hz, 1H), 6.72-6.65 (m, 2H), 5.75-5.70 (m, 1H), 5.23 (d, J=4.9 Hz, 1H), 5.05-4.96 (m, 1H), 4.66 (s, 2H), 4.46 (s, 2H), 3.82 (s, 3H), 3.81 (s, 3H), 3.39-3.32 (m, 4H), 3.20-3.12 (m, 1H), 2.82-2.69 (m, 3H), 2.62-2.49 (m, 2H), 2.37-2.00 (m, 5H), 1.78-1.30 (m, 11H), 1.24-1.08 (m, 6H), 0.81 (dt, J=32.9, 7.5 Hz, 3H). LCMS 968.55 (M+H).

Synthetic Example 62: Synthesis of dFKBP-5

A 0.1 M solution of N-(4-aminobutyl)-2-((2-(2,6-dioxopiperidin-3-yl)-1,3-dioxoisoindolin-4-yl)oxy)acetamide trifluoroacetate (0.205 mL, 0.0205 mmol, 1 eq) was added to 2-(3-((R)-3-(3,4-dimethoxyphenyl)-1-(((S)-1-(2-phenylacetyl)piperidine-2-carbonyl)oxy)propyl)phenoxy)acetic acid (11.8 mg, 0.0205 mmol, 1 eq). DIPEA (10.7 microliters, 0.0615 mmol, 3 eq) was added, followed by HATU (7.8 mg, 0.0205 mmol, 1 eq). The mixture was stirred for 29 hours, then diluted with MeOH and purified by preparative HPLC to give a white solid (10.62 mg, 0.01106 mmol, 54%).

$^1$H NMR (400 MHz, Methanol-$d_4$) δ 7.77-7.72 (m, 1H), 7.52 (s, 1H), 7.31-7.11 (m, 7H), 6.92-6.77 (m, 4H), 6.68-6.62 (m, 2H), 5.70-5.64 (m, 1H), 5.38 (d, J=3.8 Hz, 1H), 4.99 (d, J=4.6 Hz, 1H), 4.65 (s, 2H), 4.45-4.39 (m, 2H), 3.80 (dd, J=6.7, 2.4 Hz, 8H), 3.13-3.03 (m, 1H), 2.83-2.68 (m, 3H), 2.63-2.45 (m, 3H), 2.34-1.93 (m, 6H), 1.71-1.52 (m, 7H), 1.34-1.20 (m, 3H). LCMS 960.54 (M+H).

Synthetic Example 63: Synthesis of dFKBP-6

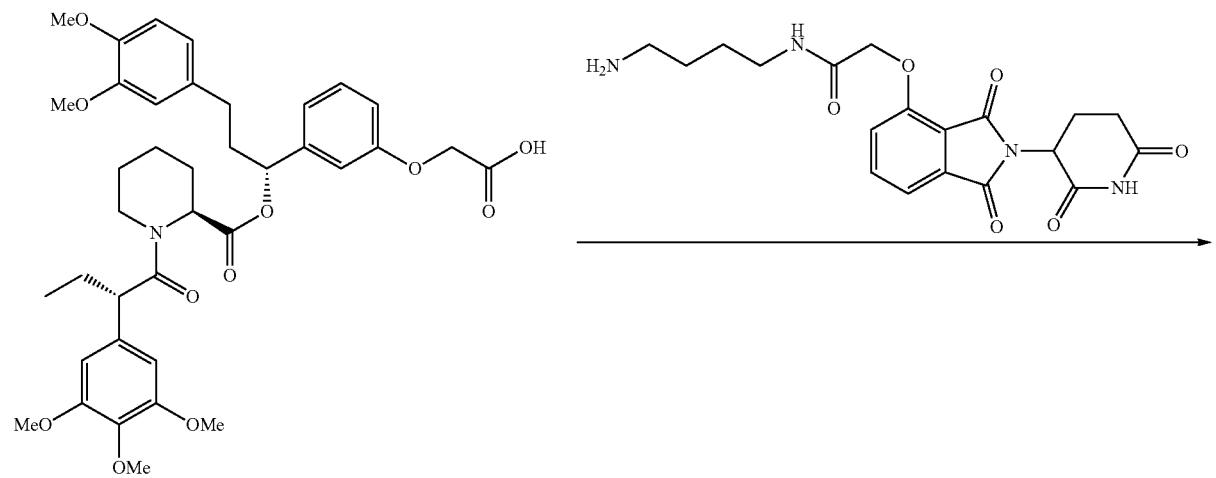

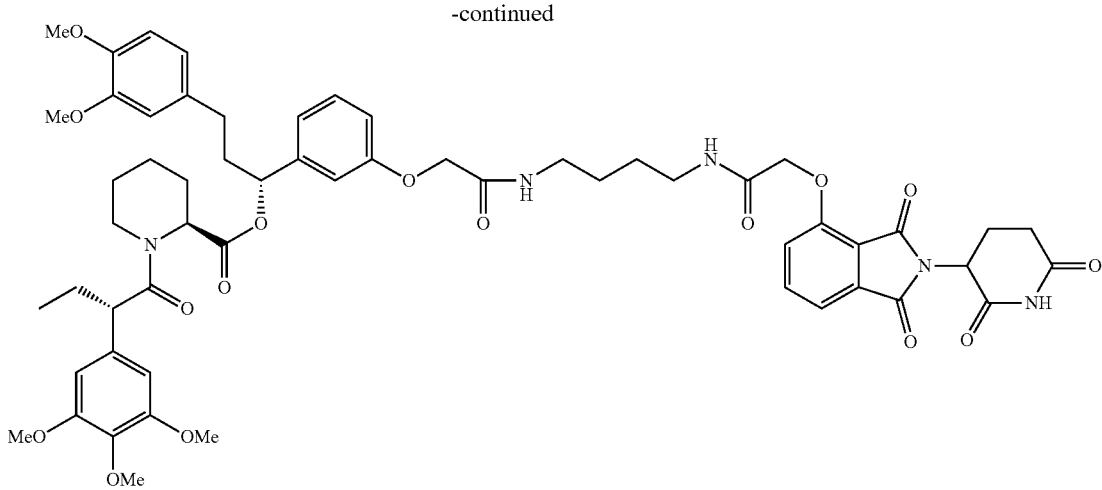

dFKBP*6

N-(4-aminobutyl)-2-((2-(2,6-dioxopiperidin-3-yl)-1,3-dioxoisoindolin-4-yl)oxy)acetamide trifluoroacetate (11.9 mg, 0.0231 mmol, 1 eq) is added to 2-(3-((R)-3-(3,4-dimethoxyphenyl)-1-(((S)-1-((S)-2-(3,4,5-trimethoxyphenyl)butanoyl)piperidine-2-carbonyl)oxy)propyl)phenoxy)acetic acid (16.0 mg, 0.0231 mmol, 1 eq) as a solution in 0.231 mL DMF (0.1 M). DIPEA (12.1 microliters, 0.0692 mmol, 3 eq) and HATU (8.8 mg, 0.0231 mmol, 1 eq) are added and the mixture is stirred for 21 hours. The mixture is diluted with EtOAc and washed with saturated sodium bicarbonate, water and brine. The organic layer is dried over sodium sulfate, filtered and concentrated under reduced pressure. The crude material is purified by column chromatography.

The above synthetic scheme can also be used to provide the analogous ortho or para bonding configuration in the dFKBP structures herein by choice of starting material, as illustrated below. Any of these positional isomers can be used in the present invention to degrade FKBP. For example:

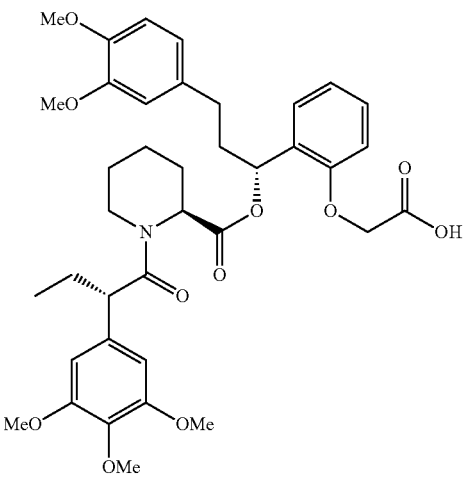 [SMILES: CC[C@H](C(=O)N1CCCC[C@H]1C(=O)O[C@H](CCc1ccc(OC)c(OC)c1)c1ccccc1OCC(=O)O)c1cc(OC)c(OC)c(OC)c1]

will produce

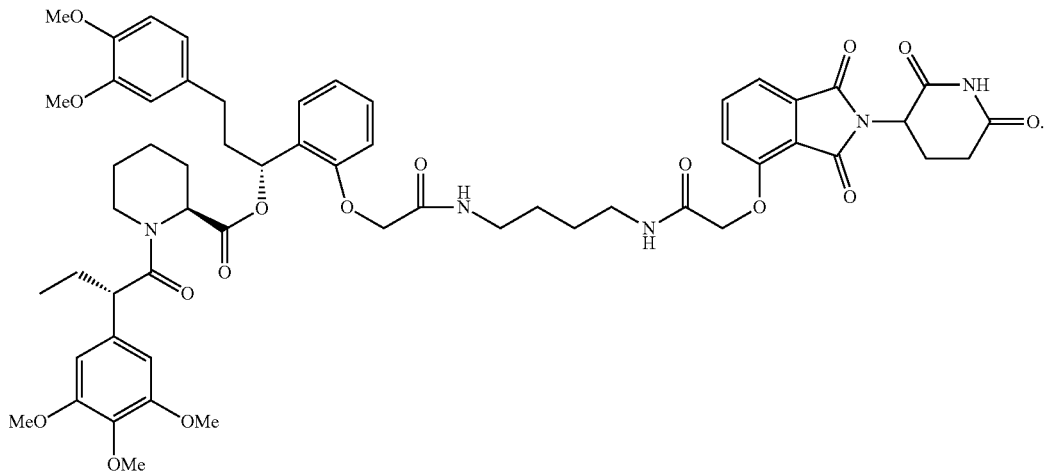

dFKBP6-o

Similarly use of:
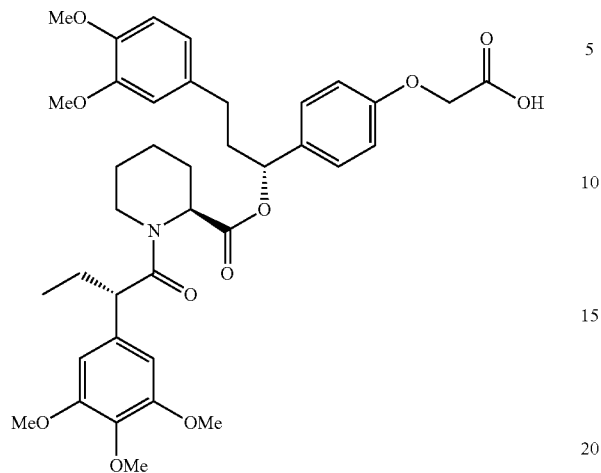
will produce
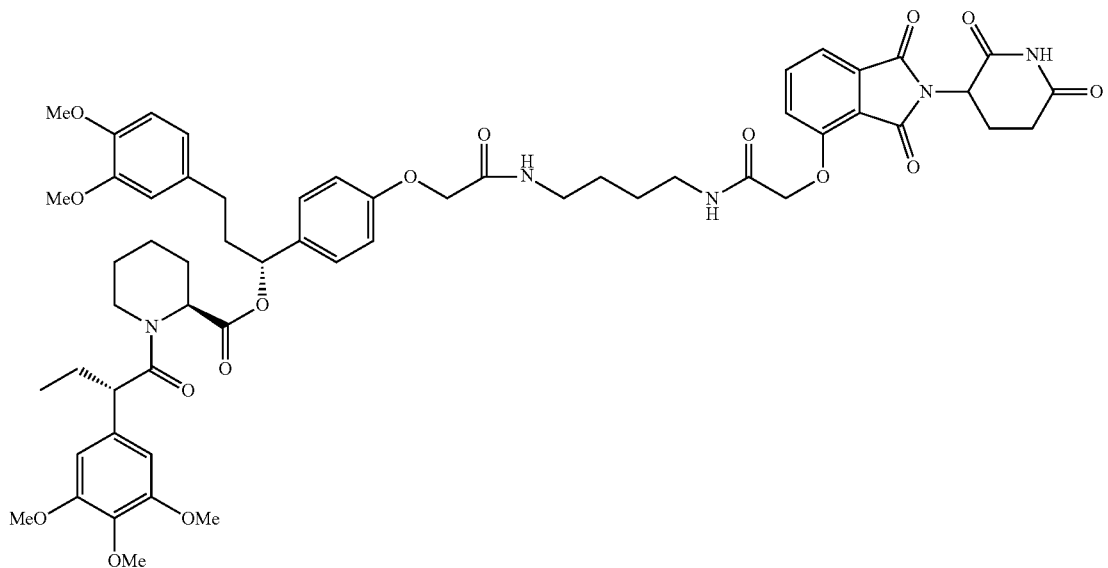
dFKBP6-p
Synthetic Example 64: Synthesis of dFKBP-7
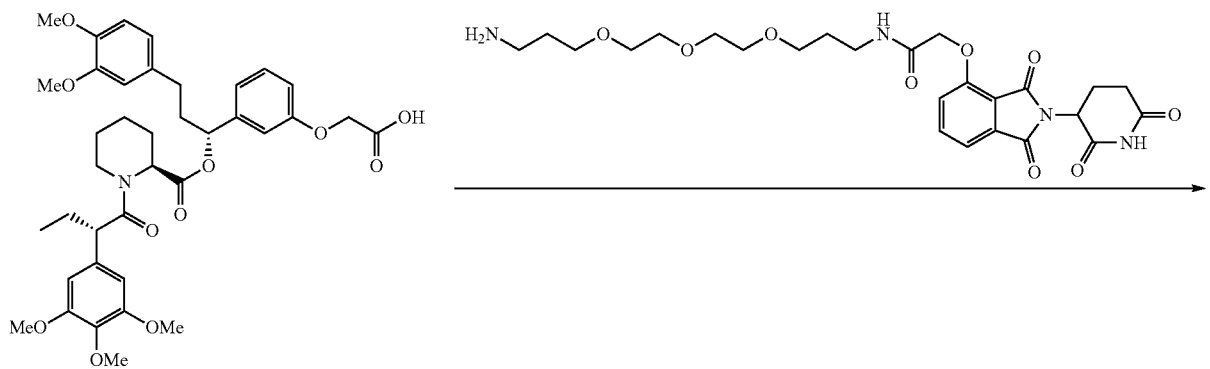

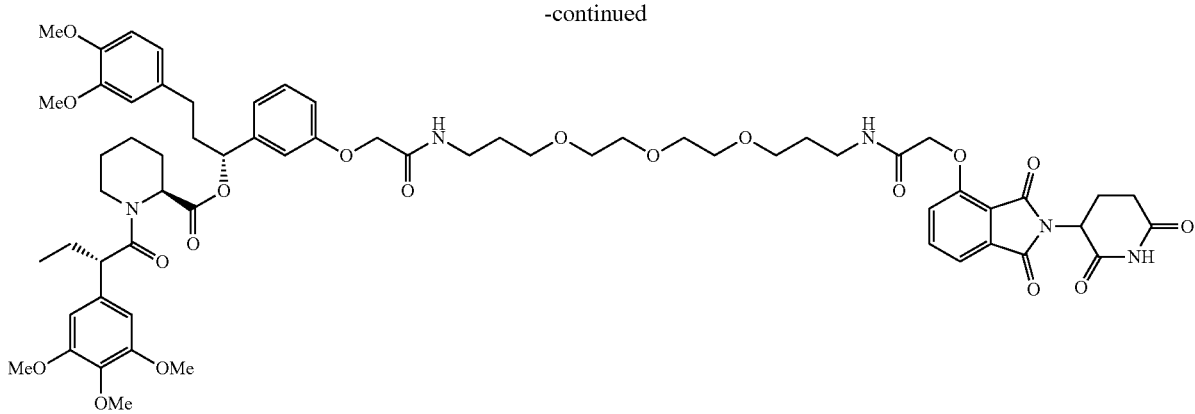

dFKBP*7

N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoracetate (12.3 mg, 0.0189 mmol, 1 eq) is added to 2-(3-((R)-3-(3,4-dimethoxyphenyl)-1-(((S)-1-((S)-2-(3,4,5-trimethoxyphenyl)butanoyl) piperidine-2-carbonyl)oxy)propyl)phenoxy)acetic acid (13.1 mg, 0.0189 mmol, 1 eq) as a solution in 0.189 mL DMF (0.1 M). DIPEA (9.9 microliters, 0.0566 mmol, 3 eq) and HATU (7.2 mg, 0.0189 mmol, 1 eq) are added and the mixture is stirred for 17 hours. The mixture is diluted with EtOAc and washed with saturated sodium bicarbonate, water and brine. The organic layer is dried over sodium sulfate, filtered and concentrated under reduced pressure. The crude material is purified by column chromatography.

Synthetic Example 65: Synthesis of dFKBP-8

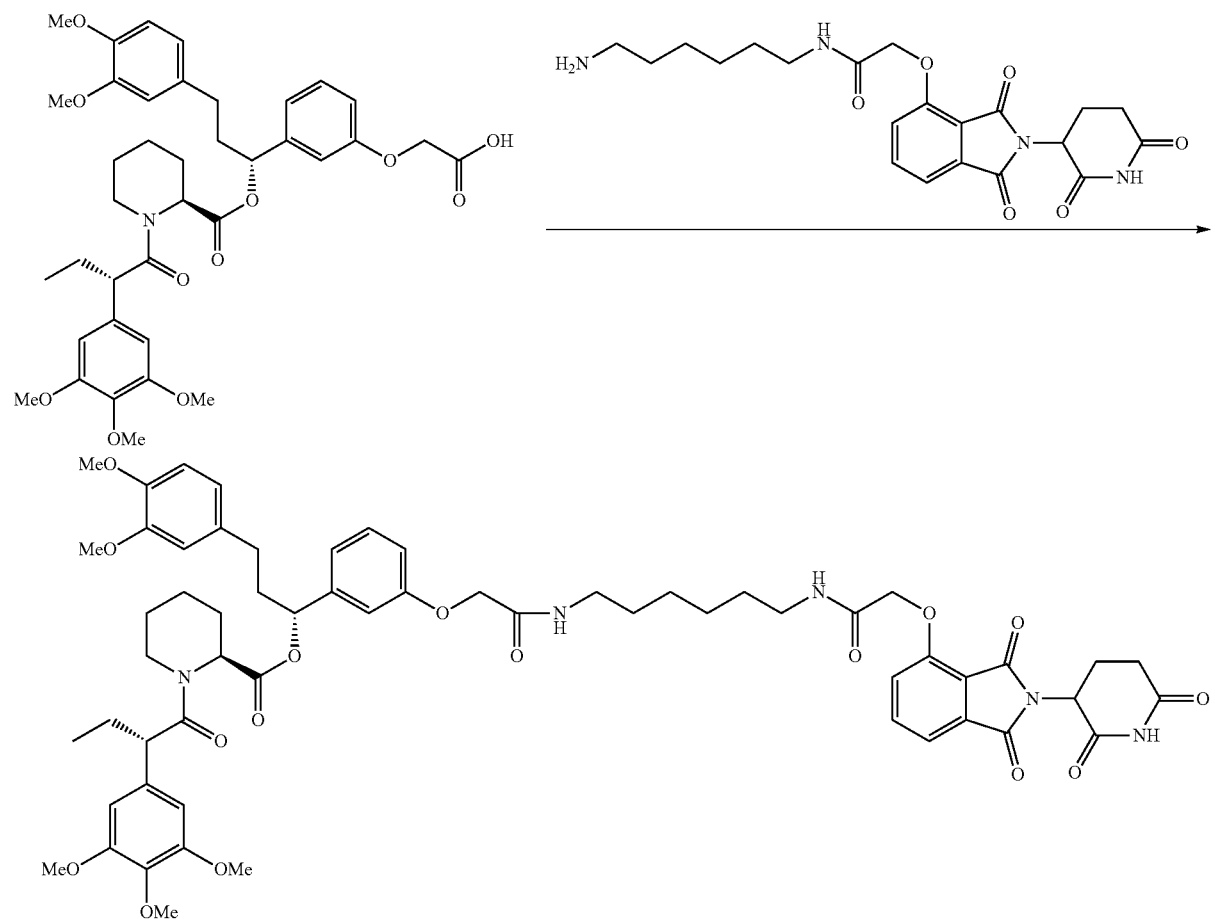

dFKBP*8

N-(6-aminohexyl)-2-((2-(2,6-dioxopiperidin-3-yl)-1,3-dioxoisoindolin-4-yl)oxy)acetamide trifluoracetate (12.7 mg, 0.0233 mmol, 1.3 eq) is added to 2-(3-((R)-3-(3,4-dimethoxyphenyl)-1-(((S)-1-((S)-2-(3,4,5-trimethoxyphenyl)butanoyl)piperidine-2-carbonyl)oxy)propyl)phenoxy)acetic acid (12.4 mg, 0.0179 mmol, 1 eq) as a solution in 0.233 mL DMF (0.1 M). DIPEA (9.3 microliters, 0.0537 mmol, 3 eq) and HATU (6.8 mg, 0.0179 mmol, 1 eq) are added and the mixture is stirred for 22 hours. The mixture is diluted with EtOAc and washed with saturated sodium bicarbonate, water and brine. The organic layer is dried over sodium sulfate, filtered and concentrated under reduced pressure. The crude material is purified by column chromatography.

Synthetic Example 66: Synthesis of dFKBP-9

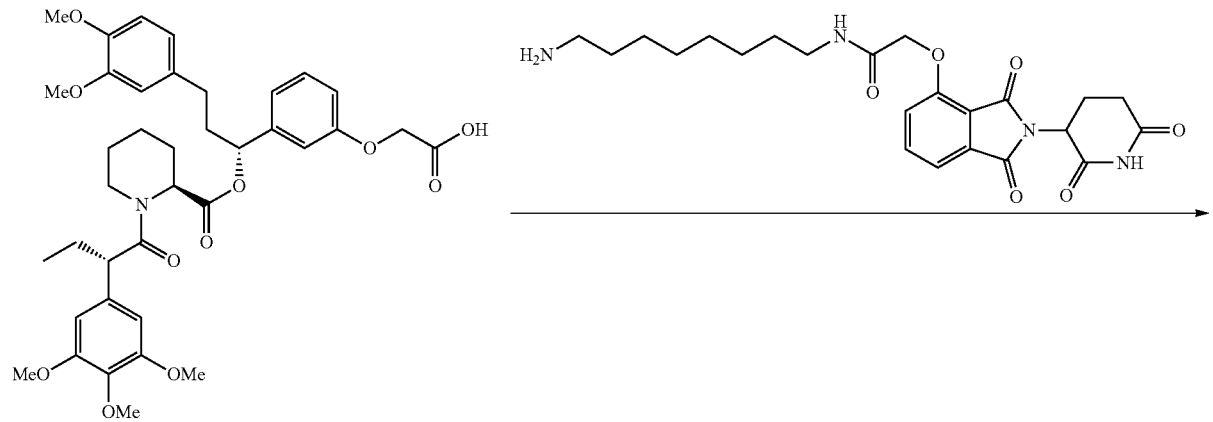

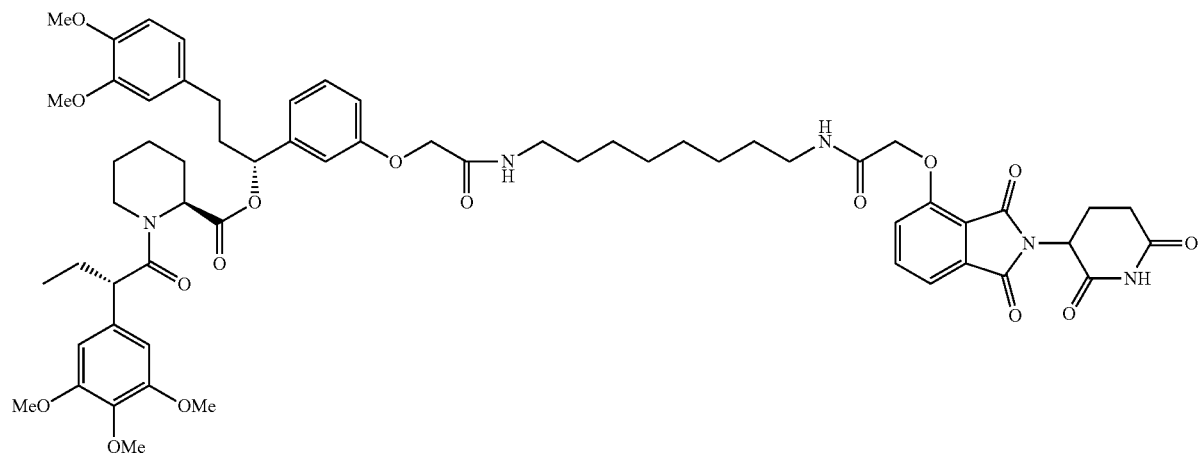

dFKBP*9

N-(8-aminooctyl)-2-((2-(2,6-dioxopiperidin-3-yl)-1,3-di-oxoisoindolin-4-yl)oxy)acetamide trifluoroacetate (10.4 mg, 0.0181 mmol, 1 eq) is added to 2-(3-((R)-3-(3,4-dimethoxy-phenyl)-1-(((S)-1-((S)-2-(3,4,5-trimethoxyphenyl)butanoyl) piperidine-2-carbonyl)oxy)propyl)phenoxy)acetic acid (12.5 mg, 0.0181 mmol, 1 eq) as a solution in 0.181 mL DMF (0.1 M). DIPEA (9.5 microliters, 0.0543 mmol, 3 eq) and HATU (6.9 mg, 0.0181 mmol, 1 eq) are added and the mixture is stirred for 22 hours. The mixture is diluted with EtOAc and washed with saturated sodium bicarbonate, water and brine. The organic layer is dried over sodium sulfate, filtered and concentrated under reduced pressure. The crude material is purified by column chromatography.

Synthetic Example 67: Synthesis of dFKBP

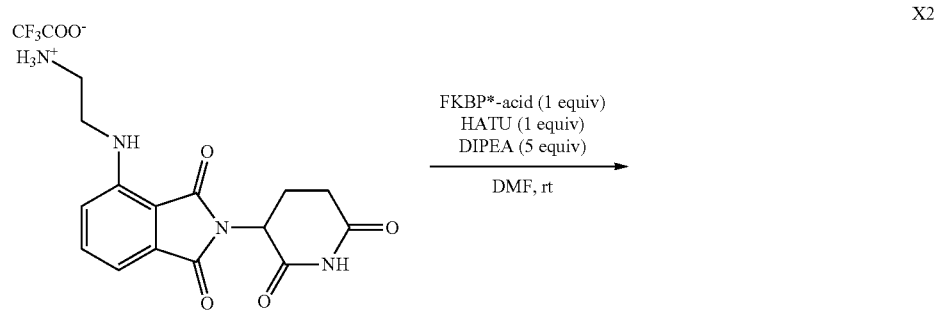

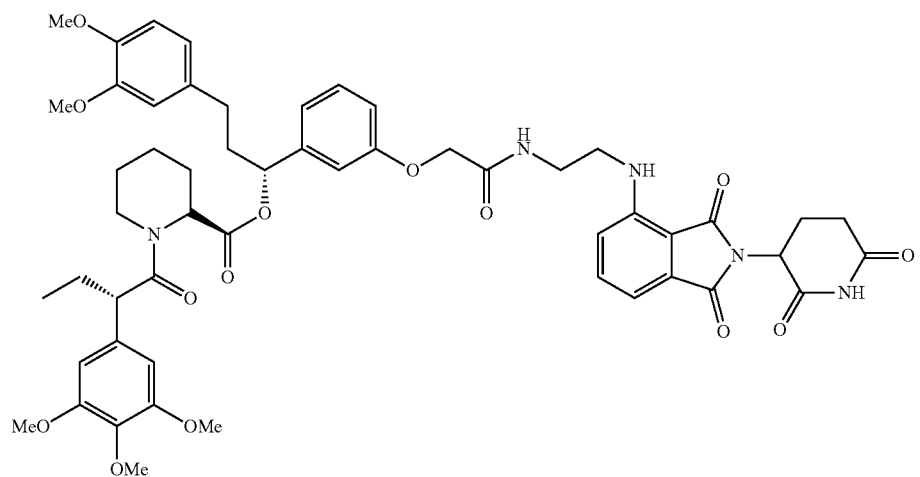

FKBP*-acid (14.0 mg, 0.0202 mmol, 1 eq) and 2-((2-(2,6-dioxopiperidin-3-yl)-1,3-dioxoisoindolin-4-yl)amino)ethan-1-aminium 2,2,2-trifluoroacetate (8.7 mg, 0.0202 mmol, 1 equiv) are dissolved in DMF (0.202 mL, 0.1 M) at room temperature. DIPEA (17.6 □L, 0.101 mmol, 5 equiv) and HATU (7.6 mg, 0.0200 mmol, 1 equiv) are then added and the mixture is stirred at room temperature overnight. The reaction mixture is taken up in EtOAc (15 mL), and washed with satd. NaHCO₃ (aq) (15 mL), water (15 mL) and brine (3×15 mL). The organic layer is dried over Na₂SO₄ and concentrated in vacuo. The crude material is purified by column chromatography.

Synthetic Example 68: Synthesis of Diaminoethyl-acetyl-O-thalidomide Trifluoroacetate

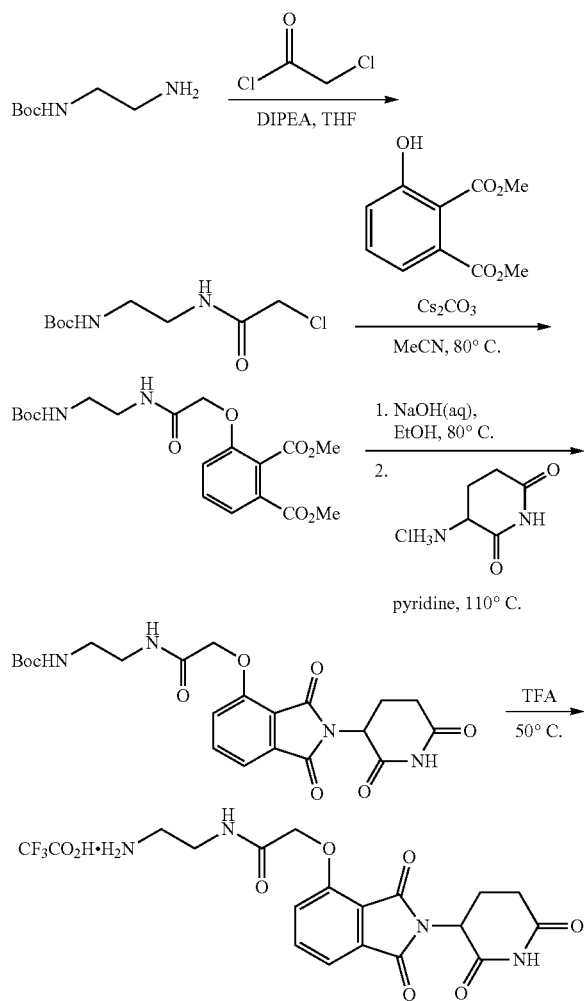

(1) Synthesis of Tert-Butyl (2-(2-chloroacetamido)ethyl)carbamate

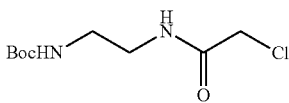 [SMILES: CC(C)(C)OC(=O)NCCNC(=O)CCl]

tert-butyl (2-aminoethyl)carbamate (0.40 mL, 2.5 mmol, 1 eq) was dissolved in THF (25 mL, 0.1 M) and DIPEA (0.44 mL, 2.5 mmol, 1 eq) at 0° C. Chloroacetyl chloride (0.21 mL, 2.75 mmol, 1.1 eq) was added and the mixture was allowed to warm to room temperature. After 22 hours, the mixture was diluted with EtOAc and washed with saturated sodium bicarbonate, water and brine. The organic layer was dried with sodium sulfate, filtered and concentrated under reduced pressure to give a white solid (0.66 g, quantitative yield) that carried forward to the next step without further purification. ¹H NMR (400 MHz, Chloroform-d) δ 7.16 (s, 1H), 4.83 (s, 1H), 4.04 (s, 2H), 3.42 (q, J=5.4 Hz, 2H), 3.32 (q, J=5.6 Hz, 2H), 1.45 (s, 9H). LCMS 237.30 (M+H).

(2) Synthesis of dimethyl 3-(2-((2-((tert-butoxycarbonyl)amino)ethyl)amino)-2-oxoethoxy)phthalate

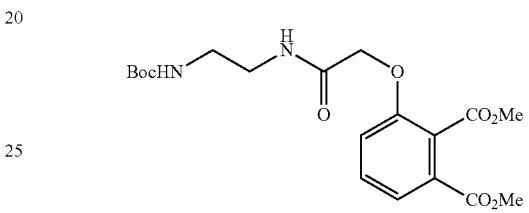

tert-butyl (2-(2-chloroacetamido)ethyl)carbamate (0.66 g, 1 eq) was dissolved in MeCN (17 mL, 0.15 M). Dimethyl 3-hydroxyphthalate (0.578 g, 2.75 mmol, 1.1 eq) and cesium carbonate (2.24 g, 6.88 mmol, 2.75 eq) were then added. The flask was fitted with a reflux condenser and heated to 80° C. for 32 hours. The mixture was then cooled to room temperature, diluted with EtOAc and washed three times with water. The organic layer was dried over sodium sulfate, filtered and concentrated under reduced pressure. Purification by column chromatography (ISCO, 4 g silica column, 0-15% MeOH/DCM over a 15 minute gradient) gave a yellow solid (0.394 g, 0.960 mmol, 38% over 2 steps). ¹H NMR (400 MHz, Chloroform-d) δ 7.65-7.56 (m, 1H), 7.50-7.41 (m, 1H), 7.27 (s, 1H), 7.11 (dd, J=8.4, 4.1 Hz, 2H), 5.17 (s, 1H), 4.57 (d, J=6.3 Hz, 2H), 3.94 (s, 2H), 3.88 (s, 2H), 3.40 (p, J=5.8 Hz, 4H), 3.32-3.19 (m, 4H), 1.39 (d, J=5.7 Hz, 13H). ¹³C NMR (100 MHz, cdcl₃) δ 168.37, 168.23, 165.73, 156.13, 154.71, 131.24, 130.09, 124.85, 123.49, 117.24, 79.42, 68.48, 53.22, 52.83, 40.43, 39.54, 28.44. LCMS 411.45 (M+H).

(3) Synthesis of Diaminoethyl-acetyl-O-thalidomide Trifluoroacetate

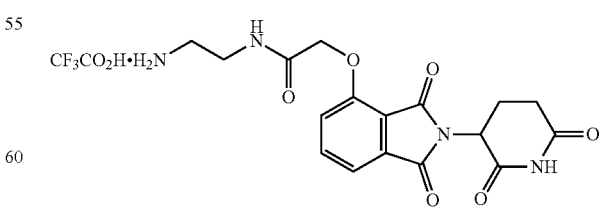

Dimethyl 3-(2-((2-((tert-butoxycarbonyl)amino)ethyl)amino)-2-oxoethoxy)phthalate (0.39 g, 0.970 mmol, 1 eq) was dissolved in EtOH (9.7 mL, 0.1 M). Aqueous 3M NaOH (0.97 mL, 2.91 mmol, 3 eq) was added and the mixture was heated to 80° C. for 3 hours. The mixture was cooled to room temperature, diluted with 50 mL DCM, 5 mL 1 M HCl and 20 mL water. The layers were separated and the organic layer was washed with 20 mL water. The combined aqueous layers were then extracted 3 times with 50 mL chloroform. The combined organic layers were dried over sodium sulfate, filtered and concentrated under reduced pressure to give a yellow solid (0.226 g) that was carried forward without further purification. LCMS 383.36.

The resultant yellow solid (0.226 g) and 3-aminopiperidine-2,6-dione hydrochloride (0.102 g, 0.6197 mmol, 1 eq) were dissolved in pyridine (6.2 mL, 0.1 M) and heated to 110° C. for 16 hours. The mixture was cooled to room temperature and concentrated under reduced pressure to give tert-butyl (2-(2-((2-(2,6-dioxopiperidin-3-yl)-1,3-dioxoisoindolin-4-yl)oxy)acetamido)ethyl)carbamate as a poorly soluble black tar (0.663 g) which was carried forward without purification (due to poor solubility). LCMS 475.42 (M+H).

The crude tert-butyl (2-(2-((2-(2,6-dioxopiperidin-3-yl)-1,3-dioxoisoindolin-4-yl)oxy)acetamido)ethyl)carbamate was dissolved in TFA (10 mL) and heated to 50° C. for 3.5 hours, then concentrated under reduced pressure. Purification by preparative HPLC gave a red oil (176.7 mg, 0.362 mmol, 37% over 3 steps). $^1$H NMR (400 MHz, Methanol-$d_4$) δ 7.85-7.76 (m, 1H), 7.57-7.50 (m, 1H), 7.48-7.41 (m, 1H), 5.13 (dd, J=12.6, 5.5 Hz, 1H), 4.81 (s, 2H), 3.62 (td, J=5.6, 1.8 Hz, 2H), 3.14 (t, J=5.8 Hz, 2H), 2.97 (s, 1H), 2.80-2.66 (m, 2H), 2.15 (dddd, J=10.1, 8.0, 5.8, 2.8 Hz, 1H). $^{13}$C NMR (100 MHz, cd$_3$od) δ 173.09, 170.00, 169.99, 166.78, 166.62, 154.93, 136.88, 133.46, 120.71, 117.93, 116.77, 68.29, 49.17, 39.37, 38.60, 30.73, 22.19. LCMS 375.30 (M+H for free base).

Synthetic Example 69: Synthesis of Diaminobutyl-acetyl-O-thalidomide Trifluoroacetate

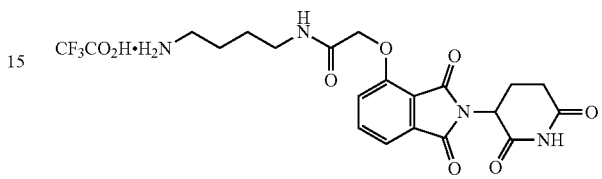

Diaminobutyl-acetyl-O-thalidomide trifluoroacetate was prepared according to the procedure in Fischer et al. *Nature*, 2014, 512, 49-53.

Synthetic Example 70: Synthesis of Diaminohexyl-acetyl-O-thalidomide Trifluoroacetate

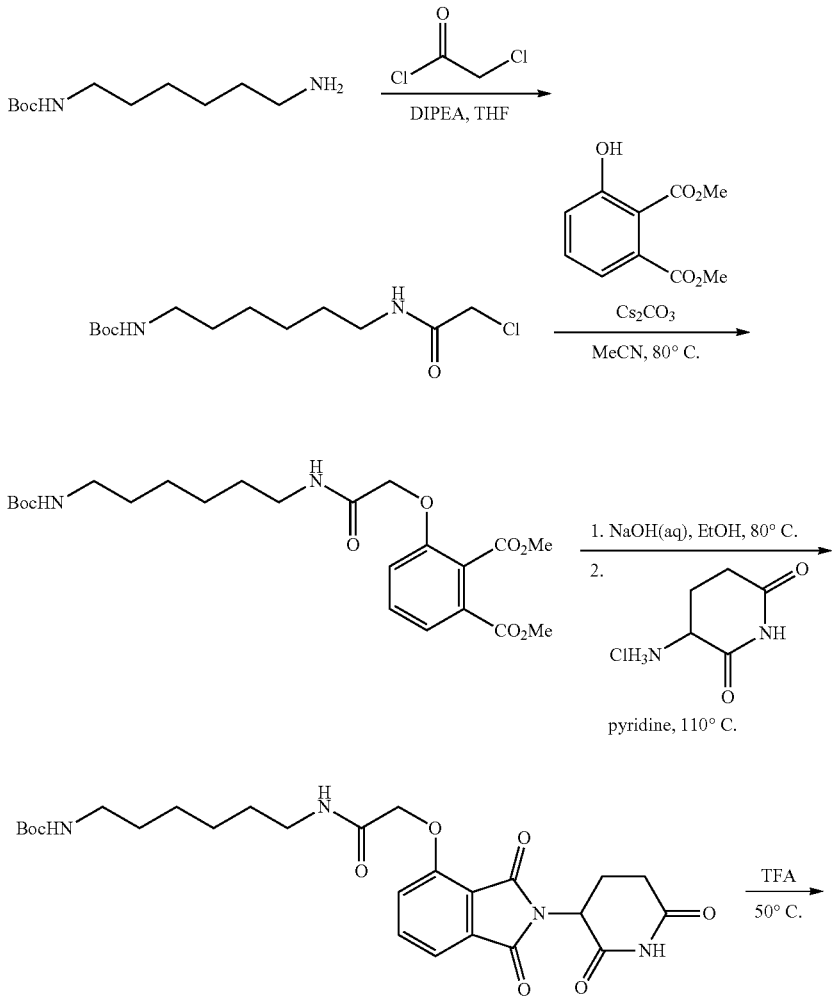

-continued

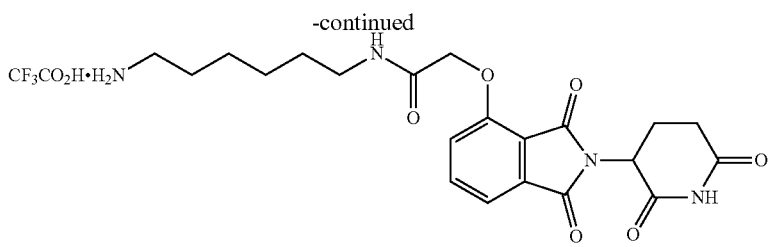

(1) Synthesis of tert-butyl (6-(2-chloroacetamido)hexyl)carbamate

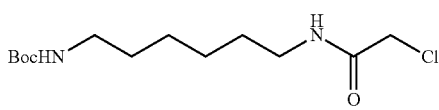 [SMILES: CC(C)(C)OC(=O)NCCCCCCNC(=O)CCl]

tert-butyl (6-aminohexyl)carbamate (0.224 mL, 1.0 mmol, 1 eq) was dissolved in THF (10 mL, 0.1 M). DIPEA (0.17 mL, 1.0 mmol, 1 eq) was added and the mixture was cooled to 0° C. Chloroacetyl chloride (88 microliters, 1.1 mmol, 1.1 eq) was added and the mixture was warmed to room temperature and stirred for 18 hours. The mixture was then diluted with EtOAc and washed with saturated sodium bicarbonate, water and brine. The organic layer was dried over sodium sulfate, filtered and concentrated under reduced pressure to give a white solid (0.2691 g, 0.919 mmol, 92%).

$^1$H NMR (400 MHz, Chloroform-d) δ 6.60 (s, 1H), 4.51 (s, 1H), 4.05 (s, 2H), 3.30 (q, J=6.9 Hz, 2H), 3.11 (d, J=6.7 Hz, 2H), 1.57-1.46 (m, 4H), 1.44 (s, 9H), 1.38-1.32 (m, 4H). LCMS 293.39 (M+H).

(2) Synthesis of Dimethyl 3-(2-((6-((tert-butoxycarbonyl)amino)hexyl)amino)-2-oxoethoxy)phthalate

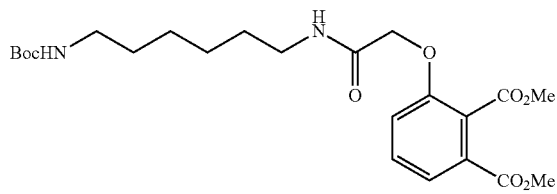 [SMILES: COC(=O)c1cccc(OCC(=O)NCCCCCCNC(=O)OC(C)(C)C)c1C(=O)OC]

tert-butyl (6-(2-chloroacetamido)hexyl)carbamate (0.2691 g, 0.919 mmol, 1 eq) was dissolved in MeCN (9.2 mL, 0.1 M). Dimethyl 3-hydroxyphthalate (0.212 g, 1.01 mmol, 1.1 eq) and cesium carbonate (0.823 g, 2.53 mmol, 2.75 eq) were added. The flask was fitted with a reflux condenser and heated to 80° C. for 14 hours. The mixture was cooled to room temperature and diluted with EtOAc, washed three times with water and back extracted once with EtOAc. The combined organic layers were dried over sodium sulfate, filtered and concentrated under reduced pressure. The crude material was purified by column chromatography (ISCO, 12 g silica column, 0-15% MeOH/DCM 15 minute gradient) to give a yellow oil (0.304 g, 0.651 mmol, 71%). $^1$H NMR (400 MHz, Chloroform-d) δ 7.66-7.58 (m, 1H), 7.44 (td, J=8.2, 1.6 Hz, 1H), 7.15-7.08 (m, 1H), 6.96 (s, 1H), 4.56 (s, 2H), 3.92 (t, J=1.6 Hz, 3H), 3.88 (t, J=1.6 Hz, 3H), 3.27 (q, J=6.9 Hz, 2H), 3.10-3.00 (m, 2H), 1.41 (s, 13H), 1.33-1.22 (m, 4H). $^{13}$C NMR (100 MHz, cdcl$_3$) δ 167.97, 167.37, 165.58, 155.95, 154.37, 130.97, 129.74, 124.94, 123.26, 116.81, 78.96, 68.04, 52.89, 52.87, 52.69, 52.67, 40.41, 38.96, 29.88, 29.13, 28.39, 26.33, 26.30. LCMS 467.49.

(3) Synthesis of Diaminohexyl-acetyl-O-thalidomide Trifluoroacetate

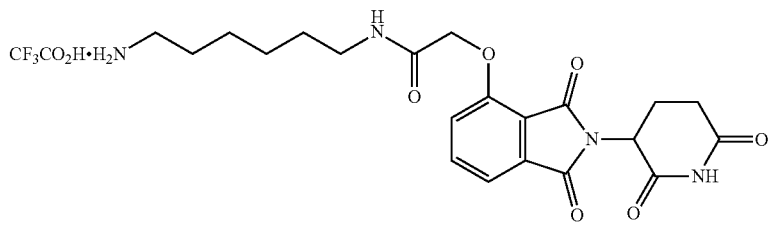

Dimethyl 3-(2-((6-((tert-butoxycarbonyl)amino)hexyl)amino)-2-oxoethoxy)phthalate (0.304 g, 0.651 mmol, 1 eq) was dissolved in EtOH (6.5 mL, 0.1 M). Aqueous 3M NaOH (0.65 mL, 1.953 mmol, 3 eq) was added and the mixture was heated to 80° C. for 18 hours. The mixture was cooled to room temperature and diluted with 50 mL DCM and 10 mL 0.5 M HCl. The layers were separated and the organic layer was washed with 20 mL water. The combined aqueous layers were then extracted 3 times with chloroform. The combined organic layers were dried over sodium sulfate, filtered and concentrated under reduced pressure to give a yellow foam (0.290 g) that was carried forward without further purification. LCMS 439.47.

The resultant yellow solid (0.290 g) and 3-aminopiperidine-2,6-dione hydrochloride (0.113 g, 0.69 mmol, 1 eq) were dissolved in pyridine (6.9 mL, 0.1 M) and heated to 110° C. for 17 hours. The mixture was cooled to room temperature and concentrated under reduced pressure to give tert-butyl (6-(2-((2-(2,6-dioxopiperidin-3-yl)-1,3-dioxoisoindolin-4-yl)oxy)acetamido)hexyl)carbamate as a black solid (0.4216 g) which was carried forward without purification (due to poor solubility). LCMS 531.41 (M+H).

The crude tert-butyl (6-(2-((2-(2,6-dioxopiperidin-3-yl)-1,3-dioxoisoindolin-4-yl)oxy)acetamido)hexyl)carbamate (0.4216 g) was dissolved in TFA (10 mL) and heated to 50° C. for 2 hours. The mixture was concentrated under reduced pressure, then concentrated under reduced pressure. Purification by preparative HPLC gave a brown solid (379.2 mg). $^1$H NMR (400 MHz, Methanol-$d_4$) δ 7.79 (dd, J=8.4, 7.4 Hz, 1H), 7.52 (d, J=7.2 Hz, 1H), 7.42 (d, J=8.4 Hz, 1H), 5.13 (dd, J=12.6, 5.5 Hz, 1H), 4.75 (s, 2H), 3.32 (t, J=7.6 Hz, 2H), 2.96-2.89 (m, 2H), 2.89-2.65 (m, 3H), 2.16 (ddt, J=10.4, 5.4, 2.9 Hz, 1H), 1.63 (dp, J=20.6, 7.1 Hz, 4H), 1.51-1.34 (m, 4H). $^{13}$C NMR (100 MHz, cd$_3$od) δ 174.57, 171.42, 169.90, 168.24, 167.79, 156.23, 138.23, 134.87, 121.69, 119.22, 117.98, 69.36, 50.53, 40.64, 39.91, 32.14, 30.01, 28.44, 27.23, 26.96, 23.63. LCMS 431.37 (M+H).

Synthetic Example 71: Synthesis of Diaminooctyl-acetyl-O-thalidomide Trifluoroacetate

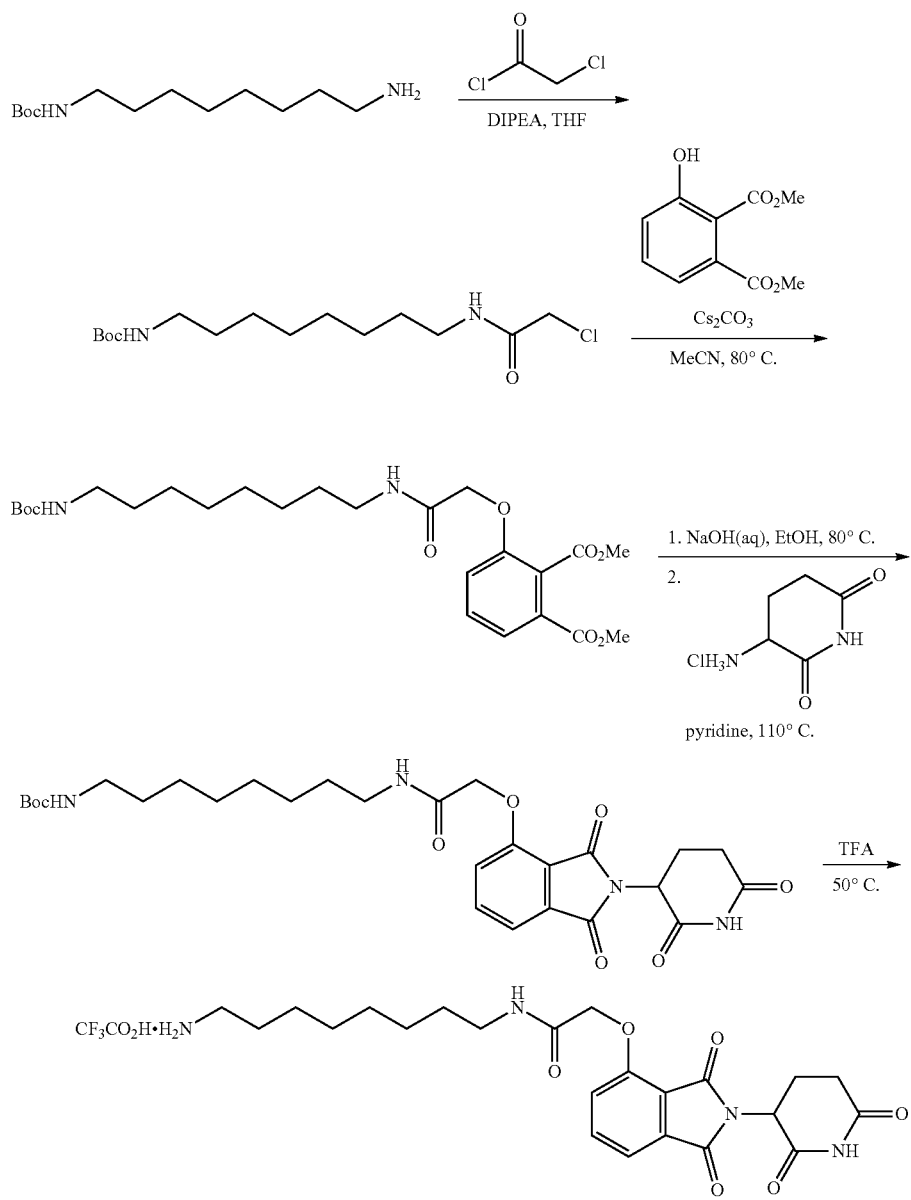

(1) Synthesis of Tert-Butyl (8-(2-chloroacetamido)octyl)carbamate

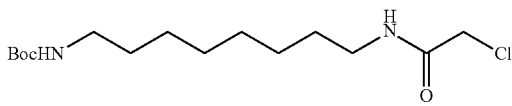 [SMILES: CC(C)(C)OC(=O)NCCCCCCCCNC(=O)CCl]

Octane-1,8-diamine (1.65 g, 11.45 mmol, 5 eq) was dissolved in chloroform (50 mL). A solution of di-tert-butyl dicarbonate (0.54 g, 2.291 mmol, 1 eq) in chloroform (10 mL) was added slowly at room temperature and stirred for 16 hours before being concentrated under reduced pressure. The solid material was resuspended in a mixture of DCM, MeOH, EtOAc and 0.5 N $NH_3$ (MeOH), filtered through celite and concentrated under reduced pressure. Purification by column chromatography (ISCO, 12 g NH2-silica column, 0-15% MeOH/DCM over a 15 minute gradient) gave a mixture (1.75 g) of the desired product and starting material which was carried forward without further purification.

This mixture was dissolved in THF (72 mL) and DIPEA (1.25 mL, 7.16 mmol) and cooled to 0° C. Chloroacetyl chloride (0.63 mL, 7.88 mmol) was added and the mixture was allowed to warm to room temperature. After 16 hours, the mixture was diluted with EtOAc and washed with saturated sodium bicarbonate, water and brine. The resultant mixture was purified by column chromatography (ISCO, dry load onto silica, 24 g column, 0-100% EtOAc/hexanes, over a 21 minute gradient) to give a white solid (0.56 g, 1.745 mmol, 76% over 2 steps). $^1$H NMR (400 MHz, Chloroform-d) δ 6.55 (s, 1H), 4.48 (s, 1H), 4.05 (s, 2H), 3.30 (q, J=6.9 Hz, 2H), 3.10 (d, J=6.2 Hz, 2H), 1.44 (s, 12H), 1.31 (s, 9H). $^{13}$C NMR (100 MHz, cdcl$_3$) δ 165.86, 156.14, 77.36, 42.86, 40.73, 40.00, 30.18, 29.44, 29.26, 28.59, 26.86, 26.82. LCMS 321.34 (M+H).

(2) Synthesis of Dimethyl 3-(2-((8-((tert-butoxycarbonyl)amino)octyl)amino)-2-oxoethoxy)phthalate

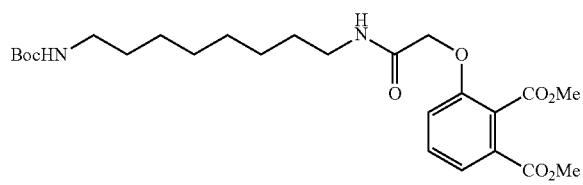 [SMILES: COC(=O)c1cccc(OCC(=O)NCCCCCCCCNC(=O)OC(C)(C)C)c1C(=O)OC]

tert-butyl (8-(2-chloroacetamido)octyl)carbamate (0.468 g, 1.46 mmol, 1 eq) was dissolved in MeCN (15 mL, 0.1 M). Dimethyl 3-hydroxyphthalate (0.337 g, 1.60 mmol, 1.1 eq) and cesium carbonate (1.308 g, 4.02 mmol, 2.75 eq) were added. The flask was fitted with a reflux condenser and heated to 80° C. for 18 hours. The mixture was cooled to room temperature and diluted water and extracted once with chloroform and twice with EtOAc. The combined organic layers were dried over sodium sulfate, filtered and concentrated under reduced pressure.

The crude material was purified by column chromatography (ISCO, 24 g silica column, 0-15% MeOH/DCM 20 minute gradient) to give a yellow oil (0.434 g, 0.878 mmol, 60%). $^1$H NMR (400 MHz, Chloroform-d) δ 7.57 (dd, J=7.9, 0.8 Hz, 1H), 7.40 (t, J=8.1 Hz, 1H), 7.07 (dd, J=8.4, 0.7 Hz, 1H), 6.89 (t, J=5.3 Hz, 1H), 4.63 (s, 1H), 4.52 (s, 2H), 3.88 (s, 3H), 3.83 (s, 3H), 3.22 (q, J=6.9 Hz, 2H), 3.01 (q, J=6.4 Hz, 2H), 1.36 (s, 12H), 1.20 (s, 9H). $^{13}$C NMR (100 MHz, cdcl$_3$) δ 167.89, 167.29, 165.54, 155.97, 154.38, 130.95, 129.69, 124.96, 123.23, 116.86, 78.82, 68.05, 52.83, 52.82, 52.66, 52.64, 40.54, 39.06, 29.97, 29.19, 29.10, 29.06, 28.40, 26.66, 26.61. LCMS 495.42 (M+H).

(3) Synthesis of Diaminooctyl-acetyl-O-thalidomide trifluoroacetate

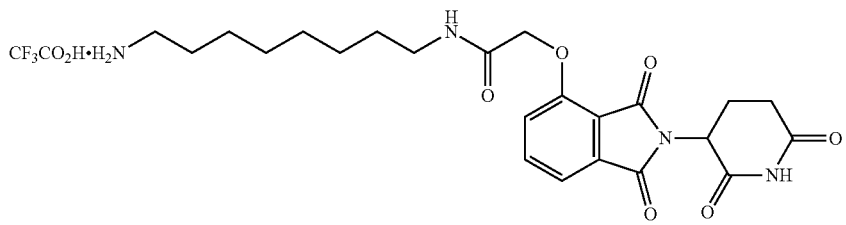

Dimethyl 3-(2-((8-((tert-butoxycarbonyl)amino)octyl)amino)-2-oxoethoxy)phthalate (0.434 g, 0.878 mmol, 1 eq) was dissolved in EtOH (8.8 mL, 0.1 M) Aqueous 3M NaOH (0.88 mL, 2.63 mmol, 3 eq) was added and the mixture was heated to 80° C. for 24 hours. The mixture was cooled to room temperature and diluted with 50 mL DCM and 10 mL 0.5 M HCl. The layers were separated and the organic layer was washed with 20 mL water. The combined aqueous layers were then extracted 3 times with chloroform. The combined organic layers were dried over sodium sulfate, filtered and concentrated under reduced pressure to give a yellow solid (0.329 g) that was carried forward without further purification. LCMS 467.41.

The resultant yellow solid (0.329 g) and 3-aminopiperidine-2,6-dione hydrochloride (0.121 g, 0.734 mmol, 1 eq) were dissolved in pyridine (7.3 mL, 0.1 M) and heated to 110° C. for 20 hours. The mixture was cooled to room temperature and concentrated under reduced pressure to give tert-butyl (8-(2-((2-(2,6-dioxopiperidin-3-yl)-1,3-dioxoisoindolin-4-yl)oxy)acetamido) octyl) carbamate as a black tar (0.293 g) which was carried forward without purification (due to poor solubility). LCMS 559.45 (M+H).

The crude tert-butyl (8-(2-((2-(2,6-dioxopiperidin-3-yl)-1,3-dioxoisoindolin-4-yl)oxy)acetamido)octyl)carbamate (0.293 g) was dissolved in TFA (10 mL) and heated to 50° C. for 4 hours. The mixture was concentrated under reduced pressure, then concentrated under reduced pressure. Purification by preparative HPLC gave a brown residue (114.69 mg, 23% over 3 steps). $^1$H NMR (400 MHz, Methanol-d$_4$) δ 7.84-7.78 (m, 1H), 7.54 (d, J=7.3 Hz, 1H), 7.43 (d, J=8.5

Hz, 1H), 5.13 (dd, J=12.5, 5.5 Hz, 1H), 4.76 (s, 2H), 3.32 (d, J=4.1 Hz, 1H), 3.30 (d, J=3.3 Hz, 1H), 2.94-2.84 (m, 3H), 2.80-2.70 (m, 2H), 2.19-2.12 (m, 1H), 1.67-1.55 (m, 4H), 1.40-1.34 (m, 8H). $^{13}$C NMR (100 MHz, cd$_3$od) δ 174.57, 171.37, 169.85, 168.26, 167.78, 156.26, 138.22, 134.91, 121.70, 119.28, 117.97, 69.37, 50.57, 40.76, 40.08, 32.17, 30.19, 30.05, 30.01, 28.52, 27.68, 27.33, 23.63. LCMS 459.41 (M+H).
Synthetic Example 72: Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy) acetamide trifluoroacetate
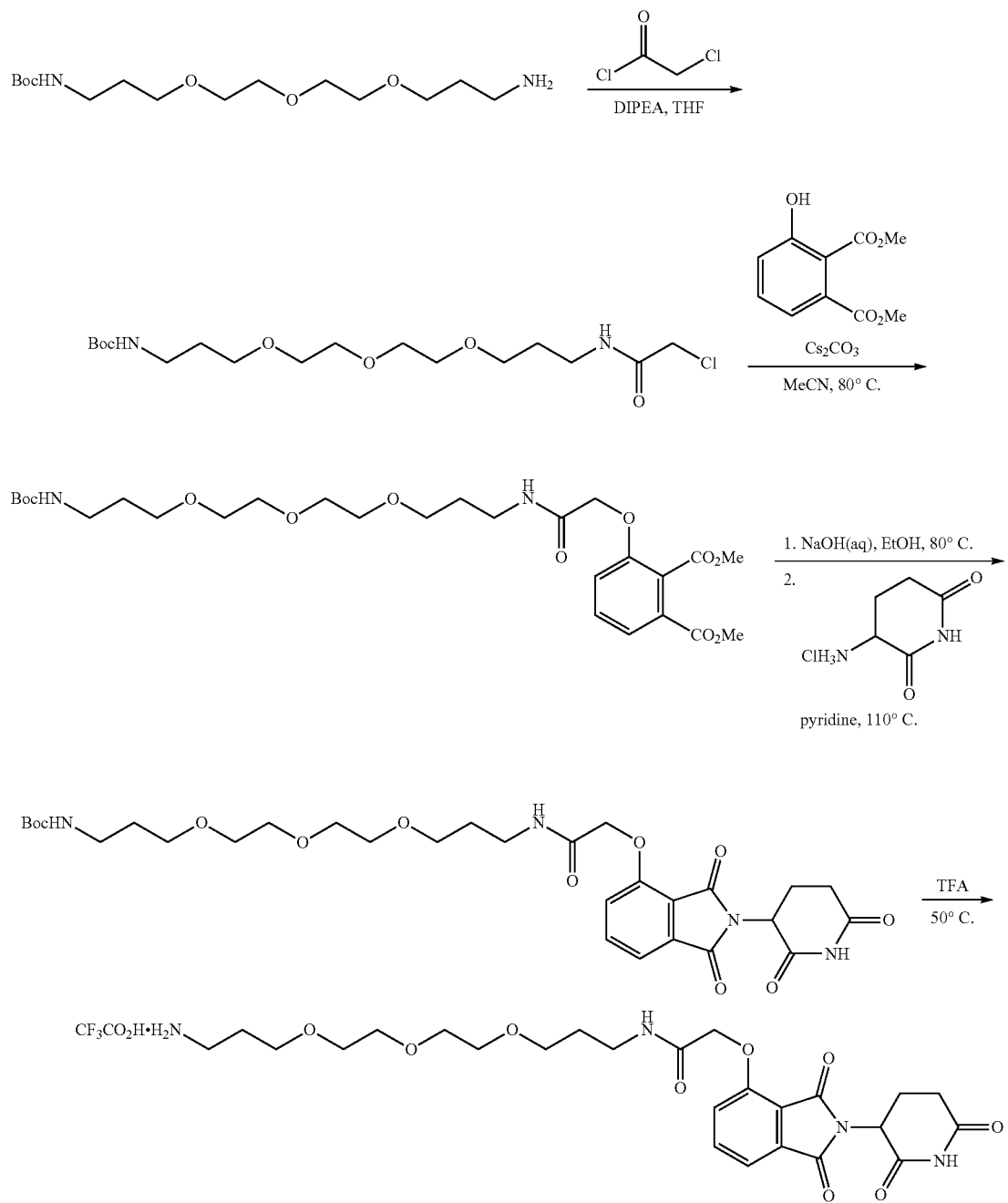

(1) Synthesis of Tert-butyl (1-chloro-2-oxo-7,10,13-trioxa-3-azahexadecan-16-yl)carbamate

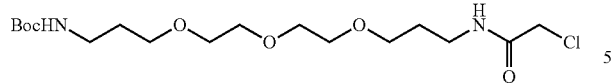

tert-butyl (3-(2-(2-(3-aminopropoxy)ethoxy)ethoxy)propyl)carbamate (1.0 g, 3.12 mmol, 1 eq) was dissolved in THF (31 mL, 0.1 M). DIPEA (0.543 mL, 3.12 mmol, 1 eq) was added and the solution was cooled to 0° C. Chloroacetyl chloride (0.273 mL, 3.43 mmol, 1.1 eq) was added and the mixture was warmed slowly to room temperature. After 24 hours, the mixture was diluted with EtOAc and washed with saturated sodium bicarbonate, water then brine. The organic layer was dried over sodium sulfate, filtered and condensed to give a yellow oil (1.416 g) that was carried forward without further purification. $^1$H NMR (400 MHz, Chloroform-d) δ 7.24 (s, 1H), 5.00 (s, 1H), 3.98-3.89 (m, 2H), 3.54 (dddt, J=17.0, 11.2, 5.9, 2.2 Hz, 10H), 3.47-3.40 (m, 2H), 3.37-3.31 (m, 2H), 3.17-3.07 (m, 2H), 1.79-1.70 (m, 2H), 1.67 (p, J=6.1 Hz, 2H), 1.35 (s, 9H). $^{13}$C NMR (100 MHz, cdcl$_3$) δ 165.83, 155.97, 78.75, 70.49, 70.47, 70.38, 70.30, 70.14, 69.48, 42.61, 38.62, 38.44, 29.62, 28.59, 28.40. LCMS 397.37 (M+H).

(2) Synthesis of dimethyl 3-((2,2-dimethyl-4,20-dioxo-3,9,12,15-tetraoxa-5,19-diazahenicosan-21-yl)oxy)phthalate

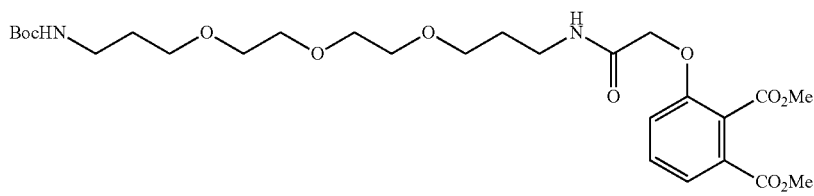 [SMILES: COC(=O)c1cccc(OCC(=O)NCCCOCCOCCOCCCNC(=O)OC(C)(C)C)c1C(=O)OC]

tert-butyl (1-chloro-2-oxo-7,10,13-trioxa-3-azahexadecan-16-yl)carbamate (1.41 g, 3.12 mmol, 1 eq) was dissolved in MeCN (32 mL, 0.1 M). Dimethyl 3-hydroxyphthalate (0.721 g, 3.43 mmol, 1.1 eq) and cesium carbonate (2.80 g, 8.58 mmol, 2.75 eq) were added. The flask was fitted with a reflux condenser and heated to 80° C. for 19 hours. The mixture was cooled to room temperature and diluted water and extracted once with chloroform and twice with EtOAc. The combined organic layers were dried over sodium sulfate, filtered and concentrated under reduced pressure. The crude material was purified by column chromatography (ISCO, 24 g silica column, 0-15% MeOH/DCM 22 minute gradient) to give a yellow oil (1.5892 g, 2.78 mmol, 89% over two steps). $^1$H NMR (400 MHz, Chloroform-d) δ 7.52 (d, J=7.8 Hz, 1H), 7.35 (t, J=8.1 Hz, 1H), 7.04 (d, J=8.3 Hz, 1H), 7.00 (t, J=5.3 Hz, 1H), 5.06 (s, 1H), 4.46 (s, 2H), 3.83 (s, 3H), 3.78 (s, 3H), 3.47 (ddd, J=14.9, 5.5, 2.8 Hz, 8H), 3.39 (dt, J=9.4, 6.0 Hz, 4H), 3.29 (q, J=6.5 Hz, 2H), 3.09 (d, J=6.0 Hz, 2H), 1.70 (p, J=6.5 Hz, 2H), 1.63 (p, J=6.3 Hz, 2H), 1.31 (s, 9H). $^{13}$C NMR (100 MHz, cdcl$_3$) δ 167.68, 167.36, 165.45, 155.93, 154.41, 130.87, 129.60, 125.01, 123.20, 117.06, 78.60, 70.40, 70.17, 70.06, 69.39, 68.67, 68.25, 52.77, 52.57, 38.38, 36.58, 29.55, 29.20, 28.34. LCMS 571.47 (M+H).

(3) Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate

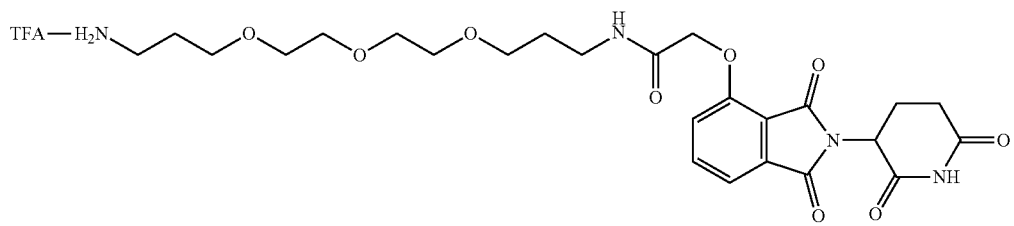

dimethyl 3-((2,2-dimethyl-4,20-dioxo-3,9,12,15-tetraoxa-5,19-diazahenicosan-21-yl)oxy)phthalate (1.589 g, 2.78 mmol, 1 eq) was dissolved in EtOH (14 mL, 0.2 M). Aqueous 3M NaOH (2.8 mL, 8.34 mmol, 3 eq) was added and the mixture was heated to 80° C. for 22 hours. The mixture was then cooled to room temperature, diluted with 50 mL DCM and 20 mL 0.5 M HCl. The layers were separated and the organic layer was washed with 25 mL water. The aqueous layers were combined and extracted three times with 50 mL chloroform. The combined organic layers were dried over sodium sulfate, filtered and condensed to give 1.53 g of material that was carried forward without further purification. LCMS 553.44.

The resultant material (1.53 g) and 3-aminopiperidine-2,6-dione hydrochloride (0.480 g, 2.92 mmol, 1 eq) were dissolved in pyridine (11.7 mL, 0.25 M) and heated to 110° C. for 17 hours. The mixture was cooled to room temperature and concentrated under reduced pressure to give crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate as a black sludge (3.1491 g) that was carried forward without further purification. LCMS 635.47.

The crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate (3.15 g) was dissolved in TFA (20 mL) and heated to 50° C. for 2.5 hours. The mixture was cooled to room temperature, diluted with MeOH and concentrated under reduced pressure. The material was purified by preparative HPLC to give N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate (1.2438 g, 1.9598 mmol, 71% over 3 steps) as a dark red oil. $^1$H NMR (400 MHz, Methanol-$d_4$) δ 7.77 (dd, J=8.3, 7.5 Hz, 1H), 7.49 (d, J=7.3 Hz, 1H), 7.40 (d, J=8.5 Hz, 1H), 5.12 (dd, J=12.8, 5.5 Hz, 1H), 4.75 (s, 2H), 3.68-3.51 (m, 12H), 3.40 (t, J=6.8 Hz, 2H), 3.10 (t, J=6.4 Hz, 2H), 2.94-2.68 (m, 3H), 2.16 (dtd, J=12.6, 5.4, 2.5 Hz, 1H), 1.92 (p, J=6.1 Hz, 2H), 1.86-1.77 (m, 2H). $^{13}$C NMR (100 MHz, cd$_3$od) δ 173.17, 169.97, 168.48, 166.87, 166.30, 154.82, 136.89, 133.41, 120.29, 117.67, 116.58, 69.96, 69.68, 69.60, 68.87, 68.12, 67.92, 49.19, 38.62, 36.14, 30.80, 28.92, 26.63, 22.22. LCMS 536.41 (M+H).

Synthetic Example 73: Synthesis of N-(6-aminohexyl)-2-(2,6-dioxopiperidin-3-yl)-1,3-dioxoisoindoline-5-carboxamide

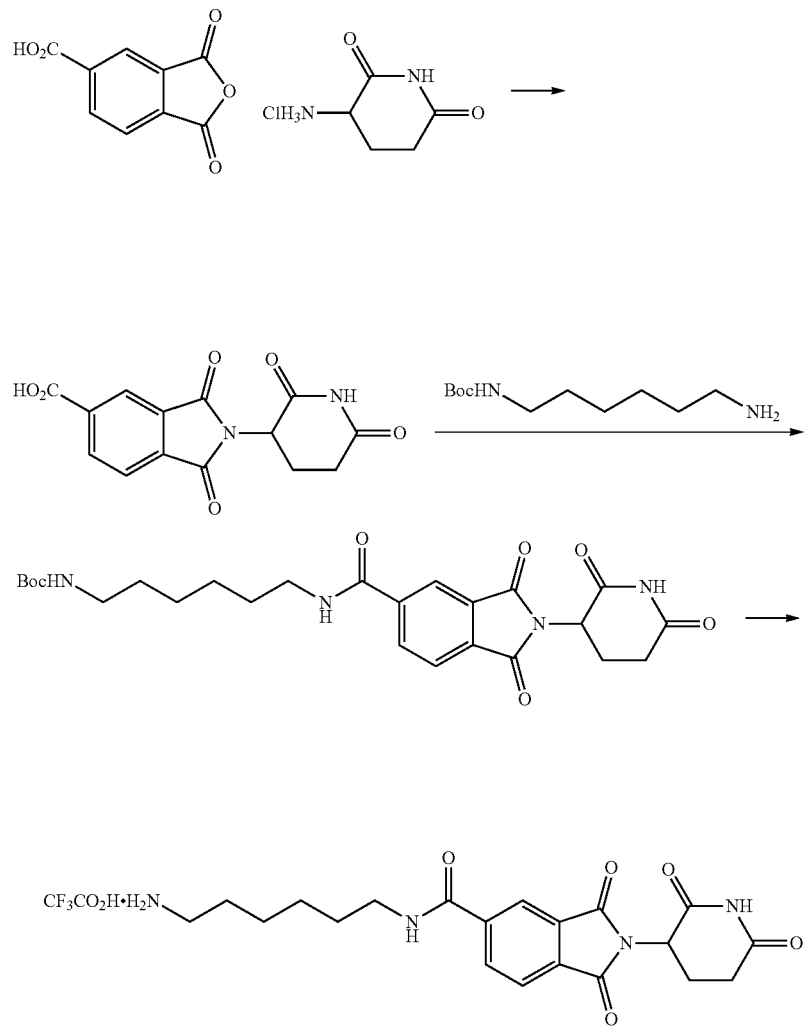

(1) Synthesis of 2-(2,6-dioxopiperidin-3-yl)-1,3-dioxoisoindoline-5-carboxylic Acid

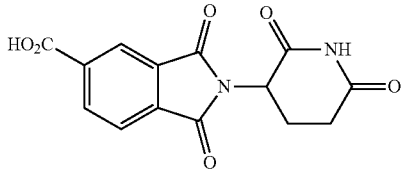 [SMILES: O=C1CCC(N2C(=O)c3ccc(C(=O)O)cc3C2=O)C(=O)N1]

1,3-dioxo-1,3-dihydroisobenzofuran-5-carboxylic acid (0.192 g, 1 mmol, 1 eq) and 3-aminopiperidine-2,6-dione hydrochloride (0.165 g, 1 mmol, 1 eq) were dissolved in DMF (2.5 mL) and acetic acid (5 mL) and heated to 80° C. for 24 hours. The mixture was then concentrated under reduced pressure and diluted with EtOH, from which a precipitate slowly formed. The precipitate was washed twice with EtOH to give a white solid (84.8 mg, 0.28 mmol, 28%). $^1$H NMR (400 MHz, DMSO-$d_6$) δ 13.74 (s, 1H), 11.12 (s, 1H), 8.39 (dd, J=7.8, 1.4 Hz, 1H), 8.26 (s, 1H), 8.04 (d, J=7.8 Hz, 1H), 5.18 (dd, J=12.8, 5.4 Hz, 1H), 2.93-2.88 (m, 1H), 2.84 (d, J=4.7 Hz, 0H), 2.66-2.50 (m, 2H), 2.12-1.99 (m, 1H). LCMS 303.19 (M+H).

(2) Synthesis of Tert-butyl (6-(2-(2,6-dioxopiperidin-3-yl)-1,3-dioxoisoindoline-5-carboxamido)hexyl)carbamate

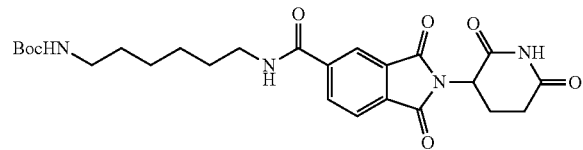 [SMILES: CC(C)(C)OC(=O)NCCCCCCNC(=O)c1ccc2c(c1)C(=O)N(C1CCC(=O)NC1=O)C2=O]

2-(2,6-dioxopiperidin-3-yl)-1,3-dioxoisoindoline-5-carboxylic acid (22.7 mg, 0.0751 mmol, 1 eq) and HATU (31.4 mg, 0.0826 mmol, 1.1 eq) were dissolved in DMF (0.75 mL). After 5 minutes, DIPA (39.2 microliters, 0.225 mmol, 3 eq) was added. After an additional 5 minutes, tert-butyl (6-aminohexyl)carbamate (19.5 mg, 0.0901 mmol, 1.2 eq) was added as a solution in DMF (0.75 mL). The mixture was stirred for 20 hours, then diluted with EtOAc. The organic layer was washed three times with brine, dried over sodium sulfate and concentrated under reduced pressure. Purification by column chromatography (ISCO, 4 g column, 0-10% MeOH/DCM, 25 minute gradient) to give a yellow oil (17.18 mg, 0.03432 mmol, 46%). $^1$H NMR (400 MHz, Chloroform-d) δ 8.29 (d, J=6.2 Hz, 2H), 8.16 (s, 1H), 7.94 (d, J=8.4 Hz, 1H), 6.91 (s, 1H), 5.00 (dd, J=12.4, 5.3 Hz, 1H), 4.58 (s, 1H), 3.47 (q, J=6.7 Hz, 2H), 3.14 (q, J=8.5, 7.3 Hz, 2H), 2.97-2.69 (m, 3H), 2.17 (ddd, J=10.4, 4.8, 2.6 Hz, 1H), 1.65 (p, J=6.9 Hz, 2H), 1.53-1.32 (m, 15H). $^{13}$C NMR (100 MHz, cdcl$_3$) δ 174.69, 170.77, 167.86, 166.67, 165.27, 156.49, 141.06, 133.95, 133.71, 132.13, 124.21, 122.27, 77.36, 49.71, 39.75, 31.54, 30.27, 29.22, 28.57, 25.70, 25.37, 22.73. LCMS 501.28 (M+H).

(3) Synthesis of N-(6-aminohexyl)-2-(2,6-dioxopiperidin-3-yl)-1,3-dioxoisoindoline-5-carboxamide

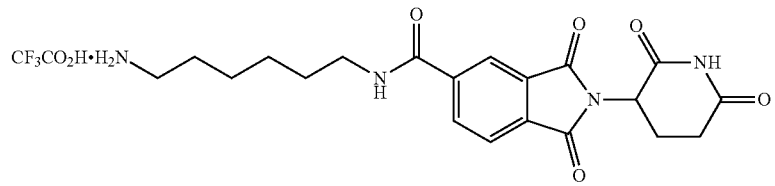

tert-butyl (6-(2-(2,6-dioxopiperidin-3-yl)-1,3-dioxoisoindoline-5-carboxamido)hexyl)carbamate (17.18 mg, 0.343 mmol, 1 eq) was dissolved in TFA (1 mL) and heated to 50° C. for 2 hours. The mixture was concentrated under reduced pressure to give a yellow oil (13.29 mg) which was deemed sufficiently pure without further purification. $^1$H NMR (400 MHz, Methanol-$d_4$) δ 8.27 (dd, J=9.3, 1.3 Hz, 2H), 7.99 (d, J=7.6 Hz, 1H), 5.18 (dd, J=12.5, 5.4 Hz, 1H), 3.48-3.40 (m, 2H), 2.96-2.84 (m, 3H), 2.76 (ddd, J=17.7, 8.1, 3.7 Hz, 2H), 2.20-2.12 (m, 1H), 1.75-1.63 (m, 4H), 1.53-1.43 (m, 4H). LCMS 401.31 (M+H).

Synthetic Example 74: Synthesis of 2-((2-(2,6-di-oxopiperidin-3-yl)-1,3-dioxoisoindolin-4-yl)oxy) acetic Acid

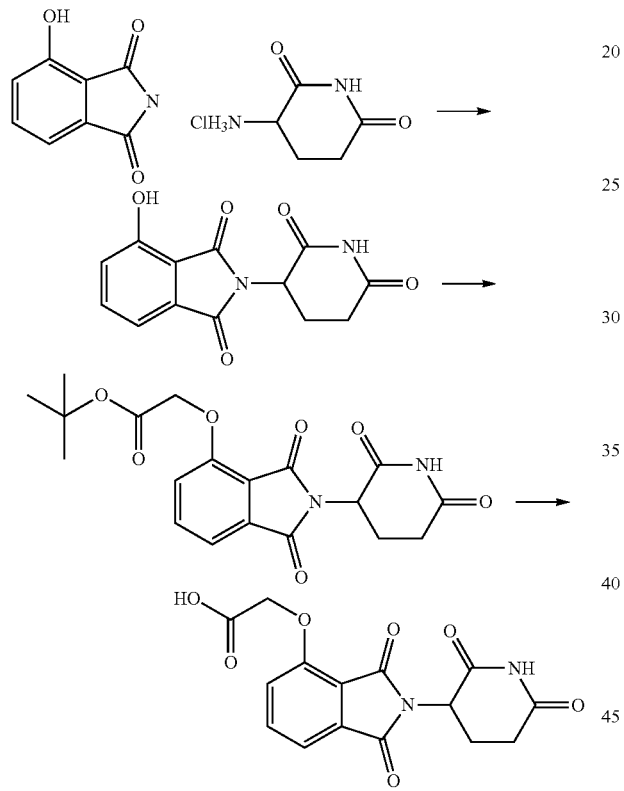

(1) Synthesis of 2-(2,6-dioxopiperidin-3-yl)-4-hydroxyisoindoline-1,3-dione

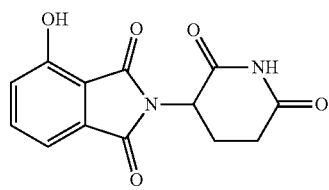 [SMILES: O=C1CCC(N2C(=O)c3cccc(O)c3C2=O)C(=O)N1]

4-hydroxyisobenzofuran-1,3-dione (0.773 g, 4.71 mmol, 1 eq) and 3-aminopiperidine-2,6-dione hydrochloride (0.775 g, 4.71 mmol, 1 eq) were dissolved in pyridine (19 mL) and heated to 110° C. for 16 hours. The mixture was concentrated under reduced pressure and purified by column chromatography (ISCO, 12 g silica column, 0-10% MeOH/DCM, 25 minute gradient) to give an off white solid (1.14 g, 4.16 mmol, 88%). $^1$H NMR (400 MHz, DMSO-$d_6$) δ 11.19 (s, 1H), 11.07 (s, 1H), 7.65 (dd, J=8.3, 7.3 Hz, 1H), 7.31 (d, J=7.2 Hz, 1H), 7.24 (d, J=8.4 Hz, 1H), 5.07 (dd, J=12.8, 5.4 Hz, 1H), 2.88 (ddd, J=17.7, 14.2, 5.4 Hz, 1H), 2.63-2.50 (m, 2H), 2.11-1.95 (m, 1H). LCMS 275.11 (M+H).

(2) Synthesis of Tert-butyl 2-((2-(2,6-dioxopiperidin-3-yl)-1,3-dioxoisoindolin-4-yl)oxy)acetate

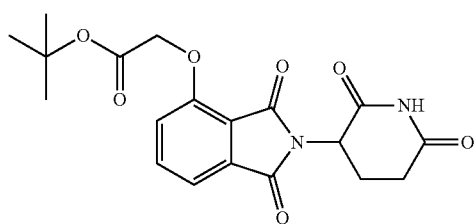 [SMILES: CC(C)(C)OC(=O)COc1cccc2c1C(=O)N(C1CCC(=O)NC1=O)C2=O]

2-(2,6-dioxopiperidin-3-yl)-4-hydroxyisoindoline-1,3-dione (218.8 mg, 0.798 mmol, 1 eq) was dissolved in DMF (8 mL). Potassium carbonate (165.9 mg, 1.20 mmol, 1.5 eq) was added, followed by tert-butyl bromoacetate (118 microliters, 0.798 mmol, 1 eq) and the mixture was stirred at room temperature for 3 hours. The mixture was diluted with EtOAc and washed once with water and twice with brine. Purification by column chromatography (ISCO, 12 g silica column, 0-100% EtOAc/hex, 17 minute gradient) gave a white solid (0.26 g, 0.669 mmol, 84%). $^1$H NMR (400 MHz, Chloroform-d) δ 8.74 (s, 1H), 7.61 (dd, J=8.4, 7.3 Hz, 1H), 7.46-7.41 (m, 1H), 7.06 (d, J=8.3 Hz, 1H), 4.98-4.92 (m, 1H), 4.74 (s, 2H), 2.83-2.69 (m, 3H), 2.12-2.04 (m, 1H), 1.43 (s, 9H). $^{13}$C NMR (100 MHz, cdcl$_3$) δ 171.58, 168.37, 166.96, 166.87, 165.49, 155.45, 136.27, 133.89, 119.78, 117.55, 116.83, 83.05, 66.52, 49.20, 31.37, 28.03, 22.55. LCMS 411.23 (M+Na).

(3) Synthesis of 2-((2-(2,6-dioxopiperidin-3-yl)-1,3-dioxoisoindolin-4-yl)oxy)acetic Acid

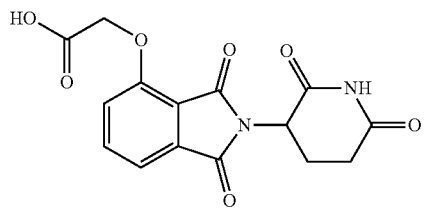 [SMILES: O=C(O)COc1cccc2c1C(=O)N(C1CCC(=O)NC1=O)C2=O]

tert-butyl 2-((2-(2,6-dioxopiperidin-3-yl)-1,3-dioxoisoindolin-4-yl)oxy)acetate (47.5 mg, 0.122 mmol, 1 eq) was dissolved in TFA (1.3 mL) at room temperature. After 3 hours, the mixture was diluted with DCM and concentrated under reduced pressure to yield a white solid (42.27 mg), which was deemed sufficiently pure without further purification. $^1$H NMR (400 MHz, Methanol-$d_4$) δ 7.76 (dd, J=8.5, 7.3 Hz, 1H), 7.50 (d, J=7.3 Hz, 1H), 7.34 (d, J=8.5 Hz, 1H), 5.11 (dd, J=12.5, 5.5 Hz, 1H), 4.96 (s, 2H), 2.87 (ddd, J=17.8, 14.2, 5.0 Hz, 1H), 2.80-2.65 (m, 2H), 2.18-2.09 (m, 1H). LCMS 333.15 (M+H).

Heterobifunctional Compound Pharmaceutical Compositions

In another aspect of the present application, pharmaceutical compositions are provided, which comprise any one of the heterobifunctional compounds described herein (or a prodrug, pharmaceutically acceptable salt or other pharmaceutically acceptable derivative thereof), and optionally comprise a pharmaceutically acceptable carrier. It will also be appreciated that certain of the heterobifunctional compounds of the present application can exist in free form for treatment, or where appropriate, as a pharmaceutically acceptable derivative thereof. According to the present application, a pharmaceutically acceptable derivative includes, but is not limited to, pharmaceutically acceptable salts, esters, salts of such esters, or a pro-drug or other adduct or derivative of a compound of this application which upon administration to a patient in need is capable of providing, directly or indirectly, a heterobifunctional compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J Pharmaceutical Sciences* 66 (1977):1-19, incorporated herein by reference. The salts can be prepared in situ during the final isolation and purification of the heterobifunctional compounds of the application, or separately by reacting a free base or free acid function with a suitable reagent, as described generally below. For example, a free base function can be reacted with a suitable acid. Furthermore, where the heterobifunctional compounds of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphor sulfonate, citrate, cyclopentane propionate, digluconate, dodecyl sulfate, ethane sulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methane sulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent heterobifunctional compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethyl succinates.

Furthermore, the term "pharmaceutically acceptable prodrugs" as used herein refers to those prodrugs of the heterobifunctional compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, (1987), both of which are incorporated herein by reference.

As described above, the pharmaceutical heterobifunctional compound compositions of the present application additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., (1980)) discloses various carriers used in formulating pharmaceutical compositions and known techniques for the preparation thereof. Except insofar as any conventional carrier medium is incompatible with the compounds of the application, such as by producing any undesirable biological effect or otherwise interacting in a deleterious manner with any other component(s) of the pharmaceutical composition, its use is contemplated to be within the scope of this application. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner.

Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active heterobifunctional compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active heterobifunctional compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present application encompasses pharmaceutically acceptable topical formulations of inventive compounds. The term "pharmaceutically acceptable topical formulation", as used herein, means any formulation which is pharmaceutically acceptable for intradermal administration of a compound of the application by application of the formulation to the epidermis. In certain embodiments of the application, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, *Remington's Pharmaceutical Sciences,* 16th Edition, (1980) and 17th Edition, (1985), both published by Mack Publishing Company, Easton, Pa., the disclosures of which are incorporated herein by reference in their entireties. In certain other embodiments, the topical formulations of the application may comprise excipients. Any pharmaceutically acceptable excipient known in the art may be used to prepare the inventive pharmaceutically acceptable topical formulations. Examples of excipients that can be included in the topical formulations of the application include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the application include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the application include, but are not limited to, vitamin E oil, allantoin, dimethicone, glycerin, petrolatum, and zinc oxide.

In certain embodiments, the pharmaceutically acceptable topical formulations of the application comprise at least a compound of the application and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Maibach H. I. and Smith H. E. (eds.), *Percutaneous Penetration Enhancers*, CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems,* Gosh T. K., Pfister W. R., Yum S. I. (eds.), Interpharm Press Inc., Buffalo Grove, Ill. (1997). In certain exemplary embodiments, penetration agents for use with the application include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the application are creams, which may further contain saturated or unsaturated fatty acids such as stearic acid, palmitic acid, oleic acid, palmito-oleic acid, cetyl or oleyl alcohols, and stearic acid being particularly preferred. Creams of the application may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this application. Additionally, the present application contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that certain of the heterobifunctional compounds of present application can exist in free form for treatment, or where appropriate, as a pharmaceutically acceptable derivative thereof. According to the present application, a pharmaceutically acceptable derivative includes, but is not limited to, pharmaceutically acceptable salts, esters, salts of such esters, or a prodrug or other adduct or derivative of a compound of this application which upon administration to a patient in need is capable of providing, directly or indirectly, a compound as otherwise described herein, or a metabolite or residue thereof.

Methods of Modulating CAR Expressing Cell Activity

In general, methods of using the heterobifunctional compounds for modulating the activity of a CAR expressing cell as described in the present application comprise administering to a subject in need thereof a therapeutically effective amount of a heterobifunctional compound of the present application, wherein the heterobifunctional compound is administered in an amount sufficient to induce degradation of the CAR.

In certain embodiments, heterobifunctional compounds are useful to modulate or downregulate the activation of the CAR expressing cell, for example a CAR T-cell, for example by degrading the intracellular signaling pathway of the CAR and thus reducing, for example, the release of cytokines by the CAR T-cell due to its activated state. In certain embodiments, according to the methods of treatment of the present application, levels of the CAR in the CAR expressing cell are modulated by contacting CAR expressing cells with a heterobifunctional compound, as described herein.

Thus, in another aspect of the application, methods for the modulating of the activity of a CAR expressing cell, for example a CAR T-cell, are provided comprising administering a therapeutically effective amount of a heterobifunctional compound to a subject in need thereof. In certain embodiments, a method for the modulation of a CAR expressing cell, for example a CAR T-cell, is provided comprising administering a therapeutically effective amount of heterobifunctional compound, or a pharmaceutical composition comprising heterobifunctional compound to a subject in need thereof, in such amounts and for such time as is necessary to achieve the desired result. Preferably, the heterobifunctional compound is administered orally or intravenously. In certain embodiments of the present application a "therapeutically effective amount" of the heterobifunctional compound is that amount effective for reducing the activity of a CAR expressing cell so that an adverse inflammatory or immune response is modulated or reduced. The heterobifunctional compound s, according to the method of the present application, may be administered using any amount and any route of administration effective for modulating the activity of a CAR expressing cell. The exact amount required will vary from subject to subject, depending on the species, age, and general condition of the subject, the activity of the CAR expressing cell, the particular CAR expressing cell, and the like. In certain embodiments of the present application a "therapeutically effective amount" of the heterobifunctional compound is that amount effective for reducing the levels of CARs in a CAR expressing cell.

The heterobifunctional compounds of the application are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the heterobifunctional compounds and compositions of the present application will be decided by the attending physician within the scope of sound medical judgment. The specific therapeutically effective dose level for any particular patient or organism will depend upon a variety of factors including the disorder being treated and the severity of the adverse CAR expressing cell inflammatory response; the activity of the specific heterobifunctional compound employed; the specific composition employed; the age, body weight, general health, sex and diet of the patient; the time of administration, route of administration, and rate of excretion of the specific heterobifunctional compound employed; the duration of the treatment; drugs used in combination or coincidental with the specific heterobifunctional compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, (2001):155-173, which is incorporated herein by reference in its entirety).

Furthermore, after formulation with an appropriate pharmaceutically acceptable carrier in a desired dosage, the pharmaceutical compositions of this application can be administered to humans and other animals orally, rectally, parenterally, intracisternally, intravaginally, intraperitoneally, topically (as by powders, ointments, creams or drops), buccally, as an oral or nasal spray, or the like, depending on the severity of the infection being treated. In certain embodiments, the heterobifunctional compound may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, heterobifunctional compounds are administered orally or parenterally.

Heterobifunctional compounds (e.g., the bifunctional compounds), once produced, can be characterized using a variety of assays known to those skilled in the art to determine whether the compounds have the desired biological activity. For example, the molecules can be characterized by conventional assays, including but not limited to those assays described below (e.g., treating cells of interest, such as MV4-11 cells, human cell line MM1S, or a human cell line MM1S that is deficient in cereblon, with a test compound and then performing immunoblotting against the indicated proteins such as BRD2, BRD3, and BRD4, or treating certain cells of interest with a test compound and then measuring BRD4 transcript levels via qRT-PCR), to determine whether they have a predicted activity, binding activity and/or binding specificity.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the application.

EXAMPLES

Examples are provided of exemplary chimeric antigen receptor (CARs) molecules having an intracellular dTAG capable of being bound by or binding to a heterobifunctional compound, which, when exposed to the heterobifunctional compound is degraded by the ubiquitin proteasomal pathway (UPP). The examples are exemplary only and are not intended to be limited, instead serving as illustrations of CAR structures incorporating a dTAG capable of being bound by a heterobifunctional compound and subsequently degraded.

Example 1: CD19-CAR-dTAG

Figure 4:
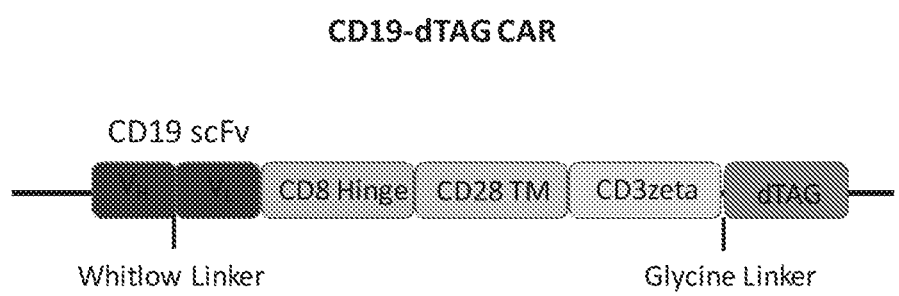
FIG. 4 is a schematic of an exemplary chimeric antigen receptor (CAR) having a scFv extracellular domain targeting the tumor antigen CD19, a CD8 Hinge transmembrane domain, a CD 28 transmembrane and signaling domain, a CD3-zeta co-stimulatory domain, and a dTAG capable of being targeted by a heterobifunctional compound. Amino acid sequences for each domain are listed in Example 1.

FIG. 4 is a schematic of an exemplary CAR targeting the tumor antigen CD19. As illustrated, the CAR has an extracellular targeting ligand domain comprising a scFv to CD19. For example, the CD19 scFv has the amino acid sequence (SEQ. ID. NO.: 10):

MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGSTSGSGKPGSGEGSTKGEVK

LQESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYGG

SYAMDYWGQGTSVTVSS, where the GMCSF signal peptide is composed of amino acid sequence (SEQ. ID. NO.: 11):

MLLLVTSLLLCELPHPAFLLIP.

The scFv to CD19 has a variable light chain (VL) composed of amino acid sequence (SEQ. ID. NO.: 12):

DIQMTQTTSSLSASLGDRVTISCRASQDISKYLNWYQQKPDGTVKLLIYH
TSRLHSGVPSRFSGSGSGTDYSLTISNLEQEDIATYFCQQGNTLPYTFGG
GTKLEIT.

The scFv variable light chain (VL) and variable heavy chain (VH) are connected by a Whitlow linker having the amino acid sequence (SEQ. ID. 13):

GSTSGSGKPGSGEGSTKG.

The scFv to CD19 has a variable heavy chain (VH) composed of the amino acid sequence (SEQ. ID. NO.: 14):

EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSS.

The scFv to CD19 is fused in frame with a modified CD8 alpha chain hinge region having the amino acid sequence (SEQ. ID. NO.: 15):

ALSNSIYFSHFVPVFLPAKPTTTPAPRPPTPAPTIASQPLSLRPEACRPA
AGGAVHTRGLD.

The effector domain is comprised of a transmembrane domain cloned in frame with 1 or more cytoplasmic signaling domains.

As exemplified herein, the Transmembrane domain (TM) can be a fragment of the co-stimulatory CD28 protein which includes the CD28 TM and cytoplasmic domain. The fragment is composed of the following amino acid sequence (SEQ. ID. NO.: 16):

KPFWVLVWGGVLACYSLLVTVAFIIFWVRSKRSRLLHSDYMNMTPRRPGP
TRKHYQPYAPPRDFAAYRS.

The CD28 cytoplasmic domain is cloned in frame with the intracellular CD3-ζ domain. CD3-ζ domain is comprised of the following amino acid sequence (SEQ. ID. NO.: 17):

RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.

The functional CAR sequence is then linked by a triple glycine linker (GGG) and cloned in frame with a dTAG composed of the following amino acid sequence (SEQ. ID. NO.: 18):

GVQVETISPGDGRTFPKRGQTCVVHYTGMLEDGKKVDSSRDRNKPFKFVL
GKQEVIRGWEEGVAQMSVGQRAKLTISPDYAYGATGHPGIIPPNATLIFD
VELLKLE.

The dTAG amino acid sequence is a derivative of FKBP12 with the F36V mutation.

As expressed, the complete amino acid sequence of the exemplary CD19-CAR-dTAG is (SEQ. ID. NO.: 19):

MLLLVTSLLLCELPHPAFLLIPDIQMTQTTSSLSASLGDRVTISCRASQD
ISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVK
LQESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYGG
SYAMDYWGQGTSVTVSSALSNSIYFSHFVPVFLPAKPTTTPAPRPPTPAP
TIASQPLSLRPEACRPAAGGAVHTRGLDKPFWVLVWGGVLACYSLLVTVA
FIIFWVRSKRSRLLHSDYMNMTPRRPGPTRKHYQPYAPPRDFAAYRSVK
FSRSADAPAYQQGQNQLYNELNLGRREEYDVLDKRRGRDPEMGGKPRRKN
PQEGLYNELQKDKMAEAYSEIGMKGERRRGKGHDGLYQGLSTATKDTYDA
LHMQALPPRGGGGVQVETISPGDGRTFPKRGQTCVVHYTGMLEDGKKVDS
SRDRNKPFKFVLGKQEVIRGWEEGVAQMSVGQRAKLTISPDYAYGATGHP
GIIPPNATLIFDVELLKLE.

Figure 5:
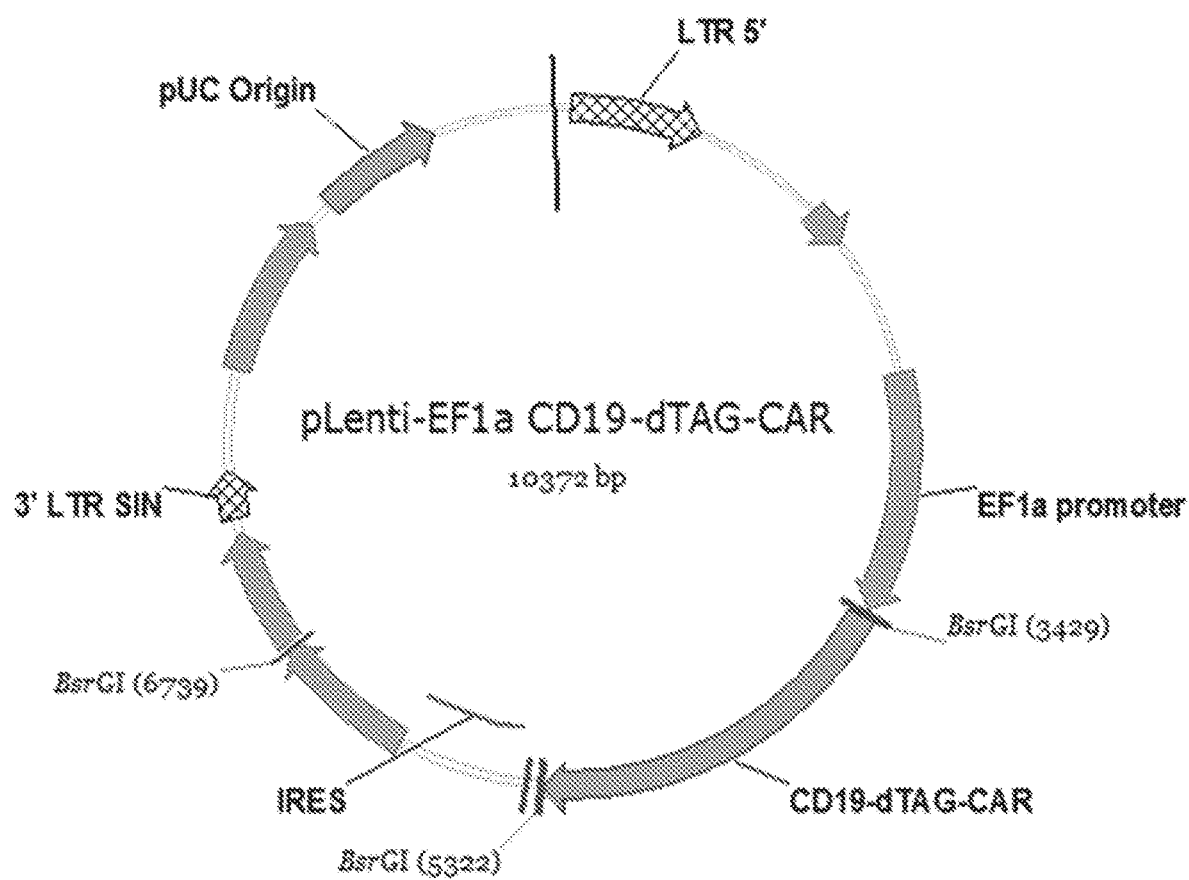
FIG. 5 is a plasmid map of the plasmid encoding CD19-CAR-dTAG. As described in Example 1, The Cd19-CAR-dTAG can be introduced to the autologous T-cell population via plasmid transfection, viral transduction, or non-viral electroporation using transposable elements.

As described in more detail above, the synthetic DNA construct expressing the CAR amino acid sequence as described is introduced into an T-cell population from a subject having a disorder, for example a cancer (in this instance ALL, for example). Autologous T-cells are isolated from the subject's blood via apheresis and the propagated ex-vivo using any of the methods described above or known in the art. The synthetic CAR plasmid DNA, for example the plasmid encoding Cd19-CAR-dTAG illustrated in FIG. 5, is then introduced to the autologous T-cell population via a mechanism including, but not limited to, plasmid transfection, viral transduction, or non-viral electroporation using transposable elements. The resultant CAR T-cells are expanded ex-vivo and then introduced to donor patients via transfusion.

Upon receiving the CAR T-cell, subjects are monitored for development of CRS and other associated toxicities. Subjects suffering from CRS or other CAR T-cell associated toxicities are administered an effective amount of a heterobifunctional compound, for example dFKBP* which targets the dTAG of the exemplary CD19-CAR-dTAG of SEQ. ID. NO.: 19. CAR degradation and T-cell load can be confirmed by FLOW cytometry.

Upon reversal of CRS and/or other associated toxicities, administration of dFKBP* can be withdrawn and CAR re-expression on T-cells monitored by FLOW Cytometry.

Example 2: ErbB2-CAR-dTAG

As an alternative example, the CAR has an extracellular targeting ligand domain comprising an scFv to Erb-B2. The Erb-B2 scFv is cloned in frame with the C8 alpha chain linker, the CD28 TM and cytoplasmic domain, the CD3-ζ cytoplasmic domain and the dTAG sequence to form a functional ErbB2-CAR-dTAG. For example, the ERB2 scFv has a variable light chain (VL) composed of the amino acid sequence (SEQ. ID. NO.: 20):

DILLTQSPVILSVSPGERVSFSCRASQSIGTNIHWYQQRTNGSPRLLIKY
ASESISGIPSRFSGSGSGTDFTLSINSVESEDIADYYCQQNNNWPTTFGA

```
GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGE,
``` where the GMCSF signal peptide is composed of amino acid sequence (SEQ. ID. NO.: 11):

```
                MLLLVTSLLLCELPHPAFLLIP.
```

The scFv to ERB2 has a variable heavy chain (VH) composed of amino acid sequence (SEQ. ID. NO.: 21):

```
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIT.
```

The scFv variable light chain (VL) and variable heavy chain (VH) are connected by a Whitlow linker having the amino acid sequence (SEQ. ID. NO.: 13):

```
                GSTSGSGKPGSGEGSTKG.
```

The scFv to Erb-B2 has a variable heavy chain (VH) composed of the amino acid sequence (SEQ. ID. NO.: 22):

```
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKS.
```

The scFv to Erb-B2 is fused in frame with a modified CD8 alpha chain hinge region having the amino acid sequence (SEQ. ID. NO.: 15):

```
ALSNSIYFSHFVPVFLPAKPTTTPAPRPPTPAPTIASQPLSLRPEACRPA

AGGAVHTRGLD.
```

The effector domain is comprised of a transmembrane domain cloned in frame with 1 or more cytoplasmic signaling domains.

As exemplified herein, the Transmembrane domain (TM) can be a fragment of the co-stimulatory CD28 protein which includes the CD28 TM and cytoplasmic domain. The fragment is composed of the following amino acid sequence (SEQ. ID. NO.: 16):

```
KPFWVLVWGGVLACYSLLVTVAFIIFWVRSKRSRLLHSDYMNMTPRRPGP

TRKHYQPYAPPRDFAAYRS.
```

The CD28 cytoplasmic domain is cloned in frame with the intracellular CD3-ζ domain. CD3-ζ domain is comprised of the following amino acid sequence (SEQ. ID. NO.: 17):

```
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.
```

The functional CAR sequence is then linked by a triple glycine linker (GGG) and cloned in frame with a dTAG composed of the following amino acid sequence (SEQ. ID. NO.: 18):

```
GVQVETISPGDGRTFPKRGQTCVVHYTGMLEDGKKVDSSRDRNKPFKFVL

GKQEVIRGWEEGVAQMSVGQRAKLTISPDYAYGATGHPGIIPPNATLIFD

VELLKLE.
```

The dTAG amino acid sequence is a derivative of FKBP12 with the F36V mutation.

As expressed, the complete amino acid sequence of the exemplary ERB2-CAR-dTAG is (SEQ. ID. NO.: 23):

```
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEGSTSGSGKPGSGEGSTKGDIQMTQTTSSLSASLGDRV

TISCRASQDISKYLNWYQQKPDGTVKLLIYHTSRLHSGVPSRFSGSGSGT

DYSLTISNLEQEDIATYFCQQGNTLPYTFGGGTKLEITALSNSIYFSHFV

PVFLPAKPTTTPAPRPPTPAPTIASQPLSLRPEACRPAAGGAVHTRGLDK

PFWVLVWGGVLACYSLLVTVAFIIFWVRSKRSRLLHSDYMNMTPRRPGPT

RKHYQPYAPPRDFAAYRSRVKFSRSADAPAYQQGQNQLYNELNLGRREEY

DVLDKRRGRDPEMGGKPRRKNPQEGLYNELQKDKMAEAYSEIGMKGERRR

GKGHDGLYQGLSTATKDTYDALHMQALPPRGGGGVQVETISPGDGRTFPK

RGQTCVVHYTGMLEDGKKVDSSRDRNKPFKFVLGKQEVIRGWEEGVAQMS

VGQRAKLTISPDYAYGATGHPGIIPPNATLIFDVELLKLE.
```

As described in more detail above, the synthetic DNA construct expressing the CAR amino acid sequence as described is introduced into an T-cell population from a subject having a disorder, for example a cancer (in this instance a solid breast cancer, for example). Autologous T-cells are isolated from the subject's blood via apheresis and the propagated ex-vivo using any of the methods described above. The synthetic CAR plasmid DNA is then introduced to the autologous T-cell population via a mechanism including, but not limited to, plasmid transfection, viral transduction, non-viral electroporation using transposable elements. The resultant CAR T-cells are expanded ex-vivo and then introduced to donor patients via transfusion.

Upon receiving the CAR T-cell, subjects are monitored for development of CRS and other associated toxicities. Subjects suffering from CRS or other CAR T-cell associated toxicities are administered an effective amount of a heterobifunctional compound, for example dFKBP* which targets the dTAG of the exemplary ERB2-CAR-dTAG of SEQ. ID. NO.: 22. CAR degradation and T-cell load can be confirmed by FLOW cytometry.

Upon reversal of CRS and/or other associated toxicities, administration of dFKBP* can be withdrawn and CAR re-expression on T-cells monitored by FLOW Cytometry.

In any of the below examples using dFKBP13 or dFKBP7 either dFKBP13-o and dFKBP 13-p or dFKBP7-o and dFKBP7-p can be used.

Example 3

Figure 6:
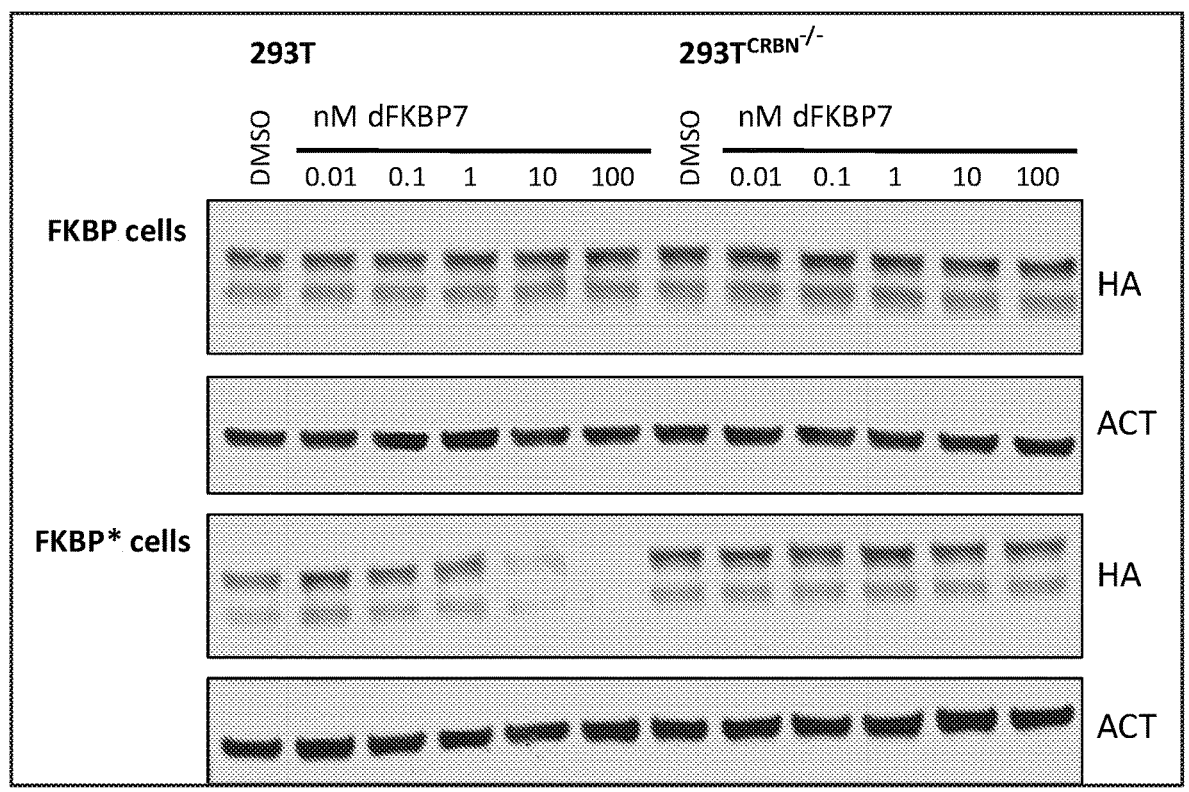
FIG. 6 is an immunoblot of cells treated with bi-functional molecules described in the present invention. As described in Example 3, 293FT cells (CRBN-WT or CRBN-/-) expressing either HA-tagged FKBP12WT or FKBP* (also referred to as dFKBP12* herein) were treated with indicated concentrations of dFKBP7 for 4 hours. CRBN-dependent degradation of FKBP* and not FKBPWT confirms selective activity of dFKBP7 for mutant FKBP*.

FIG. 6 illustrates an example to confirm selective degradation of FKBP*-fused proteins with dFKBP7.

The dTAG is predicated on the selectivity of FKBP* specific ligands over endogenous, wild type FKBP. In 293T cells expressing wild type FKBP12 or FKBP*, dFKBP7 induces targeted degradation only in FKBP* expressing cells. An immunoblot of cells treated with bi-functional molecules described in the present invention was performed. 293FT cells (CRBN-WT or CRBN-/-) expressing either HA-tagged FKBP12WT or FKBP* were treated with indicated concentrations of dFKBP7 for 4 hours. CRBN-dependent degradation of FKBP* and not FKBPWT confirms selective activity of dFKBP7 for mutant FKBP*.

Example 4

Figure 7A:
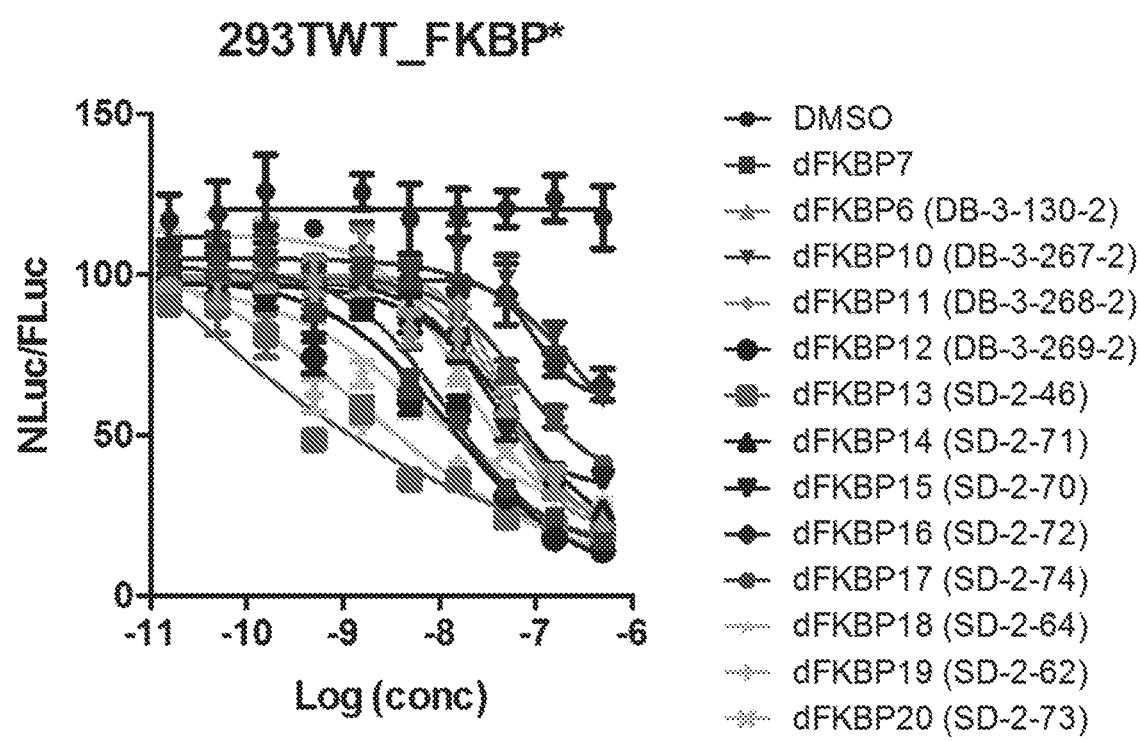
FIG. 7A and FIG. 7B are graphs measuring the activity of a panel of dFKBP heterobifunctional compounds in cells expressing FKBP* fused to Nluc. Degradation of FKBP* is measured as a signal ratio (Nluc/Fluc) between NANOluc and firefly luciferase from the same multicistronic transcript in wild type (FIG. 7A) or CRBN -/- (FIG. 7B) 293FT cells treated with indicated concentrations of dFKBPs for 4 hours. A decrease in the signal ratio indicates FKBP* (Nluc) degradation. Additional experimental details are provided in Example 4.
Figure 7B:
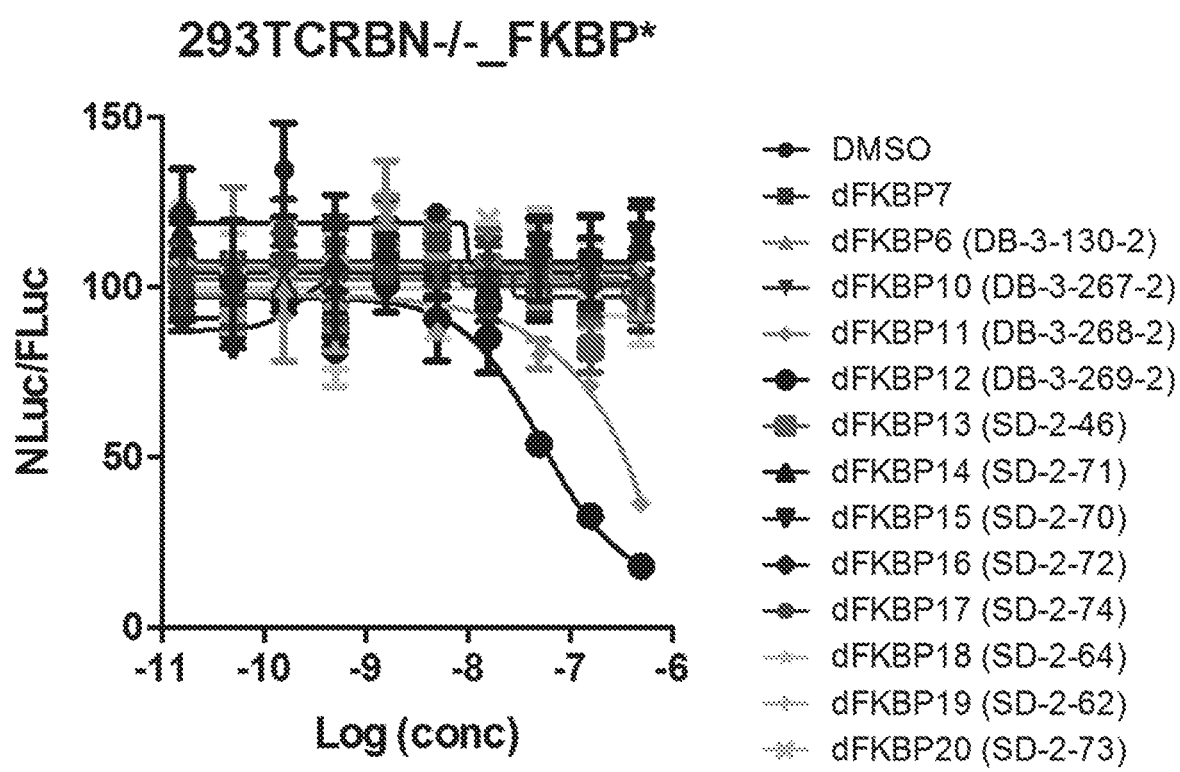

FIGS. 7A-B illustrate an example of profiling of a panel of dFKBP heterobifunctional compounds to measure differential degradation activity.

In an effort to identify potent and selective dFKPB heterobifunctional compounds, high throughput measurements of targeted FKBP* degradation were measured by surrogate levels of luciferase. Here, FKBP* is exogenously expressed as a multicistronic transcript with two types of luciferase: nano luciferase (NLuc) and firefly luciferase (FLuc) that allow for cell normalized quantification of FKBP* protein levels. Degradation of FKBP* is measured as a signal ratio (Nluc/Fluc) in wild type (FIG. 7A) or CRBN -/- (FIG. 7B) 293FT cells treated with indicated concentrations of dFKBPs for 4 hours. A decrease in the signal ratio indicates FKBP* (Nluc) degradation and molecules that effectively degrade FKBP* in a cereblon dependent manner are observed (ex. dFKBP7).

Example 5

Figure 8:
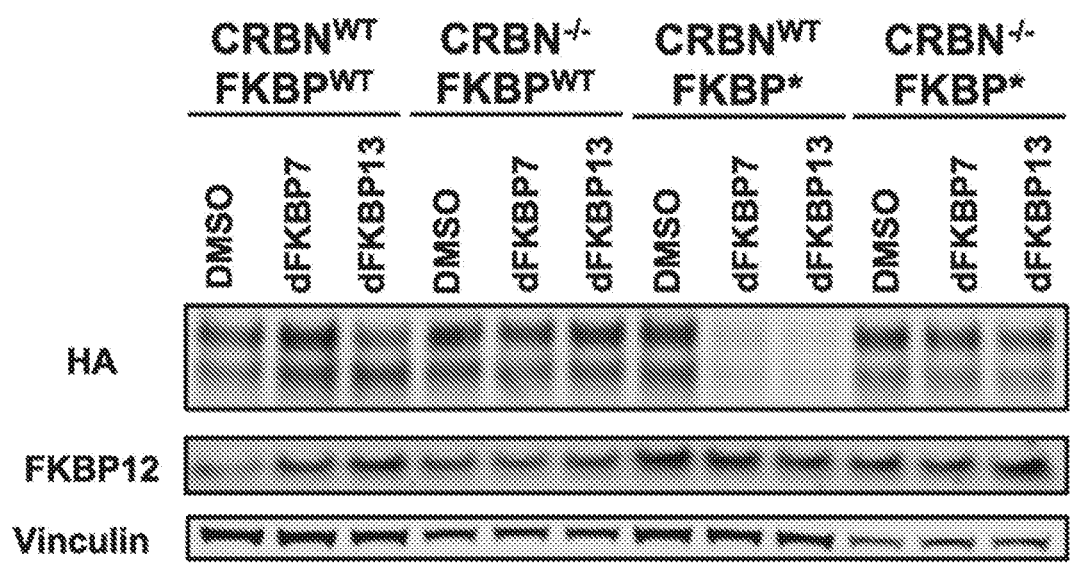
FIG. 8 is an immunoblot of cells treated with heterobifunctional compounds described in the present invention. Isogenic 293FT cells (CRBN-WT or CRBN-/-) expressing either FKBP12WT or FKBP* were treated with 100 nM of either dFKBP7 or dFKBP13 for 4 hours (Example 5). CRBN-dependent degradation of FKBP* and not FKBP12WT or endogenous FKBP12 confirms selectivity of dFKBP7 and dFKBP13 for mutant FKBP*.

FIG. 8 illustrates an example of selective degradation of FKBP*-fused proteins with heterobifunctional compounds dFKBP7 and dFKBP13.

In 293T cells expressing wild type FKBP12 or FKBP*, treatment with dFKBP7 and dFKBP13 induces targeted degradation only in FKBP* expressing cells. Isogenic 293FT cells (CRBN-WT or CRBN-/-) were engineered to express either FKBP12WT or FKBP*. Cells were treated with 100 nM of either dFKBP7 or dFKBP13 for 4 hours before lysates were prepared for western immunoblot analysis. CRBN-dependent degradation of FKBP* and not FKBP12WT or endogenous FKBP12 confirms selectivity of dFKBP7 and dFKBP13 for mutant FKBP*.

Example 6

Figure 9:
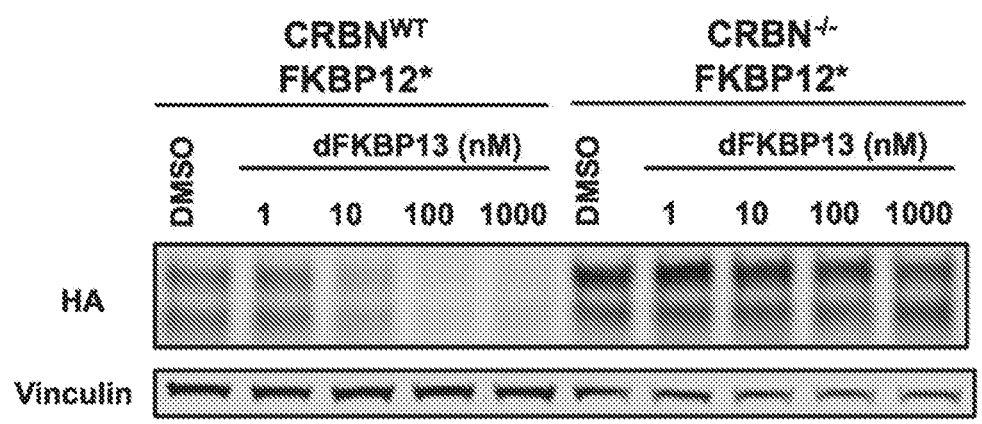
FIG. 9 is an immunoblot of cells treated with heterobifunctional compounds described in the present invention. Isogenic 293FT cells (CRBN-WT or CRBN-/-) expressing HA-tagged FKBP* were treated with the indicated dose of dFKBP13 for 4 hours (Example 6). These data confirm dose- and CRBN-dependent degradation of HA-tagged FKBP* by dFKBP13.

FIG. 9 illustrates an example of dose-dependent degradation of HA-tagged FKBP* with a heterobifunctional compound dFKBP13.

In an effort to define the optimal concentration of dFKB13 heterobifunctional compounds to induce degradation of FKBP*, degradation was measured upon treatment with increasing concentrations of dFKBP13. Isogenic 293FT cells (CRBN-WT or CRBN-/-) were engineered to expressed HA-tagged FKBP*. Cells were treated with the indicated dose of dFKBP13 for 4 hours before lysates were prepared for western immunoblot analysis. These data confirm dose- and CRBN-dependent degradation of HA-tagged FKBP* by dFKBP13.

Example 7

Figure 10:
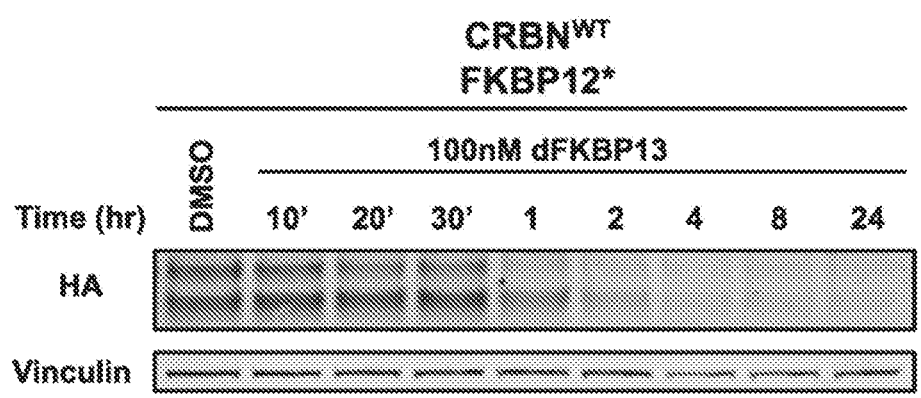
FIG. 10 is an immunoblot of cells treated with heterobifunctional compounds described in the present invention. 293FT cells (CRBN-WT) expressing HA-tagged FKBP* were treated with 100 nM dFKBP13 for the indicated times (Example 7). Cells were harvested and protein lysates immunoblotted to measure the kinetics of HA-tagged FKBP* degradation induced by dFKBP13.

FIG. 10 illustrates the kinetic control of dFKBP13-dependent degradation of HA-tagged FKBP*.

To evaluate the kinetic control of targeted degradation FKBP*, dFKBP13 was administered by increased duration. 293FT cells (CRBN-WT) were engineered to express HA-tagged FKBP*. Cells were treated with 100 nM dFKBP13 for the indicated times. Cells were harvested and protein lysates immunoblotted to measure the kinetics of HA-tagged FKBP* degradation induced by dFKBP13.

Example 8

Figure 11:
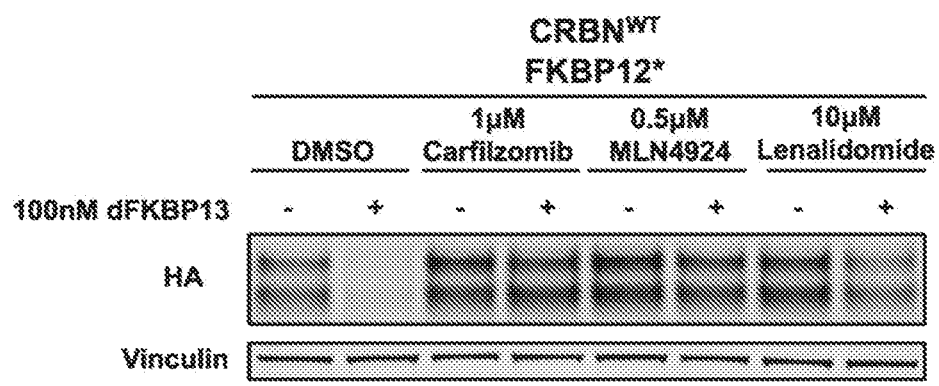
FIG. 11 is an immunoblot of cells treated with heterobifunctional compounds described in the present invention. 293FT cells (CRBN-WT) expressing FKBP* were pre-treated with 1 uM Carfilzomib (proteasome inhibitor), 0.5 uM MLN4924 (neddylation inhibitor), and 10 uM Lenalidomide (CRBN binding ligand) for two hours prior to a 4 hour treatment with dFKBP13 (Example 8). Degradation of HA-tagged FKBP* by dFKBP13 was rescued by the proteasome inhibitor Carfilzomib, establishing a requirement for proteasome function. Pre-treatment with the NAE1 inhibitor MLN4924 rescued HA-tagged FKBP* establishing dependence on CRL activity, as expected for cullin-based ubiquitin ligases that require neddylation for processive E3 ligase activity. Pre-treatment with excess Lenalidomide abolished dFKBP13-dependent FKBP* degradation, confirming the requirement of CRBN engagement for degradation.

FIG. 11 illustrates an example to confirm CRBN- and proteasome-dependent degradation of FKBP* by the heterobifunctional compound dFKBP13.

293FT cells (CRBN-WT) were engineered to express FKBP*. Cells were pretreated with 1 uM Carfilzomib (proteasome inhibitor), 0.5 uM MLN4924 (neddylation inhibitor), and 10 uM Lenalidomide (CRBN binding ligand) for two hours prior to a 4-hour treatment with dFKBP13. Lysates were prepared and western immunoblot analysis performed. Degradation of HA-tagged FKBP* by dFKBP13 was rescued by the proteasome inhibitor Carfilzomib, establishing a requirement for proteasome function. Pre-treatment with the NAE1 inhibitor MLN4924 rescued HA-tagged FKBP* establishing dependence on CRL activity, as expected for cullin-based ubiquitin ligases that require neddylation for processive E3 ligase activity. Pre-treatment with excess Lenalidomide abolished dFKBP13-dependent FKBP* degradation, confirming the requirement of CRBN engagement for degradation.

Example 9

Figure 12:
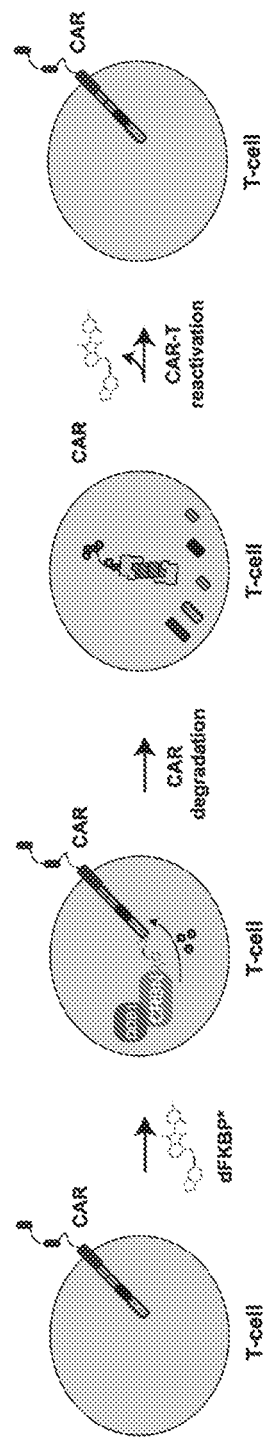
FIG. 12 is a schematic that illustrates the rheostat mechanism of CAR-dTAG. As described in Example 9, the rheostat mechanism allows for targeted degradation of CAR via a proteasome.

FIG. 12 is a schematic that illustrates the rheostat mechanism of CAR-dTAG.

The CAR-dTAG fusion protein is expressed on the membrane of T-cells to form a functional CART-dTAG. The addition of the heterobifunctional compound described in the present invention (dFKBP) leads to efficient and targeted E3 ligase mediated degradation of the CAR via the proteasome. The removal of the dFKBP heterobifunctional compound results in the reactivation of CAR expression. This figure illustrates the principle behind the rheostat mechanism described in the present invention to chemically control CAR levels while leaving the T-cell unaffected.

Example 10

Figure 13:
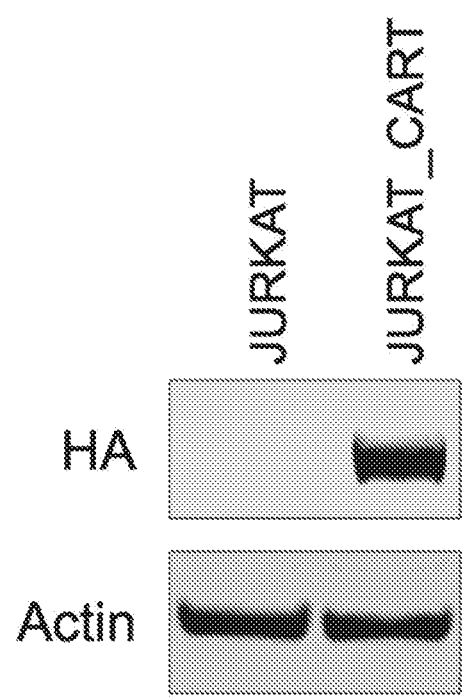
FIG. 13 is an immunoblot of cells treated with heterobifunctional compounds described in the present invention. As described in Example 10, Jurkat T-cells were transduced with lentivirus expressing CD19-CAR-dTAG. Cells were selected with blasticidin and expanded. Stable expression of CD19-CAR-dTAG was confirmed.

FIG. 13 illustrates an experiment performed to confirm ectopic expression of a CD19-CAR-dTAG (SEQ. ID. NO.: 19) in a human Jurkat T-cells.

Jurkat T-cells were transduced with lentivirus expressing CD19-CAR-dTAG. Cells were selected with blasticidin and expanded. Stable expression of CD19-CAR-dTAG in Jurkat cells was confirmed by anti-HA western immunoblotting of whole cell lysates.

Example 11

Figure 14A:
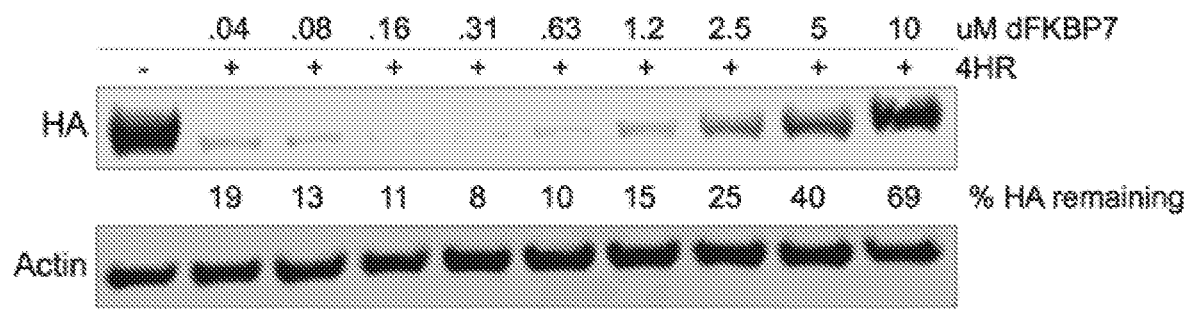
FIG. 14A and FIG. 14B are immunoblots of cells treated with heterobifunctional compounds described in the present invention. Jurkat T-cells expressing CD19-CAR-dTAG were treated with the indicated dose of dFKBP7 or dFKBP13 for 4 hours. These data, further described in Example 11, confirm dose-dependent degradation of CD19-CAR-dTAG in Jurkat T-cells.
Figure 14B:
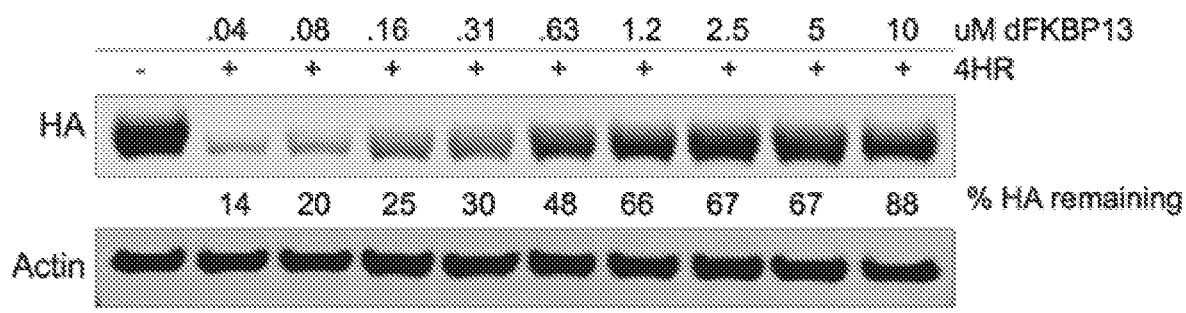

FIGS. 14A-B illustrate an example of dose-dependent degradation of CD19-CAR-dTAG in Jurkat T-cells with heterobifunctional compounds (dFKBP7 and dFKBP13).

In an effort to define the optimal concentration of bifunctional molecules to induce degradation of CD19-CAR-dTAG, degradation was measured upon treatment with increasing concentrations of dFKBP7 and dFKBP13. Jurkat T-cells were engineered to express CD19-CAR-dTAG. Cells were treated with the indicated dose of dFKBP7 or dFKBP13 for 4 hours before lysates were prepared for western immunoblot analysis. These data confirm dose-dependent degradation of CD19-CAR-dTAG in Jurkat T-cells.

Example 12

Figure 15A:
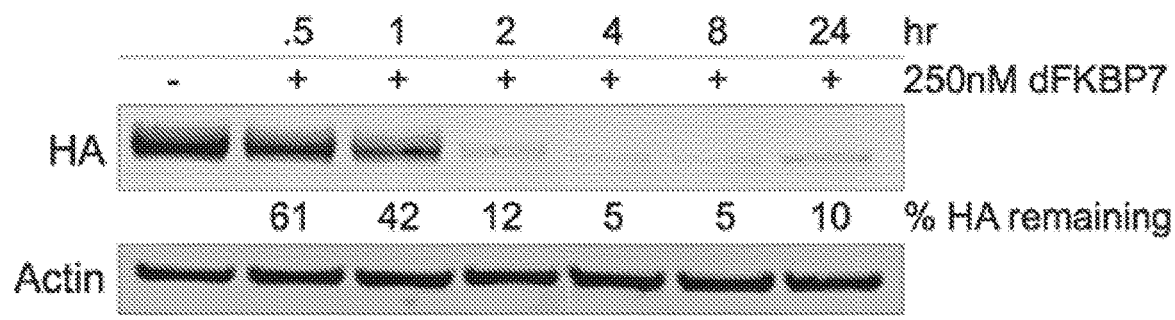
FIG. 15A and FIG. 15B are immunoblots of cells treated with bi-functional molecules described in the present invention. Jurkat T-cells expressing CD19-CAR-dTAG were treated with 250 nM of dFKBP7 or dFKBP13 for the indicated time. These data, further described in Example 12, confirm time-dependent degradation of CD19-CAR-dTAG in Jurkat T-cells.
Figure 15B:
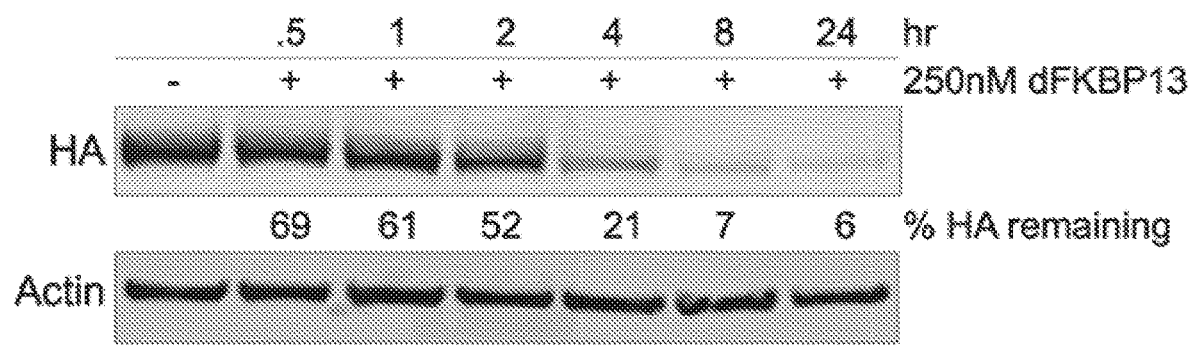

FIGS. 15A-B illustrate the kinetic control of CD19-CAR-dTAG degradation by heterobifunctional compounds dFKBP7 and dFKBP13 in Jurkat T-cells.

To evaluate the kinetic control of targeted degradation of CD19-CAR-dTAG, a fixed concentration of bi-functional molecules dFKBP7 and dFKBP13 were administered at a fixed concentration for increased duration. Jurkat T-cells were engineered to express CD19-CAR-dTAG. Cells were treated with 250 nM dFKBP7 or dFKBP13 for the indicated time before lysates were prepared for immunoblot analysis. These data confirm time-dependent degradation of CD19-CAR-dTAG in Jurkat T-cells.

Example 13

Figure 16:
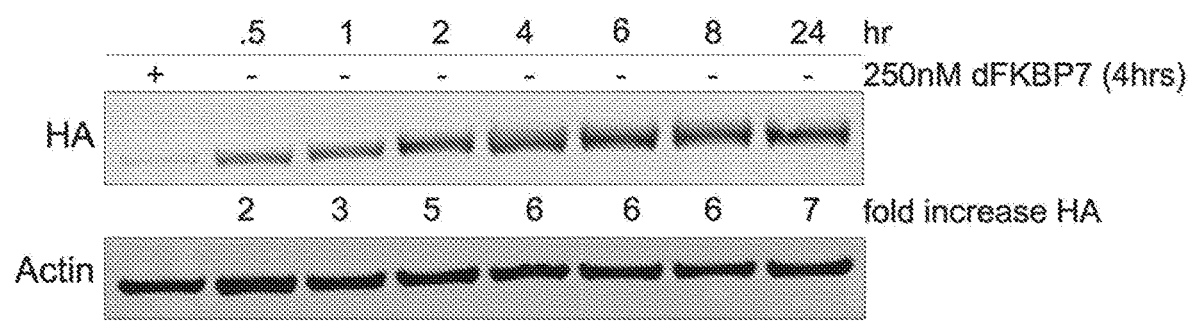
FIG. 16 is an immunoblot of cells treated with heterobifunctional compounds described in the present invention. Jurkat T-cells expressing CD19-CAR-dTAG were treated with 250 nM of dFKBP7 for 4 hours. The dFKBP7 was then removed from the Jurkat cells via washouts and the re-expression of CD19-CAR-dTAG was monitored by immunoblot analysis at the indicated time points. These data, further described in Example 13, suggest that CD19-CAR-dTAG protein levels recovered following removal of dFKBP7.

FIG. 16 illustrates the kinetics of CD19-CAR-dTAG re-expression following treatment with dFKBP7.

Immunoblot illustrating the kinetics of re-expression of the CD19-CAR-dTAG protein following targeting degradation with dFKBP7. Jurkat T-cells engineered to express CD19-CAR-dTAG were treated with 250 nM of dFKBP7 for 4 hours. The dFKBP7 was then removed from the Jurkat cells via washouts and the re-expression of CD19-CAR-dTAG was monitored by immunoblot analysis at the indicated time points. Data suggest that CD19-CAR-dTAG protein levels recovered following removal of dFKBP7.

Example 14

Figure 17A:
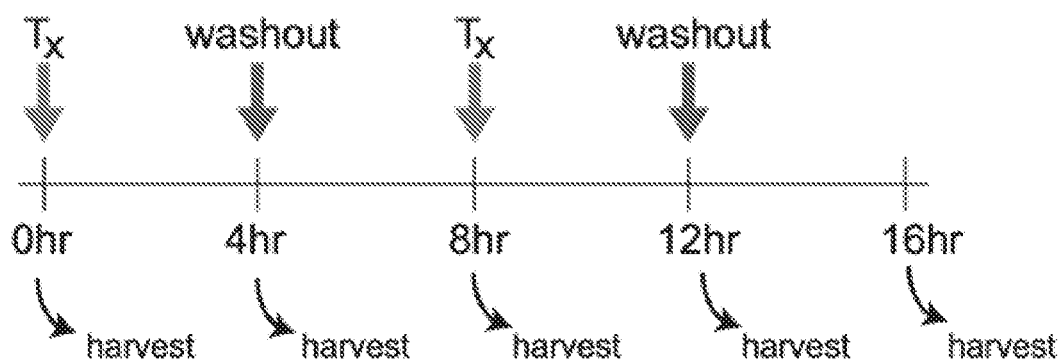
FIG. 17A and FIG. 17B illustrate the rheostat chemical control of CD19-CAR-dTAG expression in T cells treated with heterobifunctional compounds described in the present invention.
Figure 17B:
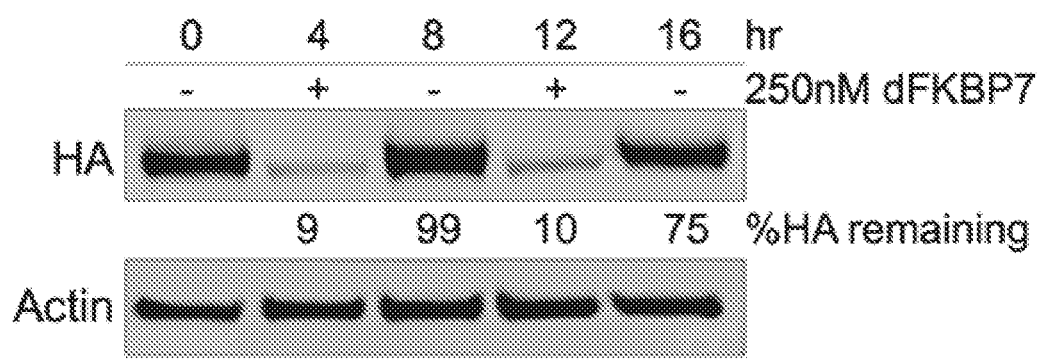

FIGS. 17A-B illustrate the rheostat chemical control of CD19-CAR-dTAG expression in T-cells.

FIG. 17A illustrates the experimental design to measure the ability to control the expression CD19-CAR-dTAG in T-cells upon addition and removal of dFKBP7. Jurkat cells engineered to express CD19-CAR-dTAG were treated with 250 nM of dFKBP7 at the indicated time points (0 and 8 hours). At 4 and 12 hours, the dFKBP7 was washed out of the Jurkat cells. At each indicated timepoint, Jurkat cells were harvest to monitor CD19-CAR-dTAG expression levels via immunoblot analysis.

FIG. 17B is an immunoblot illustrating the ability to toggle on and off expression of CD19-CAR-dTAG as described in FIG. 17A. The Heterbifunctional Compound dFKBP7 molecule allows for exquisite chemical control of CD19-CAR-dTAG protein levels allowing for modulation within hours. These data support the rheostat mechanism described in the current invention.

Example 15

Figure 18A:
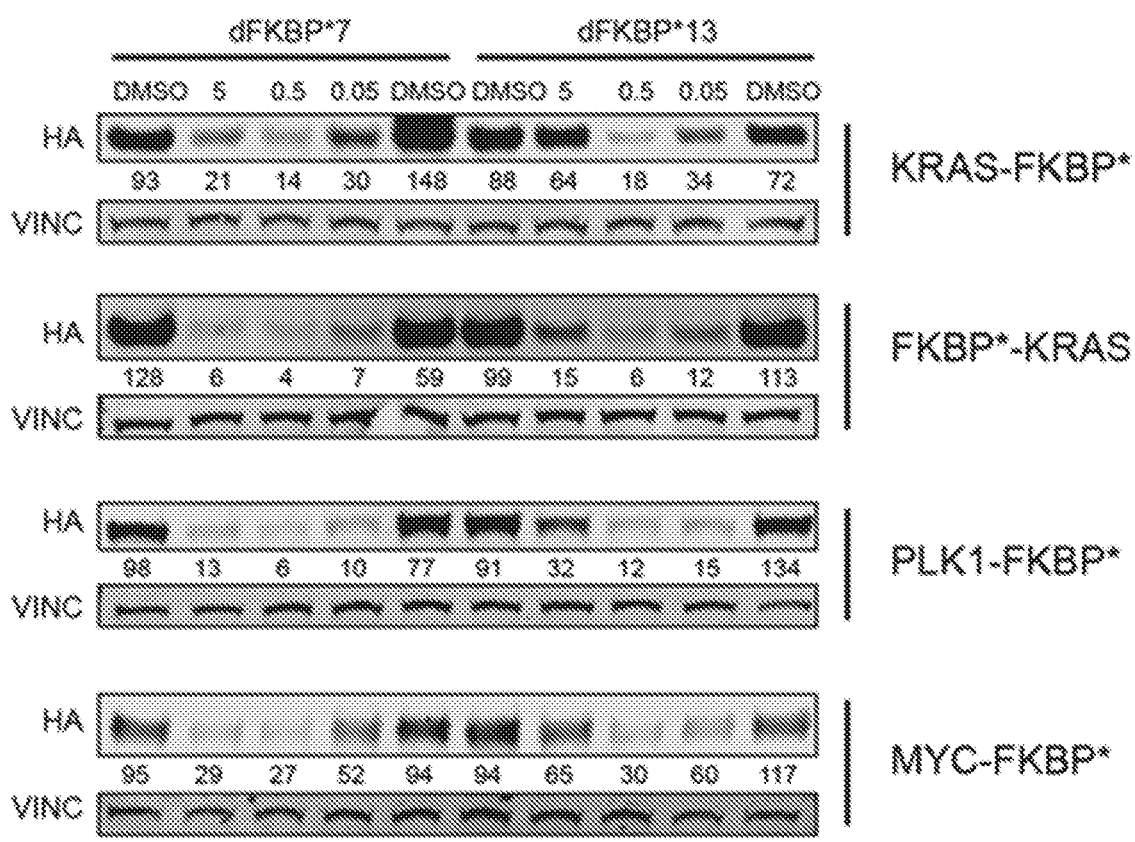
FIG. 18A and FIG. 18B are immunoblots of cells treated with heterobifunctional compounds described in the present invention. Immunoblots of MV4;11 leukemia cells expressing indicated proteins fused to mutant FKBP* with an HA tag. Cells were treated for 16 hours with indicated concentrations of FKBP* selective heterobifunctional compounds, dFKBP7 or dFKBP13 and abundance of fusion proteins measured by western immunoblot analysis. Additional experimental details are given in Example 15.
Figure 18B:
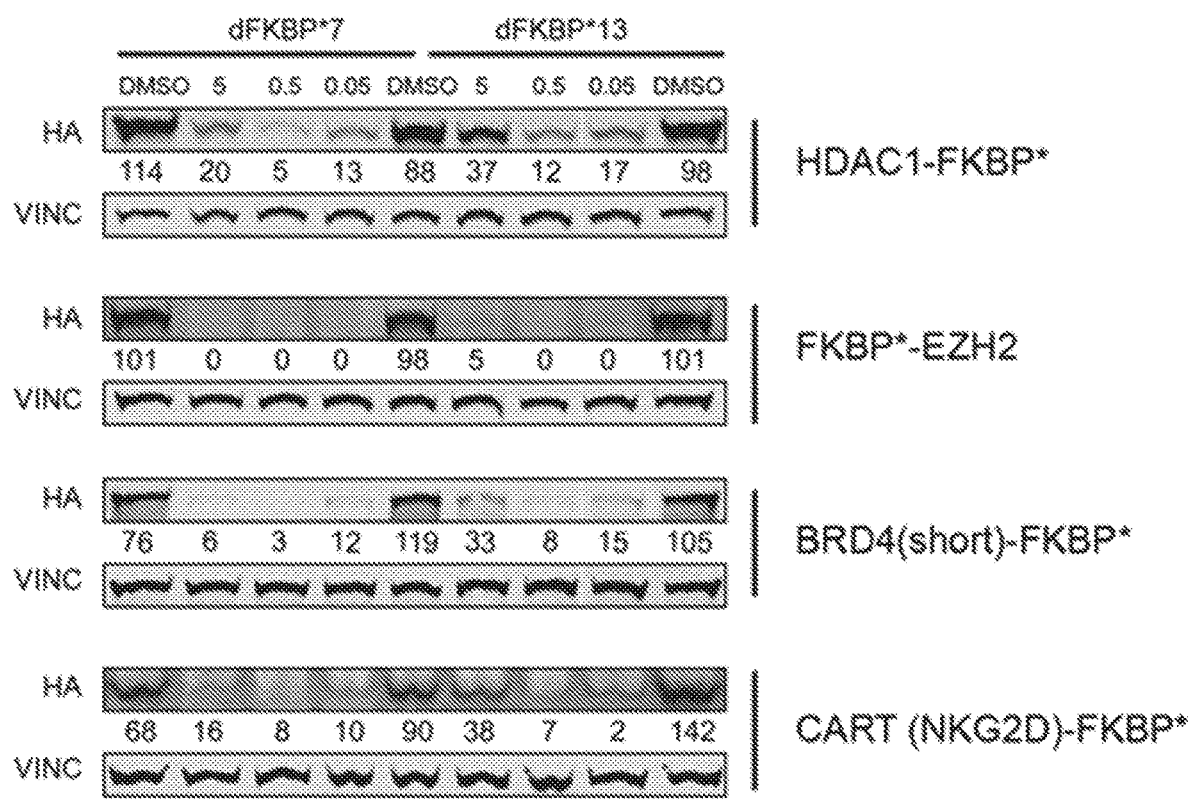

FIGS. 18A-B confirms targeted degradation of proteins of interest when fused to dTAG.

To test the general utility of the dTAG technology across several protein types, the indicated proteins fused to the dTAG in MV4; 11 leukemia cells were expressed. Upon treatment with the indicated dFKBP bifunctional molecules (dFKBP7 and dFKBP13), targeted protein degradation was observed as measured by western blot. Cells were treated for 16 hours with indicated concentrations of FKBP* selective heterobifunctional compounds and degradation was observed with nanomolar concentrations.

Example 16

Figure 19:
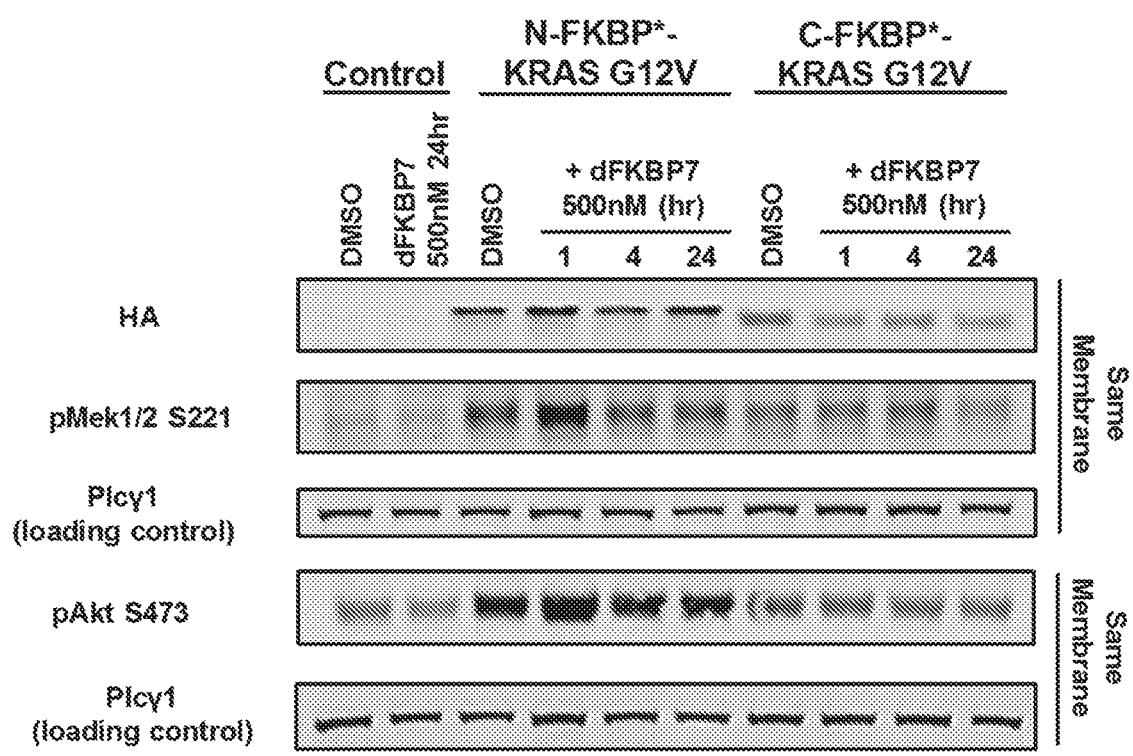
FIG. 19 is an immunoblot of NIH3T3 cells expressing KRASG12V allele fused to FKBP* in the N-terminus or C-terminus. Cells were treated with 500 nM dFKBP7 for the indicated time. Cells were harvested and immunoblotted to measure degradation of FKBP*-KRASG12V and downstream surrogates of KRAS signaling (e.g. pMEK and pAKT). The data, further described in Example 16, suggest N-terminal FKBP* fusions are active and degraded upon administration of dFKBP7.

FIG. 19 illustrates an example confirming degradation of N-terminal dTAG-KRAS.

In N-terminal dTAG-KRAS, dFKBP7 treatment resulted in potent degradation as well as a downstream decrease in p-AKT signal suggesting the biological relevance of overexpressed dTAG fusion proteins. Cells were treated with 500 nM dFKBP7 for the indicated time. Cells were harvested and immunoblotted to measure degradation of FKBP*-KRAS and downstream surrogates of KRAS signaling (e.g. pMEK and pAKT). Overexpression of dTAG KRAS resulted in the activation of the relevant downstream signaling pathways as an observed increase in p-AKT signal as measured by western blot.

Example 17

Figure 20:
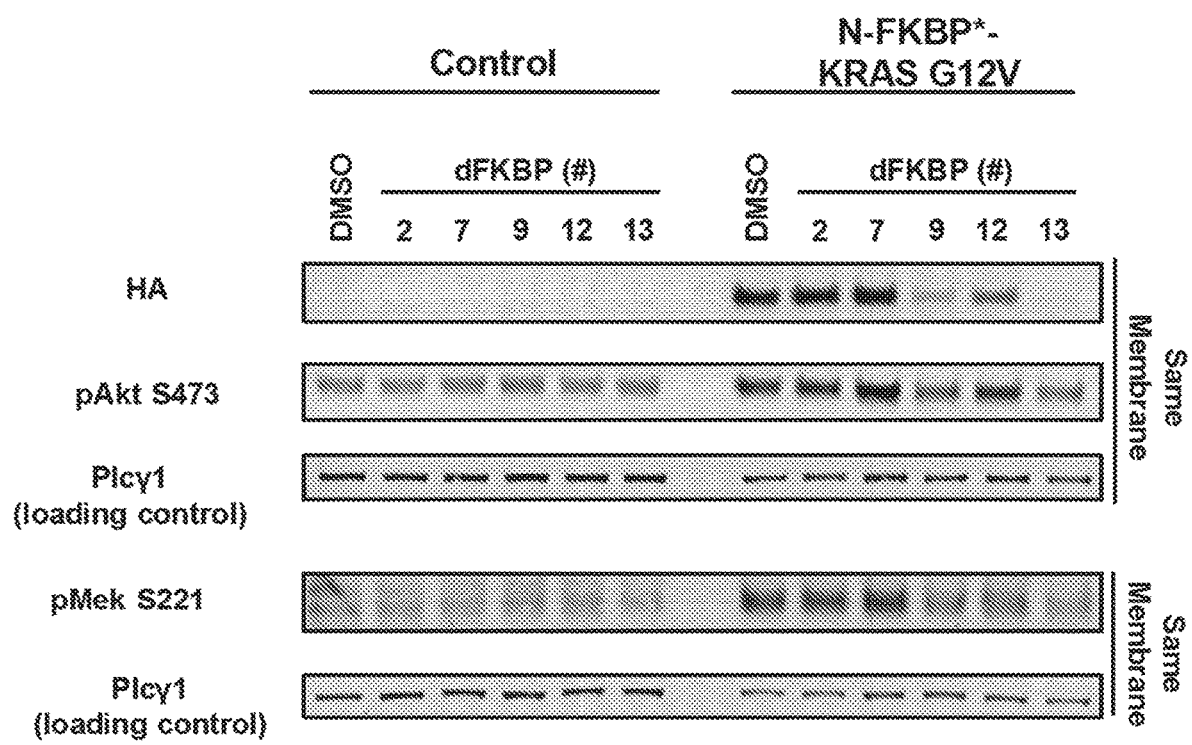
FIG. 20 is an immunoblot of NIH3T3 cells expressing FKBP* fused to the N-terminus of KRASG12V treated with 1 uM of the indicated dFKBP heterobifunctional compounds for 24 hours. Cells were harvested and immunoblotted to measure degradation of FKBP*-KRASG12V and downstream surrogates of KRAS signaling (e.g. pMEK and pAKT). The data, further described in Example 17, suggest that dFKBP9, dFKBP12, and dFKBP13 induce potent degradation of FKBP*-KRASG12V and inhibition of downstream signaling.

FIG. 20 illustrates the profiling of dFKBP heterobifunctional compounds to induce degradation of dTAG-KRAS.

In an effort to identify the best performing dFKBP molecule, dTAG-KRAS degradation was profiled across a series of dFKBP molecules. Western blotting of NIH3T3 cells expressing dTAG-KRASG12V were treated with 1 µM of the indicated dFKBP heterobifunctional compounds for 24 hours. Cells were harvested and immunoblotted to measure degradation of FKBP*-KRAS and downstream surrogates of KRAS signaling (e.g. pMEK and pAKT). The data suggest that dFKBP9, dFKBP12, and dFKBP13 induce potent degradation of FKBP*-KRAS and inhibition of downstream signaling.

Example 18

Figure 21:
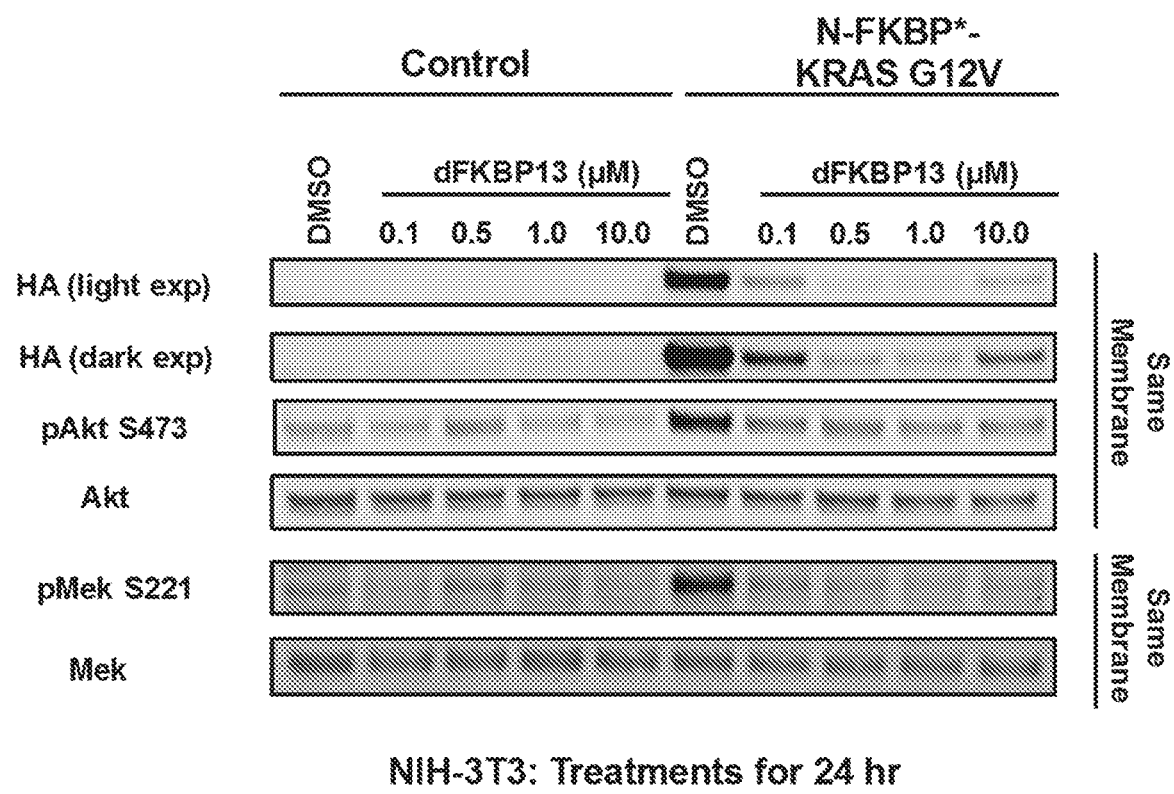
FIG. 21 is an immunoblot of NIH3T3 cells expressing FKBP* fused to the N-terminus of KRASG12V treated with the indicated concentrations of dFKBP13 for 24 hours. Cells were harvested and immunoblotted to measure degradation of FKBP*-KRASG12V and downstream surrogates of KRAS signaling (e.g. pMEK and pAKT). The data, further described in Example 18, suggest that dFKBP13 induces potent degradation of FKBP*-KRASG12V and inhibits downstream signaling potently with an IC50>100 nM.

FIG. 21 illustrates an example confirming targeted degradation of dTAG-KRAS with dFKBP13.

The dFKBP13 bifunctional molecule potently degrades dTAG-KRAS at nanomolar concentrations. Western blotting of NIH3T3 cells expressing FKBP* fused to the N-terminus of KRAS treated with the indicated concentrations of dFKBP13 for 24 hours. Cells were harvested and immunoblotted to measure degradation of FKBP*-KRAS and downstream surrogates of KRAS signaling (e.g. pMEK and pAKT). The data suggest that dFKBP13 induces potent degradation of FKBP*-KRAS and inhibits downstream signaling potently with an IC50>100 nM.

Example 19

Figure 22:
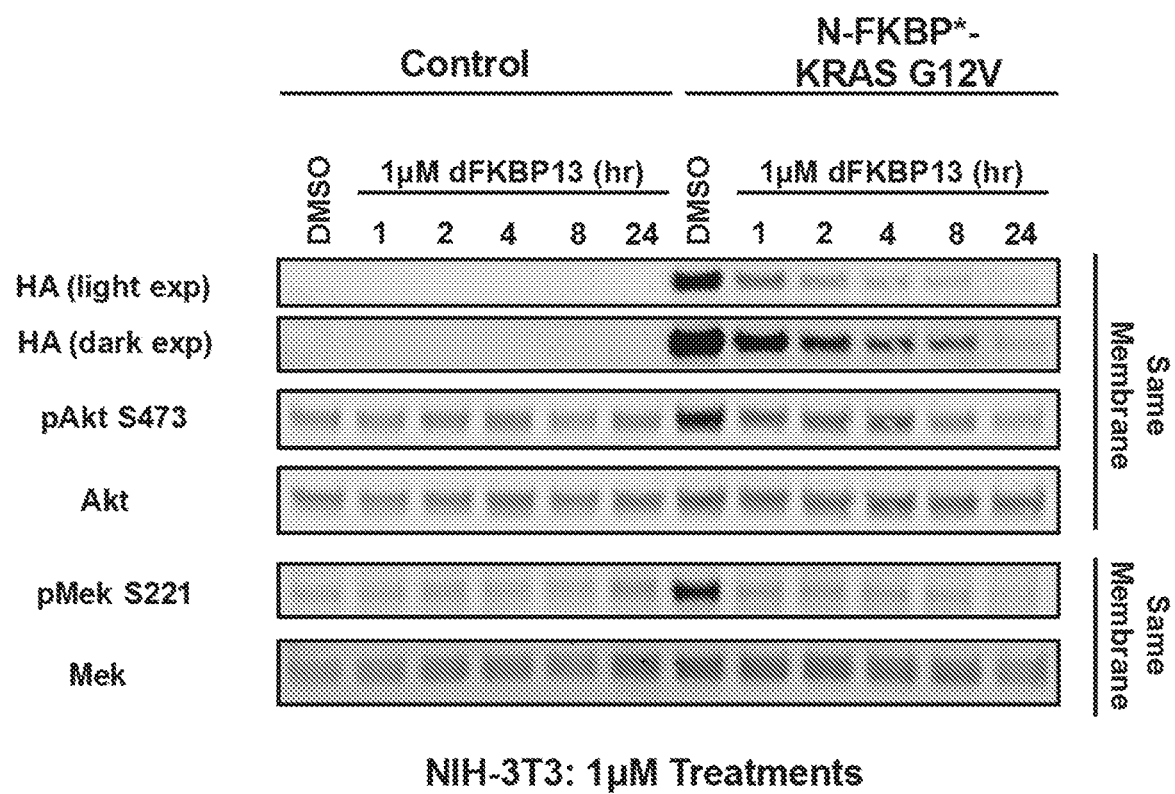
FIG. 22 is an immunoblot of NIH3T3 cells expressing FKBP* fused to the N-terminus of KRASG12V treated with 1 uM dFKBP13 for the indicated time. Cells were harvested and immunoblotted to measure degradation of FKBP*-KRASG12V and downstream surrogates of KRAS signaling (e.g. pMEK and pAKT). As described in Example 19, these data suggest that dFKBP13 induces potent degradation of FKBP*-KRASG12V and inhibition of downstream signaling as early as 1 hour post treatment.
Figure 23A:
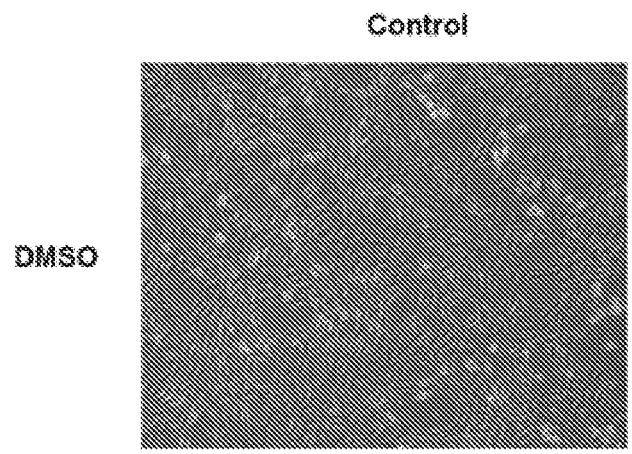
FIG. 23A, FIG. 23B, FIG. 23C, and FIG. 23D are panels of phase contrast images of control NIH3T3 cells or NIH3T3 expressing FKBP* fused to the N-terminus of KRASG12V treated with DMSO or dFKBP13 for 24 hours. Phase contrast images highlight the morphological change induced upon dFKBP13-dependent degradation of FKBP*-KRASG12V (Example 20).
Figure 23B:
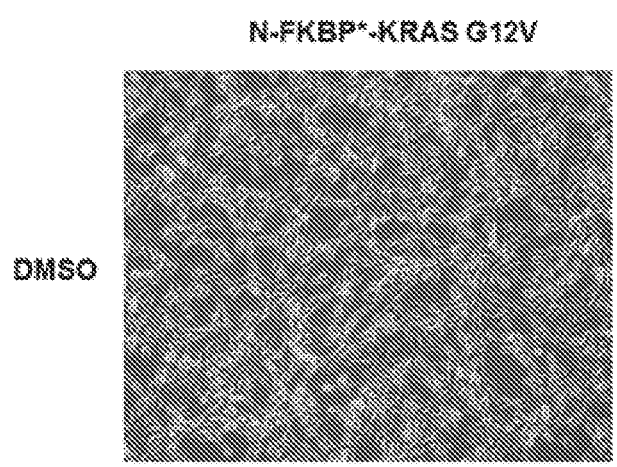
Figure 23C:
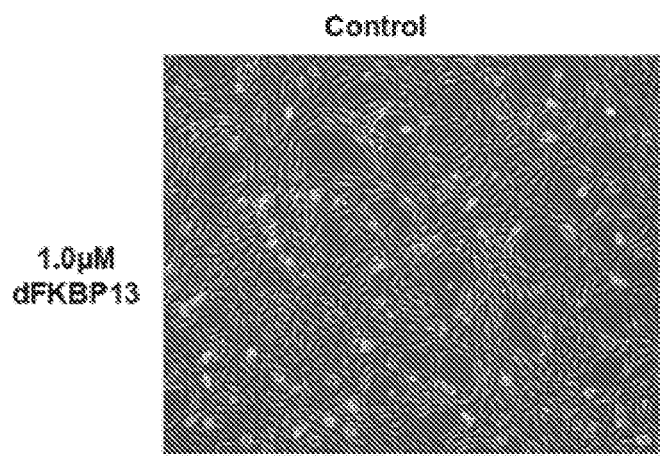
Figure 23D:
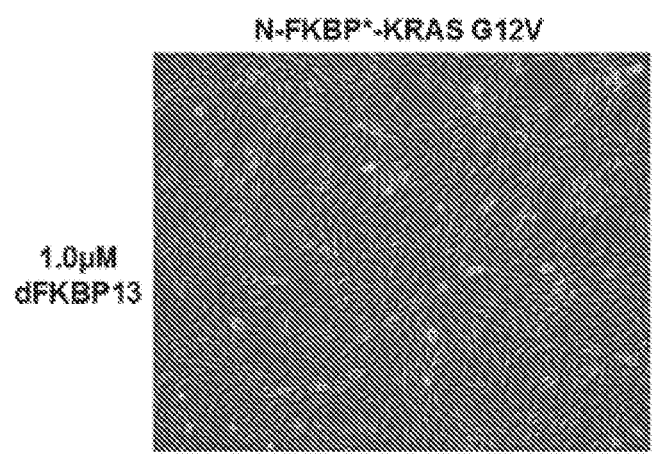
Figure 24A:
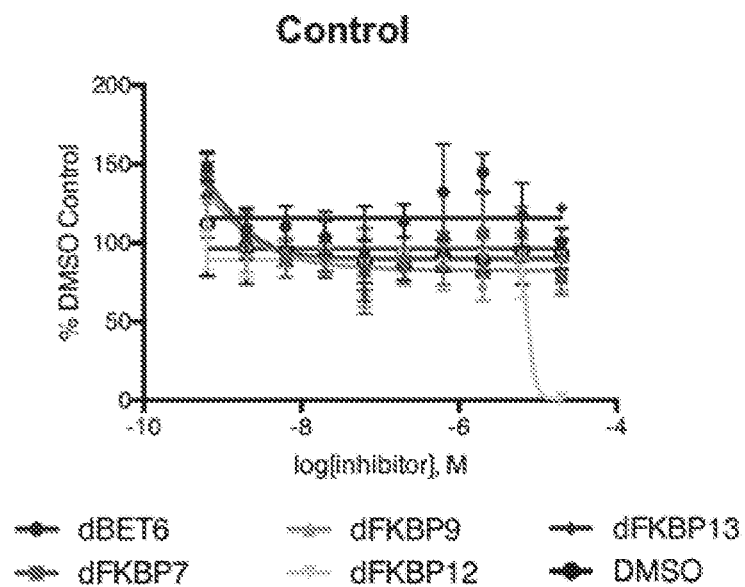
FIG. 24A, FIG. 24B, FIG. 24C, and FIG. 24D are proliferation graphs that measure the effect of dFKBP13 on the growth of NIH3T3 control cells of NIH3T3 expressing FKBP*-KRASG12V. Cells were treated with the indicated concentrations if dFKBPs for 72 hours and cell count measured using an ATPlite assay. The ATPlite 1 step luminescence assay measures cell proliferation and cytotoxicity in cells based on the production of light caused by the reaction of ATP with added luciferase and D-luciferin (Example 21). A decrease in signal indicates a reduction in cell number.
Figure 24B:
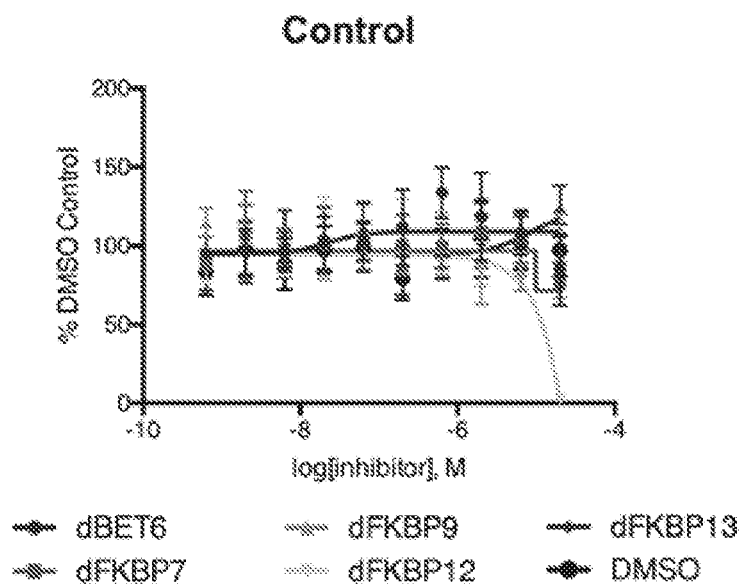
Figure 24C:
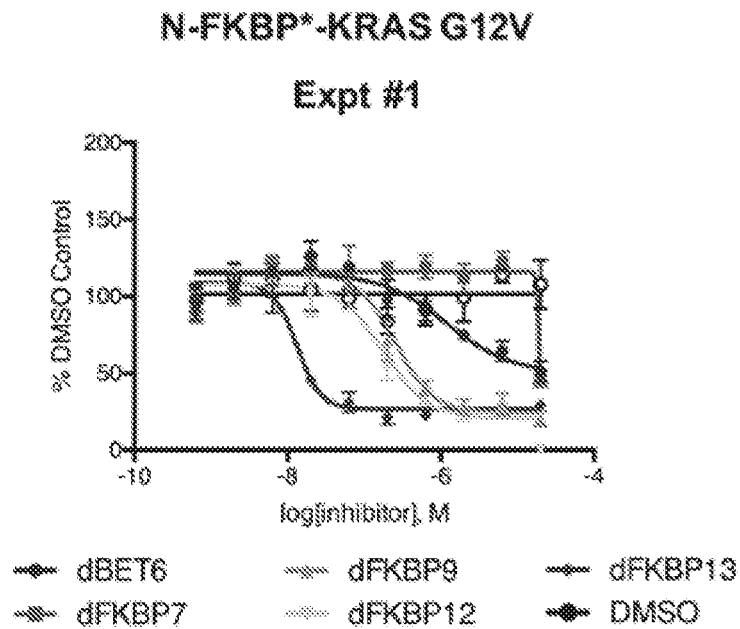
Figure 24D:
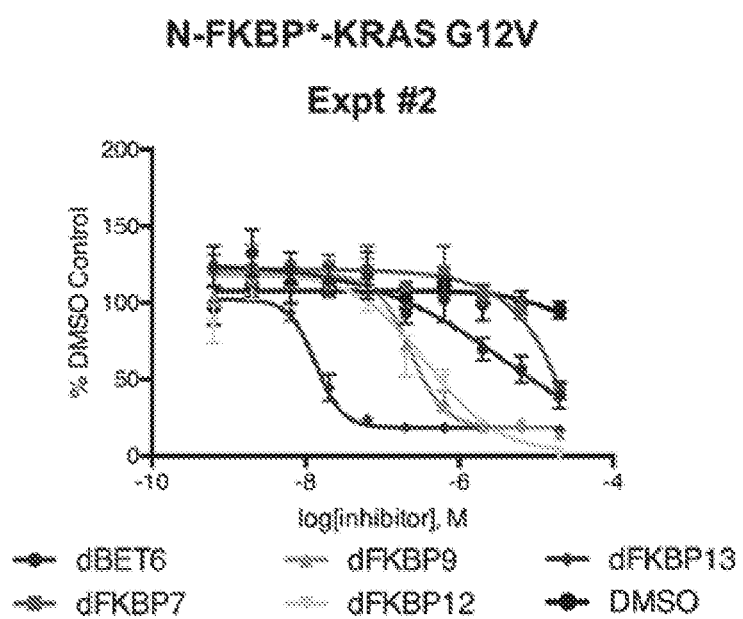

FIG. 22 illustrates an example of the kinetic control of targeted degradation of dTAG-KRAS with dFKBP13.

To evaluate the kinetic control of targeted degradation of dTAG-KRAS, dFKBP13 was administered by increased duration. Western blotting of NIH3T3 cells expressing FKBP* fused to the N-terminus of KRAS treated with 1 µM dFKBP13 for the indicated time. Cells were harvested and immunoblotted to measure degradation of FKBP*-KRAS and downstream surrogates of KRAS signaling (e.g. pMEK and pAKT). The data suggest that dFKBP13 induces potent degradation of FKBP*-KRAS and inhibition of downstream signaling as early as 1 hour post treatment.

Example 20

FIGS. 23A-D illustrate an experiment performed to confirm phenotypical changes induced upon degradation of dTAG-KRAS.

Morphological changes were observed in NIH3T3 cells upon overexpression of dTAG-KRAS as shown by phase contrast imaging. Upon treatment with dFKBP13 for 24 hours, cells morphologically revert back to the wild type (DMSO control) state.

Example 21

FIGS. 24A-D illustrate the phenotypic consequence of dTAG-KRAS degradation on the viability of NIH3T3 cells.

The ATPlite 1-step luminescence assay measures cell proliferation and cytotoxicity in cells based on the production of light caused by the reaction of ATP with added luciferase and D-luciferin. A decrease in signal indicates a reduction in cell number. To evaluate the effect of dFKBP13 on proliferation in NIH3T3 cells expressing dTAG-KRAS, viability was assessed by surrogate measurements of ATP levels. Cells were treated with the indicated concentrations of dFKBPs for 72 hours and cell viability was measured using an ATPlite assay.

Example 22

Figure 25:
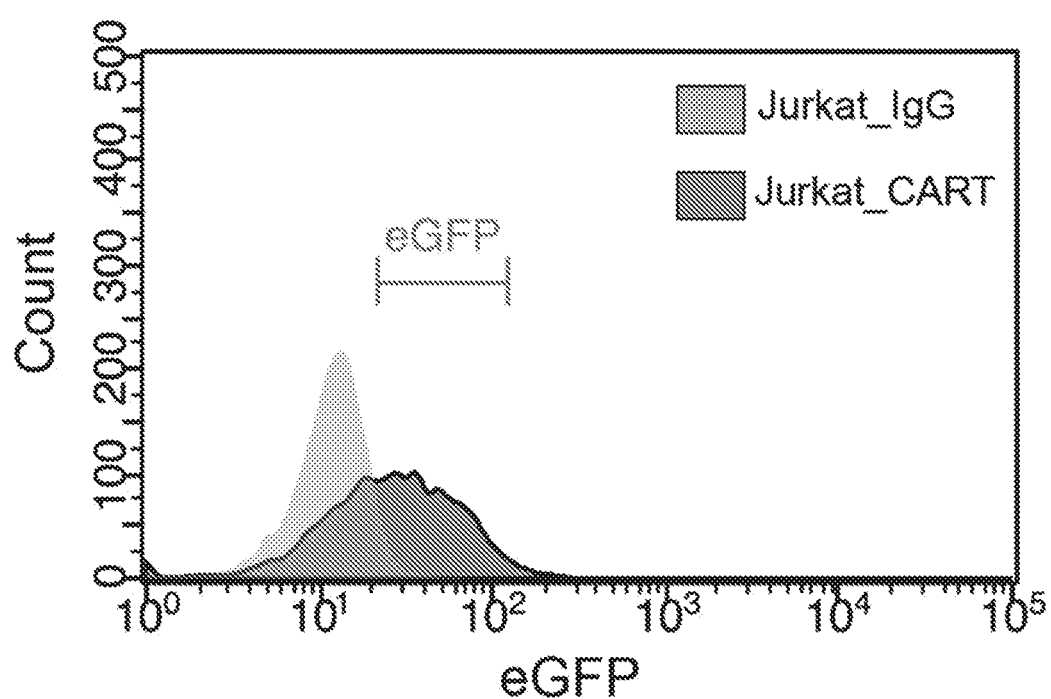
FIG. 25 is a histogram plot illustrating tracking GFP-positive SMART-CAR expressing Jurkat cells as described in Example 22. The SMART-CAR expressing cDNA was expressed in a lentiviral vector that simultaneously expressed eGFP driven off an IRES. Jurkat cells were subjected to flow cytometry with excitation with a 488 nm laser and eGFP fluorescence quantified. The observed positive shift in eGFP signal illustrates the ability to track SMART-CAR expressing T cells.

FIG. 25 illustrates the use of flow cytometry to monitor SMART-CAR expressing Jurkat T-cells. Jurkat T-cells were stably transduced with a single lentiviral vector that co-expresses the SMART-CAR and eGFP. SMART-CAR expressing T-cells can be tracked via flow cytometry. Specifically, excitation with a 488 nM laser allows for detection of eGFP and thus the ability to track SMART-CAR expressing T-cells.

Example 23

Figure 26:
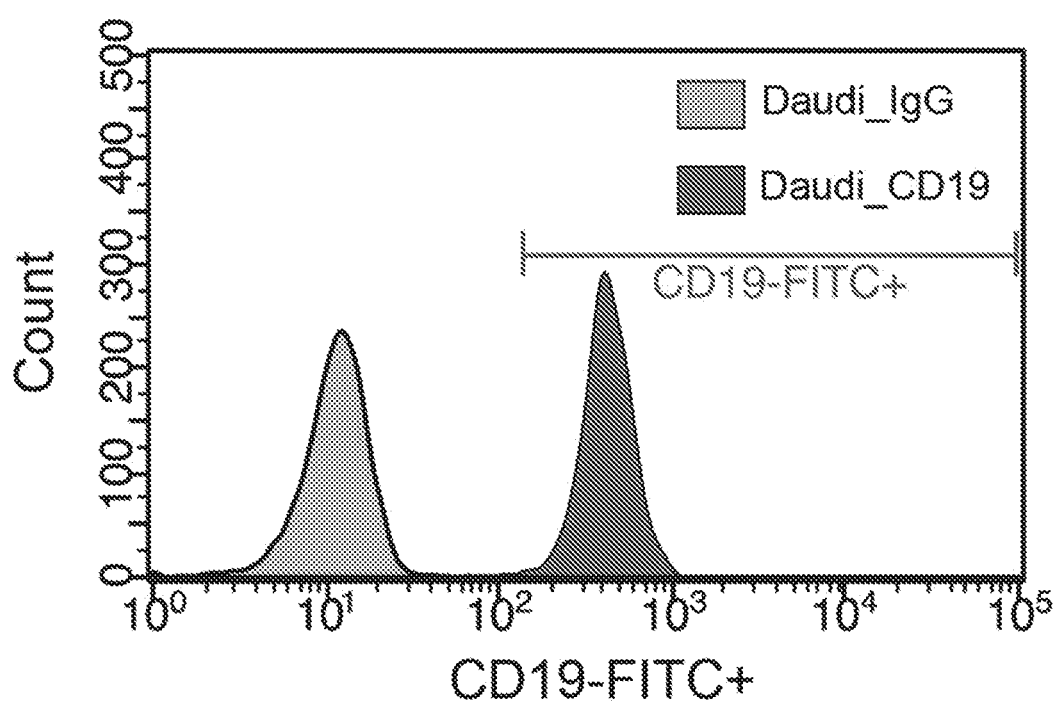
FIG. 26 is a histogram plot illustrating the ability to track CD19-positive tumor target cells. CD19-positive Daudi cells were stained with a directly conjugated CD19-FITC antibody. Stained cells were subjected to flow cytometry with excitation with a 488 nm laser and FITC fluorescence quantified (Example 23). The CD19-FITC positive signal illustrates the ability to track CD19-positive tumor cells.

FIG. 26 illustrates the use of flow cytometry to monitor CD19 positive target tumor cells. Daudi cells express the CD19 antigen endogenously and can be tracked via flow cytometry. Specifically, Duadi cells are stained with a directly conjugated CD19-FITC antibody. Excitation with a 488 nM laser allows for detection of CD19 and thus the ability to track CD19 positive target tumor cells.

Example 24

Figure 27:
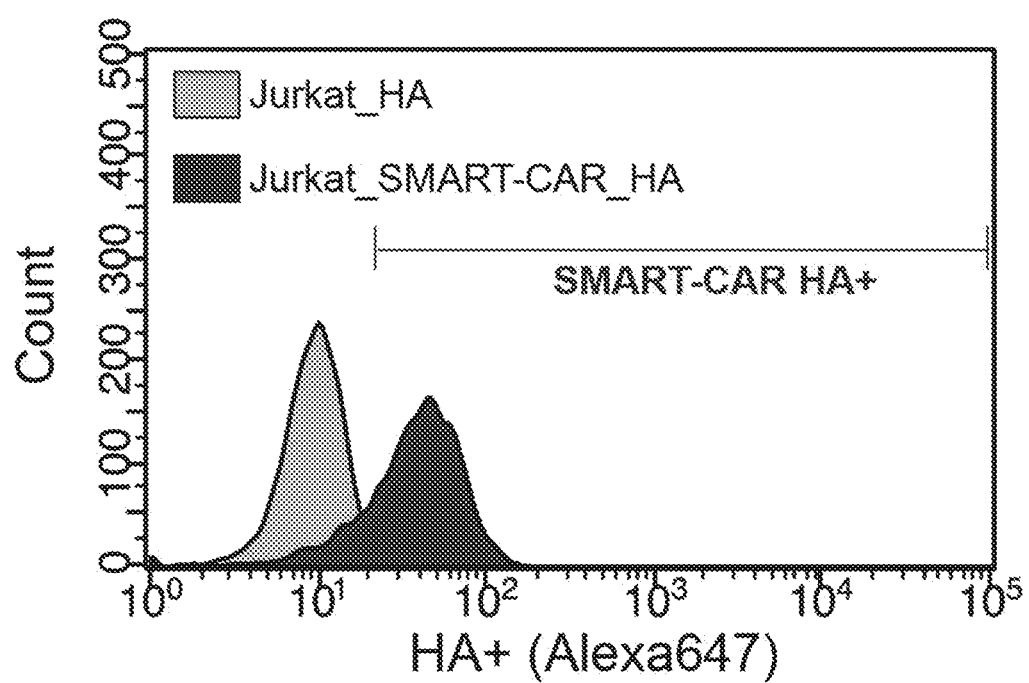
FIG. 27 is a histogram plot illustrating the ability to track SMART-CAR expression in Jurkat cells. SMART-CAR expressing Jurkat cells were stained with a HA-antibody and subsequently labelled with a secondary Alexa647 fluorescent antibody. Stained cells were subject to flow cytometry with excitation with a 647 nm laser and HA expression quantified via Alexa647 fluorescent signal (Example 24). The observed shift in signal illustrates the ability to track SMART-CAR expression in Jurkat T cells.

FIG. 27 illustrates the use of flow cytometry to monitor SMART-CAR protein expression in Jurkat T-cells. SMART-CAR expressing T-cells are fixed, permeabilized and stained with an HA antibody that allows for detection of SMART-CAR protein. After staining with HA, a fluorescent secondary antibody (Alexa 647) was conjugated to the HA to allow for detection using a 532 nM laser. This allows for quantitative measurements of SMART-CAR protein expression levels.

Example 25

Figure 28:
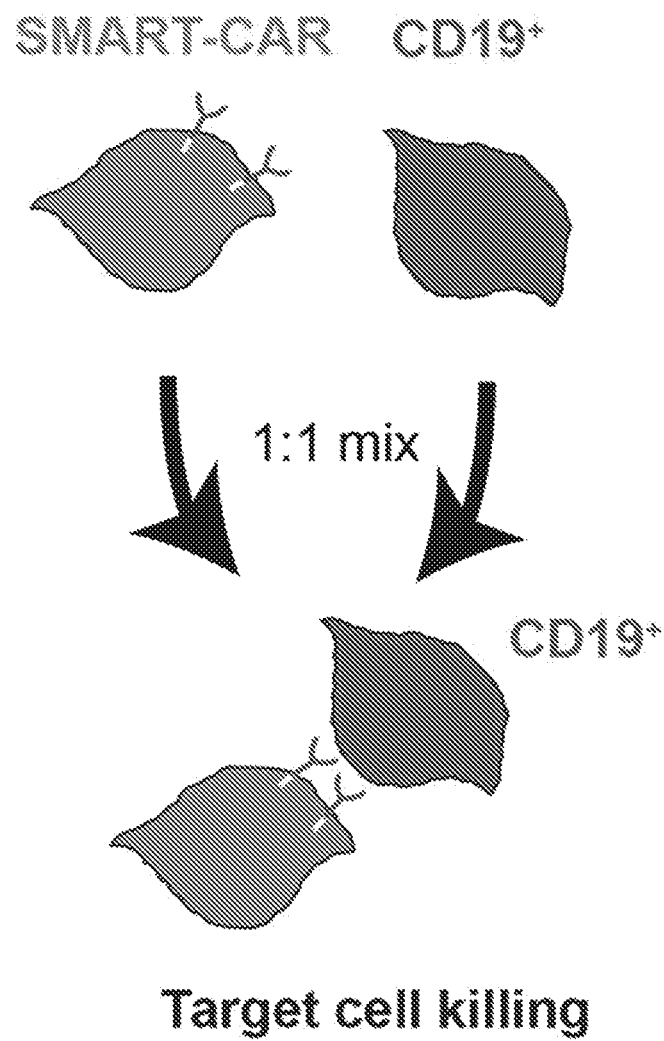
FIG. 28 is a schematic depicting the experimental setup used in FIG. 18 to evaluate the ability of SMART-CAR expressing Jurkat cells to deplete CD19-positive tumor cells. SMART-CAR expressing Jurkat cells are incubated with CD19-positive target tumor cells at the indicated ratio for a given amount of time (Example 25). CD19-positive target tumor cell depletion can be monitored by measuring levels of CD19.

FIG. 28 illustrates the experimental design to evaluate the functionality of SMART-CAR expressing Jurkat T-cells to deplete CD19 positive target tumor cells. SMART-CAR expressing Jurkat cells were co-cultured with CD19-positive target tumor cells at a 1:1 ratio. At the indicated time points, an aliquot of co-cultured cells was taken for flow cytometry. Co-cultured cells were pelleted, stained with a CD19-FITC antibody, fixed, and CD19 levels measured via flow cytometry.

Figure 29:
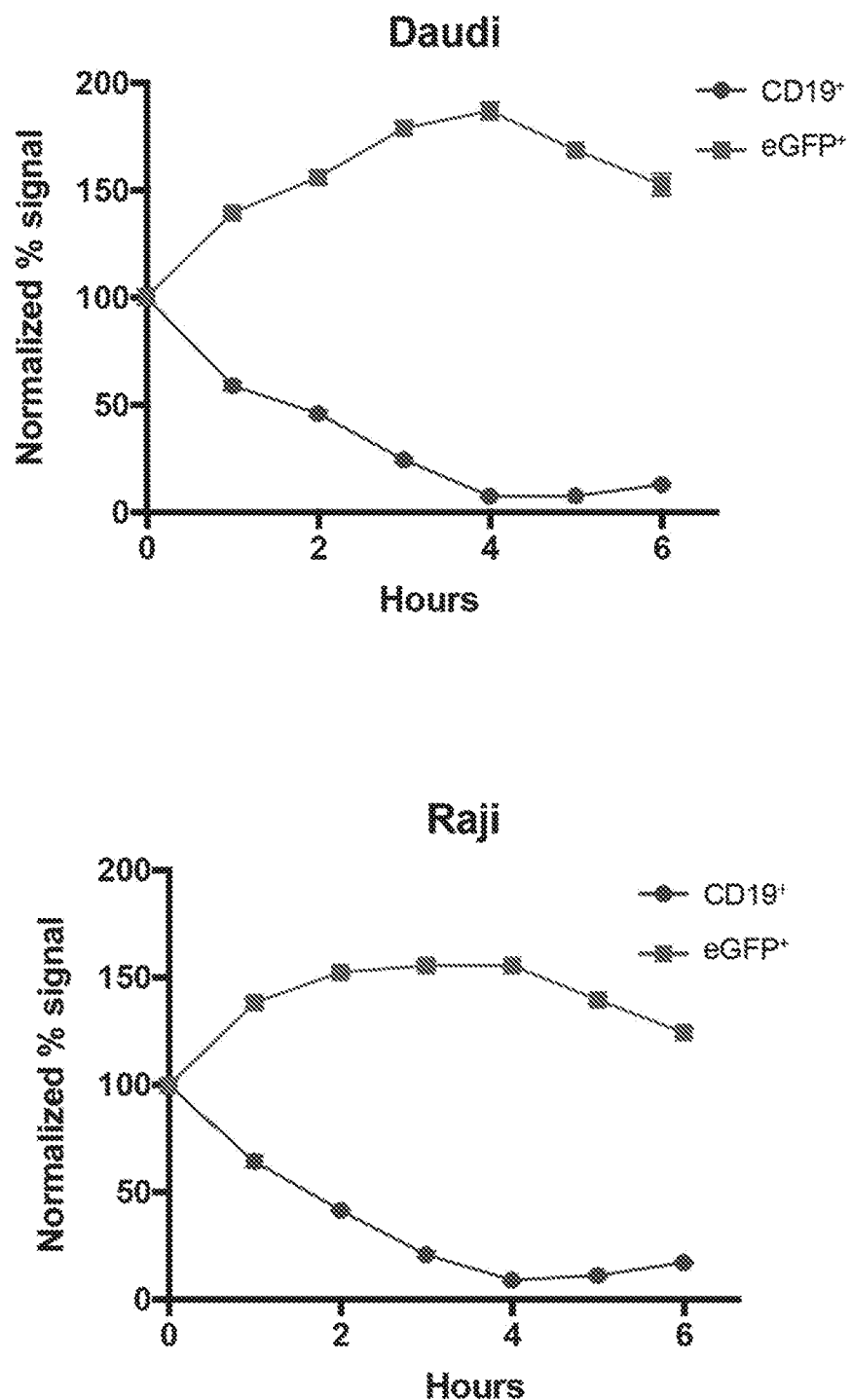
FIG. 29 are line plots tracking CD19 positive tumor cells (blue) and SMART-CAR expressing Jurkat cells (green) after mixing both cell types for a 1:1 ratio. The amount of CD19 positive tumor cells (Daudi: top and Raji: bottom) and SMART-CAR expressing Jurkat cells were quantified by flow cytometry at the indicated time points. Within two hours, SMART-CAR expressing Jurkats deplete 50% of CD19 positive tumor cells and by four hours virtually the entire CD19 positive tumor cells (Daudi: top and Raji: bottom) are depleted. Conversely, SMART-CAR expressing Jurkat cells were unaffected during the mixing of cell populations as tracked by eGFP expression. As described in Example 25, since CD19 positive tumor cells were being depleted within the population, eGFP expressing SMART-CAR Jurkats appear to increase as the mixed cell population is shifted.

FIG. 29 illustrates the functional ability of SMART-CAR expressing T-cells to kill CD19 positive target tumor cells. At the indicated time points, CD19 positive Daudi (top) and Raji (bottom) cells were quantified via flow cytometry when co-cultured with SMART-CAR expressing T-cells. Within two hours, SMART-CAR expressing Jurkats depleted 50% of CD19 positive tumor cells and by four hours virtually the entire CD19 positive tumor cells (Daudi: top and Raji: bottom) were depleted. These data support the functional ability of SMART-CAR expressing T-cells to deplete CD19 positive target tumor cells.

Example 26

Figure 30:
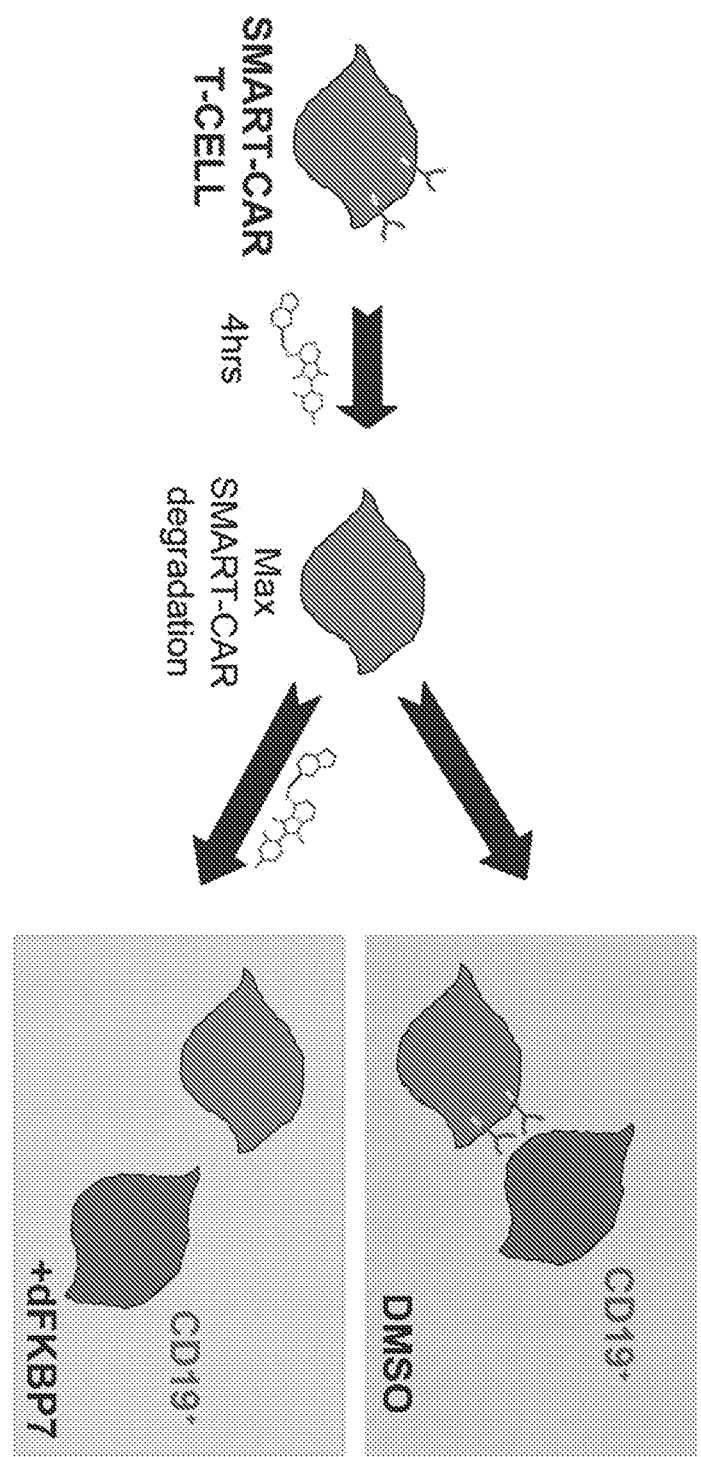
FIG. 30 is a schematic depicting the experimental setup used in FIG. 21 and described in Example 26 to illustrate the chemical control of SMART-CAR expression and subsequent activity against CD19 positive tumor cells using dFKBP7. SMART-CAR expressing Jurkat cells were pretreated with dFKBP7 at 250 nM for 4 hours to allow for maximal degradation of SMART-CAR. The Jurkat cells were then harvested and washed three times to remove dFKBP7. Jurkat cells were split into two experimental arms. The first arm (top, blue) was treated with DMSO control and the second arm (bottom, green) was retreated with 250 nM dFKBP7. The two experimental arms were then mixed at a 1:1 ratio with CD19 positive tumor cells and CD19-positive tumor cells monitored by flow cytometry.

FIG. 30 illustrates the experimental design to demonstrate chemical control of SMART-CAR expressing T-cell functional CD19 positive target tumor cell killing. SMART-CAR expressing Jurkat cells were pretreated with dFKBP7 at 250 nM for 4 hours to allow for maximal degradation of SMART-CAR. The Jurkat cells were then harvested and washed three times to remove dFKBP7. Jurkat cells were split into two experimental arms. The first arm (top, blue) was treated with DMSO control and the second arm (bottom, green) was retreated with 250 nM dFKBP7. The two experimental arms were then mixed at a 1:1 ratio with CD19 positive tumor cells and CD19-positive tumor cells monitored by flow cytometry. In addition, SMART-CAR expression was also tracked using flow cytometry with an HA-antibody (grey lines).

Figure 31:
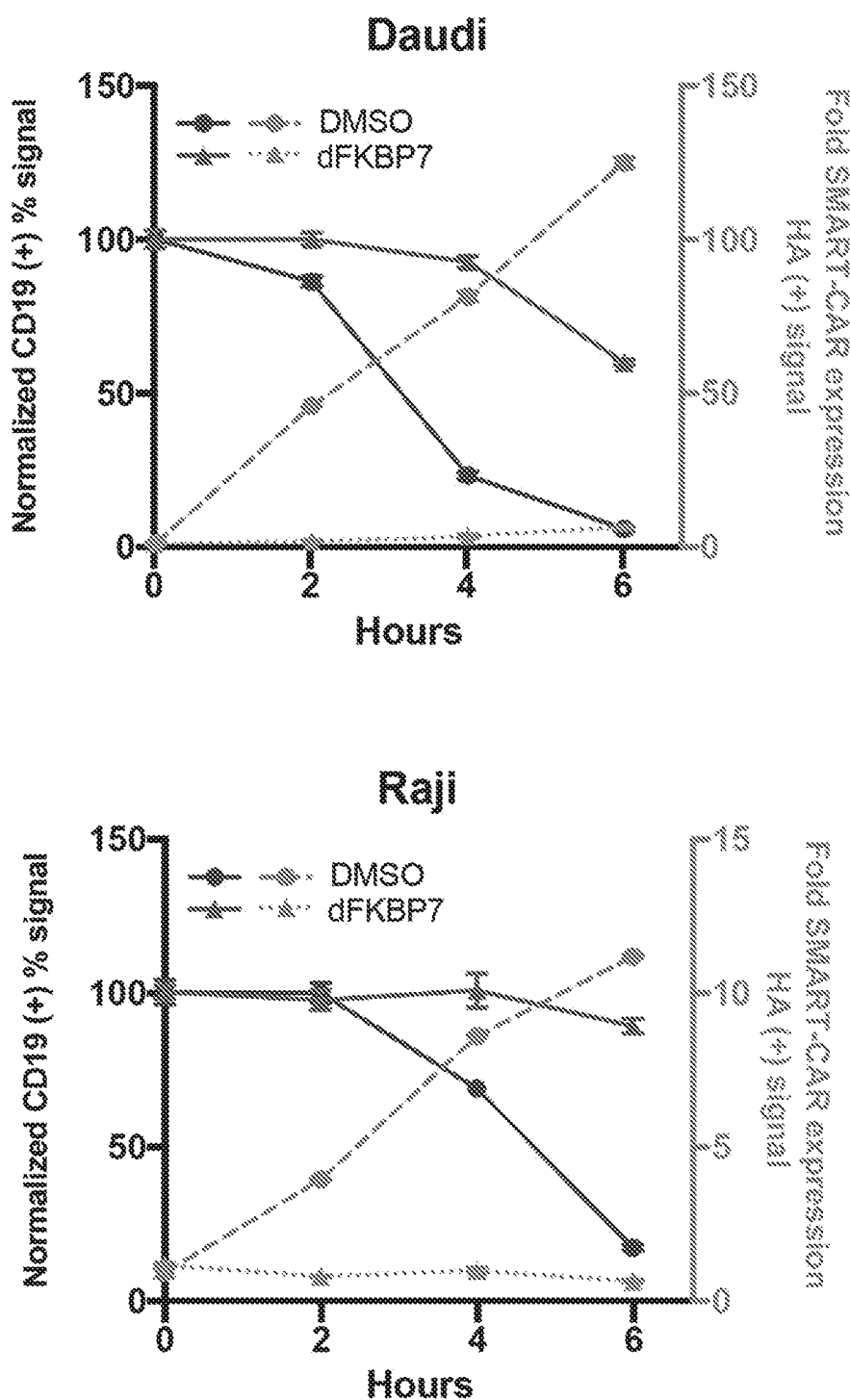
FIG. 31 are line plots tracking CD19 positive tumor cells and SMART-CAR expression levels as described in the experimental setup in FIG. 20 and described in Example 26. After the 4 hour pretreatment with 250 nM of dFKBP7, SMART-CAR expressing Jurkats were mixed in a 1:1 ratio with CD19 positive tumor cells (Daudi: top and Raji: bottom) in the presence (green line) or absence (blue line) of 250 nM of dFKBP7. CD19 positive tumor cells were then tracked by flow cytometry using a directly conjugated CD19-FITC antibody at the indicated time points. In addition, SMART-CAR expression was also tracked using flow cytometry with an HA-antibody (grey lines). With retreatment of dFKBP7, SMART-CAR expression is minimal (grey, circle, dashed lines) and consequently CD19 positive tumor cells are not affected (green lines). In contrast, when the mixed population is treated with DMSO control, SMART-CAR expression is restored and consequently CD19 positive tumor cells are rapidly depleted (blue line) with total CD19 positive tumor cell death observed within 6 hours.

FIG. 31 illustrates functional control of SMART-CAR mediated CD19 positive target tumor cell killing using the hetero bifunctional molecule dFKBP7. With retreatment of dFKBP7, SMART-CAR expression was minimal (grey, circle, dashed lines) and consequently CD19 positive tumor cells were not affected (green lines). In contrast, when the mixed population was treated with DMSO control, SMART-CAR expression was restored and consequently CD19 positive tumor cells were rapidly depleted (blue line) with total CD19 positive tumor cell death observed within 6 hours. These data illustrate that ability of the hetero bifunctional molecule dFKBP7 to modulate SMART-CAR expression, which dictates SMART-CAR mediated CD19 positive target tumor cell killing.

Example 27

Figure 32:
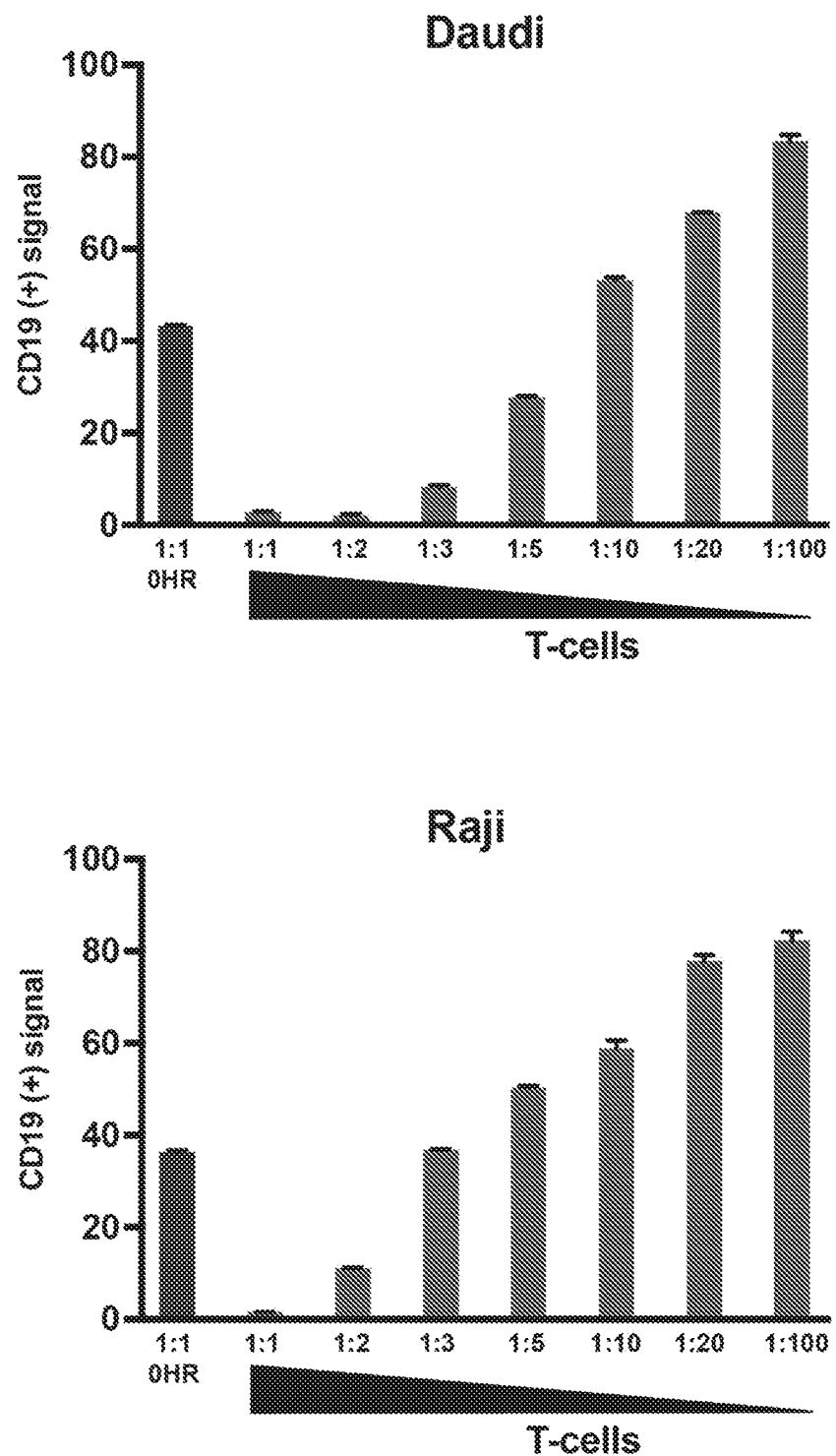
FIG. 32 is a histogram bar plot of the amount of CD19 positive tumor cells when SMART-CAR expressing Jurkat T cells are incubated at varying ratios with CD19 positive tumor cells (Daudi: top and Raji: bottom). SMART-CAR expressing Jurkat cells and CD19 positive tumor cells were mixed at the indicated ratios and allowed to incubate for 6 hours. CD19 positive tumor cells were then quantified using flow cytometry with a directly conjugated CD19-FITC antibody. The starting amount of CD19 positive tumor cells were quantified immediately following the mixing of cell populations and shown in blue. As described in Example 27, as the amount of SMART-CAR expressing Jurkat T cells is reduced, the amount of CD19 positive tumor cell depletion is reduced. Maximal depletion was observed with a 1:1 ratio, while at 1:100 ratio of T cells to CD19 positive tumor cells about 20% of the CD19 positive population is lost.

FIG. 32 is a graph that exemplifies the linear relationship between number of SMART-CAR expressing T-cells and functional killing of CD19 positive target tumor cells. SMART-CAR expressing Jurkat cells and CD19 positive tumor cells (Daudi: top, Raji: bottom) were mixed at the indicated ratios and allowed to incubate for 6 hours. CD19 positive tumor cells were then quantified using flow cytometry with a directly conjugated CD19-FITC antibody. The amount of SMART-CAR expressing Jurkat T cells was reduced and the amount of CD19 positive tumor cell depletion was reduced. Maximal depletion was observed with a 1:1 ratio, while at 1:100 ratio of T cells to CD19 positive tumor cells, about 20% of the CD19 positive population was lost. These data support the dose proportional behavior of SMART-CAR expressing T-cells in CD19 positive target tumor cell killing.

Example 28

Figure 33:
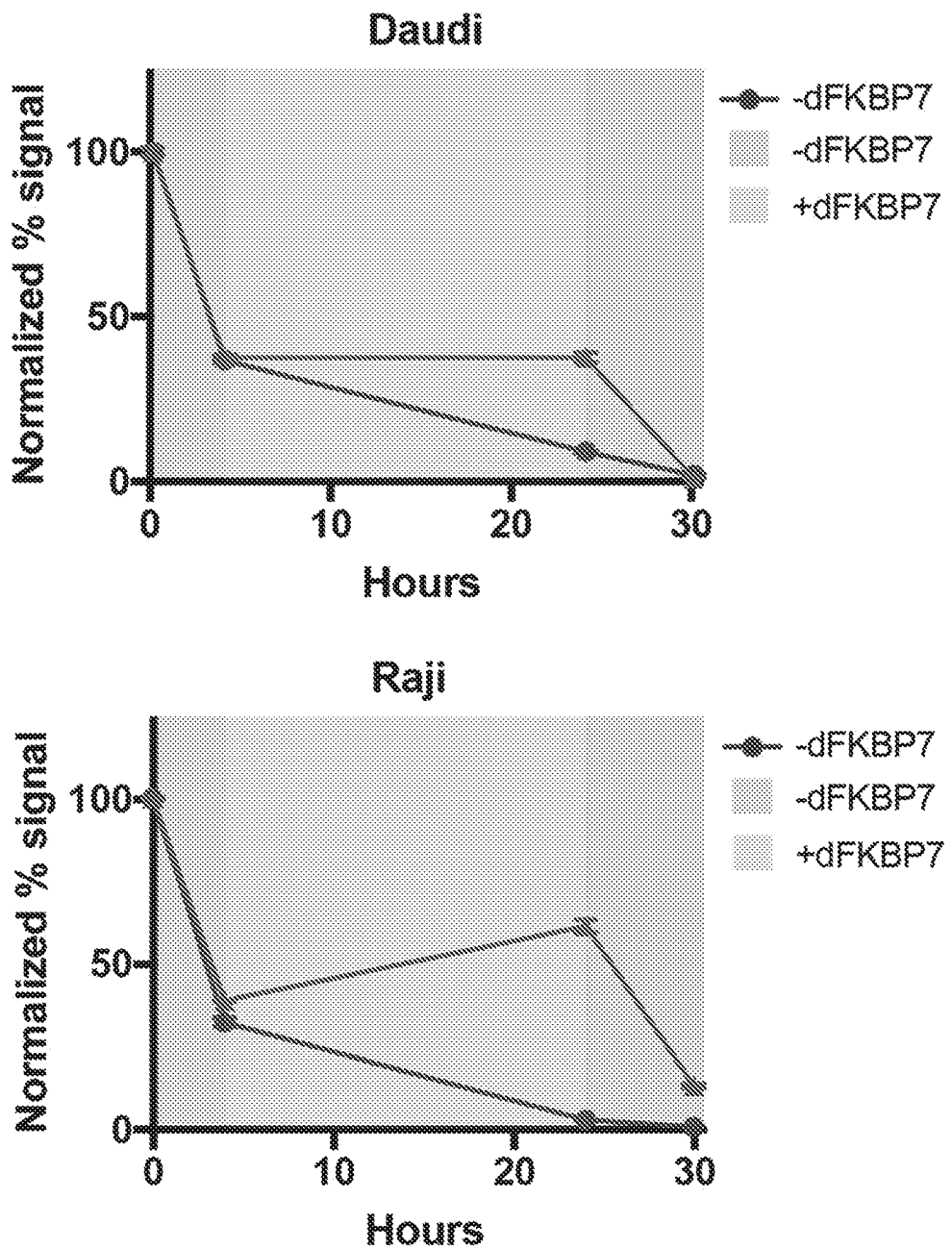
FIG. 33 is a line plot tracking CD19 positive tumor cells during alternating exposure and removal of 250 nM of dFKBP7 in a 30 hour time course. SMART-CAR expressing T-cells were mixed with CD19-positive target tumor cells (Daudi (top) and Raji (bottom) in a 1:3 ratio. At the indicated time points (time point 0 HR, 4 HR, 24 HR, and 30 HR) CD19 positive tumor cells were tracked by flow cytometry using a directly conjugated CD19-FITC antibody. In the absence of dFKBP7 (blue line), CD19 positive target tumor cells are depleted by 50% within 4 hours and completely depleted by 30 hours. In contrast, alternating exposure to dFKBP7 (green line), the rate of CD19 positive target tumor cell depletion can be controlled by chemical exposure. In the absence of dFKBP7 (blue shaded, 0 HR to 4 HR), CD19 positive target tumor cell depletion occurs. In the presence of dFKBP7 (green shaded, 4 HR to 24 HR), CD19 positive target tumor cell depletion is halted. The subsequent removal of dFKBP7 (blue shaded, 24 HR-30 HR) results in rapid target tumor cell depletion. The on-off-on control of CD19 positive target tumor cell depletion with dFKBP7 exhibits the rheostat function of the SMART-CAR technology (Example 28).

FIG. 33 demonstrates the rheostat (on-off-on) mechanism of the SMART-CAR technology. In the absence of dFKBP7 (blue line), CD19 positive target tumor cells were depleted by 50% within 4 hours and completely depleted by 30 hours. In contrast, alternating exposure to dFKBP7 (green line), the rate of CD19 positive target tumor cell depletion was controlled by chemical exposure. In the absence of dFKBP7 (blue shaded, 0 HR to 4 HR), CD19 positive target tumor cell depletion occurred. In the presence of dFKBP7 (green shaded, 4 HR to 24 HR), CD19 positive target tumor cell depletion was halted. The subsequent removal of dFKBP7 (blue shaded, 24 HR-30 HR) resulted in rapid target tumor cell depletion. The on-off-on control of CD19 positive target tumor cell depletion with dFKBP7 exhibits the rheostat function of the SMART-CAR technology. Daudi CD-19-positive target tumor cells are shown on the top and Raji cells are shown on the bottom.

Example 29

Figure 34:
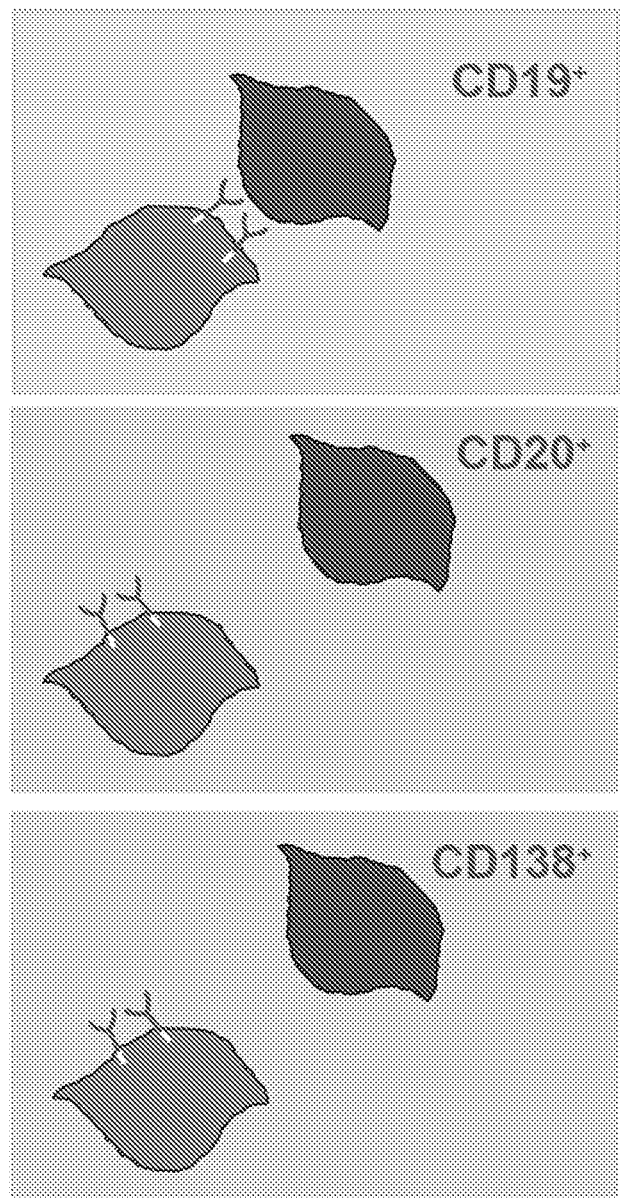
FIG. 34 is a schematic depicting the experimental setup used in FIG. 32 and described in Example 29. K562 cells were used to engineer a set of three isogenic antigens expressing cell lines (shown in red): CD19, CD20 and CD138 respectively. These cells were engineered using lentiviral based overexpression vectors expressing each respective antigen. SMART-CAR expressing T-cells (shown in green) specifically target CD19 expressing target cells and thus do not engage CD20 or CD139 expressing K562 cells.

FIG. 34 is a schematic depicting the specificity of SMART-CAR expressing T-cells for CD19 positive target tumor cells. K562 cells were engineered to express CD19, CD20, and CD139 respectively. These cells stably express each respective antigen via lentiviral infection. SMART-CAR expressing T-cells (shown in green) recognize and engage only CD19 expressing target cells.

Figure 35:
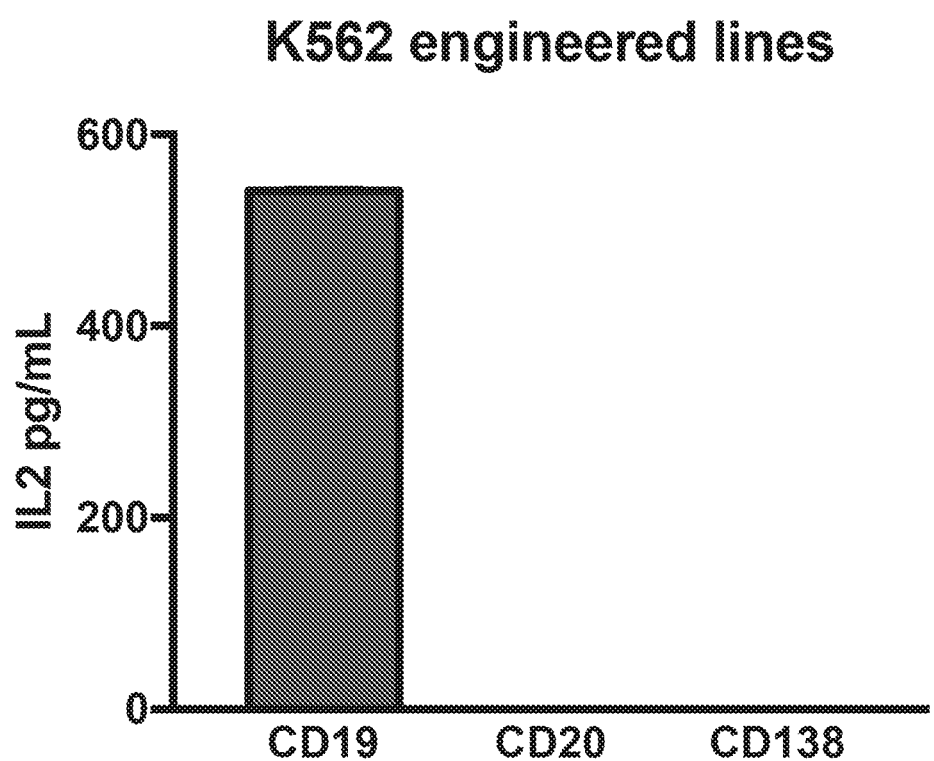
FIG. 35 is a histogram bar plot quantifying IL-2 levels produced from SMART-CAR expressing Jurkat T-cells after co-incubation with antigen expressing K562 cells in a 1:3 ratio (T cell to K562 cell) for 24 hours as described in Example 29. IL-2 levels were quantified by ELISA using co-culture supernatants. IL-2 detection was observed only in co-cultures with CD19 expressing K562 cells indicating T-cell activation was only observed in the presence of CD19 positive tumor target cells.

FIG. 35 illustrates the specificity in activation of SMART-CAR expressing T-cells for CD19 expressing target tumor cells. SMART-CAR expressing Jurkat T-cells were co-incubated with antigen expressing K562 cells in a 1:3 ratio (T cell to K562 cell) for 24 hours. IL-2 levels were quantified by ELISA using co-culture supernatants. IL-2 detection was observed only in co-cultures with CD19 expressing K562 cells indicating T-cell activation was only observed in the presence of CD19 positive tumor target cells.

Example 30

Figure 36:
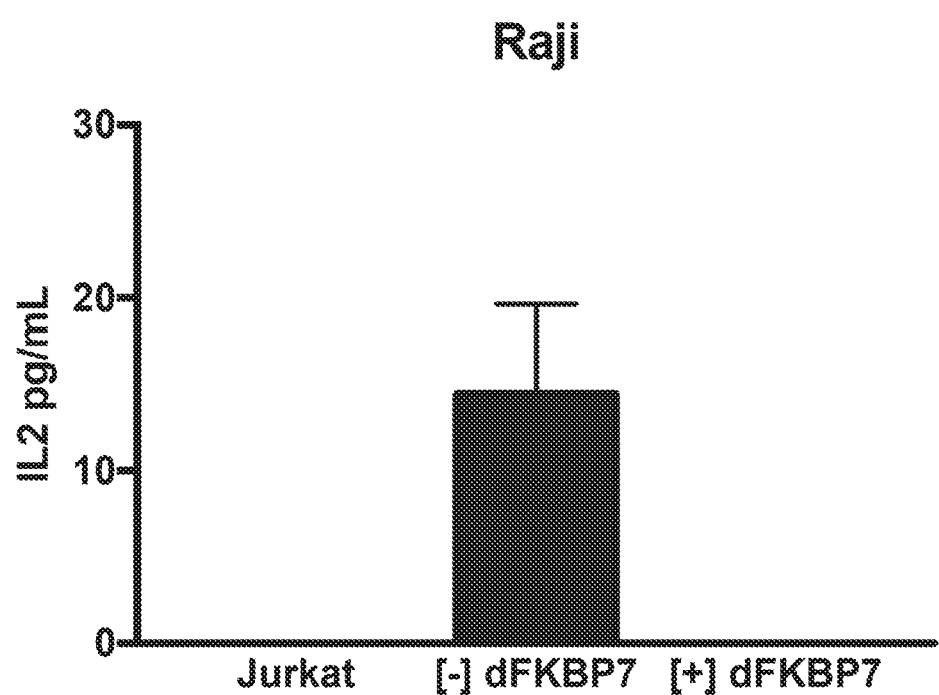
FIG. 36 is a histogram bar plot quantifying IL-2 levels produced from SMART-CAR expressing Jurkat T-cells after co-incubation with CD19 positive Raji cells in a 1:3 ratio (T cells to Raji cells) for 4 hours. Parental Jurkat cells that do not express the SMART-CAR result in no IL-2 production. In SMART-CAR expressing T-cells, IL-2 production is detected in the absence of dFKBP7 while IL-2 production is completely suppressed in the presence of 250 nM of dFKBP7 indicating a lack of SMART-CAR expressing T-cell activation. dFKBP7 was administered at the time of co-culture of T-cell and Raji target cells (Example 30).

FIG. 36 illustrates the chemical control of SMART-CAR expressing T-cell activation using the hetero bifunctional molecule dFKBP7. SMART-CAR expressing Jurkat T-cells were co-incubated with CD19 positive Raji cells in a 1:3 ratio. Parental Jurkat cells that do not express the SMART-CAR resulted in no IL-2 production. In SMART-CAR expressing T-cells, IL-2 production was detected in the absence of dFKBP7, while IL-2 production was completely suppressed in the presence of 250 nM of dFKBP7 indicating a lack of SMART-CAR expressing T-cell activation. These data demonstrate chemical control of SMART-CAR expressing T-cell activation with dFKBP7. Further, the suppression of IL2 levels suggest exquisite chemical control of cytokine production.

Example 31

Figure 37:
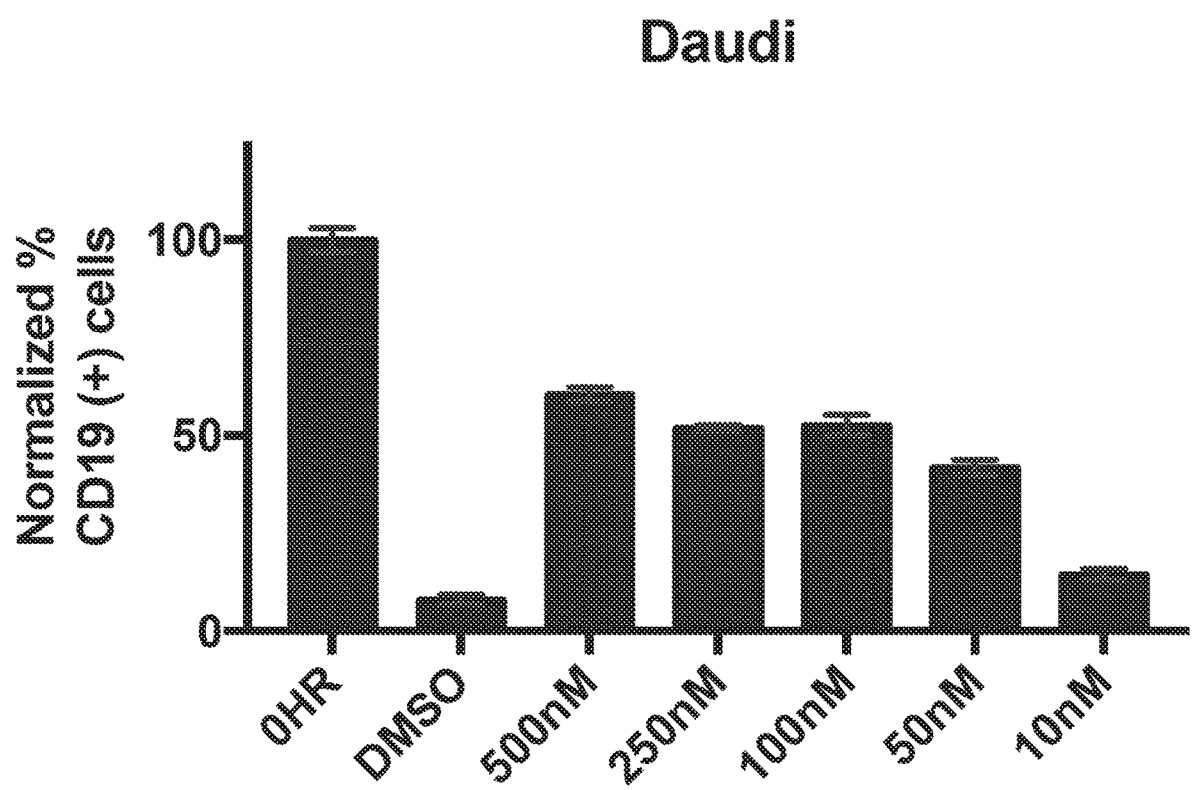
FIG. 37 is a histogram bar plot of the amount of CD19 positive tumor cells when SMART-CAR expressing Jurkat T cells are incubated with CD19 positive Daudi cells in the presence of varying amounts of dFKBP7. SMART-CAR expressing Jurkat cells were co-cultured with CD19 positive Daudi cells at a 1:3 ratio for 24 hours in the presence of the indicated concentrations of dFKBP7 (Example 31). CD19 positive Daudi were then quantified using flow cytometry with a directly conjugated CD19-FITC antibody. In the absence of dFKBP7 (DMSO control), maximal Daudi depletion is observed. In dose response fashion, Daudi cell depletion is rescued with increased concentration of dFKBP7 indicating chemical control of SMART-CAR mediated CD19 target cell depletion.

FIG. 37 demonstrates the dose proportional control of SMART-CAR expressing T-cell mediated CD19 positive target tumor cell killing. SMART-CAR expressing Jurkat T cells were incubated with CD19 positive Daudi cells in the presence of varying amounts of dFKBP7. SMART-CAR expressing Jurkat cells were co-cultured with CD19 positive Daudi cells at a 1:3 ratio for 24 hours in the presence of the indicated concentrations of dFKBP7. CD19 positive Daudi were then quantified using flow cytometry with a directly conjugated CD19-FITC antibody. In the absence of dFKBP7 (DMSO control), maximal Daudi depletion was observed. In dose response fashion, Daudi cell depletion was rescued with increased concentration of dFKBP7 indicating chemical control of SMART-CAR mediated CD19 target cell depletion.

Example 32

Figure 38:
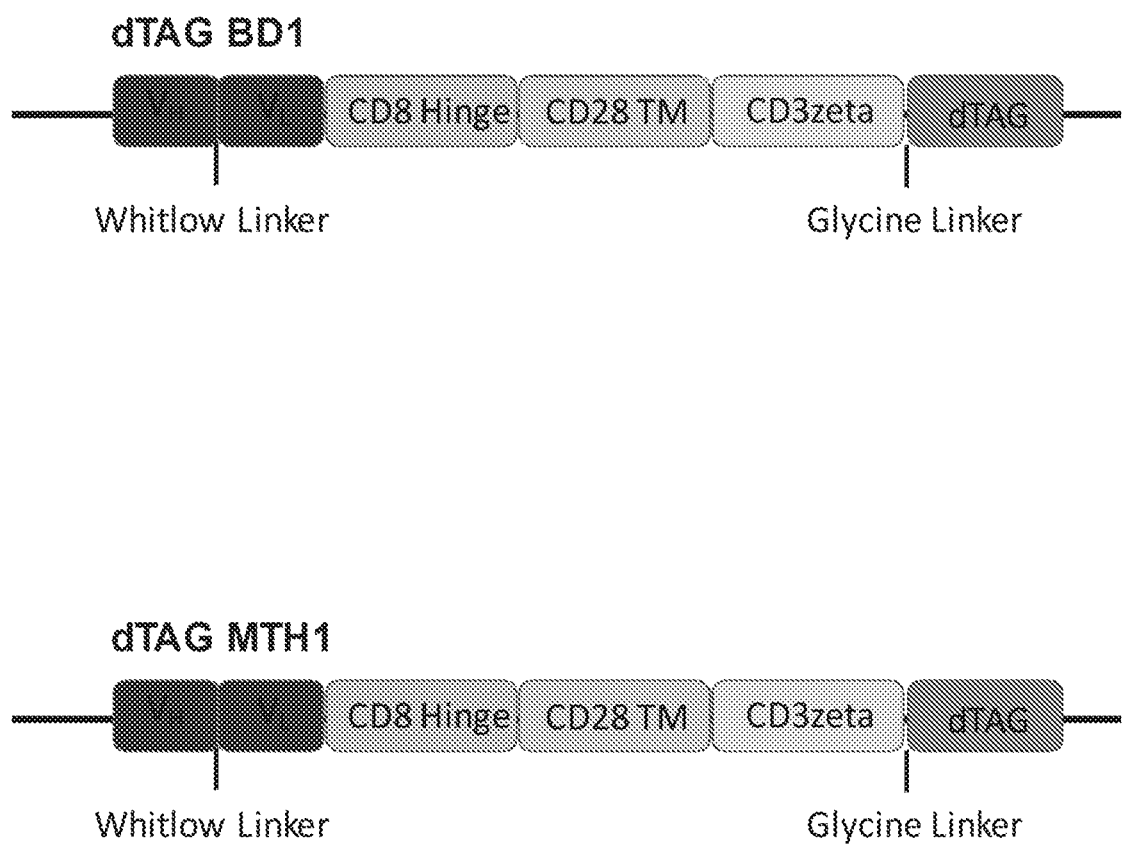
FIG. 38 is a schematic of an exemplary chimeric antigen receptors (CARs) which include a single chain antibody, hinge domain (H), transmembrane domain (TM), signaling domains responsible for T-cell activation, and a dTAG (BD1, top and MTH1, bottom) capable of being bound by a heterobifunctional compound resulting in degradation of at least a portion of the CAR. From left to right, the illustrative CARs include a CD3-derived signaling domain, a costimulatory domain and CD3-derived domain, and two costimulatory domains and a CD3-derived domain all with a 3' fused dTAG (Example 32).

FIG. 38 is a schematic showing the interchangeable nature of the dTAGs within the SMART-CAR sequence. The dTAG can be interchanged and subsequently bound by a respective paired hetero bifunctional compound resulting in targeted degradation of the SMART-CAR.

Figure 39:
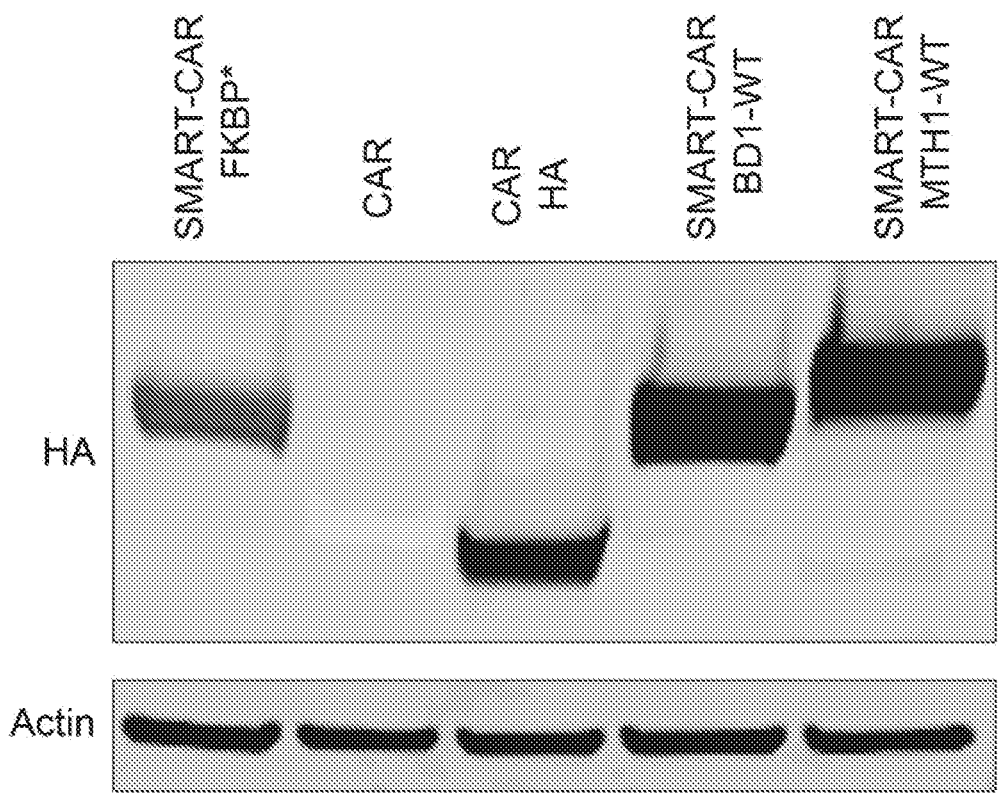
FIG. 39 is an immunoblot of a series of SMART-CAR expressing Jurkat T-cells. As described in Example 32, Jurkat T-cells were transduced with lentivirus expressing SMART-CARs (with varying dTAGs). Stable expression of CD19-CAR-dTAG for each respective SMART-CAR was confirmed by HA expression.

FIG. 39 is an immunoblot performed to confirm ectopic expression of CD19 targeted SMART-CARs with interchanged dTAGs (FKBP12*, BD1, and MTH1). Jurkat T-cells were transduced with lentivirus expressing CD19-CAR-dTAG. Cells were selected with blasticidin and expanded. Stable expression of CD19-CAR-dTAG in Jurkat cells was confirmed by anti-HA western immunoblotting of whole cell lysates.

Figure 40:
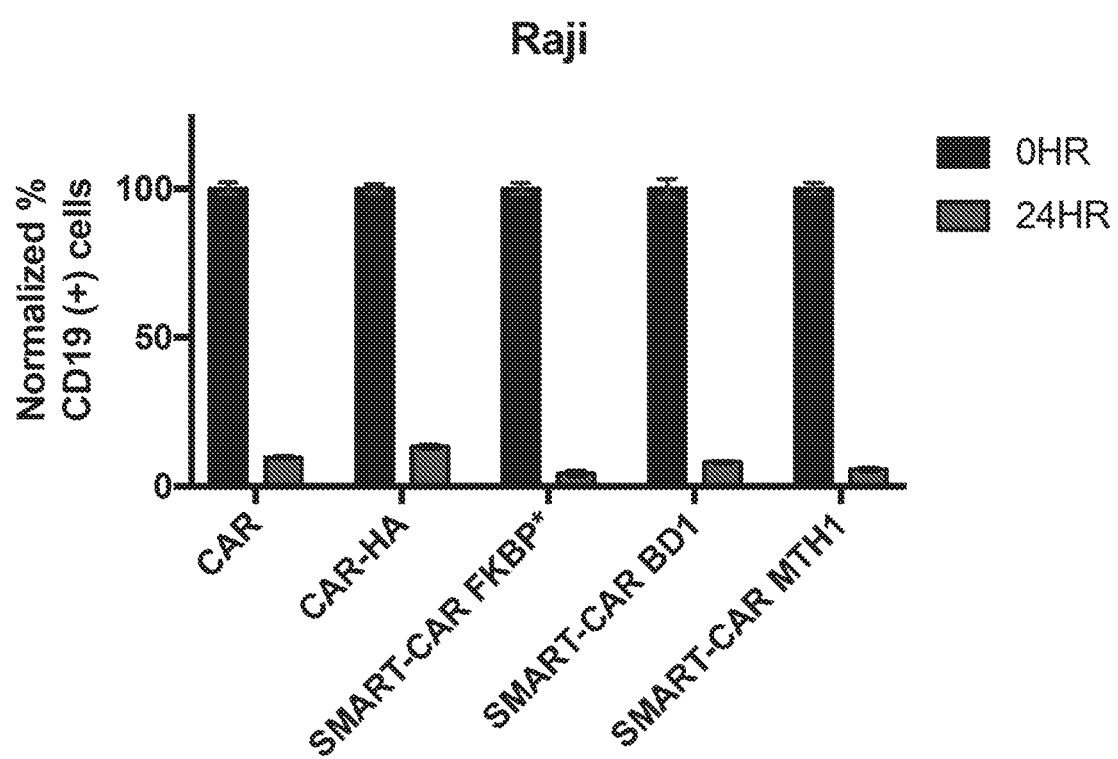
FIG. 40 is a histogram bar plot tracking CD19 positive Raji cells in co-culture with the indicated SMART-CAR expressing Jurkat T-cell. As described in Example 32, each respective SMART-CAR expressing T-cell was co-cultured with CD19 positive Raji cells in a 1:3 ratio (T-cell to Raji cell) for 24 hours. CD19 positive tumor cells were then tracked by flow cytometry using a directly conjugated CD19-FITC antibody. Relative to the 0 HR timepoint, maximal CD19 Raji cell depletion was observed with all SMART-CAR expressing T-cells validating the use of multiple dTAGs within each respective SMART-CAR.

FIG. 40 illustrates the functionality of several CD19 targeting SMART-CAR expressing T-cells. Each respective SMART-CAR expressing T-cell was co-cultured with CD19 positive Raji cells in a 1:3 ratio (T-cell to Raji cell) for 24 hours. CD19 positive tumor cells were then tracked by flow cytometry using a directly conjugated CD19-FITC antibody. Relative to the 0 HR timepoint, maximal CD19 Raji cell depletion was observed with all SMART-CAR expressing T-cells validating the use of multiple dTAGs within each respective SMART-CAR.

Figure 41:
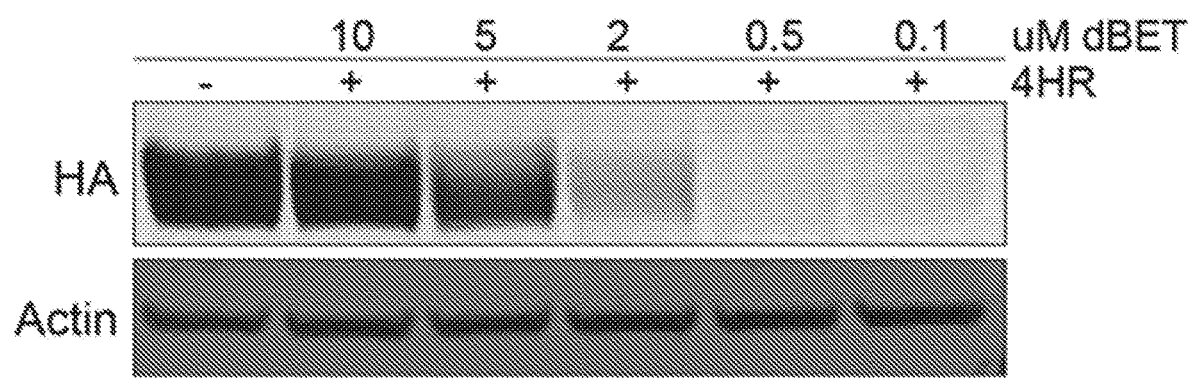
FIG. 41 is an immunoblot of SMART-CAR BD1 expressing Jurkat T-cells treated with a heterobifunctional molecule dBET as described in Example 32. SMART-CAR BD1 expressing T-cells were treated at the indicated concentrations for 4 hours and SMART-CAR BD1 degradation was observed in dose response confirming chemical control of expression.
Figure 42A:
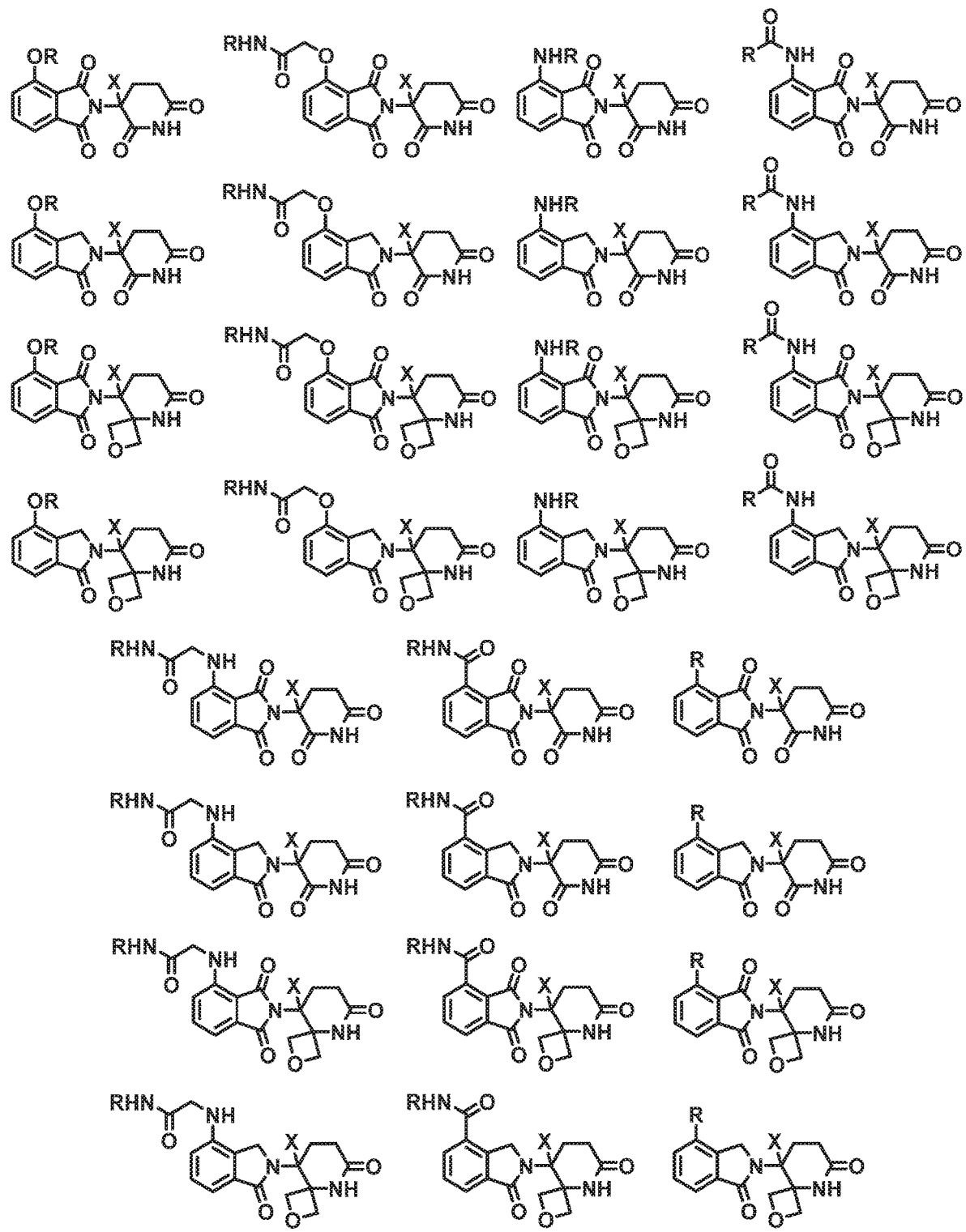
FIG. 42A, FIG. 42B, FIG. 42C, FIG. 42D, FIG. 42E, FIG. 42F, FIG. 42G, FIG. 42H and FIG. 42I provide examples of Degron moieties for use in the present invention, wherein R is the point of attachment for the Linker and X is as defined herein.
Figure 42B:
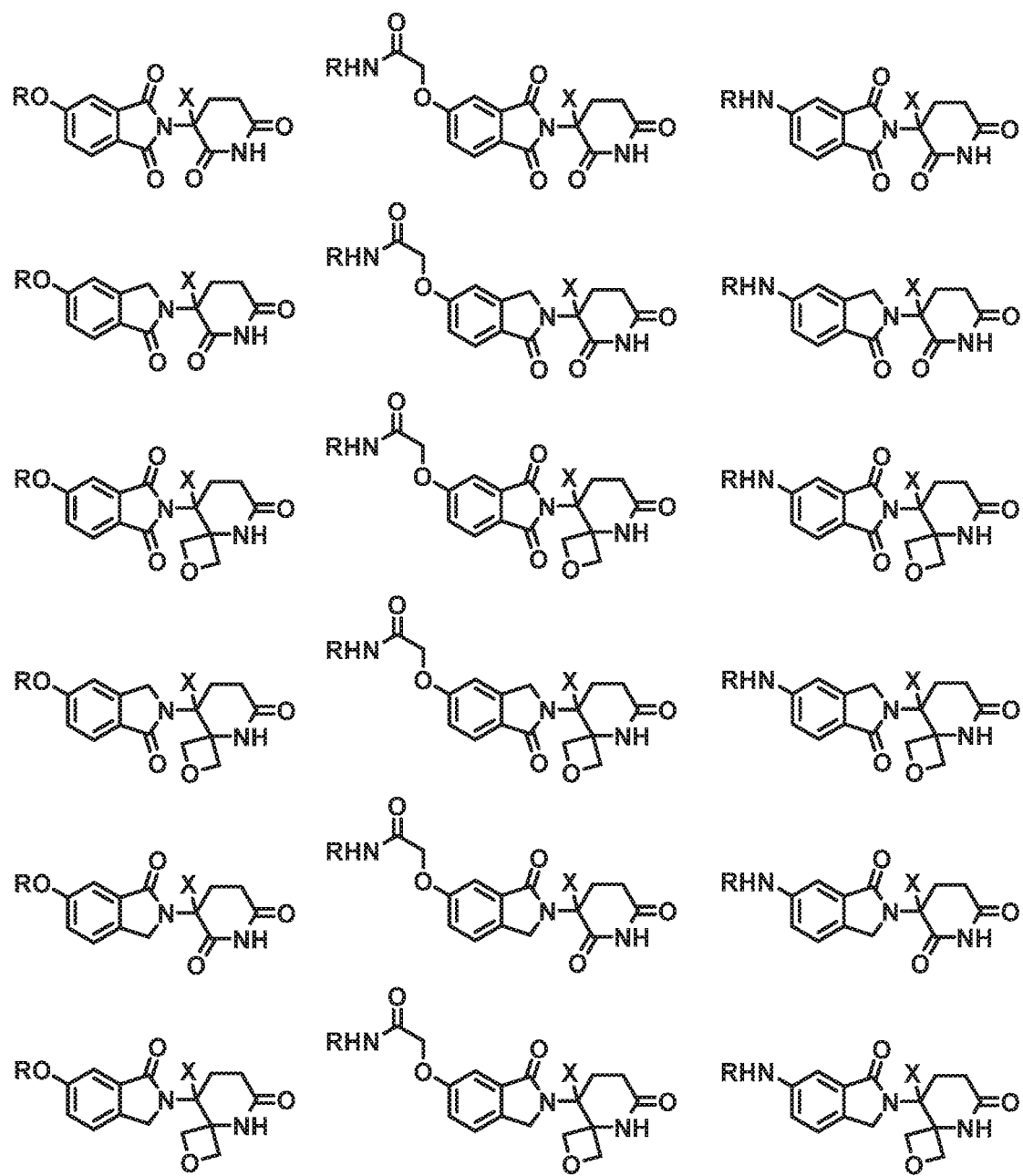
Figure 42C:
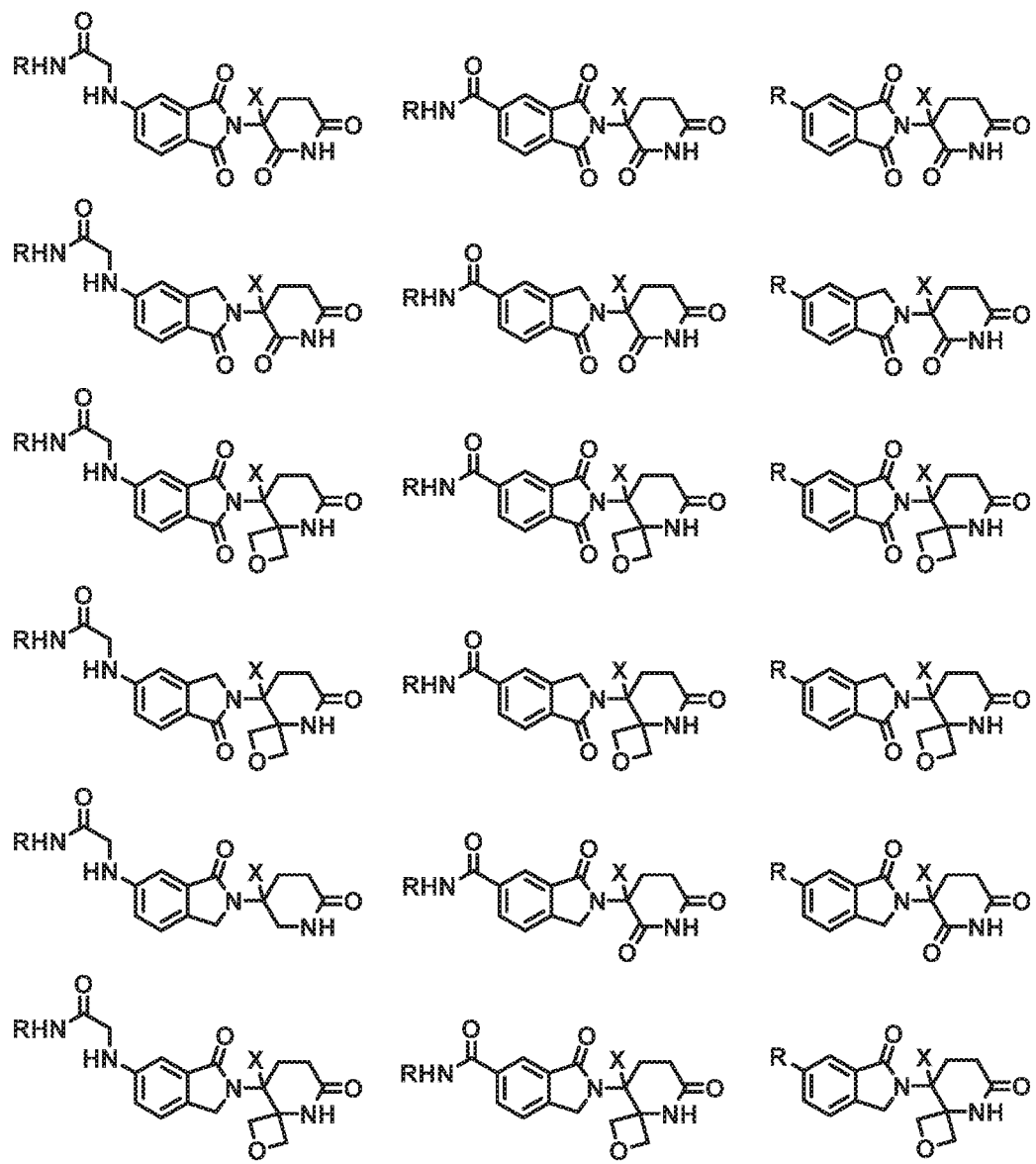
Figure 42D:
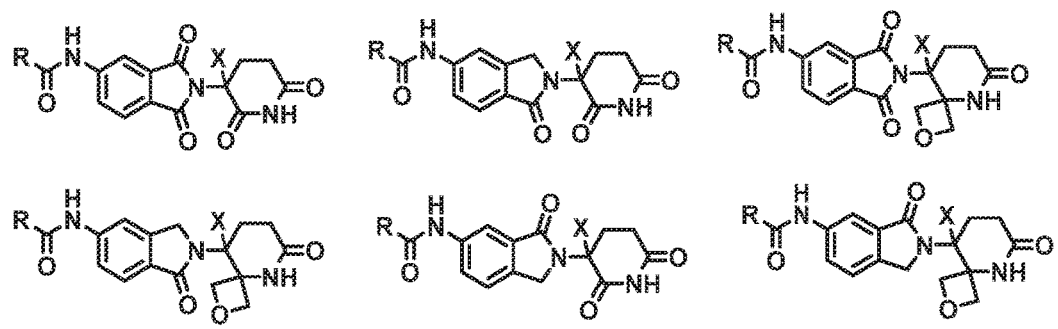
Figure 42E:
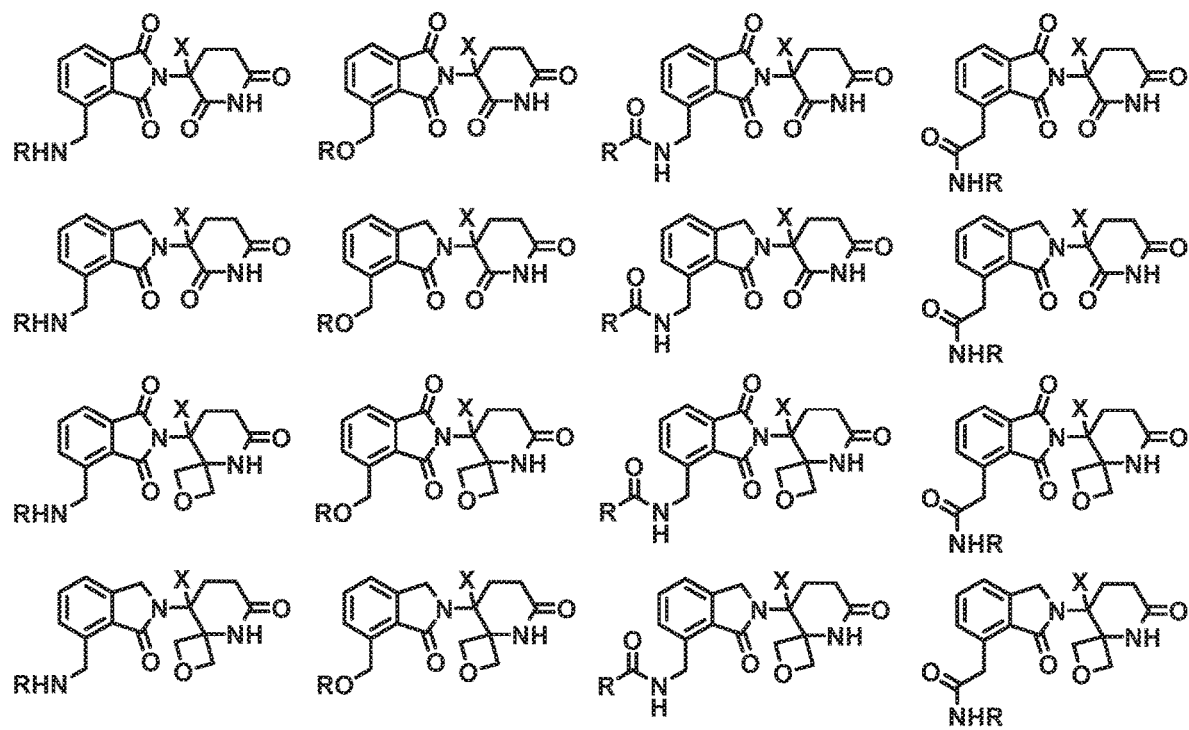
Figure 42F:
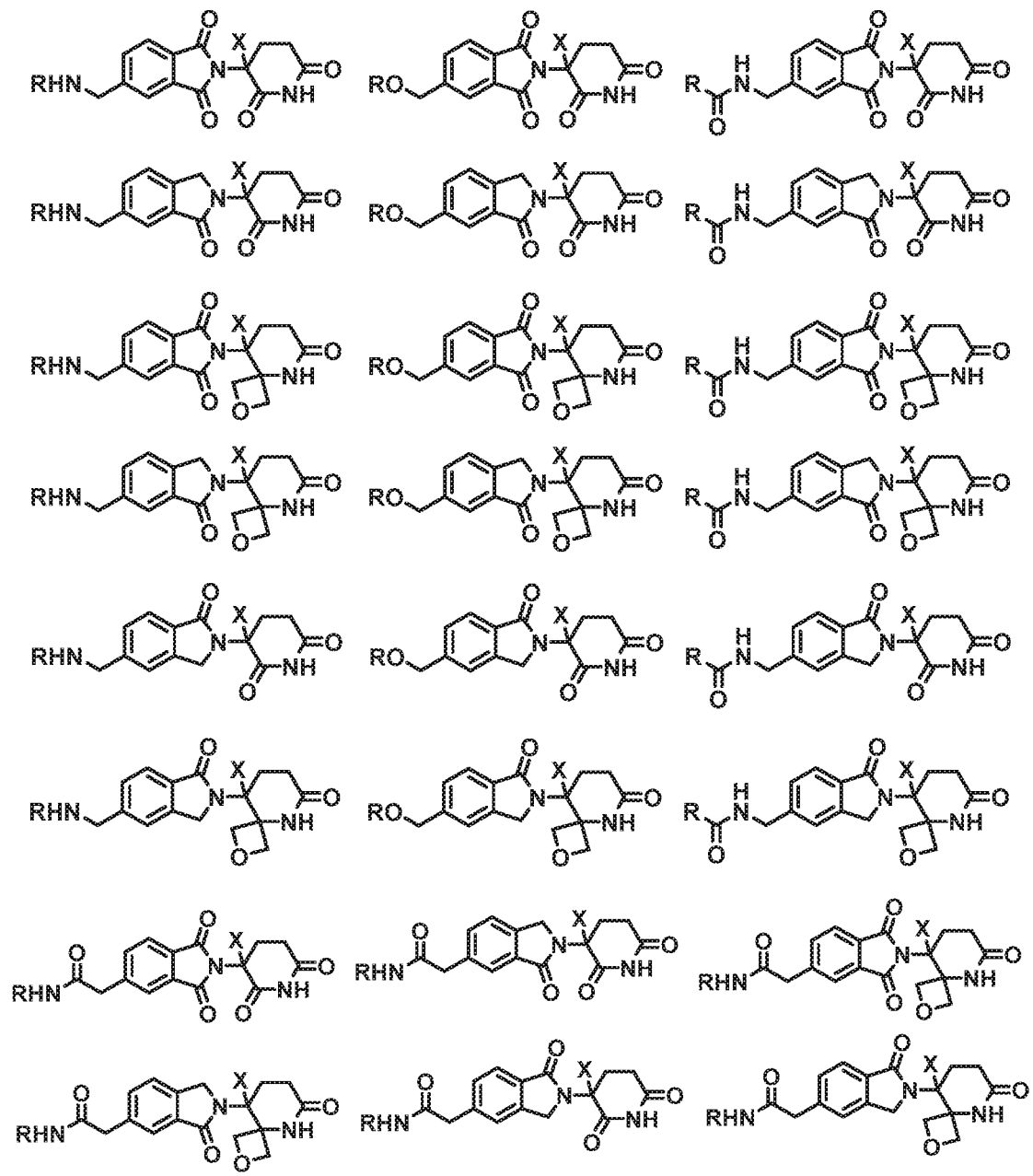
Figure 42G:
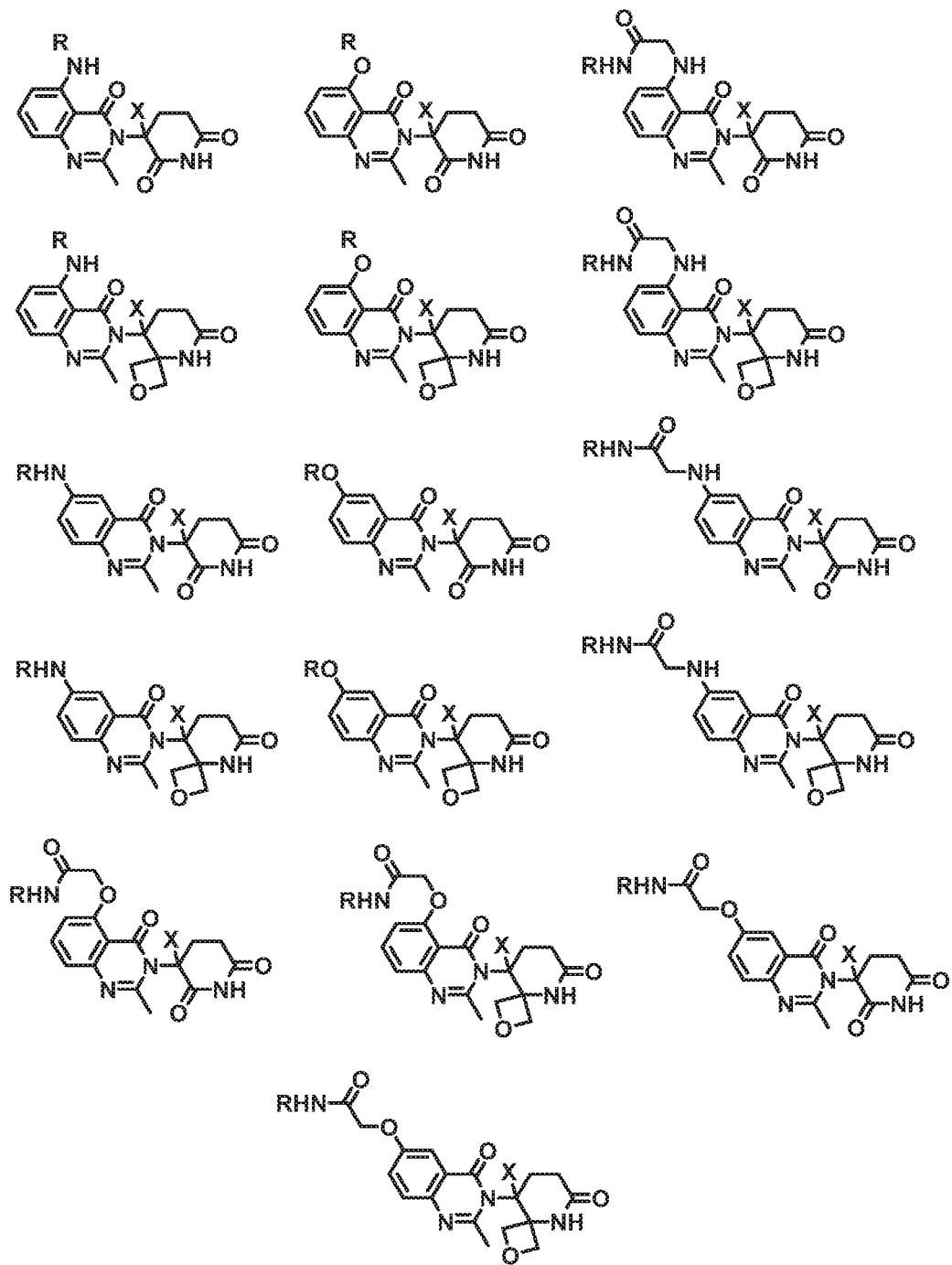
Figure 42H:
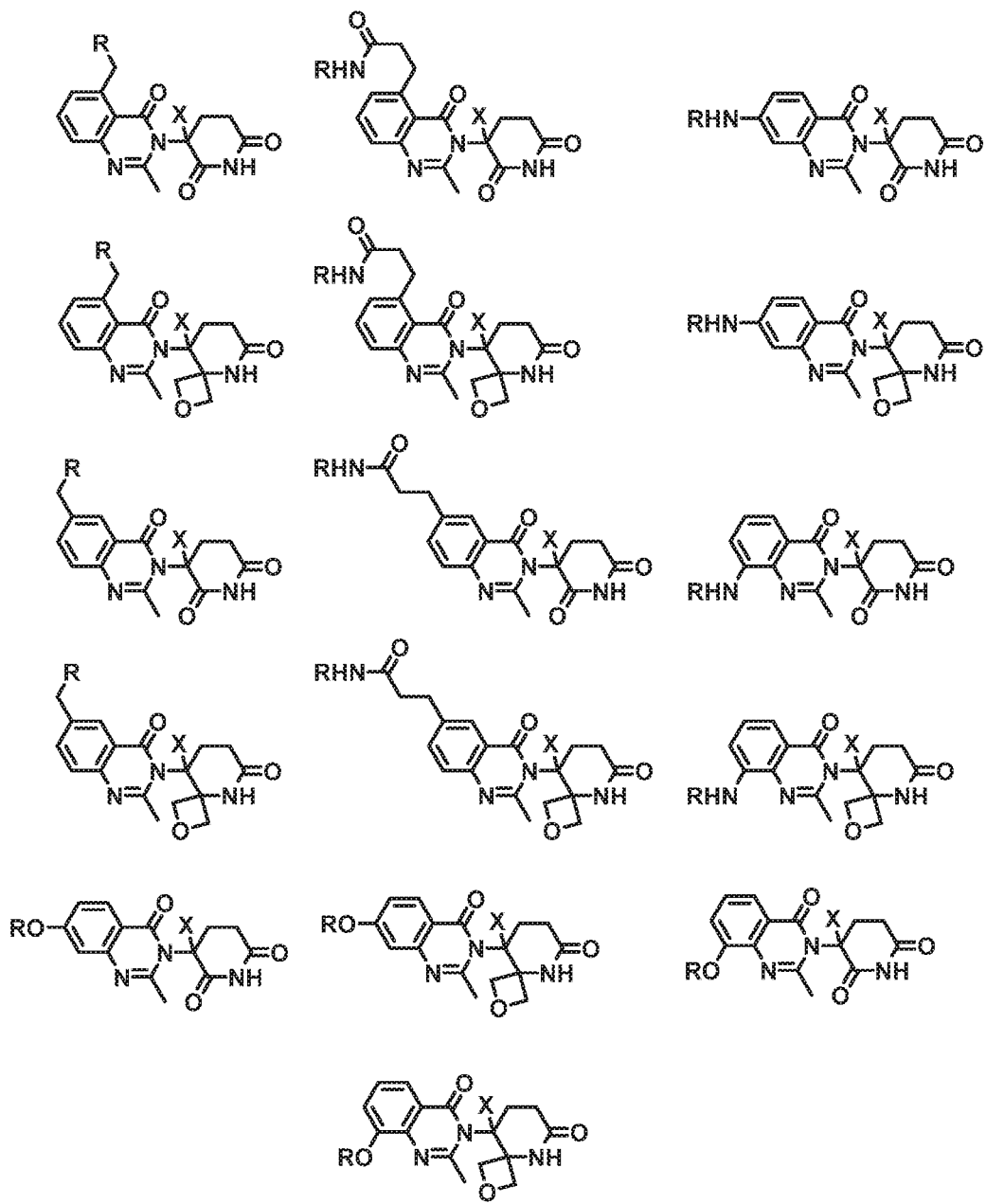
Figure 42I:
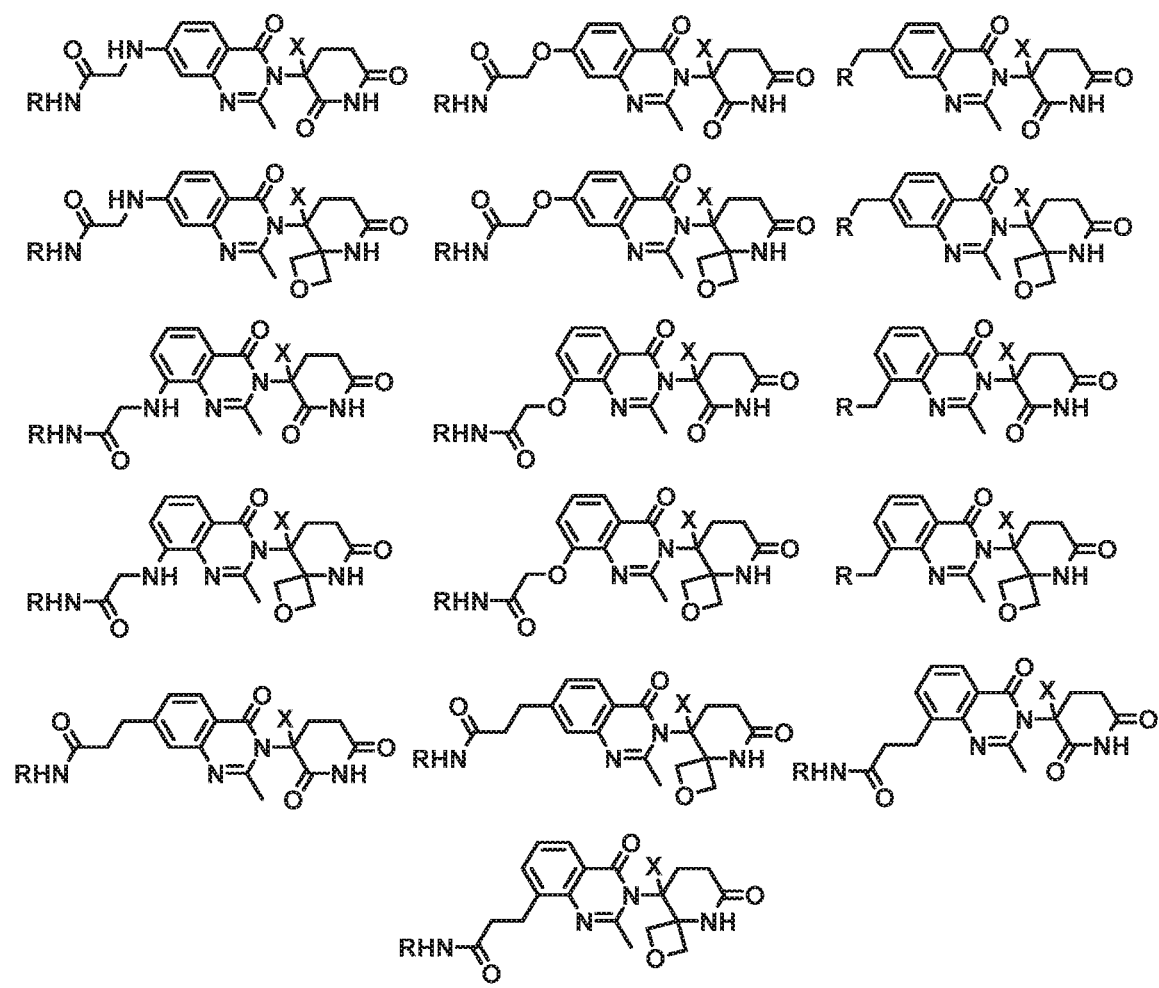

FIG. 41 is an immunoblot of SMART-CAR BD1 expressing Jurkat T-cells treated with a heterobifunctional molecule dBET.

Example 33: BCMA-CAR-dTAG

As an alternative example, the CAR has an extracellular targeting ligand domain comprising an scFv to BCMA. The BCMA scFv is cloned in frame with the C8 alpha chain linker, the 4-1BB TM and cytoplasmic domain, the CD3-ζ cytoplasmic domain and the dTAG sequence to form a functional BCMA-CAR-dTAG. For example, the BCMA scFv has a variable light chain (VL) composed of the amino acid sequence (SEQ. ID. NO.: 68):

```
DIVLTQSPPSLAMSLGKRATISCRASESVTILGSHLIYWYQQKPGQPPTL

LIQLASNVQTGVPARFSGSGSRTDFTLTIDPVEEDDVAVYYCLQSRTIPR

TFGGGTKLEIK,
``` where the CD8a signal peptide is composed of amino acid sequence (SEQ. ID. NO.: 69):

MALPVTALLLPLALLLHAARPD.

The scFv to BCMA has a variable heavy chain (VH) composed of amino acid sequence (SEQ. ID. NO.: 70):

QIQLVQSGPELKKPGETVKISCKASGYTFRHYSMNWVKQAPGKGLKWMGR

INTESGVPIYADDFKGRFAFSVETSASTAYLVINNLKDEDTASYFCSNDY

LYSLDFWGQGTALTVSS.

The scFv variable light chain (VL) and variable heavy chain (VH) are connected by a Whitlow linker having the amino acid sequence (SEQ. ID. NO.: 71):

GGGGSGGGGSGGGGS.

The scFv to BCMA is fused in frame with a modified CD8 alpha chain hinge region having the amino acid sequence (SEQ. ID. NO.: 72):

TTTPAPRPPTPAPTIASQPLSLRPEACRPAAGGAVHTRGLDFACDIYIWA

PLAGTCGVLLLSLVITLYC.

The effector domain is comprised of a transmembrane domain cloned in frame with 1 or more cytoplasmic signaling domains.

As exemplified herein, the Transmembrane domain (TM) can be a fragment of the co-stimulatory 4-1BB protein which includes the 4-1BB TM and cytoplasmic domain. The fragment is composed of the following amino acid sequence (SEQ. ID. NO.: 73):

KRGRKKLLYIFKQPFMRPVQTTQEEDGCSCRFPEEEEGGCEL.

The 4-1BB cytoplasmic domain is cloned in frame with the intracellular CD3-ζ domain. CD3-ζ domain is comprised of the following amino acid sequence (SEQ. ID. NO.: 74):

RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

The functional CAR sequence is then linked by a triple glycine linker (GGG) and cloned in frame with a dTAG composed of the following amino acid sequence (SEQ. ID. NO.: 75):

GVQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVFD

VELLKLE.

The dTAG amino acid sequence is a derivative of FKBP12 with the F36V mutation.

The dTAG is then linked to the HA tag by a double glycine linker (GG). The HA tag is composed of the following amino acid sequence (SEQ. ID. NO.: 76):

YPYDVPDYA

As expressed, the complete amino acid sequence of the exemplary BCMA-CAR-dTAG is (SEQ. ID. NO.: 77):

MALPVTALLLPLALLLHAARPDDIVLTQSPPSLAMSLGKRATISCRASES

VTILGSHLIYWYQQKPGQPPTLLIQLASNVQTGVPARFSGSGSRTDFTLT

IDPVEEDDVAVYYCLQSRTIPRTFGGGTKLEIKGGGGSGGGGSGGGGSQI

QLVQSGPELKKPGETVKISCKASGYTFRHYSMNWVKQAPGKGLKWMGRIN

TESGVPIYADDFKGRFAFSVETSASTAYLVINNLKDEDTASYFCSNDYLY

SLDFWGQGTALTVSSTTTPAPRPPTPAPTIASQPLSLRPEACRPAAGGAV

HTRGLDFACDIYIWAPLAGTCGVLLLSLVITLYCKRGRKKLLYIFKQPFM

RPVQTTQEEDGCSCRFPEEEEGGCELRVKFSRSADAPAYKQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPRGGGGVQVETISP

GDGRTFPKRGQTCVVHYTGMLEDGKKVDSSRDRNKPFKFMLGKQEVIRGW

EEGVAQMSVGQRAKLTISPDYAYGATGHPGIIPPHATLVFDVELLKLEGG

YPYDVPDYA.

As described in more detail above, the synthetic DNA construct expressing the CAR amino acid sequence as described is introduced into an T-cell population from a subject having a disorder, for example a cancer (in this instance a solid breast cancer, for example). Autologous T-cells are isolated from the subject's blood via apheresis and the propagated ex-vivo using any of the methods described above. The synthetic CAR plasmid DNA is then introduced to the autologous T-cell population via a mechanism including, but not limited to, plasmid transfection, viral transduction, non-viral electroporation using transposable elements. The resultant CAR T-cells are expanded ex-vivo and then introduced to donor patients via transfusion.

Upon receiving the CAR T-cell, subjects are monitored for development of CRS and other associated toxicities. Subjects suffering from CRS or other CAR T-cell associated toxicities are administered an effective amount of a heterobifunctional compound, for example dFKBP* which targets the dTAG of the exemplary BCMA-CAR-dTAG of SEQ. ID. NO.: 77. CAR degradation and T-cell load can be confirmed by FLOW cytometry.

Upon reversal of CRS and/or other associated toxicities, administration of dFKBP* can be withdrawn and CAR re-expression on T-cells monitored by FLOW Cytometry.

Example 34: BCMA-CAR-dTAG

As an alternative example of a BCMA-CAR-dTAG, the CAR has an extracellular targeting ligand domain comprising an scFv to BCMA. The BCMA scFv is cloned in frame with the C8 alpha chain linker, the 4-1BB TM and cytoplasmic domain, the CD3-ζ cytoplasmic domain and the dTAG sequence to form a functional BCMA-CAR-dTAG. For example, the BCMA scFv has a variable light chain (VL) composed of the amino acid sequence (SEQ. ID. NO.: 78):

DIVLTQSPPSLAMSLGKRATISCRASESVTILGSHLIYWYQQKPGQPPTL

LIQLASNVQTGVPARFSGSGSRTDFTLTIDPVEEDDVAVYYCLQSRTIPR

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC, where the CD8a signal peptide is composed of amino acid sequence (SEQ. ID. NO.: 69):

MALPVTALLLPLALLLHAARPD.

The scFv to BCMA has a variable heavy chain (VH) composed of amino acid sequence (SEQ. ID. NO.: 79):

QIQLVQSGPELKKPGETVKISCKASGYTFRHYSMNWVKQAPGKGLKWMGR

INTESGVPIYADDFKGRFAFSVETSASTAYLVINNLKDEDTASYFCSNDY

LYSLDFWGQGTTLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG.

The scFv variable light chain (VL) and variable heavy chain (VH) are connected by a Whitlow linker having the amino acid sequence (SEQ. ID. NO.: 71):

GGGGSGGGGSGGGGS.

The scFv to BCMA is fused in frame with a modified CD8 alpha chain hinge region having the amino acid sequence (SEQ. ID. NO.: 72):

TTTPAPRPPTPAPTIASQPLSLRPEACRPAAGGAVHTRGLDFACDIYIWA

PLAGTCGVLLLSLVITLYC.

The effector domain is comprised of a transmembrane domain cloned in frame with 1 or more cytoplasmic signaling domains.

As exemplified herein, the Transmembrane domain (TM) can be a fragment of the co-stimulatory 4-1BB protein which includes the 4-1BB TM and cytoplasmic domain. The fragment is composed of the following amino acid sequence (SEQ. ID. NO.: 73):

KRGRKKLLYIFKQPFMRPVQTTQEEDGCSCRFPEEEEGGCEL.

The 4-1BB cytoplasmic domain is cloned in frame with the intracellular CD3-ζ domain. CD3-ζ domain is comprised of the following amino acid sequence (SEQ. ID. NO.: 74):

RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

The functional CAR sequence is then linked by a triple glycine linker (GGG) and cloned in frame with a dTAG composed of the following amino acid sequence (SEQ. ID. NO.: 75):

GVQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVFD

VELLKLE.

The dTAG amino acid sequence is a derivative of FKBP12 with the F36V mutation.

The dTAG is then linked to the HA tag by a double glycine linker (GG). The HA tag is composed of the following amino acid sequence (SEQ. ID. NO 76):

YPYDVPDYA

As expressed, the complete amino acid sequence of the exemplary BCMA-CAR-dTAG is (SEQ. ID. NO.: 80):

MALPVTALLLPLALLLHAARPDDIVLTQSPPSLAMSLGKRATISCRASES

VTILGSHLIYWYQQKPGQPPTLLIQLASNVQTGVPARFSGSGSRTDFTLT

IDPVEEDDVAVYYCLQSRTIPRTFGGGTKLEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGECGGGGSGGGGS

GGGGSQIQLVQSGPELKKPGETVKISCKASGYTFRHYSMNWVKQAPGKGL

KWMGRINTESGVPIYADDFKGRFAFSVETSASTAYLVINNLKDEDTASYF

CSNDYLYSLDFWGQGTTLTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSP

GTTTPAPRPPTPAPTIASQPLSLRPEACRPAAGGAVHTRGLDFACDIYIW

APLAGTCGVLLLSLVITLYCKRGRKKLLYIFKQPFMRPVQTTQEEDGCSC

RFPEEEEGGCELRVKFSRSADAPAYKQGQNQLYNELNLGRREEYDVLDKR

RGRDPEMGGKPRRKNPQEGLYNELQKDKMAEAYSEIGMKGERRRGKGHDG

LYQGLSTATKDTYDALHMQALPPRGGGVQVETISPGDGRTFPKRGQTCV

VHYTGMLEDGKKVDSSRDRNKPFKFMLGKQEVIRGWEEGVAQMSVGQRAK

LTISPDYAYGATGHPGIIPPHATLVFDVELLKLEGGYPYDVPDYA.

As described in more detail above, the synthetic DNA construct expressing the CAR amino acid sequence as described is introduced into an T-cell population from a subject having a disorder, for example a cancer (in this instance a solid breast cancer, for example). Autologous T-cells are isolated from the subject's blood via apheresis and the propagated ex-vivo using any of the methods described above. The synthetic CAR plasmid DNA is then introduced to the autologous T-cell population via a mechanism including, but not limited to, plasmid transfection, viral transduction, non-viral electroporation using transposable elements. The resultant CAR T-cells are expanded ex-vivo and then introduced to donor patients via transfusion.

Upon receiving the CAR T-cell, subjects are monitored for development of CRS and other associated toxicities. Subjects suffering from CRS or other CAR T-cell associated toxicities are administered an effective amount of a heterobifunctional compound, for example dFKBP* which targets the dTAG of the exemplary BCMA-CAR-dTAG of SEQ. ID. NO.: 80. CAR degradation and T-cell load can be confirmed by FLOW cytometry.

Upon reversal of CRS and/or other associated toxicities, administration of dFKBP* can be withdrawn and CAR re-expression on T-cells monitored by FLOW Cytometry.

Example 35: CD38-CAR-dTAG

As an alternative example, the CAR has an extracellular targeting ligand domain comprising an scFv to CD38. The CD38 scFv is cloned in frame with the C8 alpha chain linker, the 4-1BB TM and cytoplasmic domain, the CD3-ζ cytoplasmic domain and the dTAG sequence to form a functional CD38-CAR-dTAG. For example, the CD38 scFv has a variable light chain (VL) composed of the amino acid sequence (SEQ. ID. NO.: 81): DIQMTQSPSSL-SASVGDRVTITCRASQGIRSWLAWYQQK-PEKAPKSLIYAASSLQSGVPS RFSGSGSGTDFTLTISSLQPEDFATYYCQQYNSY-PLTFGGGTKVEIK, where the CD8a signal peptide is composed of amino acid sequence (SEQ. ID. NO.: 69): MALPVTALLLPLALLLHAARPD.

The scFv to CD38 has a variable heavy chain (VH) composed of amino acid sequence (SEQ. ID. NO.: 82):

QVQLVQSGAEVKKPGSSVKVSCKAFGGTFSSYAISWVRQAPGQGLEWMGR

IIRFLGIANYAQKFQGRVTLIADKSTNTAYMELSSLRSEDTAVYYCAGEP

GERDPDAVDIWGQGTMVTVSS.

The scFv variable light chain (VL) and variable heavy chain (VH) are connected by a Whitlow linker having the amino acid sequence (SEQ. ID. NO.: 71):

GGGGSGGGGSGGGGS.

The scFv to CD38 is fused in frame with a modified CD8 alpha chain hinge region having the amino acid sequence (SEQ. ID. NO.: 72):

TTTPAPRPPTPAPTIASQPLSLRPEACRPAAGGAVHTRGLDFACDIYIWA

PLAGTCGVLLLSLVITLYC.

The effector domain is comprised of a transmembrane domain cloned in frame with 1 or more cytoplasmic signaling domains.

As exemplified herein, the Transmembrane domain (TM) can be a fragment of the co-stimulatory 4-1BB protein which includes the 4-1BB TM and cytoplasmic domain. The fragment is composed of the following amino acid sequence (SEQ. ID. NO.: 73):

KRGRKKLLYIFKQPFMRPVQTTQEEDGCSCRFPEEEEGGCEL.

The 4-1BB cytoplasmic domain is cloned in frame with the intracellular CD3-ζ domain. CD3-ζ domain is comprised of the following amino acid sequence (SEQ. ID. NO.: 74):

RVKFSRSADAPAYKQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR.

The functional CAR sequence is then linked by a triple glycine linker (GGG) and cloned in frame with a dTAG composed of the following amino acid sequence (SEQ. ID. NO.: 75):

GVQVETISPGDGRTFPKRGQTCVVHYTGMLEDGKKVDSSRDRNKPFKFM

LGKQEVIRGWEEGVAQMSVGQRAKLTISPDYAYGATGHPGIIPPHATLV

FDVELLKLE.

The dTAG amino acid sequence is a derivative of FKBP12 with the F36V mutation.

The dTAG is then linked to the HA tag by a double glycine linker (GG). The HA tag is composed of the following amino acid sequence (SEQ. ID. NO 76):

YPYDVPDYA

As expressed, the complete amino acid sequence of the exemplary CD38-CAR-dTAG is (SEQ. ID. NO.: 83):

MALPVTALLLPLALLLHAARPDDIQMTQSPSSLSASVGDRVTITCRASQ

GIRSWLAWYQQKPEKAPKSLIYAASSLQSGVPSRFSGSGSGTDFTLTI

SSLQPEDFATYYCQQYNSYPLTFGGGTKVEIKGGGGSGGGGSGGGGSQ

VQLVQSGAEVKKPGSSVKVSCKAFGGTFSSYAISWVRQAPGQGLEWMG

RIIRFLGIANYAQKFQGRVTLIADKSTNTAYMELSSLRSEDTAVYYCA

GEPGERDPDAVDIWGQGTMVTVSSTTTPAPRPPTPAPTIASQPLSLRP

EACRPAAGGAVHTRGLDFACDIYIWAPLAGTCGVLLLSLVITLYCKRG

RKKLLYIFKQPFMRPVQTTQEEDGCSCRFPEEEEGGCELRVKFSRSAD

APAYKQGQNQLYNELNLGRREEYDVLDKRRGRDPEMGGKPRRKNPQE

GLYNELQKDKMAEAYSEIGMKGERRRGKGHDGLYQGLSTATKDTYDAL

HMQALPPRGGGVQVETISPGDGRTFPKRGQTCVVHYTGMLEDGKKVD

SSRDRNKPFKFMLGKQEVIRGWEEGVAQMSVGQRAKLTISPDYAYGA

TGHPGIIPPHATLVFDVELLKLEGGYPYDVPDYA.

As described in more detail above, the synthetic DNA construct expressing the CAR amino acid sequence as described is introduced into an T-cell population from a subject having a disorder, for example a cancer (in this instance a solid breast cancer, for example). Autologous T-cells are isolated from the subject's blood via apheresis and the propagated ex-vivo using any of the methods described above. The synthetic CAR plasmid DNA is then introduced to the autologous T-cell population via a mechanism including, but not limited to, plasmid transfection, viral transduction, non-viral electroporation using transposable elements. The resultant CAR T-cells are expanded ex-vivo and then introduced to donor patients via transfusion.

Upon receiving the CAR T-cell, subjects are monitored for development of CRS and other associated toxicities. Subjects suffering from CRS or other CAR T-cell associated toxicities are administered an effective amount of a heterobifunctional compound, for example dFKBP* which targets the dTAG of the exemplary CD38-CAR-dTAG of SEQ. ID. NO.: 83. CAR degradation and T-cell load can be confirmed by FLOW cytometry.

Upon reversal of CRS and/or other associated toxicities, administration of dFKBP* can be withdrawn and CAR re-expression on T-cells monitored by FLOW Cytometry.

Example 36: CD38-CAR-dTAG

As an alternative example of a CD38-CAR-dTAG, the CAR has an extracellular targeting ligand domain comprising an scFv to CD38. The CD38 scFv is cloned in frame with the C8 alpha chain linker, the 4-1BB TM and cytoplasmic domain, the CD3-ζ cytoplasmic domain and the dTAG sequence to form a functional CD38-CAR-dTAG. For example, the CD38 scFv has a variable light chain (VL) composed of the amino acid sequence (SEQ. ID. NO.: 81):

DIQMTQSPSSLSASVGDRVTITCRASQGIRSWLAWYQQKPEKAPKSLIY

AASSLQSGVPSRFSGSGSGTDFTLTISSLQPEDFATYYCQQYNSYPLT

FGGGTKVEIK, where the CD8a signal peptide is composed of amino acid sequence (SEQ. ID. NO.: 69):

MALPVTALLLPLALLLHAARPD.

The scFv to CD38 has a variable heavy chain (VH) composed of amino acid sequence (SEQ. ID. NO.: 84):

QVQLVQSGAEVKKPGSSVKVSCKAFGGTFSSYAISWVRQAPGQGLEWM

GRIIRFLGKTNHAQKFQGRVTLTADKSTNTAYMELSSLRSEDTAVYYC

AGEPGDRDPDAVDIWGQGTMVTVSS.

The scFv variable light chain (VL) and variable heavy chain (VH) are connected by a Whitlow linker having the amino acid sequence (SEQ. ID. NO.: 71):

GGGGSGGGGSGGGGS.

The scFv to CD38 is fused in frame with a modified CD8 alpha chain hinge region having the amino acid sequence (SEQ. ID. NO.: 72):

TTTPAPRPPTPAPTIASQPLSLRPEACRPAAGGAVHTRGLDFACDIYIWA

PLAGTCGVLLLSLVITLYC.

The effector domain is comprised of a transmembrane domain cloned in frame with 1 or more cytoplasmic signaling domains.

As exemplified herein, the Transmembrane domain (TM) can be a fragment of the co-stimulatory 4-1BB protein which includes the 4-1BB TM and cytoplasmic domain. The fragment is composed of the following amino acid sequence (SEQ. ID. NO.: 73):

KRGRKKLLYIFKQPFMRPVQTTQEEDGCSCRFPEEEEGGCEL.

The 4-1BB cytoplasmic domain is cloned in frame with the intracellular CD3-ζ domain. CD3-ζ domain is comprised of the following amino acid sequence (SEQ. ID. NO.: 74):

RVKFSRSADAPAYKQGQNQLYNELNLGRREEYDVLDKRRGRDPEMGGKP

RRKNPQEGLYNELQKDKMAEAYSEIGMKGERRRGKGHDGLYQGLSTA

TKDTYDALHMQALPPR.

The functional CAR sequence is then linked by a triple glycine linker (GGG) and cloned in frame with a dTAG composed of the following amino acid sequence (SEQ. ID. NO.: 75):

GVQVETISPGDGRTFPKRGQTCVVHYTGMLEDGKKVDSSRDRNKPFKFM

LGKQEVIRGWEEGVAQMSVGQRAKLTISPDYAYGATGHPGIIPPHATLV

FDVELLKLE.

The dTAG amino acid sequence is a derivative of FKBP12 with the F36V mutation.

The dTAG is then linked to the HA tag by a double glycine linker (GG). The HA tag is composed of the following amino acid sequence (SEQ. ID. NO.: 76):

YPYDVPDYA

As expressed, the complete amino acid sequence of the exemplary CD38-CAR-dTAG is (SEQ. ID. NO.: 85):

MALPVTALLLPLALLLHAARPDDIQMTQSPSSLSASVGDRVTITCRASQG

IRSWLAWYQQKPEKAPKSLIYAASSLQSGVPSRFSGSGSGTDFTLTISSL

QPEDFATYYCQQYNSYPLTFGGGTKVEIKGGGGSGGGGSGGGGSQVQLVQ

SGAEVKKPGSSVKVSCKAFGGTFSSYAISWVRQAPGQGLEWMGRIIRFLG

KTNHAQKFQGRVTLTADKSTNTAYMELSSLRSEDTAVYYCAGEPGDRDPD

AVDIWGQGTMVTVSSTTTPAPRPPTPAPTIASQPLSLRPEACRPAAGGAV

HTRGLDFACDIYIWAPLAGTCGVLLLSLVITLYCKRGRKKLLYIFKQPFM

RPVQTTQEEDGCSCRFPEEEEGGCELRVKFSRSADAPAYKQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPRGGGVQVETISP

GDGRTFPKRGQTCVVHYTGMLEDGKKVDSSRDRNKPFKFMLGKQEVIRGW

EEGVAQMSVGQRAKLTISPDYAYGATGHPGIIPPHATLVFDVELLKLEGG

YPYDVPDYA.

As described in more detail above, the synthetic DNA construct expressing the CAR amino acid sequence as described is introduced into an T-cell population from a subject having a disorder, for example a cancer (in this instance a solid breast cancer, for example). Autologous T-cells are isolated from the subject's blood via apheresis and the propagated ex-vivo using any of the methods described above. The synthetic CAR plasmid DNA is then introduced to the autologous T-cell population via a mechanism including, but not limited to, plasmid transfection, viral transduction, non-viral electroporation using transposable elements. The resultant CAR T-cells are expanded ex-vivo and then introduced to donor patients via transfusion.

Upon receiving the CAR T-cell, subjects are monitored for development of CRS and other associated toxicities. Subjects suffering from CRS or other CAR T-cell associated toxicities are administered an effective amount of a heterobifunctional compound, for example dFKBP* which targets the dTAG of the exemplary CD38-CAR-dTAG of SEQ. ID. NO.: 85. CAR degradation and T-cell load can be confirmed by FLOW cytometry.

Upon reversal of CRS and/or other associated toxicities, administration of dFKBP* can be withdrawn and CAR re-expression on T-cells monitored by FLOW Cytometry.

Example 37: CD38-CAR-dTAG

As an alternative example of a CD38-CAR-dTAG, the CAR has an extracellular targeting ligand domain comprising an scFv to CD38. The CD38 scFv is cloned in frame with the C8 alpha chain linker, the 4-1BB TM and cytoplasmic domain, the CD3-ζ cytoplasmic domain and the dTAG sequence to form a functional CD38-CAR-dTAG. For example, the CD38 scFv has a variable light chain (VL) composed of the amino acid sequence (SEQ. ID. NO.: 86):

DIQMTQSPSSLSASVGDRVTITCRASQGIRSWLAWYQQKPEKAPKSLIYA

ASSLQSGVPSRFSGSGSGTDFTLTISSLQPEDFATYYCQQYNNYPLTFGG

GTKVEIK, where the CD8a signal peptide is composed of amino acid sequence (SEQ. ID. NO.: 69):

MALPVTALLLPLALLLHAARPD.

The scFv to CD38 has a variable heavy chain (VH) composed of amino acid sequence (SEQ. ID. NO.: 87):

QVQLVQSGAEVKKPGSSVKVSCKPSGGTFRSYAISWVRQAPGQGLEWMGR

IIVFLGKVNYAQRFQGRVTLTADKSTTTAYMELSSLRSEDTAVYYCTGEP

GARDPDAFDIWGQGTMVTVSS.

The scFv variable light chain (VL) and variable heavy chain (VH) are connected by a Whitlow linker having the amino acid sequence (SEQ. ID. NO.: 71):

GGGGSGGGGSGGGGS.

The scFv to CD38 is fused in frame with a modified CD8 alpha chain hinge region having the amino acid sequence (SEQ. ID. NO.: 72):

TTTPAPRPPTPAPTIASQPLSLRPEACRPAAGGAVHTRGLDFACDIYIWA

PLAGTCGVLLLSLVITLYC.

The effector domain is comprised of a transmembrane domain cloned in frame with 1 or more cytoplasmic signaling domains.

As exemplified herein, the Transmembrane domain (TM) can be a fragment of the co-stimulatory 4-1BB protein which includes the 4-1BB TM and cytoplasmic domain. The fragment is composed of the following amino acid sequence (SEQ. ID. NO.: 73):

KRGRKKLLYIFKQPFMRPVQTTQEEDGCSCRFPEEEEGGCEL.

The 4-1BB cytoplasmic domain is cloned in frame with the intracellular CD3-ζ domain. CD3-ζ domain is comprised of the following amino acid sequence (SEQ. ID. NO.: 74):

RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

The functional CAR sequence is then linked by a triple glycine linker (GGG) and cloned in frame with a dTAG composed of the following amino acid sequence (SEQ. ID. NO.: 75):

GVQVETISPGDGRTFPKRGQTCVVHYTGMLEDGKKVDSSRDRNKPFKFML

GKQEVIRGWEEGVAQMSVGQRAKLTISPDYAYGATGHPGIIPPHATLVFD

VELLKLE.

The dTAG amino acid sequence is a derivative of FKBP12 with the F36V mutation.

The dTAG is then linked to the HA tag by a double glycine linker (GG). The HA tag is composed of the following amino acid sequence (SEQ. ID. NO.: 76):

YPYDVPDYA

As expressed, the complete amino acid sequence of the exemplary CD38-CAR-dTAG is (SEQ. ID. NO.: 88):

MALPVTALLLPLALLLHAARPDDIQMTQSPSSLSASVGDRVTITCRASQG

IRSWLAWYQQKPEKAPKSLIYAASSLQSGVPSRFSGSGSGTDFTLTISSL

QPEDFATYYCQQYNNYPLTFGGGTKVEIKGGGGSGGGGSGGGGSQVQLVQ

SGAEVKKPGSSVKVSCKPSGGTFRSYAISWVRQAPGQGLEWMGRIIVFLG

KVNYAQRFQGRVTLTADKSTTTAYMELSSLRSEDTAVYYCTGEPGARDPD

AFDIWGQGTMVTVSSTTTPAPRPPTPAPTIASQPLSLRPEACRPAAGGAV

HTRGLDFACDIYIWAPLAGTCGVLLLSLVITLYCKRGRKKLLYIFKQPFM

RPVQTTQEEDGCSCRFPEEEEGGCELRVKFSRSADAPAYKQGQNQLYNEL

NLGRREEYDVLDKRRGRDPEMGGKPRRKNPQEGLYNELQKDKMAEAYSEI

-continued

GMKGERRRGKGHDGLYQGLSTATKDTYDALHMQALPPRGGGGVQVETISP

GDGRTFPKRGQTCVVHYTGMLEDGKKVDSSRDRNKPFKFMLGKQEVIRGW

EEGVAQMSVGQRAKLTISPDYAYGATGHPGIIPPHATLVFDVELLKLEGG

YPYDVPDYA.

As described in more detail above, the synthetic DNA construct expressing the CAR amino acid sequence as described is introduced into an T-cell population from a subject having a disorder, for example a cancer (in this instance a solid breast cancer, for example). Autologous T-cells are isolated from the subject's blood via apheresis and the propagated ex-vivo using any of the methods described above. The synthetic CAR plasmid DNA is then introduced to the autologous T-cell population via a mechanism including, but not limited to, plasmid transfection, viral transduction, non-viral electroporation using transposable elements. The resultant CAR T-cells are expanded ex-vivo and then introduced to donor patients via transfusion.

Upon receiving the CAR T-cell, subjects are monitored for development of CRS and other associated toxicities. Subjects suffering from CRS or other CAR T-cell associated toxicities are administered an effective amount of a heterobifunctional compound, for example dFKBP* which targets the dTAG of the exemplary CD38-CAR-dTAG of SEQ. ID. NO.: 88. CAR degradation and T-cell load can be confirmed by FLOW cytometry.

Upon reversal of CRS and/or other associated toxicities, administration of dFKBP* can be withdrawn and CAR re-expression on T-cells monitored by FLOW Cytometry.

Example 38: CD19-CAR-dTAG

As an alternative example, the CAR has an extracellular targeting ligand domain comprising an scFv to CD19. The CD19 scFv is cloned in frame with the C8 alpha chain linker, the 4-1BB TM and cytoplasmic domain, the CD3-ζ cytoplasmic domain and the dTAG sequence to form a functional CD38-CAR-dTAG. For example, the CD19 scFv has a variable light chain (VL) composed of the amino acid sequence (SEQ. ID. NO.: 89):

IQMTQTTSSLSASLGDRVTISCRASQDISKYLNWYQQKPDGTVKLLIYHT

SRLHSGVPSRFSGSGSGTDYSLTISNLEQEDIATYFCQQGNTLPYTFGGG

TKLEIT, where the CD8a signal peptide is composed of amino acid sequence (SEQ. ID. NO.: 69):

MALPVTALLLPLALLLHAARPD.

The scFv to CD19 has a variable heavy chain (VH) composed of amino acid sequence (SEQ. ID. NO.: 90):

EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS.

The scFv variable light chain (VL) and variable heavy chain (VH) are connected by a Whitlow linker having the amino acid sequence (SEQ. ID. NO.: 71):

GGGGSGGGGSGGGGS.

The scFv to CD19 is fused in frame with a modified CD8 alpha chain hinge region having the amino acid sequence (SEQ. ID. NO.: 72):

TTTPAPRPPTPAPTIASQPLSLRPEACRPAAGGAVHTRGLDFACDIYIWA

PLAGTCGVLLLSLVITLYC.

The effector domain is comprised of a transmembrane domain cloned in frame with 1 or more cytoplasmic signaling domains.

As exemplified herein, the Transmembrane domain (TM) can be a fragment of the co-stimulatory 4-1BB protein which includes the 4-1BB TM and cytoplasmic domain. The fragment is composed of the following amino acid sequence (SEQ. ID. NO.: 73):

KRGRKKLLYIFKQPFMRPVQTTQEEDGCSCRFPEEEEGGCEL.

The 4-1BB cytoplasmic domain is cloned in frame with the intracellular CD3-ζ domain. CD3-ζ domain is comprised of the following amino acid sequence (SEQ. ID. NO.: 74):

RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

The functional CAR sequence is then linked by a triple glycine linker (GGG) and cloned in frame with a dTAG composed of the following amino acid sequence (SEQ. ID. NO.: 91):

NPPPPETSNPNKPKRQTNQLQYLLRVVLKTLWKHQFAWPFQQPVDAVKLN

LPDYYKIIKTPMDMGTIKKRLENNYYWNAQECIQDFNTMFTNCYIYNKPG

DDIVLMAEALEKLFLQKINELPTEE.

The dTAG amino acid sequence is a derivative of BD1, a protein that is a portion of BD4.

The dTAG is then linked to the HA tag by a double glycine linker (GG). The HA tag is composed of the following amino acid sequence (SEQ. ID. NO 76):

YPYDVPDYA

As expressed, the complete amino acid sequence of the exemplary CD19-CAR-dTAG is (SEQ. ID. NO.: 92):

MALPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITGGGGSGGGGSGGGGSEVKLQES

GPGLVAPSQSLSVTCTVSGVSLPDYGVSWIRQPPRKGLEWLGVIWGSETT

YYNSALKSRLTIIKDNSKSQVFLKMNSLQTDDTAIYYCAKHYYYGGSYAM

-continued

```
DYWGQGTSVTVSSTTTPAPRPPTPAPTIASQPLSLRPEACRPAAGGAVHT

RGLDFACDIYIWAPLAGTCGVLLLSLVITLYCKRGRKKLLYIFKQPFMRP

VQTTQEEDGCSCRFPEEEEGGCELRVKFSRSADAPAYKQGQNQLYNELNL

GRREEYDVLDKRRGRDPEMGGKPRRKNPQEGLYNELQKDKMAEAYSEIGM

KGERRRGKGHDGLYQGLSTATKDTYDALHMQALPPRGGGNPPPPETSNPN

KPKRQTNQLQYLLRVVLKTLWKHQFAWPFQQPVDAVKLNLPDYYKIIKTP

MDMGTIKKRLENNYYWNAQECIQDFNTMFTNCYIYNKPGDDIVLMAEALE

KLFLQKINELPTEEGGYPYDVPDYA.
```

As described in more detail above, the synthetic DNA construct expressing the CAR amino acid sequence as described is introduced into an T-cell population from a subject having a disorder, for example a cancer (in this instance a solid breast cancer, for example). Autologous T-cells are isolated from the subject's blood via apheresis and the propagated ex-vivo using any of the methods described above. The synthetic CAR plasmid DNA is then introduced to the autologous T-cell population via a mechanism including, but not limited to, plasmid transfection, viral transduction, non-viral electroporation using transposable elements. The resultant CAR T-cells are expanded ex-vivo and then introduced to donor patients via transfusion.

Upon receiving the CAR T-cell, subjects are monitored for development of CRS and other associated toxicities. Subjects suffering from CRS or other CAR T-cell associated toxicities are administered an effective amount of a heterobifunctional compound, for example BD1 which targets the dTAG of the exemplary CD19-CAR-BD1 of SEQ. ID. NO.: 92. CAR degradation and T-cell load can be confirmed by FLOW cytometry.

Upon reversal of CRS and/or other associated toxicities, administration of dBD1 can be withdrawn and CAR re-expression on T-cells monitored by FLOW Cytometry.

Example 39: CD19-CAR-dTAG

As an alternative example, the CAR has an extracellular targeting ligand domain comprising an scFv to CD19. The CD19 scFv is cloned in frame with the C8 alpha chain linker, the 4-1BB TM and cytoplasmic domain, the CD3-ζ cytoplasmic domain and the dTAG sequence to form a functional CD38-CAR-dTAG. For example, the CD19 scFv has a variable light chain (VL) composed of the amino acid sequence (SEQ. ID. NO.: 89):

```
IQMTQTTSSLSASLGDRVTISCRASQDISKYLNWYQQKPDGTVKLLIYHT

SRLHSGVPSRFSGSGSGTDYSLTISNLEQEDIATYFCQQGNTLPYTFGGG

TKLEIT,
``` where the CD8a signal peptide is composed of amino acid sequence (SEQ. ID. NO.: 69):

```
MALPVTALLLPLALLLHAARPD.
```

The scFv to CD19 has a variable heavy chain (VH) composed of amino acid sequence (SEQ. ID. NO.: 90):

```
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS.
```

The scFv variable light chain (VL) and variable heavy chain (VH) are connected by a Whitlow linker having the amino acid sequence (SEQ. ID. NO.: 71):

```
GGGGSGGGGSGGGGS.
```

The scFv to CD19 is fused in frame with a modified CD8 alpha chain hinge region having the amino acid sequence (SEQ. ID. NO.: 72):

```
TTTPAPRPPTPAPTIASQPLSLRPEACRPAAGGAVHTRGLDFACDIYIWA

PLAGTCGVLLLSLVITLYC.
```

The effector domain is comprised of a transmembrane domain cloned in frame with 1 or more cytoplasmic signaling domains.

As exemplified herein, the Transmembrane domain (TM) can be a fragment of the co-stimulatory 4-1BB protein which includes the 4-1BB TM and cytoplasmic domain. The fragment is composed of the following amino acid sequence (SEQ. ID. NO.: 73):

```
KRGRKKLLYIFKQPFMRPVQTTQEEDGCSCRFPEEEEGGCEL.
```

The 4-1BB cytoplasmic domain is cloned in frame with the intracellular CD3-ζ domain. CD3-ζ domain is comprised of the following amino acid sequence (SEQ. ID. NO.: 74):

```
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.
```

The functional CAR sequence is then linked by a triple glycine linker (GGG) and cloned in frame with a dTAG composed of the following amino acid sequence (SEQ. ID. NO.: 93):

```
GASRLYTLVLVLQPQRVLLGMKKRGFGAGRWNGFGGKVQEGETIEDGARR

ELQEESGLTVDALHKVGQIVFEFVGEPELMDVHVFCTDSIQGTPVESDEM

RPCWFQLDQIPFKDMWPDDSYWFPLLLQKKKFHGYFKFQGQDTILDYTLR

EVDT.
```

The dTAG amino acid sequence is a derivative of MTH1.

The dTAG is then linked to the HA tag by a double glycine linker (GG). The HA tag is composed of the following amino acid sequence (SEQ. ID. NO.: 76):

```
YPYDVPDYA
```

As expressed, the complete amino acid sequence of the exemplary CD19-CAR-dTAG is (SEQ. ID. NO.: 94):

MALPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITGGGGSGGGGSGGGGSEVKLQES

GPGLVAPSQSLSVTCTVSGVSLPDYGVSWIRQPPRKGLEWLGVIWGSETT

YYNSALKSRLTIIKDNSKSQVFLKMNSLQTDDTAIYYCAKHYYYGGSYAM

DYWGQGTSVTVSSTTTPAPRPPTPAPTIASQPLSLRPEACRPAAGGAVHT

RGLDFACDIYIWAPLAGTCGVLLLSLVITLYCKRGRKKLLYIFKQPFMRP

VQTTQEEDGCSCRFPEEEEGGCELRVKFSRSADAPAYKQGQNQLYNELNL

GRREEYDVLDKRRGRDPEMGGKPRRKNPQEGLYNELQKDKMAEAYSEIGM

KGERRRGKGHDGLYQGLSTATKDTYDALHMQALPPRGGGGASRLYTLVLV

LQPQRVLLGMKKRGFGAGRWNGFGGKVQEGETIEDGARRELQEESGLTVD

ALHKVGQIVFEFVGEPELMDVHVFCTDSIQGTPVESDEMRPCWFQLDQIP

FKDMWPDDSYWFPLLLQKKKFHGYFKFQGQDTILDYTLREVDTVGGYPYD

VPDYA.

As described in more detail above, the synthetic DNA construct expressing the CAR amino acid sequence as described is introduced into an T-cell population from a subject having a disorder, for example a cancer (in this instance a solid breast cancer, for example). Autologous T-cells are isolated from the subject's blood via apheresis and the propagated ex-vivo using any of the methods described above. The synthetic CAR plasmid DNA is then introduced to the autologous T-cell population via a mechanism including, but not limited to, plasmid transfection, viral transduction, non-viral electroporation using transposable elements. The resultant CAR T-cells are expanded ex-vivo and then introduced to donor patients via transfusion.

Upon receiving the CAR T-cell, subjects are monitored for development of CRS and other associated toxicities. Subjects suffering from CRS or other CAR T-cell associated toxicities are administered an effective amount of a heterobifunctional compound, for example MTH1 which targets the dTAG of the exemplary CD19-CAR-MTH1 of SEQ. ID. NO.: 94. CAR degradation and T-cell load can be confirmed by FLOW cytometry.

Upon reversal of CRS and/or other associated toxicities, administration of dMTH1 can be withdrawn and CAR re-expression on T-cells monitored by FLOW Cytometry.

What is claimed is:

1. A T cell or natural killer (NK) cell comprising:
   a. a chimeric antigen receptor polypeptide, wherein the chimeric antigen receptor polypeptide comprises:
      i. an extracellular ligand binding domain comprising a single chain variable fragment (scFv) antibody that binds human CD19, BCMA, or CD38;
      ii. a CD8, CD28, or CD137 transmembrane domain; and
      iii. a cytoplasmic domain comprising at least one intracellular signaling domain, wherein the at least one intracellular signaling domain comprises CD3; and
   b. a cytoplasmic costimulatory polypeptide, wherein the cytoplasmic costimulatory polypeptide comprises:
      i. at least one intracellular signaling domain selected from a CD28, 4-1BB, OX40, CD27, ICOS, DAP-10, and DAP-12 signaling domain; and
      ii. a heterobifunctional compound targeting protein, wherein the heterobifunctional compound targeting protein comprises the amino acid sequence selected from SEQ ID NO: 1 and 2 and wherein the heterobifunctional compound targeting protein binds to a heterobifunctional compound selected from the group consisting of dFKBP-1 to dFKBP-13;
   wherein the binding of the heterobifunctional compound to the heterobifunctional compound targeting protein brings the cytoplasmic costimulatory polypeptide into proximity of a ubiquitin ligase; and wherein the cytoplasmic costimulatory polypeptide is ubiquitinated and then degraded by a proteasome.

2. The T cell or natural killer (NK) cell of claim 1, wherein the heterobifunctional compound targeting protein comprises the amino acid sequence of SEQ ID NO: 2.

3. The T cell or natural killer (NK) cell of claim 1, wherein the T cell or natural killer (NK) cell is a T cell.

4. The T cell or natural killer (NK) cell of claim 1, wherein the chimeric antigen receptor polypeptide further comprises a CD8α hinge domain.

5. The T cell or natural killer (NK) cell of claim 1, wherein the at least one intracellular signaling domain of the cytoplasmic costimulatory polypeptide is CD28.

6. A therapeutic system, comprising:
   a. the T cell or natural killer (NK) cell of claim 1; and
   b. a heterobifunctional compound comprising any one of dFKBP-1 to dFKBP-13.

7. A method of reducing an adverse immune response in a subject caused by an activated T cell or natural killer (NK) cell that expresses a chimeric antigen receptor polypeptide and a cytoplasmic costimulatory polypeptide of claim 1 comprising:
   administering to the subject experiencing an adverse immune response an effective amount of a heterobifunctional compound comprising any one of dFKBP-1 to dFKBP-13;
   wherein the subject had previously been administered the T cell or natural killer (NK) cell of claim 1.

8. A T cell or natural killer (NK) cell comprising a chimeric antigen receptor polypeptide, wherein the chimeric antigen receptor polypeptide comprises:

a. an extracellular ligand binding domain comprising a single chain variable fragment (scFv) antibody that binds human CD19, BCMA, or CD38;
b. a CD8, CD28, or CD137 transmembrane domain; and
c. a cytoplasmic domain, wherein the cytoplasmic domain comprises:
  i. at least one intracellular signaling domain, wherein the at least one intracellular signaling domain comprises CD3; and
  ii. a heterobifunctional compound targeting protein, wherein the heterobifunctional compound targeting protein comprises an amino acid sequence selected from SEQ ID NO: 1 and 2 and wherein the heterobifunctional compound targeting protein binds to a heterobifunctional compound;
wherein the binding of the heterobifunctional compound to the heterobifunctional compound targeting protein brings the chimeric antigen receptor polypeptide into proximity of a ubiquitin ligase;
and wherein the chimeric antigen receptor polypeptide is ubiquitinated and then degraded by a proteasome.

9. The T cell or natural killer (NK) cell of claim 8, wherein the T cell or natural killer (NK) cell is a T cell.

10. The T cell or natural killer (NK) cell of claim 1, wherein the chimeric antigen receptor polypeptide further comprises a CD8α hinge domain.

11. A therapeutic system for downregulating activation of a T cell or natural killer (NK) cell expressing a chimeric antigen receptor polypeptide, the system comprising:
a. the T cell or natural killer (NK) cell of claim 8; and
b. a heterobifunctional compound comprising any one of dFKBP-1 to dFKBP-13.

12. A method of reducing an adverse immune response in a subject caused by an activated T cell or natural killer (NK) cell that expresses a chimeric antigen receptor polypeptide of claim 8 comprising:
administering to the subject experiencing an adverse immune response an effective amount of a heterobifunctional compound comprising any one of dFKBP-1 to dFKBP-13;
wherein the subject had previously been administered the T cell or natural killer (NK) cell of claim 8.

13. The T cell or natural killer (NK) cell of claim 1, wherein the extracellular ligand binding domain binds CD19.

14. The T cell or natural killer (NK) cell of claim 8, wherein the extracellular ligand binding domain binds CD19.

15. The T cell or natural killer (NK) cell of claim 1, wherein the extracellular ligand binding domain that binds CD19 comprises scFv comprising the amino acid sequence of SEQ ID NO: 10 or 89.

16. The T cell or natural killer (NK) cell of claim 1, wherein the extracellular ligand binding domain that binds BCMA comprises a variable light chain (VL) and a variable heavy chain (VH) wherein the VL comprises the amino acid sequence of SEQ ID NO: 68 or SEQ ID NO: 78 and wherein the VH comprises the amino acid sequence of SEQ ID NO: 70 or SEQ ID NO: 79.

17. The T cell or natural killer (NK) cell of claim 1, wherein the extracellular ligand binding domain that binds CD38 comprises a variable light chain (VL) and a variable heavy chain (VH) wherein the VL comprises the amino acid sequence of SEQ ID NO: 81 or SEQ ID NO: 86 and the VH comprises the amino acid sequence of SEQ ID NO: 82 or SEQ ID NO: 87.

18. The T cell or natural killer (NK) cell of claim 1, wherein the CD28 transmembrane domain comprises the amino acid sequence of SEQ ID NO: 16.

19. The T cell or natural killer (NK) cell of claim 1, wherein the CD8 transmembrane domain comprises a CD8 alpha hinge comprising the amino acid sequence of SEQ ID NO: 15.

20. The T cell or natural killer (NK) cell of claim 1, wherein the CD3 intracellular signaling domain comprises the amino acid sequence of SEQ ID NO: 17.

21. The T cell or natural killer (NK) cell of claim 8, wherein the extracellular ligand binding domain that binds CD19 comprises scFv comprising the amino acid sequence of SEQ ID NO: 10.

22. The T cell or natural killer (NK) cell of claim 8, wherein the extracellular ligand binding domain that binds BCMA comprises a variable light chain (VL) and a variable heavy chain (VH) wherein the VL comprises the amino acid sequence of SEQ ID NO: 68 or SEQ ID NO: 78 and the VH comprises the amino acid sequence of SEQ ID NO: 70 or SEQ ID NO: 79.

23. The T cell or natural killer (NK) cell of claim 8, wherein the extracellular ligand binding domain that binds CD38 comprises a variable light chain (VL) and a variable heavy chain (VH) wherein the VL comprises the amino acid sequence of SEQ ID NO: 81 or SEQ ID NO: 86 and the VH comprises the amino acid sequence of SEQ ID NO: 82 or SEQ ID NO: 87.

24. The T cell or natural killer (NK) cell of claim 8, wherein the CD28 transmembrane domain comprises the amino acid sequence of SEQ ID NO: 16.

25. The T cell or natural killer (NK) cell of claim 8, wherein the CD8 transmembrane domain comprises the amino acid sequence of SEQ ID NO: 15.

26. The T cell or natural killer (NK) cell of claim 8, wherein the CD3 intracellular signaling domain comprises the amino acid sequence of SEQ ID NO: 17.

27. The T cell or natural killer (NK) cell of claim 8, wherein the chimeric antigen receptor polypeptide further comprises a CD8α hinge domain.

28. The T cell or natural killer (NK) cell of claim 1, wherein the extracellular ligand binding domain that binds CD19 comprises a variable light chain (VL) and a variable heavy chain (VH) wherein the VL comprises the amino acid sequence of SEQ ID NO: 12 or SEQ ID NO: 89 and the VH comprises the amino acid sequence of SEQ ID NO: 14 or SEQ ID NO: 90.

29. The T cell or natural killer (NK) cell of claim 8, wherein the extracellular ligand binding domain that binds CD19 comprises a variable light chain (VL) and a variable heavy chain (VH) wherein the VL comprises the amino acid sequence of SEQ ID NO: 12 or SEQ ID NO: 89 and the VH comprises the amino acid sequence of SEQ ID NO: 14 or SEQ ID NO: 90.

* * * * *